United States Patent
Ding et al.

(10) Patent No.: US 10,975,081 B2
(45) Date of Patent: *Apr. 13, 2021

(54) SUBSTITUTED FUSED PYRAZOLE COMPOUNDS AND THEIR USE AS LRRK2 INHIBITORS

(71) Applicant: GlaxoSmithKline Intellectual Property Development Limited, Middlesex (GB)

(72) Inventors: Xiao Ding, Shanghai (CN); Yun Jin, Shanghai (CN); Qian Liu, Shanghai (CN); Feng Ren, Shanghai (CN); Yingxia Sang, Shanghai (CN); Luigi Piero Stasi, Shanghai (CN); Zehong Wan, Shanghai (CN); Hailong Wang, Shanghai (CN); Weiqiang Xing, Shanghai (CN); Yang Zhan, Shanghai (CN); Baowei Zhao, Shanghai (CN)

(73) Assignee: GLAXOSMITHKLINE INTELLECTUAL PROPERTY DEVELOPMENT LIMITED, Middlesex (GB)

(*) Notice: Subject to any disclaimer, the term of this patent is extended or adjusted under 35 U.S.C. 154(b) by 464 days.

This patent is subject to a terminal disclaimer.

(21) Appl. No.: 15/746,817

(22) PCT Filed: Jul. 22, 2016

(86) PCT No.: PCT/CN2016/090962
§ 371 (c)(1),
(2) Date: Jan. 23, 2018

(87) PCT Pub. No.: WO2017/012576
PCT Pub. Date: Jan. 26, 2017

(65) Prior Publication Data
US 2020/0079777 A1    Mar. 12, 2020

(30) Foreign Application Priority Data

Jul. 23, 2015  (WO) ................ PCT/CN2015/084893

(51) Int. Cl.
*C07D 487/04* (2006.01)
*A61P 25/28* (2006.01)
*A61P 25/16* (2006.01)
*A61K 31/5377* (2006.01)

(52) U.S. Cl.
CPC ........ *C07D 487/04* (2013.01); *A61K 31/5377* (2013.01); *A61P 25/16* (2018.01); *A61P 25/28* (2018.01)

(58) Field of Classification Search
CPC .............. A61K 31/5377; C07D 413/14; C07D 487/04; A61P 25/16
USPC .................... 514/116, 262.1; 544/234.5, 262
See application file for complete search history.

(56) References Cited

U.S. PATENT DOCUMENTS

2011/0130384 A1    6/2011   Takeda

FOREIGN PATENT DOCUMENTS

| RU | 2 431 635 C2 | 10/2011 |
|----|---|---|
| WO | WO2006047516 | 5/2006 |
| WO | WO2011106168 | 9/2011 |
| WO | WO2012009258 | 1/2012 |
| WO | WO 2014/001377 A1 | 1/2014 |
| WO | WO 2014/134772 A1 | 9/2014 |
| WO | WO2015099196 | 7/2015 |
| WO | WO 2016/036586 A1 | 3/2016 |

*Primary Examiner* — Jeffrey H Murray
(74) *Attorney, Agent, or Firm* — Robert H. Brink; Duke M. Fitch; Edward R. Gimmi

(57) ABSTRACT

Disclosed are substituted fused pyrazoles, for example substituted indazoles, that inhibit LRRK2 kinase activity, pharmaceutical compositions containing them and their use in the treatment of Parkinson's disease.

18 Claims, No Drawings

Specification includes a Sequence Listing.

SEQUENCE LISTING

<160> NUMBER OF SEQ ID NOS: 10

<210> SEQ ID NO 1
<211> LENGTH: 48
<212> TYPE: DNA
<213> ORGANISM: Artificial
<220> FEATURE:
<223> OTHER INFORMATION: Primer

<400> SEQUENCE: 1
gatctcgacg ggcgcggatc caccatggat tacaaggatg acgacgat        48

<210> SEQ ID NO 2
<211> LENGTH: 49
<212> TYPE: DNA
<213> ORGANISM: Artificial
<220> FEATURE:
<223> OTHER INFORMATION: Primer

<400> SEQUENCE: 2
catggattac aaggatgacg acgataagat ggctagtggc agctgtcag        49

<210> SEQ ID NO 3
<211> LENGTH: 46
<212> TYPE: DNA
<213> ORGANISM: Artificial
<220> FEATURE:
<223> OTHER INFORMATION: Primer

<400> SEQUENCE: 3
gttcacgaga tccactattc agtaagagtt ccaccaattt gggact        46

<210> SEQ ID NO 4
<211> LENGTH: 23
<212> TYPE: DNA
<213> ORGANISM: Artificial
<220> FEATURE:
<223> OTHER INFORMATION: Primer

<400> SEQUENCE: 4
gaatagtgga tctcgtgaac aag        23

<210> SEQ ID NO 5
<211> LENGTH: 25
<212> TYPE: DNA
<213> ORGANISM: Artificial
<220> FEATURE:
<223> OTHER INFORMATION: Primer

<400> SEQUENCE: 5
gtcagacaaa ctgcttggaa ccagc        25

<210> SEQ ID NO 6

```
<211> LENGTH: 40
<212> TYPE: DNA
<213> ORGANISM: Artificial
<220> FEATURE:
<223> OTHER INFORMATION: Primer

<400> SEQUENCE: 6
ctggttccaa gcagtttgtc tgaccacagg cctgtgatag                              40

<210> SEQ ID NO 7
<211> LENGTH: 46
<212> TYPE: DNA
<213> ORGANISM: Artificial
<220> FEATURE:
<223> OTHER INFORMATION: Primer

<400> SEQUENCE: 7
gttctagcca agcttggtac cctattactc aacagatgtt cgtctc                      46

<210> SEQ ID NO 8
<211> LENGTH: 7611
<212> TYPE: DNA
<213> ORGANISM: Artificial
<220> FEATURE:
<223> OTHER INFORMATION: Wild type full length Flag-LRRK2 coding
      sequence

<400> SEQUENCE: 8
atggattaca aggatgacga cgataagatg gctagtggca gctgtcaggg gtgcgaagag        60
gacgaggaaa ctctgaagaa gttgatagtc aggctgaaca atgtccagga aggaaaacag      120
atagaaacgc tggtccaaat cctggaggat ctgctggtgt tcacgtactc cgagcacgcc      180
tccaagttat ttcaaggcaa aaatatccat gtgcctctgt tgatcgtctt ggactcctat      240
atgagagtcg cgagtgtgca gcaggtgggt tggtcacttc tgtgcaaatt aatagaagtc      300
tgtccaggta caatgcaaag cttaatggga ccccaggatg ttggaaatga ttgggaagtc      360
cttggtgttc accaattgat tcttaaaatg ctaacagttc ataatgccag tgtaaacttg      420
tcagtgattg gactgaagac cttagatctc ctcctaactt caggtaaaat caccttgctg      480
atactggatg aagaaagtga tattttcatg ttaattttg atgccatgca ctcatttcca      540
gccaatgatg aagtccagaa acttggatgc aaagctttac atgtgctgtt tgagagagtc      600
tcagaggagc aactgactga attgttgag acaaagatt atatgatatt gttaagtgcg      660
ttaacaaatt ttaaagatga agaggaaatt gtgcttcatg tgctgcattg tttacattcc      720
ctagcgattc cttgcaataa tgtggaagtc ctcatgagtg gcaatgtcag tgttataat      780 attgtggtgg aagctatgaa agcattccct atgagtgaaa gaattcaaga agtgagttgc      840
tgtttgctcc ataggcttac attaggtaat ttttcaata tcctggtatt aaacgaagtc      900
catgagtttg tggtgaaagc tgtgcagcag tacccagaga atgcagcatt gcagatctca      960
gcgctcagct gtttggccct cctcactgag actattttct taaatcaaga tttagaggaa     1020
aagaatgaga atcaagagaa tgatgatgag ggggaagaag ataaattgtt ttggctggaa     1080
gcctgttaca agcattaac gtggcataga aagaacaagc acgtgcagga ggccgcatgc     1140
tgggcactaa ataatctcct tatgtaccaa acagtttac atgagaagat ggagatgaa     1200 gatggccatt tcccagctca tagggaagtg atgctctcca tgctgatgca ttcttcatca     1260
aaggaagttt tccaggcatc tgcgaatgca ttgtcaactc tcttagaaca aaatgttaat     1320
ttcagaaaaa tactgttatc aaaaggaata cacctgaatg ttttggagtt aatgcagaag     1380
```

```
catatacatt ctcctgaagt ggctgaaagt ggctgtaaaa tgctaaatca tcttttgaa      1440 ggaagcaaca cttccctgga tataatggca gcagtggtcc ccaaaatact aacagttatg     1500
aaacgtcatg agacatcatt accagtgcag ctggaggcgc ttcgagctat tttacatttt    1560
atagtgcctg gcatgccaga agaatccagg gaggatacag aatttcatca taagctaaat    1620
atggttaaaa aacagtgttt caagaatgat attcacaaac tggtcctagc agctttgaac    1680
aggttcattg gaaatcctgg gattcagaaa tgtggattaa agtaatttc ttctattgta     1740 cattttcctg atgcattaga gatgttatcc ctggaaggtg ctatggattc agtgcttcac    1800
acactgcaga tgtatccaga tgaccaagaa attcagtgtc tgggtttaag tcttatagga    1860
tacttgatta caaagaagaa tgtgttcata ggaactggac atctgctggc aaaaattctg    1920
gtttccagct ataccgatt taaggatgtt gctgaaatac agactaaagg atttcagaca     1980
atcttagcaa tcctcaaatt gtcagcatct ttttctaagc tgctggtgca tcattcattt    2040
gacttagtaa tattccatca aatgtcttcc aatatcatgg aacaaaagga tcaacagttt    2100
ctaaacctct gttgcaagtg ttttgcaaaa gtagctatgg atgattactt aaaaaatgtg    2160
atgctagaga gagcgtgtga tcagaataac agcatcatgg ttgaatgctt gcttctattg    2220
ggagcagatg ccaatcaagc aaaggaggga tcttcttta tttgtcaggt atgtgagaaa     2280
gagagcagtc ccaaattggt ggaactctta ctgaatagtg atctcgtga acaagatgta     2340 cgaaaagcgt tgacgataag cattgggaaa ggtgacagcc agatcatcag cttgctctta    2400
aggaggctgg ccctggatgt ggccaacaat agcatttgcc ttggaggatt ttgtatagga    2460
aaagttgaac cttcttggct tggtccttta tttccagata agacttctaa tttaaggaaa    2520
caaacaaata tagcatctac actagcaaga atggtgatca gatatcagat gaaaagtgct    2580
gtggaagaag aacagcctc aggcagcgat ggaaattttt ctgaagatgt gctgtctaaa    2640
tttgatgaat ggacctttat tcctgactct tctatggaca gtgtgtttgc tcaaagtgat    2700
gacctggata gtgaaggaag tgaaggctca tttcttgtga aaaagaaatc taattcaatt    2760
agtgtaggag aattttaccg agatgccgta ttacagcgtt gctcaccaaa tttgcaaaga    2820
cattccaatt ccttggggcc cattttgat catgaagatt tactgaagcg aaaaagaaaa     2880
atattatctt cagatgattc actcaggtca tcaaaacttc aatcccatat gaggcattca    2940 gacagcatt cttctctggc ttctgagaga gaatatatta tcatcactaga cctttcagca    3000 aatgaactaa gagatattga tgccctaagc cagaaatgct gtataagtgt tcatttggag    3060
catcttgaaa agctggagct tcaccagaat gcactcacga gctttccaca acagctatgt    3120
gaaactctga agagtttgac acatttggac ttgcacagta ataaatttac atcatttcct    3180 tcttattgt tgaaaatgag ttgtattgct aatcttgatg tctctcgaaa tgacattgga    3240
ccctcagtgg tttagatcc tacagtgaaa tgtccaactc tgaaacagtt taacctgtca    3300
tataaccagc tgtctttgt acctgagaac ctcactgatg tggtagagaa actggagcag    3360 ctcatttag aaggaaataa aatatcaggg atatgctccc ccttgagact gaaggaactg    3420 aagatttaa accttagtaa gaaccacatt tcatccctat cagagaactt tcttgaggct    3480
tgtcctaaag tggagagttt cagtgccaga atgaatttc ttgctgctat gccttcttg     3540 cctccttcta tgacaatcct aaaattatct cagaacaaat tttcctgtat tccagaagca    3600
attttaaatc ttccacactt gcggtcttta gatatgagca gcaatgatat tcagtaccta    3660
ccaggtcccg cacactggaa atctttgaac ttaagggaac tcttatttag ccataatcag    3720
atcagcatct tggacttgag tgaaaaagca tatttatggt ctagagtaga gaaactgcat    3780
```

```
ctttctcaca ataaactgaa agagattcct cctgagattg gctgtcttga aaatctgaca   3840
tctctggatg tcagttacaa cttggaacta agatcctttc ccaatgaaat ggggaaatta   3900
agcaaaatat gggatcttcc tttggatgaa ctgcatctta actttgattt taaacatata   3960
ggatgtaaag ccaagacat cataaggttt cttcaacagc gattaaaaaa ggctgtgcct   4020
tataaccgaa tgaaacttat gattgtggga atactgggga gtggtaaaac caccttattg   4080
cagcaattaa tgaaaaccaa gaaatcagat cttggaatgc aaagtgccac agttggcata   4140
gatgtgaaag actggcctat ccaaataaga gacaaaagaa agagagatct cgtcctaaat   4200
gtgtgggatt ttgcaggtcg tgaggaattc tatagtactc atccccattt tatgacgcag   4260
cgagcattgt accttgctgt ctatgacctc agcaagggac aggctgaagt tgatgccatg   4320
aagccttggc tcttcaatat aaaggctcgc gcttcttctt cccctgtgat tctcgttggc   4380
acacatttgg atgtttctga tgagaagcaa cgcaaagcct gcatgagtaa aatcaccaag   4440
gaactcctga ataagcgagg gttccctgcc atacgagatt accactttgt gaatgccacc   4500
gaggaatctg atgctttggc aaaacttcgg aaaaccatca taaacgagag ccttaatttc   4560
aagatccgag atcagcttgt tgttggacag ctgattccag actgctatgt agaacttgaa   4620
aaaatcattt tatcggagcg taaaaatgtg ccaattgaat ttcccgtaat tgaccggaaa   4680
cgattattac aactagtgag agaaaatcag ctgcagttag atgaaaatga gcttcctcac   4740
gcagttcact ttctaaatga atcaggagtc cttcttcatt ttcaagaccc agcactgcag   4800
ttaagtgact tgtactttgt ggaacccaag tggctttgta aaatcatggc acagattttg   4860
acagtgaaag tggaaggttg tccaaaacac cctaagggaa ttatttcgcg tagagatgtg   4920
gaaaaatttc tttcaaagaa aaggaaattt ccaaagaact acatgtcaca gtattttaag   4980
ctcctagaaa aattccagat tgcttttgcca ataggagaag aatatttgct ggttccaagc   5040
agtttgtctg accacaggcc tgtgatagag cttccccatt gtgagaactc tgaaattatc   5100
atccgactat atgaaatgcc ttattttcca atgggatttt ggtcaagatt aatcaatcga   5160
ttacttgaga tttcaccctta catgctttca gggagagaac gagcacttcg cccaaacaga   5220
atgtattggc gacaaggcat ttacttaaat tggtctcctg aagcttattg tctggtagga   5280
tctgaagtct tagacaatca tccagagagt ttcttaaaaa ttacagttcc ttcttgtaga   5340
aaaggctgta ttcttttggg ccaagttgtg gaccacattg ttctctcat ggaagaatgg   5400 tttcctgggt tgctggagat tgatatttgt ggtgaaggag aaactctgtt gaagaaatgg   5460
gcattatata gttttaatga tggtgaagaa catcaaaaaa tcttacttga tgacttgatg   5520
aagaaagcag aggaaggaga tctcttagta aatccagatc aaccaaggct caccattcca   5580
atatctcaga ttgcccctga cttgattttg gctgacctgc ctagaaatat tatgttgaat   5640
aatgatgagt tggaatttga acaagctcca gagtttctcc taggtgatgg cagttttgga   5700
tcagtttacc gagcagccta tgaaggagaa gaagtggctg tgaagatttt taataaacat   5760
acatcactca ggctgttaag acaagagctt gtggtgcttt gccacctcca ccaccccagt   5820
ttgatatctt tgctggcagc tgggattcgt cccggatgt tggtgatgga gttagcctcc   5880
aagggttcct tggatcgcct gcttcagcag gacaaagcca gctcactag aaccctacag   5940 cacaggattg cactccacgt agctgatggt ttgagatacc tccactcagc catgattata   6000
taccgagacc tgaaacccca caatgtgctg ctttttcacac tgtatcccaa tgctgccatc   6060
attgcaaaga ttgctgacta cggcattgct cagtactgct gtagaatggg gataaaaaca   6120
```

-continued

```
tcagagggca caccagggtt tcgtgcacct gaagttgcca gaggaaatgt catttataac    6180
caacaggctg atgtttattc atttggttta ctactctatg acattttgac aactggaggt    6240
agaatagtag agggtttgaa gtttccaaat gagtttgatg aattagaaat acaaggaaaa    6300
ttacctgatc cagttaaaga atatggttgt gccccatggc ctatggttga gaaattaatt    6360
aaacagtgtt tgaagaaaaa tcctcaagaa aggcctactt ctgcccaggt ctttgacatt    6420
ttgaattcag ctgaattagt ctgtctgacg agacgcattt tattacctaa aaacgtaatt    6480
gttgaatgca tggttgctac acatcacaac agcaggaatg caagcatttg ctgggctgt     6540 gggcacaccg acagaggaca gctctcattt cttgacttaa atactgaagg atacacttct    6600
gaggaagttg ctgatagtag aatattgtgc ttagccttgg tgcatcttcc tgttgaaaag    6660
gaaagctgga ttgtgtctgg gacacagtct ggtactctcc tggtcatcaa taccgaagat    6720
gggaaaaaga gacatacccc tagaaaagatg actgattctg tcacttgttt gtattgcaat    6780
tccttttcca agcaaagcaa acaaaaaaat tttctttttgg ttggaaccgc tgatggcaag    6840
ttagcaattt ttgaagataa gactgttaag cttaaaggag ctgctccttt gaagatacta    6900
aatataggaa atgtcagtac tccattgatg tgtttgagtg aatccacaaa ttcaacggaa    6960
agaaatgtaa tgtggggagg atgtggcaca aagattttct ccttttctaa tgatttcacc    7020
attcagaaac tcattgagac aagaacaagc caactgtttt cttatgcagc tttcagtgat    7080
tccaacatca taacagtggt ggtagacact gctctctata ttgctaagca aaatagccct    7140
gttgtggaag tgtgggataa gaaaactgaa aaactctgtg gactaataga ctgcgtgcac    7200
tttttaaggg aggtaatggt aaaagaaaac aaggaatcaa aacacaaaat gtcttattct    7260
gggagagtga aaaccctctg ccttcagaag aacactgctc tttggatagg aactggagga    7320
ggccatattt tactcctgga tctttcaact cgtcgactta cgtgtaat ttacaacttt      7380 tgtaattcgg tcagagtcat gatgacagca cagctaggaa gccttaaaaa tgtcatgctg    7440
gtattgggct acaaccggaa aaatactgaa ggtacacaaa agcagaaaga gatacaatct    7500
tgcttgaccg tttgggacat caatcttcca catgaagtgc aaaatttaga aaaacacatt    7560
gaagtgagaa aagaattagc tgaaaaaatg agacgaacat ctgttgagta a            7611
```

<210> SEQ ID NO 9
<211> LENGTH: 2536
<212> TYPE: PRT
<213> ORGANISM: Artificial
<220> FEATURE:
<223> OTHER INFORMATION: Translated protein sequence for wild type full length Flag-LRRK2

<400> SEQUENCE: 9

```
Met Asp Tyr Lys Asp Asp Asp Lys Met Ala Ser Gly Ser Cys Gln
1               5                   10                  15

Gly Cys Glu Glu Asp Glu Glu Thr Leu Lys Lys Leu Ile Val Arg Leu
                20                  25                  30

Asn Asn Val Gln Glu Gly Lys Gln Ile Glu Thr Leu Val Gln Ile Leu
            35                  40                  45

Glu Asp Leu Leu Val Phe Thr Tyr Ser Glu His Ala Ser Lys Leu Phe
        50                  55                  60

Gln Gly Lys Asn Ile His Val Pro Leu Leu Ile Val Leu Asp Ser Tyr
    65                  70                  75                  80

Met Arg Val Ala Ser Val Gln Gln Val Gly Trp Ser Leu Leu Cys Lys
                85                  90                  95
```

-continued

Leu Ile Glu Val Cys Pro Gly Thr Met Gln Ser Leu Met Gly Pro Gln
            100                 105                 110

Asp Val Gly Asn Asp Trp Glu Val Leu Gly Val His Gln Leu Ile Leu
        115                 120                 125

Lys Met Leu Thr Val His Asn Ala Ser Val Asn Leu Ser Val Ile Gly
    130                 135                 140

Leu Lys Thr Leu Asp Leu Leu Thr Ser Gly Lys Ile Thr Leu Leu
145                 150                 155                 160

Ile Leu Asp Glu Glu Ser Asp Ile Phe Met Leu Ile Phe Asp Ala Met
                165                 170                 175

His Ser Phe Pro Ala Asn Asp Glu Val Gln Lys Leu Gly Cys Lys Ala
            180                 185                 190

Leu His Val Leu Phe Glu Arg Val Ser Glu Glu Gln Leu Thr Glu Phe
        195                 200                 205

Val Glu Asn Lys Asp Tyr Met Ile Leu Leu Ser Ala Leu Thr Asn Phe
    210                 215                 220

Lys Asp Glu Glu Glu Ile Val Leu His Val Leu His Cys Leu His Ser
225                 230                 235                 240

Leu Ala Ile Pro Cys Asn Asn Val Glu Val Leu Met Ser Gly Asn Val
                245                 250                 255

Arg Cys Tyr Asn Ile Val Val Glu Ala Met Lys Ala Phe Pro Met Ser
            260                 265                 270

Glu Arg Ile Gln Glu Val Ser Cys Leu Leu His Arg Leu Thr Leu
        275                 280                 285

Gly Asn Phe Phe Asn Ile Leu Val Leu Asn Glu Val His Glu Phe Val
    290                 295                 300

Val Lys Ala Val Gln Gln Tyr Pro Glu Asn Ala Ala Leu Gln Ile Ser
305                 310                 315                 320

Ala Leu Ser Cys Leu Ala Leu Leu Thr Glu Thr Ile Phe Leu Asn Gln
                325                 330                 335

Asp Leu Glu Glu Lys Asn Glu Asn Gln Glu Asn Asp Asp Glu Gly Glu
            340                 345                 350

Glu Asp Lys Leu Phe Trp Leu Glu Ala Cys Tyr Lys Ala Leu Thr Trp
        355                 360                 365

His Arg Lys Asn Lys His Val Gln Glu Ala Ala Cys Trp Ala Leu Asn
    370                 375                 380

Asn Leu Leu Met Tyr Gln Asn Ser Leu His Glu Lys Ile Gly Asp Glu
385                 390                 395                 400

Asp Gly His Phe Pro Ala His Arg Glu Val Met Leu Ser Met Leu Met
                405                 410                 415

His Ser Ser Ser Lys Glu Val Phe Gln Ala Ser Ala Asn Ala Leu Ser
            420                 425                 430

Thr Leu Leu Glu Gln Asn Val Asn Phe Arg Lys Ile Leu Leu Ser Lys
        435                 440                 445

Gly Ile His Leu Asn Val Leu Glu Leu Met Gln Lys His Ile His Ser
    450                 455                 460

Pro Glu Val Ala Glu Ser Gly Cys Lys Met Leu Asn His Leu Phe Glu
465                 470                 475                 480

Gly Ser Asn Thr Ser Leu Asp Ile Met Ala Ala Val Pro Lys Ile
                485                 490                 495

Leu Thr Val Met Lys Arg His Glu Thr Ser Leu Pro Val Gln Leu Glu
            500                 505                 510

Ala Leu Arg Ala Ile Leu His Phe Ile Val Pro Gly Met Pro Glu Glu

```
            515                 520                 525
Ser Arg Glu Asp Thr Glu Phe His His Lys Leu Asn Met Val Lys Lys
530                 535                 540

Gln Cys Phe Lys Asn Asp Ile His Lys Leu Val Leu Ala Ala Leu Asn
545                 550                 555                 560

Arg Phe Ile Gly Asn Pro Gly Ile Gln Lys Cys Gly Leu Lys Val Ile
                565                 570                 575

Ser Ser Ile Val His Phe Pro Asp Ala Leu Glu Met Leu Ser Leu Glu
            580                 585                 590

Gly Ala Met Asp Ser Val Leu His Thr Leu Gln Met Tyr Pro Asp Asp
            595                 600                 605

Gln Glu Ile Gln Cys Leu Gly Leu Ser Leu Ile Gly Tyr Leu Ile Thr
            610                 615                 620

Lys Lys Asn Val Phe Ile Gly Thr Gly His Leu Leu Ala Lys Ile Leu
625                 630                 635                 640

Val Ser Ser Leu Tyr Arg Phe Lys Asp Val Ala Glu Ile Gln Thr Lys
                645                 650                 655

Gly Phe Gln Thr Ile Leu Ala Ile Leu Lys Leu Ser Ala Ser Phe Ser
                660                 665                 670

Lys Leu Leu Val His His Ser Phe Asp Leu Val Ile Phe His Gln Met
            675                 680                 685

Ser Ser Asn Ile Met Glu Gln Lys Asp Gln Phe Leu Asn Leu Cys
690                 695                 700

Cys Lys Cys Phe Ala Lys Val Ala Met Asp Asp Tyr Leu Lys Asn Val
705                 710                 715                 720

Met Leu Glu Arg Ala Cys Asp Gln Asn Asn Ser Ile Met Val Glu Cys
                725                 730                 735

Leu Leu Leu Leu Gly Ala Asp Ala Asn Gln Ala Lys Glu Gly Ser Ser
                740                 745                 750

Leu Ile Cys Gln Val Cys Glu Lys Glu Ser Ser Pro Lys Leu Val Glu
            755                 760                 765

Leu Leu Leu Asn Ser Gly Ser Arg Glu Gln Asp Val Arg Lys Ala Leu
            770                 775                 780

Thr Ile Ser Ile Gly Lys Gly Asp Ser Gln Ile Ile Ser Leu Leu Leu
785                 790                 795                 800

Arg Arg Leu Ala Leu Asp Val Ala Asn Asn Ser Ile Cys Leu Gly Gly
                805                 810                 815

Phe Cys Ile Gly Lys Val Glu Pro Ser Trp Leu Gly Pro Leu Phe Pro
                820                 825                 830

Asp Lys Thr Ser Asn Leu Arg Lys Gln Thr Asn Ile Ala Ser Thr Leu
            835                 840                 845

Ala Arg Met Val Ile Arg Tyr Gln Met Lys Ser Ala Val Glu Glu Gly
            850                 855                 860

Thr Ala Ser Gly Ser Asp Gly Asn Phe Ser Glu Asp Val Leu Ser Lys
865                 870                 875                 880

Phe Asp Glu Trp Thr Phe Ile Pro Asp Ser Ser Met Asp Ser Val Phe
                885                 890                 895

Ala Gln Ser Asp Asp Leu Asp Ser Glu Gly Ser Glu Gly Ser Phe Leu
            900                 905                 910

Val Lys Lys Lys Ser Asn Ser Ile Ser Val Gly Glu Phe Tyr Arg Asp
            915                 920                 925

Ala Val Leu Gln Arg Cys Ser Pro Asn Leu Gln Arg His Ser Asn Ser
            930                 935                 940
```

```
Leu Gly Pro Ile Phe Asp His Glu Asp Leu Leu Lys Arg Lys Arg Lys
945                 950                 955                 960

Ile Leu Ser Ser Asp Asp Ser Leu Arg Ser Ser Lys Leu Gln Ser His
            965                 970                 975

Met Arg His Ser Asp Ser Ile Ser Ser Leu Ala Ser Glu Arg Glu Tyr
        980                 985                 990

Ile Thr Ser Leu Asp Leu Ser Ala Asn Glu Leu Arg Asp Ile Asp Ala
        995                 1000                1005

Leu Ser Gln Lys Cys Cys Ile Ser Val His Leu Glu His Leu Glu
    1010                1015                1020

Lys Leu Glu Leu His Gln Asn Ala Leu Thr Ser Phe Pro Gln Gln
    1025                1030                1035

Leu Cys Glu Thr Leu Lys Ser Leu Thr His Leu Asp Leu His Ser
    1040                1045                1050

Asn Lys Phe Thr Ser Phe Pro Ser Tyr Leu Leu Lys Met Ser Cys
    1055                1060                1065

Ile Ala Asn Leu Asp Val Ser Arg Asn Asp Ile Gly Pro Ser Val
    1070                1075                1080

Val Leu Asp Pro Thr Val Lys Cys Pro Thr Leu Lys Gln Phe Asn
    1085                1090                1095

Leu Ser Tyr Asn Gln Leu Ser Phe Val Pro Glu Asn Leu Thr Asp
    1100                1105                1110

Val Val Glu Lys Leu Glu Gln Leu Ile Leu Glu Gly Asn Lys Ile
    1115                1120                1125

Ser Gly Ile Cys Ser Pro Leu Arg Leu Lys Glu Leu Lys Ile Leu
    1130                1135                1140

Asn Leu Ser Lys Asn His Ile Ser Ser Leu Ser Glu Asn Phe Leu
    1145                1150                1155

Glu Ala Cys Pro Lys Val Glu Ser Phe Ser Ala Arg Met Asn Phe
    1160                1165                1170

Leu Ala Ala Met Pro Phe Leu Pro Pro Ser Met Thr Ile Leu Lys
    1175                1180                1185

Leu Ser Gln Asn Lys Phe Ser Cys Ile Pro Glu Ala Ile Leu Asn
    1190                1195                1200

Leu Pro His Leu Arg Ser Leu Asp Met Ser Ser Asn Asp Ile Gln
    1205                1210                1215

Tyr Leu Pro Gly Pro Ala His Trp Lys Ser Leu Asn Leu Arg Glu
    1220                1225                1230

Leu Leu Phe Ser His Asn Gln Ile Ser Ile Leu Asp Leu Ser Glu
    1235                1240                1245

Lys Ala Tyr Leu Trp Ser Arg Val Glu Lys Leu His Leu Ser His
    1250                1255                1260

Asn Lys Leu Lys Glu Ile Pro Pro Glu Ile Gly Cys Leu Glu Asn
    1265                1270                1275

Leu Thr Ser Leu Asp Val Ser Tyr Asn Leu Glu Leu Arg Ser Phe
    1280                1285                1290

Pro Asn Glu Met Gly Lys Leu Ser Lys Ile Trp Asp Leu Pro Leu
    1295                1300                1305

Asp Glu Leu His Leu Asn Phe Asp Phe Lys His Ile Gly Cys Lys
    1310                1315                1320

Ala Lys Asp Ile Ile Arg Phe Leu Gln Gln Arg Leu Lys Lys Ala
    1325                1330                1335
```

-continued

```
Val Pro Tyr Asn Arg Met Lys Leu Met Ile Val Gly Asn Thr Gly
    1340                1345                1350
Ser Gly Lys Thr Thr Leu Leu Gln Gln Leu Met Lys Thr Lys Lys
    1355                1360                1365
Ser Asp Leu Gly Met Gln Ser Ala Thr Val Gly Ile Asp Val Lys
    1370                1375                1380
Asp Trp Pro Ile Gln Ile Arg Asp Lys Arg Lys Asp Leu Val
    1385                1390                1395
Leu Asn Val Trp Asp Phe Ala Gly Arg Glu Glu Phe Tyr Ser Thr
    1400                1405                1410
His Pro His Phe Met Thr Gln Arg Ala Leu Tyr Leu Ala Val Tyr
    1415                1420                1425
Asp Leu Ser Lys Gly Gln Ala Glu Val Asp Ala Met Lys Pro Trp
    1430                1435                1440
Leu Phe Asn Ile Lys Ala Arg Ala Ser Ser Ser Pro Val Ile Leu
    1445                1450                1455
Val Gly Thr His Leu Asp Val Ser Asp Glu Lys Gln Arg Lys Ala
    1460                1465                1470
Cys Met Ser Lys Ile Thr Lys Glu Leu Leu Asn Lys Arg Gly Phe
    1475                1480                1485
Pro Ala Ile Arg Asp Tyr His Phe Val Asn Ala Thr Glu Glu Ser
    1490                1495                1500
Asp Ala Leu Ala Lys Leu Arg Lys Thr Ile Ile Asn Glu Ser Leu
    1505                1510                1515
Asn Phe Lys Ile Arg Asp Gln Leu Val Val Gly Gln Leu Ile Pro
    1520                1525                1530
Asp Cys Tyr Val Glu Leu Glu Lys Ile Ile Leu Ser Glu Arg Lys
    1535                1540                1545
Asn Val Pro Ile Glu Phe Pro Val Ile Asp Arg Lys Arg Leu Leu
    1550                1555                1560
Gln Leu Val Arg Glu Asn Gln Leu Gln Leu Asp Glu Asn Glu Leu
    1565                1570                1575
Pro His Ala Val His Phe Leu Asn Glu Ser Gly Val Leu Leu His
    1580                1585                1590
Phe Gln Asp Pro Ala Leu Gln Leu Ser Asp Leu Tyr Phe Val Glu
    1595                1600                1605
Pro Lys Trp Leu Cys Lys Ile Met Ala Gln Ile Leu Thr Val Lys
    1610                1615                1620
Val Glu Gly Cys Pro Lys His Pro Lys Gly Ile Ile Ser Arg Arg
    1625                1630                1635
Asp Val Glu Lys Phe Leu Ser Lys Lys Arg Lys Phe Pro Lys Asn
    1640                1645                1650
Tyr Met Ser Gln Tyr Phe Lys Leu Leu Glu Lys Phe Gln Ile Ala
    1655                1660                1665
Leu Pro Ile Gly Glu Glu Tyr Leu Leu Val Pro Ser Ser Leu Ser
    1670                1675                1680
Asp His Arg Pro Val Ile Glu Leu Pro His Cys Glu Asn Ser Glu
    1685                1690                1695
Ile Ile Ile Arg Leu Tyr Glu Met Pro Tyr Phe Pro Met Gly Phe
    1700                1705                1710
Trp Ser Arg Leu Ile Asn Arg Leu Leu Glu Ile Ser Pro Tyr Met
    1715                1720                1725
Leu Ser Gly Arg Glu Arg Ala Leu Arg Pro Asn Arg Met Tyr Trp
```

-continued

```
                1730                1735                1740

Arg Gln Gly Ile Tyr Leu Asn Trp Ser Pro Glu Ala Tyr Cys Leu
    1745                1750                1755

Val Gly Ser Glu Val Leu Asp Asn His Pro Glu Ser Phe Leu Lys
    1760                1765                1770

Ile Thr Val Pro Ser Cys Arg Lys Gly Cys Ile Leu Leu Gly Gln
    1775                1780                1785

Val Val Asp His Ile Asp Ser Leu Met Glu Glu Trp Phe Pro Gly
    1790                1795                1800

Leu Leu Glu Ile Asp Ile Cys Gly Glu Gly Glu Thr Leu Leu Lys
    1805                1810                1815

Lys Trp Ala Leu Tyr Ser Phe Asn Asp Gly Glu Glu His Gln Lys
    1820                1825                1830

Ile Leu Leu Asp Asp Leu Met Lys Lys Ala Glu Glu Gly Asp Leu
    1835                1840                1845

Leu Val Asn Pro Asp Gln Pro Arg Leu Thr Ile Pro Ile Ser Gln
    1850                1855                1860

Ile Ala Pro Asp Leu Ile Leu Ala Asp Leu Pro Arg Asn Ile Met
    1865                1870                1875

Leu Asn Asn Asp Glu Leu Glu Phe Glu Gln Ala Pro Glu Phe Leu
    1880                1885                1890

Leu Gly Asp Gly Ser Phe Gly Ser Val Tyr Arg Ala Ala Tyr Glu
    1895                1900                1905

Gly Glu Glu Val Ala Val Lys Ile Phe Asn Lys His Thr Ser Leu
    1910                1915                1920

Arg Leu Leu Arg Gln Glu Leu Val Val Leu Cys His Leu His His
    1925                1930                1935

Pro Ser Leu Ile Ser Leu Leu Ala Ala Gly Ile Arg Pro Arg Met
    1940                1945                1950

Leu Val Met Glu Leu Ala Ser Lys Gly Ser Leu Asp Arg Leu Leu
    1955                1960                1965

Gln Gln Asp Lys Ala Ser Leu Thr Arg Thr Leu Gln His Arg Ile
    1970                1975                1980

Ala Leu His Val Ala Asp Gly Leu Arg Tyr Leu His Ser Ala Met
    1985                1990                1995

Ile Ile Tyr Arg Asp Leu Lys Pro His Asn Val Leu Leu Phe Thr
    2000                2005                2010

Leu Tyr Pro Asn Ala Ala Ile Ile Ala Lys Ile Ala Asp Tyr Gly
    2015                2020                2025

Ile Ala Gln Tyr Cys Cys Arg Met Gly Ile Lys Thr Ser Glu Gly
    2030                2035                2040

Thr Pro Gly Phe Arg Ala Pro Glu Val Ala Arg Gly Asn Val Ile
    2045                2050                2055

Tyr Asn Gln Gln Ala Asp Val Tyr Ser Phe Gly Leu Leu Leu Tyr
    2060                2065                2070

Asp Ile Leu Thr Thr Gly Gly Arg Ile Val Glu Gly Leu Lys Phe
    2075                2080                2085

Pro Asn Glu Phe Asp Glu Leu Glu Ile Gln Gly Lys Leu Pro Asp
    2090                2095                2100

Pro Val Lys Glu Tyr Gly Cys Ala Pro Trp Pro Met Val Glu Lys
    2105                2110                2115

Leu Ile Lys Gln Cys Leu Lys Glu Asn Pro Gln Glu Arg Pro Thr
    2120                2125                2130
```

```
Ser Ala Gln Val Phe Asp Ile Leu Asn Ser Ala Glu Leu Val Cys
2135                2140                2145

Leu Thr Arg Arg Ile Leu Leu Pro Lys Asn Val Ile Val Glu Cys
2150                2155                2160

Met Val Ala Thr His His Asn Ser Arg Asn Ala Ser Ile Trp Leu
2165                2170                2175

Gly Cys Gly His Thr Asp Arg Gly Gln Leu Ser Phe Leu Asp Leu
2180                2185                2190

Asn Thr Glu Gly Tyr Thr Ser Glu Val Ala Asp Ser Arg Ile
2195                2200                2205

Leu Cys Leu Ala Leu Val His Leu Pro Val Glu Lys Glu Ser Trp
2210                2215                2220

Ile Val Ser Gly Thr Gln Ser Gly Thr Leu Leu Val Ile Asn Thr
2225                2230                2235

Glu Asp Gly Lys Lys Arg His Thr Leu Glu Lys Met Thr Asp Ser
2240                2245                2250

Val Thr Cys Leu Tyr Cys Asn Ser Phe Ser Lys Gln Ser Lys Gln
2255                2260                2265

Lys Asn Phe Leu Leu Val Gly Thr Ala Asp Gly Lys Leu Ala Ile
2270                2275                2280

Phe Glu Asp Lys Thr Val Lys Leu Lys Gly Ala Ala Pro Leu Lys
2285                2290                2295

Ile Leu Asn Ile Gly Asn Val Ser Thr Pro Leu Met Cys Leu Ser
2300                2305                2310

Glu Ser Thr Asn Ser Thr Glu Arg Asn Val Met Trp Gly Gly Cys
2315                2320                2325

Gly Thr Lys Ile Phe Ser Phe Ser Asn Asp Phe Thr Ile Gln Lys
2330                2335                2340

Leu Ile Glu Thr Arg Thr Ser Gln Leu Phe Ser Tyr Ala Ala Phe
2345                2350                2355

Ser Asp Ser Asn Ile Ile Thr Val Val Asp Thr Ala Leu Tyr
2360                2365                2370

Ile Ala Lys Gln Asn Ser Pro Val Val Glu Val Trp Asp Lys Lys
2375                2380                2385

Thr Glu Lys Leu Cys Gly Leu Ile Asp Cys Val His Phe Leu Arg
2390                2395                2400

Glu Val Met Val Lys Glu Asn Lys Glu Ser Lys His Lys Met Ser
2405                2410                2415

Tyr Ser Gly Arg Val Lys Thr Leu Cys Leu Gln Lys Asn Thr Ala
2420                2425                2430

Leu Trp Ile Gly Thr Gly Gly Gly His Ile Leu Leu Leu Asp Leu
2435                2440                2445

Ser Thr Arg Arg Leu Ile Arg Val Ile Tyr Asn Phe Cys Asn Ser
2450                2455                2460

Val Arg Val Met Met Thr Ala Gln Leu Gly Ser Leu Lys Asn Val
2465                2470                2475

Met Leu Val Leu Gly Tyr Asn Arg Lys Asn Thr Glu Gly Thr Gln
2480                2485                2490

Lys Gln Lys Glu Ile Gln Ser Cys Leu Thr Val Trp Asp Ile Asn
2495                2500                2505

Leu Pro His Glu Val Gln Asn Leu Glu Lys His Ile Glu Val Arg
2510                2515                2520
```

```
Lys Glu  Leu Ala Glu Lys Met  Arg Arg Thr Ser Val  Glu
    2525             2530                 2535

<210> SEQ ID NO 10
<211> LENGTH: 15
<212> TYPE: PRT
<213> ORGANISM: Human

<400> SEQUENCE: 10

Arg Leu Gly Arg Asp Lys Tyr Lys Thr Leu Arg Gln Ile Arg Gln
1               5                   10                  15
```

SUBSTITUTED FUSED PYRAZOLE COMPOUNDS AND THEIR USE AS LRRK2 INHIBITORS

RELATED APPLICATION

The present application is a 371 application of PCT/CN2016/090962 filed on 22 Jul. 2016 which claims priority from PCT International Application No. PCT/CN2015/084893 filed on Jul. 23, 2015 at the State Intellectual Property Office of the People's Republic of China, the entire contents of which is incorporated herein by reference.

FIELD OF THE INVENTION

The present invention relates to novel compounds that inhibit LRRK2 kinase activity, processes for their preparation, compositions containing them and their use in the treatment of diseases characterized by LRRK2 kinase activity, for example, Parkinson's disease, amyotrophic lateral sclerosis (ALS) and Alzheimer's disease.

BACKGROUND OF THE INVENTION

Parkinson's disease (PD) is a neurodegenerative disorder characterized by selective degeneration and cell death of dopaminergic neurons in the substantial nigra region of the brain. Parkinson's disease was generally considered to be sporadic and of unknown etiology, but, in the last 15 years, there has been an important development of the understanding of the genetic basis of this disease and associated pathogenic mechanisms. One area of the development is the understanding of leucine rich repeat kinase 2 (LRRK2) protein. A number of mis-sense mutations in the LRRK2 gene have been strongly linked with autosomal dominant Parkinson's disease in familial studies (See WO2006068492 and WO2006045392; Trinh and Farrer 2013, Nature Reviews in Neurology 9: 445-454; Paisan-Ruiz et al., 2013, J. Parkinson's Disease 3: 85-103). The G2019S mutation in LRRK2 is the most frequent mis-sense mutation and is associated with a clinical phenotype that closely resembles sporadic Parkinson's disease. The LRRK2 G2019S mutation is also present in approximately 1.5% of sporadic Parkinson's disease cases (See Gilks et al., 2005, Lancet, 365: 415-416). In addition to the known pathogenic coding mutations in LRRK2, additional amino acid coding variants of LRRK2 have been identified that are also associated with risk of developing Parkinson's disease (See Ross et al., 2011 Lancet Neurology 10: 898-908). Furthermore, genome-wide association studies (GWAS) have identified LRRK2 as a Parkinson's disease susceptibility locus, which indicates that LRRK2 may be also relevant to sporadic Parkinson's disease cases without mutations that cause amino acid substitutions in the LRRK2 protein. (See Satake et al., 2009 Nature Genetics 41:1303-1307; Simon-Sanchez et al 2009 Nature Genetics 41: 1308-1312)

LRRK2 is a member of the ROCO protein family and all members of this family share five conserved domains. The most common pathogenic mutation G2019S occurs in the highly conserved kinase domain of LRRK2. This mutation confers an increase in the LRRK2 kinase activity in in vitro enzyme assays of recombinant LRRK2 proteins (See Jaleel et al., 2007, Biochem J, 405: 307-317) and in LRRK2 proteins purified from G2019S PD patient-derived cells (See Dzamko et al., 2010 Biochem. J. 430: 405-413). A less frequent LRRK2 pathogenic mutation that confers amino acid substitution at a different residue, R1441, has also been shown to elevate LRRK2 kinase activity by decreasing the rate of GTP hydrolysis by the GTPase domain of LRRK2 (See Guo et al., 2007 Exp Cell Res. 313: 3658-3670; West et al., 2007 Hum. Mol Gen. 16: 223-232). Therefore, the evidence indicates that the kinase and GTPase activities of LRRK2 are important for pathogenesis, and that the LRRK2 kinase domain may regulate overall LRRK2 function (See Cookson, 2010 Nat. Rev. Neurosci. 11: 791-797).

There is evidence to show that the increased LRRK2 kinase activity is associated with neuronal toxicity in cell culture models (See Smith et al., 2006 Nature Neuroscience 9: 1231-1233) and kinase inhibitor compounds protect against LRRK2-mediated cell death (See Lee et al., 2010 Nat. Med. 16: 998-1000).

Induced pluripotent stem cells (iPSCs) derived from LRRK2 G2019S Parkinson's disease patients have been found to exhibit defects in neurite outgrowth and increased susceptibility to rotenone, that may be ameliorated by either genetic correction of the G2019S mutation or treatment of cells with small molecule inhibitors of LRRK2 kinase activity (See Reinhardt et al., 2013 Cell Stem Cell 12: 354-367). Increased mitochondrial damage associated with LRRK2 G2019S mutation in iSPCs is also blocked by genetic correction of the G2019S mutation (See Sanders et al., 2013 Neurobiol. Dis. 62: 381-386).

Additional evidence links LRRK2 function and dysfunction with autophagy-lysosomal pathways (See Manzoni and Lewis, 2013 Faseb J. 27:3234-3429). LRRK2 proteins confer defects in chaperone-mediated autophagy that negatively impact the ability of cells to degrade alpha-synuclein (Orenstein et al., 2013 Nature Neurosci. 16 394-406). In other cell models, selective LRRK2 inhibitors have been shown to stimulate macroautophagy (See Manzoni et al., 2013 BBA Mol. Cell Res. 1833: 2900-2910). These data suggest that small molecule inhibitors of LRRK2 kinase activity may have utility in the treatment of diseases characterized by defects in cellular proteostasis that result from aberrant autophagy/lysosomal degradation pathways including forms of Parkinson's disease associated with GBA mutations (See Swan and Saunders-Pullman 2013 Curr. Neurol. Neurosci Rep. 13: 368), other alpha-synucleinopathies, tauopathies, Alzheimer's disease (See Li et al., 2010 Neurodegen. Dis. 7: 265-271) and other neurodegenerative diseases (See Nixon 2013 Nat. Med. 19: 983-997) and Gaucher disease (See Westbroek et al., 2011 Trends. Mol. Med. 17: 485-493). As promoters of autophagy, small molecule inhibitors of LRRK2 kinase may also have utility in treatment of other diseases including diabetes, obesity, motor neuron disease, epilepsy and some cancers (See Rubinsztein et al., 2012 Nat. Rev. Drug Discovery 11: 709-730), pulmonary diseases such as chronic obstructive pulmonary disease and idiopathic pulmonary fibrosis (See Araya et al., 2013 Intern. Med. 52: 2295-2303) and autoimmune diseases such as systemic lupus erythematosus (See Martinez et al., 2016 Nature 533: 115-119). As promoters of autophagy and phagocytic processes, small molecule inhibitors of LRRK2 kinase may also have utility in augmenting host responses in treatment of a range of intracellular bacterial infections, parasitic infections and viral infections, including diseases such as tuberculosis (See Rubinsztein et al., 2012 Nat. Rev. Drug Discovery 11: 709-730; Araya et al., 2013 Intern. Med. 52: 2295-2303; Gutierrez, Biochemical Society Conference; Leucine rich repeat kinase 2: ten years along the road to therapeutic intervention, Henley Business School, UK 12 Jul. 2016), HIV, West Nile Virus and chikungunya virus (see Shoji-Kawata et al., 2013 Nature 494: 201-206). LRRK2 inhibitors may have utility in treatment of such diseases alone, or in combination with drugs that directly target the infectious agent. Further, significantly elevated levels of LRRK2 mRNA have also been observed in fibroblasts of Niemann-Pick Type C (NPC) disease patients compared with fibroblasts of normal subjects, which indicates that aberrant LRRK2 function may play a role in lysosomal disorders (See Reddy et al., 2006 PLOS One 1 (1):e19 doi: 10.1371/journal.pone.0000019—supporting information Dataset S1). This observation suggests that LRRK2 inhibitors may have utility for treatment of NPC.

The PD-associated G2019S mutant form of LRRK2 has also been reported to enhance phosphorylation of tubulin-associated Tau (See Kawakami et al., 2012 PLoS ONE 7: e30834, doi 10.1371), and disease models have been proposed in which LRRK2 acts upstream of the pathogenic effects of Tau and alpha-synuclein (See Taymans & Cookson, 2010, BioEssays 32: 227-235). In support of this, LRRK2 expression has been associated with increased aggregation of insoluble Tau, and increased Tau phosphorylation, in a transgenic mouse model (See Bailey et al., 2013 Acta Neuropath. 126:809-827). Over-expression of the PD pathogenic mutant protein LRRK2 R1441G is reported to cause symptoms of Parkinson's disease and hyperphosphorylation of Tau in transgenic mouse models (See Li, Y. et al. 2009, Nature Neuroscience 12: 826-828). Therefore, these data suggest that LRRK2 inhibitors of kinase catalytic activity may be useful for the treatment of tauopathy diseases characterized by hyperphosphorylation of Tau such as argyrophilic grain disease, Pick's disease, corticobasal degeneration, progressive supranuclear palsy and inherited frontotemporal dementia and parkinsonism linked to chromosome 17 (FTDP-17) (See Goedert, M and Jakes, R (2005) Biochemica et Biophysica Acta 1739, 240-250). In addition, LRRK2 inhibitors may have utility in treatment of other diseases characterized by diminished dopamine levels such as withdrawal symptoms/relapse associated with drug addiction (See Rothman et al., 2008, Prog. Brain Res, 172: 385).

Other studies have also shown that overexpression of the G2019S mutant form of LRRK2 confers defects in subventricular zone (SVZ) neuroprogenitor cell proliferation and migration in transgenic mouse models (See Winner et al., 2011 Neurobiol. Dis. 41: 706-716) and reduces neurite length and branching cell culture models (See Dachsel et al., 2010 Parkinsonism & Related Disorders 16: 650-655). Moreover, it was reported that agents that promote SVZ neuroprogenitor cell proliferation and migration also improve neurological outcomes following ischemic injury in rodent models of stroke (See Zhang et al., 2010 J. Neurosci. Res. 88: 3275-3281). These findings suggest that compounds that inhibit aberrant activity of LRRK2 may have utility for the treatments designed to stimulate restoration of CNS functions following neuronal injury, such as ischemic stroke, traumatic brain injury, spinal cord injury.

Mutations in LRRK2 have also been identified that are clinically associated with the transition from mild cognitive impairment (MCI) to Alzheimer's disease (See WO2007149798). These data suggest that inhibitors of LRRK2 kinase activity may be useful for the treatment diseases such as Alzheimer's disease, other dementias and related neurodegenerative disorders.

Aberrant regulation of normal LRRK2 proteins is also observed in some disease tissues and models of disease. Normal mechanisms of translational control of LRRK2 by miR-205 are perturbed in some sporadic PD cases, where significant decreases in miR-205 levels in PD brain samples concur with elevated LRRK2 protein levels in those samples (See Cho et al., (2013) Hum. Mol. Gen. 22: 608-620). Therefore, LRRK2 inhibitors may be used in treatment of sporadic PD patients who have elevated levels of normal LRRK2 proteins.

In an experimental model of Parkinson's disease in marmosets, an elevation of LRRK2 mRNA is observed in a manner that correlates with the level of L-Dopa induced dyskinesia (See Hurley, M. J et al., 2007 Eur. J. Neurosci. 26: 171-177). This suggests that LRRK2 inhibitors may have a utility in amelioration of such dyskinesias.

Significantly elevated levels of LRRK2 mRNA have been reported in ALS patient muscle biopsy samples (See Shtilbans et al., 2011 Amyotrophic Lateral Sclerosis 12: 250-256) It is suggested that elevated levels of LRRK2 kinase activity may be a characteristic feature of ALS. Therefore, this observation indicated that LRRK2 inhibitor may have utility for treatment of ALS.

There is also evidence indicating that LRRK2 kinase activity may play a role in mediating microglial proinflammatory responses (See Moehle et al., 2012, J. Neuroscience 32: 1602-1611). This observation suggests a possible utility of LRRK2 inhibitors for treatment of aberrant neuroinflammatory mechanisms that contribute a range of neurodegenerative diseases, including Parkinson's disease, Alzheimer's disease, multiple sclerosis, HIV-induced dementia, amyotrophic lateral sclerosis, ischemic stroke, traumatic brain injury and spinal cord injury. Some evidence also indicates that LRRK2 plays a role in regulating neuronal progenitor differentiation in vitro (See Milosevic, J. et al., 2009 Mol. Neurodegen. 4: 25). This evidence suggests that inhibitors of LRRK2 may have a utility in production of neuronal progenitor cells in vitro for consequent therapeutic application in cell based-treatment of CNS disorders.

It has been reported that Parkinson's disease patients bearing LRRK2 G2019S mutation display increased frequency of non-skin cancers, including renal, breast, lung, prostate cancers as well as acute myelogenous leukemia (AML). Since there is evidence to show that G2019S mutation in LRRK2 increases catalytic activity of the LRRK2 kinase domain, small molecule inhibitors of LRRK2 may have a utility in treatment of cancers, for example kidney cancer, breast cancer, lung cancer, prostate cancer (e.g. solid tumors) and blood cancer (See. AML; Saunders-Pullman et al., 2010, Movement Disorders, 25:2536-2541; Inzelberg et al., 2012 Neurology 78: 781-786). Amplification and over-expression of LRRK2 has also been reported in papillary renal and thyroid carcinomas, where co-operativity between LRRK2 and the MET oncogene may promote tumor cell growth and survival (See Looyenga et al., 2011 PNAS 108: 1439-1444.)

Some studies suggested that genetic association of common LRRK2 variants with susceptibility to ankylosing spondylitis (See Danoy P, et al., 2010. PLoS Genet.; 6(12): e1001195; and leprosy infection. (See Zhang F R, et al. 2009, N Engl J Med. 361:2609-18.) These findings suggest that inhibitors of LRRK2 may have a utility in the treatment of ankylosing spondylitis and leprosy infection.

Meta-analysis of three genome wide associated scans for Crohn's disease identified a number of loci associated with the disease, including the locus containing the LRRK2 gene (See Barrett et al., 2008, Nature Genetics, 40: 955-962). Evidence has also emerged that LRRK2 is an IFN-γ target gene that may be involved in signaling pathways relevant to Crohn's disease pathogenesis (See Gardet et al., 2010, J. Immunology, 185: 5577-5585). These findings suggest that inhibitors of LRRK2 may have utility in the treatment of Crohn's disease.

As an IFN-γ target gene, LRRK2 may also play a role in T cell mechanisms that underlie other diseases of the immune system such as multiple sclerosis and rheumatoid arthritis. Further potential utility of LRRK2 inhibitors comes from the reported finding that B lymphocytes constitute a major population of LRRK2 expressing cells (See Maekawa et al. 2010, BBRC 392: 431-435). This suggests that LRRK2 inhibitors may be effective in treatment of diseases of the immune system for which B cell depletion is, or may be, effective in diseases such as lymphomas, leukemias, multiple sclerosis (See Ray et al., 2011 J. Immunol. 230: 109), rheumatoid arthritis, systemic lupus erythematosus, autoimmune hemolytic anemia, pure red cell aplasia, idiopathic thrombocytopenic purpura (ITP), Evans syndrome, vasculitis, bullous skin disorders, type 1 diabetes mellitus, Sjogren's syndrome, Devic's disease and inflammatory myopathies (See Engel et al., 2011 Pharmacol. Rev. 63: 127-156; Homam et al., 2010 J. Clin. Neuromuscular Disease 12: 91-102).

SUMMARY OF THE INVENTION

The present invention provides, in a first aspect, compounds of Formula (I) and salts thereof (e.g., pharmaceutically acceptable salts)

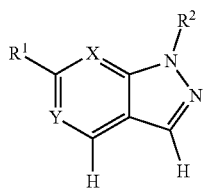

Formula (I)

Wherein

X is selected from CH or N;

Y is selected from CH, N or $CR_3$, wherein $R_3$ is selected from the group consisting of halo, $C_{1-3}$ alkyl, CN, and $C_{1-3}$ haloalkyl;

$R^1$ is selected from the group consisting of 5 or 6 membered heterocyclyl optionally substituted with one, two or three substituents independently selected from the group consisting of $C_{1-3}$ alkyl optionally further substituted with one $C_{1-3}$ alkoxyl, $C_{1-3}$ alkoxyl, halo, hydroxyl,

—$SO_2CH_3$,

—$COCH_3$, oxo group, and oxetanyl,

—O-4 to 6 membered heterocyclyl optionally substituted with one or two substituents of $C_{1-3}$ alkyl, which may be the same or different, and $C_{1-6}$ alkoxyl; and $R^2$ is

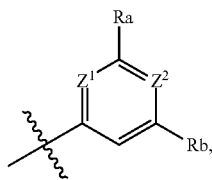

wherein $Z^1$ and $Z^2$ are independently N or $CR_7$, wherein $R_7$ is H or $C_{1-3}$alkoxy, but $Z^1$ and $Z^2$ cannot both be $CR_7$;

$R_a$ is selected from the group consisting of

H,

CN, $C_{1-3}$ alkyl, $C_{1-3}$ alkoxyl,

—O—$C_{1-3}$haloalkyl, and $C_{3-6}$cycloalkyl; and $R_b$ is selected from the group consisting of 2-oxa-6-azaspiro[3.4]octanyl, $C_{3-6}$cycloalkyl, optionally substituted with one hydroxyl,

—$CONHCH_3$,

—$NHCOCH_3$, and 4 to 6 membered heterocyclyl optionally substituted with one or two substituents independently selected from the group consisting of hydroxyl,

CN,

—$CONHCH_3$, oxetanyl, $C_{1-3}$alkyl, optionally substituted with one hydroxyl, and $C_{1-3}$alkoxyl, optionally substituted with one hydroxyl.

In a further aspect of the invention, the invention provides a pharmaceutical composition comprising a compound of Formula (I) or a pharmaceutically acceptable salt thereof and a pharmaceutically acceptable carrier.

A further aspect of the invention provides a compound of Formula (I) or a pharmaceutically acceptable salt thereof for use in the treatment or prevention of Parkinson's disease or Alzheimer's disease.

DETAILED DESCRIPTION OF THE INVENTION

The foregoing and other aspects of the present invention will now be described in more detail with respect to the description and methodologies provided herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the embodiments of the invention and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Generally, the nomenclature used herein and the laboratory procedures in organic chemistry, medicinal chemistry, biology described herein are those well known and commonly employed in the art. Unless defined otherwise, all technical and scientific terms used herein generally have the same meaning as commonly understood by one of ordinary skill in the art to which this disclosure belongs. In the event that there is a plurality of definitions for a term used herein, those in this section prevail unless stated otherwise.

All patents, patent applications and publications referred to herein are incorporated by reference in their entirety. In case of a conflict in terminology, the present specification is controlling.

A. Definitions

As used herein, "alkyl" refers to a monovalent, saturated hydrocarbon chain having a specified number of carbon atoms. For example, $C_{1-3}$ alkyl refers to an alkyl group having from 1 to 3 carbon atoms. Alkyl groups may be straight or branched. In some embodiments, branched alkyl groups may have one, two, or three branches. Exemplary alkyl groups include, but are not limited to, methyl, ethyl, and propyl (n-propyl and isopropyl).

As used herein, "alkoxyl" refers to the group —O-alkyl. For example, $C_{1-6}$ alkoxyl groups contain from 1 to 6 carbon atoms. $C_{1-3}$ alkoxyl groups contain from 1 to 3 carbon atoms. Exemplary alkoxyl groups include, but are not limited to, methoxy, ethoxy, propoxy, butoxyl, pentyloxy, and hexyloxy.

As used herein, "cycloalkyl" refers to a saturated monocyclic hydrocarbon ring of 3 to 6 carbon atoms. For example, $C_{3-6}$ cycloalkyl contains 3 to 6 carbon atoms as member atoms in the ring. Examples of cycloalkyl include cyclopropyl, cyclobutyl, cyclopentyl and cyclohexyl.

As used herein, "halogen" refers to fluorine (F), chlorine (Cl), bromine (Br), or iodine (I). "Halo" refers to the halogen radicals: fluoro (—F), chloro (—Cl), bromo (—Br), or iodo (—I).

As used herein, "haloalkyl" refers to an alkyl group, as defined above, having one or more halogen atoms selected from F, Cl, Br, or I, which are substituted on any or all of the carbon atoms of the alkyl group by replacing hydrogen atoms attached to the carbon atoms and which may be the same or different. For example, $C_{1-3}$haloalkyl refers to a $C_{1-3}$alkyl group substituted with one or more halogen atoms. In some embodiments, "haloalkyl" refers to an alkyl group substituted with one or more halogen atoms independently selected from F or Cl. Exemplary haloalkyl groups include, but are not limited to, chloromethyl, bromoethyl, trifluoromethyl, and dichloromethyl.

As used herein, "heterocyclyl" is a monovalent radical derived by removal of a hydrogen atom from a 3, 4, 5 or 6-membered saturated or unsaturated, but not aromatic, monocyclic ring, which ring consists of ring-carbon atoms and 1 or 2 ring-heteroatoms independently selected from nitrogen, oxygen, sulphur or sulphur substituted with two oxo groups (e.g., $SO_2$). In one embodiment, the heterocyclyl containing 1 or 2 ring-heteroatoms independently selected from nitrogen or oxygen. In one embodiment, "5 or 6 membered heterocyclyl" refers to saturated or containing one double bond monocyclic ring consisting of 5 or 6 ring-atoms, and 1 or 2 of which are ring-heteroatoms independently selected from nitrogen or oxygen. Exemplary "5 or 6 membered heterocyclyl" includes, but are not limited to, piperidinyl (e.g., piperidin-4-yl, piperidin-1-yl, piperidin-3-yl), pyrrolidinyl (e.g., pyrrolidin-3-yl, pyrrolidin-1-yl), 1,2,3,6-tetrahydropyridinyl (e.g., 1,2,3,6-tetrahydropyridin-4-yl), piperidinonyl (e.g. piperidin-2-onyl), tetrahydro-2H-pyranyl (e.g., tetrahydro-2H-pyran-4-yl, tetrahydro-2H-pyran-2-yl, tetrahydro-2H-pyran-3-yl), tetrahydrofuranyl (e.g., tetrahydrofuran-3-yl), morpholinyl (e.g. morpholin-2-yl, morpholin-4-yl), piperazinyl (e.g., piperazin-1-yl). In one embodiment, "4 to 6 membered heterocyclyl" refers to saturated and monocyclic ring consisting of 4 to 6 ring-atoms, and 1 or 2 of which are ring-heteroatoms independently selected from nitrogen, oxygen, sulphur or sulphur substituted with two oxo groups (e.g., $SO_2$). In one embodiment, 4 to 6 membered heterocyclyl contains 1 or 2 ring-heteroatoms independently selected from nitrogen or oxygen. Exemplary "4 to 6 membered heterocyclyl" includes, but are not limited to, piperidinyl (e.g., piperidin-4-yl, piperidin-3-yl), pyrrolidinyl (e.g., pyrrolidin-3-yl, pyrrolidin-1-yl), tetrahydrofuranyl (e.g., tetrahydrofuran-3-yl), azetidinyl (e.g., azetidin-3-yl, azetidin-1-yl), morpholinyl (e.g., morpholin-4-yl), piperazinyl (e.g., piperazin-1-yl), thiomorpholinyl 1,1-dioxide (e.g., thiomorpholin-4-yl 1,1-dioxide), tetrahydro-2H-pyranyl (e.g., tetrahydro-2H-pyran-4-yl) and oxetanyl (e.g. oxetan-3-yl). In one embodiment, "6 membered heterocyclyl" refers to saturated monocyclic ring consisting of 6 ring-atoms, and 1 or 2 of which are ring-heteroatoms independently selected from nitrogen, oxygen. Exemplary "6 membered heterocyclyl" includes, but are not limited to, piperidinyl (e.g., piperidin-4-yl, piperidin-3-yl), 1,2,3,6-tetrahydropyridinyl (e.g., 1,2,3,6-tetrahydropyridin-4-yl), piperidinonyl (e.g. piperidin-2-onyl), tetrahydro-2H-pyranyl (e.g., tetrahydro-2H-pyran-4-yl), morpholinyl (e.g., morpholin-4-yl), piperazinyl (e.g., piperazin-1-yl).

As used herein, "oxo" refers to a (=O) group.

As used herein, "substituted" in reference to a group indicates that one or more hydrogen atom attached to a member atom (e.g., carbon atom) within the group is replaced with a substituent selected from the group of defined substituents. It should be understood that the term "substituted" includes the implicit provision that such substitution is in accordance with the permitted valence of the substituted atom and the substituent and that the substitution results in a stable compound (i.e. one that does not spontaneously undergo transformation such as by rearrangement, cyclization, or elimination and that is sufficiently robust to survive isolation from a reaction mixture). When it is stated that a group may contain one or more substituent, one or more (as appropriate) member atom within the group may be substituted. In addition, a single member atom within the group may be substituted with more than one substituent as long as such substitution is in accordance with the permitted valence of the atom. Exemplary substituents include, but are not limited to, alkyl, alkoxyl, halo, hydroxy, —$SO_2CH_3$, —$COCH_3$, oxo group, oxetanyl, CN, —$CONHCH_3$, and heterocycloalkyl (e.g., piperazinyl). Suitable substituents are defined herein for each substituted or optionally substituted group.

As used herein, "optionally substituted" indicates that a group, such as heterocyclyl, alkyl, and alkoxyl may be unsubstituted, may be substituted with one, two or three substituent(s) as defined.

As used herein, the term "disease" refers to any alteration in state of the body or of some of the organs, interrupting or disturbing the performance of the functions and/or causing symptoms such as discomfort, dysfunction, distress, or even death to the person afflicted or those in contact with a person. A disease can also include a distemper, ailing, ailment, malady, disorder, sickness, illness, complain, interdisposition and/or affectation.

As used herein, "treat", "treating" or "treatment" in reference to a disease means: (1) to ameliorate the disease or one or more of the biological manifestations of the disease, (2) to interfere with (a) one or more points in the biological cascade that leads to or is responsible for the disease or (b) one or more of the biological manifestations of the disease, (3) to alleviate one or more of the symptoms or effects associated with the disease, (4) to slow the progression of the disease or one or more of the biological manifestations of the disease, and/or (5) to diminish the likelihood of severity of a disease or biological manifestations of the disease.

As used herein, "prevent", "preventing" or "prevention" means the prophylactic administration of a drug to diminish the likelihood of the onset of or to delay the onset of a disease or biological manifestation thereof.

As used herein, "subject" means a mammalian subject (e.g., dog, cat, horse, cow, sheep, goat, monkey, etc.), and human subjects including both male and female subjects, and including neonatal, infant, juvenile, adolescent, adult and geriatric subjects, and further including various races and ethnicities including, but not limited to, white, black, Asian, American Indian and Hispanic.

As used herein, "pharmaceutically acceptable salt(s)" refers to salt(s) that retain the desired biological activity of the subject compound and exhibit minimal undesired toxicological effects. These pharmaceutically acceptable salts may be prepared in situ during the final isolation and purification of the compound, or by separately reacting the purified compound in its free acid or free base form with a suitable base or acid, respectively.

As used herein, "therapeutically effective amount" in reference to a compound of the invention or other pharmaceutically-active agent means an amount of the compound sufficient to treat or prevent the patient's disease but low enough to avoid serious side effects (at a reasonable benefit/risk ratio) within the scope of sound medical judgment. A therapeutically effective amount of a compound will vary with the particular compound chosen (e.g. consider the potency, efficacy, and half-life of the compound); the route of administration chosen; the disease being treated; the severity of the disease being treated; the age, size, weight, and physical disease of the patient being treated; the medical history of the patient to be treated; the duration of the treatment; the nature of concurrent therapy; the desired therapeutic effect; and like factors, but can nevertheless be routinely determined by the skilled artisan.

B. Compounds

This invention provides, in a first aspect, a compound of Formula (I) or a salt thereof (e.g., a pharmaceutically acceptable salt thereof)

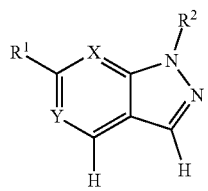

Formula (I)

Wherein
X is selected from CH or N;
Y is selected from CH, N or $CR_3$,
   wherein $R_3$ is selected from the group consisting of halo, $C_{1-3}$ alkyl, CN, and $C_{1-3}$ haloalkyl;
$R^1$ is selected from the group consisting of
   5 or 6 membered heterocyclyl optionally substituted with one, two or three substituents independently selected from the group consisting of
     $C_{1-3}$ alkyl optionally further substituted with one $C_{1-3}$ alkoxyl,
     $C_{1-3}$ alkoxyl,
     halo,
     hydroxyl,
     —$SO_2CH_3$,
     —$COCH_3$,
     oxo group, and
     oxetanyl,
   θ-4 to 6 membered heterocyclyl optionally substituted with one or two substituents of $C_{1-3}$ alkyl, which may be the same or different, and $C_{1-6}$ alkoxyl; and
$R^2$ is

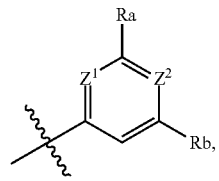

wherein
$Z^1$ and $Z^2$ are independently N or $CR_7$, and wherein $R_7$ is H or $C_{1-3}$alkoxyl, but
$Z^1$ and $Z^2$ cannot both be $CR_7$;
$R_a$ is selected from the group consisting of
   H,
   CN,
   $C_{1-3}$ alkyl,
   $C_{1-3}$ alkoxyl,
   —O—$C_{1-3}$haloalkyl, and
   $C_{3-6}$cycloalkyl; and
$R_b$ is selected from the group consisting of
   2-oxa-6-azaspiro[3.4]octanyl,
   $C_{3-6}$cycloalkyl, optionally substituted with one hydroxyl,
   —$CONHCH_3$;
   —$NHCOCH_3$;
   4 to 6 membered heterocyclyl optionally substituted with one or two substituents independently selected from the group consisting of
     hydroxyl,
     CN,
     —$CONHCH_3$,
     oxetanyl, C$_{1-3}$alkyl, optionally substituted with one hydroxyl, and C$_{1-3}$ alkoxyl, optionally substituted with one hydroxyl.

In one aspect, the present invention provides a compound of Formula (I) or a salt thereof (e.g., a pharmaceutically acceptable salt thereof)

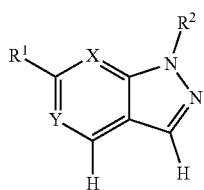

Formula (I)

wherein

X is selected from CH or N;

Y is selected from CH, N or CR$_3$,
  wherein R$_3$ is selected from the group consisting of halo and C$_{1-3}$ alkyl;

R$^1$ is selected from the group consisting of
  5 or 6 membered heterocyclyl optionally substituted with one, two or three substituents independently selected from the group consisting of
    C$_{1-3}$ alkyl optionally further substituted with one C$_{1-3}$ alkoxyl,
    halo,
    hydroxyl,
    —SO$_2$CH$_3$,
    —COCH$_3$,
    oxo group, and
    oxetanyl,
  —O-4 to 6 membered heterocyclyl optionally substituted with one or two substituents of C$_{1-3}$ alkyl, which may be the same or different, and C$_{1-6}$ alkoxyl; and R$^2$ is

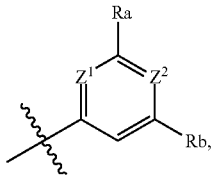

wherein

Z$^1$ and Z$^2$ are independently N or CR$_7$, wherein R$_7$ is H or C$_{1-3}$alkoxyl, but Z$^1$ and Z$^2$ cannot both be CR$_7$, R$_a$ is selected from the group consisting of
  H,
  CN,
  C$_{1-3}$ alkyl,
  C$_{1-3}$ alkoxyl,
  —O—C$_{1-3}$haloalkyl, and
  C$_{3-6}$cycloalkyl; and R$_b$ is selected from the group consisting of
  2-oxa-6-azaspiro[3.4]octanyl,
  C$_{3-6}$cycloalkyl, optionally substituted with one hydroxyl,
  —CONHCH$_3$,
  —NHCOCH$_3$, and
  4 to 6 membered heterocyclyl optionally substituted with one or two substituents independently selected from the group consisting of
    hydroxyl,
    CN,
    —CONHCH$_3$,
    oxetanyl,
    C$_{1-3}$alkyl, optionally substituted with one hydroxyl, and
    C$_{1-3}$ alkoxyl, optionally substituted with one hydroxyl.

In one embodiment, this invention relates to compounds of Formula (I), wherein X is CH.

In a further embodiment, this invention relates to compounds of Formula (I) and any of the above applicable embodiments, wherein Y is CH or CR$_3$. In another embodiment, this invention relates to compounds of Formula (I) and any of the above applicable embodiments, wherein Y is CH. In one embodiment, this invention relates to compounds of Formula (I) and any of the above applicable embodiments, wherein Y is CR$_3$ and R$_3$ is F or methyl. In one embodiment, this invention relates to compounds of Formula (I) and any of the above applicable embodiments, wherein Y is CR$_3$ and R$_3$ is methyl. In one embodiment, this invention relates to compounds of Formula (I) and any of the above applicable embodiments, wherein Y is CR$_3$ and R$_3$ is Cl or F. In one embodiment, this invention relates to compounds of Formula (I) and any of the above applicable embodiments, wherein Y is CR$_3$ and R$_3$ is Cl.

In one embodiment, this invention relates to compounds of Formula (I) and any of the above applicable embodiments, wherein R$^1$ is 5 or 6 membered heterocyclyl optionally substituted with one, two or three substituents independently selected from the group consisting of halo, hydroxyl, —SO$_2$CH$_3$, —COCH$_3$, oxetanyl, oxo group and C$_{1-3}$ alkyl optionally further substituted with one C$_{1-3}$ alkoxyl and wherein the 5 or 6 membered heterocyclyl is saturated or contains one double bond and contains one or two heteroatom ring members independently selected from nitrogen or oxygen. In another embodiment, this invention relates to compounds of Formula (I) and any of the above applicable embodiments, wherein R$^1$ is 5 or 6 membered heterocyclyl optionally substituted with one, two, or three substituents independently selected from the group consisting of halo, hydroxyl, —SO$_2$CH$_3$, —COCH$_3$, oxetanyl, oxo group and C$_{1-3}$ alkyl optionally further substituted with one C$_{1-3}$ alkoxyl, and wherein the 5 or 6 membered heterocyclyl is selected from the group consisting of piperidinyl, pyrrolidinyl (e.g., pyrrolidin-3-yl), 1,2,3,6-tetrahydropyridinyl (e.g., 1,2,3,6-tetrahydropyridin-4-yl), piperidinonyl (e.g. piperidin-2-onyl), tetrahydro-2H-pyranyl (e.g., tetrahydro-2H-pyran-4-yl), tetrahydrofuranyl (e.g., tetrahydrofuran-3-yl), morpholinyl, and piperazinyl (e.g., piperazin-1-yl). In one embodiment, this invention relates to compounds of Formula (I) and any of the above applicable embodiments, wherein R$^1$ is 6 membered heterocyclyl optionally substituted with one or two substituents independently selected from the group consisting of halo, oxetanyl and C$_{1-3}$ alkyl, and wherein the 6 membered heterocyclyl is saturated and contains one or two heteroatom ring members selected from nitrogen or oxygen. In another embodiment, this invention relates to compounds of Formula (I) and any of the above applicable embodiments, wherein R$^1$ is piperidinyl optionally substituted with one or two substituents independently selected from the group consisting of halo and C$_{1-3}$ alkyl. In one embodiment, this invention relates to compounds of Formula (I) and any of the above applicable embodiments R¹ is piperidinyl optionally substituted with one or two substituents independently selected from the group consisting of fluoro and methyl. In one embodiment, this invention relates to compounds of Formula (I) and any of the above applicable embodiments, R¹ is piperidinyl substituted with one or two substituents independently selected from the group consisting of oxetanyl and F. In one embodiment, this invention relates to compounds of Formula (I) and any of the above applicable embodiments, R¹ is piperidinyl substituted with one substituent of oxetanyl. In one embodiment, this invention relates to compounds of Formula (I) and any of the above applicable embodiments, R¹ is piperidin-4-yl substituted with one substituent of oxetanyl. In one embodiment, this invention relates to compounds of Formula (I) and any of the above applicable embodiments, R¹ is piperidin-4-yl substituted with one substituent of oxetan-3-yl.

In another embodiment, this invention relates to compounds of Formula (I) and any of the above applicable embodiments, wherein $R_1$ is —O-4 to 6 membered heterocyclyl optionally substituted with one or two substituents of $C_{1-3}$ alkyl, which may be the same or different. In another embodiment, this invention relates to compounds of Formula (I) and any of the above applicable embodiments, wherein $R_1$ is —O-4 to 6 membered heterocyclyl optionally substituted with one or two substituents independently selected from the group consisting of $C_{1-3}$ alkyl and wherein —O-4 to 6 membered heterocyclyl is selected from the group consisting of —O-piperidinyl (e.g., —O-piperidin-4-yl, —O-piperidin-3-yl), —O-pyrrolidinyl (e.g., —O-pyrrolidin-3-yl), —O-tetrahydrofuranyl (e.g., —O-tetrahydrofuran-3-yl), and —O-azetidinyl (e.g., —O-azetidin-3-yl).

In another embodiment, this invention relates to compounds of Formula (I) and any of the above applicable embodiments, wherein $R_1$ is $C_{1-6}$ alkoxyl. In another embodiment, this invention relates to compounds of Formula (I) and any of the above applicable embodiments, wherein $R_1$ is —O-isopropyl.

In another embodiment, this invention relates to compounds of Formula (I) and any of the above applicable embodiments, wherein $R^2$ is

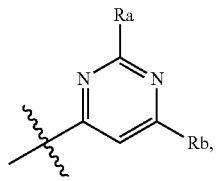

wherein
$R_a$ is selected from the group consisting of
H,
CN,
$C_{1-3}$ alkyl,
$C_{1-3}$ alkoxyl, and
$C_{3-6}$cycloalkyl; and
$R_b$ is selected from the group consisting of
2-oxa-6-azaspiro[3.4]octanyl,
$C_{3-6}$cycloalkyl, optionally substituted with one hydroxyl,
—CONHCH₃,
—NHCOCH₃, and
4 to 6 membered heterocyclyl optionally substituted with one or two substituents independently selected from the group consisting of
hydroxyl,
CN,
—CONHCH₃,
oxetanyl,
$C_{1-3}$alkyl, optionally substituted with one hydroxyl, and
$C_{1-3}$ alkoxyl, optionally substituted with one hydroxyl.

In another embodiment, this invention relates to compounds of Formula (I) and any of the above applicable embodiments, wherein $R^2$ is

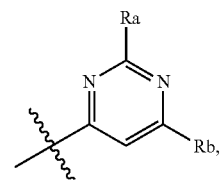

wherein
$R_a$ is selected from the group consisting of
H,
CN,
$C_{1-3}$ alkyl,
$C_{1-3}$ alkoxyl, and
cyclopropyl; and
$R_b$ is selected from the group consisting of
$C_{3-6}$cycloalkyl, optionally substituted with one hydroxyl,
—CONHCH₃,
—NHCOCH₃, and
4 to 6 membered heterocyclyl optionally substituted with one substituent selected from the group consisting of
hydroxyl,
CN,
—CONHCH₃,
oxetanyl,
$C_{1-3}$alkyl, optionally substituted with one hydroxyl, and
$C_{1-3}$ alkoxyl, optionally substituted with one hydroxyl, and the 4 to 6 membered heterocyclyl is selected from the group consisting of morpholinyl, azetinidyl, piperazinyl, thiomorpholinyl 1,1-dioxide, and oxetanyl.

In a further embodiment, this invention relates to compounds of Formula (I) and any of the above applicable embodiments, wherein $R^2$ is

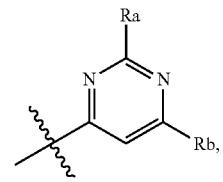

wherein
$R_a$ is $C_{1-3}$ alkyl or $C_{1-3}$ alkoxyl, and
$R_b$ is 4 to 6 membered heterocyclyl optionally substituted with one substituent selected from the group consisting of hydroxyl,
C$_{1-3}$alkyl optionally substituted with one hydroxyl, and
C$_{1-3}$ alkoxyl optionally substituted with one hydroxyl, and
the 4 to 6 membered heterocyclyl is selected from the group consisting of morpholinyl, azetinidyl, piperazinyl, and oxetanyl.

In a further embodiment, the compound of Formula (I) is a compound of Formula (A) or a pharmaceutically acceptable salt thereof

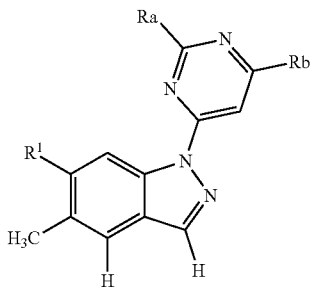

Formula (A)

wherein,
R$^1$ is piperidinyl optionally substituted with one or two substituents independently selected from the group consisting of halo and C$_{1-3}$ alkyl;
R$_a$ is C$_{1-3}$ alkyl or C$_{1-3}$ alkoxyl; and
R$_b$ is 4 to 6 membered heterocyclyl optionally substituted with one substituent selected from the group consisting of
hydroxyl,
C$_{1-3}$alkyl optionally substituted with one hydroxyl, and
C$_{1-3}$ alkoxyl optionally substituted with one hydroxyl, and
the 4 to 6 membered heterocyclyl is selected from the group consisting of morpholinyl, azetinidyl, piperazinyl, and oxetanyl.

In one embodiment, the invention relates to compounds of Formula (A) and pharmaceutically acceptable salts thereof, wherein
R$^1$ is piperidinyl optionally substituted with one or two substituents independently selected from the group consisting of F and methyl;
R$_a$ is methyl or methoxyl; and
R$_b$ is 4 to 6 membered heterocyclyl optionally substituted with one hydroxyl, and the 4 to 6 membered heterocyclyl is selected from the group consisting of morpholinyl, azetinidyl, piperazinyl, and oxetanyl.

In one embodiment, the compound of Formula (I) or Formula (A) is

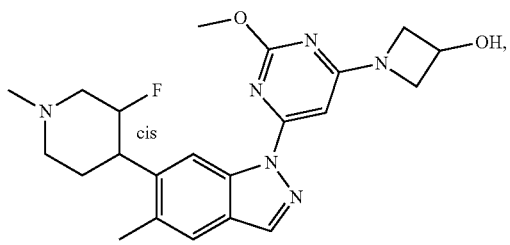 [SMILES: COc1nc(N2CC(O)C2)cc(-n2ncc3cc(C)c(C4CCN(C)CC4F)cc32)n1]

or a salt thereof.

In one embodiment, the compound of Formula (I) or Formula (A) is

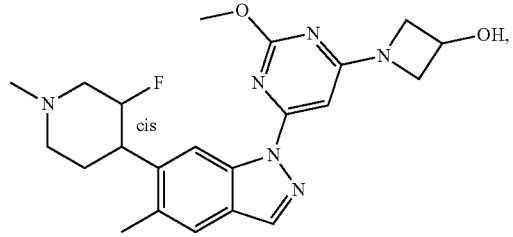 [SMILES: COc1nc(N2CC(O)C2)cc(-n2ncc3cc(C)c(C4CCN(C)CC4F)cc32)n1]

or a pharmaceutically acceptable salt thereof.

In one embodiment, the compound of Formula (I) or Formula (A) is

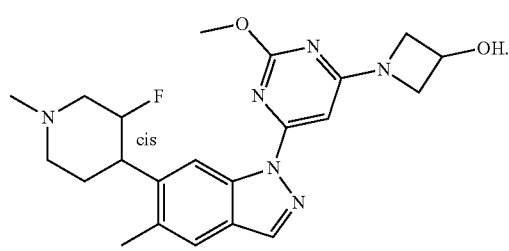 [SMILES: COc1nc(N2CC(O)C2)cc(-n2ncc3cc(C)c(C4CCN(C)CC4F)cc32)n1]

In one embodiment, the compound of Formula (I) or Formula (A) is a salt of

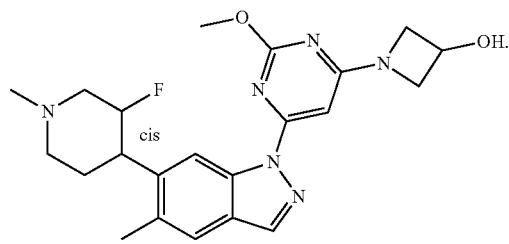 [SMILES: COc1nc(N2CC(O)C2)cc(-n2ncc3cc(C)c(C4CCN(C)CC4F)cc32)n1]

In one embodiment, the compound of Formula (I) or Formula (A) is a pharmaceutically acceptable salt of

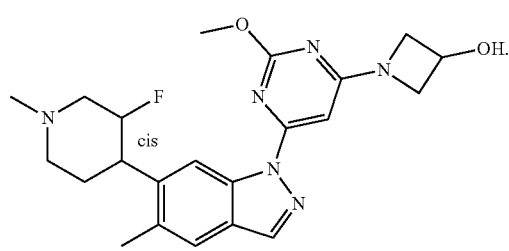 [SMILES: COc1nc(N2CC(O)C2)cc(-n2ncc3cc(C)c(C4CCN(C)CC4F)cc32)n1]

In one embodiment, the compound of Formula (I) or Formula (A) is

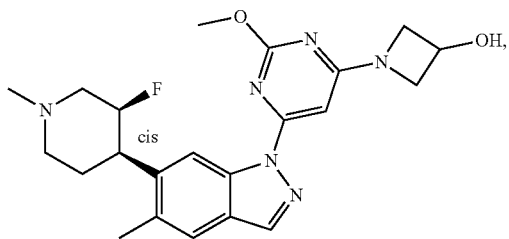 [SMILES: COc1nc(N2CC(O)C2)cc(-n2ncc3cc(C)c([C@H]4CCN(C)C[C@H]4F)cc32)n1]

or a salt thereof.

In one embodiment, the compound of Formula (I) or Formula (A) is

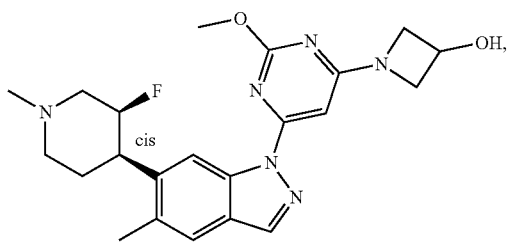 [SMILES: COc1nc(N2CC(O)C2)cc(-n2ncc3cc(C)c([C@H]4CCN(C)C[C@H]4F)cc32)n1]

or a pharmaceutically acceptable salt thereof.

In one embodiment, the compound of Formula (I) or Formula (A) is

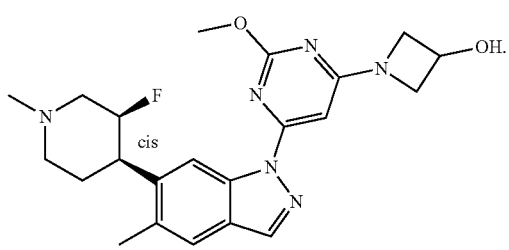 [SMILES: COc1nc(N2CC(O)C2)cc(-n2ncc3cc(C)c([C@H]4CCN(C)C[C@H]4F)cc32)n1]

In one embodiment, the compound of Formula (I) or Formula (A) is a salt of

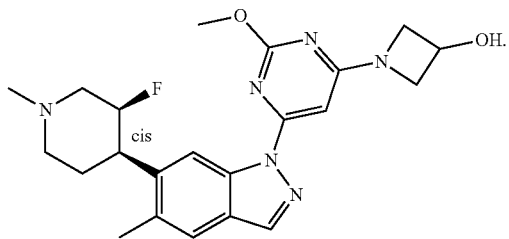 [SMILES: COc1nc(N2CC(O)C2)cc(-n2ncc3cc(C)c([C@H]4CCN(C)C[C@H]4F)cc32)n1]

In one embodiment, the compound of Formula (I) or Formula (A) is a pharmaceutically acceptable salt of

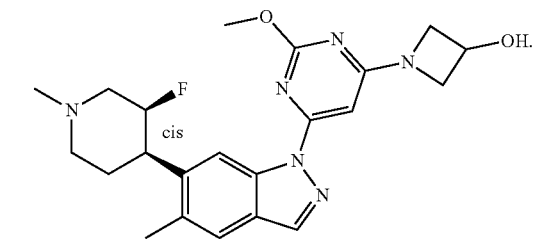 [SMILES: COc1nc(N2CC(O)C2)cc(-n2ncc3cc(C)c([C@H]4CCN(C)C[C@H]4F)cc32)n1]

In one embodiment, the compound of Formula (I) or Formula (A) is

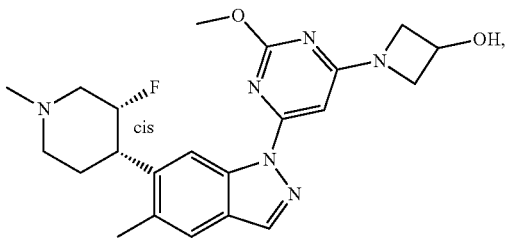 [SMILES: COc1nc(N2CC(O)C2)cc(-n2ncc3cc(C)c([C@@H]4CCN(C)C[C@@H]4F)cc32)n1]

or a salt thereof.

In one embodiment, the compound of Formula (I) or Formula (A) is

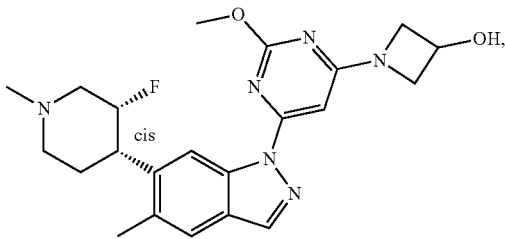 [SMILES: COc1nc(N2CC(O)C2)cc(-n2ncc3cc(C)c([C@@H]4CCN(C)C[C@@H]4F)cc32)n1]

or a pharmaceutically acceptable salt thereof.

In one embodiment, the compound of Formula (I) or Formula (A) is

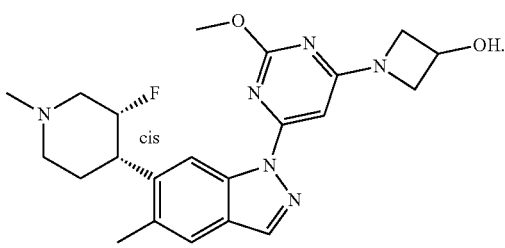 [SMILES: COc1nc(N2CC(O)C2)cc(-n2ncc3cc(C)c([C@@H]4CCN(C)C[C@@H]4F)cc32)n1]

In one embodiment, the compound of Formula (I) or Formula (A) is a salt thereof

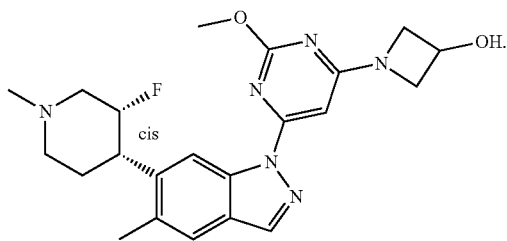 [SMILES: COc1nc(N2CC(O)C2)cc(-n2ncc3cc(C)c([C@@H]4CCN(C)C[C@@H]4F)cc32)n1]

In one embodiment, the compound of Formula (I) or Formula (A) is a pharmaceutically acceptable salt thereof

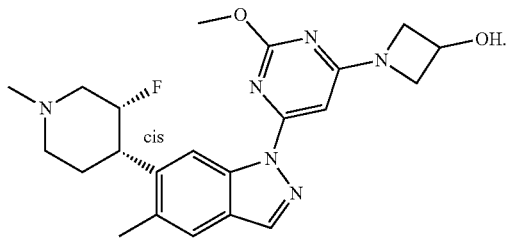 [SMILES: COc1nc(N2CC(O)C2)cc(-n2ncc3cc(C)c([C@@H]4CCN(C)C[C@@H]4F)cc32)n1]

In one embodiment, the compound of Formula (I) or Formula (A) is

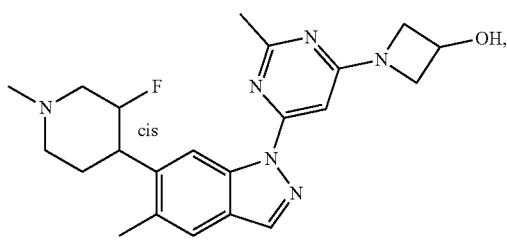 [SMILES: Cc1nc(N2CC(O)C2)cc(-n2ncc3cc(C)c(C4CCN(C)CC4F)cc32)n1]

or a salt thereof.

In one embodiment, the compound of Formula (I) or Formula (A) is

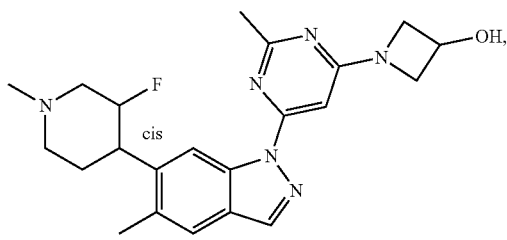 [SMILES: Cc1nc(N2CC(O)C2)cc(-n2ncc3cc(C)c(C4CCN(C)CC4F)cc32)n1]

or a pharmaceutically acceptable salt thereof.

In one embodiment, the compound of Formula (I) or Formula (A) is

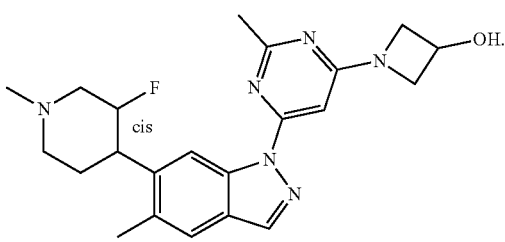 [SMILES: Cc1nc(N2CC(O)C2)cc(-n2ncc3cc(C)c(C4CCN(C)CC4F)cc32)n1]

In one embodiment, the compound of Formula (I) or Formula (A) is a salt of

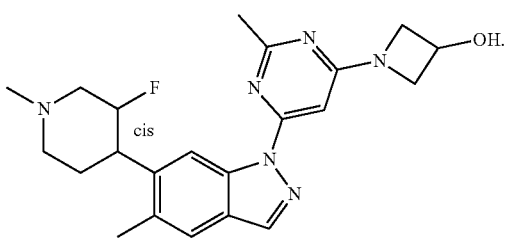 [SMILES: Cc1nc(N2CC(O)C2)cc(-n2ncc3cc(C)c(C4CCN(C)CC4F)cc32)n1]

In one embodiment, the compound of Formula (I) or Formula (A) is a pharmaceutically acceptable salt of

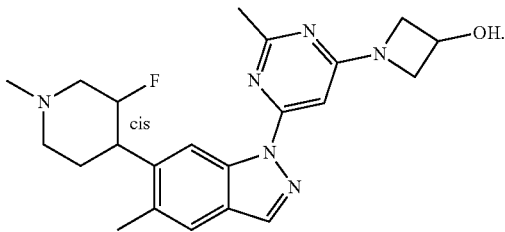

In one embodiment, the compound of Formula (I) or Formula (A) is

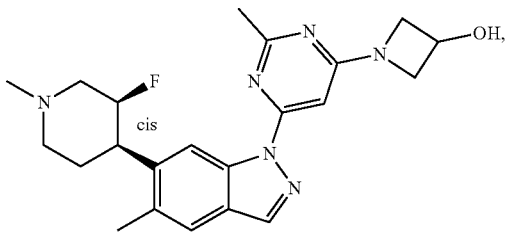 [SMILES: Cc1nc(N2CC(O)C2)cc(-n2ncc3cc(C)c([C@H]4CCN(C)C[C@H]4F)cc32)n1]

or a salt thereof.

In one embodiment, the compound of Formula (I) or Formula (A) is

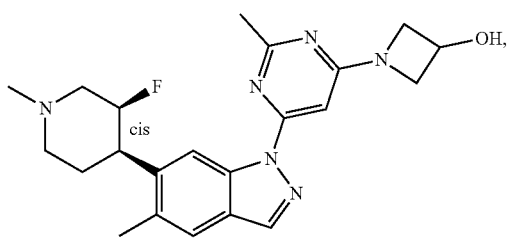 [SMILES: Cc1nc(N2CC(O)C2)cc(-n2ncc3cc(C)c([C@H]4CCN(C)C[C@H]4F)cc32)n1]

or a pharmaceutically acceptable salt thereof.

In one embodiment, the compound of Formula (I) or Formula (A) is

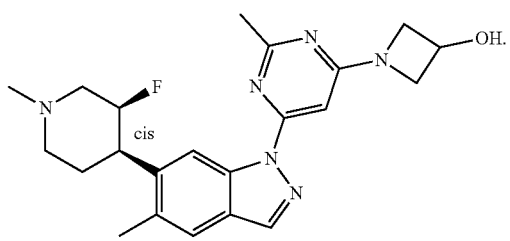 [SMILES: Cc1nc(N2CC(O)C2)cc(-n2ncc3cc(C)c([C@H]4CCN(C)C[C@H]4F)cc32)n1]

In one embodiment, the compound of Formula (I) or Formula (A) is a salt of

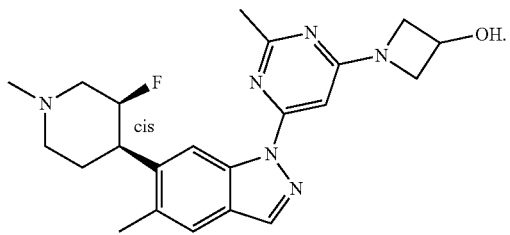 [SMILES: Cc1nc(N2CC(O)C2)cc(-n2ncc3cc(C)c([C@H]4CCN(C)C[C@H]4F)cc32)n1]

In one embodiment, the compound of Formula (I) or Formula (A) is a pharmaceutically acceptable salt of

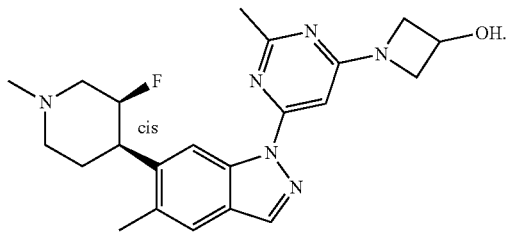 [SMILES: Cc1nc(N2CC(O)C2)cc(-n2ncc3cc(C)c([C@H]4CCN(C)C[C@H]4F)cc32)n1]

In one embodiment, the compound of Formula (I) or Formula (A) is

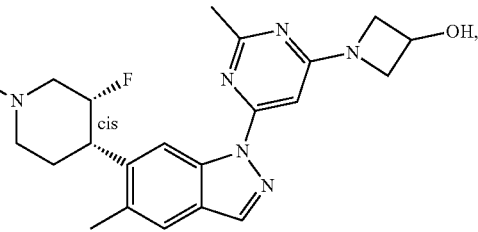

or a salt thereof.

In one embodiment, the compound of Formula (I) or Formula (A) is

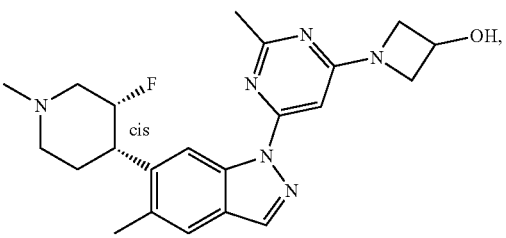

or a pharmaceutically acceptable salt thereof.

In one embodiment, the compound of Formula (I) or Formula (A) is

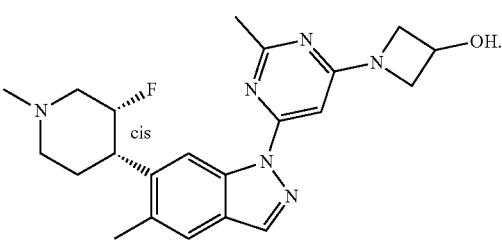 [SMILES: Cc1nc(N2CC(O)C2)cc(-n2ncc3cc(C)c([C@@H]4CCN(C)C[C@@H]4F)cc32)n1]

In one embodiment, the compound of Formula (I) or Formula (A) is a salt of

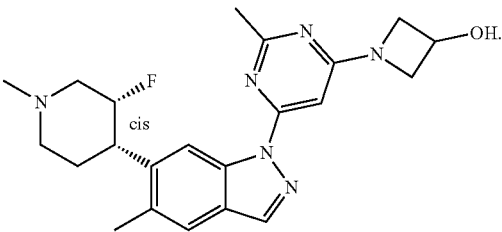 [SMILES: Cc1nc(N2CC(O)C2)cc(-n2ncc3cc(C)c([C@@H]4CCN(C)C[C@@H]4F)cc32)n1]

In one embodiment, the compound of Formula (I) or Formula (A) is a pharmaceutically acceptable salt of

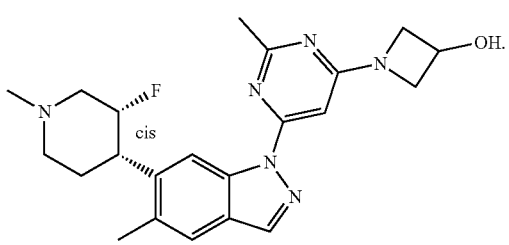

In one embodiment, the compound of Formula (I) is a compound of any one of Examples E1 to E121, a free base, a free acid, or a salt (e.g., a pharmaceutically acceptable salt) thereof.

In one embodiment, the compound of Formula (I) is a compound of any one of Examples E122 to E273, a free base, a free acid, or a salt (e.g., a pharmaceutically acceptable salt) thereof.

In some embodiment, the present invention is directed to a compound having a structure selected from the group consisting of 4-(6-(6-(3,3-difluoro-1-methylpiperidin-4-yl)-5-methyl-1H-indazol-1-yl)pyrimidin-4-yl)morpholine, 4-(6-(6-(3,3-difluoro-1-methylpiperidin-4-yl)-5-methyl-1H-indazol-1-yl)-2-methoxypyrimidin-4-yl)morpholine, 4-(6-(6-(3,3-difluoro-1-methylpiperidin-4-yl)-5-methyl-1H-indazol-1-yl)-2-ethoxypyrimidin-4-yl)morpholine, 4-(6-(6-(3,3-difluoro-1-methylpiperidin-4-yl)-5-methyl-1H-indazol-1-yl)-2-isopropoxypyrimidin-4-yl)morpholine, 4-(6-(3,3-difluoro-1-methylpiperidin-4-yl)-5-methyl-1H-indazol-1-yl)-6-morpholinopyrimidine-2-carbonitrile, 4-(6-(6-(3,3-difluoro-1-methylpiperidin-4-yl)-5-methyl-1H-indazol-1-yl)-2-ethylpyrimidin-4-yl)morpholine, 6-(6-(6-(3,3-difluoro-1-methylpiperidin-4-yl)-5-methyl-1H-indazol-1-yl)pyrimidin-4-yl)-2-oxa-6-azaspiro[3.4]octane, 4-(6-(6-(3,3-difluoro-1-methylpiperidin-4-yl)-5-methyl-1H-indazol-1-yl)pyrimidin-4-yl)-N-methylmorpholine-2-carboxamide, 4-(6-(6-(3,3-difluoro-1-methylpiperidin-4-yl)-5-methyl-1H-indazol-1-yl)-2-methoxypyrimidin-4-yl)-N-methylmorpholine-2-carboxamide, 4-(6-(6-(3,3-difluoro-1-(oxetan-3-yl)piperidin-4-yl)-5-methyl-1H-indazol-1-yl)pyrimidin-4-yl)morpholine, 4-(6-(6-(3,3-difluoro-1-(oxetan-3-yl)piperidin-4-yl)-5-methyl-1H-indazol-1-yl)-2-methoxypyrimidin-4-yl)morpholine, 4-(6-(6-(3,3-difluoro-1-(oxetan-3-yl)piperidin-4-yl)-5-methyl-1H-indazol-1-yl)-2-ethoxypyrimidin-4-yl)morpholine, 4-(6-(6-(3,3-difluoro-1-(oxetan-3-yl)piperidin-4-yl)-5-methyl-1H-indazol-1-yl)-2-isopropoxypyrimidin-4-yl)morpholine, (cis)-4-(6-(6-(3-fluoro-1-(2-methoxyethyl)piperidin-4-yl)-5-methyl-1H-indazol-1-yl)pyrimidin-4-yl)morpholine, (cis)-4-(6-(6-(3-fluoro-1-(2-methoxyethyl)piperidin-4-yl)-5-methyl-1H-indazol-1-yl)pyrimidin-4-yl)-N-methylmorpholine-2-carboxamide, (cis)-1-(2-(6-(3-fluoro-1-(2-methoxyethyl)piperidin-4-yl)-5-methyl-1H-indazol-1-yl)-5-methoxypyridin-4-yl)azetidin-3-ol, (cis)-4-(6-(6-(3-fluoro-1-(oxetan-3-yl)piperidin-4-yl)-5-methyl-1H-indazol-1-yl)pyrimidin-4-yl)-N-methylmorpholine-2-carboxamide, (cis)-1-(6-(6-(3-fluoro-1-methylpiperidin-4-yl)-5-methyl-1H-indazol-1-yl)-2-methoxypyrimidin-4-yl)azetidin-3-ol, (cis)-1-(6-(6-(3-fluoro-1-(oxetan-3-yl)piperidin-4-yl)-5-methyl-1H-indazol-1-yl)-2-methylpyrimidin-4-yl)azetidin-3-ol, (cis)-3-(6-(6-(3-fluoro-1-(oxetan-3-yl)piperidin-4-yl)-5-methyl-1H-indazol-1-yl)-2-methylpyrimidin-4-yl)cyclobutanol (cis)-1-(2-cyclopropyl-6-(6-(3-fluoro-1-methylpiperidin-4-yl)-5-methyl-1H-indazol-1-yl)pyrimidin-4-yl)azetidin-3-ol, (cis)-1-(2-(difluoromethoxy)-6-(6-(3-fluoro-1-methylpiperidin-4-yl)-5-methyl-1H-indazol-1-yl)pyrimidin-4-yl)azetidin-3-ol, (cis)-2-((1-(6-(6-(3-fluoro-1-methylpiperidin-4-yl)-5-methyl-1H-indazol-1-yl)-2-methoxypyrimidin-4-yl)azetidin-3-yl)oxy)ethanol, (cis)-1-(6-(6-(3-fluoro-1-methylpiperidin-4-yl)-5-methyl-1H-indazol-1-yl)-2-methoxypyrimidin-4-yl)pyrrolidin-3-ol, (cis)-1-(6-(6-(3-fluoro-1-methylpiperidin-4-yl)-5-methyl-1H-indazol-1-yl)-2-methoxypyrimidin-4-yl)pyrrolidin-3-ol, (cis)-6-(6-(3-fluoro-1-methylpiperidin-4-yl)-5-methyl-1H-indazol-1-yl)-2-methoxy-N-methylpyrimidine-4-carboxamide, (cis)-N-(6-(6-(3-fluoro-1-methylpiperidin-4-yl)-5-methyl-1H-indazol-1-yl)-2-methoxypyrimidin-4-yl) acetamide, (cis)-4-(6-(6-(3-fluoro-1-methylpiperidin-4-yl)-5-methyl-1H-indazol-1-yl)-2-methoxypyrimidin-4-yl)thiomorpholine 1,1-dioxide, (cis)-4-(6-(6-(3-fluoropiperidin-4-yl)-5-methyl-1H-indazol-1-yl)-2-methoxypyrimidin-4-yl)morpholine, (cis)-4-(6-(6-(3-fluoropiperidin-4-yl)-5-methyl-1H-indazol-1-yl)-2-methylpyrimidin-4-yl)morpholine, 1-(6-(6-(3,3-difluoropiperidin-4-yl)-5-methyl-1H-indazol-1-yl)-2-methoxypyrimidin-4-yl)azetidine-3-carbonitrile, (cis)-1-(6-(5-fluoro-6-(3-fluoro-1-methylpiperidin-4-yl)-1H-indazol-1-yl)-2-methoxypyrimidin-4-yl)azetidin-3-ol, (cis)-1-(6-(5-fluoro-6-(3-fluoro-1-methylpiperidin-4-yl)-1H-indazol-1-yl)-2-methylpyrimidin-4-yl)azetidin-3-ol, (cis)-1-(6-(6-(3-fluoro-1-methylpiperidin-4-yl)-1H-indazol-1-yl)-2-methoxypyrimidin-4-yl)azetidin-3-ol, (cis)-1-(6-(6-(4-fluoro-1-methylpyrrolidin-3-yl)-5-methyl-1H-indazol-1-yl)-2-methoxypyrimidin-4-yl)azetidin-3-ol, (cis)-4-(4-(6-(3-fluoro-1-(2-methoxyethyl)piperidin-4-yl)-1H-pyrazolo[3,4-d]pyrimidin-1-yl)pyridin-2-yl)morpholine, 4-(1-(6-(3-hydroxyazetidin-1-yl)-2-methoxypyrimidin-4-yl)-5-methyl-1H-indazol-6-yl)-1-methylpiperidin-2-one, 1-(2-methoxy-6-(piperazin-1-yl)pyrimidin-4-yl)-5-methyl-6-(tetrahydrofuran-3-yl)-1H-indazole, 3-(1-(2-methoxy-6-morpholinopyrimidin-4-yl)-1H-indazol-6-yl)-4-methylmorpholine, 4-(2-methoxy-6-(5-methyl-6-((1-methylpiperidin-3-yl)oxy)-1H-indazol-1-yl)pyrimidin-4-yl)morpholine, 4-(2-methoxy-6-(5-methyl-6-((1-methylpyrrolidin-3-yl)oxy)-1H-indazol-1-yl)pyrimidin-4-yl)morpholine, 1-(2-methoxy-6-(piperazin-1-yl)pyrimidin-4-yl)-5-methyl-6-((tetrahydrofuran-3-yl)oxy)-1H-indazole hydrochloride, 1-(2-methoxy-6-(4-methylpiperazin-1-yl)pyrimidin-4-yl)-5-methyl-6-((tetrahydrofuran-3-yl)oxy)-1H-indazole, and 1-(2-methoxy-6-(4-(oxetan-3-yl)piperazin-1-yl)pyrimidin-4-yl)-5-methyl-6-((tetrahydrofuran-3-yl)oxy)-1H-indazole, or a salt thereof (e.g., a pharmaceutically acceptable salt).

In some embodiment, the present invention is directed to a compound having a structure selected from the group consisting of (cis)-(1s,3s)-3-(6-(6-(3-fluoropiperidin-4-yl)-5-methyl-1H-indazol-1-yl)-2-methoxypyrimidin-4-yl)cyclobutanol hydrochloride, (cis)-(1r,3r)-3-(6-(6-(3-fluoro-1-methylpiperidin-4-yl)-5-methyl-1H-indazol-1-yl)-2-methoxypyrimidin-4-yl)cyclobutanol, 1-(6-(6-((cis)-3-fluoro-1-methylpiperidin-4-yl)-5-methyl-1H-indazol-1-yl)-2-methylpyrimidin-4-yl)pyrrolidin-3-ol, 1-(6-(6-((cis)-3-fluoro-1-methylpiperidin-4-yl)-5-methyl-1H-indazol-1-yl)-2-methylpyrimidin-4-yl)pyrrolidine-3,4-diol, (cis)-2-((1-(6-(6-(3-fluoro-1-methylpiperidin-4-yl)-5-methyl-1H-indazol-1-yl)-2-methylpyrimidin-4-yl)azetidin-3-yl)oxy)ethanol, (4-(6-(6-((cis)-3-fluoro-1-methylpiperidin-4-yl)-5-methyl-1H-indazol-1-yl)-2-methylpyrimidin-4-yl)morpholin-2-yl)methanol, (4-(6-(6-((cis)-3-fluoro-1-methylpiperidin-4-yl)-5-methyl-1H-indazol-1-yl)-2-methoxypyrimidin-4-yl)morpholin-2-yl)methanol, (4-(6-(6-(((cis)-3-fluoro-1-methylpiperidin-4-yl)-5-methyl-1H-indazol-1-yl)-2-methoxypyrimidin-4-yl)morpholin-2-yl)methanol, (cis)-1-(6-(6-(3-Fluoropiperidin-4-yl)-5-methyl-1H-indazol-1-yl)-2-methylpyrimidin-4-yl)azetidin-3-ol hydrochloride, 1-(6-(azetidin-1-yl)-2-methylpyrimidin-4-yl)-6-((cis)-3-fluoropiperidin-4-yl)-5-methyl-1H-indazole, (cis)-1-(6-(6-(1-ethyl-3-fluoropiperidin-4-yl)-5-methyl-1H-indazol-1-yl)-2-methylpyrimidin-4-yl)azetidin-3-ol, (cis)-1-(6-(6-(3-fluoro-1-isopropylpiperidin-4-yl)-5-methyl-1H-indazol-1-yl)-2-methylpyrimidin-4-yl)azetidin-3-ol, (cis)-(1r,3r)-3-(6-(6-(3-fluoro-1-(oxetan-3-yl)piperidin-4-yl)-5-methyl-1H-indazol-1-yl)-2-methylpyrimidin-4-yl)cyclobutanol, 4-(6-(6-(3-fluoro-1-(oxetan-3-yl)piperidin-4-yl)-5-methyl-1H-indazol-1-yl)-2-methoxypyrimidin-4-yl)morpholine, 6-((cis)-3-fluoro-1-(oxetan-3-yl)piperidin-4-yl)-1-(2-methoxy-6-(4-methylpiperazin-1-yl)pyrimidin-4-yl)-5-methyl-1H-indazole, 4-(6-(6-((cis)-3-fluoro-1-(oxetan-3-yl)piperidin-4-yl)-5-methyl-1H-indazol-1-yl)-2-methoxypyrimidin-4-yl)-2-methylmorpholine, 4-(6-(6-(3-fluoro-1-(oxetan-3-yl)piperidin-4-yl)-5-methyl-1H-indazol-1-yl)-2-methoxypyrimidin-4-yl)-2,6-dimethylmorpholine, 4-(6-(6-(3-fluoro-1-(oxetan-3-yl)piperidin-4-yl)-5-methyl-1H-indazol-1-yl)-2-methoxypyrimidin-4-yl)-3-methylmorpholine, 6-(6-(6-(3-fluoro-1-(oxetan-3-yl)piperidin-4-yl)-5-methyl-1H-indazol-1-yl)-2-methoxypyrimidin-4-yl)-2-oxa-6-azaspiro[3.4]octane, 4-(6-(6-(3-fluoro-1-(oxetan-3-yl)piperidin-4-yl)-5-methyl-1H-indazol-1-yl)-2-methoxypyrimidin-4-yl)morpholin-2-yl)methanol, (4-(6-(6-(3-fluoro-1-(oxetan-3-yl)piperidin-4-yl)-5-methyl-1H-indazol-1-yl)-2-methylpyrimidin-4-yl)morpholin-2-yl)methanol, 1-(6-(6-((cis)-3-fluoro-1-(oxetan-3-yl)piperidin-4-yl)-5-methyl-1H-indazol-1-yl)-2-methylpyrimidin-4-yl)-3-methylazetidin-3-ol, 1-(6-(6-((cis)-3-fluoro-1-(oxetan-3-yl)piperidin-4-yl)-5-methyl-1H-indazol-1-yl)-2-methoxypyrimidin-4-yl)-3-methylazetidin-3-ol, (4-(2-methyl-6-(5-methyl-6-(1-(oxetan-3-yl)piperidin-4-yl)-1H-indazol-1-yl)pyrimidin-4-yl)morpholin-2-yl)methanol, (4-(2-methyl-6-(5-methyl-6-(1-(oxetan-3-yl)piperidin-4-yl)-1H-indazol-1-yl)pyrimidin-4-yl)morpholin-2-yl)methanol, 1-(2-methyl-6-(5-methyl-6-(1-(oxetan-3-yl)piperidin-4-yl)-1H-indazol-1-yl)pyrimidin-4-yl)azetidin-3-ol, 1-(2-methyl-6-(5-methyl-6-(piperidin-4-yl)-1H-indazol-1-yl)pyrimidin-4-yl)azetidin-3-ol hydrochloride, 1-(2-methyl-6-(5-methyl-6-(1-methylpiperidin-4-yl)-1H-indazol-1-yl)pyrimidin-4-yl)azetidin-3-ol, (4-(2-methyl-6-(5-methyl-6-(piperidin-4-yl)-1H-indazol-1-yl)pyrimidin-4-yl)morpholin-2-yl)methanol, (4-(2-methoxy-6-(5-methyl-6-(1-(oxetan-3-yl)piperidin-4-yl)-1H-indazol-1-yl)pyrimidin-4-yl)morpholin-2-yl)methanol, (4-(2-methoxy-6-(5-methyl-6-(1-(oxetan-3-yl)piperidin-4-yl)-1H-indazol-1-yl)pyrimidin-4-yl)morpholin-2-yl)methanol, (4-(2-methoxy-6-(5-methyl-6-(piperidin-4-yl)-1H-indazol-1-yl)pyrimidin-4-yl)morpholin-2-yl)methanol, 4-(2-methyl-6-(5-methyl-6-(1-(oxetan-3-yl)piperidin-4-yl)-1H-indazol-1-yl)pyrimidin-4-yl)morpholine, 4-(2-methoxy-6-(5-methyl-6-(1-(oxetan-3-yl)piperidin-4-yl)-1H-indazol-1-yl)pyrimidin-4-yl)-2-methylmorpholine, 2-methyl-4-(2-methyl-6-(5-methyl-6-(1-(oxetan-3-yl)piperidin-4-yl)-1H-indazol-1-yl)pyrimidin-4-yl)morpholine, 4-(2-ethyl-6-(5-methyl-6-(1-(oxetan-3-yl)piperidin-4-yl)-1H-indazol-1-yl)pyrimidin-4-yl)morpholine, (4-(2-ethyl-6-(5-methyl-6-(1-(oxetan-3-yl)piperidin-4-yl)-1H-indazol-1-yl)pyrimidin-4-yl)morpholin-2-yl)methanol, 2-methyl-4-(2-methyl-6-(5-methyl-6-(piperidin-4-yl)-1H-indazol-1-yl)pyrimidin-4-yl)morpholine (HCl salt), 4-(2-methyl-6-(5-methyl-6-(piperidin-4-yl)-1H-indazol-1-yl)pyrimidin-4-yl)morpholine (HCl salt), 4-(2-methoxy-6-(5-methyl-6-(piperidin-4-yl)-1H-indazol-1-yl)pyrimidin-4-yl)-2-methylmorpholine (TFA salt), 4-(2-methoxy-6-(5-methyl-6-(piperidin-4-yl)-1H-indazol-1-yl)pyrimidin-4-yl)-2-methylmorpholine 2,2,2-trifluoroacetate, (4-(6-(5-chloro-6-(1-(oxetan-3-yl)piperidin-4-yl)-1H-indazol-1-yl)-2-methylpyrimidin-4-yl)morpholin-2-yl)methanol, 1-(6-(5-Chloro-6-(1-(oxetan-3-yl)piperidin-4-yl)-1H-indazol-1-yl)-2-methylpyrimidin-4-yl)azetidin-3-ol, (4-(6-(5-chloro-6-(piperidin-4-yl)-1H-indazol-1-yl)-2-methylpyrimidin-4-yl)morpholin-2-yl)methanol, 1-(6-(5-chloro-6-(piperidin-4-yl)-1H-indazol-1-yl)-2-methylpyrimidin-4-yl)azetidin-3-ol, 1-(2-methyl-6-(5-methyl-6-(1-(oxetan-3-yl)piperidin-4-yl)-1H-indazol-1-yl)pyrimidin-4-yl)pyrrolidin-3-ol, (trans)-4-fluoro-1-(2-methyl-6-(5-methyl-6-(1-(oxetan-3-yl)piperidin-4-yl)-1H-indazol-1-yl)pyrimidin-4-yl)pyrrolidin-3-ol, (trans)-4-fluoro-1-(2-methoxy-6-(5-methyl-6-(1-(oxetan-3-yl)piperidin-4-yl)-1H-indazol-1-yl)pyrimidin-4-yl)pyrrolidin-3-ol, N-methyl-1-(2-methyl-6-(5-methyl-6-(1-(oxetan-3-yl)piperidin-4-yl)-1H-indazol-1-yl)pyrimidin-4-yl)azetidine-3-carboxamide,
1-(6-(6-(3-fluoro-1-methylpiperidin-3-yl)-5-methyl-1H-indazol-1-yl)-2-methoxypyrimidin-4-yl)azetidin-3-ol,
(trans)-1-methyl-4-(5-methyl-1-(2-methyl-6-morpholinopyrimidin-4-yl)-1H-indazol-6-yl)piperidin-3-ol,
(trans)-4-(1-(2-methoxy-6-morpholinopyrimidin-4-yl)-5-methyl-1H-indazol-6-yl)-1-methylpiperidin-3-ol,
1-(2-methyl-6-(5-methyl-6-(4-methylmorpholin-2-yl)-1H-indazol-1-yl)pyrimidin-4-yl)azetidin-3-ol,
1-(2-methoxy-6-(5-methyl-6-(4-methylmorpholin-2-yl)-1H-indazol-1-yl)pyrimidin-4-yl)azetidin-3-ol,
1-(6-methoxy-4-(5-methyl-6-(1-(oxetan-3-yl)piperidin-4-yl)-1H-pyrazolo[3,4-b]pyridin-1-yl)pyridin-2-yl)azetidin-3-ol,
1-(6-(6-(3,3-difluoro-1-(oxetan-3-yl)piperidin-4-yl)-5-methyl-1H-indazol-1-yl)-2-methylpyrimidin-4-yl)azetidin-3-ol,
2-(4-(2-methyl-6-(5-methyl-6-(tetrahydro-2H-pyran-4-yl)-1H-indazol-1-yl)pyrimidin-4-yl)piperazin-1-yl)ethanol,
1-(2-methyl-6-(5-methyl-6-(tetrahydro-2H-pyran-4-yl)-1H-indazol-1-yl)pyrimidin-4-yl)pyrrolidine-3,4-diol,
1-(2-methoxy-6-(4-(oxetan-3-yl)piperazin-1-yl)pyrimidin-4-yl)-5-methyl-6-(tetrahydro-2H-pyran-4-yl)-1H-indazole,
2-((1-(2-methoxy-6-(5-methyl-6-(tetrahydro-2H-pyran-4-yl)-1H-indazol-1-yl)pyrimidin-4-yl)azetidin-3-yl)oxy)ethanol,
(4-(2-methyl-6-(5-methyl-6-(tetrahydro-2H-pyran-4-yl)-1H-indazol-1-yl)pyrimidin-4-yl)morpholin-2-yl)methanol,
(4-(2-methyl-6-(5-methyl-6-(tetrahydro-2H-pyran-4-yl)-1H-indazol-1-yl)pyrimidin-4-yl)morpholin-2-yl)methanol,
4-(2-methyl-6-(5-methyl-6-(tetrahydro-2H-pyran-3-yl)-1H-indazol-1-yl)pyrimidin-4-yl)morpholin-2-yl)methanol,
1-(6-(6-(3-fluorotetrahydro-2H-pyran-4-yl)-5-methyl-1H-indazol-1-yl)-2-methylpyrimidin-4-yl)azetidin-3-ol,
(4-(6-(6-(3-fluorotetrahydro-2H-pyran-4-yl)-5-methyl-1H-indazol-1-yl)-2-methylpyrimidin-4-yl)morpholin-2-yl)methanol,
1-(6-(6-isopropoxy-5-methyl-1H-indazol-1-yl)-2-methylpyrimidin-4-yl)azetidin-3-ol (HCl salt),
1-(6-(6-isopropoxy-5-methyl-1H-indazol-1-yl)-2-methoxypyrimidin-4-yl)azetidin-3-ol (TFA salt),
1-(6-(5-chloro-6-isopropoxy-1H-indazol-1-yl)-2-methylpyrimidin-4-yl)azetidin-3-ol,
1-(1-(6-(3-hydroxyazetidin-1-yl)-2-methylpyrimidin-4-yl)-5-methyl-1H-indazol-6-yl)piperidin-4-ol,
1-(1-(6-(3-hydroxyazetidin-1-yl)-2-methylpyrimidin-4-yl)-5-methyl-1H-indazol-6-yl)pyrrolidin-3-ol (HCl salt),
1-(5-chloro-1-(6-(3-hydroxyazetidin-1-yl)-2-methylpyrimidin-4-yl)-1H-indazol-6-yl)piperidin-4-ol,
5-methyl-1-(2-methyl-6-(1-(oxetan-3-yl)piperidin-4-yl)pyrimidin-4-yl)-6-(tetrahydro-2H-pyran-4-yl)-1H-indazole,
1-(2-methoxy-6-(5-methyl-6-(1-(oxetan-3-yl)piperidin-4-yl)-1H-indazol-1-yl)pyrimidin-4-yl)-3-methylpyrrolidin-3-ol,
1-(4-(2-methoxy-6-(5-methyl-6-(1-(oxetan-3-yl)piperidin-4-yl)-1H-indazol-1-yl)pyrimidin-4-yl)morpholin-2-yl)ethanol,
1-(4-(2-methyl-6-(5-methyl-6-(1-(oxetan-3-yl)piperidin-4-yl)-1H-indazol-1-yl)pyrimidin-4-yl)morpholin-2-yl)ethanol,
(4-(2-methyl-6-(5-methyl-6-(tetrahydro-2H-pyran-2-yl)-1H-indazol-1-yl)pyrimidin-4-yl)morpholin-2-yl)methanol,
(4-(2-methyl-6-(5-methyl-6-(tetrahydro-2H-pyran-2-yl)-1H-indazol-1-yl)pyrimidin-4-yl)morpholin-2-yl)methanol, and
1-(2-methyl-6-(5-methyl-6-(tetrahydro-2H-pyran-3-yl)-1H-indazol-1-yl)pyrimidin-4-yl)azetidin-3-ol,
or a salt thereof (e.g., a pharmaceutically acceptable salt).

In a further embodiment, the compound of Formula (I) is a compound of Formula (B) or a pharmaceutically acceptable salt thereof

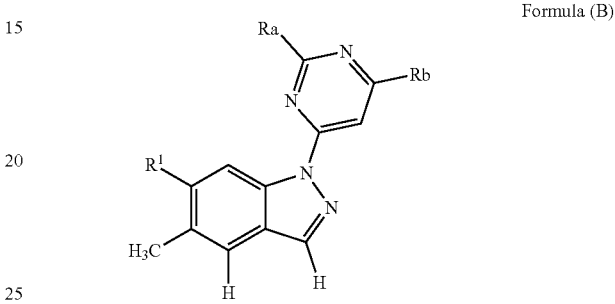

Formula (B)

wherein,
$R^1$ is piperidinyl substituted with one or two substituents independently selected from the group consisting of halo, $C_{1-3}$ alkyl and oxetanyl;
$R_a$ is $C_{1-3}$ alkyl or $C_{1-3}$ alkoxyl; and
$R_b$ is 4 to 6 membered heterocyclyl substituted with one substituent selected from the group consisting of hydroxyl,
$C_{1-3}$ alkyl optionally substituted with one hydroxyl, and
$C_{1-3}$ alkoxyl optionally substituted with one hydroxyl, and
the 4 to 6 membered heterocyclyl is selected from the group consisting of morpholinyl, azetinidyl, piperazinyl, and oxetanyl.

In one embodiment, the invention relates to compounds of Formula (B) and pharmaceutically acceptable salts thereof, wherein
$R^1$ is piperidinyl optionally substituted with one or two substituents independently selected from the group consisting of Cl, F and oxetanyl;
$R_a$ is methyl or methoxyl; and
$R_b$ is 4 to 6 membered heterocyclyl optionally substituted with one substituent of $C_{1-3}$ alkyl optionally substituted with one hydroxyl,
and the 4 to 6 membered heterocyclyl is selected from the group consisting of morpholinyl, azetinidyl, piperazinyl, and oxetanyl.

In one embodiment, the compound of Formula (I) or Formula (B) is or a salt thereof.

In one embodiment, the compound of Formula (I) or Formula (B) is

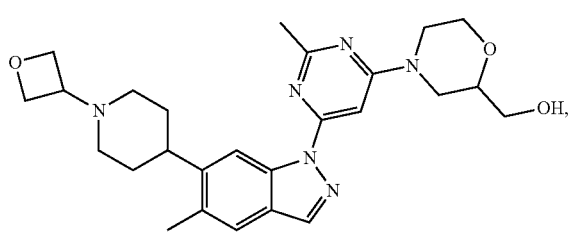

or a pharmaceutically acceptable salt thereof.

In one embodiment, the compound of Formula (I) or Formula (B) is

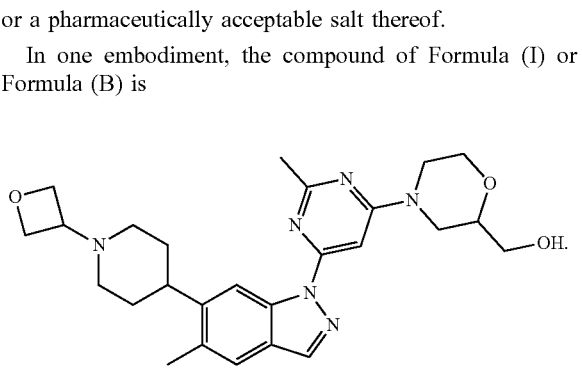

In one embodiment, the compound of Formula (I) or Formula (B) is a salt of

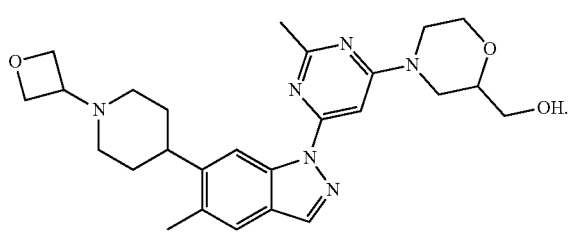

In one embodiment, the compound of Formula (I) or Formula (B) is a pharmaceutically acceptable salt of

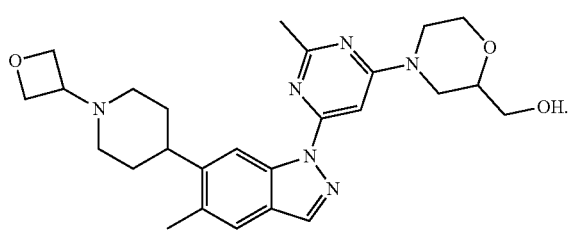

In one embodiment, the compound of Formula (I) or Formula (B) is

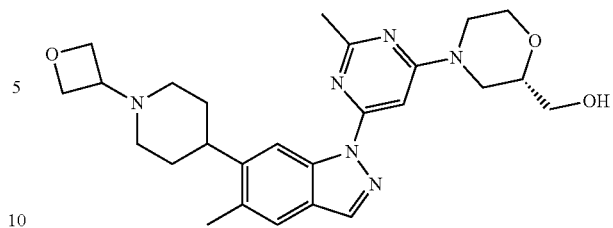

or a salt thereof.

In one embodiment, the compound of Formula (I) or Formula (B) is

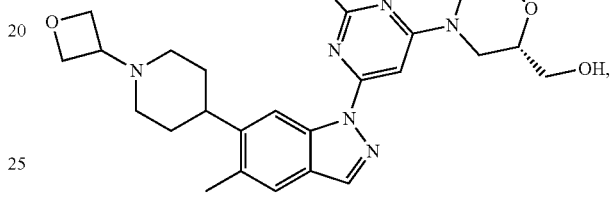

or a pharmaceutically acceptable salt thereof.

In one embodiment, the compound of Formula (I) or Formula (B) is

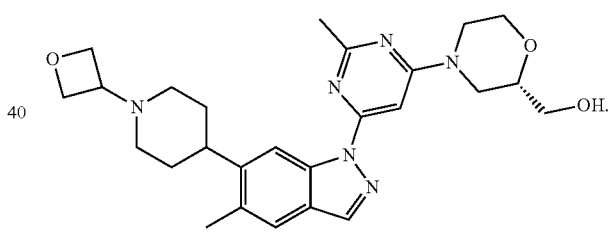

In one embodiment, the compound of Formula (I) or Formula (B) is a salt of

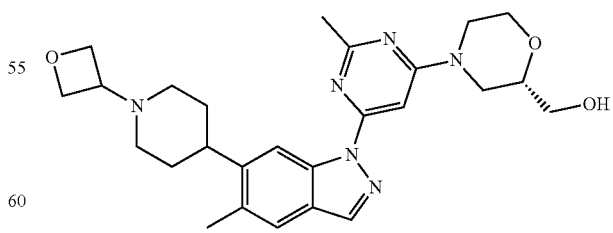

In one embodiment, the compound of Formula (I) or Formula (B) is a pharmaceutically acceptable salt of

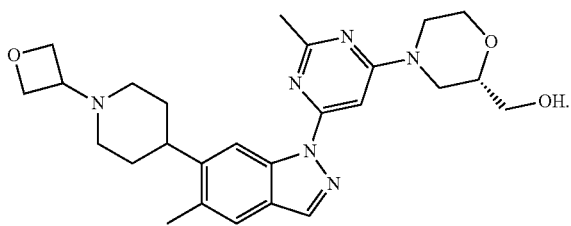

In one embodiment, the compound of Formula (I) or Formula (B) is

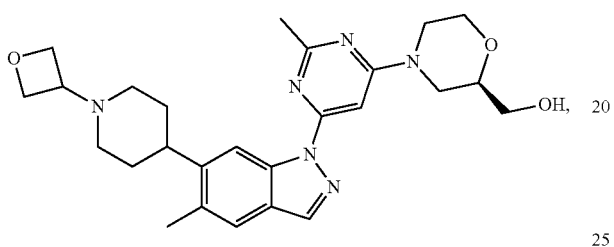

or a salt thereof.

In one embodiment, the compound of Formula (I) or Formula (B) is

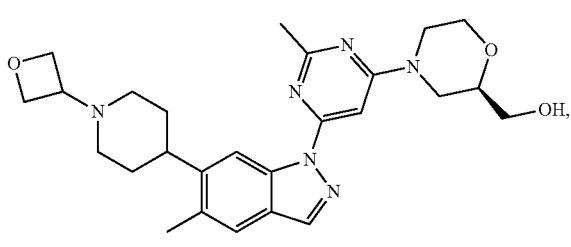 [SMILES: Cc1nc(N2CCO[C@@H](CO)C2)cc(-n2ncc3cc(C)c(C4CCN(C5COC5)CC4)cc32)n1]

or a pharmaceutically acceptable salt thereof.

In one embodiment, the compound of Formula (I) or Formula (B) is

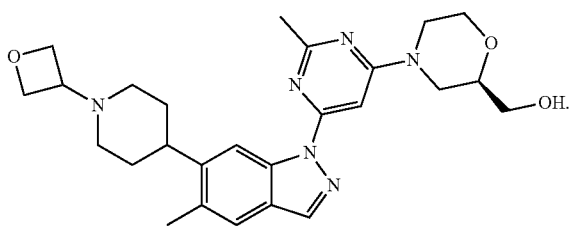 [SMILES: Cc1nc(N2CCO[C@@H](CO)C2)cc(-n2ncc3cc(C)c(C4CCN(C5COC5)CC4)cc32)n1]

In one embodiment, the compound of Formula (I) or Formula (B) is a salt of

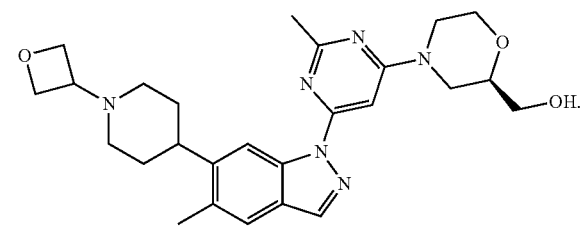 [SMILES: Cc1nc(N2CCO[C@@H](CO)C2)cc(-n2ncc3cc(C)c(C4CCN(C5COC5)CC4)cc32)n1]

In one embodiment, the compound of Formula (I) or Formula (B) is a pharmaceutically acceptable salt of

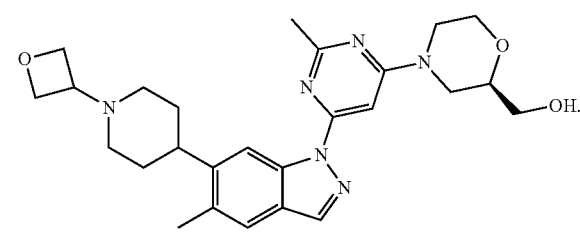 [SMILES: Cc1nc(N2CCO[C@@H](CO)C2)cc(-n2ncc3cc(C)c(C4CCN(C5COC5)CC4)cc32)n1]

In one embodiment, the compound of Formula (I) or Formula (B) is

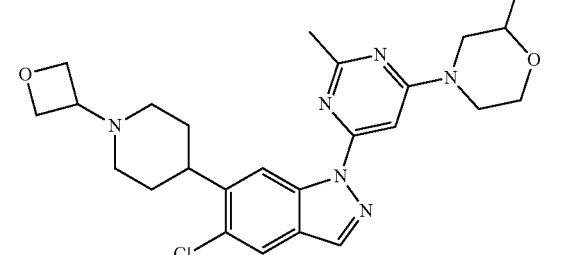

or a salt thereof.

In one embodiment, the compound of Formula (I) or Formula (B) is

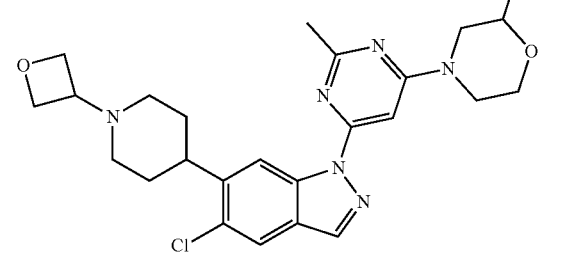

or a pharmaceutically acceptable salt thereof.

In one embodiment, the compound of Formula (I) or Formula (B) is

In one embodiment, the compound of Formula (I) or Formula (B) is a salt of

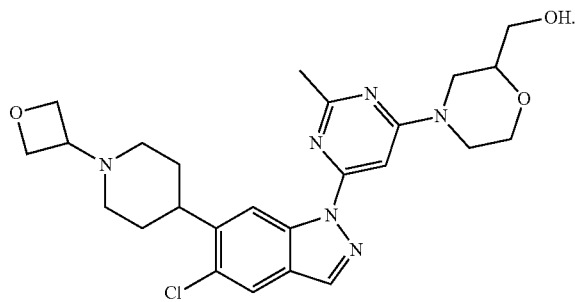

In one embodiment, the compound of Formula (I) or Formula (B) is a pharmaceutically acceptable salt of

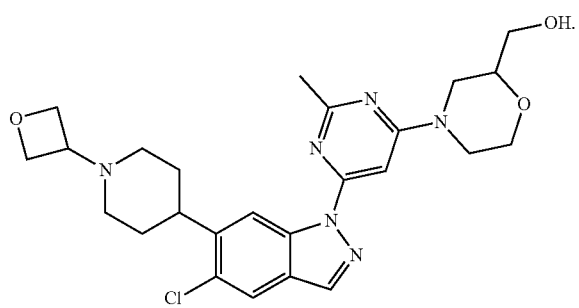 [SMILES: Cc1nc(N2CCOC(CO)C2)cc(-n2ncc3cc(Cl)c(C4CCN(C5COC5)CC4)cc32)n1]

In one embodiment, the compound of Formula (I) or Formula (B) is

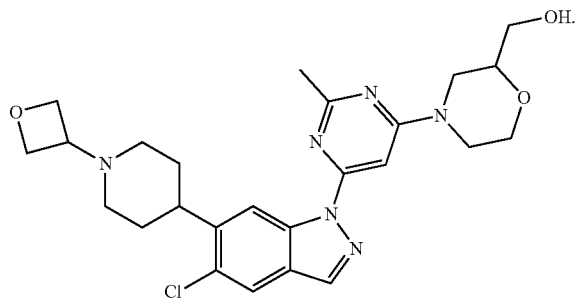 [SMILES: Cc1nc(N2CCOC(CO)C2)cc(-n2ncc3cc(Cl)c(C4CCN(C5COC5)CC4)cc32)n1]

or a salt thereof.
In one embodiment, the compound of Formula (I) or Formula (B) is

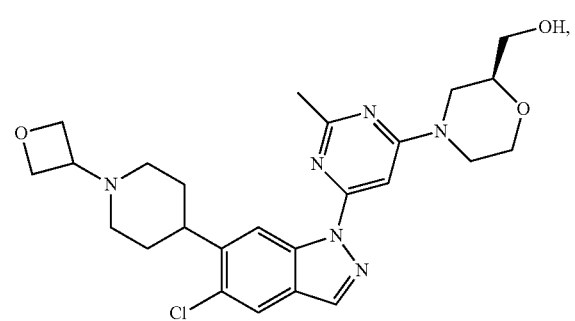 [SMILES: Cc1nc(N2CCO[C@H](CO)C2)cc(-n2ncc3cc(Cl)c(C4CCN(C5COC5)CC4)cc32)n1]

or a pharmaceutically acceptable salt thereof.
In one embodiment, the compound of Formula (I) or Formula (B) is

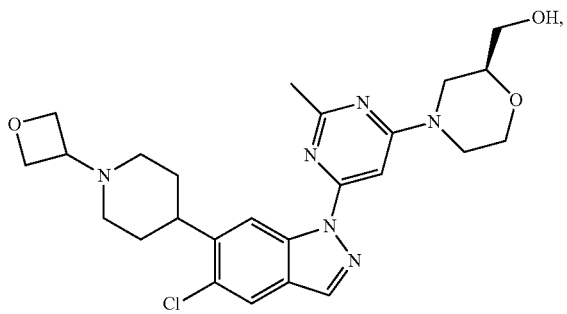 [SMILES: Cc1nc(N2CCO[C@H](CO)C2)cc(-n2ncc3cc(Cl)c(C4CCN(C5COC5)CC4)cc32)n1]

In one embodiment, the compound of Formula (I) or Formula (B) is a salt of

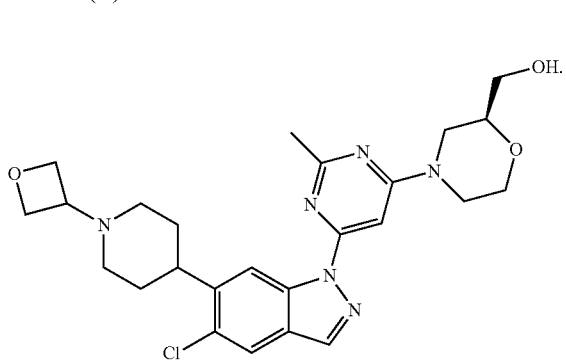

In one embodiment, the compound of Formula (I) or Formula (B) is a pharmaceutically acceptable salt of

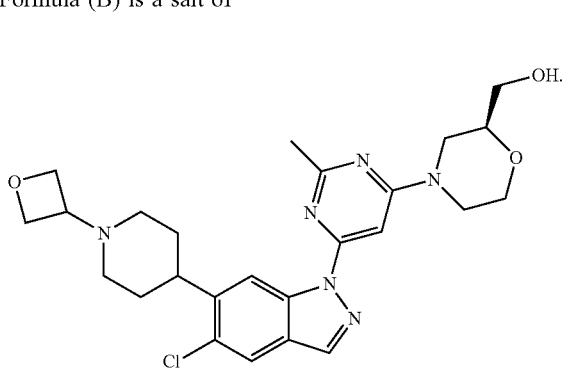

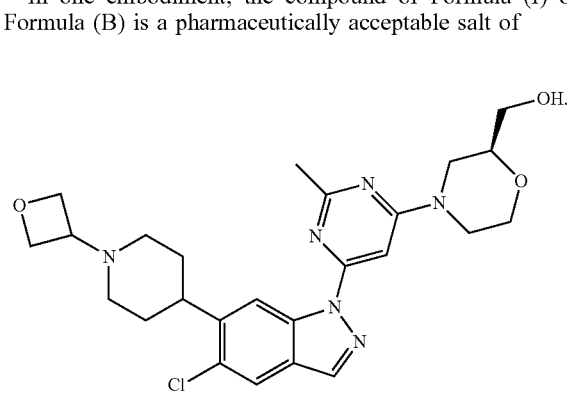

In one embodiment, the compound of Formula (I) or Formula (B) is

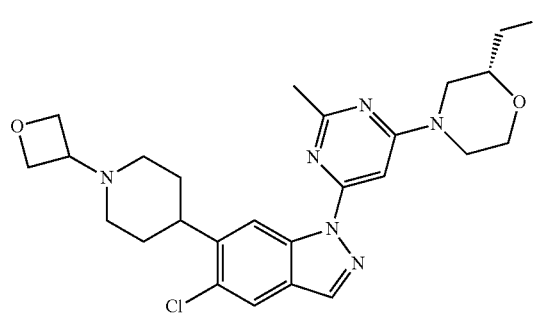

or a salt thereof.

In one embodiment, the compound of Formula (I) or Formula (B) is

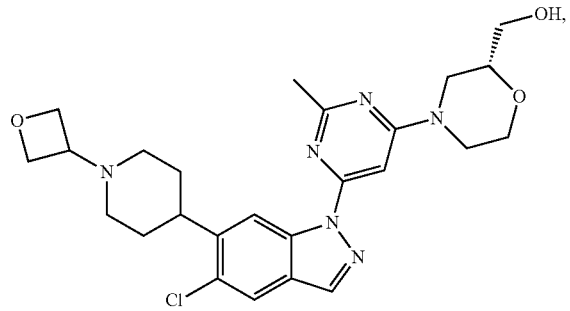 [SMILES: Cc1nc(N2CCO[C@@H](CO)C2)cc(-n2ncc3cc(Cl)c(C4CCN(C5COC5)CC4)cc32)n1]

or a pharmaceutically acceptable salt thereof.

In one embodiment, the compound of Formula (I) or Formula (B) is

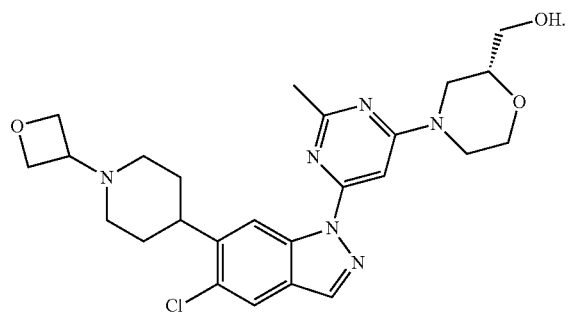

In one embodiment, the compound of Formula (I) or Formula (B) is a salt of

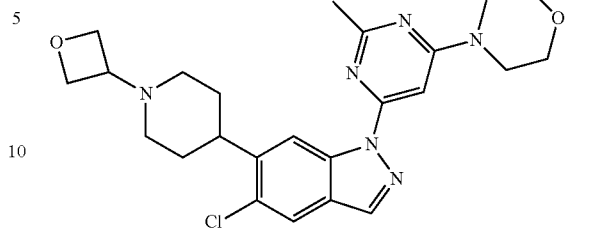

In one embodiment, the compound of Formula (I) or Formula (B) is a pharmaceutically acceptable salt of

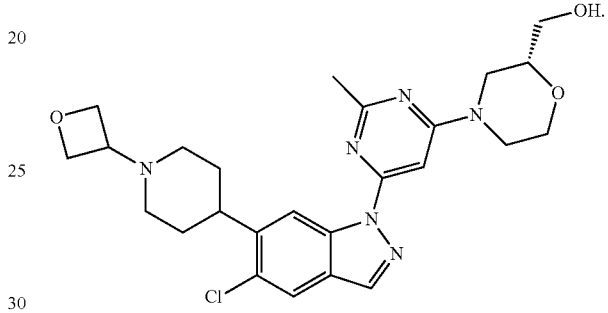

In addition to the free base form or free acid form of the compounds described herein, the salt form of the compounds is also within the scope of the present invention. The salts or pharmaceutically-acceptable salts of the compounds described herein may be prepared in situ during the final isolation and purification of the compound, or by separately reacting the purified compound in its free acid form or free base form with a suitable base or acid, respectively. For reviews on suitable pharmaceutical salts see Berge et al, J. Pharm, Sci., 66, 1-19, 1977; P L Gould, International Journal of Pharmaceutics, 33 (1986), 201-217; and Bighley et al, Encyclopedia of Pharmaceutical Technology, Marcel Dekker Inc, New York 1996, Volume 13, page 453-497.

In certain embodiments, compounds of the present invention may contain a basic group and are therefore capable of forming pharmaceutically-acceptable acid addition salts by treatment with a suitable acid. Suitable acids include pharmaceutically-acceptable inorganic acids and pharmaceutically-acceptable organic acids. These salts may be crystalline or amorphous. Exemplary pharmaceutically-acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicylate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate. In some embodiments, the pharmaceutically acceptable salts include the L-tartrate, ethanedisulfonate (edisylate), sulfate, phosphate, p-toluenesulfonate (tosylate), hydrochloride salt, methanesulfonate, citrate, fumarate, benzenesulfonate, maleate, hydrobromate, L-lactate, malonate, and S-camphor-10-sulfonate. In certain embodiments, some of these salts form solvates. In certain embodiments, some of these salts are crystalline.

The compounds of Formula (I), salts (e.g., pharmaceutically acceptable salts) thereof may exist in stereoisomeric forms (e.g., it contains one or more asymmetric carbon atoms). The individual stereoisomers (enantiomers and diastereomers) and mixtures of these are included within the scope of the present invention. The invention also covers the individual isomers of the compounds of Formula (I), salts (e.g., pharmaceutically acceptable salts) thereof as mixtures with isomers thereof in which one or more chiral centers are inverted. Likewise, it is understood that the compounds of Formula (I), salts (e.g., pharmaceutically acceptable salts) thereof may exist in tautomeric forms other than that shown in the formula and these are also included within the scope of the present invention. It is to be understood that the present invention includes all combinations and subsets of the particular groups defined hereinabove. The scope of the present invention includes mixtures of stereoisomers as well as purified enantiomers or enantiomerically/diastereomerically enriched mixtures. Also included within the scope of the invention are individual isomers of the compounds of Formula (I), salts (e.g., pharmaceutically acceptable salts) thereof, as well as any wholly or partially equilibrated mixtures thereof. The present invention also includes the individual isomers of the compounds of Formula (I), salts (e.g., pharmaceutically acceptable salts) thereof as well as mixtures with isomers thereof in which one or more chiral centers are inverted. It is to be understood that the present invention includes all combinations and subsets of the particular groups defined hereinabove. The different isomeric forms may be separated or resolved one from the other by conventional methods, or any given isomer may be obtained by conventional synthetic methods or by stereospecific or asymmetric syntheses.

The invention also includes isotopically-labelled compounds and salts, which are identical to compounds of Formula (I) or salts thereof, but for the fact that one or more atoms are replaced by an atom having an atomic mass or mass number different from the atomic mass or mass number most commonly found in nature. Examples of isotopes that can be incorporated into compounds of Formula (I) or salts thereof isotopes of hydrogen, carbon, nitrogen, fluorine, such as $^3$H, $^{11}$C, $^{14}$C and $^{18}$F. Such isotopically-labelled compound of Formula (I) or salts thereof are useful in drug and/or substrate tissue distribution assays. For example, $^{11}$C and $^{18}$F isotopes are useful in PET (positron emission tomography). PET is useful in brain imaging. Isotopically-labelled compounds of Formula (I) and salts thereof can generally be prepared by carrying out the procedures disclosed below, by substituting a readily available isotopically-labelled reagent for a non-isotopically labelled reagent. In one embodiment, compounds of Formula (I) or salts thereof are not isotopically labelled.

Certain compounds of Formula (I) or salts thereof may exist in solid or liquid form. In the solid state, compounds of Formula (I) or salts may exist in crystalline or noncrystalline form, or as a mixture thereof. For compounds of Formula (I) or salts that are in crystalline form, the skilled artisan will appreciate that pharmaceutically-acceptable solvates may be formed wherein solvent molecules are incorporated into the crystalline lattice during crystallization. Solvates may involve nonaqueous solvents such as ethanol, isopropanol, DMSO, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of Formula (I), pharmaceutically acceptable salts or solvates thereof that exist in crystalline form, including the various solvates thereof, may exhibit polymorphism (i.e. the capacity to occur in different crystalline structures). These different crystalline forms are typically known as "polymorphs." Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions. The invention includes all such polymorphs.

The skilled artisan also appreciates that this invention may contain various deuterated forms of compounds of Formula (I), or pharmaceutically acceptable salts thereof. Each available hydrogen atom attached to a carbon atom may be independently replaced with a deuterium atom. A person of ordinary skill in the art will know how to synthesize deuterated forms of compounds of Formula (I), or pharmaceutically acceptable salts thereof. Commercially available deuterated starting materials may be employed in the preparation of deuterated forms of compounds of Formula (I) or pharmaceutically acceptable salts thereof, or they may be synthesized using conventional techniques employing deuterated reagents (e.g. lithium aluminum deuteride).

The compounds described herein, their salts (e.g., pharmaceutically acceptable salts), deuterated form, solvates or hydrates thereof, may exist in one or more polymorphic form. Therefore, in a further aspect, the invention provides a polymorph of a compound defined herein, their salts (e.g., pharmaceutically acceptable salts), or a polymorph of a solvate or hydrate of a compound described herein or a salt (e.g., pharmaceutically acceptable salt) thereof.

As used herein, the terms "compound(s) of the invention" or "compound(s) of the present invention" mean a compound of the above referenced formulas, as defined herein, in any form, i.e., any salt or non-salt form (e.g., as a free acid or base form, or as a salt, for example, a pharmaceutically acceptable salt thereof), deuterated form and any physical form thereof (e.g., including non-solid forms (e.g., liquid or semi-solid forms), and solid forms (e.g., amorphous or crystalline forms, specific polymorphic forms, solvate forms, including hydrate forms (e.g., mono-, di- and hemi-hydrates)), and mixtures of various forms. In the context of pharmaceutical composition and methods of treatment discussed herein, the terms of "compounds of the invention" mean a compound of the above referenced formulas, as defined herein, in the form of any pharmaceutically acceptable salt thereof or non-salt form (e.g., as a free acid or base form), deuterated form and any physical form thereof (e.g., including non-solid forms (e.g., liquid or semi-solid forms), and solid forms (e.g., amorphous or crystalline forms, specific polymorphic forms, solvate forms, including hydrate forms (e.g., mono-, di- and hemi-hydrates)), and mixtures of various forms.

Accordingly, a compound of the invention includes a compound of Formula (I), or a salt thereof, for example a pharmaceutically acceptable salt thereof. Representative compounds of this invention include the specific compounds described.

C. Methods of Use

The compounds of Formula (I) or pharmaceutically acceptable salts thereof are inhibitors of LRRK2 kinase activity and are thus believed to be of potential use in the treatment of or prevention of neurological diseases. Exemplary neurological diseases include, but are not limited to, Parkinson's disease, Alzheimer's disease, dementia (including Lewy body dementia and vascular dementia, HIV-induced dementia), amyotrophic lateral sclerosis (ALS), age related memory dysfunction, mild cognitive impairment, argyrophilic grain disease, Pick's disease, corticobasal degeneration, progressive supranuclear palsy, inherited frontotemporal dementia and parkinsonism linked to chromosome 17 (FTDP-17), withdrawal symptoms/relapse associated with drug addiction, L-Dopa induced dyskinesia, ischemic stroke, traumatic brain injury, spinal cord injury. Other disorders include, but are not limited to, lysosomal disorders (for example, Niemann-Pick Type C disease, Gaucher disease), Crohn's disease, thyroid, renal (including papillary renal), breast, lung and prostate cancers, leukemias (including acute myelogenous leukemia (AML)), lymphomas, leukemias, multiple sclerosis, rheumatoid arthritis, systemic lupus erythematosus, autoimmune hemolytic anemia, pure red cell aplasia, idiopathic thrombocytopenic purpura (ITP), Evans syndrome, vasculitis, bullous skin disorders, type 1 diabetes mellitus, Sjogren's syndrome, Devic's disease and inflammatory myopathies.

One aspect of the invention provides a compound of Formula (I) or a pharmaceutically acceptable salt thereof for use in therapy. In one embodiment, the invention provides a compound of Formula (I) or a pharmaceutically acceptable salt thereof for use in the treatment of or prevention of a disease mediated by LRRK2. In one embodiment, the invention provides a compound of Formula (I) or a pharmaceutically acceptable salt thereof for use in the treatment of or prevention of Parkinson's disease. In one embodiment, the invention provides a compound of Formula (I) or a pharmaceutically acceptable salt thereof for use in the treatment of Parkinson's disease.

A further aspect of the invention provides the use of a compound of Formula (I) or a pharmaceutically acceptable salt thereof in the manufacture of a medicament for the treatment of or prevention of a disease mediated by LRRK2. A further aspect of the invention provides the use of a compound of Formula (I) or a pharmaceutically acceptable salt thereof in the manufacture of a medicament for the treatment of or prevention of Parkinson's disease. A further aspect of the invention provides the use of a compound of Formula (I) or a pharmaceutically acceptable salt thereof in the manufacture of a medicament for the treatment of Parkinson's disease.

A further aspect of the invention provides a method of treatment or prevention of a disease mediated by LRRK2, which comprises administering to a subject in need thereof a therapeutically effective amount of a compound of Formula (I) or a pharmaceutically acceptable salt thereof. A further aspect of the invention provides a method of treatment or prevention of Parkinson's disease, which comprises administering to a subject in need thereof a therapeutically effective amount of a compound of Formula (I) or a pharmaceutically acceptable salt thereof. In an embodiment, the subject is human.

In the context of the present invention, treatment of Parkinson's disease refers to the treatment of sporadic Parkinson's disease, and/or familial Parkinson's disease. In one embodiment, familial Parkinson's disease includes patients expressing LRRK2 kinase bearing the G2019S mutation or the R1441G mutation. In a further embodiment, familial Parkinson's disease includes patients expressing LRRK2 kinase bearing G2019S mutation, N1437H mutation, R1441G mutation, R1441C mutation, R1441H mutation, Y1699C mutation, S1761R mutation, or I2020T mutation for Parkinson's disease. In another embodiment, sporadic Parkinson's disease includes patients expressing LRRK2 kinase bearing G2019S mutation, N1437H mutation, R1441G mutation, R1441C mutation, R1441H mutation, Y1699C mutation, S1761R mutation, or I2020T mutation for Parkinson's disease. In another embodiment, Parkinson's disease includes patients expressing LRRK2 kinase bearing other coding mutations such as G2385R or non-coding single nucleotide polymorphisms at the LRRK2 locus that are associated with Parkinson's disease. In one embodiment, treatment of Parkinson's disease refers to the treatment of familial Parkinson's disease includes patients expressing LRRK2 kinase bearing G2019S mutation. In another embodiment, Parkinson's disease includes patients expressing aberrantly high levels of normal LRRK2 kinase. Treatment of Parkinson's disease may be symptomatic or may be disease modifying. In one embodiment, treatment of Parkinson's disease refers to symptomatic treatment. In one embodiment, treatment of Parkinson's disease refers to disease modifying.

Compounds of the present invention may also be useful in treating patients identified as susceptible to progression to severe Parkinsonism by means of one or more subtle features associated with disease progression such as family history, olfaction deficits, constipation, cognitive defects, gait or biological indicators of disease progression gained from molecular, biochemical, immunological or imaging technologies. In this context, treatment may be symptomatic or disease modifying.

In the context of the present invention, treatment of Alzheimer's disease refers to the treatment of sporadic Alzheimer's disease and/or familial Alzheimer's disease. Treatment of Alzheimer's disease may be symptomatic or may be disease modifying. In one embodiment, treatment of Alzheimer's disease refers to symptomatic treatment. Similarly, treatment of dementia (including Lewy body dementia vascular dementia, and HIV-induced dementia), age related memory dysfunction, mild cognitive impairment argyrophilic grain disease, amyotrophic lateral sclerosis (ALS), Pick's disease, corticobasal degeneration, progressive supranuclear palsy, inherited frontotemporal dementia and parkinsonism linked to chromosome 17 (FTDP-17), ischemic stroke, traumatic brain injury, spinal cord injury, lysosomal disorders (for example, Niemann-Pick Type C disease, Gaucher disease) Crohn's disease, thyroid, renal (including papillary renal), breast, lung and prostate cancers, leukemias (including acute myelogenous leukemia (AML)), lymphomas, leukemias, multiple sclerosis, rheumatoid arthritis, systemic lupus erythematosus, autoimmune hemolytic anemia, pure red cell aplasia, idiopathic thrombocytopenic purpura (ITP), Evans syndrome, vasculitis, bullous skin disorders, type 1 diabetes mellitus, Sjogren's syndrome, Devic's disease and inflammatory myopathies may be symptomatic or disease modifying. In some embodiments, treatment of dementia (including Lewy body dementia, vascular dementia and HIV-induced dementia), age related memory dysfunction, mild cognitive impairment, argyrophilic grain disease, amyotrophic lateral sclerosis (ALS), Pick's disease, corticobasal degeneration, progressive supranuclear palsy, inherited frontotemporal dementia and parkinsonism linked to chromosome 17 (FTDP-17), ischemic stroke, traumatic brain injury, spinal cord injury, lysosomal disorders (for example, Niemann-Pick Type C disease, Gaucher disease), Crohn's disease, thyroid, renal (including papillary renal), breast, lung and prostate cancers, leukemias (including acute myelogenous leukemia (AML)), lymphomas, leukemias, multiple sclerosis, rheumatoid arthritis, systemic lupus erythematosus, autoimmune hemolytic anemia, pure red cell aplasia, idiopathic thrombocytopenic purpura (ITP), Evans syndrome, vasculitis, bullous skin disorders, type 1 diabetes mellitus, Sjogren's syndrome, Devic's disease and inflammatory myopathies refers to symptomatic treatment.

In one embodiment, the invention also provides a method of treatment of ankylosing spondylitis and/or leprosy infection, which comprises administering to a subject in need thereof a therapeutically effective amount of a compound of Formula (I) or a pharmaceutically acceptable salt thereof. In one embodiment, the subject is human.

In the context of the present invention, treatment of withdrawal symptoms/relapse associated with drug addiction and L-Dopa induced dyskinesia refers to symptomatic treatment.

In a further aspect, the invention provides a compound of Formula (I) or a pharmaceutically acceptable salt thereof for use in the treatment of the above disorders, for example Parkinson's disease. In some embodiments, the invention provides a compound of Formula (I) or a pharmaceutically acceptable salt thereof for use in the prevention of Parkinson's disease, Alzheimer's disease, of dementia (including Lewy body dementia vascular dementia and HIV-induced dementia), age related memory dysfunction, mild cognitive impairment, argyrophilic grain disease, amyotrophic lateral sclerosis (ALS), Pick's disease, corticobasal degeneration, progressive supranuclear palsy, inherited frontotemporal dementia or parkinsonism linked to chromosome 17 (FTDP-17), lysosomal disorders (e.g., Niemann-Pick Type C disease, Gaucher disease) or renal, breast, lung, prostate cancers as well as acute myelogenous leukemia (AML). In one embodiment, the invention provides a compound of Formula (I) or a pharmaceutically acceptable salt thereof for use in the prevention of Parkinson's disease.

The invention further provides a method of treatment of the above diseases, for example Parkinson's disease in mammals including humans, which comprises administering to a subject in need thereof a therapeutically effective amount of a compound of Formula (I) or a pharmaceutically acceptable salt thereof.

The invention also provides the use of a compound of Formula (I) or a pharmaceutically acceptable salt thereof in the manufacture of a medicament for use in the treatment of the above disorders, for example, Parkinson's disease. The invention also provides the use of a compound of Formula (I) or a pharmaceutically acceptable salt thereof in the manufacture of a medicament for use in the prevention of Parkinson's disease, Alzheimer's disease, of dementia (including Lewy body dementia and vascular dementia), age related memory dysfunction, mild cognitive impairment, argyrophilic grain disease, amyotrophic lateral sclerosis (ALS), Pick's disease, corticobasal degeneration, progressive supranuclear palsy, inherited frontotemporal dementia or parkinsonism linked to chromosome 17 (FTDP-17), or renal, breast, lung, prostate cancers as well as acute myelogenous leukemia (AML), lysosomal disorders (for example, Niemann-Pick Type C disease, Gaucher disease). In some embodiments, the invention provides the use of the compound of Formula (I) or a pharmaceutically acceptable salt thereof in the manufacture of a medicament for use in the prevention of Parkinson's disease.

The invention also provides the use of inhibitors of LRRK2 in the production of neuronal progenitor cells in vitro for consequent therapeutic application in cell based-treatment of CNS disorders.

The invention further provides the use of inhibitors of LRRK2 to stimulate restoration of CNS functions following neuronal injury including, but not limited to, ischemic stroke, traumatic brain injury, and spinal cord injury.

The invention also provides the use of inhibitors of LRRK2 to treat aberrant neuroinflammatory mechanisms that contribute a range of neurodegenerative diseases, including Parkinson's disease, Alzheimer's disease, multiple sclerosis, HIV-induced dementia, amyotrophic lateral sclerosis, ischemic stroke, traumatic brain injury and spinal cord injury.

The invention also provides the use of inhibitors of LRRK2 to treat diabetes, obesity, motor neuron disease, epilepsy, cancers, pulmonary diseases such as chronic obstructive pulmonary disease, idiopathic pulmonary fibrosis and autoimmune diseases such as systemic lupus erythematosus.

The invention also provides the use of inhibitors of LRRK2 to treat bacterial infections, parasitic infections or viral infections, including tuberculosis, HIV, West Nile virus, and chikungunya virus. When a compound of Formula (I) or a pharmaceutically acceptable salt thereof is intended for use in the treatment of bacterial infections, parasitic infections or viral infections, it may be used in combination with medicaments alleged to be useful as symptomatic treatments that directly target the infectious agent.

The invention also provides the use of a compound of Formula (I) or a pharmaceutically acceptable salt thereof in the manufacture of a medicament for the treatment of tuberculosis. A further aspect of the invention provides the use of a compound of Formula (I) or a pharmaceutically acceptable salt thereof in the manufacture of a medicament for the treatment of tuberculosis.

A further aspect of the invention provides a method of treatment of tuberculosis, which comprises administering to a subject in need thereof a therapeutically effective amount of a compound of Formula (I) or a pharmaceutically acceptable salt thereof. In an embodiment, the subject is human.

When a compound of Formula (I) or a pharmaceutically acceptable salt thereof is intended for use in the treatment of Parkinson's disease, it may be used in combination with medicaments alleged to be useful as symptomatic treatments of Parkinson's disease. Suitable examples of such other therapeutic agents include L-dopa, and dopamine agonists (e.g. pramipexole, ropinirole).

When a compound of Formula (I) or a pharmaceutically acceptable salt thereof is intended for use in the treatment of Alzheimer's disease, it may be used in combination with medicaments claimed to be useful as either disease modifying or symptomatic treatments of Alzheimer's disease. Suitable examples of such other therapeutic agents may be symptomatic agents, for example those known to modify cholinergic transmission such as M1 muscarinic receptor agonists or allosteric modulators, M2 muscarinic antagonists, acetylcholinesterase inhibitors (such as tetrahydroaminoacridine, donepezil hydrochloride rivastigmine, and galantamine), nicotinic receptor agonists or allosteric modulators (such as α7 agonists or allosteric modulators or α4β2 agonists or allosteric modulators), PPAR agonists (such as PPARγ agonists), 5-HT$_4$ receptor partial agonists, 5-HT$_6$ receptor antagonists e.g. SB-742457 or 5HT1A receptor antagonists and NMDA receptor antagonists or modulators, or disease modifying agents such as β or γ-secretase inhibitors e.g semagacestat, mitochondrial stabilizers, microtubule stabilizers or modulators of Tau pathology such as Tau aggregation inhibitors (e.g. methylene blue and REMBER™), NSAIDS, e.g. tarenflurbil, tramiprosil; or antibodies for example bapineuzumab or solanezumab; proteoglycans for example tramiprosate.

When a compound of Formula (I) or a pharmaceutically acceptable salt thereof is used in combination with other therapeutic agents, the compound may be administered either sequentially or simultaneously by any convenient route.

The invention also provides, in a further aspect, a combination comprising a compound of Formula (I) or a pharmaceutically acceptable salt thereof together with one or more further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of Formula (I) or a pharmaceutically acceptable salt thereof is used in combination with a second therapeutic agent active against the same disease state the dose of each compound may differ from that when the compound is used alone. Appropriate doses will be readily appreciated by those skilled in the art.

D. Composition

The compounds of the present invention may be formulated into pharmaceutical compositions prior to administration to a subject. According to one aspect, the invention provides a pharmaceutical composition comprising a compound of the invention and a pharmaceutically acceptable excipient. According to another aspect, the invention provides a process for the preparation of a pharmaceutical composition comprising admixing a compound described herein, with a pharmaceutically acceptable excipient.

Pharmaceutical compositions may be presented in unit dose forms containing a predetermined amount of active ingredient per unit dose. Such a unit may contain, for example, 0.1 mg, 0.5 mg, or 1 mg to 50 mg, 100 mg, 200 mg, 250 mg, 500 mg, 750 mg or 1 g of a compound of the present invention, depending on the disease being treated, the route of administration and the age, weight and condition of the subject, or pharmaceutical compositions may be presented in unit dose forms containing a predetermined amount of active ingredient per unit dose. In other embodiments, the unit dosage compositions are those containing a daily dose or sub-dose as described herein, or an appropriate fraction thereof, of an active ingredient. Furthermore, such pharmaceutical compositions may be prepared by any of the methods well-known to one skilled in the art.

A therapeutically effective amount of a compound of the present invention will depend upon a number of factors including, for example, the age and weight of the intended recipient, the precise condition requiring treatment and its severity, the nature of the formulation, and the route of administration, and will ultimately be at the discretion of the attendant prescribing the medication. However, a therapeutically effective amount of a compound of present invention for the treatment of diseases described in the present invention will generally be in the range of 0.1 to 100 mg/kg body weight of recipient per day and more usually in the range of 1 to 10 mg/kg body weight per day. Thus, for a 70 kg adult mammal, the actual amount per day would usually be from 70 to 700 mg and this amount may be given in a single dose per day or in a number of sub-doses per day as such as two, three, four, five or six doses per day. Or the dosing can be done intermittently, such as once every other day, once a week or once a month. A therapeutically effective amount of a salt or solvate, etc., may be determined as a proportion of the therapeutically effective amount of the compound of Formula (I) per se. It is envisaged that similar dosages would be appropriate for treatment of the other diseases referred to above.

The pharmaceutical compositions of the invention may contain one or more compounds of the invention. In some embodiments, the pharmaceutical compositions may contain more than one compound of the invention. For example, in some embodiments, the pharmaceutical compositions may contain two or more compounds of the invention. In addition, the pharmaceutical compositions may optionally further comprise one or more additional pharmaceutically active compounds.

As used herein, "pharmaceutically acceptable excipient" means a pharmaceutically acceptable material, composition or vehicle involved in giving form or consistency to the pharmaceutical composition. Each excipient may be compatible with the other ingredients of the pharmaceutical composition when commingled such that interactions which would substantially reduce the efficacy of the compound of the invention when administered to a subject and interactions which would result in pharmaceutical compositions that are not pharmaceutically acceptable are avoided.

The compounds of the invention and the pharmaceutically-acceptable excipient or excipients may be formulated into a dosage form adapted for administration to the subject by the desired route of administration. For example, dosage forms include those adapted for (1) oral administration (including buccal or sublingual) such as tablets, capsules, caplets, pills, troches, powders, syrups, elixers, suspensions, solutions, emulsions, sachets, and cachets; (2) parenteral administration (including subcutaneous, intramuscular, intravenous or intradermal) such as sterile solutions, suspensions, and powders for reconstitution; (3) transdermal administration such as transdermal patches; (4) rectal administration such as suppositories; (5) nasal inhalation such as dry powders, aerosols, suspensions, and solutions; and (6) topical administration (including buccal, sublingual or transdermal) such as creams, ointments, lotions, solutions, pastes, sprays, foams, and gels. Such compositions may be prepared by any methods known in the art of pharmacy, for example by bringing into association a compound of Formula (I) with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Suitable pharmaceutically-acceptable excipients may vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically acceptable excipients may be chosen for their ability to facilitate carrying or transporting the compound or compounds of the invention once administered to the subject from an organ, or a portion of the body, to another organ, or a portion of the body. Certain pharmaceutically-acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, humectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a therapeutically effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmellose, alginic acid, and sodium carboxymethyl cellulose. The oral solid dosage form may further comprise a lubricant. Suitable lubricants include stearic acid, magnesium stearate, calcium stearate, and talc.

In certain embodiment, the present invention is directed to a pharmaceutical composition comprising 0.01 to 1000 mg of one or more compounds described herein or a pharmaceutically acceptable salt thereof and 0.01 to 5 g of one or more pharmaceutically acceptable excipients.

In one embodiment, the present invention is directed to a pharmaceutical composition comprising 0.01 to 1000 mg (calculated as free base) of a compound having the structure of

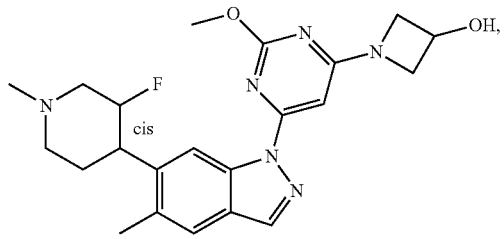 [SMILES: COc1nc(N2CC(O)C2)cc(-n2ncc3cc(C)c(C4CCN(C)CC4F)cc32)n1]

or a pharmaceutically acceptable salt thereof and 0.01 to 5 g of one or more pharmaceutically acceptable excipients.

In one embodiment, the present invention is directed to a pharmaceutical composition comprising 0.01 to 1000 mg of a compound having the structure of

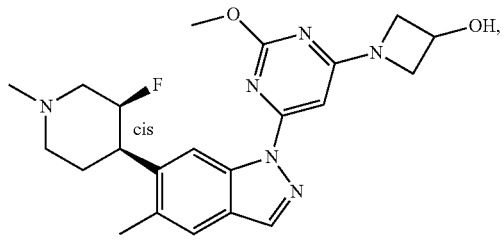 [SMILES: COc1nc(N2CC(O)C2)cc(-n2ncc3cc(C)c([C@H]4CCN(C)C[C@H]4F)cc32)n1]

or a pharmaceutically acceptable salt thereof and 0.01 to 5 g of one or more pharmaceutically acceptable excipients.

In one embodiment, the present invention is directed to a pharmaceutical composition comprising 0.01 to 1000 mg (calculated as free base) of a compound having the structure of

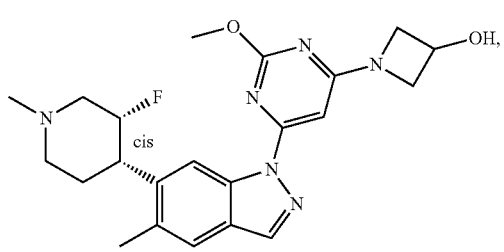 [SMILES: COc1nc(N2CC(O)C2)cc(-n2ncc3cc(C)c([C@@H]4CCN(C)C[C@@H]4F)cc32)n1]

or a pharmaceutically acceptable salt thereof and 0.01 to 5 g of one or more pharmaceutically acceptable excipients.

In one embodiment, the present invention is directed to a pharmaceutical composition comprising 0.01 to 1000 mg (calculated as free base) of a compound having the structure of

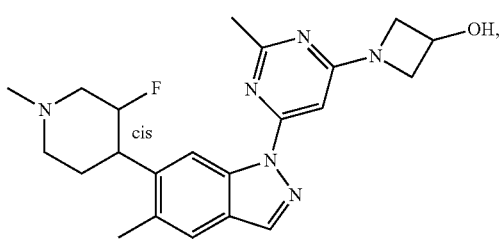 [SMILES: Cc1nc(N2CC(O)C2)cc(-n2ncc3cc(C)c(C4CCN(C)CC4F)cc32)n1]

or a pharmaceutically acceptable salt thereof and 0.01 to 5 g of one or more pharmaceutically acceptable excipients.

In one embodiment, the present invention is directed to a pharmaceutical composition comprising 0.01 to 1000 mg of a compound having the structure of

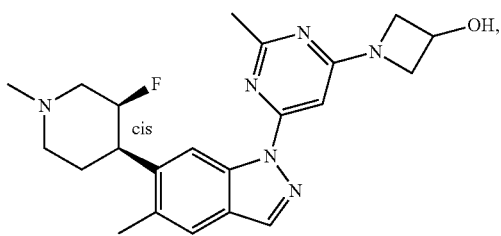 [SMILES: Cc1nc(N2CC(O)C2)cc(-n2ncc3cc(C)c([C@H]4CCN(C)C[C@H]4F)cc32)n1]

or a pharmaceutically acceptable salt thereof and 0.01 to 5 g of one or more pharmaceutically acceptable excipients.

In one embodiment, the present invention is directed to a pharmaceutical composition comprising 0.01 to 1000 mg (calculated as free base) of a compound having the structure of

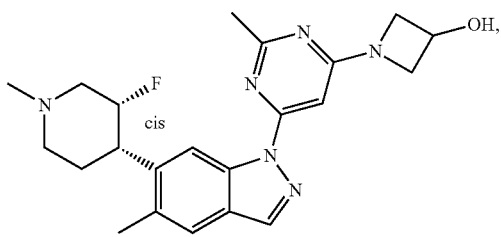 [SMILES: Cc1nc(N2CC(O)C2)cc(-n2ncc3cc(C)c([C@@H]4CCN(C)C[C@@H]4F)cc32)n1]

or a pharmaceutically acceptable salt thereof and 0.01 to 5 g of one or more pharmaceutically acceptable excipients.

In one embodiment, the present invention is directed to a pharmaceutical composition comprising 0.01 to 1000 mg (calculated as free base) of a compound having the structure of

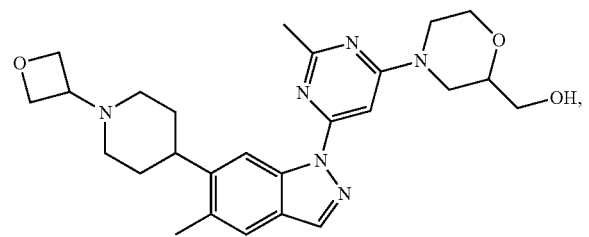 [SMILES: Cc1nc(N2CCOC(CO)C2)cc(-n2ncc3cc(C)c(C4CCN(C5COC5)CC4)cc32)n1]

or a pharmaceutically acceptable salt thereof and 0.01 to 5 g of one or more pharmaceutically acceptable excipients.

In one embodiment, the present invention is directed to a pharmaceutical composition comprising 0.01 to 1000 mg of a compound having the structure of

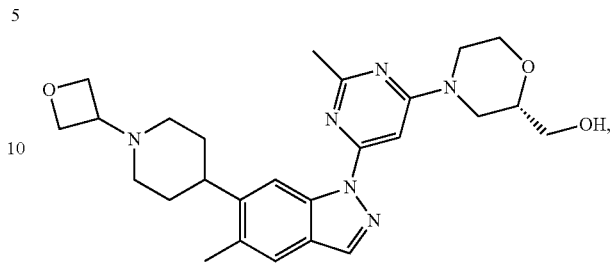

or a pharmaceutically acceptable salt thereof and 0.01 to 5 g of one or more pharmaceutically acceptable excipients.

In one embodiment, the present invention is directed to a pharmaceutical composition comprising 0.01 to 1000 mg (calculated as free base) of a compound having the structure of

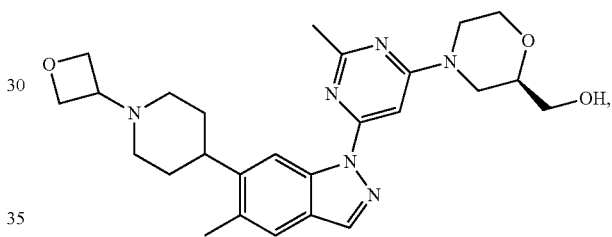

or a pharmaceutically acceptable salt thereof and 0.01 to 5 g of one or more pharmaceutically acceptable excipients.

In one embodiment, the present invention is directed to a pharmaceutical composition comprising 0.01 to 1000 mg (calculated as free base) of a compound having the structure of

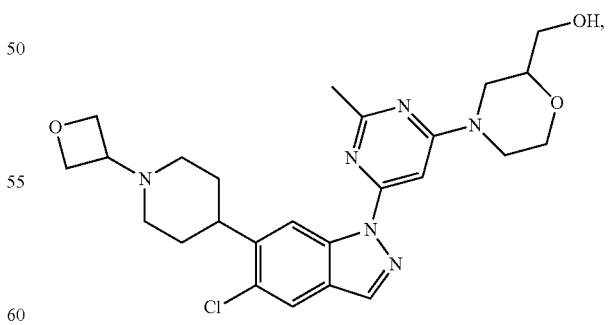

or a pharmaceutically acceptable salt thereof and 0.01 to 5 g of one or more pharmaceutically acceptable excipients.

In one embodiment, the present invention is directed to a pharmaceutical composition comprising 0.01 to 1000 mg of a compound having the structure of

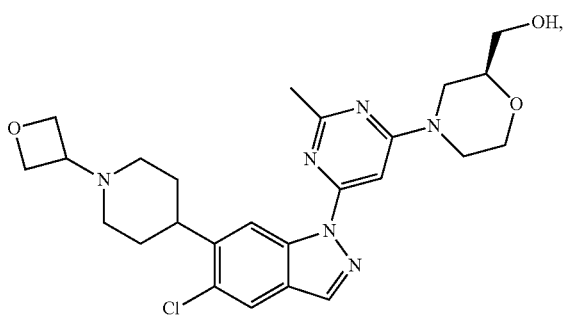 [SMILES: Cc1nc(N2CCO[C@H](CO)C2)cc(-n2ncc3cc(Cl)c(C4CCN(C5COC5)CC4)cc32)n1]

or a pharmaceutically acceptable salt thereof and 0.01 to 5 g of one or more pharmaceutically acceptable excipients.

In one embodiment, the present invention is directed to a pharmaceutical composition comprising 0.01 to 1000 mg (calculated as free base) of a compound having the structure of

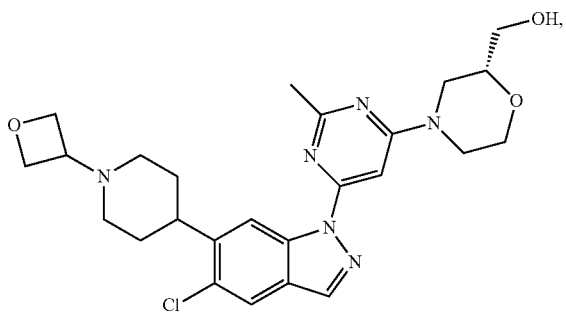 [SMILES: Cc1nc(N2CCO[C@@H](CO)C2)cc(-n2ncc3cc(Cl)c(C4CCN(C5COC5)CC4)cc32)n1]

or a pharmaceutically acceptable salt thereof and 0.01 to 5 g of one or more pharmaceutically acceptable excipients.

In another embodiment, the present invention is directed a pharmaceutical composition for the treatment of neurodegeneration disease comprising a compound described herein or a pharmaceutically acceptable salt thereof and a pharmaceutically acceptable excipient. In another embodiment, the present invention is directed a pharmaceutical composition for the treatment of Parkinson's disease comprising a compound described herein or a pharmaceutically acceptable salt thereof and a pharmaceutically acceptable excipient.

E. Process of Preparing Compounds

The process to be utilized in the preparation of the compounds described herein depends upon the desired compounds. Such factors as the selection of the specific substituent and various possible locations of the specific substituent all play a role in the path to be followed in the preparation of the specific compounds of this invention. Those factors are readily recognized by one of ordinary skill in the art.

In general, the compounds of the present invention may be prepared by standard techniques known in the art and by known processes analogous thereto. General methods for preparing compounds of the present invention are set forth below. All starting material and reagents described in the below general experimental schemes are commercially available or can be prepared by methods known to one skilled in the art.

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and deprotecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

General Scheme 1 provides exemplary processes of synthesis for preparing compounds of the present invention.

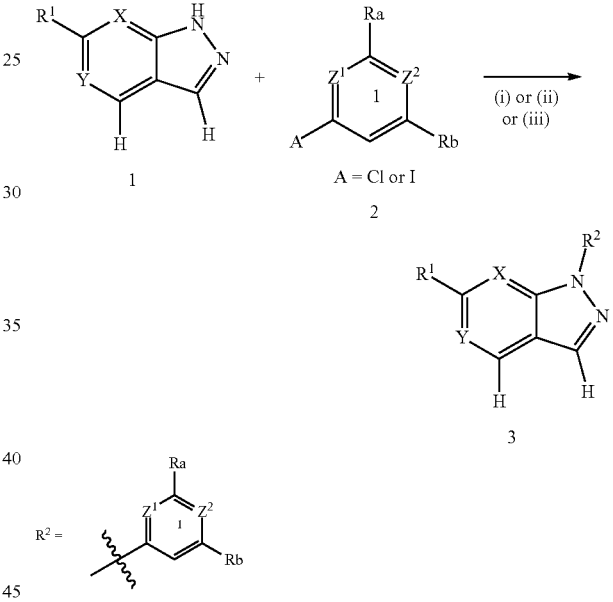

General Scheme 1

General Scheme 1 provides an exemplary synthesis for preparing compound 3 which represents compounds of Formula (I). In Scheme 1, X, Y, $R^1$ and $R^2$ are as defined in Formula I.

Step (i) may be a substitution reaction by reacting compound 1 with compound 2 using appropriate base such as $Cs_2CO_3$ in an appropriate solvent such as N,N-dimethylformamide (DMF) under suitable temperature such as about 100° C. to provide compound 3.

Step (ii) may be a coupling reaction using appropriate reagents such as CuI and N,N'-dimethyl-cyclohexane-1,2-diamine in the presence of suitable base such as $K_3PO_4$ in a suitable solvent such as toluene at suitable temperature such as reflux condition to provide compound 3.

Step (iii) may be a coupling reaction using appropriate reagents such as $Pd_2dba_3$ and di-tert-butyl(2',4',6'-triisopropyl-[1,1-biphenyl]-2-yl)phosphine in the presence of suitable base such as sodium tert-butoxide in a suitable solvent such as toluene at suitable temperature such as 100° C. to provide compound 3.

General Scheme 2

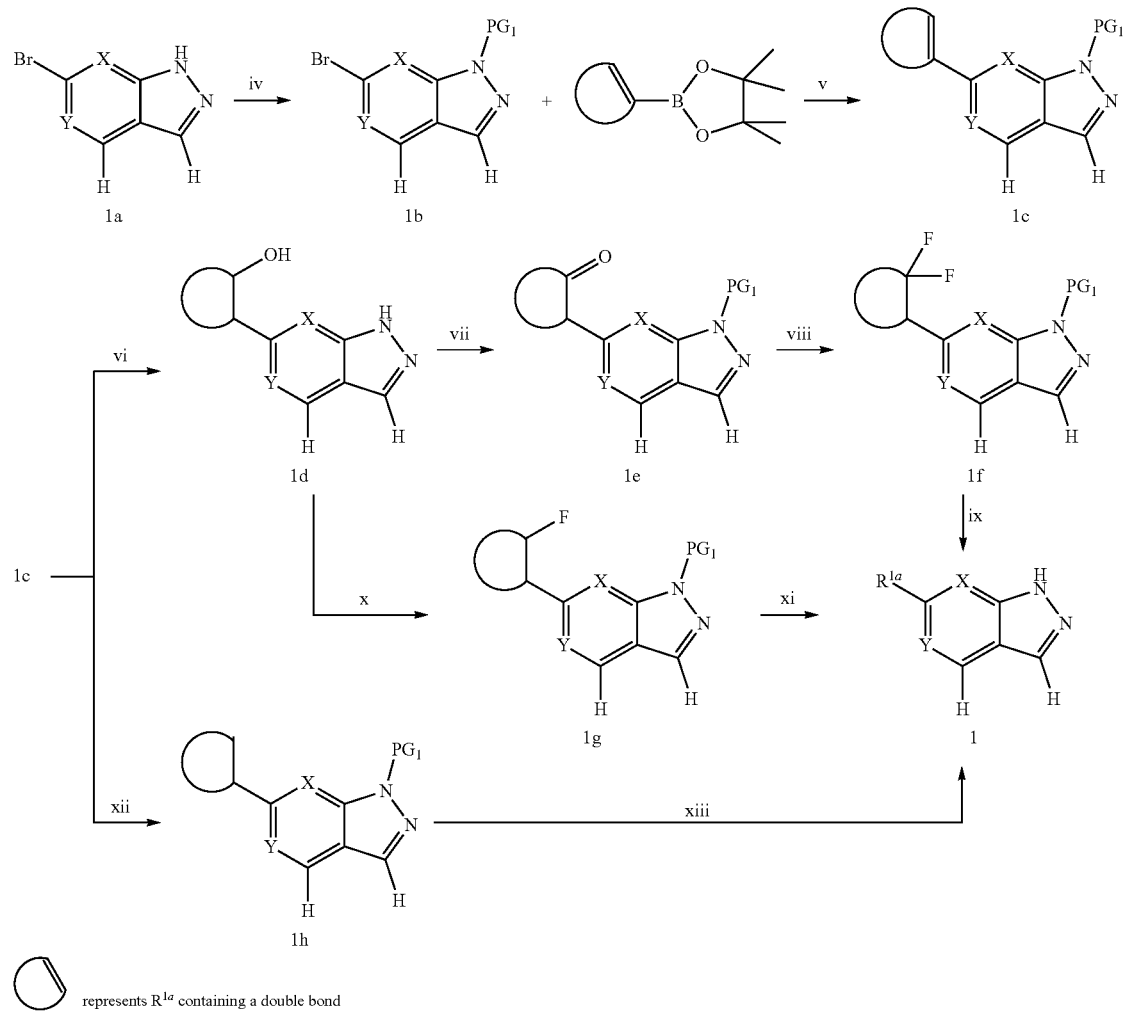

◯ represents R$^{1a}$ containing a double bond

General Scheme 2 provides an exemplary synthesis for preparing intermediates 1. R$^{1a}$ represents R$^1$ when R$^1$ is connected to the ring though a carbon atom of R$^1$. The protecting group can be any suitable protecting groups for example, tetrahydro-2H-pyran-2-yl (THP), (trimethylsilyl) ethoxy)methyl (SEM) or Acetyl (Ac).

Intermediates 1b can be obtained in step (iv) by reacting starting material 1a with suitable reagents such as DHP in the presence of suitable acids such as TsOH in appropriate solvents such as DCM under suitable temperatures such as 20° C. to 40° C. Step (v) may be a cross-coupling reaction between intermediates 1b with suitable reagents such as boronic acid or esters using appropriate palladium catalysts such as Pd(dppf)Cl$_2$ in the presence of suitable bases such as Na$_2$CO$_3$ in appropriate solvents such as 1,4-dioxane under suitable temperatures such as 60° C. to 100° C. to provide compounds 1c, which may be reacted with suitable oxidation reagents such as H$_2$O$_2$ in Step (vi) in suitable solvent such as THF under suitable temperatures such as −60° C. to −10° C. to provide intermediate 1d. Step (vii) may be an oxidation reaction by reacting intermediates 1 d with oxidants such as DMP in suitable solvents such as DCM under suitable temperatures such as 0° C. to 25° C. to give intermediate 1e. Intermediates 1f can be obtained in step (viii) by reacting 1e with fluridizer such as DAST in suitable solvents such as DCM under suitable temperatures such as −78° C. to 0° C. Step (ix) may be a de-protection reaction by reacting 1e with suitable acids such HCl in suitable solvents such as 1,4-dioxane under suitable temperatures such as 25° C. to 40° C. to give intermediate 1.

Intermediates 1d can be also directly reacted with fluridizer such as DAST in step (x) in suitable solvents such as DCM under suitable temperatures such as −78° C. to 0° C. to provide intermediate 1g, which react with suitable acids such HCl in step (xi) in suitable solvents such as 1,4-dioxane under suitable temperatures such as 25° C. to 40° C. to give intermediate 1. Intermediate 1 can be also obtained by reacting 1c with suitable reducing reagents such as hydrogen in the presence of suitable catalysts such Pd/C in polar solvents such as MeOH at appropriate temperatures such as 25° C. to 80° C. in step (xii) to provide intermediate 1 h, following by a deprotecting reaction with suitable acids such HCl in suitable solvents such as 1,4-dioxane under suitable temperatures such as 25° C. to 40° C. in step (xiii).

General scheme 3

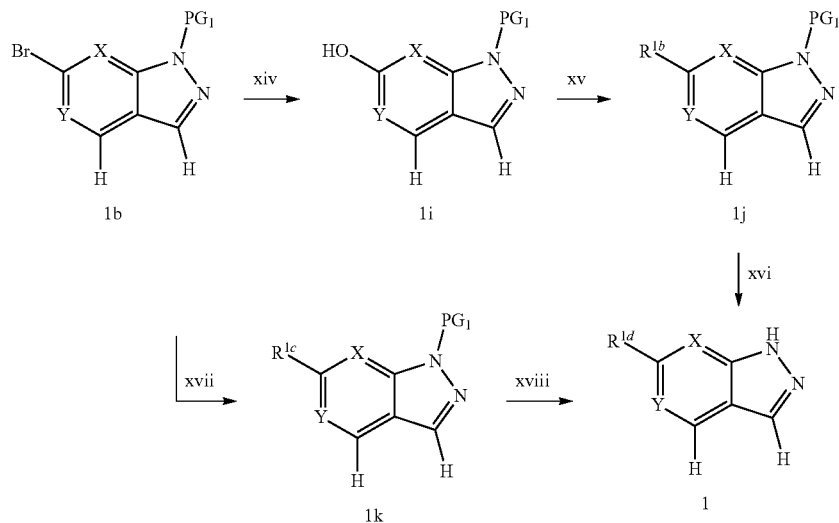

General Scheme 3 provides an exemplary synthesis for preparing intermediates 1. $R^{1b}$ represents $R^1$ when $R^1$ connects to the ring through an oxygen atom of $R^1$. $R^{1c}$ represents $R^1$ when $R^1$ connects to the ring through the nitrogen atom of $R^1$. $R^d$ represents $R^1$ when $R^1$ connects to the ring through either a nitrogen atom or an oxygen atom of $R^1$ The protecting group can be any suitable protecting group for example, tetrahydro-2H-pyran-2-yl (THP), (trimethylsilyl)ethoxy)methyl (SEM) or Acetyl (Ac).

Intermediates 1i can be obtained by reacting intermediates 1 b with suitable reagents such as 4,4,4',4',5,5,5',5'-octamethyl-2,2'-bi(1,3,2-dioxaborolane) using appropriate catalysts such as $Pd(PPh_3)_4$ in the presence of appropriate bases such as KOAc in appropriate solvents such as DMF under suitable temperatures such as 80° C. to 120° C., follow by reacting with suitable reagents such $H_2O_2$ in the presence of appropriate bases such as NaOH in suitable solvents such as THF at appropriate temperatures such as 25° C. to 80° C. in step (xiv). Intermediates 1j can be obtained by reacting 1i with suitable alkylating reagents such as 2-iodopropane in step (xv) in the presence of suitable bases such as $Cs_2CO_3$ in appropriate solvents such as $CH_3CN$ under suitable temperatures such as 25° C. to 100° C. Step (xvi) may be a deprotection reaction by reacting 1j with suitable acids such HCl in suitable solvents such as 1,4-dioxane under suitable temperatures such as 25° C. to 40° C. to give intermediate 1. Step (xvii) can be a Buchwald coupling reaction between intermediates 1b with different amines such as 1-methylpiperazine using appropriate palladium catalysts such as $Pd_2(dba)_3$ in the presence of appropriate bases such as $Cs_2CO_3$ and appropriate ligands such as BINAP in appropriate solvents such as PhMe under suitable temperatures such as 80° C. to 130° C. to provide intermediate 1k, which react with suitable acids such HCl in suitable solvents such as 1,4-dioxane under suitable temperatures such as 25° C. to 40° C. in step (xviii) to provide intermediates 1.

General scheme 4

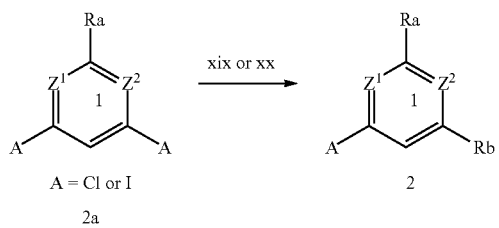

General Experimental Scheme 4 Provides an Exemplary Synthesis for Preparing Intermediates 2.

Step (xvii) can be a reaction between intermediates 2a with different amines such as morpholine using appropriate bases such as TEA in appropriate solvents such as EtOH under suitable temperatures such as 25° C. to 100° C. to provide intermediate 2. Intermediates 2 can be also obtained by a coupling reaction between intermediates 2a with suitable reagents such as bronic acid in the presence of catalysts such as $Pd(PPh_3)_2Cl_2$ in suitable solvents such as 1,4-dioxane under 25° C. to 130° C. in step (xx).

The starting material and reagents described in the above schemes are either commercially available or may be readily prepared from commercially available compounds using procedures known to a person of ordinary skill in the art.

EXAMPLES

General Experimental Procedures

The following descriptions and examples illustrate the invention. These examples are not intended to limit the scope of the present invention, but rather to provide guidance to the skilled chemist to prepare and use the compounds, compositions and methods of the present invention. While particular embodiments of the present invention are described, the skilled chemist will appreciate that various changes and modifications can be made without departing from the spirit and scope of the invention.

The chemical names of compounds described in the present application follows the principle of IUPAC nomenclature.

Heating of reaction mixtures with microwave irradiations was carried out on a Smith Creator (purchased from Personal Chemistry, Forboro/MA, now owned by Biotage), an Emrys Optimizer (purchased from Personal Chemistry) or an Explorer (provided by CEM Discover, Matthews/NC) microwave.

Conventional techniques may be used herein for work up of reactions and purification of the products of the Examples.

References in the Examples below relating to the drying of organic layers or phases may refer to drying the solution over magnesium sulfate or sodium sulfate and filtering off the drying agent in accordance with conventional techniques. Products may generally be obtained by removing the solvent by evaporation under reduced pressure.

Purification of the compounds in the examples may be carried out by conventional methods such as chromatography and/or re-crystallization using suitable solvents. Chromatographic methods are known to the skilled person and include e.g. column chromatography, flash chromatography, HPLC (high performance liquid chromatography), and MDAP (mass directed auto-preparation, also referred to as mass directed LCMS purification). MDAP is described in e.g. W. Goetzinger et al, *Int. J. Mass Spectrom.*, 2004, 238, 153-162.

Analtech Silica Gel GF and E. Merck Silica Gel 60 F-254 thin layer plates were used for thin layer chromatography. Both flash and gravity chromatography were carried out on E. Merck Kieselgel 60 (230-400 mesh) silica gel. Preparative HPLC were performed using a Gilson Preparative System using a Luna 5u C18(2) 100A reverse phase column eluting with a 10-80 gradient (0.1% TFA in acetonitrile/0.1% aqueous TFA) or a 10-80 gradient (acetonitrile/water). The CombiFlash system used for purification in this application was purchased from Isco, Inc. CombiFlash purification was carried out using a pre-packed $SiO_2$ column, a detector with UV wavelength at 254 nm and mixed solvents.

The terms "CombiFlash", "Biotage®", "Biotage 75" and "Biotage SP4®" when used herein refer to commercially available automated purification systems using pre-packed silica gel cartridges.

Final compounds were characterized with LCMS (conditions listed below) or NMR. $^1$H NMR or $^{19}$FNMR spectra were recorded using a Bruker Avance 400 MHz spectrometer. $CDCl_3$ is deuteriochloroform, DMSO-$d_6$ is hexadeuteriodimethylsulfoxide, and $CD_3OD$ is tetradeuteriomethanol. Chemical shifts are reported in parts per million (ppm) downfield from the internal standard tetramethylsilane (TMS) or the NMR solvent. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz.

All temperatures are reported in degrees Celsius. All other abbreviations are as described in the ACS Style Guide (American Chemical Society, Washington, D.C., 1986).

Absolute stereochemistry can be determined by methods known to one skilled in the art, for example X-ray or Vibrational circular dichroism (VCD).

When an enantiomer or a diastereoisomer is described and the absolute stereochemistry of a chiral center is unknown, the use of "*" at the chiral centre denotes that the absolute stereochemistry of the chiral center is unknown, i.e. the compound as drawn may be either a single R enantiomer or a single S enantiomer. Where the absolute stereochemistry is known and the compound is a single enantiomer, the bold or hashed wedge symbol ( ▬■/▪▪▪▪▪ ) are used as appropriate, without the use of "*" at the chiral centre.

In the procedures that follow, after each starting material, reference to an intermediate is typically provided. This is provided merely for assistance to the skilled chemist. The starting material may not necessarily have been prepared from the batch referred to.

LCMS Conditions:
Instruments: HPLC: Agilent 1200 and MS: Agilent 6120
1) Acidic conditions:
Mobile phase: water containing 0.05% TFA/0.05% $CH_3CN$
Column: Agilent SB-C18 4.6×30 mm-1.8 microns
Detection: MS and photodiode array detector (PDA)
2) Basic Conditions:
Mobile phase: water containing 10 mmol $NH_4HCO_3$/$CH_3CN$
Column: XBridge™ C18 4.6×50 mm-3.5 microns
Detection: MS and photodiode array detector (PDA)
3) Basic Conditions:
Mobile phase: water containing 0.02% $NH_4OAc$/$CH_3CN$
Column: Welch Ultimate XB-C18 5 μm 4.6*33 mm
Detection: MS and photodiode array detector (PDA)
Mdap Conditions:
1) Acidic Conditions:
Instrument: Waters instrument
Column: Sunfire Prep C18 column (5 urn, 19×50 mm)
Mobile phase: water containing 0.05% TFA/acetonitrile.
2) Basic Conditions:
Instrument: Waters instrument
Column: Xbridge Prep C18 column (5 urn, 19×50 mm)
Mobile phase: water containing 0.04% ammonia/acetonitrile.
Prep-HPLC Conditions
Instrument: Waters instrument
Column: Xbridge Prep C18 column OBD (10 urn, 19×250 mm)
Mobile phase: water containing 0.08% ammonia/acetonitrile.
Chiral-HPLC Isolation Instruments:
 1. Gilson Gx-281 Prep LC (Gilson 806 Manometric Module, Gilson 811D Dynamic Mixer, Gilson Gx-281 prep liquid handler, Gilson 306 Pump *2, Gilson 156 Detector),
 2. Agilent 1200 series Prep LC (Agilent G1361A Prep pump *2, Agilent G2260A Prep ALS, Agilent G1315D DAD Detector, Agilent G1364B Prep FC),
 3. Thar SFC Prep 80 (TharSFC ABPR1, TharSFC SFC Prep 80 $CO_2$ Pump, TharSFC Co-Solvent Pump, TharSFC Cooling Heat Exchanger and Circulating Bath, TharSFC Mass Flow Meter, TharSFC Static Mixer, TharSFC Injection Module, Gilson UV Detector, TharSFC Fraction Collection Module).
Chiral-HPLC Analysis Conditions:
 Instrument: Agilent 1200 series HPLC or Thar Analytical SFC
 Column and mobile phase: are described in below examples.
Chiral separation column: Chiral pak IE: particle size 5 urn; Dimensions: 4.6 mm*250 mm.
$[\alpha]_D$ was obtained by using automatic polarimeter: SGW®-1.
Abbreviations and Resource Sources
 The following abbreviations and resources are used herein below:
ACN—acetonitrile
Aq.—aqueous
BINAP—2,2'-bis(diphenylphosphino)-1,1'-binaphthyl Boc tert—butyloxycarbonyl
Boc₂O—di-tert-butyl dicarbonate
conc.—concentrated
DAST—N,N-diethylaminosulfur trifluoride
DCE—1,2-dichloroethane
DCM—dichloromethane
DEA—diethanolamine
DHP—3,4-dihydro-2H-pyran
DIBAL-H—diisobutylaluminum hydride
DIEA—N,N-diisopropylethylamine
DIPEA—N, N-diisopropylethylamine
DMA—N, N-dimethylacetamide
DMAP—4-dimethylaminopyridine
DMEDA—N,N'-dimethylethylenediamine
DMF—N, N-dimethylformamide
DMP—Dess-Martin periodinane
DMSO—dimethyl sulfoxide
DPPF—1,1'-bis(diphenylphosphino)ferrocene
EA—ethyl acetate
EDC—1-ethyl-3-(3-dimethylaminopropyl)carbodiimide hydrochloride
EDCI—3-(ethyliminomethyleneamino)-N,N-dimethylpropan-1-amine
EtOH—ethanol
EtOAc—ethyl acetate
Et₃N—triethylamine
HAc—acetic acid
HATU—2-(1H-7-azabenzotriazol-1-yl)-1,1,3,3-tetramethyl uranium hexafluorophosphate
HOBT—hydroxybenzotriazole
iPrOH—isopropyl alcohol
MOMCl—monochlorodimethyl ether
MsCl—methanesulfonyl chloride
NaHMDS—sodium bis(trimethylsilyl)amide
NIS—N-iodosuccinimide
NMP—1-methyl-2-pyrrolidone
NMO—4-methylmorpholine 4-oxide
PMB—p-methoxybenzyl
PhNTf₂—N,N-bis-(Trifluoromethanesulfonyl)aniline
PPTS—pyridinium p-toluenesulfonate
PTSA—p-toluenesulfonic acid
rt/RT—room temperature
Rt—retention time
sat.—saturated
SEM-Cl—2-(trimethylsilyl)ethoxymethyl chloride
TBDPSCl—tert-Butyl(chloro)diphenylsilane
TEA—triethylamine
TFA—trifluoroacetic acid
TFAA—trifluoroacetic anhydride
THF—tetrahydrofuran
TsCl—4-toluenesulfonyl chloride
TsOH—p-toluenesulfonic acid
PE—petroleum ether Description D1

6-Bromo-5-methyl-1H-indazole (D1)

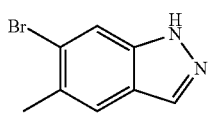

To a solution of 5-bromo-2,4-dimethylaniline (15.0 g, 75.0 mmol) in chloroform (150 mL) was added Ac₂O (15.0, 150 mmol) under ice bath. KOAc (8.00 g, 82.5 mmol), 18-crown-6 (10.0 g, 37.5 mmol) and isoamyl nitrite (26.3 g, 225 mmol) were added. The mixture was refluxed for 36 hrs. The reaction mixture was concentrated and the residue was dissolved in EtOAc (500 mL). The organic solution was washed with water (100 mL), dried over Na₂SO₄ and concentrated. The residue was dissolved in THF (100 mL) and NaOH (4 M, 40.0 mL, 160 mmol) was added. The mixture was stirred at rt for 1 h. The solvent was removed under vacuum and the residue was partitioned between EtOAc (400 mL) and water (200 mL). The organic layer was washed with brine, dried over Na₂SO₄ and concentrated. The crude was purified by column chromatography (PE:EtOAc from 10:1 to 5:1) to give the title compound (5.1 g, yield 32%) as an orange solid.

¹H NMR (300 MHz, CDCl₃): δ 10.20 (br s, 1H), 7.99 (s, 1H), 7.75 (s, 1H), 7.61 (s, 1H), 2.50 (s, 3H).

Description D2

6-Bromo-5-methyl-1-(tetrahydro-2H-pyran-2-yl)-1H-indazole (D2)

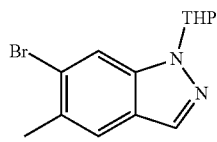

To a solution of 6-bromo-5-methyl-1H-indazole (5.10 g, 24.2 mmol) in dry DCM (120 mL) was added DHP (4.10 g, 48.4 mmol), TsOH (0.800 g, 4.80 mmol) and Mg₂SO₄ (5.0 g) at rt.

The reaction mixture was heated to 35° C. and stirred for an hour. The reaction mixture was filtered and the filtrate was washed with Na₂CO₃ (10%, 100 mL), dried over Na₂SO₄ and concentrated. The crude was purified by column chromatography (PE:EtOAc from 50:1 to 20:1) to give the title compound (6.0 g, yield 84%) as an orange solid.

¹H NMR (300 MHz, CDCl₃): δ 7.90 (s, 1H), 7.84 (s, 1H), 7.55 (s, 1H), 5.63 (dd, J=9.6, 3.0 Hz, 1H), 4.05-4.00 (m, 1H), 3.78-3.70 (m, 1H), 2.58-2.44 (m, 4H), 2.20-2.02 (m, 2H), 1.78-1.65 (m, 3H).

LCMS: (mobile phase: 5-95% CH₃CN), Rt=2.19 min in 3 min; MS Calcd: 294; MS Found: 295 [M+1]⁺.

Description D3

Tert-butyl 4-(5-methyl-1-(tetrahydro-2H-pyran-2-yl)-1H-indazol-6-yl)-5,6-dihydropyridine-1(2H)-carboxylate (D3)

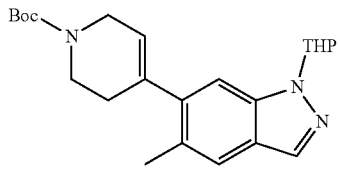

To a suspension of 6-bromo-5-methyl-1-(tetrahydro-2H-pyran-2-yl)-1H-indazole (5.50 g, 18.6 mmol), tert-butyl 4-(4,4,5,5-tetramethyl-1,3,2-dioxaborolan-2-yl)-5,6-dihydropyridine-1(2H)-(6.90 g, 22.3 mmol) and Na$_2$CO$_3$ (4.90 g, 46.5 mmol) in dioxane (150 mL) and water (130 mL) was added Pd(dppf)Cl$_2$ (658 mg, 0.900 mmol). The mixture was degassed with N$_2$ for 3 times and then stirred at 80° C. overnight. The solvent was removed under vacuum and the residue was partitioned between EtOAc (300 mL) and water (200 mL). The combined organic layers were washed with brine, dried over Na$_2$SO$_4$ and concentrated. The crude was purified by column chromatography (PE:EtOAc=10:1) to give the title compound (7.3 g, yield 99%) as a slight brown solid.

$^1$H NMR (400 MHz, CDCl$_3$): δ 7.92 (s, 1H), 7.48 (s, 1H), 7.28 (s, 1H), 5.67 (dd, J=9.6, 2.8 Hz, 1H), 5.63 (br s, 1H), 4.07-4.01 (m, 3H), 3.78-3.70 (m, 1H), 3.67-3.64 (m, 2H), 2.62-2.53 (m, 1H), 2.45-2.39 (m, 2H), 2.34 (s, 3H), 2.18-2.12 (m, 1H), 2.07-2.02 (m, 1H), 1.81-1.73 (m, 2H), 1.69-1.61 (m, 1H), 1.52 (s, 9H).

Description D4 and D5

Trans-tert-butyl 3-hydroxy-4-(5-methyl-1-(tetrahydro-2H-pyran-2-yl)-1H-indazol-6-yl)piperidine-1-carboxylate (D4) and tert-Butyl 4-(5-methyl-1-(tetrahydro-2H-pyran-2-yl)-1H-indazol-6-yl)piperidine-1-carboxylate (D5)

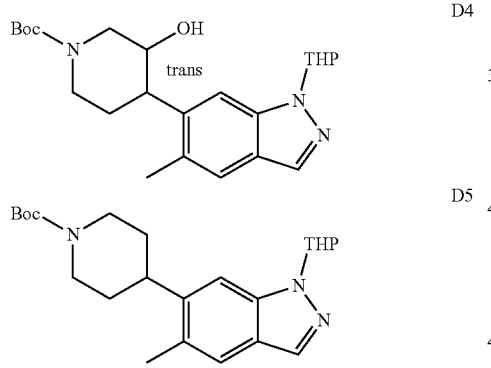

To a solution of tert-butyl 4-(5-methyl-1-(tetrahydro-2H-pyran-2-yl)-1H-indazol-6-yl)-5,6-(6.00 g, 15.1 mmol) in dry THF (120 mL) was added BH$_3$-THF solution (1 M, 151 mL, 151 mmol) under N$_2$ and kept the internal temperature below 10° C. The mixture was warmed to rt and stirred overnight. After the reaction mixture was cooled to 0° C., NaOH (aq, 2 M, 22.7 mL, 45.3 mmol) was added carefully and the internal temperature was kept below 10° C. Then, H$_2$O$_2$ (30%, 20.0 mL, 151 mmol) was added dropwise and the internal temperature was kept below 10° C. The mixture was stirred at 40° C. for an hour. The solvent was evaporated and EtOAc (50 mL×2) was added. The combined organic layers were washed with brine, dried over Na$_2$SO$_4$ and evaporated. The residue was purified by column chromatography (PE:EtOAc from 5:1 to 2:1) to give the title compound tert-butyl 3-hydroxy-4-(5-methyl-1-(tetrahydro-2H-pyran-2-yl)-1H-indazol-6-yl)piperidine-1-carboxylate (D4) (2.0 g of pure and 3.45 g with 80% purity) as a white solid.

$^1$H NMR (300 MHz, CDCl$_3$): δ 7.89 (s, 1H), 7.51 (s, 1H), 7.41 (s, 1H), 5.68-5.65 (m, 1H), 4.48-4.45 (m, 1H), 4.22 (br s, 1H), 4.02-4.00 (m, 1H), 3.96-3.89 (m, 1H), 3.80-3.71 (m, 1H), 3.03-2.95 (m, 1H), 2.83-2.68 (m, 2H), 2.60-2.50 (m, 1H), 2.47 (s, 3H), 2.20-2.10 (m, 1H), 2.06-2.02 (m, 1H), 1.94-1.62 (m, 6H), 1.51 (s, 9H).

To a solution of tert-butyl 4-(5-methyl-1-(tetrahydro-2H-pyran-2-yl)-1H-indazol-6-yl)-5,6-dihydropyridine-1(2H)-carboxylate (33.0 g, 83.0 mmol) in dry THF (300 mL) was added BH$_3$-THF (1 M, 332 mL, 332 mmol) at 10° C. The mixture was gradually warmed to rt and stirred overnight. The reaction mixture was cooled to 0° C. and NaOH (aq, 2 M, 125 mL, 249 mmol) was added carefully. H$_2$O$_2$ (30%, 87 mL, 830 mmol) was followed. The temperature was kept below 10° C. during the addition of NaOH and H$_2$O$_2$. The mixture was stirred for an hour at rt. Na$_2$SO$_3$ (10%, 100 mL) was added to the reaction mixture and stirred for 20 min. The organic layer was separated and the aqueous was extracted with EtOAc (100 mL×2). The combined organic layers were washed with brine, dried over Na$_2$SO$_4$ and evaporated. The crude was purified by column chromatography (PE:EtOAc from 3:1 to 1:1) to give tert-butyl 3-hydroxy-4-(5-methyl-1-(tetrahydro-2H-pyran-2-yl)-1H-indazol-6-yl)piperidine-1-carboxylate as major product (D4) (23 g, yield 67%) as a white solid and tert-butyl 4-(5-methyl-1-(tetrahydro-2H-pyran-2-yl)-1H-indazol-6-yl)piperidine-1-carboxylate (D5) as minor product (6.7 g, yield 20%) as a slight brown solid.

D4 obtained in this batch $^1$H NMR (300 MHz, CDCl$_3$): δ 7.89 (s, 1H), 7.51 (s, 1H), 7.41 (s, 1H), 5.68-5.65 (m, 1H), 4.48-4.45 (m, 1H), 4.22 (br s, 1H), 4.02-4.00 (m, 1H), 3.96-3.89 (m, 1H), 3.80-3.71 (m, 1H), 3.03-2.95 (m, 1H), 2.83-2.68 (m, 2H), 2.62-2.50 (m, 1H), 2.47 (s, 3H), 2.20-2.10 (m, 1H), 2.06-2.02 (m, 1H), 1.94-1.62 (m, 6H), 1.51 (s, 9H).

D5: $^1$H NMR (300 MHz, CDCl$_3$): δ 7.90 (s, 1H), 7.48 (s, 1H), 7.34 (s, 1H), 5.68 (dd, J=9.6 Hz, 2.7 Hz, 1H), 4.33-4.28 (m, 2H), 4.06-4.02 (m, 1H), 3.80-3.72 (m, 1H), 3.00-2.82 (m, 3H), 2.65-2.51 (m, 1H), 2.44 (s, 3H), 2.22-2.11 (m, 1H), 2.08-2.00 (m, 1H), 1.88-1.80 (m, 2H), 1.77-1.63 (m, 5H), 1.51 (s, 9H).

Description D6 tert-Butyl 4-(5-methyl-1-(tetrahydro-2H-pyran-2-yl)-1H-indazol-6-yl)-3-oxopiperidine-1-carboxylate (D6)

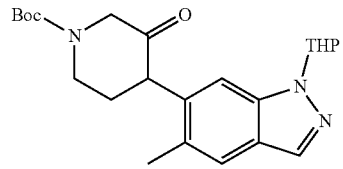

To a solution of tert-butyl 3-hydroxy-4-(5-methyl-1-(tetrahydro-2H-pyran-2-yl)-1H-indazol-6-yl) piperidine-1-carboxylate (3.45 g, 8.30 mmol) in dry dichloromethane (80 mL) was added DMP (7.04 g, 16.6 mmol) under ice bath. After stirred for 30 min under ice bath the mixture was warmed to rt and stirred for an additional 1.5 hour. The reaction mixture was gradually poured into an aqueous solution (100 mL, 10% of NaHCO$_3$ and 10% of Na$_2$S$_2$O$_3$) and stirred for 15 min. The organic layer was separated and the aqueous was extracted with dichloromethane (200 mL). The combined organic layers were washed with brine, dried over Na$_2$SO$_4$ and evaporated. The residue was purified by column chromatography (PE:EtOAc from 10:1 to 5:1) to give the title compound (1.6 g, yield 47%) as a white solid.

¹H NMR (300 MHz, CDCl₃): δ 7.92 (s, 1H), 7.53 (s, 1H), 7.29 (s, 1H), 5.68-5.65 (m, 1H), 4.36-4.29 (m, 1H), 4.13-3.87 (m, 4H), 3.76-3.68 (m, 1H), 3.59-3.47 (m, 1H), 2.62-2.47 (m, 1H), 2.40-2.27 (m, 5H), 2.21-2.09 (m, 1H), 2.09-1.97 (m, 1H), 1.78-1.64 (m, 3H), 1.51 (s, 9H).

LCMS: (mobile phase: 5-95% CH₃CN), Rt=2.15 min in 3 min; MS Calcd: 413; MS Found: 414 [M+1]⁺.

Description D7 tert-Butyl 3,3-difluoro-4-(5-methyl-1-(tetrahydro-2H-pyran-2-yl)-1H-indazol-6-yl)piperidine-1-carboxylate (D7)

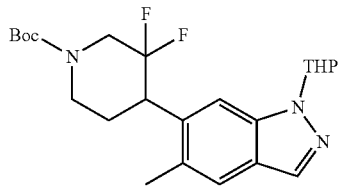

To a solution of tert-butyl 4-(5-methyl-1-(tetrahydro-2H-pyran-2-yl)-1H-indazol-6-yl)-3-oxopiperidine-1-carboxylate (1.60 g, 3.90 mmol) in dry DCM (80 mL) was added DAST (6.30 g, 39.0 mmol) under N₂ at −65° C. After stirred at −60° C. for 30 min the mixture was warmed to rt and stirred overnight. The reaction mixture was carefully poured into Na₂CO₃ aqueous solution (10%, 100 mL) and stirred for 15 min. The organic layer was separated and the aqueous was extracted with DCM (80 mL×2). The combined organic layers were washed with brine, dried over Na₂SO₄ and evaporated. The crude was purified by column chromatography (PE:EtOAc from 10:1) to give the title compound (1.0 g, yield 59%) as a slight yellow solid.

¹H NMR (400 MHz, CDCl₃): δ 7.93 (s, 1H), 7.52 (s, 2H), 5.74-5.67 (m, 1H), 4.42 (br s, 2H), 4.07-3.99 (m, 1H), 3.80-3.71 (m, 1H), 3.51-3.41 (m, 1H), 3.17-2.83 (m, 2H), 2.65-2.51 (m, 1H), 2.45 (s, 3H), 2.34-2.07 (m, 3H), 1.93-1.83 (m, 1H), 1.83-1.71 (m, 2H), 1.71-1.62 (m, 1H), 1.52 (s, 9H). LCMS: (mobile phase: 5-95% CH₃CN), Rt=2.39 min in 3 min; MS Calcd: 435; MS Found: 436 [M+1]⁺.

Description D8

6-(3,3-Difluoropiperidin-4-yl)-5-methyl-1H-indazole hydrochloride (D8)

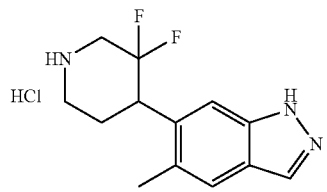 [SMILES: Cl ; Cc1cc2cn[nH]c2cc1C1CCNCC1(F)F]

To a solution of tert-butyl 3,3-difluoro-4-(5-methyl-1-(tetrahydro-2H-pyran-2-yl)-1H-indazol-6-yl) piperidine-1-carboxylate (1.00 g, 2.30 mmol) in dioxane (2 mL) was added sat. HCl/dioxane (5 mL). The mixture was stirred at rt overnight. The reaction mixture was concentrated to give the title compound (770 mg, yield >100%) as a slight brown solid.

LCMS: (mobile phase: 5-95% CH₃CN), Rt=1.89 min in 3 min; MS Calcd: 251; MS Found: 252 [M+1]⁺.

Description D9

6-(3,3-Difluoro-1-methylpiperidin-4-yl)-5-methyl-1H-indazole (D9)

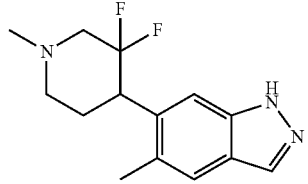

To a solution of 6-(3,3-difluoropiperidin-4-yl)-5-methyl-1H-indazole hydrochloride (420 mg, 1.70 mmol) in methanol (4 mL) was added formaldehyde (37%, 3 mL) and NaBH₃CN (536 mg, 8.50 mmol) at rt. Then the mixture was stirred at rt for 2 hrs. The reaction mixture was poured into Na₂CO₃ (10%, 20 mL). After stirring for 15 min the aqueous layer was extracted with DCM (15 mL×3). The combined organic layers were washed with brine, dried over Na₂SO₄ and concentrated. The crude was dissolved in sat. NH₃/MeOH (3 mL) and stirred overnight. The mixture was evaporated under vacuum to give the title compound (380 mg, yield 86%) as a yellow solid.

LCMS: (mobile phase: 5-95% Acetonitrile), Rt=1.81 min in 3 min; MS Calcd: 265; MS Found: 266 [M+1]⁺.

Description D10 and D11

6-(3,3-Difluoro-1-methylpiperidin-4-yl)-5-methyl-1H-indazole (Enantiomer 1) (D10) and 6-(3,3-Difluoro-1-methylpiperidin-4-yl)-5-methyl-1H-indazole (Enantiomer 2) (D11)

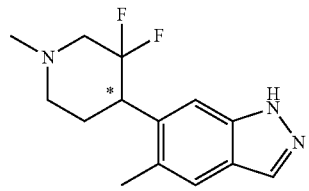 [SMILES: Cc1cc2cn[nH]c2cc1C1CCN(C)CC1(F)F]

enantiomer 1

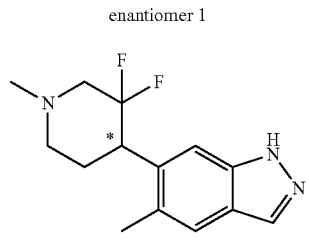

enantiomer 2

The racemate 6-(3,3-difluoro-1-methylpiperidin-4-yl)-5-methyl-1H-indazole (380 mg, 1.43 mmol) was separated by chiral-HPLC (Chiralpak IC 5 μm 4.6×250 mm, Phase: Hex/EtOH=80/20, flowrate: 1 mL/min, temperature: 30° C.) to give 6-(3,3-difluoro-1-methylpiperidin-4-yl)-5-methyl-1H-indazole (enantiomer 1) (D10) (Rt: 6.740 min, 120 mg, yield 32%) as a white solid and 6-(3,3-difluoro-1-methylpiperidin-4-yl)-5-methyl-1H-indazole (enantiomer 2) (D11) (Rt: 7.990 min, 110 mg, yield 29%) as a white solid.

D10: $^1$H NMR (300 MHz, CDCl$_3$): δ 11.60 (s, 1H), 7.97 (s, 1H), 7.72 (s, 1H), 7.57 (s, 1H), 3.46-3.27 (m, 2H), 3.17-3.12 (m, 1H), 2.59 (s, 3H), 2.53-2.25 (s, 6H), 2.00-1.92 (m, 1H).

D11: $^1$H NMR (300 MHz, CDCl$_3$): δ 11.71 (s, 1H), 7.97 (s, 1H), 7.73 (s, 1H), 7.57 (s, 1H), 3.44-3.30 (m, 2H), 3.17-3.13 (m, 1H), 2.60 (s, 3H), 2.53-2.26 (s, 6H), 1.99-1.92 (m, 1H).

Description D12

4-(6-Chloropyrimidin-4-yl)morpholine (D12)

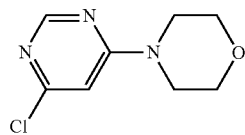 [SMILES: Clc1cc(N2CCOCC2)ncn1]

To a solution of 4,6-dichloro-pyrimidine (10.0 g, 67.1 mmol) in i-PrOH (70 mL) was added morpholine (5.84 g, 67.1 mmol). The mixture was stirred for 2.5 hrs at reflux. After cooling down, the solid was obtained through filtration. The solid was partitioned between DCM (50 mL) and water (50 mL). The organic phase was concentrated to afford the title compound (6.6 g, yield 50%).

$^1$H NMR (300 MHz, CDCl$_3$): δ 8.38 (m, 1H), 6.48 (m, 1H), 3.75-3.78 (m, 4H), 3.60-3.63 (m, 4H).

Description D13

4-(6-Chloro-2-methoxypyrimidin-4-yl)morpholine (D13)

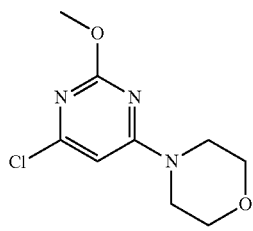

A mixture of 4,6-dichloro-2-methoxypyrimidine (700 mg, 3.91 mmol), morpholine (340 mg, 3.91 mmol) and NaHCO$_3$ (822 mg, 9.78 mmol) in ethanol (20 mL) was refluxed for 3 hrs. Then the reaction was cooled to rt and diluted with 20 mL of water. The mixture was stirred for 30 min and filtered. The solid was collected and washed with water and ether. The title compound (660 mg, yield 73%) was obtained after dried under vacuum as a white solid.

$^1$H NMR (300 MHz, CDCl$_3$): δ 6.18 (s, 1H), 3.93 (s, 3H), 3.77-3.74 (m, 4H), 3.63-3.61 (m, 4H).

Description D14

4-(6-Chloro-2-ethoxypyrimidin-4-yl)morpholine (D14)

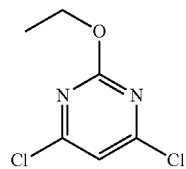

To a suspension of NaH (60%, 536 mg, 13.4 mmol) in dry THF (20 mL) was added EtOH (617 mg, 13.4 mmol) at 0° C. under N$_2$. The suspension was stirred at 0° C. for 1 h. Then, the suspension was cooled to −78° C. and a solution of 4,6-dichloro-2-methanesulfonyl-pyrimidine (2.03 g, 8.90 mmol) in THF (20 mL) was added to the stirring mixture slowly, then the mixture was stirred at −78° C. for 1 h. Sat. NH$_4$Cl solution (10 mL) and EtOAc (40 mL) was added. The organic layer was dried and concentrated in vacuo. The residue was purified by column (PE:EtOAc=50:1) to give the title compound (1.62 g, yield 94%) as a colorless oil.

$^1$H NMR (300 MHz, CDCl$_3$): δ 7.01 (s, 1H), 4.45 (q, J=7.2 Hz, 2H), 1.41 (t, J=7.2 Hz, 3H).

Description D15

4-(6-Chloro-2-ethoxypyrimidin-4-yl)morpholine (D15)

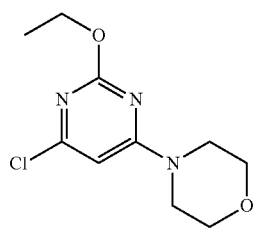 [SMILES: CCOc1nc(Cl)cc(N2CCOCC2)n1]

To a solution of 4,6-dichloro-2-ethoxypyrimidine (2.10 g, 10.9 mmol) in i-PrOH (50 mL) was added morpholine (1.99 g, 22.8 mmol) at room temperature. The resulting mixture was heated to 90° C. for 1 h. The reaction mixture was cooled and concentrated under vacuum. The residue was diluted with H$_2$O (100 mL) and extracted with EtOAc (100 mL×3). The organic layers were dried over Na$_2$SO$_4$ and concentrated. The residue was purified by column (PE: EtOAc=10:1) to give the title compound (2.1 g, yield 80%) as a white solid.

$^1$H NMR (300 MHz, CDCl$_3$): δ 6.16 (s, 1H), 4.35 (q, J=7.2 Hz, 2H), 3.77-3.73 (m, 4H), 3.62-3.60 (m, 4H), 1.38 (t, J=7.2 Hz, 3H).

Description D16

4,6-Dichloro-2-isopropoxypyrimidine (D16)

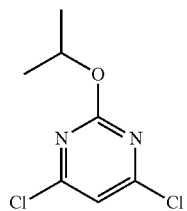

To a suspension of NaH (60%, 248 mg, 6.20 mmol) in dry THF (10 mL) was added i-PrOH (373 mg, 6.20 mmol) under ice bath and N₂ atmosphere. After stirring for 20 min, the suspension was cooled to −60° C. and 4,6-dichloro-2-(methylsulfonyl)pyrimidine (1.0 g, 4.4 mmol) in dry THF (10 mL) was added dropwise and kept the temperature below −55° C. The resulting mixture was stirred for an hour at −55° C. The reaction mixture was poured into water (100 mL) slowly and the aqueous layer was extracted with EtOAc (30 mL×3). The combined organic layers were washed with brine, dried over Na₂SO₄ and concentrated to give the title compound (700 mg, yield 77%) as a slight yellow liquid.

$^1$H NMR (300 MHz, CDCl₃): δ 6.98 (s, 1H), 5.34-5.21 (m, 1H), 1.40-1.37 (m, 6H).

Description D17

4-(6-chloro-2-isopropoxypyrimidin-4-yl)morpholine (D17)

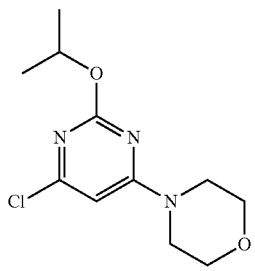 [SMILES: CC(C)Oc1nc(Cl)cc(N2CCOCC2)n1]

A solution of 4,6-dichloro-2-isopropoxypyrimidine (660 mg, 3.19 mmol) and morpholine (584 mg, 6.69 mmol) in i-PrOH (20 mL) was refluxed for an hour. The reaction mixture was concentrated and the residue was partitioned between water (30 mL) and EtOAc (20 mL). The organic layer was washed with brine, dried over Na₂SO₄ and concentrated. The crude was purified by column chromatography (PE:EtOAc from 10:1 to 5:1) to give the title compound (600 mg, yield 73%) as a white solid.

LCMS: 5-95% CH₃CN in 3 min; Rt=1.99 min; MS Calcd.: 257, MS Found: 258 [M+H]⁺.

$^1$H NMR (300 MHz, CDCl₃): δ 6.14 (s, 1H), 5.27-5.14 (m, 1H), 3.76-3.73 (m, 4H), 3.61-3.58 (m, 4H), 1.35 (d, J=6.3 Hz, 6H).

Description D18

4-Chloro-6-morpholinopyrimidin-2-amine (D18)

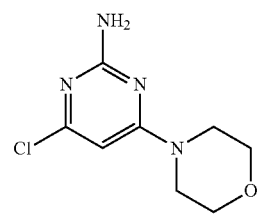 [SMILES: Nc1nc(Cl)cc(N2CCOCC2)n1]

To a suspension of 4,6-dichloropyrimidin-2-amine (10 g, 61 mmol) in MeOH (100 mL) were added morpholine (7.97 mL, 91 mmol), DIPEA (22.5 mL, 121 mmol) and the mixture was stirred at 65° C. overnight. The reaction mixture was cooled to room temperature. About half of the methanol was evaporated under the reduced pressure and then filtered. The solid was collected, washed with Et₂O (20 mL) and then dried to afford 4-chloro-6-morpholinopyrimidin-2-amine (9.6 g, 73% yield) as a white solid. ESI(MS): 215.1[M+H]

Description D19

4-(6-Chloro-2-iodopyrimidin-4-yl)morpholine (D19)

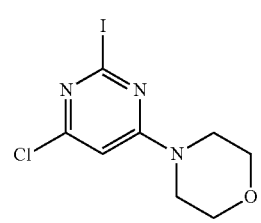 [SMILES: Clc1cc(N2CCOCC2)nc(I)n1]

To a stirred mixture of 4-chloro-6-morpholinopyrimidin-2-amine (3 g, 14 mmol), diiodomethane (5.63 mL, 70 mmol) and CuI (2.66 g, 14 mmol) in THF (50 mL) was added 2-methyl-2-nitropropane (4.99 mL, 43 mmol) dropwise at 70° C. After the addition, the reaction mixture was stirred at 90° C. for 3 hrs. The mixture was cooled down to the room temperature, EtOAc (200 mL) was added to dilute the solution, Na₂S₂O₃ (sa, 30 mL) was added and the organic layer was washed with water (50 mL×2). The organic layer was then dried over anhydrous Na₂SO₄ and concentrated. The crude product was purified by normal phase chromatography (PE:EtOAc=100:0 to 60:40) to afford the 4-(6-chloro-2-iodopyrimidin-4-yl)morpholine (2.2 g, 48.4% yield) as a white solid. ESI (MS): 325.9[M+H].

Description D20

4-Chloro-6-morpholinopyrimidine-2-carbonitrile (D20)

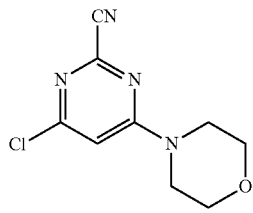 [SMILES: N#Cc1nc(Cl)cc(N2CCOCC2)n1]

4-(6-chloro-2-iodopyrimidin-4-yl)morpholine (500 mg, 1.54 mmol) and Zn(CN)$_2$ (90 mg, 0.77 mmol) was dissolved in DMF (10 mL), tetrakis(triphenylphosphine)palladium(0) (170 mg, 0.15 mmol) was added and the mixture was stirred at 90° C. for 2 hrs. The mixture was cooled down to the room temperature, EtOAc (30 mL) was added to dilute the solution, water (10 mL) was added and the organic layer was separated. The organic layer was further washed with water (20 mL×3) and dried over anhydrous Na$_2$SO$_4$ and concentrated. The crude product was purified by normal phase chromatography (PE:EtOAc=100:0→60:40) to afford the 4-chloro-6-morpholinopyrimidine-2-carbonitrile (280 mg, 81.3% yield) as a white solid.

$^1$H NMR (400 MHz, CD$_3$OD): 7.06 (s, 1H), 3.66-3.87 (m, 8H).

ESI(MS): 225.1[M+H].

Description D21

2-Ethylpyrimidine-4,6-diol (D21)

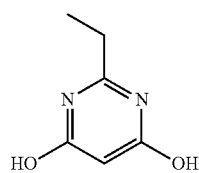

Sodium (1.27 g, 55.3 mmol) was added to anhydrous methanol (50 mL) under ice bath. Once sodium was completely dissolved propionimidamide hydrochloride (2.00 g, 18.4 mmol) was added and the reaction mixture was stirred for 15 min. Then diethyl malonate (3.80 g, 23.9 mmol) was added dropwise. The reaction mixture was warmed to rt and stirred for 4 hrs. The mixture was concentrated under vacuum. The resulting residue was dissolved in water (120 mL) and the solution was acidified with conc. HCl to pH=5. The mixture was filtered and the solid was collected. The solid was successively washed with H$_2$O (15 mL), isopropanol (10 ml) and PE (10 ml), and dried under vacuum to afford the title compound (0.96 g, yield: 38%) as a white solid.

$^1$H NMR (300 MHz, DMSO-d$_6$): δ 11.59 (br s, 2H), 5.01 (s, 1H), 2.46 (q, J=7.8 Hz, 2H), 0.97 (t, J=7.8 Hz, 3H).

LC-MS: 5-95% CH$_3$CN in 3 min, Rt=0.25 min; MS Calcd.: 140, MS Found: 141 [M+H]$^+$.

Description D22

4,6-Dichloro-2-ethylpyrimidine (D22)

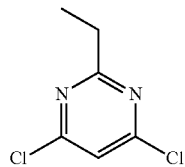

To a flask (50 mL) containing 2-ethylpyrimidine-4,6-diol (963 mg, 6.87 mmol) was added POCl$_3$ (10 mL). Then the mixture was heated to 100° C. for 2 hrs. The mixture was cooled to rt and poured into water (100 mL) and basified with saturated NaHCO$_3$ to pH=6-7. Then the mixture was extracted with ethyl acetate (40 mL×2). The organic layer was dried over Na$_2$SO$_4$ and concentrated. The residue was purified by column (PE:EtOAc=20:1) give the title compound (920 mg, yield 76%) as a colorless oil.

$^1$H NMR (300 MHz, CDCl$_3$): δ 7.25 (s, 1H), 2.95 (q, J=7.8 Hz, 2H), 1.35 (t, J=7.8 Hz, 3H).

Description D23

4-(6-Chloro-2-ethylpyrimidin-4-yl)morpholine (D23)

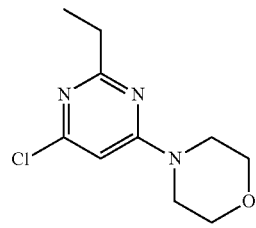

To a solution of 4,6-dichloro-2-ethylpyrimidine (920 mg, 5.20 mmol) in isopropanol (25 mL) was added morpholine (0.949 g, 10.9 mmol). The mixture was heated to 90° C. and stirred for 1 h. Then the reaction was cooled to rt and concentrated. Then the residue was purified by column (PE:EtOAc=5:1) to give the title compound (960 mg, yield 81%) as a white solid.

$^1$H NMR (300 MHz, CDCl$_3$): δ 6.31 (s, 1H), 3.79-3.75 (m, 4H), 3.64-3.61 (m, 4H), 2.74 (q, J=7.5 Hz, 2H), 1.28 (t, J=7.5 Hz, 3H). LC-MS: 5-95% CH$_3$CN in 3 min, Rt=1.49 min; MS Calcd.: 227, MS Found: 228 [M+H]$^+$.

Description D24

6-(6-Chloropyrimidin-4-yl)-2-oxa-6-azaspiro[3.4]octane (D24)

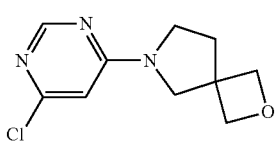 [SMILES: Clc1cc(N2CCC3(COC3)C2)ncn1]

A mixture of 4,6-dichloro-pyrimidine (0.800 g, 5.36 mmol), 1-oxa-6-azaspiro[3.4]octane oxalate (0.850 g, 5.36 mmol) and Et$_3$N (1.35 g, 13.4 mmol) in i-PrOH (10 mL) was stirred at 90° C. for 3 hrs. Then the mixture was diluted with water (50 mL) and extracted with ethyl acetate (20 mL×3). The combined organic layers were washed with brine, dried over Na$_2$SO$_4$ and concentrated. The residue was treated with ethyl acetate (1 mL) and ether (15 mL). The mixture was stirred at room temperature for 15 min and filtered. The solid was dried to give desired compound (1.0 g, yield 82%) as a yellow solid.

$^1$H NMR (300 MHz, CDCl$_3$): 8.38 (s, 1H), 6.30 (s, 1H), 4.72-4.63 (m, 4H), 3.87-3.33 (m, 4H), 2.37-2.27 (m, 2H).

Description D25

(R)-Methyl morpholine-2-carboxylate hydrochloride (D25)

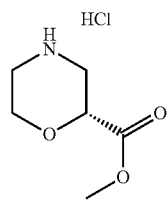

To a solution of morpholine-2-carboxylic acid (850 mg, 3.68 mmol) in MeOH (15 mL) was added SOCl$_2$ (1 mL) dropwise at 0° C. Then the mixture was stirred at rt for 30 mins and stirred at 60° C. for 2 hrs. The mixture was concentrated under reduced pressure to afford the desired compound (670 mg, yield >100%) as a white solid which was used for next step without purification.

LC-MS: 5-95% CH$_3$CN, Rt=0.35 min, MS Calcd.: 145, MS Found: 146 [M+H]$^+$.

Description D26

(R)-Methyl 4-(6-chloropyrimidin-4-yl)morpholine-2-carboxylate (D26)

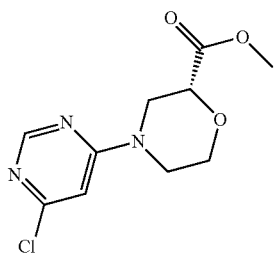 [SMILES: COC(=O)[C@H]1CN(c2cc(Cl)ncn2)CCO1]

To a solution of (R)-Methyl morpholine-2-carboxylate hydrochloride (335 mg, 1.85 mmol) and TEA (2 mL) in EtOH (15 mL) was added 4,6-dichloro-pyrimidine (412 mg, 2.77 mmol). The mixture was heated to 40° C. for 1 hour. Then the reaction was cooled and diluted with water (25 mL) and extracted with EtOAc (20 mL×3). The combined organic layers were washed with brine (20 mL), dried over Na$_2$SO$_4$, filtered and concentrated to give the desired compound (460 mg, yield 97%) as a white solid.

LC-MS: 5-95% CH$_3$CN, Rt=1.68 min; MS Calcd.: 257, MS Found: 258 [M+H]$^+$.

Description D27

(R)-4-(6-Chloropyrimidin-4-yl)-N-methylmorpholine-2-carboxamide (D27)

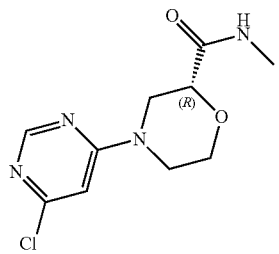

A solution of (R)-Methyl 4-(6-chloropyrimidin-4-yl)morpholine-2-carboxylate (460 mg, 1.79 mmol) in CH$_3$NH$_2$/CH$_3$OH (28-32%, 10 mL) was stirred at rt for 1 h. The reaction mixture was concentrated and purified by column (PE/EtOAc=1/1) to give the desired compound (440 mg, yield 95%) as a white solid.

$^1$H NMR (300 MHz, CDCl$_3$): δ 8.41 (brs, 1H), 6.62 (s, 2H), 4.46-4.38 (m, 2H), 4.12-3.98 (m, 2H), 3.72-3.60 (m, 1H), 3.12-2.91 (m, 2H), 2.86 (d, J=4.8 Hz, 3H).

LC-MS: 5-95% CH$_3$CN, Rt=1.21 min; MS Calcd.: 256, MS Found: 257 [M+H]$^+$.

Description D28

(S)-Methyl morpholine-2-carboxylate hydrochloride (D28)

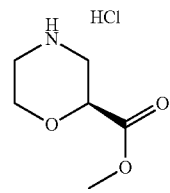

To a solution of (S)-4-(tert-Butoxycarbonyl)morpholine-2-carboxylic acid (1.00 g, 4.33 mmol) in MeOH (15 mL) was added SOCl$_2$ (2 mL) dropwise at 0° C. Then the mixture was refluxed for 1 h. The mixture was cooled to rt and concentrated under reduced pressure to afford a white solid (780 mg, yield 99%) which was used for next step without purification.

$^1$H NMR (400 MHz, DMSO-d$_6$): δ 9.85 (br s, 1H), 9.56 (br s, 1H), 4.56-4.51 (m, 1H), 4.02-3.96 (m, 1H), 3.84-3.79 (m, 1H), 3.68 (s, 3H), 3.40-3.35 (m, 1H), 3.19-2.94 (m, 3H).

Description D29

(S)-Methyl 4-(6-chloropyrimidin-4-yl)morpholine-2-carboxylate (D29)

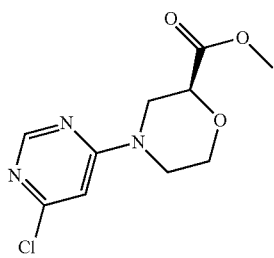 [SMILES: COC(=O)[C@@H]1CN(c2cc(Cl)ncn2)CCO1]

To a solution of (S)-methyl morpholine-2-carboxylate hydrochloride (780 mg, 4.30 mmol) in EtOH (15 mL) was added 4,6-dichloro-pyrimidine (769 mg, 5.16 mmol) and TEA (2 mL).

The mixture was heated to 40° C. for 1 hour. Then the reaction was cooled and concentrated. The residue was diluted with water (20 mL) and extracted with EtOAc (20 mL×3). The combined organic layers were washed with brine (20 mL), dried over $Na_2SO_4$, filtered and concentrated to give the desired compound (1.0 g, yield 90%) as a white solid.

LC-MS: 5-95% $CH_3CN$, Rt=1.68 min; MS Calcd.: 257, MS Found: 258 [M+H].

Description D30

(S)-4-(6-Chloropyrimidin-4-yl)-N-methylmorpholine-2-carboxamide (D30)

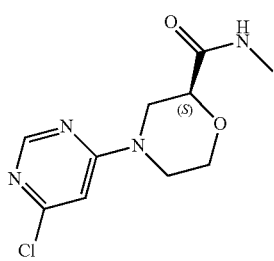

To a solution (S)-methyl 4-(6-chloropyrimidin-4-yl)morpholine-2-carboxylate (1.00 g, 3.89 mmol) in MeOH (20 mL) was added $CH_3NH_2/CH_3OH$ (28-32%, 4 mL). The mixture was stirred at rt for 1 h and concentrated. The residue was purified by column (PE:EtOAc=1:1) to give the desired compound (709 mg, yield 70%) as a white solid.

$^1$H NMR (300 MHz, $CDCl_3$): δ 8.40 (s, 1H), 6.62 (s, 2H), 4.45-4.36 (m, 2H), 4.10-3.99 (m, 2H), 3.71-3.63 (m, 1H), 3.11-2.91 (m, 2H), 2.86 (d, J=4.8 Hz, 3H).

Description D31

(R)-Methyl 4-(6-chloro-2-methoxypyrimidin-4-yl) morpholine-2-carboxylate (D31)

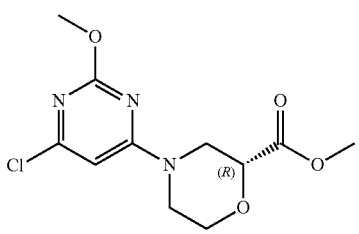

To a solution of (R)-methyl morpholine-2-carboxylate hydrochloride (335 mg, 1.85 mmol) and TEA (1 mL) in EtOH (10 mL) was added a solution of 4,6-dichloro-2-methoxy-pyrimidine (496 mg, 2.77 mmol) in EtOH (5 mL). The mixture was heated to 40° C. for 1 hour. Then the reaction was diluted with water (25 mL) and extracted with EtOAc (20 mL×3). The combined organic layers were washed with brine (20 mL), dried over $Na_2SO_4$, filtered and concentrated to give the title compound (450 mg, yield 95%) as a white solid.

LC-MS: 5-95% $CH_3CN$, Rt=1.68 min; MS Calcd.: 287, MS Found: 288 [M+H]$^+$.

Description D32

(R)-4-(6-Chloro-2-methoxypyrimidin-4-yl)-N-methylmorpholine-2-carboxamide (D32)

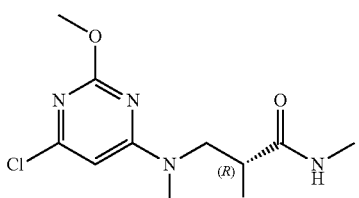

A solution of (R)-methyl 4-(6-chloro-2-methoxypyrimidin-4-yl)morpholine-2-carboxylate (450 mg, 1.57 mmol) in $CH_3NH_2/CH_3OH$ (30%, 10 mL) was stirred at rt for 1 h. The reaction mixture was concentrated and purified by column (PE:EtOAc=1:1) to give the title compound (420 mg, yield: 93%) as a white solid.

$^1$H NMR (300 MHz, $CDCl_3$): δ 6.59 (br s, 1H), 6.29 (s, 1H), 4.42-4.32 (m, 2H), 4.06-3.97 (m, 2H), 3.93 (s, 3H), 3.70-3.61 (m, 1H), 3.09-2.91 (m, 2H), 2.86 (d, J=5.1 Hz, 3H). LC-MS: 5-95% $CH_3CN$, Rt=1.31 min; MS Calcd.: 286, MS Found: 287 [M+H]$^+$.

Description D33

6-(3,3-Difluoro-1-(oxetan-3-yl)piperidin-4-yl)-5-methyl-1H-indazole (D33)

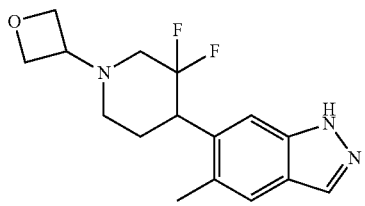 [SMILES: Cc1cc2cn[nH]c2cc1C1CCN(C2COC2)CC1(F)F]

To a solution of 6-(3,3-difluoropiperidin-4-yl)-5-methyl-1H-indazole hydrochloride (300 mg, 1.05 mmol) in methanol (1 mL) and 1,2-dichloro-ethane (5 mL) was added oxetan-3-one (864 mg, 12.0 mmol). Then, the mixture was stirred for 40 min. NaBH$_3$CN (756 mg, 12.0 mmol) was added slowly and stirred for another 2 hrs. The reaction mixture was poured into Na$_2$CO$_3$ aqueous solution (10%, 20 mL) and stirred for 20 min. The aqueous layer was extracted with dichloromethane (15 mL×3). The combined organic layers were washed with brine, dried over Na$_2$SO$_4$ and concentrated. The crude was purified by column chromatography (DCM:MeOH=30:1) to give the title compound (200 mg, yield 62%) as a yellow solid.

LC-MS: (mobile phase: from 40% water and 60% CH$_3$CN to 5% water and 95% CH$_3$CN in 3 min), Rt=0.97 min; MS Calcd.: 307, MS Found: 308 [M+H]$^+$.

Description D34 and D35

6-(3,3-Difluoro-1-(oxetan-3-yl)piperidin-4-yl)-5-methyl-1H-indazole (Enantiomer 1) (D34) and 6-(3,3-difluoro-1-(oxetan-3-yl)piperidin-4-yl)-5-methyl-1H-indazole (Enantiomer 2) (D35)

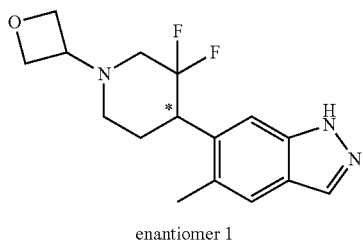
enantiomer 1
D34

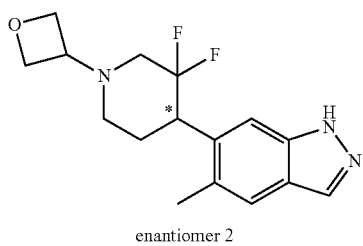
enantiomer 2
D35

The racemate 6-(3,3-difluoro-1-(oxetan-3-yl)piperidin-4-yl)-5-methyl-1H-indazole (300 mg, 0.98 mmol) was separated by chiral HPLC (Chiralpak IB 5 μm 4.6×250 mm; phase: Hex/EtOH=50/50; flow rate: 1.0 mL/min) to give 6-(3,3-difluoro-1-(oxetan-3-yl)piperidin-4-yl)-5-methyl-1H-indazole (enantiomer 1) (D34) (80 mg, Rt=9.1 min, yield 27%) and 6-(3,3-difluoro-1-(oxetan-3-yl)piperidin-4-yl)-5-methyl-1H-indazole (enantiomer 2) (D35) (90 mg, Rt=12.0 min, yield 30%) both as white solid.

D34: $^1$H NMR (300 MHz, CDCl$_3$): δ 10.00 (s, 1H), 7.98 (s, 1H), 7.57 (s, 2H), 4.74-4.66 (m, 4H), 3.77-3.68 (m, 1H), 3.45-3.29 (m, 1H), 3.19-3.10 (m, 1H), 3.02-2.97 (m, 1H), 2.46 (s, 3H), 2.41-2.13 (m, 3H), 1.96-1.88 (m, 1H).

D35: $^1$H NMR (300 MHz, CDCl$_3$): δ 10.00 (s, 1H), 7.98 (s, 1H), 7.57 (s, 2H), 4.74-4.66 (m, 4H), 3.77-3.68 (m, 1H), 3.46-3.29 (m, 1H), 3.19-3.09 (m, 1H), 3.02-2.97 (m, 1H), 2.46 (s, 3H), 2.41-2.13 (m, 3H), 1.94-1.90 (m, 1H).

Description D36

6-Bromo-5-methyl-1-((2-(trimethylsilyl)ethoxy)methyl)-1H-indazole (D36)

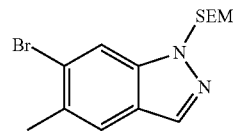

To a solution of 6-bromo-5-methyl-1H-indazole (22.0 g, 104 mmol) in DMF (100 mL) was added NaH (8.32 g, 208 mmol, 60% in material oil) at 0° C. After the mixture was stirred at 0° C. for 30 min, SEMCl (26.0 g, 208 mmol) was added and the resulting mixture was stirred at 0° C. for 2 hrs. Then the mixture was stirred at rt for 1 hrs. To the reaction mixture was added ice-water (400 mL) and extracted with ethyl acetate (2×300 mL). The combined organic layers were washed with water (100 mL) and brine (100 mL), dried over Na$_2$SO$_4$, filtered and concentrated. The residue was purified by column chromatography (petroleum ether:ethyl acetate=20:1) to give the title product (19.5 g, yield 55%) as a yellow oil.

$^1$H NMR (300 MHz, CDCl$_3$): δ 7.88 (s, 1H), 7.82 (s, 1H), 7.56 (s, 1H), 5.66 (s, 2H), 3.54-3.49 (m, 2H), 2.48 (s, 3H), 0.90-0.85 (m, 2H), 0.06 (s, 9H).

LCMS [mobile phase: 5-95% CH$_3$CN in 4 min]: Rt=3.141 min; MS Calcd: 340; MS Found: 341 [M+H]$^+$.

Description D37 tert-Butyl 4-(5-methyl-1-((2-(trimethylsilyl)ethoxy)methyl)-1H-indazol-6-yl)-5,6-dihydropyridine-1(2H)-carboxylate (D37)

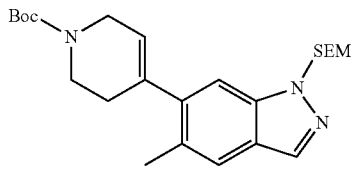 [SMILES: Cc1cc2cnn(COCC[Si](C)(C)C)c2cc1C1=CCN(C(=O)OC(C)(C)C)CC1]

To a solution of 6-bromo-5-methyl-1-((2-(trimethylsilyl)ethoxy)methyl)-1H-indazole (19.5 g, 57.2 mmol) in dioxane (400 mL) was added tert-butyl 4-(4,4,5,5-tetramethyl-1,3,2-dioxaborolan-2-yl)-5,6-dihydropyridine-1(2H)-carboxylate (19.5 g, 62.9 mmol) and Na$_2$CO$_3$ (15.2 g, 143 mmol), water (80 mL) and Pd(dppf)Cl$_2$ (2.12 g, 2.86 mmol). The mixture was stirred at 80° C. overnight under N$_2$ atmosphere. The solvent was removed under vacuum and the residue was extracted EtOAc (2×200 mL). The combined organic layers were washed with water (100 mL) and brine (100 mL), dried over Na$_2$SO$_4$ and concentrated. The crude was purified by column chromatography (petroleum ether:ethyl acetate=10:1) to give the title compound (21.5 g, yield 85%) as a colorless oil.

$^1$H NMR (300 MHz, CDCl$_3$): 7.91 (s, 1H), 7.51 (s, 1H), 7.30 (s, 1H), 5.71 (s, 2H), 5.63 (br s, 1H), 4.08-4.07 (m, 2H), 3.68-3.64 (m, 2H), 3.55 (t, J=8.1 Hz, 2H), 2.40-2.37 (m, 5H), 1.52 (s, 9H), 0.89 (t, J=8.1 Hz, 2H), 0.06 (s, 9H).

LCMS [mobile phase: 5-95% CH$_3$CN in 4 min]: Rt=3.568 min; MS Calcd: 443; MS Found: 444 [M+H]$^+$.

Description D38

(trans)-tert-Butyl 3-hydroxy-4-(5-methyl-1-((2-(trimethylsilyl)ethoxy)methyl)-1H-indazol-6-yl)piperidine-1-carboxylate (D38)

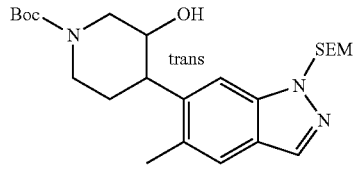 [SMILES: Cc1cc2cnn(COCC[Si](C)(C)C)c2cc1C1CCN(C(=O)OC(C)(C)C)CC1O]

To a solution of tert-butyl 4-(5-methyl-1-((2-(trimethylsilyl)ethoxy)methyl)-1H-indazol-6-yl)-5,6-dihydropyridine-1(2H)-carboxylate (16.0 g, 36.1 mmol) in THF (160 mL) was added BH$_3$-THF solution (1 M, 144 mL, 144 mmol) at 0° C. The mixture was warmed to rt and stirred overnight. The reaction mixture was cooled to 0° C. and NaOH (aq, 2 M, 54 mL, 108 mmol) was added carefully at 0° C. Then H$_2$O$_2$ (30%, 38.0 mL, 361 mmol) was added dropwise at 0° C. The mixture was stirred at rt for an hour. The mixture was poured into sat. Na$_2$S$_2$O$_3$ solution (400 mL) and extracted with EtOAc (300 mL×2). The combined organic layers were washed with brine (100 mL×2), dried over Na$_2$SO$_4$ and evaporated. The residue was purified by column chromatography (petroleum ether:ethyl acetate from 10:1 to 2:1) to give the title compound (10.0 g, yield 60%) as a white solid.

$^1$H NMR (300 MHz, CDCl$_3$): δ 7.89 (s, 1H), 7.55 (s, 1H), 7.42 (s, 1H), 5.66 (s, 2H), 4.50-4.42 (m, 1H), 4.27-4.18 (m, 1H), 3.97-3.89 (m, 1H), 3.56-3.51 (m, 2H), 3.04-2.96 (m, 1H), 2.84-2.68 (m, 2H), 2.49 (s, 3H), 1.85-1.80 (m, 1H), 1.73-1.67 (m, 1H), 1.50 (s, 9H), 0.89-0.84 (m, 2H), −0.08 (s, 9H).

LCMS [mobile phase: 5-95% CH$_3$CN in 4 min]: Rt=2.851 min; MS Calcd: 461; MS Found: 462 [M+H]$^+$.

Description D39

(cis)-tert-Butyl 3-fluoro-4-(5-methyl-1-((2-(trimethylsilyl)ethoxy)methyl)-1H-indazol-6-yl)piperidine-1-carboxylate (D39)

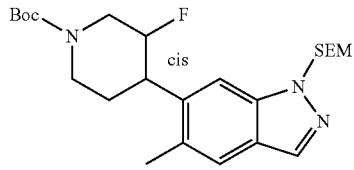 [SMILES: Cc1cc2cnn(COCC[Si](C)(C)C)c2cc1C1CCN(C(=O)OC(C)(C)C)CC1F]

To a solution of (trans)-tert-butyl 3-hydroxy-4-(5-methyl-1-((2-(trimethylsilyl)ethoxy)methyl)-1H-indazol-6-yl)piperidine-1-carboxylate (11.0 g, 23.7 mmol) in dry DCM (100 mL) was added DAST (11.4 g, 71.1 mmol) under N$_2$ at −78° C. The mixture was warmed to rt and stirred for 1 h. To the reaction mixture was added sat. NaHCO$_3$ solution (200 mL). The mixture was extracted with DCM (100 mL×2). The combined organic layers were washed with brine (100 mL), dried over Na$_2$SO$_4$ and evaporated. The crude was purified by column chromatography (petroleum ether:ethyl acetate from 10:1 to 5:1) to give the title compound (4.20 g, yield 38%) as a yellow oil.

$^1$H NMR (300 MHz, CDCl$_3$): δ 7.91 (s, 1H), 7.56 (s, 1H), 7.47 (s, 1H), 5.73 (s, 2H), 4.83-4.56 (m, 2H), 4.31-4.17 (m, 1H), 3.58-3.53 (m, 2H), 3.26-3.18 (m, 1H), 2.92-2.80 (m, 2H), 2.49 (s, 3H), 1.95-1.87 (m, 1H), 1.83-1.72 (m, 1H), 1.53 (s, 9H), 0.92-0.87 (m, 2H), −0.06 (s, 9H).

Description D40

(cis)-6-(3-Fluoropiperidin-4-yl)-5-methyl-1-((2-(trimethylsilyl)ethoxy)methyl)-1H-indazole (D40)

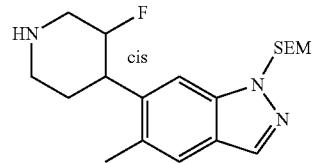 [SMILES: Cc1cc2cnn(COCC[Si](C)(C)C)c2cc1C1CCNCC1F]

To a solution of (cis)-tert-butyl 3-fluoro-4-(5-methyl-1-((2-(trimethylsilyl)ethoxy)methyl)-1H-indazol-6-yl)piperidine-1-carboxylate (2.60 g, 5.61 mmol) in dioxane (10 mL) was added sat. HCl/dioxane (20 mL). The mixture was stirred at rt for 30 min. The reaction mixture was poured into sat. NaHCO$_3$ solution (200 mL). The mixture was extracted with EtOAc (50 mL×3). The combined organic layers were washed with brine (50 mL×2), dried over Na$_2$SO$_4$ and concentrated to give the title compound (1.9 g, yield 93%) as yellow oil.

LCMS: (mobile phase: 5-95% Acetonitrile in 3 min), Rt=2.12 min; MS Calcd: 363; MS Found: 364 (M+1)$^+$.

Description D41, D42 and D43

(cis)-6-(3-Fluoro-1-(2-methoxyethyl)piperidin-4-yl)-5-methyl-1-((2-(trimethylsilyl)ethoxy)methyl)-1H-indazole (D41), (cis)-6-(3-Fluoro-1-(2-methoxyethyl)piperidin-4-yl)-5-methyl-1-((2-(trimethylsilyl)ethoxy)methyl)-1H-indazole (Enantiomer 1) (D42) and (cis)-6-(3-Fluoro-1-(2-methoxyethyl)piperidin-4-yl)-5-methyl-1-((2-(trimethylsilyl)ethoxy)methyl)-1H-indazole (Enantiomer 2) (D43)

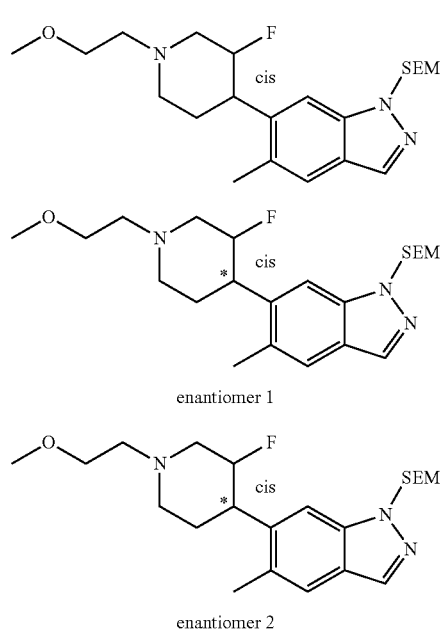

To a solution of (cis)-6-(3-Fluoropiperidin-4-yl)-5-methyl-1-((2-(trimethylsilyl)ethoxy)methyl)-1H-indazole (1.60 g, 4.41 mmol) in CH₃CN (20 mL) was added 1-bromo-2-methoxy-ethane (1.23 g, 8.82 mmol) and K₂CO₃ (1.22 g, 8.82 mmol). Then the mixture was heated to 60° C. and stirred overnight. The reaction mixture was cooled to rt and filtered. The organic layer was concentrated. The residue was purified by column chromatography (petroleum ether:ethyl acetate=2:1) to give crude product (720 mg). The crude product was purified by prep-TLC (petroleum ether:ethyl acetate=1:1) to give the tiled compound (cis)-6-(3-fluoro-1-(2-methoxyethyl)piperidin-4-yl)-5-methyl-1-((2-(trimethylsilyl)ethoxy)methyl)-1H-indazole (D41) (520 mg, yield 28%) as yellow oil. The product (cis)-6-(3-fluoro-1-(2-methoxyethyl)piperidin-4-yl)-5-methyl-1-((2-(trimethylsilyl)ethoxy)methyl)-1H-indazole (D41) was separated by chiral prep-HPLC (Chiralpak AD-3 33 μm 4.6×150 mm, Phase: Hex/EtOH=95/5, flowrate: 1 mL/min, temperature: 30° C.) to give (cis)-6-(3-Fluoro-1-(2-methoxyethyl)piperidin-4-yl)-5-methyl-1-((2-(trimethylsilyl)ethoxy)methyl)-1H-indazole (enantiomer 1) (D42) (Rt: 4.501 min, 230 mg, yield 12%) as a yellow oil and (cis)-6-(3-Fluoro-1-(2-methoxyethyl)piperid in-4-yl)-5-methyl-1-((2-(trimethylsilyl)ethoxy)methyl)-1H-indazole (enantiomer 2) (D43) (Rt: 7.828 min, 230 mg, yield 12%) as a yellow oil.

D41: ¹H NMR (400 MHz, CDCl₃): δ 7.88 (s, 1H), 7.53 (s, 1H), 7.51 (s, 1H), 5.68 (s, 2H), 5.01-4.83 (m, 1H), 3.56-3.46 (m, 5H), 3.39 (s, 3H), 3.10-2.99 (m, 2H), 2.74-2.68 (m, 2H), 2.46 (s, 3H), 2.28-2.17 (m, 2H), 1.91-1.90 (m, 2H), 0.87 (t, J=8.0 Hz, 2H), −0.07 (s, 9H).

LCMS: (mobile phase: 5-95% Acetonitrile in 2.5 min), Rt=1.72 min; MS Calcd: 421. MS Found: 422 [M+1]⁺.

Description D44

(cis)-6-(3-Fluoro-1-(2-methoxyethyl)piperidin-4-yl)-5-methyl-1H-indazole (Enantiomer 1) (D44)

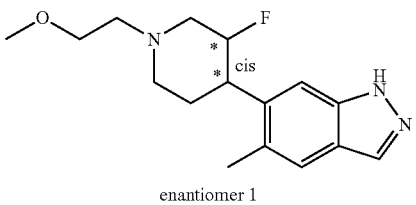 [SMILES: COCCN1CCC(c2cc3[nH]ncc3cc2C)C(F)C1]

enantiomer 1

A solution of (cis)-6-(3-Fluoro-1-(2-methoxyethyl)piperidin-4-yl)-5-methyl-1-((2-(trimethylsilyl)ethoxy)methyl)-1H-indazole (enantiomer 1) (230 mg, 0.546 mmol) in dioxane (4 mL) was added con. HCl (2 mL). The reaction mixture was stirred at rt for 1 h. The reaction mixture was poured into sat. NaHCO₃ solution (60 mL). The mixture was extracted with EtOAc (20 mL×3). The combined organic layers were washed with brine (20 mL), dried over Na₂SO₄ and concentrated. The residue was dissolved in NH₃—CH₃OH (10 mL, 5 M) and stirred overnight. The mixture was concentrated to give the title compound (160 mg, yield 100%) as white solid.

LCMS: (mobile phase: 5-95% Acetonitrile in 2.5 min), Rt=1.48 min; MS Calcd: 291. MS Found: 292 [M+1]⁺.

Description D45

(cis)-6-(3-Fluoro-1-(2-methoxyethyl)piperidin-4-yl)-5-methyl-1H-indazole (Enantiomer 2) (D45)

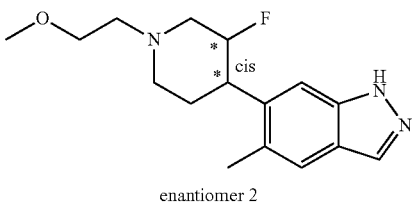 [SMILES: COCCN1CCC(c2cc3[nH]ncc3cc2C)C(F)C1]

enantiomer 2

A solution of (cis)-6-(3-fluoro-1-(2-methoxyethyl)piperidin-4-yl)-5-methyl-1-((2-(trimethylsilyl)ethoxy)methyl)-1H-indazole (enantiomer 2) (230 mg, 0.546 mmol) in dioxane (4 mL) was added con. HCl (2 mL). The reaction mixture was stirred at rt for 1 h. The reaction mixture was poured into sat. NaHCO₃ solution (60 mL). The mixture was extracted with EtOAc (20 mL×3). The combined organic layers were washed with brine (20 mL), dried over Na₂SO₄ and concentrated. The residue was dissolved in NH₃—CH₃OH (10 mL, 5 M) and stirred overnight. The mixture was concentrated to give the title compound (160 mg, yield 100%) as a white solid.

LCMS: (mobile phase: 5-95% Acetonitrile in 2.5 min), Rt=1.40 min; MS Calcd: 291. MS Found: 292 [M+1]⁺.

Description D46

(cis)-tert-Butyl 3-fluoro-4-(5-methyl-1-(tetrahydro-2H-pyran-2-yl)-1H-indazol-6-yl) piperidine-1-carboxylate (D46)

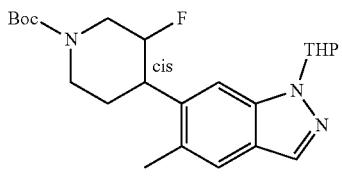

To a solution of (trans)-tert-butyl 3-hydroxy-4-(5-methyl-1-(tetrahydro-2H-pyran-2-yl)-1H-indazol-6-yl)piperidine-1-carboxylate (24.5 g, 59.0 mmol) in dry DCM (200 mL) was added DAST (38.0 g, 236 mmol) under $N_2$ at −65° C. The mixture was gradually warmed to rt and stirred for 2 hrs. The reaction mixture was carefully poured into $Na_2CO_3$ aqueous solution (10%, 300 mL) and stirred for 20 min. The organic layer was separated and the aqueous was extracted with DCM (250 mL×2). The combined organic layers were washed with brine, dried over $Na_2SO_4$ and evaporated. The crude was purified by column chromatography (PE:EtOAc=10:1) to give the title compound (11.8 g, yield 48%) as a white solid.

$^1$H NMR (400 MHz, CDCl$_3$): δ 7.92 (s, 1H), 7.52 (s, 1H), 7.41 (s, 1H), 5.74-5.67 (m, 1H), 4.80-4.59 (m, 2H), 4.21 (br s, 1H), 4.07-3.99 (m, 1H), 3.80-3.71 (m, 1H), 3.25-3.19 (m, 1H), 2.89-2.79 (m, 2H), 2.65-2.51 (m, 1H), 2.45 (s, 3H), 2.19-2.15 (m, 1H), 2.15-2.04 (m, 1H), 1.93-1.88 (m, 1H), 1.80-1.74 (m, 5H), 1.52 (s, 9H).

LCMS: 5-95% CH$_3$CN, Rt=2.25 min in 3 min; MS Calcd: 417; MS Found: 418 (M+1)$^+$.

Description D47

((cis)-6-(3-Fluoropiperidin-4-yl)-5-methyl-1-(tetrahydro-2H-pyran-2-yl)-1H-indazole (D47)

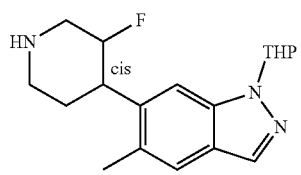

To a solution of (cis)-tert-butyl 3-fluoro-4-(5-methyl-1-(tetrahydro-2H-pyran-2-yl)-1H-indazol-6-yl) piperidine-1-carboxylate (1.60 g, 3.84 mmol) in CH$_3$OH (10 mL) was added HCl/CH$_3$OH (5 M, 20 mL). The mixture was stirred at 0° C. for 1 h. The reaction mixture was poured into sat. NaHCO$_3$ solution (200 mL). The mixture was extracted with EtOAc (50 mL×3). The combined organic layers were washed with brine (50 mL), dried over Na$_2$SO$_4$ and concentrated. The residue was purified by column C18 (5%-60% CH$_3$CN in water) to give the title compound (600 mg, yield 49%) as a yellow oil.

LCMS: (mobile phase: 5-95% Acetonitrile in 2.5 min), Rt=1.46 min; MS Calcd: 317; MS Found: 318 [M+1]$^+$.

Description D48

(cis)-6-(3-Fluoro-1-(2-methoxyethyl)piperidin-4-yl)-5-methyl-1-(tetrahydro-2H-pyran-2-yl)-1H-indazole (D48)

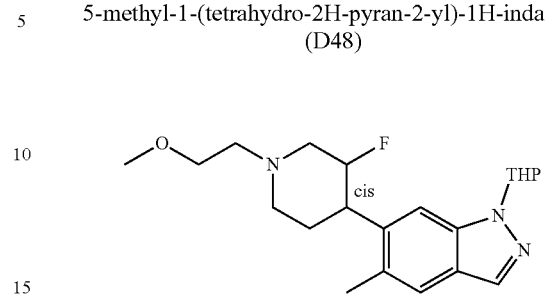

To a solution of (cis)-6-(3-fluoropiperidin-4-yl)-5-methyl-1-(tetrahydro-2H-pyran-2-yl)-1H-indazole (600 mg, 1.89 mmol) in CH$_3$CN (5 mL) was added 1-bromo-2-methoxy-ethane (525 mg, 3.78 mmol) and K$_2$CO$_3$ (521 mg, 3.78 mmol). Then the mixture was heated to 60° C. under microwave for 1.5 h. The mixture was concentrated. The residue was purified by prep-TLC (PE:EtOAc=1:1) to give the title compound (500 mg, yield 71%) as a yellow oil.

$^1$H NMR (300 MHz, CDCl$_3$): δ 7.90 (s, 1H), 7.55 (d, =8.4 Hz, 1H), 7.49 (s, 1H), 5.67-5.64 (m, 1H), 5.10-4.87 (m, 1H), 4.05-4.02 (m, 1H), 3.78-3.71 (m, 1H), 3.61-3.50 (m, 3H), 3.38 (s, 3H), 3.15-3.03 (m, 2H), 2.84-2.79 (m, 2H), 2.60-2.52 (m, 1H), 2.44 (s, 3H), 2.31-1.95 (m, 7H), 1.79-1.72 (m, 2H).

LCMS: (mobile phase: 5-95% acetonitrile in 2.5 min), Rt=1.66 min; MS Calcd: 375. MS Found: 376 [M+1]$^+$.

Description D49

(cis)-6-(3-Fluoro-1-(2-methoxyethyl)piperidin-4-yl)-5-methyl-1H-indazole (D49)

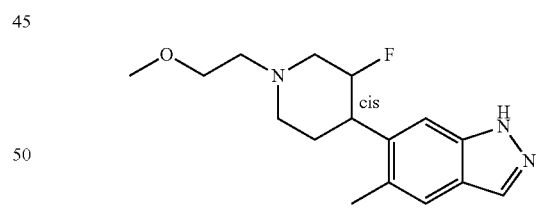

A solution of (cis)-6-(3-fluoro-1-(2-methoxyethyl)piperidin-4-yl)-5-methyl-1-(tetrahydro-2H-pyran-2-yl)-1H-indazole (500 mg, 1.33 mmol) in dioxane (4 mL) was added con. HCl (8 mL). The reaction mixture was stirred at rt for 1 h. The reaction mixture was poured into sat. NaHCO$_3$ solution (200 mL). The mixture was extracted with EtOAc (50 mL×3). The combined organic layers were washed with brine (50 mL), dried over Na$_2$SO$_4$ and concentrated to give the title compound (350 mg, yield 90%) as a white solid.

LCMS: (mobile phase: 5-95% acetonitrile in 2.5 min), Rt=1.49 min; MS Calcd: 291. MS Found: 292 [M+1]$^+$.

Description D50 and D51

(cis)-6-(3-Fluoro-1-(2-methoxyethyl)piperidin-4-yl)-5-methyl-1H-indazole (Enantiomer 1') (D50) and (cis)-6-(3-Fluoro-1-(2-methoxyethyl)piperidin-4-yl)-5-methyl-1H-indazole (Enantiomer 2') (D51)

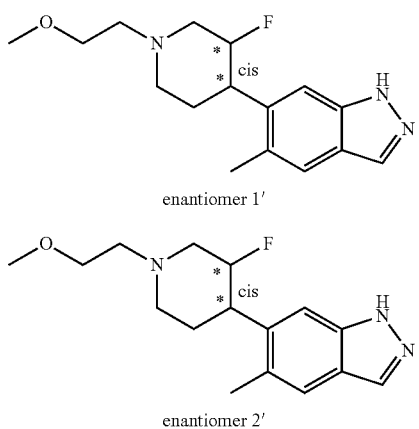

(cis)-6-(3-Fluoro-1-(2-methoxyethyl)piperidin-4-yl)-5-methyl-1H-indazole (350 mg, 1.20 mmol) was separated by chiral prep-HPLC with the method (Chiralpak IC 33 μm 4.6×250 mm, Phase: Hex/EtOH=70/30, flowrate: 1 mL/min, temperature: ambient) to give (cis)-6-(3-Fluoro-1-(2-methoxyethyl)piperidin-4-yl)-5-methyl-1H-indazole (enantiomer 1') (D50) (100 mg, yield 29%, Rt: 11.255 min, 100% ee) as a white solid and (cis)-6-(3-fluoro-1-(2-methoxyethyl)piperidin-4-yl)-5-methyl-1H-indazole (enantiomer 2') (D51) (100 mg, yield 29%, Rt: 13.747 min, 99.3% ee) as a white solid.

D50: LCMS: (mobile phase: 5-95% Acetonitrile in 2.5 min), Rt=1.50 min; MS Calcd: 291 MS Found: 292 [M+1]$^+$.

D51: LCMS: (mobile phase: 5-95% Acetonitrile in 2.5 min), Rt=1.49 min; MS Calcd: 291 MS Found: 292 [M+1]$^+$.

Description D52

1-Benzhydryl-3-((tetrahydro-2H-pyran-2-yl)oxy)azetidine (D52)

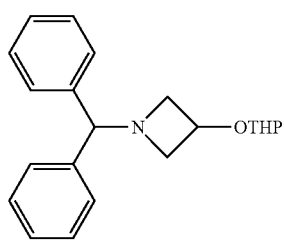

To a solution of 1-benzhydrylazetidin-3-ol, hydrochloride (5 g, 18.13 mmol) in DCM (50 mL) was added PPTS (2.278 g, 9.07 mmol) and DHP (6.63 mL, 72.5 mmol). The reaction solution was stirred at room temperature for 16 hours. After concentration, the residue was purified by silica gel column chromatography (30-50% MeOH in PE) to give 1-benzhydryl-3-((tetrahydro-2H-pyran-2-yl)oxy)azetidine (5 g, 15.46 mmol, 85% yield).

LCMS: (mobile phase: 5-95% Acetonitrile), Rt=2.76 min in 5 min; MS Calcd: 323; MS Found: 324 [M+1]$^+$.

Description D53

3-((Tetrahydro-2H-pyran-2-yl)oxy)azetidine (D53)

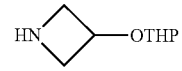

A mixture of 1-benzhydryl-3-((tetrahydro-2H-pyran-2-yl)oxy)azetidine (1 g, 3.09 mmol) and Pd—C (3.29 g, 3.09 mmol) and methanol (15 mL) was stirred under hydrogen balloon atmosphere at room temperature for 16 hours. After filtration, the filtrate was concentrated to give 3-((tetrahydro-2H-pyran-2-yl)oxy)azetidine (450 mg, 2.86 mmol, 93% yield) as a crude product.

LCMS: (mobile phase: 5-95% CH$_3$CN), Rt=0.63 min in 5 min; MS Calcd: 157; MS Found: 158 [M+1]$^+$.

Description D54

2-Chloro-5-(methoxymethoxy)pyridine (D54)

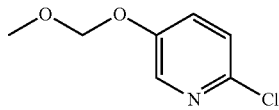

To a solution of 6-chloropyridin-3-ol (5.0 g, 38.5 mmol) and N,N-diisopropylethylamine (9.92 g, 76.9 mmol) in anhydrous DCM (120 mL) at 0° C. under an atmosphere of nitrogen was added methyl chloromethyl ether (6.15 g, 76.9 mmol) dropwise. The resulting mixture was allowed to warm to room temperature overnight. The reaction mixture was extracted with DCM and washed with sat NaHCO$_3$ several times. The organic phase was combined, washed with brine, dried over Na$_2$SO$_4$ and concentrated in vacuum to give the crude product which was purified by column eluting with PE/EtOAc (10:1 to 7:1) to give the title compound (4.16 g, 63%) as yellow oil.

$^1$H NMR (300 MHz, CDCl$_3$): 8.15 (d, J=2.7 Hz, 1H), 7.34 (dd, J=8.4, 3.0 Hz 1H) 7.21 (d, J=9.0 Hz, 1H), 5.16 (s, 2H), 3.47 (s, 3H).

LC-MS: (mobile phase: from 90% water (0.02% NH$_4$Ac) and 10% CH$_3$CN to 5% water (0.02% NH$_4$Ac) and 95% CH$_3$CN in 6.5 min, purity is >95%, Rt=3.642 min; MS Calcd.: 173, MS Found: 174 [M+H]$^+$.

Description D55

2-Chloro-4-iodo-5-(methoxymethoxy)pyridine (D55)

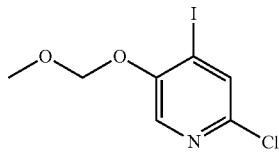

nBuLi (7.92 mL, 15.84 mmol) was added dropwise over 30 min to a cooled −78° C. solution of 2-chloro-5-(methoxymethoxy)pyridine (2.5 g, 14.40 mmol) dissolved in THF (50 mL). The reaction mixture was stirred for 1 h at −78° C. A solution of iodine (4.39 g, 17.28 mmol) in THF (5 mL) was added and the reaction was warmed to room temperature and stirred for 16 hours. The reaction was quenched with sat. NH₄Cl and sodium thiofulfite was added. The mixture was stirred for 30 min and then extracted with ethyl acetate. The organic extracts were washed with sodium thiosulfite, dried over sodium sulphate, filtered and concentrated. Purification by silica gel chromatography (20-30% EA in PE) gave 2-chloro-4-iodo-5-(methoxymethoxy)pyridine (3.9 g, 13.02 mmol, 90% yield).

LCMS: (mobile phase: 5-95% Acetonitrile), Rt=3.29 min in 5 min; MS Calcd: 299; MS Found: 300 [M+1]⁺.

Description D56

6-Chloro-4-iodopyridin-3-ol (D56)

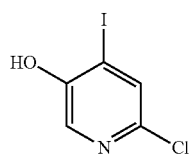

To a solution of 2-chloro-4-iodo-5-(methoxymethoxy)pyridine (3.9 g, 13.02 mmol) and methanol (30 mL) was added aq. concentrated HCl (0.989 mL, 32.6 mmol). The reaction solution was heated to reflux for 4 h, allowed to cool to room temperature, and concentrated in vacuo, the residue 6-chloro-4-iodopyridin-3-ol (3.33 g, 13.02 mmol, 100% yield) was used directly without further purification.

LCMS: (mobile phase: 5-95% acetonitrile), Rt=2.71 min in 5 min; MS Calcd: 255; MS Found: 256 [M+1]⁺.

Description D57

2-Chloro-4-iodo-5-methoxypyridine (D57)

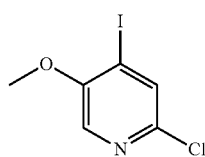

6-Chloro-4-iodopyridin-3-ol (3.3 g, 12.92 mmol) was dissolved in DMF (30 mL) and treated with potassium carbonate (12.50 g, 90 mmol), followed by methyl iodide (1.212 mL, 19.38 mmol). The reaction mixture was stirred at room temperature for 16 hours. The mixture was poured into 20% aqueous citric acid and extracted with ethyl acetate. The organic extracts were washed with water, brine, dried over Na₂SO₄ and concentrated. Purification by silica gel chromatography (20-25% EA in PE) gave 2-chloro-4-iodo-5-methoxypyridine (2.8 g, 10.39 mmol, 80% yield).

¹H NMR (400 MHz, DMSO-d₆): δ 8.05 (1H, s), 7.97 (1H, s), 3.95 (3H, m)

LCMS: (mobile phase: 5-95% CH₃CN), Rt=3.18 min in 5 min; MS Calcd: 269; MS Found: 270 [M+1]⁺.

Description D58

2-Chloro-5-methoxy-4-(3-((tetrahydro-2H-pyran-2-yl)oxy)azetidin-1-yl)pyridine (D58)

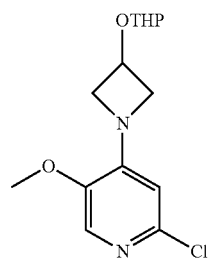

A mixture of 3-((tetrahydro-2H-pyran-2-yl)oxy)azetidine (210 mg, 1.336 mmol), 2-chloro-4-iodo-5-methoxypyridine (300 mg, 1.113 mmol), 18-crown-6 (294 mg, 1.113 mmol), potassium carbonate (308 mg, 2.227 mmol) and DMA (5 mL) was irradiated by microwave to 180° C. for 4 hours, then diluted with ethyl acetate, washed with water, brine, dried over sodium sulfite, concentrated and purified by C18 column (0.5% TFA in water, water/acetonitrile) to give 2-chloro-5-methoxy-4-(3-((tetrahydro-2H-pyran-2-yl)oxy)azetidin-1-yl)pyridine (200 mg, 0.669 mmol, 60.1% yield).

¹H NMR (400 MHz, DMSO-d₆): δ 7.69 (1H, s) 6.29 (1H, s) 4.64 (1H, m) 4.56 (1H, m) 4.28 (2H, m) 3.90 (2H, dt) 3.78 (4H, m) 3.46 (1H, dd) 1.68 (2H, m) 1.47 (4H, m)

LCMS: (mobile phase: 5-95% Acetonitrile), Rt=2.42 min in 5 min; MS Calcd: 298; MS Found: 299 [M+1]⁺.

Description D59

(cis)-6-(3-Fluoropiperidin-4-yl)-5-methyl-1H-indazole hydrochloride (D59)

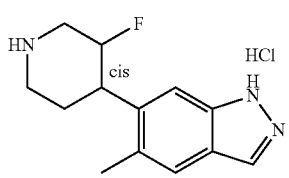 [SMILES: Cc1cc2cn[nH]c2cc1C1CCNCC1F ; Cl]

A mixture of (cis)-tert-butyl 3-fluoro-4-(5-methyl-1-(tetrahydro-2H-pyran-2-yl)-1H-indazol-6-yl) piperidine-1-carboxylate (2.50 g, 6.00 mmol) in HCl/dioxane (6 mol/L, 40 mL) was stirred at rt for 6 hrs. The reaction mixture was cooled to 0° C. and filtered. The solid was washed with cold 1,4-dioxane (5 mL) to get the title compound (1.4 g, yield 100%) as a white solid which was used for next step directly.

LC-MS: 5-95% CH₃CN, Rt=1.73 min; MS Calcd.: 233, MS Found: 234 [M+H]⁺.

Description D60

(cis)-6-(3-Fluoro-1-(oxetan-3-yl)piperidin-4-yl)-5-methyl-1H-indazole (D60)

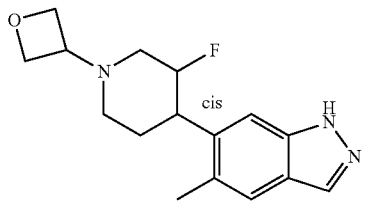

To a solution of (cis)-6-(3-fluoropiperidin-4-yl)-5-methyl-1H-indazole hydrochloride (1.40 g, 6.00 mmol) and oxetan-3-one (2.16 g, 30.0 mmol) in methanol (5 mL) and 1,2-dichloroethane (50 mL) was added NaBH$_3$CN (1.13 g, 18.0 mmol). Then the mixture was stirred at rt for 3 hrs. The reaction mixture was diluted with water (100 mL) and extracted with dichloromethane (100 mL×3). The combined organic layers were dried over MgSO$_4$, filtered and concentrated. The crude was purified by column chromatography (DCM:MeOH=30:1) to give the title compound (1.0 g, yield 57.6%) as a white solid.

LC-MS: 5%-95% CH$_3$CN, Rt=1.85 min; MS Calcd.: 289, MS Found: 290 [M+H]$^+$.

Description D61 and D62

(cis)-6-(3-Fluoro-(oxetan-3-yl)piperidin-4-yl)-5-methyl-1H-indazole (Enantiomer 1) (D61) and (cis)-6-(3-Fluoro-1-(oxetan-3-yl)piperidin-4-yl)-5-methyl-1H-indazole (Enantiomer 2) (D62)

enantiomer 1

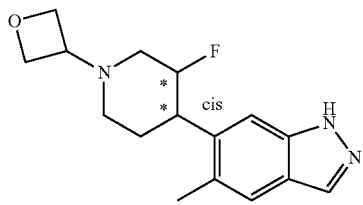 [SMILES: Cc1cc2cn[nH]c2cc1C1CCN(C2COC2)CC1F]
enantiomer 2

The racemate (cis)-6-(3-Fluoro-1-(oxetan-3-yl)piperidin-4-yl)-5-methyl-1H-indazole (1.20 g, 4.15 mmol) was separated by chiral HPLC (Chiralpak OJ-H 5 μm 4.6×250 mm; phase: Hex/EtOH=50/50; flow rate: 1.0 mL/min) to give (cis)-6-(3-fluoro-1-(oxetan-3-yl)piperidin-4-yl)-5-methyl-1H-indazole (enantiomer 1) (D61) (350 mg, Rt=8.07 min, yield 29%) and (cis)-6-(3-Fluoro-1-(oxetan-3-yl)piperidin-4-yl)-5-methyl-1H-indazole (enantiomer 2) (D62) (350 mg, Rt=14.21 min, yield 29%) both as white solid.

D61: $^1$H NMR (400 MHz, CDCl$_3$): δ 10.02 (br s, 1H), 7.97 (s, 1H), 7.56 (s, 1H), 7.45 (s, 1H), 4.95-4.76 (m, 1H), 4.73-4.69 (m, 2H), 4.69-4.64 (m, 2H), 3.66-3.63 (m, 1H), 3.26-3.23 (m, 1H), 3.15-3.07 (m, 1H), 2.84-2.81 (m, 1H), 2.46 (s, 3H), 2.13-2.08 (m, 1H), 2.07-1.93 (m, 2H), 1.86-1.83 (m, 1H).

D62: $^1$H NMR (400 MHz, CDCl$_3$): δ 10.02 (br s, 1H), 7.97 (s, 1H), 7.56 (s, 1H), 7.46 (s, 1H), 4.95-4.76 (m, 1H), 4.73-4.69 (m, 2H), 4.69-4.64 (m, 2H), 3.67-3.61 (m, 1H), 3.28-3.22 (m, 1H), 3.14-3.04 (m, 1H), 2.84-2.81 (m, 1H), 2.46 (s, 3H), 2.13-2.08 (m, 1H), 2.07-1.93 (m, 2H), 1.86-1.83 (m, 1H).

Description D63

(cis)-6-(3-Fluoro-1-methylpiperidin-4-yl)-5-methyl-1H-indazole (D63)

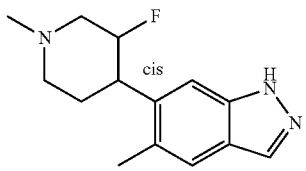 [SMILES: Cc1cc2cn[nH]c2cc1C1CCN(C)CC1F]

To a solution of (cis)-6-(3-fluoropiperidin-4-yl)-5-methyl-1H-indazole hydrochloride (2.1 g, crude, 6.2 mmol) in methanol (14 mL) was added CH$_2$O (37%, 14 mL) under ice bath. NaBH$_3$CN (1.2 g, 18.6 mmol) was followed. The reaction mixture was stirred at rt for 30 min. The reaction mixture was poured into Na$_2$CO$_3$ (10%, 150 mL) and stirred for 15 min. The aqueous was extracted with DCM (70 mL×3) and the combined organic layers were washed with brine, dried over Na$_2$SO$_4$ and concentrated. The crude was dissolved in NH$_3$/MeOH (5 M, 20 mL) and stirred overnight. LCMS showed the reaction completed. The reaction mixture was poured into water (150 mL) and the aqueous was extracted with DCM (50 mL×3). The combined organic layers were washed with brine, dried over Na$_2$SO$_4$ and concentrated. The crude was purified by column chromatography (DCM/MeOH=40/1) to give the title compound (1.04 g, yield 68%) as a white solid.

LCMS: 5-95% CH$_3$CN in 2.5 min; Rt=1.43 min, [M+H]$^+$= 248.

Description D64 and D65

(cis)-6-(3-Fluoro-1-methylpiperidin-4-yl)-5-methyl-1H-indazole (Enantiomer 1) (D64) and (cis)-6-(3-fluoro-1-methylpiperidin-4-yl)-5-methyl-1H-indazole (Enantiomer 2) (D65)

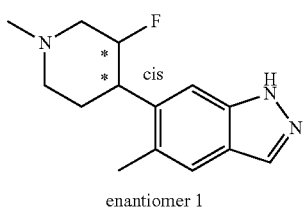
enantiomer 1

D65

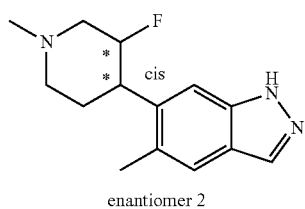

enantiomer 2

(cis)-6-(3-Fluoro-1-methylpiperidin-4-yl)-5-methyl-1H-indazole (1.2 g, 4.9 mmol) was separated by Chiral-HPLC (Chiralpak OJ-H 5 μm 4.6×250 mm, Phase: Hex/EtOH=80/20, flowrate: 1 mL/min, temperature: 30° C.) to give (cis)-6-(3-fluoro-1-methylpiperidin-4-yl)-5-methyl-1H-indazole (enantiomer 1) (D64) (430 mg, yield 36%, Rt=7.203 min, 100% ee) and (cis)-6-(3-fluoro-1-methylpiperidin-4-yl)-5-methyl-1H-indazole (enantiomer 2) (D65) (430 mg, yield 36%, Rt=12.351 min, 99.1% ee) both as white solid.

D64: $^1$H NMR (300 MHz, CDCl$_3$): δ 10.61 (br s, 1H), 7.97 (s, 1H), 7.56 (s, 1H), 7.44 (s, 1H), 5.01-5.76 (m, 1H), 3.40-3.34 (m, 1H), 3.14-3.01 (m, 1H), 2.97-2.93 (m, 1H), 2.47 (s, 6H), 2.27-2.10 (m, 2H), 1.98-1.79 (m, 2H).

D65: $^1$H NMR (300 MHz, CDCl$_3$): δ 10.92 (br s, 1H), 7.97 (s, 1H), 7.56 (s, 1H), 7.45 (s, 1H), 5.02-5.77 (m, 1H), 3.42-3.35 (m, 1H), 3.15-3.01 (m, 1H), 2.99-2.94 (m, 1H), 2.49 (s, 3H), 2.47 (s, 3H), 2.28-2.11 (m, 2H), 1.98-1.79 (m, 2H).

Description D66

1-(6-Chloro-2-methoxypyrimidin-4-yl)azetidin-3-ol (D66)

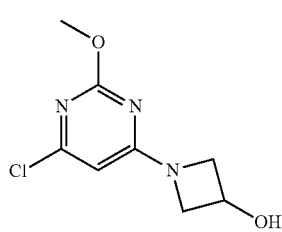

A suspension of 4,6-dichloro-2-methoxypyrimidine (1.0 g, 5.6 mmol), azetidin-3-ol hydrochloride (614 mg, 5.60 mmol) and TEA (1.70 g, 16.8 mmol) in i-PrOH (20 mL) was heated to 85° C. and stirred for 2 hrs. The solvent was removed under vacuum and the residue was partitioned with EtOAc (50 mL) and water (50 mL). The aqueous layer was extracted with EtOAc (30 mL×3) and the combined organic layers were washed with brine, dried over Na$_2$SO$_4$ and concentrated to give the title compound (1.17 g, yield 97%) as a white solid.

$^1$H NMR (400 MHz, CDCl$_3$): δ 5.86 (s, 1H), 4.84-4.79 (m, 1H), 4.34-4.30 (m, 2H), 3.98-3.95 (m, 2H), 3.92 (s, 3H), 3.13 (br s, 1H).

LCMS: 5-95% CH$_3$CN in 2.5 min; Rt=1.27 min, [M+H]$^+$=216.

Description D67

4-Chloro-2-methoxy-6-(3-((tetrahydro-2H-pyran-2-yl)oxy)azetidin-1-yl)pyrimidine (D67)

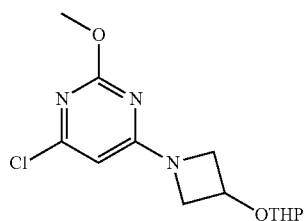

To a suspension of 1-(6-chloro-2-methoxypyrimidin-4-yl)azetidin-3-ol (500 mg, 2.32 mmol) in dry DCM (10 mL) was added DHP (390 mg, 4.64 mmol) and TsOH (79 mg, 0.46 mmol) at rt. The reaction mixture was stirred overnight. The reaction mixture was washed with Na$_2$CO$_3$ (10%, 40 mL) and then extracted with DCM (20 mL×3). The combined organic layers were washed with brine, dried over Na$_2$SO$_4$ and concentrated. The crude was purified by column chromatography (PE/EtOAc=5/1) to give the title compound (690 mg, yield 99%) as slight yellow oil.

$^1$H NMR (300 MHz, CDCl$_3$): δ 5.88 (s, 1H), 4.72-4.64 (m, 2H), 4.35-4.23 (m, 2H), 4.09-3.96 (m, 2H), 3.92 (s, 3H), 3.90-3.83 (m, 1H), 3.57-3.50 (m, 1H), 1.88-1.69 (m, 2H), 1.66-1.49 (m, 4H).

LCMS: 5-95% CH$_3$CN in 2.5 min; Rt=1.46 min, [M+H]$^+$=300.

Description D68

(cis)-tert-Butyl 3-fluoro-4-(5-methyl-1H-indazol-6-yl)piperidine-1-carboxylate (D68)

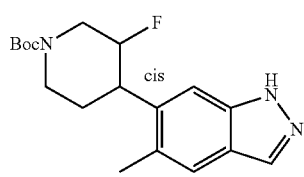 [SMILES: Cc1cc2cn[nH]c2cc1C1CCN(C(=O)OC(C)(C)C)CC1F]

To a solution of (cis)-6-(3-fluoropiperidin-4-yl)-5-methyl-1H-indazole hydrochloride (500 mg, 2.14 mmol) in CH$_3$OH (5 mL) and H$_2$O (1 mL) was added KOH (242 mg, 4.29 mmol) and (Boc)$_2$O (700 mg, 3.21 mmol) under ice bath. The reaction mixture was stirred at rt for 2 hrs. The reaction mixture was diluted with water (30 mL) and extracted with EtOAc (3×20 mL). The combined organic layers were concentrated. The residue was purified by column chromatograph (PE:EtOAc=20:1) to give the title compound (180 mg, yield 25%) as colorless oil.

$^1$H NMR (300 MHz, CDCl$_3$): δ 9.98 (s, 1H), 7.96 (s, 1H), 7.56 (s, 1H), 7.39 (s, 1H), 4.76-4.54 (m, 2H), 4.27-4.10 (m, 1H), 3.25-3.14 (m, 1H), 2.91-2.76 (m, 2H), 2.48 (s, 3H), 1.97-1.84 (m, 1H), 1.71-1.62 (m, 1H), 1.51 (s, 9H).

Description D69 and D70

(cis)-tert-Butyl 3-fluoro-4-(5-methyl-1H-indazol-6-yl)piperidine-1-carboxylate (Enantiomer 1) (D69) and (cis)-tert-Butyl 3-fluoro-4-(5-methyl-1H-indazol-6-yl)piperidine-1-carboxylate (Enantiomer 2) (D70)

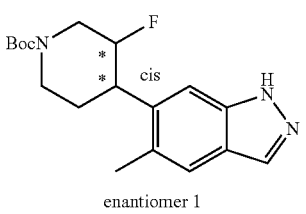

D69 enantiomer 1

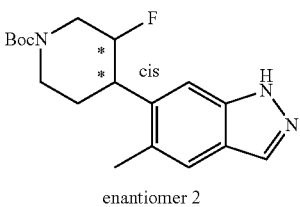

D70 enantiomer 2

(cis)-tert-Butyl 3-fluoro-4-(5-methyl-1H-indazol-6-yl)piperidine-1-carboxylate (140 mg, 0.420 mmol) was separated by chiral prep. HPLC with the method (Chiralpak IB 5 um 20*250 nm, Hex:i-PrOH=80:20, Flow: 20 mL/min, 205 nm, T=30° C.) to give (cis)-tert-butyl 3-fluoro-4-(5-methyl-1H-indazol-6-yl)piperidine-1-carboxylate (enantiomer 1) (D69) (68 mg, yield 48%) as a white solid and (cis)-tert-Butyl 3-fluoro-4-(5-methyl-1H-indazol-6-yl)piperidine-1-carboxylate (enantiomer 2) (D70) (47 mg, yield 33%) as a white solid.

D69: LCMS: (mobile phase: 5-95% acetonitrile in 2.5 min), Rt=1.64 min; MS Calcd: 333. MS Found: 332 [M−1]$^-$.

$^1$H NMR (300 MHz, CDCl$_3$): δ 10.07 (s, 1H), 7.97 (s, 1H), 7.56 (s, 1H), 7.39 (s, 1H), 4.78-4.53 (m, 2H), 4.32-4.12 (m, 1H), 3.26-3.13 (m, 1H), 2.93-2.75 (m, 2H), 2.47 (s, 3H), 1.94-1.79 (m, 1H), 1.69-1.60 (m, 1H), 1.49 (s, 9H).

Chiral HPLC: Chiralpak IB 5 μm 4.6×250 mm, Phase: Hex/IPA=80/20, flowrate: 1 mL/min, temperature: 30° C., Rt: 6.142 min, 100% ee.

D70: LCMS: (mobile phase: 5-95% Acetonitrile in 2.5 min), Rt=1.64 min; MS Calcd: 333 MS Found: 332 [M−1]$^-$.

$^1$H NMR (300 MHz, CDCl$_3$): δ 10.45 (s, 1H), 7.97 (s, 1H), 7.56 (s, 1H), 7.39 (s, 1H), 4.75-4.55 (m, 2H), 4.26-4.16 (m, 1H), 3.24-3.17 (m, 1H), 2.90-2.74 (m, 2H), 2.46 (s, 3H), 1.93-1.87 (m, 1H), 1.70-1.61 (m, 1H), 1.50 (s, 9H).

Chiral HPLC: Chiralpak IB 5 μm 4.6×250 mm, Phase: Hex/IPA=80/20, flowrate: 1 mL/min, temperature: 30° C., Rt: 7.671 min, 100% ee.

Description D71

4,6-Diiodo-2-methylpyrimidine (D71)

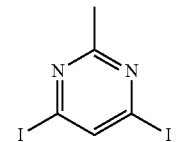

To a solution of NaI (11.9 g, 79.7 mmol) in HI (55%, 50 mL) was added 4,6-dichloro-2-methylpyrimidine (10.0 g, 61.3 mmol) in portions. The resulting suspension was heated to 40° C. and stirred for 1 hour. The reaction mixture was cooled and filtered. The solid was washed with water and then triturated with methanol (50 mL). The mixture was filtered to give the title compound (9.0 g, yield 42%) as white solid.

$^1$H NMR (400 MHz, CDCl$_3$): δ 8.07 (s, 1H), 2.67 (s, 3H).

LCMS: (mobile phase: 5-95% acetonitrile in 2.5 min), Rt=1.59 min, MS Calcd: 346; MS Found: 347 [M+H]$^+$.

Description D72

1-(6-Iodo-2-methylpyrimidin-4-yl)azetidin-3-ol (D72)

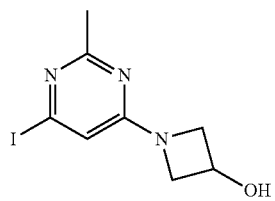

A suspension of 4,6-diiodo-2-methylpyrimidine (2.00 g, 5.80 mmol), azetidin-3-ol hydrochloride (700 mg, 6.38 mmol) and TEA (1.76 g, 17.4 mmol) in i-PrOH (12 mL) was heated to 75° C. and stirred for 1 h. The reaction mixture was concentrated and the residue was triturated with water (50 mL), filtered and dried to give the title compound (1.2 g, yield 71%) as white solid.

$^1$H NMR (400 MHz, DMSO-d$_6$): δ 6.69 (s, 1H), 5.79 (d, J=6.4 Hz, 1H), 4.59-4.52 (m, 1H), 4.22-4.18 (m, 2H), 3.72 (dd, J=9.6, 4.4 Hz, 2H), 2.29 (s, 3H).

LCMS: (mobile phase: 5-95% Acetonitrile in 2.5 min), Rt=1.18 min, MS Calcd: 291; MS Found: 292 [M+H]$^+$.

Description D73

4-Iodo-2-methyl-6-(3-((tetrahydro-2H-pyran-2-yl)oxy)azetidin-1-yl)pyrimidine (D73)

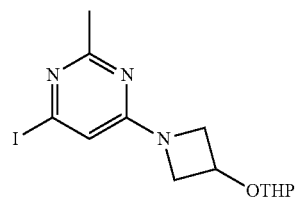

To a suspension of 1-(6-iodo-2-methylpyrimidin-4-yl) azetidin-3-ol (1.20 g, 4.12 mmol) in dry DCM (20 mL) was added DHP (1.38 g, 16.4 mmol) and TsOH (280 mg, 1.64 mmol) at rt.

The resulting mixture was heated to reflux and stirred for 20 hrs. The reaction mixture was diluted with DCM to 100 mL and then washed with $Na_2CO_3$ (sat., 50 mL) and brine, dried over $MgSO_4$ and concentrated. The crude was purified by column chromatography (PE:EtOAc=5:1) to give the title compound (1.5 g, yield 97%) as a colorless oil.

$^1$H NMR (300 MHz, CDCl$_3$): δ 6.48 (s, 1H), 4.70-4.60 (m, 2H), 4.33-4.18 (m, 2H), 4.08-3.92 (m, 2H), 3.90-3.80 (m, 1H), 3.57-3.48 (m, 1H), 2.45 (s, 3H), 1.89-1.69 (m, 2H), 1.64-1.49 (m, 4H).

LCMS: (mobile phase: 5-95% Acetonitrile in 2.5 min), Rt=1.59 min, MS Calcd: 375; MS Found: 376 [M+H]$^+$.

Description D74

(cis)-tert-Butyl 3-fluoro-4-(5-methyl-1-(2-methyl-6-(3-((tetrahydro-2H-pyran-2-yl)oxy)azetidin-1-yl) pyrimidin-4-yl)-1H-indazol-6-yl)piperidine-1-carboxylate (Enantiomer 1) (D74)

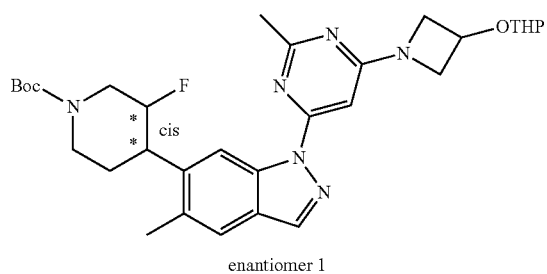

enantiomer 1

To a solution of (cis)-tert-butyl 3-fluoro-4-(5-methyl-1H-indazol-6-yl)piperidine-1-carboxylate (enantiomer 1) (83 mg, 0.25 mmol) in toluene (5 mL) was added 4-iodo-2-methyl-6-(3-((tetrahydro-2H-pyran-2-yl)oxy)azetidin-1-yl) pyrimidine (112 mg, 0.300 mmol), CuI (142 mg, 0.750 mmol), $K_3PO_4$ (159 mg, 0.750 mmol) and N,N'-dimethylcyclohexane-1,2-diamine (106 mg, 0.750 mmol). The mixture was refluxed for 2 hrs. The reaction mixture was cooled to rt and then poured into $NH_3.H_2O$ (5 mL) and extracted with EtOAc (10 mL×3). The combined organic layers were washed with water (10 mL) and brine (10 mL), dried over $Na_2SO_4$ and concentrated. The crude was purified by prep. HPLC (condition: from 65% water (0.1% TFA) and 35% $CH_3CN$ to 20% water (0.1% TFA) and 80% $CH_3CN$ in 20 min) to give the title compound (80 mg, yield 55%) as white solid.

LCMS: [mobile phase: 5-95% $CH_3CN$ in water in 3 min], Rt=2.38 min; MS Calcd: 580; MS Found: 581 [M+H]$^+$.

Description D75

(cis)-1-(6-(6-(3-Fluoropiperidin-4-yl)-5-methyl-1H-indazol-1-yl)-2-methylpyrimidin-4-yl)azetidin-3-ol hydrochloride (Enantiomer 1) (D75)

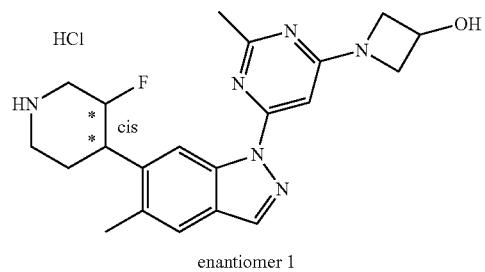 [SMILES: Cc1nc(N2CC(O)C2)cc(-n2ncc3cc(C)c(C4CCNCC4F)cc32)n1 ; Cl]

enantiomer 1

To a solution of (cis)-tert-butyl 3-fluoro-4-(5-methyl-1-(2-methyl-6-(3-((tetrahydro-2H-pyran-2-yl)oxy)azetidin-1-yl)pyrimidin-4-yl)-1H-indazol-6-yl)piperidine-1-carboxylate (enantiomer 1) (80 mg, 0.14 mmol) in methanol (5 mL) was added HCl/methanol (8 mol/L, 5 mL) and stirred at rt for 2 hrs. The reaction mixture was concentrated to give the title compound (80 mg, yield >100%) as a yellow solid.

$^1$H NMR (300 MHz, DMSO-d$_6$): δ 10.02 (br s, 1H), 9.46 (br s, 1H), 8.78 (s, 1H), 8.40 (s, 1H), 7.69 (s, 1H), 6.62 (s, 1H), 5.36-5.04 (m, 1H), 4.66-4.57 (m, 1H), 4.43-4.29 (m, 2H), 3.97-3.85 (m, 2H), 3.73-3.63 (m, 1H), 3.58-3.42 (m, 1H), 3.38-3.28 (m, 1H), 3.21-3.04 (m, 2H), 2.65 (s, 3H), 2.44 (s, 6H), 2.10-1.94 (m, 2H).

LCMS: [mobile phase: 5-95% $CH_3CN$ in water in 2.5 min], Rt=1.25 min; MS Calcd: 396; MS Found: 397[M+H]$^+$.

Description D76

(cis)-tert-Butyl 3-fluoro-4-(5-methyl-1-(2-methyl-6-(3-((tetrahydro-2H-pyran-2-yl)oxy)azetidin-1-yl) pyrimidin-4-yl)-1H-indazol-6-yl)piperidine-1-carboxylate (Enantiomer 2) (D76)

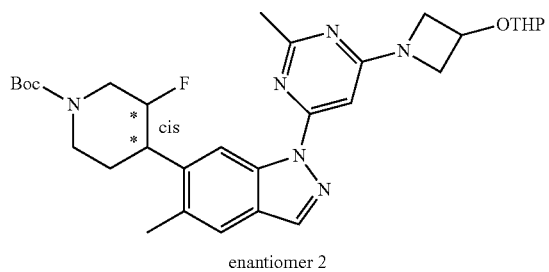

enantiomer 2

To a solution of (cis)-tert-butyl 3-fluoro-4-(5-methyl-1H-indazol-6-yl)piperidine-1-carboxylate (enantiomer 2) (83 mg, 0.25 mmol) in toluene (5 mL) was added 4-iodo-2-methyl-6-(3-((tetrahydro-2H-pyran-2-yl)oxy)azetidin-1-yl) pyrimidine (112 mg, 0.300 mmol), CuI (142 mg, 0.750 mmol), $K_3PO_4$ (159 mg, 0.750 mmol) and N,N'-dimethylcyclohexane-1,2-diamine (106 mg, 0.750 mmol). The mixture was refluxed for 2 hrs. The reaction mixture was cooled to rt and then poured into $NH_3.H_2O$ (5 mL) and extracted with EtOAc (10 mL×3). The combined organic layers were washed with water (10 mL) and brine (10 mL), dried over Na$_2$SO$_4$ and concentrated. The crude was purified by prep. HPLC (condition: from 65% water (0.1% TFA) and 35% CH$_3$CN to 20% water (0.1% TFA) and 80% CH$_3$CN in 20 min) to give the title compound (80 mg, yield 55%) as white solid.

LCMS: [mobile phase: 5-95% CH$_3$CN in water in 2.5 min], Rt=1.89 min; MS Calcd: 580; MS Found: 581 [M+H]$^+$.

Description D77

(cis)-1-(6-(6-(3-Fluoropiperidin-4-yl)-5-methyl-1H-indazol-1-yl)-2-methylpyrimidin-4-yl)azetidin-3-ol hydrochloride (Enantiomer 2) (D77)

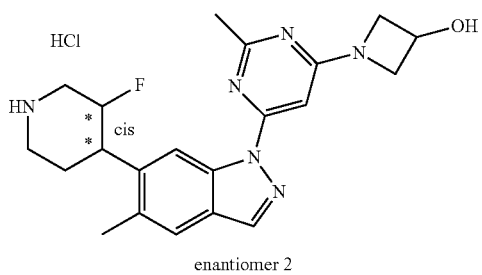 [SMILES: Cc1nc(N2CC(O)C2)cc(-n2ncc3cc(C)c(C4CCNCC4F)cc32)n1 ; Cl]

enantiomer 2

To a solution of (cis)-tert-butyl 3-fluoro-4-(5-methyl-1-(2-methyl-6-(3-((tetrahydro-2H-pyran-2-yl)oxy)azetidin-1-yl)pyrimidin-4-yl)-1H-indazol-6-yl)piperidine-1-carboxylate (enantiomer 2) (80 mg, 0.14 mmol) in methanol (5 mL) was added HCl/methanol (8 mol/L, 5 mL) and stirred at rt for 2 hrs. The reaction mixture was concentrated to give the title compound (80 mg, yield >100%) as a yellow solid.

$^1$H NMR (300 MHz, DMSO-d$_6$): δ 10.23 (brs, 1H), 9.50 (brs, 1H), 8.77 (s, 1H), 8.43 (s, 1H), 7.69 (s, 1H), 6.64 (s, 1H), 5.38-5.14 (m, 1H), 4.69-4.58 (m, 1H), 4.46-4.35 (m, 2H), 3.99-3.89 (m, 2H), 3.72-3.62 (m, 1H), 3.58-3.47 (m, 1H), 3.38-3.30 (m, 1H), 3.22-3.04 (m, 2H), 2.69 (s, 3H), 2.44 (s, 6H), 2.15-1.92 (m, 2H).

LCMS: [mobile phase: 5-95% CH$_3$CN in water in 2.5 min], Rt=1.20 min; MS Calcd: 396; MS Found: 397 [M+H]$^+$.

Description D78

5-(3-(Benzyloxy)cyclobutanecarbonyl)-2,2-dimethyl-1,3-dioxane-4,6-dione (D78)

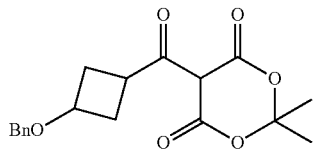 [SMILES: CC1(C)OC(=O)C(C(=O)C2CC(OCc3ccccc3)C2)C(=O)O1]

To a solution of 3-(benzyloxy)cyclobutanecarboxylic acid (5.00 g, 24.3 mmol), 2,2-dimethyl-1,3-dioxane-4,6-dione (3.84 g, 26.7 mmol) and DMAP (4.45 g, 36.5 mmol) in DCM (100 mL) was added EDCl (5.60 g, 29.2 mmol). The mixture was stirred at room temperature for 20 hrs. To the mixture was added KHSO$_4$ solution (5%, 100 mL). The mixture was stirred at room temperature for 10 min. The organic layer was separated and washed with KHSO$_4$ solution (5%, 50 mL×2) and brine (50 mL), dried over Na$_2$SO$_4$ and concentrated to give the desired compound (8.6 g, yield >100%) as a yellow oil.

$^1$H NMR (300 MHz, CDCl$_3$): δ 7.34-7.28 (m, 5H), 4.46 (s, 2H), 4.32-3.97 (m, 2H), 2.69-2.32 (m, 4H), 1.73 (s, 6H).

Description D79

Ethyl 3-(3-(benzyloxy)cyclobutyl)-3-oxopropanoate (D79)

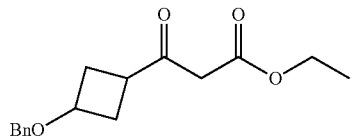 [SMILES: CCOC(=O)CC(=O)C1CC(OCc2ccccc2)C1]

To a solution of 5-(3-(benzyloxy)cyclobutanecarbonyl)-2,2-dimethyl-1,3-dioxane-4,6-dione (8.60 g, 25.9 mmol) in ethanol (80 mL) was refluxed for 2 hrs. The reaction mixture was cooled to rt and concentrated. The residue was purified by column chromatograph (PE:EtOAc=20:1) to give the title compound (6.2 g, yield 87%) as colorless oil.

$^1$H NMR (300 MHz, CDCl$_3$): δ 7.34-7.30 (m, 5H), 4.42-4.40 (m, 2H), 4.22-3.94 (m, 3H), 3.44-3.41 (m, 2H), 3.37-2.83 (m, 1H), 2.56-2.41 (m, 2H), 2.28-2.13 (m, 2H), 1.29-1.24 (m, 3H).

Description D80

6-(3-(Benzyloxy)cyclobutyl)-2-methylpyrimidin-4-ol (D80)

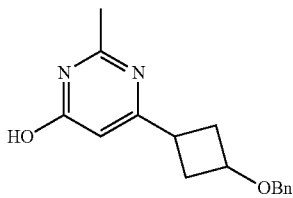 [SMILES: Cc1nc(O)cc(C2CC(OCc3ccccc3)C2)n1]

To a solution of CH$_3$ONa (1.17 g, 21.7 mmol) in CH$_3$OH (40 mL) was added acetimidamide hydrochloride (1.03 g, 10.9 mmol) at 0° C. Then ethyl 3-(3-(benzyloxy)cyclobutyl)-3-oxopropanoate (2.00 g, 7.25 mmol) was added to the mixture. The reaction mixture was stirred at rt for 2 hrs. Then the reaction mixture was refluxed for 6 hrs. The reaction mixture was cooled to rt and concentrated. The residue was dissolved in water (100 mL). To the mixture was added con. HCl solution to pH=5. The mixture was filtered and the solid was collected and dried. The solid was triturated with (PE:EtOAc=10:1, 20 mL) to give the title compound (1.42 g, yield 73%) as a white solid.

$^1$H NMR (300 MHz, CDCl$_3$): δ 13.12 (s, 1H), 7.35-7.29 (m, 5H), 6.20-6.16 (m, 1H), 4.46-4.44 (m, 2H), 4.36-3.97 (m, 1H), 3.40-2.80 (m, 1H), 2.64-2.55 (m, 1.5H), 2.47-2.42 (m, 4H), 2.17-2.12 (m, 1.5H).

Description D81 and D82

4-((1s,3s)-3-(Benzyloxy)cyclobutyl)-6-chloro-2-methylpyrimidine and 4-((1r,3r)-3-(benzyloxy)cyclobutyl)-6-chloro-2-methylpyrimidine

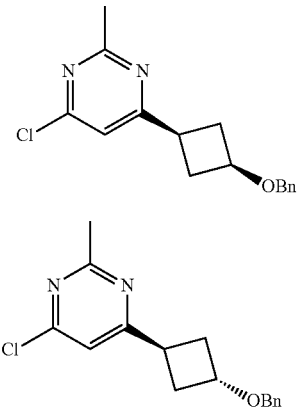

To a solution of 6-(3-(benzyloxy)cyclobutyl)-2-methylpyrimidin-4-ol (1.24 g, 4.59 mmol) in toluene (50 mL) was added TEA (556 mg, 5.51 mmol) and POCl₃ (843 mg, 5.51 mmol). The reaction mixture was refluxed for 2 hrs. The mixture was cooled to rt and poured into sat. NaHCO₃ solution (100 mL). The resulting mixture was extracted with EtOAc (50 mL×3). The combined organic layers were washed with brine (50 mL), dried over Na₂SO₄ and concentrated. The residue was purified by column chromatography (PE:EtOAc=20:1) to give the title compound cis-isomer (D81) (600 mg, yield 45%) as colorless oil and trans-isomer (D82) (200 mg, yield 15%) as colorless oil.

D81: $^1$H NMR (300 MHz, CDCl₃): δ 7.36-7.29 (m, 5H), 7.04 (s, 1H), 4.47 (s, 2H), 4.14-4.04 (m, 1H), 3.10-3.04 (m, 1H), 2.72-2.63 (m, 5H), 2.32-2.22 (m, 2H).

D82: $^1$H NMR (300 MHz, CDCl₃): δ 7.36-7.29 (m, 5H), 7.01 (s, 1H), 4.46 (s, 2H), 4.41-4.36 (m, 1H), 3.58-3.47 (m, 1H), 2.70 (s, 3H), 2.55-2.52 (m, 4H).

LC-MS: N/A.

Description D83

(cis)-tert-Butyl 4-(1-(6-((1s,3s)-3-(benzyloxy)cyclobutyl)-2-methylpyrimidin-4-yl)-5-methyl-1H-indazol-6-yl)-3-fluoropiperidine-1-carboxylate (Enantiomer 1) (D83)

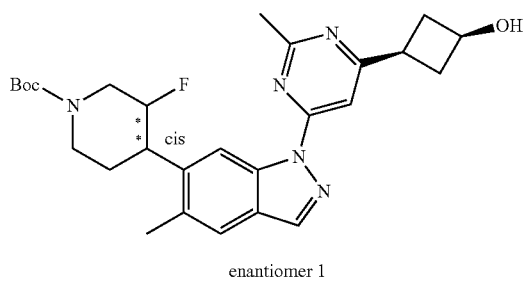 [SMILES: Cc1nc(-n2ncc3cc(C)c(C4CCN(C(=O)OC(C)(C)C)CC4F)cc32)cc([C@H]2C[C@@H](O)C2)n1]

enantiomer 1

To a solution of (cis)-tert-butyl 3-fluoro-4-(5-methyl-1H-indazol-6-yl)piperidine-1-carboxylate (enantiomer 1) (83 mg, 0.25 mmol) in toluene (5 mL) was added 4-((1s,3s)-3-(benzyloxy)cyclobutyl)-6-chloro-2-methylpyrimidine (144 mg, 0.500 mmol), CuI (142 mg, 0.750 mmol), K₃PO₄ (159 mg, 0.750 mmol) and N,N'-dimethyl-cyclohexane-1,2-diamine (106 mg, 0.750 mmol). The mixture was refluxed for 4 hrs. The reaction mixture was cooled to rt and then poured into NH₃·H₂O (30%, 5 mL) and extracted with EtOAc (10 mL×3). The combined organic layers were washed with water (10 mL) and brine (10 mL), dried over Na₂SO₄ and concentrated. The crude was purified by prep. HPLC (Condition: from 55% water (0.1% TFA) and 45% CH₃CN to 5% water (0.1% TFA) and 95% CH₃CN in 20 min) to give the title compound (60 mg, yield 41%) as a yellow solid.

$^1$H NMR (300 MHz, CDCl₃): δ 8.67 (s, 1H), 8.28 (s, 1H), 8.02 (s, 1H), 7.63 (s, 1H), 7.36-7.30 (m, 5H), 4.80-4.56 (m, 2H), 4.48 (s, 2H), 4.30-4.14 (m, 2H), 3.37-3.23 (m, 2H), 2.94-2.82 (m, 7H), 2.54 (s, 3H), 2.34-2.23 (m, 2H), 2.06-1.91 (m, 1H), 1.83-1.73 (m, 1H), 1.52 (s, 9H).

LC-MS: N/A.

Description D84

(cis)-tert-butyl 3-fluoro-4-(1-(6-((1s,3s)-3-hydroxycyclobutyl)-2-methylpyrimidin-4-yl)-5-methyl-1H-indazol-6-yl)piperidine-1-carboxylate (Enantiomer 1) (D84)

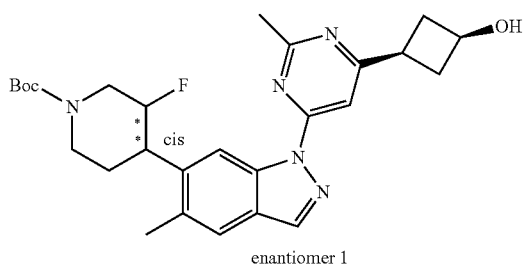 [SMILES: Cc1nc(-n2ncc3cc(C)c(C4CCN(C(=O)OC(C)(C)C)CC4F)cc32)cc([C@H]2C[C@@H](O)C2)n1]

enantiomer 1

To a solution of (cis)-tert-butyl 4-(1-(6-((1s,3s)-3-(benzyloxy)cyclobutyl)-2-methylpyrimidin-4-yl)-5-methyl-1H-indazol-6-yl)-3-fluoropiperidine-1-carboxylate (enantiomer 1) (60 mg, 0.10 mmol) in CH₃OH (3 mL) was added Pd/C (30 mg). The mixture was stirred at rt under H₂ (balloon) overnight. The mixture was filtered. The filtrate was concentrated to give the title compound (40 mg, yield 80%) as a yellow solid.

LCMS [mobile phase: 5-95% CH₃CN in 3 min]: Rt=2.03 min; MS Calcd: 495; MS Found: 496 [M+H]⁺.

Description D85

(cis)-(1s,3s)-3-(6-(6-(3-fluoropiperidin-4-yl)-5-methyl-1H-indazol-1-yl)-2-methylpyrimidin-4-yl)cyclobutanol hydrochloride (Enantiomer 1) (D85)

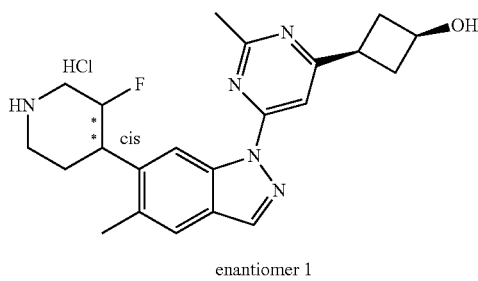 [SMILES: Cc1nc(-n2ncc3cc(C)c(C4CCNCC4F)cc32)cc([C@H]2C[C@@H](O)C2)n1 ; Cl]

enantiomer 1

To a solution of (cis)-tert-butyl 3-fluoro-4-(1-(6-((1s,3s)-3-hydroxycyclobutyl)-2-methyl pyrimidin-4-yl)-5-methyl-1H-indazol-6-yl)piperidine-1-carboxylate (enantiomer 1) (40 mg, 0.081 mmol) in CH$_3$OH (2.5 mL) was added HCl/CH$_3$OH (8 mol/L, 2.5 mL) at 0° C. The mixture was stirred at rt for 1 h. The reaction mixture was concentrated to give the title compound (35 mg, yield 100%) as a white solid.

LCMS [mobile phase: 5-95% CH$_3$CN in 3 min]: Rt=1.80 min; MS Calcd: 395; MS Found: 396 [M+H]$^+$.

Description D86

(cis)-tert-Butyl 4-(1-(6-((1s,3s)-3-(benzyloxy)cyclobutyl)-2-methylpyrimidin-4-yl)-5-methyl-1H-indazol-6-yl)-3-fluoropiperidine-1-carboxylate (Enantiomer 2) (D86)

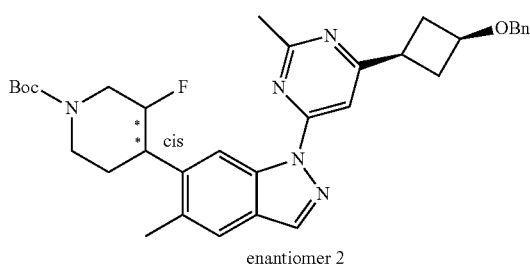 [SMILES: Cc1nc(-n2ncc3cc(C)c(C4CCN(C(=O)OC(C)(C)C)CC4F)cc32)cc([C@H]2C[C@@H](OCc3ccccc3)C2)n1]

enantiomer 2

To a solution of (cis)-tert-butyl 3-fluoro-4-(5-methyl-1H-indazol-6-yl)piperidine-1-carboxylate (enantiomer 2) (83 mg, 0.25 mmol) in toluene (5 mL) was added 4-((1s,3s)-3-(benzyloxy)cyclobutyl)-6-chloro-2-methylpyrimidine (144 mg, 0.500 mmol), CuI (142 mg, 0.750 mmol), K$_3$PO$_4$ (159 mg, 0.750 mmol) and N,N'-dimethyl-cyclohexane-1,2-diamine (106 mg, 0.750 mmol). The mixture was refluxed for 4 hrs. The reaction mixture was cooled to rt and then poured into NH$_3$.H$_2$O (30%, 5 mL) and extracted with EtOAc (10 mL×3). The combined organic layers were washed with brine (10 mL), dried over Na$_2$SO$_4$ and concentrated. The crude was purified by prep. HPLC (prep-HPLC: from 55% water (0.1% TFA) and 45% CH$_3$CN to 5% water (0.1% TFA) and 95% CH$_3$CN in 20 min) to give the title compound (60 mg, yield 41%) as a yellow solid.

$^1$H NMR (300 MHz, CDCl$_3$): δ 8.72 (s, 1H), 8.23 (s, 1H), 7.91 (s, 1H), 7.61 (s, 1H), 7.36-7.29 (m, 5H), 4.82-4.54 (m, 2H), 4.48 (s, 2H), 4.30-4.15 (m, 2H), 3.36-3.20 (m, 2H), 2.90-2.80 (m, 7H), 2.53 (s, 3H), 2.37-2.25 (m, 2H), 2.03-1.90 (m, 1H), 1.84-1.71 (m, 1H), 1.52 (s, 9H).
LC-MS: N/A.

Description D87

(cis)-tert-Butyl 3-fluoro-4-(1-(6-((1s,3s)-3-hydroxycyclobutyl)-2-methylpyrimidin-4-yl)-5-methyl-1H-indazol-6-yl)piperidine-1-carboxylate (Enantiomer 2) (D87)

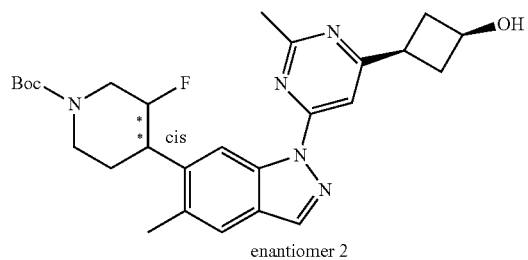 [SMILES: Cc1nc(-n2ncc3cc(C)c(C4CCN(C(=O)OC(C)(C)C)CC4F)cc32)cc([C@H]2C[C@@H](O)C2)n1]

enantiomer 2

To a solution of (cis)-tert-butyl 4-(1-(6-((1s,3s)-3-(benzyloxy)cyclobutyl)-2-methylpyrimidin-4-yl)-5-methyl-1H-indazol-6-yl)-3-fluoropiperidine-1-carboxylate (enantiomer 2) (60 mg, 0.10 mmol) in CH$_3$OH (3 mL) was added Pd/C (30 mg). The mixture was stirred at rt under H$_2$ (balloon) overnight. The mixture was filtered. The filtrate was concentrated to give the title compound (40 mg, yield 80%) as a yellow solid.

LCMS [mobile phase: 5-95% CH$_3$CN in 3 min]: Rt=2.03 min; MS Calcd: 495; MS Found: 496 [M+H]$^+$.

Description D88

(cis)-(1s,3s)-3-(6-(6-(3-Fluoropiperidin-4-yl)-5-methyl-1H-indazol-1-yl)-2-methylpyrimidin-4-yl)cyclobutanol hydrochloride (Enantiomer 2) (D88)

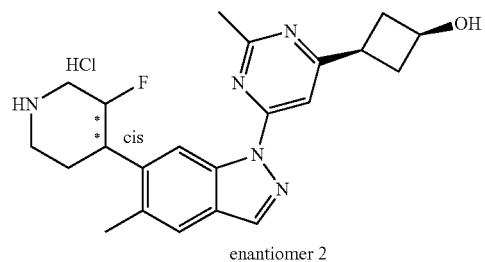 [SMILES: Cc1nc(-n2ncc3cc(C)c(C4CCNCC4F)cc32)cc([C@H]2C[C@@H](O)C2)n1 ; Cl]

enantiomer 2

To a solution of (cis)-tert-butyl 3-fluoro-4-(1-(6-((1s,3s)-3-hydroxycyclobutyl)-2-methyl pyrimidin-4-yl)-5-methyl-1H-indazol-6-yl)piperidine-1-carboxylate (enantiomer 2) (40 mg, 0.081 mmol) in CH$_3$OH (2.5 mL) was added HCl/CH$_3$OH (8 mol/L, 2.5 mL) was stirred at rt for 1 h. The reaction mixture was concentrated to give the title compound (35 mg, yield 100%) as a white solid.

LCMS [mobile phase: 5-95% CH$_3$CN in 3 min]: Rt=1.80 min; MS Calcd: 395; MS Found: 396 [M+H]$^+$.

Description D89

2-Cyclopropyl-4,6-diiodopyrimidine (D89)

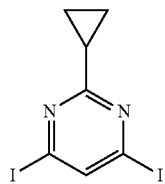 [SMILES: Ic1cc(I)nc(C2CC2)n1]

To a suspension of NaI (2.10 g, 13.7 mmol) in HI (55%, 10 mL) was added 4,6-dichloro-2-cyclopropylpyrimidine (2.00 g, 10.6 mmol). The resulting mixture was warmed to 40° C. and stirred for 1 hour. The reaction mixture was cooled to rt and diluted with H$_2$O (100 mL) and stirred for 15 min. The mixture was filtered to give the title compound (2.9 g, yield 74%) as a yellow solid.

$^1$H NMR (300 MHz, CDCl$_3$): δ 7.95 (s, 1H), 2.21-2.12 (m, 1H), 1.15-1.09 (m, 4H).

Description D90

1-(2-Cyclopropyl-6-iodopyrimidin-4-yl)azetidin-3-ol (D90)

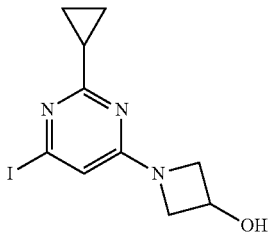 [SMILES: OC1CN(c2cc(I)nc(C3CC3)n2)C1]

A suspension of 2-cyclopropyl-4,6-diiodopyrimidine (1.00 g, 2.69 mmol), azetidin-3-ol hydrochloride (323 mg, 2.95 mmol) and TEA (678 mg, 6.72 mmol) in i-PrOH (10 mL) was heated to 90° C. and stirred for 1 h. The mixture was cooled and concentrated. Then the residue was diluted with water (20 mL) and filtered to give the title compound (1.1 g, yield 100%) as a white solid.

$^1$H NMR (300 MHz, DMSO-d$_6$): δ 6.59 (s, 1H), 5.77-5.73 (m, 1H), 4.55-4.48 (m, 1H), 4.21-4.12 (m, 2H), 3.74-3.66 (m, 2H), 1.88-1.79 (m, 1H), 0.90-0.81 (m, 4H).

Description D91

2-Cyclopropyl-4-iodo-6-(3-((tetrahydro-2H-pyran-2-yl)oxy)azetidin-1-yl)pyrimidine (D91)

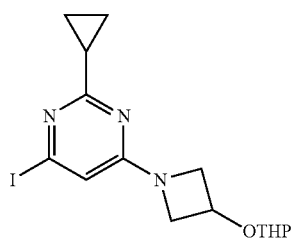

To a solution of 1-(2-cyclopropyl-6-iodopyrimidin-4-yl)azetidin-3-ol (1.10 g, 3.47 mmol) in DCM (20 mL) was added DHP (1.16 g, 13.9 mmol) and TsOH.H$_2$O (640 mg, 3.47 mmol) at rt. The reaction mixture was stirred at 40° C. overnight. The reaction mixture was cooled and poured into saturated NaHCO$_3$ (100 mL) and then extracted with DCM (50 mL×2). The combined organic layers were dried over Na$_2$SO$_4$, filtered and concentrated. The crude was purified by column chromatography (PE:EtOAc=10:1) to give a light yellow oil. The oil was purified by C18 to give the title compound (250 mg, yield 18%) as yellow oil.

$^1$H NMR (300 MHz, CDCl$_3$): δ 6.42 (s, 1H), 4.67-4.62 (m, 2H), 4.25-4.17 (m, 2H), 3.98-3.82 (m, 3H), 3.56-3.49 (m, 1H), 1.99-1.94 (m, 1H), 1.84-1.79 (m, 2H), 1.70-1.62 (m, 4H), 1.06-1.03 (m, 2H), 0.96-0.88 (m, 2H).

Description D92

(cis)-tert-Butyl 4-(1-(2-cyclopropyl-6-(3-((tetrahydro-2H-pyran-2-yl)oxy)azetidin-1-yl) pyrimidin-4-yl)-5-methyl-1H-indazol-6-yl)-3-fluoropiperidine-1-carboxylate (Enantiomer 1) (D92)

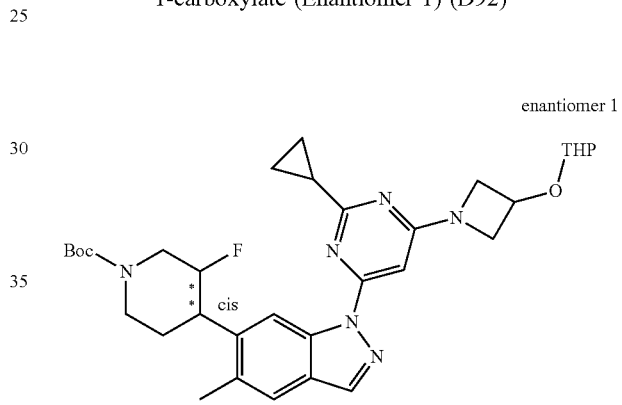

enantiomer 1

To a suspension of (cis)-tert-butyl 3-fluoro-4-(5-methyl-1H-indazol-6-yl)piperidine-1-carboxylate (enantiomer 1) (80 mg, 0.24 mmol), 2-cyclopropyl 4-iodo-6-(3-((tetrahydro-2H-pyran-2-yl)oxy)azetidin-1-yl)pyrimidine (106 mg, 0.264 mmol), CuI (46 mg, 0.24 mmol), K$_3$PO$_4$ (102 mg, 0.480 mmol) in dry toluene (3 mL) was added N,N'-dimethyl-cyclohexane-1,2-diamine (68 mg, 0.48 mmol). The mixture was degassed with N$_2$ for 3 times and stirred at 110° C. for 2 hrs. The reaction mixture was cooled to rt and then diluted with NH$_3$.H$_2$O (5%, 20 mL) and extracted with EtOAc (15 mL×2). The combined organic layers were washed with brine, dried over Na$_2$SO$_4$ and concentrated. The crude was purified by prep-TLC (DCM:MeOH=25:1) to give the title compound (120 mg, yield: 83%) as a light yellow solid.

$^1$H NMR (300 MHz, CDCl$_3$): δ 8.79 (s, 1H), 8.05 (s, 1H), 7.52 (s, 1H), 6.55 (s, 1H), 4.71-4.62 (m, 4H), 4.38-4.30 (m, 2H), 4.29-4.20 (m, 1H), 4.18-4.04 (m, 2H), 3.93-3.86 (m, 1H), 3.57-3.49 (m, 1H), 3.27-3.16 (m, 1H), 2.95-2.76 (m, 2H), 2.49 (s, 3H), 2.16-2.06 (m, 1H), 2.01-1.93 (m, 1H), 1.83-1.74 (m, 4H), 1.63-1.58 (m, 3H), 1.51 (s, 9H), 1.25-1.23 (m, 2H), 1.05-1.03 (m, 2H).

Description D93

(cis)-tert-Butyl 4-(1-(2-cyclopropyl-6-(3-((tetra-hydro-2H-pyran-2-yl)oxy)azetidin-1-yl) pyrimidin-4-yl)-5-methyl-1H-indazol-6-yl)-3-fluoropiperidine-1-carboxylate (Enantiomer 2) (D93)

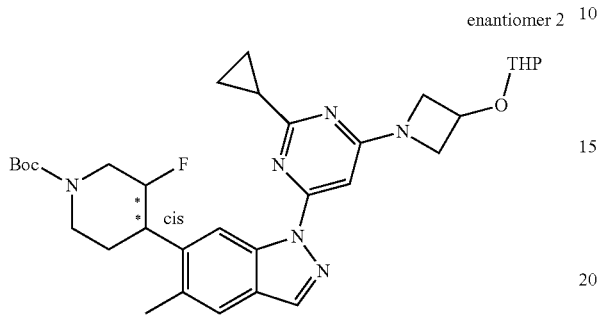

To a suspension of (cis)-tert-butyl 3-fluoro-4-(5-methyl-1H-indazol-6-yl)piperidine-1-carboxylate (enantiomer 2) (80 mg, 0.24 mmol), 2-cyclopropyl-4-iodo-6-(3-((tetra-hydro-2H-pyran-2-yl)oxy)azetidin-1-yl)pyrimidine (106 mg, 0.264 mmol), CuI (46 mg, 0.24 mmol), K$_3$PO$_4$ (102 mg, 0.480 mmol) in dry toluene (3 mL) was added N,N'-dimethyl-cyclohexane-1,2-diamine (68 mg, 0.48 mmol). The mixture was degassed with N$_2$ for 3 times and stirred at 110° C. for 2 hrs. The reaction mixture was cooled to rt and then diluted with NH$_3$.H$_2$O (5%, 20 mL) and extracted with EtOAc (15 mL×2). The combined organic layers were washed with brine, dried over Na$_2$SO$_4$ and concentrated. The crude was purified by prep-TLC (DCM:MeOH=25:1) to give the title compound (110 mg, yield 76%) as a light yellow solid.

$^1$H NMR (300 MHz, CDCl$_3$): δ 8.80 (s, 1H), 8.05 (s, 1H), 7.52 (s, 1H), 6.55 (s, 1H), 4.71-4.62 (m, 4H), 4.38-4.20 (m, 3H), 4.18-4.04 (m, 2H), 3.93-3.86 (m, 1H), 3.57-3.49 (m, 1H), 3.27-3.16 (m, 1H), 2.95-2.76 (m, 2H), 2.49 (s, 3H), 2.16-2.06 (m, 1H), 2.01-1.93 (m, 1H), 1.83-1.58 (m, 7H), 1.51 (s, 9H), 1.25-1.23 (m, 2H), 1.05-1.03 (m, 2H).

Description D94

4-(3-Hydroxyazetidin-1-yl)-6-iodopyrimidin-2-ol (D94)

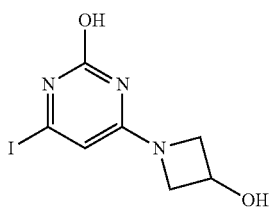 [SMILES: Oc1nc(I)cc(N2CC(O)C2)n1]

A mixture of 1-(6-iodo-2-methoxypyrimidin-4-yl)azetidin-3-ol (450 mg, 2.17 mmol) in HBr (40%, 5 mL) was stirred at 80° C. for 2 hrs. The reaction mixture was concentrated, and the residue was evaporated with toluene (5 mL×3) to give the title compound (390 mg, yield 91%) as a yellow solid.

LCMS: [mobile phase: 5-95% CH$_3$CN in 4 min], Rt=1.312 min, MS Calcd: 293, MS Found: 294 [M+H]$^+$.

Description 95

1-(2-(Difluoromethoxy)-6-iodopyrimidin-4-yl)azetidin-3-ol (D95)

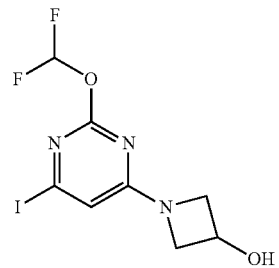 [SMILES: OC1CN(c2cc(I)nc(OC(F)F)n2)C1]

To a mixture of 4-(3-hydroxyazetidin-1-yl)-6-iodopyrimidin-2-ol (390 mg, 1.33 mmol) and K$_2$CO$_3$ (918 mg, 6.65 mmol) in DMF (20 mL) was added methyl 2-chloro-2,2-difluoroacetate (961 mg, 6.65 mmol). The mixture was stirred at 115° C. for 2 hrs. The reaction mixture was cooled to rt, diluted with EtOAc (50 mL) and washed with brine (30 mL×2). The organic layer was dried over Na$_2$SO$_4$, filtered and concentrated. The residue was purified by prep-TLC to give the title compound (100 mg, yield 22%) as a yellow solid.

$^1$H NMR (300 MHz, CDCl$_3$): δ 7.35 (t, J=72.0 Hz, 1H), 6.47 (s, 1H), 4.86-4.80 (m, 1H), 4.40-4.27 (m, 2H), 4.01-3.92 (m, 2H), 2.31 (br s, 1H).

LCMS: [mobile phase: 10-95% CH$_3$CN in 3 min], Rt=1.74 min; MS Calcd: 343; MS Found: 344 [M+H]$^+$.

Description D96

Ethyl 2-((1-(6-iodo-2-methoxypyrimidin-4-yl)azetidin-3-yl)oxy)acetate (D96)

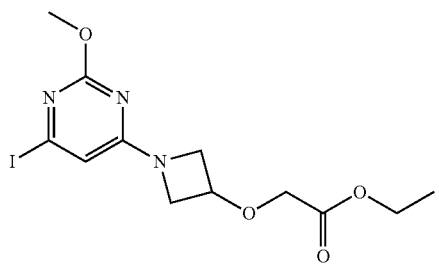 [SMILES: CCOC(=O)COC1CN(c2cc(I)nc(OC)n2)C1]

To a solution of 1-(6-iodo-2-methoxypyrimidin-4-yl)azetidin-3-ol (921 mg, 3.00 mmol) in DMF (15 mL) was added Cs$_2$CO$_3$ (1.95 g, 6.00 mmol) and ethyl 2-bromoacetate (752 mg, 4.50 mmol). The mixture was stirred at room temperature for 2 hrs. To the mixture was added water (60 mL) and EtOAc (20 mL×3) was added to extract the desired compound. The combined organic layers were washed with brine (20 mL×2), dried over Na$_2$SO$_4$ and concentrated. The residue was purified by column chromatograph (PE:EtOAc=4:1) to give the desired compound (1.0 g, yield 85%) as a white solid.

¹H NMR (400 MHz, CDCl₃): δ 6.33 (s, 1H), 4.54-4.49 (m, 1H), 4.26-4.21 (m, 4H), 4.09 (s, 2H), 4.05-4.02 (m, 2H), 3.88 (s, 3H), 1.28 (t, J=7.2 Hz, 3H).

Description D97

2-((1-(6-Iodo-2-methoxypyrimidin-4-yl)azetidin-3-yl)oxy)ethanol (D97)

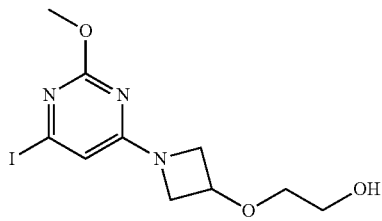 [SMILES: COc1nc(I)cc(N2CC(OCCO)C2)n1]

To a solution of ethyl 2-((1-(6-iodo-2-methoxypyrimidin-4-yl)azetidin-3-yl)oxy)acetate (1.00 g, 2.54 mmol) in THF (15 mL) was added DIBAL-H (1 M in toluene, 8.9 mL, 8.9 mmol) by dropwise at 0° C. The reaction mixture was stirred at 0° C. for 3 hrs. To the mixture was added ice-water (20 mL). The resulting mixture was extracted with EtOAc (50 mL×3). The combined organic layers were washed with brine (20 mL×2), dried over Na₂SO₄ and concentrated to give the desired compound (800 mg, yield 90%) as a white solid.

LCMS: (mobile phase: 5-95% acetonitrile in 3 min), Rt=1.47 min; MS Calcd: 351; MS Found: 352 [M+H]⁺.

Description D98

4-iodo-2-methoxy-6-(3-(2-((tetrahydro-2H-pyran-2-yl)oxy)ethoxy)azetidin-1-yl)pyrimidine (D98)

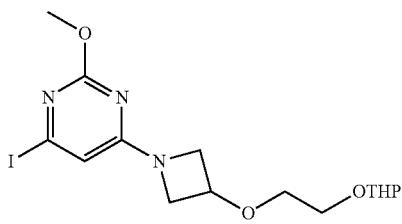

To a solution of 2-((1-(6-iodo-2-methoxypyrimidin-4-yl)azetidin-3-yl)oxy)ethanol (800 mg, 2.28 mmol) in DCM (15 mL) was added DHP (383 mg, 4.56 mmol) and TsOH (78 mg, 0.46 mmol). The reaction mixture was stirred at rt overnight. To the mixture was added sat. Na₂CO₃ solution (20 mL) and stirred for 10 min. The resulting mixture was extracted with DCM (20 mL×2). The combined organic layers were washed with brine (20 mL), dried over Na₂SO₄, and concentrated. The residue was purified by column chromatography (PE:EtOAc=5:1) to give the title compound (620 mg, yield 63%) as colorless oil.

¹H NMR (300 MHz, CDCl₃): δ 6.32 (s, 1H), 4.61-4.54 (m, 1H), 4.49-4.34 (m, 1H), 4.30-3.19 (m, 2H), 3.98-3.86 (m, 7H), 3.64-3.52 (m, 4H), 1.89-1.73 (m, 2H), 1.60-1.53 (m, 4H).

Description D99

(cis)-tert-Butyl 3-fluoro-4-(1-(2-methoxy-6-(3-(2-((tetrahydro-2H-pyran-2-yl)oxy)ethoxy) azetidin-1-yl)pyrimidin-4-yl)-5-methyl-1H-indazol-6-yl)piperidine-1-carboxylate (Enantiomer 1) (D99)

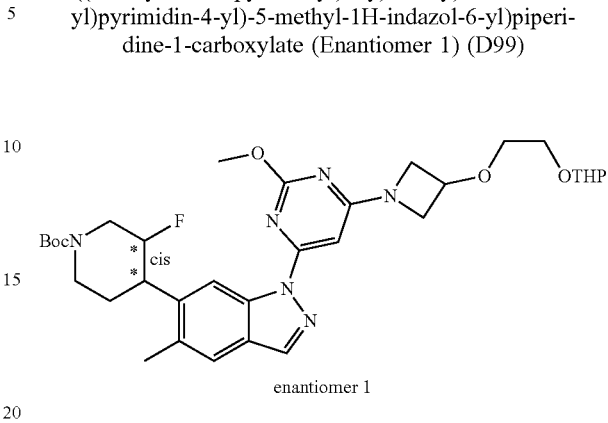

enantiomer 1

To a solution of (cis)-tert-butyl 3-fluoro-4-(5-methyl-1H-indazol-6-yl)piperidine-1-carboxylate (enantiomer 1) (80 mg, 0.24 mmol) in toluene (5 mL) was added 4-iodo-2-methoxy-6-(3-(2-((tetrahydro-2H-pyran-2-yl)oxy)ethoxy) azetidin-1-yl)pyrimidine (156 mg, 0.360 mmol), CuI (137 mg, 0.720 mmol), K₃PO₄ (153 mg, 0.720 mmol) and N,N'-dimethyl-cyclohexane-1,2-diamine (102 mg, 0.720 mmol). The mixture was refluxed for 2 hrs. The reaction mixture was cooled to rt and then poured into NH₃·H₂O (sat., 5 mL). EtOAc (10 mL×3) was added to extract the desired compound. The combined organic layers were washed with water (10 mL) and brine (10 mL), dried over Na₂SO₄ and concentrated. The crude was purified by prep. HPLC (prep-HPLC: from 30% water (0.1% NH₄HCO₃) and 70% CH₃CN to 15% water (0.1% NH₄HCO₃) and 85% CH₃CN in 20 min) to give the title compound (80 mg, yield 52%) as a white solid.

¹H NMR (300 MHz, CDCl₃): δ 8.83 (s, 1H), 8.08 (s, 1H), 7.54 (s, 1H), 6.47 (s, 1H), 4.80-4.49 (m, 4H), 4.36-4.15 (m, 3H), 4.09-4.02 (m, 5H), 3.91-3.82 (m, 2H), 3.68-3.64 (m, 4H), 3.30-3.17 (m, 1H), 2.95-2.75 (m, 2H), 2.49 (s, 3H), 2.02-1.63 (m, 8H), 1.51 (s, 9H).

Description D100

(cis)-2-((1-(6-(6-(3-Fluoropiperidin-4-yl)-5-methyl-1H-indazol-1-yl)-2-methoxypyrimidin-4-yl)azetidin-3-yl)oxy)ethanol hydrochloride (Enantiomer 1) (D100)

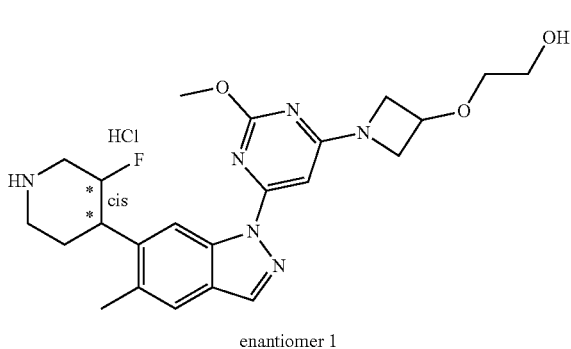

enantiomer 1

To a solution of (cis)-tert-butyl 3-fluoro-4-(1-(2-methoxy-6-(3-(2-((tetrahydro-2H-pyran-2-yl)oxy) ethoxy)azetidin-1-yl)pyrimidin-4-yl)-5-methyl-1H-indazol-6-yl)piperidine-1-carboxylate (enantiomer 1) (80 mg, 0.13 mmol) in dioxane (2 mL) was added HCl/dioxane (4 mol/L, 4 mL) and the resulting mixture was stirred at rt for 2 hrs. The reaction mixture was concentrated to give the title compound (60 mg, yield 100%) as a white solid.

LCMS [mobile phase: 5-95% CH$_3$CN in water in 3 min]: Rt=1.62 min; MS Calcd: 456; MS Found: 457[M+H]$^+$.

Description D101

(cis)-tert-butyl 3-fluoro-4-(1-(2-methoxy-6-(3-(2-((tetrahydro-2H-pyran-2-yl)oxy)ethoxy) azetidin-1-yl)pyrimidin-4-yl)-5-methyl-1H-indazol-6-yl)piperidine-1-carboxylate (Enantiomer 2) (D101)

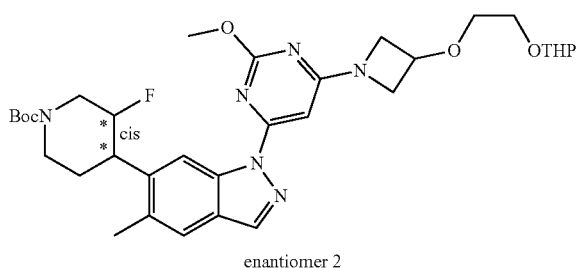

enantiomer 2

To a solution of (cis)-tert-butyl 3-fluoro-4-(5-methyl-1H-indazol-6-yl)piperidine-1-carboxylate (enantiomer 2) (80 mg, 0.24 mmol) in toluene (5 mL) was added 4-iodo-2-methoxy-6-(3-(2-((tetrahydro-2H-pyran-2-yl)oxy)ethoxy) azetidin-1-yl)pyrimidine (156 mg, 0.360 mmol), CuI (137 mg, 0.720 mmol), K$_3$PO$_4$ (153 mg, 0.720 mmol) and N,N'-dimethyl-cyclohexane-1,2-diamine (102 mg, 0.720 mmol). The mixture was refluxed for 2 hrs. The reaction mixture was cooled to rt and then poured into NH$_3$·H$_2$O (sat., 5 mL) and extracted with EtOAc (10 mL×3). The combined organic layers were washed with water (10 mL) and brine (10 mL), dried over Na$_2$SO$_4$ and concentrated. The crude was purified by prep. HPLC (prep-HPLC: from 30% water (0.1% NH$_4$HCO$_3$) and 70% CH$_3$CN to 15% water (0.1% NH$_4$HCO$_3$) and 85% CH$_3$CN in 20 min) to give the title compound (80 mg, yield 52%) as a white solid.

$^1$H NMR (300 MHz, CDCl$_3$): δ 8.83 (s, 1H), 8.08 (s, 1H), 7.54 (s, 1H), 6.47 (s, 1H), 4.79-4.50 (m, 4H), 4.36-4.17 (m, 3H), 4.09-4.03 (m, 5H), 3.92-3.84 (m, 2H), 3.67-3.58 (m, 4H), 3.28-3.17 (m, 1H), 2.96-2.75 (m, 2H), 2.49 (s, 3H), 2.00-1.64 (m, 8H), 1.51 (s, 9H).

Description D102

(cis)-2-((1-(6-(6-(3-Fluoropiperidin-4-yl)-5-methyl-1H-indazol-1-yl)-2-methoxypyrimidin-4-yl)azetidin-3-yl)oxy)ethanol hydrochloride (Enantiomer 2) (D102)

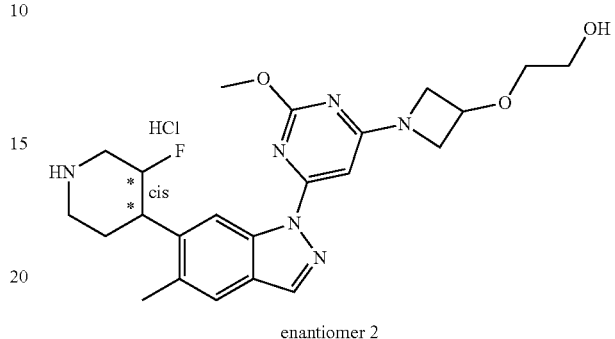

enantiomer 2

To a solution of (cis)-tert-butyl 3-fluoro-4-(1-(2-methoxy-6-(3-(2-((tetrahydro-2H-pyran-2-yl)oxy) ethoxy)azetidin-1-yl)pyrimidin-4-yl)-5-methyl-1H-indazol-6-yl)piperidine-1-carboxylate (enantiomer 2) (80 mg, 0.13 mmol) in dioxane (2 mL) was added HCl/dioxane (4 mol/L, 4 mL) and the resulting mixture was stirred at rt for 2 hrs. The reaction mixture was concentrated to give the title compound (60 mg, yield 100%) as a white solid.

LCMS [mobile phase: 5-95% CH$_3$CN in water in 3 min]: Rt=1.60 min; MS Calcd: 456; MS Found: 457 [M+H]$^+$.

Description D103

(S)-1-(6-Iodo-2-methoxypyrimidin-4-yl)pyrrolidin-3-ol (D103)

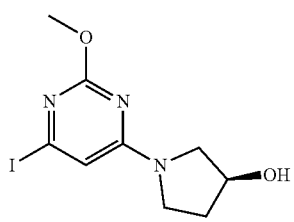

To a suspension of 4,6-diiodo-2-methoxypyrimidine (300 mg, 0.829 mmol) and (S)-pyrrolidin-3-ol hydrochloride (113 mg, 0.912 mmol) in i-PrOH (8 mL) was added TEA (252 mg, 2.49 mmol). The resulting mixture was heated to 75° C. and stirred for 1 hour. The reaction mixture was cooled to rt and then partitioned between water (50 mL) and EtOAc (40 mL). The organic layer was washed with brine, dried over MgSO$_4$ and concentrated to give the title compound (255 mg, yield 96%) as white solid.

$^1$H NMR (300 MHz, CDCl$_3$): δ 6.45 (s, 1H), 4.60 (s, 1H), 3.89 (s, 3H), 3.82-3.25 (m, 4H), 2.31-2.04 (m, 3H).

Description D104

(cis)-tert-Butyl 3-fluoro-4-(1-(6-((S)-3-hydroxypyrrolidin-1-yl)-2-methoxypyrimidin-4-yl)-5-methyl-1H-indazol-6-yl)piperidine-1-carboxylate (Diastereoisomer 1) (D104)

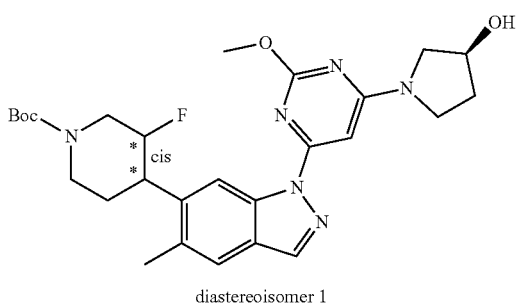 [SMILES: COc1nc(N2CC[C@H](O)C2)cc(-n2ncc3cc(C)c(C4CCN(C(=O)OC(C)(C)C)CC4F)cc32)n1]

diastereoisomer 1

To a suspension of (cis)-tert-butyl 3-fluoro-4-(5-methyl-1H-indazol-6-yl)piperidine-1-carboxylate (enantiomer 1) (80 mg, 0.24 mmol), (S)-1-(6-iodo-2-methoxypyrimidin-4-yl)pyrrolidin-3-ol (83 mg, 0.26 mmol), CuI (46 mg, 0.24 mmol) and $K_3PO_4$ (102 mg, 0.480 mmol) in dry toluene (4 mL) was added N,N'-dimethyl-cyclohexane-1,2-diamine (68 mg, 0.48 mmol). The resulting mixture was degassed with $N_2$ and stirred at 110° C. for 2 hrs. TLC showed the reaction was completed. The reaction mixture was cooled to rt and then partitioned between diluted ammonia (10%, 100 mL) and EtOAc (70 mL). The aqueous layer was extracted with EtOAc (70 mL). The combined organic layers were washed with brine, dried over $MgSO_4$ and concentrated to give the title compound (140 mg, crude; two isomers in a ratio of 10:3) as a slight brown solid.

LCMS: (mobile phase: 5-95% Acetonitrile in 3 min), Rt=2.36 min; MS Calcd: 526; MS Found: 527 [M+1]$^+$.

Description D105

(cis)-(3S)-1-(6-(6-(3-Fluoropiperidin-4-yl)-5-methyl-1H-indazol-1-yl)-2-methoxypyrimidin-4-yl)pyrrolidin-3-ol hydrochloride (Diastereoisomer 1) (D105)

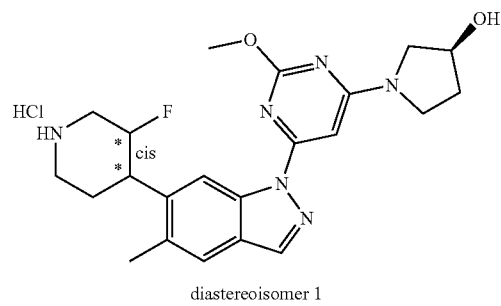 [SMILES: Cl ; COc1nc(N2CC[C@H](O)C2)cc(-n2ncc3cc(C)c(C4CCNCC4F)cc32)n1]

diastereoisomer 1

To a suspension of (cis)-tert-butyl 3-fluoro-4-(1-(6-((S)-3-hydroxypyrrolidin-1-yl)-2-methoxypyrimidin-4-yl)-5-methyl-1H-indazol-6-yl)piperidine-1-carboxylate (diastereoisomer 1) (140 mg crude, 0.240 mmol) in dioxane (2 mL) was added HCl/dioxane (4 M, 5 mL). The mixture was stirred at rt for 2 hrs. The reaction mixture was concentrated to give the title compound (140 mg crude, yield >100%) as a white solid which was used for next step directly.

LCMS: (mobile phase: 5-95% acetonitrile in 3 min), Rt=1.64 min; MS Calcd: 426; MS Found: 427 [M+1]$^+$.

Description D106

(cis)-tert-Butyl 3-fluoro-4-(1-(6-((S)-3-hydroxypyrrolidin-1-yl)-2-methoxypyrimidin-4-yl)-5-methyl-1H-indazol-6-yl)piperidine-1-carboxylate (Diastereoisomer 2) (D106)

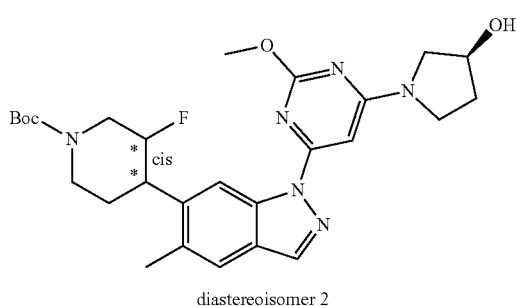 [SMILES: COc1nc(N2CC[C@H](O)C2)cc(-n2ncc3cc(C)c(C4CCN(C(=O)OC(C)(C)C)CC4F)cc32)n1]

diastereoisomer 2

To a suspension of (cis)-tert-butyl 3-fluoro-4-(5-methyl-1H-indazol-6-yl)piperidine-1-carboxylate (diastereoisomer 2) (80 mg, 0.24 mmol), (S)-1-(6-Iodo-2-methoxypyrimidin-4-yl)pyrrolidin-3-ol (83 mg, 0.26 mmol), CuI (46 mg, 0.24 mmol) and $K_3PO_4$ (102 mg, 0.480 mmol) in dry toluene (4 mL) was added N,N'-dimethyl-cyclohexane-1,2-diamine (68 mg, 0.48 mmol). The resulting mixture was degassed with $N_2$ and heated to 110° C. for 2 hrs. The reaction mixture was cooled and then partitioned between dilute ammonia (10%, 100 mL) and EtOAc (70 mL). The aqueous layer was extracted with EtOAc (70 mL). The combined organic layers were washed with brine, dried over $MgSO_4$ and concentrated to give the title compound (140 mg, crude) as a slight brown solid.

LC-MS: 3.0 min, 5-95%; Rt: 2.36 min, 527 [M+H]$^+$.

Description D107

(cis)-(3S)-1-(6-(6-(3-Fluoropiperidin-4-yl)-5-methyl-1H-indazol-1-yl)-2-methoxypyrimidin-4-yl)pyrrolidin-3-ol hydrochloride (Diastereoisomer 2) (D107)

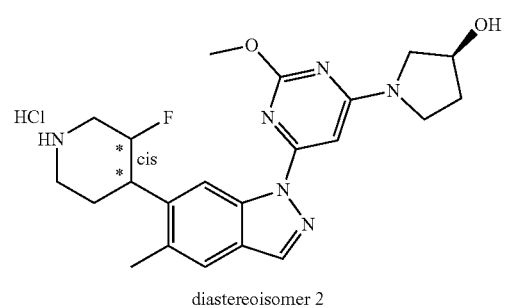 [SMILES: Cl ; COc1nc(N2CC[C@H](O)C2)cc(-n2ncc3cc(C)c(C4CCNCC4F)cc32)n1]

diastereoisomer 2

To a suspension of (cis)-tert-butyl 3-fluoro-4-(1-(6-((S)-3-hydroxypyrrolidin-1-yl)-2-methoxypyrimidin-4-yl)-5-methyl-1H-indazol-6-yl)piperidine-1-carboxylate (diastereoisomer 2) (140 mg crude, 0.24 mmol) in dioxane (2 mL) was added HCl/dioxane (4 M, 5 mL). The mixture was stirred at rt for 2 hrs. The reaction mixture was concentrated to give the title compound (140 mg crude) as a white solid.

LCMS: 3.0 min, 5-95%; Rt: 1.64 min, 427 [M+H]⁺.

Description D108

(R)-Pyrrolidin-3-ol hydrochloride (D108)

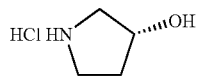

(R)-tert-Butyl 3-hydroxypyrrolidine-1-carboxylate (250 mg, 1.34 mmol) was dissolved in HCl/dioxane (4 M, 5 mL) and stirred at rt for 1 h. The reaction mixture was concentrated to give the title compound (150 mg, yield 90%) as a white solid.

$^1$H NMR (300 MHz, DMSO-d$_6$): δ 9.47 (br s, 1H), 9.24 (br s, 1H), 4.38 (s, 1H), 3.57-2.96 (m, 4H), 1.95-1.79 (m, 2H).

Description D109

(R)-1-(6-Iodo-2-methoxypyrimidin-4-yl)pyrrolidin-3-ol (D109)

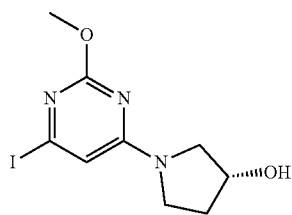

To a suspension of 4,6-diiodo-2-methoxypyrimidine (366 mg, 1.01 mmol) and (R)-pyrrolidin-3-ol hydrochloride (150 mg, 1.21 mmol) in i-PrOH (10 mL) was added TEA (307 mg, 3.03 mmol). The resulting mixture was stirred at 75° C. for 1 h. The reaction mixture was cooled to rt and then partitioned between water (50 mL) and EtOAc (40 mL). The organic layer was washed with brine, dried over MgSO₄ and concentrated to give the title compound (255 mg, yield 96%) as a white solid.

$^1$H NMR (300 MHz, CDCl$_3$): δ 6.45 (s, 1H), 4.60 (s, 1H), 3.90 (s, 3H), 3.81-3.28 (m, 4H), 2.10-1.88 (m, 3H).

LCMS: (mobile phase: 5-95% Acetonitrile in 2.5 min), Rt=1.28 min; MS Calcd: 321; MS Found: 322 [M+1]⁺.

Description D110

(cis)-tert-Butyl 3-fluoro-4-(1-(6-((R)-3-hydroxypyrrolidin-1-yl)-2-methoxypyrimidin-4-yl)-5-methyl-1H-indazol-6-yl)piperidine-1-carboxylate (Diastereoisomer 1) (D110)

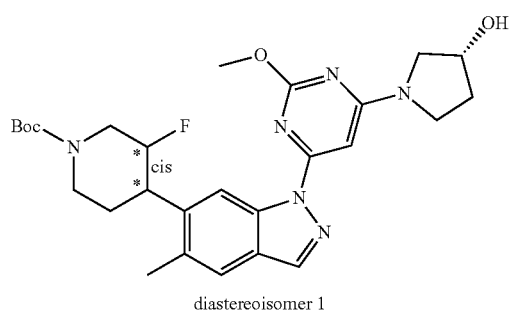 [SMILES: COc1nc(N2CC[C@@H](O)C2)cc(-n2ncc3cc(C)c(C4CCN(C(=O)OC(C)(C)C)CC4F)cc32)n1]

diastereoisomer 1

To a suspension of (cis)-tert-butyl 3-fluoro-4-(5-methyl-1H-indazol-6-yl)piperidine-1-carboxylate (enantiomer 1) (80 mg, 0.24 mmol), (R)-1-(6-iodo-2-methoxypyrimidin-4-yl) pyrrolidin-3-ol (85 mg, 0.26 mmol), CuI (46 mg, 0.24 mmol) and K₃PO₄ (102 mg, 0.480 mmol) in dry toluene (4 mL) was added N1,N2-dimethylcyclohexane-1,2-diamine (68 mg, 0.48 mmol). The resulting mixture was degassed with N₂ and stirred at 110° C. for 2 hrs. The reaction mixture was cooled to rt and then partitioned between dilute ammonia (10%, 70 mL) and EtOAc (50 mL). The aqueous layer was extracted with EtOAc (50 mL). The combined organic layers were washed with brine, dried over MgSO₄ and concentrated to give the title compound (150 mg, crude; two isomers in a ratio of 10:3) as a slight brown solid.

LCMS: (mobile phase: 5-95% acetonitrile in 3.0 min), Rt=2.05 min; MS Calcd: 526; MS Found: 527 (M+1)⁺.

Description D111

(cis)-(3R)-1-(6-(6-(3-Fluoropiperidin-4-yl)-5-methyl-1H-indazol-1-yl)-2-methoxypyrimidin-4-yl) pyrrolidin-3-ol hydrochloride (Diastereoisomer 1) (D111)

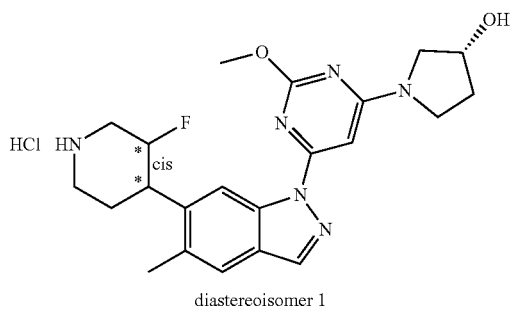 [SMILES: Cl ; COc1nc(N2CC[C@@H](O)C2)cc(-n2ncc3cc(C)c(C4CCNCC4F)cc32)n1]

diastereoisomer 1

To a suspension of (cis)-tert-butyl 3-fluoro-4-(1-(6-((R)-3-hydroxypyrrolidin-1-yl)-2-methoxy pyrimidin-4-yl)-5-methyl-1H-indazol-6-yl)piperidine-1-carboxylate (diastereoisomer 1) (150 mg crude, 0.240 mmol) in dioxane (3 mL) was added HCl/dioxane (4 M, 5 mL). The mixture was stirred at rt for 2 hrs. The reaction mixture was concentrated to give the title compound (200 mg crude) as a white solid.

LCMS: (mobile phase: 5-95% Acetonitrile in 3.0 min), Rt=1.89 min; MS Calcd: 426; MS Found: 427 [M+1]+.

Description D112

(cis)-tert-Butyl 3-fluoro-4-(1-(6-((R)-3-hydroxypyrrolidin-1-yl)-2-methoxypyrimidin-4-yl)-5-methyl-1H-indazol-6-yl)piperidine-1-carboxylate (Diastereoisomer 2) (D112)

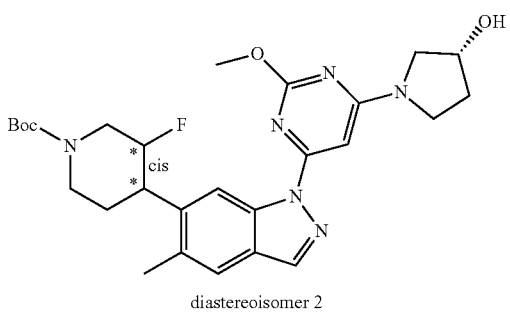 [SMILES: COc1nc(N2CC[C@@H](O)C2)cc(-n2ncc3cc(C)c(C4CCN(C(=O)OC(C)(C)C)CC4F)cc32)n1]

diastereoisomer 2

To a suspension of (cis)-tert-butyl 3-fluoro-4-(5-methyl-1H-indazol-6-yl)piperidine-1-carboxylate (enantiomer 2) (80 mg, 0.24 mmol), (R)-1-(6-iodo-2-methoxypyrimidin-4-yl) pyrrolidin-3-ol (85 mg, 0.26 mmol), CuI (46 mg, 0.24 mmol) and K₃PO₄ (102 mg, 0.480 mmol) in dry toluene (4 mL) was added N1,N2-dimethylcyclohexane-1,2-diamine (68 mg, 0.48 mmol). The resulting mixture was degassed with N₂ and stirred to 110° C. for 2 hrs. The reaction mixture was cooled and then partitioned between dilute ammonia (10%, 70 mL) and EtOAc (50 mL). The aqueous layer was extracted with EtOAc (50 mL). The combined organic layers were washed with brine, dried over MgSO₄ and concentrated to give the title compound (150 mg, crude) as a white solid.

LCMS: (mobile phase: 5-95% Acetonitrile in 3.0 min), Rt=2.06 min; MS Calcd: 526; MS Found: 527 [M+1]+.

Description D113

(cis)-(3R)-1-(6-(6-(3-Fluoropiperidin-4-yl)-5-methyl-1H-indazol-1-yl)-2-methoxypyrimidin-4-yl) pyrrolidin-3-ol hydrochloride (Diastereoisomer 2) (D113)

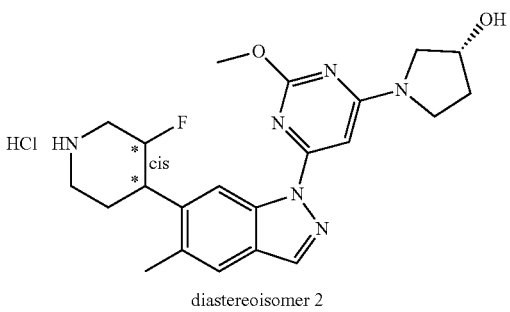 [SMILES: Cl ; COc1nc(N2CC[C@@H](O)C2)cc(-n2ncc3cc(C)c(C4CCNCC4F)cc32)n1]

diastereoisomer 2

To a suspension of (cis)-tert-butyl 3-fluoro-4-(1-(6-((R)-3-hydroxypyrrolidin-1-yl)-2-methoxy pyrimidin-4-yl)-5-methyl-1H-indazol-6-yl)piperidine-1-carboxylate (diastereoisomer 2) (150 mg crude, 0.24 mmol) in dioxane (3 mL) was added HCl/dioxane (4 M, 5 mL). The mixture was stirred at rt for 2 hrs. The reaction mixture was concentrated to give the title compound (180 mg crude) as a white solid. The crude product was used directly for next step.

Description D114

Ethyl 4-(benzyloxy)-3-oxobutanoate (D114)

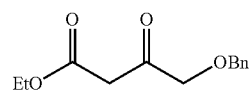

Benzyl alcohol (6.90 g, 63.8 mmol) was added dropwise to a stirred suspension of sodium hydride (60%, 5.37 g, 134 mmol) in dry THF (50 mL) under ice bath to keep the temperature below 10° C. The mixture was stirred for an hour. Ethyl 4-chloro-3-oxobutanoate (10.0 g, 60.8 mmol) was added dropwise within 40 min at rt, and the resulting mixture was stirred overnight. The reaction mixture was carefully added to HCl (5%, 100 mL) at 5° C. and then extracted with EtOAc (20 mL×3). The combined organic layers were washed with brine, dried over Na₂SO₄, filtered and concentrated. The crude was purified by column chromatography (PE/EtOAc=10/1) to give the title compound (12.1 g, yield 85%) as a yellow oil.

LCMS: [mobile phase: 5-95% CH₃CN in 2.5 min], Rt=1.55 min, MS Calcd: 236; MS Found: 237 [M+H]+.

¹H NMR (300 MHz, CDCl₃): δ 7.38-7.30 (m, 5H), 4.59 (s, 2H), 4.22-4.10 (m, 4H), 3.53 (s, 2H), 1.25 (t, J=7.2 Hz, 3H).

Description D115

6-((Benzyloxy)methyl)-2-methoxypyrimidin-4-ol (D115)

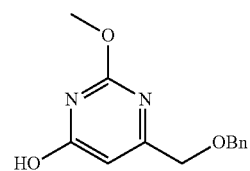 [SMILES: COc1nc(O)cc(COCc2ccccc2)n1]

To a suspension of MeONa (7.99 g, 148 mmol) in MeOH (120 mL) was added methyl carbamimidate hydrochloride (7.02 g, 63.5 mmol) under ice bath. Ethyl 4-(benzyloxy)-3-oxobutanoate (10.0 g, 42.3 mmol) was followed. The mixture was warmed to rt and stirred for 2 hrs. Then, the reaction mixture was heated to reflux for 4 hrs. The solvent was removed under vacuum and the residue was partitioned between water (300 ml) and EtOAc (100 ml). The aqueous layer was acidified by conc. HCl to pH=5. The white precipitate was collected by filtration. The solid was washed with water and dried under vacuum to give the title compound (6.0 g, yield 58%) as a white solid.

LCMS: [mobile phase: 5-95% CH₃CN in 2.5 min], Rt=1.39 min, MS Calcd: 246; MS Found: 247 [M+H]+.

¹H NMR (300 MHz, CDCl₃): δ 7.37-7.29 (m, 5H), 6.38 (s, 1H), 4.64 (s, 2H), 4.35 (s, 2H), 3.96 (s, 3H).

Description D116

4-((Benzyloxy)methyl)-6-chloro-2-methoxypyrimidine (D116)

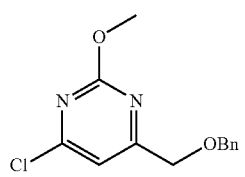 [SMILES: COc1nc(Cl)cc(COCc2ccccc2)n1]

To a solution of 6-((benzyloxy)methyl)-2-methoxypyrimidin-4-ol (2.9 g, 12 mmol) in DCM (60 mL) was added SOCl₂ (1.7 g, 14 mmol) and DMF (1 mL). The resulting white suspension was heated to 40° C. for 2 hrs. The reaction mixture was cooled to rt and then gradually poured into Na₂CO₃ (10%, 100 mL) and stirred for 10 min. The organic layer was separated and the aqueous was extracted with EtOAc (50 mL×2). The combined organic layers were washed with brine, dried over Na₂SO₄ and concentrated. The crude was purified by column chromatography (PE/EtOAc=4/1) to give the title compound (1.8 g, yield 58%) as a yellow oil.

LCMS: [mobile phase: 5-95% CH₃CN in 2.5 min], Rt=1.71 min, MS Calcd: 264; MS Found: 265 [M+H]⁺.

¹H NMR (300 MHz, CDCl₃): δ 7.38-7.29 (m, 5H), 7.22 (s, 1H), 4.65 (s, 2H), 4.55 (s, 2H), 4.00 (s, 3H).

Description D117

(6-Chloro-2-methoxypyrimidin-4-yl)methanol (D117)

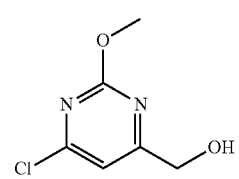

A suspension of 4-((benzyloxy)methyl)-6-chloro-2-methoxypyrimidine (1.8 g, 6.8 mmol) in TFA (12 mL) was heated to 70° C. and stirred for 6.5 hrs. The reaction mixture was cooled to rt and gradually poured into Na₂CO₃ (10%, 50 mL). The aqueous was extracted with EtOAc (20 mL×3). The combined organic layers were washed with brine, dried over Na₂SO₄ and concentrated. The crude was purified by column chromatography (PE/EtOAc from 5/1 to 2/1) to give the title compound (450 mg, yield 38%) as a white solid.

¹H NMR (300 MHz, CDCl₃): δ 7.05 (s, 1H), 4.69 (s, 2H), 4.03 (s, 3H), 2.46 (br s, 1H).

Description D118

6-Chloro-2-methoxypyrimidine-4-carbaldehyde (D118)

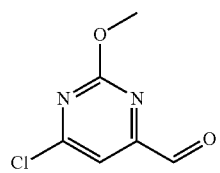

To a solution of (6-chloro-2-methoxypyrimidin-4-yl)methanol (450 mg, 2.58 mmol) in dry DCM (25 mL) was added NaHCO₃ (2.17 g, 25.8 mmol). DMP (1.64 g, 3.87 mmol) was added in portions under ice bath. The resulting suspension was warmed to rt and stirred for 2 hrs. The reaction mixture was poured into Na₂S₂O₃ (10%, 50 mL) and stirred for 20 min. The organic layer was separated and the aqueous was extracted with DCM (20 mL×2). The combined organic layers were washed with brine, dried over Na₂SO₄ and concentrated to give the title compound (390 mg, yield 79%) as a yellow solid.

LCMS: [mobile phase: 5-95% CH₃CN in 2.5 min], Rt=1.02 min, MS Calcd: 172; MS Found: 191 [M+19]⁺.

¹H NMR (300 MHz, CDCl₃): δ 9.90 (s, 1H), 7.45 (s, 1H), 4.11 (s, 3H).

Description D119

Methyl 6-chloro-2-methoxypyrimidine-4-carboxylate (D119)

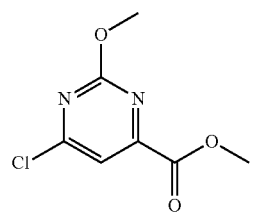

To a suspension of 6-chloro-2-methoxypyrimidine-4-carbaldehyde (350 mg, 2.03 mmol) and NaHCO₃ (3.41 g, 40.6 mmol) in MeOH (10 mL) and water (1 mL) was added a solution of Br₂ in MeOH (10 mL) and water (1 mL) dropwise under ice bath. The resulting mixture was stirred at rt for 5 hrs. The reaction mixture was poured into NaHSO₃ (10%, 100 mL) and stirred for 15 min. The aqueous was extracted with EtOAc (50 mL×3) and the combined organic layers were washed with brine, dried over Na₂SO₄ and concentrated to give the title compound (320 g, yield 78%) as a white solid.

¹H NMR (300 MHz, CDCl₃): δ 7.64 (s, 1H), 4.10 (s, 3H), 4.00 (s, 3H).

LC-MS (mobile phase: from 95% water and 5% CH₃CN to 5% water and 95% CH₃CN in 2.5 min, Rt=1.45 min; MS Calcd.: 202; MS Found: 203 [M+H]⁺.

Description D120

(cis)-Methyl 6-(6-(3-fluoro-1-methylpiperidin-4-yl)-5-methyl-1H-indazol-1-yl)-2-methoxy pyrimidine-4-carboxylate (Enantiomer 2) (D120)

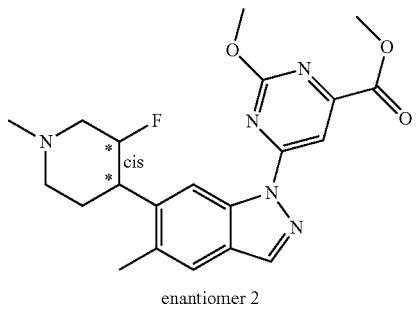 [SMILES: COC(=O)c1cc(-n2ncc3cc(C)c(C4CCN(C)CC4F)cc32)nc(OC)n1]

enantiomer 2

A suspension of (cis)-6-(3-fluoro-1-methylpiperidin-4-yl)-5-methyl-1H-indazole (enantiomer 2) (50 mg, 0.20 mmol), methyl 6-chloro-2-methoxypyrimidine-4-carboxylate (81 mg, 0.40 mmol) and $Cs_2CO_3$ (130 mg, 0.400 mmol) in NMP (2 mL) was heated to 100° C. for 4 hrs. The reaction mixture was cooled to rt and then poured into water (30 mL). The aqueous was extracted with EtOAc (15 mL×3) and the combined organic layers were washed with brine for 3 times, dried over $Na_2SO_4$ and concentrated. The crude was purified by prep. TLC (DCM/MeOH=15/1) to give the title compound (20 mg, yield 24%) as a white solid.

$^1$H NMR (300 MHz, $CDCl_3$): δ 8.82 (s, 1H), 8.28 (s, 1H), 8.17 (s, 1H), 7.57 (s, 1H), 5.06-4.77 (m, 1H), 4.23 (s, 3H), 4.02 (s, 3H), 3.42-3.34 (m, 1H), 3.18-3.05 (m, 1H), 3.02-2.92 (m, 1H), 2.50 (s, 3H), 2.44 (s, 3H), 2.28-2.11 (m, 2H), 2.01-1.86 (m, 2H).

LC-MS (mobile phase: from 95% water and 5% $CH_3CN$ to 5% water and 95% $CH_3CN$ in 2.5 min, Rt=1.85 min; MS Calcd.: 413; MS Found: 414 [M+H]$^+$.

Description D121

(cis)-Methyl 6-(6-(3-fluoro-1-methylpiperidin-4-yl)-5-methyl-1H-indazol-1-yl)-2-methoxy pyrimidine-4-carboxylate (Enantiomer 1) (D121)

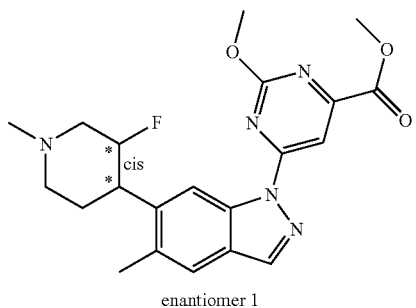 [SMILES: COC(=O)c1cc(-n2ncc3cc(C)c(C4CCN(C)CC4F)cc32)nc(OC)n1]

enantiomer 1

A suspension of (cis)-6-(3-fluoro-1-methylpiperidin-4-yl)-5-methyl-1H-indazole (enantiomer 1) (50 mg, 0.20 mmol), methyl 6-chloro-2-methoxypyrimidine-4-carboxylate (81 mg, 0.40 mmol) and $Cs_2CO_3$ (130 mg, 0.400 mmol) in NMP (2 mL) was heated to 100° C. for 4 hrs. The reaction mixture was cooled to rt and then poured into water (30 mL). The aqueous was extracted with EtOAc (15 mL×3) and the combined organic layers were washed with brine for 3 times, dried over $Na_2SO_4$ and concentrated. The crude was purified by prep. TLC (DCM/MeOH=15/1) to give the title compound (20 mg, yield 25%) as a white solid.

$^1$H NMR (300 MHz, $CDCl_3$): δ 8.82 (s, 1H), 8.28 (s, 1H), 8.17 (s, 1H), 7.58 (s, 1H), 5.05-4.82 (m, 1H), 4.23 (s, 3H), 4.02 (s, 3H), 3.41-3.39 (m, 1H), 3.17-3.07 (m, 1H), 3.01-2.99 (m, 1H), 2.50 (s, 3H), 2.46 (s, 3H), 2.33-2.13 (m, 2H), 1.96 (br s, 2H).

LC-MS (mobile phase: from 95% water and 5% $CH_3CN$ to 5% water and 95% $CH_3CN$ in 2.5 min, Rt=1.84 min; MS Calcd.: 413; MS Found: 414 [M+H]$^+$.

Description D122

6-Iodo-2-methoxy-N-(4-methoxybenzyl)pyrimidin-4-amine (D122)

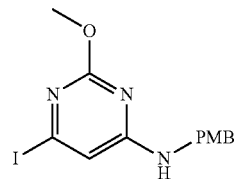

To a solution of 4,6-diiodo-2-methoxypyrimidine (527 mg, 1.45 mmol) in EtOH (10 mL) was added 4-methoxybenzylamine (600 mg, 4.38 mmol) and $Et_3N$ (3.64 mmol, 367 mg). The mixture was stirred at 70° C. for 3 hrs. Then the mixture was cooled and concentrated. The residue was purified by column (PE:EtOAc=5:1) to give the title compound (512 mg, yield 95%) as a white solid.

$^1$H NMR (300 MHz, $CDCl_3$): δ 7.21 (d, J=8.7 Hz, 2H), 6.87 (d, J=8.7 Hz, 1H), 6.49 (s, 1H), 4.44 (br s, 2H), 3.90 (s, 3H), 3.80 (s, 3H).

Description D123

(cis)-6-(6-(3-Fluoro-1-methylpiperidin-4-yl)-5-methyl-1H-indazol-1-yl)-2-methoxy-N-(4-methoxybenzyl)pyrimidin-4-amine (Enantiomer 2) (D123)

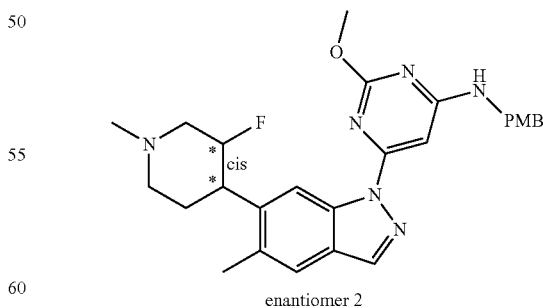

enantiomer 2

To a suspension of (cis)-6-(3-fluoro-1-methylpiperidin-4-yl)-5-methyl-1H-indazole (enantiomer 2) (100 mg, 0.405 mmol), 6-iodo-2-methoxy-N-(4-methoxybenzyl) pyrimidin-4-amine (225 mg, 0.607 mmol), $K_3PO_4$ (172 mg, 0.809 mmol), CuI (154 mg, 0.809 mmol) in dry touenel (5 mL)

was added N,N'-dimethyl-cyclohexane-1,2-diamine (230 mg, 1.62 mmol). The resulting green suspension was degassed with N₂ for 3 times and stirred at 110° C. for 2 hrs. The reaction mixture was concentrated. The residue was diluted with H₂O (10 mL) and EtOAc (10 mL×4). The organic layer was washed with brine, dried over Na₂SO₄ and concentrated. The residue was purified by prep-TLC (CH₂Cl₂:MeOH=15:1) to give the title compound (108 mg, yield 44%) as a light yellow solid.

¹H NMR (300 MHz, CDCl₃): δ 8.84 (s, 1H), 8.05 (s, 1H), 7.52 (s, 1H), 7.29-7.25 (m, 2H), 6.90-6.87 (m, 2H), 6.68 (s, 1H), 5.30-5.17 (m, 1H), 4.95-4.76 (m, 1H), 4.55-4.50 (m, 2H), 4.11 (s, 3H), 3.80 (s, 3H), 3.36-3.30 (m, 1H), 3.10-3.00 (m, 1H), 2.94-2.89 (m, 1H), 2.48 (s, 3H), 2.41 (s, 3H), 2.26-2.10 (m, 2H), 1.92-1.87 (m, 2H).

Description D124

(cis)-6-(6-(3-Fluoro-1-methylpiperidin-4-yl)-5-methyl-1H-indazol-1-yl)-2-methoxypyrimidin-4-amine (Enantiomer 2) (D124)

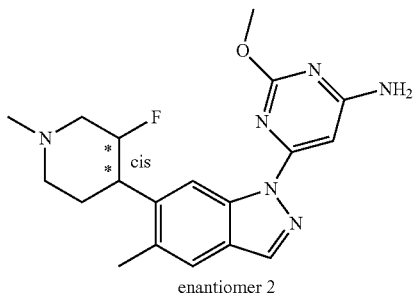 [SMILES: COc1nc(N)cc(-n2ncc3cc(C)c(C4CCN(C)CC4F)cc32)n1]

enantiomer 2

To a solution of (cis)-6-(6-(3-fluoro-1-methylpiperidin-4-yl)-5-methyl-1H-indazol-1-yl)-2-methoxy-N-(4-methoxybenzyl)pyrimidin-4-amine (enantiomer 2) (105 mg, 0.214 mmol) in DCM (20 mL) was added TFA (20 mL) at rt slowly. Then the mixture was stirred at 40° C. for 48 hrs. Then the mixture was cooled and adjusted to pH=7-8 with saturated NaHCO₃ under ice bath. Then the mixture was extracted with DCM (50 mL×4). The combined organic layers were washed with brine, dried over Na₂SO₄ and concentrated. The residue was purified by prep-TLC (CH₂Cl₂:MeOH=15:1) to give the title compound (83 mg, yield 100%) as a white solid.

¹H NMR (300 MHz, CDCl₃): δ 8.83 (s, 1H), 8.07 (s, 1H), 7.53 (s, 1H), 6.73 (s, 1H), 4.97-4.72 (m, 3H), 4.11 (s, 3H), 3.36-3.31 (m, 1H), 3.12-3.00 (m, 1H), 2.96-2.87 (m, 1H), 2.48 (s, 3H), 2.40 (s, 3H), 2.23-2.05 (m, 2H), 1.99-1.82 (m, 2H).

Description D125

(cis)-6-(6-(3-Fluoro-1-methylpiperidin-4-yl)-5-methyl-1H-indazol-1-yl)-2-methoxy-N-(4-methoxybenzyl)pyrimidin-4-amine (Enantiomer 1) (D125)

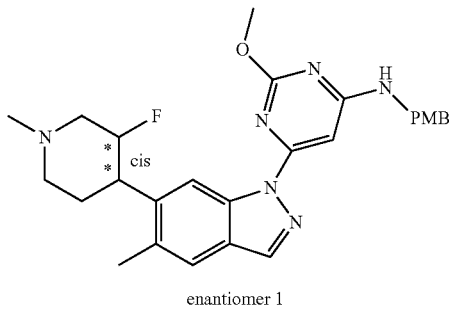

enantiomer 1

To a suspension of (cis)-6-(3-fluoro-1-methylpiperidin-4-yl)-5-methyl-1H-indazole (enantiomer 1) (60 mg, 0.24 mmol), 6-iodo-2-methoxy-N-(4-methoxybenzyl) pyrimidin-4-amine (90 mg, 0.24 mmol), K₃PO₄ (103 mg, 0.485 mmol), CuI (92 mg, 0.585 mmol) in dry toluene (3 mL) was added N,N'-dimethyl-cyclohexane-1,2-diamine (138 mg, 0.970 mmol). The resulting green suspension was degassed with N₂ for 3 times and stirred at 110° C. for 2 hrs. The reaction mixture was concentrated and the residue was partitioned with NH₃.H₂O (5%, 10 mL) and EtOAc (20 mL). The organic layer was washed with brine, dried over Na₂SO₄ and concentrated. The residue was purified by prep-TLC (CH₂Cl₂:MeOH=15:1) to give the title compound (61 mg, yield 50%) as a white solid.

¹H NMR (300 MHz, CDCl₃): δ 8.86 (s, 1H), 8.07 (s, 1H), 7.54 (s, 1H), 7.31-7.27 (m, 2H), 6.92-6.89 (m, 2H), 6.69 (s, 1H), 5.19 (br s, 1H), 4.97-4.75 (m, 1H), 4.57-4.56 (m, 2H), 4.12 (s, 3H), 3.82 (s, 3H), 3.38-3.32 (m, 1H), 3.11-3.02 (m, 1H), 2.95-2.89 (m, 1H), 2.49 (s, 3H), 2.41 (s, 3H), 2.23-2.10 (m, 2H), 1.96-1.82 (m, 2H).

Description D126

(cis)-6-(6-(3-Fluoro-1-methylpiperidin-4-yl)-5-methyl-1H-indazol-1-yl)-2-methoxypyrimidin-4-amine (Enantiomer 1) (D126)

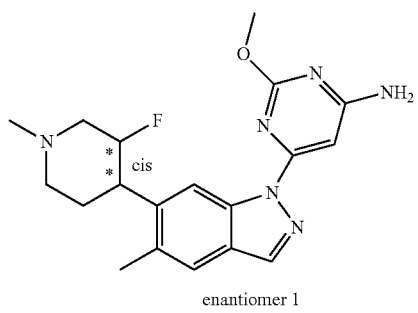 [SMILES: COc1nc(N)cc(-n2ncc3cc(C)c(C4CCN(C)CC4F)cc32)n1]

enantiomer 1

To a solution of (cis)-6-(6-(3-fluoro-1-methylpiperidin-4-yl)-5-methyl-1H-indazol-1-yl)-2-methoxy-N-(4-methoxybenzyl)pyrimidin-4-amine (enantiomer 1) (61 mg, 0.124 mmol) in CH₂Cl₂ (10 mL) was added TFA (10 mL) at rt slowly. The mixture was stirred at 40° C. overnight. Then, the mixture was stirred at 45° C. for 4 hrs. The mixture was cooled and adjusted to pH=7-8 with saturated NaHCO$_3$ under ice bath. DCM (30 mL×3) was added to extract the desired. The combined organic solutions were washed with brine, dried over Na$_2$SO$_4$ and concentrated. The residue was purified by prep-TLC (DCM:MeOH=15:1) to give the title compound (39 mg, yield 85%) as a white solid.

$^1$H NMR (300 MHz, CDCl$_3$): δ 8.82 (s, 1H), 8.07 (s, 1H), 7.53 (s, 1H), 6.73 (s, 1H), 4.94-4.72 (m, 3H), 4.12 (s, 3H), 3.36-3.31 (m, 1H), 3.11-3.02 (m, 1H), 2.94-2.88 (m, 1H), 2.48 (s, 3H), 2.40 (s, 3H), 2.23-2.06 (m, 2H), 1.95-1.82 (m, 2H).

LCMS: (mobile phase: 5-95% Acetonitrile in 2.5 min), Rt=1.53 min; MS Calcd: 370; MS Found: 371 [M+1]$^+$.

Description D127

4-(6-Iodo-2-methoxypyrimidin-4-yl)thiomorpholine 1,1-dioxide (D127)

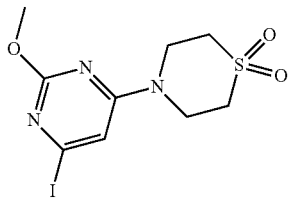 [SMILES: COc1nc(I)cc(N2CCS(=O)(=O)CC2)n1]

To a solution of thiomorpholine 1,1-dioxide hydrochloride (0.950 g, 5.52 mmol) and DIPEA (1.78 g, 13.8 mmol) in NMP (5 mL) was added 4,6-diiodo-2-methoxypyrimidine (1.00 g, 2.76 mmol) at rt. The resulting mixture was heated to 110° C. and stirred for 1 h. The mixture was poured into water (20 mL). EtOAc (30 mL×3) was added to extract the desired compound. The combined organic layers were washed with water (20 mL) and brine (20 mL×2), dried over Na$_2$SO$_4$ and concentrated under vacuum. The residue was slurried with EtOAc (15 mL) and filtered. The solid was collected and dried to give the title compound (0.65 g, yield 64%) as white solid.

$^1$H NMR (300 MHz, CDCl$_3$): δ 6.77 (s, 1H), 4.16-4.13 (m, 4H), 3.93 (s, 3H), 3.08-3.05 (m, 4H).

Description D128

(cis)-tert-Butyl 4-(1-(6-(1,1-dioxidothiomorpholino)-2-methoxypyrimidin-4-yl)-5-methyl-1H-indazol-6-yl)-3-fluoropiperidine-1-carboxylate (Enantiomer 1) (D128)

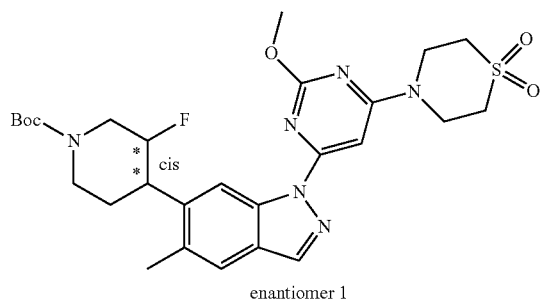 [SMILES: COc1nc(N2CCS(=O)(=O)CC2)cc(-n2ncc3cc(C)c(C4CCN(C(=O)OC(C)(C)C)CC4F)cc32)n1]

enantiomer 1

A mixture of (cis)-tert-butyl 3-fluoro-4-(5-methyl-1H-indazol-6-yl)piperidine-1-carboxylate (enantiomer 1) (80 mg, 0.24 mmol), 4-(6-iodo-2-methoxypyrimidin-4-yl) thiomorpholine 1,1-dioxide (106 mg, 0.288 mmol), CuI (46 mg, 0.24 mmol), K$_3$PO$_4$ (254 mg, 1.20 mmol), and N,N'-dimethyl-cyclohexane-1,2-diamine (29 mg, 0.24 mmol) in NMP (2 mL) was stirred at 100° C. under N$_2$ atmosphere for 2 hrs. The reaction mixture was cooled to room temperature and partitioned with ethyl acetate (50 mL) and water (30 mL). The organic solution was washed with water (2×50 mL), brine (50 mL), dried over Na$_2$SO$_4$ and concentrated. The residue was slurried with EtOAc/ether (0.5 mL/5 mL) to give 130 mg of white solid. The solid was further purified by chiral prep. HPLC with the method (Chiralpak IB 5 μm 20×250 mm, Phase: MeOH/EtOH=50/50, flow rate: 10 mL/min, temperature: 30° C., 230 nm)) to give the title compound (38 mg, yield 28%) as white solid.

$^1$H NMR (300 MHz, CDCl$_3$): δ 8.80 (s, 1H), 8.09 (s, 1H), 7.56 (s, 1H), 6.97 (s, 1H), 4.79-4.51 (m, 2H), 4.27-4.18 (m, 5H), 4.10 (s, 3H), 3.30-3.20 (m, 1H), 3.12-3.07 (m, 4H), 2.93-2.77 (m, 2H), 2.50 (s, 3H), 1.97-1.94 (m, 1H), 1.81-1.69 (m, 1H), 1.52 (s, 9H).

LCMS: (mobile phase: 20-95% Acetonitrile in 4 min), Rt=2.603 min; MS Calcd: 574; MS Found: 575 [M+H]$^+$.

Description D129

(cis)-4-(6-(6-(3-Fluoropiperidin-4-yl)-5-methyl-1H-indazol-1-yl)-2-methoxypyrimidin-4-yl)thiomorpholine 1,1-dioxide hydrochloride (Enantiomer 1) (D129)

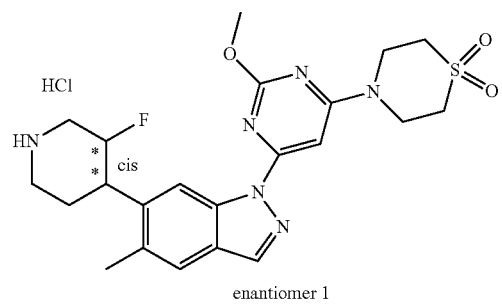 [SMILES: COc1nc(N2CCS(=O)(=O)CC2)cc(-n2ncc3cc(C)c(C4CCNCC4F)cc32)n1 ; Cl]

enantiomer 1

To a mixture of (cis)-tert-butyl 4-(1-(6-(1,1-dioxidothiomorpholino)-2-methoxypyrimidin-4-yl)-5-methyl-1H-indazol-6-yl)-3-fluoropiperidine-1-carboxylate (enantiomer 1) (38 mg, 0.066 mmol) in methanol (2 mL) was added conc. HCl (2 mL) dropwise at 0° C. The resulting mixture was stirred at rt for 2 hrs. The reaction mixture was concentrated to give the title compound (37 mg, yield >100%) as a white solid which was used for next step directly.

LCMS: (mobile phase: 5-95% Acetonitrile in 4 min), Rt=2.216 min; MS Calcd: 474; MS Found: 475 [M+H]$^+$.

Description D130

(cis)-tert-Butyl 4-(1-(6-(1,1-dioxidothiomorpholino)-2-methoxypyrimidin-4-yl)-5-methyl-1H-indazol-6-yl)-3-fluoropiperidine-1-carboxylate (Enantiomer 2) (D130)

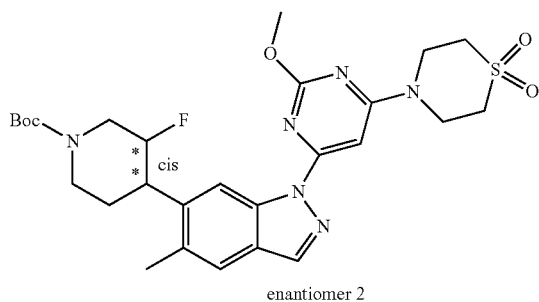 [SMILES: COc1nc(N2CCS(=O)(=O)CC2)cc(-n2ncc3cc(C)c(C4CCN(C(=O)OC(C)(C)C)CC4F)cc32)n1]

enantiomer 2

A mixture of (cis)-tert-butyl 3-fluoro-4-(5-methyl-1H-indazol-6-yl)piperidine-1-carboxylate (enantiomer 2) (80 mg, 0.24 mmol), 4-(6-iodo-2-methoxypyrimidin-4-yl)thiomorpholine 1,1-dioxide (106 mg, 0.288 mmol), CuI (46 mg, 0.24 mmol), K$_3$PO$_4$ (254 mg, 1.20 mmol) and N,N'-dimethyl-cyclohexane-1,2-diamine (29 mg, 0.24 mmol) in NMP (2 mL) was stirred at 100° C. under N$_2$ atmosphere for 1 h. The reaction mixture was cooled to room temperature and partitioned with ethyl acetate (50 mL) and water (30 mL). The organic solution was washed with water (2×30 mL), dried over Na$_2$SO$_4$ and concentrated. The residue was purified by chiral prep. HPLC with the method (Chiralpak IB 5 μm 20×250 mm, Phase: MeOH/EtOH=50/50, flow rate: 10 mL/min, temperature: 30° C., 230 nm)) to give the title compound (51 mg, yield 37%) as white solid.

$^1$H NMR (300 MHz, CDCl$_3$): δ 8.80 (s, 1H), 8.09 (s, 1H), 7.56 (s, 1H), 6.96 (s, 1H), 4.78-4.49 (m, 2H), 4.31-4.19 (m, 5H), 4.09 (s, 3H), 3.30-3.23 (m, 1H), 3.12-3.06 (m, 4H), 2.91-2.77 (m, 2H), 2.50 (s, 3H), 1.98-1.93 (m, 1H), 1.81-1.68 (m, 1H), 1.52 (s, 9H).

Description D131

(cis)-4-(6-(6-(3-Fluoropiperidin-4-yl)-5-methyl-1H-indazol-1-yl)-2-methoxypyrimidin-4-yl)thiomorpholine 1,1-dioxide hydrochloride (Enantiomer 2) (D131)

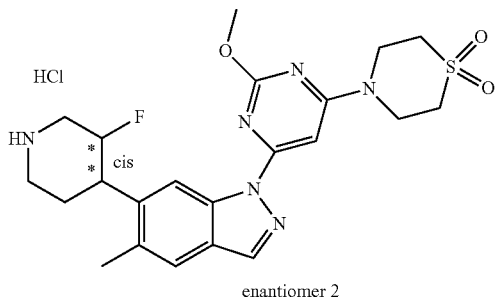 [SMILES: COc1nc(N2CCS(=O)(=O)CC2)cc(-n2ncc3cc(C)c(C4CCNCC4F)cc32)n1 ; Cl]

enantiomer 2

To a mixture of (cis)-tert-butyl 4-(1-(6-(1,1-dioxidothiomorpholino)-2-methoxypyrimidin-4-yl)-5-methyl-1H-indazol-6-yl)-3-fluoropiperidine-1-carboxylate (enantiomer 2) (51 mg, 0.087 mmol) in methanol (2 mL) was added conc. HCl (2 mL) dropwise at 0° C. The resulting mixture was stirred at rt for 2 hrs. The reaction mixture was concentrated to give the title compound (45 mg, yield >100%) as a white solid which was used for next step directly.

LCMS: (mobile phase: 5-95% Acetonitrile in 4 min), Rt=2.239 min; MS Calcd: 474; MS Found: 475 [M+H]$^+$.

Description D132

(cis)-tert-Butyl 3-fluoro-4-(1-(2-methoxy-6-morpholinopyrimidin-4-yl)-5-methyl-1H-indazol-6-yl)piperidine-1-carboxylate (Enantiomer 2) (D132)

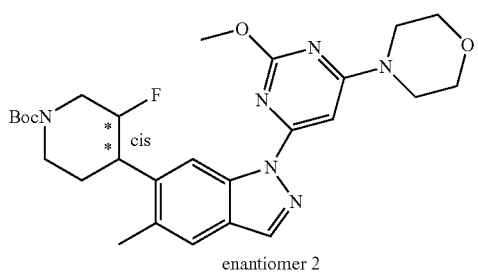 [SMILES: COc1nc(N2CCOCC2)cc(-n2ncc3cc(C)c(C4CCN(C(=O)OC(C)(C)C)CC4F)cc32)n1]

enantiomer 2

To a solution of (cis)-tert-butyl 3-fluoro-4-(5-methyl-1H-indazol-6-yl)piperidine-1-carboxylate (enantiomer 2) (45 mg, 0.14 mmol) in toluene (10 mL) was added 4-(6-iodo-2-methoxypyrimidin-4-yl)morpholine (64 mg, 0.20 mmol), K$_3$PO$_4$ (86 mg, 0.41 mmol), CuI (77 mg, 0.41 mmol) and N,N'-dimethyl-cyclohexane-1,2-diamine (58 mg, 0.41 mmol). The reaction mixture was refluxed overnight. The reaction mixture was cooled to room temperature and poured into NH$_3$.H$_2$O (10 mL). The desired was extracted with EtOAc (3×10 mL). The combined organic layers were washed with brine (2×10 mL), dried over Na$_2$SO$_4$ and concentrated. The residue was purified by prep. HPLC to give the title compound (37 mg, yield 52%) as a white solid.

$^1$H NMR (300 MHz, CDCl$_3$): δ 8.82 (s, 1H), 8.07 (s, 1H), 7.54 (s, 1H), 6.83 (s, 1H), 4.82-4.51 (m, 2H), 4.29-4.17 (m, 1H), 4.07 (s, 3H), 3.81-3.78 (m, 4H), 3.73-3.71 (m, 4H), 3.29-3.18 (m, 1H), 2.93-2.78 (m, 2H), 2.50 (s, 3H), 1.98-1.92 (m, 1H), 1.82-1.73 (m, 1H), 1.51 (s, 9H).

LCMS: (mobile phase: 5-95% Acetonitrile in 2.5 min), Rt=1.89 min; MS Calcd: 526. MS Found: 527 [M+1]$^+$.

Description D133

(cis)-tert-Butyl 3-fluoro-4-(1-(2-methoxy-6-morpholinopyrimidin-4-yl)-5-methyl-1H-indazol-6-yl)piperidine-1-carboxylate (Enantiomer 1) (D133)

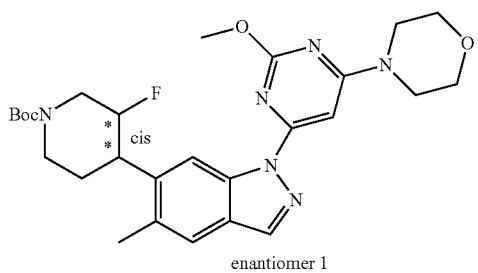 [SMILES: COc1nc(N2CCOCC2)cc(-n2ncc3cc(C)c(C4CCN(C(=O)OC(C)(C)C)CC4F)cc32)n1]

enantiomer 1

To a solution of (cis)-tert-butyl 3-fluoro-4-(5-methyl-1H-indazol-6-yl)piperidine-1-carboxylate (enantiomer 1) (65 mg, 0.20 mmol) in toluene (10 mL) was added 4-(6-iodo-2-methoxypyrimidin-4-yl)morpholine (93 mg, 0.29 mmol), $K_3PO_4$ (124 mg, 0.585 mmol), CuI (111 mg, 0.585 mmol) and N,N'-dimethyl-cyclohexane-1,2-diamine (83 mg, 0.59 mmol). The reaction mixture was refluxed overnight. The reaction mixture was cooled to room temperature and poured into $NH_3.H_2O$ (10 mL). The mixture was extracted with EtOAc (3×10 mL). The combined organic layers were washed with brine (2×10 mL), dried over $Na_2SO_4$ and concentrated. The residue was purified by prep. HPLC to give the title compound (37 mg, yield 36%) as a white solid.

$^1$H NMR (300 MHz, CDCl$_3$): δ 8.82 (s, 1H), 8.07 (s, 1H), 7.54 (s, 1H), 6.83 (s, 1H), 4.81-4.56 (m, 2H), 4.28-4.17 (m, 1H), 4.07 (s, 3H), 3.80-3.77 (m, 4H), 3.73-3.71 (m, 4H), 3.28-3.20 (m, 1H), 2.92-2.79 (m, 2H), 2.50 (s, 3H), 1.97-1.91 (m, 1H), 1.82-1.71 (m, 1H), 1.51 (s, 9H).

LCMS: (mobile phase: 5-95% Acetonitrile in 2.5 min), Rt=1.90 min; MS Calcd: 526, MS Found: 527 [M+1]$^+$.

Description D134

4-(6-Iodo-2-methylpyrimidin-4-yl)morpholine (D134)

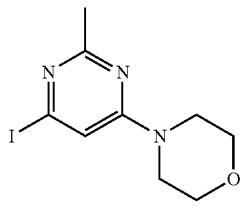

To a mixture of 4,6-diiodo-2-methylpyrimidine (1.10 g, 3.18 mmol) in i-PrOH (20 mL) was added morpholine (1.11 g, 12.7 mmol). The mixture was stirred at 45° C. for 2 hrs. Then the reaction was warmed to 65° C. and stirred for 30 min. The mixture was cooled to rt and poured into water (50 mL). EtOAc (50 mL×2) was added to extract the desired. The combined organic layers were washed with brine (30 mL×2), dried over $Na_2SO_4$ and concentrated to give the title compound as colorless oil (980 mg, yield 100%).

$^1$H NMR (300 MHz, CDCl$_3$): δ 6.76 (s, 1H), 3.76-3.73 (m, 4H), 3.59-3.56 (m, 4H), 2.45 (s, 3H).

Description D135

(cis)-tert-Butyl 3-fluoro-4-(5-methyl-1-(2-methyl-6-morpholinopyrimidin-4-yl)-1H-indazol-6-yl) piperidine-1-carboxylate (Enantiomer 1) (D135)

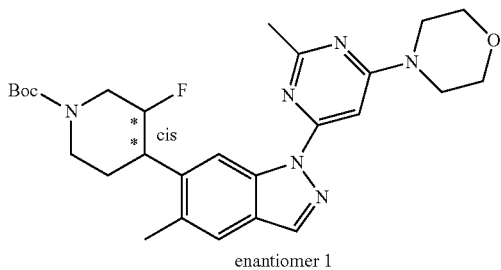 [SMILES: Cc1nc(N2CCOCC2)cc(-n2ncc3cc(C)c(C4CCN(C(=O)OC(C)(C)C)CC4F)cc32)n1]

enantiomer 1

To a suspension of (cis)-tert-butyl 3-fluoro-4-(5-methyl-1H-indazol-6-yl)piperidine-1-carboxylate (enantiomer 1) (50 mg, 0.15 mmol), 4-(6-iodo-2-methylpyrimidin-4-yl)morpholine (50 mg, 0.17 mmol), CuI (28 mg, 0.15 mmol), $K_3PO_4$ (64 mg, 0.30 mmol) in dry toluene (3 mL) was added N,N'-dimethyl-cyclohexane-1,2-diamine (43 mg, 0.30 mmol). The mixture was degassed with $N_2$ for 3 times and stirred at 110° C. for 2 hrs. The reaction mixture was cooled to rt and then poured into $NH_3.H_2O$ (5%, 15 mL) and extracted with EtOAc (15 mL×2). The combined organic layers were washed with brine, dried over $Na_2SO_4$ and concentrated. The crude was purified by prep. HPLC (prep-HPLC: from 50% water (0.1% HCl) and 50% $CH_3CN$ to 20% water (0.1% HCl) and 80% $CH_3CN$ in 20 min) to give a mixture (63 mg with 60% de-Boc compound) as a white solid.

LC-MS: (mobile phase: 5-95% Acetonitrile in 3 min), Rt=1.89 min; MS Calcd.: 510, MS Found: 411 (M−100+H)$^+$, purity: 60%; Rt=2.39 min, MS Calcd.: 510, MS Found: 511 (M+H)$^+$, purity: 40%.

Description D136

(cis)-tert-Butyl 3-fluoro-4-(5-methyl-1-(2-methyl-6-morpholinopyrimidin-4-yl)-1H-indazol-6-yl) piperidine-1-carboxylate (Enantiomer 2) (D136)

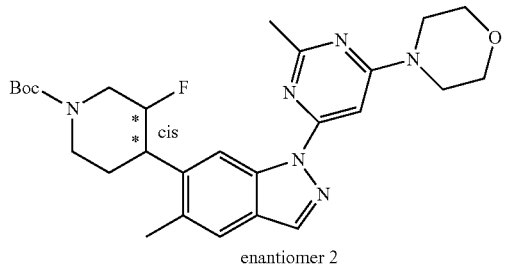 [SMILES: Cc1nc(N2CCOCC2)cc(-n2ncc3cc(C)c(C4CCN(C(=O)OC(C)(C)C)CC4F)cc32)n1]

enantiomer 2

To a suspension of tert-butyl 3-fluoro-4-(5-methyl-1H-indazol-6-yl)piperidine-1-carboxylate (enantiomer 2) (50 mg, 0.15 mmol), 4-(6-iodo-2-methylpyrimidin-4-yl)morpholine (50 mg, 0.17 mmol), CuI (28 mg, 0.15 mmol), $K_3PO_4$ (64 mg, 0.30 mmol) in dry toluene (3 mL) was added N,N'-dimethyl-cyclohexane-1,2-diamine (43 mg, 0.30 mmol). The mixture was degassed with $N_2$ for 3 times and stirred at 110° C. for 2 hrs. The reaction mixture was cooled to rt and then poured into $NH_3.H_2O$ (5%, 15 mL) and extracted with EtOAc (15 mL×2). The combined organic layers were washed with brine, dried over $Na_2SO_4$ and concentrated. The crude was purified by prep. HPLC (prep-HPLC: from 50% water (0.1% HCl) and 50% $CH_3CN$ to 20% water (0.1% HCl) and 80% $CH_3CN$ in 20 min) to give a mixture (63 mg with 60% de-Boc compound) as a white solid.

LC-MS: (mobile phase: 5-95% Acetonitrile in 3 min), Rt=1.89 min; MS Calcd.: 410, MS Found: 411 (M−100+H)$^+$, purity: 60%; Rt=2.39 min; MS Calcd.: 510, MS Found: 511 [M+H]$^+$, purity: 40%.

Description D137

1-(6-Iodo-2-methoxypyrimidin-4-yl)azetidine-3-carbonitrile (D137)

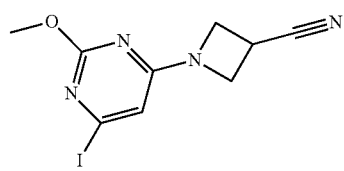

A solution of 4,6-diiodo-2-methoxypyrimidine (1.00 g, 2.76 mmol), azetidine-3-carbonitrile hydrochloride (0.52 g, 4.42 mmol) and DIPEA (1.78 g, 13.8 mmol) in NMP (5 mL) was heated to 100° C. and stirred for 1 h. The mixture was partitioned with EtOAc (100 mL) and water (100 mL). The organic layer was washed with water (100 mL) and brine (50 mL), dried over $Na_2SO_4$ and concentrated. The residue was purified by column (DCM) to give the title compound (600 mg, yield 69%) as a white solid.

$^1$H NMR (300 MHz, $CDCl_3$): δ 6.36 (s, 1H), 4.40-4.27 (m, 4H), 3.91 (s, 3H), 3.66-3.58 (m, 1H).

Description D138 tert-Butyl 3,3-difluoro-4-(5-methyl-1H-indazol-6-yl)piperidine-1-carboxylate (D138)

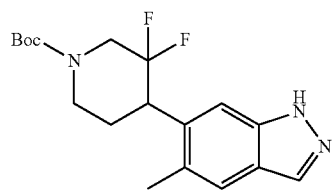 [SMILES: Cc1cc2cn[nH]c2cc1C1CCN(C(=O)OC(C)(C)C)CC1(F)F]

To a solution of 6-(3,3-difluoropiperidin-4-yl)-5-methyl-1H-indazole hydrochloride (1.00 g, 3.48 mmol) in MeOH (8 mL) and water (2 mL) was added KOH (471 mg, 8.40 mmol) and $Boc_2O$ (917 mg, 4.20 mmol) under ice bath. The mixture was warmed to 25° C. and stirred for 2 hrs. The reaction mixture was poured into water (50 mL) and then extracted with DCM (30 mL×3). The combined organic layers were washed with brine, dried over $MgSO_4$, and concentrated. The crude was purified by column chromatography (PE:EtOAc=5:1) to give the title compound (660 mg, yield 54%) as white solid.

LCMS: (mobile phase: 5-95% Acetonitrile in 3 min), Rt=2.03 min; MS Calcd: 351; MS Found: 352 $[M+1]^+$.

Description D139 and D140 tert-Butyl 3,3-difluoro-4-(5-methyl-1H-indazol-6-yl)piperidine-1-carboxylate (Enantiomer 1) (D139) and tert-Butyl 3,3-difluoro-4-(5-methyl-1H-indazol-6-yl)piperidine-1-carboxylate (Enantiomer 2) (D140)

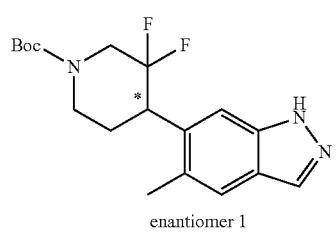

enantiomer 1

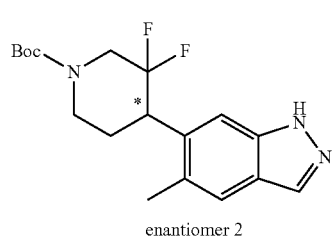

enantiomer 2

Racemic tert-butyl 3,3-difluoro-4-(5-methyl-1H-indazol-6-yl)piperidine-1-carboxylate (660 mg, 1.88 mmol) was separated by Chiral-HPLC (Chiralpak IB 250 mm×20 mm. Phase: Hex/EtOH=90/10, flowrate: 15 mL/min, W: 214 nm, temperature: ambient) to give tert-butyl 3,3-difluoro-4-(5-methyl-1H-indazol-6-yl)piperidine-1-carboxylate (enantiomer 1) (D139) (290 mg, yield 44%) as white solid and tert-butyl 3,3-difluoro-4-(5-methyl-1H-indazol-6-yl)piperidine-1-carboxylate (enantiomer 2) (D140) (260 mg, yield 39%) as white solid.

D139: $^1$H NMR (300 MHz, $CDCl_3$): δ 10.10 (br s, 1H), 7.97 (s, 1H), 7.57 (s, 1H), 7.53 (s, 1H), 4.68-4.22 (m, 2H), 3.55-3.36 (m, 1H), 3.22-2.79 (m, 2H), 2.47 (s, 3H), 2.28-2.11 (m, 1H), 1.89-1.84 (m, 1H), 1.51 (s, 9H).

Chiral HPLC: Chiralpak IB 250 mm×4.6 mm, 5 μm. Phase: Hex/EtOH=90/10, flowrate: 1.0 mL/min, W: 230 nm; Rt: 7.543 min, 100% ee.

D140: $^1$H NMR (300 MHz, $CDCl_3$): δ 7.97 (s, 1H), 7.57 (s, 1H), 7.54 (s, 1H), 4.67-4.20 (m, 2H), 3.56-3.37 (m, 1H), 3.22-2.80 (m, 2H), 2.47 (s, 3H), 2.30-2.11 (m, 1H), 1.91-1.83 (m, 1H), 1.51 (s, 9H).

Chiral HPLC: Chiralpak IB 250 mm×4.6 mm, 5 μm. Phase: Hex/EtOH=90/10, flowrate: 1.0 mL/min, W: 230 nm; Rt: 10.446 min, 100% ee.

Description D141 tert-Butyl 4-(1-(6-(3-cyanoazetidin-1-yl)-2-methoxypyrimidin-4-yl)-5-methyl-1H-indazol-6-yl)-3,3-difluoropiperidine-1-carboxylate (Enantiomer 1) (D141)

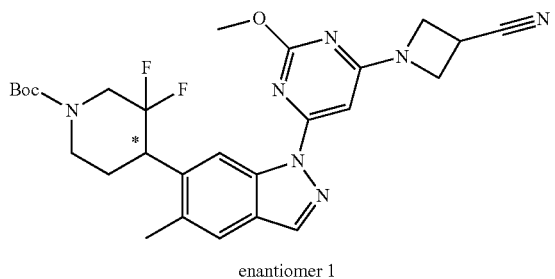 [SMILES: COc1nc(N2CC(C#N)C2)cc(-n2ncc3cc(C)c(C4CCN(C(=O)OC(C)(C)C)CC4(F)F)cc32)n1]

enantiomer 1

A mixture of tert-butyl 3,3-difluoro-4-(5-methyl-1H-indazol-6-yl)piperidine-1-carboxylate (enantiomer 1) (100 mg, 0.285 mmol), 1-(6-iodo-2-methoxypyrimidin-4-yl)azetidine-3-carbonitrile (135 mg, 0.427 mmol), N,N'-dimethylcyclohexane-1,2-diamine (81 mg, 0.57 mmol), CuI (108 mg, 0.570 mmol) and $K_3PO_4$ (120 mg, 0.570 mmol) in toluene (10 mL) was heated to 110° C. and stirred for 4 hrs under $N_2$. The reaction mixture was diluted with EtOAc (30 mL) and washed with $NH_3.H_2O$ (10%, 20 mL×3). The combined organic layers were dried over $Na_2SO_4$ and concentrated. The residue was dispersed in 1.5 mL of EtOAc and stirred at ambient temperature for 20 min. The solid was collected by filtration to give the title compound (90 mg, yield 58%) as white solid.

$^1$H NMR (300 MHz, $CDCl_3$): δ 8.95 (s, 1H), 8.10 (s, 1H), 7.56 (s, 1H), 6.50 (s, 1H), 4.49-4.36 (m, 6H), 4.09 (s, 3H), 3.69-3.59 (m, 1H), 3.56-3.42 (m, 1H), 3.22-3.06 (m, 1H), 2.98-2.81 (m, 1H), 2.49 (s, 3H), 2.28-2.12 (m, 1H), 1.93-1.89 (m, 1H), 1.51 (s, 9H).

LCMS: (mobile phase: 30-95% Acetonitrile in 3 min), Rt=2.12 min, MS Calcd: 539; MS Found: 540 [M+1]$^+$.

Description D142 tert-Butyl 4-(1-(6-(3-cyanoazetidin-1-yl)-2-methoxypyrimidin-4-yl)-5-methyl-1H-indazol-6-yl)-3,3-difluoropiperidine-1-carboxylate (Enantiomer 2) (D142)

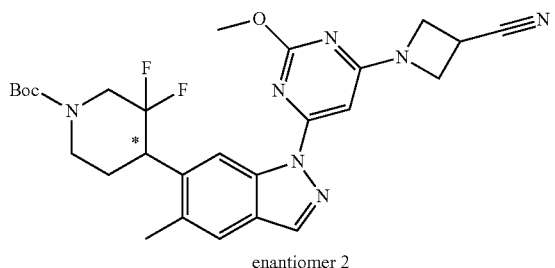 [SMILES: COc1nc(N2CC(C#N)C2)cc(-n2ncc3cc(C)c(C4CCN(C(=O)OC(C)(C)C)CC4(F)F)cc32)n1]

enantiomer 2

A mixture of tert-butyl 3,3-difluoro-4-(5-methyl-1H-indazol-6-yl)piperidine-1-carboxylate (enantiomer 2) (100 mg, 0.285 mmol), 1-(6-iodo-2-methoxypyrimidin-4-yl)azetidine-3-carbonitrile (135 mg, 0.427 mmol), N,N'-dimethylcyclohexane-1,2-diamine (81 mg, 0.57 mmol), CuI (108 mg, 0.570 mmol) and $K_3PO_4$ (120 mg, 0.570 mmol) in toluene (10 mL) was heated to 110° C. and stirred for 4 hrs under $N_2$. The reaction mixture was diluted with EtOAc (30 mL) and washed with $NH_3.H_2O$ (10%, 20 mL×2) and brine (30 mL). The organic layer was dried over $Na_2SO_4$ and concentrated. The residue was dispersed in EtOAc (1 mL) and stirred for 15 min. The solid was collected by filtration to give the title compound (80 mg, yield 52%) as white solid.

$^1$H NMR (300 MHz, $CDCl_3$): δ 8.95 (s, 1H), 8.10 (s, 1H), 7.56 (s, 1H), 6.50 (s, 1H), 4.49-4.36 (m, 6H), 4.09 (s, 3H), 3.69-3.61 (m, 1H), 3.57-3.43 (m, 1H), 3.26-3.04 (m, 1H), 2.99-2.80 (m, 1H), 2.49 (s, 3H), 2.27-2.12 (m, 1H), 1.93-1.88 (m, 1H), 1.51 (s, 9H).

LCMS: (mobile phase: 30-95% Acetonitrile in 2.5 min), Rt=1.43 min, MS Calcd: 539; MS Found: 540 [M+1]$^+$.

Description D143

1-(6-Bromo-5-fluoro-1H-indazol-1-yl)ethanone (D143)

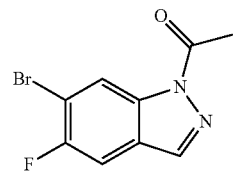

To a solution of 5-bromo-4-fluoro-2-methylaniline (15.0 g, 73.5 mmol) in $CHCl_3$ (300 mL) was added $Ac_2O$ (22.7 g, 222 mmol) under ice bath. The resulting mixture was stirred for another 30 min. 18-Crown-6 (9.70 g, 36.8 mmol), KOAc (2.2 g, 22 mmol) and isoamyl nitrite (17.3 g, 148 mmol) were added to the reaction mixture at rt. The mixture was refluxed overnight. The solvent was removed under vacuum and the residue was partitioned with water (500 mL) and EtOAc (600 mL). The organic layer was separated and the aqueous was extracted with EtOAc (200 mL×2). The combined organic layers were washed with brine, dried over $MgSO_4$ and concentrated. The crude was purified by column chromatography (from PE:EtOAc=50:1 to DCM:EtOAc=5:1) to give the title compound (5.0 g, yield 26%) as orange solid.

$^1$H NMR (300 MHz, $CDCl_3$): δ 8.74 (d, J=5.7 Hz, 1H), 8.07 (s, 1H), 7.43 (d, J=7.5 Hz, 1H), 2.78 (s, 3H).

Description D144

6-Bromo-5-fluoro-1H-indazole (D144)

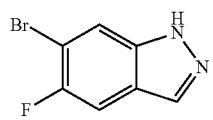

To a solution of 1-(6-bromo-5-fluoro-1H-indazol-1-yl)ethanone (6.4 g, 25 mmol) in THF (100 mL) was added NaOH (4 M, 13 mL, 50 mmol) at rt. The resulting mixture was stirred for 2 hrs at rt. The solvent was removed under vacuum and the residue was partitioned between water (300 mL) and EtOAc (200 mL). The organic layer was separated and the aqueous layer was extracted with EtOAc (200 mL). The combined organic layers were washed with brine, dried over MgSO$_4$ and concentrated. The crude was triturated with PE (20 mL) and filtered to give the title compound (4.4 g, yield 81%) as a brown solid.

$^1$H NMR (300 MHz, CDCl$_3$): δ 10.10 (br s, 1H), 8.04 (s, 1H), 7.75 (d, J=5.4 Hz, 1H), 7.47 (d, J=8.4 Hz, 1H).

LCMS: (mobile phase: 5-95% Acetonitrile in 2.5 min), Rt=1.45 min, MS Calcd: 214, 216; MS Found: 215, 217 [M+H]$^+$.

Description D145

6-Bromo-5-fluoro-1-(tetrahydro-2H-pyran-2-yl)-1H-indazole (D145)

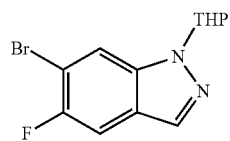

To a suspension of 6-bromo-5-fluoro-1H-indazole (4.4 g, 20 mmol) in dry DCM (100 mL) was added DHP (3.4 g, 40 mmol) and TsOH (0.7 g, 4 mmol) at rt. The resulting mixture was warmed to 30° C. and stirred for 3 hrs. The reaction mixture was washed with Na$_2$CO$_3$ (sat. 200 mL) and then the aqueous layer was extracted with DCM (100 mL). The combined organic layers were washed with brine, dried over MgSO$_4$ and concentrated. The crude was purified by column chromatography (PE:EtOAc=20:1) to give the title compound (6.0 g, yield 98%) as a slight orange solid.

$^1$H NMR (300 MHz, CDCl$_3$): δ 7.95 (s, 1H), 7.85 (d, J=5.4 Hz, 1H), 7.41 (d, J=8.1 Hz, 1H), 5.66 (dd, J=9.3, 2.7 Hz, 1H), 4.03-3.99 (m, 1H), 3.79-3.71 (m, 1H), 2.57-2.44 (m, 1H), 2.21-2.07 (m, 2H), 1.90-1.60 (m, 3H).

LCMS: (mobile phase: 5-95% Acetonitrile in 2.5 min), Rt=1.71 min, MS Calcd: 298, 300; MS Found: 299, 301 [M+H]$^+$.

Description D146 tert-Butyl 4-(5-fluoro-1-(tetrahydro-2H-pyran-2-yl)-1H-indazol-6-yl)-5,6-dihydropyridine-1 (2H)-carboxylate (D146)

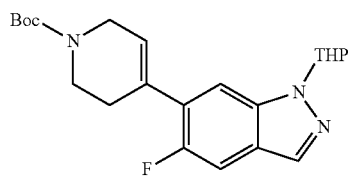

A suspension of 6-bromo-5-fluoro-1-(tetrahydro-2H-pyran-2-yl)-1H-indazole (5.0 g, 17 mmol), tert-butyl 4-(4, 4,5,5-tetramethyl-1,3,2-dioxaborolan-2-yl)-5,6-dihydropyridine-1(2H)-carboxylate (5.6 g, 18 mmol), Na$_2$CO$_3$ (4.6 g, 43 mmol), Pd(dppf)Cl$_2$ (622 mg, 0.850 mmol) in dioxane (50 mL) and water (10 mL) was degassed with N$_2$ for 3 times. The mixture was heated to 90° C. and stirred for 5 hrs. The reaction mixture was cooled and the solvent was removed under vacuum. The residue was partitioned between water (200 mL) and EtOAc (100 mL). The organic layer was separated and the aqueous layer was extracted with EtOAc (100 mL×2). The combined organic layers were washed with brine, dried over MgSO$_4$ and concentrated. The crude was purified by column chromatography (PE:EtOAc from 20:1 to 10:1) to give the title compound (5.6 g, yield 83%) as an oily solid.

$^1$H NMR (300 MHz, CDCl$_3$): δ 7.95 (s, 1H), 7.40 (d, J=5.7 Hz, 1H), 7.32 (d, J=10.5 Hz, 1H), 5.96 (br s, 1H), 5.70-5.67 (m, 1H), 4.10-4.02 (m, 3H), 3.80-3.61 (m, 3H), 2.61-2.42 (m, 3H), 2.21-2.03 (m, 2H), 1.82-1.63 (m, 3H), 1.50 (s, 9H).

Description D147

(trans)-tert-butyl 4-(5-fluoro-1-(tetrahydro-2H-pyran-2-yl)-1H-indazol-6-yl)-3-hydroxy piperidine-1-carboxylate (D147)

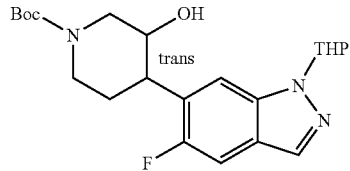

To a solution of tert-butyl 4-(5-fluoro-1-(tetrahydro-2H-pyran-2-yl)-1H-indazol-6-yl)-5,6-dihydropyridine-1(2H)-carboxylate (6.2 g, 15 mmol) in dry THF (45 mL) was added BH$_3$/THF (1 M, 45 mL, 45 mmol) at 0° C. under N$_2$. The resulting mixture was warmed to 20° C. and stirred overnight. The reaction mixture was cooled under ice bath and NaOH (4 M, 11 mL, 45 mmol) was added dropwise and carefully. H$_2$O$_2$ (30%, 17.0 g, 150 mmol) was followed and kept the temperature below 5° C. Then the reaction mixture was warmed to 30° C. and stirred for 1 h. The reaction mixture was gradually poured into Na$_2$S$_2$O$_3$ (20%, 200 mL) and stirred for 20 min. The organic layer was separated and the aqueous was extracted with EtOAc (50 mL×2). The combined organic layers were washed with brine, dried over MgSO$_4$ and concentrated. The crude was purified by column chromatography (PE:EtOAc from 5:1 to 1:1) to give the title compound (4.5 g, yield 69%) as a white solid.

$^1$H NMR (300 MHz, CDCl$_3$): δ 7.94 (s, 1H), 7.44 (d, J=5.1 Hz, 1H), 7.35 (d, J=10.2 Hz, 1H), 5.67 (dd, J=9.3, 2.4 Hz, 1H), 4.53-4.35 (m, 1H), 4.31-4.08 (m, 1H), 4.05-3.85 (m, 2H), 3.78-3.70 (m, 1H), 3.07-2.95 (m, 1H), 2.85-2.47 (m, 3H), 2.20-2.00 (m, 2H), 1.86-1.66 (m, 6H), 1.49 (s, 9H).

LCMS: (mobile phase: 5-95% Acetonitrile in 2.5 min), Rt=1.62 min, MS Calcd: 419; MS Found: 420 [M+H]$^+$.

Description D148

(cis)-tert-Butyl 3-fluoro-4-(5-fluoro-1-(tetrahydro-2H-pyran-2-yl)-1H-indazol-6-yl) piperidine-1-carboxylate (D148)

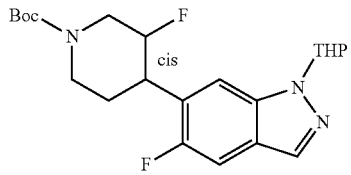

A solution of (trans)-tert-butyl 4-(5-fluoro-1-(tetrahydro-2H-pyran-2-yl)-1H-indazol-6-yl)-3-hydroxy piperidine-1-carboxylate (4.7 g, 11 mmol) in dry DCM (100 mL) was cooled to −60° C. under $N_2$ protected. DAST (7.1 g, 44 mmol) was added dropwise. The resulting mixture was stirred at −60° C. for 1 h and then gradually warmed to 20° C. and stirred for 3 hrs. The reaction mixture was gradually poured into $Na_2CO_3$ (sat., 150 mL) and stirred for 15 min. The organic layer was separated and the aqueous was extracted with DCM (100 mL). The combined organic layers were washed with brine, dried over $MgSO_4$ and concentrated. The crude was purified by column chromatography (PE:EtOAc from 10:1 to 5:1) to give the title compound (2.8 g, yield 60%) as a white solid.

$^1$H NMR (300 MHz, $CDCl_3$): δ 7.96 (s, 1H), 7.45 (d, J=5.4 Hz, 1H), 7.35 (d, J=10.2 Hz, 1H), 5.69 (dd, J=9.0, 2.4 Hz, 1H), 4.92-4.65 (m, 1H), 4.65-4.41 (m, 1H), 4.27-4.10 (m, 1H), 4.04-4.00 (m, 1H), 3.81-3.71 (m, 1H), 3.30-3.15 (m, 1H), 2.92-2.76 (m, 2H), 2.62-2.48 (m, 1H), 2.20-2.04 (m, 3H), 1.81-1.66 (m, 4H), 1.50 (s, 9H).

LCMS: (mobile phase: 5-95% Acetonitrile in 2.5 min), two peaks, Rt=1.76, 1.82 min, MS Calcd: 421; MS Found: 422 [M+H]$^+$.

Description D149

(cis)-5-Fluoro-6-(3-fluoropiperidin-4-yl)-1H-indazole hydrochloride (D149)

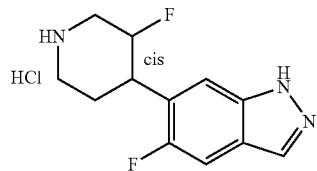 [SMILES: Cl ; Fc1cc2cn[nH]c2cc1C1CCNCC1F]

(cis)-tert-Butyl 3-fluoro-4-(5-fluoro-1-(tetrahydro-2H-pyran-2-yl)-1H-indazol-6-yl) piperidine-1-carboxylate (1.2 g, 2.8 mmol) was dissolved in HCl/MeOH (8 M, 20 mL) and stirred at 30° C. overnight. The reaction mixture was concentrated to give the title compound (900 mg, crude) as a pale yellow solid. The crude was used for next step directly.

LCMS: (mobile phase: 5-95% Acetonitrile in 2.5 min), Rt=1.15 min, MS Calcd: 237; MS Found: 238 [M+H]$^+$, purity: 91% (254 nm).

Description D150

(cis)-5-Fluoro-6-(3-fluoro-1-methylpiperidin-4-yl)-1H-indazole (D150)

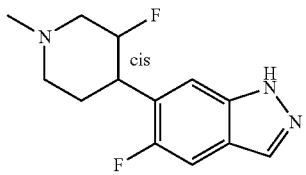 [SMILES: CN1CCC(c2cc3[nH]ncc3cc2F)C(F)C1]

To a solution of (cis)-5-fluoro-6-(3-fluoropiperidin-4-yl)-1H-indazole hydrochloride (0.90 g crude, 2.8 mmol) in methanol (20 mL) was added formaldehyde (37%, 6 mL) and $NaBH_3CN$ (352 mg, 5.60 mmol) in portions at rt. The resulting mixture was stirred for 1 h. The reaction mixture was poured into $Na_2CO_3$ (sat., 100 mL) and stirred for 15 min. The aqueous layer was extracted with DCM (50 mL×3) and the combined organic layers were washed with brine, dried over $MgSO_4$ and concentrated. The crude was dissolved in $NH_3$/MeOH (3M, 20 mL) and stirred at rt overnight. The reaction mixture was concentrated and the crude was triturated with PE/DCM (50 mL, 3/1) to give the title compound (270 mg) as a white solid. The liquid portion was concentrated and then purified by prep. TLC (DCM: MeOH=10:1) to give the title compound (150 mg) as a white solid. The compound was obtained in 57% yield.

$^1$H NMR (300 MHz, $CD_3OD$): δ 7.99 (s, 1H), 7.52 (d, J=5.4 Hz, 1H), 7.43 (d, J=10.8 Hz, 1H), 5.29-4.87 (m, 1H), 3.31-3.29 (m, 1H), 3.18-3.05 (m, 1H), 2.96-2.93 (m, 1H), 2.43 (s, 3H), 2.28-2.18 (m, 2H), 2.02-1.83 (m, 2H).

LCMS: (mobile phase: 20-95% Acetonitrile in 3 min), Rt=1.63 min, MS Calcd: 251; MS Found: 252 [M+H]$^+$.

Description D151 and D152

(cis)-5-Fluoro-6-(3-fluoro-1-methylpiperidin-4-yl)-1H-indazole (Enantiomer 1) (D151) and (cis)-5-Fluoro-6-(3-fluoro-1-methylpiperidin-4-yl)-1H-indazole (Enantiomer 2) (D152)

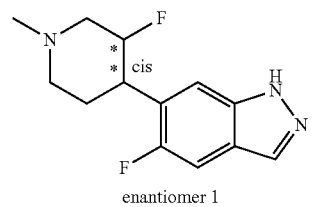

enantiomer 1

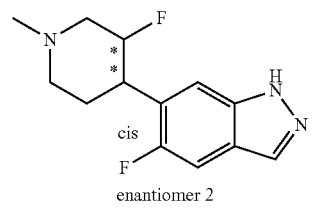

enantiomer 2

(cis)-5-Fluoro-6-(3-fluoro-1-methylpiperidin-4-yl)-1H-indazole (500 mg, 1.99 mmol) was separated by Chiral HPLC [Chiral condition: Chiralpak IC 5 μm 20*250 mm, Phase: Hex/IPA=80/20, flow rate: 15 mL/min, 205 nm, T=30° C.] to give the title compounds (cis)-5-fluoro-(enantiomer 1) (D151) (140 mg, yield 28%) and (cis)-5-Fluoro-6-(3-fluoro-1-methylpiperidin-4-yl)-1H-indazole (enantiomer 2) (D152) (90 mg, yield 18%) both as white solid.

D151: $^1$H NMR (300 MHz, CDCl$_3$): δ 10.53 (br s, 1H), 8.01 (s, 1H), 7.43-7.37 (m, 2H), 5.02-4.78 (m, 1H), 3.38-3.31 (m, 1H), 3.19-3.07 (m, 1H), 2.94-2.89 (m, 1H), 2.43 (s, 3H), 2.24-2.09 (m, 2H), 2.04-1.80 (m, 2H).

Chiral HPLC [Chiralpak IF 5 um 4.6*250 mm, Phase: Hex/EtOH/DEA=80/20/0.2, flow rate: 1.0 mL/min, 230 nm, T=30° C.], Rt=6.236 min, 99.31% ee.

D152: $^1$H NMR (300 MHz, CDCl$_3$): δ 10.53 (br s, 1H), 8.01 (s, 1H), 7.43-7.37 (m, 2H), 5.02-4.78 (m, 1H), 3.38-3.31 (m, 1H), 3.19-3.07 (m, 1H), 2.94-2.89 (m, 1H), 2.43 (s, 3H), 2.24-2.09 (m, 2H), 2.04-1.80 (m, 2H).

Chiral HPLC [Chiralpak IF 5 um 4.6*250 mm, Phase: Hex/EtOH/DEA=80/20/0.2, flow rate: 1.0 mL/min, 230 nm, T=30° C.], Rt=6.236 min, 97.19% ee.

Description D153

(cis)-5-Fluoro-6-((3S,4R)-3-fluoro-1-methylpiperidin-4-yl)-1-(2-methoxy-6-(3-((tetrahydro-2H-pyran-2-yl)oxy)azetidin-1-yl)pyrimidin-4-yl)-1H-indazole (Enantiomer 1) (D153)

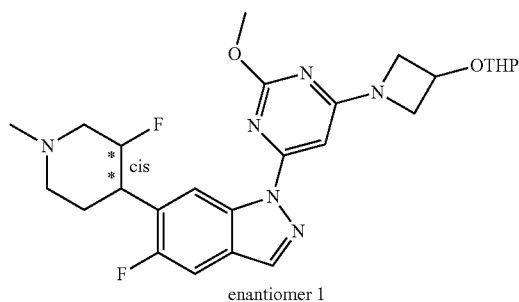

enantiomer 1

To a suspension of (cis)-5-fluoro-6-((3S,4R)-3-fluoro-1-methylpiperidin-4-yl)-1H-indazole (enantiomer 1) (56 mg, 0.22 mmol), 4-iodo-2-methoxy-6-(3-((tetrahydro-2H-pyran-2-yl)oxy)azetidin-1-yl)pyrimidine (105 mg, 0.269 mmol), CuI (42 mg, 0.22 mmol) and K$_3$PO$_4$ (95 mg, 0.45 mmol) in dry toluene (4 mL) was added N,N'-dimethyl-cyclohexane-1,2-diamine (63 mg, 0.44 mmol). The suspension was degassed with N$_2$ and heated to 110° C. for 2 hrs. The solvent was removed under vacuum and the residue was purified by C-18 column (CH$_3$CN/H$_2$O: 50-90%) to give a crude product as a yellow solid. The yellow solid was scattered in CH$_3$CN (1 mL). The solid was collected by filtration and washed with CH$_3$CN (1 mL) to give the title compound (50 mg, yield 44%) as a white solid.

LC-MS [mobile phase: from 50% water and 50% CH$_3$CN to 5% water and 95% CH$_3$CN in 3.0 min], Rt=1.91 min; MS Calcd: 514; MS Found: 515 [M+H]$^+$.

Description D154

(cis)-5-Fluoro-6-((3S,4R)-3-fluoro-1-methylpiperidin-4-yl)-1-(2-methoxy-6-(3-((tetrahydro-2H-pyran-2-yl)oxy)azetidin-1-yl)pyrimidin-4-yl)-1H-indazole (Enantiomer 2) (D154)

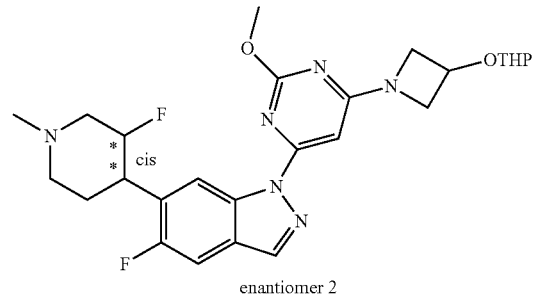

enantiomer 2

To a suspension of (cis)-5-fluoro-6-((3S,4R)-3-fluoro-1-methylpiperidin-4-yl)-1H-indazole (enantiomer 2) (52 mg, 0.21 mmol), 4-iodo-2-methoxy-6-(3-((tetrahydro-2H-pyran-2-yl)oxy)azetidin-1-yl)pyrimidine (97 mg, 0.25 mmol), CuI (39 mg, 0.21 mmol) and K$_3$PO$_4$ (88 mg, 0.42 mmol) in dry toluene (4 mL) was added N,N'-dimethyl-cyclohexane-1,2-diamine (59 mg, 0.42 mmol). The suspension was degassed with N$_2$ and heated to 110° C. for 2 hrs. The solvent was removed under vacuum and the residue was purified by prep-TLC (DCM:MeOH=10:1) to give the title compound (40 mg, yield 38%) as a white solid.

LC-MS [mobile phase: from 70% water and 30% CH$_3$CN to 5% water and 95% CH$_3$CN in 2.5 min], Rt=1.66 min; MS Calcd: 514; MS Found: 515 [M+H]$^+$.

Description D155

(cis)-5-Fluoro-6-(3-fluoro-1-methylpiperidin-4-yl)-1-(2-methyl-6-(3-((tetrahydro-2H-pyran-2-yl)oxy)azetidin-1-yl)pyrimidin-4-yl)-1H-indazole (Enantiomer 1) (D155)

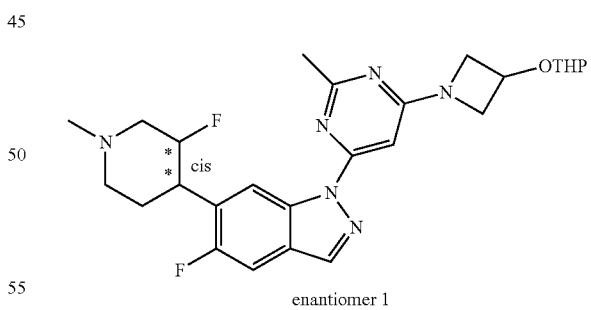

enantiomer 1

To a suspension of (cis)-5-fluoro-6-(3-fluoro-1-methylpiperidin-4-yl)-1H-indazole (enantiomers 1) (40 mg, 0.16 mmol), 4-iodo-2-methyl-6-(3-((tetrahydro-2H-pyran-2-yl)oxy)azetidin-1-yl)pyrimidine (72 mg, 0.19 mmol), CuI (30 mg, 0.06 mmol) and K$_3$PO$_4$ (68 mg, 0.32 mmol) in dry toluene (2 mL) was added N,N'-dimethyl-cyclohexane-1,2-diamine (46 mg, 0.32 mmol). The suspension was degassed with N$_2$ and stirred at 110° C. for 3 hrs. The reaction mixture was cooled to rt and partitioned between diluted ammonia (30 mL) and EtOAc (30 mL). The organic layer was washed with brine, dried over MgSO$_4$ and concentrated. The crude was purified by prep. TLC (DCM:MeOH=10:1) to give the title compound (70 mg, yield 89%) as a white solid.

$^1$H NMR (300 MHz, CDCl$_3$): δ 8.94 (d, J=6.6 Hz, 1H), 8.10 (s, 1H), 7.36 (d, J=9.9 Hz, 1H), 6.59 (s, 1H), 5.12-4.84 (m, 1H), 4.76-4.67 (m, 2H), 4.41-4.33 (m, 2H), 4.15-4.03 (m, 2H), 3.93-3.85 (m, 1H), 3.59-3.51 (m, 1H), 3.41-3.32 (m, 1H), 3.22-3.10 (m, 1H), 2.99-2.94 (m, 1H), 2.62 (s, 3H), 2.44 (s, 3H), 2.30-2.13 (m, 2H), 2.13-2.02 (m, 2H), 1.90-1.65 (m, 6H).

LCMS: (mobile phase: 5-95% Acetonitrile in 3 min), Rt=2.40 min, MS Calcd: 499; MS Found: 500 [M+H]$^+$.

Description D156

(cis)-5-Fluoro-6-(3-fluoro-1-methylpiperidin-4-yl)-1-(2-methyl-6-(3-((tetrahydro-2H-pyran-2-yl)oxy)azetidin-1-yl)pyrimidin-4-yl)-1H-indazole (Enantiomer 2) (D156)

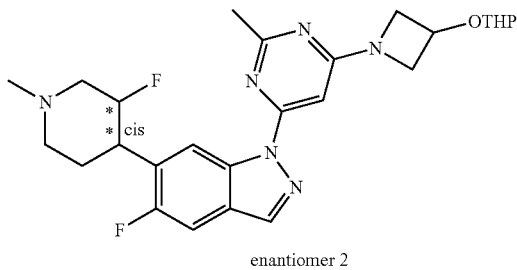

enantiomer 2

To a suspension of (cis)-5-fluoro-6-(3-fluoro-1-methylpiperidin-4-yl)-1H-indazole (enantiomer 2) (40 mg, 0.16 mmol), 4-iodo-2-methyl-6-(3-((tetrahydro-2H-pyran-2-yl)oxy)azetidin-1-yl)pyrimidine (72 mg, 0.19 mmol), CuI (30 mg, 0.06 mmol) and K$_3$PO$_4$ (68 mg, 0.32 mmol) in dry toluene (2 mL) was added N,N'-dimethyl-cyclohexane-1,2-diamine (46 mg, 0.32 mmol). The suspension was degassed with N$_2$ and heated to 110° C. for 3 hrs. The reaction mixture was cooled to rt and partitioned between diluted ammonia (30 mL) and EtOAc (30 mL). The organic layer was washed with brine, dried over MgSO$_4$ and concentrated. The crude was purified by prep. TLC (DCM/MeOH=10/1) to give the title compound (68 mg, yield 86%) as a white solid.

$^1$H NMR (300 MHz, CDCl$_3$): δ 8.94 (d, J=6.6 Hz, 1H), 8.10 (s, 1H), 7.36 (d, J=9.9 Hz, 1H), 6.59 (s, 1H), 5.12-4.84 (m, 1H), 4.76-4.67 (m, 2H), 4.41-4.33 (m, 2H), 4.15-4.03 (m, 2H), 3.93-3.85 (m, 1H), 3.59-3.51 (m, 1H), 3.41-3.32 (m, 1H), 3.22-3.10 (m, 1H), 2.99-2.94 (m, 1H), 2.62 (s, 3H), 2.44 (s, 3H), 2.30-2.13 (m, 2H), 2.13-2.02 (m, 2H), 1.90-1.65 (m, 6H).

LCMS: (mobile phase: 5-95% Acetonitrile in 3 min), Rt=2.39 min, MS Calcd: 499; MS Found: 500 [M+H]$^+$.

Description D157

6-Bromo-1-(tetrahydro-2H-pyran-2-yl)-1H-indazole (D157)

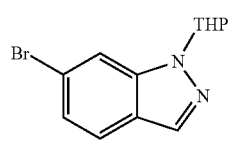

A mixture of 6-bromo-1H-indazole (10.0 g, 0.051 mol), DHP (8.57 g, 0.102 mol), PTSA (1.75 g, 10.2 mmol) and MgSO$_4$ (18.0 g, 0.153 mol) in THF (50 mL) was heated to reflux and stirred overnight. The mixture was filtered. The filtrate was diluted with water (50 mL) and extracted with EtOAc (30 mL×3). The combination organic layers were washed with sat. NaHCO$_3$ aqueous and brine, dried over Na$_2$SO$_4$ and concentrated in vacuo. The residue was purified by silica column (PE:EtOAc=40:1) to give the desired compound (12.0 g, yield 84%) as a yellow solid.

$^1$H NMR (300 MHz, CDCl$_3$): δ 7.99 (s, 1H), 7.80 (s, 1H), 7.58 (d, J=8.7 Hz, 1H), 7.30-7.26 (m, 1H), 5.67 (dd, J=9.3, 2.7 Hz, 1H), 4.06-4.02 (m, 1H), 3.81-3.72 (m, 1H), 2.60-2.47 (m, 1H), 2.19-2.04 (m, 2H), 1.81-1.64 (m, 3H).

LC-MS (mobile phase: from 90% water and 10% CH$_3$CN to 5% water and 95% CH$_3$CN in 4.0 min, purity is >95%, Rt=2.632 min; MS Calcd.: 280; MS Found: 281 [M+H]$^+$.

Description D158 tert-Butyl 4-(1-(tetrahydro-2H-pyran-2-yl)-1H-indazol-6-yl)-5,6-dihydropyridine-1(2H)-carboxylate (D158)

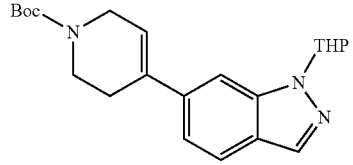

A suspension of 6-bromo-1-(tetrahydro-2H-pyran-2-yl)-1H-indazole (4.00 g, 14.2 mmol), tert-butyl 4-(4,4,5,5-tetramethyl-1,3,2-dioxaborolan-2-yl)-5,6-dihydropyridine-1(2H)-carboxylate (4.82 g, 15.6 mmol), Pd(dppf)Cl$_2$ (0.5 g, 0.7 mmol) and Na$_2$CO$_3$ (3.70 g, 34.9 mmol) in dioxane (140 mL) and water (28 mL) was degassed with N$_2$ for 3 times. Then the mixture was stirred at 85° C. for 2 hrs. The reaction mixture was cooled and the solvent was removed under vacuum. The residue was partitioned between water (200 mL) and EtOAc (100 mL). The organic layer was separated and the aqueous layer was extracted with EtOAc (100 mL×3). The combined organic layers were washed with brine, dried over Na$_2$SO$_4$ and concentrated. The crude was purified by column chromatography (PE:EtOAc from 10:1 to 5:1) to give the title compound (5.32 g, yield 97%) as brown oily solid.

$^1$H NMR (300 MHz, CDCl$_3$): δ 7.98 (s, 1H), 7.65 (d, J=8.4 Hz, 1H), 7.49 (s, 1H), 7.23 (d, J=8.7 Hz, 1H), 6.11 (br s, 1H), 5.72 (dd, J=9.3, 2.4 Hz, 1H), 4.11-4.01 (m, 3H), 3.80-3.72 (m, 1H), 3.67 (t, J=5.4 Hz, 2H), 2.67-2.53 (m, 3H), 2.22-2.04 (m, 2H), 1.84-1.63 (m, 3H), 1.50 (s, 9H).

LCMS: (mobile phase: 5-95% Acetonitrile in 3 min), Rt=2.48 min; MS Calcd: 383; MS Found: 384 [M+H]$^+$.

Description D159

(Trans)-tert-Butyl 3-hydroxy-4-(1-(tetrahydro-2H-pyran-2-yl)-1H-indazol-6-yl)piperidine-1-carboxylate (D159)

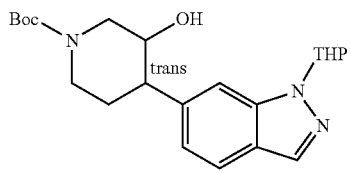

To a solution of tert-butyl 4-(1-(tetrahydro-2H-pyran-2-yl)-1H-indazol-6-yl)-5,6-dihydropyridine-1(2H)-carboxylate (5.32 g, 13.8 mmol) in dry THF (140 mL) was added BH$_3$/THF (1 M, 55.2 mL, 55.2 mmol) at 0° C. under N$_2$. The resulting mixture was stirred at rt overnight. The reaction mixture was cooled to 3° C. and NaOH (2 M, 20.7 mL, 41.4 mmol) was added dropwise carefully. H$_2$O$_2$ (30%, 15.6 g, 138 mmol) was followed and kept the internal temperature below 5° C. Then the reaction mixture was warmed to 30° C. and stirred for 1 h. The reaction mixture was gradually poured into Na$_2$S$_2$O$_3$ (10%, 200 mL) and stirred for 15 min. The organic layer was separated and the aqueous was extracted with EtOAc (100 mL×2). The combined organic layers were washed with brine, dried over Na$_2$SO$_4$ and concentrated. The crude was purified by column chromatography (PE:EtOAc from 4:1 to 1:1) to give the title compound (5.2 g, yield 93%) as white solid.

$^1$H NMR (300 MHz, CDCl$_3$): δ 7.99 (s, 1H), 7.70 (d, J=8.4 Hz, 1H), 7.46 (s, 1H), 7.08 (d, J=8.4 Hz, 1H), 5.70 (dd, J=11.7, 2.4 Hz, 1H), 4.52-4.36 (m, 1H), 4.36-4.17 (m, 1H), 4.08-4.03 (m, 1H), 3.85-3.70 (m, 2H), 2.84-2.52 (m, 4H), 2.23-2.01 (m, 2H), 1.87-1.67 (m, 6H), 1.50 (s, 9H).

LCMS: (mobile phase: 5-95% Acetonitrile in 2.5 min), Rt=1.62 min; MS Calcd: 401; MS Found: 402 [M+H]$^+$.

Description D160

(cis)-tert-Butyl 3-fluoro-4-(1-(tetrahydro-2H-pyran-2-yl)-1H-indazol-6-yl)piperidine-1-carboxylate (D160)

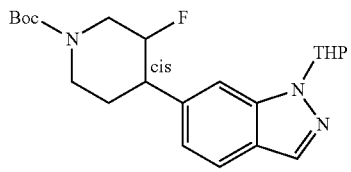

A solution of tert-butyl 3-hydroxy-4-(1-(tetrahydro-2H-pyran-2-yl)-1H-indazol-6-yl)piperidine-1-carboxylate (5.20 g, 13.0 mmol) in dry DCM (200 mL) was cooled to −60° C. and DAST (8.40 g, 52.1 mmol) was added dropwise. The resulting mixture was gradually warmed to rt and stirred for 3 hrs. The reaction mixture was gradually poured into Na$_2$CO$_3$ (10%, 300 mL) and stirred for 15 min. The organic layer was separated and the aqueous was extracted with DCM (100 mL×2). The combined organic layers were washed with brine, dried over Na$_2$SO$_4$ and concentrated. The crude was purified by column chromatography (PE:EtOAc=5:1) to give the title compound (4.0 g, yield 75%) as white solid.

$^1$H NMR (300 MHz, CDCl$_3$): δ 7.99 (s, 1H), 7.69 (dd, J=8.4, 2.4 Hz, 1H), 7.49-7.40 (m, 1H), 7.09-7.06 (m, 1H), 5.71 (dd, J=9.3, 2.7 Hz, 1H), 4.79-4.46 (m, 2H), 4.21 (br s, 1H), 4.07-4.03 (m, 1H), 3.80-3.72 (m, 1H), 3.05-2.74 (m, 3H), 2.66-2.52 (m, 1H), 2.23-1.91 (m, 3H), 1.89-1.59 (m, 4H), 1.50 (s, 9H).

Description D161

(cis)-6-(3-Fluoropiperidin-4-yl)-1H-indazole hydrochloride (D161)

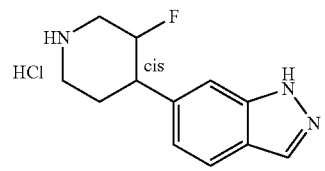 [SMILES: Cl ; FC1CNCCC1c1ccc2cn[nH]c2c1]

tert-Butyl 3-fluoro-4-(1-(tetrahydro-2H-pyran-2-yl)-1H-indazol-6-yl)piperidine-1-carboxylate (1.0 g, 2.5 mmol) was dissolved in HCl/MeOH (5M, 20 mL) and stirred overnight. The reaction mixture was concentrated to give the title compound (740 mg, crude) as white solid which was used for next step directly.

LCMS: (mobile phase: 5-95% Acetonitrile in 2.5 min), Rt=1.19 min; MS Calcd: 219; MS Found: 220 [M+H]$^+$.

Description D162

(cis)-6-(3-Fluoro-1-methylpiperidin-4-yl)-1H-indazole (D162)

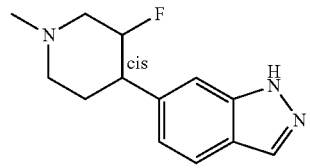 [SMILES: CN1CCC(c2ccc3cn[nH]c3c2)C(F)C1]

To a solution of 6-(3-fluoropiperidin-4-yl)-1H-indazole hydrochloride (740 mg, 2.48 mmol) in methanol (20 mL) was added formaldehyde (37%, 5 mL) and NaBH$_3$CN (314 mg, 5.00 mmol) in portions under ice bath. The resulting solution was warmed to rt and stirred for 1 h. The reaction mixture was poured into Na$_2$CO$_3$ (10%, 100 mL) and stirred for 15 min. The aqueous was extracted with DCM (40 mL×3) and the combined organic layers were washed with brine, dried over Na$_2$SO$_4$ and concentrated. The crude was dissolved in NH$_3$/MeOH (3M, 20 mL) and stirred overnight. The reaction mixture was concentrated and purified by C18 (water:acetonitrile from 95:5 to 50:50) to give the title compound (320 mg, yield 55%) as white solid.

$^1$H NMR (300 MHz, CDCl$_3$): δ 10.15 (br s, 1H), 8.04 (s, 1H), 7.72 (d, J=8.4 Hz, 1H), 7.39 (s, 1H), 7.11 (d, J=8.4 Hz, 1H), 4.89-4.65 (m, 1H), 3.36-3.28 (m, 1H), 2.94-2.90 (m, 1H), 2.85-2.72 (m, 1H), 2.42 (s, 3H), 2.20-2.06 (m, 2H), 2.00-1.90 (m, 2H).

LCMS: (mobile phase: 5-95% Acetonitrile in 2.5 min), Rt=1.36 min; MS Calcd: 233; MS Found: 234 [M+H]+.

Description D163

(cis)-1-(6-(6-(3-Fluoro-1-methylpiperidin-4-yl)-1H-indazol-1-yl)-2-methoxypyrimidin-4-yl)azetidin-3-ol (D163)

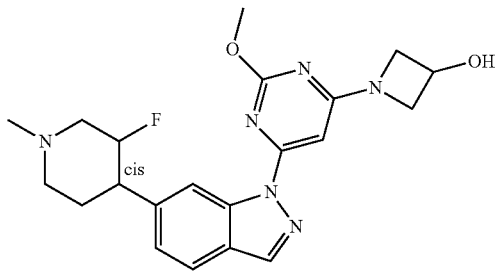 [SMILES: COc1nc(N2CC(O)C2)cc(-n2ncc3ccc(C4CCN(C)CC4F)cc32)n1]

To a suspension of 6-(3-fluoro-1-methylpiperidin-4-yl)-1H-indazole (150 mg, 0.643 mg), 1-(6-iodo-2-methoxypyrimidin-4-yl)azetidin-3-ol (217 mg, 0.707 mmol), CuI (122 mg, 0.643 mmol) and K$_3$PO$_4$ (274 mg, 1.29 mmol) in dry toluene (10 mL) was added N,N'-dimethyl-cyclohexane-1,2-diamine (183 mg, 1.29 mmol). The dark blue suspension was degassed with N$_2$ and heated to 110° C. for 2 hrs. The reaction mixture was concentrated and the residue was partitioned between water (50 mL) and EtOAc (30 mL). The organic layer was separated and the aqueous was extracted with EtOAc (20 mL×3). The combined organic layers were washed with brine, dried over MgSO$_4$ and concentrated. The crude was purified by column chromatography (DCM:MeOH from 40:1 to 20:1) to give the title compound (210 mg, yield 79%; two isomers in the ratio of 85:15) as a white solid.

$^1$H NMR (300 MHz, CDCl$_3$): δ 8.81 (s, 1H), 8.15 (s, 1H), 7.71 (d, J=6.0 Hz, 1H), 7.22 (d, J=6.3 Hz, 1H), 6.49 (s, 1H), 4.86-4.68 (m, 2H), 4.49-4.38 (m, 2H), 4.10 (s, 1H), 4.04-4.03 (m, 2H), 3.34-3.27 (m, 1H), 2.94-2.76 (m, 2H), 2.40 (s, 3H), 2.19-1.91 (m, 4H).

LCMS: (mobile phase: 5-95% Acetonitrile in 2.5 min), Rt=1.46 min; MS Calcd: 412; MS Found: 413 [M+H]+.

Description D164 tert-Butyl 3-(((trifluoromethyl)sulfonyl)oxy)-2,5-dihydro-1H-pyrrole-1-carboxylate (D164)

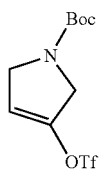

To a solution of NaHMDS (2 mol/L, 52 mL, 104 mmol) in THF (100 mL) was added a solution of tert-butyl 3-oxopyrrolidine-1-carboxylate (16.0 g, 86.5 mmol) in THF (100 mL) at −70° C. dropwise. The reaction mixture was stirred at −70° C. for 15 min. Then a solution of PhNTf$_2$ (37.0 g, 104 mmol) in THF (200 mL) was added dropwise to the mixture at −70° C. The reaction mixture was stirred at −70° C. for 1 h. The mixture was warmed to −30° C. and quenched with ice water (100 mL). The mixture was warmed to rt and extracted with EtOAc (400 mL×2). The combined organic layers were washed with brine (100 mL×3), dried over Na$_2$SO$_4$ and concentrated. The residue was purified by column chromatograph (PE:EtOAc=10:1) to give a crude title compound (40 g, yield 100%) as a yellow oil.

$^1$H NMR (300 MHz, CDCl$_3$): δ 5.75-5.70 (m, 1H), 4.28-4.14 (m, 4H), 1.48 (s, 9H).

Description D165 tert-Butyl 3-(4,4,5,5-tetramethyl-1,3,2-dioxaborolan-2-yl)-2,5-dihydro-1H-pyrrole-1-carboxylate (D165)

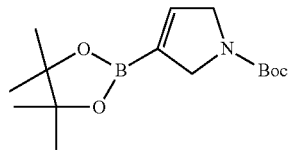 [SMILES: CC(C)(C)OC(=O)N1CC=C(B2OC(C)(C)C(C)(C)O2)C1]

To a solution of tert-butyl 3-(((trifluoromethyl)sulfonyl)oxy)-2,5-dihydro-1H-pyrrole-1-carboxylate (40.0 g crude, 86.5 mmol) in dioxane (400 mL) was added KOAc (25.5 g, 260 mmol), Pin$_2$B$_2$ (25.4 g, 100 mmol), DPPF (4.77 g, 8.65 mmol) and Pd(dppf)Cl$_2$ (7.00 g, 8.65 mmol). The reaction mixture was stirred at 90° C. overnight. The mixture was cooled to rt and filtered. The filtrate was concentrated and purified by column chromatograph (PE:EtOAc from 40:1 to 10:1) to give the title compound (19 g, yield 74%) as a colorless oil.

$^1$H NMR (300 MHz, CDCl$_3$): δ 6.49-6.43 (m, 1H), 4.21-4.14 (m, 4H), 1.46 (s, 9H), 1.27 (s, 12H).

Description D166 tert-Butyl 3-(5-methyl-1-(tetrahydro-2H-pyran-2-yl)-1H-indazol-6-yl)-2,5-dihydro-1H-pyrrole-1-carboxylate (D166)

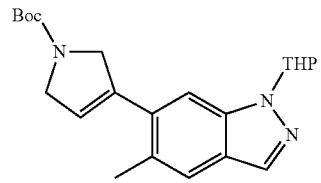

To a suspension of 6-bromo-5-methyl-1-(tetrahydro-2H-pyran-2-yl)-1H-indazole (3.00 g, 10.2 mmol), tert-butyl 3-(4,4,5,5-tetramethyl-1,3,2-dioxaborolan-2-yl)-2,5-dihydro-1H-pyrrole-1-carboxylate (4.40 g, 15.2 mmol) and Na$_2$CO$_3$ (3.23 g, 30.5 mmol) in dioxane (75 mL) and water (15 mL) was added Pd(dppf)Cl$_2$ (823 mg, 1.02 mmol). The mixture was heated to 100° C. under N$_2$ for 1.5 h. The mixture was cooled and concentrated and the residue was partitioned between EtOAc (50 mL) and water (50 mL). The aqueous layer was extracted with EtOAc (50 mL×3). The combined EtOAc layers were concentrated. The crude was purified by column chromatography (PE:EtOAc from 20:1 to 10:1) to give the title compound (3.44 g, yield 90%) as a white solid.
¹H NMR (300 MHz, CDCl₃): δ 7.93 (s, 1H), 7.53 (s, 1H), 7.40-7.38 (m, 1H), 5.85 (s, 1H), 5.69-5.64 (m, 1H), 4.53 (s, 1H), 4.42 (s, 1H), 4.37-4.34 (m, 2H), 4.05-4.02 (m, 1H), 3.77-3.70 (m, 1H), 2.55 (br s, 1H), 2.45 (d, J=5.1 Hz, 3H), 2.15-2.04 (m, 2H), 1.79-1.66 (m, 3H), 1.52 (s, 9H).

Description D167

(Trans)-tert-butyl 3-hydroxy-4-(5-methyl-1-(tetrahydro-2H-pyran-2-yl)-1H-indazol-6-yl) pyrrolidine-1-carboxylate (D167)

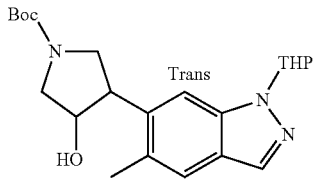

To a solution of tert-butyl 3-(5-methyl-1-(tetrahydro-2H-pyran-2-yl)-1H-indazol-6-yl)-2,5-dihydro-1H-pyrrole-1-carboxylate (5.80 g, 15.1 mmol) in dry THF (120 mL) was added BH₃-THF solution (1 M, 60.6 mL, 60.6 mmol) under ice bath with N₂ protected. The mixture was warmed to rt and stirred overnight. After cooled the reaction mixture to 0° C., NaOH (aq, 2 M, 23 mL, 45.4 mmol) was added and kept the internal temperature below 5° C. Then H₂O₂ (30%, 15.2 mL, 151 mmol) was added dropwise and kept the internal temperature below 5° C. Then the mixture was stirred at rt and stirred for 3 hours. Na₂S₂O₃ (10%, 200 mL) was added and stirred for 15 min under ice bath. The organic layer was separated and the aqueous was extracted with EtOAc (100 mL×3). The combined organic layers were washed with brine, dried over Na₂SO₄ and evaporated. The residue was purified by column chromatography (PE:EtOAc from 10:1 to 4:1) to give the title compound (2.53 g, yield 42%) as a white solid.
¹H NMR (300 MHz, CDCl₃): δ 7.91 (s, 1H), 7.51 (s, 1H), 7.34 (s, 1H), 5.67-5.61 (m, 1H), 4.38 (br s, 1H), 4.05-4.01 (m, 1H), 3.94 (br s, 1H), 3.76-3.69 (m, 3H), 3.60 (br s, 2H), 3.38 (br s, 1H), 2.55 (br s, 1H), 2.47 (s, 3H), 2.13-1.99 (m, 2H), 1.78-1.63 (m, 3H), 1.51 (s, 9H).

Description D168

(cis)-tert-Butyl 3-fluoro-4-(5-methyl-1-(tetrahydro-2H-pyran-2-yl)-1H-indazol-6-yl) pyrrolidine-1-carboxylate (D168)

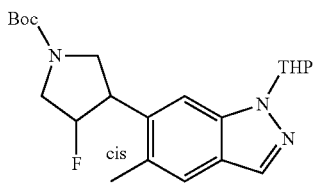

To a solution of (trans)-tert-butyl 3-hydroxy-4-(5-methyl-1-(tetrahydro-2H-pyran-2-yl)-1H-indazol-6-yl)pyrrolidine-1-carboxylate (2.50 g, 6.23 mmol) in dry DCM (100 mL) was added DAST (4.02 g, 24.9 mmol) under N₂ and kept the inner temperature below −65° C. The mixture was gradually warmed to rt and stirred for 2 hrs. The reaction mixture was carefully poured into saturated Na₂CO₃ aqueous solution (100 mL) and stirred for 20 min. The organic layer was separated and the aqueous was extracted with DCM (100 mL×2). The combined organic layers were washed with brine, dried over Na₂SO₄ and evaporated. The crude was purified by column chromatography (PE:EtOAc=10:1) to give the title compound (1.2 g, yield 48%) as a white solid.
¹H NMR (300 MHz, CDCl₃): δ 7.92 (s, 1H), 7.53 (s, 1H), 7.26 (s, 1H), 5.65-5.58 (m, 1H), 5.08-4.89 (m, 1H), 4.04-3.68 (m, 7H), 2.56-2.49 (m, 1H), 2.49 (s, 3H), 2.15-2.05 (m, 2H), 1.75-1.66 (m, 3H), 1.52 (s, 9H).

Description D169

(cis)-6-(4-Fluoropyrrolidin-3-yl)-5-methyl-1H-indazole hydrochloride (D169)

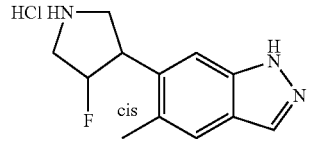

A mixture of (cis)-tert-Butyl 3-fluoro-4-(5-methyl-1-(tetrahydro-2H-pyran-2-yl)-1H-indazol-6-yl) pyrrolidine-1-carboxylate (1.40 g, 3.47 mmol) in HCl/dioxane (5 mol/L, 30 mL) was stirred at 35° C. overnight. The reaction mixture was cooled to 0° C. and filtered. The solid was washed with cold 1,4-dioxane (5 mL) to get the crude compound as a white solid (1.1 g, yield 100%) without further purification.
LCMS: (mobile phase: 5-95% Acetonitrile in 2.5 min), Rt=1.17 min, MS Calcd: 219; MS Found: 220 [M+H]⁺.

Description D170

(cis)-6-(4-fluoro-1-methylpyrrolidin-3-yl)-5-methyl-1H-indazole (D170)

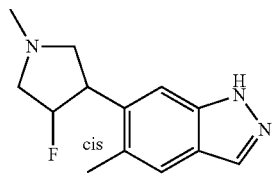 [SMILES: Cc1cc2cn[nH]c2cc1C1CN(C)CC1F]

To a suspension of (cis)-6-(4-fluoropyrrolidin-3-yl)-5-methyl-1H-indazole hydrochloride (1.10 g, 4.30 mmol) in methanol (20 mL) was added formaldehyde solution (37%, 10 mL), CH₃COOH (cat.) and NaBH₃CN (811 mg, 12.9 mmol). Then the mixture was stirred for 2 hrs. The reaction mixture was poured into NaHCO₃ (saturated, 100 mL) and stirred for 10 min. Then the mixture was extracted with dichloromethane (50 mL×5). The combined organic layers were dried over Na₂SO₄, filtered and concentrated. The residue was dissolved in NH₃/MeOH (3M, 20 mL) and stirred overnight. The mixture was concentrated and purified by column chromatography (DCM:MeOH from 80:1 to 40:1) to give the title compound (450 mg, yield 45%) as white solid.

¹H NMR (300 MHz, CDCl₃): δ 10.01 (br s, 1H), 7.96 (s, 1H), 7.55 (s, 1H), 7.43 (s, 1H), 5.22-5.00 (m, 1H), 3.94-3.78 (m, 1H), 3.31-3.28 (m, 1H), 3.06-3.04 (m, 1H), 2.97-2.95 (m, 1H), 2.69-2.62 (m, 1H), 2.48 (s, 6H).

Description D171 and D172

(cis)-6-(4-Fluoro-1-methylpyrrolidin-3-yl)-5-methyl-1H-indazole (Enantiomer 1) (D171) and (cis)-6-(4-Fluoro-1-methylpyrrolidin-3-yl)-5-methyl-1H-indazole (Enantiomer 2) (D172)

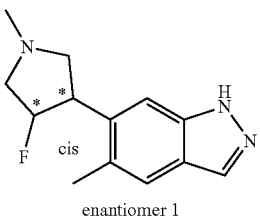

enantiomer 1
D171

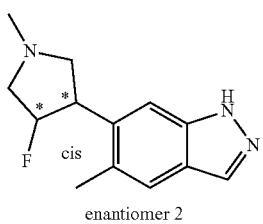

enantiomer 2
D172

The racemate (cis)-6-(4-fluoro-1-methylpyrrolidin-3-yl)-5-methyl-1H-indazole (450 mg, 1.93 mmol) was separated by chiral HPLC with the method (Chiralpak IA 5 µm 30*250 mm, Phase: Hex/EtOH=90/10, flow rate: 25 mL/min, 205 nm, T=30° C.) to give (cis)-6-(4-fluoro-1-methylpyrrolidin-3-yl)-5-methyl-1H-indazole (enantiomer 1) (D171) (120 mg, yield 27%) and (cis)-6-(4-Fluoro-1-methylpyrrolidin-3-yl)-5-methyl-1H-indazole (enantiomer 2) (D172) (120 mg, yield 27%) both as white solid.

D171: ¹H NMR (400 MHz, CDCl₃): δ 10.66-10.20 (m, 1H), 7.98 (s, 1H), 7.55 (s, 1H), 7.42 (s, 1H), 5.18-5.03 (m, 1H), 3.91-3.79 (m, 1H), 3.31-3.27 (m, 1H), 3.05-2.93 (m, 2H), 2.66-2.62 (m, 1H), 2.48 (s, 6H).

D172: ¹H NMR (400 MHz, CDCl₃): δ 11.11 (br s, 1H), 7.99 (s, 1H), 7.54 (s, 1H), 7.40 (s, 1H), 5.17-5.02 (m, 1H), 3.91-3.78 (m, 1H), 3.30-3.28 (m, 1H), 3.10-2.89 (m, 2H), 2.62-2.61 (m, 1H), 2.48 (s, 6H).

Description D173

(cis)-6-(4-Fluoro-1-methylpyrrolidin-3-yl)-1-(2-methoxy-6-(3-((tetrahydro-2H-pyran-2-yl)oxy)azetidin-1-yl)pyrimidin-4-yl)-5-methyl-1H-indazole (Enantiomer 1) (D173)

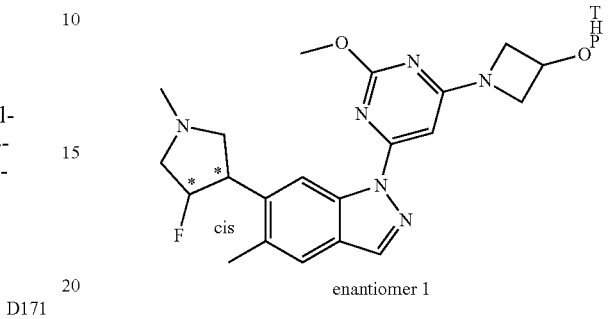

enantiomer 1

To a suspension of 6-(4-fluoro-1-methylpyrrolidin-3-yl)-5-methyl-1H-indazole (enantiomer 1) (50 mg, 0.21 mmol), 4-iodo-2-methoxy-6-(3-((tetrahydro-2H-pyran-2-yl)oxy)azetidin-1-yl)pyrimidine (92 mg, 0.24 mmol), CuI (41 mg, 0.214 mmol), K₃PO₄ (91 mg, 0.43 mmol) in dry toluene (3 mL) was added N,N'-dimethyl-cyclohexane-1,2-diamine (61 mg, 0.43 mmol). The mixture was degassed with N₂ for 3 times and stirred at 110° C. for 2 hrs. The reaction mixture was cooled to rt and then poured into NH₃.H₂O (5%, 15 mL) and extracted with EtOAc (15 mL×3). The combined organic layers were washed with brine, dried over Na₂SO₄ and concentrated. The crude was purified by prep. HPLC to give the title compound (83 mg, yield 78%) as a white solid.

¹H NMR (300 MHz, CDCl₃): δ 8.77 (s, 1H), 8.08 (s, 1H), 7.53 (s, 1H), 6.48 (s, 1H), 5.24-5.04 (m, 1H), 4.76-4.67 (m, 2H), 4.40-4.33 (m, 2H), 4.12-4.07 (m, 6H), 3.96-3.89 (m, 2H), 3.59-3.50 (m, 1H), 3.36-3.28 (m, 1H), 3.13-3.01 (m, 1H), 2.93-2.78 (m, 1H), 2.64-2.58 (m, 1H), 2.50 (s, 3H), 2.41 (s, 3H), 1.90-1.70 (m, 2H), 1.61-1.51 (m, 3H).

Description D174

(cis)-6-(4-Fluoro-1-methylpyrrolidin-3-yl)-1-(2-methoxy-6-(3-((tetrahydro-2H-pyran-2-yl)oxy)azetidin-1-yl)pyrimidin-4-yl)-5-methyl-1H-indazole (Enantiomer 2) (D174)

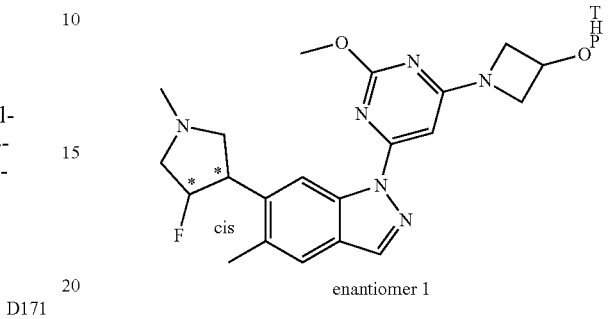

enantiomer 2

To a suspension of (cis)-6-(4-fluoro-1-methylpyrrolidin-3-yl)-5-methyl-1H-indazole (enantiomer 2) (15 mg, 0.064 mmol), 4-iodo-2-methoxy-6-(3-((tetrahydro-2H-pyran-2-yl)oxy)azetidin-1-yl)pyrimidine (28 mg, 0.071 mmol), CuI (13 mg, 0.064 mmol), K₃PO₄ (27 mg, 0.13 mmol) in dry toluene (1 mL) was added N,N'-dimethyl-cyclohexane-1,2-diamine (18 mg, 0.13 mmol). The mixture was degassed with $N_2$ for 3 times and stirred at 110° C. for 2 hrs. The reaction mixture was cooled to rt and then poured into NH₃.H₂O (5%, 5 mL) and extracted with EtOAc (5 mL×3). The combined organic layers were washed with brine, dried over Na₂SO₄ and concentrated. The crude was purified by prep. HPLC to give the title compound (23 mg, yield 74%) as white solid.

¹H NMR (400 MHz, CDCl₃): δ 8.77 (s, 1H), 8.08 (s, 1H), 7.54 (s, 1H), 6.48 (s, 1H), 5.22-5.06 (m, 1H), 4.71-4.64 (m, 2H), 4.42-4.35 (m, 2H), 4.12-4.07 (m, 6H), 3.95-3.89 (m, 2H), 3.57-3.51 (m, 1H), 3.35-3.29 (m, 1H), 3.12-3.01 (m, 1H), 2.90-2.78 (m, 1H), 2.64-2.58 (m, 1H), 2.51 (s, 3H), 2.42 (s, 3H), 1.90-1.71 (m, 2H), 1.61-1.52 (m, 3H).

Description D175

(trans)-tert-Butyl 4-cyano-3-hydroxypiperidine-1-carboxylate and (trans)-tert-Butyl 3-cyano-4-hydroxypiperidine-1-carboxylate (D175)

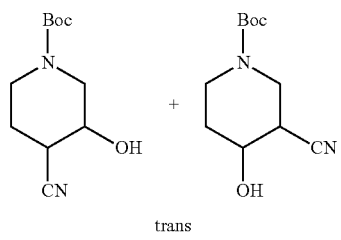 [SMILES: CC(C)(C)OC(=O)N1CCC(C#N)C(O)C1 ; CC(C)(C)OC(=O)N1CCC(O)C(C#N)C1]

trans

A suspension of tert-Butyl 7-oxa-3-azabicyclo[4.1.0]heptane-3-carboxylate (13.0 g, 65.3 mmol) NaCN (10.6 g, 0.216 mol) and LiClO₄ (22.2 g, 0.209 mol) in CH₃CN (150 mL) was heated to 95° C. under $N_2$ atmosphere for two days. The mixture was cooled to room temperature, and diluted with water (150 mL) and EtOAc (200 mL). The organic layer was separated, and the aqueous layer was extracted with EtOAc (200 mL×2). The combined organic layers were dried over Na₂SO₄, concentrated in vacuo. The residue was purified by column on silica gel eluting with PE/EtOAc (from 5/1 to 1:1) to give a mixture of the title compound and (trans)-tert-butyl 3-cyano-4-hydroxypiperidine-1-carboxylate (D172) (7.06 g, yield 48%) in 3:1 ratio as a yellow oil.

¹H NMR of major product (400 MHz, CDCl₃): δ 3.98 (dd, J=13.6 Hz, 3.2 Hz, 1H), 3.89-3.75 (m, 2H), 3.18-2.99 (m, 2H), 2.70-2.65 (m, 1H), 2.16-2.06 (m, 1H), 1.80-1.72 (m, 1H), 1.46 (s, 9H).

Description D176

(trans)-tert-Butyl 4-carbamothioyl-3-hydroxypiperidine-1-carboxylate and (trans)-tert-Butyl 3-carbamothioyl-4-hydroxypiperidine-1-carboxylate (D176)

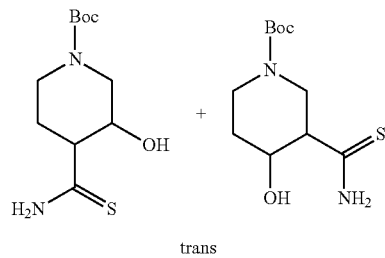 [SMILES: CC(C)(C)OC(=O)N1CCC(C(N)=S)C(O)C1 ; CC(C)(C)OC(=O)N1CCC(O)C(C(N)=S)C1]

trans

A mixture of (trans)-tert-butyl 4-cyano-3-hydroxypiperidine-1-carboxylate and (trans)-tert-Butyl 3-cyano-4-hydroxypiperidine-1-carboxylate (7.00 g, 30.6 mmol, 3:1) was dissolved into DMF (40 mL), and (NH₄)₂S aqueous solution (S % 40 mL) was added. After addition the resulting solution was stirred for two days. The reaction was diluted with water (100 mL), and extracted with EtOAc (100 mL×3) and DCM (100 mL). The combined organic layers were dried over Na₂SO₄, filtered and concentrated in vacuo to give the crude product as black oil. The black oil was further purified by C18 column eluting with CH₃CN/water to give a mixture of the title compound and (trans)-tert-butyl 3-carbamothioyl-4-hydroxypiperidine-1-carboxylate (4.05 g, yield 51%) in 3:1 ratio as a white solid.

¹H NMR of major product (400 MHz, CDCl₃): δ 7.80 (s, 2H), 4.38-4.27 (m, 1H), 4.22-4.09 (m, 1H), 3.97-3.87 (m, 1H), 2.76-2.65 (m, 1H), 2.64-2.50 (m, 2H), 1.89-1.84 (m, 2H), 1.46 (s, 9H).

Description D177

(trans)-tert-Butyl 3-hydroxy-4-(imino(methylthio) methyl)piperidine-1-carboxylate and (trans)-tert-Butyl 4-hydroxy-3-(imino(methylthio)methyl)piperidine-1-carboxylate (D177)

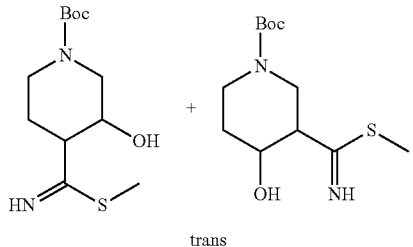 [SMILES: CSC(=N)C1CCN(C(=O)OC(C)(C)C)CC1O ; CSC(=N)C1CN(C(=O)OC(C)(C)C)CCC1O]

trans

A mixture of (trans)-tert-butyl 4-carbamothioyl-3-hydroxypiperidine-1-carboxylate and (trans)-tert-Butyl 3-carbamothioyl-4-hydroxypiperidine-1-carboxylate (4.05 g, 15.6 mmol, 3:1) in acetone (100 mL) was added CH₃I (3.32 g, 23.4 mmol). After addition the resulting solution was stirred overnight at room temperature. The mixture was concentrated in vacuo to give a mixture of the title compound and (trans)-tert-Butyl 4-hydroxy-3-(imino(methylthio)methyl)piperidine-1-carboxylate (4.24 g, yield 100%) in 3:1 ratio as a yellow solid.

¹H NMR of major product (400 MHz, CDCl₃): δ 4.44-4.14 (m, 2H), 4.04-3.87 (m, 1H), 3.52-3.38 (m, 1H), 2.93 (s, 3H), 2.84-2.69 (m, 2H), 2.05-1.98 (m, 1H), 1.91-1.73 (m, 1H), 1.47 (s, 9H).

Description D178

3-Amino-1-(4-methoxy-benzyl)-1H-pyrazole-4-carbonitrile (D178)

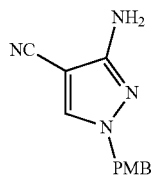

To a solution of 5-amino-1H-pyrazole-4-carbonitrile (20.0 g, 185.2 mmol) in DMF (80 mL) was added PMBCl (32.8 g, 207 mmol) and K₂CO₃ (30.7 g, 222 mmol) at room temperature. The resulting mixture was stirred at 70° C. for 2 hrs. The mixture was partitioned between H₂O (400 mL) and EtOAc (400 mL). The organic layers were washed with brine (200 mL×2), dried over Na₂SO₄, filtered and concentrated under reduced pressure. Then the residue was purified by column (petroleum ether:EtOAc from 5:1 to 2:1) to give the title compound (25 g, yield: 59%) as a white solid.

¹H NMR (300 MHz, DMSO-d₆): δ 8.16 (s, 1H), 7.18 (d, J=9.0 Hz, 2H), 6.88 (d, J=9.0 Hz, 2H), 5.53 (s, 2H), 4.97 (s, 2H), 3.71 (s, 3H). LC-MS (5-95%) Rt=1.86 min; MS Calcd.: 228, MS Found: 229 [M+H]⁺.

Description D179

3-Amino-1-(4-methoxy-benzyl)-1H-pyrazole-4-carbaldehyde (D179)

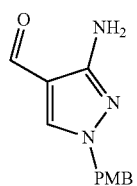

DIBAL-H (151 mL, 151 mmol) was added slowly to a solution of 3-amino-1-(4-methoxy-benzyl)-1H-pyrazole-4-carbonitrile (8.60 g, 37.7 mmol) in toluene (200 mL) at −78° C. under N₂. After addition, the solution was stirred for 20 min and then warmed to 0° C. The solution was slowly poured into HCl (4N, 220 mL). The mixture was diluted with H₂O (400 mL) and extracted with EtOAc (150 mL×3). The organic phase was washed with H₂O (100 mL), saturated NaHCO₃ (100 mL), dried over anhydrous Na₂SO₄, filtered and evaporated to give the title compound (5.13 g, yield 59%) as a yellow solid.

¹H NMR (300 MHz, DMSO-d₆): δ 9.61 (s, 1H), 8.13 (s, 1H), 7.22 (d, J=8.4 Hz, 2H), 6.89 (d, J=8.4 Hz, 2H), 5.64 (br s, 2H), 5.01 (s, 2H), 3.71 (s, 3H).

Description D180

(trans)-tert-Butyl 3-hydroxy-4-(2-(4-methoxybenzyl)-2H-pyrazolo[3,4-d]pyrimidin-6-yl) piperidine-1-carboxylate (D180)

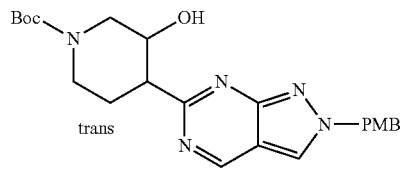

A mixture of (trans)-tert-butyl 3-hydroxy-4-(imino(methylthio)methyl)piperidine-1-carboxylate and (trans)-tert-Butyl 4-hydroxy-3-(imino(methylthio)methyl)piperidine-1-carboxylate (4.24 g, 15.5 mmol, 3:1) and 3-amino-1-(4-methoxybenzyl)-1H-pyrazole-4-carbaldehyde (4.29 g, 18.6 mmol) were dissolved in dry DCM (150 mL). The resulting solution was heated to reflux for two days. The mixture was cooled to room temperature and concentrated. The residue was purified by C18 column eluting with CH₃CN/water (from 0/100 to 100/0) to give a crude product. The crude product was washed with EtOAc (6 mL) to give (trans)-tert-Butyl 3-hydroxy-4-(2-(4-methoxybenzyl)-2H-pyrazolo[3,4-d]pyrimidin-6-yl)piperidine-1-carboxylate (568 mg, yield 8%) as a white solid.

¹H NMR (400 MHz, CD₃OD): δ 9.35 (s, 1H), 8.56 (s, 1H), 7.38 (d, J=8.4 Hz, 2H), 6.94 (d, J=8.4 Hz, 2H), 5.63 (s, 2H), 4.34-4.30 (m, 1H), 4.17-4.10 (m, 2H), 3.80 (s, 3H), 3.06-3.00 (m, 1H), 2.95-2.82 (m, 1H), 2.81-2.65 (m, 1H), 2.03-1.97 (m, 1H), 1.90-1.78 (m, 1H), 1.51 (s, 9H).

Description D181

(cis)-tert-Butyl 3-fluoro-4-(2-(4-methoxybenzyl)-2H-pyrazolo[3,4-d]pyrimidin-6-yl)piperidine-1-carboxylate (D181)

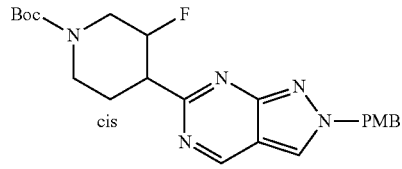

DAST (1.50 mL) was added slowly to a solution of (trans)-tert-butyl 3-hydroxy-4-(2-(4-methoxybenzyl)-2H-pyrazolo[3,4-d]pyrimidin-6-yl) piperidine-1-carboxylate (300 mg, 0.683 mmol) in dry DCM (20 mL) under N₂ atmosphere under at −68° C. After addition the mixture was warmed to room temperature slowly and stirred overnight. The mixture was diluted with sat. NaHCO₃ aqueous solution (50 mL) and extracted with EtOAc (100 mL×3). The combined organic layers were dried over Na₂SO₄, filtered, concentrated in vacuo to give the title compound (305 mg, yield 100%) as a yellow oil which was used in next step without further purification.

LC-MS (mobile phase: from 95% water and 5% CH₃CN to 5% water and 95% CH₃CN in 2.5 min, purity >90%, Rt=1.62 min; MS Calcd.: 441; MS Found: 442, [M+H]⁺.

Description D182

(cis)-6-(3-Fluoropiperidin-4-yl)-2-(4-methoxybenzyl)-2H-pyrazolo[3,4-d]pyrimidine hydrochloride (D182)

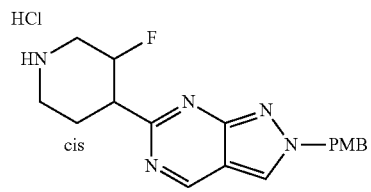

A solution of (cis)-tert-Butyl 3-fluoro-4-(2-(4-methoxybenzyl)-2H-pyrazolo[3,4-d]pyrimidin-6-yl)piperidine-1-carboxylate (305 mg, 0.692 mmol) in HCl/MeOH (5 M, 20 mL) was stirred at room temperature for two hours. The mixture was concentrated in vacuo to give the title product (265 mg, yield 100%) as yellow oil which was used for next step directly.

LC-MS (mobile phase: from 95% water and 5% $CH_3CN$ to 5% water and 95% $CH_3CN$ in 2.5 min, Rt=1.27 min; MS Calcd.: 341; MS Found: 342 $[M+H]^+$.

Description D183

(cis)-6-(3-Fluoro-1-(2-methoxyethyl)piperidin-4-yl)-2-(4-methoxybenzyl)-2H-pyrazolo[3,4-d]pyrimidine (D183)

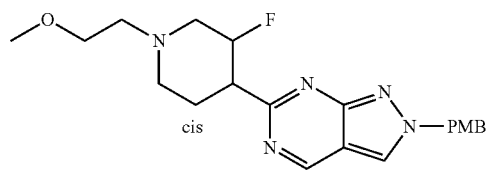

To a solution of (cis)-6-(3-Fluoropiperidin-4-yl)-2-(4-methoxybenzyl)-2H-pyrazolo[3,4-d]pyrimidine hydrochloride (265 mg, 0.701 mmol) in $CH_3CN$ (30 mL) was added 1-bromo-2-methoxy-ethane (484 mg, 3.51 mmol), and $K_2CO_3$ (484 mg, 3.51 mmol). The resulting suspension was heated to 65° C. and stirred overnight. The mixture was cooled to room temperature, filtered, concentrated in vacuo. The residue was purified by C18 column eluting with $CH_3CN$/water (from 0/100 to 100/0) to give the title compound (140 mg, yield 52%) as a yellow oil.

$^1$H NMR (300 MHz, $CDCl_3$): δ 9.21 (s, 1H), 7.95 (s, 1H), 7.33 (d, J=8.4 Hz, 2H), 6.90 (d, J=8.4 Hz, 2H), 5.53 (s, 2H), 5.50-5.24 (m, 1H), 3.80 (s, 3H), 3.55 (t, J=5.4 Hz, 2H), 3.39-3.37 (m, 4H), 3.22-3.12 (m, 1H), 2.96-2.91 (m, 1H), 2.70-2.67 (m, 2H), 2.36-2.21 (m, 2H), 2.06-2.00 (m, 2H).

Description D184 and D185

(cis)-6-(3-Fluoro-1-(2-methoxyethyl)piperidin-4-yl)-1H-pyrazolo[3,4-d]pyrimidine (Enantiomer 1) (D184) and (cis)-6-(3-Fluoro-1-(2-methoxyethyl)piperidin-4-yl)-1H-pyrazolo[3,4-d]pyrimidine (Enantiomer 2) (D185)

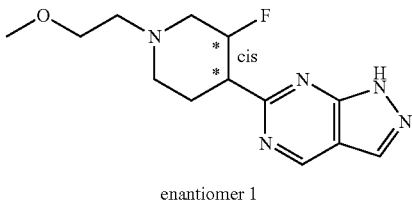

enantiomer 1

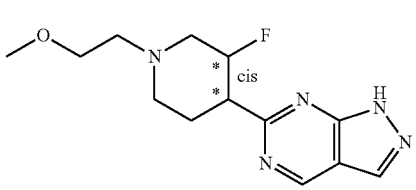

enantiomer 2

A solution of (cis)-6-(3-fluoro-1-(2-methoxyethyl)piperidin-4-yl)-2-(4-methoxybenzyl)-2H-pyrazolo[3,4-d]pyrimidine (140 mg, 0.351 mmol) in TFA (6 mL) was stirred at room temperature for two days. The mixture was concentrated in vacuo and dissolved into water (30 mL). EtOAc (30 mL) was added. The two phases was separated and $Cs_2CO_3$ (10 eq) was added to aqueous solution. EtOAc (20 mL×4) was added to the aqueous solution to extract the desired. The combined organic layers were dried over $Na_2SO_4$, filtered and concentrated in vacuo. The residue was purified by Chiral HPLC with the method (Chiral condition: Chiralpak IF-5 um 4.6*250 mm, Hex/EtOH=70/30, Flow Rate: 1.0 ml/min, 230 nm, T=30° C.) to give (cis)-6-(3-Fluoro-1-(2-methoxyethyl)piperidin-4-yl)-1H-pyrazolo[3,4-d]pyrimidine (enantiomer 1) (D184) (35 mg, yield 36%, Rt=8.487 min, 100% ee) and (cis)-6-(3-Fluoro-1-(2-methoxyethyl)piperidin-4-yl)-1H-pyrazolo[3,4-d]pyrimidine (enantiomer 2) (D185) (35 mg, yield 36%, Rt=13.986 min, 99.5% ee.) both as colorless oil.

D184: $^1$H NMR (300 MHz, $CD_3OD$): δ 8.94 (s, 1H), 7.96 (s, 1H), 5.05-4.81 (m, 1H), 3.29 (t, J=5.4 Hz, 2H), 3.13-3.02 (m, 4H), 2.88-2.75 (m, 1H), 2.75-2.66 (m, 1H), 2.42 (t, J=5.4 Hz, 2H), 2.02-1.92 (m, 2H), 1.76-1.65 (m, 2H).

D185: $^1$H NMR (300 MHz, $CD_3OD$): δ 8.95 (s, 1H), 7.97 (s, 1H), 5.09-4.84 (m, 1H), 3.30 (t, J=5.4 Hz, 2H), 3.15-3.03 (m, 4H), 2.94-2.79 (m, 1H), 2.75-2.67 (m, 1H), 2.44 (t, J=5.4 Hz, 2H), 2.06-1.92 (m, 2H), 1.79-1.66 (m, 2H).

Description D186

4-(4-iodopyridin-2-yl)morpholine (D186)

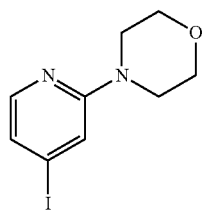 [SMILES: Ic1ccnc(N2CCOCC2)c1]

A suspension of 2-fluoro-4-iodopyridine (1.78 g, 7.98 mmol), morpholine (1.0 mL, 11.5 mmol) and $K_2CO_3$ (3.32 g, 24.1 mmol) in dry DMSO (12 mL) was heated to 70° C. overnight. The mixture was cooled to room temperature, diluted with EtOAc (100 mL) and water (100 mL). The organic layer was dried over $Na_2SO_4$ and concentrated in vacuo. The residue was purified by column on silica gel (PE:EtOAc from 1:0 to 30:1) to afford the desired compound (2.15 g, yield 93%) as a white solid.

$^1$H NMR (300 MHz, $CDCl_3$): δ 7.84 (d, J=4.8 Hz, 1H), 7.00-6.99 (m, 2H), 3.80 (d, J=4.8 Hz, 4H), 3.49 (d, J=4.8 Hz, 4H). LC-MS (mobile phase: from 95% water and 5% $CH_3CN$ to 5% water and 95% $CH_3CN$ in 3 min, Rt=1.92 min; MS Calcd.: 290; MS Found: 291, $[M+H]^+$.

Description D187

5-Methyl-6-(piperidin-4-yl)-1H-indazole hydrochloride (D187)

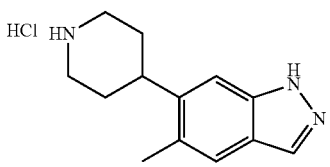 [SMILES: Cl ; Cc1cc2cn[nH]c2cc1C1CCNCC1]

tert-Butyl 4-(5-methyl-1-(tetrahydro-2H-pyran-2-yl)-1H-indazol-6-yl)piperidine-1-carboxylate (1.0 g, 2.5 mmol) was dissolved in HCl/MeOH (5 mol/L, 10 mL). Then, the mixture was stirred for 6 hrs. The mixture was concentrated under reduced pressure to afford the title compound (820 mg, yield >100%) as a light yellow solid used for next step without purification.

LC-MS: 5-95% $CH_3CN$, Rt=1.13 min, MS Calcd.: 215, MS Found: 216 $[M+H]^+$.

Description D188

5-Methyl-6-(1-(oxetan-3-yl)piperidin-4-yl)-1H-indazole (D188)

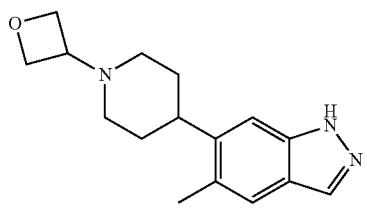 [SMILES: Cc1cc2cn[nH]c2cc1C1CCN(C2COC2)CC1]

To a solution of 5-methyl-6-(piperidin-4-yl)-1H-indazole hydrochloride (820 mg of crude, 2.50 mmol) in DCE (15 mL) was added oxetan-3-one (1.80 g, 25.0 mmol). The mixture was stirred at room temperature for 40 min. Then the mixture was cooled under ice bath and $NaBH_3CN$ (473 mg, 7.50 mmol) was added to the mixture. The mixture was warmed to room temperature and stirred for 2 hrs. Then, the reaction mixture was poured into $Na_2CO_3$ aqueous solution (10%, 100 mL) and stirred for 15 min. Then the mixture was extracted with EtOAc (30 mL×3). The combined organic layers were washed with brine, dried over $Na_2SO_4$ and concentrated. The residue was purified by column chromatography (DCM:MeOH=40:1) to afford the title compound (473 mg, yield 70%) as a white solid $^1$H NMR (300 MHz, $CDCl_3$): δ 10.11 (br s, 1H), 7.96 (s, 1H), 7.53 (s, 1H), 7.38 (s, 1H), 4.72-4.69 (m, 4H), 3.61-3.52 (m, 1H), 2.96-2.93 (m, 2H), 2.88-2.78 (m, 1H), 2.44 (s, 3H), 2.06-1.98 (m, 2H), 1.90-1.82 (m, 4H).

LC-MS: [mobile phase: 5-95% acetonitrile in 2.5 min], Rt=1.37 min; MS Calcd: 271; MS Found: 272 $[M+H]^+$.

Description D189

1-(2-Methoxy-6-(3-((tetrahydro-2H-pyran-2-yl)oxy) azetidin-1-yl)pyrimidin-4-yl)-5-methyl-6-(1-(oxetan-3-yl)piperidin-4-yl)-1H-indazole (D189)

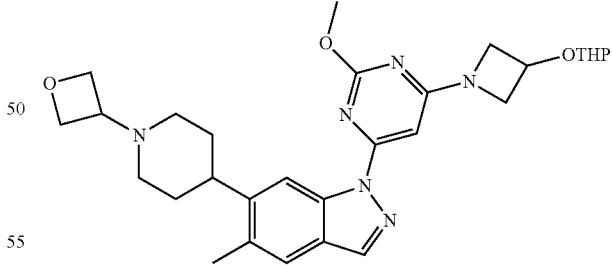

To a solution of 5-methyl-6-(1-(oxetan-3-yl)piperidin-4-yl)-1H-indazole (60 mg, 0.22 mmol) in toluene (10 mL) was added 4-iodo-2-methoxy-6-(3-((tetrahydro-2H-pyran-2-yl)oxy)azetidin-1-yl)pyrimidine (105 mg, 0.270 mmol), $K_3PO_4$ (140 mg, 0.660 mmol), CuI (125 mg, 0.660 mmol) and N,N'-dimethyl-cyclohexane-1,2-diamine (94 mg, 0.66 mmol). The reaction mixture was refluxed for 2 hrs. The reaction mixture was cooled to room temperature and poured into $NH_3.H_2O$ (10 mL). The desired was extracted with EtOAc (3×20 mL). The combined organic layers were washed with brine (2×20 mL), dried over Na$_2$SO$_4$ and concentrated. The residue was triturated with PE:EtOAc=5:1 (3 mL) to give the title compound (80 mg, yield 68%) as white solid.

$^1$H NMR (300 MHz, CDCl$_3$): δ 8.76 (s, 1H), 8.07 (s, 1H), 7.50 (s, 1H), 6.47 (s, 1H), 4.74-4.65 (m, 6H), 4.42-4.33 (m, 2H), 4.15-4.00 (m, 5H), 3.93-3.85 (m, 1H), 3.59-3.50 (m, 2H), 2.98-2.79 (m, 3H), 2.45 (s, 3H), 2.06-1.74 (m, 8H), 1.68-1.58 (m, 4H).

LCMS: (mobile phase: 5-95% acetonitrile in 2.5 min), Rt=1.763 min; MS Calcd: 534; MS Found: 535 [M+H]$^+$.

Description D190

1-(6-Iodo-2-methoxypyrimidin-4-yl)-3-methylazetidin-3-ol (D190)

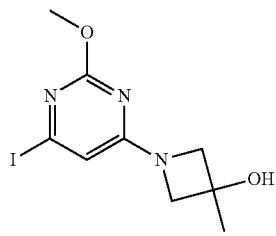

A mixture of 4,6-diiodo-2-methoxypyrimidine (300 mg, 0.829 mmol), 3-methylazetidin-3-ol hydrochloride (122 mg, 0.99 mmol) and TEA (251 mg, 2.49 mmol) in MeOH (10 mL) was heated at 50° C. and stirred at for 1.5 hrs. The mixture was concentrated and the residue was purified by column (PE:EtOAc=2:1) to give the title compound (250 mg, yield 94%) as white solid.

$^1$H NMR (300 MHz, CDCl$_3$): δ 6.33 (s, 1H), 3.98 (s, 4H), 3.89 (s, 3H), 2.27-2.23 (m, 1H), 1.60 (s, 3H).

Description D191

1-(6-Iodo-2-methylpyrimidin-4-yl)-3-methylazetidin-3-ol (D191)

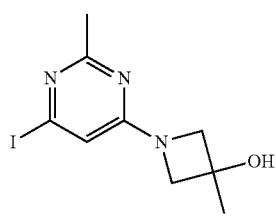

A suspension of 4,6-diiodo-2-methylpyrimidine (300 mg, 0.867 mmol), 3-methylazetidin-3-ol hydrochloride (118 mg, 0.954 mmol) and TEA (263 mg, 2.60 mmol) in i-PrOH (8 mL) was heated to 75° C. and stirred for 2 hrs. The reaction mixture was cooled to rt and poured into water (50 mL). EtOAc (30 mL×3) was added to extract the desired. The combined organic layers were washed with brine, dried over MgSO$_4$ and concentrated to give the title compound (270 mg, yield 100%) as a white solid.

$^1$H NMR (300 MHz, CDCl$_3$): δ 6.48 (s, 1H), 4.03-3.92 (m, 4H), 2.63 (s, 1H), 2.45 (s, 3H), 1.59 (s, 3H).

LCMS: (mobile phase: 5-95% Acetonitrile in 2.5 min), Rt=1.09 min; MS Calcd: 305; MS Found: 306 [M+H]$^+$.

Description D192

5-Methyl-6-(1-(methylsulfonyl)piperidin-4-yl)-1H-indazole (D192)

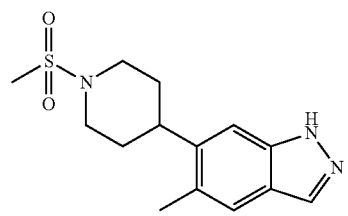 [SMILES: Cc1cc2cn[nH]c2cc1C1CCN(S(C)(=O)=O)CC1]

To a mixture of 5-methyl-6-(piperidin-4-yl)-1H-indazole hydrochloride (252 mg, 1.00 mmol) in CH$_2$Cl$_2$ (10 mL) was added TEA (2 mL). To the mixture was added methanesulfonyl chloride (171 mg, 1.50 mmol). The reaction mixture was poured into water (10 mL). The mixture was extracted with CH$_2$Cl$_2$ (2×10 mL). The combined organic layers were washed with brine (10 mL), dried over Na$_2$SO$_4$ and concentrated. The residue was dissolved in CH$_3$OH (10 mL). K$_2$CO$_3$ (1.38 g, 10.0 mmol) was added to the solution. The mixture was stirred at rt for 1 h. The reaction mixture was poured into water (30 mL). The mixture was extracted with CH$_2$Cl$_2$ (3×30 mL). The combined organic layers were washed with brine (30 mL), dried over Na$_2$SO$_4$ and concentrated. The residue was purified by prep. TLC (CH$_2$Cl$_2$:CH$_3$OH=10:1) to give the title compound (60 mg, yield 20%) as white solid.

$^1$H NMR (300 MHz, CDCl$_3$): δ 7.97 (s, 1H), 7.54 (s, 1H), 7.33 (s, 1H), 4.02-3.98 (m, 2H), 2.96-2.78 (m, 6H), 2.44 (s, 3H), 2.00-1.80 (m, 4H).

LCMS: (mobile phase: 5-95% Acetonitrile in 2.5 min), Rt=1.40 min; MS Calcd: 293; MS Found: 294 [M+H]$^+$.

Description D193

1-(2-Methoxy-6-(3-((tetrahydro-2H-pyran-2-yl)oxy)azetidin-1-yl)pyrimidin-4-yl)-5-methyl-6-(1-(methylsulfonyl)piperidin-4-yl)-1H-indazole (D193)

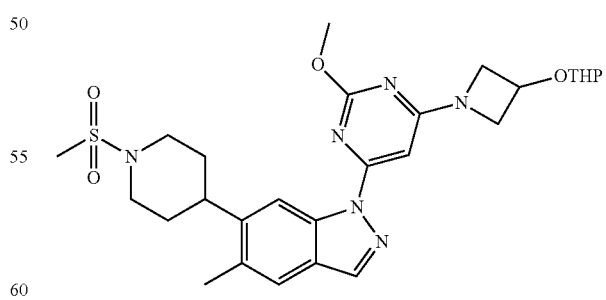

To a solution of 5-methyl-6-(1-(methylsulfonyl)piperidin-4-yl)-1H-indazole (60 mg, 0.20 mmol) in toluene (10 mL) was added 4-iodo-2-methoxy-6-(3-((tetrahydro-2H-pyran-2-yl)oxy)azetidin-1-yl) pyrimidine (102 mg, 0.260 mmol), K$_3$PO$_4$ (127 mg, 0.600 mmol), CuI (114 mg, 0.600 mmol) and N,N'-dimethyl-cyclohexane-1,2-diamine (85 mg, 0.60 mmol). The reaction mixture was refluxed for 1.5 hrs. The reaction mixture was cooled to room temperature and poured into NH$_3$.H$_2$O (10 mL). The desired was extracted with EtOAc (3×10 mL). The combined organic layers were washed with brine (2×10 mL), dried over Na$_2$SO$_4$ and concentrated. The residue was triturated with EtOAc (3 mL) to give the title compound (70 mg, yield 63%) as white solid.

$^1$H NMR (300 MHz, CDCl$_3$): δ 8.75 (s, 1H), 8.07 (s, 1H), 7.52 (s, 1H), 6.47 (s, 1H), 4.72-4.66 (m, 2H), 4.41-4.33 (m, 2H), 4.15-3.97 (m, 7H), 3.91-3.84 (m, 1H), 3.57-3.50 (m, 1H), 2.98-2.80 (m, 6H), 2.46 (s, 3H), 1.99-1.66 (m, 6H), 1.62-1.57 (m, 4H).

LCMS: (mobile phase: 5-95% Acetonitrile in 2.5 min), Rt=1.75 min; MS Calcd: 556. MS Found: 557[M+H]$^+$.

Description D194

1-(4-(5-Methyl-1H-indazol-6-yl)piperidin-1-yl)ethanone (D194)

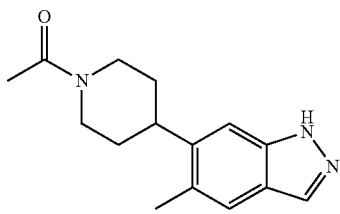 [SMILES: CC(=O)N1CCC(c2cc3[nH]ncc3cc2C)CC1]

To a mixture of 5-methyl-6-(piperidin-4-yl)-1H-indazole hydrochloride (280 mg, 1.30 mmol) in THF (5 mL) was added TEA (1 mL) and acetic anhydride (204 mg, 2.00 mmol). The reaction mixture was stirred at rt overnight. The reaction mixture was concentrated. The residue was dispersed in water (10 mL). The mixture was extracted with EtOAc (3×10 mL). The combined organic layers were washed with brine (10 mL), dried over Na$_2$SO$_4$ and concentrated. The residue was dissolved in THF (5 mL). NaOH (1 M, 1 mL) was added to the solution. The mixture was stirred at rt for 2 hrs. EtOAc (2×20 mL) was added to extract the desired compound. The combined organic layers were washed with brine (20 mL), dried over Na$_2$SO$_4$ and concentrated. The residue was purified by prep. TLC (CH$_2$Cl$_2$:CH$_3$OH=20:1) to give the title compound (100 mg, yield 30%) as a yellow solid.

$^1$H NMR (300 MHz, CDCl$_3$): δ 8.00 (s, 1H), 7.53 (s, 1H), 7.29 (s, 1H), 4.87-4.82 (m, 1H), 4.00-3.95 (m, 1H), 3.26-3.18 (m, 1H), 3.07-2.99 (m, 1H), 2.72-2.63 (m, 1H), 2.45 (s, 3H), 2.17 (s, 3H), 1.94-1.85 (m, 2H), 1.70-1.62 (m, 2H).

Description D195

Benzyl 4-(1H-indazol-6-yl)-5,6-dihydropyridine-1(2H)-carboxylate (D195)

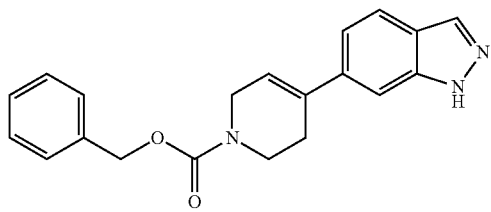 [SMILES: O=C(OCc1ccccc1)N1CC=C(c2ccc3cn[nH]c3c2)CC1]

A reaction mixture of 6-iodo-1H-indazole (1 g, 4.10 mmol), benzyl 4-(4,4,5,5-tetramethyl-1,3,2-diox-aborolan-2-yl)-5,6-dihydropyridine-1(2H)-carboxylate (1.41 g, 4.10 mmol), PdCl$_2$(dppf)-CH$_2$Cl$_2$ adduct (0.335 g, 0.410 mmol) and sodium carbonate (1.30 g, 12.3 mmol) was bubbled with nitrogen and stirred at 74° C. (oil bath) overnight. Then the reaction mixture was filtered, concentrated to remove solvent and diluted with ethyl acetate (180 mL) and water (50 mL). Separated organic part was dried over anhydrous Na$_2$SO$_4$, filtered and concentrated. Purification via ISCO system (ethyl acetate/petroleum ether) afforded the title product.

LC-MS (ESI) [mobile phase: from 95% water (0.05% TFA) and 5% CH$_3$CN to 5% water (0.05% TFA) and 95% CH$_3$CN in 5.0 min]: m/z 334 [M+H]$^+$; Rt=3.50 min.

Description D196

Benzyl 4-(1-(6-morpholinopyrimidin-4-yl)-1H-indazol-6-yl)-5,6-dihydropyridine-1(2H)-carboxylate (D196)

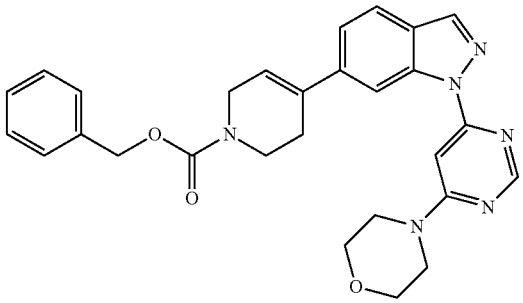 [SMILES: O=C(OCc1ccccc1)N1CC=C(c2ccc3cnn(-c4cc(N5CCOCC5)ncn4)c3c2)CC1]

A mixture of benzyl 4-(1H-indazol-6-yl)-5,6-dihydropyridine-1(2H)-carboxylate (300 mg, 0.900 mmol), 4-(6-chloropyrimidin-4-yl)morpholine (180 mg, 0.900 mmol) and cesium carbonate (586 mg, 1.80 mmol) in DMF (8 mL) was sealed in microwave vial and irradiated with a microwave at 120° C. for 2 h. Then the reaction mixture was filtered and diluted with ethyl acetate (200 mL) and water (60 mL). Separated organic part was dried over anhydrous Na$_2$SO$_4$, filtered and concentrated. Purification via Biotage system with inverse phase column (0.5% TFA in water and acetonitrile) afforded the title product.

LC-MS (ESI) [mobile phase: from 95% water (0.05% TFA) and 5% CH$_3$CN to 5% water (0.05% TFA) and 95% CH$_3$CN in 5.0 min]: m/z 497 [M+H]$^+$; Rt=4.30, 4.40 min.

Description D197

4-(6-(6-(Piperidin-4-yl)-1H-indazol-1-yl)pyrimidin-4-yl)morpholine (D197)

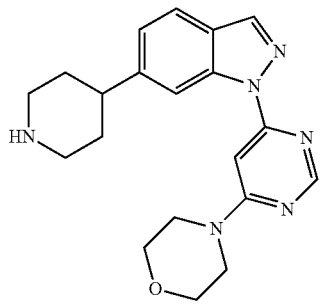 [SMILES: c1nc(N2CCOCC2)cc(-n2ncc3ccc(C4CCNCC4)cc32)n1]

A mixture of benzyl 4-(1-(6-morpholinopyrimidin-4-yl)-1H-indazol-6-yl)-5,6-dihydropyridine-1(2H)-carboxylate (100 mg, 0.200 mmol) and Pd—C (21.4 mg, 0.0200 mmol) in methanol (40 mL) was stirred at 60° C. under hydrogen overnight (50 ps) for two days. The reaction mixture was filtered and concentrated. The crude was directly used into next step without further purification.

LC-MS (ESI) [mobile phase: from 95% water (0.0.05% TFA) and 5% $CH_3CN$ to 5% water (0.05% TFA) and 95% $CH_3CN$ in 5.0 min]: m/z 365 [M+H]$^+$; Rt=2.21 min.

Description D198

Benzyl 4-(5-methyl-1-(6-morpholinopyrimidin-4-yl)-1H-indazol-6-yl)-5,6-dihydropyridine-1(2H)-carboxylate (D198)

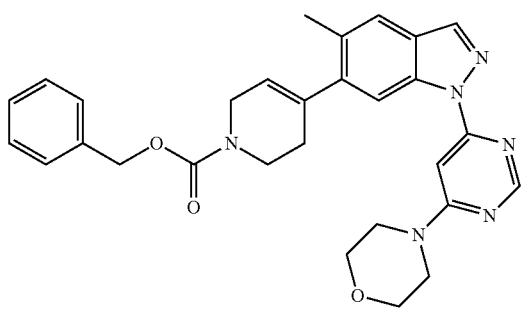 [SMILES: Cc1cc2cnn(-c3cc(N4CCOCC4)ncn3)c2cc1C1=CCN(C(=O)OCc2ccccc2)CC1]

A mixture of 4-(6-(6-bromo-5-methyl-1H-indazol-1-yl)pyrimidin-4-yl)morpholine (1.4 g, 3.74 mmol), benzyl 4-(4,4,5,5-tetramethyl-1,3,2-dioxaborolan-2-yl)-5,6-dihydropyridine-1(2H)-carboxylate (1.284 g, 3.74 mmol), $PdCl_2$(dppf)-$CH_2Cl_2$ adduct (0.306 g, 0.374 mmol) and sodium carbonate (0.793 g, 7.48 mmol) in 1,4-dioxane (30 mL) and water (10.00 mL) was equally split into two batches, sealed in a microwave vials and irradiated with a microwave at 120° C. for 2 h. Combined reaction mixture was concentrated to remove solvent, diluted with ethyl acetate (120 mL) and water (40 mL). Separated organic part was dried over anhydrous Na2SO4, filtered and concentrated. The crude was directly used into next step without further purification.

LC-MS (ESI) [mobile phase: from 95% water (0.05% TFA) and 5% $CH_3CN$ to 5% water (0.05% TFA) and 95% $CH_3CN$ in 5.0 min]: m/z 511 [M+H]$^+$; Rt=4.43 min.

Description D199

5-methyl-1-(tetrahydro-2H-pyran-2-yl)-6-(4,4,5,5-tetramethyl-1,3,2-dioxaborolan-2-yl)-1H-indazole (D199)

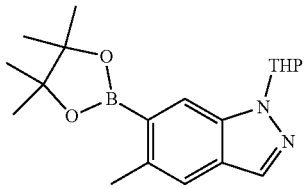

To a mixture of 6-bromo-5-methyl-1-(tetrahydro-2H-pyran-2-yl)-1H-indazole (5.78 g, 19.6 mmol), bis(pinacolato)diboron (9.95 g, 39.2 mmol) and $CH_3COO^-$ $K^+$ (7.68 g, 78.3 mmol) in dioxane (50 mL) was added Pd(PPh$_3$)$_4$ (6.60 g, 5.09 mmol). The mixture was heated to 90° C. and stirred under N$_2$ overnight. The mixture was filtered and the filtrate was concentrated under vacuum. The residue was purified by silica column (PE:EtOAc from 100:1 to 60:1) to give the desired product (2.7 g, yield 41%) as a yellow solid.

$^1$H NMR (400 MHz, CDCl$_3$): δ 7.98 (s, 1H), 7.94 (s, 1H), 7.47 (s, 1H), 5.77 (dd, J=9.6, 2.8 Hz, 1H), 4.05-4.02 (m, 1H), 3.81-3.75 (m, 1H), 2.61 (s, 3H), 2.19-2.13 (m, 1H), 2.04-2.00 (m, 1H), 1.84-1.72 (m, 2H), 1.65-1.59 (m, 2H), 1.38 (s, 12H).

LC-MS: [mobile phase: from 90% water (0.02% NH$_4$OAc) and 10% $CH_3CN$ to 5% water (0.02% NH$_4$OAc) and 95% $CH_3CN$ in 4 min], Rt=2.914 min MS Calcd.: 342, MS Found: 343 [M+H]$^+$.

Description D200

6-(2-Fluoropyridin-4-yl)-5-methyl-1-(tetrahydro-2H-pyran-2-yl)-1H-indazole (D200)

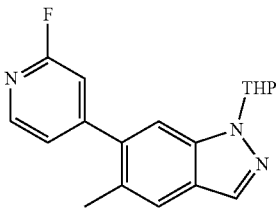

To a solution of 5-methyl-1-(tetrahydro-2H-pyran-2-yl)-6-(4,4,5,5-tetramethyl-1,3,2-dioxaborolan-2-yl)-1H-indazole (2.40 g, 7.02 mmol) in dioxane (50 mL) was added 4-bromo-2-fluoropyridine (1.85 g, 10.5 mmol), Na$_2$CO$_3$ (2.24 g, 21.1 mmol), water (10 mL) and Pd(dppf)Cl$_2$ (816 mg, 1.00 mmol). The mixture was stirred at 90° C. for 2 hrs. The solvent was removed under vacuum and the residue was partitioned with water (20 mL) and extracted EtOAc (3×20 mL). The combined organic layers were washed with brine (2×10 mL), dried over Na$_2$SO$_4$ and concentrated. The residue was purified by column chromatography (PE:EtOAc from 20:1 to 10:1) to give the title compound (1.40 g, yield 64%) as a white solid.

LCMS: [mobile phase: 5-95% CH$_3$CN in water in 2.5 min], Rt=1.66 min; MS Calcd: 311; MS Found: 312 [M+H]$^+$.

$^1$H NMR (300 MHz, CDCl$_3$): δ 8.28 (d, J=5.1 Hz, 1H), 8.00 (s, 1H), 7.63 (s, 1H), 7.41 (s, 1H), 7.20 (d, J=5.1 Hz, 1H), 6.96 (s, 1H), 5.72-5.68 (m, 1H), 4.07-4.01 (m, 1H), 3.77-3.69 (m, 1H), 2.65-2.49 (m, 1H), 2.32 (s, 3H), 2.19-2.06 (m, 2H), 1.79-1.66 (m, 3H).

Description D201

6-(2-(Benzyloxy)pyridin-4-yl)-5-methyl-1-(tetra-hydro-2H-pyran-2-yl)-1H-indazole (D201)

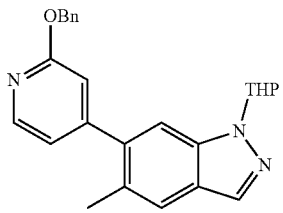

NaH (500 mg, 12.5 mmol) was dispersed in DMF (10 mL). Phenylmethanol (729 mg, 6.75 mmol) was added to the mixture. The mixture was stirred at rt for 10 min. To the mixture was added a solution of 6-(2-fluoropyridin-4-yl)-5-methyl-1-(tetrahydro-2H-pyran-2-yl)-1H-indazole (1.40 g, 4.50 mmol) in DMF (10 mL). The mixture was heated to 40° C. and stirred for 1 h. The mixture was quenched with ice-water (60 mL). The mixture was extracted EtOAc (3×50 mL). The combined organic layers were washed with water (2×40 mL) and brine (2×50 mL), dried over Na$_2$SO$_4$ and concentrated to give the title compound (2.10 g, yield >100%) as a white solid.

LCMS: [mobile phase: 5-95% CH$_3$CN in 2.5 min], Rt=1.71 min; MS Calcd: 399; MS Found: 400 [M+H]$^+$.

$^1$H NMR (300 MHz, CDCl$_3$): δ 8.23 (d, J=5.1 Hz, 1H), 7.98 (s, 1H), 7.59 (s, 1H), 7.59-7.51 (m, 2H), 7.42-7.36 (m, 4H), 6.93 (d, J=4.8 Hz, 1H), 6.83 (s, 1H), 5.69-5.66 (m, 1H), 5.45 (s, 2H), 4.05-4.02 (m, 1H), 3.75-3.69 (m, 1H), 2.61-2.51 (m, 1H), 2.32 (s, 3H), 2.13-2.04 (m, 2H), 1.74-1.61 (m, 3H).

Description D202

4-(5-Methyl-1-(tetrahydro-2H-pyran-2-yl)-1H-inda-zol-6-yl)pyridin-2(1H)-one (D202)

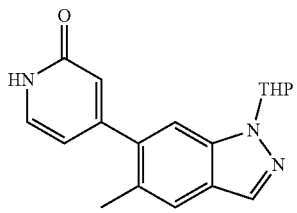

To a solution of 6-(2-(benzyloxy)pyridin-4-yl)-5-methyl-1-(tetrahydro-2H-pyran-2-yl)-1H-indazole (2.10 g, 5.26 mmol) in CH$_3$OH (40 mL) was added Pd/C (200 mg). The reaction mixture was stirred at rt for 3 hrs under H$_2$ balloon. The reaction mixture was filtered. The filtrate was concentrated to give the title compound (1.50 g, yield 92%) as white solid.

LCMS: [mobile phase: 5-95% CH$_3$CN in water in 2.5 min], Rt=1.37 min; MS Calcd: 309; MS Found: 310 [M+H]$^+$.

$^1$H NMR (300 MHz, CDCl$_3$): δ 13.27 (br s, 1H), 7.99 (s, 1H), 7.60 (s, 1H), 7.45-7.38 (m, 2H), 6.62 (s, 1H), 6.37-6.35 (m, 1H), 5.71-5.67 (m, 1H), 4.07-4.03 (m, 1H), 3.75-3.71 (m, 1H), 2.61-2.50 (m, 1H), 2.37 (s, 3H), 2.16-2.07 (m, 2H), 1.83-1.59 (m, 3H).

Description D203

1-Methyl-4-(5-methyl-1-(tetrahydro-2H-pyran-2-yl)-1H-indazol-6-yl)pyridin-2(1H)-one (D203)

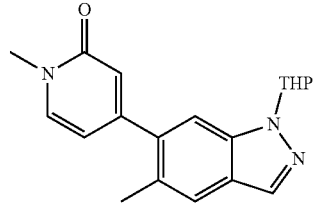

NaH (584 mg, 14.6 mmol) was dispersed in DMF (5 mL), and a solution of 4-(5-methyl-1-(tetrahydro-2H-pyran-2-yl)-1H-indazol-6-yl)pyridin-2(1H)-one (1.50 g, 4.85 mmol) in DMF (10 mL) was added to the mixture. The mixture was stirred at 0° C. for 10 min. To the mixture was added CH$_3$I (1.38 g, 9.70 mmol) at 0° C. The mixture was stirred at rt for 1 h. The mixture was quenched with ice-water (80 mL). The mixture was extracted EtOAc (3×50 mL). The combined organic layers were washed with brine (3×50 mL), dried over Na$_2$SO$_4$ and concentrated. The crude product was purified by column chromatograph (CH$_2$Cl$_2$:CH$_3$OH=100: 1) to give the title compound (1.06 g, yield 68%) as a white solid.

LCMS: [mobile phase: 5-95% CH$_3$CN in water in 2.5 min], Rt=1.43 min; MS Calcd: 323; MS Found: 324 [M+H]$^+$.

$^1$H NMR (300 MHz, CDCl$_3$): δ 7.97 (s, 1H), 7.57 (s, 1H), 7.41 (s, 1H), 7.33-7.30 (m, 1H), 6.59 (s, 1H), 6.22-6.19 (m, 1H), 5.69-5.65 (m, 1H), 4.06-4.02 (m, 1H), 3.75-3.69 (m, 1H), 3.61 (s, 3H), 2.59-2.47 (m, 1H), 2.35 (s, 3H), 2.16-2.04 (m, 2H), 1.81-1.63 (m, 3H).

Description D204

1-Methyl-4-(5-methyl-1-(tetrahydro-2H-pyran-2-yl)-1H-indazol-6-yl)piperidin-2-one (D204)

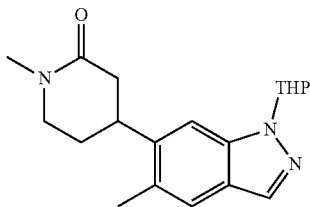

To a solution of 1-methyl-4-(5-methyl-1-(tetrahydro-2H-pyran-2-yl)-1H-indazol-6-yl) pyridin-2(1H)-one (1.10 g, 3.4 mmol) in $CH_3OH$ (20 mL) was added Pd/C (200 mg). The reaction mixture was stirred at 60° C. overnight under $H_2$ atmosphere (50 psi). The reaction mixture was filtered. The filtrate was concentrated to give the title compound (1.10 g, yield 99%) as white solid.

LCMS: [mobile phase: 5-95% $CH_3CN$ in water in 2.5 min], Rt=1.45 min; MS Calcd: 327; MS Found: 328 $[M+H]^+$.

$^1H$ NMR (300 MHz, $CDCl_3$): δ 7.90 (s, 1H), 7.50 (s, 1H), 7.35-7.31 (m, 1H), 5.68-5.65 (m, 1H), 4.05-4.01 (m, 1H), 3.78-3.71 (m, 1H), 3.51-3.37 (m, 3H), 3.02 (s, 3H), 2.80-2.75 (m, 1H), 2.60-2.56 (m, 2H), 2.51 (s, 3H), 2.12-2.03 (m, 4H), 1.77-1.68 (m, 3H).

Description D205

1-Methyl-4-(5-methyl-1H-indazol-6-yl)piperidin-2-one (D205)

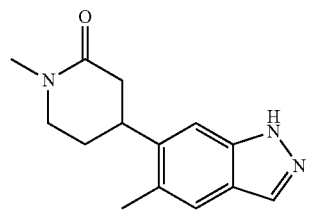 [SMILES: Cc1cc2cn[nH]c2cc1C1CCN(C)C(=O)C1]

To a solution of 1-methyl-4-(5-methyl-1-(tetrahydro-2H-pyran-2-yl)-1H-indazol-6-yl) piperidin-2-one (1.10 g, 3.36 mmol) in dioxane (12 mL) was added conc. HCl (3 mL). The reaction mixture was stirred at rt for 2 hrs. The reaction mixture was poured into sat. $NaHCO_3$ solution (100 mL). The mixture was extracted with EtOAc (50 mL×3). The combined organic layers were washed with brine (50 mL), dried over $Na_2SO_4$ and concentrated. The crude product was purified by column chromatograph ($CH_2Cl_2$:$CH_3OH$=100:1) to give the title compound (500 mg, yield 61%) as a white solid.

LCMS: [mobile phase: 5-95% acetonitrile in 2.5 min], Rt=1.28 min; MS Calcd: 243 MS Found: 244 $(M+1)^+$.

$^1H$ NMR (300 MHz, $CDCl_3$): δ 7.96 (s, 1H), 7.54 (s, 1H), 7.28 (s, 1H), 3.49-3.30 (m, 3H), 3.03 (s, 3H), 2.81-2.73 (m, 1H), 2.56-2.50 (m, 1H), 2.43 (s, 3H), 2.15-1.97 (m, 2H).

Description D206 and D207

1-Methyl-4-(5-methyl-1H-indazol-6-yl)piperidin-2-one (Enantiomer 1) (D206) and 1-Methyl-4-(5-methyl-1H-indazol-6-yl)piperidin-2-one (Enantiomer 2) (D207)

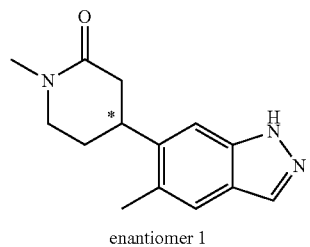

D206 enantiomer 1

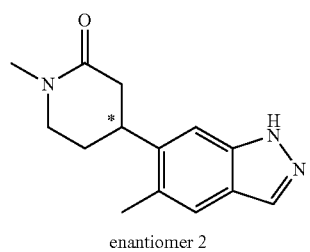

D207 enantiomer 2

1-Methyl-4-(5-methyl-1H-indazol-6-yl)piperidin-2-one (500 mg, 2.06 mmol) was separated by SFC (Chiralpak OD-H 33 μm 4.6×150 mm, Phase: $CO_2$/$CH_3OH$=70/30, flowrate: 50 mL/min, temperature: 30° C.) to give 1-methyl-4-(5-methyl-1H-indazol-6-yl)piperidin-2-one (enantiomer 1) (D206) (190 mg, yield 42%) as a white solid and 1-methyl-4-(5-methyl-1H-indazol-6-yl)piperidin-2-one (enantiomer 2) (D207) (200 mg, yield 44%) as a white solid.

D206: $^1H$ NMR (400 MHz, $CDCl_3$): δ 7.97 (s, 1H), 7.55 (s, 1H), 7.29 (s, 1H), 3.49-3.33 (m, 3H), 3.04 (s, 3H), 2.80-2.74 (m, 1H), 2.57-2.50 (m, 1H), 2.44 (s, 3H), 2.16-2.12 (m, 1H), 2.07-1.97 (m, 1H).

LCMS: (mobile phase: 5-95% acetonitrile in 2.5 min), Rt=1.30 min; MS Calcd: 243. MS Found: 244 $(M+1)^+$.

SFC: (Chiralpak OD-H 5 μm 4.6×150 mm, Phase: $CO_2$/$CH_3OH$=70/30, flowrate: 2.1 mL/min, temperature: 30° C.), Rt=3.31 min, 100% ee.

D207: $^1H$ NMR (400 MHz, $CDCl_3$): δ 7.97 (s, 1H), 7.55 (s, 1H), 7.28 (s, 1H), 3.49-3.33 (m, 3H), 3.04 (s, 3H), 2.80-2.75 (m, 1H), 2.56-2.49 (m, 1H), 2.44 (s, 3H), 2.18-2.12 (m, 1H), 2.08-1.97 (m, 1H).

LCMS: (mobile phase: 5-95% acetonitrile in 2.5 min), Rt=1.29 min; MS Calcd: 243 MS Found: 244 $(M+1)^+$.

SFC: (Chiralpak OD-H 5 μm 4.6×150 mm, Phase: $CO_2$/$CH_3OH$=70/30, flowrate: 2.1 mL/min, temperature: 30° C.), Rt=4.37 min, 99.3% ee.

Description D208

4-(1-(2-Methoxy-6-(3-((tetrahydro-2H-pyran-2-yl)oxy)azetidin-1-yl)pyrimidin-4-yl)-5-methyl-1H-indazol-6-yl)-1-methylpiperidin-2-one (Enantiomer 1) (D208)

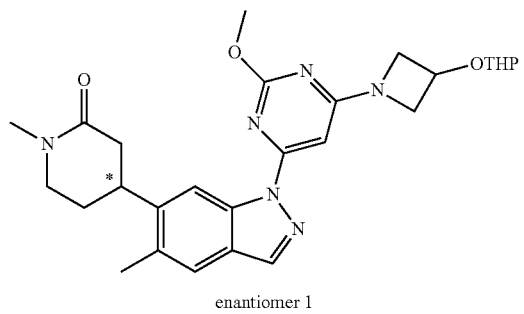

enantiomer 1

To a solution of 1-methyl-4-(5-methyl-1H-indazol-6-yl)piperidin-2-one (enantiomer 1) (enantiomer 1) (60 mg, 0.25 mmol) in toluene (5 mL) was added 4-iodo-2-methoxy-6-(3-((tetrahydro-2H-pyran-2-yl) oxy)azetidin-1-yl)pyrimidine (106 mg, 0.270 mmol), K$_3$PO$_4$ (105 mg, 0.494 mmol), CuI (94 mg, 0.494 mmol) and N,N'-dimethyl-cyclohexane-1,2-diamine (70 mg, 0.49 mmol). The reaction mixture was refluxed for 2 hrs. The reaction mixture was cooled to room temperature and poured into NH$_3$.H$_2$O (5 mL). The desired was extracted with EtOAc (3×20 mL). The combined organic layers were washed with brine (2×20 mL), dried over Na$_2$SO$_4$ and concentrated. The residue was triturated with EtOAc (5 mL) to give the title compound (52 mg, yield 42%) as a white solid.

$^1$H NMR (300 MHz, CDCl$_3$): δ 8.72 (s, 1H), 8.08 (s, 1H), 7.53 (s, 1H), 6.48 (s, 1H), 4.74-4.65 (m, 2H), 4.40-4.34 (m, 2H), 4.15-4.00 (m, 5H), 3.92-3.84 (m, 1H), 3.55-3.34 (m, 4H), 3.03 (s, 3H), 2.81-2.74 (m, 1H), 2.51-2.39 (m, 4H), 2.19-2.01 (m, 2H), 1.88-1.62 (m, 6H).

Description D209

Description of 4-(1-(2-Methoxy-6-(3-((tetrahydro-2H-pyran-2-yl)oxy)azetidin-1-yl)pyrimidin-4-yl)-5-methyl-1H-indazol-6-yl)-1-methylpiperidin-2-one (Enantiomer 2) (D209)

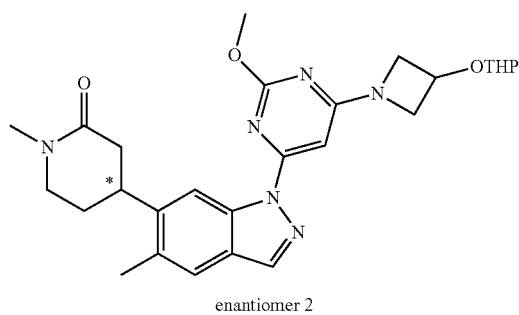

enantiomer 2

To a solution of 1-methyl-4-(5-methyl-1H-indazol-6-yl)piperidin-2-one (60 mg, 0.25 mmol) (enantiomer 2) in toluene (5 mL) was added 4-iodo-2-methoxy-6-(3-((tetrahydro-2H-pyran-2-yl)oxy)azetidin-1-yl)pyrimidine (106 mg, 0.270 mmol), K$_3$PO$_4$ (105 mg, 0.494 mmol), CuI (94 mg, 0.494 mmol) and N,N'-dimethyl-cyclohexane-1,2-diamine (70 mg, 0.49 mmol). The reaction mixture was refluxed for 2 hrs. The reaction mixture was cooled to room temperature and poured into NH$_3$.H$_2$O (5 mL). The desired was extracted with EtOAc (3×10 mL). The combined organic layers were washed with brine (10 mL), dried over Na$_2$SO$_4$ and concentrated. The residue was triturated with EtOAc/PE (2/1, 10 mL) to give the title compound (50 mg, yield 40%) as a white solid.

$^1$H NMR (300 MHz, CDCl$_3$): δ 8.71 (s, 1H), 8.08 (s, 1H), 7.53 (s, 1H), 6.48 (s, 1H), 4.74-4.67 (m, 2H), 4.41-4.31 (m, 2H), 4.15-4.02 (m, 5H), 3.91-3.84 (m, 1H), 3.56-3.34 (m, 4H), 3.03 (s, 3H), 2.81-2.75 (m, 1H), 2.49-2.39 (m, 4H), 2.17-2.05 (m, 2H), 1.86-1.70 (m, 2H), 1.70-1.50 (m, 4H).

Description D210

6-(3,6-dihydro-2H-pyran-4-yl)-5-methyl-1-(tetrahydro-2H-pyran-2-yl)-1H-indazole (D210)

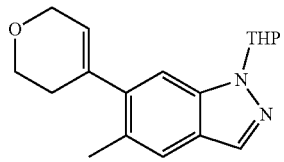

To a mixture of 2-(3,6-dihydro-2H-pyran-4-yl)-4,4,5,5-tetramethyl-1,3,2-dioxaborolane (939 mg, 4.47 mmol), 6-bromo-5-methyl-1-(tetrahydro-2H-pyran-2-yl)-1H-indazole (1200 mg, 4.07 mmol), PdCl$_2$(dppf)-CH$_2$Cl$_2$ adduct (332 mg, 0.407 mmol) and tripotassium phosphate (2589 mg, 12.20 mmol) was added DMF (10 mL) and water (2.500 mL). The reaction mixture was heated to 100° C. for 3 h. The reaction mixture was diluted with ethyl acetate, after filtration, the filtrate was concentrated and purified by silica column (30% EA in PE) to give 6-(3,6-dihydro-2H-pyran-4-yl)-5-methyl-1-(tetrahydro-2H-pyran-2-yl)-1H-indazole (610 mg, 2.044 mmol, 50.3% yield).

MS: 299.0 [M+H]$^+$.

Description D211

5-methyl-1-(tetrahydro-2H-pyran-2-yl)-6-(tetrahydro-2H-pyran-4-yl)-1H-indazole (D211)

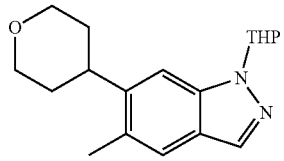

A mixture of 6-(3,6-dihydro-2H-pyran-4-yl)-5-methyl-1-(tetrahydro-2H-pyran-2-yl)-1H-indazole (610 mg, 2.044 mmol), Pd—C (435 mg, 0.409 mmol, 10%) and methanol (10 mL) was stirred under hydrogen balloon atmosphere at rt for 16 h. After filtration, the filtrate was concentrated to afford a crude 5-methyl-1-(tetrahydro-2H-pyran-2-yl)-6-(tetrahydro-2H-pyran-4-yl)-1H-indazole (614 mg, 2.044 mmol, 100% yield).

MS: 301.1 [M+H]$^+$.

Description D212

5-Methyl-6-(tetrahydro-2H-pyran-4-yl)-1H-indazole (D212)

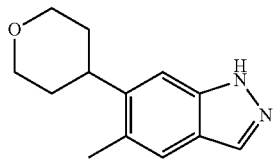 [SMILES: Cc1cc2cn[nH]c2cc1C1CCOCC1]

A solution of 5-methyl-1-(tetrahydro-2H-pyran-2-yl)-6-(tetrahydro-2H-pyran-4-yl)-1H-indazole (610 mg, 2.031 mmol), HCl (4.06 mL, 20.31 mmol) and methanol (5 mL) was stirred at rt for 16 h. The reaction solution was neutralized by aq. NaHCO$_3$ to pH=7, and extracted with ethyl acetate. The combined organic phases were dried and concentrated to give 5-methyl-6-(tetrahydro-2H-pyran-4-yl)-1H-indazole (430 mg, 1.988 mmol, 98% yield).

MS: 217.1 [M+H]$^+$.

Description D213 tert-Butyl 4-(6-iodo-2-methylpyrimidin-4-yl)piperazine-1-carboxylate (D213)

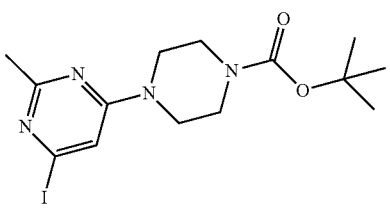 [SMILES: Cc1nc(I)cc(N2CCN(C(=O)OC(C)(C)C)CC2)n1]

A reaction mixture of tert-butyl piperazine-1-carboxylate (0.610 g, 3.28 mmol), 4,6-diiodo-2-methylpyrimidine (1.03 g, 2.98 mmol) and DIPEA (1.300 mL, 7.44 mmol) and Isopropanol (20 mL) was heated at 70° C. for 16 h. The reaction was not completed and after concentration in vacuo, the residue was purified by silica column (30-40% EA in PE) to give tert-butyl 4-(6-iodo-2-methylpyrimidin-4-yl)piperazine-1-carboxylate (330 mg, 0.816 mmol, 27.4% yield).

LCMS: (mobile phase: 5-95% acetonitrile), Rt=2.75 min in 5 min; MS Calcd: 404; MS Found: 405 [M+1]$^+$.

Description D214 tert-Butyl 4-(2-methyl-6-(5-methyl-6-(tetrahydro-2H-pyran-4-yl)-1H-indazol-1-yl)pyrimidin-4-yl)piperazine-1-carboxylate (D214)

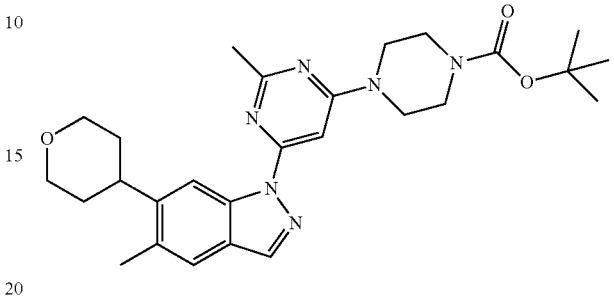

To a round bottom bottle were added tripotassium phosphate (263 mg, 1.237 mmol), 5-methyl-6-(tetrahydro-2H-pyran-4-yl)-1H-indazole (112 mg, 0.519 mmol), copper(I) iodide (37.7 mg, 0.198 mmol), and a stir bar. The reaction vessel was fitted with a rubber septum, was evacuated and back-filled with argon, and this sequence was repeated an additional time. tert-Butyl 4-(6-iodo-2-methylpyrimidin-4-yl)piperazine-1-carboxylate (200 mg, 0.495 mmol), N1,N2-dimethylcyclohexane-1,2-diamine (113 mg, 0.792 mmol) and toluene (5 mL) were then added successively under a stream of argon. The mixture was stirred at 120° C. for 16 hours. After filtration, the filtrate was concentrated and purified by silica gel column (30-40% EA in PE) to give tert-butyl 4-(2-methyl-6-(5-methyl-6-(tetrahydro-2H-pyran-4-yl)-1H-indazol-1-yl)pyrimidin-4-yl)piperazine-1-carboxylate (90 mg, 0.183 mmol), which was used directly in the next step.

Description D215

5-Methyl-1-(2-methyl-6-(piperazin-1-yl)pyrimidin-4-yl)-6-(tetrahydro-2H-pyran-4-yl)-1H-indazole (D215)

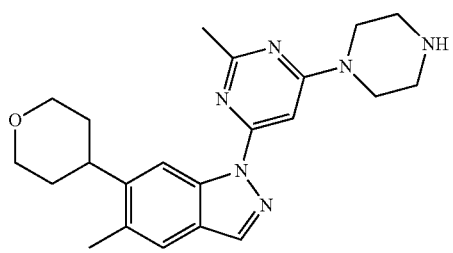 [SMILES: Cc1nc(N2CCNCC2)cc(-n2ncc3cc(C)c(C4CCOCC4)cc32)n1]

A solution of tert-butyl 4-(2-methyl-6-(5-methyl-6-(tetrahydro-2H-pyran-4-yl)-1H-indazol-1-yl)pyrimidin-4-yl)piperazine-1-carboxylate (90 mg, 0.183 mmol) and HCl (0.365 mL, 1.827 mmol, 5 M in isopropanol) and methanol (5 mL) was stirred at room temperature for 16 h. The solvent was removed in vacuo and the residue was used directly without further purification.

MS: 393.3 [M+H]$^+$.

Description D216 tert-butyl 4-(6-iodo-2-methoxypyrimidin-4-yl)piperazine-1-carboxylate (D216)

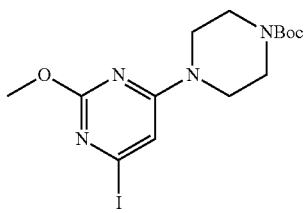 [SMILES: COc1nc(I)cc(N2CCN(C(=O)OC(C)(C)C)CC2)n1]

To a solution of 4,6-diiodo-2-methoxypyrimidine (1.50 g, 4.14 mmol) in CH₃CN (20 mL) was added tert-butyl piperazine-1-carboxylate (1.16 g, 6.21 mmol) and K$_2$CO$_3$ (1.14 g, 8.28 mmol). The mixture was stirred at 60° C. for 1 h. The reaction mixture was cooled to rt and filtered. The filtrate was concentrated. The residue was purified by column chromatography (PE:EtOAc=10:1) to give the title compound (1.73 g, yield 100%) as a white solid.

LCMS: [mobile phase: 5-95% CH$_3$CN in 2.5 min], Rt=1.73 min, MS Calcd: 420, MS Found: 421 [M+H]$^+$.

$^1$H NMR (300 MHz, CDCl$_3$): δ 6.63 (s, 1H), 3.90 (s, 3H), 3.60-3.59 (m, 4H), 3.51-3.47 (m, 4H), 1.47 (s, 9H).

Description D217

6-(Furan-3-yl)-5-methyl-1-(tetrahydro-2H-pyran-2-yl)-1H-indazole (D217)

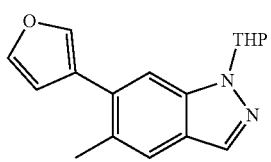

To a solution of 6-bromo-5-methyl-1-(tetrahydro-2H-pyran-2-yl)-1H-indazole (295 mg, 1.00 mmol) in dioxane (10 mL) was added furan-3-ylboronic acid (468 mg, 1.50 mmol), Na$_2$CO$_3$ (265 mg, 2.50 mmol), water (2 mL) and Pd(dppf)Cl$_2$ (74 mg, 0.10 mmol). The mixture was stirred at 90° C. for 3 hrs. The solvent was removed under vacuum and the residue was poured into water (10 mL) and extracted with EtOAc (3×20 mL). The combined organic layers were washed with brine (20 mL), dried over Na$_2$SO$_4$ and concentrated. The residue was purified by column chromatography (PE:EtOAc=20:1) to give the title compound (240 mg, yield 85%) as a yellow oil.

$^1$H NMR (300 MHz, CDCl$_3$): δ 7.95 (s, 1H), 7.56 (s, 2H), 7.52-7.50 (m, 2H), 6.62 (s, 1H), 5.69 (dd, J=9.6, 2.4 Hz, 1H), 4.06-4.02 (m, 1H), 3.77-3.70 (m, 1H), 2.63-2.54 (m, 1H), 2.42 (s, 3H), 2.17-2.03 (m, 2H), 1.79-1.68 (m, 3H).

LCMS: [mobile phase: 5-95% CH$_3$CN in 2.5 min], Rt=1.73 min; MS Calcd: 282, MS Found: 283 [M+H]$^+$.

Description D218

5-methyl-1-(tetrahydro-2H-pyran-2-yl)-6-(tetrahydrofuran-3-yl)-1H-indazole (D218)

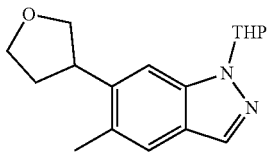

To a solution of 6-(furan-3-yl)-5-methyl-1-(tetrahydro-2H-pyran-2-yl)-1H-indazole (360 mg, 1.28 mmol) in CH$_3$OH (5 mL) was added Pd/C (10%, 50 mg). The reaction mixture was heated to 50° C. and stirred overnight under H$_2$ atmosphere (50 psi). The reaction mixture was filtered. The filtrate was concentrated to give the title compound (300 mg, yield 82%) as colorless oil.

$^1$H NMR (400 MHz, CDCl$_3$): δ 7.91 (s, 1H), 7.49-7.46 (m, 2H), 5.71-5.68 (m, 1H), 4.18-3.89 (m, 5H), 3.79-3.67 (m, 2H), 2.62-2.53 (m, 1H), 2.46-2.38 (m, 4H), 2.18-2.14 (m, 1H), 2.06-1.98 (m, 2H), 1.81-1.73 (m, 3H).

LCMS: [mobile phase: 5-95% CH$_3$CN in 2.5 min], Rt=1.69 min; MS Calcd: 286; MS Found: 287 [M+H]$^+$.

Description D219

5-Methyl-6-(tetrahydrofuran-3-yl)-1H-indazole (D219)

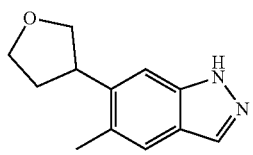

A solution of 5-methyl-1-(tetrahydro-2H-pyran-2-yl)-6-(tetrahydrofuran-3-yl)-1H-indazole (300 mg, 1.05 mmol) in dioxane (5 mL) was added conc. HCl (5 mL). The reaction mixture was stirred at rt for 2 hrs. The reaction mixture was poured into sat. NaHCO$_3$ solution (100 mL). The mixture was extracted with EtOAc (20 mL×3). The combined organic layers were washed with brine (20 mL), dried over Na$_2$SO$_4$ and concentrated to give the title compound (200 mg, yield 94%) as a yellow oil.

$^1$H NMR (300 MHz, CDCl$_3$): δ 7.96 (s, 1H), 7.53 (s, 1H), 7.44 (s, 1H), 4.17-4.00 (m, 2H), 3.95-3.88 (m, 2H), 3.74-3.66 (m, 1H), 2.46-2.37 (m, 4H), 2.04-1.93 (m, 1H).

LCMS: [mobile phase: 5-95% acetonitrile in 2.5 min], Rt=1.42 min; MS Calcd: 202, MS Found: 203 [M+1]$^+$.

Description D220

Tert-butyl 4-(2-methoxy-6-(5-methyl-6-(tetrahydrofuran-3-yl)-1H-indazol-1-yl)pyrimidin-4-yl) piperazine-1-carboxylate (D220)

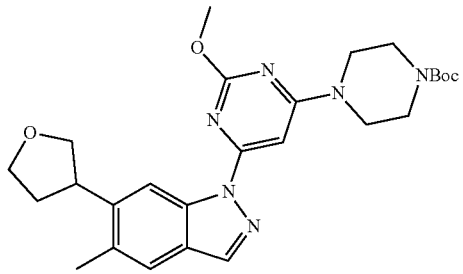 [SMILES: COc1nc(N2CCN(C(=O)OC(C)(C)C)CC2)cc(-n2ncc3cc(C)c(C4CCOC4)cc32)n1]

To a solution of 5-methyl-6-(tetrahydrofuran-3-yl)-1H-indazole (180 mg, 0.891 mmol) in toluene (15 mL) was added tert-butyl 4-(6-iodo-2-methoxypyrimidin-4-yl)piperazine-1-carboxylate (563 mg, 1.34 mmol), K₃PO₄.3H₂O (754 mg, 3.56 mmol), CuI (676 mg, 3.56 mmol), and N1,N2-dimethylcyclohexane-1,2-diamine (505 mg, 3.56 mmol). The reaction mixture was refluxed for 2 hrs. The reaction mixture was cooled to room temperature and poured into NH₃.H₂O (30%, 50 mL). EtOAc (3×20 mL) was added to extract the desired. The combined organic layers were washed with brine (2×20 mL), dried over Na₂SO₄ and concentrated. The residue was purified by column chromatograph (PE:EtOAc from 10:1 to 5:1) to give the title compound (260 mg, yield 59%) as a white solid.

¹H NMR (300 MHz, CDCl₃): δ 8.84 (s, 1H), 8.06 (s, 1H), 7.51 (s, 1H), 6.84 (s, 1H), 4.19-4.13 (m, 4H), 4.07-4.02 (m, 1H), 3.98-3.94 (m, 2H), 3.74-3.71 (m, 5H), 3.54-3.51 (m, 4H), 2.48-2.39 (m, 4H), 2.04-1.97 (m, 1H), 1.48 (s, 9H).

LCMS: [mobile phase: 5-95% acetonitrile in 2.5 min], Rt=1.94 min; MS Calcd: 494, MS Found: 495 [M+1]⁺.

Description D221 and D222 tert-butyl 4-(2-methoxy-6-(5-methyl-6-(tetrahydrofuran-3-yl)-1H-indazol-1-yl)pyrimidin-4-yl) piperazine-1-carboxylate (Enantiomer 1) (D221) and tert-butyl 4-(2-methoxy-6-(5-methyl-6-(tetrahydrofuran-3-yl)-1H-indazol-1-yl)pyrimidin-4-yl) piperazine-1-carboxylate (Enantiomer 2) (D222)

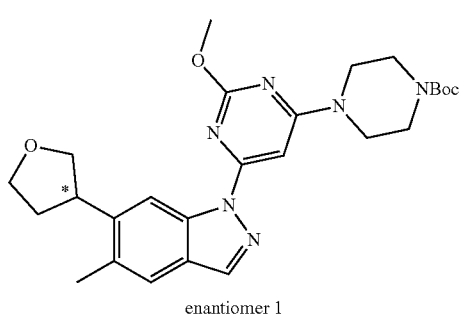

enantiomer 1

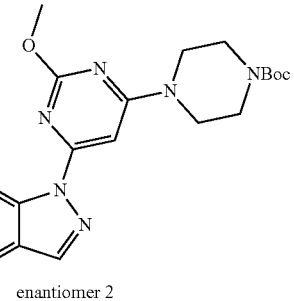

enantiomer 2 tert-Butyl 4-(2-methoxy-6-(5-methyl-6-(tetrahydrofuran-3-yl)-1H-indazol-1-yl)pyrimidin-4-yl) piperazine-1-carboxylate (260 mg, 0.526 mmol) was separated by chiral prep. HPLC with the method (Chiralpak IA 5 μm 4.6×250 mm, Phase: Hex/IPA=70/30, flow rate: 1 mL/min, temperature: 30° C.) to give tert-butyl 4-(2-methoxy-6-(5-methyl-6-(tetrahydrofuran-3-yl)-1H-indazol-1-yl)pyrimidin-4-yl) piperazine-1-carboxylate (enantiomer 1) (D221) (90 mg, yield 34%, Rt: 5.170 min, 100% ee) as a white solid and tert-butyl 4-(2-methoxy-6-(5-methyl-6-(tetrahydrofuran-3-yl)-1H-indazol-1-yl)pyrimidin-4-yl) piperazine-1-carboxylate (enantiomer 2) (D222) (90 mg, yield 34%, Rt: 6.099 min, 95% ee) as a white solid.

D221: ¹H NMR (300 MHz, CDCl₃): δ 8.84 (s, 1H), 8.07 (s, 1H), 7.51 (s, 1H), 6.85 (s, 1H), 4.19-4.03 (m, 5H), 3.98-3.93 (m, 2H), 3.74-3.71 (m, 5H), 3.54-3.51 (m, 4H), 2.51-2.42 (m, 4H), 2.06-1.98 (m, 1H), 1.48 (s, 9H).

LCMS: [mobile phase: 5-95% acetonitrile in 2.5 min], Rt=1.95 min; MS Calcd: 494, MS Found: 495 [M+1]⁺.

D222: ¹H NMR (300 MHz, CDCl₃): δ 8.84 (s, 1H), 8.07 (s, 1H), 7.51 (s, 1H), 6.85 (s, 1H), 4.19-4.03 (m, 5H), 3.98-3.94 (m, 2H), 3.74-3.71 (m, 5H), 3.54-3.51 (m, 4H), 2.50-2.42 (m, 4H), 2.05-1.96 (m, 1H), 1.48 (s, 9H).

LCMS: [mobile phase: 5-95% acetonitrile in 2.5 min], Rt=1.94 min; MS Calcd: 494, MS Found: 495 [M+1]⁺.

Description D223 tert-Butyl 3-oxomorpholine-4-carboxylate (D223)

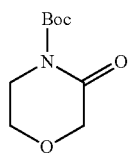 [SMILES: CC(C)(C)OC(=O)N1CCOCC1=O]

Morpholin-3-one (8.00 g, 79.2 mmol) was dissolved in dry THF (100 mL), and then (Boc)₂O (25.9 g, 0.119 mol) and DMAP (966 mg, 7.92 mmol) were added. The mixture was stirred at room temperature under N₂ atmosphere overnight. Imidazole (5.39 g, 79.2 mmol) was added. After stirred for 30 min EtOAc (150 mL) was added. The organic layer was washed with brine (100 mL), dried over Na₂SO₄, filtered and concentrated in vacuo to give oil which was solidified after standing. The solid was washed with PE (100 mL) to afford the desired compound (10.5 g, yield 66%) as a white solid.

¹H NMR (300 MHz, CDCl₃): δ 4.20 (s, 2H), 3.88-3.85 (m, 2H), 3.74-3.70 (m, 2H), 1.51 (s, 9H).

LC-MS (mobile phase: from 95% water and 5% CH$_3$CN to 5% water and 95% CH$_3$CN in 3.0 min, purity is >95%, Rt=1.56 min; MS Calcd.: 201; MS Found: 202 [M+H]$^+$; 146 [M−56+H]$^+$.

Description D224 tert-Butyl (2-(2-oxo-2-(1-(tetrahydro-2H-pyran-2-yl)-1H-indazol-6-yl)ethoxy)ethyl)carbamate (D224)

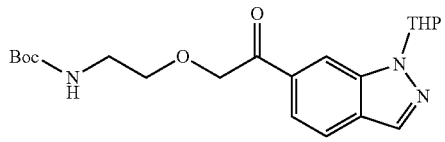

n-BuLi (3.86 mL, 9.25 mmol, 2.4 M in hexane) was injected slowly to a solution of 6-bromo-1-(tetrahydro-2H-pyran-2-yl)-1H-indazole (2.00 g, 7.12 mmol) in dry THF (20 mL) under N$_2$ atmosphere at −78° C. After addition, the mixture was stirred for another half an hour. Then a solution of tert-butyl 3-oxomorpholine-4-carboxylate (2.15 g, 10.7 mmol) in dry THF (4 mL) was added slowly. And then the mixture was stirred for another three hours. The mixture was quenched with water (30 mL) at −78° C. and warmed to room temperature. The mixture was diluted with EtOAc (100 mL). The organic layer was washed with water (50 mL×3) and brine (50 mL), dried over Na$_2$SO$_4$ and concentrated in vacuo. The residue was purified by column on silica gel eluting with PE/EtOAc (from 10/1 to 4/1) to afford the title compound (950 mg, yield 33%) as a colorless oil.

$^1$H NMR (300 MHz, CDCl$_3$): δ 8.24 (s, 1H), 8.09 (s, 1H), 7.80 (dd, J=8.7, 0.6 Hz, 1H), 7.69 (dd, J=8.7, 1.5 Hz, 1H), 5.823-5.80 (m, 1H), 5.24 (br s, 1H), 4.88 (s, 2H), 4.07-3.99 (m, 1H), 3.85-3.76 (m, 1H), 3.72-3.68 (m, 2H), 3.44-3.36 (m, 2H), 2.64-2.53 (m, 1H), 2.23-2.07 (m, 2H), 1.85-1.66 (m, 3H), 1.45 (s, 9H).

Description D225

5-(1H-Indazol-6-yl)-3,6-dihydro-2H-1,4-oxazine (D225)

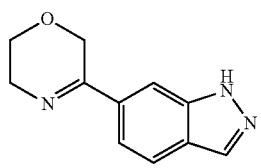 [SMILES: c1cc2cn[nH]c2cc1C1=NCCOC1]

HCl/dioxane (5 M, 10 mL) was added slowly to a solution of tert-butyl (2-(2-oxo-2-(1-(tetrahydro-2H-pyran-2-yl)-1H-indazol-6-yl)ethoxy)ethyl)carbamate (950 mg, 2.36 mmol) in dioxane (10 mL) at ice bath. After addition, the mixture was stirred at room temperature for four hours. The mixture was concentrated in vacuo to give the crude product (560 mg, yield >100%) as a yellow solid.

LC-MS (mobile phase: from 95% water and 5% CH$_3$CN to 5% water and 95% CH$_3$CN in 2.5 min, Rt=1.22 min; MS Calcd.: 201; MS Found: 202 [M+H]$^+$.

Description D226

3-(1H-Indazol-6-yl)morpholine (D226)

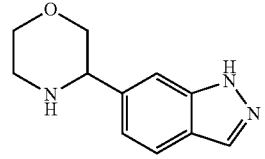 [SMILES: c1cc2cn[nH]c2cc1C1COCCN1]

NaBH$_4$ (179 mg, 4.72 mmol) was added slowly to a solution of the crude 5-(1H-indazol-6-yl)-3,6-dihydro-2H-1,4-oxazine (560 mg, 2.36 mmol) in MeOH (50 mL) under ice bath. After addition the mixture was stirred at room temperature for one hour, water (10 mL) was added, and the mixture was concentrated in vacuo to give the crude product (600 mg, yield >100%) as a yellow oil which was used in next step without further purification.

LC-MS (mobile phase: from 95% water and 5% CH$_3$CN to 5% water and 95% CH$_3$CN in 2.5 min, Rt=1.12 min; MS Calcd.: 203; MS Found: 204 [M+H]$^+$.

Description D227 and D228

3-(1H-Indazol-6-yl)-4-methylmorpholine (Enantiomer 1) (D227) and 3-(1H-indazol-6-yl)-4-methylmorpholine (Enantiomer 2) (D228)

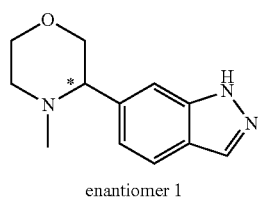

enantiomer 1

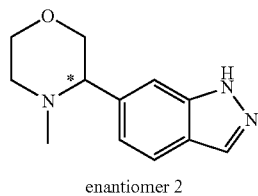

enantiomer 2

NaBH$_3$CN (474 mg, 7.55 mmol) was added slowly to a solution of the crude 3-(1H-indazol-6-yl)morpholine (600 mg, 2.36 mmol), HCHO aqueous (37%, 4 mL) and CH$_3$COOH (10 drops) in MeOH (50 mL) under ice bath. After added the mixture was stirred at room temperature for another 1.5 hrs. The mixture was quenched with NaHCO$_3$ aqueous (sat. 50 mL). The mixture was diluted with water (50 mL) and extracted with DCM (100 mL×3). The organic layers were washed with water (100 mL) and brine (100 mL), dried over Na$_2$SO$_4$ and concentrated in vacuo to give the crude product. The crude product was dissolved in NH$_3$/MeOH (5 M, 20 mL) and stirred at room temperature for 3 hrs. The mixture was concentrated in vacuo and purified by C18 column eluting with CH$_3$CN/H$_2$O to give the desired compound (300 mg, yield 59%) as a colorless oil. The colorless oil was separated by Chiral HPLC with the method (Chiral condition: Chiralpak IE-5 um 20 mm*250 mm, Hex/EtOH=70/30, Flow Rate: 12 ml/min, 205 nm, T=30° C.) to give 3-(1H-indazol-6-yl)-4-methylmorpholine (enantiomer 1) (D227) (97 mg, yield 32%, Rt=5.853 min, 100% ee) and 3-(1H-indazol-6-yl)-4-methylmorpholine (enantiomer 2) (D228) (111 mg, yield 37%, Rt=7.949 min, 94% ee.) both as colorless oil.

D227: $^1$H NMR (300 MHz, CDCl$_3$): δ 8.09 (s, 1H), 7.73 (d, J=8.4 Hz, 1H), 7.59 (s, 1H), 7.18 (d, J=8.1 Hz, 1H), 3.99-3.96 (m, 1H), 3.90-3.78 (m, 2H), 3.54-3.46 (m, 1H), 3.28-3.24 (m, 1H), 2.98 (d, J=12.0 Hz, 1H), 2.50 (td, J=11.7, 3.3 Hz, 1H), 2.13 (s, 3H).

D228: $^1$H NMR (300 MHz, CDCl$_3$): δ 8.08 (s, 1H), 7.73 (d, J=8.4 Hz, 1H), 7.58 (s, 1H), 7.18 (d, J=8.4 Hz, 1H), 3.99-3.98 (m, 1H), 3.89-3.77 (m, 2H), 3.53-3.46 (m, 1H), 3.28-3.24 (m, 1H), 2.97 (d, J=11.7 Hz, 1H), 2.50 (td, J=11.7, 3.6 Hz, 1H), 2.13 (s, 3H).

Description D229

1-(6-Bromo-5-methyl-1H-indazol-1-yl)ethanone (D229)

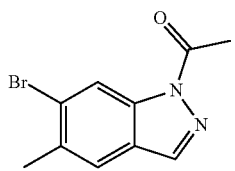

Acetic anhydride (4.69 mL, 50 mmol) was added to a solution of 5-bromo-2,4-dimethylaniline (5 g, 25.0 mmol) in chloroform (100 mL) under ice-bath cooling and the mixture was stirred at rt for 5 min. Potassium acetate (2.58 g, 26.25 mmol) was then added and the mixture was stirred at rt for 5 min. A solution of 18-crown-6 (1.32 g, 5.00 mmol) in chloroform (10 mL) was then added followed by addition of tert-butyl nitrite (6.54 mL, 55 mmol). The resulting mixture was stirred at 60° C. for 18 hrs. The reaction mixture was cooled and the pH value of the organic layer was adjusted to 8 using saturated aqueous sodium bicarbonate solution. The organic layer was separated, dried over anhydrous Na$_2$SO$_4$ and concentrated. The residue was purified by normal phase chromatography (PE:EtOAc=100:0 to 20:80) to afford the 1-(6-bromo-5-methyl-1H-indazol-1-yl)ethanone (5.8 g, 91.7% yield) as yellow solid.

LCMS: (mobile phase: 5-95% acetonitrile), Rt=3.72 min in 5 min; MS Calcd: 252; MS Found: 253 [M+1]$^+$.

Description D230

1-(6-Hydroxy-5-methyl-1H-indazol-1-yl)ethanone (D230)

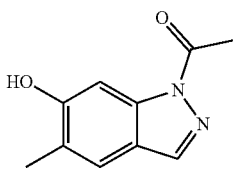

Step 1:

To a stirred solution of 1-(6-bromo-5-methyl-1H-indazol-1-yl)ethanone (2.3 g, 9.09 mmol) in DMF (50 mL) was added 4,4,4',4',5,5,5',5'-octamethyl-2,2'-bi(1,3,2-dioxaborolane) (4.6 g, 18 mmol) and KOAc (2.6 g, 26.5 mmol). The mixture was stirred at 90° C. for 15 min under nitrogen atmosphere, then, tetrakis(triphenylphosphine)palladium(0) (1 g, 0.64 mmol) was added and the resulting solution was stirred at 90° C. under nitrogen atmosphere overnight. EtOAc (150 mL) was added to dilute the solution and the organic layer was washed with water (50 mL×3), dried over anhydrous Na$_2$SO$_4$ and concentrated. The crude product 1-(5-methyl-6-(4,4,5,5-tetramethyl-1,3,2-dioxaborolan-2-yl)-1H-indazol-1-yl)ethanone was used in next step without further purification.

LCMS: (mobile phase: 5-95% Acetonitrile), Rt=4.25 min in 5 min; MS Calcd: 300; MS Found: 301 [M+1]$^+$.

Step 2:

The crude product (obtained in step 1) was dissolved in THF (15 mL). NaOH (1N, 18 mL) was added and the solution was cooled to 0° C., H$_2$O$_2$ was added and the solution was stirred at this temperature for an additional 1 hr. The pH value of the reaction mixture was adjusted to 5 using 1N HCl and then extracted with EtOAc (100 mL). The organic layer was separated, dried over anhydrous Na$_2$SO$_4$ and concentrated. The crude product was purified by normal phase chromatography (PE:EtOAc=100:0→80:20) to afford 1-(6-hydroxy-5-methyl-1H-indazol-1-yl)ethanone (370 mg, 21.41% yield) as a white solid.

LCMS: (mobile phase: 5-95% Acetonitrile), Rt=2.57 min in 5 min; MS Calcd: 190; MS Found: 191 [M+1]$^+$.

Description D231

1-(6-Isopropoxy-5-methyl-1H-indazol-1-yl)ethanone (D231)

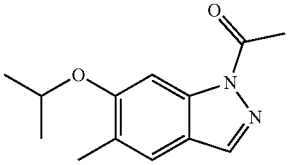 [SMILES: CC(=O)n1ncc2cc(C)c(OC(C)C)cc21]

To a stirred solution of 1-(6-hydroxy-5-methyl-1H-indazol-1-yl)ethanone (200 mg, 1.05 mmol) and 2-iodopropane (157 μL, 1.5 mmol) was added DIPEA (388 μL, 2.1 mmol) and the resulting solution was stirred at 40° C. for 1 hr. K$_2$CO$_3$ (290 mg, 2.1 mmol) was then added and the reaction temperature was raised to 60° C. and stirred at that temperature for 4 hrs. The reaction mixture was cooled to room temperature, and EtOAc (30 mL) was added to dilute the reaction mixture. The organic layer was washed with water (30 mL×3), dried over anhydrous Na$_2$SO$_4$ and then concentrated. The residue was purified by normal phase chromatography (PE:EtOAc=100:0 to 80:20) to afford 1-(6-isopropoxy-5-methyl-1H-indazol-1-yl)ethanone (140 mg, 57% yield) as a white solid.

LCMS: (mobile phase: 5-95% Acetonitrile), Rt=3.91 min in 5 min; MS Calcd: 232; MS Found: 233 [M+1]$^+$.

Description D232 tert-Butyl 4-((1-acetyl-5-methyl-1H-indazol-6-yl)oxy)piperidine-1-carboxylate (D232)

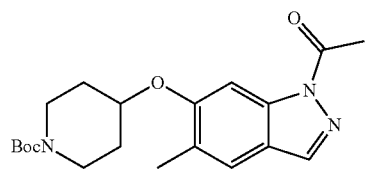 [SMILES: CC(=O)n1ncc2cc(C)c(OC3CCN(C(=O)OC(C)(C)C)CC3)cc21]

Step 1:

To an ice-cooled solution of tert-butyl 4-hydroxypiperidine-1-carboxylate (600 mg, 2.98 mmol) in PhMe (20 mL) was added DIPEA (1.65 mL, 8.9 mmol) and MsCl (461 μL, 6 mmol) sequentially. The resulting mixture was then stirred at that temperature for 1 hr. Water (10 mL) was added to quench the reaction and the mixture was extracted with EtOAc (20 mL). The organic layer was separated, dried over anhydrous $Na_2SO_4$ and concentrated. The crude product tert-butyl 4-((methylsulfonyl)oxy)piperidine-1-carboxylate was used in next step without further purifications.

Step 2:

The intermediate (obtained in step 1) was dissolved in DMF (10 mL). 1-(6-hydroxy-5-methyl-1H-indazol-1-yl)ethanone (160 mg, 841 μmol), DIPEA (310 μL, 1.6 mmol) and $K_2CO_3$ (232 mg, 1.68 mmol) were then added and the mixture was stirred at 90° C. overnight. EtOAc (50 mL) and water (20 mL) were added to the reaction mixture and the layer was separated, the organic layer was washed with water (20 mL×2), dried over anhydrous $Na_2SO_4$ and then concentrated. The residue was purified by normal phase chromatography (PE:EtOAc=100:0 to 80:20) to afford the tert-butyl 4-((1-acetyl-5-methyl-1H-indazol-6-yl)oxy)piperidine-1-carboxylate (285 mg, 91% yield) as a white solid.

LCMS: (mobile phase: 5-95% acetonitrile), Rt=4.23 min in 5 min; MS Calcd: 373; MS Found: 374 [M+1]+.

Description D233

1-(5-Methyl-6-(piperidin-4-yloxy)-1H-indazol-1-yl)ethanone (D233)

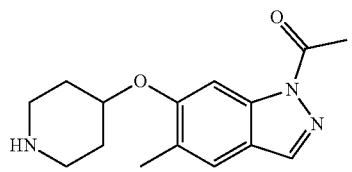 [SMILES: CC(=O)n1ncc2cc(C)c(OC3CCNCC3)cc21]

tert-Butyl 4-((1-acetyl-5-methyl-1H-indazol-6-yl)oxy)piperidine-1-carboxylate (285 mg, 763 μmol) was dissolved in DCM (20 mL). TFA (2 mL) was added and the solution was stirred at room temperature for 3 hrs. The solvent was removed and the residue (200 mg, 96% yield) was used in next step without further purifications.

LCMS: (mobile phase: 5-95% acetonitrile), Rt=2.3 min in 5 min; MS Calcd: 273; MS Found: 274 [M+1]+.

Description D234

1-(5-Methyl-6-((1-methylpiperidin-4-yl)oxy)-1H-indazol-1-yl)ethanone (D234)

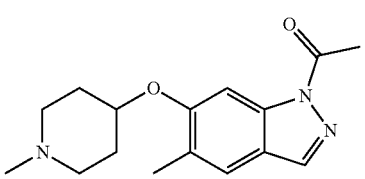 [SMILES: CC(=O)n1ncc2cc(C)c(OC3CCN(C)CC3)cc21]

1-(5-Methyl-6-(piperidin-4-yloxy)-1H-indazol-1-yl)ethanone (200 mg, 732 μmol) was dissolved in DMF (5 mL). 30% aqueous formaldehyde (366 μmol, 3.66 mmol), $NaBH(OAc)_2$ (310 mg, 1.5 mmol), AcOH (1 drop) were then added and the solution was stirred at room temperature for 1 hr. EtOAc (20 mL) was added to dilute the reaction mixture and the organic layer was washed by aqueous $NaHCO_3$ (sat. 20 mL) and water (10 mL×2) sequentially. The organic layer was then dried over anhydrous $Na_2SO_4$ and concentrated. The crude product was used in next steps without further purifications. (180 mg, 86% yield)

LCMS: (mobile phase: 5-95% acetonitrile), Rt=2.34 min in 5 min; MS Calcd: 287; MS Found: 288 [M+1]+.

Description D235

(S)-tert-Butyl 3-((methylsulfonyl)oxy)piperidine-1-carboxylate (D235)

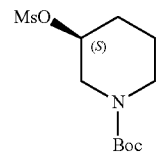

To a solution of (S)-tert-butyl 3-hydroxypiperidine-1-carboxylate (750 mg, 3.73 mmol) and TEA (1.88 g, 18.7 mmol) in DCM (10 mL) was added MsCl (550 mg, 4.85 mmol) at 0° C. The solution was warmed to room temperature and stirred for 2 hrs. The mixture was washed with $H_2O$ (10 mL×2) and brine (10 mL×2), dried over $Na_2SO_4$ and concentrated to give the desired product (970 mg, yield 93%) as a yellow solid.

$^1$H NMR (300 MHz, $CDCl_3$): δ 4.76-4.68 (m, 1H), 3.67-3.57 (m, 2H), 3.48-3.40 (m, 1H), 3.35-3.27 (m, 1H), 3.04 (s, 3H), 2.07-1.77 (m, 3H), 1.57-1.50 (m, 1H), 1.45 (s, 9H).

LC-MS: N/A

Description D236

5-Methyl-1-(tetrahydro-2H-pyran-2-yl)-1H-indazol-6-ol (D236)

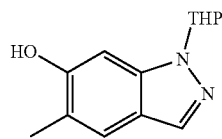

To a solution of 5-methyl-1-(tetrahydro-2H-pyran-2-yl)-6-(4,4,5,5-tetramethyl-1,3,2-dioxaborolan-2-yl)-1H-indazole (2.70 g, 7.89 mmol) in THF (80 mL) and NaOH aqueous solution (1 N, 40 mL) was added $H_2O_2$ aqueous (37%, 4.48 g, 39.5 mmol) at 0-15° C. The mixture was diluted with sat. $NaHSO_3$ (100 mL) and extracted with EtOAc (3×50 mL). The combined organic layers were washed with brine, dried over $Na_2SO_4$ and concentrated under vacuum. The residue was purified by silica column (PE:EtOAc=6:1) and the crude was slurried with PE (3.5 mL) to give the desired product (1.70 g, yield 94%) as a yellow solid.

$^1$H NMR (300 MHz, $CDCl_3$): δ 7.85 (s, 1H), 7.42 (s, 1H), 6.93 (s, 1H), 5.58 (dd, J=9.6, 2.7 Hz, 1H), 5.44 (s, 1H), 4.04-3.99 (m, 1H), 3.75-3.66 (m, 1H), 2.60-2.47 (m, 1H), 2.32 (s, 3H), 2.17-2.01 (m, 2H), 1.81-1.63 (m, 3H).

LC-MS [mobile phase: from 90% water (0.02% $NH_4OAc$) and 10% $CH_3CN$ to 5% water (0.02% $NH_4OAc$) and 95% $CH_3CN$ in 4 min], Rt=2.113 min, MS Calcd.: 232, MS Found: 233 [M+H]$^+$.

Description D237

(3R)-tert-Butyl 3-((5-methyl-1-(tetrahydro-2H-pyran-2-yl)-1H-indazol-6-yl)oxy)piperidine-1-carboxylate (D237)

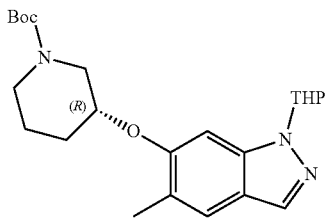

A mixture of 5-methyl-1-(tetrahydro-2H-pyran-2-yl)-1H-indazol-6-ol (500 mg, 2.16 mmol) and $Cs_2CO_3$ (3.51 g, 10.8 mmol) in $CH_3CN$ (20 mL) was stirred at 80° C. for 10 min. Then a solution of (S)-tert-butyl 3-((methylsulfonyl)oxy) piperidine-1-carboxylate (960 mg, 3.46 mmol) in $CH_3CN$ (10 mL) was added dropwise. The resulting mixture was stirred in reflux overnight. After the mixture was cooled the mixture was concentrated. The mixture was partitioned with $H_2O$ (20 mL) and EtOAc (30 mL). The organic layer was washed with brine (20 mL), dried over $Na_2SO_4$ and concentrated under vacuum. The residue was purified by silica column (PE:EtOAc=6:1) to give the desired product (0.19 g, yield 21%) as a yellow oil.

$^1$H NMR (300 MHz, $CDCl_3$): δ 7.83 (s, 1H), 7.42 (s, 1H), 6.94 (br s, 1H), 5.66-5.63 (m, 1H), 4.42 (br s, 1H), 4.01-3.94 (m, 1H), 3.79-3.70 (m, 1H), 3.61-3.24 (m, 3H), 2.63-2.52 (m, 1H), 2.25 (s, 3H), 2.21-2.11 (m, 1H), 2.08-1.83 (m, 5H), 1.81-1.63 (m, 4H), 1.32-1.23 (m, 9H).

LC-MS: [mobile phase: from 80% water (0.02% $NH_4OAc$) and 20% $CH_3CN$ to 5% water (0.02% $NH_4OAc$) and 95% $CH_3CN$ in 4 min], Rt=2.752 min, MS Calcd.: 415, MS Found: 416 [M+H]$^+$.

Description D238

(R)-5-Methyl-6-(piperidin-3-yloxy)-1H-indazole (D238)

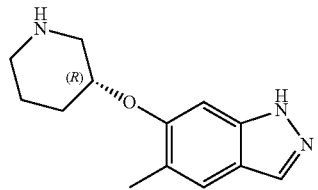

To a solution of (3R)-tert-butyl 3-((5-methyl-1-(tetrahydro-2H-pyran-2-yl)-1H-indazol-6-yl)oxy) piperidine-1-carboxylate (190 mg, 0.458 mmol) in methanol (2 mL) at 0° C. was added dropwise conc. HCl (2 mL). The mixture was warmed to room temperature and stirred for 30 min. The reaction mixture was concentrated and 2 mL of sat. $NH_3.H_2O$ was added. The mixture was stirred at rt for 5 min and concentrated to give the title compound (120 mg, yield 95%) as a yellow solid which was used for next step directly.

LC-MS: [mobile phase: from 95% water (0.02% $NH_4OAc$) and 5% $CH_3CN$ to 5% water (0.02% $NH_4OAc$) and 95% $CH_3CN$ in 4 min], Rt=1.752 min, MS Calcd.: 231, MS Found: 232 [M+H]$^+$.

Description D239

(R)-5-Methyl-6-((1-methylpiperidin-3-yl)oxy)-1H-indazole (D239)

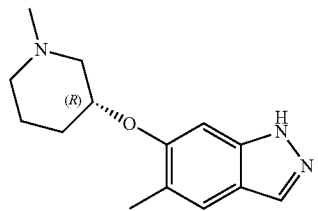

To a solution of (R)-5-methyl-6-(piperidin-3-yloxy)-1H-indazole (100 mg, 0.433 mmol) and HCHO aqueous solution (37%, 1.5 mL) in MeOH (4 mL) was added $NaBH_3CN$ (136 mg, 2.16 mmol). The resulting mixture was stirred at rt overnight. The mixture was poured into sat. $NaHCO_3$ solution (5 mL). EtOAc (2×10 mL) was added to extract the desired compound. The combined organic layers were washed with brine, dried over $Na_2SO_4$ and concentrated. The residue was dissolved in sat. $NH_3$-methanol (10 mL) and stirred at rt for 2 hrs. The mixture was concentrated and the residue was purified by silica column (PE:EtOAc=2:1) to give the desired product (75 mg, yield 71%) as a slight yellow oil.

LC-MS: [mobile phase: from 90% water (0.02% NH₄OAc) and 10% CH₃CN to 5% water (0.02% NH₄OAc) and 95% CH₃CN in 4 min], Rt=1.903 min, MS Calcd.: 245, MS Found: 246 [M+H]⁺.

Description D240

(R)-tert-Butyl 3-((methylsulfonyl)oxy)piperidine-1-carboxylate (D240)

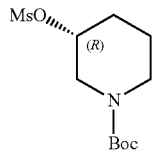

To a solution of (R)-tert-butyl 3-hydroxypiperidine-1-carboxylate (800 mg, 4.00 mmol) and TEA (2.02 g, 20.0 mmol) in DCM (10 mL) was added MsCl (590 mg, 5.20 mmol) at 0° C. The solution was warmed to room temperature and stirred for 2 hrs. The mixture was washed with H₂O (10 mL×2) and brine (20 mL), dried over Na₂SO₄ and concentrated to give the desired product (1.08 g, yield 97%) as a yellow solid.

¹H NMR (300 MHz, CDCl₃): δ 4.70 (br s, 1H), 3.75-3.60 (m, 2H), 3.47-3.39 (m, 1H), 3.35-3.27 (m, 1H), 3.04 (s, 3H), 2.00-1.75 (m, 3H), 1.54-1.45 (m, 1H), 1.45 (s, 9H).

Description D241

(3S)-tert-Butyl 3-((5-methyl-1-(tetrahydro-2H-pyran-2-yl)-1H-indazol-6-yl)oxy)piperidine-1-carboxylate (D241)

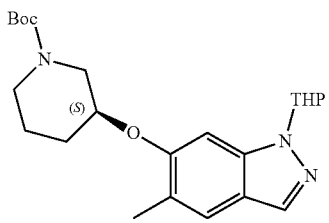

A mixture of 5-methyl-1-(tetrahydro-2H-pyran-2-yl)-1H-indazol-6-ol (560 mg, 2.42 mmol) and Cs₂CO₃ (2.36 g, 7.26 mmol) in CH₃CN (20 mL) was stirred at 80° C. for 15 min. Then a solution of (R)-tert-butyl 3-((methylsulfonyl)oxy)piperidine-1-carboxylate (1.08 g, 3.87 mmol) in CH₃CN (10 mL) was added dropwise. The resulting mixture was stirred in reflux overnight. After cooled the mixture was concentrated. The mixture was partitioned with H₂O (20 mL) and EtOAc (30 mL). The organic layer was washed with brine (20 mL), dried over Na₂SO₄ and concentrated under vacuum. The residue was purified by silica column (PE: EtOAc=6:1) to give the desired product (0.18 g, yield 18%) as a yellow solid.

¹H NMR (300 MHz, CDCl₃): δ 7.84 (s, 1H), 7.42 (s, 1H), 7.01-6.85 (m, 1H), 5.66-5.63 (m, 1H), 4.42 (br s, 1H), 4.03-3.90 (m, 1H), 3.77-3.64 (m, 1H), 3.62-3.21 (m, 3H), 2.63-2.52 (m, 1H), 2.25 (s, 3H), 2.20-2.14 (m, 1H), 2.10-1.85 (m, 5H), 1.81-1.62 (m, 4H), 1.38-1.21 (m, 9H).

Description D242

(S)-5-Methyl-6-((1-methylpiperidin-3-yl)oxy)-1H-indazole (D242)

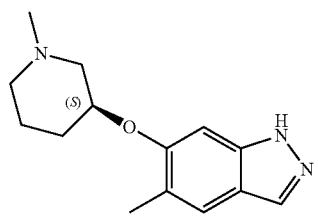

To a solution of (3S)-tert-butyl 3-((5-methyl-1-(tetrahydro-2H-pyran-2-yl)-1H-indazol-6-yl)oxy) piperidine-1-carboxylate (180 mg, 0.430 mmol) in methanol (2 mL) at 0° C. was added dropwise conc. HCl (2 mL). The mixture was warmed to room temperature and stirred for 20 min. The reaction mixture was concentrated and 2 mL of sat. NH₃.H₂O was added. The mixture was concentrated to give the crude intermediate. The intermediate and H₂C(=O) aqueous solution (37%, 1.0 mL) in MeOH (4 mL) was added NaBH₃CN (275 mg, 4.40 mmol). The resulting mixture was stirred at rt for 2 hrs. The mixture was poured into sat. NaHCO₃ solution (5 mL). EtOAc (2×30 mL) was added to extract the desired compound. The combined organic layers were washed with brine, dried over Na₂SO₄ and concentrated. The residue was dissolved in sat. NH₃-methanol (5 mL) and stirred overnight. The mixture was concentrated and the residue was purified by prep. TLC (PE:EtOAc=1:1) to give the desired product (95 mg, yield 91%) as a slight yellow oil.

LC-MS: [mobile phase: from 90% water (0.02% NH₄OAc) and 10% CH₃CN to 5% water (0.02% NH₄OAc) and 95% CH₃CN in 4 min], Rt=1.903 min, MS Calcd.: 245, MS Found: 246 [M+H]⁺.

Description D243

(R)-tert-Butyl 3-((methylsulfonyl)oxy)pyrrolidine-1-carboxylate (D243)

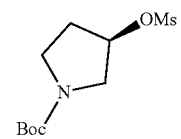

To a solution of (R)-tert-butyl 3-hydroxypyrrolidine-1-carboxylate (1.00 g, 5.35 mmol) and TEA (1.62 mg, 16.1 mmol) in DCM (15 mL) was added MsCl (0.920 g, 8.03 mmol) at 0° C. under N₂. The mixture was warmed to room temperature and stirred for another 1 h. The mixture was diluted with H₂O (40 mL) and extracted with EtOAc (3×20 mL). The combined organic layers were washed with sat. NaHCO₃ aq. brine, dried over Na₂SO₄ and concentrated in vacuum to give the desired product (1.4 g, yield 100%) as yellow oil.

¹H NMR (300 MHz, CDCl₃): δ 5.29-5.24 (m, 1H), 3.72-3.43 (m, 4H), 3.05 (s, 3H), 2.35-2.08 (m, 2H), 1.47 (s, 9H).

LC-MS: [mobile phase: from 90% water (0.02% NH₄OAc) and 10% CH₃CN to 5% water (0.02% NH₄OAc) and 95% CH₃CN in 4 min], Rt=2.152 min MS Calcd.: 265, MS Found: 210 [M−56+H]⁺.

Description D244

(3S)-tert-Butyl 3-((5-methyl-1-(tetrahydro-2H-pyran-2-yl)-1H-indazol-6-yl)oxy)pyrrolidine-1-carboxylate (D244)

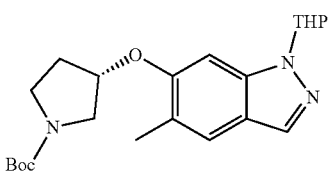

To a mixture of 5-methyl-1-(tetrahydro-2H-pyran-2-yl)-1H-indazol-6-ol (300 mg, 1.29 mmol) and K₂CO₃ (534 mg, 3.87 mmol) in DMF (15 mL) was added (R)-tert-butyl 3-((methylsulfonyl)oxy)pyrrolidine-1-carboxylate (513 mg, 1.94 mmol). The mixture was heated to 80° C. and stirred for 6 hrs. The mixture was diluted with H₂O (30 mL) and extracted with EtOAc (3×15 mL). The combined organic layers were washed with brine, dried over Na₂SO₄ and concentrated under vacuum. The residue was purified by silica column (PE:EtOAc=6:1) to give the desired product (0.55 g, yield >100%) as a yellow oil.

¹H NMR (300 MHz, CDCl₃): δ 7.85 (s, 1H), 7.43 (s, 1H), 6.84 (s, 1H), 5.64 (dd, J=9.0, 3.0 Hz, 1H), 5.03-4.99 (m, 1H), 4.01-3.93 (m, 1H), 3.77-3.54 (m, 5H), 2.64-2.50 (m, 1H), 2.24-2.02 (m, 7H), 1.83-1.65 (m, 3H), 1.47 (s, 9H).

LC-MS: [mobile phase: from 90% water (0.02% NH₄OAc) and 10% CH₃CN to 5% water (0.02% NH₄OAc) and 95% CH₃CN in 4 min], Rt=2.726 min MS Calcd.: 401, MS Found: 402 [M+H]⁺.

Description D245

(S)-5-Methyl-6-((1-methylpyrrolidin-3-yl)oxy)-1H-indazole (D245)

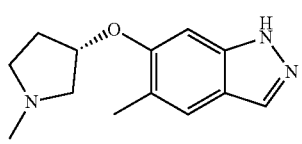 [SMILES: Cc1cc2cn[nH]c2cc1O[C@H]1CCN(C)C1]

To a solution of (3S)-tert-butyl 3-((5-methyl-1-(tetrahydro-2H-pyran-2-yl)-1H-indazol-6-yl)oxy) pyrrolidine-1-carboxylate (552 mg, 1.38 mmol) in dioxane (2 mL) was added sat. HCl/dioxane (5 mL). The solution was heated to 40° C. and stirred overnight. The solution was directly concentrated under vacuum. The residue was dissolved in MeOH (10 mL) and HCHO aqueous solution (37%, 4 mL) was added. The solution was stirred for 1 h at room temperature. NaBH₃CN (520 mg, 8.28 mmol) was added to the solution and the mixture was stirred for 1 h. The mixture was diluted with sat Na₂CO₃ (30 mL) and extracted with EtOAc (3×15 mL). The combined organic layer was washed with brine, dried over Na₂SO₄ and concentrated under vacuum. The residue was dissolved in sat. NH₃/MeOH (15 mL) and the solution was stirred overnight at room temperature. The solution was evaporated under vacuum and the residue was purified by silica column (DCM:MeOH=10:1) to give the desired product (230 mg, yield 72%) as a yellow oil.

¹H NMR (400 MHz, CDCl₃): δ 7.89 (s, 1H), 7.45 (s, 1H), 6.71 (s, 1H), 4.91-4.73 (m, 1H), 3.23-3.19 (m, 1H), 2.88-2.76 (m, 3H), 2.51 (s, 3H), 2.43-2.38 (m, 1H), 2.27 (s, 3H), 2.14-2.09 (m, 1H).

LC-MS: [mobile phase: from 90% water (0.02% NH₄OAc) and 10% CH₃CN to 5% water (0.02% NH₄OAc) and 95% CH₃CN in 4 min], Rt=1.670 min MS Calcd.: 231, MS Found: 232 [M+H]⁺.

Description D246

(S)-tert-Butyl 3-((methylsulfonyl)oxy)pyrrolidine-1-carboxylate (D246)

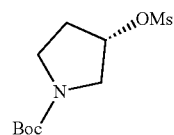

To a solution of (S)-tert-butyl 3-hydroxypyrrolidine-1-carboxylate (1.00 g, 5.35 mmol) and TEA (1.62 g, 16.1 mmol) in DCM (15 mL) was added MsCl (920 mg, 8.03 mmol) at 0° C. under N₂. The solution was warmed to room temperature and stirred for another 1 hour. The mixture was diluted with H₂O (30 mL) and extracted with DCM (3×15 mL). The combined organic layers were washed with sat. NaHCO₃ solution and brine, dried over Na₂SO₄ and concentrated under vacuum to give the desired product (1.5 g, yield 100%) as yellow oil.

¹H NMR (300 MHz, CDCl₃): δ 5.28-5.25 (m, 1H), 3.73-3.43 (m, 4H), 3.05 (s, 3H), 2.36-2.09 (m, 2H), 1.47 (s, 9H).

LC-MS: [mobile phase: from 90% water (0.02% NH₄OAc) and 10% CH₃CN to 5% water (0.02% NH₄OAc) and 95% CH₃CN in 4 min], Rt=2.153 min MS Calcd.: 265. MS Found: 210 [M−56+H]⁺.

Description D247

(3R)-tert-Butyl 3-((5-methyl-1-(tetrahydro-2H-pyran-2-yl)-1H-indazol-6-yl)oxy)pyrrolidine-1-carboxylate (D247)

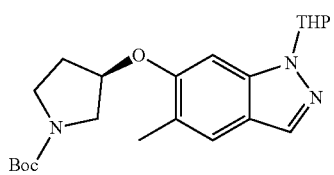

To a mixture of 5-methyl-1-(tetrahydro-2H-pyran-2-yl)-1H-indazol-6-ol (300 mg, 1.29 mmol) and K₂CO₃ (534 mg, 3.87 mmol) in DMF (8 mL) was added (S)-tert-butyl 3-((methylsulfonyl)oxy)pyrrolidine-1-carboxylate (513 mg, 1.94 mmol). The mixture was heated to 60° C. and stirred overnight. The mixture was diluted with H₂O (20 mL) and extracted with EtOAc (3×15 mL). The combined organic layers were washed with brine, dried over Na₂SO₄ and concentrated under vacuum. The residue was purified by silica column (PE:EtOAc=10:1) and further purified by C18 (CH₃CN/H₂O=5-50%) to give the desired product (0.37 g, yield 71%) as a yellow oil.

¹H NMR (300 MHz, CDCl₃): δ 7.85 (s, 1H), 7.47 (s, 1H), 6.84 (s, 1H), 5.64 (dd, J=8.7, 3.0 Hz, 1H), 5.03-4.99 (m, 1H), 4.02-3.94 (m, 1H), 3.78-3.50 (m, 5H), 2.64-2.50 (m, 1H), 2.24-2.03 (m, 7H), 1.82-1.65 (m, 3H), 1.48 (s, 9H).

LC-MS: [mobile phase: from 90% water (0.02% NH₄OAc) and 10% CH₃CN to 5% water (0.02% NH₄OAc) and 95% CH₃CN in 4 min], Rt=3.011 min, MS Calcd.: 401. MS Found: 402 [M+H]⁺.

Description D248

(R)-5-Methyl-6-((1-methylpyrrolidin-3-yl)oxy)-1H-indazole (D248)

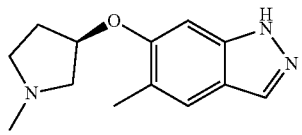 [SMILES: Cc1cc2cn[nH]c2cc1O[C@@H]1CCN(C)C1]

To a solution of (3R)-tert-butyl 3-((5-methyl-1-(tetrahydro-2H-pyran-2-yl)-1H-indazol-6-yl)oxy)pyrrolidine-1-carboxylate (370 mg, 0.922 mmol) in DCM (6 mL) was added CF₃COOH (3 mL) at 0° C. The mixture was warmed to room temperature and stirred for 30 min. The solution was adjusted to pH 8-9 with sat. NaHCO₃ aqueous and extracted with DCM (3×20 mL). The combined organic layers were washed with brine, dried over Na₂SO₄ and concentrated under vacuum. The residue was added MeOH (3 mL), HCHO aqueous solution (37%, 1 mL). The solution was stirred for 30 min at room temperature. Then, NaBH₃CN (500 mg, 7.97 mmol) was added and the mixture was stirred for 12 hrs. The mixture was diluted with H₂O (20 mL) and extracted with EtOAc (3×15 mL). The combined organic layers were washed with brine, dried over Na₂SO₄ and concentrated under vacuum. The residue was dissolved in dioxane (3 mL) and con. HCl (6 mL) was added. The mixture was heated to 40° C. and stirred for 3 hrs. Then the mixture was adjusted to pH 8-9 with sat. Na₂CO₃ aq and extracted with EtOAc (3×15 mL). The combined organic layers were washed with brine, dried over Na₂SO₄ and concentrated under vacuum. The residue was purified by C18 (CH₃CN/H₂O=5-35%) to give the desired product (70 mg, yield 33%) as a yellow oil.

¹H NMR (300 MHz, CDCl₃): δ 7.89 (s, 1H), 7.45 (s, 1H), 6.69 (s, 1H), 4.90-4.84 (m, 1H), 3.13-3.07 (m, 1H), 2.84-2.76 (m, 2H), 2.70-2.62 (m, 1H), 2.45 (s, 3H), 2.42-2.32 (m, 1H), 2.27 (s, 3H), 2.13-2.07 (m, 1H).

LC-MS: [mobile phase: from 90% water (0.02% NH₄OAc) and 10% CH₃CN to 5% water (0.02% NH₄OAc) and 95% CH₃CN in 4 min], Rt=1.714 min, MS Calcd.: 231, MS Found: 232 [M+H]⁺.

Description D249 tert-Butyl 4-(6-chloro-2-methoxypyrimidin-4-yl)piperazine-1-carboxylate (D249)

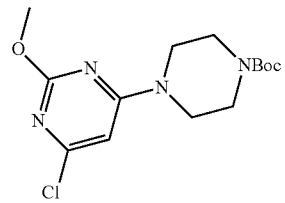 [SMILES: COc1nc(Cl)cc(N2CCN(C(=O)OC(C)(C)C)CC2)n1]

To a solution of 4,6-dichloro-2-methoxy-pyrimidine (1.50 g, 8.38 mmol) and TEA (2.50 g, 25.1 mmol) in methanol (100 mL) was added a solution of piperazine-1-carboxylic acid tert-butyl ester (1.55 g, 8.38 mmol), and the mixture was stirred at room temperature for 2 hrs. The reaction mixture was concentrated and the residue was washed with 5 mL of cold MeOH (5 mL) to get the title compound (2.4 g, yield 87%) as a white solid.

¹H NMR (400 MHz, CDCl₃): δ 6.19 (s, 1H), 3.94 (s, 3H), 3.63-3.50 (m, 8H), 1.48 (s, 9H).

LC-MS: [mobile phase: from 80% water (0.02% NH₄OAc) and 20% CH₃CN to 5% water (0.02% NH₄OAc) and 95% CH₃CN in 4 min], Rt=2.418 min, MS Calcd.: 328, MS Found: 329 [M+H]⁺.

Description D250

(R)-tert-Butyl 4-(2-methoxy-6-(5-methyl-6-((tetrahydrofuran-3-yl)oxy)-1H-indazol-1-yl) pyrimidin-4-yl)piperazine-1-carboxylate (D250)

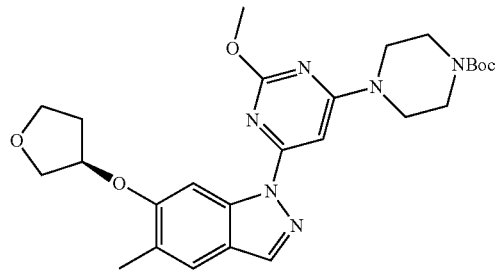 [SMILES: COc1nc(N2CCN(C(=O)OC(C)(C)C)CC2)cc(-n2ncc3cc(C)c(O[C@@H]4CCOC4)cc32)n1]

A mixture of (R)-5-methyl-6-((tetrahydrofuran-3-yl)oxy)-1H-indazole (400 mg, 1.83 mmol), tert-butyl 4-(6-chloro-2-methoxypyrimidin-4-yl)piperazine-1-carboxylate (900 mg, 2.75 mmol) and Cs₂CO₃ (1.79 g, 5.49 mmol) in DMF (40 mL) was heated to 100° C. and stirred overnight. The mixture was diluted with H₂O (100 mL) and extracted with EtOAc (30 mL×3). The combined organic layer were washed with brine (50 mL), dried over Na₂SO₄, filtered and concentrated. The residue was purified by column chromatography on silica gel (PE:EtOAc=3:1) to give the title compound (210 mg, yield 22%) as a white solid.

¹H NMR (300 MHz, CDCl₃): δ 8.25 (s, 1H), 8.01 (s, 1H), 7.45 (s, 1H), 6.86 (s, 1H), 5.11-5.06 (m, 1H), 4.16-3.95 (m, 7H), 3.75-3.72 (m, 4H), 3.55-3.49 (m, 4H), 2.30-2.23 (m, 5H), 1.49 (s, 9H).

LC-MS: [mobile phase: from 70% water (0.02% NH₄OAc) and 30% CH₃CN to 5% water (0.02% NH₄OAc) and 95% CH₃CN in 3 min], Rt=2.24 min, MS Calcd.: 510, MS Found: 511 [M+H]⁺.

Description D251

(S)-tert-Butyl 4-(2-methoxy-6-(5-methyl-6-((tetrahydrofuran-3-yl)oxy)-1H-indazol-1-yl) pyrimidin-4-yl) piperazine-1-carboxylate (D251)

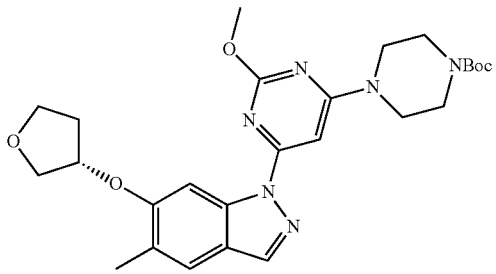 [SMILES: COc1nc(N2CCN(C(=O)OC(C)(C)C)CC2)cc(-n2ncc3cc(C)c(O[C@H]4CCOC4)cc32)n1]

A mixture of (S)-5-methyl-6-((tetrahydrofuran-3-yl)oxy)-1H-indazole (330 mg, 1.51 mmol), tert-butyl 4-(6-chloro-2-methoxypyrimidin-4-yl)piperazine-1-carboxylate (744 mg, 2.27 mmol) and Cs₂CO₃ (1.47 g, 4.53 mmol) in DMF (50 mL) was heated to 100° C. and stirred overnight. The mixture was diluted with H₂O (100 mL) and extracted with EtOAc (40 mL×3). The combined organic layer were washed with brine (50 mL), dried over Na₂SO₄, filtered and concentrated. The residue was purified by column chromatography on silica gel (PE:EtOAc=3:1) to give the title compound (180 mg, yield 23%) as a white solid.

¹H NMR (300 MHz, CDCl₃): δ 8.25 (s, 1H), 8.01 (s, 1H), 7.46 (s, 1H), 6.86 (s, 1H), 5.12-5.06 (m, 1H), 4.09-3.94 (m, 7H), 3.75-3.72 (m, 4H), 3.55-3.52 (m, 4H), 2.30-2.23 (m, 5H), 1.50 (s, 9H).

LC-MS: [mobile phase: from 95% water (0.02% NH₄OAc) and 5% CH₃CN to 5% water (0.02% NH₄OAc) and 95% CH₃CN in 2.5 min], Rt=2.37 min, MS Calcd.: 510, MS Found: 511 [M+H]⁺.

Description D252 tert-Butyl 3-((methylsulfonyl)oxy)azetidine-1-carboxylate (D252)

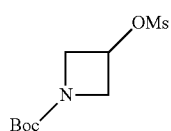

To a solution of tert-butyl 3-hydroxyazetidine-1-carboxylate (1.00 g, 6.01 mmol) and TEA (1.82 g, 18.0 mmol) in DCM (15 mL) was added MsCl (1.03 g, 9.02 mmol) at 0° C. under N₂. The solution was warmed to room temperature and stirred for another 1 hour. The mixture was diluted with H₂O (30 mL) and extracted with EtOAc (3×15 mL). The combined organic layers were washed with sat. NaHCO₃ aqueous solution, brine, dried over Na₂SO₄ and concentrated under vacuum to give the desired product (1.5 g, yield >100%) as a yellow oil.

¹H NMR (300 MHz, CDCl₃): δ 5.22-5.15 (m, 1H), 4.29-4.24 (m, 2H), 4.11-4.06 (m, 2H), 3.06 (s, 3H), 1.43 (s, 9H).

LC-MS: [mobile phase: from 90% water (0.02% NH₄OAc) and 10% CH₃CN to 5% water (0.02% NH₄OAc) and 95% CH₃CN in 4 min], Rt=2.103 min MS Calcd.: 251, MS Found: 196 [M−56+H]⁺.

Description D253 tert-Butyl 3-((5-methyl-1-(tetrahydro-2H-pyran-2-yl)-1H-indazol-6-yl)oxy)azetidine-1-carboxylate (D253)

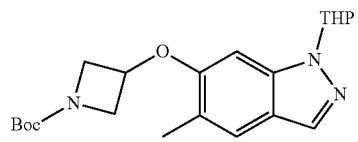

To a mixture of 5-methyl-1-(tetrahydro-2H-pyran-2-yl)-1H-indazol-6-ol (340 mg, 1.47 mmol) and Cs₂CO₃ (1.44 g, 4.41 mmol) was added tert-butyl 3-((methylsulfonyl)oxy) azetidine-1-carboxylate (552 mg, 2.20 mmol). The mixture was heated to 80° C. and stirred for 8 hrs. The mixture was diluted with H₂O (20 mL) and extracted with EtOAc (3×15 mL). The combined organic layers were washed with brine, dried over Na₂SO₄ and concentrated under vacuum. The residue was purified by silica column (PE:EtOAc=10:1) to give the desired product (0.52 g, yield 92%) as a yellow oil.

¹H NMR (400 MHz, CDCl₃): δ 7.85 (s, 1H), 7.45 (s, 1H), 6.53 (s, 1H), 5.60 (dd, J=8.8, 2.8 Hz, 1H), 5.02-4.97 (m, 1H), 4.41-4.36 (m, 2H), 4.10-4.05 (m, 2H), 4.01-3.97 (m, 1H), 3.75-3.69 (m, 1H), 2.57-2.48 (m, 1H), 2.30 (s, 3H), 2.18-2.13 (m, 1H), 2.09-2.04 (m, 1H), 1.79-1.66 (m, 3H), 1.47 (s, 9H).

LC-MS: [mobile phase: from 90% water (0.02% NH₄OAc) and 10% CH₃CN to 5% water (0.02% NH₄OAc) and 95% CH₃CN in 4 min], Rt=2.741 min MS Calcd.: 387, MS Found: 388 [M+H]⁺.

Description D254

5-Methyl-6-((1-methylazetidin-3-yl)oxy)-1H-indazole (D254)

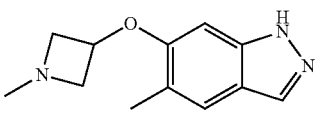 [SMILES: Cc1cc2cn[nH]c2cc1OC1CN(C)C1]

A solution of tert-butyl 3-((5-methyl-1-(tetrahydro-2H-pyran-2-yl)-1H-indazol-6-yl)oxy)azetidine-1-carboxylate (520 mg, 1.34 mmol) in sat. HCl/dioxane (10 mL) was heated to 45° C. and stirred for 1 hour. Then, the solution was concentrated under vacuum. The residue was dissolved in MeOH (10 mL). HCHO aqueous solution (37%, 4 mL) was added. The solution was stirred for 1 hour at room temperature. NaBH₃CN (520 mg, 8.22 mmol) was added and the mixture was stirred for 1 hour. The mixture was diluted with H$_2$O (20 mL) and extracted with DCM (3×15 mL). The combined organic layer was washed with brine, dried over Na$_2$SO$_4$ and concentrated under vacuum. The residue was dissolved in sat. NH$_3$/MeOH (10 mL) and the solution was stirred at room temperature for 12 hrs. The solution was evaporated under vacuum and the residue was purified by silica column (DCM:MeOH=10:1) to give the desired product (0.28 g, yield 95%) as a yellow oil.

$^1$H NMR (300 MHz, DMSO-d$_6$): δ 12.66 (br s, 1H), 7.84 (s, 1H), 7.48 (s, 1H), 6.64 (m, 1H), 4.86-4.82 (m, 1H), 3.86-3.81 (m, 2H), 3.11-3.07 (m, 2H), 2.35 (s, 3H), 2.22 (s, 3H).

LC-MS: [mobile phase: from 90% water (0.02% NH$_4$OAc) and 10% CH$_3$CN to 5% water (0.02% NH$_4$OAc) and 95% CH$_3$CN in 4 min], Rt=1.812 min MS Calcd.: 217, MS Found: 218 [M+H]$^+$.

Description D255

(Z/E)-Methyl 3-(3-amino-1-(4-methoxybenzyl)-1H-pyrazol-4-yl)acrylate (D255)

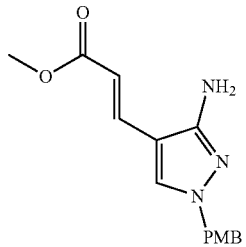

To a semi-solid mixture of 18-crown-6 (29.1 g, 108 mmol) in THF (200 mL) at −40° C. under N$_2$ was added methyl 2-(dimethoxyphosphoryl)acetate (3.90 g, 21.6 mmol) followed by a solution of KHMDS (21.6 mL, 21.6 mmol). A solution of 5-amino-1-(4-methoxy-benzyl)-1H-pyrazole-4-carbaldehyde (5.00 g, 21.6 mmol) in THF (100 mL) was added dropwise. Then the mixture was warmed to room temperature and stirred for 20 hrs. The mixture was partitioned between saturated aqueous NH$_4$Cl (100 mL) and EtOAc (150 mL). The aqueous phase was extracted a second time with EtOAc (150 mL). The organic layer was washed with brine, dried and concentrated, then purified by column (PE:EtOAc from 10:1 to 2:1) to give a yellow solid. The solid was slurried with EtOAc (30 mL) to give the title compound (2.9 g, yield: 47%) as a slight yellow solid.

LC-MS (5-95%) Rt=1.71 min; MS Calcd.: 287, MS Found: 288 [M+H]$^+$.

Description D256

2-(4-Methoxybenzyl)-2H-pyrazolo[3,4-b]pyridin-6-ol (D256)

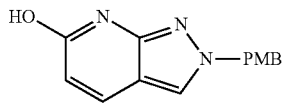

To a flask containing (Z/E)-methyl 3-(3-amino-1-(4-methoxybenzyl)-1H-pyrazol-4-yl)acrylate (2.9 g, 10.1 mmol) was added HCl (3 N, 300 mL). The mixture was heated to 100° C. for 2 hrs. The mixture was cooled and filtered to give the title compound (1.6 g, yield: 62%) as a slight yellow solid.

$^1$H NMR (300 MHz, DMSO-d$_6$): δ 8.11 (s, 1H), 7.70 (d, J=9.6 Hz, 1H), 7.25 (d, J=8.7 Hz, 2H), 6.90 (d, J=9.6 Hz, 1H), 6.05 (d, J=9.3 Hz, 1H), 5.26 (s, 2H), 3.71 (s, 3H).

LC-MS (mobile phase: 5-95% Acetonitrile), Rt=1.58 min; MS Calcd: 255, MS Found: 256 [M+H]$^+$.

Description D257

5-Bromo-2-(4-methoxy-benzyl)-2H-pyrazolo[3,4-b]pyridin-6-ol (D257)

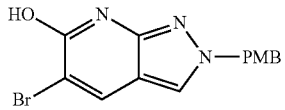

Br$_2$ (212 L, 4.10 mmol) was added to a suspension of 2-(4-methoxybenzyl)-2H-pyrazolo[3,4-b]pyridin-6-ol (2.1 g, 8.2 mmol) in AcOH (50 mL). The mixture was stirred for 30 mins. Then the suspension was added Br$_2$ (426 L, 8.20 mmol) and stirred for 30 mins. The mixture was filtered and the solid was washed with H$_2$O (30 mL), dried to give the title compound (1.32 g, yield 48%) as a yellow solid.

$^1$H NMR (400 MHz, DMSO-d$_6$): δ 12.22 (br s, 1H), 8.27 (s, 1H), 8.13 (s, 1H), 7.26 (d, J=8.8 Hz, 2H), 6.91 (d, J=8.8 Hz, 2H), 5.28 (s, 2H), 3.73 (s, 3H). LC-MS (5-95%) Rt=1.74 min; MS Calcd.: 333, MS Found: 334 [M+1]$^+$.

Description D258

5-Bromo-6-isopropoxy-2-(4-methoxy-benzyl)-2H-pyrazolo[3,4-b]pyridine (D258) and 5-bromo-7-isopropyl-2-(4-methoxybenzyl)-2H-pyrazolo[3,4-b]pyridin-6(7H)-one

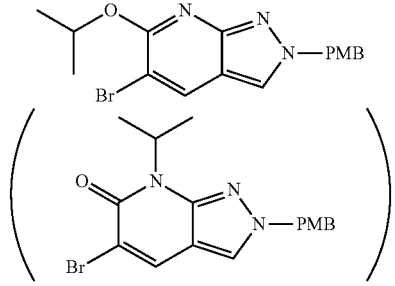

By-product

To a solution of 5-bromo-2-(4-methoxy-benzyl)-2H-pyrazolo[3,4-b]pyridin-6-ol (1.51 g, 4.50 mmol) in DMF (20 mL) under N$_2$ was added Cs$_2$CO$_3$ (2.95 g, 9.06 mmol) followed by 2-Iodopropane (1.15 g, 6.80 mmol). The mixture was heated at 60° C. and stirred for 2 hrs. The mixture was cooled to rt and partitioned with H$_2$O (100 mL) and EtOAc (100 mL). The organic layer was washed with brine (100 mL), dried and concentrated. The residue was purified by column using (PE:EtOAc=10:1) to give a mixture (1.45 g, yield 86%) as a brown oil which was used for next step directly.

LC-MS (5-95% CH$_3$CN): Peak 1, Rt=2.01 min; MS Calcd.: 375, MS Found: 376 (M+H)$^+$; Peak 2, Rt=2.20 min; MS Calcd.: 375, MS Found: 376 [M+H]$^+$.

Description D259

6-Isopropoxy-2-(4-methoxy-benzyl)-5-methyl-2H-pyrazolo[3,4-b]pyridine (D259)

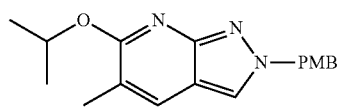

To a suspension of 5-bromo-6-isopropoxy-2-(4-methoxybenzyl)-2H-pyrazolo[3,4-b]pyridine and 5-bromo-7-isopropyl-2-(4-methoxybenzyl)-2H-pyrazolo[3,4-b]pyridin-6(7H)-one (1.27 g, 3.39 mmol), methyl boronic acid (1.02 g, 16.7 mmol) and K$_2$CO$_3$ (1.40 g, 10.2 mmol) in 1,4-dioxane (50 mL) was added Pd(PPh$_3$)$_4$ (0.42 g, 0.33 mmol) quickly at room temperature under N$_2$ atmosphere. Then the mixture solution was heated to 100° C. and stirred for 8 hrs under N$_2$ atmosphere. The mixture was cooled to room temperature, concentrated and purified by column on silica gel eluting with PE/EtOAc (10/1) to afford crude product as yellow oil. The crude was further purified by C18 to give the title compound (254 mg, yield 24%) as brown oil.

$^1$H NMR (400 MHz, CDCl$_3$): δ 7.55 (s, 1H), 7.52 (s, 1H), 7.28 (d, J=8.4 Hz, 2H), 6.87 (d, J=8.4 Hz, 2H), 5.59-5.53 (m, 1H), 5.40 (s, 2H), 3.79 (s, 3H), 2.19 (s, 3H), 1.39 (d, J=6.0 Hz, 6H).

LC-MS: (5-95% CH$_3$CN) Rt=2.20 min; MS Calcd.: 311, MS Found: 312 [M+H]$^+$.

Description D260

6-Isopropoxy-5-methyl-2H-pyrazolo[3,4-b]pyridine (D260)

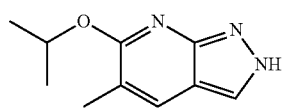

The solution of 6-isopropoxy-2-(4-methoxy-benzyl)-5-methyl-2H-pyrazolo[3,4-b]pyridine (101 mg, 0.320 mmol) in TFA (5 mL) was stirred at 60° C. for 48 hrs. The mixture was cooled and concentrated. The residue was diluted with H$_2$O (5 mL) and EtOAc (5 mL). The aqueous layer was extracted with EtOAc (5 mL). Then combined organic layers were concentrated. The residue was purified by prep-TLC (PE:EtOAc=10:1) to give the title compound (43 mg, yield: 69%, purity >70%) as a yellow solid.

LC-MS: (5-95% CH$_3$CN) Rt=1.58 min; MS Calcd.: 191, MS Found: 192 [M+H]$^+$.

Description D261

1-(4-Iodopyridin-2-yl)-4-methylpiperazine (D261)

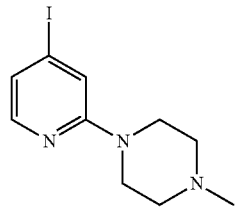

To a solution of 2-fluoro-4-iodopyridine (2.00 g, 8.97 mmol) in DMSO (8 mL) was added 1-methylpiperazine (1.34 g, 13.4 mmol) and K$_2$CO$_3$ (2.47 g, 17.9 mmol). The mixture was heated to 60° C. and stirred overnight. The mixture was cooled to rt and poured into water (50 mL). EtOAc (2×50 mL) was added to extract the desired. The combined organic layers were washed with brine (3×20 mL), dried over Na$_2$SO$_4$ and concentrated. The residue was triturated with petroleum ether (20 mL) to give the title compound (1.20 g, yield 44%) as a white solid.

$^1$H NMR (300 MHz, CDCl$_3$): δ 7.82 (d, J=5.4 Hz, 1H), 7.01 (s, 1H), 6.94 (d, J=5.4 Hz, 1H), 3.55-3.52 (m, 4H), 2.51-2.47 (m, 4H), 2.33 (s, 3H).

Description D262

2,4,6-Trichloropyrimidine-5-carbaldehyde (D262)

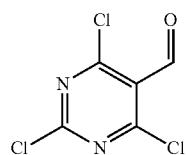 [SMILES: O=Cc1c(Cl)nc(Cl)nc1Cl]

A mixture of pyrimidine-2,4,6-triol (20.0 g, 156 mmol) in DMF (20 mL) and POCl$_3$ (200 mL) was refluxed overnight. The mixture was concentrated. The residue was poured into ice-water (1 L) and filtered. The solid was collected and purified by column chromatography (petroleum ether:ethyl acetate=10:1) to give the title compound (12.0 g, yield 36%) as a yellow solid.

$^1$H NMR (CDCl$_3$, 300 MHz): δ 10.41 (s, 1H).

Description D263

4,6-Dichloro-1H-pyrazolo[3,4-d]pyrimidine (D263)

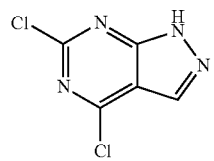 [SMILES: Clc1nc(Cl)c2cn[nH]c2n1]

To a solution of 2,4,6-trichloropyrimidine-5-carbaldehyde (3.50 g, 16.6 mmol) in THF (50 mL) was added N$_2$H$_4$.H$_2$O (830 mg, 16.6 mmol) slowly at −10° C. Then, Et₃N (2.51 g, 24.9 mmol) was added to the mixture at −10° C. The mixture was stirred at −10° C. for 30 min. The mixture was concentrated. The residue was purified by column chromatography (petroleum ether:ethyl acetate=10:1) to give the title compound (1.25 g, yield 40%) as a yellow solid.

¹H NMR (300 MHz, CDCl₃): δ 11.61 (br s, 1H), 8.25 (s, 1H).

LCMS [mobile phase: 5-95% CH₃CN]: Rt=2.005 min; MS Calcd: 188; MS Found: 189 [M+H]⁺.

Description D264

4,6-Dichloro-1-(tetrahydro-2H-pyran-2-yl)-1H-pyrazolo[3,4-d]pyrimidine (D264)

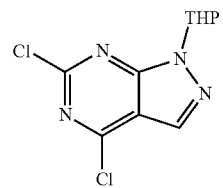

To a solution of 4,6-dichloro-1H-pyrazolo[3,4-d]pyrimidine (2.60 g, 13.7 mmol) in DCM (100 mL) was added DHP (2.31 g, 27.4 mmol) and TsOH (0.471 g, 2.70 mmol). The reaction mixture was stirred at rt for 1 h. The reaction mixture was poured into sat. NaHCO₃ solution (30 mL). The organic layer was separated and the aqueous was extracted with DCM (2×100 mL). The combined organic layers were washed with brine (50 mL), dried over Na₂SO₄ and concentrated. The crude was purified by column chromatography (petroleum ether:EtOAc=20:1) to give the title compound (3.1 g, yield 83%) as a white solid.

¹H NMR (400 MHz, CDCl₃): δ 8.19 (s, 1H), 6.00 (dd, J=10.8, 2.4 Hz, 1H), 4.13-4.10 (m, 1H), 3.84-3.77 (m, 1H), 2.61-2.51 (m, 1H), 2.16-2.13 (m, 1H), 1.97-1.93 (m, 1H), 1.82-1.75 (m, 2H), 1.64-1.57 (m, 1H).

Description D265

6-Chloro-1-(tetrahydro-2H-pyran-2-yl)-1H-pyrazolo[3,4-d]pyrimidine (D265)

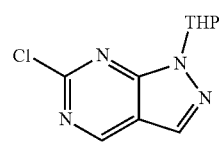

To a solution of 4,6-dichloro-1-(tetrahydro-2H-pyran-2-yl)-1H-pyrazolo[3,4-d]pyrimidine (3.10 g, 11.3 mmol) in dioxane (120 mL) was added sodium formate hydrate (3.50 g, 33.9 mmol), H₂O (12 mL) and Pd(dppf)Cl₂ (1.83 g, 2.06 mmol). The mixture was heated to 80° C. for 5 hrs under N₂ atmosphere. The reaction mixture was cooled to rt and concentrated. The residue was purified by column chromatography (petroleum ether:EtOAc=5:1) to give the title compound (1.07 g, yield 40%) as a white solid.

¹H NMR (400 MHz, CDCl₃): δ 9.04 (s, 1H), 8.20 (s, 1H), 6.05 (dd, J=10.4, 2.4 Hz, 1H), 4.14-4.10 (m, 1H), 3.83-3.79 (m, 1H), 2.63-2.54 (m, 1H), 2.16-2.14 (m, 1H), 1.97-1.94 (m, 1H), 1.82-1.76 (m, 2H), 1.65-1.61 (m, 1H).

LCMS [mobile phase: 5-95% CH₃CN] Rt=2.22 min; MS Calcd: 238; MS Found: 239 [M+H]⁺.

Description D266

6-Isopropoxy-1-(tetrahydro-2H-pyran-2-yl)-1H-pyrazolo[3,4-d]pyrimidine (D266)

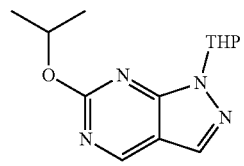

To a mixture of NaH (60% in oil) (302 mg, 7.75 mmol) in THF (10 mL) was added propan-2-ol (465 mg, 7.75 mmol) and stirred at 0° C. for 10 min. Then a solution of 6-chloro-1-(tetrahydro-2H-pyran-2-yl)-1H-pyrazolo[3,4-d]pyrimidine (370 mg, 1.55 mmol) was added. The resulting mixture was stirred at rt for 1 h. To the mixture was added water (5 mL), then extracted with ethyl acetate (3×10 mL). The combined organic layers were washed with brine (10 mL), dried over Na₂SO₄, and concentrated. The residue was purified by prep. TLC (petroleum ether:EtOAc=3:1) to give the title compound (200 mg, yield 49%) as a yellow oil.

¹H NMR (300 MHz, CDCl₃): δ 8.92 (s, 1H), 8.05 (s, 1H), 5.96 (dd, J=10.5, 2.1 Hz, 1H), 5.47-5.40 (m, 1H), 4.16-4.11 (m, 1H), 3.84-3.75 (m, 1H), 2.65-2.54 (m, 1H), 2.17-2.11 (m, 1H), 1.98-1.92 (m, 1H), 1.83-1.74 (m, 2H), 1.65-1.61 (m, 1H), 1.46 (t, J=6.0 Hz, 6H).

LCMS [mobile phase: 5-95% CH₃CN] RT=2.36 min; MS Calcd: 263; MS Found: 264[M+H]⁺.

Description D267

6-Isopropoxy-1H-pyrazolo[3,4-d]pyrimidine (D267)

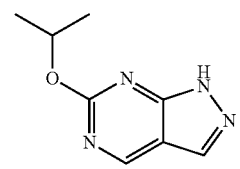

To a solution of 6-isopropoxy-1-(tetrahydro-2H-pyran-2-yl)-1H-pyrazolo[3,4-d]pyrimidine (200 mg, 0.760 mmol) in dioxane (3 mL) was added sat. HCl-dioxane (2 mL). The mixture was stirred at rt for 2 hrs. The mixture was poured into sat. NaHCO₃ solution (10 mL). Ethyl acetate (3×10 mL) was added to extract the desired. The combined organic layers were washed with brine (10 mL), dried over Na₂SO₄, and concentrated to give the title compound (130 mg, yield 96%) as a yellow solid.

LCMS [mobile phase: 5-95% CH₃CN] RT=1.84 min; MS Calcd: 178; MS Found: 179[M+H]⁺.

Description D268 tert-Butyl 4-(1-acetyl-5-methyl-1H-indazol-6-yl)piperazine-1-carboxylate (D268)

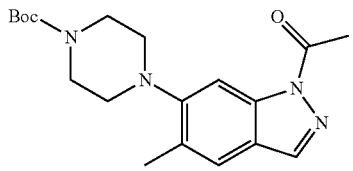 [SMILES: CC(=O)n1ncc2cc(C)c(N3CCN(C(=O)OC(C)(C)C)CC3)cc21]

To a solution of 1-(6-bromo-5-methyl-1H-indazol-1-yl)ethanone (1 g, 3.95 mmol) in toluene (30 mL) was added Pd$_2$(dba)$_3$ (0.362 g, 0.395 mmol), BINAP (0.492 g, 0.790 mmol), tert-butyl piperazine-1-carboxylate (1.472 g, 7.90 mmol) and Cs$_2$CO$_3$ (2.57 g, 7.90 mmol). The mixture was stirred at 120° C. under nitrogen atmosphere for 3 hrs. The mixture was cooled to room temperature. EtOAc (100 mL) and water (50 mL) were added. The layers were separated and the aqueous layer was extracted with EtOAc (30 mL). The combined layers were washed with saturated aqueous sodium chloride, dried over anhydrous Na$_2$SO$_4$ and then concentrated under the reduced pressure. The residue was then purified by normal phase chromatography (ISCO, 40 g column, PE:EtOAc=100:0→40:60) to afford tert-butyl 4-(1-acetyl-5-methyl-1H-indazol-6-yl)piperazine-1-carboxylate (600 mg, 1.674 mmol, 42.4% yield) as a pale yellow solid.

LCMS: (mobile phase: 5-95% Acetonitrile), Rt=4.11 min in 5 min; MS Calcd: 358; MS Found: 359 [M+1]$^+$.

$^1$H NMR (DMSO-d$_6$) δ: 8.29 (s, 1H), 7.88 (s, 1H), 7.67 (s, 1H), 3.51 (br. s., 4H), 2.87 (t, J=4.6 Hz, 4H), 2.68 (s, 3H), 2.37 (s, 3H), 1.43 (s, 9H)

Description D269 tert-Butyl 4-(5-methyl-1H-indazol-6-yl)piperazine-1-carboxylate (D269)

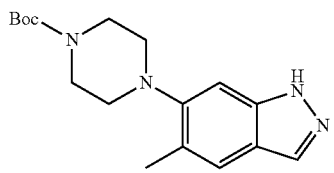

tert-Butyl 4-(1-acetyl-5-methyl-1H-indazol-6-yl)piperazine-1-carboxylate (200 mg, 0.558 mmol) was dissolved in THF (10 mL)/water (1.00 mL). Sodium hydroxide (1.116 mL, 1.116 mmol) was added and the reaction was stirred at 25° C. for 3 hrs. EtOAc (50 mL) and water (30 mL) were added to the reaction mixture and the layers were separated. The organic layer was collected, dried over anhydrous Na$_2$SO$_4$ and concentrated. The residue tert-butyl 4-(5-methyl-1H-indazol-6-yl)piperazine-1-carboxylate was used in next step without further purification.

LCMS: (mobile phase: 5-95% Acetonitrile), Rt=3.49 min in 5 min; MS Calcd: 316; MS Found: 317 [M+1]$^+$.

Description D270 tert-Butyl 4-(5-methyl-1-(6-morpholinopyrimidin-4-yl)-1H-indazol-6-yl)piperazine-1-carboxylate (D270)

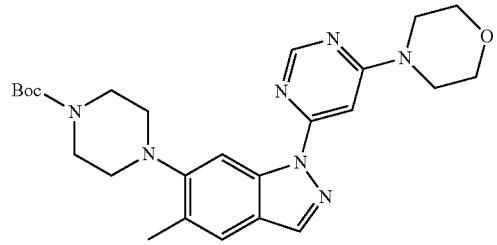 [SMILES: Cc1cc2cnn(-c3cc(N4CCOCC4)ncn3)c2cc1N1CCN(C(=O)OC(C)(C)C)CC1]

To a round bottle charged with tert-butyl 4-(5-methyl-1H-indazol-6-yl)piperazine-1-carboxylate (obtained in above step) were added copper(I) iodide (42.5 mg, 0.223 mmol), 4-(6-iodopyrimidin-4-yl)morpholine (162 mg, 0.558 mmol) and potassium phosphate trihydrate (371 mg, 1.395 mmol). Subsequently, N1,N2-dimethylcyclohexane-1,2-diamine (0.141 mL, 0.893 mmol) and toluene (10.00 mL) were added under the nitrogen atmosphere. The mixture was then stirred at 120° C. for 2 days under nitrogen atmosphere. The mixture was cooled to room temperature, EtOAc (40 mL) and water (30 mL) were added and the layers were separated. The aqueous layer was extracted by EtOAc (30 mL). The combined organic layers was washed with saturated aqueous NaCl (50 mL×2), dried over anhydrous Na$_2$SO$_4$ and then concentrated under the reduced pressure. The residue was purified by normal phase chromatography (ISCO, 24 g column, PE: (EtOAc/EtOH (3:1, v:v))=100:0→60:40) to afford tert-butyl 4-(5-methyl-1-(6-morpholinopyrimidin-4-yl)-1H-indazol-6-yl)piperazine-1-carboxylate (200 mg, 0.417 mmol, 74.7% yield) as a white solid.

LCMS: (mobile phase: 5-95% Acetonitrile), Rt=4.41 min in 5 min; MS Calcd: 479; MS Found: 480 [M+1]$^+$.

$^1$H NMR (DMSO-d$_6$): 8.60 (s, 1H), 8.41 (s, 1H), 8.32 (s, 1H), 7.66 (s, 1H), 7.16 (s, 1H), 3.63-3.76 (m, 8H), 3.53 (br. s., 4H), 2.90 (t, J=4.4 Hz, 4H), 2.39 (s, 3H), 1.42-1.51 (m, 9H).

Description D271

5-Methyl-6-(4-methylpiperazin-1-yl)-1H-indazole (D271)

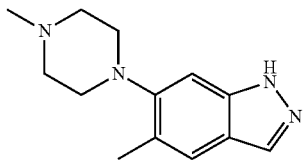 [SMILES: Cc1cc2cn[nH]c2cc1N1CCN(C)CC1]

Step 1:

6-Bromo-5-methyl-1-(tetrahydro-2H-pyran-2-yl)-1H-indazole (260 mg, 0.88 mmol), Pd$_2$(dba)$_3$ (161 mg, 0.17 mmol), BINAP (219 mg, 0.35 mmol) and Cs$_2$CO$_3$ (574 mg, 1.76 mmol) were placed at a microwave tube. PhMe (5 mL) was added followed by the addition of 1-methylpiperazine (500 μL, 4.49 mmol). The tube was sealed with nitrogen ad heated at 120° C. for 1 hr under the microwave irradiation. The tube was cooled to room temperature, EtOAc (30 mL) was added to the mixture and the organic layer was washed with water (50 mL×2), then dried over anhydrous Na₂SO₄ and concentrated. The crude product was used in next step without further purification.

LCMS: (mobile phase: 5-95% Acetonitrile), Rt=2.27 min in 5 min; MS Calcd: 314; MS Found: 315 [M+1]⁺.

Step 2:

The crude product (obtained from step 1) was dissolved in MeOH (10 mL), HCl (12N, 1 mL) was added and the mixture was stirred at 40° C. for 1 hr. The solvent was then removed and the residue was used in next step without further purification.

LCMS: (mobile phase: 5-95% Acetonitrile), Rt=1.75 min in 5 min; MS Calcd: 230; MS Found: 231 [M+1]⁺.

Description D272

4-(6-(6-Bromo-5-methyl-1H-indazol-1-yl)-2-ethylpyrimidin-4-yl)morpholine (D272)

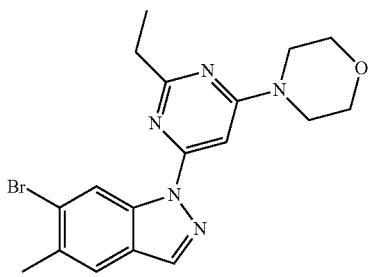 [SMILES: CCc1nc(N2CCOCC2)cc(-n2ncc3cc(C)c(Br)cc32)n1]

To a solution of 1-(6-bromo-5-methyl-1H-indazol-1-yl) ethanone (300 mg, 1.185 mmol) in DMF (20 mL) was added potassium carbonate (164 mg, 1.185 mmol) and 4-(6-chloro-2-ethylpyrimidin-4-yl)morpholine (270 mg, 1.185 mmol), then the reaction mixture was stirred at 120° C. under microwave irradiation for 2 hrs. Water (50 mL) and EtOAc (100 mL) were added to the reaction mixture. The layers were separated and the aqueous layer was extracted by EtOAc (30 mL). The combined organic layers was washed with saturated aqueous NaCl (50 mL×2 times), dried over anhydrous Na₂SO₄ and then concentrated under the reduced pressure. The residue was purified by normal phase chromatography (ISCO, 40 g column, PE:EtOAc/EtOH=100: 0→50:50) to afford 4-(6-(6-bromo-5-methyl-1H-indazol-1-yl)-2-ethylpyrimidin-4-yl)morpholine (260 mg, 0.646 mmol, 54.5% yield).

LCMS: (mobile phase: 5-95% Acetonitrile), Rt=4.47 min in 5 min; MS Calcd: 401; MS Found: 402 [M+1]⁺.

¹H NMR (DMSO-d₆) δ: 9.14 (s, 1H), 8.43 (s, 1H), 7.87 (s, 1H), 7.00 (s, 1H), 3.68 (d, J=7.1 Hz, 11H), 2.82 (q, J=7.6 Hz, 2H), 2.48 (s, 3H), 1.36 (t, J=7.5 Hz, 3H).

Description D273

6-Bromo-1-(6-chloro-2-methoxypyrimidin-4-yl)-5-methyl-1H-indazole (D273)

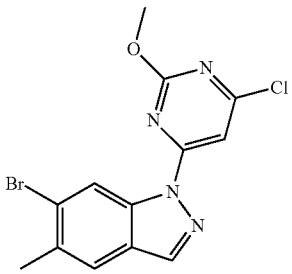 [SMILES: COc1nc(Cl)cc(-n2ncc3cc(C)c(Br)cc32)n1]

6-Bromo-5-methyl-1H-indazole (50 mg, 0.237 mmol) and 4,6-dichloro-2-methoxypyrimidine (127 mg, 0.711 mmol) was dissolved in DMF (3 mL), Cs₂CO₃ (154 mg, 0.474 mmol) was added and the mixture was stirred at 120° C. for 1.5 h under microwave irradiation. Water (20 mL) and EtOAc (50 mL) were added to the reaction mixture. The layers were separated and the aqueous layer was extracted by EtOAc (30 mL). The combined organic layers was washed with saturated aqueous NaCl (50 mL×2 times), dried over anhydrous Na₂SO₄ and then concentrated under the reduced pressure. The residue was purified by normal phase chromatography (ISCO, 24 g column, PE:EtOAc=100: 0→80:20) to afford 6-bromo-1-(6-chloro-2-methoxypyrimidin-4-yl)-5-methyl-1H-indazole (48 mg, 0.136 mmol, 57.3% yield) as a white solid.

LCMS: (mobile phase: 5-95% acetonitrile), Rt=4.47 min in 5 min; MS Calcd: 352; MS Found: 353 [M+1]⁺.

¹H NMR (DMSO-d₆): 8.92 (s, 1H), 8.59 (s, 1H), 7.93 (s, 1H), 7.60 (s, 1H), 4.08 (s, 3H) (Note: a CH₃ peak is masked by the solvent DMSO)

Description D274 tert-Butyl 4-(6-(6-bromo-5-methyl-1H-indazol-1-yl)-2-methoxypyrimidin-4-yl) piperazine-1-carboxylate (D274)

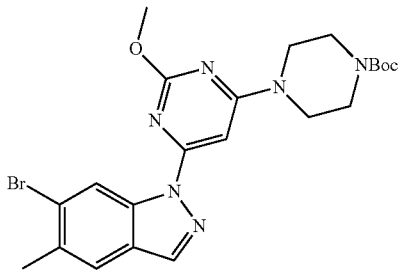 [SMILES: COc1nc(N2CCN(C(=O)OC(C)(C)C)CC2)cc(-n2ncc3cc(C)c(Br)cc32)n1]

To a solution of 6-bromo-1-(6-chloro-2-methoxypyrimidin-4-yl)-5-methyl-1H-indazole (40 mg, 0.113 mmol) in DMF (3 mL) was added tert-butyl piperazine-1-carboxylate (31.6 mg, 0.170 mmol) and K₂CO₃ (31.3 mg, 0.226 mmol). The resulting mixture was stirred at 120° C. for 1 hr under microwave irradiation. Water (10 mL) and EtOAc (30 mL) were added to the reaction mixture. The layers were separated and the aqueous layer was extracted by EtOAc (20 mL). The combined organic layers was washed with saturated aqueous NaCl (50 mL×2 times), dried over anhydrous Na$_2$SO$_4$ and then concentrated under the reduced pressure. The residue was used in next step without further purification.

LCMS: (mobile phase: 5-95% Acetonitrile), Rt=4.93 min in 5 min; MS Calcd: 502; MS Found: 503 [M+1]$^+$.

$^1$H NMR (DMSO-d$_6$): 9.02 (s, 1H), 8.45 (s, 1H), 7.88 (s, 1H), 6.86 (s, 1H), 3.97 (s, 3H), 3.70 (br. s., 4H), 3.45 (br. s., 4H), 1.44 (s, 9H) (Note: a CH$_3$ peak is masked by the solvent DMSO).

Description D275

6-Bromo-1-(6-chloropyrimidin-4-yl)-5-methyl-1H-indazole (D275)

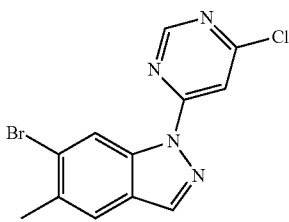 [SMILES: Cc1cc2cnn(-c3cc(Cl)ncn3)c2cc1Br]

6-Bromo-5-methyl-1H-indazole (440 mg, 2.085 mmol) and 4,6-dichloropyrimidine (932 mg, 6.25 mmol) was dissolved in DMF (3 mL), Cs$_2$CO$_3$ (1358 mg, 4.17 mmol) was added and the mixture was stirred at 120° C. for 1.5 h under microwave irradiation. Water (50 mL) and EtOAc (100 mL) were added to the reaction mixture. The layers were separated and the aqueous layer was extracted by EtOAc (30 mL). The combined organic layers were washed with saturated aqueous NaCl (50 mL×2 times), dried over anhydrous Na$_2$SO$_4$ and then concentrated under the reduced pressure. The residue was purified by normal phase chromatography (ISCO, 80 g column, PE:EtOAc=100:0→80:20) to afford 6-bromo-1-(6-chloropyrimidin-4-yl)-5-methyl-1H-indazole (400 mg, 1.236 mmol, 59.3% yield) as a white solid.

LCMS: (mobile phase: 5-95% acetonitrile), Rt=4.36 min in 5 min; MS Calcd: 322; MS Found: 323 (M+1)$^+$.

$^1$H NMR (DMSO-d$_6$) δ: 9.05 (s, 1H), 8.98 (s, 1H), 8.60 (s, 1H), 7.98 (s, 1H), 7.87-7.94 (m, 1H), 2.50 (s, 3H)

Description D276 tert-Butyl 4-(6-(5-methyl-6-morpholino-1H-indazol-1-yl)pyrimidin-4-yl)piperazine-1-carboxylate (D276)

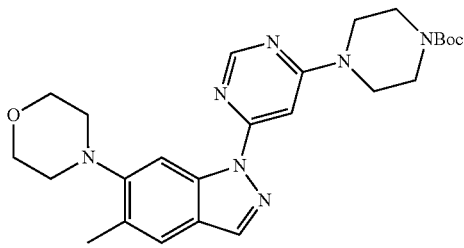 [SMILES: Cc1cc2cnn(-c3cc(N4CCN(C(=O)OC(C)(C)C)CC4)ncn3)c2cc1N1CCOCC1]

Step 1:

6-Bromo-1-(6-chloropyrimidin-4-yl)-5-methyl-1H-indazole (400 mg, 1.236 mmol) and K$_2$CO$_3$ (342 mg, 2.472 mmol) was dissolved in DMF (10 mL), tert-butyl piperazine-1-carboxylate (230 mg, 1.236 mmol) was added and the mixture was stirred at 120° C. for 1 hr under microwave irradiation. Water (30 mL) and EtOAc (50 mL) were added to the reaction mixture. The layers were separated and the aqueous layer was extracted by EtOAc (30 mL). The combined organic layers was washed with saturated aqueous NaCl (50 mL×2 times), dried over anhydrous Na$_2$SO$_4$ and then concentrated. The crude product was used in next step without further purification.

LCMS: (mobile phase: 5-95% Acetonitrile), Rt=4.80 min in 5 min; MS Calcd: 472; MS Found: 473 [M+1]$^+$.

Step 2:

Pd$_2$(dba)$_3$ (56.6 mg, 0.062 mmol), xantphos (71.5 mg, 0.124 mmol), morpholine (1.077 mL, 12.36 mmol) and Cs$_2$CO$_3$ (806 mg, 2.472 mmol) were added to a solution of crude product (obtained in step 1) in toluene (20.00 mL) and then the mixture was stirred at 120° C. under nitrogen atmosphere for 3 hrs. The mixture was cooled to room temperature. EtOAc (100 mL) and water (50 mL) were added. The layers were separated and the aqueous layer was extracted with EtOAc (30 mL). The combined layers were washed with saturated aqueous sodium chloride, dried over anhydrous Na$_2$SO$_4$ and then concentrated under the reduced pressure. The residue was then purified by normal phase chromatography (ISCO, 40 g column, PE:EtOAc=100:0 to 40:60) to afford tert-butyl 4-(2-methoxy-6-(5-methyl-6-morpholino-1H-indazol-1-yl)pyrimidin-4-yl)piperazine-1-carboxylate as a pale yellow solid.

LCMS: (mobile phase: 5-95% Acetonitrile), Rt=4.29 min in 5 min; MS Calcd: 479; MS Found: 480 [M+1]$^+$.

Description D277

6-Bromo-1-((2-(trimethylsilyl)ethoxy)methyl)-1H-indazole (D277)

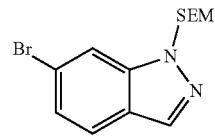 [SMILES: C[Si](C)(C)CCOCn1ncc2ccc(Br)cc21]

To a solution of 6-bromo-1H-indazole (2.00 g, 10.2 mmol) in THF (30 mL) was added NaH (0.820 g, 20.4 mmol) at 0° C. The mixture was stirred at rt for 30 min. SEM-Cl (2.55 g, 15.3 mmol) was added to the mixture at 0° C. The mixture was stirred at room temperature for another 1 h. The mixture was diluted with H$_2$O (50 mL) and extracted with EtOAc (3×20 mL). The combined organic layers were washed with brine, dried over Na$_2$SO$_4$ and concentrated under vacuum. The residue was purified by silica column (PE:EtOAc=60:1) to give the desired product (2.62 g, yield 79%) as a red oil.

$^1$H NMR (300 MHz, CDCl$_3$): δ 7.97 (s, 1H), 7.77 (s, 1H), 7.60 (d, J=8.7 Hz, 1H), 7.30 (dd, J=8.7, 1.5 Hz, 1H), 5.69 (s, 2H), 3.53 (t, J=8.1 Hz, 2H), 0.89 (t, J=8.1 Hz, 2H), −0.06 (s, 9H).

LC-MS: [mobile phase: from 90% water (0.02% NH$_4$OAc) and 10% CH$_3$CN to 5% water (0.02% NH$_4$OAc) and 95% CH$_3$CN in 4 min], Rt=2.981 min MS Calcd.: 326, MS Found: 327 [M+H]$^+$.

Description D278 tert-Butyl 4-(1-((2-(trimethylsilyl)ethoxy)methyl)-1H-indazol-6-yl)piperazine-1-carboxylate (D278)

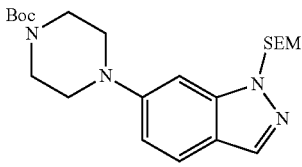 [SMILES: C[Si](C)(C)CCOCn1ncc2ccc(N3CCNCC3)cc21]

To a mixture of 6-bromo-1-((2-(trimethylsilyl)ethoxy)methyl)-1H-indazole (1.00 g, 3.07 mmol), tert-butyl piperazine-1-carboxylate (0.860 g, 4.61 mmol), $Cs_2CO_3$ (2.00 g, 6.14 mmol) and BINAP (0.770 g, 1.23 mmol) in toluene (20 mL) was added $Pd_2(dba)_3$ (0.57 g, 0.62 mmol).

The mixture was heated to 105° C. and stirred overnight under $N_2$. The mixture was filtered and the filtrate was directly concentrated in vacuum. The residue was purified by silica column (PE:EtOAc=6:1) to give the desired product (330 g, yield 24%) as a yellow oil.

LC-MS: [mobile phase: from 90% water (0.02% $NH_4OAc$) and 10% $CH_3CN$ to 5% water (0.02% $NH_4OAc$) and 95% $CH_3CN$ in 4 min], Rt=2.939 min MS Calcd.: 432, MS Found: 433 $[M+H]^+$.

Description D279 tert-Butyl 4-(1H-indazol-6-yl)piperazine-1-carboxylate (D279)

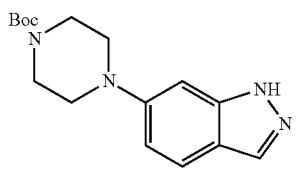 [SMILES: c1cc2cn[nH]c2cc1N1CCNCC1]

To a solution of tert-butyl 4-(1-((2-(trimethylsilyl)ethoxy)methyl)-1H-indazol-6-yl)piperazine-1-carboxylate (410 mg, 0.950 mmol) in methanol (5 mL) was added conc. HCl (5 mL). The solution was stirred at rt for 1 h. The solution was concentrated in vacuum. The residue was dissolved in methanol (4 mL). KOH (161 mg, 2.88 mmol) in $H_2O$ (1 mL) and $Boc_2O$ (314 mg, 1.44 mmol) were added to the solution. The mixture was stirred for 2 hrs. The mixture was diluted with $H_2O$ (20 mL) and extracted with DCM/MeOH (20/1, 3×20 mL). The combined organic layers were washed with brine, dried over $Na_2SO_4$ and concentrated in vacuum. The residue was purified by C18 ($CH_3CN/H_2O$ from 5% to 80%) to give the desired product (110 mg, yield 38%) as a yellow solid.

$^1$H NMR (300 MHz, $CDCl_3$): δ 7.93 (s, 1H), 7.61 (d, J=8.7 Hz, 1H), 6.93 (dd, J=9.0, 1.8 Hz, 1H), 6.82 (s, 1H), 3.63-3.60 (m, 4H), 3.20-3.17 (m, 4H), 1.49 (s, 9H).

LC-MS: [mobile phase: from 90% water (0.02% $NH_4OAc$) and 10% $CH_3CN$ to 5% water (0.02% $NH_4OAc$) and 95% $CH_3CN$ in 4 min], Rt=2.218 min MS Calcd.: 302, MS Found: 303 $[M+H]^+$.

Description D280 tert-Butyl 4-(1-(2-methoxy-6-morpholinopyrimidin-4-yl)-1H-indazol-6-yl)piperazine-1-carboxylate (D280)

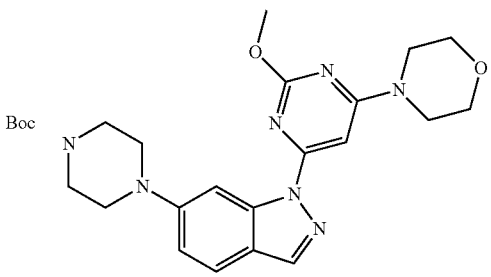 [SMILES: COc1nc(N2CCOCC2)cc(-n2ncc3ccc(N4CCNCC4)cc32)n1 ; "Boc"]

To a mixture of tert-butyl 4-(1H-indazol-6-yl)piperazine-1-carboxylate (110 mg, 0.364 mmol) and $Cs_2CO_3$ (234 mg, 0.720 mmol) in DMF (3 mL) was added 4-(6-chloro-2-methoxypyrimidin-4-yl)morpholine (108 mg, 0.470 mmol). The mixture was heated to 100° C. and stirred overnight. The mixture was diluted with $H_2O$ (20 mL) and extracted with EtOAc (3×15 mL). The combined organic layers were washed with brine, dried over $Na_2SO_4$ and concentrated under vacuum. The residue was purified by prep. TLC (PE:EtOAc=1:1) and further purified by prep. HPLC to give the desired product (60 mg, yield 33%) as a yellow solid.

$^1$H NMR (300 MHz, $CDCl_3$): δ 8.34 (s, 1H), 8.03 (s, 1H), 7.59 (d, J=9.0 Hz, 1H), 7.00 (dd, J=9.0, 1.8 Hz, 1H), 6.84 (s, 1H), 4.09 (s, 3H), 3.81-3.71 (m, 8H), 3.64-3.60 (m, 4H), 3.29-3.26 (m, 4H), 1.50 (s, 9H).

Description D281

6-Bromo-1-(2-methoxy-6-(4-methylpiperazin-1-yl)pyrimidin-4-yl)-5-methyl-1H-indazole (D281)

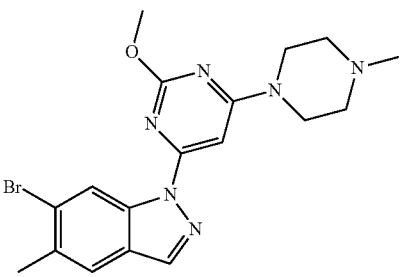 [SMILES: COc1nc(N2CCN(C)CC2)cc(-n2ncc3cc(C)c(Br)cc32)n1]

6-Bromo-1-(6-chloro-2-methoxypyrimidin-4-yl)-5-methyl-1H-indazole (200 mg, 0.566 mmol) was dissolved in DMF (5 mL), 1-methylpiperazine (113 mg, 1.131 mmol) and $Cs_2CO_3$ (369 mg, 1.131 mmol) were added and the mixture was stirred at 120° C. for 30 min under microwave irradiation. Water (30 mL) and EtOAc (50 mL) were added to the reaction mixture. The layers were separated and the aqueous layer was extracted by EtOAc (30 mL). The combined organic layers was washed with saturated aqueous NaCl (50 mL×2 times), dried over anhydrous $Na_2SO_4$ and then concentrated. The crude product was used in next step without further purification.

LCMS: (mobile phase: 5-95% acetonitrile), Rt=3.07 min in 5 min; MS Calcd: 416; MS Found: 416.9 [M+1]⁺.

Description D282

4,6-Diiodo-2-methoxypyrimidine (D282)

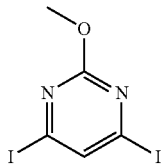

To a solution of NaI (2.20 g, 14.6 mmol) in HI (55%, 15 mL) was added 4,6-dichloro-2-methoxypyrimidine (2.00 g, 11.2 mmol). The mixture was heated to 40° C. and stirred for 10 hours. The reaction mixture was cooled to room temperature and poured into ice water (50 mL). The solid collected by filtrated and purified by column chromatography (PE:EtOAc=10:1) to give the title compound (1.2 g, yield 30%) as a white solid.

¹H NMR (400 MHz, CDCl3): δ 7.85 (s, 1H), 4.00 (s, 3H).

LC-MS (mobile phase: from 95% water (0.02% NH₄Ac) and 5% CH₃CN to 5% water (0.02% NH₄Ac) and 95% CH₃CN in 2.5 min, Rt=1.66 min; MS Calcd.: 362; MS Found: 363 [M+H]⁺.

Description D283

4-Iodo-2-methoxy-6-(piperidin-1-yl)pyrimidine (D283)

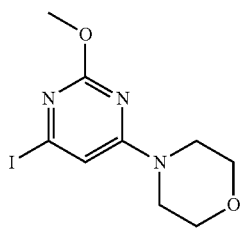

To a suspension of 4,6-diiodo-2-methoxypyrimidine (1.40 g, 3.90 mmol) in EtOH (30 mL) was added morpholine (714 mg, 8.2 mmol) at room temperature. The mixture was stirred for 4 hours. The mixture was concentrated until a lot of white solid precipitated. The solid was collected and washed with EtOH to give a crude product (900 mg). The crude was partitioned with EtOAc (30 mL) and water (50 mL). The organic layer was washed with brine, dried over Na₂SO₄, and concentrated. The residue was triturated with EtOAc/PE (10 mL, 1/10) and filtered to give the title compound (800 mg, yield 65%) as a white solid.

¹H NMR (400 MHz, CDCl3): δ 6.62 (s, 1H), 3.89 (s, 3H), 3.76-3.72 (m, 4H), 3.59-3.56 (m, 4H).

LC-MS (mobile phase: from 95% water (0.02% NH₄Ac) and 5% CH₃CN to 5% water (0.02% NH₄Ac) and 95% CH₃CN in 3.0 min, Rt=1.67 min; MS Calcd.: 320; MS Found: 321 [M+H]+.

Description D284

1-(6-Iodo-2-methoxypyrimidin-4-yl)azetidin-3-ol (D284)

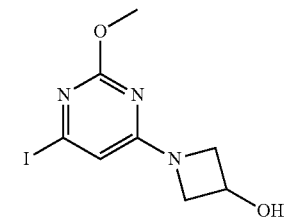

To a mixture of 4,6-diiodo-2-methoxypyrimidine (1.25 g, 3.45 mmol) in i-PrOH (20 mL) was added azetidin-3-ol hydrochloride (374 mg, 3.45 mmol) and TEA (3 mL). The mixture was heated to 75° C. and stirred for 2 hrs. The solvent was removed under vacuum and the residue was dispersed in water (20 mL). The mixture was extracted with EtOAc (100 mL×2) and the combined organic layers were washed with brine (50 mL), dried over Na₂SO₄ and concentrated to give the title compound (1.06 g, yield 100%) as white solid.

LCMS: (mobile phase: 5-95% Acetonitrile in 2.5 min), Rt=1.33 min, MS Calcd: 307; MS Found: 308 [M+H]⁺.

¹H NMR (300 MHz, DMSO-d₆): δ 6.51 (s, 1H), 5.76 (br s, 1H), 4.57-4.49 (m, 1H), 4.20-4.15 (m, 2H), 3.76-3.68 (m, 5H).

Description D285

4-Iodo-2-methoxy-6-(3-((tetrahydro-2H-pyran-2-yl)oxy)azetidin-1-yl)pyrimidine (D285)

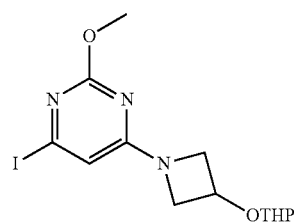

To a mixture of 1-(6-iodo-2-methoxy-pyrimidin-4-yl)-azetidin-3-ol (700 mg, 2.28 mmol) in DCM (10 mL) was added DHP (383 mg, 4.56 mmol) and TsOH.H₂O (87 mg, 0.46 mmol). The reaction mixture was stirred at rt overnight. The mixture was concentrated. The residue was purified by column chromatography (PE:EtOAc=5:1) to give the title compound (700 mg, yield 78%) as yellow oil.

LCMS: (mobile phase: 5-95% acetonitrile in 2.5 min), Rt=1.68 min; MS Calcd: 391; MS Found: 392 [M+H]⁺.

¹H NMR (400 MHz, CDCl₃): δ 6.33 (s, 1H), 4.69-4.64 (m, 2H), 4.32-4.22 (m, 2H), 4.08-3.96 (m, 2H), 4.02-3.84 (m, 4H), 3.55-3.51 (m, 1H), 1.87-1.71 (m, 2H), 1.60-1.54 (m, 4H).

Description D286

4-(6-Iodopyrimidin-4-yl)morpholine (D286)

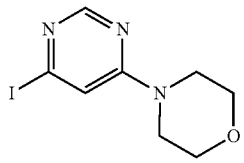

4-(6-chloropyrimidin-4-yl)morpholine (2.5 g, 12.52 mmol) and sodium iodide (2.82 g, 18.78 mmol) was dissolved in hydrogen iodide (24.78 ml, 188 mmol) (water solution) and the solution was stirred at 40° C. for 3 days. The pH of the reaction mixture was adjusted to 8 using 1N NaOH. EtOAc (200 mL) was added to dissolve the precipitate. The organic layer was then separated, dried over Na$_2$SO$_4$ and then concentrated. The crude was purified by normal phase chromatography (PE:EtOAc=100:0→60:40) to afford the 4-(6-iodopyrimidin-4-yl)morpholine (2.3 g, 7.11 mmol, 56.8% yield) as white solid.

LCMS: (mobile phase: 5-95% Acetonitrile), Rt=2.16 min in 5 min; MS Calcd: 291; MS Found: 292.0 [M+1]$^+$.

Description D287

(S)-Tetrahydrofuran-3-yl methanesulfonate (D287)

To a solution of (S)-tetrahydrofuran-3-ol (600 mg, 6.82 mmol) and TEA (2.07 g, 20.5 mmol) in DCM (10 mL) was added MsCl (1.17 mg, 10.2 mmol) with ice-bath. The solution was warmed to room temperature and stirred for 1 h. The mixture was diluted with H$_2$O (40 mL) and extracted with DCM (20 mL×3). The combined organic layers were dried over Na$_2$SO$_4$, filtered and concentrated to give the desired product (1.1 g, yield 96%) as a brown oil.

1H NMR (300 MHz, CDCl$_3$): δ 5.33-5.28 (m, 1H), 4.04-3.84 (m, 4H), 3.03 (s, 3H), 2.26-2.20 (m, 2H).

Description D288

5-Methyl-1-(tetrahydro-2H-pyran-2-yl)-6-(((R)-tetrahydrofuran-3-yl)oxy)-1H-indazole (D288)

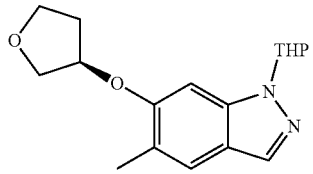

A mixture of 5-methyl-1-(tetrahydro-2H-pyran-2-yl)-1H-indazol-6-ol (600 mg, 2.59 mmol), (S)-tetrahydrofuran-3-yl methanesulfonate (644 mg, 3.88 mmol), and Cs$_2$CO$_3$ (2.50 g, 7.76 mmol) in DMF (40 mL) was stirred at 100° C. for 3 hrs. The mixture was diluted with H$_2$O (100 mL) and extracted with EtOAc (40 mL×3). The combined organic layer were washed with brine (50 mL), dried over Na$_2$SO$_4$, filtered and concentrated under vacuum. The residue was purified by column chromatography on silica gel (PE:EtOAc=3:1) to give the desired product (610 g, yield 78%) as white solid.

$^1$H NMR (300 MHz, CDCl3): δ 7.84 (s, 1H), 7.43 (s, 1H), 6.79 (d, J=2.1 Hz, 1H), 5.63 (dd, J=11.1, 2.7 Hz, 1H), 5.07-5.02 (m, 1H), 4.13-3.92 (m, 5H), 3.77-3.69 (m, 1H), 2.63-2.51 (m, 1H), 2.26-2.05 (m, 7H), 1.82-1.67 (m, 3H).

LC-MS: [mobile phase: from 90% water (0.02% NH$_4$OAc) and 10% CH$_3$CN to 5% water (0.02% NH$_4$OAc) and 95% CH3CN in 4 min], Rt=2.413 min, MS Calcd.: 302, MS Found: 303 [M+H]$^+$.

Description D289

(R)-5-methyl-6-((tetrahydrofuran-3-yl)oxy)-1H-indazole (D289)

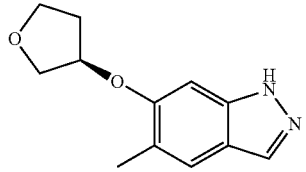 [SMILES: Cc1cc2cn[nH]c2cc1O[C@@H]1CCOC1]

A mixture of 5-methyl-1-(tetrahydro-2H-pyran-2-yl)-6-(((R)-tetrahydrofuran-3-yl)oxy)-1H-indazole (610 mg, 2.02 mmol) in HCl/1,4-dioxane (6 M, 50 mL) was stirred at room temperature for 2 hrs. The reaction mixture was concentrated, and the residue was washed with 10 mL of cold EtOAc to get the title compound (400 mg, yield 91%) as a white solid.

$^1$H NMR (300 MHz, DMSO-d6): δ 7.84 (s, 1H), 7.46 (s, 1H), 6.84 (s, 1H), 5.08-5.06 (m, 1H), 3.96-3.74 (m, 4H), 2.30-2.17 (m, 4H), 2.06-1.95 (m, 1H).

Description D290

(R)-Tetrahydrofuran-3-yl methanesulfonate (D290)

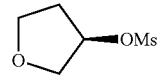

To a solution of (R)-tetrahydrofuran-3-ol (600 mg, 6.82 mmol) and TEA (3.07 g, 20.5 mmol) in DCM (10 mL) was added MsCl (1.17 mg, 10.2 mmol) with ice-bath. The solution was warmed to room temperature and stirred for 1 h. The mixture was diluted with H$_2$O (40 mL) and extracted with DCM (20 mL×3). The combined organic layers were dried over Na$_2$SO$_4$, filtered and concentrated to give the desired product (1 g, yield 88%) as a brown oil.

1H NMR (300 MHz, CDCl$_3$): δ 5.32-5.29 (m, 1H), 4.33-3.86 (m, 4H), 3.03 (s, 3H), 2.26-2.19 (m, 2H).

Description D291

5-Methyl-1-(tetrahydro-2H-pyran-2-yl)-6-(((S)-tetra-hydrofuran-3-yl)oxy)-1H-indazole (D291)

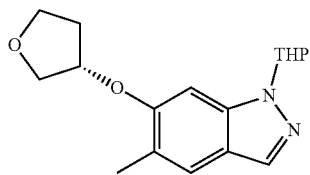

A mixture of 5-methyl-1-(tetrahydro-pyran-2-yl)-1H-indazol-6-ol (550 mg, 2.37 mmol), (R)-tetrahydrofuran-3-yl methanesulfonate (590 mg, 3.56 mmol), and $Cs_2CO_3$ (3.47 g, 10.7 mmol) in DMF (20 mL) was stirred at 100° C. for 2 hrs. The mixture was diluted with $H_2O$ (100 mL) and extracted with EtOAc (20 mL×3). The combined organic layer were washed with brine (20 mL), dried over $Na_2SO_4$, filtered and concentrated. The residue was purified by column chromatography on silica gel (PE:EtOAc=3:1) to give the desired product (600 g, yield 84%) as white solid.

$^1$H NMR (300 MHz, $CDCl_3$): δ 7.84 (s, 1H), 7.42 (s, 1H), 6.79 (d, J=2.1 Hz, 1H), 5.62 (dd, J=9.0, 2.1 Hz, 1H), 5.05-5.01 (m, 1H), 4.12-3.86 (m, 5H), 3.76-3.68 (m, 1H), 2.62-2.49 (m, 1H), 2.32-2.04 (m, 7H), 1.83-1.64 (m, 3H).

Description D292

(S)-5-Methyl-6-((tetrahydrofuran-3-yl)oxy)-1H-indazole (D292)

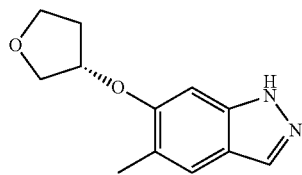 [SMILES: Cc1cc2cn[nH]c2cc1O[C@H]1CCOC1]

A mixture of 5-methyl-1-(tetrahydro-2H-pyran-2-yl)-6-(((S)-tetrahydrofuran-3-yl)oxy)-1H-indazole (540 mg, 1.79 mmol) in HCl/1,4-dioxane (6 M, 100 mL) was stirred at room temperature overnight. The reaction mixture was concentrated under reduced pressure, and the residue was washed with 20 mL of EtOAc to get the title compound (300 mg, yield 77%) as a white solid.

LC-MS: [mobile phase: from 80% water (0.02% $NH_4OAc$) and 20% $CH_3CN$ to 5% water (0.02% $NH_4OAc$) and 95% $CH_3CN$ in 3 min], Rt=1.74 min, MS Calcd.: 218, MS Found: 218 [M]$^+$.

Description D293

4-(6-(6-Bromo-5-methyl-1H-indazol-1-yl)pyrimidin-4-yl)morpholine (D293)

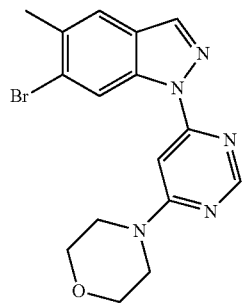 [SMILES: Cc1cc2cnn(-c3cc(N4CCOCC4)ncn3)c2cc1Br]

A mixture of 6-bromo-5-methyl-1H-indazole, hydrochloride (4.4 g, 17.78 mmol), $Cs_2CO_3$ (17.38 g, 53.3 mmol) and 4-(6-chloropyrimidin-4-yl)morpholine (3.55 g, 17.78 mmol) in DMF (35 mL) was equally splited into two microwave vials, sealed in a microwave vials and irradiated with a microwave at 100° C. for 2 h. Desired product and regioselective byproduct 4-(6-(6-bromo-5-methyl-2H-indazol-2-yl)pyrimidin-4-yl)morpholine were also found in LCMS monitoring. Then the reaction mixture was diluted with water (100 mL), filtered, extracted with ethyl acetate (80×3 mL). Combined organic parts were dried over anhydrous $Na_2SO_4$, filtered and concentrated. Purification via ISCO system (ethyl acetate/petroleum ether) afforded the mixture which included the title product and regioselective byproduct.

LC-MS (ESI) [mobile phase: from 95% water (0.05% TFA) and 5% $CH_3CN$ to 5% water (0.05% TFA) and 95% $CH_3CN$ in 5.0 min]: m/z 375 [M+H]+; Rt=4.06, 4.26 min.

Description D294

6-(3-(Benzyloxy)cyclobutyl)-2-methoxypyrimidin-4-ol (D294)

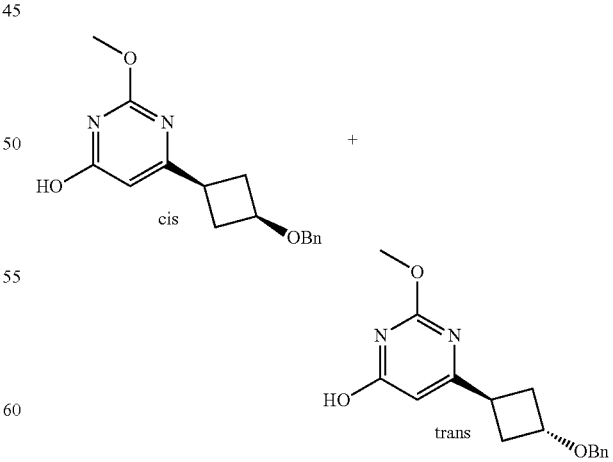

To a solution of $CH_3ONa$ (2.40 g, 44.5 mmol) in $CH_3OH$ (70 mL) was added methyl carbamimidate hydrochloride (2.10 g, 19.1 mmol) and ethyl 3-(3-(benzyloxy)cyclobutyl)-3-oxopropanoate (3.50 g, 12.7 mmol). The reaction mixture was stirred at rt for 2 hrs. Then, the reaction mixture was refluxed for 6 hrs. The reaction mixture was cooled to rt and concentrated. The residue was dissolved in water (50 mL). To the mixture was added conc. HCl solution to pH=5. The resulting mixture was extracted with EtOAc (50 mL×2). The combined organic layers were washed with brine (50 mL), dried over Na$_2$SO$_4$ and concentrated. The residue was triturated with (PE:EtOAc=5:1, 50 mL) to give the title compound (1.87 g, yield 51%) as white solid.

$^1$H NMR (300 MHz, CDCl$_3$): δ 7.35-7.28 (m, 5H), 5.94 (s, 1H), 4.46-4.44 (m, 2H), 4.03-3.96 (m, 4H), 2.83-2.74 (m, 1H), 2.55-2.42 (m, 2.5H), 2.30-2.21 (m, 1.5H).

Description D295 and D296

4-((1S,3S)-3-(benzyloxy)cyclobutyl)-6-chloro-2-methoxypyrimidine (D295) 4-((1R,3R)-3-(benzyloxy)cyclobutyl)-6-chloro-2-methoxypyrimidine (D296)

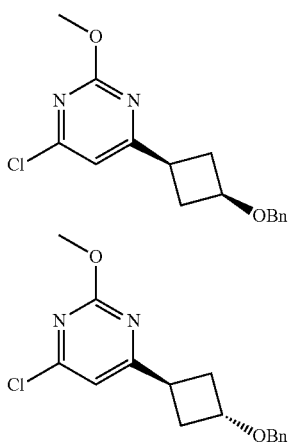

To a solution of 6-(3-(benzyloxy)cyclobutyl)-2-methoxypyrimidin-4-ol (1.60 g, 5.59 mmol) in toluene (40 mL) was added TEA (677 mg, 6.71 mmol) and POCl$_3$ (1.03 g, 6.71 mmol). The reaction mixture was refluxed for 2 hrs. The mixture was cooled to rt and poured into sat. NaHCO$_3$ solution (150 mL) and stirred for 10 min. The resulting mixture was extracted with EtOAc (50 mL×3). The combined organic layers were washed with brine (50 mL), dried over Na$_2$SO$_4$ and concentrated. The residue was purified by column chromatography (PE:EtOAc=20:1) to give the title compound cis-isomer (1.00 g, yield 59%) as colorless oil and trans-isomer (260 mg, yield 15%) as colorless oil.

D295 (cis-isomer): $^1$H NMR (400 MHz, CDCl$_3$): δ 7.35-7.27 (m, 5H), 6.84 (s, 1H), 4.46 (s, 2H), 4.08-4.02 (m, 4H), 3.02-2.97 (m, 1H), 2.67-2.61 (m, 2H), 2.33-2.26 (m, 2H).

D296 (trans-isomer): $^1$H NMR (300 MHz, CDCl$_3$): δ 7.35-7.26 (m, 5H), 6.82 (s, 1H), 4.47-4.37 (m, 3H), 4.01 (s, 3H), 3.55-3.45 (m, 1H), 2.58-2.43 (m, 4H).

Description D297

(cis)-tert-Butyl 4-(1-(6-((1s,3s)-3-(benzyloxy)cyclobutyl)-2-methoxypyrimidin-4-yl)-5-methyl-1H-indazol-6-yl)-3-fluoropiperidine-1-carboxylate (Enantiomer 1, D297)

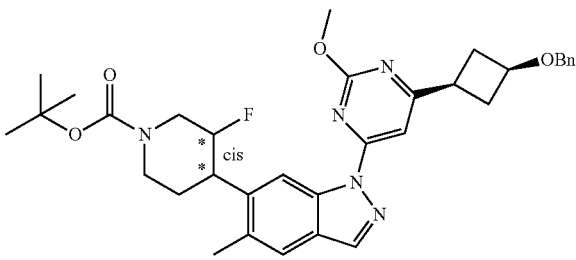 [SMILES: COc1nc(-n2ncc3cc(C)c(C4CCN(C(=O)OC(C)(C)C)CC4F)cc32)cc([C@H]2C[C@@H](OCc3ccccc3)C2)n1]

To a solution of (cis)-tert-butyl 3-fluoro-4-(5-methyl-1H-indazol-6-yl)piperidine-1-carboxylate (100 mg, 0.300 mmol) (enantiomer 1) in toluene (5 mL) was added 4-((1S,3S)-3-(benzyloxy)cyclobutyl)-6-chloro-2-methoxypyrimidine (182 mg, 0.600 mmol), CuI (171 mg, 0.900 mmol), K$_3$PO$_4$ (212 mg, 1.00 mmol) and N,N'-dimethyl-cyclohexane-1,2-diamine (128 mg, 0.900 mmol). The mixture was refluxed overnight. The reaction mixture was cooled to rt and filtered. The filtrate was concentrated. The residue was purified by column chromatography (PE:EtOAc=10:1) to give the crude (160 mg). The crude was purified by C18 column (from 95% water and 5% CH$_3$CN to 20% water and 80% CH$_3$CN in 60 min) to give the title compound (100 mg, yield 55%) as colorless oil.

D297 $^1$H NMR (300 MHz, CDCl$_3$): δ 8.82 (s, 1H), 8.12 (s, 1H), 7.57 (s, 1H), 7.48 (s, 1H), 7.37-7.26 (m, 5H), 4.83-4.54 (m, 2H), 4.49 (s, 2H), 4.29-4.19 (m, 1H), 4.14-4.07 (m, 4H), 3.31-3.19 (m, 1H), 3.14-3.03 (m, 1H), 2.95-2.78 (m, 2H), 2.73-2.63 (m, 2H), 2.51 (s, 3H), 2.44-2.34 (m, 2H), 2.04-1.91 (m, 1H), 1.84-1.74 (m, 1H), 1.53 (s, 9H).

Description D298

(cis)-tert-Butyl 3-fluoro-4-(1-(6-((1s,3s)-3-hydroxycyclobutyl)-2-methoxypyrimidin-4-yl)-5-methyl-1H-indazol-6-yl)piperidine-1-carboxylate (Enantiomer 1, D298)

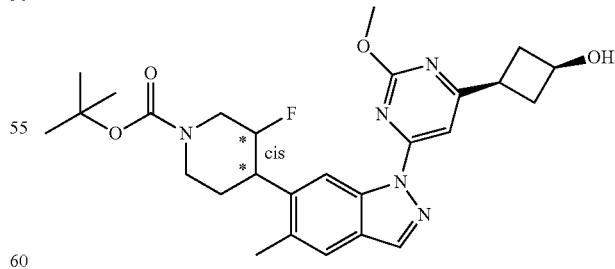

To a solution of (cis)-tert-butyl 4-(1-(6-((1s,3s)-3-(benzyloxy)cyclobutyl)-2-methoxypyrimidin-4-yl)-5-methyl-1H-indazol-6-yl)-3-fluoropiperidine-1-carboxylate (enantiomer 1, 100 mg, 0.166 mmol) in CH$_3$OH (5 mL) was added Pd/C (10%, 100 mg). The mixture was stirred at rt under H$_2$ balloon overnight. The mixture was filtered and the filtrate was concentrated. The residue was triturated with (PE:EtOAc=5:1, 5 mL) to give the title compound (45 mg, yield 53%) as white solid.

D298 $^1$H NMR (300 MHz, CDCl$_3$): δ 8.81 (s, 1H), 8.13 (s, 1H), 7.57 (s, 1H), 7.46 (s, 1H), 4.64-4.37 (m, 2H), 4.25-4.09 (m, 5H), 3.31-3.06 (m, 2H), 2.91-2.76 (m, 5H), 2.50 (s, 3H), 2.35-2.24 (m, 2H), 1.98-1.87 (m, 2H), 1.52 (s, 9H).

Description D299

(cis)-3-{6-[6-(3-fluoro-piperidin-4-yl)-5-methyl-indazol-1-yl]-2-methoxy-pyrimidin-4-yl}-cyclobutanol hydrochloride (Enantiomer 1, D299)

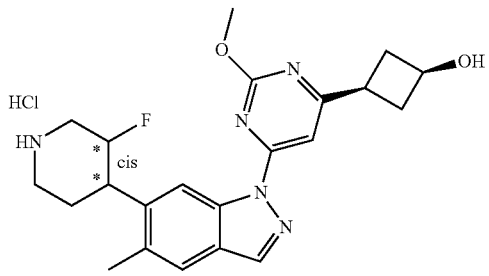 [SMILES: Cl ; COc1nc(-n2ncc3cc(C)c(C4CCNCC4F)cc32)cc([C@H]2C[C@@H](O)C2)n1]

To a solution of (cis)-tert-butyl 3-fluoro-4-(1-(6-((1S,3S)-3-hydroxycyclobutyl)-2-methoxypyrimidin-4-yl)-5-methyl-1H-indazol-6-yl)piperidine-1-carboxylate (enantiomer 1, 45 mg, 0.088 mmol) in CH$_3$OH (2.5 mL) was added HCl/CH$_3$OH (8 mol/L, 2.5 mL). The mixture was stirred at rt for 1 h. The reaction mixture was concentrated to give the title compound (35 mg, yield 90%) as a white solid.

D299 LCMS [mobile phase: 5-95% CH$_3$CN in 3 min]: Rt=1.80 min; MS Calcd: 411; MS Found: 412[M+H]$^+$.

Description D300

(cis)-tert-butyl 4-(1-(6-((1s,3s)-3-(benzyloxy)cyclobutyl)-2-methoxypyrimidin-4-yl)-5-methyl-1H-indazol-6-yl)-3-fluoropiperidine-1-carboxylate (Enantiomer 2, D300)

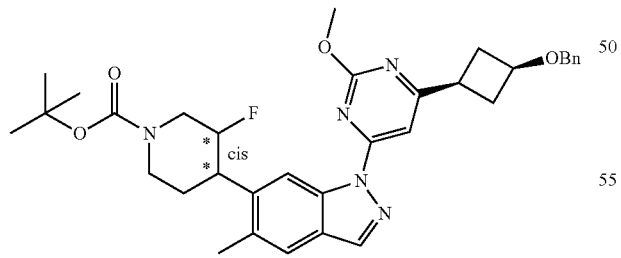

To a solution of (cis)-tert-butyl 3-fluoro-4-(5-methyl-1H-indazol-6-yl)piperidine-1-carboxylate (enantiomer 2, 150 mg, 0.450 mmol) in toluene (5 mL) was added 4-((1S,3S)-3-(benzyloxy)cyclobutyl)-6-chloro-2-methoxypyrimidine (273 mg, 0.900 mmol), CuI (171 mg, 0.900 mmol), K$_3$PO$_4$ (286 mg, 1.35 mmol) and N,N'-dimethyl-cyclohexane-1,2-diamine (128 mg, 0.900 mmol). The mixture was refluxed overnight. The reaction mixture was cooled to rt and filtered. The filtrate was concentrated. The residue was purified by column chromatography (PE:EtOAc=10:1) to give the title compound (240 mg, yield 88%) as colorless oil.

D300 LCMS [mobile phase: 5-95% CH$_3$CN in 3 min]: Rt=2.46 min; MS Calcd: 601; MS Found: 602 [M+H]$^+$.

Description D301

(cis)-tert-Butyl 3-fluoro-4-(1-(6-((1S,3S)-3-hydroxycyclobutyl)-2-methoxypyrimidin-4-yl)-5-methyl-1H-indazol-6-yl)piperidine-1-carboxylate (Enantiomer 2, D301)

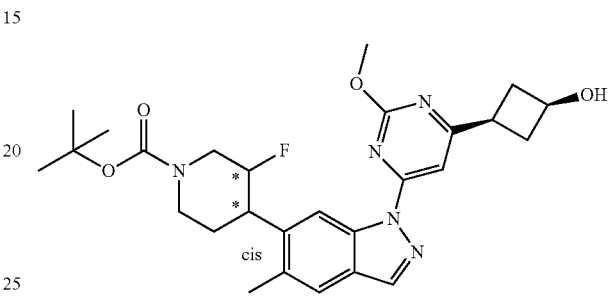

To a solution of (cis)-tert-butyl 4-(1-(6-((1S,3S)-3-(benzyloxy)cyclobutyl)-2-methoxypyrimidin-4-yl)-5-methyl-1H-indazol-6-yl)-3-fluoropiperidine-1-carboxylate (enantiomer 2, 240 mg, 0.399 mmol) in CH$_3$OH (5 mL) was added Pd/C (10%, 200 mg). The mixture was stirred at rt under H$_2$ balloon overnight. The mixture was filtered and the filtrate was concentrated. The residue was purified by prep-TLC (DCM:CH$_3$OH=20:1) to give the crude (100 mg). The crude was triturated with (PE:EtOAc=5:1, 10 mL) to give the title compound (70 mg, yield 34%) as white solid.

D301 $^1$H NMR (300 MHz, CDCl$_3$): δ 8.81 (s, 1H), 8.12 (s, 1H), 7.57 (s, 1H), 7.46 (s, 1H), 4.82-4.52 (m, 2H), 4.35-4.05 (m, 5H), 3.310-3.09 (m, 2H), 2.92-2.69 (m, 5H), 2.51 (s, 3H), 2.33-2.25 (m, 2H), 2.00-1.89 (m, 1H), 1.82-1.73 (m, 1H), 1.52 (s, 9H).

Description D302

(cis)-3-{6-[6-(3-fluoro-piperidin-4-yl)-5-methyl-indazol-1-yl]-2-methoxy-pyrimidin-4-yl}-cyclobutanol hydrochloride (Enantiomer 2, D302)

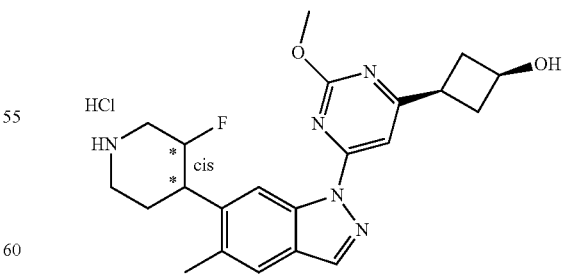

To a solution of (cis)-tert-butyl 3-fluoro-4-(1-(6-((1s,3s)-3-hydroxycyclobutyl)-2-methoxypyrimidin-4-yl)-5-methyl-1H-indazol-6-yl)piperidine-1-carboxylate (enantiomer 2, 70 mg, 0.14 mmol) in CH$_3$OH (2.5 mL) was added HCl/CH$_3$OH (8 mol/L, 2.5 mL). The mixture was stirred at rt for 1 h. The reaction mixture was concentrated to give the title compound (62 mg, yield 100%) as a white solid.

D302 LCMS [mobile phase: 20-95% CH₃CN in 3 min]: Rt=1.26 min; MS Calcd: 411; MS Found: 412 [M+H]⁺.

Description D303

(cis)-tert-butyl 4-(1-(6-(((1r,3r)-3-(benzyloxy)cyclobutyl)-2-methoxypyrimidin-4-yl)-5-methyl-1H-indazol-6-yl)-3-fluoropiperidine-1-carboxylate (Enantiomer 1, D303)

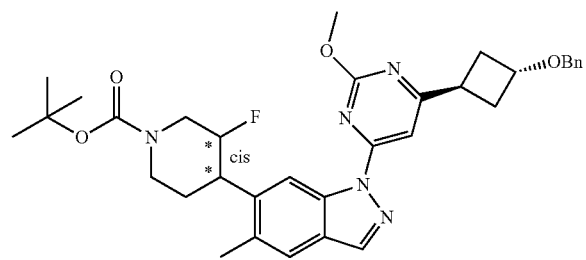 [SMILES: COc1nc(-n2ncc3cc(C)c(C4CCN(C(=O)OC(C)(C)C)CC4F)cc32)cc([C@H]2C[C@H](OCc3ccccc3)C2)n1]

To a solution of (cis)-tert-butyl 3-fluoro-4-(5-methyl-1H-indazol-6-yl)piperidine-1-carboxylate (100 mg, 0.300 mmol) (enantiomer 1) in toluene (5 mL) was added 4-((1R,3R)-3-(benzyloxy)cyclobutyl)-6-chloro-2-methoxypyrimidine (120 mg, 0.395 mmol), CuI (171 mg, 0.900 mmol), K₃PO₄ (191 mg, 0.900 mmol) and N,N'-dimethyl-cyclohexane-1,2-diamine (128 mg, 0.900 mmol). The mixture was refluxed overnight. The reaction mixture was cooled to rt and filtered. The filtrate was concentrated. The residue was purified by column chromatography (PE:EtOAc=10:1) to give the crude (180 mg). The crude was purified by prep-HPLC (prep-HPLC: from 40% water (0.1% NH₄HCO₃) and 60% CH₃CN to 5% water (0.1% NH₄HCO₃) and 95% CH₃CN in 20 min) to give the title compound (80 mg, yield 44%) as colorless oil.

D303 ¹H NMR (300 MHz, CDCl₃): δ 8.82 (s, 1H), 8.12 (s, 1H), 7.56 (s, 1H), 7.46 (s, 1H), 7.36-7.27 (m, 5H), 4.81-4.58 (m, 2H), 4.53-4.43 (m, 3H), 4.30-4.18 (m, 1H), 4.13 (s, 3H), 3.67-3.57 (m, 1H), 3.30-3.19 (m, 1H), 2.93-2.79 (m, 2H), 2.69-2.61 (m, 2H), 2.56-2.47 (m, 5H), 2.01-1.93 (m, 1H), 1.84-1.74 (m, 1H), 1.53 (s, 9H).

Description D304

(cis)-tert-Butyl 3-fluoro-4-(1-(6-(((1r,3r)-3-hydroxycyclobutyl)-2-methoxypyrimidin-4-yl)-5-methyl-1H-indazol-6-yl)piperidine-1-carboxylate (Enantiomer 1, D304)

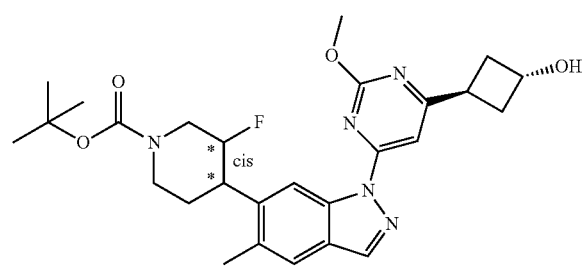 [SMILES: COc1nc(-n2ncc3cc(C)c(C4CCN(C(=O)OC(C)(C)C)CC4F)cc32)cc([C@H]2C[C@H](O)C2)n1]

To a solution of (cis)-tert-butyl 4-(1-(6-(((1R,3R)-3-(benzyloxy)cyclobutyl)-2-methoxypyrimidin-4-yl)-5-methyl-1H-indazol-6-yl)-3-fluoropiperidine-1-carboxylate (enantiomer 1, 80 mg, 0.13 mmol) in CH₃OH (10 mL) was added Pd/C (10%, 80 mg). The mixture was stirred at rt under H₂ balloon overnight. The mixture was filtered and the filtrate was concentrated to give the title compound (60 mg, yield 90%) as white solid.

D304 LCMS [mobile phase: 5-95% CH₃CN in 3 min]: Rt=2.02 min; MS Calcd: 511; MS Found: 512 [M+H]⁺.

Description D305

(cis)-(1R,3R)-3-(6-(6-(3-fluoropiperidin-4-yl)-5-methyl-1H-indazol-1-yl)-2-methoxypyrimidin-4-yl)cyclobutanol hydrochloride (Enantiomer 1, D305)

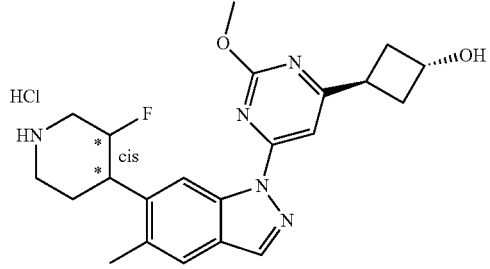

To a solution of (cis)-tert-butyl 3-fluoro-4-(1-(6-(((1R,3R)-3-hydroxycyclobutyl)-2-methoxypyrimidin-4-yl)-5-methyl-1H-indazol-6-yl)piperidine-1-carboxylate (enantiomer 1, 60 mg, 0.12 mmol) in CH₃OH (5 mL) was added HCl/CH₃OH (8 mol/L, 5 mL). The mixture was stirred at rt for 1 h. The reaction mixture was concentrated to give the title compound (54 mg, yield 100%) as white solid.

D305 LCMS [mobile phase: 20-95% CH₃CN in 3 min]: Rt=1.76 min; MS Calcd: 411; MS Found: 412 [M+H]⁺.

Description D306

(cis)-tert-Butyl 4-(1-(6-(((1R,3R)-3-(benzyloxy)cyclobutyl)-2-methoxypyrimidin-4-yl)-5-methyl-1H-indazol-6-yl)-3-fluoropiperidine-1-carboxylate (Enantiomer 2, D306)

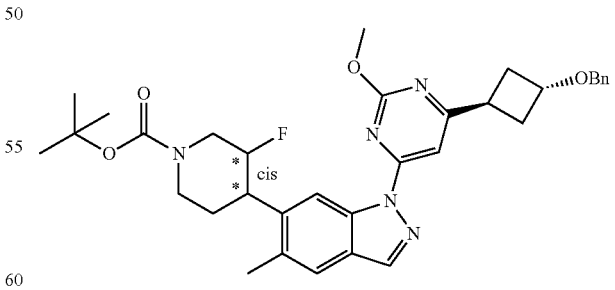

To a solution of (cis)-tert-butyl 3-fluoro-4-(5-methyl-1H-indazol-6-yl)piperidine-1-carboxylate (enantiomer 2, 100 mg, 0.300 mmol) in toluene (5 mL) was added 4-((1R,3R)-3-(benzyloxy)cyclobutyl)-6-chloro-2-methoxypyrimidine (120 mg, 0.395 mmol), CuI (171 mg, 0.900 mmol), K₃PO₄ (191 mg, 0.900 mmol) and N,N'-dimethyl-cyclohexane-1,2- diamine (128 mg, 0.900 mmol). The mixture was refluxed overnight. The reaction mixture was cooled to rt and filtered. The filtrate was concentrated. The residue was purified by column chromatography (PE:EtOAc=10:1) to give the crude (185 mg). The crude was purified by prep-HPLC (prep-HPLC: from 40% water (0.1% NH₄HCO₃) and 60% CH₃CN to 5% water (0.1% NH₄HCO₃) and 95% CH₃CN in 20 min) to give the title compound (80 mg, yield 44%) as colorless oil.

D306 $^1$H NMR (300 MHz, CDCl₃): δ 8.82 (s, 1H), 8.11 (s, 1H), 7.56 (s, 1H), 7.46 (s, 1H), 7.46-7.27 (m, 5H), 4.81-4.57 (m, 2H), 4.52-4.43 (m, 3H), 4.28-4.18 (m, 1H), 4.13 (s, 3H), 3.66-3.57 (m, 1H), 3.31-3.19 (m, 1H), 2.94-2.77 (m, 2H), 2.69-2.60 (m, 2H), 2.56-2.47 (m, 5H), 2.00-1.90 (m, 1H), 1.83-1.72 (m, 1H), 1.52 (s, 9H).

Description D307

(cis)-tert-butyl 3-fluoro-4-(1-(6-((1R,3R)-3-hydroxycyclobutyl)-2-methoxypyrimidin-4-yl)-5-methyl-1H-indazol-6-yl)piperidine-1-carboxylate (Enantiomer 2, D307)

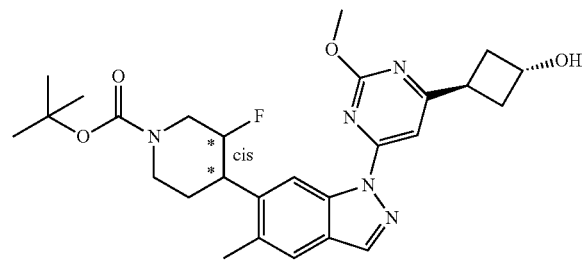 [SMILES: COc1nc(-n2ncc3cc(C)c(C4CCN(C(=O)OC(C)(C)C)CC4F)cc32)cc([C@H]2C[C@H](O)C2)n1]

To a solution of (cis)-tert-butyl 4-(1-(6-((1R,3R)-3-(benzyloxy)cyclobutyl)-2-methoxypyrimidin-4-yl)-5-methyl-1H-indazol-6-yl)-3-fluoropiperidine-1-carboxylate (enantiomer 2, 60 mg, 0.10 mmol) in CH₃OH (10 mL) was added Pd/C (10%, 80 mg). The mixture was stirred at rt under H₂ balloon overnight. The mixture was filtered and the filtrate was concentrated to give the title compound (45 mg, yield 88%) as white solid.

D307 LCMS [mobile phase: 5-95% CH₃CN in 3 min]: Rt=2.02 min; MS Calcd: 511; MS Found: 512 [M+H]⁺.

Description D308

(cis)-(1R,3R)-3-(6-(6-(3-fluoropiperidin-4-yl)-5-methyl-1H-indazol-1-yl)-2-methoxypyrimidin-4-yl)cyclobutanol hydrochloride (Enantiomer 2, D308)

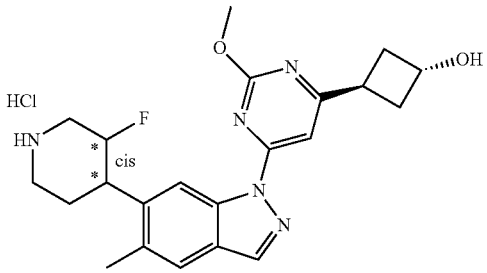 [SMILES: Cl ; COc1nc(-n2ncc3cc(C)c(C4CCNCC4F)cc32)cc([C@H]2C[C@H](O)C2)n1]

To a solution of (cis)-tert-butyl 3-fluoro-4-(1-(6-((1R,3R)-3-hydroxycyclobutyl)-2-methoxypyrimidin-4-yl)-5-methyl-1H-indazol-6-yl)piperidine-1-carboxylate (enantiomer 2, 60 mg, 0.12 mmol) in CH₃OH (5 mL) was added HCl/CH₃OH (8 mol/L, 5 mL). The mixture was stirred at rt for 1 h. The reaction mixture was concentrated to give the title compound (54 mg, yield 100%) as a white solid.

D308 LCMS [mobile phase: 5-95% CH₃CN in 3 min]: Rt=1.73 min; MS Calcd: 411; MS Found: 412 [M+H]⁺.

Description D309

(R)-1-(6-iodo-2-methylpyrimidin-4-yl)pyrrolidin-3-ol (D309)

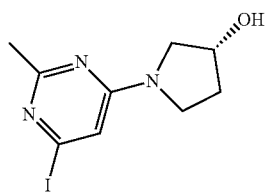

To a solution of 4,6-diiodo-2-methylpyrimidine (600 mg, 1.73 mmol) in DMF (10 mL) was added (R)-pyrrolidin-3-ol (151 mg, 1.73 mmol) and DIPEA (447 mg, 3.46 mmol). The mixture was stirred at room temperature for 3 hrs. The reaction mixture was poured into KF solution water (100 mL), extracted with EtOAc (50 mL×3). The combined organic layers were washed with brine (50 mL), dried over anhydrous Na₂SO₄ and concentrated to give the crude product (530 mg) as a white solid.

D309 LC-MS: (mobile phase: from 90% water (0.1% FA) and 10% CH₃CN (0.1% FA) to 5% water (0.1% FA) and 95% CH₃CN (0.1% FA) in 2.5 min), Rt=0.66 min; MS Calcd.: 305.1; MS Found: 305.8 [M+H]⁺.

Description D310

(cis)-tert-butyl 3-fluoro-4-(1-(6-((R)-3-hydroxypyrrolidin-1-yl)-2-methylpyrimidin-4-yl)-5-methyl-1H-indazol-6-yl)piperidine-1-carboxylate (Diastereoisomer 1, D310)

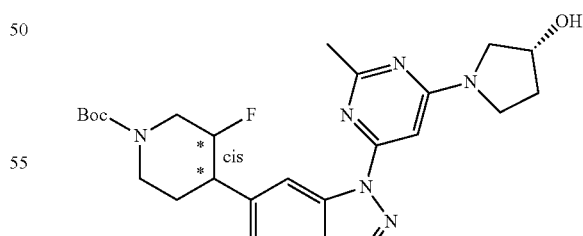

To a solution of (R)-1-(6-iodo-2-methylpyrimidin-4-yl)pyrrolidin-3-ol (88 mg, 0.29 mmol) in toluene (8 mL) was added (cis)-tert-butyl 3-fluoro-4-(5-methyl-1H-indazol-6-yl)piperidine-1-carboxylate (enantiomer 1, 80 mg, 0.24 mmol), K₃PO₄ (102 mg, 0.48 mmol), CuI (46 mg, 0.24 mmol) and N1,N2-dimethylethane-1,2-diamine (42 mg, 0.48 mmol). The mixture was stirred at 110° C. for 2 hrs under N₂. The reaction mixture was cooled to rt and concentrated. The residue was purified by silica gel chromatography eluted with (EtOAc:petroleum ether=1:5~1:1) to give the product (cis)-tert-butyl 3-fluoro-4-(1-(6-((R)-3-hydroxypyrrolidin-1-yl)-2-methylpyrimidin-4-yl)-5-methyl-1H-indazol-6-yl)piperidine-1-carboxylate (diastereoisomer 1) (120 mg, 97.9% yield) as a yellow solid.

D310 LC-MS (mobile phase: from 90% water (0.1% FA) and 10% CH₃CN (0.1% FA) to 5% water (0.1% FA) and 95% CH₃CN (0.1% FA) in 2.5 min), Rt=1.61 min; MS Calcd.: 510; MS Found: 511 [M+H]⁺.

Description D311

(R)-1-(6-(6-((cis)-3-fluoropiperidin-4-yl)-5-methyl-1H-indazol-1-yl)-2-methylpyrimidin-4-yl)pyrrolidin-3-ol (Diastereoisomer 1, D311)

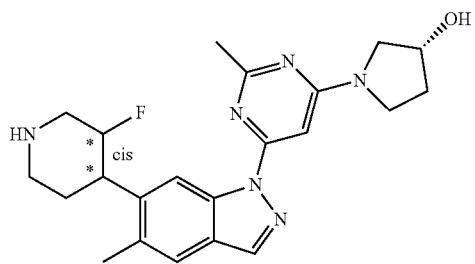 [SMILES: Cc1nc(N2CC[C@@H](O)C2)cc(-n2ncc3cc(C)c(C4CCNCC4F)cc32)n1]

A solution of (cis)-tert-butyl 3-fluoro-4-(1-(6-((R)-3-hydroxypyrrolidin-1-yl)-2-methyl pyrimidin-4-yl)-5-methyl-1H-indazol-6-yl)piperidine-1-carboxylate (diastereoisomer 1, 120 mg, 0.24 mmol) in 4 mol/L HCl/EtOAc (10 mL) was stirred at room temperature for 1 hr. The mixture was poured into sat. NaHCO₃ (30 mL) and then the mixture was extracted with EtOAc (30 mL×3). The combined organic layers were washed with brine (30 mL), dried over anhydrous Na₂SO₄ and filtered. The filtrate was concentrated to give the crude product (R)-1-(6-(6-((cis)-3-fluoropiperidin-4-yl)-5-methyl-1H-indazol-1-yl)-2-methylpyrimidin-4-yl)pyrrolidin-3-ol (diastereoisomer 1) (110 mg, yield ~100%) as yellow crude solid.

D311 LC-MS (mobile phase: from 90% water (0.1% FA) and 10% CH₃CN (0.1% FA) to 5% water (0.1% FA) and 95% CH₃CN (0.1% FA) in 2.5 min), Rt=1.06 min; MS Calcd.: 410; MS Found: 411 [M+H]⁺.

Description D312

(cis)-tert-butyl 3-fluoro-4-(1-(6-((R)-3-hydroxypyrrolidin-1-yl)-2-methyl pyrimidin-4-yl)-5-methyl-1H-indazol-6-yl)piperidine-1-carboxylate (Diastereoisomer 2, D312)

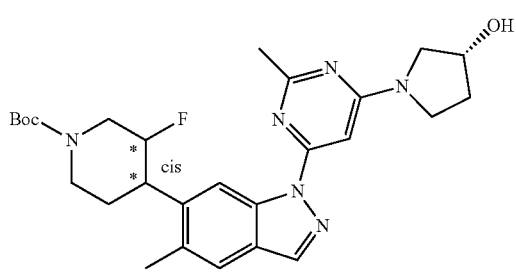 [SMILES: Cc1nc(N2CC[C@@H](O)C2)cc(-n2ncc3cc(C)c(C4CCN(C(=O)OC(C)(C)C)CC4F)cc32)n1]

To a solution of (R)-1-(6-iodo-2-methylpyrimidin-4-yl)pyrrolidin-3-ol (88 mg, 0.29 mmol) in toluene (8 mL) was added (cis)-tert-butyl 3-fluoro-4-(5-methyl-1H-indazol-6-yl)piperidine-1-carboxylate (enantiomer 2) (80 mg, 0.24 mmol), K₃PO₄ (102 mg, 0.48 mmol), CuI (46 mg, 0.24 mmol) and N1,N2-dimethylethane-1,2-diamine (42 mg, 0.48 mmol). The mixture was stirred at 130° C. for 2 hrs under N₂. The reaction mixture was cooled to rt and concentrated. The residue was purified by silica gel chromatography eluted with (EtOAc:petroleum ether=1:5~1:1) to give the product (cis)-tert-butyl 3-fluoro-4-(1-(6-((R)-3-hydroxypyrrolidin-1-yl)-2-methyl pyrimidin-4-yl)-5-methyl-1H-indazol-6-yl)piperidine-1-carboxylate (diastereoisomer 2) (120 mg, 97.9% yield) as a yellow solid.

D312 LC-MS (mobile phase: from 90% water (0.1% FA) and 10% CH₃CN (0.1% FA) to 5% water (0.1% FA) and 95% CH₃CN (0.1% FA) in 2.5 min), Rt=1.61 min; MS Calcd.: 510; MS Found: 511 [M+H]⁺.

Description D313

(R)-1-(6-(6-((cis)-3-fluoropiperidin-4-yl)-5-methyl-1H-indazol-1-yl)-2-methylpyrimidin-4-yl)pyrrolidin-3-ol (Enantiomer 2, D313)

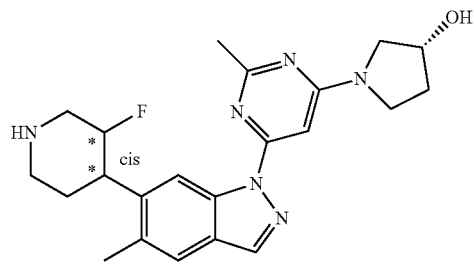 [SMILES: Cc1nc(N2CC[C@@H](O)C2)cc(-n2ncc3cc(C)c(C4CCNCC4F)cc32)n1]

A solution of (cis)-tert-butyl 3-fluoro-4-(1-(6-((R)-3-hydroxypyrrolidin-1-yl)-2-methyl pyrimidin-4-yl)-5-methyl-1H-indazol-6-yl)piperidine-1-carboxylate (diastereoisomer 2) (120 mg, 0.24 mmol) in 4 mol/L HCl/EtOAc (10 mL) was stirred at room temperature for overnight. The mixture was poured into sat. NaHCO₃ (30 mL) and then the mixture was extracted with EtOAc (30 mL×3). The combined organic layers were washed with brine (30 mL), and dried over anhydrous Na₂SO₄ and filtered. The filtrate was concentrated to give the crude product (R)-1-(6-(6-((cis)-3-fluoropiperidin-4-yl)-5-methyl-1H-indazol-1-yl)-2-methylpyrimidin-4-yl)pyrrolidin-3-ol (diastereoisomer 2) (110 mg, yield ~100%) as yellow solid.

D313 LC-MS (mobile phase: from 90% water (0.1% FA) and 10% CH₃CN (0.1% FA) to 5% water (0.1% FA) and 95% CH₃CN (0.1% FA) in 2.5 min), Rt=1.06 min; MS Calcd.: 410; MS Found: 411 [M+H]⁺.

Description D314

(S)-1-(6-iodo-2-methylpyrimidin-4-yl)pyrrolidin-3-ol (D314)

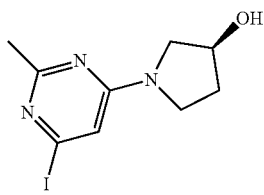

To a solution of 4,6-diiodo-2-methylpyrimidine (600 mg, 1.73 mmol) in DMF (10 mL) was added (S)-pyrrolidin-3-ol (151 mg, 1.73 mmol) and DIPEA (447 mg, 3.46 mmol). The mixture was stirred at room temperature for 3 hrs. The reaction mixture was poured into water (100 mL), extracted with EtOAc (50 mL×3). The combined organic layers were washed with brine (50 mL), dried over anhydrous $Na_2SO_4$ and concentrated to give the crude product (500 mg, yield=94.7%) as a white solid.

D314 LC-MS: (mobile phase: from 90% water (0.1% FA) and 10% $CH_3CN$ (0.1% FA) to 5% water (0.1% FA) and 95% $CH_3CN$ (0.1% FA) in 2.5 min), Rt=0.68 min; MS Calcd.: 305.1; MS Found: 305.8 $[M+H]^+$.

Description D315

(cis)-tert-Butyl 3-fluoro-4-(1-(6-((S)-3-hydroxypyrrolidin-1-yl)-2-methylpyrimidin-4-yl)-5-methyl-1H-indazol-6-yl)piperidine-1-carboxylate (Diastereoisomer 1, D315)

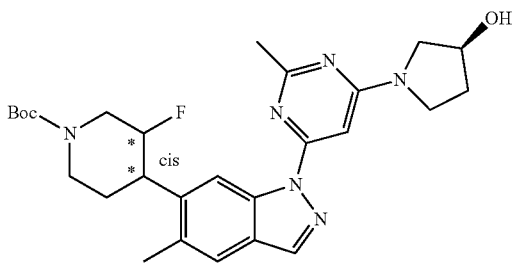 [SMILES: Cc1nc(N2CC[C@H](O)C2)cc(-n2ncc3cc(C)c(C4CCN(C(=O)OC(C)(C)C)CC4F)cc32)n1]

To a solution of (S)-1-(6-iodo-2-methylpyrimidin-4-yl)pyrrolidin-3-ol (150 mg, 0.49 mmol) in toluene (10 mL) was added (cis)-tert-butyl 3-fluoro-4-(5-methyl-1H-indazol-6-yl)piperidine-1-carboxylate (enantiomer 1, 136 mg, 0.41 mmol), $K_3PO_4$ (174 mg, 0.82 mmol), CuI (78 mg, 0.41 mmol) and N1,N2-dimethylethane-1,2-diamine (72 mg, 0.82 mmol). The mixture was stirred at 100° C. for 2 hrs under $N_2$. The reaction mixture was cooled to rt and concentrated. The residue was purified by silica gel chromatography eluted with (EtOAc:petroleum ether=1:10~1:2) to give the product (cis)-tert-butyl 3-fluoro-4-(1-(6-((S)-3-hydroxypyrrolidin-1-yl)-2-methylpyrimidin-4-yl)-5-methyl-1H-indazol-6-yl)piperidine-1-carboxylate (diastereoisomer 1) (90 mg, 43.1% yield) as a yellow solid.

D315 LC-MS (mobile phase: from 90% water (0.1% FA) and 10% $CH_3CN$ (0.1% FA) to 5% water (0.1% FA) and 95% $CH_3CN$ (0.1% FA) in 2.5 min), Rt=1.75 min; MS Calcd.: 510; MS Found: 511 $[M+H]^+$.

Description D316

(S)-1-(6-(6-((cis)-3-fluoropiperidin-4-yl)-5-methyl-1H-indazol-1-yl)-2-methylpyrimidin-4-yl)pyrrolidin-3-ol (Diastereoisomer 1, D316)

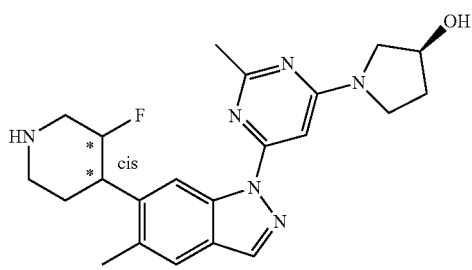 [SMILES: Cc1nc(N2CC[C@H](O)C2)cc(-n2ncc3cc(C)c(C4CCNCC4F)cc32)n1]

A solution of (cis)-tert-butyl 3-fluoro-4-(1-(6-((S)-3-hydroxypyrrolidin-1-yl)-2-methylpyrimidin-4-yl)-5-methyl-1H-indazol-6-yl)piperidine-1-carboxylate (diastereoisomer 1) (90 mg, 0.176 mmol) in 4 mol/L HCl/EtOAc (10 mL) was stirred at room temperature overnight. The mixture was poured into sat. $NaHCO_3$ (50 mL) and then the mixture was extracted with EtOAc (50 mL×3). The combined organic layers were washed with brine (50 mL), dried over anhydrous $Na_2SO_4$ and filtered. The filtrate was concentrated to give the crude product (S)-1-(6-(6-((cis)-3-fluoropiperidin-4-yl)-5-methyl-1H-indazol-1-yl)-2-methylpyrimidin-4-yl)pyrrolidin-3-ol (diastereoisomer 1) (50 mg, yield=69.3%) as yellow solid.

D316 LC-MS (mobile phase: from 90% water (0.1% FA) and 10% $CH_3CN$ (0.1% FA) to 5% water (0.1% FA) and 95% $CH_3CN$ (0.1% FA) in 2.5 min), Rt=1.03 min; MS Calcd.: 410; MS Found: 411 $[M+H]^+$.

Description D317

(cis)-tert-butyl 3-fluoro-4-(1-(6-((S)-3-hydroxypyrrolidin-1-yl)-2-methylpyrimidin-4-yl)-5-methyl-1H-indazol-6-yl)piperidine-1-carboxylate (Diastereoisomer 2, D317)

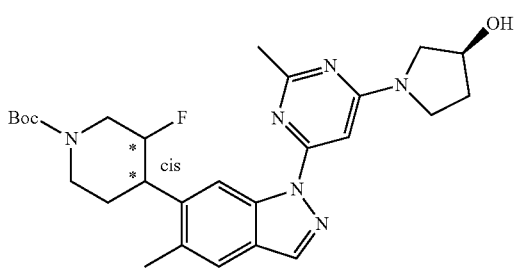 [SMILES: Cc1nc(N2CC[C@H](O)C2)cc(-n2ncc3cc(C)c(C4CCN(C(=O)OC(C)(C)C)CC4F)cc32)n1]

To a solution of (S)-1-(6-iodo-2-methylpyrimidin-4-yl)pyrrolidin-3-ol (150 mg, 0.49 mmol) in toluene (10 mL) was added (cis)-tert-butyl 3-fluoro-4-(5-methyl-1H-indazol-6-yl)piperidine-1-carboxylate (enantiomer 2, 136 mg, 0.41 mmol), $K_3PO_4$ (174 mg, 0.82 mmol), CuI (78 mg, 0.41 mmol) and N1,N2-dimethylethane-1,2-diamine (72 mg, 0.82 mmol). The mixture was stirred at 100° C. for 2 hrs under N₂. The reaction mixture was cooled to rt and concentrated. The residue was purified by silica gel chromatography eluted with (EtOAc:petroleum ether=1:10~1:2) to give the product (cis)-tert-butyl 3-fluoro-4-(1-(6-((S)-3-hydroxypyrrolidin-1-yl)-2-methylpyrimidin-4-yl)-5-methyl-1H-indazol-6-yl)piperidine-1-carboxylate (diastereoisomer 2, 132 mg, 63.5% yield) as a yellow solid.

D317 LC-MS (mobile phase: from 90% water (0.1% FA) and 10% CH₃CN (0.1% FA) to 5% water (0.1% FA) and 95% CH₃CN (0.1% FA) in 2.5 min), Rt=1.74 min; MS Calcd.: 510; MS Found: 511 [M+H]⁺.

Description D318

(S)-1-(6-(6-(((cis)-3-fluoropiperidin-4-yl)-5-methyl-1H-indazol-1-yl)-2-methylpyrimidin-4-yl)pyrrolidin-3-ol (Diastereoisomer 2, D318)

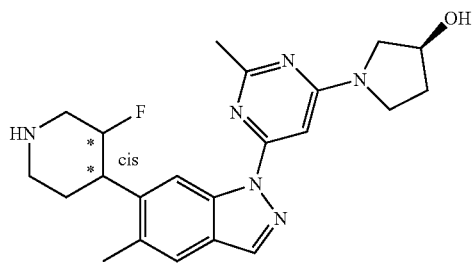 [SMILES: Cc1nc(N2CC[C@H](O)C2)cc(-n2ncc3cc(C)c(C4CCNCC4F)cc32)n1]

A solution of (cis)-tert-butyl 3-fluoro-4-(1-(6-((S)-3-hydroxypyrrolidin-1-yl)-2-methylpyrimidin-4-yl)-5-methyl-1H-indazol-6-yl)piperidine-1-carboxylate (diastereoisomer 2) (132 mg, 0.258 mmol) in 4 mol/L HCl/EtOAc (10 mL) was stirred at room temperature for 2 hrs. The mixture was poured into sat. NaHCO₃ (30 mL) and then the mixture was extracted with EtOAc (30 mL×3). The combined organic layers were washed with brine (30 mL), dried over anhydrous Na₂SO₄ and filtered. The filtrate was concentrated to give the crude product (S)-1-(6-(6-((cis)-3-fluoropiperidin-4-yl)-5-methyl-1H-indazol-1-yl)-2-methylpyrimidin-4-yl)pyrrolidin-3-ol (diastereoisomer 2, 90 mg, yield=84.9%) as yellow solid.

D318 LC-MS (mobile phase: from 90% water (0.1% FA) and 10% CH₃CN (0.1% FA) to 5% water (0.1% FA) and 95% CH₃CN (0.1% FA) in 2.5 min), Rt=1.04 min; MS Calcd.: 410; MS Found: 411 [M+H]⁺.

Description D319

4-(2,5-Dihydro-1H-pyrrol-1-yl)-6-iodo-2-methylpyrimidine (D319)

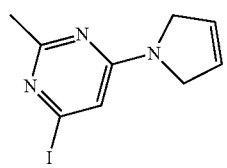

To a solution of 4,6-diiodo-2-methylpyrimidine (1.0 g, 2.89 mmol) in DMF (10 mL) was added 2,5-dihydro-1H-pyrrole (200 mg, 2.89 mmol) and DIPEA (747 mg, 5.78 mmol). The mixture was stirred at room temperature for 3 hrs. The reaction mixture was poured into water (100 mL), extracted with EtOAc (50 mL×3). The combined organic layers were washed with brine (50 mL), dried over anhydrous Na₂SO₄ and concentrated to dryness, the residue was purified by silica gel chromatography eluted with EtOAc: petroleum ether=1:10 to 1:5 to give the product 4-(2,5-dihydro-1H-pyrrol-1-yl)-6-iodo-2-methyl pyrimidine (660 mg, 79.5% yield) as a white solid.

D319 LC-MS: (mobile phase: from 90% water (0.1% FA) and 10% CH₃CN (0.1% FA) to 5% water (0.1% FA) and 95% CH₃CN (0.1% FA) in 2.5 min), Rt=1.28 min; MS Calcd.: 287.1; MS Found: 287.8 [M+H]⁺.

Description D320 cis-1-(6-Iodo-2-methylpyrimidin-4-yl)pyrrolidine-3,4-diol (D320)

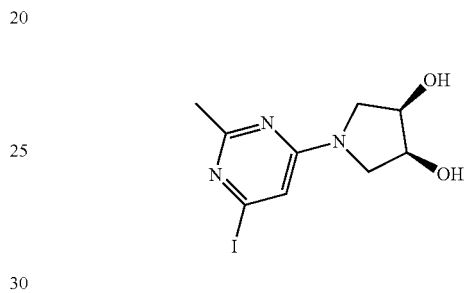

To a solution of 4-(2,5-dihydro-1H-pyrrol-1-yl)-6-iodo-2-methylpyrimidine (560 mg, 1.95 mmol) in THF/H₂O (30/4 mL) was added 50% NMO (aq.) (1371 mg, 5.85 mmol) and OsO₄ (50 mg, 0.19 mmol). The mixture was stirred at room temperature for 4 hrs. The reaction mixture concentrated to dryness, the residue was purified by silica gel chromatography eluted with (EtOAc:petroleum ether=1:5 to 1:0) to give the product cis-1-(6-iodo-2-methylpyrimidin-4-yl)pyrrolidine-3,4-diol (500 mg, 79.9% yield) as a white solid.

D320 LC-MS: (mobile phase: from 90% water (0.1% FA) and 10% CH₃CN (0.1% FA) to 5% water (0.1% FA) and 95% CH₃CN (0.1% FA) in 2.5 min), Rt=1.01 min; MS Calcd.: 321.1; MS Found: 321.8 [M+H]⁺.

Description D321 tert-Butyl 4-(1-(6-(cis-3,4-dihydroxypyrrolidin-1-yl)-2-methylpyrimidin-4-yl)-5-methyl-1H-indazol-6-yl)-3-fluoropiperidine-1-carboxylate (Diastereoisomer 1, D321)

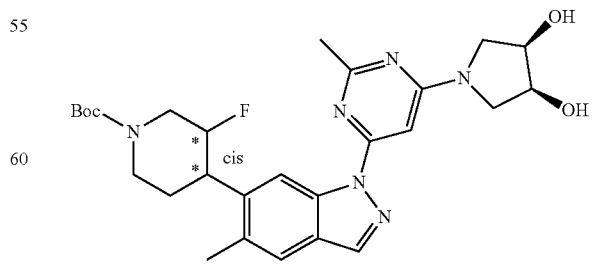

To a solution of cis-1-(6-iodo-2-methylpyrimidin-4-yl)pyrrolidine-3,4-diol (58 mg, 0.18 mmol) in toluene (8 mL)

was added (cis)-tert-butyl 3-fluoro-4-(5-methyl-1H-indazol-6-yl)piperidine-1-carboxylate (enantiomer 1, 50 mg, 0.15 mmol), $K_3PO_4$ (64 mg, 0.30 mmol), CuI (29 mg, 0.15 mmol) and N1,N2-dimethylethane-1,2-diamine (26 mg, 0.30 mmol). The mixture was stirred at 110° C. for 2 hrs under $N_2$. The reaction mixture was cooled to rt and concentrated. The residue was purified by silica gel chromatography eluted with (EtOAc:Petroleum Ether=1:5 to 1:0) to give the product (cis)-tert-butyl 4-(1-(6-(cis-3,4-dihydroxypyrrolidin-1-yl)-2-methylpyrimidin-4-yl)-5-methyl-1H-indazol-6-yl)-3-fluoropiperidine-1-carboxylate (diastereoisomer 1, 60 mg, 75.9% yield) as a yellow oil.

D321 LC-MS (mobile phase: from 90% water (0.1% FA) and 10% $CH_3CN$ (0.1% FA) to 5% water (0.1% FA) and 95% $CH_3CN$ (0.1% FA) in 2.5 min), Rt=1.68 min; MS Calcd.: 526.6; MS Found: 527.1 $[M+H]^+$.

Description D322 cis-1-(6-(6-(3-Fluoropiperidin-4-yl)-5-methyl-1H-indazol-1-yl)-2-methylpyrimidin-4-yl)pyrrolidine-3,4-diol (Diastereoisomer 1, D322)

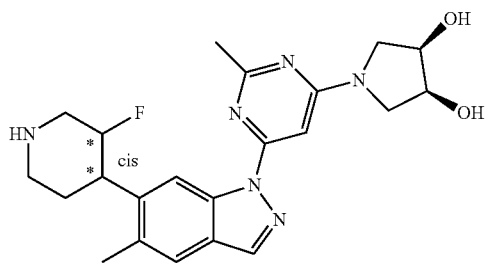 [SMILES: Cc1nc(N2C[C@@H](O)[C@@H](O)C2)cc(-n2ncc3cc(C)c(C4CCNCC4F)cc32)n1]

To a solution of (cis)-tert-butyl 4-(1-(6-(cis-3,4-dihydroxypyrrolidin-1-yl)-2-methylpyrimidin-4-yl)-5-methyl-1H-indazol-6-yl)-3-fluoropiperidine-1-carboxylate (diastereoisomer 1) (60 mg, 0.11 mmol) in DCM (5 mL) was added TFA (1 mL), the reaction was stirred at room temperature for 3 hrs. The mixture was concentrated to dryness, the residue was dissolved with DCM (100 mL), washed with sat. $NaHCO_3$ (30 mL), brine (30 mL), dried over anhydrous $Na_2SO_4$ and filtered. The filtrate was concentrated to give the crude product cis-1-(6-(6-(3-fluoropiperidin-4-yl)-5-methyl-1H-indazol-1-yl)-2-methylpyrimidin-4-yl) pyrrolidine-3,4-diol (diastereoisomer 1) (42 mg, yield: 89.6%) as a yellow solid.

D322 LC-MS (mobile phase: from 90% water (0.1% FA) and 10% $CH_3CN$ (0.1% FA) to 5% water (0.1% FA) and 95% $CH_3CN$ (0.1% FA) in 2.5 min), Rt=1.02 min; MS Calcd.: 426.5; MS Found: 427.0 $[M+H]^+$.

Description D323

(cis)-tert-Butyl 4-(1-(6-(cis-3,4-dihydroxypyrrolidin-1-yl)-2-methylpyrimidin-4-yl)-5-methyl-1H-indazol-6-yl)-3-fluoropiperidine-1-carboxylate (Diastereoisomer 2, D323)

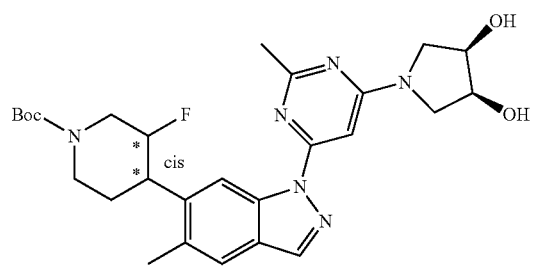 [SMILES: Cc1nc(N2C[C@@H](O)[C@@H](O)C2)cc(-n2ncc3cc(C)c(C4CCN(C(=O)OC(C)(C)C)CC4F)cc32)n1]

To a solution of cis-1-(6-iodo-2-methylpyrimidin-4-yl) pyrrolidine-3,4-diol (116 mg, 0.36 mmol) in toluene (10 mL) was added (cis)-tert-butyl 3-fluoro-4-(5-methyl-1H-indazol-6-yl)piperidine-1-carboxylate (enantiomer 2, 100 mg, 0.30 mmol), $K_3PO_4$ (127 mg, 0.60 mmol), CuI (57 mg, 0.30 mmol) and N1,N2-dimethylethane-1,2-diamine (53 mg, 0.60 mmol). The mixture was stirred at 110° C. for 2 hrs under $N_2$. The reaction mixture was cooled to rt and concentrated. The residue was purified by silica gel chromatography eluted with (EtOAc:petroleum ether=1:2 to 1:0) to give the product (cis)-tert-butyl 4-(1-(6-(cis-3,4-dihydroxypyrrolidin-1-yl)-2-methylpyrimidin-4-yl)-5-methyl-1H-indazol-6-yl)-3-fluoropiperidine-1-carboxylate (diastereoisomer 2) (160 mg, yield ~100%) as a yellow solid.

D323 LC-MS (mobile phase: from 90% water (0.1% FA) and 10% $CH_3CN$ (0.1% FA) to 5% water (0.1% FA) and 95% $CH_3CN$ (0.1% FA) in 2.5 min), Rt=1.66 min; MS Calcd.: 526.6; MS Found: 527.0 $[M+H]^+$.

Description D324

(cis)-1-(6-(6-(3-Fluoropiperidin-4-yl)-5-methyl-1H-indazol-1-yl)-2-methylpyrimidin-4-yl)pyrrolidine-3,4-diol (Diastereoisomer 2, D324)

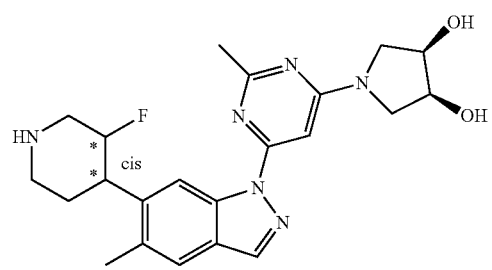 [SMILES: Cc1nc(N2C[C@@H](O)[C@@H](O)C2)cc(-n2ncc3cc(C)c(C4CCNCC4F)cc32)n1]

To a solution of (cis)-tert-butyl 4-(1-(6-(cis-3,4-dihydroxypyrrolidin-1-yl)-2-methylpyrimidin-4-yl)-5-methyl-1H-indazol-6-yl)-3-fluoropiperidine-1-carboxylate (diastereoisomer 2) (160 mg, 0.30 mmol) in 4 mol/L HCl/EtOAc (10 mL), the reaction was stirred at room temperature for 1 hr. The mixture was concentrated to dryness, the residue was dissolved with DCM (100 mL), washed with sat. $NaHCO_3$ (30 mL), brine (30 mL), dried over anhydrous $Na_2SO_4$ and filtered. The filtrate was concentrated to give the crude product cis-1-(6-(6-(3-fluoropiperidin-4-yl)-5-methyl-1H-indazol-1-yl)-2-methylpyrimidin-4-yl) pyrrolidine-3,4-diol (diastereoisomer 2, D324) (120 mg, yield: 94.1%) as a yellow solid.

D324 LC-MS (mobile phase: from 90% water (0.1% FA) and 10% CH$_3$CN (0.1% FA) to 5% water (0.1% FA) and 95% CH$_3$CN (0.1% FA) in 2.5 min), Rt=1.02 min; MS Calcd.: 426.5; MS Found: 427.0 [M+H]$^+$.

Description D325

Ethyl 2-((1-(6-iodo-2-methylpyrimidin-4-yl)azetidin-3-yl)oxy)acetate (D325)

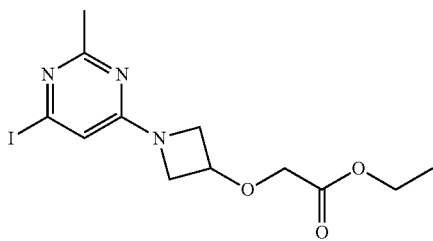 [SMILES: CCOC(=O)COC1CN(c2cc(I)nc(C)n2)C1]

To a solution of 1-(6-iodo-2-methylpyrimidin-4-yl)azetidin-3-ol (2.3 g, 8.0 mmol) in DMF (10 mL) was added ethyl 2-bromoacetate (2.0 g, 12 mmol) and Cs$_2$CO$_3$ (5.2 g, 16 mmol). The resulting mixture was stirred at rt for 2 hrs. The reaction mixture was poured into water (50 mL) and extracted with CH$_2$Cl$_2$ (30 mL×3). The combined organic layers were washed with brine (20 mL), dried over Na$_2$SO$_4$ and concentrated. The residue was purified by column (PE:EtOAc=6:1) to give the title compound (2.6 g, yield 87%) as a white solid.

D325 $^1$H NMR (300 MHz, CDCl$_3$): δ 6.48 (s, 1H), 4.55-4.49 (m, 1H), 4.26-4.21 (m, 4H), 4.09 (s, 2H), 4.05-4.01 (m, 2H), 2.45 (s, 3H), 1.31-1.25 (m, 3H).

Description D326

2-((1-(6-Iodo-2-methylpyrimidin-4-yl)azetidin-3-yl)oxy)ethanol (D326)

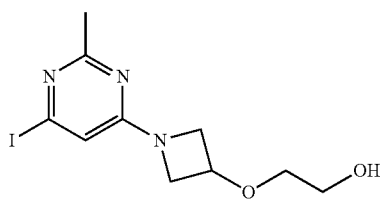 [SMILES: Cc1nc(I)cc(N2CC(OCCO)C2)n1]

To a solution of ethyl 2-((1-(6-iodo-2-methylpyrimidin-4-yl)azetidin-3-yl)oxy)acetate (2.6 g, 6.9 mmol) in THF (15 mL) was added DIBAL-H (1 M hexane, 24 mL, 24 mmol) dropwise under N$_2$ at 0° C. The resulting mixture was stirred at 0° C. for 3 hrs and at rt. overnight. The reaction mixture was poured into ice-water (50 mL) slowly. The solid was removed by filtration. The filtrate was extracted with EtOAc (30 mL×3). The combined organic layers were washed with brine (20 mL), dried over Na$_2$SO$_4$ and concentrated to give the title compound (2.3 g, yield 100%) as yellow oil.

D326 $^1$H NMR (300 MHz, CDCl$_3$): δ 6.48 (s, 1H), 4.50-4.453 (m, 1H), 4.26-4.21 (m, 2H), 3.97-3.92 (m, 2H), 3.77 (br s, 2H), 3.56-3.53 (m, 2H), 2.45 (s, 3H), 2.12 (br s, 1H).

Description D327

4-Iodo-2-methyl-6-(3-(2-((tetrahydro-2H-pyran-2-yl)oxy)ethoxy)azetidin-1-yl)pyrimidine (D327)

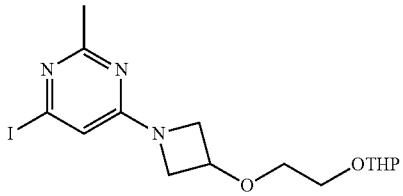

To a solution of 2-((1-(6-iodo-2-methylpyrimidin-4-yl)azetidin-3-yl)oxy)ethanol (2.3 g, 6.9 mmol) in CH$_2$Cl$_2$ (20 mL) was added DHP (2.3 g, 28 mmol) and TsOH (1.2 g, 6.9 mmol) at rt. The resulting mixture was warmed to 50° C. and stirred for 2 hrs. The reaction mixture was cooled to rt and diluted with CH$_2$Cl$_2$ (80 mL). The mixture was washed with saturated Na$_2$CO$_3$ solution (20 mL×2) and brine (20 mL), dried over Na$_2$SO$_4$ and concentrated. The residue was purified by column (PE:EtOAc=5:1) to give the title compound (2.1 g, yield 71%) as colorless oil.

D327 $^1$H NMR (300 MHz, CDCl$_3$): δ 6.47 (s, 1H), 4.62-4.60 (m, 1H), 4.53-4.45 (m, 1H), 4.24-4.19 (m, 2H), 3.98-3.92 (m, 2H), 3.90-3.82 (m, 2H), 3.65-3.50 (m, 4H), 2.45 (s, 3H), 2.32-2.19 (m, 1H), 1.85-1.71 (m, 2H), 1.62-1.52 (m, 3H).

Description D328

(cis)-tert-Butyl 3-fluoro-4-(5-methyl-1-(2-methyl-6-(3-(2-((tetrahydro-2H-pyran-2-yl)oxy)ethoxy)azetidin-1-yl)pyrimidin-4-yl)-1H-indazol-6-yl)piperidine-1-carboxylate (Isomer 1, D328)

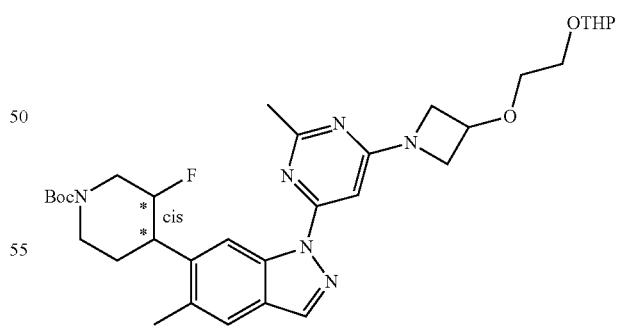

To a solution of (cis)-tert-butyl 3-fluoro-4-(5-methyl-1H-indazol-6-yl)piperidine-1-carboxylate (100 mg, 0.300 mmol) (enantiomer 1) in toluene (5 mL) was added 4-iodo-2-methyl-6-(3-(2-((tetrahydro-2H-pyran-2-yl)oxy)ethoxy)azetidin-1-yl)pyrimidine (151 mg, 0.360 mmol), N,N'-dimethyl-cyclohexane-1,2-diamine (128 mg, 0.900 mmol), CuI (171 mg, 0.900 mmol) and K$_3$PO$_4$ (191 mg, 0.900 mmol) at rt. The resulting mixture was warmed to 110° C. and stirred for 2 hrs. The reaction mixture was cooled to rt and poured into NH₃.H₂O (30%, 50 mL). The mixture was extracted with EtOAc (30 mL×3). The combined organic layers were washed with water (20 mL) and brine (20 mL), dried over Na₂SO₄ and concentrated. The residue was purified by prep. HPLC (condition: from 55% water (0.1% TFA) and 45% CH₃CN to 15% water (0.1% TFA) and 85% CH₃CN in 12 min). The eluents were collected and concentrated. The THP protected-group was moved during evaporation. The white solid was collected to give the title compound (120 mg, yield 64%).

D328 ¹H NMR (300 MHz, CD₃OD): δ 8.67 (s, 1H), 8.32 (s, 1H), 7.66 (s, 1H), 6.86 (s, 1H), 4.64-4.52 (m, 3H), 4.27-4.24 (m, 2H), 4.18-4.13 (m, 1H), 3.73-3.70 (m, 2H), 3.62-3.61 (m, 2H), 3.41-3.36 (m, 1H), 3.32-3.30 (m, 2H), 3.04-2.92 (m, 3H), 2.69 (s, 3H), 2.51 (s, 3H), 1.98-1.94 (m, 1H), 1.72-1.61 (m, 1H), 1.52 (s, 9H).

Description D329

(cis)-2-((1-(6-(6-(3-Fluoropiperidin-4-yl)-5-methyl-1H-indazol-1-yl)-2-methylpyrimidin-4-yl)azetidin-3-yl)oxy)ethanol hydrochloride (Enantiomer 1, D329)

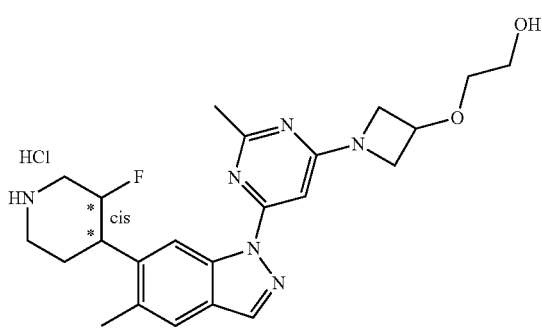

To a solution of (cis)-tert-butyl 3-fluoro-4-(5-methyl-1-(2-methyl-6-(3-(2-((tetrahydro-2H-pyran-2-yl)oxy)ethoxy) azetidin-1-yl)pyrimidin-4-yl)-1H-indazol-6-yl)piperidine-1-carboxylate (isomer 1, 120 mg, 0.220 mmol) in methanol (4 mL) was added HCl/methanol (8 mol/L, 4 mL) at rt. The resulting mixture was stirred at rt for 2 hrs. The reaction mixture was concentrated to give the title compound (85 mg, yield 94%) as a yellow solid.

D329 ¹H NMR (300 MHz, DMSO-d₆): δ 9.80 (br s, 1H), 9.43 (br s, 1H), 8.79 (s, 1H), 8.39 (s, 1H), 7.69 (s, 1H), 6.63 (s, 1H), 5.31-5.10 (m, 1H), 4.50-4.47 (m, 1H), 4.39-4.34 (m, 2H), 4.00-3.93 (m, 2H), 3.75-3.64 (m, 4H), 3.37-3.29 (m, 3H), 3.22-3.04 (m, 3H), 2.65 (s, 3H), 2.44 (s, 3H), 2.04-1.94 (m, 2H).

Description D330

(cis)-tert-Butyl 3-fluoro-4-(5-methyl-1-(2-methyl-6-(3-(2-((tetrahydro-2H-pyran-2-yl)oxy)ethoxy)azetidin-1-yl)pyrimidin-4-yl)-1H-indazol-6-yl)piperidine-1-carboxylate (Isomer 2, D330)

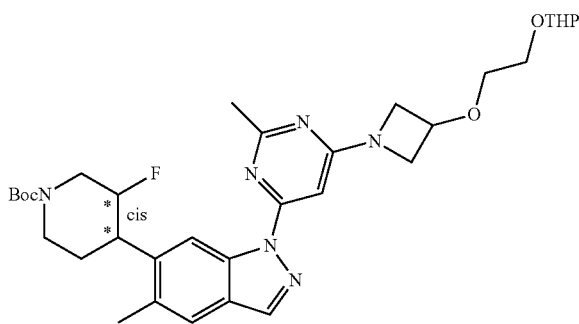

To a solution of (cis)-tert-butyl 3-fluoro-4-(5-methyl-1H-indazol-6-yl)piperidine-1-carboxylate (enantiomer 2, 100 mg, 0.30 mmol) in toluene (5 mL) was added 4-iodo-2-methyl-6-(3-(2-((tetrahydro-2H-pyran-2-yl)oxy)ethoxy) azetidin-1-yl)pyrimidine (151 mg, 0.36 mmol), N,N'-dimethyl-cyclohexane-1,2-diamine (128 mg, 0.90 mmol), CuI (171 mg, 0.90 mmol) and K₃PO₄ (191 mg, 0.90 mmol) at rt. The resulting mixture was warmed to 110° C. and stirred for 2 hrs. The reaction mixture was cooled to rt and poured into NH₃.H₂O (50 mL). The mixture was extracted with EtOAc (30 mL×3). The combined organic layers were washed with water (20 mL) and brine (20 mL) and dried over Na₂SO₄ and concentrated. The residue was purified by prep. HPLC (condition: from 60% water (0.1% TFA) and 40% CH₃CN to 20% water (0.1% TFA) and 80% CH₃CN in 12 min). The eluents were collected and concentrated. The THP protected-group was moved during evaporation. The white solid was collected to give the title compound (100 mg, yield 53%) as white solid.

D330 LCMS: [mobile phase: 40-95% CH₃CN in water (0.1% TFA) in 6.5 min], Rt=3.398 min; MS Calcd: 624; MS Found: 625 [M+H]⁺.

Description D331

(cis)-2-((1-(6-(6-(3-Fluoropiperidin-4-yl)-5-methyl-1H-indazol-1-yl)-2-methylpyrimidin-4-yl)azetidin-3-yl)oxy)ethanol hydrochloride (Enantiomer 2, D331)

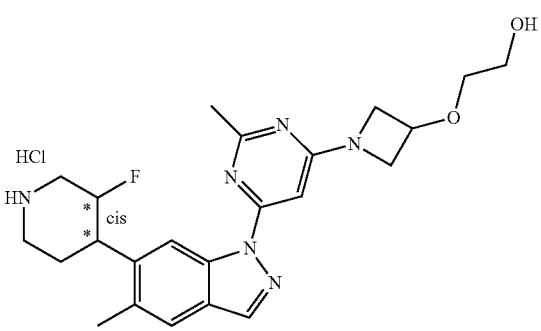 [SMILES: Cl ; Cc1nc(N2CC(OCCO)C2)cc(-n2ncc3cc(C)c(C4CCNCC4F)cc32)n1]

To a solution of (cis)-tert-butyl 3-fluoro-4-(5-methyl-1-(2-methyl-6-(3-(2-((tetrahydro-2H-pyran-2-yl)oxy)ethoxy)azetidin-1-yl)pyrimidin-4-yl)-1H-indazol-6-yl)piperidine-1-carboxylate (isomer 2, 100 mg, 0.16 mmol) in methanol (4 mL) was added HCl/methanol (8 mol/L, 4 mL) and stirred at rt for 2 hrs. The reaction mixture was concentrated to give the title compound (75 mg, yield 98%) as a yellow solid.

D331 $^1$H NMR (300 MHz, DMSO-d$_6$): δ 9.77 (br s, 1H), 9.39 (br s, 1H), 8.79 (s, 1H), 8.38 (s, 1H), 7.68 (s, 1H), 6.61 (s, 1H), 5.22-5.06 (m, 1H), 4.49-4.47 (m, 1H), 4.37-4.32 (m, 2H), 3.98-3.94 (m, 2H), 3.75-3.68 (m, 4H), 3.47-3.38 (m, 3H), 3.20-3.08 (m, 3H), 2.58 (s, 3H), 2.44 (s, 3H), 2.05-1.95 (m, 2H).

Description D332

(R)-(4-(6-iodo-2-methylpyrimidin-4-yl)morpholin-2-yl)methanol (D332)

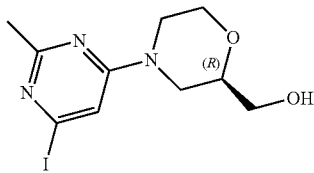

To a solution of (R)-morpholin-2-ylmethanol (300 mg, 2.56 mmol) and DIEA (992 mg, 7.68 mmol) in EtOH (10 mL) was added 4,6-diiodo-2-methylpyrimidine (885 mg, 2.56 mmol). The reaction was stirred at room temperature overnight. Solvent was removed in vacuum and the residue was purified by silica gel chromatography (eluted with PE/EtOAc=4:1) to give product (470 mg, yield 54.8%) as a pale yellow solid.

D332 $^1$H (400 MHz, CDCl$_3$): δ 6.79 (s, 1H), 4.16~4.06 (m, 2H), 4.06~4.02 (m, 1H), 3.79~3.73 (m, 1H), 3.70~3.57 (m, 3H), 3.04 (td, J=13.2, 3.6 Hz, 1H), 2.91 (dd, J=12.8, 10.4 Hz, 1H), 2.47 (s, 3H), 1.94 (t, J=6.0 Hz, 1H).

Description D333

(cis)-tert-Butyl 3-fluoro-4-(1-(6-((R)-2-(hydroxymethyl)morpholino)-2-methylpyrimidin-4-yl)-5-methyl-1H-indazol-6-yl)piperidine-1-carboxylate (Diastereoisomer 1, D333)

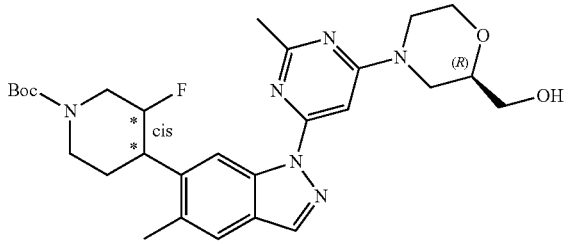

To a suspension of (cis)-tert-butyl 3-fluoro-4-(5-methyl-1H-indazol-6-yl)piperidine-1-carboxylate (enantiomer 1, 150 mg, 0.45 mmol), (R)-(4-(6-iodo-2-methylpyrimidin-4-yl)morpholin-2-yl)methanol (180 mg, 0.54 mmol), CuI (86 mg, 0.45 mmol) and K$_3$PO$_4$ (201 mg, 0.94 mmol) in dry toluene (10 mL) was added N,N-dimethyl-1,2-ethanediamine (80 mg, 0.90 mmol). The suspension was degassed with N$_2$ and stirred at 100° C. for 2 h. EtOAc (50 mL) was added and the resulting mixture was washed with water (50 mL), dried over anhydrous Na$_2$SO$_4$ and concentrated under reduced pressure. The residue was purified by silica gel chromatography (eluted with PE/EtOAc=2:1) to give product (185 mg, yield 76.1%) as a white solid.

D333 LC-MS (mobile phase: from 90% water (0.1% FA) and 10% CH$_3$CN (0.1% FA) to 5% water (0.1% FA) and 95% CH$_3$CN (0.1% FA) in 2.0 min, Rt=1.48 min; MS Calcd.: 540.6. MS Found: 541.3 (M+H)$^+$.

Description D334

((R)-4-(6-(6-((cis)-3-fluoropiperidin-4-yl)-5-methyl-1H-indazol-1-yl)-2-methylpyrimidin-4-yl)morpholin-2-yl)methanol (Diastereoisomer 1, D334)

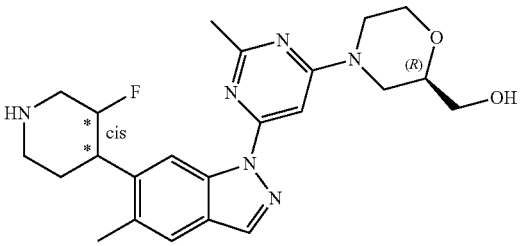

A mixture of (cis)-tert-butyl 3-fluoro-4-(1-(6-((R)-2-(hydroxymethyl)morpholino)-2-methyl pyrimidin-4-yl)-5-methyl-1H-indazol-6-yl)piperidine-1-carboxylate (diastereoisomer 1) (180 mg, 0.33 mmol) in HCl/EtOAc (1.0 M, 10 mL) was stirred at room temperature overnight. Sat. NaHCO$_3$ (20 mL) was added and the resulting mixture was extracted with EtOAc (2×30 mL). The combined extracts were dried over anhydrous Na$_2$SO$_4$ and concentrated under reduced pressure to give product (130 mg, yield 88.6%) as a white solid.

D334 LC-MS (mobile phase: from 90% water (0.1% FA) and 10% CH$_3$CN (0.1% FA) to 5% water (0.1% FA) and 95% CH$_3$CN (0.1% FA) in 2.0 min, Rt=0.96 min; MS Calcd.: 440.5. MS Found: 441.3 (M+H)$^+$.

Description D335

(cis)-tert-Butyl 3-fluoro-4-(1-(6-((R)-2-(hydroxymethyl)morpholino)-2-methylpyrimidin-4-yl)-5-methyl-1H-indazol-6-yl)piperidine-1-carboxylate (Diastereoisomer 2, D335)

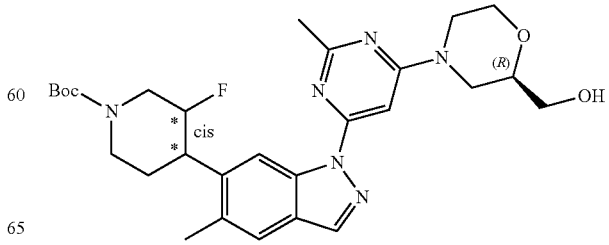

To a suspension of (cis)-tert-butyl 3-fluoro-4-(5-methyl-1H-indazol-6-yl)piperidine-1-carboxylate (enantiomer 2, 150 mg, 0.45 mmol), (R)-(4-(6-iodo-2-methylpyrimidin-4-yl)morpholin-2-yl)methanol (180 mg, 0.54 mmol), CuI (86 mg, 0.45 mmol) and K$_3$PO$_4$ (201 mg, 0.94 mmol) in dry toluene (10 mL) was added N,N-dimethyl-1,2-ethanediamine (80 mg, 0.90 mmol). The suspension was degassed with N$_2$ and stirred at 100° C. for 2 h. EtOAc (50 mL) was added and the resulting mixture was washed with water (50 mL), dried over anhydrous Na$_2$SO$_4$ and concentrated under reduced pressure. The residue was purified by pre-HPLC (Waters 2767/Qda, Waters XBridge 30*150 mm 5 um, Phase: MeCN/H$_2$O (0.1% TFA): 10%~95%, Flow rate: 20 mL/min, 214 nm/254 nm) to give product (130 mg, yield 53.4%) as a white solid.

D335 LC-MS (mobile phase: from 90% water (0.1% FA) and 10% CH$_3$CN (0.1% FA) to 5% water (0.1% FA) and 95% CH$_3$CN (0.1% FA) in 2.0 min, Rt=1.49 min; MS Calcd.: 540.6. MS Found: 541.3 (M+H)$^+$.

Description D336

((R)-4-(6-(6-((cis)-3-fluoropiperidin-4-yl)-5-methyl-1H-indazol-1-yl)-2-methylpyrimidin-4-yl)morpholin-2-yl)methanol (Diastereoisomer 2, D336)

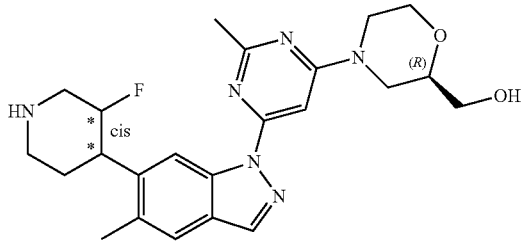

A mixture of (cis)-tert-butyl 3-fluoro-4-(1-(6-((R)-2-(hydroxymethyl)morpholino)-2-methyl pyrimidin-4-yl)-5-methyl-1H-indazol-6-yl)piperidine-1-carboxylate (diastereoisomer 2, 125 mg, 0.23 mmol) in HCl/EtOAc (1.0 M, 10 mL) was stirred at room temperature for 5.0 h. Sat. NaHCO$_3$ (25 mL) was added and the resulting mixture was extracted with EtOAc (2×30 mL). The combined extracts were washed with brine (30 mL), dried over anhydrous Na$_2$SO$_4$ and concentrated under reduced pressure to give product (104 mg, yield 100%) as a white solid.

D336 LC-MS (mobile phase: from 90% water (0.1% FA) and 10% CH$_3$CN (0.1% FA) to 5% water (0.1% FA) and 95% CH$_3$CN (0.1% FA) in 2.0 min, Rt=0.25 min; MS Calcd.: 440.5. MS Found: 441.3 (M+H)$^+$.

Description D337

(S)-(4-(6-iodo-2-methylpyrimidin-4-yl)morpholin-2-yl)methanol (D337)

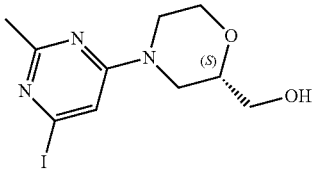

To a solution of (S)-morpholin-2-ylmethanol (300 mg, 2.56 mmol) and DIEA (992 mg, 7.68 mmol) in EtOH (10 mL) and THF (20 mL) was added 4,6-diiodo-2-methylpyrimidine (885 mg, 2.56 mmol). The reaction was stirred at room temperature overnight. Solvent was removed in vacuum and the residue was purified by silica gel chromatography (eluted with PE/EtOAc=4:1) to give product (420 mg, yield 48.8%) as a pale yellow solid.

D337 LC-MS (mobile phase: from 90% water (0.1% FA) and 10% CH$_3$CN (0.1% FA) to 5% water (0.1% FA) and 95% CH$_3$CN (0.1% FA) in 2.0 min, Rt=0.25 min; MS Calcd.: 335.1. MS Found: 336.0 (M+H)$^+$.

Description D338

(cis)-tert-Butyl 3-fluoro-4-(1-(6-((S)-2-(hydroxymethyl)morpholino)-2-methylpyrimidin-4-yl)-5-methyl-1H-indazol-6-yl)piperidine-1-carboxylate (Diastereoisomer 1, D338)

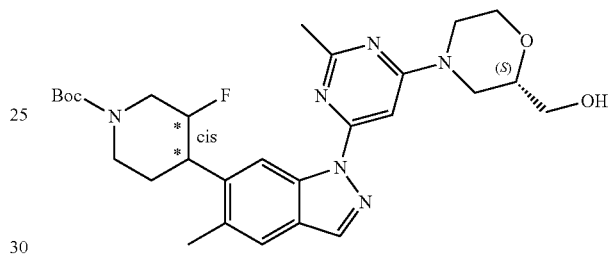

To a suspension of (cis)-tert-butyl 3-fluoro-4-(5-methyl-1H-indazol-6-yl)piperidine-1-carboxylate (enantiomer 1, 150 mg, 0.45 mmol), (S)-(4-(6-iodo-2-methylpyrimidin-4-yl)morpholin-2-yl)methanol (180 mg, 0.54 mmol), CuI (86 mg, 0.45 mmol) and K$_3$PO$_4$ (201 mg, 0.94 mmol) in dry toluene (10 mL) was added N,N-dimethyl-1,2-ethanediamine (80 mg, 0.90 mmol). The suspension was degassed with N$_2$ and stirred at 100° C. for 2 h. EtOAc (50 mL) was added and the resulting mixture was washed with water (50 mL), dried over anhydrous Na$_2$SO$_4$ and concentrated under reduced pressure. The residue was purified by silica gel chromatography (eluted with PE/EtOAc=2:1) to give product (185 mg, yield 76.1%) as a white solid.

D338 LC-MS (mobile phase: from 90% water (0.1% FA) and 10% CH$_3$CN (0.1% FA) to 5% water (0.1% FA) and 95% CH$_3$CN (0.1% FA) in 2.0 min, Rt=1.69 min; MS Calcd.: 540.6. MS Found: 541.3 (M+H)$^+$.

Description D339

((S)-4-(6-(6-((cis)-3-fluoropiperidin-4-yl)-5-methyl-1H-indazol-1-yl)-2-methylpyrimidin-4-yl)morpholin-2-yl)methanol (Enantiomer 1, D339)

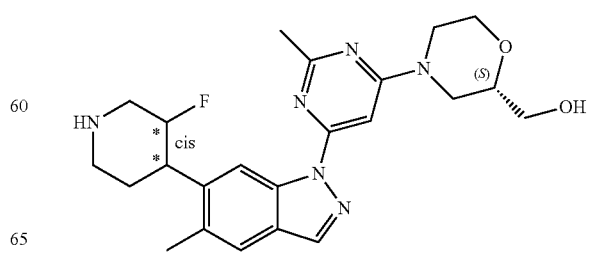

A mixture of (cis)-tert-butyl 3-fluoro-4-(1-(6-((S)-2-(hydroxymethyl)morpholino)-2-methyl pyrimidin-4-yl)-5-methyl-1H-indazol-6-yl)piperidine-1-carboxylate (diastereoisomer 1, 180 mg, 0.33 mmol) in HCl/EtOAc (1.0 M, 10 mL) was stirred at room temperature for 5.0 h. Water (30 mL) was added and the aqueous phase was basified with sat. NaHCO₃ to pH≈9. The resulting suspension was filtered and the filter cake was washed with water to give product (135 mg, yield 92.0%) as a white solid.

D339 LC-MS (mobile phase: from 90% water (0.1% FA) and 10% CH₃CN (0.1% FA) to 5% water (0.1% FA) and 95% CH₃CN (0.1% FA) in 2.0 min, Rt=1.13 min; MS Calcd.: 440.5. MS Found: 441.3 (M+H)⁺.

Description D340

(cis)-tert-Butyl 3-fluoro-4-(1-(6-((S)-2-(hydroxymethyl)morpholino)-2-methylpyrimidin-4-yl)-5-methyl-1H-indazol-6-yl)piperidine-1-carboxylate (Diastereoisomer 2, D340)

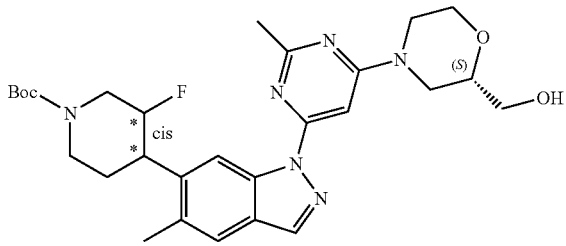

To a suspension of (cis)-tert-butyl 3-fluoro-4-(5-methyl-1H-indazol-6-yl)piperidine-1-carboxylate (enantiomer 2, 150 mg, 0.45 mmol), (S)-(4-(6-iodo-2-methylpyrimidin-4-yl)morpholin-2-yl)methanol (180 mg, 0.54 mmol), CuI (86 mg, 0.45 mmol) and K₃PO₄ (201 mg, 0.94 mmol) in dry toluene (10 mL) was added N,N-dimethyl-1,2-ethanediamine (80 mg, 0.90 mmol). The suspension was degassed with N₂ and stirred at 100° C. for 2 h. EtOAc (50 mL) was added and the resulting mixture was washed with water (50 mL), dried over anhydrous Na₂SO₄ and concentrated under reduced pressure. The residue was purified by silica gel chromatography (eluted with PE/EtOAc=2:1) to give product (180 mg, yield 74.0%) as a white solid.

D340 LC-MS (mobile phase: from 90% water (0.1% FA) and 10% CH₃CN (0.1% FA) to 5% water (0.1% FA) and 95% CH₃CN (0.1% FA) in 2.0 min, Rt=1.26 min; MS Calcd.: 540.6. MS Found: 541.3 (M+H)⁺.

Description D341

((S)-4-(6-(6-((cis)-3-Fluoropiperidin-4-yl)-5-methyl-1H-indazol-1-yl)-2-methylpyrimidin-4-yl)morpholin-2-yl)methanol (Diastereoisomer 2, D341)

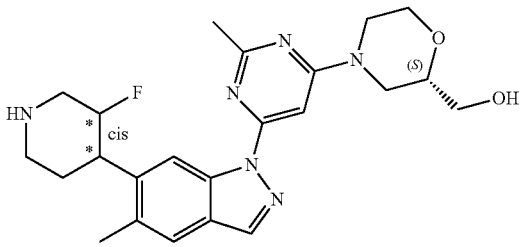

A mixture of (cis)-tert-butyl 3-fluoro-4-(1-(6-((S)-2-(hydroxymethyl)morpholino)-2-methyl pyrimidin-4-yl)-5-methyl-1H-indazol-6-yl)piperidine-1-carboxylate (diastereoisomer 2) (178 mg, 0.33 mmol) in HCl/EtOAc (1.0 M, 10 mL) was stirred at room temperature overnight. Water (40 mL) was added and the aqueous layer was basified with sat. NaHCO₃ to pH≈9. The resulting suspension was filtered and the filter cake was washed with water to give product (120 mg, yield 82.7%) as a white solid.

LC-MS (mobile phase: from 90% water (0.1% FA) and 10% CH₃CN (0.1% FA) to 5% water (0.1% FA) and 95% CH₃CN (0.1% FA) in 2.0 min, Rt=0.95 min; MS Calcd.: 440.5. MS Found: 441.3 (M+H)⁺.

Description D342

(R)-(4-(6-Iodo-2-methoxypyrimidin-4-yl)morpholin-2-yl)methanol (D342)

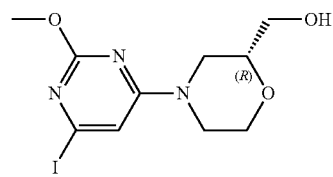

4,6-Diiodo-2-methoxypyrimidine (724 mg, 2.0 mmol) was added to the solution of (R)-morpholin-2-ylmethanol (235 mg, 2.0 mmol) and Et₃N (0.4 mL in MeOH (15 mL) at rt and the reaction was stirred at rt for 1 hour until all solid was dissolved. Then the reaction solution was concentrated and the residue was purified by silica gel chromatography (eluted with PE/EtOAc=2/1~1/1) to give product (680 mg, yield 97%) as a white solid.

D342 ¹H NMR (400 MHz, CDCl₃): δ 6.65 (s, 1H), 4.15~4.01 (m, 3H), 3.91 (s, 3H), 3.77~3.72 (m, 1H), 3.69~3.57 (m, 3H), 3.10~3.06 (m, 1H), 2.95~2.88 (m, 1H), 1.96~1.92 (m, 1H).

Description D343

(cis)-tert-Butyl 3-fluoro-4-(1-(6-((R)-2-(hydroxymethyl)morpholino)-2-methoxypyrimidin-4-yl)-5-methyl-1H-indazol-6-yl)piperidine-1-carboxylate (Diastereoisomer 1, D343)

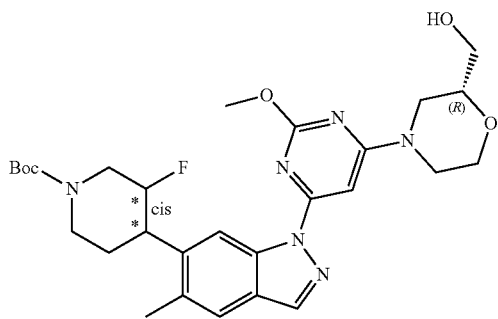

The mixture of (cis)-tert-butyl 3-fluoro-4-(5-methyl-1H-indazol-6-yl)piperidine-1-carboxylate (enantiomer 1, 150 mg, 0.45 mmol), (R)-(4-(6-iodo-2-methoxypyrimidin-4-yl)morpholin-2-yl) methanol (180 mg, 0.52 mmol), CuI (190 mg, 1.0 mmol) and $K_3PO_4$ (212 mg, 1.0 mmol) in toluene (10 mL) was degassed and protected with $N_2$ before N,N-dimethyl-1,2-ethanediamine (88 mg, 1.0 mmol) was added. Then the reaction mixture was stirred at 100° C. for 1 hour. The reaction mixture was concentrated and the residue was purified by silica column chromatography (EtOAc/PE=1/1) to give the desired product as a white solid. (165 mg, 64% yield)

D343 $^1$H NMR (400 MHz, $CDCl_3$): δ 8.83 (s, 1H), 8.09 (s, 1H), 7.55 (s, 1H), 6.85 (s, 1H), 4.75~4.62 (m, 2H), 4.28 (br, 3H), 4.07~4.05 (m, 1H), 4.07 (s, 3H), 3.81~3.66 (m, 4H), 3.25~3.08 (m, 2H), 3.01~2.804 (m, 3H), 2.50 (s, 4H), 1.98~1.92 (m, 2H), 1.79~1.71 (m, 1H), 1.51 (s, 9H).

LC-MS (mobile phase: mobile phase: from 40% water (0.1% FA) and 60% $CH_3CN$ (0.1% FA) to 5% water (0.1% FA) and 95% $CH_3CN$ (0.1% FA) in 10.0 min, Rt=7.10 min; MS Calcd.: 556.2, MS Found: 557.8 $[M+H]^+$.

Description D344

((R)-4-(6-(6-(3-fluoropiperidin-4-yl)-5-methyl-1H-indazol-1-yl)-2-methoxypyrimidin-4-yl)morpholin-2-yl)methanol (Diastereoisomer 1, D344)

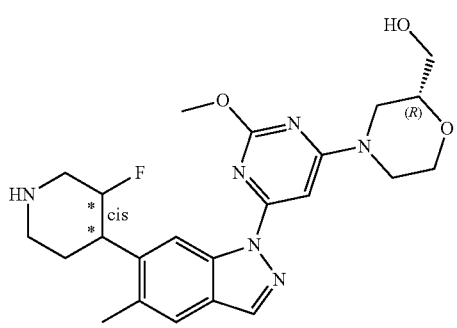

TFA (1.0 mL) was added to the solution of (cis)-tert-butyl 3-fluoro-4-(1-(6-((R)-2-(hydroxymethyl) morpholino)-2-methoxypyrimidin-4-yl)-5-methyl-1H-indazol-6-yl)piperidine-1-carboxylate (diastereoisomer 1, 165 mg, 0.30 mmol) in DCM (5 mL). The reaction was stirred at rt for 2 hours and then the reaction solution was concentrated. The residue was diluted with MeOH (5 mL) and then $K_2CO_3$ (138 mg, 1.0 mmol) was added before the mixture was stirred at RT for 1 hour. Then, the mixture was diluted with brine (10 mL) and extracted with DCM/MeOH (10/1, 3×20 mL). The obtained solution was dried over anhydrous $Na_2SO_4$ and concentrated to crude product as an off-white solid. (155 mg, 100% yield). The crude product was used to next step without further purification.

D344 LC-MS (mobile phase: mobile phase: from 90% water (0.1% FA) and 10% $CH_3CN$ (0.1% FA) to 5% water (0.1% FA) and 95% $CH_3CN$ (0.1% FA) in 2.0 min, Rt=1.17 min; MS Calcd.: 456.2, MS Found: 457.3 $[M+H]^+$.

Description D345

(cis)-tert-Butyl 3-fluoro-4-(1-(6-((R)-2-(hydroxymethyl)morpholino)-2-methoxypyrimidin-4-yl)-5-methyl-1H-indazol-6-yl)piperidine-1-carboxylate (Diastereoisomer 2, D345)

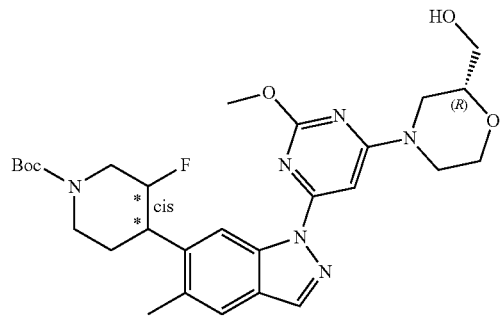

The mixture of (cis)-tert-butyl 3-fluoro-4-(5-methyl-1H-indazol-6-yl)piperidine-1-carboxylate (enantiomer 2, 150 mg, 0.45 mmol), (R)-(4-(6-iodo-2-methoxypyrimidin-4-yl)morpholin-2-yl) methanol (180 mg, 0.52 mmol), CuI (190 mg, 1.0 mmol) and $K_3PO_4$ (212 mg, 1.0 mmol) in toluene (10 mL) was degassed and protected with $N_2$ before N,N-dimethyl-1,2-ethanediamine (88 mg, 1.0 mmol) was added. Then the reaction mixture was stirred at 100° C. for 1 hour. The reaction mixture was concentrated and the residue was purified by silica column chromatography (EtOAc/PE=1/1) to give the desired product as a white solid. (170 mg, 71% yield)

D345 LC-MS (mobile phase: mobile phase: from 40% water (0.1% FA) and 60% $CH_3CN$ (0.1% FA) to 5% water (0.1% FA) and 95% $CH_3CN$ (0.1% FA) in 10.0 min, Rt=7.12 min; MS Calcd.: 556.2, MS Found: 557.8 $[M+H]^+$.

Description D346

((R)-4-(6-(6-(3-fluoropiperidin-4-yl)-5-methyl-1H-indazol-1-yl)-2-methoxypyrimidin-4-yl)morpholin-2-yl)methanol (Diastereoisomer 2, D346)

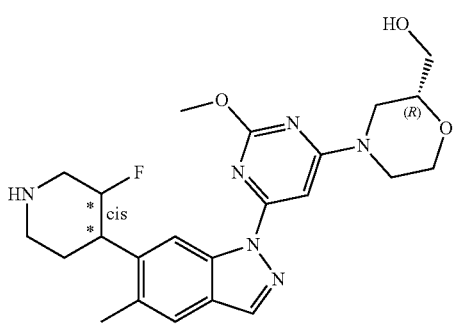

TFA (1.0 mL) was added to the solution of (cis)-tert-butyl 3-fluoro-4-(1-(6-((R)-2-(hydroxymethyl)morpholino)-2-methoxypyrimidin-4-yl)-5-methyl-1H-indazol-6-yl)piperidine-1-carboxylate (diastereoisomer 2, 170 mg, 0.31 mmol) in DCM (5 mL). The reaction was stirred at RT for 2 hours and then the reaction solution was concentrated. The residue was diluted with MeOH (5 mL) and then $K_2CO_3$ (138 mg, 1.0 mmol) was added before the mixture was stirred at RT for 1 hour. Then, the mixture was diluted with brine (10 mL) and extracted with DCM/MeOH (10/1, 3×20 mL). The obtained solution was dried over anhydrous $Na_2SO_4$ and concentrated to crude product as an off-white solid. (140 mg, 100% yield). The crude product was used to next step without further purification.

D346 LC-MS (mobile phase: mobile phase: from 90% water (0.1% FA) and 10% $CH_3CN$ (0.1% FA) to 5% water (0.1% FA) and 95% $CH_3CN$ (0.1% FA) in 2.0 min, Rt=1.18 min; MS Calcd.: 456.2, MS Found: 457.3 $[M+H]^+$.

Description D347

(S)-(4-(6-iodo-2-methoxypyrimidin-4-yl)morpholin-2-yl)methanol (D347)

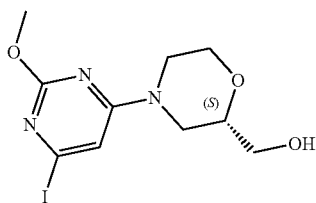

4,6-Diiodo-2-methoxypyrimidine (680 mg, 1.9 mmol) was added to the solution of (S)-morpholin-2-yl-methanol (235 mg, 2.0 mmol) and $Et_3N$ (0.4 mL0 in MeOH (15 mL) at RT and the reaction was stirred at RT for 1 hour until all solid was dissolved. Then the reaction solution was concentrated and the residue was purified by silica gel chromatography (eluted with PE/EtOAc=2/1~2/1) to give product (680 mg, yield 97%) as a colorless oil.

D347 $^1$H NMR (400 MHz, $CDCl_3$): δ 6.65 (s, 1H), 4.15~4.01 (m, 3H), 3.91 (s, 3H), 3.77~3.72 (m, 1H), 3.69~3.57 (m, 3H), 3.10~3.06 (m, 1H), 2.95~2.88 (m, 1H), 1.96~1.92 (m, 1H).

Description D348

(cis)-tert-Butyl 3-fluoro-4-(1-(6-((S)-2-(hydroxymethyl)morpholino)-2-methoxypyrimidin-4-yl)-5-methyl-1H-indazol-6-yl)piperidine-1-carboxylate (Diastereoisomer 1, D348)

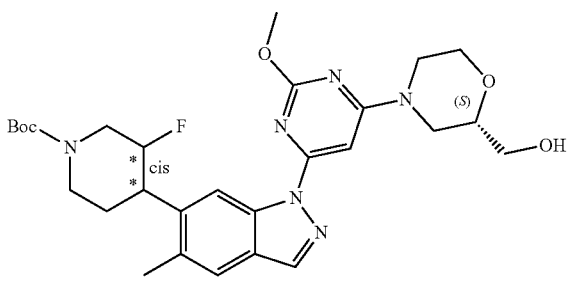

The mixture of (cis)-tert-butyl 3-fluoro-4-(5-methyl-1H-indazol-6-yl)piperidine-1-carboxylate (enantiomer 1, 150 mg, 0.45 mmol), (S)-(4-(6-Iodo-2-methoxypyrimidin-4-yl)morpholin-2-yl)methanol (173.7 mg, 0.50 mmol), CuI (171 mg, 0.90 mmol) and $K_3PO_4$ (191 mg, 0.90 mmol) in toluene (20 mL) was degassed and protected with $N_2$ before N,N-dimethyl-1,2-ethanediamine (80 mg, 0.90 mmol) was added. Then the reaction mixture was stirred at 95° C. for 1 hour. The reaction mixture was concentrated and the residue was purified by silica column chromatography (EtOAc/PE=1/1) to give the desired product as a white solid. (110 mg, 42% yield)

D348 LC-MS (mobile phase: mobile phase: from 40% water (0.1% FA) and 60% $CH_3CN$ (0.1% FA) to 5% water (0.1% FA) and 95% $CH_3CN$ (0.1% FA) in 10.0 min, Rt=7.07 min; MS Calcd.: 556.2, MS Found: 557.8 $[M+H]^+$.

Description D349

((S)-4-(6-(6-((3-fluoropiperidin-4-yl)-5-methyl-1H-indazol-1-yl)-2-methoxypyrimidin-4-yl)morpholin-2-yl)methanol (Diastereoisomer 1, D349)

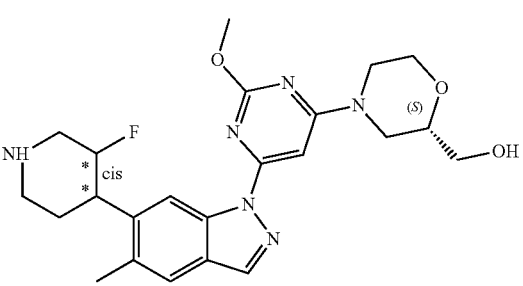

TFA (1.2 mL) was added to the solution of tert-butyl 3-fluoro-4-(1-(6-((S)-2-(hydroxyl methyl)morpholino)-2-methoxypyrimidin-4-yl)-5-methyl-1H-indazol-6-yl)piperidine-1-carboxylate (diastereoisomer 1, 110 mg, 0.197 mmol) in DCM (7 mL). The reaction was stirred at rt for 2 hours and then the reaction solution was concentrated. The residue was diluted with MeOH (10 mL) and then K₂CO₃ (500 mg, 2.0 mmol) was added before the mixture was stirred at RT for 2 hours. Then, the mixture was diluted with water (80 mL) and extracted with DCM (2×50 mL). The obtained solution was washed with brine (2×100 mL). The organic solution was dried over anhydrous Na₂SO₄ and concentrated to give the crude product as a yellow solid. (80 mg, 88% yield). The crude product was used to next step without further purification.

D349 LC-MS (mobile phase: mobile phase: from 90% water (0.1% FA) and 10% CH₃CN (0.1% FA) to 5% water (0.1% FA) and 95% CH₃CN (0.1% FA) in 2.5 min, Rt=1.123 min; MS Calcd.: 456.2, MS Found: 457.3 [M+H]⁺.

Description D350

(cis)-tert-Butyl 3-fluoro-4-(1-(6-(((S)-2-(hydroxymethyl)morpholino)-2-methoxypyrimidin-4-yl)-5-methyl-1H-indazol-6-yl)piperidine-1-carboxylate (Diastereoisomer 2, D350)

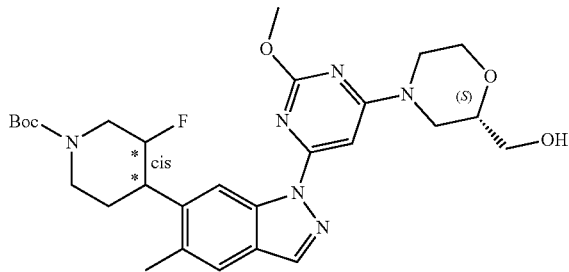

The mixture of (cis)-tert-butyl 3-fluoro-4-(5-methyl-1H-indazol-6-yl)piperidine-1-carboxylate (enantiomer 2, 150 mg, 0.45 mmol), (S)-(4-(6-Iodo-2-methoxypyrimidin-4-yl)morpholin-2-yl)methanol (173.7 mg, 0.50 mmol), CuI (171 mg, 0.90 mmol) and K₃PO₄ (191 mg, 0.90 mmol) in toluene (20 mL) was degassed and protected with N₂ before N,N-dimethyl-1,2-ethanediamine (80 mg, 0.90 mmol) was added. Then the reaction mixture was stirred at 95° C. for 2 hour. The reaction mixture was concentrated and the residue was purified by silica column chromatography (EtOAc/PE=1/1) to give the desired product as a white solid. (200 mg, 80% yield).

D350 LC-MS (mobile phase: mobile phase: from 40% water (0.1% FA) and 60% CH₃CN (0.1% FA) to 5% water (0.1% FA) and 95% CH₃CN (0.1% FA) in 10.0 min, Rt=7.10 min; MS Calcd.: 556.2, MS Found: 557.8 [M+H]⁺.

Description D351

((S)-4-(6-(6-((3-fluoropiperidin-4-yl)-5-methyl-1H-indazol-1-yl)-2-methoxypyrimidin-4-yl)morpholin-2-yl)methanol (Diastereoisomer 2, D351)

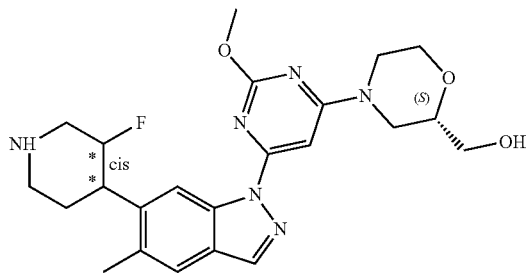

TFA (1.2 mL) was added to the solution of (cis)-tert-butyl 3-fluoro-4-(1-(6-(((S)-2-(hydroxyl methyl)morpholino)-2-methoxypyrimidin-4-yl)-5-methyl-1H-indazol-6-yl)piperidine-1-carboxylate (diastereoisomer 2, 200 mg, 0.34 mmol) in DCM (8 mL). The reaction was stirred at RT for 2 hours and then the reaction solution was concentrated. The residue was diluted with MeOH (15 mL) and then K₂O₃ (500 mg, 3.4 mmol) was added before the mixture was stirred at RT for overnight. Then the mixture was diluted with water (50 mL) and extracted with DCM (2×80 mL). The obtained solution was washed with brine (2×100 mL). The organic solution was dried over anhydrous Na₂SO₄ and concentrated to crude product as an off-white solid (130 mg, 83.8% yield). The crude product was used to next step without further purification.

D351 LC-MS (mobile phase: mobile phase: from 90% water (0.1% FA) and 10% CH₃CN (0.1% FA) to 5% water (0.1% FA) and 95% CH₃CN (0.1% FA) in 2.5 min, Rt=1.136 min; MS Calcd.: 456.2, MS Found: 457.3 [M+H]⁺.

Description D352

4-(Azetidin-1-yl)-6-iodo-2-methylpyrimidine (D352)

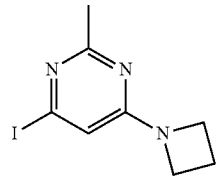

To a solution of 4,6-diiodo-2-methylpyrimidine (1.38 g, 4.0 mmol) and azetidine (228 mg, 4.0 mmol) in THF/EtOH (30 mL/30 mL) was added DIEA (1.55 g, 12.0 mmol). Then, the reaction was stirred at room temperature for 16 hours. Then, the reaction was concentrated and purified by column (PE:EtOAc=8:1-6:1-4:1-3:1~EtOAc) to get a white solid (774 g, yield 70.6%).

D352 ¹H NMR (400 MHz, DMSO-d₆): δ 6.64 (s, 1H), 4.01-3.97 (t, J=7.6 Hz, 4H), 2.35-2.30 (m, 2H), 2.28 (s, 3H).

Description D353

(cis)-tert-Butyl 4-(1-(6-(azetidin-1-yl)-2-methylpyrimidin-4-yl)-5-methyl-1H-indazol-6-yl)-3-fluoropiperidine-1-carboxylate (Enantiomer 1, D353)

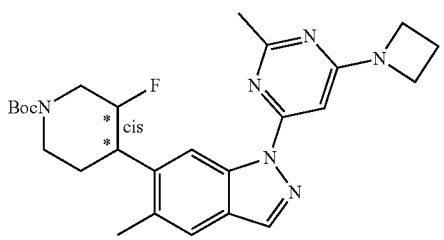 [SMILES: Cc1nc(N2CCC2)cc(-n2ncc3cc(C)c(C4CCN(C(=O)OC(C)(C)C)CC4F)cc32)n1]

To a suspension of (cis)-tert-butyl 3-fluoro-4-(5-methyl-1H-indazol-6-yl)piperidine-1-carboxylate (enantiomer 1, 80 mg, 0.24 mmol), 4-(azetidin-1-yl)-6-iodo-2-methylpyrimidine (99 mg, 0.36 mmol), CuI (45 mg, 0.24 mmol) and K$_3$PO$_4$ (100 mg, 0.48 mmol) in dry toluene (2 mL) was added N,N-dimethyl-1,2-ethanediamine (45 mg, 0.24 mmol). The suspension was degassed with Ar and refluxed at 90° C. for 2 h. The solvent was removed under vacuum and the residue was purified by silica gel chromatography (eluted with PE/EtOAc=5:1) to give product (60 mg, yield 52.1%) as a white solid.

D353 $^1$H NMR (400 MHz, CDCl$_3$): δ 8.87 (s, 1H), 8.07 (s, 1H), 7.53 (s, 1H), 6.54 (s, 1H), 4.79-4.64 (m, 2H), 4.18-4.15 (m, 5H), 3.28-3.19 (m, 1H), 2.88-2.85 (m, 2H), 2.58 (s, 3H), 2.49 (s, 3H), 2.46-2.38 (m, 2H), 1.96-1.77 (m, 2H), 1.51 (s, 9H).

Description D354

(cis)-tert-Butyl 4-(1-(6-(azetidin-1-yl)-2-methylpyrimidin-4-yl)-5-methyl-1H-indazol-6-yl)-3-fluoropiperidine-1-carboxylate (Enantiomer 2, D354)

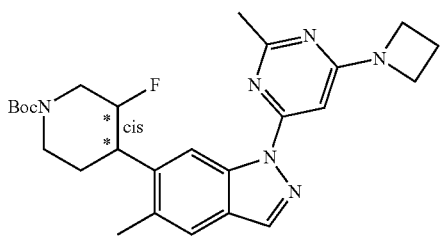 [SMILES: Cc1nc(N2CCC2)cc(-n2ncc3cc(C)c(C4CCN(C(=O)OC(C)(C)C)CC4F)cc32)n1]

To a suspension of (cis)-tert-butyl 3-fluoro-4-(5-methyl-1H-indazol-6-yl)piperidine-1-carboxylate (enantiomer 2, 80 mg, 0.24 mmol), 4-(azetidin-1-yl)-6-iodo-2-methylpyrimidine (99 mg, 0.36 mmol), CuI (45 mg, 0.24 mmol) and K$_3$PO$_4$ (100 mg, 0.48 mmol) in dry toluene (2 mL) was added N,N-dimethyl-1,2-ethanediamine (45 mg, 0.24 mmol). The suspension was degassed with N$_2$ and refluxed for 2 h. The solvent was removed under vacuum and the residue was purified by silica gel chromatography (eluted with PE/EtOAc=4:1 to 2:1) to give product (72 mg, yield 62%) as a white solid.

D354 LC-MS (mobile phase: from 50% water (0.1% FA) and 50% CH$_3$CN (0.1% FA) to 50% water (0.1% FA) and 50% CH$_3$CN (0.1% FA) in 2.5 min, Rt=1.45 min; MS Calcd.: 480.26, MS Found: 481.4 (M+H)$^+$.

Description D355

(cis)-tert-Butyl 4-(1-(6-(((1R,3R)-3-(benzyloxy)cyclobutyl)-2-methylpyrimidin-4-yl)-5-methyl-1H-indazol-6-yl)-3-fluoropiperidine-1-carboxylate (Enantiomer 1, D355)

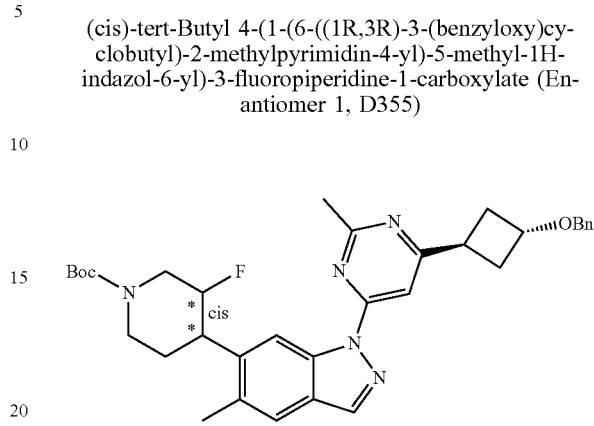

To a solution of (cis)-tert-butyl 3-fluoro-4-(5-methyl-1H-indazol-6-yl)piperidine-1-carboxylate (100 mg, 0.300 mmol) (enantiomer 1) in toluene (5 mL) was added 4-((1R,3R)-3-(benzyloxy)cyclobutyl)-6-chloro-2-methylpyrimidine (130 mg, 0.450 mmol), CuI (171 mg, 0.900 mmol), K$_3$PO$_4$ (191 mg, 0.900 mmol) and N,N'-dimethyl-cyclohexane-1,2-diamine (128 mg, 0.900 mmol). The mixture was refluxed under N$_2$ protected for 4 hrs. The reaction mixture was cooled to rt and then poured into NH$_3$.H$_2$O (30%, 100 mL) and extracted with EtOAc (100 mL×2). The combined organic layers were washed with brine (100 mL), dried over Na$_2$SO$_4$ and concentrated. The crude was purified by column chromatography (PE:EA=15:1) to give the crude compound (160 mg) as a white solid. The crude was separated by chiral HPLC under the condition (Chiralpak ID 5 um 20*250 mm, Hex/EtOH=70/30, Flow Rate: 15 ml/min, 205 nm, T=30° C.) to give the title compound (97 mg, yield 55%) as white solid.

D355 $^1$H NMR (400 MHz, CDCl$_3$): δ 8.87 (s, 1H), 8.12 (s, 1H), 7.65 (s, 1H), 7.57 (s, 1H), 7.37-7.26 (m, 5H), 4.84-4.49 (m, 2H), 4.48 (s, 2H), 4.44-4.41 (m, 1H), 4.40-4.26 (m, 1H), 3.68-3.61 (m, 1H), 3.30-3.25 (m, 1H), 2.96-2.79 (m, 2H), 2.77 (s, 3H), 2.64-2.62 (m, 2H), 2.57-2.55 (m, 2H), 2.51 (s, 3H), 1.98-1.94 (m, 1H), 1.86-1.80 (m, 1H), 1.53 (s, 9H).

LC-MS: N/A.

Description D356

(cis)-tert-Butyl 3-fluoro-4-(1-(6-((1r,3r)-3-hydroxycyclobutyl)-2-methylpyrimidin-4-yl)-5-methyl-1H-indazol-6-yl)piperidine-1-carboxylate (Enantiomer 1, D356)

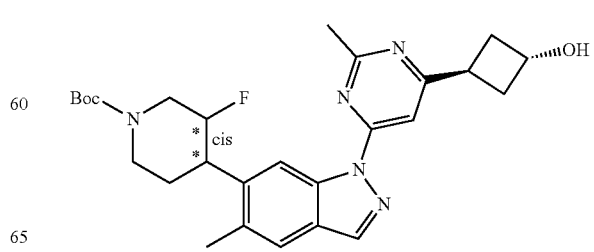

To a solution of (cis)-tert-butyl 4-(1-(6-((1R,3R)-3-(benzyloxy)cyclobutyl)-2-methylpyrimidin-4-yl)-5-methyl-1H-indazol-6-yl)-3-fluoropiperidine-1-carboxylate (enantiomer 1, 97 mg, 0.17 mmol) in CH₃OH (10 mL) was added Pd/C (10%, 60 mg). The mixture was stirred under H₂ (50 psi) at 40° C. overnight. The mixture was filtered and the filtrate was concentrated. To the residue was added CH₃OH (10 mL) and Pd/C (10%, 50 mg). And the mixture was stirred under H₂ (50 psi) at 40° C. for 2.5 days. The mixture was filtered and the filtrate was concentrated. The residue was purified by prep. TLC (CH₂Cl₂:CH₃OH=50:1) to give the title compound (27 mg, yield 32%) as yellow solid.

D356 ¹H NMR (300 MHz, CDCl₃): δ 8.85 (s, 1H), 8.12 (s, 1H), 7.65 (s, 1H), 7.56 (s, 1H), 4.84-4.54 (m, 3H), 4.29-4.11 (m, 1H), 3.67-3.58 (m, 1H), 3.30-3.21 (m, 1H), 2.97-2.78 (m, 2H), 2.76-2.66 (m, 5H), 2.51-2.40 (m, 5H), 2.03-1.73 (m, 3H), 1.52 (m, 9H).

Description D357

(cis)-(1R,3R)-3-(6-(6-(3-fluoropiperidin-4-yl)-5-methyl-1H-indazol-1-yl)-2-methylpyrimidin-4-yl)cyclobutanol hydrochloride (Enantiomer 1, D357)

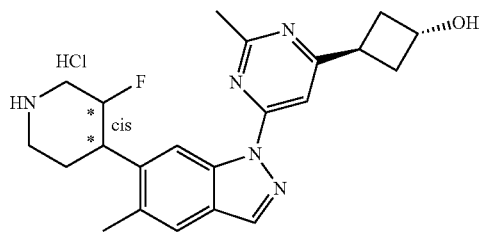 [SMILES: Cc1nc(-n2ncc3cc(C)c(C4CCNCC4F)cc32)cc([C@H]2C[C@H](O)C2)n1 ; Cl]

To a solution of (cis)-tert-butyl 3-fluoro-4-(1-(6-((1r,3r)-3-hydroxycyclobutyl)-2-methylpyrimidin-4-yl)-5-methyl-1H-indazol-6-yl)piperidine-1-carboxylate (enantiomer 1, 27 mg, 0.05 mmol) in CH₃OH (1.5 mL) was added HCl/CH₃OH (8 mol/L, 1.0 mL). The mixture was stirred at rt for 1 h. The reaction mixture was concentrated to give the title compound (21 mg, yield 97%) as a yellow solid.

D357 LCMS [mobile phase: 5-95% CH₃CN in 3 min]: Rt=1.41 min; MS Calcd: 395; MS Found: 396 [M+H]⁺.

Description D358

(cis)-tert-Butyl 4-(1-(6-((1R,3R)-3-(benzyloxy)cyclobutyl)-2-methylpyrimidin-4-yl)-5-methyl-1H-indazol-6-yl)-3-fluoropiperidine-1-carboxylate (Enantiomer 2, D358)

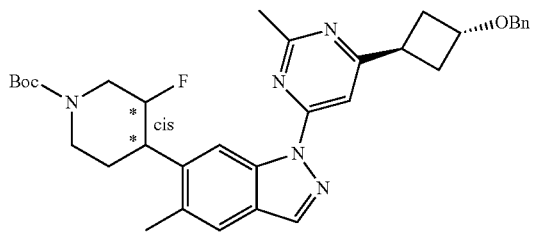 [SMILES: Cc1nc(-n2ncc3cc(C)c(C4CCN(C(=O)OC(C)(C)C)CC4F)cc32)cc([C@H]2C[C@H](OCc3ccccc3)C2)n1]

To a solution of (cis)-tert-butyl 3-fluoro-4-(5-methyl-1H-indazol-6-yl)piperidine-1-carboxylate (enantiomer 2, 100 mg, 0.300 mmol) in toluene (5 mL) was added 4-((1R,3R)-3-(benzyloxy)cyclobutyl)-6-chloro-2-methylpyrimidine (100 mg, 0.350 mmol), CuI (171 mg, 0.900 mmol), K₃PO₄ (191 mg, 0.900 mmol) and N,N'-dimethyl-cyclohexane-1,2-diamine (128 mg, 0.900 mmol). The mixture was refluxed for 4 hrs under N₂. Then the reaction mixture was cooled to rt and poured into NH₃.H₂O (30%, 100 mL). EtOAc (100 mL×2) was added to extract the desired compound. The combined organic layers were washed with brine (100 mL), dried over Na₂SO₄ and concentrated. The residue was purified by column chromatography (PE:EA=15:1) to give the crude compound (166 mg) as yellow liquid. The crude was separated by chiral HPLC under the condition (Chiralpak ID 5 um 20*250 mm, Hex/EtOH=70/30, Flow Rate: 15 ml/min, 205 nm, T=30° C.) to give the title compound to give the title compound (70 mg, yield 40%) as white solid.

D358 ¹H NMR (300 MHz, CDCl₃): δ 8.86 (s, 1H), 8.12 (s, 1H), 7.65 (s, 1H), 7.56 (s, 1H), 7.37-7.26 (m, 5H), 4.81-4.49 (m, 2H), 4.48 (s, 2H), 4.45-4.01 (m, 1H), 4.30-4.19 (m, 1H), 3.68-3.62 (m, 1H), 3.30-3.24 (m, 1H), 2.91-2.78 (m, 2H), 2.77 (s, 3H), 2.64-2.52 (m, 4H), 2.51 (s, 3H), 1.97-1.94 (m, 1H), 1.83-1.79 (m, 1H), 1.53 (s, 9H).

Description D359

(cis)-tert-Butyl 3-fluoro-4-(1-(6-((1R,3R)-3-hydroxycyclobutyl)-2-methylpyrimidin-4-yl)-5-methyl-1H-indazol-6-yl)piperidine-1-carboxylate (Enantiomer 2, D359)

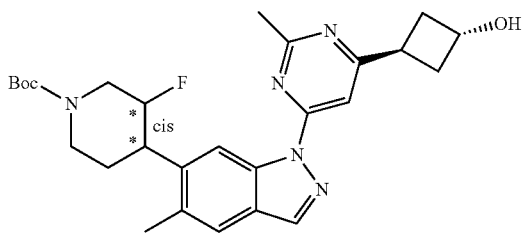 [SMILES: Cc1nc(-n2ncc3cc(C)c(C4CCN(C(=O)OC(C)(C)C)CC4F)cc32)cc([C@H]2C[C@H](O)C2)n1]

To a solution of (cis)-tert-butyl 4-(1-(6-((1r,3r)-3-(benzyloxy)cyclobutyl)-2-methylpyrimidin-4-yl)-5-methyl-1H-indazol-6-yl)-3-fluoropiperidine-1-carboxylate (enantiomer 2, 70 mg, 0.12 mmol) in CH₃OH (4.5 mL) was added Pd/C (10%, 50 mg). The mixture was stirred under H₂ (50 psi) at 40° C. overnight. The mixture was filtered and the filtrate was concentrated. To the residue was added CH₃OH (3 mL) and Pd/C (10%, 40 mg). And the mixture was stirred under H₂ (50 psi) at 40° C. overnight. Then the mixture was filtered and the filtrate was concentrated. The residue was purified by preparative TLC (CH₂Cl₂:CH₃OH=15:1) to give the title compound (21 mg, yield 35%) as white solid.

D359 ¹H NMR (300 MHz, CDCl₃): δ 8.86 (s, 1H), 8.12 (s, 1H), 7.65 (s, 1H), 7.56 (s, 1H), 4.86-4.57 (m, 3H), 4.29-4.17 (m, 1H), 3.68-3.59 (m, 1H), 3.27-3.24 (m, 1H), 2.97-2.83 (m, 2H), 2.77 (s, 3H), 2.74-2.66 (m, 2H), 2.51-2.40 (m, 5H), 2.03-1.79 (m, 3H), 1.53 (m, 9H).

Description D360

(cis)-(1R,3R)-3-(6-(6-(3-Fluoropiperidin-4-yl)-5-methyl-1H-indazol-1-yl)-2-methylpyrimidin-4-yl)cyclobutanol hydrochloride (Enantiomer 2, D360)

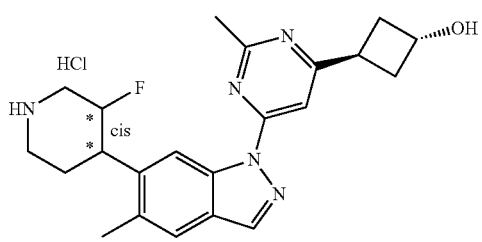 [SMILES: Cc1nc(-n2ncc3cc(C)c(C4CCNCC4F)cc32)cc([C@H]2C[C@H](O)C2)n1 ; Cl]

To a solution of (cis)-tert-butyl 3-fluoro-4-(1-(6-((1r,3r)-3-hydroxycyclobutyl)-2-methylpyrimidin-4-yl)-5-methyl-1H-indazol-6-yl)piperidine-1-carboxylate (enantiomer 2, 37 mg, 0.075 mmol) in CH$_3$OH (1.5 mL) was added HCl/CH$_3$OH (8 mol/L, 1.3 mL). The mixture was stirred at rt for 1 h. The reaction mixture was concentrated to give the title compound (32 mg, yield 99%) as a yellow solid.

D360 LCMS [mobile phase: 5-95% CH$_3$CN in 3 min]: Rt=1.817 min; MS Calcd: 395; MS Found: 397.

Description D361

(cis)-tert-Butyl 3-fluoro-4-(1-(2-methoxy-6-morpholinopyrimidin-4-yl)-5-methyl-1H-indazol-6-yl)piperidine-1-carboxylate (Enantiomer 1, D361)

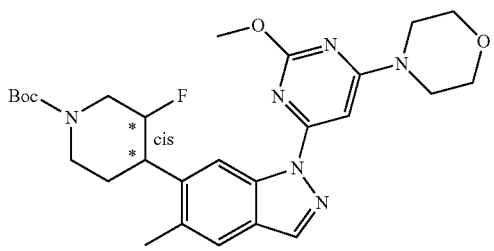 [SMILES: COc1nc(N2CCOCC2)cc(-n2ncc3cc(C)c(C4CCN(C(=O)OC(C)(C)C)CC4F)cc32)n1]

To a suspension of (cis)-tert-butyl 3-fluoro-4-(5-methyl-1H-indazol-6-yl)piperidine-1-carboxylate (enantiomer 1, 100 mg, 0.30 mmol), 4-(6-iodo-2-methoxypyrimidin-4-yl)morpholine (116 mg, 0.36 mmol), CuI (57 mg, 0.30 mmol) and K$_3$PO$_4$ (134 mg, 0.63 mmol) in dry toluene (5 mL) was added N,N-dimethyl-1,2-ethanediamine (53 mg, 0.60 mmol). The suspension was degassed with N$_2$ and stirred at 80° C. for 2 h. CH$_2$Cl$_2$ (30 mL) was added and the resulting mixture was washed with brine (2×30 mL), dried over anhydrous Na$_2$SO$_4$ and concentrated under reduced pressure. The residue was purified by pre-TLC (CH$_2$Cl$_2$) to give product (135 mg, yield 85.5%) as a white solid.

D361 LC-MS (mobile phase: from 90% water (0.1% FA) and 10% CH$_3$CN (0.1% FA) to 5% water (0.1% FA) and 95% CH$_3$CN (0.1% FA) in 2.5 min, Rt=2.11 min; MS Calcd.: 526.3. MS Found: 527.2 (M+H)$^+$.

Description D362

4-(6-(6-(3-Fluoropiperidin-4-yl)-5-methyl-1H-indazol-1-yl)-2-methoxypyrimidin-4-yl)morpholine (Enantiomer 1, D362)

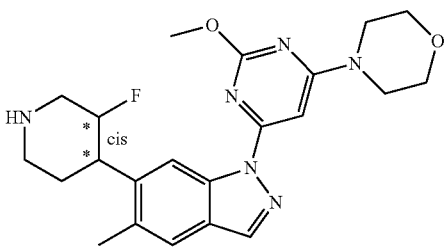 [SMILES: COc1nc(N2CCOCC2)cc(-n2ncc3cc(C)c(C4CCNCC4F)cc32)n1]

To a solution of (cis)-tert-butyl 3-fluoro-4-(1-(2-methoxy-6-morpholinopyrimidin-4-yl)-5-methyl-1H-indazol-6-yl)piperidine-1-carboxylate (enantiomer 1, 132 mg, 0.25 mmol) in CH$_2$Cl$_2$ (10 mL) was added TFA (2 mL). The reaction was stirred at room temperature for 2 h. Solvent and most of TFA were removed in vacuum and the residue was diluted with CH$_2$Cl$_2$ (30 mL). The resulting solution was washed with sat. NaHCO$_3$ (5 mL) and brine (20 mL), dried over anhydrous Na$_2$SO$_4$ and concentrated under reduced pressure to give product (90 mg, yield 84.2%) as a white solid.

D362 LC-MS (mobile phase: from 90% water (0.1% FA) and 10% CH$_3$CN (0.1% FA) to 5% water (0.1% FA) and 95% CH$_3$CN (0.1% FA) in 2.5 min, Rt=1.07 min; MS Calcd.: 426.2. MS Found: 427.2 (M+H)$^+$.

Description D363

(cis)-tert-Butyl 3-fluoro-4-(1-(2-methoxy-6-morpholinopyrimidin-4-yl)-5-methyl-1H-indazol-6-yl)piperidine-1-carboxylate (Enantiomer 2, D363)

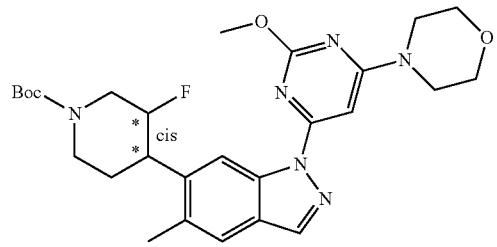 [SMILES: COc1nc(N2CCOCC2)cc(-n2ncc3cc(C)c(C4CCN(C(=O)OC(C)(C)C)CC4F)cc32)n1]

To a suspension of (cis) tert-butyl 3-fluoro-4-(5-methyl-1H-indazol-6-yl)piperidine-1-carboxylate (enantiomer 2, 100 mg, 0.30 mmol), 4-(6-iodo-2-methoxypyrimidin-4-yl)morpholine (116 mg, 0.36 mmol), CuI (57 mg, 0.30 mmol) and K$_3$PO$_4$ (134 mg, 0.63 mmol) in dry toluene (5 mL) was added N,N-dimethyl-1,2-ethanediamine (53 mg, 0.60 mmol). The suspension was degassed with N$_2$ and stirred at 80° C. for 2 h. CH$_2$Cl$_2$ (30 mL) was added and the resulting mixture was washed with brine (2×30 mL), dried over anhydrous Na$_2$SO$_4$ and concentrated under reduced pressure. The residue was purified by pre-TLC (CH$_2$Cl$_2$) to give product (120 mg, yield 76.0%) as a white solid.

D363 LC-MS (mobile phase: from 90% water (0.1% FA) and 10% CH$_3$CN (0.1% FA) to 5% water (0.1% FA) and 95% CH₃CN (0.1% FA) in 2.0 min, Rt=1.84 min; MS Calcd.: 526.3 MS Found: 527.3 (M+H)⁺.

Description D364

4-(6-(6-(3-Fluoropiperidin-4-yl)-5-methyl-1H-indazol-1-yl)-2-methoxypyrimidin-4-yl)morpholine (Enantiomer 2, D364)

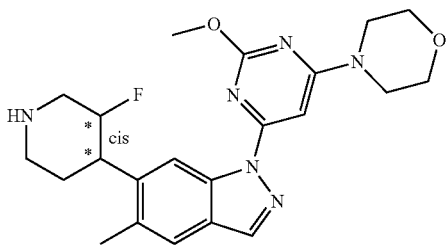 [SMILES: COc1nc(N2CCOCC2)cc(-n2ncc3cc(C)c(C4CCNCC4F)cc32)n1]

To a solution of (cis)-tert-butyl 3-fluoro-4-(1-(2-methoxy-6-morpholinopyrimidin-4-yl)-5-methyl-1H-indazol-6-yl)piperidine-1-carboxylate (enantiomer 2, 115 mg, 0.22 mmol) in CH₂Cl₂ (10 mL) was added TFA (2 mL). The reaction was stirred at room temperature for 2 h. Solvent and most of TFA were removed in vacuum and the residue was diluted with CH₂Cl₂ (30 mL). The resulting solution was washed with sat. NaHCO₃ (5 mL) and brine (20 mL), dried over anhydrous Na₂SO₄ and concentrated under reduced pressure to give product (80 mg, yield 83.7%) as a white solid.

D364 LC-MS (mobile phase: from 90% water (0.1% FA) and 10% CH₃CN (0.1% FA) to 5% water (0.1% FA) and 95% CH₃CN (0.1% FA) in 2.0 min, Rt=1.18 min; MS Calcd.: 426.2 MS Found: 427.3 (M+H)⁺.

Description D365

4-Iodo-2-methoxy-6-(4-methylpiperazin-1-yl)pyrimidine (D365)

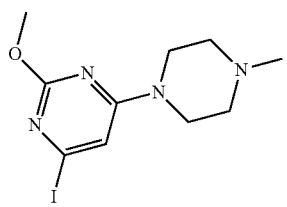 [SMILES: COc1nc(I)cc(N2CCN(C)CC2)n1]

To a solution of N-methyl piperazine (42 mg, 0.41 mmol) and DIEA (161 mg, 1.24 mmol) in EtOH (5 mL) was added 4,6-diiodo-2-methoxypyrimidine (150 mg, 0.41 mmol). The reaction was stirred at room temperature overnight. Solvent was removed in vacuum and the residue was diluted with EtOAc (25 mL). The resulting solution was washed with brine (20 mL), dried over anhydrous Na₂SO₄ and concentrated under reduced pressure. The residue was purified by silica gel chromatography (eluted with CH₂Cl₂/MeOH=20:1) to give product (132 mg, yield 95.3%) as a pale yellow oil.

D365 ¹H NMR (400 MHz, CDCl₃): δ 6.64 (s, 1H), 3.90 (s, 3H), 3.62 (s, 4H), 2.45 (t, J=5.2 Hz, 4H), 2.33 (s, 3H).

Description D366

(cis)-tert-Butyl 3-fluoro-4-(1-(2-methoxy-6-(4-methylpiperazin-1-yl)pyrimidin-4-yl)-5-methyl-1H-indazol-6-yl)piperidine-1-carboxylate (Enantiomer 1, D366)

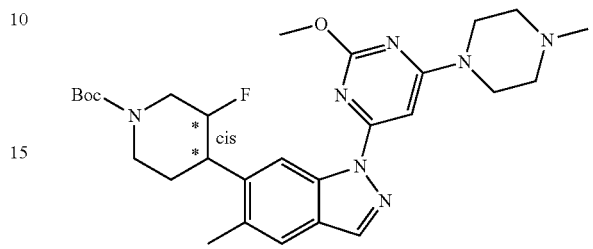

The mixture of (cis)-tert-butyl 3-fluoro-4-(5-methyl-1H-indazol-6-yl)piperidine-1-carboxylate (enantiomer 1, 150 mg, 0.45 mmol), 4-iodo-2-methoxy-6-(4-methylpiperazin-1-yl)pyrimidine (174 mg, 0.52 mmol), CuI (190 mg, 1.0 mmol) and K₃PO₄ (212 mg, 1.0 mmol) in toluene (10 mL) was degassed and protected with N₂ before N,N-dimethyl-1,2-ethanediamine (53 mg, 0.60 mmol) was added. Then, the reaction mixture was stirred at 100° C. for 1 hour. The reaction mixture was concentrated and the residue was purified by silica column chromatography (MeOH:DCM=1:15, 15 g of silica gel) to give the desired product (210 mg, 87% yield) as an off-white solid. The solid was washed by hexane to give pure product as an off-white solid. (175 mg, 72% yield)

D366 ¹H NMR (400 MHz, CD₃OD): δ 8.76 (br, 1H), 8.16 (br, 1H), 7.60 (br, 1H), 6.91 (br, 1H), 4.82~4.61 (m, 1H), 4.49~4.45 (m, 1H), 4.17~4.14 9M, 1H), 4.04 (s, 3H), 3.74 (br, 4H), 3.38 (m, 1H), 2.94 (br, 2H), 2.60 (br, 4H), 2.54 (s, 3H), 2.36 (s, 3H), 1.95~1.92 (m, 1H), 1.75~1.72 (m, 1H), 1.52 (s, 9H).

LC-MS (mobile phase: mobile phase: from 90% water (0.1% FA) and 10% CH₃CN (0.1% FA) to 5% water (0.1% FA) and 95% CH₃CN (0.1% FA) in 10.0 min, Rt=6.73 min; MS Calcd.: 539.6, MS Found: 540.6 [M+H]⁺.

Description D367

6-((cis)-3-Fluoropiperidin-4-yl)-1-(2-methoxy-6-(4-methylpiperazin-1-yl)pyrimidin-4-yl)-5-methyl-1H-indazole TFA Salt (Enantiomer 1, D367)

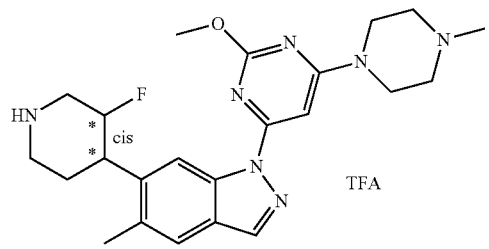 [SMILES: COc1nc(N2CCN(C)CC2)cc(-n2ncc3cc(C)c(C4CCNCC4F)cc32)n1]

TFA (1.0 mL) was added to the solution of (cis)-tert-butyl 3-fluoro-4-(1-(2-methoxy-6-(4-methylpiperazin-1-yl)pyrimidin-4-yl)-5-methyl-1H-indazol-6-yl)piperidine-1-carboxylate (enantiomer 1, 175 mg, 0.33 mmol) in DCM (5 mL). The reaction was stirred at rt for 2 hours and then the reaction solution was concentrated to give crude product as a colorless oil (220 mg, 100% yield). The crude product was used to next step without further purification.

D367 LC-MS (mobile phase: mobile phase: from 90% water (0.1% FA) and 10% CH$_3$CN (0.1% FA) to 5% water (0.1% FA) and 95% CH$_3$CN (0.1% FA) in 2.6 min, Rt=0.96 min; MS Calcd.: 439.2, MS Found: 440.4 [M+H]$^+$.

Description D368

(cis)-tert-Butyl 3-fluoro-4-(1-(2-methoxy-6-(4-methylpiperazin-1-yl)pyrimidin-4-yl)-5-methyl-1H-indazol-6-yl)piperidine-1-carboxylate (Enantiomer 2, D368)

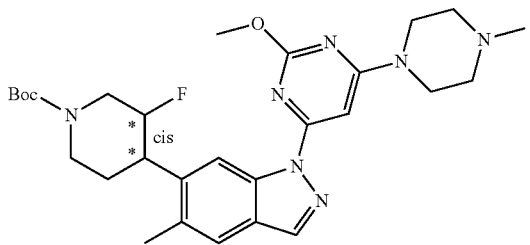 [SMILES: COc1nc(N2CCN(C)CC2)cc(-n2ncc3cc(C)c(C4CCN(C(=O)OC(C)(C)C)CC4F)cc32)n1]

The mixture of tert-butyl 3-fluoro-4-(5-methyl-1H-indazol-6-yl)piperidine-1-carboxylate (enantiomer 2, 150 mg, 0.45 mmol), 4-iodo-2-methoxy-6-(4-methylpiperazin-1-yl)pyrimidine (174 mg, 0.52 mmol), CuI (190 mg, 1.0 mmol) and K$_3$PO$_4$ (212 mg, 1.0 mmol) in toluene (10 mL) was degassed and protected with N$_2$ before N,N-dimethyl-1,2-ethanediamine (53 mg, 0.60 mmol) was added. Then, the reaction mixture was stirred at 100° C. for 1 hour. The reaction mixture was concentrated and the residue was purified by silica column chromatography (MeOH:DCM=1:10, 15 g of silica gel) to give the desired product (280 mg, 100% yield) as a light green solid.

D368 LC-MS (mobile phase: mobile phase: from 90% water (0.1% FA) and 10% CH$_3$CN (0.1% FA) to 5% water (0.1% FA) and 95% CH$_3$CN (0.1% FA) in 2.5 min, Rt=1.132 min; MS Calcd.: 539.6, MS Found: 540.6 [M+H]$^+$.

Description D369

6-((cis)-3-Fluoropiperidin-4-yl)-1-(2-methoxy-6-(4-methylpiperazin-1-yl)pyrimidin-4-yl)-5-methyl-1H-indazole (Enantiomer 2, D369)

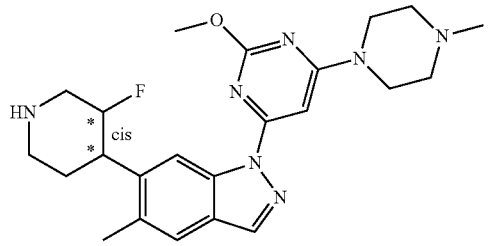 [SMILES: COc1nc(N2CCN(C)CC2)cc(-n2ncc3cc(C)c(C4CCNCC4F)cc32)n1]

HCl/EtOAc (6.2M/L, 7.0 mL) was added to the solution of (cis)-tert-butyl 3-fluoro-4-(1-(2-methoxy-6-(4-methylpiperazin-1-yl)pyrimidin-4-yl)-5-methyl-1H-indazol-6-yl)piperidine-1-carboxylate (enantiomer 2, 280 mg, 0.52 mmol) in EtOAc (8 mL). The reaction was stirred at RT overnight. Then, the reaction solution was concentrated. The residue was diluted with sat NaHCO$_3$ (100 mL). extracted by DCM (2×100 mL). The combined organic layer was washed with brine. dried over Na$_2$SO$_4$ and concentrated to give crude product as a green oil (280 mg, 100% yield). The crude product was used to next step without further purification.

D369 LC-MS (mobile phase: mobile phase: from 90% water (0.1% FA) and 10% CH$_3$CN (0.1% FA) to 5% water (0.1% FA) and 95% CH$_3$CN (0.1% FA) in 2.6 min, Rt=1.009 min; MS Calcd.: 439.2, MS Found: 440.4 [M+H]$^+$.

Description D370

6-(3-Fluoro-1-(oxetan-3-yl)piperidin-4-yl)-5-methyl-1H-indazole (Enantiomer 1, D370)

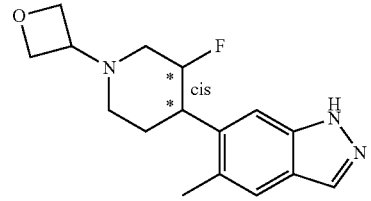 [SMILES: Cc1cc2cn[nH]c2cc1C1CCN(C2COC2)CC1F]

To the solution of 6-(3-fluoropiperidin-4-yl)-5-methyl-1H-indazole hydrochloride (enantiomer 1, 2.0 g, 7.0 mmol) in MeOH (150 mL) was added oxetan-3-one (2.1 g, 30 mmol) at RT and the reaction was stirred overnight. Then NaBH$_3$CN (3.3 g, 52 mmol) was added to the reaction and the reaction was stirred at RT for 5 hours. The reaction was poured in to water (50 mL) and the mixture was extracted with DCM (2×150 mL). The organic solution was washed with brine (2×200 mL) and dried over anhydrous Na$_2$SO$_4$. The dry solution was concentrated and the residue was purified by chromatography (EtOAc/MeOH=12/1) to the desired product as a white solid. (1.3 mg, 100 yield).

D370 $^1$H NMR (400 MHz, CDCl$_3$): δ7.98 (s, 1H), 7.56 (s, 1H), 7.45 (s, 1H), 4.94~4.73 (m, 1H), 4.73~4.63 (m, 4H), 3.67~3.63 (m, 1H), 3.25~3.21 (m, 1H), 3.14~3.05 (m, 1H), 2.83 (d, J=9.6 Hz, 1H), 2.46 (s, 3H), 2.10~1.80 (m, 4H).

Description D371

6-(3-Fluoro-1-(oxetan-3-yl)piperidin-4-yl)-5-methyl-1H-indazole (Enantiomer 2, D371)

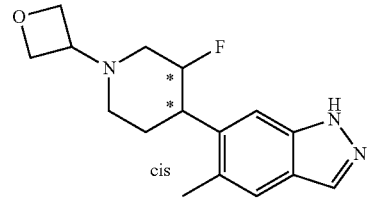 [SMILES: Cc1cc2cn[nH]c2cc1C1CCN(C2COC2)CC1F]

To the solution of 6-(3-fluoropiperidin-4-yl)-5-methyl-1H-indazole hydrochloride (enantiomer 2, 1.02 g, 3.6 mmol) in DCM/MeOH (1/1, 20 mL) was added oxetan-3-one (1.1 g, 15.3 mmol) at RT and the reaction was stirred overnight.

Then, NaBH₃CN (1.1 g, 17.5 mmol) was added to the reaction and the reaction was stirred at RT for 0.5 hour. The reaction was poured in to water (50 mL) and the mixture was extracted with DCM (2×20 mL). The organic solution was washed with brine (2×20 mL) and dried over anhydrous Na₂SO₄. The dry solution was concentrated and the residue was purified by chromatography (MeOH/DCM=1/20) to the desired product as a white solid. (720 mg, 69% yield).

D371 ¹H NMR (400 MHz, CDCl₃): δ 10.09 (br, 1H), 7.98 (s, 1H), 7.56 (s, 1H), 7.45 (s, 1H), 4.94~4.73 (m, 1H), 4.73~4.63 (m, 4H), 3.67~3.63 (m, 1H), 3.25~3.21 (m, 1H), 3.14~3.05 (m, 1H), 2.83 (d, J=9.6 Hz, 1H), 2.46 (s, 3H), 2.10~1.80 (m, 4H).

Description D372

(R)-(4-(6-iodo-2-methoxypyrimidin-4-yl)morpholin-2-yl)methanol (D372)

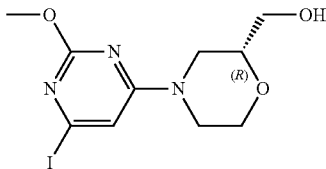

4,6-Diiodo-2-methoxypyrimidine (362 mg, 1.0 mmol) was added to the solution of (R)-morpholin-2-ylmethanol 169 mg, 1.1 mmol) and Et₃N (404 mg, 4.0 mmol) in MeOH (15 mL) at RT overnight. Then the reaction solution was concentrated and the residue was purified by silica gel chromatography (eluted with PE/EtOAc=2/1~1/1) to give product (320 mg, yield 91%) as a light yellow oil.

D372 ¹H NMR (400 MHz, CDCl₃): δ 6.65 (s, 1H), 4.15~4.01 (m, 3H), 3.91 (s, 3H), 3.77~3.72 (m, 1H), 3.69~3.57 (m, 3H), 3.10~3.06 (m, 1H), 2.95~2.88 (m, 1H), 2.0~1.96 (m, 1H)

Description D373

(S)-(4-(6-iodo-2-methoxypyrimidin-4-yl)morpholin-2-yl)methanol (D373)

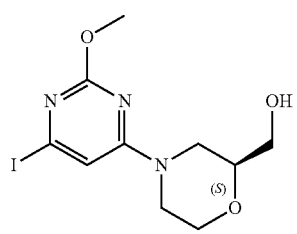

4,6-Diiodo-2-methoxypyrimidine (362 mg, 1.0 mmol) was added to the solution of (S)-morpholin-2-ylmethanol 169 mg, 1.1 mmol) and Et₃N (404 mg, 4.0 mmol) in MeOH (15 mL) at RT overnight. Then, the reaction solution was concentrated and the residue was purified by silica gel chromatography (eluted with PE/EtOAc=2/1~1/1) to give product (330 mg, yield 94%) as a colorless oil.

D373 ¹H NMR (400 MHz, CDCl₃): δ 6.65 (s, 1H), 4.15~4.01 (m, 3H), 3.91 (s, 3H), 3.77~3.72 (m, 1H), 3.69~3.57 (m, 3H), 3.10~3.06 (m, 1H), 2.92~2.88 (m, 1H), 2.36 (s, 1H)

Description D374

(R)-4-(6-iodo-2-methoxypyrimidin-4-yl)-2-methyl-morpholine (D374)

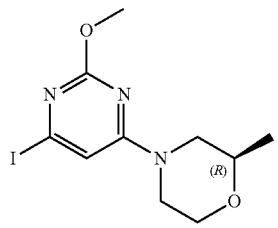

To a solution of 4,6-diiodo-2-methoxypyrimidine (600 mg, 1.66 mmol) in DMF (10 mL) was added (R)-2-methylmorpholine (201 mg, 1.99 mmol) and DIPEA (429 mg, 3.32 mmol). The mixture was stirred at room temperature overnight. The reaction mixture was poured into water (100 mL), extracted with EtOAc (50 mL×3). The combined organic layers were washed with brine (50 mL), dried over anhydrous Na₂SO₄ and concentrated to dryness. The residue was purified by silica gel chromatography eluted with (EtOAc:petroleum ether=1:10~1:5) to give the product (R)-4-(6-iodo-2-methoxypyrimidin-4-yl)-2-methylmorpholine (520 mg, 93.6% yield) as a yellow oil.

LC-MS: (mobile phase: from 90% water (0.1% FA) and 10% CH₃CN (0.1% FA) to 5% water (0.1% FA) and 95% CH₃CN (0.1% FA) in 2.5 min), Rt=1.55 min; MS Calcd.: 335; MS Found: 336 [M+H]⁺.

Description D375

(S)-4-(6-iodo-2-methoxypyrimidin-4-yl)-2-methyl-morpholine (D375)

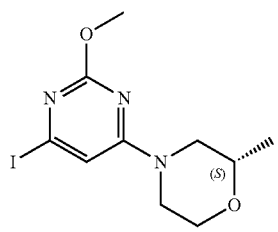

To a solution of 4,6-diiodo-2-methoxypyrimidine (600 mg, 1.66 mmol) in DMF (10 mL) was added (S)-2-methylmorpholine (201 mg, 1.99 mmol) and DIPEA (429 mg, 3.32 mmol). The mixture was stirred at room temperature overnight. The reaction mixture was poured into water (100 mL), extracted with EtOAc (50 mL×3). The combined organic layers were washed with brine (50 mL), dried over anhydrous Na₂SO₄ and concentrated to dryness. The residue was purified by silica gel chromatography eluted with (EtOAc:Petroleum Ether=1:10~1:5) to give the product (S)-

4-(6-iodo-2-methoxypyrimidin-4-yl)-2-methylmorpholine (500 mg, 89.9% yield) as a yellow oil.

D375 LC-MS: (mobile phase: from 90% water (0.1% FA) and 10% CH$_3$CN (0.1% FA) to 5% water (0.1% FA) and 95% CH$_3$CN (0.1% FA) in 2.5 min), Rt=1.69 min; MS Calcd.: 335; MS Found: 336 [M+H]$^+$.

Description D376

(cis)-tert-Butyl 3-fluoro-4-(1-(2-methoxy-6-((S)-2-methylmorpholino)pyrimidin-4-yl)-5-methyl-1H-indazol-6-yl)piperidine-1-carboxylate (Diastereoisomer 1, D376)

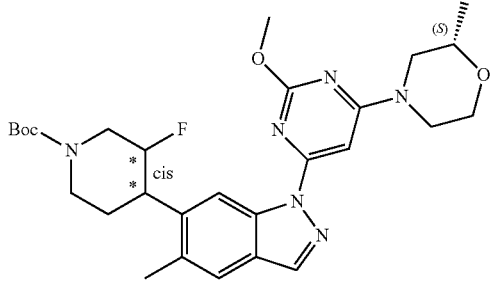

To a solution of (S)-4-(6-iodo-2-methoxypyrimidin-4-yl)-2-methylmorpholine (181 mg, 0.54 mmol) in toluene (10 mL) was added (cis)-tert-butyl 3-fluoro-4-(5-methyl-1H-indazol-6-yl)piperidine-1-carboxylate (enantiomer 1) (150 mg, 0.45 mmol), K$_3$PO$_4$ (191 mg, 0.90 mmol), CuI (86 mg, 0.45 mmol) and N1,N2-dimethylethane-1,2-diamine (79 mg, 0.90 mmol). The mixture was stirred at 90° C. for 2 hrs under N$_2$. The reaction mixture was poured into water (100 mL), extracted with EtOAc (50 mL×3). The combined organic layers were washed with brine (50 mL), dried over anhydrous Na$_2$SO$_4$ and concentrated to dryness. The residue was purified by silica gel chromatography eluted with (EtOAc:petroleum ether=1:10~1:5) to give the product (cis)-tert-butyl 3-fluoro-4-(1-(2-methoxy-6-((S)-2-methylmorpholino)pyrimidin-4-yl)-5-methyl-1H-indazol-6-yl)piperidine-1-carboxylate (diastereoisomer 1) (180 mg, 74.1% yield) as a white solid.

D376 LC-MS: (mobile phase: from 90% water (0.1% FA) and 10% CH$_3$CN (0.1% FA) to 5% water (0.1% FA) and 95% CH$_3$CN (0.1% FA) in 2.5 min), Rt=2.09 min; MS Calcd.: 540; MS Found: 541 [M+H]$^+$.

Description D377

(S)-4-(6-(6-((cis)-3-fluoropiperidin-4-yl)-5-methyl-1H-indazol-1-yl)-2-methoxypyrimidin-4-yl)-2-methylmorpholine (Diastereoisomer 1, D377)

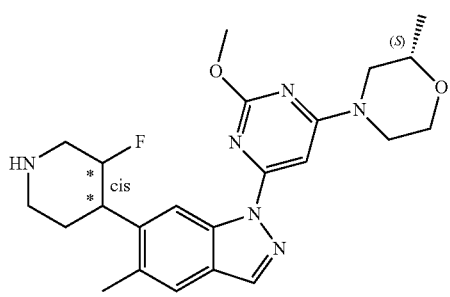

A solution of (cis)-tert-butyl 3-fluoro-4-(1-(2-methoxy-6-((S)-2-methylmorpholino)pyrimidin-4-yl)-5-methyl-1H-indazol-6-yl)piperidine-1-carboxylate (diastereoisomer 1, 180 mg, 0.33 mmol) in 4 mol/L HCl/EtOAc (10 mL) was stirred at room temperature for 2 hr. The mixture was poured into sat. NaHCO$_3$ (100 mL) and then the mixture was extracted with EtOAc (30 mL×3). The combined organic layers were washed with brine (30 mL), dried over anhydrous Na$_2$SO$_4$ and filtered. The filtrate was concentrated to give the crude product (S)-4-(6-(6-((cis)-3-fluoropiperidin-4-yl)-5-methyl-1H-indazol-1-yl)-2-methoxypyrimidin-4-yl)-2-methylmorpholine (diastereoisomer 1) (140 mg, yield=95.4%) as a light yellow solid.

D377 LC-MS: (mobile phase: from 90% water (0.1% FA) and 10% CH$_3$CN (0.1% FA) to 5% water (0.1% FA) and 95% CH$_3$CN (0.1% FA) in 2.5 min), Rt=0.97 min; MS Calcd.: 440; MS Found: 441 [M+H]$^+$.

Description D378

(cis)-tert-Butyl 3-fluoro-4-(1-(2-methoxy-6-((S)-2-methylmorpholino)pyrimidin-4-yl)-5-methyl-1H-indazol-6-yl)piperidine-1-carboxylate (Diastereoisomer 2, D378)

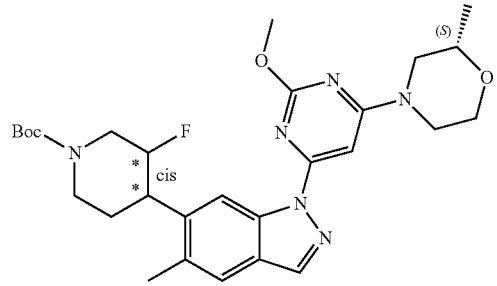

To a solution of (S)-4-(6-iodo-2-methoxypyrimidin-4-yl)-2-methylmorpholine (181 mg, 0.54 mmol) in toluene (10 mL) was added (cis)-tert-butyl 3-fluoro-4-(5-methyl-1H-indazol-6-yl)piperidine-1-carboxylate (enantiomer 2) (150 mg, 0.45 mmol), K$_3$PO$_4$ (191 mg, 0.90 mmol), CuI (86 mg, 0.45 mmol) and N1,N2-dimethylethane-1,2-diamine (79 mg, 0.90 mmol). The mixture was stirred at 90° C. for 2 hrs under N$_2$. The reaction mixture was poured into water (100 mL), extracted with EtOAc (50 mL×3). The combined organic layers were washed with brine (50 mL), dried over anhydrous Na$_2$SO$_4$ and concentrated to dryness. The residue was purified by silica gel chromatography eluted with (EtOAc:petroleum ether=1:10~1:5) to give the product (cis)-tert-butyl 3-fluoro-4-(1-(2-methoxy-6-((S)-2-methylmorpholino)pyrimidin-4-yl)-5-methyl-1H-indazol-6-yl)piperidine-1-carboxylate (diastereoisomer 2) (140 mg, 57.6% yield) as a white solid.

D378 LC-MS: (mobile phase: from 90% water (0.1% FA) and 10% CH$_3$CN (0.1% FA) to 5% water (0.1% FA) and 95% CH$_3$CN (0.1% FA) in 2.5 min), Rt=2.09 min; MS Calcd.: 540; MS Found: 541 [M+H]$^+$.

Description D379

(S)-4-(6-(6-(((cis)-3-fluoropiperidin-4-yl)-5-methyl-1H-indazol-1-yl)-2-methoxypyrimidin-4-yl)-2-methyl morpholine (Diastereoisomer 2, D379)

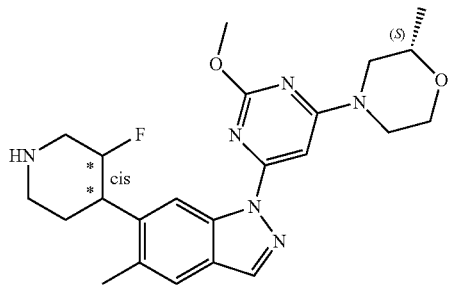

A solution of (cis)-tert-butyl 3-fluoro-4-(1-(2-methoxy-6-((S)-2-methylmorpholino)pyrimidin-4-yl)-5-methyl-1H-indazol-6-yl)piperidine-1-carboxylate (diastereoisomer 2) (140 mg, 0.26 mmol) in 4 mol/L HCl/EtOAc (10 mL) was stirred at room temperature overnight. The mixture was poured into sat. NaHCO$_3$ (100 mL) and then the mixture was extracted with EtOAc (30 mL×3). The combined organic layers were washed with brine (30 mL), dried over anhydrous Na$_2$SO$_4$ and filtered. The filtrate was concentrated to give the crude product (S)-4-(6-(6-(((cis)-3-fluoropiperidin-4-yl)-5-methyl-1H-indazol-1-yl)-2-methoxypyrimidin-4-yl)-2-methylmorpholine (diastereoisomer 2) (95 mg, yield=83.3%) as a white solid.

D379 LC-MS: (mobile phase: from 90% water (0.1% FA) and 10% CH$_3$CN (0.1% FA) to 5% water (0.1% FA) and 95% CH$_3$CN (0.1% FA) in 2.5 min), Rt=1.36 min; MS Calcd.: 440; MS Found: 441 [M+H]$^+$.

Description D380

(2S,6R)-4-(6-iodo-2-methoxypyrimidin-4-yl)-2,6-dimethylmorpholine (D380)

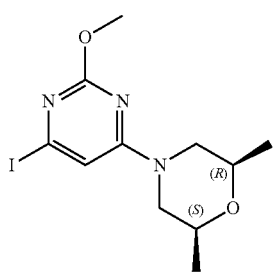

4,6-Diiodo-2-methoxypyrimidine (680 mg, 1.88 mmol) was added to the solution of (2S,6R)-2,6-dimethylmorpholine (230 mg, 2.0 mmol) and Et$_3$N (0.6 mL) in MeOH (10 mL) at RT and the reaction was stirred at RT for 2 hours until all solid was dissolved. Then the reaction solution was concentrated and the residue was purified by silica gel chromatography (eluted with PE/EtOAc=3/1) to give product (570 mg, yield 87%) as a white solid.

D380 $^1$H NMR (400 MHz, CDCl$_3$): δ 6.62 (s, 1H), 4.09 (br, 2H), 3.91 (s, 3H), 3.65~3.57 (m, 2H), 2.59 (t, J=12.0 Hz, 2H), 1.24 (d, J=6.4 Hz, 6H).

Description D381

(2S,6S)-4-(6-iodo-2-methoxypyrimidin-4-yl)-2,6-dimethylmorpholine (D381)

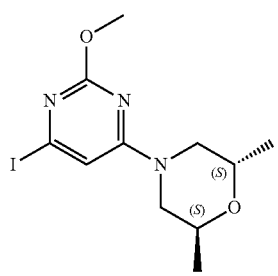

4,6-Diiodo-2-methoxypyrimidine (723.8 mg, 2.0 mmol) was added to the solution of (2S,6S)-2,6-dimethylmorpholine (230 mg, 2.0 mmol) and Et$_3$N (607 mg) in MeOH (10 mL) at RT and the reaction was stirred at RT overnight. Then the reaction solution was concentrated and the residue was purified by silica gel column chromatography (PE/EtOAc=1:0~3:1) to give product (510 mg, yield 72%) as a light yellow liquid.

D381 $^1$H NMR (400 MHz, CDCl$_3$): δ 6.60 (s, 1H), 4.09 (br, 2H), 3.90 (s, 3H), 3.55~3.25 (m, 2H), 2.59~2.50 (m, 2H), 1.22 (d, J=6.4 Hz, 6H).

Description D382

(R)-4-(6-iodo-2-methoxypyrimidin-4-yl)-3-methylmorpholine (D382)

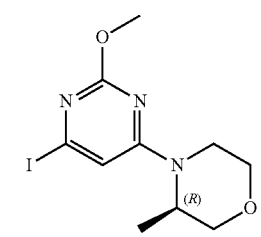

A solution of 4,6-diiodo-2-methoxypyrimidine (500 mg, 1.38 mmol), (R)-3-methylmorpholine (167.5 mg, 1.65 mmol), DIEA (534.1 mg, 4.14 mmol) in DMF (30 mL) was heated to 60° C. and stirred overnight. The reaction mixture was cooled to RT, poured into water, extracted with EtOAc (2×120 mL), washed by brine, dried over anhydrous Na$_2$SO$_4$ and concentrated. The residue was purified by column chromatography (PE:EtOAc=1:0~6:1) to give the title compound (270 mg, 58% yield, Lot #:FP111303-011A1) as a colorless oil.

D382 $^1$H NMR (400 MHz, CDCl$_3$): δ 6.59 (s, 1H), 4.26 (s, 1H), 3.99 (M, 1H), 3.95~3.90 (m, 5H), 3.78~3.66 (m, 2H), 3.56~3.50 (m, 1H), 3.26~3.21 (m, 1H), 1.29 (S, 3H).

Description D383

(S)-4-(6-Iodo-2-methoxypyrimidin-4-yl)-3-methyl-morpholine (D383)

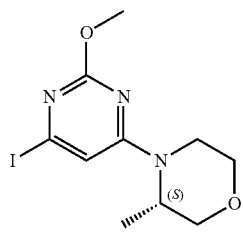

A solution of 4,6-diiodo-2-methoxypyrimidine (500 mg, 1.38 mmol), (R)-3-methylmorpholine (167.5 mg, 1.65 mmol), DIEA (534.1 mg, 4.14 mmol) in DMF (30 mL) was heated to 60° C. and stirred overnight. The reaction mixture was cooled to RT, poured into water, extracted with EtOAc (2×120 mL), washed by brine, dried over anhydrous $Na_2SO_4$ and concentrated. The residue was purified by column chromatography (PE:EtOAc=1:0~6:1) to give the title compound (300 mg, 65% yield) as a colorless oil.

D383 $^1$H NMR (400 MHz, $CDCl_3$): δ 6.59 (s, 1H), 4.26 (s, 1H), 3.99 (M, 1H), 3.95~3.90 (m, 5H), 3.78~3.66 (m, 2H), 3.56~3.50 (m, 1H), 3.26~3.21 (m, 1H), 1.29 (S, 3H).

Description D384

6-(6-Iodo-2-methoxypyrimidin-4-yl)-2-oxa-6-azaspiro[3.4]octane (D384)

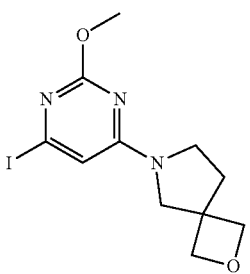 [SMILES: COc1nc(I)cc(N2CCC3(COC3)C2)n1]

The mixture of 4,6-diiodo-2-methoxypyrimidine (680 mg, 1.88 mmol) and 2-oxa-6-azaspiro[3.4]octane (377 mg, 2.0 mmol) in $Et_3N$ (0.6 mL) and MeOH (10 mL) was stirred at RT for 2 hours and concentrated. The residue was purified by column chromatography (PE/EtOAc=2/1~2/3) to give the desired product as a white solid (570 mg, 87% yield).

D384 $^1$H NMR (400 MHz, $CDCl_3$): δ 6.45 (s, 1H), 4.70~4.61 (m, 4H), 3.91 (s, 3H), 3.82 (br, 1H), 3.59 (br, 2H), 3.40 (br, 1H), 2.30 (br, 2H).

Description D385

(R)-(4-(6-iodo-2-methylpyrimidin-4-yl)morpholin-2-yl)methanol (D385)

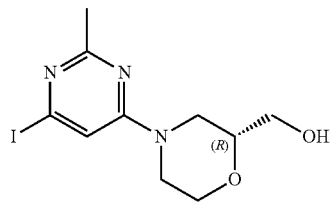

To a solution of (R)-morpholin-2-ylmethanol (203 mg, 1.73 mmol) and DIEA (670 mg, 5.19 mmol) in DMF (10 mL) was added 4,6-diiodo-2-methylpyrimidine (600 mg, 1.73 mmol). The reaction was stirred at room temperature for 3 hrs. The reaction mixture was poured into water (100 mL), extracted with EtOAc (30 mL×3). The combined organic layers were washed with brine (30 mL), dried over anhydrous $Na_2SO_4$ and concentrated to dryness. The residue was purified by silica gel chromatography eluted with (EtOAc:Petroleum Ether=1:5-1:1) to give the product (R)-(4-(6-iodo-2-methylpyrimidin-4-yl) morpholin-2-yl)methanol (450 mg, 77.6% yield) as a white solid.

D385 LC-MS (mobile phase: from 90% water (0.1% FA) and 10% $CH_3CN$ (0.1% FA) to 5% water (0.1% FA) and 95% $CH_3CN$ (0.1% FA) in 2.5 min, Rt=1.02 min; MS Calcd.: 335.1. MS Found: 335.9 $(M+H)^+$.

Description D386

(S)-(4-(6-iodo-2-methylpyrimidin-4-yl)morpholin-2-yl)methanol (D386)

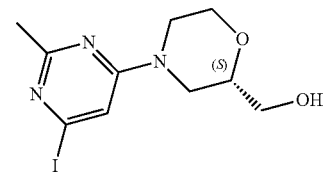

To a solution of (S)-morpholin-2-ylmethanol (300 mg, 2.56 mmol) and DIEA (992 mg, 7.68 mmol) in EtOH (10 mL) and THF (20 mL) was added 4,6-diiodo-2-methylpyrimidine (885 mg, 2.56 mmol). The reaction was stirred at room temperature overnight. Solvent was removed in vacuum and the residue was purified by silica gel chromatography (eluted with PE/EtOAc=4:1) to give product (420 mg, yield 48.8%) as a pale yellow solid.

D386 LC-MS (mobile phase: from 90% water (0.1% FA) and 10% $CH_3CN$ (0.1% FA) to 5% water (0.1% FA) and 95% $CH_3CN$ (0.1% FA) in 2.0 min, Rt=0.25 min; MS Calcd.: 335.1. MS Found: 336.0 $(M+H)^+$.

Description D387

(2R)-4-(6-Iodo-2-methylpyrimidin-4-yl)-2-(((tetrahydro-2H-pyran-2-yl)oxy)methyl)morpholine (D387)

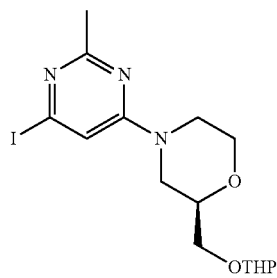

To a solution of (R)-(4-(6-iodo-2-methylpyrimidin-4-yl)morpholin-2-yl)methanol (639 mg, 1.90 mmol) in DCM (20 mL) was added DHP (639 mg, 7.60 mmol) and TsOH (327 mg, 1.90 mmol) at rt. The resulting mixture was warmed to 55° C. and stirred overnight. The reaction mixture was diluted with DCM (100 mL). The organic layer was washed with sat. $Na_2CO_3$ (40 mL) and brine (40 mL), dried over $Na_2SO_4$ and concentrated. The residue was purified by column (PE:EA=5:1) to give the title compound (723 mg, yield 91%) as a light yellow oil.

D387 $^1$H NMR (300 MHz, $CDCl_3$): δ 6.79 (s, 1H), 4.63-4.01 (m, 1H), 4.22-4.01 (m, 3H), 3.91-9.79 (m, 2H), 3.65-3.51 (m, 4H), 3.11-2.78 (m, 2H), 2.46 (s, 3H), 1.91-1.65 (m, 3H), 1.57-1.48 (m, 3H).

Description D388 tert-Butyl 4-(5-methyl-1-(2-methyl-6-((2R)-2-(((tetrahydro-2H-pyran-2-yl)oxy)methyl)morpholino)pyrimidin-4-yl)-1H-indazol-6-yl)piperidine-1-carboxylate (D388)

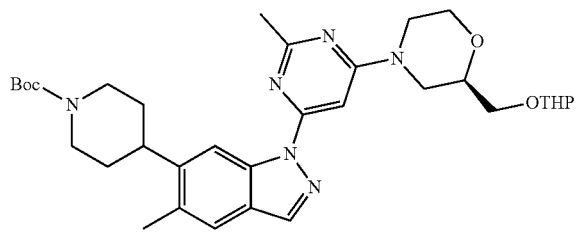

To a solution of tert-butyl 4-(5-methyl-1H-indazol-6-yl)piperidine-1-carboxylate (100 mg, 0.320 mmol) in toluene (7 mL) was added (2R)-4-(6-iodo-2-methylpyrimidin-4-yl)-2-(((tetrahydro-2H-pyran-2-yl)oxy)methyl)morpholine (160 mg, 0.380 mmol), $K_3PO_4$ (202 mg, 0.950 mmol), N,N'-dimethyl-cyclohexane-1,2-diamine (135 mg, 0.950 mmol) and CuI (180 mg, 0.950 mmol). The resulting mixture was warmed to 110° C. and stirred for 3 hrs. LCMS showed that the reaction was completed. To the mixture was added $NH_3 \cdot H_2O$ (30%, 40 mL) and extracted with ethyl acetate (40 mL×3). The combined organic layers were washed with water (40 mL) and brine (40 mL), dried over $Na_2SO_4$ and concentrated. The residue was purified by prep-HPLC (from 40% water (0.1% TFA) and 60% $CH_3CN$ to 10% water (0.1% TFA) and 90% $CH_3CN$ in 18 min, Flow rate: 20 mL/min) to give the title compound (118 mg, yield 61%) as a light yellow solid.

$^1$H NMR (300 MHz, $CDCl_3$) showed that 55% of THP group of target compound was moved.

Description D389

(R)-(4-(2-Methyl-6-(5-methyl-6-(piperidin-4-yl)-1H-indazol-1-yl)pyrimidin-4-yl)morpholin-2-yl)methanol hydrochloride (D389)

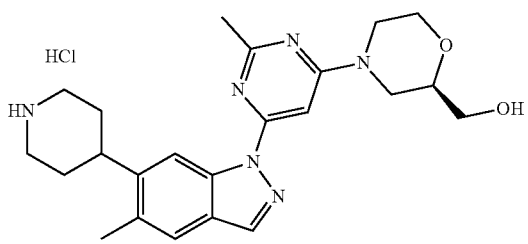 [SMILES: Cc1nc(N2CCO[C@@H](CO)C2)cc(-n2ncc3cc(C)c(C4CCNCC4)cc32)n1 ; Cl]

To a solution of tert-butyl 4-(5-methyl-1-(2-methyl-6-((2R)-2-(((tetrahydro-2H-pyran-2-yl)oxy)methyl)morpholino)pyrimidin-4-yl)-1H-indazol-6-yl)piperidine-1-carboxylate (118 mg, 0.194 mmol) in $CH_3OH$ (2 mL) was added HCl/$CH_3OH$ (4 M, 4 mL) and stirred for 2 hrs at rt. TLC showed that the reaction was completed. The reaction mixture was concentrated to the title compound (119 mg, yield >100%) as yellow solid which was used for next step directly.

D395 LC-MS (mobile phase: from 95% water and 5% $CH_3CN$ to 5% water and 95% $CH_3CN$ in 2.5 min, Rt=1.41 min; MS Calcd: 422; MS Found: 423 (M+H)$^+$.

Description D390

(2S)-4-(6-Iodo-2-methylpyrimidin-4-yl)-2-(((tetrahydro-2H-pyran-2-yl)oxy)methyl)morpholine (D390)

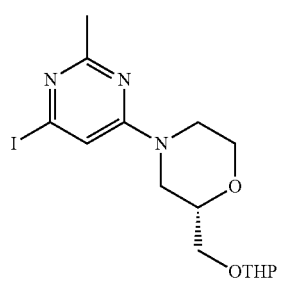

To a solution of (S)-(4-(6-iodo-2-methylpyrimidin-4-yl)morpholin-2-yl)methanol (760 mg, 2.30 mmol) in DCM (20 mL) was added DHP (774 mg, 9.20 mmol) and TsOH (396 mg, 2.30 mmol). The resulting mixture was stirred at 50° C. overnight. The mixture was washed with water (20 mL) and extracted with DCM (20 mL×2). The combined organic layers were washed with brine, dried over $Na_2SO_4$ and concentrated. The crude was purified by column (PE:EA=5:1) to give the title compound (750 mg, yield 78%) as a light yellow oil.

D390 ¹H NMR (300 MHz, CDCl₃): δ 6.79 (s, 1H), 4.63-4.61 (m, 1H), 4.15-4.00 (m, 3H), 3.901-3.77 (m, 2H), 3.73-3.51 (m, 4H), 3.11-2.78 (m, 2H), 2.46 (s, 3H), 1.88-1.48 (m, 6H).

Description D391 tert-Butyl 4-(5-methyl-1-(2-methyl-6-((2S)-2-(((tetrahydro-2H-pyran-2-yl)oxy)methyl)morpholino)pyrimidin-4-yl)-1H-indazol-6-yl)piperidine-1-carboxylate (D391)

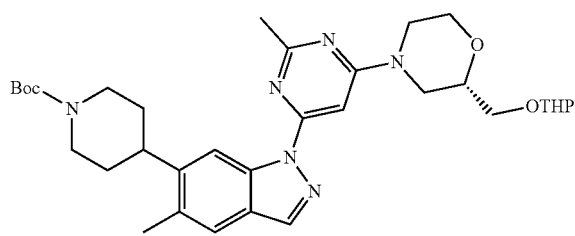

To a solution of tert-butyl 4-(5-methyl-1H-indazol-6-yl)piperidine-1-carboxylate (100 mg, 0.320 mmol) in toluene (4 mL) was added (2S)-4-(6-iodo-2-methylpyrimidin-4-yl)-2-(((tetrahydro-2H-pyran-2-yl)oxy)methyl)morpholine (160 mg, 0.380 mmol), CuI (180 mg, 0.950 mmol), K₃PO₄ (202 mg, 0.950 mmol) and N,N'-dimethyl-cyclohexane-1,2-diamine (135 mg, 0.950 mmol). The resulting mixture was stirred at 115° C. for 3 hrs. The mixture was cooled to rt and NH₃.H₂O (30%, 10 mL) was added. Ethyl acetate (10 mL×2) was added to extract the desired compound. The combined organic layers were washed with brine, dried over Na₂SO₄ and concentrated. The crude was purified by prep-HPLC (from 40% water (0.1% TFA) and 60% CH₃CN to 10% water (0.1% TFA) and 90% CH₃CN in 18 min, Flow rate: 20 mL/min) to give the crude title compound (120 mg) as a light yellow solid and it was used directly in next step without further purification.

Description D392

5-Methyl-1-(2-methyl-6-(3-((tetrahydro-2H-pyran-2-yl)oxy)azetidin-1-yl)pyrimidin-4-yl)-6-(1-(oxetan-3-yl)piperidin-4-yl)-1H-indazole (D392)

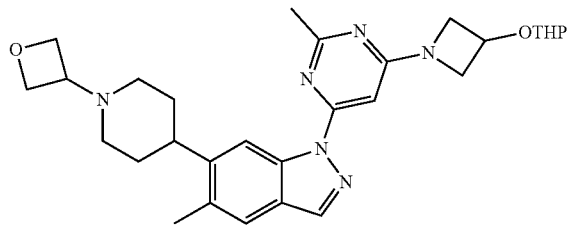

A mixture of 5-methyl-6-(1-(oxetan-3-yl)piperidin-4-yl)-1H-indazole (130 mg, 0.480 mmol), 4-iodo-2-methyl-6-(3-((tetrahydro-2H-pyran-2-yl)oxy)azetidin-1-yl)pyrimidine (105 mg, 0.270 mmol), N,N'-dimethyl-cyclohexane-1,2-diamine (136 mg, 0.960 mmol), CuI (182 mg, 0.960 mmol) and K₃PO₄ (204 mg, 0.960 mmol) in toluene (8 mL) was stirred at 115° C. for 13 hrs. The reaction mixture was cooled to room temperature. The mixture was filtered and concentrated in vacuo. The residue was purified by column on C18 using CH₃CN/H₂O (10%-80%) to give the desired product (100 mg, yield 40%) as a white solid.

D392 LC-MS (XB-C18, ⌀4.6*50 mm*5 um; mobile phase: from 95% water (0.02% NH₄OAc) and 5% CH₃CN to 5% water (0.02% NH₄OAc) and 95% CH₃CN in 4 min, purity is >95%, Rt=2.804 min; MS Calcd.: 518, MS Found: 519 (M+H)⁺.

Description D393 tert-Butyl 4-(5-methyl-1-(2-methyl-6-(3-((tetrahydro-2H-pyran-2-yl)oxy)azetidin-1-yl)pyrimidin-4-yl)-1H-indazol-6-yl)piperidine-1-carboxylate (D393)

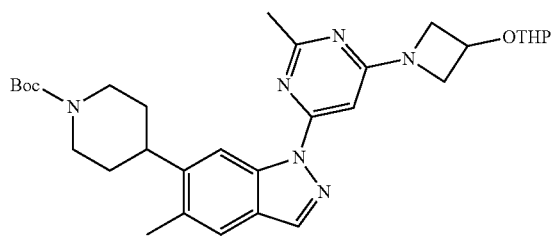

To a suspension of tert-butyl 4-(5-methyl-1H-indazol-6-yl)piperidine-1-carboxylate (103 mg, 0.32 mmol) and 4-iodo-2-methyl-6-(3-((tetrahydro-2H-pyran-2-yl)oxy)azetidin-1-yl)pyrimidine (123 mg, 0.32 mmol) in toluene (10 mL) was added N1,N2-dimethylcyclohexane-1,2-diamine (91 mg, 0.64 mmol), CuI (61 mg, 0.32 mmol) and K₃PO₄ (136 mg, 0.64 mmol). The mixture was stirred at 115° C. under nitrogen for 2 hrs. The reaction mixture was cooled to rt and filtered. The filtrate was concentrated and the residue was purified by pre-TLC (PE:EtOAc=2:1, twice) and column C18 (5-70% ACN in water) to give the title compound (70 mg, yield 38%) as a grey solid.

D393 ¹H NMR (300 MHz, CDCl₃): δ 8.76 (s, 1H), 8.06 (s, 1H), 7.50 (s, 1H), 6.59 (s, 1H), 4.75-4.68 (m, 2H), 4.36-4.28 (m, 4H), 4.15-4.04 (m, 2H), 3.93-3.85 (m, 1H), 3.59-3.52 (m, 1H), 3.01-2.84 (m, 3H), 2.61 (s, 3H), 2.47 (s, 3H), 1.90-1.86 (m, 3H), 1.79-1.72 (m, 2H), 1.62-1.54 (m, 5H), 1.50 (s, 9H).

Description D394

(S)-tert-Butyl 4-(1-(6-(2-(hydroxymethyl)morpholino)-2-methylpyrimidin-4-yl)-5-methyl-1H-indazol-6-yl)piperidine-1-carboxylate (D394)

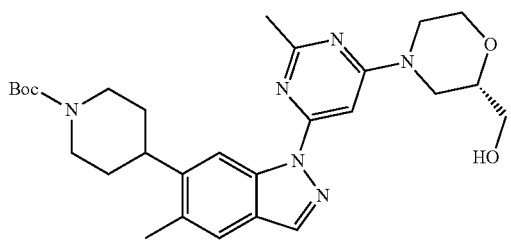 [SMILES: Cc1nc(N2CCO[C@H](CO)C2)cc(-n2ncc3cc(C)c(C4CCN(C(=O)OC(C)(C)C)CC4)cc32)n1]

To a solution of tert-butyl 4-(5-methyl-1H-indazol-6-yl)piperidine-1-carboxylate (80 mg, 0.25 mmol), (S)-(4-(6-iodo-2-methylpyrimidin-4-yl)morpholin-2-yl)methanol (102 mg, 0.305 mmol), K$_3$PO$_4$ (162 mg, 0.762 mmol) and CuI (145 mg, 0.762 mmol) in toluene (2 mL) was added N,N'-dimethyl-cyclohexane-1,2-diamine (108 mg, 0.762 mmol) at rt. The resulting mixture was stirred at 110° C. under N$_2$ atmosphere for 2 hrs. Then, the reaction mixture was cooled and poured into diluted ammonia (10%, 30 mL) and extracted with EtOAc (30 mL×2). The combined organic layers was washed with brine, dried over Na$_2$SO$_4$ and concentrated. The crude was purified by prep-HPLC (from 55% water (0.1% TFA) and 45% CH$_3$CN to 25% water (0.1% TFA) and 75% CH$_3$CN) to give the title compound (50 mg, yield 38%) as colorless oil.

D394 $^1$H NMR (300 MHz, CDCl$_3$): δ 8.74 (s, 1H), 8.06 (s, 1H), 7.50 (s, 1H), 6.95 (s, 1H), 4.35-4.25 (m, 3H), 4.16-4.02 (m, 2H), 3.81-3.65 (m, 4H), 3.20-3.05 (m, 1H), 3.01-2.83 (m, 4H), 2.61 (s, 3H), 2.47 (s, 3H), 2.07-2.01 (m, 1H), 1.93-1.85 (m, 2H), 1.82-1.70 (m, 2H), 1.51 (s, 9H).

Description D395

(R)-tert-Butyl 4-(1-(6-(2-(hydroxymethyl)morpholino)-2-methoxypyrimidin-4-yl)-5-methyl-1H-indazol-6-yl)piperidine-1-carboxylate (D395)

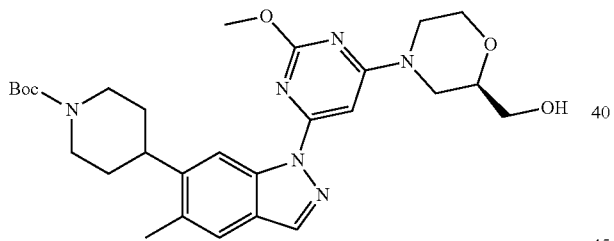

To a solution of tert-butyl 4-(5-methyl-1H-indazol-6-yl)piperidine-1-carboxylate (50 mg, 0.16 mmol) in toluene (10 mL) was added (2R)-4-(6-iodo-2-methoxypyrimidin-4-yl)-2-(((tetrahydro-2H-pyran-2-yl)oxy)methyl)morpholine (69 mg, 0.16 mmol), N,N'-dimethyl-cyclohexane-1,2-diamine (68 mg, 0.48 mmol), K$_3$PO$_4$ (102 mg, 0.48 mmol) and CuI (91 mg, 0.48 mmol) at rt. The resulting mixture was warmed to 110° C. and stirred overnight. To the reaction mixture was added NH$_3$H$_2$O (30%, 20 mL) and extracted with EtOAc (20 mL×3). The combined organic layers were washed with water (20 mL×2) and brine (20 mL), dried over Na$_2$SO$_4$ and concentrated. The residue was purified by prep-HPLC (from 13% water (0.1% TFA) and 87% CH$_3$CN to 5% water (0.1% TFA) and 95% CH$_3$CN in 20 min, Flow rate: 15 mL/min) to give the title compound (55 mg, yield 56%) as white solid.

D395 $^1$H NMR (300 MHz, CDCl$_3$): δ 8.71 (s, 1H), 8.07 (s, 1H), 7.52 (s, 1H), 6.85 (s, 1H), 4.36-4.23 (m, 3H), 4.11-4.04 (m, 4H), 3.80-3.66 (m, 4H), 3.19-2.82 (m, 4H), 2.48 (s, 3H), 1.90-1.77 (m, 3H), 1.67-1.58 (m, 3H), 1.50 (s, 9H).

Description D396

(R)-(4-(2-Methoxy-6-(5-methyl-6-(piperidin-4-yl)-1H-indazol-1-yl)pyrimidin-4-yl)morpholin-2-yl)methanol hydrochloride (D396)

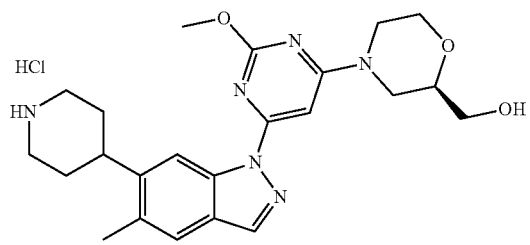 [SMILES: Cl ; COc1nc(N2CCO[C@@H](CO)C2)cc(-n2ncc3cc(C)c(C4CCNCC4)cc32)n1]

To a solution of (R)-tert-butyl 4-(1-(6-(2-(hydroxymethyl)morpholino)-2-methoxypyrimidin-4-yl)-5-methyl-1H-indazol-6-yl)piperidine-1-carboxylate (55 mg, 0.09 mmol) in dioxane (2 mL) was added HCl/dioxane (4 M, 6 mL) and stirred for 1 h. The reaction mixture was concentrated to give the title compound (42 mg, yield >100%) as a white solid.

D396 $^1$H NMR (300 MHz, CD$_3$OD): δ 8.37 (s, 1H), 8.35 (s, 1H), 7.72 (s, 1H), 7.08 (s, 1H), 4.36-4.26 (m, 5H), 4.14-4.10 (m, 1H), 3.80-3.75 (m, 5H), 3.59-3.56 (m, 3H), 3.44-3.35 (m, 1H), 3.26-3.21 (m, 2H), 2.54 (s, 3H), 2.16-2.08 (m, 4H).

Description D397

(S)-tert-Butyl 4-(1-(6-(2-(hydroxymethyl)morpholino)-2-methoxypyrimidin-4-yl)-5-methyl-1H-indazol-6-yl)piperidine-1-carboxylate (D397)

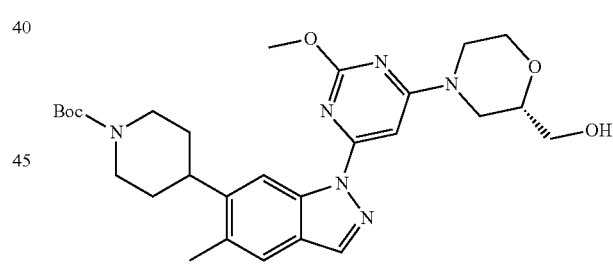

To a solution of tert-butyl 4-(5-methyl-1H-indazol-6-yl)piperidine-1-carboxylate (50 mg, 0.16 mmol) in toluene (10 mL) was added (2S)-4-(6-iodo-2-methoxypyrimidin-4-yl)-2-(((tetrahydro-2H-pyran-2-yl)oxy)methyl)morpholine (69 mg, 0.16 mmol), N,N'-dimethyl-cyclohexane-1,2-diamine (68 mg, 0.48 mmol), K$_3$PO$_4$ (102 mg, 0.48 mmol) and CuI (91 mg, 0.48 mmol) at rt. The resulting mixture was warmed to 110° C. and stirred overnight. To the reaction mixture was added NH$_3$H$_2$O (30%, 20 mL) and extracted with EtOAc (20 mL×3). The combined organic layers were washed with water (20 mL×2) and brine (20 mL), dried over Na$_2$SO$_4$ and concentrated. The residue was purified by prep-HPLC (from 13% water (0.1% TFA) and 87% CH$_3$CN to 5% water (0.1% TFA) and 95% CH$_3$CN in 20 min, Flow rate: 15 mL/min) to give the title compound (47 mg, yield 48%) as white solid.

D397 $^1$H NMR (300 MHz, CDCl$_3$): δ 8.71 (s, 1H), 8.07 (s, 1H), 7.52 (s, 1H), 6.85 (s, 1H), 4.34-4.22 (m, 3H), 4.11-4.03 (m, 4H), 3.80-3.66 (m, 4H), 3.18-2.83 (m, 4H), 2.48 (s, 3H), 1.90-1.76 (m, 3H), 1.67-1.62 (m, 3H), 1.50 (s, 9H).

Description D398

(S)-(4-(2-Methoxy-6-(5-methyl-6-(piperidin-4-yl)-1H-indazol-1-yl)pyrimidin-4-yl)morpholin-2-yl)methanol hydrochloride (D398)

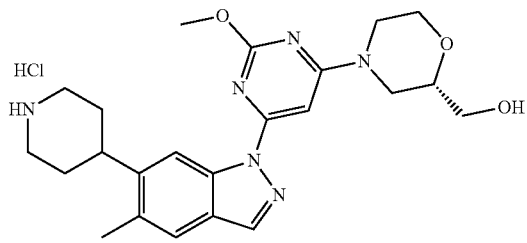 [SMILES: Cl ; COc1nc(N2CCO[C@H](CO)C2)cc(-n2ncc3cc(C)c(C4CCNCC4)cc32)n1]

To a solution of (S)-tert-butyl 4-(1-(6-(2-(hydroxymethyl)morpholino)-2-methoxypyrimidin-4-yl)-5-methyl-1H-indazol-6-yl)piperidine-1-carboxylate (47 mg, 0.08 mmol) in dioxane (2 mL) was added HCl/dioxane (4 M, 6 mL) and stirred for 1 h. The reaction mixture was concentrated to give the title compound (40 mg, yield >100%) as a white solid.

D398 $^1$H NMR (300 MHz, CD$_3$OD): δ 8.45 (s, 1H), 8.31 (s, 1H), 7.70 (s, 1H), 7.05 (s, 1H), 4.38-4.26 (m, 5H), 4.12-4.08 (m, 1H), 3.75-3.68 (m, 5H), 3.59-3.53 (m, 3H), 3.39-3.31 (m, 1H), 3.26-3.11 (m, 2H), 2.53 (s, 3H), 2.18-2.00 (m, 4H).

Description D399 tert-Butyl 4-(5-methyl-1-(2-methyl-6-morpholinopyrimidin-4-yl)-1H-indazol-6-yl)piperidine-1-carboxylate (D399)

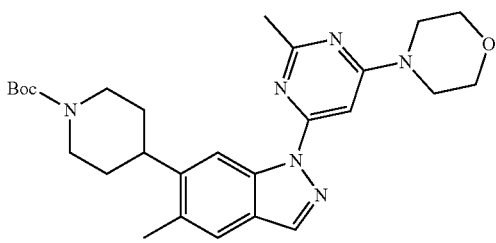 [SMILES: Cc1nc(N2CCOCC2)cc(-n2ncc3cc(C)c(C4CCN(C(=O)OC(C)(C)C)CC4)cc32)n1]

To a solution of 4-(6-iodo-2-methylpyrimidin-4-yl)morpholine (100 mg, 0.328 mmol) in toluene (10 mL) was added tert-butyl 4-(5-methyl-1H-indazol-6-yl)piperidine-1-carboxylate (103 mg, 0.328 mmol), N,N'-dimethyl-cyclohexane-1,2-diamine (140 mg, 0.984 mmol), K$_3$PO$_4$ (208 mg, 0.984 mmol) and CuI (187 mg, 0.984 mmol) at rt. The resulting mixture was warmed to 110° C. and stirred overnight. To the reaction mixture was added NH$_3$H$_2$O (30%, 20 mL) and extracted with EtOAc (20 mL×3). The combined organic layers were washed with water (20 mL×2) and brine (20 mL), dried over Na$_2$SO$_4$ and concentrated. The residue was purified by prep-HPLC (from 40% water (0.1% TFA) and 60% CH$_3$CN to 5% water (0.1% TFA) and 95% CH$_3$CN in 12 min, Flow rate: 15 mL/min) to give the title compound (112 mg, yield 70%) as a white solid.

D399 $^1$H NMR (300 MHz, CDCl$_3$): δ 8.69 (s, 1H), 8.09 (s, 1H), 7.52 (s, 1H), 7.00 (s, 1H), 4.34-4.30 (m, 2H), 3.83-3.81 (m, 4H), 3.77-3.75 (m, 4H), 3.02-2.84 (m, 3H), 2.69 (s, 3H), 2.48 (s, 3H), 1.90-1.79 (m, 2H), 1.75-1.65 (m, 2H), 1.51 (s, 9H).

Description D400

4-(2-Methyl-6-(5-methyl-6-(piperidin-4-yl)-1H-indazol-1-yl)pyrimidin-4-yl)morpholine hydrochloride (D400)

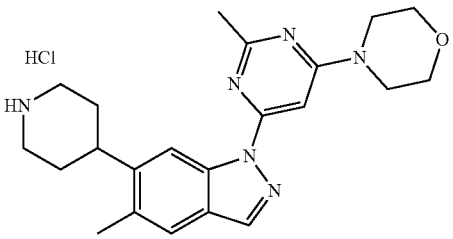 [SMILES: Cc1nc(N2CCOCC2)cc(-n2ncc3cc(C)c(C4CCNCC4)cc32)n1 ; Cl]

To a solution of tert-butyl 4-(5-methyl-1-(2-methyl-6-morpholinopyrimidin-4-yl)-1H-indazol-6-yl)piperidine-1-carboxylate (112 mg, 0.228 mmol) in dioxane (5 mL) was added HCl/dioxane (4 M, 5 mL). The mixture was stirred at rt for 1 h. The reaction mixture was concentrated to give the title compound (91 mg) as a white solid which was used for the next step without further purification.

Description D401 tert-Butyl 4-(1-(2-methoxy-6-morpholinopyrimidin-4-yl)-5-methyl-1H-indazol-6-yl)piperidine-1-carboxylate (D401)

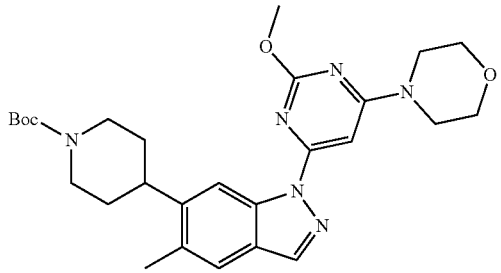 [SMILES: COc1nc(N2CCOCC2)cc(-n2ncc3cc(C)c(C4CCN(C(=O)OC(C)(C)C)CC4)cc32)n1]

To a solution of 4-(6-iodo-2-methoxypyrimidin-4-yl)morpholine (90 mg, 0.28 mmol) in toluene (10 mL) was added tert-butyl 4-(5-methyl-1H-indazol-6-yl)piperidine-1-carboxylate (89 mg, 0.28 mmol), N,N'-dimethyl-cyclohexane-1,2-diamine (120 mg, 0.84 mmol), K$_3$PO$_4$ (179 mg, 0.84 mmol) and CuI (160 mg, 0.84 mmol) at rt. The resulting mixture was warmed to 110° C. and stirred overnight. To the reaction mixture was added NH$_3$H$_2$O (30%, 20 mL) and extracted with EtOAc (20 mL×3). The combined organic layers were washed with water (20 mL×2) and brine (20 mL), dried over Na$_2$SO$_4$ and concentrated. The residue was purified by prep-HPLC (from 40% water (0.1% TFA) and 60% CH$_3$CN to 5% water (0.1% TFA) and 95% CH$_3$CN in 12 min, Flow rate: 15 mL/min) to give the title compound (56 mg, yield 39%) as a white solid.

D401 $^1$H NMR (300 MHz, CDCl$_3$): δ 8.71 (s, 1H), 8.08 (s, 1H), 7.53 (s, 1H), 6.84 (s, 1H), 4.35-4.22 (m, 2H), 4.11 (s, 3H), 3.82-3.77 (m, 4H), 3.75-3.69 (m, 4H), 2.99-2.82 (m, 3H), 2.48 (s, 3H), 1.93-1.87 (m, 2H), 1.75-1.65 (m, 2H), 1.51 (s, 9H).

Description D402

4-(2-Methoxy-6-(5-methyl-6-(piperidin-4-yl)-1H-indazol-1-yl)pyrimidin-4-yl)morpholine hydrochloride (D402)

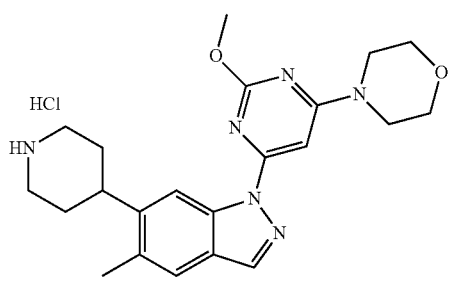 [SMILES: COc1nc(N2CCOCC2)cc(-n2ncc3cc(C)c(C4CCNCC4)cc32)n1 ; Cl]

To a solution of tert-butyl 4-(1-(2-methoxy-6-morpholinopyrimidin-4-yl)-5-methyl-1H-indazol-6-yl)piperidine-1-carboxylate (56 mg, 0.11 mmol) in dioxane (5 mL) was added HCl/dioxane (4 M, 5 mL) and the mixture was stirred for 1 h. The reaction mixture was concentrated to give the title compound (52 mg) as a white solid which was used for the next step directly.

D402 $^1$H NMR (300 MHz, CD$_3$OD): δ 8.54 (s, 1H), 8.27 (s, 1H), 7.69 (s, 1H), 7.02 (s, 1H), 4.21 (s, 3H), 3.83-3.77 (m, 4H), 3.69-3.3.65 (m, 4H), 3.57-3.54 (m, 3H), 3.28-3.22 (m, 2H), 2.53 (s, 3H), 2.16-2.00 (m, 4H).

Description D403

(R)-tert-Butyl 4-(1-(2-methoxy-6-(2-methylmorpholino)pyrimidin-4-yl)-5-methyl-1H-indazol-6-yl)piperidine-1-carboxylate (D403)

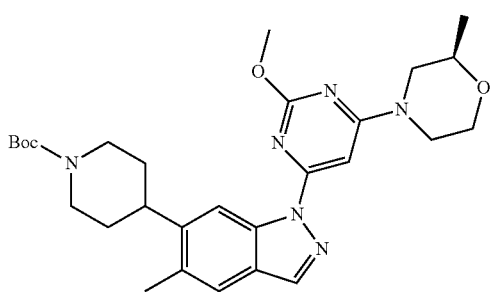 [SMILES: COc1nc(N2CCO[C@H](C)C2)cc(-n2ncc3cc(C)c(C4CCN(C(=O)OC(C)(C)C)CC4)cc32)n1]

To a suspension of (R)-4-(6-iodo-2-methoxypyrimidin-4-yl)-2-methylmorpholine (94 mg, 0.28 mmol), tert-butyl 4-(5-methyl-1H-indazol-6-yl)piperidine-1-carboxylate (97 mg, 0.31 mmol), CuI (54 mg, 0.28 mmol), K$_3$PO$_4$ (119 mg, 0.562 mmol) in toluene (2 mL) was added N,N'-dimethylcyclohexane-1,2-diamine (80 mg, 0.56 mmol) at rt. The resulting mixture was stirred at 110° C. under N$_2$ atmosphere for 4 hrs. The resulting mixture was poured into diluted ammonia (10%, 60 mL) and extracted with EtOAc (60 mL). The organic solution was washed with brine, dried over Na$_2$SO$_4$ and then concentrated. The crude was purified by prep-HPLC (from 35% water (0.1% NH$_4$HCO$_3$) and 65% CH$_3$CN to 5% water (0.1% NH$_4$HCO$_3$) and 95% CH$_3$CN in 15 min) to give the title compound (50 mg, yield 38%) as colorless oil.

D403 $^1$H NMR (300 MHz, CDCl$_3$): δ 8.72 (s, 1H), 8.07 (s, 1H), 7.52 (s, 1H), 6.83 (s, 1H), 4.41-4.19 (m, 4H), 4.11 (s, 3H), 4.04-3.96 (m, 1H), 3.72-3.60 (m, 2H), 3.18-2.71 (m, 5H), 2.48 (s, 3H), 1.92-1.66 (m, 4H), 1.50 (s, 9H), 1.26 (d, J=6.0 Hz, 3H).

Description D404

(R)-4-(2-Methoxy-6-(5-methyl-6-(piperidin-4-yl)-1H-indazol-1-yl)pyrimidin-4-yl)-2-methylmorpholine hydrochloride (D404)

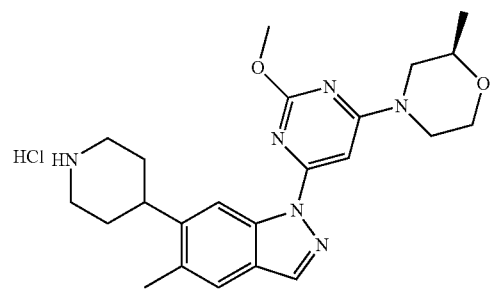 [SMILES: Cl ; COc1nc(N2CCO[C@H](C)C2)cc(-n2ncc3cc(C)c(C4CCNCC4)cc32)n1]

To a solution of (R)-tert-butyl 4-(1-(2-methoxy-6-(2-methylmorpholino)pyrimidin-4-yl)-5-methyl-1H-indazol-6-yl)piperidine-1-carboxylate (50 mg, 0.096 mmol) in dioxane (2 mL) was added HCl/dioxane (4 M, 5 mL) at rt. The resulting mixture was stirred at rt for 4 hrs. The resulting mixture was concentrated to give the title compound (100 mg, crude) as white solid.

D404 LCMS: 5-95% CH$_3$CN in 3 min; Rt=1.79 min; MS Calcd.: 422, MS Found: 423 [M+H]$^+$.

Description D405

(S)-tert-Butyl 4-(1-(2-methoxy-6-(2-methylmorpholino)pyrimidin-4-yl)-5-methyl-1H-indazol-6-yl)piperidine-1-carboxylate (D405)

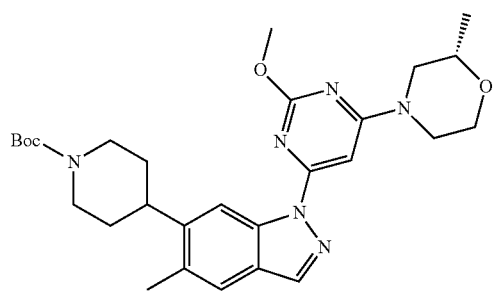 [SMILES: COc1nc(N2CCO[C@@H](C)C2)cc(-n2ncc3cc(C)c(C4CCN(C(=O)OC(C)(C)C)CC4)cc32)n1]

To a suspension of (S)-4-(6-iodo-2-methoxypyrimidin-4-yl)-2-methylmorpholine (94 mg, 0.28 mmol), tert-butyl 4-(5-methyl-1H-indazol-6-yl)piperidine-1-carboxylate (97 mg, 0.31 mmol), CuI (54 mg, 0.28 mmol), K$_3$PO$_4$ (119 mg, 0.562 mmol) in toluene (2 mL) was added N,N'-dimethylcyclohexane-1,2-diamine (80 mg, 0.56 mmol) at rt. The resulting mixture was stirred at 110° C. under N$_2$ atmosphere for 4 hrs. The resulting mixture was poured into diluted ammonia (10%, 60 mL) and extracted with EtOAc (60 mL). The organic solution was washed with brine, dried over Na$_2$SO$_4$ and then concentrated. The crude was purified by prep-TLC (PE:EtOAc=3:1) to give the title compound (50 mg, yield 38%) as colorless oil.

D405 $^1$H NMR (300 MHz, CDCl$_3$): δ 8.72 (s, 1H), 8.08 (s, 1H), 7.52 (s, 1H), 6.83 (s, 1H), 4.39-4.15 (m, 4H), 4.11 (s, 3H), 4.04-3.96 (m, 1H), 3.71-3.60 (m, 2H), 3.15-2.69 (m, 5H), 2.48 (s, 3H), 1.92-1.64 (m, 4H), 1.50 (s, 9H), 1.26 (d, J=6.3 Hz, 3H).

Description D406

(S)-4-(2-Methoxy-6-(5-methyl-6-(piperidin-4-yl)-1H-indazol-1-yl)pyrimidin-4-yl)-2-methylmorpholine hydrochloride (D406)

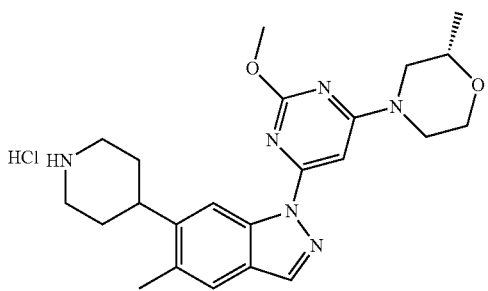 [SMILES: Cl ; COc1nc(N2CCO[C@@H](C)C2)cc(-n2ncc3cc(C)c(C4CCNCC4)cc32)n1]

To a solution of (S)-tert-butyl 4-(1-(2-methoxy-6-(2-methylmorpholino)pyrimidin-4-yl)-5-methyl-1H-indazol-6-yl)piperidine-1-carboxylate (50 mg, 0.096 mmol) in dioxane (2 mL) was added HCl/dioxane (4 M, 5 mL) at rt. The resulting mixture was stirred at rt for 4 hrs. The resulting mixture was concentrated to give the title compound (60 mg, yield 100%) as white solid.

D406 LCMS: 5-95% CH$_3$CN in 3 min; Rt=1.80 min; MS Calcd.: 422, MS Found: 423 [M+H]$^+$.

Description D407

(R)-4-(6-Iodo-2-methylpyrimidin-4-yl)-2-methylmorpholine (D407)

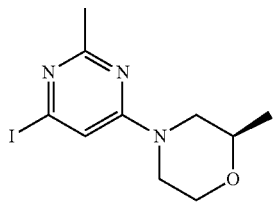

To a suspension of 4,6-diiodo-2-methylpyrimidine (150 mg, 0.434 mmol) in i-PrOH (2 mL) was added (R)-2-methylmorpholine (53 mg, 0.52 mmol) and TEA (131 mg, 1.30 mmol) at rt. The resulting mixture was stirred at 65° C. for 2 hrs. The resulting mixture was poured into water (60 mL) and extracted with EtOAc (60 mL). The organic solution was washed with brine, dried over Na$_2$SO$_4$ and then concentrated. The crude was purified by column chromatography (PE:EtOAc=7:1) to give the title compound (110 mg, yield 80%) as colorless oil.

D407 $^1$H NMR (300 MHz, CDCl$_3$): δ 6.77 (s, 1H), 4.24-3.96 (m, 3H), 3.67-3.54 (m, 2H), 3.07-2.95 (m, 1H), 2.71-2.60 (m, 1H), 2.46 (s, 3H), 1.25 (d, J=6.0 Hz, 3H).

Description D408

(R)-tert-Butyl 4-(5-methyl-1-(2-methyl-6-(2-methylmorpholino)pyrimidin-4-yl)-1H-indazol-6-yl)piperidine-1-carboxylate (D408)

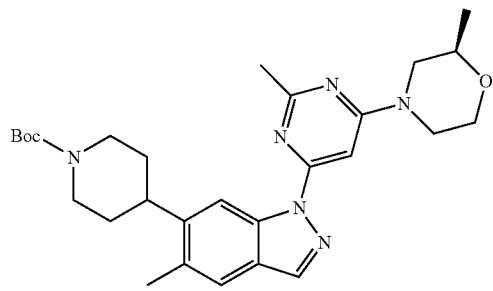 [SMILES: Cc1nc(N2CCO[C@H](C)C2)cc(-n2ncc3cc(C)c(C4CCN(C(=O)OC(C)(C)C)CC4)cc32)n1]

To a suspension of tert-butyl 4-(5-methyl-1H-indazol-6-yl)piperidine-1-carboxylate (110 mg, 0.345 mmol), (R)-4-(6-iodo-2-methylpyrimidin-4-yl)-2-methylmorpholine (119 mg, 0.379 mmol), CuI (66 mg, 0.35 mmol), K$_3$PO$_4$ (146 mg, 0.690 mmol) in toluene (2 mL) was added N,N'-dimethylcyclohexane-1,2-diamine (98 mg, 0.69 mmol) at rt. The resulting mixture was stirred at 110° C. under N$_2$ atmosphere for 4 hrs. The resulting mixture was poured into diluted ammonia (10%, 60 mL) and extracted with EtOAc (60 mL). The organic solution was washed with brine, dried over Na$_2$SO$_4$ and then concentrated. The crude was purified by prep-TLC (DCM:EtOAc=5:1) to give the title compound (100 mg, yield 57%) as colorless oil.

D408 $^1$H NMR (300 MHz, CDCl$_3$): δ 8.76 (s, 1H), 8.06 (s, 1H), 7.51 (s, 1H), 6.93 (s, 1H), 4.41-4.23 (m, 4H), 4.06-3.98 (m, 1H), 3.76-3.60 (m, 2H), 3.13-2.81 (m, 4H), 2.79-2.67 (m, 1H), 2.62 (s, 3H), 2.47 (s, 3H), 1.94-1.66 (m, 4H), 1.51 (s, 9H), 1.28 (d, J=6.3 Hz, 3H).

Description D409

(R)-2-Methyl-4-(2-methyl-6-(5-methyl-6-(piperidin-4-yl)-1H-indazol-1-yl)pyrimidin-4-yl)morpholine hydrochloride (D409)

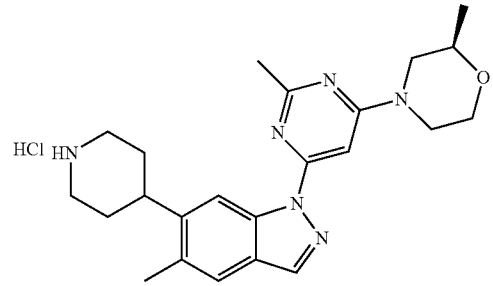 [SMILES: Cl ; Cc1nc(N2CCO[C@H](C)C2)cc(-n2ncc3cc(C)c(C4CCNCC4)cc32)n1]

To a solution of (R)-tert-butyl 4-(5-methyl-1-(2-methyl-6-(2-methylmorpholino)pyrimidin-4-yl)-1H-indazol-6-yl)piperidine-1-carboxylate (100 mg, 0.198 mmol) in dioxane (2 mL) was added HCl/dioxane (4 M, 5 mL) at rt. The resulting mixture was stirred at rt for 4 hrs. The resulting mixture was concentrated to give the title compound (140 mg, yield 100%) as yellow oil.

D409 LCMS: 5-95% CH₃CN in 3 min; Rt=1.68 min; MS Calcd.: 406, MS Found: 407 [M+H]⁺.

Description D410

(S)-4-(6-Iodo-2-methylpyrimidin-4-yl)-2-methylmorpholine (D410)

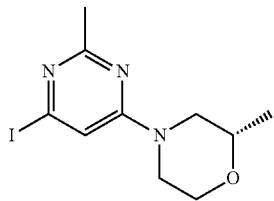

To a suspension of 4,6-diiodo-2-methylpyrimidine (150 mg, 0.434 mmol) in i-PrOH (2 mL) was added (S)-2-methylmorpholine (53 mg, 0.52 mmol) and TEA (131 mg, 1.30 mmol) at rt. The resulting mixture was stirred at 65° C. for 4 hrs. The resulting mixture was poured into water (60 mL) and extracted with EtOAc (60 mL). The organic solution was washed with brine, dried over Na₂SO₄ and then concentrated. The crude was purified by column chromatography (PE:EtOAc=7:1)) to give the title compound (110 mg, yield 80%) as colorless oil.

D410 ¹H NMR (300 MHz, CDCl₃): δ 6.77 (s, 1H), 4.23-3.96 (m, 3H), 3.65-3.54 (m, 2H), 3.07-2.94 (m, 1H), 2.71-2.60 (m, 1H), 2.46 (s, 3H), 1.26-1.24 (m, 3H).

Description D411

(S)-tert-Butyl 4-(5-methyl-1-(2-methyl-6-(2-methylmorpholino)pyrimidin-4-yl)-1H-indazol-6-yl)piperidine-1-carboxylate (D411)

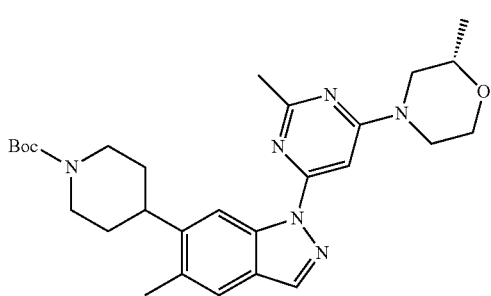 [SMILES: Cc1nc(N2CCO[C@@H](C)C2)cc(-n2ncc3cc(C)c(C4CCN(C(=O)OC(C)(C)C)CC4)cc32)n1]

To a suspension of tert-butyl 4-(5-methyl-1H-indazol-6-yl)piperidine-1-carboxylate (110 mg, 0.345 mmol), (S)-4-(6-iodo-2-methylpyrimidin-4-yl)-2-methylmorpholine (119 mg, 0.379 mmol), CuI (66 mg, 0.35 mmol), K₃PO₄ (146 mg, 0.690 mmol) in toluene (2 mL) was added N,N'-dimethylcyclohexane-1,2-diamine (98 mg, 0.69 mmol) at rt. The resulting mixture was stirred at 110° C. under N₂ atmosphere for 4 hrs. The resulting mixture was poured into diluted ammonia (10%, 60 mL) and extracted with EtOAc (60 mL). The organic solution was washed with brine, dried over Na₂SO₄ and then concentrated. The crude was purified by prep-TLC (DCM:EtOAc=5:1) to give the title compound (78 mg, yield 45%) as colorless oil.

D411 ¹H NMR (300 MHz, CDCl₃): δ 8.76 (s, 1H), 8.06 (s, 1H), 7.51 (s, 1H), 6.93 (s, 1H), 4.40-4.24 (m, 4H), 4.05-3.96 (m, 1H), 3.73-3.60 (m, 2H), 3.13-2.82 (m, 4H), 2.76-2.68 (m, 1H), 2.62 (s, 3H), 2.47 (s, 3H), 1.93-1.68 (m, 4H), 1.51 (s, 9H), 1.29-1.27 (m, 3H).

Description D412

(S)-2-Methyl-4-(2-methyl-6-(5-methyl-6-(piperidin-4-yl)-1H-indazol-1-yl)pyrimidin-4-yl)morpholine hydrochloride (D412)

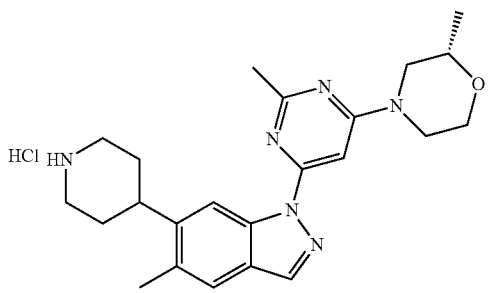 [SMILES: Cl ; Cc1nc(N2CCO[C@@H](C)C2)cc(-n2ncc3cc(C)c(C4CCNCC4)cc32)n1]

To a solution of (S)-tert-butyl 4-(5-methyl-1-(2-methyl-6-(2-methylmorpholino)pyrimidin-4-yl)-1H-indazol-6-yl)piperidine-1-carboxylate (78 mg, 0.15 mmol) in dioxane (2 mL) was added HCl/dioxane (4 M, 5 mL) at rt. The resulting mixture was stirred at rt for 4 hrs. The resulting mixture was concentrated to give the title compound (120 mg, yield >100%) as yellow oil.

D412 LCMS: 5-95% CH₃CN in 3 min; Rt=1.63 min; MS Calcd.: 406, MS Found: 407 [M+H]⁺.

Description D413

4-(1-(2-ethyl-6-morpholinopyrimidin-4-yl)-5-methyl-1H-indazol-6-yl)piperidine-1-carboxylate (Isomer 1, D413) and tert-butyl 4-(2-(2-ethyl-6-morpholinopyrimidin-4-yl)-5-methyl-2H-indazol-6-yl)piperidine-1-carboxylate (Isomer 2)

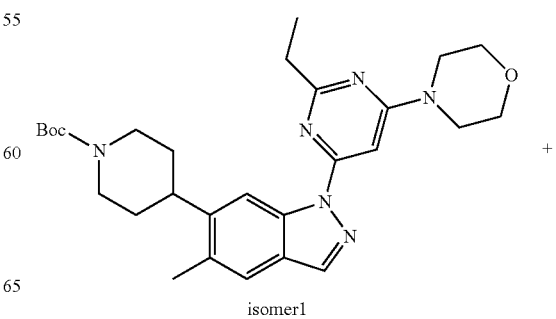

isomer1

-continued

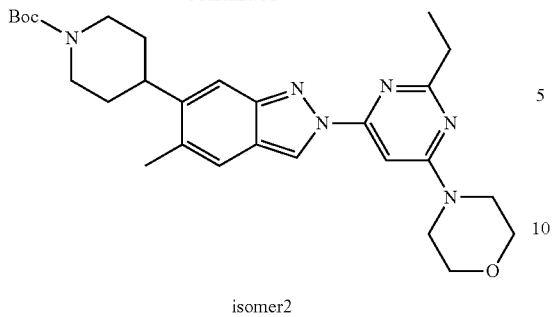

isomer2

To a solution of tert-butyl 4-(5-methyl-1H-indazol-6-yl)piperidine-1-carboxylate (100 mg, 0.317 mmol) and 4-(6-chloro-2-ethylpyrimidin-4-yl)morpholine (108 mg, 0.47 mmol) in NMP (6 mL) was added $Cs_2CO_3$ (207 mg, 0.634 mmol). The resulting mixture was heated to 100° C. and stirred overnight. The mixture was cooled to rt and poured into water (200 mL). EtOAc (50 mL×4) was added to extract the desired compound. The combined organic layers were washed with brine, dried over $Na_2SO_4$ and concentrated. The residue was purified by prep-TLC (EtOAc:DCM=10:1) to give isomer 1 (D431, 27 mg, yield 17%) and isomer 2 (12 mg, yield 8%) both as a white solid.

D413 (isomer 1) $^1$H NMR (300 MHz, $CDCl_3$): δ 8.83 (s, 1H), 8.06 (s, 1H), 7.51 (s, 1H), 6.96 (s, 1H), 4.40-4.25 (m, 2H), 3.83-3.80 (m, 4H), 3.74-3.71 (m, 4H), 3.02-2.86 (m, 5H), 2.48 (s, 3H), 1.90-1.69 (m, 4H), 1.51 (s, 9H), 1.48-1.43 (m, 3H).

isomer 2: $^1$H NMR (300 MHz, $CDCl_3$): δ 8.99 (s, 1H), 7.49 (s, 1H), 7.46 (s, 1H), 7.20 (s, 1H), 4.37-4.21 (m, 2H), 3.80-3.78 (m, 8H), 2.89-2.78 (m, 5H), 2.42 (s, 3H), 1.89-1.64 (m, 4H), 1.50 (s, 9H), 1.36 (t, J=7.5 Hz, 3H).

Description D414

4-(2-Ethyl-6-(5-methyl-6-(piperidin-4-yl)-1H-indazol-1-yl)pyrimidin-4-yl)morpholine hydrochloride (D414)

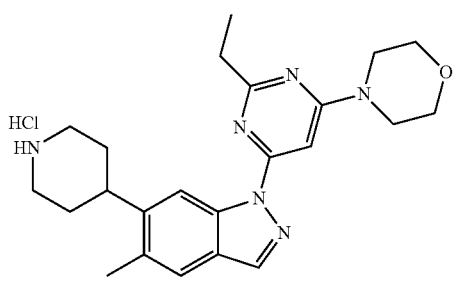 [SMILES: Cl ; CCc1nc(N2CCOCC2)cc(-n2ncc3cc(C)c(C4CCNCC4)cc32)n1]

To a solution of tert-butyl 4-(1-(2-ethyl-6-morpholinopyrimidin-4-yl)-5-methyl-1H-indazol-6-yl)piperidine-1-carboxylate (27 mg, 0.05 mmol) in dioxane (6 mL) was added HCl/dioxane (4 M, 6 mL). The resulting mixture was stirred at rt for 1 h. The mixture was concentrated to give the title compound (30 mg) as a white solid which was used for the next step directly.

Description D415

(S)-(4-(6-Chloro-2-ethylpyrimidin-4-yl)morpholin-2-yl)methanol (D415)

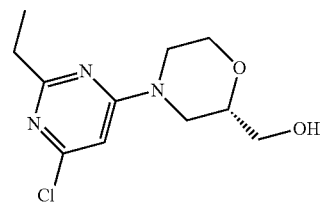 [SMILES: CCc1nc(Cl)cc(N2CCO[C@H](CO)C2)n1]

To a solution of 4,6-dichloro-2-ethylpyrimidine (84 mg, 0.48 mmol) in i-PrOH (5 mL) was added (S)-morpholin-2-ylmethanol hydrochloride (120 mg, 0.784 mmol) and TEA (0.5 mL). The resulting mixture was stirred at 90° C. for 1 h. The mixture was concentrated and purified by column (PE:EtOAc from 5:1 to 1:1) to give the title compound (130 mg, yield >100%) as colorless oil.

D415 $^1$H NMR (300 MHz, $CDCl_3$): δ 6.34 (s, 1H), 4.22-4.03 (m, 3H), 3.80-3.60 (m, 4H), 3.13-3.03 (m, 1H), 2.96-2.88 (m, 1H), 2.78-2.71 (m, 2H), 1.97-1.93 (m, 1H), 1.33-1.26 (m, 3H).

Description D416

(S)-tert-Butyl 4-(1-(2-ethyl-6-(2-(hydroxymethyl)morpholino)pyrimidin-4-yl)-5-methyl-1H-indazol-6-yl)piperidine-1-carboxylate (D416)

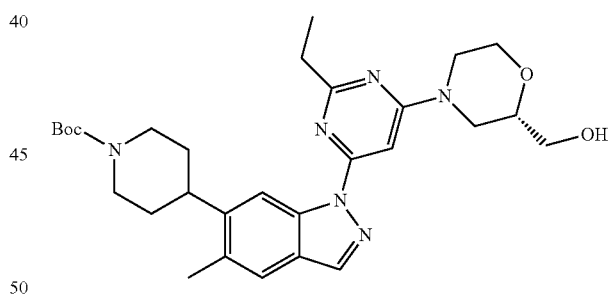

To a solution of tert-butyl 4-(5-methyl-1H-indazol-6-yl)piperidine-1-carboxylate (110 mg, 0.349 mmol) and (S)-(4-(6-chloro-2-ethylpyrimidin-4-yl)morpholin-2-yl)methanol (130 mg, 0.506 mmol) in NMP (5 mL) was added $Cs_2CO_3$ (210 mg, 0.644 mmol). The resulting mixture was stirred at 120° C. overnight. The mixture was poured into water (10 mL). EtOAc (50 mL) was added to extract the desired compound. The organic layer was concentrated and the residue was purified by prep-HPLC to give the title compound (30 mg, yield 16%) as a white solid.

D416 $^1$H NMR (300 MHz, $CDCl_3$): δ 8.82 (s, 1H), 8.06 (s, 1H), 7.51 (s, 1H), 6.96 (s, 1H), 4.33-4.29 (m, 4H), 4.08-4.05 (m, 1H), 3.80-3.67 (m, 4H), 3.15-3.11 (m, 1H), 3.06-2.86 (m, 6H), 2.47 (s, 3H), 1.89-1.80 (m, 2H), 1.75-1.62 (m, 2H), 1.51 (s, 9H), 1.48-1.43 (m, 3H).

Description D417

(S)-(4-(2-Ethyl-6-(5-methyl-6-(piperidin-4-yl)-1H-indazol-1-yl)pyrimidin-4-yl)morpholin-2-yl)methanol hydrochloride (D417)

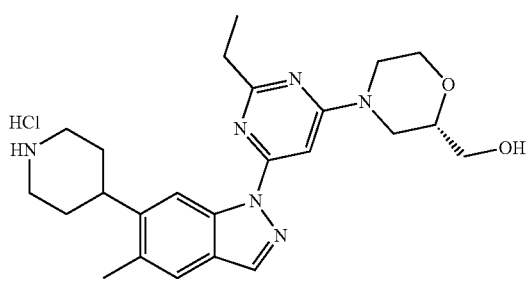 [SMILES: Cl ; CCc1nc(N2CCO[C@H](CO)C2)cc(-n2ncc3cc(C)c(C4CCNCC4)cc32)n1]

To a solution of (S)-tert-butyl 4-(1-(2-ethyl-6-(2-(hydroxymethyl)morpholino)pyrimidin-4-yl)-5-methyl-1H-indazol-6-yl)piperidine-1-carboxylate (30 mg, 0.056 mmol) in dioxane (3 mL) was added HCl/dioxane (5 M, 5 mL). The resulting mixture was stirred at rt for 2 hrs. The mixture was concentrated to give the title compound (40 mg, yield >100%) as a white solid.

D417 LC-MS (mobile phase: from 95% water and 5% CH$_3$CN to 5% water and 95% CH$_3$CN in 3 min), Rt=1.84 min; MS Calcd.: 436, MS Found: 437 [M+H]$^+$.

Description D418

(R)-(4-(6-Chloro-2-ethylpyrimidin-4-yl)morpholin-2-yl)methanol (D418)

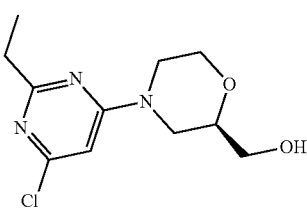 [SMILES: CCc1nc(Cl)cc(N2CCO[C@@H](CO)C2)n1]

To a solution of 4,6-dichloro-2-ethylpyrimidine (84 mg, 0.46 mmol) in i-PrOH (8 mL) was added (R)-morpholin-2-yl)methanol hydrochloride (123 mg, 0.691 mmol) and TEA (209 mg, 1.38 mmol). The resulting mixture was stirred at 90° C. for 1 h. The mixture was concentrated and purified by column (PE:EtOAc from 5:1 to 1:1) to give the title compound (139 mg, yield >100%) as a slight yellow solid.

D418 $^1$H NMR (300 MHz, CDCl$_3$): δ 6.34 (s, 1H), 4.26-4.03 (m, 3H), 3.80-3.61 (m, 4H), 3.13-3.03 (m, 1H), 2.96-2.89 (m, 1H), 2.75 (q, J=7.5 Hz, 2H), 2.05-1.94 (m, 1H), 1.28 (t, J=7.5 Hz, 3H).

Description D419

(R)-tert-Butyl 4-(1-(2-ethyl-6-(2-(hydroxymethyl)morpholino)pyrimidin-4-yl)-5-methyl-1H-indazol-6-yl)piperidine-1-carboxylate (D419)

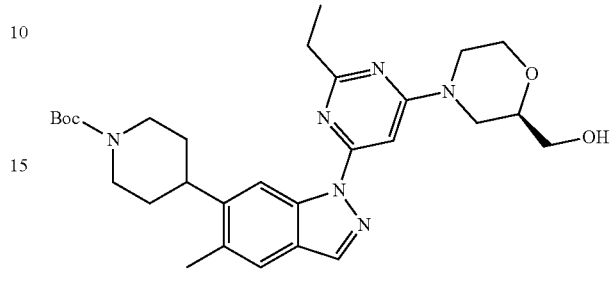

To a solution of tert-butyl 4-(5-methyl-1H-indazol-6-yl)piperidine-1-carboxylate (82 mg, 0.26 mmol) and (R)-(4-(6-chloro-2-ethylpyrimidin-4-yl)morpholin-2-yl)methanol (139 mg, 0.461 mmol) in NMP (5 mL) was added Cs$_2$CO$_3$ (201 mg, 0.635 mmol). The resulting mixture was stirred at 120° C. overnight. The mixture was cooled to r.t and poured into water (200 mL). EtOAc (50 mL) was added to extract the desired compound. The organic layers were washed with brine, dried over Na$_2$SO$_4$ and concentrated. The residue was purified by prep-HPLC (from 60% water (0.1% NH$_4$HCO$_3$) and 40% CH$_3$CN to 5% water (0.1% NH$_4$HCO$_3$) and 95% CH$_3$CN in 20 min, Flow rate: 15 mL/min) to give the title compound (15 mg, yield 7%) as a white solid.

D419 $^1$H NMR (300 MHz, CDCl$_3$): δ 8.82 (s, 1H), 8.06 (s, 1H), 7.51 (s, 1H), 6.96 (s, 1H), 4.36-4.28 (m, 4H), 4.09-4.05 (m, 1H), 3.82-3.68 (m, 4H), 3.15-3.07 (m, 1H), 2.99-2.86 (m, 6H), 2.48 (s, 3H), 2.02-1.80 (m, 3H), 1.76-1.72 (m, 2H), 1.51 (s, 9H), 1.48-1.42 (m, 3H).

Description D420

(R)-(4-(2-Ethyl-6-(5-methyl-6-(piperidin-4-yl)-1H-indazol-1-yl)pyrimidin-4-yl)morpholin-2-yl)methanol hydrochloride (D420)

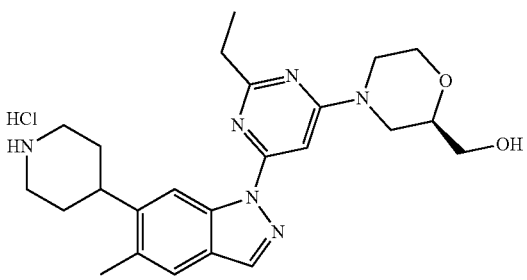 [SMILES: Cl ; CCc1nc(N2CCO[C@@H](CO)C2)cc(-n2ncc3cc(C)c(C4CCNCC4)cc32)n1]

To a solution of (R)-tert-butyl 4-(1-(2-ethyl-6-(2-(hydroxymethyl)morpholino)pyrimidin-4-yl)-5-methyl-1H-indazol-6-yl)piperidine-1-carboxylate (15 mg, 0.03 mmol) in dioxane (10 mL) was added HCl/dioxane (5 M, 5 mL). The resulting mixture was stirred at r.t for 1 h. The mixture was concentrated to give the title compound (20 mg) as a white solid which was used for next step directly.

Description D421

5-Bromo-2-methyl-4-nitroaniline (D421)

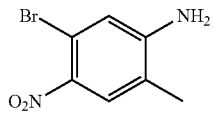

To a solution of 5-bromo-2-methylaniline (5.0 g, 27 mmol) in conc. H₂SO₄ (40 mL) was added KNO₃ (2.7 g, 27 mmol) in portions and kept the internal temperature below 5° C. The resulting mixture stirred for 2 hrs under ice bath. The resulting mixture was poured into ice water and stirred for 10 min. The mixture was filtered and the cake was washed with water (100 mL). The cake was purified by column chromatography (PE:EtOAc from 20:1 to 10:1) to give the title compound (3.1 g, yield 50%).

D421 $^1$H NMR (300 MHz, CDCl₃): δ 7.88 (s, 1H), 6.91 (s, 1H), 4.25 (br s, 2H), 2.16 (s, 3H).

Description D422

1-(6-Bromo-5-nitro-1H-indazol-1-yl)ethanone (D422)

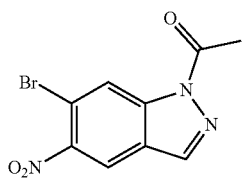 [SMILES: CC(=O)n1ncc2cc([N+](=O)[O-])c(Br)cc21]

To a solution of 5-bromo-2-methyl-4-nitroaniline (3.1 g, 13 mmol) in CHCl₃ (50 mL) was added Ac₂O (5.5 g, 54 mmol) under ice bath. Then, KOAc (2.6 g, 27 mmol), 18-crown-6 (1.1 g, 4.1 mmol) and isoamyl nitrite (3.2 g, 27 mmol) was added. The resulting mixture was refluxed overnight. The reaction mixture was washed with water (100 mL) and the aqueous layer was extracted with DCM (200 mL). The organic layer was concentrated and the residue was purified by column chromatography (PE:EtOAc=10:1) to give the title compound (2.2 g, yield 58%) as a brown solid.

D422 $^1$H NMR (300 MHz, CDCl₃): δ 8.90 (s, 1H), 8.29 (s, 1H), 8.24 (s, 1H), 2.82 (s, 3H).

Description D423

6-Bromo-5-nitro-1H-indazole (D423)

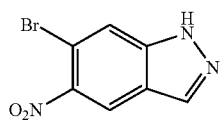 [SMILES: O=[N+]([O-])c1cc2cn[nH]c2cc1Br]

To a solution of 1-(6-bromo-5-nitro-1H-indazol-1-yl)ethanone (2.2 g, 7.8 mmol) in THF (10 mL) was added aqueous NaOH (5 M, 6 mL). The resulting mixture was stirred at rt for 1 h. DCM (100 mL) was added to extract the desired compound. The organic solution was washed with water (30 mL) and brine, dried over Na₂SO₄ and concentrated to give the title compound (1.0 g, yield 53%) as a brown solid which was used for next step directly.

D423 $^1$H NMR (300 MHz, DMSO-d₆): δ 13.74 (s, 1H), 8.63 (s, 1H), 8.35 (s, 1H), 8.07 (s, 1H).

Description D424

6-Bromo-5-nitro-1-(tetrahydro-2H-pyran-2-yl)-1H-indazole (D424)

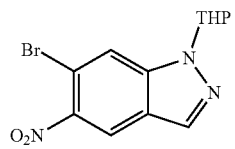

To a suspension of 6-bromo-5-nitro-1H-indazole (1.03 g, 4.26 mmol) and DHP (717 mg, 8.25 mmol) in DCM (10 mL) was added TsOH (146 mg, 0.825 mmol) at rt. The resulting mixture was stirred at rt (5° C.) for 20 min. The reaction mixture was diluted with DCM (50 mL) and then washed with sat. Na₂CO₃ (30 mL) and brine, dried over MgSO₄ and concentrated. The crude was purified by column chromatography (PE:EtOAc=5:1) to give the title compound (1.08 g, yield 78%) as an orange solid.

D424 $^1$H NMR (300 MHz, CDCl₃): δ 8.35 (s, 1H), 8.14 (s, 1H), 8.00 (s, 1H), 5.75-5.71 (m, 1H), 4.04-3.99 (m 1H), 3.82-3.74 (m, 1H), 2.54-2.41 (m, 1H), 2.21-2.08 (m, 2H), 1.85-1.66 (m, 3H).

Description D425 tert-Butyl 4-(5-nitro-1-(tetrahydro-2H-pyran-2-yl)-1H-indazol-6-yl)-5,6-dihydropyridine-1(2H)-carboxylate (D425)

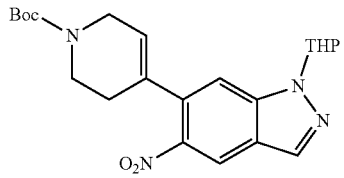

To a suspension of 6-bromo-5-nitro-1-(tetrahydro-2H-pyran-2-yl)-1H-indazole (1.08 g, 3.31 mmol), tert-butyl 4-(4,4,5,5-tetramethyl-1,3,2-dioxaborolan-2-yl)-5,6-dihydropyridine-1(2H)-carboxylate (1.08 g, 3.48 mmol) and Na₂CO₃ (878 mg, 8.28 mmol) in dioxane (12 mL) and water (2.5 mL) was added Pd(dppf)Cl₂ (121 mg, 0.166 mmol) at rt. The resulting mixture was stirred at 100° C. under N₂ atmosphere overnight. The reaction mixture was cooled and filtered. The filtrate was concentrated and the crude was purified by column chromatography (PE:EtOAc=5:1) to give the title compound (1.2 g, yield 85%) as an orange solid.

D425 $^1$H NMR (300 MHz, CDCl₃): δ 8.48 (s, 1H), 8.17 (s, 1H), 7.43 (s, 1H), 5.76-5.61 (m, 2H), 4.13-4.01 (m 3H), 3.83-3.74 (m, 1H), 3.72-3.65 (m, 2H), 2.58-2.45 (m, 1H), 2.41-2.28 (m, 2H), 2.22-2.06 (m, 2H), 1.85-1.65 (m, 3H), 1.51 (s, 9H).

Description D426 tert-Butyl 4-(5-amino-1-(tetrahydro-2H-pyran-2-yl)-1H-indazol-6-yl)piperidine-1-carboxylate (D426)

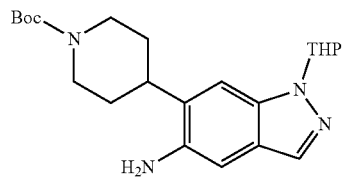

To a solution of tert-butyl 4-(5-nitro-1-(tetrahydro-2H-pyran-2-yl)-1H-indazol-6-yl)-5,6-dihydropyridine-1(2H)-carboxylate (1.0 g, 2.3 mmol) in MeOH (15 mL) was added Pd/C (10%, 100 mg) at rt. The resulting mixture was stirred at 50° C. under H₂ atmosphere (1 atm) for 3 hrs. The reaction mixture was cooled and filtered. The filtrate was concentrated to give the title compound (876 mg, yield 95%) as a white solid.

D426 ¹H NMR (300 MHz, CDCl₃): δ 7.82 (s, 1H), 7.28 (s, 1H), 6.98 (s, 1H), 5.66-5.62 (m, 1H), 4.41-4.24 (m, 2H), 4.07-4.01 (m 1H), 3.79-3.71 (m, 1H), 3.57 (s, 2H), 2.92-2.75 (m, 3H), 2.64-2.48 (m, 1H), 2.20-2.10 (m, 1H), 2.07-1.93 (m, 3H), 1.83-1.63 (m, 5H), 1.50 (s, 9H).

Description D427

5-Chloro-6-(piperidin-4-yl)-1H-indazole (D427)

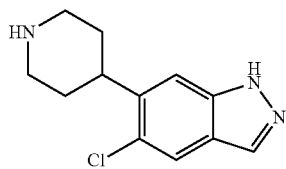 [SMILES: Clc1cc2cn[nH]c2cc1C1CCNCC1]

A solution of NaNO₂ (165 mg, 2.39 mmol) in water (5 mL) was added dropwise to a solution of tert butyl-4-(5-amino-1-(tetrahydro-2H-pyran-2-yl)-1H-indazol-6-yl)piperidine-1-carboxylate (870 mg, 2.17 mmol) in conc. HCl (3 mL) under ice bath (0-5° C.). Then, the resulting mixture was stirred for additional 15 min under ice bath. Then, the mixture was added to a suspension of CuCl (387 mg, 3.91 mmol) in water (5 mL) at 60° C. in one portion. The resulting mixture was stirred for 30 min at 60° C. The reaction mixture was cooled and gradually added to sat. Na₂CO₃ (50 mL) and stirred for 15 min. Then, ammonia (30%, 5 mL) was added to the mixture and stirred for 5 min. Then, the mixture was extracted with EtOAc (30 mL×3) and the combined organic layers were washed with brine, dried over MgSO₄ and concentrated to give the title compound (400 mg, yield 78%) as a pale yellow solid.

D427 ¹H NMR (300 MHz, DMSO-d₆): δ 13.15 (br s, 1H), 8.01 (s, 1H), 7.86 (s, 1H), 7.43 (s, 1H), 3.10-3.06 (m, 3H), 2.69-2.62 (m, 2H), 1.81-1.77 (m, 2H), 1.62-1.47 (m, 2H).

Description D428

5-Chloro-6-(1-(oxetan-3-yl)piperidin-4-yl)-1H-indazole (D428)

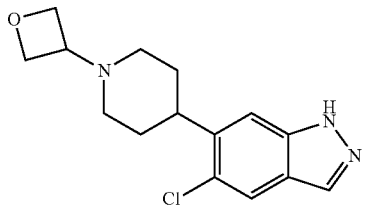 [SMILES: Clc1cc2cn[nH]c2cc1C1CCN(C2COC2)CC1]

To a solution of 5-chloro-6-(piperidin-4-yl)-1H-indazole (350 mg, 1.48 mmol) and oxetan-3-one (534 mg, 7.40 mmol) in DCE (10 mL) and MeOH (2 mL) was added HCl/MeOH (8 M, two drops) at rt. After the resulting mixture was stirred for 20 min, NaBH₃CN (279 mg, 4.44 mmol) was added in portions and the mixture was stirred for 3 hrs. The reaction mixture was poured into sat. Na₂CO₃ (50 mL) and extracted with DCM (30 mL×3). The combined organic layers were washed with brine, dried over Na₂SO₄ and concentrated. The crude was purified by column chromatography (DCM:MeOH=20:1) to give the title compound (160 mg, yield 37%) as a white solid.

D428 ¹H NMR (400 MHz, CDCl₃): δ 10.39 (br s, 1H), 7.99 (s, 1H), 7.78 (s, 1H), 7.43 (s, 1H), 4.77-4.68 (m, 4H), 3.61-3.54 (m, 1H), 3.20-3.10 (m, 1H), 2.96-2.93 (m, 2H), 2.09-1.99 (m, 4H), 1.84-1.74 (m, 2H).

Description D429

5-Chloro-1-(2-methyl-6-(3-((tetrahydro-2H-pyran-2-yl)oxy)azetidin-1-yl)pyrimidin-4-yl)-6-(1-(oxetan-3-yl)piperidin-4-yl)-1H-indazole (D429)

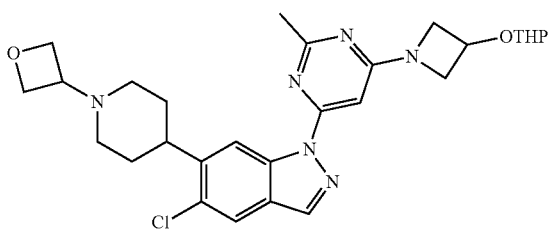

To a suspension of 5-chloro-6-(1-(oxetan-3-yl)piperidin-4-yl)-1H-indazole (50 mg, 0.17 mmol), 4-iodo-2-methyl-6-(3-((tetrahydro-2H-pyran-2-yl)oxy)azetidin-1-yl)pyrimidine (64 mg, 0.17 mmol), CuI (32 mg, 0.17 mmol) and K₃PO₄ (72 mg, 0.34 mmol) in toluene (3 mL) was added N,N'-dimethyl-cyclohexane-1,2-diamine (48 mg, 0.34 mmol) at rt. The resulting mixture was stirred at 110° C. under N₂ atmosphere for 3 hrs. Then, the reaction mixture was cooled and partitioned between diluted ammonia (10%, 30 mL) and EtOAc (30 mL). The organic layer was washed with brine, dried over Na₂SO₄ and concentrated. The crude was purified by prep-HPLC [Preparative HPLC was performed at conditions: Column: XBridge C18 5 μm 19*150 mm; Mobile phase: A acetonitrile; B water (0.1% NH₄HCO₃); Method: 60-80% A; Flow rate: 15 mL/min] to give the title compound (34 mg, yield 37%) as a white solid.

D429 $^1$H NMR (300 MHz, CDCl$_3$): δ 8.93 (s, 1H), 8.08 (s, 1H), 7.74 (s, 1H), 6.60 (s, 1H), 4.76-4.65 (m, 6H), 4.43-4.32 (m, 2H), 4.16-4.04 (m, 2H), 3.94-3.84 (m, 1H), 3.61-3.51 (m, 2H), 3.19-3.07 (m, 1H), 2.98-2.94 (m, 2H), 2.64 (s, 3H), 2.12-2.00 (m, 4H), 1.96-1.70 (m, 4H), 1.66-1.51 (m, 4H).

Description D430 tert-Butyl 4-(5-chloro-1H-indazol-6-yl)piperidine-1-carboxylate (D430)

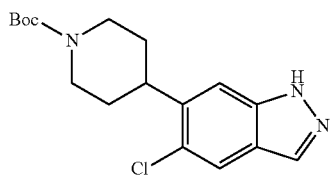 [SMILES: CC(C)(C)OC(=O)N1CCC(c2cc3[nH]ncc3cc2Cl)CC1]

To a solution of 5-chloro-6-(piperidin-4-yl)-1H-indazole (500 mg, 2.12 mmol) in DCM (10 mL) was added Boc$_2$O (1.39 g, 6.36 mmol) and DMAP (259 mg, 2.12 mmol) at rt. The resulting mixture was stirred for 30 min. The reaction mixture was then concentrated and the residue was dissolved in MeOH (5 mL). KOH (356 mg, 6.36 mmol) was added to the system and the solution was stirred for 30 min. The reaction mixture was poured into water (50 mL) and extracted with EtOAc (30 mL×2). The combined organic layers were washed with brine, dried over MgSO$_4$ and concentrated. The residue was purified by column chromatography (PE:EtOAc=2:1) to give the title compound (280 mg, yield 39%) as a white solid.

D430 $^1$H NMR (300 MHz, CDCl$_3$): δ 10.30 (br s, 1H), 8.00 (s, 1H), 7.79 (s, 1H), 7.36 (s, 1H), 4.40-4.21 (m, 2H), 3.33-3.20 (m, 1H), 2.94-2.85 (m, 2H), 1.98-1.93 (m, 2H), 1.68-1.62 (m, 2H), 1.50 (s, 9H).

Description D431

(S)-tert-Butyl 4-(5-chloro-1-(6-(2-(hydroxymethyl)morpholino)-2-methylpyrimidin-4-yl)-1H-indazol-6-yl)piperidine-1-carboxylate (D431)

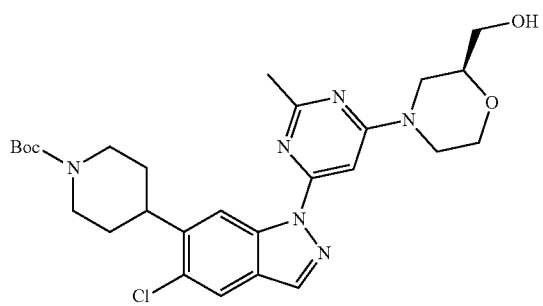 [SMILES: Cc1nc(N2CCO[C@H](CO)C2)cc(-n2ncc3cc(Cl)c(C4CCN(C(=O)OC(C)(C)C)CC4)cc32)n1]

To a suspension of tert-butyl 4-(5-chloro-1H-indazol-6-yl)piperidine-1-carboxylate (95 mg, 0.28 mmol), (S)-(4-(6-iodo-2-methylpyrimidin-4-yl)morpholin-2-yl)methanol (94 mg, 0.28 mmol), CuI (53 mg, 0.28 mmol) and K$_3$PO$_4$ (119 mg, 0.560 mmol) in toluene (2 mL) was added N,N'-dimethyl-cyclohexane-1,2-diamine (80 mg, 0.56 mmol) at rt. The resulting mixture was stirred at 110° C. under N$_2$ atmosphere for 3 hrs. Then, the reaction mixture was cooled and partitioned between NH$_4$Cl (sat, 30 mL) and EtOAc (30 mL). The organic layer was washed with brine, dried over MgSO$_4$ and concentrated. The crude was purified by prep-HPLC [Preparative HPLC was performed at conditions: Column: XBridge C18 5 μm 19*150 mm; Mobile phase: A acetonitrile; B water (0.1% TFA); Method: 83% A; Flow rate: 15 mL/min, 254 nm] to give the title compound (80 mg, yield 53%) as a white solid.

D431 $^1$H NMR (400 MHz, CDCl$_3$): δ 8.82 (s, 1H), 8.11 (s, 1H), 7.77 (s, 1H), 7.00 (s, 1H), 4.39-4.24 (m, 4H), 4.11-4.07 (m, 1H), 3.82-3.66 (m, 4H), 3.32-3.24 (m, 1H), 3.20-3.13 (m, 1H), 3.05-2.88 (m, 3H), 2.66 (s, 3H), 1.96-1.92 (m, 2H), 1.75-1.62 (m, 2H), 1.51 (s, 9H).

Description D432

(R)-tert-Butyl 4-(5-chloro-1-(6-(2-(hydroxymethyl)morpholino)-2-methylpyrimidin-4-yl)-1H-indazol-6-yl)piperidine-1-carboxylate (D432)

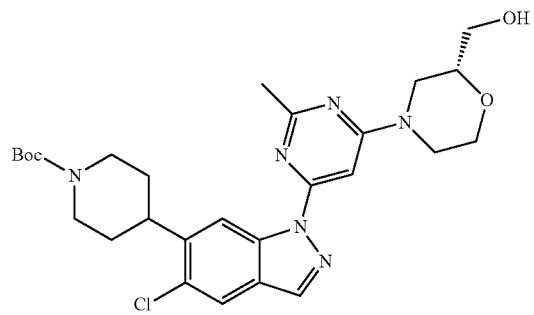 [SMILES: Cc1nc(N2CCO[C@@H](CO)C2)cc(-n2ncc3cc(Cl)c(C4CCN(C(=O)OC(C)(C)C)CC4)cc32)n1]

To a suspension of tert-butyl 4-(5-chloro-1H-indazol-6-yl)piperidine-1-carboxylate (95 mg, 0.28 mmol), (R)-(4-(6-iodo-2-methylpyrimidin-4-yl)morpholin-2-yl)methanol (94 mg, 0.28 mmol), CuI (53 mg, 0.28 mmol) and K$_3$PO$_4$ (119 mg, 0.560 mmol) in toluene (2 mL) was added N,N'-dimethyl-cyclohexane-1,2-diamine (80 mg, 0.56 mmol) at rt. The resulting mixture was stirred at 110° C. under N$_2$ atmosphere for 3 hrs. Then, the reaction mixture was cooled and partitioned between NH$_4$Cl (sat, 30 mL) and EtOAc (30 mL). The organic layer was washed with brine, dried over MgSO$_4$ and concentrated. The crude was purified by prep-HPLC [Preparative HPLC was performed at conditions: Column: XBridge C18 5 μm 19*150 mm; Mobile phase: A acetonitrile; B water (0.1% TFA); Method: 83% A; Flow rate: 15 mL/min, 254 nm] to give the title compound (74 mg, yield 49%) as a white solid.

D432 $^1$H NMR (400 MHz, CDCl$_3$): δ 8.81 (s, 1H), 8.11 (s, 1H), 7.76 (s, 1H), 7.00 (s, 1H), 4.40-4.22 (m, 4H), 4.11-4.07 (m, 1H), 3.83-3.67 (m, 4H), 3.31-3.24 (m, 1H), 3.21-3.14 (m, 1H), 3.05-2.88 (m, 3H), 2.67 (s, 3H), 2.04-1.98 (m, 2H), 1.74-1.60 (m, 2H), 1.51 (s, 9H).

Description D433 tert-Butyl 4-(5-chloro-1-(2-methyl-6-(3-((tetrahydro-2H-pyran-2-yl)oxy)azetidin-1-yl)pyrimidin-4-yl)-1H-indazol-6-yl)piperidine-1-carboxylate (D433)

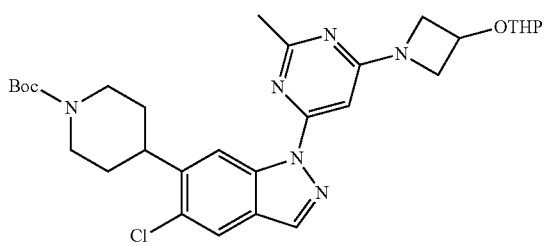

To a suspension of tert-butyl 4-(5-chloro-1H-indazol-6-yl)piperidine-1-carboxylate (80 mg, 0.24 mmol), 4-iodo-2-methyl-6-(3-((tetrahydro-2H-pyran-2-yl)oxy)azetidin-1-yl)pyrimidine (90 mg, 0.24 mmol), CuI (46 mg, 0.24 mmol) and $K_3PO_4$ (102 mg, 0.480 mmol) in toluene (2 mL) was added N,N'-dimethyl-cyclohexane-1,2-diamine (68 mg, 0.48 mmol) at rt. The resulting mixture was stirred at 110° C. under $N_2$ atmosphere for 3 hrs. Then, the reaction mixture was cooled and partitioned between $NH_4Cl$ (sat, 30 mL) and EtOAc (30 mL). The organic layer was washed with brine, dried over $MgSO_4$ and concentrated. The crude was purified by prep. HPLC [Preparative HPLC was performed at conditions: Column: XBridge C18 5 μm 19*150 mm; Mobile phase: A acetonitrile; B water (0.1% TFA); Method: 50-90% A; Flow rate: 20 mL/min, 254 nm] to give the title compound (70 mg, yield 53%) as a white solid.

D433 $^1$H NMR (300 MHz, $CDCl_3$): δ 8.73 (s, 1H), 8.15 (s, 1H), 7.78 (s, 1H), 6.69 (s, 1H), 4.78-4.26 (m, 8H), 3.92-3.82 (m, 1H), 3.59-3.51 (m, 1H), 3.34-3.23 (m, 1H), 2.98-2.85 (m, 2H), 2.75 (s, 3H), 2.02-1.94 (m, 2H), 1.87-1.55 (m, 8H), 1.50 (s, 9H).

Description D434

(S)-1-(6-iodo-2-methylpyrimidin-4-yl)pyrrolidin-3-ol (D434)

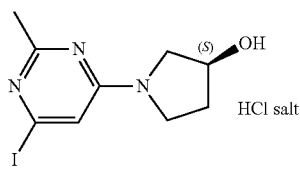

To a solution of 4,6-diiodo-2-methylpyrimidine (2 g, 5.8 mmol) and (S)-pyrrolidin-3-ol (717 mg, 5.8 mmol) in THF/EtOH (40 mL/40 mL) was added DIEA (2.25 g, 17.4 mmol). Then, the reaction was stirred at room temperature for 48 hours. Then, the reaction was concentrated and purified by column (PE:EtOAc=10:1-6:1~DCM:MeOH=50:1-40:1-30:1) to get a creamy-white solid (2.8 g).

D434 $^1$H NMR (400 MHz, DMSO-$d_6$): δ 8.17 (s, 1H), 6.76 (s, 1H), 5.05-4.96 (d, J=35.2 Hz, 1H), 4.38-4.32 (d, J=24.4 Hz, 1H), 3.64-3.60 (m, 2H), 3.16-3.13 (m, 2H), 2.30 (s, 3H), 1.99-1.88 (m, 2H).

Description D435

(R)-1-(6-iodo-2-methylpyrimidin-4-yl)pyrrolidin-3-ol (D435)

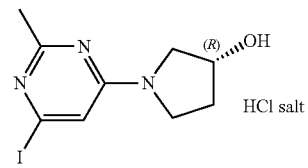

To a solution of 4,6-diiodo-2-methylpyrimidine (2 g, 5.8 mmol) and (R)-pyrrolidin-3-ol (717 mg, 5.8 mmol) in THF/EtOH (40 mL/40 mL) was added DIEA (2.25 g, 17.4 mmol). Then, the reaction mixture was stirred at room temperature for 48 hours. Then, the reaction mixture was concentrated and purified by column (PE:EtOAc=6:1-1:1~DCM:MeOH=40:1) to get a yellow solid (2.64 g).

D435 $^1$H NMR (400 MHz, DMSO-$d_6$): δ 8.16 (s, 1H), 6.76 (s, 1H), 5.04-4.95 (d, J=35.2 Hz, 1H), 4.38-4.31 (d, J=27.2 Hz, 1H), 3.66-3.58 (m, 2H), 3.18-3.11 (m, 2H), 2.30 (s, 3H), 1.98-1.81 (m, 2H).

Description D436

(trans)-4-Fluoro-1-(6-iodo-2-methylpyrimidin-4-yl)pyrrolidin-3-ol (D436)

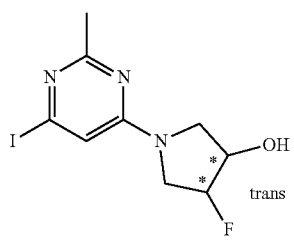

A mixture of 4,6-diiodo-2-methylpyrimidine (692 mg, 2 mmol), (trans)-4-fluoropyrrolidin-3-ol hydrochloride (283 mg, 2 mmol) and DIPEA (774 mg, 6 mmol) in THF/EtOH (40 mL/40 mL) was stirred at rt for 14 h. The solvent was removed, and the residue was purified by column to give a white solid. (490 mg, 75% yield).

D436 $^1$H NMR (400 MHz, DMSO-$d_6$) δ 6.87 (s, 1H), 5.64-5.56 (m, 1H), 5.15-4.96 (m, 1H), 4.35-4.30 (m, 1H), 3.80-3.51 (m, 3H), 2.33 (s, 3H).

Description D437

(trans)-4-Fluoro-1-(2-methyl-6-(5-methyl-6-(1-(oxetan-3-yl)piperidin-4-yl)-1H-indazol-1-yl)pyrimidin-4-yl)pyrrolidin-3-ol (D437)

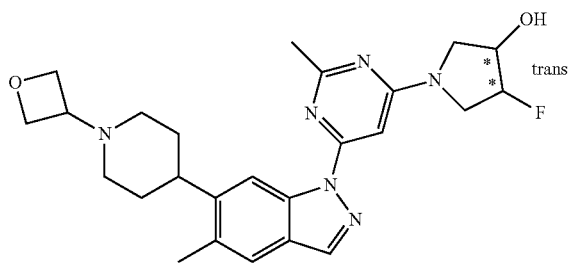 [SMILES: Cc1nc(N2CC(O)C(F)C2)cc(-n2ncc3cc(C)c(C4CCN(C5COC5)CC4)cc32)n1]

To a suspension of (trans)-4-fluoro-1-(6-iodo-2-methylpyrimidin-4-yl)pyrrolidin-3-ol (200 mg, 0.62 mmol), 5-methyl-6-(1-(oxetan-3-yl)piperidin-4-yl)-1H-indazole (138 mg, 0.51 mmol), CuI (97 mg, 0.51 mmol) and $K_3PO_4$ (216 mg, 1.02 mmol) in dry toluene (20 mL) was added N,N-dimethyl-1,2-ethanediamine (90 mg, 1.02 mmol). The suspension was degassed with $N_2$ and refluxed for 2 h. The solvent was removed under vacuum and the residue was purified by silica gel chromatography (eluted with DCM/MeOH=15:1) to give product (80 mg, yield 33.6%) as a white solid. (45 mg, yield: 19%)

D437 $^1$H NMR (400 MHz, CDCl$_3$) δ 8.82 (s, 1H), 8.06 (s, 1H), 7.50 (s, 1H), 6.75 (s, 1H), 5.01-5.15 (m, 1H), 4.71 (d, J=6.8 Hz, 4H), 4.53 (s, 1H), 3.93 (s, 1H), 3.73-3.86 (m, 2H), 3.54-3.57 (m, 1H); 2.97-2.99 (m, 2H); 2.83-2.87 (m, 1H), 2.66 (s, 3H); 2.46 (s, 3H); 2.17 (s, 1H), 1.85-2.11 (m, 7H).

Description D438

(trans)-4-Fluoro-1-(6-iodo-2-methoxypyrimidin-4-yl)pyrrolidin-3-ol (D438)

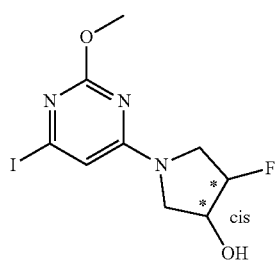 [SMILES: COc1nc(I)cc(N2CC(O)C(F)C2)n1]

A mixture of 4,6-diiodo-2-methoxypyrimidine (600 mg, 2 mmol), (trans)-4-fluoropyrrolidin-3-ol hydrochloride (235 mg, 1.66 mmol) and DIPEA (641 mg, 4.97 mmol) in THF/EtOH (40 mL/40 mL) was stirred at rt for 14 h. The solvent was removed, and the residue was purified by column to give a white solid (300 mg) and it was used directly in the next step without further purification.

Description D439

(trans)-4-Fluoro-1-(2-methoxy-6-(5-methyl-6-(1-(oxetan-3-yl)piperidin-4-yl)-1H-indazol-1-yl)pyrimidin-4-yl)pyrrolidin-3-ol (D439)

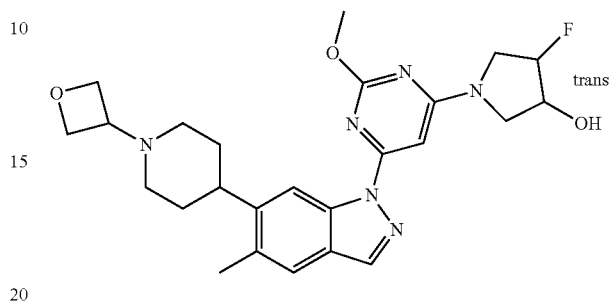

To a suspension of (trans)-4-fluoro-1-(6-iodo-2-methoxypyrimidin-4-yl)pyrrolidin-3-ol (300 mg, 0.88 mmol), 5-methyl-6-(1-(oxetan-3-yl)piperidin-4-yl)-1H-indazole (286 mg, 0.88 mmol), CuI (170 mg, 0.88 mmol) and $K_3PO_4$ (373 mg, 1.76 mmol) in dry toluene (30 mL) was added N,N-dimethyl-1,2-ethanediamine (156 mg, 1.76 mmol). The suspension was degassed with $N_2$ and refluxed for 2 h. The solvent was removed under vacuum and the residue was purified by silica gel chromatography (eluted with DCM/MeOH=15:1) to give product (220 mg, yield 52%) as a white solid.

D439 $^1$H NMR (400 MHz, CDCl$_3$) δ 8.77 (s, 1H), 8.07 (s, 1H), 7.51 (s, 1H), 6.64 (s, 1H), 5.10 (d, J=6.4 Hz, 1H); 4.65 (d, J=6.4 Hz, 4H), 4.53-4.59 (m, 1H), 4.16 (s, 3H), 3.84-3.87 (m, 3H), 3.49-3.56 (m, 1H); 2.94 (m, 2H); 2.92 (m, 1H), 2.46 (s, 3H); 1.86-2.04 (m, 7H).

Description D440

Methyl 1-(6-iodo-2-methylpyrimidin-4-yl)azetidine-3-carboxylate (D440)

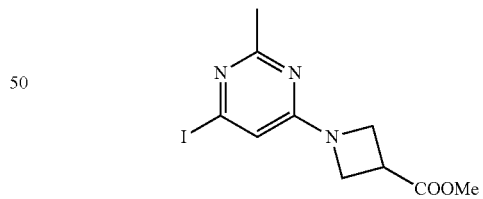

Methyl azetidine-3-carboxylate hydrochloride (437 mg, 2.89 mmol) was added to the solution of 4,6-diiodo-2-methylpyrimidine (230 mg, 2.0 mmol) and Et$_3$N (5 mL) in iPrOH (100 mL) at RT and the reaction was stirred at RT for 2 overnights. Then, the reaction mixture was concentrated and the residue was purified by silica gel chromatography (eluted with PE/EtOAc=6/1) to give the product as yellow oil (680 mg, yield 70.7%).

D440 $^1$H NMR (400 MHz, CDCl$_3$): δ 6.50 (s, 1H), 4.20, 4.23, 4.24, 4.25 (dd, J1=8.4 Hz, J2=5.6 Hz). 3.77 (s, 3H), 3.56~3.60 (m, 1H), 2.46 (s, 3H)

Description D441

Methyl 1-(2-methyl-6-(5-methyl-6-(1-(oxetan-3-yl)piperidin-4-yl)-1H-indazol-1-yl)pyrimidin-4-yl)azetidine-3-carboxylate (D441)

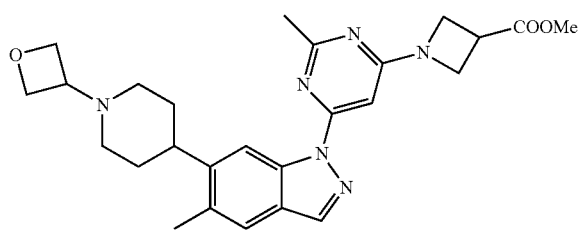 [SMILES: COC(=O)C1CN(c2cc(-n3ncc4cc(C)c(C5CCN(C6COC6)CC5)cc43)nc(C)n2)C1]

The mixture of methyl 1-(6-iodo-2-methylpyrimidin-4-yl)azetidine-3-carboxylate (300 mg, 0.9 mmol), 5-methyl-6-(1-(oxetan-3-yl)piperidin-4-yl)-1H-indazole (245 mg, 0.9 mmol), CuI (171 mg, 0.9 mmol) and $K_3PO_4$ (383 mg, 1.8 mmol) in toluene (15 mL) was degassed and protected with $N_2$ before N,N-dimethyl-1,2-ethanediamine (159 mg, 1.8 mmol) was added. Then, the reaction mixture was stirred at 80° C. for 1 hour. The reaction mixture was concentrated. The residue was purified by column (DCM/MeOH=50/1) to give the desired product as a white solid (30 mg, yield=7.0%).

D441 LC-MS (mobile phase: from 80% water (0.1% FA) and 20% $CH_3CN$ (0.1% FA). Rt=1.07 min; MS Calcd.: 476.2; MS Found: 477.4 $[M+H]^+$.

Description D442 tert-Butyl 3-hydroxy-3-(5-methyl-1-(tetrahydro-2H-pyran-2-yl)-1H-indazol-6-yl)piperidine-1-carboxylate (D442)

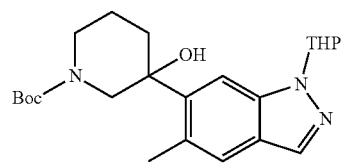

n-BuLi (2.0 mL, 2.5 M, 5.0 mmol) was slowly added to the solution of 6-bromo-5-methyl-1-(tetrahydro-2H-pyran-2-yl)-1H-indazole (1.18 g, 4.0 mmol) in dry THF (15 mL) at −80° C. Then, the solution of tert-butyl 3-oxopiperidine-1-carboxylate (1.0 g, 5.0 mmol) in dry THF (5.0 mL) was added to the reaction mixture before the reaction mixture was stirred at −78° C. for 10 mins. The reaction mixture was stirred at −75° C. for 1 hour and then the reaction mixture was quenched with water (20 mL). The mixture was extracted with EtOAc (2×20 mL) and the organic layers were dried over anhydrous $Na_2SO_4$ and filtered. The filtrate was concentrated and the residue was purified by silica column chromatography (EtOAc:PE=1:3~1:1) to give the desired product (920 mg, 55% yield) as a white solid.

D442 $^1$H NMR (400 MHz, $CDCl_3$): δ 7.92 (s, 1H), 7.67 (s, 1H), 7.52 (s, 1H), 5.71 (d, J=6.4 Hz, 1H), 4.5~4.01 (m, 1H), 3.78~3.75 (m, 1H), 2.71 (s, 3H), 2.61~2.56 (m, 1H), 2.29~2.00 (m, 6H), 1.80~1.58 (4H), 1.50 (s, 9H), 1.50~1.44 (m, 4H).

Description D443 tert-Butyl 3-fluoro-3-(5-methyl-1-(tetrahydro-2H-pyran-2-yl)-1H-indazol-6-yl)piperidine-1-carboxylate (D443)

DAST (715 mg, 4.42 mmol) was slowly added to the solution of tert-butyl 3-hydroxy-3-(5-methyl-1-(tetrahydro-2H-pyran-2-yl)-1H-indazol-6-yl)piperidine-1-carboxylate (920 mg, 2.21 mmol) in DCM (10 mL) at 0° C. slowly and the reaction was stirred at RT for 1 hour. Sat. $NaHCO_3$ (20 mL) was added to the reaction mixture and the mixture was extracted with DCM (2×20 mL). The organic layers were dried over anhydrous $Na_2SO_4$ and filtered. The filtrate was concentrated and the residue was purified by silica column chromatography (EtOAc:PE=1:10) to give the desired product (420 mg, 46% yield) as a light brown oil.

D443 $^1$H NMR (400 MHz, $CDCl_3$): δ 7.94 (s, 1H), 7.54 (s, 2H), 5.72 (d, J=1.6 Hz, 1H), 4.57~4.51 (m, 1H), 4.40~4.30 (m, 1H), 4.04~4.000 (m, 1H), 3.80~3.73 (m, 1H), 3.30~2.73 (m, 2H), 2.65 (s, 3H), 2.65~2.55 (m, 1H), 2.40~2.00 (m, 6H), 1.80~1.58 (4H), 1.50 (s, 9H).

Description D444

6-(3-Fluoropiperidin-3-yl)-5-methyl-1H-indazole TFA Salt (D444)

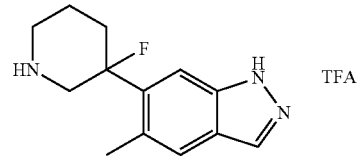 [SMILES: Cc1cc2cn[nH]c2cc1C1(F)CCCNC1]

TFA (0.5 mL) was added to the solution of tert-butyl 3-fluoro-3-(5-methyl-1-(tetrahydro-2H-pyran-2-yl)-1H-indazol-6-yl)piperidine-1-carboxylate (420 mg, 1.0 mmol) in DCM (5 mL) at RT and the reaction was stirred at RT overnight. Then, the reaction solution was concentrated to give the desired product as a brown oil. (400 mg, 100% yield) The crude product was used to next step without further purification.

D444 LC-MS (mobile phase: mobile phase: from 80% water (0.1% FA) and 20% $CH_3CN$ (0.1% FA) to 5% water (0.1% FA) and 95% $CH_3CN$ (0.1% FA) in 2.6 min, Rt=0.779 min; MS Calcd.: 233.1, MS Found: 234.3 $[M+H]^+$.

Description D445

6-(3-Fluoro-1-methylpiperidin-3-yl)-5-methyl-1H-indazole (D445)

CH$_2$O (0.4 mL, 5.0 mmol) was added to the solution of 6-(3-fluoropiperidin-3-yl)-5-methyl-1H-indazole TFA salt (400 mg, 1.0 mmol) in MeOH (4.0 mL) at RT and the resulting solution was stirred at room temperature overnight. NaBH$_3$CN (252 mg, 4.0 mmol) was added and the reaction was stirred at room temperature for 1 hour. Then, the reaction solution was concentrated. The residue was purified by perp-TLC (MeOH:DCM=1:5) to give the desired product (210 mg, 85% yield) as a colorless oil.

D445 LC-MS (mobile phase: mobile phase: from 90% water (0.1% FA) and 80% CH$_3$CN (0.1% FA) to 5% water (0.1% FA) and 95% CH$_3$CN (0.1% FA) in 2.0 min, Rt=0.63 min & 0.86 min; MS Calcd.: 247.1, MS Found: 248.3 [M+H]$^+$.

Description D446

6-(3-Fluoro-1-methylpiperidin-3-yl)-1-(2-methoxy-6-(3-((tetrahydro-2H-pyran-2-yl)oxy)azetidin-1-yl)pyrimidin-4-yl)-5-methyl-1H-indazole (D446)

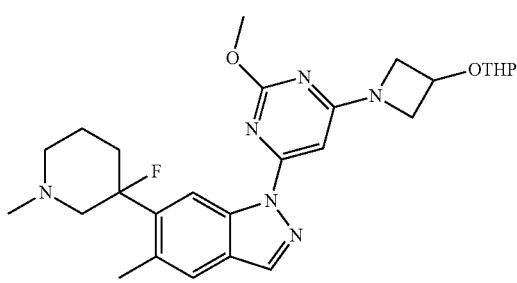

The mixture of 6-(3-fluoro-1-methylpiperidin-3-yl)-5-methyl-1H-indazole (210 mg, 0.8 mmol), 4-iodo-2-methoxy-6-(3-((tetrahydro-2H-pyran-2-yl)oxy)azetidin-1-yl)pyrimidine (340 mg, 0.87 mmol), CuI (200 mg, 1.05 mmol) and K$_3$PO$_4$ (424 mg, 2.0 mmol) in toluene (5 mL) and DMF (2 mL) was degassed and protected with N$_2$ before N,N-dimethyl-1,2-ethanediamine (176 mg, 2.0 mmol) was added. Then, the reaction mixture was stirred at 110° C. for 2 hours. The reaction mixture was cooled and diluted with EtOAc (50 mL). The mixture was washed with brine (3×50 mL) and the organic solution was dried over anhydrous Na$_2$SO$_4$ and filtered. The filtrate was concentrated and the residue was purified by silica column chromatography (MeOH/DCM=1/20) to give an off-white solid (210 mg, 42% yield). The solid was washed with hexane to give the desired product as a white solid. (180 mg, 36% yield)

D446 $^1$H NMR (400 MHz, CDCl$_3$): δ 8.97 (s, 1H), 8.09 (s, 1H), 7.54 (s, 1H), 6.67 (s, 1H), 4.73~4.67 (m, 2H), 4.40~4.34 (m, 2H), 4.16~4.05 (m, 2H), 4.15 (s, 3H), 3.91~3.86 (m, 1H), 3.56~3.52 (m, 1H), 3.29~3.23 (m, 1H), 2.96 (d, J=10.0 Hz, 1H), 2.85 (s, 3H), 2.66 (d, J=4.4 Hz, 3H), 2.45~1.55 (m, 12H).

Description D447

(trans)-4-(5-Methyl-1H-indazol-6-yl)piperidin-3-ol hydrochloride (D447)

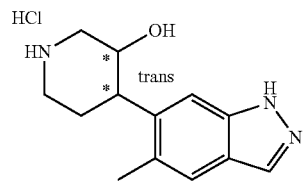 [SMILES: Cl ; Cc1cc2cn[nH]c2cc1C1CCNCC1O]

To a solution of (trans)-tert-butyl 3-hydroxy-4-(5-methyl-1-(tetrahydro-2H-pyran-2-yl)-1H-indazol-6-yl)piperidine-1-carboxylate (7.30 g, 17.6 mmol) in CH$_3$OH (60 mL) was added HCl/CH$_3$OH (8 M, 20 mL). The mixture was stirred at r.t overnight. The mixture was concentrated to give the title compound (5.9 g) as white solid which was used for next step directly.

Description D448

(trans)-tert-Butyl 3-hydroxy-4-(5-methyl-1H-indazol-6-yl)piperidine-1-carboxylate (D448)

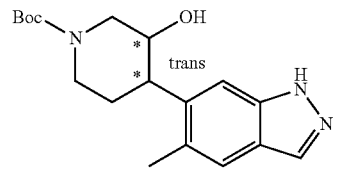 [SMILES: Cc1cc2cn[nH]c2cc1C1CCN(C(=O)OC(C)(C)C)CC1O]

To a solution of (trans)-4-(5-methyl-1H-indazol-6-yl)piperidin-3-ol hydrochloride (5.90 g crude, 17.6 mmol) in methanol (120 mL) was added a solution of KOH (2.50 g in 50 mL of water, 43.9 mmol) at rt. Then, (Boc)$_2$O (4.60 g, 21.1 mmol) was added slowly. The mixture was stirred at rt for 30 min. The mixture was extracted with DCM (150 mL×2). The combined organic phases were washed with brine, dried over Na$_2$SO$_4$, filtered and concentrated to give the crude product. The crude was purified by column chromatography on silica gel (petroleum ether:ethyl acetate from 10:1 to 5:1 to 2:1) to give the title compound (4.83 g, yield 83% after two steps) as white solid.

D448 $^1$H NMR (300 MHz, CDCl$_3$): δ 10.17 (br s, 1H) 7.94 (s, 1H), 7.56 (s, 1H), 7.34 (s, 1H), 4.49-4.48 (m, 1H), 4.21-4.11 (m, 1H), 3.92-3.38 (m, 1H), 3.02-2.95 (m, 1H), 2.85-2.69 (m, 2H), 2.48 (s, 3H), 1.87-1.81 (m, 1H), 1.63-1.59 (m, 2H), 1.51 (s, 9H)

Description D449 and D450

(trans)-tert-Butyl 3-hydroxy-4-(5-methyl-1H-indazol-6-yl)piperidine-1-carboxylate (Enantiomer 1, D449; Enantiomer 2, D450)

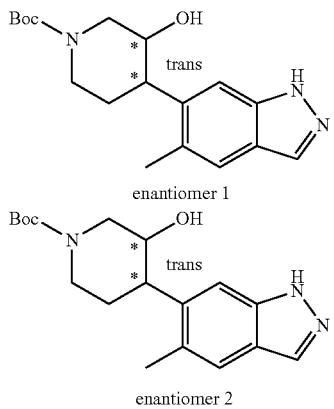

enantiomer 1 enantiomer 2

(trans)-tert-Butyl 3-hydroxy-4-(5-methyl-1H-indazol-6-yl)piperidine-1-carboxylate (1.24 g, 3.75 mmol) was separated by chiral prep-HPLC with the method (Chiralpak IC 5 um 4.6*250 mm; phase: Hex:EtOH=70:30; F: 15 mL/min; W: 230 nm; T: 30° C.) to obtain enantiomer 1 (440 mg, yield 36%) as a white solid and enantiomer 2 (460 mg, yield 37%) as a white solid.

D449 (enantiomer 1) $^1$H NMR (300 MHz, CDCl$_3$): δ 10.11 (m, 1H) 7.96 (s, 1H), 7.58 (s, 1H), 7.39 (s, 1H), 4.53-4.43 (m, 1H), 4.25-4.17 (m, 1H), 3.91-3.84 (m, 1H), 3.00-2.96 (m, 1H), 2.82-2.69 (m, 2H), 2.49 (s, 3H), 1.82-1.80 (m, 1H), 1.64-1.58 (m, 2H), 1.50 (s, 9H). Chiral HPLC: Chiralpak IC, 5 um 4.6*250 nm; Phase: Hex:EtOH=70:30; F=0.5 mL/min; W: 230 nm; T: 30° C.; Rt=6.417 min, 98.95% ee.

D450 (enantiomer 2) $^1$H NMR (300 MHz, CDCl$_3$): δ 10.23 (m, 1H) 7.93 (s, 1H), 7.56 (s, 1H), 7.37 (s, 1H), 4.49-4.47 (m, 1H), 4.27-4.15 (m, 1H), 3.92-3.84 (m, 1H), 3.04-2.94 (m, 1H), 2.80-2.69 (m, 2H), 2.48 (s, 3H), 1.83-1.80 (m, 1H), 1.61-1.59 (m, 3H), 1.51 (s, 9H). Chiral HPLC: Chiralpak IC, 5 um 4.6*250 nm; Phase: Hex:EtOH=70:30; F=0.5 mL/min; W: 230 nm; T: 30° C.; Rt=7.967 min, 96.31% ee.

Description D451

(trans)-tert-Butyl 3-hydroxy-4-(5-methyl-1-(2-methyl-6-morpholinopyrimidin-4-yl)-1H-indazol-6-yl)piperidine-1-carboxylate (Enantiomer 1, D451)

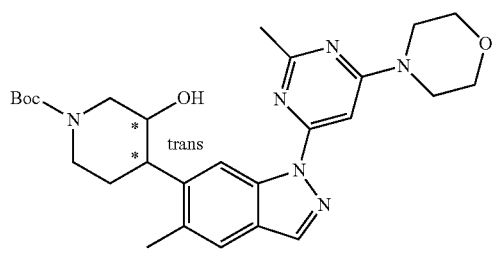 [SMILES: Cc1nc(N2CCOCC2)cc(-n2ncc3cc(C)c(C4CCN(C(=O)OC(C)(C)C)CC4O)cc32)n1]

To a solution of (trans)-tert-butyl 3-hydroxy-4-(5-methyl-1H-indazol-6-yl)piperidine-1-carboxylate (80 mg, 0.24 mmol, enantiomer 1) in toluene (3 mL) was added 4-(6-iodo-2-methylpyrimidin-4-yl)morpholine (56 mg, 0.29 mmol), CuI (46 mg, 0.24 mmol), K$_3$PO$_4$ (102 mg, 0.48 mmol) and N,N'-dimethyl-cyclohexane-1,2-diamine (69 mg, 0.48 mmol). The mixture was stirred at 110° C. under N$_2$ protected for 3 hrs. After cooled to rt the mixture was added ammonia hydrate (25%, 5 mL) and extracted with EtOAc (10 mL×4). The combined organic phase was dried over Na$_2$SO$_4$, filtered and concentrated. The crude was purified by prep-HPLC with the method (40-80% CH$_3$CN in H$_2$O (0.01% TFA)) to give the title compound (60 mg, yield 49%) as a white solid.

D451 $^1$H NMR (300 MHz, CD$_3$OD): δ 8.68 (s, 1H), 8.20 (s, 1H), 7.62 (s, 1H), 7.08 (s, 1H), 4.40-4.34 (m, 1H), 4.20-4.12 (m, 1H), 3.93-3.84 (m, 1H), 3.80-3.71 (m, 8H), 3.12-3.04 (m, 1H), 2.92-2.69 (m, 2H), 2.59 (s, 3H), 2.52 (s, 3H), 1.90-1.83 (m, 1H), 1.68-1.58 (m, 1H), 1.51 (s, 9H).

Description D452

(trans)-4-(5-Methyl-1-(2-methyl-6-morpholinopyrimidin-4-yl)-1H-indazol-6-yl)piperidin-3-ol hydrochloride (Enantiomer 1, D452)

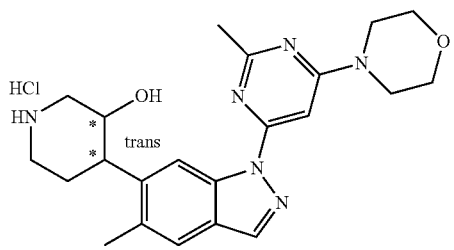 [SMILES: Cl ; Cc1nc(N2CCOCC2)cc(-n2ncc3cc(C)c(C4CCNCC4O)cc32)n1]

To a solution of (trans)-tert-butyl 3-hydroxy-4-(5-methyl-1-(2-methyl-6-morpholinopyrimidin-4-yl)-1H-indazol-6-yl)piperidine-1-carboxylate (enantiomer 1, 60 mg, 0.12 mmol) in dioxane (2 mL) was added HCl/dioxane (4 M, 2 mL). The mixture was stirred at rt for 1 hour. The mixture was concentrated to give the crude product (70 mg, yield >100%) as white solid which was used for next step directly.

D452 LC-MS: [mobile phase: 5-95% Acetonitrile in 2.5 min], Rt=1.49 min; MS Calcd.: 408; MS Found: 409 [M+1]$^+$.

Description D453

(trans)-tert-Butyl 3-hydroxy-4-(5-methyl-1-(2-methyl-6-morpholinopyrimidin-4-yl)-1H-indazol-6-yl)piperidine-1-carboxylate (Enantiomer 2, D453)

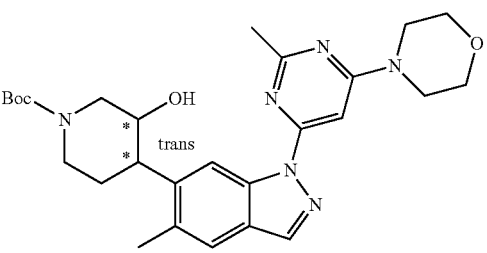 [SMILES: Cc1nc(N2CCOCC2)cc(-n2ncc3cc(C)c(C4CCN(C(=O)OC(C)(C)C)CC4O)cc32)n1]

To a solution of (trans)-tert-butyl 3-hydroxy-4-(5-methyl-1H-indazol-6-yl)piperidine-1-carboxylate (82 mg, 0.25 mmol) (enantiomer 2) in toluene (3 mL) was added 4-(6-iodo-2-methylpyrimidin-4-yl)morpholine (57 mg, 0.30 mmol), CuI (47 mg, 0.25 mmol), $K_3PO_4$ (105 mg, 0.50 mmol) and N,N'-dimethyl-cyclohexane-1,2-diamine (70 mg, 0.50 mmol). The mixture was stirred at 110° C. under $N_2$ protected for 3 hrs. After cooled to rt, the mixture was added ammonia hydrate (25%, 5 mL) and extracted with EtOAc (10 mL×4). The combined organic phase was dried over $Na_2SO_4$, filtered and concentrated. The crude was purified by prep-HPLC to give the title compound (63 mg, yield 51%) as a white solid.

D453 $^1$H NMR (300 MHz, $CD_3OD$): δ 8.73 (s, 1H), 8.18 (s, 1H), 7.60 (s, 1H), 7.05 (s, 1H), 4.39-4.34 (m, 1H), 4.18-4.13 (m, 1H), 3.92-3.84 (m, 1H), 3.81-3.71 (m, 8H), 3.13-3.04 (m, 1H), 2.94-2.68 (m, 2H), 2.57 (s, 3H), 2.51 (s, 3H), 1.90-1.85 (m, 1H), 1.62-1.58 (m, 1H), 1.51 (s, 9H).

Description D454

(trans)-4-(5-Methyl-1-(2-methyl-6-morpholinopyrimidin-4-yl)-1H-indazol-6-yl)piperidin-3-ol hydrochloride (Enantiomer 2, D454)

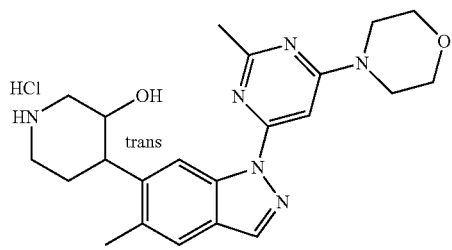 [SMILES: Cl ; Cc1nc(N2CCOCC2)cc(-n2ncc3cc(C)c(C4CCNCC4O)cc32)n1]

To a solution of (trans)-tert-butyl 3-hydroxy-4-(5-methyl-1-(2-methyl-6-morpholinopyrimidin-4-yl)-1H-indazol-6-yl)piperidine-1-carboxylate (enantiomer 2, 63 mg, 0.12 mmol) in dioxane (2 mL) was added HCl/dioxane (4 M, 2 mL). The mixture was stirred at rt for 1 hour. The mixture was concentrated to give the crude product (75 mg, yield >100%) as white solid which was used for next step directly.

D454 LC-MS: [mobile phase: 5-95% Acetonitrile in 2.5 min], Rt=1.49 min; MS Calcd.: 408; MS Found: 409 $[M+1]^+$.

Description D455

(trans)-tert-Butyl 3-hydroxy-4-(1-(2-methoxy-6-morpholinopyrimidin-4-yl)-5-methyl-1H-indazol-6-yl)piperidine-1-carboxylate (Enantiomer 1, D455)

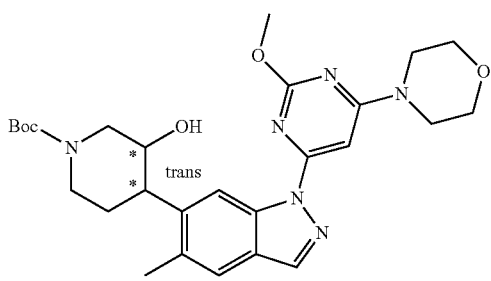 [SMILES: COc1nc(N2CCOCC2)cc(-n2ncc3cc(C)c(C4CCN(C(=O)OC(C)(C)C)CC4O)cc32)n1]

To a solution of (trans)-tert-butyl 3-hydroxy-4-(5-methyl-1H-indazol-6-yl)piperidine-1-carboxylate (80 mg, 0.24 mmol) (enantiomer 1) in toluene (2 mL) was added 4-(6-iodo-2-methoxypyrimidin-4-yl)morpholine (93 mg, 0.29 mmol), CuI (46 mg, 0.24 mmol), $K_3PO_4$ (102 mg, 0.48 mmol) and N,N'-dimethyl-cyclohexane-1,2-diamine (68 mg, 0.48 mmol). The mixture was stirred at 115° C. under $N_2$ protected for 3 hrs. After cooled to rt the mixture was added ammonia hydrate (25%, 10 mL) and extracted with EtOAc (20 mL). The organic phase was washed with brine, dried over $Na_2SO_4$ and concentrated. The crude was purified by prep-HPLC to give the title compound (31 mg, yield 24%) as white solid.

D455 $^1$H NMR (300 MHz, $CD_3OD$): δ 8.74 (s, 1H), 8.12 (s, 1H), 7.57 (s, 1H), 6.85 (s, 1H), 4.39-4.31 (m, 1H), 4.17-4.12 (m, 1H), 4.03 (s, 3H), 3.92-3.83 (m, 1H), 3.77-3.75 (m, 4H), 3.67-3.64 (m, 4H), 3.11-3.02 (m, 1H), 2.92-2.66 (m, 2H), 2.50 (s, 3H), 1.88-1.83 (m, 1H), 1.67-1.57 (m, 1H), 1.52 (s, 9H).

Description D456

(trans)-4-(1-(2-Methoxy-6-morpholinopyrimidin-4-yl)-5-methyl-1H-indazol-6-yl)piperidin-3-ol hydrochloride (Enantiomer 1, D456)

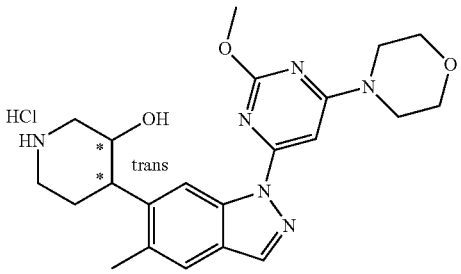 [SMILES: Cl ; COc1nc(N2CCOCC2)cc(-n2ncc3cc(C)c(C4CCNCC4O)cc32)n1]

To a solution of (trans)-tert-butyl 3-hydroxy-4-(1-(2-methoxy-6-morpholinopyrimidin-4-yl)-5-methyl-1H-indazol-6-yl)piperidine-1-carboxylate (enantiomer 1, 31 mg, 0.06 mmol) in dioxane (2 mL) was added HCl/dioxane (4 M, 2 mL). The mixture was stirred at rt for 1 hour. The mixture was concentrated to give the crude product (430 mg) as white solid which was used for next step directly.

Description D457

(trans)-tert-Butyl 3-hydroxy-4-(1-(2-methoxy-6-morpholinopyrimidin-4-yl)-5-methyl-1H-indazol-6-yl)piperidine-1-carboxylate (Enantiomer 2, D457)

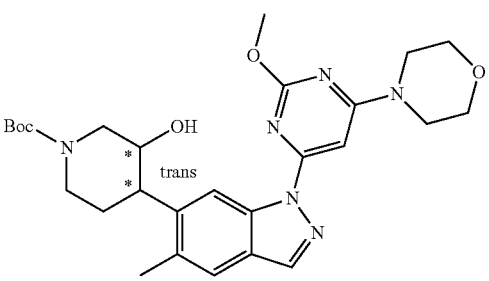 [SMILES: COc1nc(N2CCOCC2)cc(-n2ncc3cc(C)c(C4CCN(C(=O)OC(C)(C)C)CC4O)cc32)n1]

To a solution of (trans)-tert-butyl 3-hydroxy-4-(5-methyl-1H-indazol-6-yl)piperidine-1-carboxylate (80 mg, 0.24 mmol) (enantiomer 2) in toluene (2 mL) was added 4-(6-iodo-2-methylpyrimidin-4-yl)morpholine (93 mg, 0.29 mmol), CuI (46 mg, 0.24 mmol), K$_3$PO$_4$ (102 mg, 0.48 mmol) and N,N'-dimethyl-cyclohexane-1,2-diamine (68 mg, 0.48 mmol). The mixture was stirred at 115° C. under N$_2$ protected for 3 hrs. After cooled to rt the mixture was added ammonia hydrate (25%, 10 mL) and extracted with EtOAc (20 mL). The organic layer was washed with brine, dried over Na$_2$SO$_4$ and concentrated. The crude was purified by prep-HPLC to give the title compound (68 mg, yield 54%) as white solid.

D457 $^1$H NMR (300 MHz, CD$_3$OD): δ 8.76 (s, 1H), 8.14 (s, 1H), 7.59 (s, 1H), 6.89 (s, 1H), 4.38-4.31 (m, 1H), 4.17-4.12 (m, 1H), 4.05 (s, 3H), 3.92-3.82 (m, 1H), 3.79-3.76 (m, 4H), 3.70-3.66 (m, 4H), 3.12-3.01 (m, 1H), 2.97-2.63 (m, 2H), 2.51 (s, 3H), 1.89-1.82 (m, 1H), 1.73-1.57 (m, 1H), 1.51 (s, 9H).

Description D458

(trans)-4-(5-Methyl-1-(2-methyl-6-morpholinopy-rimidin-4-yl)-1H-indazol-6-yl)piperidin-3-ol (HCl Salt) (Enantiomer 2, D458)

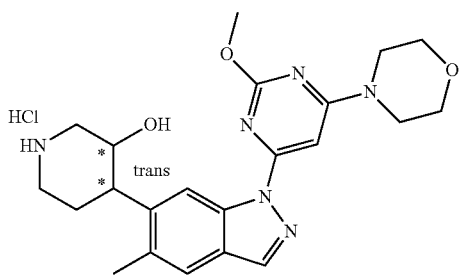 [SMILES: Cl ; COc1nc(N2CCOCC2)cc(-n2ncc3cc(C)c(C4CCNCC4O)cc32)n1]

To a solution of (trans)-tert-butyl 3-hydroxy-4-(5-methyl-1-(2-methyl-6-morpholinopyrimidin-4-yl)-1H-indazol-6-yl)piperidine-1-carboxylate (68 mg, 0.13 mmol) in dioxane (2 mL) was added HCl/dioxane (4 M, 2 mL). The mixture was stirred at rt for 1 hour. The mixture was concentrated to give the crude product (62 mg, yield >100%) as white solid which was used for next step directly.

D458 LC-MS: [mobile phase: 5-95% acetonitrile in 3 min], Rt=1.77 min; MS Calcd.: 424; MS Found: 425 [M+1]$^+$.

Description D459

5-Methyl-1-(tetrahydro-2H-pyran-2-yl)-1H-inda-zole-6-carbaldehyde (D459)

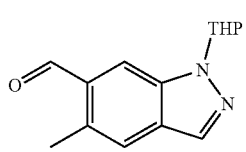

To a solution of 6-bromo-5-methyl-1-(tetrahydro-2H-pyran-2-yl)-1H-indazole (6.90 g, 23.5 mmo) in 100 mL of dry THF was added dropwise of n-BuLi (2.5 M in THF, 18.8 mL, 46.9 mmol) at −78° C. After addition the reaction mixture was stirred at −78° C. for 1 hour. Dry DMF (34.2 g, 46.8 mmol) was added to the reaction mixture and stirred at −78° C. for 3 hrs. The reaction mixture was poured into water (200 mL) and extracted with EtOAc (150 mL×2). The combined organic layers were washed with brine (200 mL), dried over Na$_2$SO$_4$ and concentrated under reduced pressure to give the crude product as brown oil. The crude was purified by column chromatography (petroleum ether:E-tOAc=6:1) to give the title compound (3.2 g, yield 56%) as pale yellow solid.

D459 $^1$H NMR (300 MHz, CDCl$_3$): δ 10.37 (s, 1H), 8.08 (s, 1), 8.00 (s, 1H), 7.56 (s, 1H), 5.80-5.76 (m, 1H), 4.05-4.01 (m, 1H), 3.82-3.74 (m, 1H), 2.74 (s, 3H), 2.58-2.50 (m, 1H), 2.18-2.07 (m, 2H), 1.81-1.65 (m, 3H).

Description D460

5-Methyl-6-(oxiran-2-yl)-1-(tetrahydro-2H-pyran-2-yl)-1H-indazole (D460)

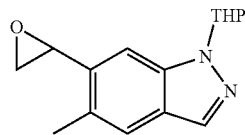

To an ice-cooled solution of NaH (60% in mineral oil, 74 mg, 3.08 mmol) in dry THF (20 mL) was added dropwise a solution of trimethylsulfoxinium iodide (677 mg, 3.08 mmol) in DMSO (4 mL). The mixture was stirred at 0° C. for 10 min. Then 5-methyl-1-(tetrahydro-2H-pyran-2-yl)-1H-indazole-6-carbaldehyde (500 mg, 2.05 mmol) was added to the reaction mixture and stirred at 0° C. to rt for 2 hrs. The reaction mixture was poured into water (50 mL) and extracted with EtOAc (30 mL×2). The combined organic layers were washed with brine (30 mL), dried over anhydrous sodium sulfate and concentrated. The residue was purified by column chromatography (petroleum ether:E-tOAc=6:1) to give the title compound (87 mg, yield 16%) as yellow solid.

D460 $^1$H NMR (300 MHz, CDCl$_3$): δ 7.93 (s, 1H), 7.48-7.45 (m, 2H), 5.68 (dd, J=9.6, 2.1 Hz, 1H), 4.13-4.03 (m, 2H), 3.78-3.71 (m, 1H), 3.24-3.20 (m, 1H), 2.72-2.54 (m, 2H), 2.49 (s, 3H), 2.14-2.01 (m, 2H), 1.79-1.69 (m, 3H).

Description D461

2-((2-Hydroxyethyl)amino)-1-(5-methyl-1-(tetra-hydro-2H-pyran-2-yl)-1H-indazol-6-yl)ethanol (D461)

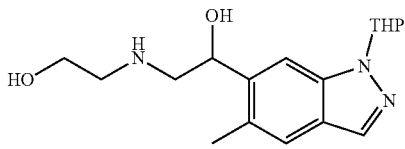

A mixture of 5-methyl-6-(oxiran-2-yl)-1-(tetrahydro-2H-pyran-2-yl)-1H-indazole (560 mg, 2.17 mmol) and 2-ami-noethanol (2.03 g, 33.3 mmol) in THF (8 mL) was refluxed for 18 hrs. The reaction mixture was concentrated in reduced pressure to give yellow oil. The yellow oil was purified by C18 column eluting with ACN/H₂O (0-60% in 40 min) to give the title compound (370 mg, yield 53%) as colorless oil.

D461 ¹H NMR (300 MHz, CDCl₃): δ 7.92 (s, 1H), 7.77 (s, 1H), 7.45 (s, 1H), 5.72-5.69 (m, 1H), 5.09-5.05 (m, 1H), 4.02-3.99 (m, 1H), 3.76-3.69 (m, 3H), 2.95-2.53 (m, 8H), 2.40 (s, 3H), 2.14-2.00 (m, 2H), 1.78-1.63 (m, 3H).

Description D462 tert-Butyl (2-hydroxy-2-(5-methyl-1-(tetrahydro-2H-pyran-2-yl)-1H-indazol-6-yl)ethyl)(2-hydroxyethyl)carbamate (D462)

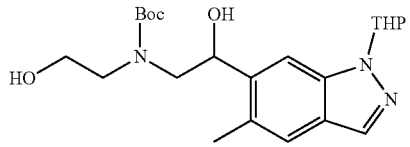

To a mixture of 2-((2-hydroxyethyl)amino)-1-(5-methyl-1-(tetrahydro-2H-pyran-2-yl)-1H-indazol-6-yl)ethanol (2.30 g, 7.21 mmol) and triethylamine (1.46 g, 14.42 mmol) in dry THF (35 mL) was added Boc₂O (1.57 g, 7.21 mmol) at ambient temperature. The reaction mixture was stirred at rt for 4 hrs. The reaction mixture was directly concentrated under reduced pressure. The residue was purified by chromatography column on silica gel (petroleum ether:EtOAc from 10:1 to 1:1) to give the title compound (2.2 g, yield 73%) as white solid.

D462 ¹H NMR (300 MHz, CDCl₃): δ 7.92 (s, 1H), 7.76 (s, 1H), 7.45 (s, 1H), 5.72-5.68 (m, 1H), 5.39-5.28 (m, 1H), 4.04-3.13 (m, 9H), 2.59-2.46 (m, 1H), 2.40 (s, 3H), 2.12-1.99 (m, 2H), 1.79-1.64 (m, 3H), 1.48 (s, 9H).

Description D463 tert-Butyl 2-(5-methyl-1-(tetrahydro-2H-pyran-2-yl)-1H-indazol-6-yl)morpholine-4-carboxylate (D463)

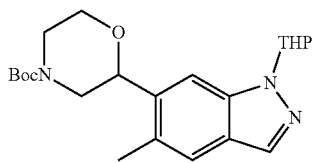

To a solution of tert-butyl (2-hydroxy-2-(5-methyl-1-(tetrahydro-2H-pyran-2-yl)-1H-indazol-6-yl)ethyl)(2-hydroxyethyl)carbamate (1.30 g, 3.10 mmol) in dry THF (120 mL) was added sodium hydride (60% in mineral oil, 310 mg, 7.76 mmol) at 0° C. The resulting mixture was allowed to warm to ambient temperature and stirred for 30 min. The reaction was cooled to 0° C. and 1-(4-tolylsulfonyl)imidazole (758 mg, 3.41 mmol) was added. The reaction mixture was warmed to ambient temperature and stirred for 2 hrs. Then the reaction mixture was poured into saturated NH₄Cl solution (150 mL) and extracted with EtOAc (100 mL×2). The combined organic layers were washed with brine (100 mL), dried over Na₂SO₄ and concentrated under reduced pressure. The residue was purified by flash chromatography (petroleum ether:EtOAc=4:1) to give the title compound (0.93 g, yield 75%) as colorless oil.

D463 ¹H NMR (300 MHz, CDCl₃): δ 7.95 (s, 1H), 7.70-7.68 (m, 1H), 7.50 (s, 1H), 5.74 (dd, J=9.3, 2.7 Hz, 1H), 4.67-4.63 (m, 1H), 4.20-4.04 (m, 4H), 3.81-3.74 (m, 2H), 3.17-3.09 (m, 1H), 2.86-2.73 (m, 1H), 2.63-2.55 (m, 1H), 2.46 (s, 3H), 2.34-2.14 (m, 2H), 2.06-2.01 (m, 1H), 1.78-1.67 (m, 2H), 1.50 (s, 9H).

Description D464 tert-Butyl 2-(5-methyl-1H-indazol-6-yl)morpholine-4-carboxylate (D464)

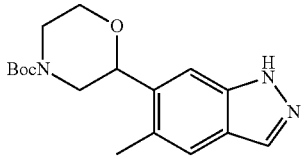 [SMILES: Cc1cc2cn[nH]c2cc1C1CN(C(=O)OC(C)(C)C)CCO1]

A mixture of tert-butyl 2-(5-methyl-1-(tetrahydro-2H-pyran-2-yl)-1H-indazol-6-yl)morpholine-4-carboxylate (930 mg, 2.32 mmol) in HCl/MeOH (4 M, 10 mL) was stirred at room temperature for 2 hrs. The reaction was directly concentrated in reduced pressure to give a white solid. The solid was dissolved in MeOH (30 mL) and water (6 mL). Then, KOH (390 mg, 6.96 mmol) and Boc₂O (759 mg, 3.48 mmol) were added. The mixture was stirred at room temperature for 1 hour. The reaction mixture was poured into water (100 mL) and extracted with EtOAc (80 mL×2). The combined organic layers were washed with brine, dried over Na₂SO₄ and concentrated in reduced pressure to give the crude title compound (840 mg, quantitative) as a pale yellow gel which was used for next step directly.

D464 LC-MS: [mobile phase: 5-95% acetonitrile+0.02% NH₄OAc in 3.0 min], Rt=1.62 min; MS Calcd.: 317; MS Found: 262 [M−56+1]⁺.

Description D465 and D466 tert-Butyl 2-(5-methyl-1H-indazol-6-yl)morpholine-4-carboxylate (Enantiomer 1, D465; Enantiomer 2 D466)

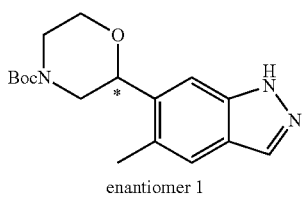

enantiomer 1

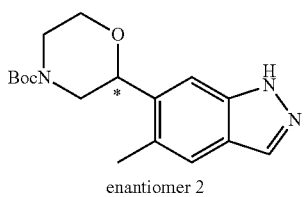

enantiomer 2

Racemic tert-butyl 2-(5-methyl-1H-indazol-6-yl)morpholine-4-carboxylate (900 mg, 2.84 mmol) was resolved with chiral-HPLC column under the chiral condition (chiral pak, IB, 5 urn, 4.6*250 nm, Phase: Hex:EtOH=70:30, F: 15 mL/min, W: 214 nm, T: 30) to give enantiomer 1 (320 mg, yield 36%) as white solid and enantiomer 2 (280 mg, yield 31%) as white solid.

D465 (enantiomer 1): $^1$H NMR (300 MHz, CDCl$_3$): δ 10.19 (br s, 1H), 7.98 (s, 1H), 7.65 (s, 1H), 7.53 (s, 1H), 4.65-4.62 (m, 1H), 4.18-3.98 (m, 3H), 3.80-3.72 (m, 1H), 3.13-3.05 (m, 1H), 2.78-2.70 (m, 1H), 2.46 (s, 3H), 1.49 (s, 9H).

Chiral condition: Chiralpak IB 5 um 4.6*250 nm, Hex:EtOH=70:30; Flow: 1.0 ml/min; W: 230 nm; T=30° C. Rt=4.531 min, 99.4% ee.

D466 (enantiomer 2): $^1$H NMR (300 MHz, CDCl$_3$): δ 10.31 (br s, 1H), 7.98 (s, 1H), 7.65 (s, 1H), 7.53 (s, 1H), 4.65-4.62 (m, 1H), 4.15-3.98 (m, 3H), 3.80-3.72 (m, 1H), 3.12-3.04 (m, 1H), 2.78-2.70 (m, 1H), 2.45 (s, 3H), 1.49 (s, 9H).

Chiral condition: Chiralpak IB 5 um 4.6*250 nm, ACN:IPA=70:30, Flow: 1.0 ml/min, 230 nm, T=30° C. Rt=6.997 min, 100% ee.

Description D467 tert-Butyl 2-(5-methyl-1-(2-methyl-6-(3-((tetrahydro-2H-pyran-2-yl)oxy)azetidin-1-yl)pyrimidin-4-yl)-1H-indazol-6-yl)morpholine-4-carboxylate (Enantiomer 1, D467)

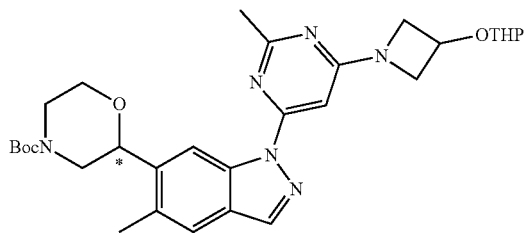

A mixture of tert-butyl 2-(5-methyl-1H-indazol-6-yl)morpholine-4-carboxylate (enantiomer 1) (80 mg, 0.25 mmol) and 4-iodo-2-methyl-6-(3-((tetrahydro-2H-pyran-2-yl)oxy)azetidin-1-yl)pyrimidine (104 mg, 0.278 mmol), CuI (48 mg. 0.25 mmol), N,N'-dimethyl-cyclohexane-1,2-diamine (72 mg, 0.51 mmol) and potassium phosphate (107 mg, 0.506 mmol) in toluene (4 mL) was degassed with nitrogen and stirred at 110° C. for 2 hrs. After cooling down to room temperature the reaction mixture was poured into ammonia solution (6%, 60 mL) and extracted with ethyl acetate (30 mL×2). The combined organic layers were washed with brine (50 mL), dried over Na$_2$SO$_4$ and concentrated. The residue was purified by prep-TLC (petroleum ether:EtOAc=1:1) to give the title compound (76 mg, yield 54%) as white foam.

D467 $^1$H NMR (300 MHz, CDCl$_3$): δ 9.00 (s, 1H), 8.08 (s, 1H), 7.51 (s, 1H), (s, 1H), 6.59 (s, 1H), 4.73-4.62 (m, 3H), 4.41-4.33 (m, 2H), 4.26-3.92 (m, 5H), 3.85-3.73 (m, 2H), 3.56-3.52 (m, 1H), 3.15-3.09 (m, 1H), 2.97-2.90 (m, 1H), 2.62 (s, 3H), 2.49 (s, 3H), 1.86-1.55 (m, 6H), 1.49 (s, 9H).

Description D468

1-(2-Methyl-6-(5-methyl-6-(morpholin-2-yl)-1H-indazol-1-yl)pyrimidin-4-yl)azetidin-3-ol (Enantiomer 1, D468)

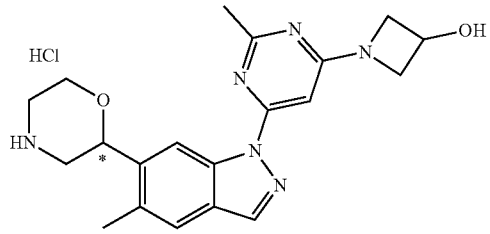 [SMILES: Cc1nc(N2CC(O)C2)cc(-n2ncc3cc(C)c(C4CNCCO4)cc32)n1 ; Cl]

A mixture of tert-butyl 2-(5-methyl-1-(2-methyl-6-(3-((tetrahydro-2H-pyran-2-yl)oxy)azetidin-1-yl)pyrimidin-4-yl)-1H-indazol-6-yl)morpholine-4-carboxylate (enantiomer 1, 70 mg, 0.12 mmol) in HCl/dioxane (4 M, 4 mL) was stirred at room temperature for 2 hrs. The reaction mixture was directly concentrated under reduced pressure to give the title compound (58 mg, yield 100%) as white solid.

D468 LC-MS: [mobile phase: 2-60% acetonitrile+0.02% NH$_4$OAc in 3.0 min], Rt=2.20 min; MS Calcd.: 380; MS Found: 381 [M+1]$^+$.

Description D469 tert-Butyl 2-(5-methyl-1-(2-methyl-6-(3-((tetrahydro-2H-pyran-2-yl)oxy)azetidin-1-yl)pyrimidin-4-yl)-1H-indazol-6-yl)morpholine-4-carboxylate (Enantiomer 2, D469)

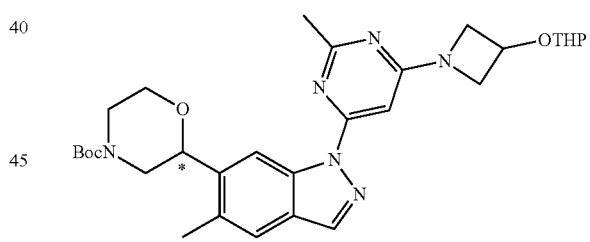

A mixture of tert-butyl 2-(5-methyl-1H-indazol-6-yl)morpholine-4-carboxylate (80 mg, 0.25 mmol) (enantiomer 2) and 4-iodo-2-methyl-6-(3-((tetrahydro-2H-pyran-2-yl)oxy)azetidin-1-yl)pyrimidine (113 mg, 0.301 mmol), CuI (38 mg. 0.20 mmol), N,N'-dimethyl-cyclohexane-1,2-diamine (56 mg, 0.40 mmol) and potassium phosphate (85 mg, 0.40 mmol) in toluene (4 mL) was degassed with nitrogen and stirred at 110° C. for 2 hrs. After cooling down to room temperature the reaction mixture was poured into diluted ammonia solution (6%, 50 mL) and extracted with ethyl acetate (30 mL×2). The combined organic layers were washed with brine (50 mL), dried and concentrated. The residue was purified by prep-TLC (EtOAc:petroleum ether=2:3) to give the title compound (125 mg, yield 87%) as white solid.

D469 $^1$H NMR (300 MHz, CDCl$_3$): δ 9.00 (s, 1H), 8.08 (s, 1H), 7.50 (s, 1H), 6.59 (s, 1H), 4.73-4.64 (m, 3H), 4.40-4.33 (m, 2H), 4.23-3.99 (m, 5H), 3.88-3.73 (m, 2H), 3.56-3.52 (m, 1H), 3.12-2.89 (m, 2H), 2.62 (s, 3H), 2.49 (s, 3H), 1.86-1.53 (m, 6H), 1.49 (s, 9H).

Description D470

1-(2-Methyl-6-(5-methyl-6-(morpholin-2-yl)-1H-indazol-1-yl)pyrimidin-4-yl)azetidin-3-ol (HCl Salt) (Enantiomer 2, D470)

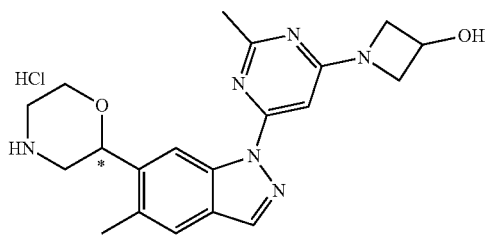 [SMILES: Cl ; Cc1nc(N2CC(O)C2)cc(-n2ncc3cc(C)c(C4CNCCO4)cc32)n1]

A mixture of tert-butyl 2-(5-methyl-1-(2-methyl-6-(3-((tetrahydro-2H-pyran-2-yl)oxy)azetidin-1-yl)pyrimidin-4-yl)-1H-indazol-6-yl)morpholine-4-carboxylate (enantiomer 2, 125 mg, 0.222 mmol) in HCl/dioxane (4 M, 4 mL) was stirred at room temperature for 3 hrs. The reaction mixture was directly concentrated under reduced pressure to give the title compound (110 mg, yield 100%) as white solid.

D470 LC-MS: [mobile phase: 2-60% acetonitrile+0.02% NH$_4$OAc in 3.0 min], Rt=1.35 min; MS Calcd.: 380; MS Found: 381 [M+1]$^+$.

Description D471 tert-Butyl 2-(1-(6-(3-hydroxyazetidin-1-yl)-2-methoxypyrimidin-4-yl)-5-methyl-1H-indazol-6-yl)morpholine-4-carboxylate (Enantiomer 1, D471)

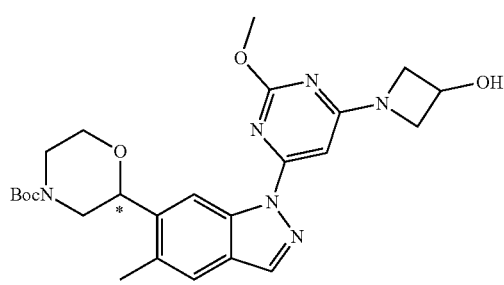 [SMILES: COc1nc(N2CC(O)C2)cc(-n2ncc3cc(C)c(C4CN(C(=O)OC(C)(C)C)CCO4)cc32)n1]

A mixtures of 2-(5-methyl-1H-indazol-6-yl)-morpholine-4-carboxylic acid tert-butyl ester (95 mg, 0.30 mmol) (enantiomer 1) and 1-(6-iodo-2-methoxypyrimidin-4-yl)azetidin-3-ol (138 mg, 0.45 mmol), CuI (57 mg. 0.30 mmol), N,N'-dimethyl-cyclohexane-1,2-diamine (85 mg, 0.60 mmol) and potassium phosphate (127 mg, 0.600 mmol) in toluene (5 mL) was degassed with nitrogen and stirred at 110° C. for 3 hrs. After cooling down to room temperature the reaction mixture was poured into diluted ammonia solution (10%, 40 mL) and extracted with ethyl acetate (30 mL×2). The combined organic layers were washed with brine (50 mL), dried and concentrated. The residue was purified by triturated in EtOAc (1 mL) and petroleum ether (5 mL) to give the title compound (130 mg, yield 87%) as pale yellow solid.

D471 $^1$H NMR (300 MHz, DMSO-d$_6$): δ 8.91 (s, 1H), 8.34 (s, 1H), 7.63 (s, 1H), 6.39 (s, 1H), 4.63-4.58 (m, 2H), 4.29-4.24 (m, 2H), 3.98 (s, 3H), 3.90-3.65 (m, 6H), 3.05-2.48 (m, 2H), 2.41 (s, 3H), 1.41 (s, 9H).

Description D472

1-(2-Methoxy-6-(5-methyl-6-(morpholin-2-yl)-1H-indazol-1-yl)pyrimidin-4-yl)azetidin-3-ol (HCl Salt) (Enantiomer 1, D472)

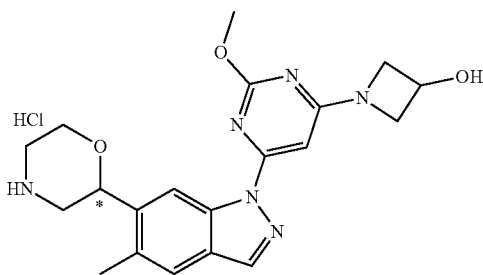 [SMILES: Cl ; COc1nc(N2CC(O)C2)cc(-n2ncc3cc(C)c(C4CNCCO4)cc32)n1]

A mixture of tert-butyl 2-(1-(6-(3-hydroxyazetidin-1-yl)-2-methoxypyrimidin-4-yl)-5-methyl-1H-indazol-6-yl)morpholine-4-carboxylate (enantiomer 1, 130 mg, 0.262 mmol) in HCl/dioxane (4 M, 5 mL) was stirred at room temperature for 2 hrs. The reaction mixture was directly concentrated under reduced pressure to give the crude compound (109 mg, yield >100%) as yellow solid which was used for next step directly.

D472 LC-MS: [mobile phase: 2-60% acetonitrile+0.02% NH$_4$OAc in 3.0 min], Rt=1.52 min; MS Calcd.: 396; MS Found: 397 [M+1]$^+$.

Description D473 tert-Butyl 2-(1-(6-(3-hydroxyazetidin-1-yl)-2-methoxypyrimidin-4-yl)-5-methyl-1H-indazol-6-yl)morpholine-4-carboxylate (Enantiomer 2, D473)

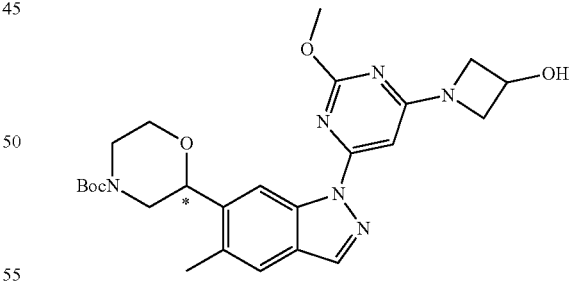

A mixture of tert-butyl 2-(5-methyl-1H-indazol-6-yl)morpholine-4-carboxylate (95 mg, 0.30 mmol) (enantiomer 2) and 1-(6-iodo-2-methoxypyrimidin-4-yl)azetidin-3-ol (138 mg, 0.450 mmol), CuI (57 mg. 0.30 mmol), N,N'-dimethyl-cyclohexane-1,2-diamine (85 mg, 0.60 mmol) and potassium phosphate (127 mg, 0.600 mmol) in toluene (5 mL) was degassed with nitrogen and stirred at 110° C. for 3 hrs. After cooling down to room temperature the reaction mixture was poured into diluted ammonia solution (6%, 50 mL) and extracted with ethyl acetate (50 mL×2). The combined organic layers were washed with brine (50 mL), dried and concentrated. The residue was triturated in petroleum ether (4 mL) and EtOAc (0.5 mL) to give the title compound (150 mg, yield 100%) as yellow solid.

D473 $^1$H NMR (300 MHz, CDCl$_3$): δ 9.05 (s, 1H), 8.08 (s, 1H), 7.50 (s, 1H), 6.45 (s, 1H), 4.84-4.76 (m, 1H), 4.67-4.63 (m, 1H), 4.43-4.37 (m, 2H), 4.14 (s, 3H), 4.05-3.97 (m, 4H), 3.91-3.87 (m, 2H), 3.79-3.07 (m, 1H), 3.08-2.96 (m, 1H), 2.84-2.72 (m, 1H), 2.48 (s, 3H), 1.49 (s, 9H).

Description D474

1-(2-Methoxy-6-(5-methyl-6-(morpholin-2-yl)-1H-indazol-1-yl)pyrimidin-4-yl)azetidin-3-ol (HCl Salt) (Enantiomer 2, D474)

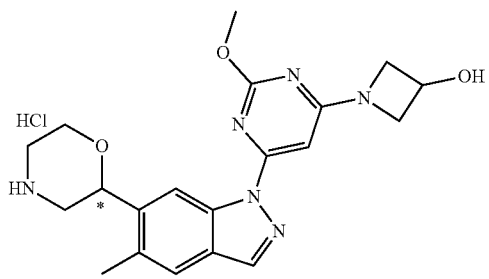 [SMILES: Cl ; COc1nc(N2CC(O)C2)cc(-n2ncc3cc(C)c(C4CNCCO4)cc32)n1]

A mixture of tert-butyl 2-(1-(6-(3-hydroxyazetidin-1-yl)-2-methoxypyrimidin-4-yl)-5-methyl-1H-indazol-6-yl)morpholine-4-carboxylate (enantiomer 2, 150 mg, 0.262 mmol) in HCl/dioxane (4 M, 5 mL) was stirred at room temperature for 2 hrs. The reaction mixture was directly concentrated under reduced pressure to give the crude compound (150 mg, yield >100%) as white solid which was used for next step directly.

D474 LC-MS: [mobile phase: 2-60% acetonitrile+0.02% NH$_4$OAc in 3.0 min], Rt=2.39 min; MS Calcd.: 396; MS Found: 397 [M+1]$^+$.

Description D475

6-Chloro-1-(4-methoxybenzyl)-1H-pyrazolo[3,4-b]pyridine (D475)

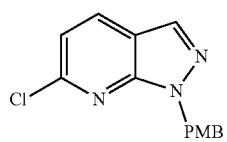

To a mixture of 6-chloro-1H-pyrazolo[3,4-b]pyridine (6.00 g, 39.1 mmol) and K$_2$CO$_3$ (16.2 g, 117 mmol) in CH$_3$CN (30 mL) was added PMB-Cl (10.4 g, 66.5 mmol). The mixture was heated to 60° C. and stirred overnight. The mixture was directly concentrated in vacuum. The residue was purified by silica column (PE:EtOAc=15:1) to give the desired product (4.8 g, yield 44%) as a yellow solid.

D475 $^1$H NMR (300 MHz, CDCl$_3$): δ 7.99 (s, 1H), 7.97 (d, J=8.4 Hz, 1H), 7.33 (d, J=8.7 Hz, 2H), 7.13 (d, J=8.4 Hz, 1H), 6.84 (d, J=8.7 Hz, 2H), 5.59 (s, 2H), 3.76 (s, 3H).

LCMS: [mobile phase: 10-95% Acetonitrile+0.02% NH$_4$OAc in 4 min] Rt=2.518 min; MS Calcd.: 273; MS Found: 274 [M+1]$^+$.

Description D476

1-(4-Methoxybenzyl)-1H-pyrazolo[3,4-b]pyridin-6-ol (D476)

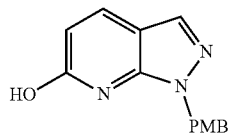

To a solution of 6-chloro-1-(4-methoxybenzyl)-1H-pyrazolo[3,4-b]pyridine (5.20 g, 19.0 mmol) and TMSOK (3.65 g, 28.5 mmol) in DMF (30 mL) was added NaH (60% in material oil, 2.30 g, 57.0 mmol). The mixture was stirred at 60° C. overnight. The mixture was diluted with H$_2$O (40 mL) and extracted with EtOAc (20 mL×3). The aqueous layer was adjusted to pH=7 with conc. HCl. The suspension was filtered. The cake was washed with H$_2$O (10 mL×3) and dried in vacuum to give the desired product (3.2 g, yield 66%) as a yellow solid.

D476 $^1$H NMR (300 MHz, DMSO-d$_6$): δ 11.78 (br s, 1H), 7.92 (d, J=9.0 Hz, 1H), 7.85 (s, 1H), 7.17 (d, J=8.7 Hz, 2H), 6.87 (d, J=9.0 Hz, 2H), 6.37-6.34 (m, 1H), 5.40 (s, 2H), 3.70 (s, 3H).

Description D477

5-Bromo-1-(4-methoxybenzyl)-1H-pyrazolo[3,4-b]pyridin-6-ol (D477)

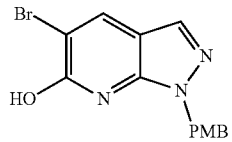

To a solution of 1-(4-methoxybenzyl)-1H-pyrazolo[3,4-b]pyridin-6-ol (3.20 g, 12.5 mmol) in AcOH (30 mL) was added Br$_2$ (2.11 g, 13.2 mmmol). The reaction was stirred for 1 h. The suspension was filtered. The cake was washed with AcOH (5 mL×3) and then dried in vacuum to give the desired product (4.54 g, yield >100%) as a yellow solid.

D477 $^1$H NMR (300 MHz, DMSO-d$_6$): δ 8.33 (s, 1H), 7.80 (s, 1H), 7.18 (d, J=8.4 Hz, 2H), 6.88 (d, J=8.4 Hz, 2H), 5.39 (s, 2H), 3.71 (s, 3H).

Description D478

5-Bromo-1-(4-methoxybenzyl)-6-(methoxymethoxy)-1H-pyrazolo[3,4-b]pyridine (D478)

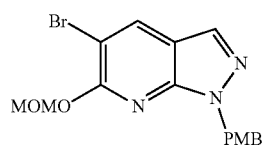

To a suspension of 5-bromo-1-(4-methoxybenzyl)-1H-pyrazolo[3,4-b]pyridin-6-ol (4.34 g, 13.0 mmol) in DCM (20 mL) was added DIPEA (5.03 g, 39.0 mmol). Then, MOMCl (2.08 g, 26.0 mmol) was added at 0° C. The reaction was stirred at room temperature for 1 h. The solution was diluted with H$_2$O (20 mL) and extracted with DCM (20 mL×3). The combined organic layers were washed with brine, dried over Na$_2$SO$_4$ and evaporated. The residue was purified by silica column (PE:EtOAc=8:1) to give the desired product (3.70 g, yield 73%) as a yellow solid.

D478 $^1$H NMR (300 MHz, CDCl$_3$): δ 8.14 (s, 1H), 7.82 (s, 1H), 7.30 (d, J=8.7 Hz, 2H), 6.82 (d, J=8.4 Hz, 2H), 5.70 (s, 2H), 5.48 (s, 2H), 3.76 (s, 3H), 3.60 (s, 3H).

Description D479

1-(4-Methoxybenzyl)-6-(methoxymethoxy)-5-methyl-1H-pyrazolo[3,4-b]pyridine (D479)

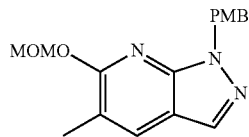

To a mixture of 5-bromo-1-(4-methoxybenzyl)-6-(methoxymethoxy)-1H-pyrazolo[3,4-b]pyridine (3.70 g, 9.79 mmol), methylboronic acid (5.87 g, 97.9 mmol) and Na$_2$CO$_3$ (4.16 g, 39.2 mmol) in dioxane/H$_2$O (50/5 mL) was added Pd(dppf)Cl$_2$ (1.60 g, 1.96 mmol). The mixture was stirred at 90° C. overnight under N$_2$. The mixture was filtered and the filtrate was concentrated in vacuum. The residue was purified by silica column (PE:EtOAc=15:1) to give the desired product (2.20 g, yield 73%) as a yellow oil.

D479 $^1$H NMR (300 MHz, CDCl$_3$): δ 7.78 (s, 1H), 7.70 (s, 1H), 7.30 (d, J=8.7 Hz, 2H), 6.81 (d, J=8.7 Hz, 2H), 5.69 (s, 2H), 5.49 (s, 2H), 3.75 (s, 3H), 3.58 (s, 3H), 2.29 (s, 3H).

LCMS: [mobile phase: 10-95% acetonitrile+0.02% NH$_4$OAc in 4 min] Rt=2.549 min; MS Calcd.: 313; MS Found: 314 [M+1]$^+$.

Description D480

1-(4-Methoxybenzyl)-5-methyl-1H-pyrazolo[3,4-b]pyridin-6-ol (D480)

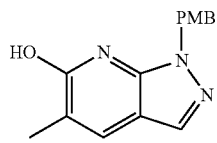

A solution of 1-(4-methoxybenzyl)-6-(methoxymethoxy)-5-methyl-1H-pyrazolo[3,4-b]pyridine (2.20 g, 7.03 mmol) in dioxane (30 mL) was added conc. HCl (0.5 mL). The suspension was stirred at room temperature for 1 h. The suspension was filtered. The cake was washed with dioxane (5 mL×3) and dried in vacuum to give the desired product (1.89 g, yield 100%) as a white solid.

D480 $^1$H NMR (300 MHz, DMSO-d$_6$): δ 10.90 (br s, 1H), 7.71 (s, 1H), 7.69 (s, 1H), 7.16 (d, J=8.4 Hz, 2H), 6.87 (d, J=8.7 Hz, 2H), 5.38 (s, 2H), 3.70 (s, 3H), 2.05 (s, 3H).

LCMS: [mobile phase: 10-95% acetonitrile+0.02% NH$_4$OAc in 4 min] Rt=1.948 min; MS Calcd.: 269; MS Found: 270 [M+1]$^+$.

Description D481

1-(4-methoxybenzyl)-5-methyl-1H-pyrazolo[3,4-b]pyridin-6-yl trifluoromethanesulfonate (D481)

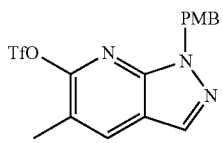

To a solution of 1-(4-methoxybenzyl)-5-methyl-1H-pyrazolo[3,4-b]pyridin-6-ol (1.89 g, 7.03 mmol) in DCM (20 mL) was added pyridine (1.67 g, 21.1 mmol). Then, Tf$_2$O (3.96 g, 14.1 mmol) was added dropwise at 0° C. under N$_2$. The suspension was stirred at room temperature for 1 h. The solution was diluted with H$_2$O (20 mL) and extracted with DCM (15 mL×3). The combined organic layers were washed with brine, dried over Na$_2$SO$_4$ and evaporated to give the desired product (2.47 g, yield 87%) as a yellow solid.

D481 $^1$H NMR (300 MHz, CDCl$_3$): δ 7.99 (s, 1H), 7.97 (s, 1H), 7.37 (d, J=8.7 Hz, 2H), 6.83 (d, J=8.4 Hz, 2H), 5.52 (s, 2H), 3.76 (s, 3H), 2.44 (s, 3H).

LCMS: [mobile phase: 10-95% acetonitrile+0.02% NH$_4$OAc in 5 min] Rt=2.751 min; MS Calcd.: 401; MS Found: 402 [M+1]$^+$.

Description D482

4-[1-(4-Methoxy-benzyl)-5-methyl-1H-pyrazolo[3,4-b]pyridin-6-yl]-3,6-dihydro-2H-pyridine-1-carboxylic acid tert-butyl ester (D482)

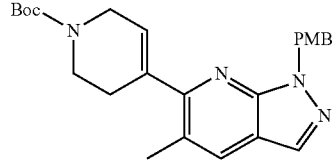

To a mixture of 1-(4-methoxybenzyl)-5-methyl-1H-pyrazolo[3,4-b]pyridin-6-yl trifluoromethane sulfonate (2.47 g, 6.16 mmol), tert-butyl 4-(4,4,5,5-tetramethyl-1,3,2-dioxaborolan-2-yl)-5,6-dihydropyridine-1(2H)-carboxylate (3.81 g, 12.3 mmol) and Na$_2$CO$_3$ (2.62 g, 24.6 mmol) in dioxane/H$_2$O (50/5 mL) was added Pd(dppf)Cl$_2$ (1.01 g, 1.23 mmol). The mixture was stirred at 90° C. under N$_2$ overnight. The mixture was filtered and the filtrate was concentrated in vacuum. The residue was purified by silica column (PE:EtOAc=8:1) to give the desired product (2.71 g, yield >100%) as a yellow oil.

D482 $^1$H NMR (300 MHz, CDCl$_3$): δ 7.88 (s, 1H), 7.82 (s, 1H), 7.30 (d, J=9.0 Hz, 2H), 6.81 (d, J=9.0 Hz, 2H), 5.88-5.86 (m, 1H), 5.60 (s, 2H), 4.14-4.13 (m, 2H), 3.76 (s, 3H), 3.71 (t, J=8.7 Hz, 2H), 2.64-2.60 (m, 2H), 2.44 (s, 3H), 1.52 (s, 9H).

LCMS [mobile phase: 10-95% acetonitrile+0.02% NH₄OAc in 5 min] Rt=2.767 min; MS Calcd.: 434, MS Found: 435 [M+1]⁺.

Description D483 tert-Butyl 4-(1-(4-methoxybenzyl)-5-methyl-1H-pyrazolo[3,4-b]pyridin-6-yl)piperidine-1-carboxylate (D483)

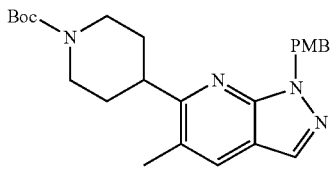

To a solution of tert-butyl 4-(1-(4-methoxybenzyl)-5-methyl-1H-pyrazolo[3,4-b]pyridin-6-yl)-(2.71 g, 6.24 mmol) in EtOH (30 mL) was added Pd/C (0.27 g). The mixture was stirred for 2 days under H₂. The mixture was filtered and the filtrate was concentrated in vacuum to give the desired product (2.37 g, yield 87%) as a yellow oil.

D483 ¹H NMR (300 MHz, CDCl₃): δ 7.84 (s, 1H), 7.73 (s, 1H), 7.35 (d, J=8.4 Hz, 2H), 6.81 (d, J=8.7 Hz, 2H), 5.58 (s, 2H), 4.33-4.26 (m, 2H), 3.76 (s, 3H), 3.13-3.06 (m, 1H), 2.94-2.86 (m, 2H), 2.44 (s, 3H), 2.07-1.93 (m, 2H), 1.82-1.77 (m, 2H), 1.52 (s, 9H).

Description D484

5-Methyl-6-(piperidin-4-yl)-1H-pyrazolo[3,4-b]pyridine TFA Salt (D484)

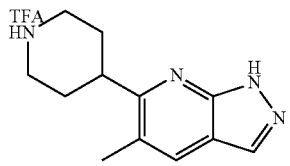 [SMILES: Cc1cc2cn[nH]c2nc1C1CCNCC1 ; "TFA"]

To a solution of tert-butyl 4-(1-(4-methoxybenzyl)-5-methyl-1H-pyrazolo[3,4-b]pyridin-6-yl) piperidine-1-carboxylate (2.15 g, 4.93 mmol) in CH₂Cl₂ (15 mL) was added TFA (50 mL) at ° C. Then, the mixture was warmed to 45° C. and stirred overnight. The mixture was concentrated under vacuum to give the crude compound (2.8 g, yield >100%) as a black oil which was used for next step directly.

D484 LC-MS: (mobile phase: from 95% water and 5% CH₃CN to 5% water and 95% CH₃CN in 4 min, Rt=1.561 min; MS Calcd.: 216; MS Found: 217 (M+H)⁺.

Description D485 tert-Butyl 4-(5-methyl-1H-pyrazolo[3,4-b]pyridin-6-yl)piperidine-1-carboxylate (D485)

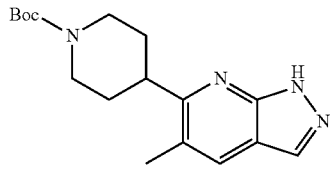 [SMILES: Cc1cc2cn[nH]c2nc1C1CCN(C(=O)OC(C)(C)C)CC1]

To a solution of 5-methyl-6-(piperidin-4-yl)-1H-pyrazolo [3,4-b]pyridine TFA salt (2.60 g of crude, 4.93 mmol) in methanol (100 mL) was added a solution of KOH (4.65 g, 83.1 mmol) in water (40 mL). Then, Boc₂O (2.72 g, 12.5 mmol) was added. The resulting mixture was stirred at rt overnight. The mixture was diluted with CH₂Cl₂ (200 mL) and water (50 mL). The organic solution was washed with brine (100 mL×2), dried over Na₂SO₄ and concentrated. The residue was purified by column (PE:ethyl acetate=5:1) to give the title compound (620 mg, yield 40% in two steps) as a white solid.

D485 ¹H NMR (400 MHz, CDCl₃): δ 7.96 (s, 1H), 7.84 (s, 1H), 4.40-4.23 (m, 2H), 3.15-3.09 (m, 1H), 2.94-2.80 (m, 2H), 2.48 (s, 3H), 2.01-1.87 (m, 2H), 1.81-1.78 (m, 2H).

Description D486 tert-Butyl 3-hydroxyazetidine-1-carboxylate (D486)

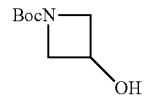

To a solution of azetidin-3-ol hydrochloride (2.00 g, 18.3 mmol) in CH₂Cl₂ (20 mL) was added TEA (5 mL) and (Boc)₂O (4.80 g, 22.0 mmol). The mixture was stirred at rt overnight. The reaction mixture was concentrated. The residue was dissolved in EtOAc (20 mL). The mixture was washed with water (20 mL×2) and brine (20 mL), dried over Na₂SO₄ and concentrated to give the title compound (2.80 g, yield 88%) as yellow oil.

D486 ¹H NMR (300 MHz, CDCl₃): δ 4.58-4.56 (m, 1H), 4.17-4.11 (m, 2H), 3.82-3.77 (m, 2H), 2.51-2.49 (m, 1H), 1.43 (s, 9H).

Description D487 tert-Butyl 3-(benzyloxy)azetidine-1-carboxylate (D487)

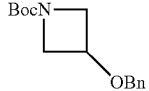

To a mixture of NaH (60% in material oil, 464 mg, 11.6 mmol) in DMF (10 mL) was added tert-butyl 3-hydroxyazetidine-1-carboxylate (1.00 g, 5.78 mmol) at 0° C. After stirred at 0° C. for 20 min (chloromethyl)benzene (874 mg, 6.94 mmol) was added at 0° C. Then, the mixture was stirred at rt for 2 hrs. To the mixture was added ice-water (70 mL) and the mixture was extracted with EtOAc (50 mL×2). The combined organic layers were washed with water (50 mL) and brine (50 mL), dried over Na₂SO₄ and concentrated. The residue was purified by column chromatography (PE:EtOAc=10:1) to give the title compound (600 mg, yield 39%) as a colorless oil.

D487 ¹H NMR (300 MHz, CDCl₃): δ 7.41-7.31 (m, 5H), 4.45 (s, 2H), 4.35-4.27 (m, 1H), 4.08-4.02 (m, 2H), 3.88-3.83 (m, 2H), 1.43 (s, 9H).

Description D488

3-(Benzyloxy)azetidine (D488)

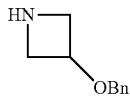

To a solution of tert-butyl 3-(benzyloxy)azetidine-1-carboxylate (600 mg, 2.28 mmol) in CH₂Cl₂ (10 mL) was added TFA (2 mL). The mixture was stirred at rt for 1 h. The mixture was concentrated. The residue was dissolved in water (5 mL) and added sat. Na₂CO₃ solution (10 mL). The mixture was extracted with EtOAc (50 mL×2). The combined organic layers were washed with brine (20 mL), dried over Na₂SO₄ and concentrated to give the title compound (200 mg, yield 54%) as yellow oil.

D488 ¹H NMR (300 MHz, CDCl₃): δ 7.38-7.30 (m, 5H), 4.50-4.42 (m, 3H), 3.88-3.75 (m, 4H).

Description D489

2-Chloro-6-methoxypyridin-4-amine (D489)

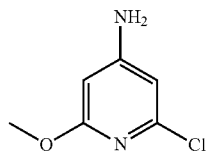

To a solution of 2,6-dichloropyridin-4-amine (2.80 g, 17.2 mmol) in NMP (25 mL) was added CH₃ONa (3.72 g, 68.8 mmol). The mixture was stirred at 140° C. overnight. The reaction mixture was cooled to rt and poured into water (150 mL). The mixture was extracted with EtOAc (50 mL×3). The combined organic layers were washed with water (50 mL) and brine (50 mL), dried over Na₂SO₄ and concentrated. The residue was purified by column chromatography (PE:EtOAc=10:1) to give the title compound (2.0 g, yield 74%) as a white solid.

D489 ¹H NMR (300 MHz, CDCl₃): δ 6.23 (s, 1H), 5.83 (s, 1H), 4.16 (br s, 2H), 3.86 (s, 3H).

Description D490

2-Chloro-4-iodo-6-methoxypyridine (D490)

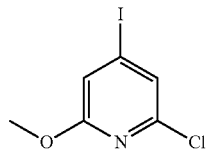

To a solution of 2-chloro-6-methoxypyridin-4-amine (790 mg, 5.00 mmol) in CH₃CN (5 mL) was added water (5 mL) and conc. HCl (5 mL). Then a solution of NaNO₂ (690 mg, 10.0 mmol) in water (5 mL) was added dropwise at 0° C. After stirred at 0° C. for 10 min a solution of KI (1.66 g, 10.0 mmol) in water (5 mL) was added dropwise at 0° C. The mixture was stirred at 0° C. for 20 min. Then, the reaction was quenched with sat. Na₂S₂O₃ solution (50 mL). EtOAc (20 mL×3) was added to extract desired compound. The combined organic layers were washed with brine (20 mL), dried over Na₂SO₄ and concentrated. The residue was purified by column chromatography (PE) to give the title compound (1.1 g, yield 82%) as white solid.

D490 ¹H NMR (300 MHz, CDCl₃): δ 7.26 (s, 1H), 7.07 (s, 1H), 3.91 (s, 3H).

Description D491 tert-Butyl 4-(1-(2-chloro-6-methoxypyridin-4-yl)-5-methyl-1H-pyrazolo[3,4-b]pyridin-6-yl)piperidine-1-carboxylate (D491)

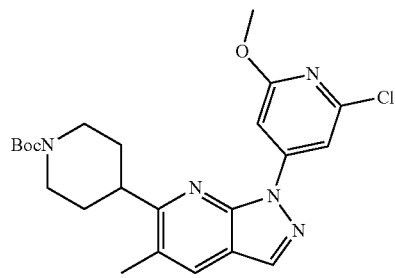 [SMILES: COc1cc(-n2ncc3cc(C)c(C4CCN(C(=O)OC(C)(C)C)CC4)nc32)cc(Cl)n1]

To a solution of tert-butyl 4-(5-methyl-1H-pyrazolo[3,4-b]pyridin-6-yl)piperidine-1-carboxylate (160 mg, 0.506 mmol) in toluene (5 mL) was added 2-chloro-4-iodo-6-methoxypyridine (204 mg, 0.759 mmol), CuI (95 mg, 0.51 mmol), K₃PO₄ (424 mg, 2.00 mmol) and N,N'-dimethylcyclohexane-1,2-diamine (71.0 mg, 0.506 mmol). The mixture was refluxed for 2 hrs. The reaction mixture was cooled to rt and filtered. The filtrate was concentrated. The residue was purified by column chromatography (PE:EtOAc=10:1) to give the title compound (150 mg, yield 65%) as white solid.

D491 ¹H NMR (300 MHz, CDCl₃): δ 8.12 (s, 1H), 8.08 (s, 1H), 7.99 (s, 1H), 7.84 (s, 1H), 4.38-4.26 (m, 2H), 4.00 (s, 3H), 3.19-3.10 (m, 1H), 2.95-2.83 (m, 2H), 2.50 (s, 3H), 2.01-1.80 (m, 4H), 1.52 (s, 9H).

Description D492 tert-Butyl 4-(1-(2-(3-(benzyloxy)azetidin-1-yl)-6-methoxypyridin-4-yl)-5-methyl-1H-pyrazolo[3,4-b]pyridin-6-yl)piperidine-1-carboxylate (D492)

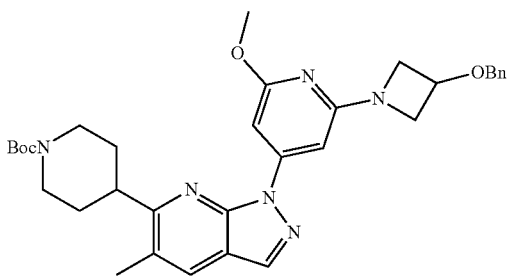 [SMILES: COc1cc(-n2ncc3cc(C)c(C4CCN(C(=O)OC(C)(C)C)CC4)nc32)cc(N2CC(OCc3ccccc3)C2)n1]

To a solution of tert-butyl 4-(1-(2-chloro-6-methoxypyridin-4-yl)-5-methyl-1H-pyrazolo[3,4-b]pyridin-6-yl)piperidine-1-carboxylate (150 mg, 0.328 mmol) in toluene (8 mL) was added 3-(benzyloxy)azetidine (107 mg, 0.656 mmol), Pd$_2$(dba)$_3$ (30 mg, 0.033 mmol), xphos (62 mg, 0.13 mmol) and Cs$_2$CO$_3$ (426 mg, 1.31 mmol). The mixture was refluxed overnight under N$_2$ atmosphere. The reaction mixture was cooled to rt and filtered. The filtrate was concentrated. The residue was purified by prep-TLC (PE:EtOAc=5:1) to give the title compound (90 mg, yield 47%) as yellow oil.

D492 $^1$H NMR (300 MHz, CDCl$_3$): δ 8.04 (s, 1H), 7.81 (s, 1H), 7.41-7.31 (m, 6H), 7.19 (s, 1H), 4.53 (s, 3H), 4.37-4.25 (m, 4H), 4.04-3.97 (m, 2H), 3.93 (s, 3H), 3.20-3.08 (m, 1H), 2.97-2.84 (m, 2H), 2.48 (s, 3H), 2.02-1.80 (m, 4H), 1.49 (s, 9H).

Description D493

1-(2-(3-(Benzyloxy)azetidin-1-yl)-6-methoxypyridin-4-yl)-5-methyl-6-(piperidin-4-yl)-1H-pyrazolo[3,4-b]pyridine 2,2,2-trifluoroacetate (D493)

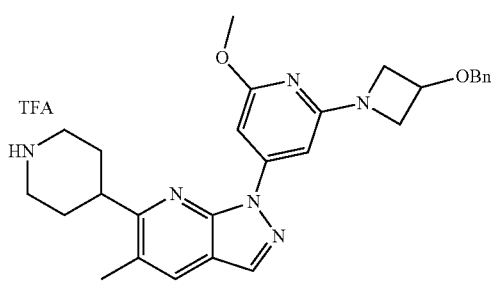 [SMILES: COc1cc(-n2ncc3cc(C)c(C4CCNCC4)nc32)cc(N2CC(OCc3ccccc3)C2)n1]

To a solution of tert-butyl 4-(1-(2-(3-(benzyloxy)azetidin-1-yl)-6-methoxypyridin-4-yl)-5-methyl-1H-pyrazolo[3,4-b]pyridin-6-yl)piperidine-1-carboxylate (90 mg, 0.15 mmol) in CH$_2$Cl$_2$ (5 mL) was added TFA (1 mL). The mixture was stirred at rt for 30 min. The mixture was concentrated to give the title compound (100 mg, yield >100%) as yellow solid.

D493 LCMS [mobile phase: 30-95% CH$_3$CN in 2.5 min]: Rt=1.28 min; MS Calcd: 484; MS Found: 485 [M+H]$^+$.

Description D494

1-(2-(3-(Benzyloxy)azetidin-1-yl)-6-methoxypyridin-4-yl)-5-methyl-6-(1-(oxetan-3-yl)piperidin-4-yl)-1H-pyrazolo[3,4-b]pyridine (D494)

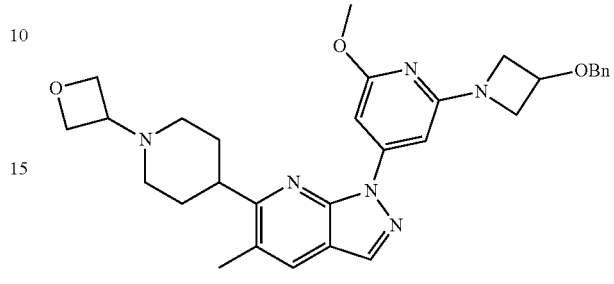

To a solution of 1-(2-(3-(benzyloxy)azetidin-1-yl)-6-methoxypyridin-4-yl)-5-methyl-6-(piperidin-4-yl)-1H-pyrazolo[3,4-b]pyridine 2,2,2-trifluoroacetate (100 mg, 0.15 mmol) in DCE (5 mL) was added oxetan-3-one (0.5 mL) and CH$_3$OH (1 mL). The mixture was stirred at rt for 30 min. NaBH$_3$CN (62 mg, 1.0 mmol) was added and the reaction mixture was stirred at rt for 2 hrs. To the reaction mixture was added sat. Na$_2$CO$_3$ solution (15 mL). The mixture was stirred at rt for 10 min. The mixture was extracted with CH$_2$Cl$_2$ (20 mL×3). The combined organic layers were washed with brine (20 mL), dried over Na$_2$SO$_4$ and concentrated. The residue was purified by prep-TLC (DCM:CH$_3$OH=20:1) to give the title compound (50 mg, yield 62%) as a white solid.

D494 $^1$H NMR (300 MHz, CDCl$_3$): δ 8.04 (s, 1H), 7.80 (s, 1H), 7.37-7.26 (m, 6H), 7.23 (s, 1H), 4.69-4.67 (m, 4H), 4.60-4.53 (m, 3H), 4.33-4.80 (m, 2H), 4.05-4.01 (m, 2H), 3.96 (s, 3H), 3.58-3.53 (m, 1H), 3.03-2.88 (m, 3H), 2.46 (s, 3H), 2.21-2.09 (m, 2H), 2.04-1.96 (m, 2H), 1.91-1.85 (m, 2H).

Description D495

6-(3,3-Difluoro-1-(oxetan-3-yl)piperidin-4-yl)-5-methyl-1-(2-methyl-6-(3-((tetrahydro-2H-pyran-2-yl)oxy)azetidin-1-yl)pyrimidin-4-yl)-1H-indazole (Isomer 1, D495)

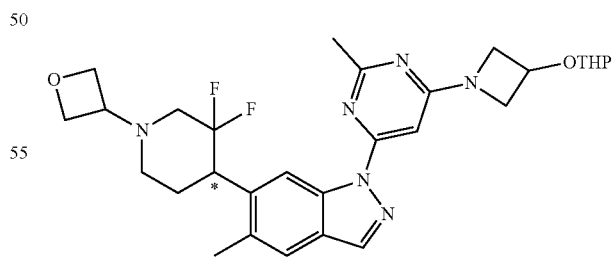

To a solution of 6-(3,3-difluoro-1-(oxetan-3-yl)piperidin-4-yl)-5-methyl-1H-indazole (50 mg, 0.16 mmol) (enantiomer 1) in toluene (10 mL) was added 4-iodo-2-methyl-6-(3-((tetrahydro-2H-pyran-2-yl)oxy)azetidin-1-yl)pyrimidine (73 mg, 0.19 mmol), K$_3$PO$_4$ (103 mg, 0.490 mmol), N,N'-dimethyl-cyclohexane-1,2-diamine (69 mg, 0.49 mmol) and CuI (93 mg, 0.49 mmol). The resulting mixture was warmed to 110° C. and stirred for 3 hrs. To the mixture was added NH$_3$.H$_2$O (30%, 40 mL) and extracted with ethyl acetate (40 mL×3). The combined organic layers were washed with water (40 mL) and brine (40 mL), dried over Na$_2$SO$_4$ and concentrated. The residue was purified by prep-TLC (CH$_2$Cl$_2$:CH$_3$OH=20:1) to give the title compound (68 mg, yield 76%) as a white solid.

D495 $^1$H NMR (300 MHz, CDCl$_3$): δ 9.01 (s, 1H), 8.07 (s, 1H), 7.53 (s, 1H), 6.59 (s, 1H), 4.78-4.65 (m, 8H), 4.41-4.33 (m, 2H), 4.14-4.03 (m, 2H), 3.93-3.85 (m, 1H), 3.78-3.69 (m, 1H), 3.58-3.45 (m, 1H), 3.40-3.30 (m, 1H), 3.19-3.10 (m, 1H), 3.05-3.01 (m, 1H), 2.64 (s, 3H), 2.47 (s, 3H), 2.43-2.16 (m, 4H), 2.04-1.71 (m, 4H).

Description D496

6-(3,3-Difluoro-1-(oxetan-3-yl)piperidin-4-yl)-5-methyl-1-(2-methyl-6-(3-((tetrahydro-2H-pyran-2-yl)oxy)azetidin-1-yl)pyrimidin-4-yl)-1H-indazole (Isomer 2, D496)

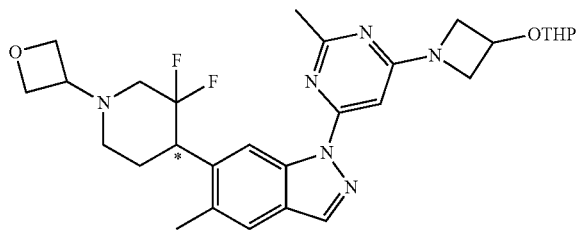

To a solution of 6-(3,3-difluoro-1-oxetan-3-yl-piperidin-4-yl)-5-methyl-1H-indazole (50 mg, 0.16 mmol) (enantiomer 2) in toluene (10 mL) was 4-iodo-2-methyl-6-(3-((tetrahydro-2H-pyran-2-yl)oxy)azetidin-1-yl)pyrimidine (73 mg, 0.19 mmol), K$_3$PO$_4$ (103 mg, 0.49 mmol), N,N'-dimethyl-cyclohexane-1,2-diamine (69 mg, 0.49 mmol) and CuI (93 mg, 0.49 mmol). The resulting mixture was warmed to 110° C. and stirred for 3 hrs. To the mixture was added NH$_3$.H$_2$O (30%, 40 mL) and extracted with ethyl acetate (40 mL×3). The combined organic layers were washed with water (40 mL) and brine (40 mL), dried over Na$_2$SO$_4$ and concentrated. The residue was purified by prep-TLC (CH$_2$Cl$_2$:CH3OH=20:1) to give the title compound (93 mg, yield >100%) as a white solid.

D496 $^1$H NMR (300 MHz, CDCl$_3$): δ 9.01 (s, 1H), 8.07 (s, 1H), 7.53 (s, 1H), 6.59 (s, 1H), 4.76-4.68 (m, 8H), 4.43-4.33 (m, 2H), 4.14-4.04 (m, 2H), 3.92-3.84 (m, 1H), 3.79-3.70 (m, 1H), 3.59-3.51 (m, 1H), 3.45-3.29 (m, 1H), 3.19-3.10 (m, 1H), 3.06-3.01 (m, 1H), 2.64 (s, 3H), 2.47 (s, 3H), 2.43-2.28 (m, 4H), 2.24-2.15 (m, 4H), 2.02-1.71 (m, 4H).

Description D497

2-(4-(6-Iodo-2-methylpyrimidin-4-yl)piperazin-1-yl) ethanol (D497)

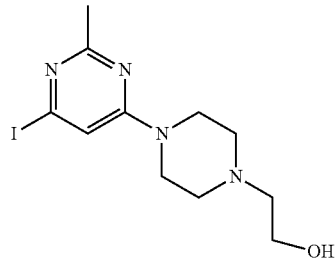 [SMILES: Cc1nc(I)cc(N2CCN(CCO)CC2)n1]

To a suspension of 4,6-diiodo-2-methylpyrimidine (150 mg, 0.434 mmol) and Et$_3$N (220 mg, 2.17 mmol) in i-PrOH (5 mL) was added 2-(piperazin-1-yl)ethanol (85 mg, 0.65 mmol) at rt. The resulting mixture was stirred at 60° C. for 1 h. The mixture was concentrated and the residue was purified by C18 to give the title compound (150 mg, yield 99%) as white solid.

D497 $^1$H NMR (300 MHz, CDCl$_3$): δ 6.78 (s, 1H), 3.68-3.61 (m, 6H), 2.60-2.54 (m, 6H), 2.45 (s, 3H).

Description D498

(3S,4S)-1-(6-Iodo-2-methylpyrimidin-4-yl)pyrrolidine-3,4-diol (D498)

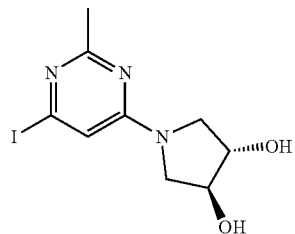

A mixture of (3S,4S)-pyrrolidine-3,4-diol (96 mg, 0.95 mmol) and 4,6-diiodo-2-methylpyrimidine (300 mg, 0.867 mmol) in MeOH (10 mL) was stirred at 70° C. for 2 hrs. The mixture was cooled to room temperature and concentrated in vacuo. The residue was purified by column on C18 using CH$_3$CN/H$_2$O (5%-95%) to give the desired product (170 mg, yield 61%) as a white solid.

D498 $^1$H NMR (300 Hz, DMSO-d$_6$): δ 6.75 (s, 1H), 5.19-5.11 (m, 2H), 4.02-3.96 (m, 2H), 3.48-3.42 (m, 3H), 3.15-3.12 (m, 1H), 2.28 (s, 3H).

LC-MS (XB-C18, ¢4.6*50 mm*5 um; mobile phase: from 95% water (0.02% NH$_4$OAc) and 5% CH$_3$CN to 5% water (0.02% NH$_4$OAc) and 95% CH$_3$CN in 4 min, purity is >95%, Rt=1.478 min; MS Calcd.: 321, MS Found: 322 (M+H)$^+$.

Description D499 tert-Butyl 4-(2-methoxy-6-(5-methyl-6-(tetrahydro-2H-pyran-4-yl)-1H-indazol-1-yl)pyrimidin-4-yl)piperazine-1-carboxylate (D499)

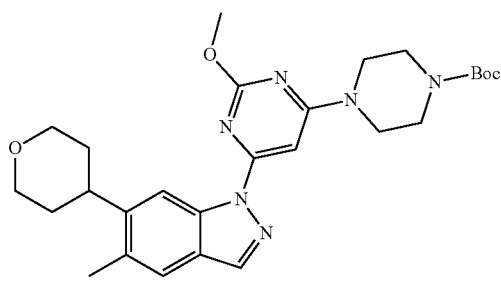 [SMILES: COc1nc(N2CCN(C(=O)OC(C)(C)C)CC2)cc(-n2ncc3cc(C)c(C4CCOCC4)cc32)n1]

To a solution of 5-methyl-6-(tetrahydro-2H-pyran-4-yl)-1H-indazole (500 mg, 1.98 mmol) in toluene (30 mL) was added tert-butyl 4-(6-iodo-2-methoxypyrimidin-4-yl)piperazine-1-carboxylate (998 mg, 2.78 mmol), $K_3PO_4$ (1.26 g, 5.94 mmol), N,N'-dimethyl-cyclohexane-1,2-diamine (1.12 g, 7.92 mmol) and CuI (1.13 mg, 5.94 mmol). The resulting mixture was warmed to 110° C. and stirred overnight. To the mixture was added $NH_3.H_2O$ (30%, 80 mL) and extracted with ethyl acetate (100 mL×3). The combined organic layers were washed with water (100 mL) and brine (100 mL), dried over $Na_2SO_4$ and concentrated. The residue was purified by prep-HPLC (from 15% water (0.1% $NH_4OAc$) and 85% $CH_3CN$ to 15% water (0.1% $NH_4OAc$) and 85% $CH_3CN$ in 20 min, Flow rate: 50 mL/min) to give the title compound (693 mg, yield 69%) as white solid.

D499 $^1H$ NMR (300 MHz, $CDCl_3$): δ 8.76 (s, 1H), 8.07 (s, 1H), 7.52 (s, 1H), 6.85 (s, 1H), 4.14-4.09 (m, 5H), 3.76-3.69 (m, 4H), 3.64-3.59 (m, 1H), 3.56-3.49 (m, 5H), 3.14-3.05 (m, 1H), 2.47 (s, 3H), 1.92-1.78 (m, 4H), 1.49 (s, 9H).

Description D500

1-(2-Methoxy-6-(piperazin-1-yl)pyrimidin-4-yl)-5-methyl-6-(tetrahydro-2H-pyran-4-yl)-1H-indazole hydrochloride (D500)

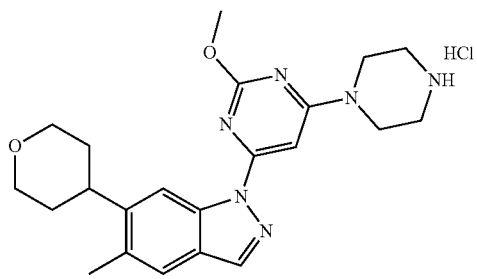 [SMILES: COc1nc(N2CCNCC2)cc(-n2ncc3cc(C)c(C4CCOCC4)cc32)n1 ; Cl]

To a solution of tert-butyl 4-(2-methoxy-6-(5-methyl-6-(tetrahydro-2H-pyran-4-yl)-1H-indazol-1-yl)pyrimidin-4-yl)piperazine-1-carboxylate (696 mg, 1.37 mmol) in dioxane (10 mL) was added HCl/dioxane (4 M, 10 mL). The mixture was stirred for 2 hrs at rt. The reaction mixture was concentrated to give the title compound (732 mg, yield >100%) as white solid.

D500 $^1H$ NMR (300 MHz, DMSO-$d_6$): δ 9.40 (br s, 2H), 8.65 (s, 1H), 8.33 (s, 1H), 7.63 (s, 1H), 6.93 (s, 1H), 4.02 (s, 3H), 3.98-3.87 (m, 6H), 3.63-3.62 (m, 1H), 3.55-3.47 (m, 2H), 3.38-3.37 (1H), 3.33-3.27 (m, 2H), 3.18-3.06 (m, 1H), 2.43 (s, 3H), 1.89-1.62 (m, 4H).

Description D501

(2S)-4-(2-Methyl-6-(5-methyl-6-(tetrahydro-2H-pyran-4-yl)-1H-indazol-1-yl)pyrimidin-4-yl)-2-(((tetrahydro-2H-pyran-2-yl)oxy)methyl)morpholine (D501)

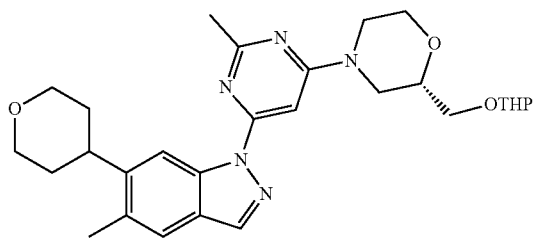

To a solution of 5-methyl-6-(tetrahydro-2H-pyran-4-yl)-1H-indazole (100 mg, 0.463 mmol), (2S)-4-(6-iodo-2-methylpyrimidin-4-yl)-2-(((tetrahydro-2H-pyran-2-yl)oxy)methyl)morpholine (194 mg, 0.463 mmol), N,N'-dimethyl-cyclohexane-1,2-diamine (131 mg, 0.923 mmol) and $K_3PO_4$ (195 mg, 0.920 mmol) in dry toluene (5 mL) was added CuI (175 mg, 0.920 mmol) under $N_2$. Then, the mixture was stirred 110° C. for 3 hrs. After cooled to rt the reaction mixture was filtered. The filtrate was concentrated and the crude was purified by prep-TLC (DCM) to give the desired product (180 mg, yield 77%) as yellow oil.

D501 $^1H$ NMR (300 MHz, $CDCl_3$): δ 8.82 (s, 1H), 8.06 (s, 1H), 7.51 (s, 1H), 6.96 (s, 1H), 4.70-4.62 (m, 1H), 4.41-4.01 (m, 5H), 3.95-3.46 (m, 8H), 3.21-2.81 (m, 3H), 2.63 (s, 3H), 2.47 (s, 3H), 2.05-1.58 (m, 10H).

Description D502

(2R)-4-(2-Methyl-6-(5-methyl-6-(tetrahydro-2H-pyran-4-yl)-1H-indazol-1-yl)pyrimidin-4-yl)-2-(((tetrahydro-2H-pyran-2-yl)oxy)methyl)morpholine (D502)

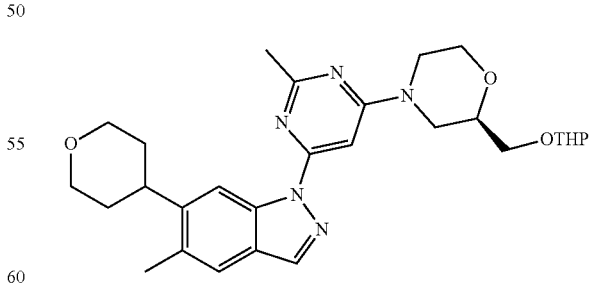

To a solution of 5-methyl-6-(tetrahydro-2H-pyran-4-yl)-1H-indazole (100 mg, 0.463 mmol), (2R)-4-(6-iodo-2-methylpyrimidin-4-yl)-2-(((tetrahydro-2H-pyran-2-yl)oxy)methyl)morpholine (194 mg, 0.463 mmol), N,N'-dimethyl-cyclohexane-1,2-diamine (131 mg, 0.923 mmol) and $K_3PO_4$ (195 mg, 0.920 mmol) in dry toluene (5 mL) was added CuI (175 mg, 0.920 mmol) under $N_2$. Then, the mixture was stirred 110° C. for 3 hrs. After cooled to rt the reaction mixture was filtered. The filtrate was concentrated and the crude was purified by prep-TLC (DCM) to give the desired product (165 mg, yield 71%) as yellow oil.

D502 $^1$H NMR (300 MHz, $CDCl_3$): δ 8.82 (s, 1H), 8.06 (s, 1H), 7.50 (s, 1H), 6.96 (s, 1H), 4.69-4.63 (m, 1H), 4.42-4.01 (m, 5H), 3.95-3.48 (m, 8H), 3.21-2.82 (m, 3H), 2.63 (s, 3H), 2.47 (s, 3H), 2.08-1.60 (m, 10H).

Description D503

Methyl 5-methyl-1-(tetrahydro-2H-pyran-2-yl)-1H-indazole-6-carboxylate (D503)

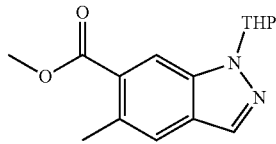

To a solution of 6-bromo-5-methyl-1-(tetrahydro-2H-pyran-2-yl)-1H-indazole (5.00 g, 16.9 mmol) in $CH_3OH$ (100 mL) was added $Pd(OAc)_2$ (757 mg, 3.38 mmol), DPPF (1.87 g, 3.38 mmol) and NaOAc (4.60 g, 33.8 mmol). The mixture was stirred at 100° C. under CO atmosphere (5 MPa) overnight. The mixture was cooled to rt and concentrated. The residue was dispersed in water (100 mL). EtOAc (100 mL×3) was added to extract the desired compound. The combined organic layers were washed with brine (100 mL), dried over $Na_2SO_4$ and concentrated. The residue was purified by chromatography (PE:EtOAc=10:1) to give the title compound (4.20 g, yield 91%) as a yellow solid.

D503 $^1$H NMR (300 MHz, $CDCl_3$): δ 8.18 (s, 1H), 7.98 (s, 1H), 7.56 (s, 1H), 5.75 (dd, J=9.3, 2.7 Hz, 1H), 4.05-4.00 (m, 1H), 3.5 (s, 3H), 3.81-3.73 (m, 1H), 2.65 (s, 3H), 2.61-2.51 (m, 1H), 2.21-2.05 (m, 2H), 1.81-1.63 (m, 3H).

Description D504

(5-Methyl-1-(tetrahydro-2H-pyran-2-yl)-1H-indazol-6-yl)methanol (D504)

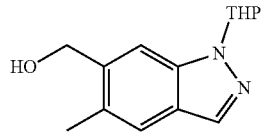

To a solution of methyl 5-methyl-1-(tetrahydro-2H-pyran-2-yl)-1H-indazole-6-carboxylate (4.20 g, 15.3 mmol) in THF (40 mL) was added DIBAl-H (1 M in toluene, 31 mL, 31 mmol) at 0° C. The mixture was stirred at 0° C. for 1 h. To the mixture was added sat. $Na_2SO_4$ solution (10 mL). The mixture was filtered. The filtrates were dissolved in EtOAc (100 mL). The mixture was washed with brine (50 mL), dried over $Na_2SO_4$ and concentrated to give the title compound (3.60 g, yield 96%) as yellow oil.

D504 $^1$H NMR (300 MHz, $CDCl_3$): δ 7.93 (s, 1H), 7.63 (s, 1H), 7.49 (s, 1H), 5.71 (dd, J=9.9, 2.7 Hz, 1H), 4.81 (d, J=5.1 Hz, 2H), 4.06-4.01 (m, 1H), 4.79-3.71 (m, 1H), 2.65-2.52 (m, 1H), 2.40 (s, 3H), 2.21-2.07 (m, 2H), 1.81-1.73 (m, 3H).

Description D505

(5-Methyl-1-(tetrahydro-2H-pyran-2-yl)-1H-indazol-6-yl)methyl methanesulfonate (D505)

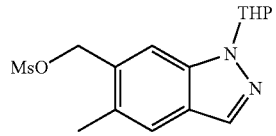

To a solution of (5-methyl-1-(tetrahydro-2H-pyran-2-yl)-1H-indazol-6-yl)methanol (3.60 g, 14.6 mmol) in THF (30 mL) was added $NEt_3$ (2.95 g, 29.2 mmol) and methanesulfonyl chloride (1.99 g, 17.5 mmol) at 0° C. The mixture was stirred at 0° C. for 1 h. The mixture was filtered. The filtrate was concentrated to give the title compound (5.80 g, yield >100%) as a yellow oil.

D505 $^1$H NMR (300 MHz, $CDCl_3$): δ 7.95 (s, 1H), 7.64 (s, 1H), 7.56 (s, 1H), 5.71 (dd, J=9.3, 2.7 Hz, 1H), 5.39 (s, 2H), 4.04-4.00 (m, 1H), 3.80-3.76 (m, 1H), 2.92 (s, 3H), 2.60-2.51 (m, 1H), 2.48 (s, 3H), 2.17-2.04 (m, 2H), 1.76-1.62 (m, 3H).

Description D506

2-(5-Methyl-1-(tetrahydro-2H-pyran-2-yl)-1H-indazol-6-yl)acetonitrile (D506)

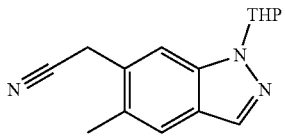

To a solution of (5-methyl-1-(tetrahydro-2H-pyran-2-yl)-1H-indazol-6-yl)methyl methanesulfonate (5.80 g, crude, 14.6 mmol) in DMSO (30 mL) was added NaCN (1.43 g, 29.2 mmol). The mixture was stirred to 60° C. overnight. The mixture was cooled to rt and poured into water (150 mL). The mixture was extracted with EtOAc (50 mL×3). The combined organic layers were washed with water (50 mL×2) and brine (50 mL), dried over $Na_2SO_4$ and concentrated. The residue was purified by chromatography (PE:EtOAc from 10:1 to 2:1) to give the title compound (680 mg, yield 18%) as yellow oil.

D506 $^1$H NMR (300 MHz, $CDCl_3$): δ 7.95 (s, 1H), 7.64 (s, 1H), 7.55 (s, 1H), 5.72 (dd, J=9.6, 2.7 Hz, 1H), 4.07-4.02 (m, 1H), 3.80-3.72 (m, 3H), 2.61-2.50 (m, 1H), 2.41 (s, 3H), 2.19-2.03 (m, 2H), 1.80-1.64 (m, 3H).

Description D507

2-(5-Methyl-1-(tetrahydro-2H-pyran-2-yl)-1H-indazol-6-yl)acetic acid (D507)

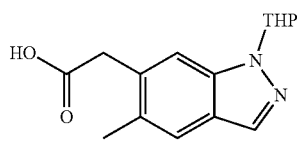

To a solution of 2-(5-methyl-1-(tetrahydro-2H-pyran-2-yl)-1H-indazol-6-yl)acetonitrile (7.80 g, 30.6 mmol) in ethanol (240 mL) was added a solution of KOH (10.3 g, 184 mmol) in water (100 mL). The reaction was stirred in reflux overnight. Then, the mixture was evaporated to remove ethanol. Ethyl acetate (100 mL) was added and separated. The aqueous layer was added HCl (4 M) to adjust pH=5. Ethyl acetate (200 mL×3) was added to extract the desired compound. The combined organic layers were dried over $Na_2SO_4$ and concentrated to give the title compound (7.6 g, yield 91%) as a pale yellow solid.

D507 $^1$H NMR (300 MHz, $CDCl_3$): δ 7.92 (s, 1H), 7.51 (s, 1H), 7.44 (s, 1H), 5.67 (dd, J=9.3, 2.4 Hz, 1H), 4.03-3.99 (m, 1H), 3.80 (s, 2H), 3.77-3.69 (m, 1H), 2.60-2.49 (m, 1H), 2.40 (s, 3H), 2.16-2.02 (m, 2H), 1.78-1.64 (m, 3H).

Description D508

Methyl 2-(5-methyl-1-(tetrahydro-2H-pyran-2-yl)-1H-indazol-6-yl)acetate (D508)

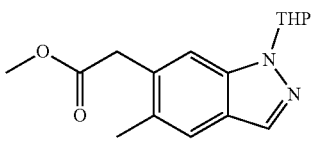

To a mixture of 2-(5-methyl-1-(tetrahydro-2H-pyran-2-yl)-1H-indazol-6-yl)acetic acid (1.15 g, 4.20 mmol) and potassium carbonate (1.16 g, 8.40 mmol) in DMF (10 mL) was added MeI (1.19 g, 8.40 mmol). The reaction mixture was stirred at room temperature for 3 hrs. The reaction mixture was poured into water (100 mL) and extracted with ethyl acetate (100 mL×2). The combined organic layers were washed with water (100 mL) and brine (100 mL×2), dried and concentrated. The residue was purified by column chromatography (petroleum ether:EtOAc from 15:1 to 5:1) to give the title compound (1.20 g, yield 99%) as a pale yellow oil.

D508 $^1$H NMR (300 MHz, $CDCl_3$): δ 7.92 (s, 1H), 7.51 (s, 1H), 7.43 (s, 1H), 5.68 (dd, J=9.6, 2.4 Hz, 1H), 4.05-4.01 (m, 1H), 3.78-3.70 (m, 6H), 2.59-2.54 (m, 1H), 2.38 (s, 3H), 2.17-2.02 (m, 2H), 1.79-1.63 (m, 3H).

Description D509

Dimethyl 2-(5-methyl-1-(tetrahydro-2H-pyran-2-yl)-1H-indazol-6-yl)pentanedioate (D509)

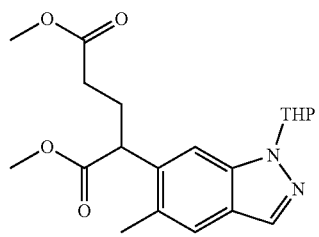

To a stirred solution of methyl 2-(5-methyl-1-(tetrahydro-2H-pyran-2-yl)-1H-indazol-6-yl)acetate (1.50 g, 5.21 mmol) and potassium tert-butyloxide (1.17 g, 10.4 mmol) in toluene (30 mL) was added methyl acrylate (0.900 g, 10.4 mmol) at 0° C. The reaction mixture was stirred at 0° C. for 3 hrs. Then the mixture was poured into saturated ammonium chloride solution (100 mL) and extracted with EtOAc (50 mL×2). The combined organic layers were washed with brine (100 mL), dried and concentrated. The residue was purified by flash column chromatography (petroleum ether:EtOAc from 10:1 to 5:1) to give the title compound (0.65 g, yield 33%) as pale yellow oil.

D509 $^1$H NMR (300 MHz, $CDCl_3$): δ 7.92 (s, 1H), 7.50 (s, 1H), 7.46 (s, 1H), 5.66 (dd, J=9.6, 2.1 Hz, 1H), 4.05-4.02 (m, 2H), 3.79-3.71 (m, 1H), 3.65 (s, 6H), 2.59-2.49 (m, 1H), 2.46 (s, 3H), 2.39-2.29 (m, 3H), 2.19-2.08 (m, 2H), 2.04-2.00 (m, 1H), 1.79-1.62 (m, 3H).

Description D510

2-(5-Methyl-1-(tetrahydro-2H-pyran-2-yl)-1H-indazol-6-yl)pentane-1,5-diol (D510)

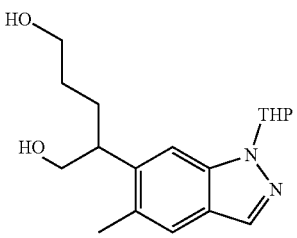

To an ice-water cooled solution of dimethyl 2-(5-methyl-1-(tetrahydro-2H-pyran-2-yl)-1H-indazol-6-yl)pentanedioate (1.63 g, 4.36 mmol) in dry THF (20 mL) was added $LiAlH_4$ (0.550 g, 13.1 mmol). After the reaction mixture was stirred at 0° C. for 1 hour water (50 mL) was carefully added. The mixture was extracted with EtOAc (50 mL×2). The combined organic layers were washed with brine (100 mL), dried over $Na_2SO_4$ and concentrated. The residue was purified by column chromatography (petroleum ether:EtOAc from 1:1 to 0:1) to give the title compound (1.10 g, yield 79%) as colorless oil.

D510 $^1$H NMR (300 MHz, $CDCl_3$): δ 7.91 (s, 1H), 7.50 (s, 1H), 7.37 (s, 1H), 5.69-5.66 (m, 1H), 4.03-3.99 (m, 1H), 3.81-3.70 (m, 3H), 3.62-3.56 (m, 2H), 3.29-3.25 (m, 1H), 2.59-2.53 (m, 1H), 2.43 (s, 3H), 2.18-2.04 (m, 2H), 1.95-1.90 (m, 1H), 1.76-1.48 (m, 6H).

Description D511

5-Methyl-1-(tetrahydro-2H-pyran-2-yl)-6-(tetrahydro-2H-pyran-3-yl)-1H-indazole (D511)

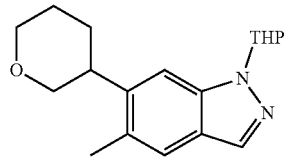

To a solution of 2-(5-methyl-1-(tetrahydro-2H-pyran-2-yl)-1H-indazol-6-yl)pentane-1,5-diol (1.10 g, 3.46 mmol) in dry THF (60 mL) was added sodium hydride (60% in mineral oil, 415 mg, 10.4 mmol) at 0° C. After the mixture was stirred at 0° C. for 30 min 1-tosyl-1H-imidazole (0.850 g, 3.81 mmol) was added. The resulting reaction mixture was warmed to ambient temperature and stirred for 18 hours. The reaction mixture was poured into water (100 mL) and extracted with EtOAc (60 mL×2). The combined organic layers were washed with brine (100 mL), dried and concentrated. The residue was purified by column chromatography (petroleum ether:EtOAc=5:1) to give the title compound (0.31 g, yield 30%) as yellow gel.

D511 $^1$H NMR (300 MHz, CDCl$_3$): δ 7.90 (s, 1H), 7.49 (s, 1H), 7.37 (s, 1H), 5.69 (dd, J=9.0, 3.0 Hz, 1H), 4.08-3.97 (m, 3H), 3.81-3.72 (m, 1H), 3.58-3.39 (m, 2H), 3.21-3.16 (m, 1H), 2.61-2.57 (m, 1H), 2.45 (s, 3H), 2.17-2.04 (m, 3H), 1.87-1.74 (m, 6H).

Description D512 and D513

5-Methyl-6-(tetrahydro-2H-pyran-3-yl)-1H-indazole (Enantiomer 1, D512) and 5-Methyl-6-(tetrahydro-2H-pyran-3-yl)-1H-indazole (Enantiomer 2, D513)

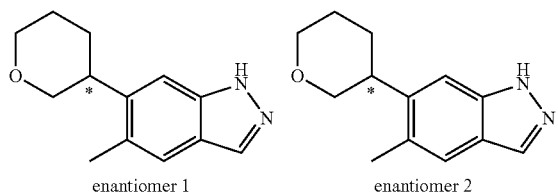

enantiomer 1    enantiomer 2

A mixture of 5-methyl-1-(tetrahydro-2H-pyran-2-yl)-6-(tetrahydro-2H-pyran-3-yl)-1H-indazole (0.310 g, 1.03 mmol) in HCl/methanol (4 M, 5 mL) was stirred at 0° C. for 2 hrs. The reaction mixture was concentrated under vacuum. The residue was partitioned between EtOAc (20 mL) and NaHCO$_3$ (sat., 20 mL). The organic layer was separated and the aqueous layer was extracted with EtOAc (20 mL). The combined organic layers were washed with brine, dried and concentrated under vacuum. The residue was separated by chiral prep-HPLC (IC, CAN:IPA=90:10, 18 mL/min, 254 nm) to give enantiomer 1 (65 mg, yield 21%) and enantiomer 2 (83 mg, yield 27%) both as yellow gel.

D512 (enantiomer 1): $^1$H NMR (300 MHz, CDCl$_3$): δ 7.95 (s, 1H), 7.53 (s, 1H), 7.36 (s, 1H), 4.05-3.97 (m, 2H), 3.56-3.38 (m, 2H), 3.20-3.13 (m, 1H), 2.46 (s, 3H), 2.07-2.04 (m, 1H), 1.87-1.72 (m, 3H). Chiral HPLC: Chiral pak IF 5 um 4.6*250 mm, Hex:EtOH=85:15, Flow: 0.5 ml/min, 230 nm, T=30° C. Rt=6.753 min, 100% ee.

D513 (enantiomer 2): $^1$H NMR (300 MHz, CDCl$_3$): δ 7.96 (s, 1H), 7.53 (s, 1H), 7.36 (s, 1H), 4.06-3.97 (m, 2H), 3.58-3.38 (m, 2H), 3.20-3.13 (m, 1H), 2.46 (s, 3H), 2.06-2.01 (m, 1H), 1.87-1.73 (m, 3H). Chiral HPLC: Chiral pak IF 5 um 4.6*250 mm, Hex:EtOH=85:15, Flow: 0.5 ml/min, 230 nm, T=30° C. Rt=8.997 min, 98.77% ee.

Description D514

(But-3-yn-1-yloxy)(tert-butyl)diphenylsilane (D514)

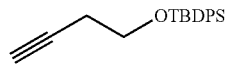

To a cooled solution of but-3-yn-1-ol (2.10 g, 30.0 mmol) and imidazole (4.08 g, 60.0 mmol) in dichloromethane (100 mL) was added a solution of TBDPSCl (9.9 g, 36.0 mmol) in dichloromethane (20 mL). The resulting mixture was stirred at 0° C. to rt under nitrogen for 16 hrs. The reaction mixture was diluted with water (100 mL) and extracted with dichloromethane (50 mL×2). The combined organic layers were washed with brine (100 mL), dried over Na$_2$SO$_4$ and concentrated. The residue was purified by column chromatography on silica gel (PE:EtOAC=50:1) to give the title compound (8.5 g, yield 92%) as a yellow oil.

D514 $^1$H NMR (300 MHz, CDCl$_3$): δ 7.69 (dd, J=7.5, 1.8 Hz, 4H), 7.44-7.37 (m, 6H), 3.80 (t, J=6.9 Hz, 2H), 2.49-2.43 (m, 2H), 1.97-1.95 (m, 1H), 1.07 (s, 9H).

Description D515

5-Methyl-1-(tetrahydro-2H-pyran-2-yl)-1H-indazole-6-carbaldehyde (D515)

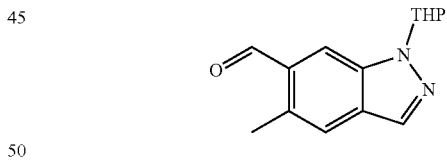

To a solution of 6-bromo-5-methyl-1-(tetrahydro-2H-pyran-2-yl)-1H-indazole (6.90 g, 23.5 mmo) in 100 mL of dry THF was added dropwise of n-BuLi (2.5 M in THF, 18.8 mL, 46.9 mmol) at −78° C. After addition the reaction mixture was stirred at −78° C. for 1 hour. Dry DMF (34.2 g, 46.8 mmol) was added to the reaction mixture and stirred at −78° C. for 3 hrs. The reaction mixture was poured into water (200 mL) and extracted with EtOAc (150 mL×2). The combined organic layers were washed with brine (200 mL), dried over Na$_2$SO$_4$ and concentrated under reduced pressure to give the crude product as brown oil. The crude was purified by column chromatography (petroleum ether:EtOAc=6:1) to give the title compound (3.2 g, yield 56%) as pale yellow solid.

D515 $^1$H NMR (300 MHz, CDCl$_3$): δ 10.37 (s, 1H), 8.08 (s, 1), 8.00 (s, 1H), 7.56 (s, 1H), 5.80-5.76 (m, 1H), 4.05-4.01 (m, 1H), 3.82-3.74 (m, 1H), 2.74 (s, 3H), 2.58-2.50 (m, 1H), 2.18-2.07 (m, 2H), 1.81-1.65 (m, 3H).

Description D516

5-((tert-Butyldiphenylsilyl)oxy)-1-(5-methyl-1-(tetrahydro-2H-pyran-2-yl)-1H-indazol-6-yl)pent-2-yn-1-ol (D516)

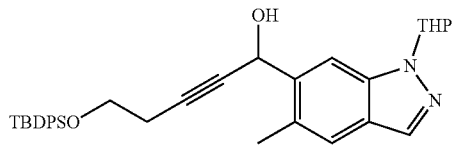

A solution of (but-3-yn-1-yloxy)(tert-butyl)diphenylsilane (308 mg, 1.0 mmol) in dry THF (10 mL) was treated with n-BuLi (2.5 mol/L in hexane, 0.5 mL) at −78° C. over 5 min. After the reaction mixture was stirred for 15 min a solution of 5-methyl-1-(tetrahydro-2H-pyran-2-yl)-1H-indazole-6-carbaldehyde (122 mg, 0.50 mmol) in THF (2 mL) was added. The resulting mixture was stirred at room temperature overnight. The reaction mixture was quenched with sat. NH$_4$Cl solution (30 mL) and extracted with EtOAc (30 mL×2). The combined organic layers were washed with brine (50 mL), dried over Na$_2$SO$_4$ and concentrated. The residue was purified by column chromatography on silica gel (PE:EtOAC from 10:1 to 5:1) and prep-TLC (PE:EtOAc=3:1) to give the title compound (143 mg, yield 51%) as a grey solid.

D516 $^1$H NMR (300 MHz, CDCl$_3$): δ 7.93 (s, 1H), 7.86 (s, 1H), 7.68-7.65 (m, 4H), 7.48 (s, 1H), 7.42-7.33 (m, 6H), 5.69-5.66 (m, 2H), 4.02-3.97 (m, 1H), 3.81 (t, J=6.9 Hz, 2H), 3.72-3.63 (m, 1H), 2.57-2.52 (m, 3H), 2.49 (s, 3H), 2.15-2.05 (m, 2H), 2.05-1.99 (m, 1H), 1.76-1.69 (m, 3H), 1.04 (s, 9H).

Description D517

5-((tert-Butyldiphenylsilyl)oxy)-1-(5-methyl-1-(tetrahydro-2H-pyran-2-yl)-1H-indazol-6-yl)pentan-1-ol (D517)

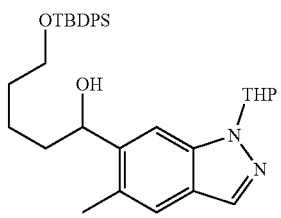

A mixture of 5-((tert-butyldiphenylsilyl)oxy)-1-(5-methyl-1-(tetrahydro-2H-pyran-2-yl)-1H-indazol-6-yl)pent-2-yn-1-ol (680 mg, 1.23 mmol) and platinum dioxide (68 mg) in EtOAc (40 mL) was hydrogenated under H$_2$ atmosphere at room temperature overnight. The mixture was filtered and concentrated to give the title compound (720 mg, yield 95%) as a white solid.

D517 $^1$H NMR (300 MHz, CDCl$_3$): δ 7.93 (s, 1H), 7.71 (s, 1H), 7.67-7.61 (m, 4H), 7.46 (s, 1H), 7.41-7.34 (m, 6H), 5.72-5.68 (m, 1H), 5.02-5.00 (m, 1H), 4.07-4.04 (m, 1H), 3.78-3.75 (m, 1H), 3.74-3.66 (m, 2H), 2.62-2.54 (m, 1H), 2.39 (s, 3H), 2.19-2.12 (m, 1H), 2.05-2.04 (m, 1H), 2.01-1.93 (m, 1H), 1.79-1.70 (m, 8H), 1.64-1.60 (m, 1H), 1.03 (s, 9H).

Description D518

1-(5-Methyl-1-(tetrahydro-2H-pyran-2-yl)-1H-indazol-6-yl)pentane-1,5-diol (D518)

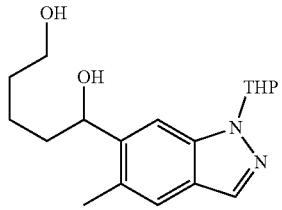

To a solution of 5-((tert-butyldiphenylsilyl)oxy)-1-(5-methyl-1-(tetrahydro-2H-pyran-2-yl)-1H-indazol-6-yl)pentan-1-ol (5.34 g, 9.60 mmol) in THF (50 mL) was added tetrabutylammonium fluoride (9.50 g, 36.3 mmol). The resulting mixture was stirred at room temperature overnight. The reaction mixture was concentrated under vacuum and purified by column C18 (5-60% ACN in water) to give the title compound (2.34 g, yield 76%) as a colorless oil.

D518 $^1$H NMR (300 MHz, CDCl$_3$): δ 7.91 (s, 1H), 7.71 (s, 1H), 7.45 (s, 1H), 5.72-5.68 (m, 1H), 5.04-5.00 (m, 1H), 4.10-4.02 (m, 1H), 3.75-3.66 (m, 3H), 2.61-2.51 (m, 1H), 2.39 (s, 3H), 2.22-2.14 (m, 1H), 2.14-2.12 (m, 1H), 2.03-1.93 (m, 1H), 1.77-1.71 (m, 4H), 1.68-1.52 (m, 4H).

Description D519

5-Methyl-1,6-bis(tetrahydro-2H-pyran-2-yl)-1H-indazole (D519)

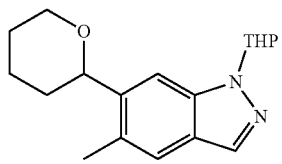

To a solution of 1-(5-methyl-1-(tetrahydro-2H-pyran-2-yl)-1H-indazol-6-yl)pentane-1,5-diol (2.34 g, 7.35 mmol) in dry THF (100 mL) was added NaH (60% in material oil, 1.18 g, 29.4 mmol) at 0-5° C. under nitrogen. After the mixture was stirred at this temperature for 30 min 1-tosyl-1H-imidazole (1.96 g, 8.82 mmol) was added. The resulting mixture was stirred at rt overnight. Then the reaction mixture was gradually poured into water (100 mL) and extracted with EtOAc (100 mL×3). The combined organic layers were washed with brine (50 mL×2), dried over Na$_2$SO$_4$ and concentrated. The crude was purified by column chromatography on silica gel (PE:EtOAC=10:1) to give the title compound (965 mg, yield 43%) as a white solid.

D519 $^1$H NMR (300 MHz, CDCl$_3$): δ 7.92 (s, 1H), 7.65 (d, J=7.8 Hz, 1H), 7.45 (s, 1H), 5.75-5.71 (m, 1H), 4.59-4.55 (m, 1H), 4.23-4.20 (m, 1H), 4.08-4.00 (m, 1H), 3.81-3.64

(m, 2H), 2.61-2.54 (m, 1H), 2.40 (s, 3H), 2.19-2.12 (m, 1H), 2.04-1.99 (m, 2H), 1.97-1.92 (m, 1H), 1.87-1.76 (m, 4H), 1.76-1.68 (m, 3H).

Description D520

5-Methyl-6-(tetrahydro-2H-pyran-2-yl)-1H-indazole (D520)

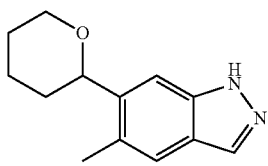 [SMILES: Cc1cc2cn[nH]c2cc1C1CCCCO1]

To a solution of 5-methyl-1,6-bis(tetrahydro-2H-pyran-2-yl)-1H-indazole (960 mg, 3.20 mmol) in dioxane (30 mL) and methanol (10 mL) was added HCl/dioxane (4 M, 8 mL) at room temperature. The resulting mixture was stirred at rt overnight and then concentrated. 50% EtOAc in PE (30 mL) was added and the mixture was stirred at room temperature for 10 min. The reaction mixture was filtered and concentrated under vacuum to give a white solid (700 mg). Sat. NaHCO$_3$ (30 mL) was added and stirred for 10 min the aqueous was extracted with EtOAc (50 mL×2). The combined organic layers were washed with brine (50 mL), dried over Na$_2$SO$_4$ and concentrated to give the title compound (570 mg, yield 82%) as a white solid.

D520 $^1$H NMR (300 MHz, CDCl$_3$): δ 10.41 (br s, 1H), 7.96 (s, 1H), 7.63 (s, 1H), 7.49 (s, 1H), 4.59-4.56 (m, 1H), 4.24-4.20 (m, 1H), 3.73-3.65 (m, 1H), 2.42 (s, 3H), 1.99-1.96 (m, 1H), 1.92-1.87 (m, 1H), 1.79-1.61 (m, 3H), 1.54-1.50 (m, 1H).

LC-MS [mobile phase: from 95% water (0.02% NH$_4$OAc) and 5% CH$_3$CN to 5% water (0.02% NH$_4$OAc) and 95% CH$_3$CN in 6.5 min], Rt=3.398 min; MS Calcd.: 216, MS Found: 217 [M+H]$^+$.

Description D521 and D522

5-Methyl-6-(tetrahydro-2H-pyran-2-yl)-1H-indazole (Enantiomer 1, D521) and 5-Methyl-6-(tetrahydro-2H-pyran-2-yl)-1H-indazole (Enantiomer 2, D522)

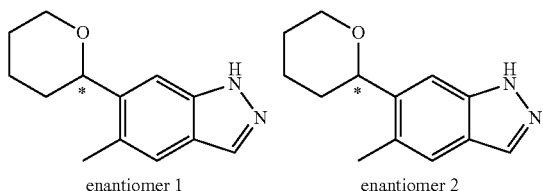

enantiomer 1    enantiomer 2

Racemic 5-methyl-6-(tetrahydro-pyran-2-yl)-1H-indazole (639 mg, 2.95 mmol) was separated by chiral prep-HPLC to give enantiomer 1 (290 mg) and enantiomer 2 (298 mg) both as yellow solid.

D521 (enantiomer 1): $^1$H NMR (300 MHz, CDCl$_3$): δ 7.95 (s, 1H), 7.64 (s, 1H), 7.49 (s, 1H), 4.57 (d, J=10.8 Hz, 1H), 4.22 (d, J=11.4 Hz, 1H), 3.73-3.66 (m, 1H), 2.42 (s, 3H), 1.99-1.96 (m, 1H), 1.92-1.87 (m, 1H), 1.79-1.61 (m, 3H), 1.54-1.50 (m, 1H).

Chiral HPLC [Chiralpak OD-H, Phase: CO$_2$/MeOH=70/30, flow rate (CO$_2$: 2.1 mL/min; MeOH: 0.899 mL/min), T=40° C.], Rt=2.70 min, 99.33% ee.

D522 (enantiomer 2): $^1$H NMR (300 MHz, CDCl$_3$): δ 7.96 (s, 1H), 7.64 (s, 1H), 7.49 (s, 1H), 4.57 (d, J=10.8 Hz, 1H), 4.22 (d, J=13.8 Hz, 1H), 3.69 (t, J=11.4 Hz, 1H), 2.42 (s, 3H), 1.99-1.96 (m, 1H), 1.92-1.87 (m, 1H), 1.79-1.61 (m, 3H), 1.54-1.50 (m, 1H).

Chiral HPLC [Chiralpak OD-H, Phase: CO$_2$/MeOH=70/30, flow rate (CO$_2$: 2.1 mL/min; MeOH: 0.899 mL/min), T=40° C.], Rt=5.63 min, 99.23% ee.

Description D523

4-(5-Methyl-1-(tetrahydro-2H-pyran-2-yl)-1H-indazol-6-yl)tetrahydro-2H-pyran-3-ol and 4-(5-methyl-1-(tetrahydro-2H-pyran-2-yl)-1H-indazol-6-yl)tetrahydro-2H-pyran-4-ol (Isomer) (D523)

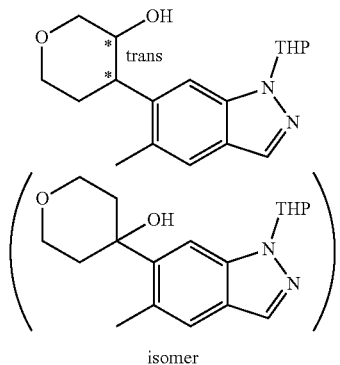

isomer

To a solution of 6-(3,6-dihydro-2H-pyran-4-yl)-5-methyl-1-(tetrahydro-2H-pyran-2-yl)-1H-indazole (2.0 g, 6.7 mmol) in dry THF (20 mL) was added BH$_3$.THF (1 M, 20 mL, 20 mmol) dropwise under ice bath and N$_2$ atmosphere. The reaction mixture was stirred at rt for 2 hrs. Then the mixture was cooled to 0° C. and MeOH (4 mL) was added dropwise carefully. After the resulting mixture was stirred for 30 min under ice bath, NaOH (4 M, 5.0 mL, 20 mmol) and H$_2$O$_2$ (30%, 2.3 g, 20 mmol) were followed. The resulting mixture was stirred at rt overnight. The reaction mixture was gradually poured into Na$_2$S$_2$O$_3$ (10%, 100 mL) and stirred for 15 min. Then the organic layer was separated and the aqueous layer was extracted with EtOAc (100 mL). The combined organic layers were washed with brine, dried over Na$_2$SO$_4$ and concentrated. The crude was purified by column chromatography (PE:EtOAc=2:1). The crude was triturated with PE/EtOAc (5/1, 5 mL) and filtered to give the title compound (1.0 g with 9% of isomer, yield 31%) as a white solid.

D523 $^1$H NMR (300 MHz, CDCl$_3$): δ 7.90 (s, 1H), 7.52 (s, 1H), 7.48 (s, 1H), 5.68-5.65 (m, 1H), 4.21-4.14 (m, 1H), 4.10-3.97 (m, 3H), 3.80-3.70 (m, 1H), 3.58-3.46 (m, 1H), 3.34-3.27 (m, 1H), 3.14-3.00 (m, 1H), 2.64-2.51 (m, 1H), 2.48 (s, 3H), 2.20-1.99 (m, 2H), 1.91-1.70 (m, 6H).

Description D524

6-(3-Fluorotetrahydro-2H-pyran-4-yl)-5-methyl-1-(tetrahydro-2H-pyran-2-yl)-1H-indazole and 6-(4-fluorotetrahydro-2H-pyran-4-yl)-5-methyl-1-(tetrahydro-2H-pyran-2-yl)-1H-indazole (Isomer) (D524)

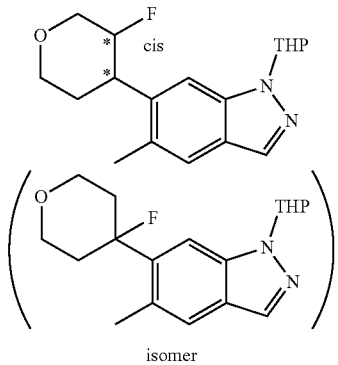

To a solution of 4-(5-methyl-1-(tetrahydro-2H-pyran-2-yl)-1H-indazol-6-yl)tetrahydro-2H-pyran-3-ol (1.0 g with 9% of isomer, 3.2 mmol) in dry DCM (150 mL) was added DAST (2.06 g, 12.8 mmol) at −60° C. under $N_2$ atmosphere. After stirring at −60° C. for 20 min, the reaction mixture was warmed to rt for 30 min. The reaction mixture was gradually poured into $Na_2CO_3$ (10%, 150 mL) and stirred for 15 min. The organic layer was washed with brine, dried over $Na_2SO_4$ and concentrated to give the title compound (1.0 g with 9% of isomer, yield 99%) as slightly brown oil.

D524 $^1$H NMR (300 MHz, $CDCl_3$): δ 7.92 (s, 1H), 7.53-7.51 (m, 2H), 5.74-5.70 (m, 1H), 5.10-4.84 (m, 1H), 4.19-4.10 (m, 1H), 4.06-3.94 (m, 2H), 3.80-3.72 (m, 1H), 3.69-3.62 (m, 1H), 3.55-3.34 (m, 2H), 2.59-2.52 (m, 1H), 2.48 (s, 3H), 2.28-1.93 (m, 4H), 1.86-1.63 (m, 3H).

Description D525

6-(3-Fluorotetrahydro-2H-pyran-4-yl)-5-methyl-1H-indazole and 6-(4-fluorotetrahydro-2H-pyran-4-yl)-5-methyl-1H-indazole (Isomer) (D525)

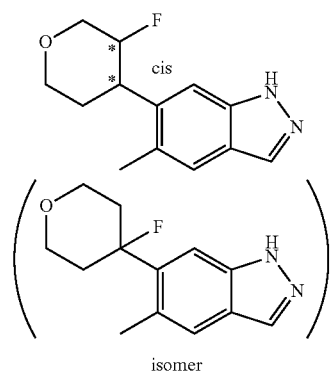

To a solution of 6-(3-fluorotetrahydro-2H-pyran-4-yl)-5-methyl-1-(tetrahydro-2H-pyran-2-yl)-1H-indazole (1.0 g with 9% of isomer, 3.1 mmol) in EtOH (10 mL) was added conc. HCl (5 mL) dropwise at rt. The resulting mixture was stirred for 30 min. Then $Na_2CO_3$ (sat) was added dropwise to the mixture to adjust pH=11. Then the aqueous layer was extracted with EtOAc (50 mL×2). The combined organic layers were washed with brine, dried over $Na_2SO_4$ and concentrated. The crude was purified by column chromatography (PE:EtOAc from 2:1 to 1:1) to give the title compound (650 mg with 8% of isomer, yield 88%) as a white semi-solid.

D525 $^1$H NMR (300 MHz, $CDCl_3$): δ 10.01 (br s, 1H), 7.98 (s, 1H), 7.58 (s, 1H), 7.51 (s, 1H), 5.05-4.81 (m, 1H), 4.18-3.95 (m, 2H), 3.68-3.59 (m, 1H), 3.52-3.33 (m, 2H), 2.49 (s, 3H), 2.29-2.14 (m, 1H), 2.06-1.90 (m, 1H).

Description D526 and D527

6-(3-Fluorotetrahydro-2H-pyran-4-yl)-5-methyl-1H-indazole (Enantiomer 1) with 6-(4-fluorotetrahydro-2H-pyran-4-yl)-5-methyl-1H-indazole (Isomer) (D526) and 6-(3-Fluoro-tetrahydro-pyran-4-yl)-5-methyl-1H-indazole (Enantiomer 2, D527)

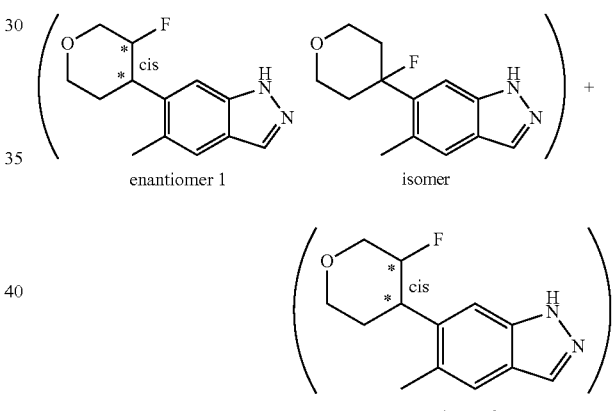

6-(3-Fluoro-tetrahydro-pyran-4-yl)-5-methyl-1H-indazole (650 mg with 8% of isomer, 2.77 mmol) was separated by chiral prep. HPLC [Column: Chiralpak OJ (20 mm×250 mm, 5 μm); Wavelength: 214 nm; Mobile phase: hexane/ethanol=60/40 (v/v); Flow rate: 13 mL/min] to give the title compound enantiomer 1 (280 mg with 18% of isomer, yield 35%) and enantiomer 2 (210 mg, yield 32%) both as a white solid.

D526: $^1$H NMR (300 MHz, $CDCl_3$): δ 10.10 (br s, 1H), 7.98 (s, 1H), 7.58 (s, 1H), 7.51 (s, 1H), 5.06-4.80 (m, 1H), 4.18-3.95 (m, 2H), 3.67-3.59 (m, 1H), 3.52-3.32 (m, 2H), 2.49 (s, 3H), 2.29-2.15 (m, 1H), 2.09-1.89 (m, 1H).

D527: $^1$H NMR (300 MHz, $CDCl_3$): δ 10.00 (br s, 1H), 7.98 (s, 1H), 7.58 (s, 1H), 7.51 (s, 1H), 5.06-4.79 (m, 1H), 4.20-3.98 (m, 2H), 3.68-3.60 (m, 1H), 3.52-3.32 (m, 2H), 2.49 (s, 3H), 2.29-2.15 (m, 1H), 2.09-1.89 (m, 1H).

Description D528 and D529

6-(3-Fluorotetrahydro-2H-pyran-4-yl)-5-methyl-1-(2-methyl-6-(3-((tetrahydro-2H-pyran-2-yl)oxy)azetidin-1-yl)pyrimidin-4-yl)-1H-indazole (Isomer 1, D528) and 6-(4-fluorotetrahydro-2H-pyran-4-yl)-5-methyl-1-(2-methyl-6-(3-((tetrahydro-2H-pyran-2-yl)oxy)azetidin-1-yl)pyrimidin-4-yl)-1H-indazole (Isomer, D529)

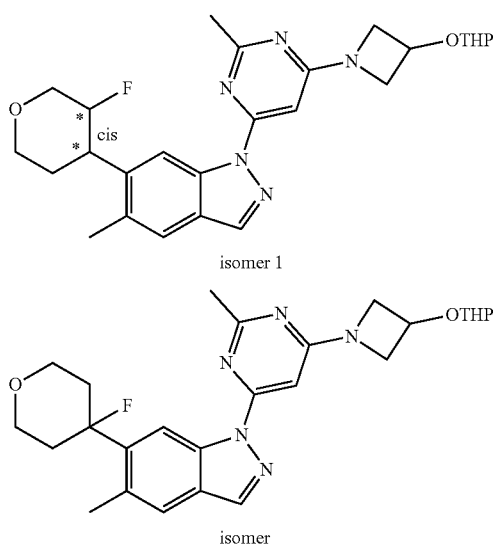

isomer 1 isomer

To a suspension of 6-(3-fluorotetrahydro-2H-pyran-4-yl)-5-methyl-1H-indazole (enantiomer 1) (70 mg with 18% of isomer, 0.30 mmol), 4-iodo-2-methyl-6-(3-((tetrahydro-2H-pyran-2-yl)oxy)azetidin-1-yl)pyrimidine (113 mg, 0.300 mmol), CuI (57 mg, 0.30 mmol) and $K_3PO_4$ (127 mg, 0.60 mmol) in toluene (3 mL) was added N,N'-dimethyl-cyclohexane-1,2-diamine (85 mg, 0.60 mmol) at rt. The resulting mixture was stirred at 110° C. under $N_2$ atmosphere for 3 hrs. Then the reaction mixture was cooled and partitioned between dilute ammonia (10%, 30 mL) and EtOAc (30 mL). The organic layer was washed with brine, dried over $Na_2SO_4$ and concentrated. The crude was purified by prep. TLC (PE:EtOAc=2:1) to give the title compound (60 mg, yield 42%) as a white solid and the isomer (30 mg).

D528 $^1$H NMR (300 MHz, CDCl$_3$): δ 8.94 (s, 1H), 8.07 (s, 1H), 7.54 (s, 1H), 6.59 (s, 1H), 5.11-4.86 (m, 1H), 4.75-4.68 (m, 2H), 4.41-4.33 (m, 2H), 4.22-4.01 (m, 4H), 3.92-3.85 (m, 1H), 3.69-3.61 (m, 1H), 3.58-3.50 (m, 2H), 3.46-3.36 (m, 1H), 2.61 (s, 3H), 2.50 (s, 3H), 2.35-2.22 (m, 1H), 2.10-1.95 (m, 1H), 1.89-1.55 (m, 6H).

D529 (isomer): $^1$H NMR (300 MHz, CDCl$_3$): δ 9.00 (s, 1H), 8.09 (s, 1H), 7.54 (s, 1H), 6.60 (s, 1H), 4.77-4.69 (m, 2H), 4.42-4.34 (m, 2H), 4.16-3.86 (m, 7H), 3.56-3.49 (m, 1H), 2.65-2.61 (m, 6H), 2.52-2.18 (m, 4H), 1.90-1.60 (m, 6H).

Description D530

6-(3-Fluorotetrahydro-2H-pyran-4-yl)-5-methyl-1-(2-methyl-6-(3-((tetrahydro-2H-pyran-2-yl)oxy)azetidin-1-yl)pyrimidin-4-yl)-1H-indazole (Isomer 2, D530)

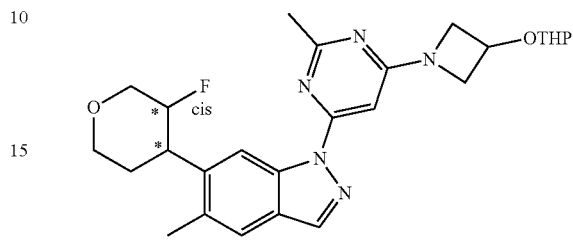

To a suspension of 6-(3-fluorotetrahydro-2H-pyran-4-yl)-5-methyl-1H-indazole (enantiomer 2) (60 mg, 0.26 mmol), 4-iodo-2-methyl-6-(3-((tetrahydro-2H-pyran-2-yl)oxy)azetidin-1-yl)pyrimidine (98 mg, 0.26 mmol), CuI (50 mg, 0.26 mmol) and $K_3PO_4$ (110 mg, 0.52 mmol) in toluene (3 mL) was added N,N'-dimethyl-cyclohexane-1,2-diamine (74 mg, 0.52 mmol) at rt. The resulting mixture was stirred at 110° C. under $N_2$ atmosphere for 3 hrs. Then the reaction mixture was cooled and partitioned between diluted ammonia (10%, 30 mL) and EtOAc (30 mL). The organic layer was washed with brine, dried over $Na_2SO_4$ and concentrated. The crude was purified by prep-TLC (PE:EtOAc=1:1) to give the title compound (100 mg, yield 81%) as a white solid.

D530 $^1$H NMR (300 MHz, CDCl$_3$): δ 8.94 (s, 1H), 8.07 (s, 1H), 7.54 (s, 1H), 6.60 (s, 1H), 5.12-4.86 (m, 1H), 4.76-4.65 (m, 2H), 4.42-4.33 (m, 2H), 4.22-4.01 (m, 4H), 3.93-3.85 (m, 1H), 3.69-3.60 (m, 1H), 3.57-3.50 (m, 2H), 3.47-3.36 (m, 1H), 2.62 (s, 3H), 2.51 (s, 3H), 2.34-2.23 (m, 1H), 2.09-1.95 (m, 1H), 1.91-1.71 (m, 2H), 1.66-1.58 (m, 4H).

Description D531

6-Isopropoxy-5-methyl-1H-indazole (D531)

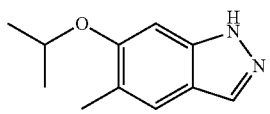

Step 1:

To a solution of 5-methyl-1-(tetrahydro-2H-pyran-2-yl)-1H-indazol-6-ol (463 mg, 1.993 mmol) in DMF (4 mL), added to a suspension of sodium hydride (159 mg, 3.99 mmol) in DMF (4.00 mL) at 0° C., and the reaction mixture stirred for 30 min. 2-bromopropane (0.225 mL, 2.392 mmol) was added and the reaction stirred at rt for 10 h. The reaction was cooled to 0° C., quenched with sat. NH$_4$Cl solution and the mixture was evaporated in vacuo and purified by normal phase column chromatography (EA/PE: 0% to 100%) to furnished 6-isopropoxy-5-methyl-1-(tetrahydro-2H-pyran-2-yl)-1H-indazole (368 mg, 1.341 mmol, 67.3% yield).

LC-MS (mobile phase: from 95% water (0.1% TFA) and 5% CH$_3$CN (0.1% TFA) to 5% water (0.1% TFA) and 95%

CH₃CN (0.1% TFA) in 5 min, Rt=3.942 min; MS Calcd.: 275.1. MS Found: 275.1 (M+H)⁺.

Step 2:

To a 25 mL round bottle charged with 6-isopropoxy-5-methyl-1-(tetrahydro-2H-pyran-2-yl)-1H-indazole (203 mg, 0.740 mmol) were added ethanol (2 mL) and hydrochloric acid (conc.) (1 ml, 32.9 mmol). The mixture was stirred for 1 hr at room temperature. Then the mixture was evaporated in vacuo and furnished 6-isopropoxy-5-methyl-1H-indazole directly used in the next step without purification.

D531 LC-MS (mobile phase: from 95% water (0.1% TFA) and 5% CH₃CN (0.1% TFA) to 5% water (0.1% TFA) and 95% CH₃CN (0.1% TFA) in 5 min, Rt=3.068 min; MS Calcd.: 191.1 MS Found: 191.1 (M+H)⁺.

Description D532

6-Isopropoxy-1-(2-methoxy-6-(3-((tetrahydro-2H-pyran-2-yl)oxy)azetidin-1-yl)pyrimidin-4-yl)-5-methyl-1H-indazole (D532)

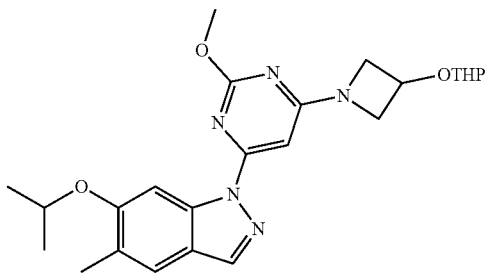

To a 50 mL round bottle charged with the 6-isopropoxy-5-methyl-1H-indazole (114 mg, 0.601 mmol) were added copper(I) iodide (114 mg, 0.601 mmol), 4-iodo-2-methoxy-6-(3-((tetrahydro-2H-pyran-2-yl)oxy)azetidin-1-yl)pyrimidine (235 mg, 0.601 mmol), potassium phosphate (128 mg, 0.601 mmol) and toluene (6 mL). Subsequently, N1,N2-dimethylcyclohexane-1,2-diamine (0.095 mL, 0.601 mmol) were added under the nitrogen atmosphere. The mixture was then stirred at 120° C. for 2 hrs under nitrogen atmosphere. The mixture was cooled to room temperature, EtOAc (40 mL) and water (20 mL) were added and the layers were separated. The aqueous layer was extracted by EtOAc (40 mL). The combined organic layers was washed with saturated aqueous NaCl (30 mL), dried over anhydrous Na₂SO₄. Then the mixture was evaporated in vacuo and purified by normal phase column chromatography (EA/PE: 0% to 60%) to afford 6-isopropoxy-1-(2-methoxy-6-(3-((tetrahydro-2H-pyran-2-yl)oxy)azetidin-1-yl)pyrimidin-4-yl)-5-methyl-1H-indazole (59 mg, 0.130 mmol, 21.65% yield).

D532 LC-MS (mobile phase: from 95% water (0.1% TFA) and 5% CH₃CN (0.1% TFA) to 5% water (0.1% TFA) and 95% CH₃CN (0.1% TFA) in 5 min, Rt=4.599 min; MS Calcd.: 454.2 MS Found: 454.1 (M+H)⁺.

Description D533

1-Bromo-2-chloro-4-methyl-5-nitrobenzene (D533)

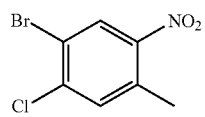

Con. HNO₃ (15 mL) was added to the solution of 1-bromo-2-chloro-4-methylbenzene (20 g, 100 mmol) in con. H₂SO₄ (65 mL) at −20° C. slowly. The reaction was stirred for 5 mins and then poured into ice-water (500 g). Then, the mixture was filtered and the solid was washed by water and dried to give the crude product as a yellow solid. (23 g, 95% yield).

D533 ¹H NMR (400 MHz, CDCl₃) δ 8.27 (s, 1H), 7.46 (s, 1H), 2.56 (s, 3H).

Description D534

5-Bromo-4-chloro-2-methylaniline (D534)

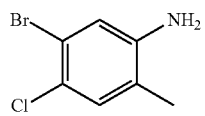

Con. HCl was slowly added to the stirred mixture of Fe (22.4 g, 400 mmol) and 1-bromo-2-chloro-4-methyl-5-nitrobenzene (20 g, 80 mmol) in THF (100 mL) at RT until the reaction completed (The temperature of the reaction rise to ~60° C.). Then the reaction mixture was poured into K₂CO₃ (200 g) and EtOAc (500 mL) and the mixture was stirred for 0.5 hour. The mixture was filtered and the solution was washed with sat. NaHCO₃ (2×200 mL). Then the solution was dried and concentrated. The residue was purified by chromatography (EtOAc/PE=1/10) to give 5-bromo-4-chloro-2-methylaniline as a yellow solid (11 g, 62% yield).

D534 ¹H NMR (400 MHz, CDCl₃) δ 7.10 (s, 1H), 6.90 (s, 1H), 3.63 (br, 2H), 2.09 (s, 3H)

Description D535

6-Bromo-5-chloro-1H-indazole (D535)

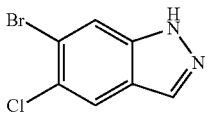

A solution of NaNO₂ (3.04 g, 44 mmol) in water (10 mL) was added to the solution of 5-bromo-4-chloro-2-methylaniline (9.3 g, 40 mmol) in HOAc (50 mL) at RT and the mixture was refluxed for 2 hours. The reaction was then concentrated and the residue was diluted with EtOAc (200 mL). The mixture was washed with sat. NaHCO₃ (2×100 mL) and dried. Then, the solution was filtered and concentrated to give the crude product as a brown solid (4.7 g, 50% yield).

Description D536

6-Bromo-5-chloro-1-(tetrahydro-2H-pyran-2-yl)-1H-indazole (D536)

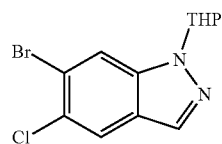

The solution of 6-bromo-5-chloro-1H-indazole (4.7 g, 20 mmol), DHP (4.7 mL) and p-TsOH (30 mg) in THF (50 mL) was refluxed for 2 hours. The reaction was diluted with EtOAc (50 mL) and washed with sat. NaHCO$_3$ (2×100 mL). Then the solution was dried and concentrated. The residue was purified by silica gel column (PE/EtOAc=10/1) to give 6-bromo-5-chloro-1-(tetrahydro-2H-pyran-2-yl)-1H-indazole as a yellow solid (2.5 g, 40% yield).

D536 $^1$H NMR (400 MHz, CDCl$_3$) δ 7.95 (s, 2H), 7.83 (s, 1H), 5.66 (dd, J=9.6 2.8 Hz, 1H), 4.02-4.00 (m, 1H), 3.78-3.73 (m, 1H), 2.50-2.48 (m, 1H), 2.16-2.05 (m, 1H), 1.80-1.66 (m, 1H).

Description D537

5-Chloro-1-(tetrahydro-2H-pyran-2-yl)-6-(4,4,5,5-tetramethyl-1,3,2-dioxaborolan-2-yl)-1H-indazole (D537)

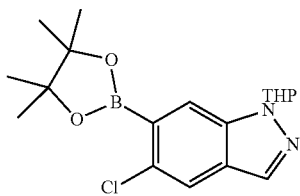

The solution of 6-bromo-5-chloro-1-(tetrahydro-2H-pyran-2-yl)-1H-indazole (400 mg, 1.26 mmol, 1.0 eq), bis(pinacolato)diboron (481 mg, 1.89 mmol, 1.5 eq) and KOAc (483 mg, 5.04 mmol, 4.0 eq) in dioxane (15 mL) was degassed and refilled with Ar for 3 times with water pump. Pd(dppf)Cl$_2$ (96 mg, 0.126 mmol, 0.1 eq) was added quickly in one portion under Ar. After being degassed for another 3 times with water pump, the reaction was stirred at 90° C. for 5 h. 30 mL H$_2$O was added and extracted with DCM three times. The organic phase was combined and dried over Na$_2$SO4. Flash chromatography with PE:EtOAc=10:1 gave compound 5-chloro-1-(tetrahydro-2H-pyran-2-yl)-6-(4,4,5,5-tetramethyl-1,3,2-dioxaborolan-2-yl)-1H-indazole as a yellow solid (220 mg, yield 48%).

D537 $^1$H NMR (400 MHz, CDCl$_3$) δ 7.96 (s, 1H), 7.89 (s, 1H), 7.71 (s, 1H), 5.75 (d, J=9.1 Hz, 1H), 4.01 (m, 1H), 3.77 (t, J=10.6 Hz, 1H), 2.57 (d, J=11.1 Hz, 1H), 2.16 (s, 1H), 2.03 (d, J=11.6 Hz, 1H), 1.88-1.54 (m, 3H), 1.41 (s, 12H).

Description D538

5-Chloro-1-(tetrahydro-2H-pyran-2-yl)-1H-indazol-6-ol (D538)

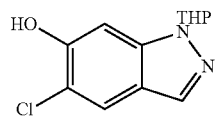

To a solution of 5-chloro-1-(tetrahydro-2H-pyran-2-yl)-6-(4,4,5,5-tetramethyl-1,3,2-dioxaborolan-2-yl)-1H-indazole (220 mg, 0.6 mmol) in THF (2 mL) and 1N NaOH solution (1 mL) was added 30% H$_2$O$_2$ (0.2 g) at 0° C. After a few minutes the mixture was diluted with H$_2$O and extracted with DCM three times. The combined organic payer were dried over anhydrous Na$_2$SO$_4$ and concentrated under reduced pressure. The residue was purified by silica gel chromatography (eluted with PE/EtOAc=2:1) to give product (141 mg, yield 91.0%) as a white solid.

D538 $^1$H NMR (400 MHz, CDCl$_3$) δ 7.89 (s, 1H), 7.69 (s, 1H), 7.20 (s, 1H), 5.80 (s, 1H), 5.60 (dd, J=9.3, 2.1 Hz, 1H), 4.03 (d, J=11.8 Hz, 1H), 3.73 (t, J=9.5 Hz, 1H), 2.66-2.41 (m, 1H), 2.18-1.91 (m, 2H), 1.93-1.45 (m, 4H).

Description D539

5-Chloro-6-isopropoxy-1-(tetrahydro-2H-pyran-2-yl)-1H-indazole (D539)

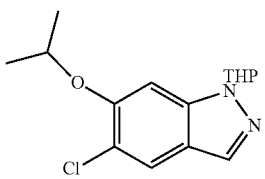

To a solution of 5-chloro-1-(tetrahydro-2H-pyran-2-yl)-1H-indazol-6-ol (141 mg, 0.56 mmol) and K$_2$CO$_3$ (154 mg, 1.12 mmol) in DMF (2 mL) was added 2-bromopropane (103 mg, 0.84 mmol) at rt. The resulting mixture was stirred at rt. over night. 10 mL H$_2$O was added and extracted with EtOAc three times. The combined organic payer were dried over anhydrous Na$_2$SO$_4$ and concentrated under reduced pressure. The residue was purified by silica gel chromatography (eluted with PE/EtOAc=6:1) to give product (140 mg, yield 95.7%) as yellow oil.

D539 LC-MS (mobile phase: mobile phase: from 90% water (0.1% FA) and 10% CH$_3$CN (0.1% FA) to 5% water (0.1% FA) and 95% CH$_3$CN (0.1% FA) in 2.0 min, Rt=1.31 min; MS Calcd.: 294.1, MS Found: 295.1 [M+H]$^+$.

Description D540

5-Chloro-6-isopropoxy-1H-indazole (D540)

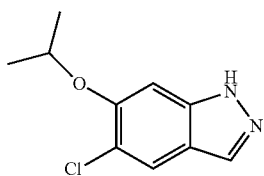

To a solution of 5-chloro-6-isopropoxy-1-(tetrahydro-2H-pyran-2-yl)-1H-indazole (140 mg, 0.47 mmol) in MeOH (1.0 mL) was added HCl/MeOH (3M, 2 mL) drop-wise at 0° C. The reaction was stirred at room temperature overnight. Solvent and most of TFA was removed in vacuum and the residue was diluted with $CH_2Cl_2$ (20 mL). The resulting solution was washed with sat. $NaHCO_3$ (10 mL) and brine (20 mL), dried over anhydrous $Na_2SO_4$ and concentrated under reduced pressure to give the crude product 5-chloro-6-isopropoxy-1H-indazole (90 mg, yield 89.9%) as a white solid.

D540 $^1$H NMR (400 MHz, DMSO) δ 7.99 (s, 1H), 7.89 (s, 1H), 7.18 (s, 1H), 4.78 (dt, J=11.9, 6.0 Hz, 2H), 4.53 (br, 1H), 1.40 (d, J=6.0 Hz, 6H).

Description D541

5-Chloro-6-isopropoxy-1-(2-methyl-6-(3-((tetrahydro-2H-pyran-2-yl)oxy)azetidin-1-yl)pyrimidin-4-yl)-1H-indazole (D541)

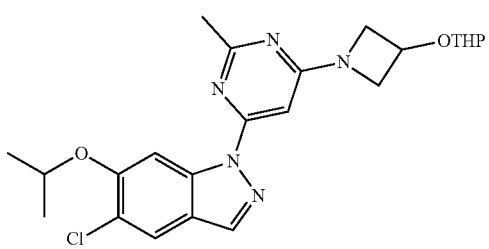

To a suspension of 5-chloro-6-isopropoxy-1H-indazole (90 mg, 0.428 mmol), 4-iodo-2-methyl-6-(3-((tetrahydro-2H-pyran-2-yl)oxy)azetidin-1-yl)pyrimidine (160 mg, 0.428 mmol), CuI (81 mg, 0.43 mmol) and $K_3PO_4$ (181 mg, 0.856 mmol) in dry toluene (2 mL) was added N,N-dimethyl-1,2-ethanediamine (46 mg, 0.856 mmol). The suspension was degassed with $N_2$ and refluxed for 2 h. The solvent was removed under vacuum and the residue was purified by silica gel chromatography (eluted with PE/EtOAc=3:1) to give product (72 mg, yield 37%) as a white solid.

D541 $^1$H NMR (400 MHz, $CDCl_3$) δ 8.60 (s, 1H), 8.02 (s, 1H), 7.70 (s, 1H), 6.60 (s, 1H), 4.89-4.52 (m, 3H), 4.37 (dd, J=15.7, 8.1 Hz, 2H), 4.09 (m, 2H), 3.89 (t, J=9.5 Hz, 1H), 3.62-3.36 (m, 1H), 2.58 (s, 3H), 1.92-1.70 (m, 2H), 1.68-1.53 (m, 5H), 1.50 (d, J=6.0 Hz, 6H).

Description D542

6-Bromo-5-methyl-1-(2-methyl-6-(3-((tetrahydro-2H-pyran-2-yl)oxy)azetidin-1-yl)pyrimidin-4-yl)-1H-indazole (D542)

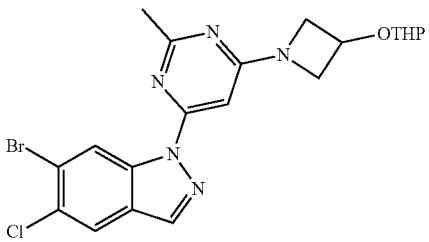

To a 100 ml round bottle charged with the 4-iodo-2-methyl-6-(3-((tetrahydro-2H-pyran-2-yl)oxy) azetidin-1-yl) pyrimidine (1.778 g, 4.74 mmol) were added 6-bromo-5-methyl-1H-indazole (1 g, 4.74 mmol), N1,N2-dimethylcyclohexane-1,2-diamine (0.747 mL, 4.74 mmol) and copper(I) iodide (0.902 g, 4.74 mmol). Subsequently, potassium phosphate (1.006 g, 4.74 mmol) and Toluene (20 mL) were added under the nitrogen atmosphere. The mixture was then stirred at 120° C. overnight under nitrogen atmosphere. The mixture was cooled to room temperature, EtOAc (20 mL) and water (10 mL) were added and the layers were separated. The aqueous layer was extracted by EtOAc (30 mL). The combined organic layers was washed with saturated aqueous NaCl (50 mL), dried over anhydrous $Na_2SO_4$ and then concentrated under the reduced pressure. The residue was purified by normal phase chromatography (PE:EtOAc=100:0→50:50) to afford 6-bromo-5-methyl-1-(2-methyl-6-(3-((tetrahydro-2H-pyran-2-yl)oxy)azetidin-1-yl) pyrimidin-4-yl)-1H-indazole (1.29 g, 1.689 mmol, 35.6% yield) as a yellow solid.

D542 LC-MS (mobile phase: from 95% water (0.1% TFA) and 5% $CH_3CN$ (0.1% TFA) to 5% water (0.1% TFA) and 95% $CH_3CN$ (0.1% TFA) in 5 min, Rt=3.805 min; MS Calcd.: 458.1 MS Found: 458.0 (M+H)$^+$.

Description D543

(3R)-1-(5-methyl-1-(2-methyl-6-(3-((tetrahydro-2H-pyran-2-yl)oxy)azetidin-1-yl)pyrimidin-4-yl)-1H-indazol-6-yl)pyrrolidin-3-ol (D543)

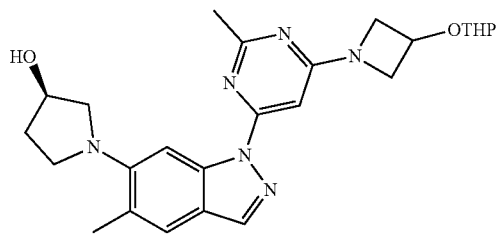

To a solution of (R)-pyrrolidin-3-ol (0.013 mL, 0.159 mmol) in THF (10 mL) was added dicyclohexyl(2',6'-diisopropoxy-[1,1'diisopropoxy-[1,1'osphine (RuPhos) (29.7 mg, 0.064 mmol), 6-bromo-5-methyl-1-(2-methyl-6-(3-((tetrahydro-2H-pyran-2-yl)oxy)azetidin-1-yl)pyrimidin-4-yl)-

1H-indazole (73 mg, 0.159 mmol), diacetoxypalladium (7.15 mg, 0.032 mmol) and sodium 2-methylpropan-2-olate (0.159 mL, 0.319 mmol). The mixture was stirred at 70° C. under nitrogen atmosphere for 3 hrs. The reaction mixture was cooled down to room temperature and then water (20 mL) and EtOAc (50 mL) were added to the mixture. The layers were separated and the aqueous layer was extracted by EtOAc (40 mL). The combined organic layers were washed with brine (40 mL), dried over anhydrous $Na_2SO_4$ and then concentrated under the reduced pressure. The residue was purified by reverse phase chromatography (KP-C18-HS 60 g column, $ACN:H_2O$=5:95→95:5) to afford the desired product (3R)-1-(5-methyl-1-(2-methyl-6-(3-((tetrahydro-2H-pyran-2-yl)oxy) azetidin-1-yl)pyrimidin-4-yl)-1H-indazol-6-yl)pyrrolidin-3-ol (20 mg, 0.043 mmol, 27.0% yield) as a colorless gel.

D543 LC-MS (mobile phase: from 95% water (0.1% TFA) and 5% $CH_3CN$ (0.1% TFA) to 5% water (0.1% TFA) and 95% $CH_3CN$ (0.1% TFA) in 5 min, Rt=2.666 min; MS Calcd.: 465.2 MS Found: 465.0 $(M+H)^+$.

Description D544

(3S)-1-(5-Methyl-1-(2-methyl-6-(3-((tetrahydro-2H-pyran-2-yl)oxy)azetidin-1-yl)pyrimidin-4-yl)-1H-indazol-6-yl)pyrrolidin-3-ol (D544)

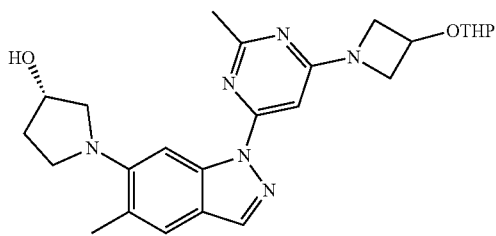

To a solution of (S)-pyrrolidin-3-ol (0.053 mL, 0.655 mmol) in THF (10 mL) was added dicyclohexyl (2',6'-diisopropoxy-[1,1'-biphenyl]-2-yl)phosphine (RuPhos) (122 mg, 0.262 mmol), 6-bromo-5-methyl-1-(2-methyl-6-(3-((tetrahydro-2H-pyran-2-yl)oxy)azetidin-1-yl) pyrimidin-4-yl)-1H-indazole (300 mg, 0.655 mmol), diacetoxypalladium (29.4 mg, 0.131 mmol) and sodium 2-methylpropan-2-olate (0.655 mL, 1.309 mmol). The mixture was stirred at 70° C. under nitrogen atmosphere for 3 hrs. The reaction mixture was cooled down to room temperature and then water (40 mL) and EtOAc (100 mL) were added to the mixture. The layers were separated and the aqueous layer was extracted by EtOAc (60 mL). The combined organic layers were washed with brine (40 mL), dried over anhydrous $Na_2SO_4$ and then concentrated under the reduced pressure. The residue was purified by normal phase chromatography (EA:PE=5:95→95:5) to afford the desired product (3S)-1-(5-methyl-1-(2-methyl-6-(3-((tetrahydro-2H-pyran-2-yl)oxy) azetidin-1-yl)pyrimidin-4-yl)-1H-indazol-6-yl)pyrrolidin-3-ol (124 mg, 0.267 mmol, 40.8% yield) as a colorless gel.

D544 LC-MS (mobile phase: from 95% water (0.1% TFA) and 5% $CH_3CN$ (0.1% TFA) to 5% water (0.1% TFA) and 95% $CH_3CN$ (0.1% TFA) in 5 min, Rt=2.773 min; MS Calcd.: 465.2 MS Found: 465.1 $(M+H)^+$.

Description D545

8-(5-Chloro-1-(tetrahydro-2H-pyran-2-yl)-1H-indazol-6-yl)-1,4-dioxa-8-azaspiro[4.5]decane (D545)

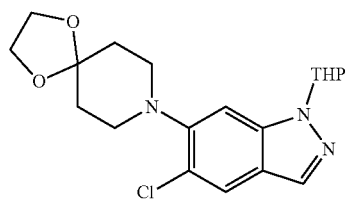

To a solution of 6-bromo-5-chloro-1-(tetrahydro-2H-pyran-2-yl)-1H-indazole (900 mg, 2.85 mmol) and 1,4-dioxa-8-azaspiro[4.5]decane (1.21 g, 8.56 mmol) in toluene (30 mL) was added $^tBuONa$ (1.28 g, 13.3 mmol), XPhos (270 mg, 0.56 mmol), and $Pd_2(dba)_3$ (270 mg, 0.29 mmol) under $N_2$ atmosphere. The mixture was stirred at 45° C. for 6 hr. The reactive solution was diluted with EtOAc (60 mL) and filtered through a pad of Celite. The filtrate was concentrated and purified with silica gel chromotograph to obtain 8-(5-chloro-1-(tetrahydro-2H-pyran-2-yl)-1H-indazol-6-yl)-1,4-dioxa-8-azaspiro[4.5]decane as a light yellow solid (390 mg, 36%).

D545 $^1H$ NMR (400 MHz, $CDCl_3$): δ 7.87 (s, 1H), 7.71 (s, 1H), 7.18 (s, 1H), 5.63-5.61 (d, 1H), 4.03 (s, 4H), 3.75-3.71 (t, 1H), 3.19 (s, 4H), 2.54-2.51 (q, 1H), 2.17-2.14 (m, 1H), 2.07-2.04 (d, 1H), 1.97-1.95 (t, 3H), 1.78-1.75 (m, 4H), 1.73-1.70 (m, 1H), 1.16-1.14 (m, 1H).

Description D546

1-(5-Chloro-1H-indazol-6-yl)piperidin-4-one (D546)

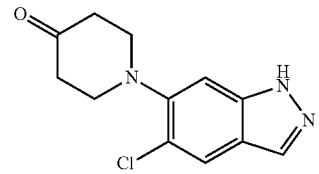 [SMILES: O=C1CCN(c2cc3[nH]ncc3cc2Cl)CC1]

To a solution of 8-(5-chloro-1-(tetrahydro-2H-pyran-2-yl)-1H-indazol-6-yl)-1,4-dioxa-8-azaspiro[4.5]decane (390 mg, 1.03 mmol) in dioxane (5 mL) was added HCl solution (3M, in water, 5 mL). The mixture was stirred at 50° C. for 4 hr. The reactive solution was cooled down to room temperature and then quenched with saturated $Na_2CO_3$ solution. The mixture was extracted with EtOAc (50 mL×3). The combined organic layers were dried over $Na_2SO_4$, concentrated and purified with prep-TLC (DCM/MeOH, 10/1) to get the title product, 1-(5-chloro-1H-indazol-6-yl)piperidin-4-one as a light yellow solid (100 mg, 38.8%).

D546 MS Calcd.: 249.0, MS Found: 250.0 $(M+H)^+$.

Description D547

1-(5-Chloro-1-(2-methyl-6-(3-((tetrahydro-2H-pyran-2-yl)oxy)azetidin-1-yl)pyrimidin-4-yl)-1H-indazol-6-yl)piperidin-4-one (D547)

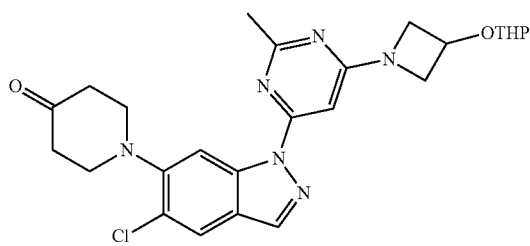

To a solution of 1-(5-chloro-1H-indazol-6-yl)piperidin-4-one (100 mg, 0.40 mmol)(100 mg, 0.40 mmol), 4-iodo-2-methyl-6-(3-((tetrahydro-2H-pyran-2-yl)oxy)azetidin-1-yl)pyrimidine (165.3 mg, 0.44 mmol), CuI (114 mg, 0.60 mmol), $K_3PO_4$ (170.4 mg, 0.80 mmol), N1,N2-dimethylethane-1,2-diamine (70.0 mg, 0.80 mmol) in toluene (5 mL) was stirred at 100° C. for 4 h. Then, the mixture was cooled down to rt. The organic phase was diluted with EtOAc (20 mL) and filtered through a pad of celite. The filtrate was concentrated to obtain the crude. The crude was re-dissolved in DCM (5 mL) and further purified with prep-TLC (DCM/MeOH, 20/1) to get 1-(5-chloro-1-(2-methyl-6-(3-((tetrahydro-2H-pyran-2-yl)oxy)azetidin-1-yl)pyrimidin-4-yl)-1H-indazol-6-yl)piperidin-4-one as a white solid (130 mg) and used directly in the next step.

Description D548

1-(5-Chloro-1-(6-(3-hydroxyazetidin-1-yl)-2-methylpyrimidin-4-yl)-1H-indazol-6-yl)piperidin-4-one (D548)

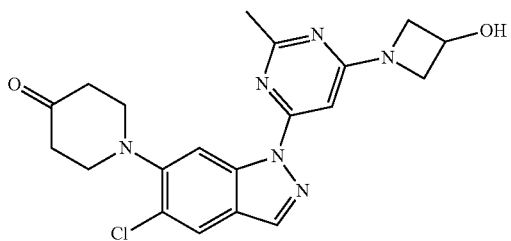 [SMILES: Cc1nc(N2CC(O)C2)cc(-n2ncc3cc(Cl)c(N4CCC(=O)CC4)cc32)n1]

To a solution of 1-(5-chloro-1-(2-methyl-6-(3-((tetrahydro-2H-pyran-2-yl)oxy)azetidin-1-yl)pyrimidin-4-yl)-1H-indazol-6-yl)piperidin-4-one (130 mg, 0.26 mmol) in THF (5 mL) was added 2M HCl (5 mL, water solution). The mixture was stirred at 50° C. for 4 hr. The reactive solution was cooled down to room temperature and quenched with saturated $Na_2CO_3$. The mixture was extracted with EtOAc (50 mL×3). The combined organic layer was dried over $Na_2SO_4$, concentrated and then purified with prep-TLC (DCM/MeOH, 10/1) to get the title product 1-(5-chloro-1-(6-(3-hydroxyazetidin-1-yl)-2-methylpyrimidin-4-yl)-1H-indazol-6-yl)piperidin-4-one as a white solid (95 mg, yield 88%)

D548 $^1$H NMR (400 MHz, CDCl3): δ 8.70 (s, 1H), 8.09 (s, 1H), 7.78 (s, 1H), 6.61 (s, 1H), 4.85-4.84 (s, 1H), 4.44-4.40 (t, 2H), 4.03-4.00 (t, 2H), 3.49-3.46 (t, 2H), 2.73-2.70 (t, 2H), 2.59-2.56 (s, 3H).

Description D549

6-(3,6-Dihydro-2H-pyran-4-yl)-5-methyl-1H-indazole (D549)

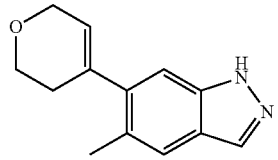 [SMILES: Cc1cc2cn[nH]c2cc1C1=CCOCC1]

To a solution of 6-(3,6-dihydro-2H-pyran-4-yl)-5-methyl-1-(tetrahydro-2H-pyran-2-yl)-1H-indazole (400 mg, 1.341 mmol) in methanol (30 mL) was added HCl (0.335 mL, 4.02 mmol) and the solution was stirred at 40° C. for 1 hr. The solvent was removed and the residue was used in next steps without further purification.

D549 LCMS: (mobile phase: 5-95% acetonitrile), Rt=2.735 min in 5 min; MS Calcd: 214; MS Found: 215.1 $(M+1)^+$.

Description D550

1-(6-Chloro-2-methylpyrimidin-4-yl)-6-(3,6-dihydro-2H-pyran-4-yl)-5-methyl-1H-indazole (D550)

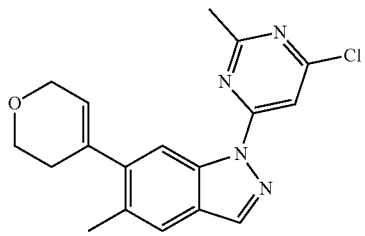 [SMILES: Cc1nc(Cl)cc(-n2ncc3cc(C)c(C4=CCOCC4)cc32)n1]

To a solution of 6-(3,6-dihydro-2H-pyran-4-yl)-5-methyl-1H-indazole (287 mg, 1.339 mmol) and 4,6-dichloro-2-methylpyrimidine (240 mg, 1.473 mmol) in DMF (20 mL) was added $K_2CO_3$ (370 mg, 2.68 mmol). The mixture was stirred at 90° C. for 1 hr under microwave irradiation. Water (100 mL) and EtOAc (100 mL) were added to the reaction mixture. The layers were separated and the aqueous layer was extracted by EtOAc (50 mL×3 time). The combined organic layers was washed with saturated aqueous NaCl (50 mL×2 times), dried over anhydrous Na2SO4 and then concentrated. The residue was purified by normal phase chromatography (Biotage, 120 g column, EtOAc:PE=5:95→60:40) to afford 1-(6-chloro-2-methylpyrimidin-4-yl)-6-(3,6-dihydro-2H-pyran-4-yl)-5-methyl-1H-indazole (100 mg, 0.264 mmol, 19.72% yield) as a white solid.

D550 LCMS: (mobile phase: 5-95% acetonitrile), Rt=4.352 min in 5 min; MS Calcd: 340; MS Found: 341.0 $(M+1)^+$.

Description D551 tert-Butyl 4-(6-(6-(3,6-dihydro-2H-pyran-4-yl)-5-methyl-1H-indazol-1-yl)-2-methylpyrimidin-4-yl)-5,6-dihydropyridine-1(2H)-carboxylate (D551)

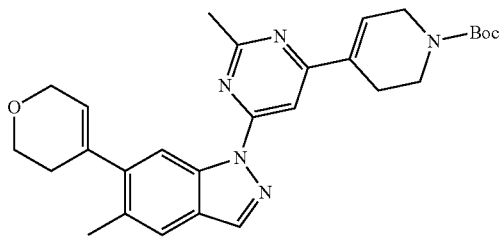 [SMILES: Cc1nc(C2=CCN(C(=O)OC(C)(C)C)CC2)cc(-n2ncc3cc(C)c(C4=CCOCC4)cc32)n1]

To a solution tert-butyl 4-(4,4,5,5-tetramethyl-1,3,2-dioxaborolan-2-yl)-5,6-dihydropyridine-1(2H)-carboxylate (91 mg, 0.293 mmol) in 1,4-dioxane (10 mL)/water (1.0 mL) were added 1-(6-chloro-2-methylpyrimidin-4-yl)-6-(3,6-dihydro-2H-pyran-4-yl)-5-methyl-1H-indazole (100 mg, 0.293 mmol), PdCl$_2$(dppf) (21.47 mg, 0.029 mmol) and K$_2$CO$_3$ (81 mg, 0.587 mmol). The mixture was stirred at 90° C. for 2 hrs under nitrogen atmosphere. Water (200 mL) and EtOAc (200 mL) were added to the reaction mixture. The layers were separated and the aqueous layer was extracted by EtOAc (50 mL). The combined organic layers was washed with saturated aqueous NaCl (50 mL×2 times), dried over anhydrous Na$_2$SO$_4$ and then concentrated. The residue was purified by normal phase chromatography (Biotage, 120 g column, EtOAc:PE=5:95→60:40) to afford the product (53 mg).

D551 LCMS: (mobile phase: 5-95% acetonitrile), Rt=2.720 min in 5 min; MS Calcd: 487; MS Found: 488.0 (M+1)$^+$.

Description D552

6-(3,6-Dihydro-2H-pyran-4-yl)-5-methyl-1-(2-methyl-6-(1,2,3,6-tetrahydropyridin-4-yl)pyrimidin-4-yl)-1H-indazole (D552)

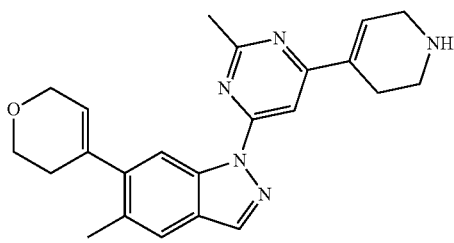 [SMILES: Cc1nc(C2=CCNCC2)cc(-n2ncc3cc(C)c(C4=CCOCC4)cc32)n1]

To a solution tert-butyl 4-(6-(6-(3,6-dihydro-2H-pyran-4-yl)-5-methyl-1H-indazol-1-yl)-2-methylpyrimidin-4-yl)-5,6-dihydropyridine-1(2H)-carboxylate (53 mg, 0.109 mmol) in DCM (10 mL) was added TFA (100 µl, 1.298 mmol). The solution was stirred at rt overnight. The solvent was removed under reduced pressure. The residue (42.1 mg) was used in next steps without further purification.

D552 LCMS: (mobile phase: 5-95% Acetonitrile), Rt=2.800 min in 5 min; MS Calcd: 387; MS Found: 388.1 (M+1)$^+$.

Description D553

6-(3,6-Dihydro-2H-pyran-4-yl)-5-methyl-1-(2-methyl-6-(1-(oxetan-3-yl)-1,2,3,6-tetrahydropyridin-4-yl)pyrimidin-4-yl)-1H-indazole (D553)

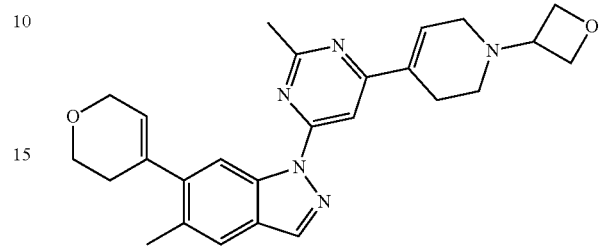

To a solution of 6-(3,6-dihydro-2H-pyran-4-yl)-5-methyl-1-(2-methyl-6-(1,2,3,6-tetrahydropyridin-4-yl)pyrimidin-4-yl)-1H-indazole (42 mg, 0.108 mmol) in DMF (5 mL) was added oxetan-3-one (15.62 mg, 0.217 mmol) and NaBH(OAc)$_3$ (45.9 mg, 0.217 mmol). The solution was stirred at rt for 1 hr. Water (100 mL) and EtOAc (100 mL) were added to the reaction mixture. The layers were separated and the aqueous layer was extracted by EtOAc (50 mL). The combined organic layers was washed with saturated aqueous NaCl (50 mL×3 times), dried over anhydrous Na$_2$SO$_4$ and then concentrated. The residue (42 mg) was used in next steps without further purification.

D553 LCMS: (mobile phase: 5-95% acetonitrile), Rt=2.794 min in 5 min; MS Calcd: 443; MS Found: 444.0 (M+1)$^+$.

Description D554

1-(2-Methoxy-6-(5-methyl-6-(1-(oxetan-3-yl)piperidin-4-yl)-1H-indazol-1-yl)pyrimidin-4-yl)pyrrolidin-3-one (D554)

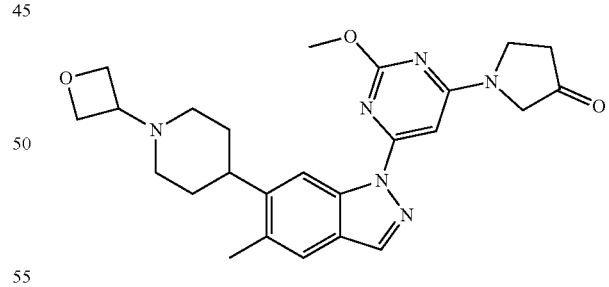

To a mixture of (S)-1-(2-methoxy-6-(5-methyl-6-(1-(oxetan-3-yl)piperidin-4-yl)-1H-indazol-1-yl)pyrimidin-4-yl)pyrrolidin-3-ol (220 mg, 0.47 mmol) in DCM (30 mL) was added DMP (402 mg, 0.94 mmol), then the mixture was stirred at rt for 12 h. The solvent was removed, and the residue was purified by column to give a solid. (106 mg; 49% yield).

D554 LC-MS [mobile phase: from 30% water (0.1% FA) and 70% CH$_3$CN (0.1% FA) to 30% water (0.1% FA) and 70% CH$_3$CN (0.1% FA) in 2 min]. MS Calcd: 462.24, MS Found: 463.4[M+H]$^+$, Rt=1.52 min

Description D555

1-(2-Methoxy-6-(5-methyl-6-(1-(oxetan-3-yl)piperidin-4-yl)-1H-indazol-1-yl)pyrimidin-4-yl)-3-methylpyrrolidin-3-ol (D555)

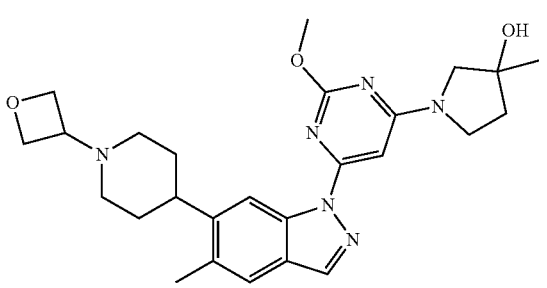 [SMILES: COc1nc(N2CCC(C)(O)C2)cc(-n2ncc3cc(C)c(C4CCN(C5COC5)CC4)cc32)n1]

To a suspension of 1-(2-methoxy-6-(5-methyl-6-(1-(oxetan-3-yl)piperidin-4-yl)-1H-indazol-1-yl)pyrimidin-4-yl)pyrrolidin-3-one (106 mg, 0.23 mmol) in THF (20 mL) was added MeMgBr (0.345 mmol) at 0° C. Then warmed to rt for 4 h. Water was added, and extracted with EtOAc. The organics were washed with brine, concentrated, and the residue was purified by silica gel chromatography to give a white solid (65 mg, yield 59%)

D555 $^1$H NMR (400 MHz, CDCl$_3$) δ 8.78 (s, 1H), 8.06 (s, 1H), 7.50 (s, 1H), 6.60 (s, 1H), 4.69 (d, J=6.0 Hz, 4H), 4.15 (s, 3H), 3.48-3.77 (m, 5H), 2.92-2.95 (m, 3H); 2.45 (s, 3H); 1.91-2.03 (m, 8H), 1.51 (s, 3H).

Description D556 tert-Butyl 2-(methoxy(methyl)carbamoyl)morpholine-4-carboxylate (D556)

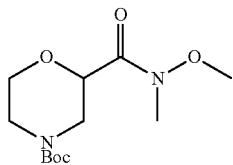 [SMILES: CON(C)C(=O)C1CN(C(=O)OC(C)(C)C)CCO1]

DIEA (2.79 g, 21.6 mmol) was added to a solution of 4-(tert-butoxycarbonyl)morpholine-2-carboxylic acid (1.0 g, 4.3 mmol), N,O-dimethylhydroxylamine hydrochloride (1.26 g, 13.0 mmol) and HATU (1.81 g, 4.8 mmol) in DMF (10 mL). The reaction was stirred at r.t for 2 h. The mixture was added in water (10 mL) and extracted with EtOAc (15 mL×3). The combine layers were washed with 1N HCl (10 mL), 1N NaOH (10 mL×3), water (10 mL×2) and brine (10 mL), dried over Na$_2$SO$_4$, and then evaporated to get a light yellow oil (1.03 g, yield: 86.8%).

D556 $^1$H NMR (400 MHz, CDCl3): δ 4.34 (s, 1H), 4.15-4.00 (m, 2H), 3.87, 3.87 (d, J=2 Hz, 1H), 3.76 (s, 3H), 3.62, 3.59, 3.59, 3.57 (dd, J$_1$=10 Hz, J$_2$=1.6 Hz, 1H), 3.22 (s, 3H), 3.06, 3.06 (d, J=1.2 Hz, 2H), 1.47 (s, 9H).

Description D557 tert-Butyl 2-acetylmorpholine-4-carboxylate (D557)

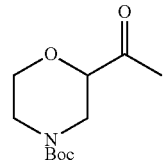 [SMILES: CC(=O)C1CN(C(=O)OC(C)(C)C)CCO1]

EtMgBr (1.79 mL, 5.36 mmol) was added to a solution of tert-butyl 2-(methoxy(methyl)carbamoyl)morpholine-4-carboxylate (980 mg, 3.57 mmol) in THF (20 mL) under Ar at 0° C. The reaction was stirred at r.t for overnight. The mixture was added in NH$_4$Cl aqueous solution (2 mL) and extracted with EtOAc (50 mL), washed with water and brine, and dried over Na$_2$SO$_4$. Purified by column (PE:EtOAc=10:1 to 2:1) to get colourless oil (528 mg, yield: 64.5%)

D557 $^1$H NMR (400 MHz, CDCl$_3$) δ 4.15 (s, 1H), 3.97 (d, J=10.9 Hz, 1H), 3.85 (s, 2H), 3.57 (s, 1H), 2.96 (s, 1H), 2.80 (t, J=11.7 Hz, 1H), 2.24 (s, 3H), 1.47 (s, 9H).

Description D558

1-(Morpholin-2-yl)ethanone hydrochloride (D558)

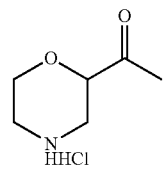

HCl/EtOAc (3M, 10 mL) was added to a solution of tert-butyl 2-acetylmorpholine-4-carboxylate (1.5 g, 6.5 mmol) in EtOAc (40 mL) at 0° C. The reaction was stirred at r.t for overnight. Removed the solvent to got a crude yellow solid (0.9 g, yield: 95%).

D558 LC-MS (mobile phase: from 70% water (0.1% FA) and 30% CH$_3$CN (0.1% FA), Rt=0.28 min; MS Calcd.: 129.08; MS Found: 130.0 [M+H]$^+$.

Description D559

1-(4-(6-Iodo-2-methylpyrimidin-4-yl)morpholin-2-yl)ethanone (D559)

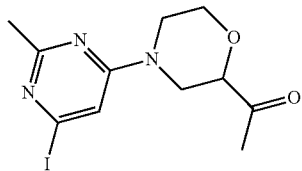 [SMILES: CC(=O)C1CN(c2cc(I)nc(C)n2)CCO1]

DIEA (469 mg, 3.6 mmol) was added to a solution of 1-(morpholin-2-yl)ethanone hydrochloride (200 mg, 1.2 mmol) and 4,6-diiodo-2-methylpyrimidine (628 mg, 1.82 mmol) in EtOH/THF (20 mL/20 mL). The reaction was stirred at 40° C. under Ar for 4 hr. The solvent was removed and the water (20 mL) was added to the mixture. Extracted with EtOAc (100 mL), washed with H$_2$O (20 mL) and brine (20 mL). Purified by column (PE:EtOAc=6:1 to 2:1) to gave a white solid (260 mg, yield: 62.1%)

D559 LC-MS (mobile phase: from 60% water (0.1% FA) and 40% CH$_3$CN (0.1% FA), Rt=0.47 min; MS Calcd.: 347.01; MS Found: 348.0 [M+H]$^+$.

Description D560

1-(4-(2-Methyl-6-(5-methyl-6-(1-(oxetan-3-yl)piperidin-4-yl)-1H-indazol-1-yl)pyrimidin-4-yl)morpholin-2-yl)ethanone (D560)

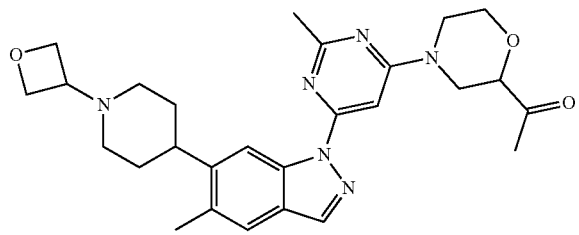 [SMILES: CC(=O)C1CN(c2cc(-n3ncc4cc(C)c(C5CCN(C6COC6)CC5)cc43)nc(C)n2)CCO1]

N,N'-dimethylethylenediamine (145 mg, 1.65 mmol) was added to a solution of 1-(4-(6-iodo-2-methylpyrimidin-4-yl)morpholin-2-yl)ethanone (287 mg, 0.83 mmol), 5-methyl-6-(1-(oxetan-3-yl)piperidin-4-yl)-1H-indazole (224 mg, 0.83 mmol), CuI (157 mg, 0.83 mmol) and K$_3$PO$_4$ (350 mg, 1.65 mmol) in toluene (10 mL). The mixture was stirred at 100° C. for 4 h. The solvent was removed and purified by column (DCM:MeOH=50:1) to gave product as a white solid (187 mg, yield: 46.1%).

D560 LC-MS (mobile phase: from 80% water (0.1% FA) and 20% CH$_3$CN (0.1% FA), Rt=1.20 min; MS Calcd.: 490.6; MS Found: 491.5 [M+H]$^+$.

Description D561

1-(4-(2-Methyl-6-(5-methyl-6-(1-(oxetan-3-yl)piperidin-4-yl)-1H-indazol-1-yl)pyrimidin-4-yl)morpholin-2-yl)ethanol (D561)

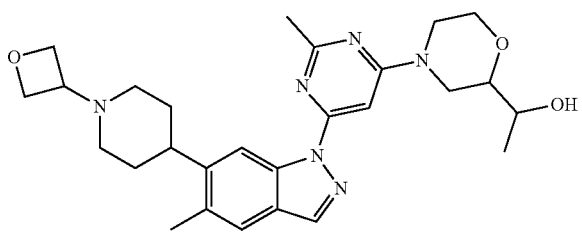 [SMILES: Cc1nc(N2CCOC(C(C)O)C2)cc(-n2ncc3cc(C)c(C4CCN(C5COC5)CC4)cc32)n1]

NaBH$_4$ (36 mg, 0.57 mmol) was added to a solution of 1-(4-(2-methyl-6-(5-methyl-6-(1-(oxetan-3-yl)piperidin-4-yl)-1H-indazol-1-yl)pyrimidin-4-yl)morpholin-2-yl)ethanone (187 mg, 0.38 mmol) in MeOH (5 mL). The mixture was added in water (10 mL) and extracted with DCM (20 mL×2). Then, the reaction mixture was washed with water (10 mL) and brine (10 mL). It was then dried over Na$_2$SO$_4$. Purified by column (DCM:MeOH=50:1) to give product as a white solid (122 mg, yield: 65%).

D561 LC-MS (mobile phase: from 80% water (0.1% FA) and 20% CH$_3$CN (0.1% FA), Rt=4.97 min, Rt=5.12 min; MS Calcd.: 492.6; MS Found: 493.4 [M+H]$^+$.

Description D562

1-(4-(6-Iodo-2-methoxypyrimidin-4-yl)morpholin-2-yl)ethanone (D562)

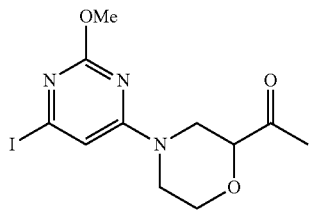 [SMILES: COc1nc(I)cc(N2CCOC(C(C)=O)C2)n1]

DIEA (1.2 g, 9.06 mmol) was added to a solution of 1-(morpholin-2-yl)ethanone hydrochloride (500 mg, 3.02 mmol), 4,6-diiodo-2-methoxypyrimidine (1.3 g, 3.63 mmol) in EtOH/THF (10 mL/10 mL). The mixture was stirred at r.t for 36 h. After the solvent is removed, the mixture was purified by column (PE:EtOAC=5:1) to give product as a white solid (990 mg, yield: 90.3%).

D562 LC-MS (mobile phase: from 60% water (0.1% FA) and 40% CH$_3$CN (0.1% FA), Rt=0.58 min; MS Calcd.: 363.2; MS Found: 364.1 [M+H]$^+$.

Description D563

1-(4-(2-Methoxy-6-(5-methyl-6-(1-(oxetan-3-yl)piperidin-4-yl)-1H-indazol-1-yl)pyrimidin-4-yl)morpholin-2-yl)ethanone (D563)

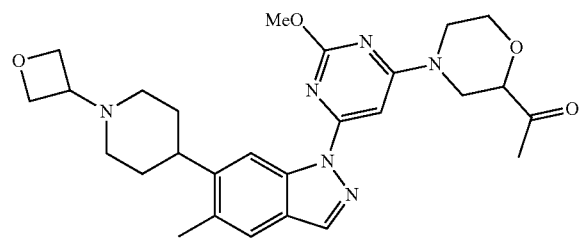 [SMILES: COc1nc(N2CCOC(C(C)=O)C2)cc(-n2ncc3cc(C)c(C4CCN(C5COC5)CC4)cc32)n1]

DMEDA (456 mg, 5.17 mmol) was added to a solution of 1-(4-(6-iodo-2-methoxypyrimidin-4-yl)morpholin-2-yl) ethanone (6990 mg, 2.59 mmol), 5-methyl-6-(1-(oxetan-3-yl)piperidin-4-yl)-1H-indazole (701 mg, 2.59 mmol), CuI (492 mg, 2.59 mmol) and K$_3$PO$_4$ (1097 mg, 5.17 mmol) in toluene (10 mL). The mixture was stirred at 100° C. for 5 h. The solvent was removed and purified by column (DCM:MeOH=50:1) to give product as a white solid (250 mg, yield: 19.1%).

D563 LC-MS (mobile phase: from 80% water (0.1% FA) and 20% CH$_3$CN (0.1% FA), Rt=1.12 min; MS Calcd.: 506.6; MS Found: 507.4 [M+H]$^+$.

345
Description D564

1-(4-(2-Methoxy-6-(5-methyl-6-(1-(oxetan-3-yl)piperidin-4-yl)-1H-indazol-1-yl)pyrimidin-4-yl)morpholin-2-yl)ethanol (D564)

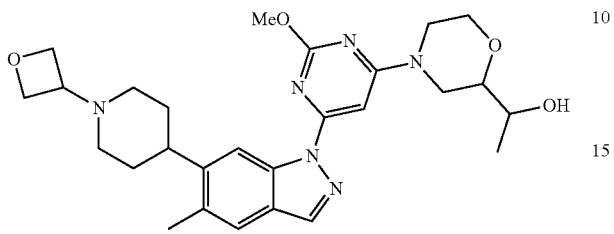

NaBH$_4$ (47 mg, 0.74 mmol) was added to a solution of 1-(4-(2-methoxy-6-(5-methyl-6-(1-(oxetan-3-yl)piperidin-4-yl)-1H-indazol-1-yl)pyrimidin-4-yl)morpholin-2-yl)ethanol (250 mg, 0.49 mmol) in MeOH (10 mL). The mixture was added in water (10 mL) and extracted with DCM (20 mL×2). The reaction mixture was washed with water (10 mL) and brine (10 mL). It was then dried over Na$_2$SO$_4$. The reaction mixture was purified by Pre-plate to give product as a white solid (150 mg, yield: 59.8%).

D564 LC-MS (mobile phase: from 80% water (0.1% FA) and 20% CH$_3$CN (0.1% FA), Rt=99 min; MS Calcd.: 508.6; MS Found: 509.5 [M+H]$^+$.

Description D565 tert-Butyl 4-(5-methyl-1H-indazol-6-yl)piperidine-1-carboxylate (D565)

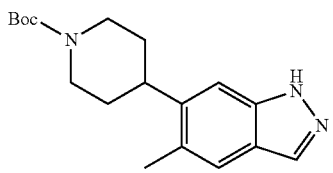 [SMILES: Cc1cc2cn[nH]c2cc1C1CCN(C(=O)OC(C)(C)C)CC1]

To a solution of 5-methyl-6-(piperidin-4-yl)-1H-indazole hydrochloride (600 mg, 2.39 mmol) in CH$_3$OH (10 mL) and H$_2$O (2 mL) was added KOH (268 mg, 4.78 mmol) and (Boc)$_2$O (781 mg, 3.58 mmol) under ice bath. The reaction mixture was stirred at rt for 2 hrs. The reaction mixture was diluted with water (50 mL) and extracted with EtOAc (50 mL×3). The combined organic layers were dried over Na$_2$SO$_4$ and concentrated. The residue was purified by column chromatograph (PE:EtOAc from 10:1 to 4:1) to give the title compound (353 mg, yield 47%) as a yellow oil.

D565 $^1$H NMR (300 MHz, CDCl$_3$): δ 10.15 (br s, 1H), 7.95 (s, 1H), 7.53 (s, 1H), 7.29 (s, 1H), 4.34 (br s, 2H), 2.95-2.81 (m, 3H), 2.45 (s, 3H), 1.86-1.81 (m, 2H), 1.69-1.61 (m, 2H), 1.51 (s, 9H).

346
EXAMPLES

Example 1

4-(6-(6-(3,3-Difluoro-1-methylpiperidin-4-yl)-5-methyl-1H-indazol-1-yl)pyrimidin-4-yl)morpholine (Enantiomer 1) (E1)

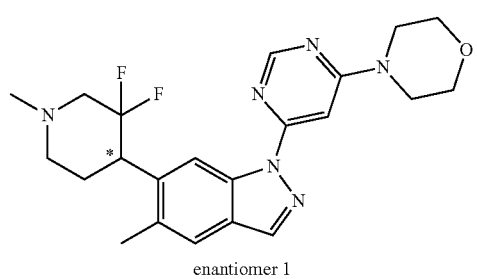 [SMILES: Cc1cc2cnn(-c3cc(N4CCOCC4)ncn3)c2cc1C1CCN(C)CC1(F)F]

enantiomer 1

A suspension of 6-(3,3-difluoro-1-methylpiperidin-4-yl)-5-methyl-1H-indazole (enantiomer 1) (120 mg, 0.450 mmol), 4-(6-chloro-pyrimidin-4-yl)-morpholine (180 mg, 0.900 mmol) and Cs$_2$CO$_3$ (293 mg, 0.900 mmol) in DMF (8 mL) was heated to 100° C. and stirred overnight. The reaction mixture was cooled to rt and then poured into water (40 mL) and extracted with EtOAc (20 mL×3). The combined organic layers were washed with brine, dried over Na$_2$SO$_4$ and concentrated. The residue was purified by prep. TLC (PE:EtOAc=2:3) to give E1 (16.3 mg, yield 8%) as white solid. E1 is a single unknown enantiomer.

E1: $^1$H NMR (300 MHz, CDCl$_3$): δ 9.00 (s, 1H), 8.56 (s, 1H), 8.07 (s, 1H), 7.54 (s, 1H), 7.11 (s, 1H), 3.81-3.76 (m, 4H), 3.75-3.71 (m, 4H), 3.43-3.22 (m, 2H), 3.13-3.09 (m, 1H), 2.61-2.33 (m, 8H), 2.27-2.19 (m, 1H), 1.98-1.91 (m, 1H). $^{19}$F NMR (376 MHz, CDCl$_3$): δ −102.85 (d, J=243.3 Hz, 1F), −111.76 (d, J=244.0 Hz, 1F).

LC-MS (mobile phase: from 80% water (0.02% NH$_4$OAc) and 20% CH$_3$CN to 5% water (0.02% NH$_4$OAc) and 95% CH$_3$CN in 6 min), Rt=4.103 min; MS Calcd.: 428, MS Found: 429 [M+H]$^+$.

Chiral condition: Chiralpak IC 5 μm 4.6*250 mm, Hex/EtOH=85/15, Flow Rate: 1.0 ml/min, 230 nm, T=30° C. Rt=10.897 min, 99.5% ee.

Example 2

4-(6-(6-(3,3-Difluoro-1-methylpiperidin-4-yl)-5-methyl-1H-indazol-1-yl)pyrimidin-4-yl)morpholine (Enantiomer 2) (E2)

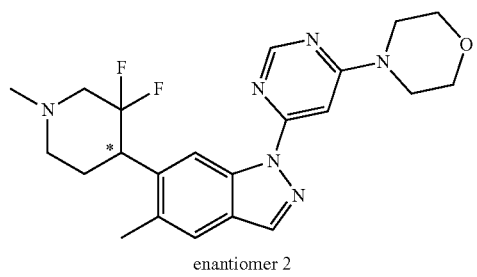 [SMILES: Cc1cc2cnn(-c3cc(N4CCOCC4)ncn3)c2cc1C1CCN(C)CC1(F)F]

enantiomer 2

A suspension of 6-(3,3-difluoro-1-methylpiperidin-4-yl)-5-methyl-1H-indazole (enantiomer 2) (110 mg, 0.415 mmol), 4-(6-chloro-pyrimidin-4-yl)-morpholine (164 mg, 0.820 mmol) and Cs$_2$CO$_3$ (267 mg, 0.822 mmol) in DMF (8 mL) was heated to 100° C. and stirred overnight. The reaction mixture was cooled to rt and then poured into water (40 mL) and extracted with EtOAc (20 mL×3). The combined organic layers were washed with brine, dried over Na$_2$SO$_4$ and concentrated. The crude was purified by prep. TLC (PE:EtOAc=2:3) and each was triturated with Hex/EtOAc (3/1, 5 mL) to give E2 (26.6 mg, yield 15%) as white solid. E2 is a single unknown enantiomer.

E2: $^1$H NMR (300 MHz, CDCl$_3$): δ 9.00 (s, 1H), 8.56 (s, 1H), 8.07 (s, 1H), 7.54 (s, 1H), 7.11 (s, 1H), 3.84-3.76 (m, 4H), 3.76-3.64 (m, 4H), 3.41-3.21 (m, 2H), 3.13-3.09 (m, 1H), 2.60-2.33 (m, 8H), 2.27-2.19 (m, 1H), 1.96-1.91 (m, 1H). $^{19}$F NMR (376 MHz, CDCl$_3$): δ −102.85 (d, J=243.3 Hz, 1F), −111.77 (d, J=243.3 Hz, 1F).

LC-MS (mobile phase: from 80% water (0.02% NH$_4$OAc) and 20% CH$_3$CN to 5% water (0.02% NH$_4$OAc) and 95% CH$_3$CN in 6 min), purity >95%, Rt=4.077 min; MS Calcd.: 428, MS Found: 429 [M+H]$^+$.

Chiral condition: Chiralpak IC 5 μm 4.6*250 mm, Hex/EtOH=85/15, Flow Rate: 1.0 ml/min, 230 nm, T=30° C. Rt=9.901 min, 95.3% ee.

Example 3

4-(6-(6-(3,3-Difluoro-1-methylpiperidin-4-yl)-5-methyl-1H-indazol-1-yl)-2-methoxypyrimidin-4-yl)morpholine (Enantiomer 1) (E3)

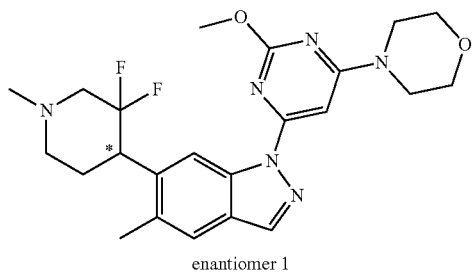 [SMILES: COc1nc(N2CCOCC2)cc(-n2ncc3cc(C)c(C4CCN(C)CC4(F)F)cc32)n1]

enantiomer 1

A suspension of 6-(3,3-difluoro-1-methylpiperidin-4-yl)-5-methyl-1H-indazole (enantiomer 1) (80 mg, 0.30 mmol), 4-(6-chloro-2-methoxypyrimidin-4-yl)morpholine (138 mg, 0.600 mmol) and Cs$_2$CO$_3$ (195 mg, 0.600 mmol) in DMF (5 mL) was heated to 100° C. and stirred overnight. The reaction mixture was cooled to rt and then poured into water (50 mL) and extracted with EtOAc (20 mL×3). The combined organic layers were washed with brine, dried over Na$_2$SO$_4$ and concentrated. The crude was purified by prep. TLC (PE:EtOAc=1:2) and triturated with Hex/EtOAc (3/1, 10 mL) to give E3 (16.8 mg, yield 12%) as white solid. E3 is a single unknown enantiomer.

E3: $^1$H NMR (400 MHz, CDCl$_3$): δ 8.97 (s, 1H), 8.07 (s, 1H), 7.54 (s, 1H), 6.83 (s, 1H), 4.13 (s, 3H), 3.79-3.77 (m, 4H), 3.72-3.70 (m, 4H), 3.38-3.26 (m, 1H), 3.24-3.18 (m, 1H), 3.06-3.03 (m, 1H), 2.47 (s, 3H), 2.41 (s, 3H), 2.39-2.28 (m, 2H), 2.23-2.17 (m, 1H), 1.92-1.89 (m, 1H).

$^{19}$F NMR (376 MHz, CDCl$_3$): δ −102.98 (d, J=243.3 Hz, 1F), −112.51 (d, J=241.0 Hz, 1F).

LC-MS (mobile phase: from 60% water (0.02% NH$_4$OAc) and 40% CH$_3$CN to 5% water (0.02% NH$_4$OAc) and 95% CH$_3$CN in 6 min), purity >95%, Rt=3.466 min; MS Calcd.: 458, MS Found: 459 [M+H]$^+$.

Chiral condition: Chiralpak IB 5 μm 4.6*250 mm, Hex/EtOH=70/30, Flow Rate: 1.0 ml/min, 230 nm, T=30° C. Rt=7.681 min, 96.7% ee.

Example 4

4-(6-(6-(3,3-Difluoro-1-methylpiperidin-4-yl)-5-methyl-1H-indazol-1-yl)-2-methoxypyrimidin-4-yl)morpholine (Enantiomer 2) (E4)

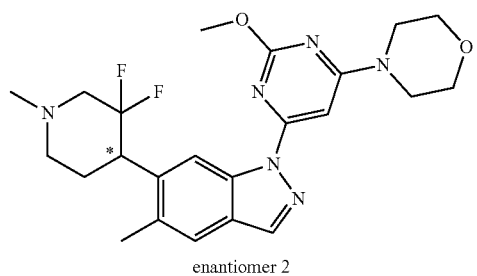 [SMILES: COc1nc(N2CCOCC2)cc(-n2ncc3cc(C)c(C4CCN(C)CC4(F)F)cc32)n1]

enantiomer 2

A suspension of 6-(3,3-difluoro-1-methylpiperidin-4-yl)-5-methyl-1H-indazole (enantiomer 2) (80 mg, 0.30 mmol), 4-(6-chloro-2-methoxypyrimidin-4-yl)morpholine (138 mg, 0.600 mmol) and Cs$_2$CO$_3$ (195 mg, 0.600 mmol) in DMF (5 mL) was heated to 100° C. and stirred overnight. The reaction mixture was cooled to rt and then poured into water (50 mL) and extracted with EtOAc (20 mL×3). The combined organic layers were washed with brine, dried over Na$_2$SO$_4$ and concentrated. The crude was purified by prep. TLC (PE:EtOAc=1:2) and triturated with Hex/EtOAc (3/1, 10 mL) to give E4 (22.5 mg, yield 16%) as white solid. E4 is a single unknown enantiomer.

E4: $^1$H NMR (300 MHz, CDCl$_3$): δ 8.97 (s, 1H), 8.07 (s, 1H), 7.54 (s, 1H), 6.83 (s, 1H), 4.13 (s, 3H), 3.79-3.77 (m, 4H), 3.72-3.70 (m, 4H), 3.38-3.26 (m, 1H), 3.24-3.18 (m, 1H), 3.07-3.05 (m, 1H), 2.47 (s, 3H), 2.41 (s, 3H), 2.39-2.28 (m, 2H), 2.25-2.16 (m, 1H), 1.93-1.88 (m, 1H).

$^{19}$F NMR (376 MHz, CDCl$_3$): δ −102.98 (d, J=241.4 Hz, 1F), −112.50 (d, J=242.9 Hz, 1F).

LC-MS (mobile phase: from 60% water (0.02% NH$_4$OAc) and 40% CH$_3$CN to 5% water (0.02% NH$_4$OAc) and 95% CH$_3$CN in 6 min), purity >95%, Rt=3.500 min; MS Calcd.: 458, MS Found: 459 [M+H]$^+$.

Chiral condition: Chiralpak IB 5 μm 4.6*250 mm, Hex/EtOH=70/30, Flow Rate: 1.0 ml/min, 230 nm, T=30° C. Rt=6.244 min, 98.3% ee.

Example 5

4-(6-(6-(3,3-Difluoro-1-methylpiperidin-4-yl)-5-methyl-1H-indazol-1-yl)-2-ethoxypyrimidin-4-yl)morpholine (Enantiomer 1) (E5)

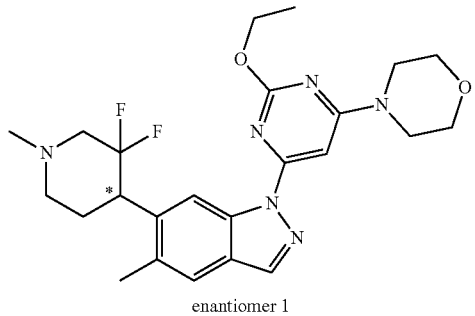 [SMILES: CCOc1nc(N2CCOCC2)cc(-n2ncc3cc(C)c(C4CCN(C)CC4(F)F)cc32)n1]

enantiomer 1

A suspension of 6-(3,3-difluoro-1-methylpiperidin-4-yl)-5-methyl-1H-indazole (enantiomer 1) (80 mg, 0.30 mmol), 4-(6-chloro-2-ethoxypyrimidin-4-yl)morpholine (146 mg, 0.600 mmol) and $Cs_2CO_3$ (195 mg, 0.600 mmol) in DMF (5 mL) was heated to 110° C. and stirred overnight. The reaction mixture was cooled to rt and then poured into water (40 mL) and extracted with EtOAc (20 mL×3). The combined organic layers were washed with brine, dried over $Na_2SO_4$ and concentrated. The crude was purified by prep. HPLC to give E5 (18.8 mg, yield 13%) as white solid. E5 is a single unknown enantiomer.

E5: 1H NMR (400 MHz, $CDCl_3$): δ 8.92 (s, 1H), 8.07 (s, 1H), 7.55 (s, 1H), 6.83 (s, 1H), 4.58 (q, J=7.2 Hz, 2H), 3.80-3.77 (m, 4H), 3.72-3.70 (m, 4H), 3.39-3.27 (m, 1H), 3.25-3.18 (m, 1H), 3.06-3.03 (m, 1H), 2.48 (s, 3H), 2.42 (s, 3H), 2.40-2.29 (m, 2H), 2.25-2.19 (m, 1H), 1.92-1.89 (m, 1H), 1.51 (t, J=7.2 Hz, 3H).

$^{19}F$ NMR (376 MHz, $CDCl_3$): δ -103.00 (d, J=241.8 Hz, 1F), -112.11 (d, J=241.4 Hz, 1F).

LC-MS (mobile phase: from 70% water (0.02% $NH_4OAc$) and 30% $CH_3CN$ to 5% water (0.02% $NH_4OAc$) and 95% $CH_3CN$ in 6.5 min), Rt=4.380 min, purity >95%; MS Calcd.: 472, MS Found: 473 [M+H]$^+$.

Chiral condition: Chiralpak IB 5 μm 4.6*250 mm, Hex/EtOH=70/30, Flow Rate: 1.0 ml/min, 230 nm, T=30° C. Rt=6.353 min, 97.3% ee.

Example 6

4-(6-(6-(3,3-Difluoro-1-methylpiperidin-4-yl)-5-methyl-1H-indazol-1-yl)-2-ethoxypyrimidin-4-yl)morpholine (Enantiomer 2) (E6)

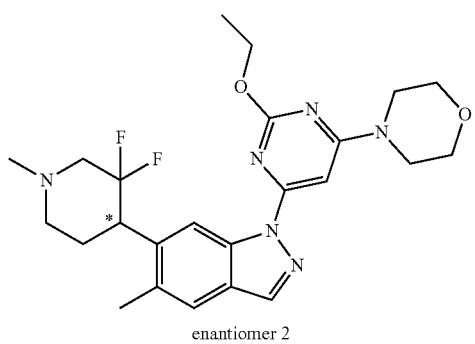 [SMILES: CCOc1nc(N2CCOCC2)cc(-n2ncc3cc(C)c(C4CCN(C)CC4(F)F)cc32)n1]

enantiomer 2

A mixture of 6-(3,3-difluoro-1-methylpiperidin-4-yl)-5-methyl-1H-indazole (enantiomer 2) (80 mg, 0.30 mmol), 4-(6-chloro-2-ethoxypyrimidin-4-yl)morpholine (146 mg, 0.600 mmol) and $Cs_2CO_3$ (195 mg, 0.600 mmol) in DMF (10 mL) was heated to 100° C. and stirred overnight. The reaction mixture was cooled to rt. Water (20 mL) and EtOAc (20 mL) were added, and the mixture was separated. The aqueous was extracted with EtOAc (15 mL×3). The combined organic layers were washed with brine (20 mL) and water (20 mL), dried over $Na_2SO_4$, filtered and concentrated. The residue was purified by prep. HPLC to give E6 (40.9 mg, yield 29%) as white solid. E6 is a single unknown enantiomer.

E6: $^1H$ NMR (400 MHz, $CDCl_3$): δ 8.92 (s, 1H), 8.07 (s, 1H), 7.53 (s, 1H), 6.83 (s, 1H), 4.58 (q, J=7.2 Hz, 2H), 3.79-3.69 (m, 8H), 3.36-3.19 (m, 2H), 3.05-3.02 (m, 1H), 2.47 (s, 3H), 2.41-2.29 (m, 5H), 2.24-2.18 (m, 1H), 1.91-1.84 (m, 1H), 1.52 (t, J=7.2 Hz, 3H).

$^{19}F$ NMR (376 MHz, $CDCl_3$): δ -102.78 (d, J=242.1 Hz, 1F), -112.09 (d, J=242.1 Hz, 1F).

LC-MS (mobile phase: from 70% water (0.02% $NH_4OAc$) and 30% $CH_3CN$ to 5% water (0.02% $NH_4OAc$) and 95% $CH_3CN$ in 6 min), purity >95%, Rt=4.189 min; MS Calcd.: 472, MS Found: 473 [M+H]$^+$.

Chiral condition: Chiralpak IB 5 μm 4.6*250 mm, Hex/EtOH=70/30, Flow Rate: 1.0 ml/min, 230 nm, T=30° C. Rt=5.515 min, 97.1% ee.

Example 7

4-(6-(6-(3,3-Difluoro-1-methylpiperidin-4-yl)-5-methyl-1H-indazol-1-yl)-2-isopropoxypyrimidin-4-yl)morpholine (Enantiomer 1) (E7)

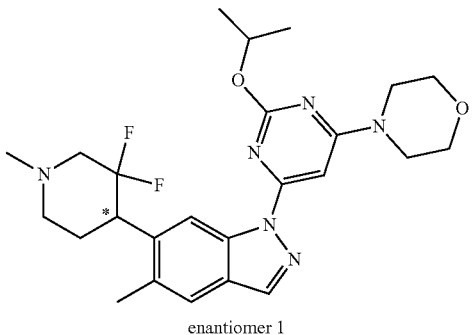 [SMILES: Cc1cc2cnn(-c3cc(N4CCOCC4)nc(OC(C)C)n3)c2cc1C1CCN(C)CC1(F)F]

enantiomer 1

A suspension of 6-(3,3-difluoro-1-methylpiperidin-4-yl)-5-methyl-1H-indazole (enantiomer 1) (100 mg, 0.377 mmol), 4-(6-chloro-2-isopropoxypyrimidin-4-yl)morpholine (196 mg, 0.760 mmol) and $Cs_2CO_3$ (248 mg, 0.763 mmol) in DMF (5 mL) was heated to 100° C. and stirred overnight. The reaction mixture was cooled to rt and then poured into water (40 mL) and extracted with EtOAc (20 mL×3). The combined organic layers were washed with brine, dried over $Na_2SO_4$ and concentrated. The crude was purified by prep. HPLC to give E7 (36.4 mg, yield 20%) as white solid. E7 is a single unknown enantiomer.

E7: $^1H$ NMR (400 MHz, $CDCl_3$): δ 8.86 (s, 1H), 8.07 (s, 1H), 7.55 (s, 1H), 6.83 (s, 1H), 5.55-5.45 (m, 1H), 3.79-3.77 (m, 4H), 3.72-3.70 (m, 4H), 3.39-3.27 (m, 1H), 3.23-3.16 (m, 1H), 3.04-3.00 (m, 1H), 2.48 (s, 3H), 2.41 (s, 3H), 2.39-2.32 (m, 2H), 2.24-2.18 (m, 1H), 1.91-1.87 (m, 1H), 1.51-1.49 (m, 6H).

$^{19}$F NMR (376 MHz, CDCl$_3$): δ −102.58 (d, J=242.1 Hz, 1F), −111.66 (d, J=242.1 Hz, 1F).

LC-MS [mobile phase: from 60% water (0.02% NH$_4$OAc) and 40% CH$_3$CN to 5% water (0.02% NH$_4$OAc) and 95% CH$_3$CN in 6.5 min]: Rt=4.234 min, purity >95%; MS Calcd.: 486, MS Found: 487 [M+H]$^+$.

Chiral HPLC [Chiral condition: Chiralpak IB 5 μm 4.6*250 mm, Hex/IPA/DEA=80/20/0.2, Flow Rate: 1.0 ml/min, 230 nm, T=30° C.]: Rt=7.372 min, 95.4% ee.

Example 8

4-(6-(6-(3,3-Difluoro-1-methylpiperidin-4-yl)-5-methyl-1H-indazol-1-yl)-2-isopropoxypyrimidin-4-yl)morpholine (Enantiomer 2) (E8)

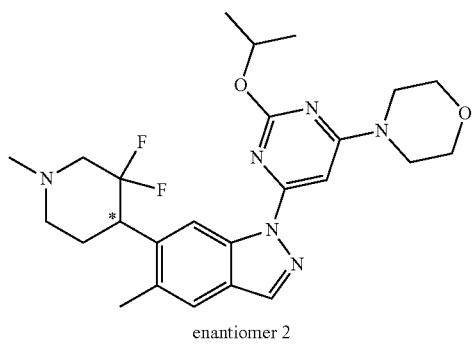 [SMILES: Cc1cc2cnn(-c3cc(N4CCOCC4)nc(OC(C)C)n3)c2cc1C1CCN(C)CC1(F)F]

enantiomer 2

A suspension of 6-(3,3-difluoro-1-methylpiperidin-4-yl)-5-methyl-1H-indazole (enantiomer 2) (70 mg, 0.26 mmol), 4-(6-chloro-2-isopropoxypyrimidin-4-yl)morpholine (134 mg, 0.52 mmol) and Cs$_2$CO$_3$ (169 mg, 0.52 mmol) in DMF (5 mL) was heated to 100° C. and stirred overnight. TLC showed the starting material was consumed. The reaction mixture was cooled to rt and then poured into water (40 mL) and extracted with EtOAc (20 mL×3). The combined organic layers were washed with brine, dried over Na$_2$SO$_4$ and concentrated. The crude was purified by prep. HPLC [XBridge, C18, 5 μm, 19*150 mm, 50-95% B; A: H$_2$O (0.1% NH$_4$HCO$_3$), B: CH$_3$CN; UV: 214 nm; flow rate: 20 mL/min] to give E8 (13.2 mg, yield 10%) as white solid. E8 is a single unknown enantiomer.

E8: $^1$H NMR (400 MHz, CDCl$_3$): δ 8.86 (s, 1H), 8.07 (s, 1H), 7.55 (s, 1H), 6.83 (s, 1H), 5.55-5.46 (m, 1H), 3.79-3.77 (m, 4H), 3.72-3.70 (m, 4H), 3.39-3.26 (m, 1H), 3.23-3.17 (m, 1H), 3.03-3.01 (m, 1H), 2.48 (s, 3H), 2.41 (s, 3H), 2.39-2.32 (m, 2H), 2.24-2.18 (m, 1H), 1.91-1.87 (m, 1H), 1.51-1.49 (m, 6H).

$^{19}$F NMR (376 MHz, CDCl$_3$): δ −102.58 (d, J=242.1 Hz, 1F), −111.66 (d, J=241.8 Hz, 1F)

LC-MS [mobile phase: from 60% water (0.02% NH$_4$OAc) and 40% CH$_3$CN to 5% water (0.02% NH$_4$OAc) and 95% CH$_3$CN in 6.5 min]: Rt=4.235 min, purity >95%; MS Calcd.: 486, MS Found: 487 [M+H]$^+$.

Chiral HPLC [Chiral condition: Chiralpak IB 5 μm 4.6*250 mm, Hex/IPA/DEA=80/20/0.2, Flow Rate: 1.0 ml/min, 230 nm, T=30° C.]: Rt=6.502 min, ee 97.1%.

Example 9

4-(6-(3,3-Difluoro-1-methylpiperidin-4-yl)-5-methyl-1H-indazol-1-yl)-6-morpholinopyrimidine-2-carbonitrile (Enantiomer 1) (E9)

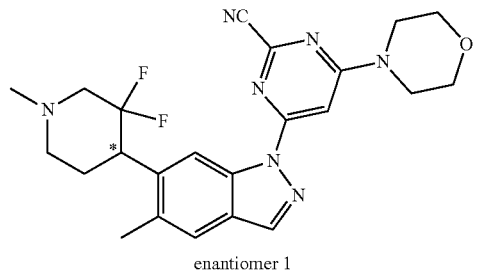 [SMILES: Cc1cc2cnn(-c3cc(N4CCOCC4)nc(C#N)n3)c2cc1C1CCN(C)CC1(F)F]

enantiomer 1

A suspension of 6-(3,3-difluoro-1-methylpiperidin-4-yl)-5-methyl-1H-indazole (enantiomer 1) (80 mg, 0.30 mmol), 4-chloro-6-morpholinopyrimidine-2-carbonitrile (101 mg, 0.450 mmol) and Cs$_2$CO$_3$ (196 mg, 0.602 mmol) in DMF (3 mL) was heated to 100° C. and stirred overnight. The reaction mixture was cooled to rt and then poured into water (40 mL) and extracted with EtOAc (15 mL×3). The combined organic layers were washed with brine, dried over Na$_2$SO$_4$ and concentrated. The crude was purified by prep. HPLC [Sunfire, C18, 5 μm, 19*150 mm, 45-95% B; A: H$_2$O (0.1% NH$_4$HCO$_3$), B: CH$_3$CN; UV: 214 nm; flow rate: 20 mL/min] to give the title compound E9 (40.4 mg, yield 30%) as white solid. E9 is a single unknown enantiomer.

E9: $^1$H NMR (400 MHz, CDCl$_3$): 8.79 (s, 1H), 8.09 (s, 1H), 7.55 (s, 1H), 7.19 (s, 1H), 3.82-3.74 (m, 8H), 3.41-3.29 (m, 1H), 3.26-3.20 (m, 1H), 3.13-3.10 (m, 1H), 2.56-2.36 (m, 2H), 2.49 (s, 3H), 2.44 (s, 3H), 2.26-2.21 (m, 1H), 1.96-1.92 (m, 1H).

$^{19}$F NMR (376 MHz, CDCl$_3$): δ −102.53 (d, J=241.4 Hz, 1F), −112.12 (d, J=243.3 Hz, 1F).

LC-MS [mobile phase: from 60% water (0.02% NH$_4$OAc) and 40% CH$_3$CN to 5% water (0.02% NH$_4$OAc) and 95% CH$_3$CN in 6.5 min], purity >95%, Rt=3.933 min; MS Calcd.: 453, MS Found: 454 [M+H]$^+$.

Chiral HPLC (Chiral condition: Chiralpak ID 5 μm 4.6*250 mm, CO$_2$/MeOH=70/30, Co-Solvent: IPA, CO$_2$ Flow Rate: 2.1 mL/min, Co-Solvent Flow Rate: 0.9 mL/min, 254 nm, T=39° C.), Rt=3.58 min, 97.5% ee.

Example 10

4-(6-(3,3-Difluoro-1-methylpiperidin-4-yl)-5-methyl-1H-indazol-1-yl)-6-morpholinopyrimidine-2-carbonitrile (Enantiomer 2) (E10)

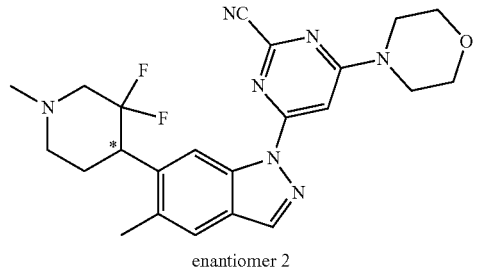 [SMILES: Cc1cc2cnn(-c3cc(N4CCOCC4)nc(C#N)n3)c2cc1C1CCN(C)CC1(F)F]

enantiomer 2

A suspension of 6-(3,3-difluoro-1-methylpiperidin-4-yl)-5-methyl-1H-indazole (enantiomer 2) (80 mg, 0.30 mmol), 4-chloro-6-morpholinopyrimidine-2-carbonitrile (101 mg, 0.450 mmol) and $Cs_2CO_3$ (196 mg, 0.602 mmol) in DMF (3 mL) was heated to 100° C. and stirred overnight. The reaction mixture was cooled to rt and then poured into water (40 mL) and extracted with EtOAc (15 mL×3). The combined organic layers were washed with brine, dried over $Na_2SO_4$ and concentrated. The crude was purified by prep. HPLC [Sunfire, C18, 5 μm, 19*150 mm, 45-95% B; A: $H_2O$ (0.1% $NH_4HCO_3$), B: $CH_3CN$; UV: 214 nm; flow rate: 20 mL/min] to give the title compound E10 (22.4 mg, yield 16%) as a white solid. E10 is a single unknown enantiomer.

E10: $^1$H NMR (400 MHz, $CDCl_3$): 8.79 (s, 1H), 8.09 (s, 1H), 7.54 (s, 1H), 7.19 (s, 1H), 3.82-3.73 (m, 8H), 3.41-3.29 (m, 1H), 3.26-3.20 (m, 1H), 3.13-3.10 (m, 1H), 2.56-2.36 (m, 2H), 2.49 (s, 3H), 2.44 (s, 3H), 2.26-2.21 (m, 1H), 1.96-1.92 (m, 1H).

$^{19}$F NMR (376 MHz, $CDCl_3$): δ −102.52 (d, J=242.1 Hz, 1F), −112.11 (d, J=241.0 Hz, 1F).

LC-MS [mobile phase: from 60% water (0.02% $NH_4OAc$) and 40% $CH_3CN$ to 5% water (0.02% $NH_4OAc$) and 95% $CH_3CN$ in 6.5 min], purity >95%, Rt=3.913 min; MS Calcd.: 453, MS Found: 454 $[M+H]^+$.

Chiral HPLC (Chiral condition: Chiralpak ID 5 μm 4.6*250 mm, $CO_2$/MeOH=70/30, Co-Solvent: IPA, $CO_2$ Flow Rate: 2.1 mL/min, Co-Solvent Flow Rate: 0.9 mL/min, 254 nm, T=40° C.), Rt=3.99 min, 98.5% ee.

Example 11

4-(6-(6-(3,3-Difluoro-1-methylpiperidin-4-yl)-5-methyl-1H-indazol-1-yl)-2-ethylpyrimidin-4-yl)morpholine (Enantiomer 1) (E11)

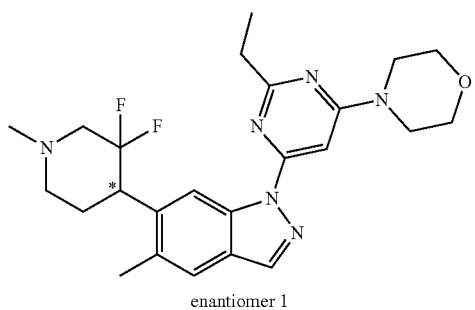 [SMILES: CCc1nc(N2CCOCC2)cc(-n2ncc3cc(C)c(C4CCN(C)CC4(F)F)cc32)n1]

enantiomer 1

A suspension of 6-(3,3-difluoro-1-methylpiperidin-4-yl)-5-methyl-1H-indazole (enantiomer 1) (80 mg, 0.30 mmol), 4-(6-chloro-2-ethylpyrimidin-4-yl)morpholine (103 mg, 0.450 mmol) and $Cs_2CO_3$ (196 mg, 0.603 mmol) in DMF (3 mL) was heated to 100° C. and stirred overnight. The reaction mixture was cooled to rt and then poured into water (40 mL) and extracted with EtOAc (15 mL×3). The combined organic layers were washed with brine, dried over $Na_2SO_4$ and concentrated. The crude was purified by prep-HPLC to give the title compound E11 (25.8 mg, yield 19%) as white solid. E11 is a single unknown enantiomer.

E11: $^1$H NMR (400 MHz, $CDCl_3$): 9.04 (s, 1H), 8.07 (s, 1H), 7.54 (s, 1H), 6.95 (s, 1H), 3.82-3.79 (m, 4H), 3.73-3.70 (m, 4H), 3.43-3.21 (m, 2H), 3.10-3.07 (m, 1H), 2.89 (q, J=7.6 Hz, 2H), 2.48 (s, 3H), 2.44 (s, 3H), 2.44-2.38 (m, 2H), 2.26-2.21 (m, 1H), 1.96-1.92 (m, 1H), 1.43 (t, J=7.6 Hz, 3H).

$^{19}$F NMR (376 MHz, $CDCl_3$): δ −102.94 (d, J=241.0 Hz, 1F), −112.73 (d, J=241.0 Hz, 1F).

LC-MS (mobile phase: from 60% water (0.02% $NH_4OAc$) and 40% $CH_3CN$ to 5% water (0.02% $NH_4OAc$) and 95% $CH_3CN$ in 6 min), purity>95%, Rt=4.178 min; MS Calcd.: 456, MS Found: 457 $[M+H]^+$.

Chiral condition: Chiralpak IC 5 μm 4.6*250 mm, Hex/IPA=90/10, Flow Rate: 1.0 ml/min, 230 nm, T=30° C. Rt=14.155 min, 100% ee.

Example 12

4-(6-(6-(3,3-Difluoro-1-methylpiperidin-4-yl)-5-methyl-1H-indazol-1-yl)-2-ethylpyrimidin-4-yl)morpholine (Enantiomer 2) (E12)

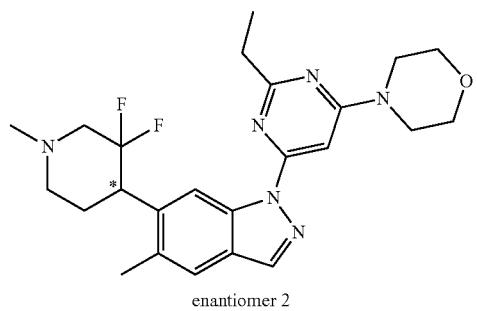 [SMILES: CCc1nc(N2CCOCC2)cc(-n2ncc3cc(C)c(C4CCN(C)CC4(F)F)cc32)n1]

enantiomer 2

A suspension of 6-(3,3-difluoro-1-methylpiperidin-4-yl)-5-methyl-1H-indazole (enantiomer 2) (80 mg, 0.30 mmol), 4-(6-chloro-2-ethylpyrimidin-4-yl)morpholine (103 mg, 0.450 mmol) and $Cs_2CO_3$ (196 mg, 0.600 mmol) in DMF (3 mL) was heated to 100° C. and stirred overnight. The reaction mixture was cooled to rt and then poured into water (40 mL) and extracted with EtOAc (15 mL×3). The combined organic layers were washed with brine, dried over $Na_2SO_4$ and concentrated. The crude was purified by prep-HPLC to give the title compound E12 (35.8 mg, yield 26%) as white solid. E12 is a single unknown enantiomer.

E12: 1H NMR (400 MHz, $CDCl_3$): 9.04 (s, 1H), 8.07 (s, 1H), 7.54 (s, 1H), 6.95 (s, 1H), 3.84-3.81 (m, 4H), 3.73-3.68 (m, 4H), 3.37-3.19 (m, 2H), 3.12-3.07 (m, 1H), 2.89 (q, J=7.6 Hz, 2H), 2.48 (s, 3H), 2.44 (s, 3H), 2.44-2.35 (m, 2H), 2.26-2.20 (m, 1H), 1.95-1.90 (m, 1H), 1.43 (t, J=7.6 Hz, 3H).

$^{19}$F NMR (376 MHz, $CDCl_3$): δ −102.93 (d, J=242.9 Hz, 1F), −112.73 (d, J=242.9 Hz, 1F).

LC-MS (mobile phase: from 60% water (0.02% $NH_4OAc$) and 40% $CH_3CN$ to 5% water (0.02% $NH_4OAc$) and 95% $CH_3CN$ in 6 min), purity>95%, Rt=4.154 min; MS Calcd.: 456, MS Found: 457 $[M+H]^+$.

Chiral condition: Chiralpak IC 5 μm 4.6*250 mm, Hex/IPA=90/10, Flow Rate: 1.0 ml/min, 230 nm, T=30° C. Rt=12.122 min, 100% ee.

Example 13

6-(6-(6-(3,3-Difluoro-1-methylpiperidin-4-yl)-5-methyl-1H-indazol-1-yl)pyrimidin-4-yl)-2-oxa-6-azaspiro[3.4]octane (Enantiomer 1) (E13)

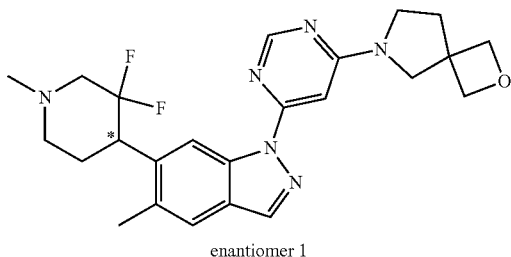 [SMILES: Cc1cc2cnn(-c3cc(N4CCC5(COC5)C4)ncn3)c2cc1C1CCN(C)CC1(F)F]

enantiomer 1

A suspension of 6-(3,3-difluoro-1-methylpiperidin-4-yl)-5-methyl-1H-indazole (enantiomer 1) (80 mg, 0.30 mmol), 6-(6-chloropyrimidin-4-yl)-2-oxa-6-azaspiro[3.4]octane (135 mg, 0.60 mmol) and $Cs_2CO_3$ (195 mg, 0.60 mmol) in DMF (3 mL) was heated to 100° C. and stirred overnight. The reaction mixture was cooled to rt and then poured into water (40 mL) and extracted with EtOAc (15 mL×3). The combined organic layers were washed with brine, dried over $Na_2SO_4$ and concentrated. The crude was purified by prep. HPLC [Sunfire, C18, 5 μm, 19*150 mm, 20-95% B; A: $H_2O$ (0.1% $NH_4HCO_3$), B: $CH_3CN$; UV: 214 nm; flow rate: 20 mL/min] to give E13 (32.2 mg, yield 24%) as white solid. E13 is a single unknown enantiomer.

E13: $^1$H NMR (400 MHz, $CDCl_3$): 9.01 (s, 1H), 8.55 (s, 1H), 8.09 (s, 1H), 7.54 (s, 1H), 6.87 (s, 1H), 4.74 (d, J=6.0 Hz, 2H), 4.65 (d, J=6.0 Hz, 2H), 3.83 (br s, 2H), 3.60 (br s, 2H), 3.41-3.22 (m, 2H), 3.13-3.10 (m, 1H), 2.64-2.42 (m, 2H), 2.48 (s, 3H), 2.46 (s, 3H), 2.38-2.34 (m, 2H), 2.26-2.20 (m, 1H), 1.98-1.91 (m, 1H).

$^{19}$F NMR (376 MHz, $CDCl_3$): δ −102.86 (d, J=243.3 Hz, 1F), −111.79 (d, J=243.6 Hz, 1F).

LC-MS [mobile phase: from 70% water (0.02% $NH_4OAc$) and 30% $CH_3CN$ to 5% water (0.02% $NH_4OAc$) and 95% $CH_3CN$ in 6.5 min], purity >95%, Rt=3.498 min; MS Calcd.: 454, MS Found: 455 [M+H]$^+$.

Chiral HPLC (Chiral condition: Chiralpak IF 5 μm 4.6*250 mm, MeOH/EtOH=50/50, Flow Rate: 1.0 ml/min, 230 nm, T=30° C.), Rt=14.710 min, 98.7% ee.

Example 14

6-(6-(6-(3,3-Difluoro-1-methylpiperidin-4-yl)-5-methyl-1H-indazol-1-yl)pyrimidin-4-yl)-2-oxa-6-azaspiro[3.4]octane (Enantiomer 2) (E14)

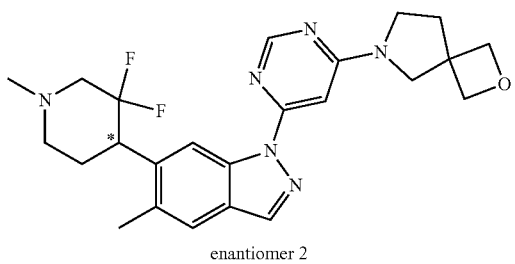 [SMILES: Cc1cc2cnn(-c3cc(N4CCC5(COC5)C4)ncn3)c2cc1C1CCN(C)CC1(F)F]

enantiomer 2

A suspension of 6-(3,3-difluoro-1-methylpiperidin-4-yl)-5-methyl-1H-indazole (enantiomer 2) (80 mg, 0.30 mmol), 6-(6-chloropyrimidin-4-yl)-2-oxa-6-azaspiro[3.4]octane (135 mg, 0.60 mmol) and $Cs_2CO_3$ (195 mg, 0.60 mmol) in DMF (3 mL) was heated to 100° C. and stirred overnight. The reaction mixture was cooled to rt and then poured into water (40 mL) and extracted with EtOAc (15 mL×3). The combined organic layers were washed with brine, dried over $Na_2SO_4$ and concentrated. The crude was purified by prep. HPLC [Sunfire, C18, 5 μm, 19'150 mm, 20-95% B; A: $H_2O$ (0.1% $NH_4HCO_3$), B: $CH_3CN$; UV: 214 nm; flow rate: 20 mL/min] to give E14 (25.2 mg, yield 18%) as white solid. E14 is a single unknown enantiomer.

E14: $^1$H NMR (400 MHz, $CDCl_3$): 9.01 (s, 1H), 8.55 (s, 1H), 8.09 (s, 1H), 7.54 (s, 1H), 6.87 (s, 1H), 4.74 (d, J=6.4 Hz, 2H), 4.66 (d, J=6.0 Hz, 2H), 3.83 (br s, 2H), 3.60 (br s, 2H), 3.41-3.22 (m, 2H), 3.13-3.09 (m, 1H), 2.64-2.42 (m, 2H), 2.48 (s, 3H), 2.46 (s, 3H), 2.38-2.34 (m, 2H), 2.26-2.20 (m, 1H), 1.97-1.93 (m, 1H).

$^{19}$F NMR (376 MHz, $CDCl_3$): δ −102.87 (d, J=243.6 Hz, 1F), −111.79 (d, J=243.3 Hz, 1F).

LC-MS [mobile phase: from 70% water (0.02% $NH_4OAc$) and 30% $CH_3CN$ to 5% water (0.02% $NH_4OAc$) and 95% $CH_3CN$ in 6.5 min], purity >95%, Rt=3.567 min; MS Calcd.: 454, MS Found: 455 [M+H]$^+$.

Chiral HPLC (Chiral condition: Chiralpak IF 5 μm 4.6*250 mm, MeOH/EtOH=50/50, Flow Rate: 1.0 ml/min, 230 nm, T=30° C.), Rt=13.072 min, 100% ee.

Example 15

(2R)-4-(6-(6-(3,3-Difluoro-1-methylpiperidin-4-yl)-5-methyl-1H-indazol-1-yl)pyrimidin-4-yl)-N-methylmorpholine-2-carboxamide (Diastereoisomer 1)(E15)

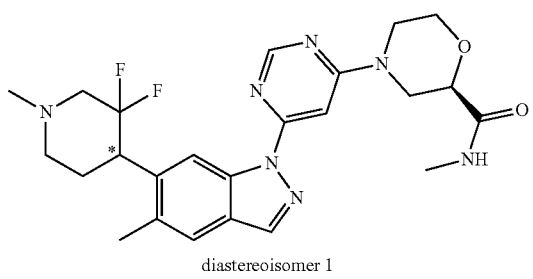 [SMILES: CNC(=O)[C@H]1CN(c2cc(-n3ncc4cc(C)c(C5CCN(C)CC5(F)F)cc43)ncn2)CCO1]

diastereoisomer 1

A suspension of 6-(3,3-difluoro-1-methylpiperidin-4-yl)-5-methyl-1H-indazole (enantiomer 1) (80 mg, 0.30 mmol), (R)-4-(6-chloropyrimidin-4-yl)-N-methylmorpholine-2-carboxamide (116 mg, 0.452 mmol) and $Cs_2CO_3$ (195 mg, 0.599 mmol) in DMF (3 mL) was heated to 100° C. and stirred overnight. The reaction mixture was cooled to rt and then poured into water (40 mL) and extracted with EtOAc (15 mL×3). The combined organic layers were washed with brine, dried over $Na_2SO_4$ and concentrated. The crude was purified by prep. HPLC [Sunfire, C18, 5 μm, 19*150 mm, 30-60% B; A: $H_2O$ (0.1% $NH_4HCO_3$), B: $CH_3CN$; UV: 214 nm; flow rate: 20 mL/min] to give E15 (48.3 mg, yield 33%) as white solid. E15 is a single unknown diastereoisomer.

E15: $^1$H NMR (400 MHz, $CDCl_3$): 8.99 (s, 1H), 8.57 (s, 1H), 8.09 (s, 1H), 7.54 (s, 1H), 7.23 (s, 1H), 6.62-6.61 (m, 1H), 4.66-4.63 (m, 1H), 4.49-4.50 (m, 1H), 4.12-4.05 (m, 2H), 3.76-3.69 (m, 1H), 3.41-3.21 (m, 2H), 3.14-3.03 (m,

2H), 2.99-2.93 (m, 1H), 2.88 (d, J=4.8 Hz, 3H), 2.59-2.35 (m, 8H), 2.26-2.21 (m, 1H), 1.96-1.92 (m, 1H).

$^{19}$F NMR (376 MHz, CDCl$_3$): δ −102.85 (d, J=243.3 Hz, 1F), −111.78 (d, J=243.6 Hz, 1F).

LC-MS [mobile phase: from 80% water (0.02% NH$_4$OAc) and 20% CH$_3$CN to 5% water (0.02% NH$_4$OAc) and 95% CH$_3$CN in 6.5 min], purity >95%, Rt=3.784 min; MS Calcd.: 485, MS Found: 486 [M+H]$^+$.

Chiral HPLC (Chiral condition: Chiralpak AD-3 3 μm 4.6*150 mm, Hex/IPA=70/30, Flow Rate: 1.0 ml/min, 230 nm, T=30° C.), Rt=6.360 min, 75.7% de.

Example 16

(2R)-4-(6-(6-(3,3-Difluoro-1-methylpiperidin-4-yl)-5-methyl-1H-indazol-1-yl)pyrimidin-4-yl)-N-methylmorpholine-2-carboxamide (Diastereoisomer 2) (E16)

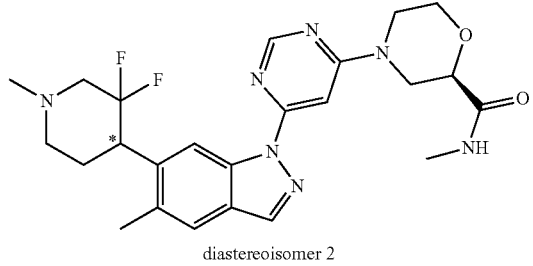 [SMILES: CNC(=O)[C@H]1CN(c2cc(-n3ncc4cc(C)c(C5CCN(C)CC5(F)F)cc43)ncn2)CCO1]

diastereoisomer 2

A suspension of 6-(3,3-difluoro-1-methylpiperidin-4-yl)-5-methyl-1H-indazole (enantiomer 2) (80 mg, 0.30 mmol), (R)-4-(6-chloropyrimidin-4-yl)-N-methylmorpholine-2-carboxamide (116 mg, 0.452 mmol) and Cs$_2$CO$_3$ (195 mg, 0.599 mmol) in DMF (3 mL) was heated to 100° C. and stirred overnight. The reaction mixture was cooled to rt and then poured into water (40 mL) and extracted with EtOAc (15 mL×3). The combined organic layers were washed with brine, dried over Na$_2$SO$_4$ and concentrated. The crude was purified by prep. HPLC [Sunfire, C18, 5 μm, 19'150 mm, 30-60% B; A: H$_2$O (0.1% NH$_4$HCO$_3$), B: CH$_3$CN; UV: 214 nm; flow rate: 20 mL/min] to give E16 (35.1 mg, yield 24%) as white solid. E16 is a single unknown diastereoisomer.

E16: $^1$H NMR (400 MHz, CDCl$_3$): 8.99 (s, 1H), 8.57 (s, 1H), 8.08 (s, 1H), 7.54 (s, 1H), 7.23 (s, 1H), 6.65-6.60 (m, 1H), 4.67-4.64 (m, 1H), 4.47-4.44 (m, 1H), 4.11-4.05 (m, 2H), 3.76-3.69 (m, 1H), 3.41-3.22 (m, 2H), 3.13-3.04 (m, 2H), 2.96 (dd, J=13.2, 10.8 Hz, 1H), 2.88 (d, J=5.2 Hz, 3H), 2.59-2.35 (m, 8H), 2.26-2.20 (m, 1H), 1.96-1.92 (m, 1H).

$^{19}$F NMR (376 MHz, CDCl$_3$): δ −102.84 (d, J=243.6 Hz, 1F), −111.77 (d, J=242.9 Hz, 1F).

LC-MS [mobile phase: from 80% water (0.02% NH$_4$OAc) and 20% CH$_3$CN to 5% water (0.02% NH$_4$OAc) and 95% CH$_3$CN in 6.5 min], purity >95%, Rt=3.791 min; MS Calcd.: 485, MS Found: 486 [M+H]$^+$.

Chiral HPLC (Chiral condition: Chiralpak AD-3 3 μm 4.6*150 mm, Hex/IPA=70/30, Flow Rate: 1.0 ml/min, 230 nm, T=30° C.), Rt=9.425 min, 76.9% de.

Example 17

(2R)-4-(6-(6-(3,3-Difluoro-1-methylpiperidin-4-yl)-5-methyl-1H-indazol-1-yl)-2-methoxypyrimidin-4-yl)-N-methylmorpholine-2-carboxamide (E17)

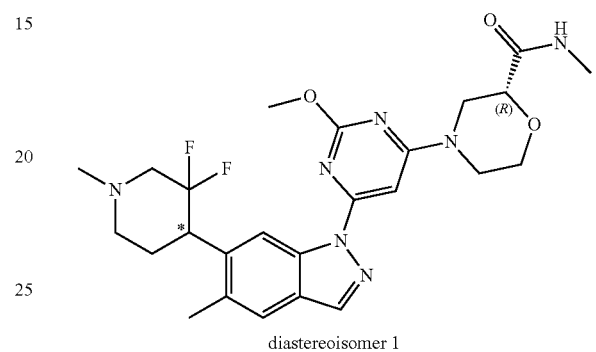

diastereoisomer 1

A suspension of 6-(3,3-difluoro-1-methylpiperidin-4-yl)-5-methyl-1H-indazole (enantiomer 1) (80 mg, 0.30 mmol), (R)-4-(6-chloro-2-methoxypyrimidin-4-yl)-N-methylmorpholine-2-carboxamide (129 mg, 0.451 mmol) and Cs$_2$CO$_3$ (196 mg, 0.603 mmol) in 3 mL of DMF was heated to 100° C. and stirred overnight. The reaction mixture was cooled to room temperature and then poured into 40 mL of water and extracted with EtOAc (15 mL×3). The combined organic layers were washed with brine, dried over Na$_2$SO$_4$ and concentrated. The crude was purified by prep-HPLC to give the title compound E17 (27.1 mg, yield 18%) as white solid. E17 is a single unknown enantiomer.

E17: $^1$H NMR (400 MHz, CDCl$_3$): δ 8.95 (s, 1H), 8.08 (s, 1H), 7.54 (s, 1H), 6.95 (s, 1H), 6.61 (br s, 1H), 4.66-4.59 (m, 1H), 4.53-4.45 (m, 1H), 4.12 (s, 3H), 4.06-4.00 (m, 2H), 3.75-3.64 (m, 1H), 3.37-3.19 (m, 2H), 3.10-3.00 (m, 2H), 3.00-2.91 (m, 1H), 2.87 (d, J=4.8 Hz, 3H), 2.47 (s, 3H), 2.42 (s, 3H), 2.42-2.32 (m, 2H), 2.28-2.17 (m, 1H), 1.96-1.87 (m, 1H).

$^{19}$F NMR (376 MHz, CDCl3): δ −103.02 (d, J=244.4 Hz, 1F), −112.53 (d, J=244.4 Hz, 1F).

LC-MS (mobile phase: from 65% water (0.02% NH$_4$OAc) and 35% CH$_3$CN to 35% water (0.02% NH$_4$OAc) and 65% CH$_3$CN in 6 min, purity is >95%, Rt=3.915 min; MS Calcd.: 515, MS Found: 516 [M+H]$^+$.

Chiral condition: Chiralpak IB 5 μm 4.6*250 mm, Hex: EtOH=80:20, Flow Rate: 1.0 ml/min, 230 nm, T=30° C. Rt=19.26 min, 72.8% de.

Example 18

(2R)-4-(6-(6-(3,3-Difluoro-1-methylpiperidin-4-yl)-5-methyl-1H-indazol-1-yl)-2-methoxypyrimidin-4-yl)-N-methylmorpholine-2-carboxamide (Diastereoisomer 2) (E18)

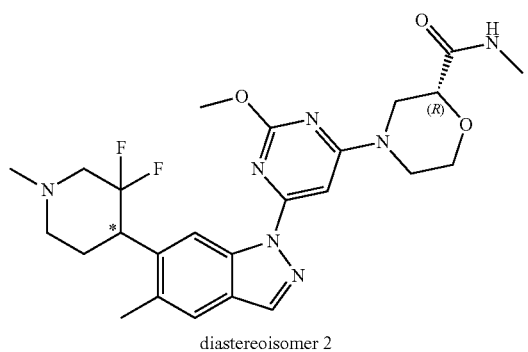

diastereoisomer 2

A suspension of 6-(3,3-difluoro-1-methyl-piperidin-4-yl)-5-methyl-1H-indazole (enantiomer 2) (80 mg, 0.30 mmol), (R)-4-(6-chloro-2-methoxypyrimidin-4-yl)-N-methylmorpholine-2-carboxamide (129 mg, 0.451 mmol) and $Cs_2CO_3$ (196 mg, 0.603 mmol) in 3 mL of DMF was heated to 100° C. and stirred overnight. The reaction mixture was cooled to room temperature and then poured into 40 mL of water and extracted with EtOAc (15 mL×3). The combined organic layers were washed with brine, dried over $Na_2SO_4$ and concentrated. The crude was purified by prep-HPLC to give the title compound E18 (29.1 mg, yield 19%) as white solid. E18 is a single unknown diastereoisomer.

E18: $^1$H NMR (400 MHz, $CDCl_3$): δ 8.95 (s, 1H), 8.08 (s, 1H), 7.54 (s, 1H), 6.95 (s, 1H), 6.65-6.56 (m, 1H), 4.68-4.59 (m, 1H), 4.51-4.45 (m, 1H), 4.12 (s, 3H), 4.07-4.02 (m, 2H), 3.73-3.66 (m, 1H), 3.37-3.26 (m, 2H), 3.20-3.01 (m, 2H), 3.00-2.91 (m, 1H), 2.87 (d, J=4.8 Hz, 3H), 2.47 (s, 3H), 2.42 (s, 3H), 2.42-2.32 (m, 2H), 2.28-2.17 (m, 1H), 1.94-1.85 (m, 1H).

$^{19}$F NMR (376 MHz, $CDCl_3$): δ -103.02 (d, J=242.5 Hz, 1F), -112.54 (d, J=242.5 Hz, 1F).

LC-MS (mobile phase: from 65% water (0.02% $NH_4OAc$) and 35% $CH_3CN$ to 35% water (0.02% $NH_4OAc$) and 65% $CH_3CN$ in 6 min, purity is >95%, Rt=3.940 min; MS Calcd.: 515, MS Found: 516 $[M+H]^+$.

Chiral condition: Chiralpak IB 5 μm 4.6*250 mm, Hex:EtOH=80:20, Flow Rate: 1.0 ml/min, 230 nm, T=30° C. Rt=16.508 min, 100% de.

Example 19

4-(6-(6-(3,3-Difluoro-1-(oxetan-3-yl)piperidin-4-yl)-5-methyl-1H-indazol-1-yl)pyrimidin-4-yl)morpholine (Enantiomer 1) (E19)

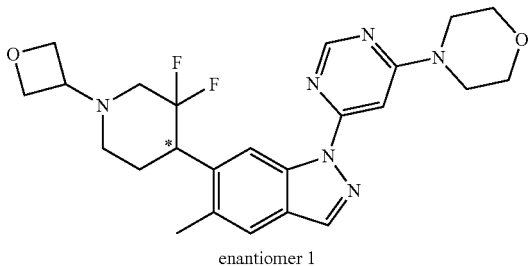 [SMILES: Cc1cc2cnn(-c3cc(N4CCOCC4)ncn3)c2cc1C1CCN(C2COC2)CC1(F)F]

enantiomer 1

A suspension of 6-(3,3-difluoro-1-(oxetan-3-yl)piperidin-4-yl)-5-methyl-1H-indazole (enantiomer 1) (80 mg, 0.26 mmol), 4-(6-chloro-pyrimidin-4-yl)-morpholine (104 mg, 0.52 mmol) and $Cs_2CO_3$ (169 mg, 0.520 mmol) in DMF (5 mL) was heated to 100° C. and stirred overnight. The reaction mixture was cooled to rt and then poured into water (40 mL) and extracted with EtOAc (20 mL×3). The combined organic layers were washed with brine, dried over $Na_2SO_4$ and concentrated. The crude was purified by prep. TLC (PE:EtOAc=2:3) to give E19 (19.6 mg, yield 16%) as white solid. E19 is a single unknown enantiomer.

E19: $^1$H NMR (400 MHz, $CDCl_3$): δ 8.98 (s, 1H), 8.61 (s, 1H), 8.06 (s, 1H), 7.54 (s, 1H), 7.12 (s, 1H), 4.78-4.68 (m, 4H), 3.82-3.80 (m, 4H), 3.74-3.70 (m, 5H), 3.45-3.34 (m, 1H), 3.20-3.14 (m, 1H), 3.06-3.03 (m, 1H), 2.59-2.48 (m, 1H), 2.48 (s, 3H), 2.40-2.31 (m, 1H), 2.20-2.15 (m, 1H), 1.99-1.96 (m, 1H).

$^{19}$F NMR (376 MHz, $CDCl_3$): δ -102.34 (d, J=244.0 Hz, 1F), -111.54 (d, J=242.5 Hz, 1F).

LC-MS (mobile phase: from 90% water (0.02% $NH_4OAc$) and 10% $CH_3CN$ to 5% water (0.02% $NH_4OAc$) and 95% $CH_3CN$ in 6 min), purity >95%, Rt=4.407 min; MS Calcd.: 470, MS Found: 471 $[M+H]^+$.

Chiral condition: Chiralpak ID 5 μm 4.6*250 nm, $CO_2$/MeOH/DEA=60/40/0.2, $CO_2$ Flow Rate: 1.8 ml/min, Co-Solvent Flow Rate: 1.2 ml/min, 230 nm, T=40° C. Rt=6.67 min, 100% ee.

Example 20

4-(6-(6-(3,3-Difluoro-1-(oxetan-3-yl)piperidin-4-yl)-5-methyl-1H-indazol-1-yl)pyrimidin-4-yl)morpholine (Enantiomer 2) (E20)

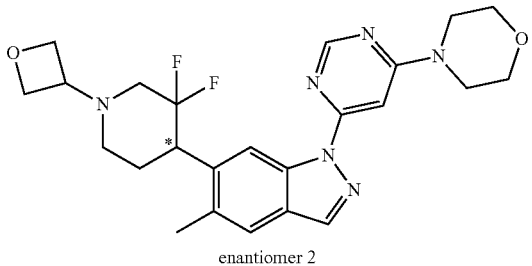 [SMILES: Cc1cc2cnn(-c3cc(N4CCOCC4)ncn3)c2cc1C1CCN(C2COC2)CC1(F)F]

enantiomer 2

A suspension of 6-(3,3-difluoro-1-(oxetan-3-yl)piperidin-4-yl)-5-methyl-1H-indazole (enantiomer 2) (90 mg, 0.29 mmol), 4-(6-chloro-pyrimidin-4-yl)-morpholine (116 mg, 0.580 mmol) and Cs$_2$CO$_3$ (189 mg, 0.582 mmol) in DMF (5 mL) was heated to 100° C. and stirred overnight. The reaction mixture was cooled to rt and then poured into water (40 mL) and extracted with EtOAc (20 mL×3). The combined organic layers were washed with brine, dried over Na$_2$SO$_4$ and concentrated. The crude was purified by prep. TLC (PE:EtOAc=2:3) to give E20 (38.1 mg, yield 28%) and as white solid. E20 is a single unknown enantiomer.

E20: $^1$H NMR (400 MHz, CDCl$_3$): δ 8.97 (s, 1H), 8.61 (s, 1H), 8.08 (s, 1H), 7.54 (s, 1H), 7.12 (s, 1H), 4.77-4.70 (m, 4H), 3.82-3.80 (m, 4H), 3.74-3.70 (m, 5H), 3.45-3.33 (m, 1H), 3.20-3.14 (m, 1H), 3.06-3.03 (m, 1H), 2.58-2.47 (m, 1H), 2.47 (s, 3H), 2.41-2.31 (m, 1H), 2.21-2.15 (m, 1H), 1.97-1.95 (m, 1H).

$^{19}$F NMR (376 MHz, CDCl$_3$): δ −102.33 (d, J=242.9 Hz, 1F), −111.54 (d, J=243.3 Hz, 1F).

LC-MS (mobile phase: from 90% water (0.02% NH$_4$OAc) and 10% CH$_3$CN to 5% water (0.02% NH$_4$OAc) and 95% CH$_3$CN in 6 min), purity >95%, Rt=4.406 min; MS Calcd.: 470, MS Found: 471 [M+H]$^+$.

Chiral condition: Chiralpak ID 5 μm 4.6×250 nm, CO$_2$/MeOH/DEA=60/40/0.2, CO$_2$ Flow Rate: 1.8 ml/min, Co-Solvent Flow Rate: 1.2 ml/min, 230 nm, T=40° C. Rt=5.97 min, 100% ee.

Example 21

4-(6-(6-(3,3-Difluoro-1-(oxetan-3-yl)piperidin-4-yl)-5-methyl-1H-indazol-1-yl)-2-methoxypyrimidin-4-yl)morpholine (Enantiomer 1) (E21)

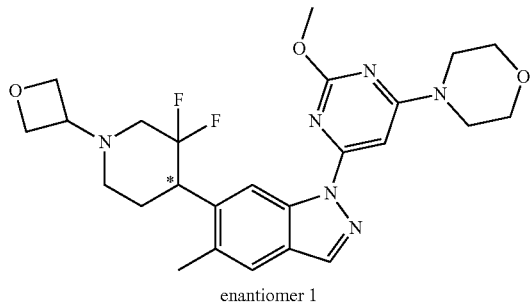 [SMILES: COc1nc(N2CCOCC2)cc(-n2ncc3cc(C)c(C4CCN(C5COC5)CC4(F)F)cc32)n1]

enantiomer 1

A suspension of 6-(3,3-difluoro-1-(oxetan-3-yl)piperidin-4-yl)-5-methyl-1H-indazole (enantiomer 1) (100 mg, 0.325 mmol), 4-(6-chloro-2-methoxypyrimidin-4-yl)morpholine (152 mg, 0.662 mmol) and Cs$_2$CO$_3$ (215 mg, 0.660 mmol) in DMF (5 mL) was heated to 100° C. and stirred overnight. The reaction mixture was cooled to rt and then poured into water (40 mL) and extracted with EtOAc (20 mL×3). The combined organic layers were washed with brine, dried over Na$_2$SO$_4$ and concentrated. The crude was purified by prep. HPLC [Sunfire, C18, 5 μm, 19*150 mm, 35-80% B; A: H2O (0.1% NH4HCO3), B: CH$_3$CN; UV: 214 nm; flow rate: 20 mL/min] to give E21 (46.9 mg, yield 29%) as white solid. E21 is a single unknown enantiomer.

E21: $^1$H NMR (400 MHz, CDCl$_3$): δ 8.99 (s, 1H), 8.08 (s, 1H), 7.55 (s, 1H), 6.84 (s, 1H), 4.74-4.67 (m, 4H), 4.15 (s, 3H), 3.80-3.78 (m, 4H), 3.75-3.72 (m, 5H), 3.44-3.31 (m, 1H), 3.16-3.10 (m, 1H), 2.99-2.97 (m, 1H), 2.48 (s, 3H), 2.40-2.27 (m, 2H), 2.21-2.15 (m, 1H), 1.97-1.93 (m, 1H).

$^{19}$F NMR (376 MHz, CDCl$_3$): δ −102.51 (d, J=242.1 Hz, 1F), −112.10 (d, J=241.8 Hz, 1F).

LC-MS [mobile phase: from 80% water (0.02% NH$_4$OAc) and 20% CH$_3$CN to 5% water (0.02% NH$_4$OAc) and 95% CH$_3$CN in 6.5 min]: purity >95%, Rt=4.177 min; MS Calcd.: 500, MS Found: 501 [M+H]$^+$.

Chiral HPLC [Chiral condition: Chiralpak IC 5 μm 4.6*250 nm, MeOH/EtOH=50/50, Flow Rate: 1 ml/min, 230 nm, T=30° C.]: Rt=13.548 min, 100% ee.

Example 22

4-(6-(6-(3,3-Difluoro-1-(oxetan-3-yl)piperidin-4-yl)-5-methyl-1H-indazol-1-yl)-2-methoxypyrimidin-4-yl)morpholine (Enantiomer 2) (E22)

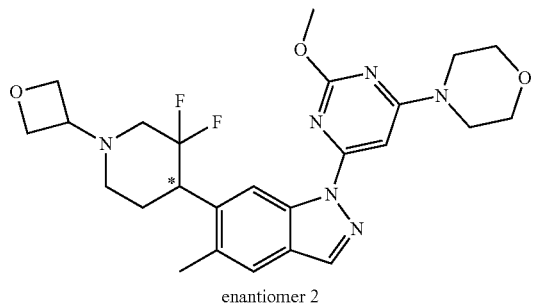 [SMILES: COc1nc(N2CCOCC2)cc(-n2ncc3cc(C)c(C4CCN(C5COC5)CC4(F)F)cc32)n1]

enantiomer 2

A suspension of 6-(3,3-difluoro-1-(oxetan-3-yl)piperidin-4-yl)-5-methyl-1H-indazole (enantiomer 2) (100 mg, 0.325 mmol), 4-(6-chloro-2-methoxypyrimidin-4-yl)morpholine (152 mg, 0.662 mmol) and Cs$_2$CO$_3$ (215 mg, 0.660 mmol) in DMF (5 mL) was heated to 100° C. and stirred overnight. The reaction mixture was cooled to rt and then poured into water (40 mL) and extracted with EtOAc (20 mL×3). The combined organic layers were washed with brine, dried over Na$_2$SO$_4$ and concentrated. The crude was purified by prep. HPLC [Sunfire, C18, 5 μm, 19*150 mm, 35-80% B; A: H$_2$O (0.1% NH$_4$HCO$_3$), B: CAN; UV: 214 nm; flow rate: 20 mL/min] to give E22 (32.8 mg, yield 20%) as white solid. E22 is a single unknown enantiomer.

E22: $^1$H NMR (400 MHz, CDCl$_3$): δ 8.99 (s, 1H), 8.08 (s, 1H), 7.55 (s, 1H), 6.84 (s, 1H), 4.72-4.68 (m, 4H), 4.15 (s, 3H), 3.80-3.78 (m, 4H), 3.74-3.72 (m, 5H), 3.44-3.32 (m, 1H), 3.16-3.10 (m, 1H), 2.99-2.96 (m, 1H), 2.48 (s, 3H), 2.40-2.27 (m, 2H), 2.21-2.15 (m, 1H), 1.97-1.93 (m, 1H).

$^{19}$F NMR (376 MHz, CDCl$_3$): δ −102.52 (d, J=241.4 Hz, 1F), −112.10 (d, J=242.5 Hz, 1F).

LC-MS [mobile phase: from 80% water (0.02% NH$_4$OAc) and 20% CH$_3$CN to 5% water (0.02% NH$_4$OAc) and 95% CH$_3$CN in 6.5 min]: purity >95%, Rt=4.174 min; MS Calcd.: 500, MS Found: 501 [M+H]$^+$.

Chiral HPLC (Chiral condition: Chiralpak IC 5 μm 4.6*250 nm, MeOH/EtOH=50/50, Flow Rate: 1 ml/min, 230 nm, T=30° C.): Rt=12.047 min, 100% ee.

Example 23

4-(6-(6-(3,3-Difluoro-1-(oxetan-3-yl)piperidin-4-yl)-5-methyl-1H-indazol-1-yl)-2-ethoxypyrimidin-4-yl)morpholine (Enantiomer 1) (E23)

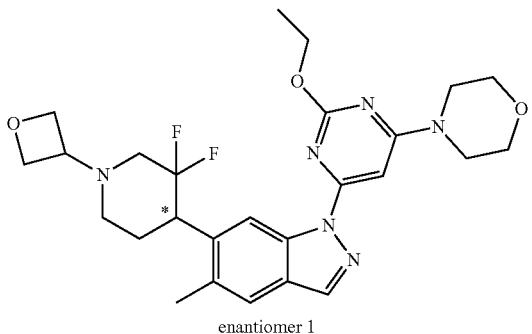 [SMILES: CCOc1nc(N2CCOCC2)cc(-n2ncc3cc(C)c(C4CCN(C5COC5)CC4(F)F)cc32)n1]

enantiomer 1

A mixture of 6-(3,3-difluoro-1-(oxetan-3-yl)piperidin-4-yl)-5-methyl-1H-indazole (enantiomer 1) (80 mg, 0.26 mmol), 4-(6-chloro-2-ethoxypyrimidin-4-yl)morpholine (127 mg, 0.52 mmol) and $Cs_2CO_3$ (169 mg, 0.520 mmol) in DMF (6 mL) was heated to 100° C. and stirred overnight. The reaction mixture was cooled to rt, diluted with water (20 mL) and extracted with EtOAc (20 mL×3). The combined organic layers were washed with brine (20 mL), dried over $Na_2SO_4$, filtered and concentrated. The residue was purified by prep. HPLC to give E23 (26 mg, yield 19%) as white solid. E23 is a single unknown enantiomer.

E23: $^1$H NMR (300 MHz, $CDCl_3$): δ 8.98 (s, 1H), 8.08 (s, 1H), 7.55 (s, 1H), 6.84 (s, 1H), 4.74-4.58 (m, 6H), 3.80-3.70 (m, 9H), 3.46-3.30 (m, 1H), 3.15-3.06 (m, 1H), 2.97-2.93 (m, 1H), 2.47 (s, 3H), 2.41-2.13 (m, 3H), 1.97-1.91 (m, 1H), 1.56 (t, J=7.2 Hz, 3H).

$^{19}$F NMR (376 MHz, $CDCl_3$): δ −102.29 (d, J=243.3 Hz, 1F), −111.52 (d, J=243.3 Hz, 1F).

LC-MS (mobile phase: from 70% water (0.02% $NH_4OAc$) and 30% $CH_3CN$ to 5% water (0.02% $NH_4OAc$) and 95% $CH_3CN$ in 6 min), purity >95%, Rt=4.134 min; MS Calcd.: 514, MS Found: 515[M+H]$^+$.

Chiral condition: Chiralpak IB 5 μm 4.6*250 mm, Hex/EtOH=50/50, Flow Rate: 1.0 ml/min, 230 nm, T=30° C. Rt=7.860 min, 100% ee.

Example 24

4-(6-(6-(3,3-Difluoro-1-(oxetan-3-yl)piperidin-4-yl)-5-methyl-1H-indazol-1-yl)-2-ethoxypyrimidin-4-yl)morpholine (Enantiomer 2) (E24)

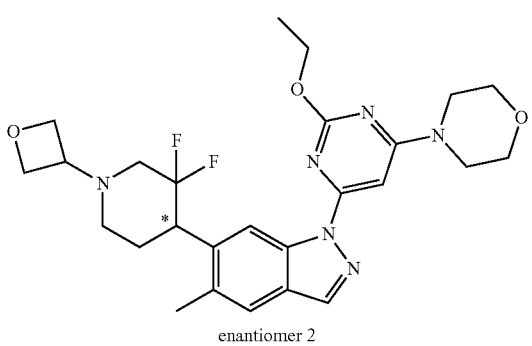 [SMILES: CCOc1nc(N2CCOCC2)cc(-n2ncc3cc(C)c(C4CCN(C5COC5)CC4(F)F)cc32)n1]

enantiomer 2

A mixture of 6-(3,3-difluoro-1-(oxetan-3-yl)piperidin-4-yl)-5-methyl-1H-indazole (enantiomer 2) (80 mg, 0.26 mmol), 4-(6-chloro-2-ethoxypyrimidin-4-yl)morpholine (127 mg, 0.520 mmol) and $Cs_2CO_3$ (169 mg, 0.520 mmol) in DMF (8 mL) was heated to 100° C. and stirred overnight. After cooled to rt the reaction mixture was diluted with water (20 mL) and extracted with EtOAc (20 mL×3). The combined organic layers were washed with brine (20 mL) and water (20 mL), dried over $Na_2SO_4$ and concentrated. The residue was purified by prep. HPLC to give E24 (33 mg, yield 24%) as white solid. E24 is a single unknown enantiomer.

E24: $^1$H NMR (300 MHz, $CDCl_3$): δ 8.98 (s, 1H), 8.08 (s, 1H), 7.55 (s, 1H), 6.84 (s, 1H), 4.74-4.58 (m, 6H), 3.83-3.70 (m, 9H), 3.46-3.30 (m, 1H), 3.15-3.07 (m, 1H), 2.97-2.93 (m, 1H), 2.47 (s, 3H), 2.35-2.12 (m, 3H), 1.98-1.92 (m, 1H), 1.59-1.54 (m, 3H).

$^{19}$F NMR (376 MHz, $CDCl_3$): δ −102.29 (d, J=242.1 Hz, 1F), −111.52 (d, J=242.1 Hz, 1F).

LC-MS (mobile phase: from 70% water (0.02% $NH_4OAc$) and 30% $CH_3CN$ to 5% water (0.02% $NH_4OAc$) and 95% $CH_3CN$ in 6 min), purity >95%, Rt=4.142 min; MS Calcd.: 514, MS Found: 515[M+H]$^+$.

Chiral condition: Chiralpak IB 5 μm 4.6*250 mm, Hex/EtOH=50/50, Flow Rate: 1.0 ml/min, 230 nm, T=30° C. Rt=6.996 min, 100% ee.

Example 25

4-(6-(6-(3,3-Difluoro-1-(oxetan-3-yl)piperidin-4-yl)-5-methyl-1H-indazol-1-yl)-2-isopropoxypyrimidin-4-yl)morpholine (Enantiomer 1) (E25)

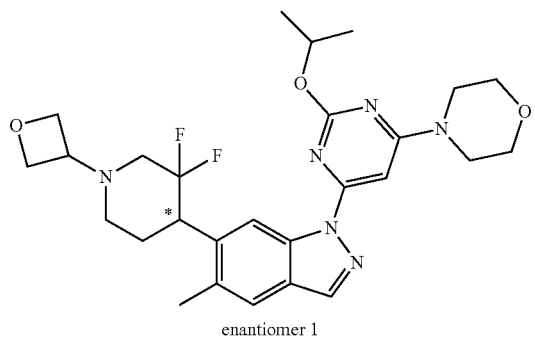 [SMILES: Cc1cc2cnn(-c3cc(N4CCOCC4)nc(OC(C)C)n3)c2cc1C1CCN(C2COC2)CC1(F)F]

enantiomer 1

A suspension of 6-(3,3-difluoro-1-(oxetan-3-yl)piperidin-4-yl)-5-methyl-1H-indazole (enantiomer 1) (100 mg, 0.325 mmol), 4-(6-chloro-2-isopropoxy-pyrimidin-4-yl)-morpholine (127 mg, 0.500 mmol) and $Cs_2CO_3$ (215 mg, 0.660 mmol) in DMF (8 mL) was heated to 100° C. and stirred overnight. The reaction mixture was cooled to rt and then poured into water (20 mL) and extracted with EtOAc (20 mL×3). The combined organic layers were washed with brine (20 mL), dried over $Na_2SO_4$ and concentrated. The crude was purified by prep. HPLC to give E25 (35 mg, yield 20%) as white solid. E25 is a single unknown enantiomer.

E25: $^1$H NMR (400 MHz, $CDCl_3$): δ 8.93 (s, 1H), 8.08 (s, 1H), 7.55 (s, 1H), 6.84 (s, 1H), 5.60-5.53 (m, 1H), 4.73-4.68 (m, 2H), 4.66-4.63 (m, 2H), 3.79-3.70 (m, 9H), 3.44-3.33 (m, 1H), 3.13-3.07 (m, 1H), 2.95-2.91 (m, 1H), 2.48 (s, 3H), 2.38-2.27 (m, 2H), 2.19-2.13 (m, 1H), 1.95-1.91 (m, 1H), 1.58-1.53 (m, 6H).

¹⁹F NMR (376 MHz, CDCl₃): δ −102.05 (d, J=238.4 Hz, 1F), −111.73 (d, J=242.1 Hz, 1F).

LC-MS [mobile phase: from 70% water (0.02% NH₄OAc) and 30% CH₃CN to 5% water (0.02% NH₄OAc) and 95% CH₃CN in 6.5 min]: purity >95%, Rt=4.316 min; MS Calcd.: 528, MS Found: 529 [M+H]⁺.

Chiral HPLC (Chiral condition: Chiralpak IC 5 μm 4.6*250 mm, CO₂/MeOH=70/30, Co-Solvent: MeOH, CO₂ Flow Rate: 2.1 ml/min, Co-Solvent Flow Rate: 0.899 ml/min, 254 nm, T=40.1° C.): Rt=10.87 min, 100% ee.

Example 26

4-(6-(6-(3,3-Difluoro-1-(oxetan-3-yl)piperidin-4-yl)-5-methyl-1H-indazol-1-yl)-2-isopropoxypyrimidin-4-yl)morpholine (E26)

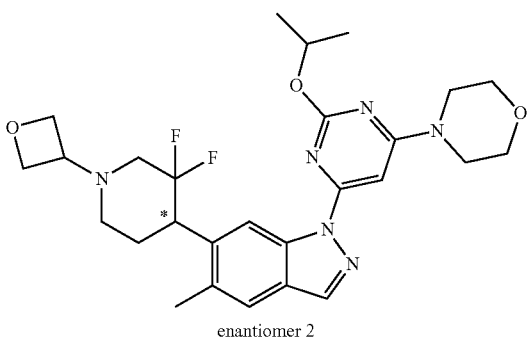 [SMILES: Cc1cc2cnn(-c3cc(N4CCOCC4)nc(OC(C)C)n3)c2cc1C1CCN(C2COC2)CC1(F)F]

enantiomer 2

A suspension of 6-(3,3-difluoro-1-(oxetan-3-yl)piperidin-4-yl)-5-methyl-1H-indazole (enantiomer 2) (100 mg, 0.325 mmol), 4-(6-chloro-2-isopropoxypyrimidin-4-yl)morpholine (127 mg, 0.500 mmol) and Cs₂CO₃ (215 mg, 0.660 mmol) in DMF (8 mL) was heated to 100° C. and stirred overnight. The reaction mixture was cooled to rt and then poured into water (20 mL) and extracted with EtOAc (20 mL×3). The combined organic layers were washed with brine (20 mL), dried over Na₂SO₄ and concentrated. The crude was purified by prep. HPLC to give E26 (36 mg, yield 21%) as white solid. E26 is a single unknown enantiomer.

E26: ¹H NMR (400 MHz, CDCl₃): δ 8.93 (s, 1H), 8.08 (s, 1H), 7.55 (s, 1H), 6.84 (s, 1H), 5.61-5.52 (m, 1H), 4.74-4.63 (m, 4H), 3.79-3.70 (m, 9H), 3.45-3.33 (m, 1H), 3.13-3.07 (m, 1H), 2.94-2.91 (m, 1H), 2.48 (s, 3H), 2.40-2.28 (m, 2H), 2.19-2.13 (m, 1H), 1.95-1.92 (m, 1H), 1.56-1.53 (m, 6H).

¹⁹F NMR (376 MHz, CDCl₃): δ −102.05 (d, J=242.1 Hz, 1F), −110.73 (d, J=242.1 Hz, 1F).

LC-MS [mobile phase: from 70% water (0.02% NH₄OAc) and 30% CH₃CN to 5% water (0.02% NH₄OAc) and 95% CH₃CN in 6.5 min]: purity >95%, Rt=4.340 min; MS Calcd.: 528, MS Found: 529 [M+H]⁺.

Chiral HPLC (Chiral condition: Chiralpak IC 5 μm 4.6*250 mm, CO₂/MeOH=70/30, Co-Solvent: MeOH, CO₂ Flow Rate: 2.1 ml/min, Co-Solvent Flow Rate: 0.899 ml/min, 254 nm, T=40° C.): Rt=9.42 min, 100% ee.

Example 27

(cis)-4-(6-(6-(3-Fluoro-1-(2-methoxyethyl)piperidin-4-yl)-5-methyl-1H-indazol-1-yl)pyrimidin-4-yl)morpholine (Enantiomer 1) (E27)

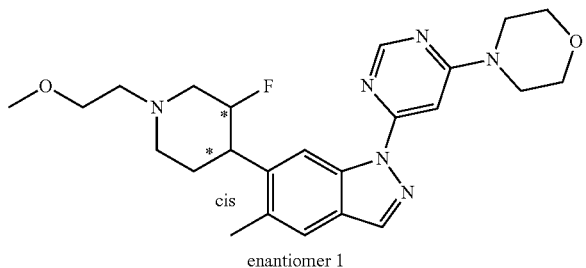 [SMILES: COCCN1CCC(c2cc3c(cnn3-c3cc(N4CCOCC4)ncn3)cc2C)C(F)C1]

enantiomer 1

A solution of (cis)-6-(3-fluoro-1-(2-methoxyethyl)piperidin-4-yl)-5-methyl-1H-indazole (enantiomer 1) (80 mg, 0.27 mmol), 4-(6-chloro-pyrimidin-4-yl)-morpholine (108 mg, 0.540 mmol) and Cs₂CO₃ (176 mg, 0.540 mmol) in DMF (3 mL) was heated to 100° C. and stirred for 2 hrs. The reaction mixture was cooled to rt and then poured into water (30 mL). EtOAc (20 mL×3) was added to extract the desired. The combined organic layers were washed with brine (20 mL), dried over Na₂SO₄ and concentrated. The residue was purified by prep. HPLC to give E27 (24.2 mg, yield 20%) as white solid. E27 is a single unknown enantiomer.

E27: ¹H NMR (400 MHz, CDCl₃): δ 8.89 (s, 1H), 8.62 (s, 1H), 8.06 (s, 1H), 7.52 (s, 1H), 7.12 (s, 1H), 5.12-4.94 (m, 1H), 3.83-3.80 (m, 4H), 3.73-3.71 (m, 4H), 3.58-3.53 (m, 2H), 3.49-3.47 (m, 1H), 3.41 (s, 3H), 3.14-3.05 (m, 2H), 2.78-2.68 (m, 2H), 2.48 (s, 3H), 2.23-2.01 (m, 3H), 1.94-1.88 (m, 1H).

¹⁹F NMR (376 MHz, CDCl₃): δ −183.95 (s, 1F).

LC-MS (mobile phase: from 80% water (0.02% NH₄OAc) and 20% CH₃CN to 5% water (0.02% NH₄OAc) and 95% CH₃CN in 6.5 min), purity >95%, Rt=4.331 min; MS Calcd.: 454, MS Found: 455 [M+H]⁺.

Chiral condition: Chiralpak IC 5 μm 4.6*250 mm, Hex/EtOH=80/20, Flow Rate: 1.0 ml/min, 230 nm, T=30° C. Rt=11.215 min, 94.3% ee.

Example 28

(cis)-4-(6-(6-(3-Fluoro-1-(2-methoxyethyl)piperidin-4-yl)-5-methyl-1H-indazol-1-yl)pyrimidin-4-yl)morpholine (Enantiomer 2) (E28)

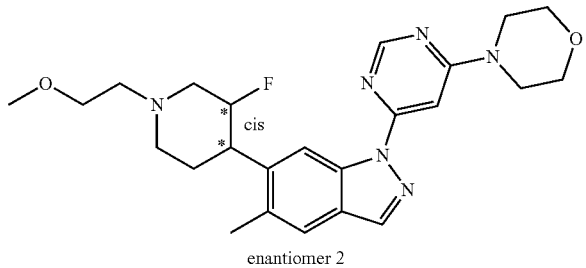 [SMILES: COCCN1CCC(c2cc3c(cnn3-c3cc(N4CCOCC4)ncn3)cc2C)C(F)C1]

enantiomer 2

A solution of (cis)-6-(3-fluoro-1-(2-methoxyethyl)piperidin-4-yl)-5-methyl-1H-indazole (enantiomer 2) (80 mg, 0.27 mmol), 4-(6-chloropyrimidin-4-yl)morpholine (108 mg, 0.540 mmol) and Cs$_2$CO$_3$ (176 mg, 0.540 mmol) in DMF (3 mL) was heated to 100° C. and stirred for 2 hrs. The reaction mixture was cooled to rt and then poured into water (30 mL). EtOAc (20 mL×3) was added to extract the desired. The combined organic layers were washed with brine (20 mL), dried over Na$_2$SO$_4$ and concentrated. The residue was purified by prep. HPLC to give E28 (23.4 mg, yield 19%) as white solid. E28 is a single unknown enantiomer.

E28: $^1$H NMR (400 MHz, CDCl$_3$): δ 8.89 (s, 1H), 8.62 (s, 1H), 8.07 (s, 1H), 7.52 (s, 1H), 7.12 (s, 1H), 5.13-4.94 (m, 1H), 3.83-3.80 (m, 4H), 3.73-3.71 (m, 4H), 3.59-3.57 (m, 2H), 3.52-3.47 (m, 1H), 3.41 (s, 3H), 3.14-3.05 (m, 2H), 2.78-2.68 (m, 2H), 2.48 (s, 3H), 2.26-2.00 (m, 3H), 1.94-1.87 (m, 1H).

$^{19}$F NMR (376 MHz, CDCl$_3$): δ −183.95 (s, 1F).

LC-MS (mobile phase: from 80% water (0.02% NH$_4$OAc) and 20% CH$_3$CN to 5% water (0.02% NH$_4$OAc) and 95% CH$_3$CN in 6 min), purity >95%, Rt=4.335 min; MS Calcd.: 454, MS Found: 455 [M+H]$^+$.

Chiral condition: Chiralpak IC 5 μm 4.6*250 mm, Hex/EtOH=80/20, Flow Rate: 1.0 ml/min, 230 nm, T=30° C. Rt=10.692 min, 100% ee.

Example 29

(cis)-(2R)-4-(6-(6-(3-Fluoro-1-(2-methoxyethyl)piperidin-4-yl)-5-methyl-1H-indazol-1-yl)pyrimidin-4-yl)-N-methylmorpholine-2-carboxamide (Diastereoisomer 2) (E29)

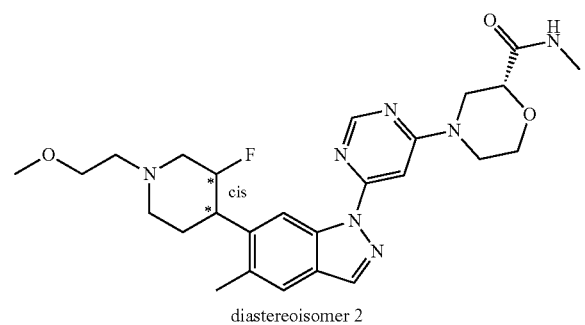

diastereoisomer 2

A solution of (cis)-6-(3-fluoro-1-(2-methoxyethyl)piperidin-4-yl)-5-methyl-1H-indazole (enantiomer 2) (80 mg, 0.27 mmol), (R)-4-(6-Chloropyrimidin-4-yl)-N-methylmorpholine-2-carboxamide (105 mg, 0.41 mmol) and Cs$_2$CO$_3$ (134 mg, 0.412 mmol) in DMF (3 mL) was heated to 100° C. and stirred for 3 hrs. The reaction mixture was cooled to rt and then poured into water (30 mL) and extracted with EtOAc (30 mL×3). The combined organic layers were washed with brine (30 mL), dried over Na$_2$SO$_4$ and concentrated. The residue was purified by prep-HPLC to give crude product (27 mg). The crude product was separated by chiral prep-HPLC to give the title compound E29 (20 mg, yield 14%) as white solid. E29 is a single unknown diastereoisomer.

E29: $^1$H NMR (400 MHz, CDCl$_3$): δ 8.88 (s, 1H), 8.63 (s, 1H), 8.07 (s, 1H), 7.52 (s, 1H), 7.24 (s, 1H), 6.63 (s, 1H), 5.11-4.94 (m, 1H), 4.68-4.65 (m, 1H), 4.48-4.45 (m, 1H), 4.12-4.06 (m, 2H), 3.77-3.70 (m, 1H), 3.59-3.57 (m, 2H), 3.53-3.46 (m, 1H), 3.41 (s, 3H), 3.11-3.05 (m, 3H), 3.00-2.93 (m, 1H), 2.88 (d, J=4.8 Hz, 3H), 2.78-2.69 (m, 2H), 2.48 (s, 3H), 2.24-2.01 (m, 3H), 1.95-1.88 (m, 1H).

$^{19}$F NMR (376 MHz, CDCl$_3$): δ −183.95 (s, 1F).

LC-MS (mobile phase: from 95% water (0.02% NH$_4$OAc) and 5% CH$_3$CN to 5% water (0.02% NH$_4$OAc) and 95% CH$_3$CN in 6 min), purity >95%, Rt=4.348 min; MS Calcd.: 511, MS Found: 512 [M+H]$^+$.

Chiral condition: Chiralpak OD-H 5 μm 4.6*250 mm, Hex/EtOH=80/20, Flow Rate: 1.0 ml/min, 230 nm, T=30° C. Rt=12.855 min, 100% de.

Example 30

(cis)-(2S)-4-(6-(6-(3-Fluoro-1-(2-methoxyethyl)piperidin-4-yl)-5-methyl-1H-indazol-1-yl)pyrimidin-4-yl)-N-methylmorpholine-2-carboxamide (Diastereoisomer 2) (E30)

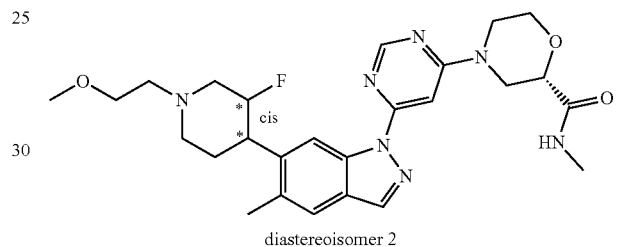

diastereoisomer 2

A solution of (cis)-6-(3-fluoro-1-(2-methoxyethyl)piperidin-4-yl)-5-methyl-1H-indazole (enantiomer 2) (100 mg, 0.334 mmol), (S)-4-(6-chloropyrimidin-4-yl)-N-methylmorpholine-2-carboxamide (132 mg, 0.516 mmol) and Cs$_2$CO$_3$ (168 mg, 0.516 mmol) in DMF (3 mL) was heated to 100° C. and stirred for 3 hrs. The reaction mixture was cooled to rt and then poured into water (30 mL) and extracted with EtOAc (30 mL×3). The combined organic layers were washed with brine (30 mL), dried over Na$_2$SO$_4$ and concentrated. The residue was purified by prep-HPLC to give crude product (45 mg). The crude product was further separated by chiral prep-HPLC to give the title compound E30 (26 mg, yield 15%) as white solid. E30 is a single unknown diastereoisomer.

E30: $^1$H NMR (400 MHz, CDCl$_3$): δ 8.88 (s, 1H), 8.63 (s, 1H), 8.07 (s, 1H), 7.52 (s, 1H), 7.23 (s, 1H), 6.63 (s, 1H), 5.12-4.94 (m, 1H), 4.68-4.64 (m, 1H), 4.49-4.45 (m, 1H), 4.12-4.05 (m, 2H), 3.76-3.71 (m, 1H), 3.59-3.57 (m, 2H), 3.51-3.47 (m, 1H), 3.41 (s, 3H), 3.10-3.08 (m, 3H), 2.99-2.93 (m, 1H), 2.88 (d, J=4.8 Hz, 3H), 2.78-2.71 (m, 2H), 2.48 (s, 3H), 2.26-2.01 (m, 3H), 1.94-1.83 (m, 1H).

$^{19}$F NMR (376 MHz, CDCl$_3$): δ −183.934 (s, 1F).

LC-MS (mobile phase: from 95% water (0.02% NH$_4$OAc) and 5% CH$_3$CN to 5% water (0.02% NH$_4$OAc) and 95% CH$_3$CN in 6 min), purity >95%, Rt=4.351 min; MS Calcd.: 511, MS Found: 512 [M+H]$^+$.

Chiral condition: Chiralpak OD-H 5um 4.6*250 mm, Hex/EtOH=80/20, Flow Rate: 1.0 ml/min, 230 nm, T=30° C. Rt=9.907 min, 98.9% de.

Example 31

(cis)-(2S)-4-(6-(6-(3-Fluoro-1-(2-methoxyethyl)piperidin-4-yl)-5-methyl-1H-indazol-1-yl)pyrimidin-4-yl)-N-methylmorpholine-2-carboxamide (Diastereoisomer 1') (E31)

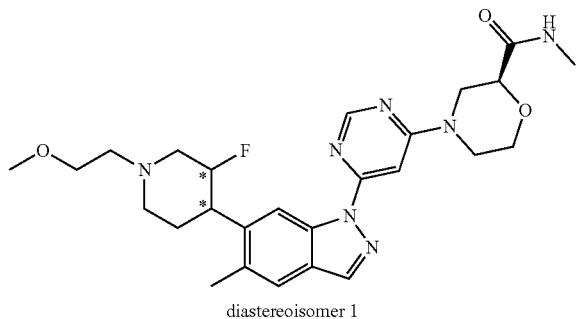

diastereoisomer 1

A solution of (cis)-6-(3-fluoro-1-(2-methoxyethyl)piperidin-4-yl)-5-methyl-1H-indazole (enantiomer 1') (60 mg, 0.21 mmol), (S)-4-(6-chloro-pyrimidin-4-yl)-morpholine-2-carboxylic acid methylamide (79 mg, 0.31 mmol) and Cs$_2$CO$_3$ (101 mg, 0.309 mmol) in DMF (3 mL) was heated to 100° C. and stirred for 3 hrs. The reaction mixture was cooled to rt and then poured into water (30 mL) and extracted with EtOAc (20 mL×3). The combined organic layers were washed with brine (20 mL×2), dried over Na$_2$SO$_4$ and concentrated. The residue was purified by prep. TLC (CH$_2$Cl$_2$:CH$_3$OH=15:1) to give crude product (40 mg). The crude product was purified by prep. chiral HPLC to give the title compound E31 (29.3 mg, yield 28%) as white solid. E31 is a single unknown diastereoisomer.

E31: $^1$H NMR (400 MHz, CDCl$_3$): δ 8.88 (s, 1H), 8.64 (s, 1H), 8.08 (s, 1H), 7.53 (s, 1H), 7.24 (s, 1H), 6.64 (br s, 1H), 5.13-4.94 (m, 1H), 4.69-4.65 (m, 1H), 4.48-4.45 (m, 1H), 4.12-4.06 (m, 2H), 3.76-3.71 (m, 1H), 3.59-3.57 (m, 2H), 3.51-3.48 (m, 1H), 3.41 (s, 3H), 3.11-3.08 (m, 3H), 3.00-2.94 (m, 1H), 2.88 (d, J=4.4 Hz, 3H), 2.79-2.68 (m, 2H), 2.48 (s, 3H), 2.24-2.01 (m, 3H), 1.94-1.88 (m, 1H). $^{19}$F NMR (376 MHz, CDCl$_3$): δ -183.9 (s, 1F).

LC-MS (mobile phase: 20-95% CH$_3$CN in water in 6.5 min), purity >95%, Rt=3.899 min; MS Calcd.: 511, MS Found: 512 [M+H]$^+$.

Chiral condition: Chiralpak OD-H, 5 μm 4.6*250 mm, Hex/EtOH=80/20, Flow Rate: 1.0 nil/min, 230 nm, T=ambient. Rt=10.346 min, 100% de.

Example 32

(cis)-(2R)-4-(6-(6-(3-Fluoro-1-(2-methoxyethyl)piperidin-4-yl)-5-methyl-1H-indazol-1-yl)pyrimidin-4-yl)-N-methylmorpholine-2-carboxamide (Diastereoisomer 1) (E32)

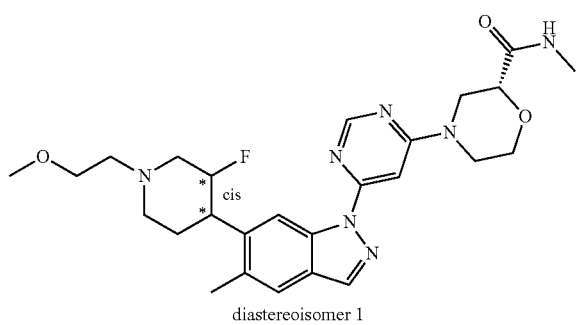

diastereoisomer 1

A solution of (cis)-6-(3-fluoro-1-(2-methoxyethyl)piperidin-4-yl)-5-methyl-1H-indazole (enantiomer 1) (80 mg, 0.27 mmol), (R)-4-(6-chloropyrimidin-4-yl)-N-methylmorpholine-2-carboxamide (105 mg, 0.410 mmol) and Cs$_2$CO$_3$ (134 mg, 0.412 mmol) in DMF (3 mL) was heated to 100° C. and stirred for 3 hrs. The reaction mixture was cooled to rt and then poured into water (30 mL) and extracted with EtOAc (30 mL×3). The combined organic layers were washed with brine (30 mL), dried over Na$_2$SO$_4$ and concentrated. The residue was purified by prep-HPLC to give crude product (40 mg). The crude product was separated by chiral pep-HPLC to give the title compound E32 (25.6 mg, yield 18%) as a white solid. E32 is a single unknown diastereoisomer.

E30: $^1$H NMR (400 MHz, CDCl$_3$): δ 8.88 (s, 1H), 8.64 (s, 1H), 8.07 (s, 1H), 7.52 (s, 1H), 7.24 (s, 1H), 6.62 (br s, 1H), 5.10-4.93 (m, 1H), 4.68-4.64 (m, 1H), 4.49-4.45 (m, 1H), 4.12-4.06 (m, 2H), 3.76-3.70 (m, 1H), 3.60-3.57 (m, 2H), 3.51-3.48 (m, 1H), 3.41 (s, 3H), 3.11-3.08 (m, 3H), 3.00-2.93 (m, 1H), 2.88 (d, J=4.4 Hz, 3H), 2.79-2.69 (m, 2H), 2.48 (s, 3H), 2.25-2.01 (m, 3H), 1.95-1.88 (m, 1H).

$^{19}$F NMR (376 MHz, CDCl$_3$): δ -183.95 (s, 1F).

LC-MS (mobile phase: from 95% water (0.02% NH$_4$OAc) and 5% CH$_3$CN to 5% water (0.02% NH$_4$OAc) and 95% CH$_3$CN in 6.5 min), purity >95%, Rt=4.350 min; MS Calcd.: 511, MS Found: 512 [M+H]$^+$.

Chiral condition: Chiralpak OD-H 5 μm 4.6*250 mm, Hex/EtOH=80/20, Flow Rate: 1.0 ml/min, 230 nm, T=ambient. Rt=15.399 min, 100% de.

Example 33

(cis)-1-(2-(6-(3-Fluoro-1-(2-methoxyethyl)piperidin-4-yl)-5-methyl-1H-indazol-1-yl)-5-methoxypyridin-4-yl)azetidin-3-ol (Enantiomer 2) (E33)

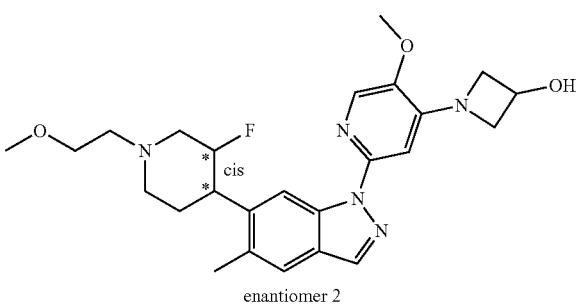 [SMILES: COCCN1CCC(c2cc3c(cnn3-c3cc(N4CC(O)C4)c(OC)cn3)cc2C)C(F)C1]

enantiomer 2

Step 1:

A reaction mixture of 6-(3-fluoro-1-(2-methoxyethyl)piperidin-4-yl)-5-methyl-1H-indazole (enantiomer 2) (38.0 mg, 0.131 mmol), 2-chloro-5-methoxy-4-(3-((tetrahydro-2H-pyran-2-yl)oxy)azetidin-1-yl)pyridine (30 mg, 0.100 mmol), sodium tert-butoxide (38.6 mg, 0.402 mmol), Pd$_2$dba$_3$ (9.20 mg, 10.04 μmol), di-tert-butyl(2',4',6'-triisopropyl-[1,1-biphenyl]-2-yl)phosphine (8.53 mg, 0.020 mmol) and toluene (2 mL) was heated to 100° C. for 16 hours. After cooling and diluted with ethyl acetate, the mixture was filtered and the filtrate was concentrated and the residue was purified by C18 column (0.5% TFA in water, water/acetonitrile) to give 6-(3-fluoro-1-(2-methoxyethyl)piperidin-4-yl)-1-(5-methoxy-4-(3-((tetrahydro-2H-pyran-2-yl)oxy)azetidin-1-yl)pyridin-2-yl)-5-methyl-1H-indazole (26 mg, 0.047 mmol, 46.8% yield).

MS: 554.0 [M+H]$^+$.

Step 2:

To a solution of rel-6-(3-fluoro-1-(2-methoxyethyl)piperidin-4-yl)-1-(5-methoxy-4-(3-((tetrahydro-2H-pyran-2-yl)oxy)azetidin-1-yl)pyridin-2-yl)-5-methyl-1H-indazole (26 mg, 0.047 mmol) and Methanol (3 mL) was added HCl (0.094 mL, 0.470 mmol, 5M in isopropanol). The reaction solution was aged at room temperature for 3 hours. The solvent was removed in vacuo and the residue was purified by MDAP to give cis-1-(2-(6-(3-fluoro-1-(2-methoxyethyl)piperidin-4-yl)-5-methyl-1H-indazol-1-yl)-5-methoxypyridin-4-yl)azetidin-3-ol (2 mg, 4.26 μmol, 9.07% yield). E33 is a single unknown enantiomer.

MS: 470.1 [M+H]$^+$.

$^1$H NMR (400 MHz, DMSO-d$_6$): δ 8.70 (1H, s) 8.20 (1H, s) 7.99 (1H, s) 7.62 (1H, s) 6.83 (1H, s) 5.69 (1H, d) 4.77 (1H, m) 4.56 (1H, m) 4.33 (2H, t) 3.81 (5H, m) 3.50 (2H, t) 3.41 (1H, m) 3.27 (3H, s) 3.06 (1H, m) 2.94 (1H, d) 2.65 (2H, m) 2.42 (3H, s) 2.21 (2H, m) 1.86 (1H, br. s.) 1.63 (1H, m).

Example 34

(cis)-(2S)-4-(6-(6-(3-fluoro-1-(oxetan-3-yl)piperidin-4-yl)-5-methyl-1H-indazol-1-yl)pyrimidin-4-yl)-N-methylmorpholine-2-carboxamide (Diastereoisomer 1) (E34)

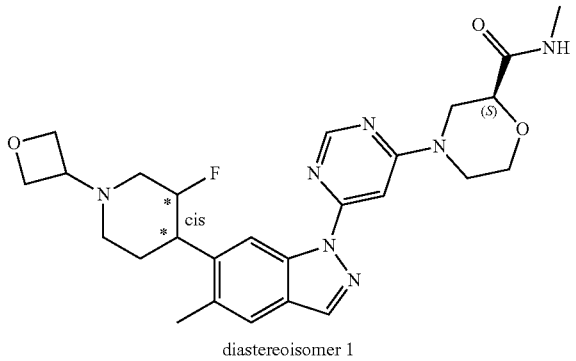

diastereoisomer 1

To a solution of (cis)-6-(3-fluoro-1-(oxetan-3-yl)piperidin-4-yl)-5-methyl-1H-indazole (enantiomer 1) (145 mg, 0.500 mmol) in DMF (5 mL) was added Cs$_2$CO$_3$ (327 mg, 1.00 mmol) and (S)-4-(6-chloropyrimidin-4-yl)-N-methylmorpholine-2-carboxamide (192 mg, 0.750 mmol). The mixture was heated to 100° C. and stirred overnight. The reaction mixture was cooled to rt and then poured into water (40 mL) and extracted with EtOAc (20 mL×3). The combined organic layers were washed with brine, dried over Na$_2$SO$_4$ and concentrated. The crude was purified by prep. HPLC [Waters XBridge, C18, 5 μm, 19*200 mm, 15-60%; A: H$_2$O (0.1% NH$_4$HCO$_3$), B: CH$_3$CN; UV: 214 nm; flow rate: 20 mL/min] to give a white solid. The solid was further purified by chiral-HPLC (ID, 5 μm, 4.6*250 mm, phase: MeOH:EtOH=50:50; flow rate: 1 mL/min) to give a white solid E34 (54.4 mg, yield 21%). E34 is a single unknown diastereoisomer.

E34: $^1$H NMR (400 MHz, CDCl$_3$): δ 8.89 (s, 1H), 8.65 (s, 1H), 8.09 (s, 1H), 7.54 (s, 1H), 7.25 (s, 1H), 6.62 (br s, 1H), 5.08-4.90 (m, 1H), 4.75-4.64 (m, 5H), 4.50-4.46 (m, 1H), 4.12-4.07 (m, 2H), 3.77-3.71 (m, 1H), 3.70-3.64 (m, 1H), 3.30-3.26 (m, 1H), 3.15-3.08 (m, 2H), 3.00-2.94 (m, 1H), 2.89-2.88 (m, 4H), 2.48 (m, 3H), 2.13-2.10 (m, 1H), 2.07-1.97 (m, 3H).

$^{19}$F NMR (376 MHz, CDCl$_3$): δ −184.04 (s, 1F).

LC-MS [mobile phase: from 95% water (0.02% NH$_4$OAc) and 5% CH$_3$CN to 5% water (0.02% NH$_4$OAc) and 95% CH$_3$CN in 6.5 min], purity >95%, Rt=4.111 min; MS Calcd.: 509, MS Found: 510 [M+H]$^+$.

Chiral HPLC (Chiral condition: Chiralpak ID—5 μm 4.6*250 mm, MeOH/EtOH=50/50, Flow Rate: 1.0 ml/min, 230 nm, T=30° C.), Rt=14.45 min, 99.2% de.

Example 35

(cis)-(2R)-4-(6-(6-(3-Fluoro-1-(oxetan-3-yl)piperidin-4-yl)-5-methyl-1H-indazol-1-yl)pyrimidin-4-yl)-N-methylmorpholine-2-carboxamide (Diastereoisomer 1) (E35)

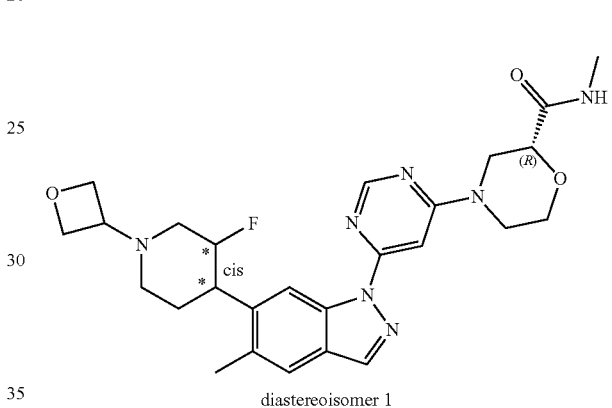

diastereoisomer 1

To a solution of (cis)-6-(3-Fluoro-1-(oxetan-3-yl)piperidin-4-yl)-5-methyl-1H-indazole (enantiomer 1) (145 mg, 0.500 mmol) in DMF (5 mL) was added Cs$_2$CO$_3$ (327 mg, 1.00 mmol) and (R)-4-(6-chloropyrimidin-4-yl)-N-methylmorpholine-2-carboxamide (192 mg, 0.750 mmol). The mixture was heated to 100° C. and stirred overnight. The reaction mixture was cooled to rt and then poured into water (40 mL) and extracted with EtOAc (20 mL×3). The combined organic layers were washed with brine, dried over Na$_2$SO$_4$ and concentrated. The crude was purified by prep. HPLC [Waters XBridge, C18, 5 μm, 19*200 mm, 15-60%; A: H$_2$O (0.1% NH$_4$HCO$_3$), B: CH$_3$CN; UV: 214 nm; flow rate: 20 mL/min] to give a white solid. The solid was further purified by chiral-HPLC (ID, 5 μm, 4.6*250 mm, phase: MeOH:EtOH=50:50; flow rate: 1 mL/min) to give a white solid E35 (37.2 mg, yield 15%). E35 is a single unknown diastereoisomer.

E35: $^1$H NMR (400 MHz, CDCl$_3$): δ 8.89 (s, 1H), 8.65 (s, 1H), 8.09 (s, 1H), 7.54 (s, 1H), 7.25 (s, 1H), 6.62 (br s, 1H), 5.08-4.90 (m, 1H), 4.75-4.64 (m, 5H), 4.50-4.43 (m, 1H), 4.14-4.04 (m, 2H), 3.75-3.71 (m, 1H), 3.66-3.61 (m, 1H), 3.29-3.23 (m, 1H), 3.15-3.07 (m, 2H), 3.00-2.93 (m, 1H), 2.89-2.88 (m, 4H), 2.48 (s, 3H), 2.13-2.07 (m, 1H), 2.07-1.97 (m, 3H). $^{19}$F NMR (376 MHz, CDCl$_3$): δ −184.04 (s, 1F).

LC-MS [mobile phase: from 95% water (0.02% NH$_4$OAc) and 5% CH$_3$CN to 5% water (0.02% NH$_4$OAc) and 95% CH$_3$CN in 6.5 min], purity >95%, Rt=4.104 min; MS Calcd.: 509, MS Found: 510 [M+H]$^+$.

Example 36

(cis)-(2S)-4-(6-(6-(3-fluoro-1-(oxetan-3-yl)piperidin-4-yl)-5-methyl-1H-indazol-1-yl)pyrimidin-4-yl)-N-methylmorpholine-2-carboxamide (Diastereoisomer 2) (E36)

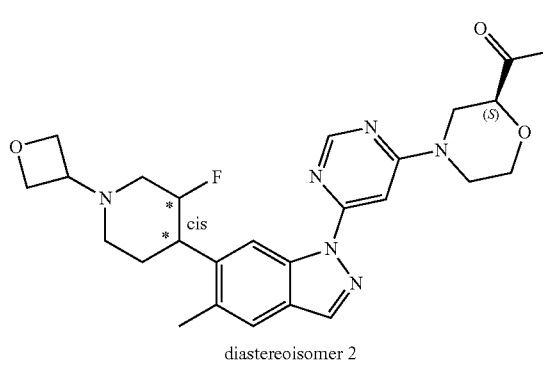

diastereoisomer 2

To a solution of (cis)-6-(3-fluoro-1-(oxetan-3-yl)piperidin-4-yl)-5-methyl-1H-indazole (enantiomer 2) (145 mg, 0.502 mmol) in DMF (5 mL) was added Cs$_2$CO$_3$ (327 mg, 1.00 mmol) and (S)-4-(6-Chloropyrimidin-4-yl)-N-methylmorpholine-2-carboxamide (192 mg, 0.750 mmol). The mixture was heated to 100° C. and stirred overnight. The reaction mixture was cooled to rt and then poured into water (40 mL) and extracted with EtOAc (20 mL×3). The combined organic layers were washed with brine (20 mL), dried over Na$_2$SO$_4$ and concentrated. The crude was purified by prep. HPLC [Waters XBridge, C18, 5 μm, 19*200 mm, 15-60%; A: H$_2$O (0.1% NH$_4$HCO$_3$), B: CH$_3$CN; UV: 214 nm; flow rate: 20 mL/min] to give a white solid. The solid was further purified by chiral-HPLC (ID, 5 μm, 4.6*250 mm, phase: MeOH:EtOH=50:50; flow rate: 1 mL/min) to give the title compound E36 (31 mg, yield 12%) as a white solid. E36 is a single unknown diastereoisomer.

E36: $^1$H NMR (400 MHz, CDCl$_3$): δ 8.89 (s, 1H), 8.65 (s, 1H), 8.09 (s, 1H), 7.54 (s, 1H), 7.25 (s, 1H), 6.64-6.62 (m, 1H), 5.08-4.90 (m, 1H), 4.75-4.64 (m, 5H), 4.50-4.46 (m, 1H), 4.12-4.07 (m, 2H), 3.77-3.71 (m, 1H), 3.67-3.64 (m, 1H), 3.30-3.26 (m, 1H), 3.15-3.08 (m, 2H), 3.00-2.94 (m, 1H), 2.89-2.88 (m, 4H), 2.48 (m, 3H), 2.13-2.10 (m, 1H), 2.07-1.97 (m, 3H).

$^{19}$F NMR (376 MHz, CDCl$_3$): δ −184.04 (s, 1F).

LC-MS [mobile phase: from 95% water (0.02% NH$_4$OAc) and 5% CH$_3$CN to 5% water (0.02% NH$_4$OAc) and 95% CH$_3$CN in 6.5 min], purity >95%, Rt=4.112 min; MS Calcd.: 509, MS Found: 510 [M+H]$^+$.

Chiral HPLC (Chiral condition: Chiralpak ID—5 μm 4.6*250 mm, MeOH/EtOH=50/50, Flow Rate: 1.0 ml/min, 230 nm, T=30° C.), Rt=17.857 min, 99.1% de.

Example 37

(cis)-(2R)-4-(6-(6-(3-Fluoro-1-(oxetan-3-yl)piperidin-4-yl)-5-methyl-1H-indazol-1-yl)pyrimidin-4-yl)-N-methylmorpholine-2-carboxamide (Diastereoisomer 2) (E37)

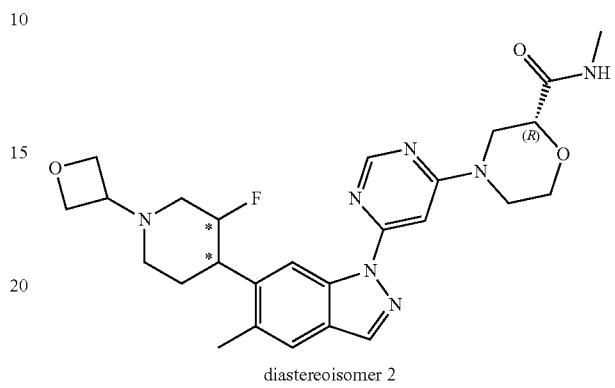

diastereoisomer 2

To a solution of (cis)-6-(3-fluoro-1-(oxetan-3-yl)piperidin-4-yl)-5-methyl-1H-indazole (enantiomer 2) (145 mg, 0.502 mmol) in DMF (5 mL) was added Cs$_2$CO$_3$ (327 mg, 1.00 mmol) and (R)-4-(6-chloropyrimidin-4-yl)-N-methylmorpholine-2-carboxamide (192 mg, 0.750 mmol). The mixture was heated to 100° C. and stirred overnight. The reaction mixture was cooled to rt and then poured into water (40 mL) and extracted with EtOAc (20 mL×3). The combined organic layers were washed with brine (20 mL), dried over Na$_2$SO$_4$ and concentrated. The crude was purified by prep. HPLC [Waters XBridge, C18, 5 μm, 19*200 mm, 15-60%; A: H$_2$O (0.1% NH$_4$HCO$_3$), B: CH$_3$CN; UV: 214 nm; flow rate: 20 mL/min] to give a white solid. The solid was further purified by chiral-HPLC (ID, 5 μm, 4.6*250 mm, phase: MeOH:EtOH=50:50; flow rate: 1 ml/min) to give the desired compound E37 (43.2 mg, yield 17%) as a white solid. E37 is a single unknown diastereoisomer.

E37: $^1$H NMR (400 MHz, CDCl$_3$): δ 8.89 (s, 1H), 8.65 (s, 1H), 8.09 (s, 1H), 7.54 (s, 1H), 7.25 (s, 1H), 6.64-6.62 (m, 1H), 5.08-4.88 (m, 1H), 4.75-4.64 (m, 5H), 4.50-4.46 (m, 1H), 4.12-4.07 (m, 2H), 3.77-3.71 (m, 1H), 3.67-3.64 (m, 1H), 3.30-3.26 (m, 1H), 3.15-3.08 (m, 2H), 3.00-2.94 (m, 1H), 2.89-2.88 (m, 4H), 2.48 (m, 3H), 2.13-2.10 (m, 1H), 2.07-1.97 (m, 3H).

$^{19}$F NMR (376 MHz, CDCl$_3$): δ −184.04 (s, 1F).

LC-MS [mobile phase: from 95% water (0.02% NH$_4$OAc) and 5% CH$_3$CN to 5% water (0.02% NH$_4$OAc) and 95% CH$_3$CN in 6.5 min], purity >95%, Rt=4.113 min; MS Calcd.: 509, MS Found: 510 [M+H]$^+$.

Chiral HPLC (Chiral condition: Chiralpak ID—5 μm 4.6*250 mm, MeOH/EtOH=50/50, Flow Rate: 1.0 ml/min, 230 nm, T=30° C.), Rt=11.541 min, 100% de.

Example 38

(cis)-1-(6-(6-(3-Fluoro-1-methylpiperidin-4-yl)-5-methyl-1H-indazol-1-yl)-2-methoxypyrimidin-4-yl)azetidin-3-ol (Enantiomer 2) (E38)

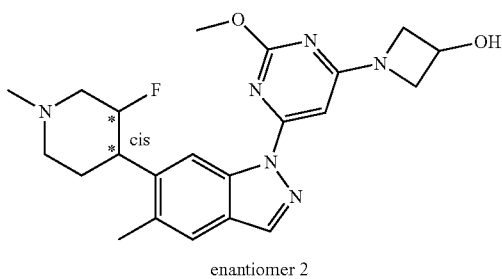 [SMILES: COc1nc(N2CC(O)C2)cc(-n2ncc3cc(C)c(C4CCN(C)CC4F)cc32)n1]

enantiomer 2

Step 1:

A suspension of (cis)-6-(3-fluoro-1-methylpiperidin-4-yl)-5-methyl-1H-indazole (enantiomer 2) (80 mg, 0.32 mmol), 4-chloro-2-methoxy-6-(3-((tetrahydro-2H-pyran-2-yl)oxy)azetidin-1-yl)pyrimidine (144 mg, 0.480 mmol) and $Cs_2CO_3$ (209 mg, 0.641 mmol) in DMF (3 mL) was heated to 100° C. and stirred overnight. The reaction mixture was cooled to rt and then poured into water (40 mL) and extracted with EtOAc (20 mL×3). The combined organic layers were washed with brine, dried over $Na_2SO_4$ and concentrated. The crude was purified by prep. HPLC [XUnion, C18, 5 μm, 20*150 mm, 50-85% B; A: $H_2O$ (0.1% $NH_4HCO_3$), B: $CH_3CN$; UV: 214 nm; flowrate: 20 mL/min] to give (cis)-6-(3-fluoro-1-methylpiperidin-4-yl)-1-(2-methoxy-6-(3-((tetrahydro-2H-pyran-2-yl)oxy)azetidin-1-yl)pyrimidin-4-yl)-5-methyl-1H-indazole (enantiomer 2) (60 mg, yield 36%) and (cis)-6-(3-fluoro-1-methylpiperidin-4-yl)-2-(2-methoxy-6-(3-((tetrahydro-2H-pyran-2-yl)oxy)azetidin-1-yl)pyrimidin-4-yl)-5-methyl-2H-indazole (isomer 2) (48 mg, yield 29%) both as white solid.

(cis)-6-(3-fluoro-1-methylpiperidin-4-yl)-1-(2-methoxy-6-(3-((tetrahydro-2H-pyran-2-yl)oxy)azetidin-1-yl)pyrimidin-4-yl)-5-methyl-1H-indazole (isomer 2) (300 MHz, $CDCl_3$): δ 8.83 (s, 1H), 8.06 (s, 1H), 7.52 (s, 1H), 6.44 (s, 1H), 5.04-4.77 (m, 1H), 4.74-4.67 (m, 2H), 4.41-4.29 (m, 2H), 4.13 (s, 3H), 4.12-4.00 (m, 2H), 3.92-3.85 (m, 1H), 3.58-3.50 (m, 1H), 3.43-3.37 (m, 1H), 3.14-2.96 (m, 2H), 2.47 (s, 6H), 2.32-2.13 (m, 2H), 2.00-1.71 (m, 5H), 1.66-1.51 (m, 3H).

(cis)-6-(3-fluoro-1-methylpiperidin-4-yl)-2-(2-methoxy-6-(3-((tetrahydro-2H-pyran-2-yl)oxy)azetidin-1-yl)pyrimidin-4-yl)-5-methyl-2H-indazole (enantiomer 2): $^1$H NMR (300 MHz, $CDCl_3$): δ 8.91 (s, 1H), 7.66 (s, 1H), 7.46 (s, 1H), 6.71 (s, 1H), 5.00-4.77 (m, 1H), 4.74-4.65 (m, 2H), 4.45-4.36 (m, 2H), 4.19-4.07 (m, 2H), 4.02 (s, 3H), 3.92-3.84 (m, 1H), 3.59-3.51 (m, 1H), 3.43-3.33 (m, 1H), 3.00-2.94 (m, 2H), 2.45 (s, 3H), 2.42 (s, 3H), 2.26-2.07 (m, 2H), 1.94-1.64 (m, 8H).

Step 2:

To a suspension of (cis)-6-(3-fluoro-1-methylpiperidin-4-yl)-1-(2-methoxy-6-(3-((tetrahydro-2H-pyran-2-yl)oxy)azetidin-1-yl)pyrimidin-4-yl)-5-methyl-1H-indazole (enantiomer 2) (50 mg, 0.098 mmol) in methanol (5 mL) was added TsOH (3 mg, 0.02 mmol). The resulting mixture was stirred at rt for 2 hours. The reaction mixture was poured into $Na_2CO_3$ aqueous solution (10%, 30 mL) and stirred for 15 min. The aqueous was extracted with EtOAc (15 mL×3) and the combined organic layers were washed with water, brine, dried over $Na_2SO_4$ and concentrated to give the title compound E38 (22.1 mg, yield 53%) as a white solid. E38 is a single unknown enantiomer.

E38: $^1$H NMR (400 MHz, $CDCl_3$): δ 8.85 (s, 1H), 8.07 (s, 1H), 7.53 (s, 1H), 6.46 (s, 1H), 4.95-4.76 (m, 2H), 4.41 (t, J=7.6 Hz, 2H), 4.12 (s, 3H), 4.02-4.00 (m, 2H), 3.35-3.32 (m, 1H), 3.12-3.02 (m, 1H), 2.94-2.91 (m, 1H), 2.48 (s, 3H), 2.40 (s, 3H), 2.24-2.17 (m, 1H), 2.16-2.09 (m, 1H), 1.97-1.83 (m, 2H). $^{19}$F NMR (376 MHz, $CDCl_3$): δ −184.29 (s, 1F).

LC-MS [mobile phase: from 90% water (0.1% TFA) and 10% $CH_3CN$ to 5% water (0.1% TFA) and 95% $CH_3CN$ in 6.5 min], purity is >95%, Rt=2.969 min; MS Calcd.: 426, MS Found: 427 $[M+H]^+$.

Chiral HPLC [Chiral condition: Chiralpak ID 5 μm 4.6*250 mm, $CO_2$-MeOH=70/30, Co-Solvent: IPA (0.2DEA), $CO_2$ Flow Rate: 2.1 ml/min, Co-Solvent Flow Rate: 0.9 ml/min, 230 nm, T=40° C.], Rt=7.37 min, 97.2% ee.

Example 39

(cis)-1-(6-(6-(3-Fluoro-1-methylpiperidin-4-yl)-5-methyl-1H-indazol-1-yl)-2-methoxypyrimidin-4-yl)azetidin-3-ol (Enantiomer 1) (E39)

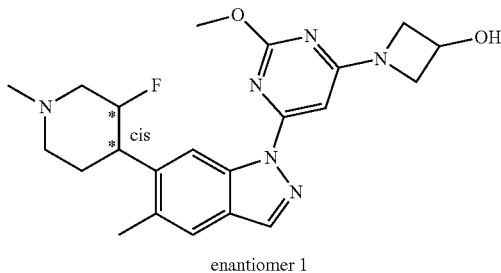 [SMILES: COc1nc(N2CC(O)C2)cc(-n2ncc3cc(C)c(C4CCN(C)CC4F)cc32)n1]

enantiomer 1

Step 1:

A suspension of (cis)-6-(3-fluoro-1-methylpiperidin-4-yl)-5-methyl-1H-indazole (enantiomer 1) (80 mg, 0.32 mmol), 4-chloro-2-methoxy-6-(3-((tetrahydro-2H-pyran-2-yl)oxy)azetidin-1-yl)pyrimidine (144 mg, 0.480 mmol) and $Cs_2CO_3$ (209 mg, 0.641 mmol) in DMF (3 mL) was heated to 100° C. and stirred overnight. The reaction mixture was cooled to rt and then poured into water (40 mL) and extracted with EtOAc (20 mL×3). The combined organic layers were washed with brine, dried over $Na_2SO_4$ and concentrated. The crude was purified by prep. HPLC [XUnion, C18, 5 μm, 20*150 mm, 50-85% B; A: $H_2O$ (0.1% $NH_4HCO_3$), B: $CH_3CN$; UV: 214 nm; flowrate: 20 mL/min] to give (cis)-6-(3-fluoro-1-methylpiperidin-4-yl)-1-(2-methoxy-6-(3-((tetrahydro-2H-pyran-2-yl)oxy)azetidin-1-yl)pyrimidin-4-yl)-5-methyl-1H-indazole (enantiomer 1) (44 mg, yield 27%) and (cis)-6-(3-fluoro-1-methylpiperidin-4-yl)-2-(2-methoxy-6-(3-((tetrahydro-2H-pyran-2-yl)oxy)azetidin-1-yl)pyrimidin-4-yl)-5-methyl-2H-indazole (isomer 1) (46 mg, yield 28%) both as white solid.

(cis)-6-(3-fluoro-1-methylpiperidin-4-yl)-1-(2-methoxy-6-(3-((tetrahydro-2H-pyran-2-yl)oxy)azetidin-1-yl)pyrimidin-4-yl)-5-methyl-1H-indazole (enantiomer 1): 1H NMR (300 MHz, CDCl3): δ 8.83 (s, 1H), 8.06 (s, 1H), 7.52 (s, 1H), 6.42 (s, 1H), 5.05-4.78 (m, 1H), 4.73-4.66 (m, 2H), 4.40-4.28 (m, 2H), 4.13 (s, 3H), 4.12-4.00 (m, 2H), 3.93-

3.84 (m, 1H), 3.58-3.51 (m, 1H), 3.44-3.38 (m, 1H), 3.13-2.99 (m, 2H), 2.49 (s, 3H), 2.47 (s, 3H), 2.32-2.14 (m, 2H), 2.00-1.71 (m, 5H), 1.66-1.52 (m, 3H).

(cis)-6-(3-fluoro-1-methylpiperidin-4-yl)-2-(2-methoxy-6-(3-((tetrahydro-2H-pyran-2-yl)oxy)azetidin-1-yl)pyrimidin-4-yl)-5-methyl-2H-indazole (isomer 1): $^1$H NMR (300 MHz, CDCl3): δ 8.91 (s, 1H), 7.64 (s, 1H), 7.46 (s, 1H), 6.72 (s, 1H), 4.97-4.66 (m, 3H), 4.45-4.35 (m, 2H), 4.20-4.07 (m, 2H), 4.02 (s, 3H), 3.93-3.84 (m, 1H), 3.59-3.51 (m, 1H), 3.36-3.28 (m, 1H), 3.02-2.87 (m, 2H), 2.42 (s, 3H), 2.40 (s, 3H), 2.22-2.04 (m, 2H), 1.94-1.71 (m, 4H), 1.67-1.51 (m, 4H).

Step 2:

To a suspension of (cis)-6-(3-fluoro-1-methylpiperidin-4-yl)-1-(2-methoxy-6-(3-((tetrahydro-2H-pyran-2-yl)oxy)azetidin-1-yl)pyrimidin-4-yl)-5-methyl-1H-indazole (enantiomer 1) (44 mg, 0.086 mmol) in methanol (5 mL) was added TsOH (3 mg, 0.02 mmol). The resulting solution was stirred at rt for 2 hours. The reaction mixture was poured into Na$_2$CO$_3$ aqueous solution (10%, 30 mL) and stirred for 15 min. The aqueous was extracted with EtOAc (15 mL×3) and the combined organic layers were washed with water, brine, dried over Na$_2$SO$_4$ and concentrated to give the title compound E39 (33.2 mg, yield 90%) as a white solid. E39 is a single unknown enantiomer.

E39: $^1$H NMR (400 MHz, CDCl$_3$): δ 8.85 (s, 1H), 8.07 (s, 1H), 7.53 (s, 1H), 6.46 (s, 1H), 4.94-4.74 (m, 2H), 4.40 (t, J=7.6 Hz, 2H), 4.10 (s, 3H), 4.02-3.99 (m, 2H), 3.34-3.30 (m, 1H), 3.11-3.01 (m, 1H), 2.92-2.89 (m, 1H), 2.48 (s, 3H), 2.39 (s, 3H), 2.22-2.15 (m, 1H), 2.15-2.13 (m, 1H), 1.98-1.90 (m, 1H), 1.88-1.81 (m, 1H). $^{19}$F NMR (376 MHz, CDCl$_3$): δ−184.24 (s, 1F).

LC-MS [mobile phase: from 95% water (0.02% NH$_4$OAc) and 5% CH$_3$CN to 5% water (0.02% NH$_4$OAc) and 95% CH$_3$CN in 6.5 min], purity is >95%, Rt=4.192 min; MS Calcd.: 426, MS Found: 427 [M+H]$^+$.

Chiral HPLC [Chiral condition: Chiralpak ID 5 μm 4.6*250 mm, CO$_2$-MeOH=70/30, Co-Solvent: IPA (0.2DEA), CO$_2$ Flow Rate: 2.1 ml/min, Co-Solvent Flow Rate: 0.9 ml/min, 230 nm, T=41° C.], Rt=6.77 min, 97.5% ee.

Example 40

(cis)-1-(6-(6-(3-Fluoro-1-methylpiperidin-4-yl)-5-methyl-1H-indazol-1-yl)-2-methylpyrimidin-4-yl)azetidin-3-ol (Enantiomer 1) (E40)

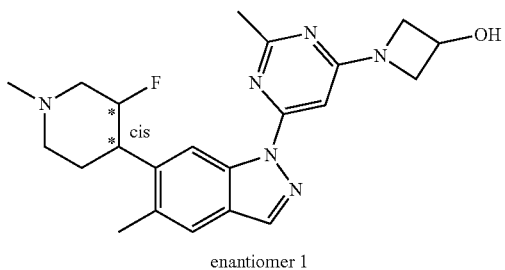 [SMILES: Cc1nc(N2CC(O)C2)cc(-n2ncc3cc(C)c(C4CCN(C)CC4F)cc32)n1]

enantiomer 1

To a solution of (cis)-1-(6-(6-(3-fluoropiperidin-4-yl)-5-methyl-1H-indazol-1-yl)-2-methylpyrimidin-4-yl)azetidin-3-ol hydrochloride (enantiomer 1) (80 mg, 0.18 mmol) in methanol (5 mL) and was added HCHO (14%, 1 mL) and stirred for 30 min. NaBH$_3$CN (80 mg, 1.3 mmol) was added slowly and the mixture was stirred for 2 hrs. To the mixture was added sat. NaHCO$_3$ aqueous solution (20 mL). The mixture was extracted with EtOAc (20 mL×3). The combined organic layers were washed with brine (20 mL), dried over Na$_2$SO$_4$ and concentrated. The crude was purified by prep. TLC (DCM:MeOH=10:1) to give the title compound (40 mg, yield 54%) as white solid. E40 is a single unknown enantiomer.

$^1$H NMR (400 MHz, CDCl$_3$): 8.90 (s, 1H), 8.07 (s, 1H), 7.53 (s, 1H), 6.58 (s, 1H), 5.02-4.82 (m, 2H), 4.41-4.38 (m, 2H), 4.02-3.98 (m, 2H), 3.39-3.35 (m, 1H), 3.12-3.04 (m, 1H), 3.00-2.94 (m, 1H), 2.61 (s, 3H), 2.48 (s, 3H), 2.44 (s, 3H), 2.29-2.14 (m, 2H), 1.99-1.93 (m, 2H).

$^{19}$F NMR (376 MHz, CDCl$_3$): δ −184.23 (s, 1F).

LC-MS: [mobile phase: from 95% water (0.1% NH$_4$OAc) and 5% CH$_3$CN to 5% water (0.1% NH$_4$OAc) and 95% CH$_3$CN in 6.5 min], purity is >95%, Rt=4.053 min; MS Calcd.: 410, MS Found: 411 [M+H]$^+$.

Chiral condition: Supercritical Fluid Chromatography (SFC), IF, CO$_2$/CH$_3$OH=70/30, CO$_2$ Flow Rate: 2.1, 254 nm, T=41.8° C., Rt=7.46 min, 100% ee.

Example 41

(cis)-1-(6-(6-(3-Fluoro-1-methylpiperidin-4-yl)-5-methyl-1H-indazol-1-yl)-2-methylpyrimidin-4-yl)azetidin-3-ol (Enantiomer 2) (E41)

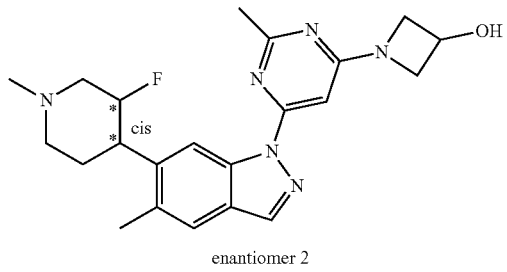 [SMILES: Cc1nc(N2CC(O)C2)cc(-n2ncc3cc(C)c(C4CCN(C)CC4F)cc32)n1]

enantiomer 2

To a solution of (cis)-1-(6-(6-(3-fluoropiperidin-4-yl)-5-methyl-1H-indazol-1-yl)-2-methylpyrimidin-4-yl)azetidin-3-ol hydrochloride (enantiomer 2) (80 mg, 0.18 mmol) in methanol (5 mL) and was added HCHO (14%, 1 mL) and stirred for 30 min. NaBH$_3$CN (80 mg, 1.3 mmol) was added slowly and the mixture was stirred for 2 hrs. To the mixture was added sat. NaHCO$_3$ aqueous solution (20 mL). The mixture was extracted with EtOAc (20 mL×3). The combined organic layers were washed with brine (20 mL), dried over Na$_2$SO$_4$ and concentrated. The crude was purified by prep. TLC (DCM:MeOH=10:1) to give the title compound (30 mg, yield 41%) as a white solid. E41 is a single unknown enantiomer.

$^1$H NMR (400 MHz, CDCl$_3$): 8.90 (s, 1H), 8.07 (s, 1H), 7.53 (s, 1H), 6.58 (s, 1H), 5.04-4.79 (m, 2H), 4.42-4.38 (m, 2H), 4.02-3.98 (m, 2H), 3.41-3.35 (m, 1H), 3.13-3.04 (m, 1H), 3.01-2.94 (m, 1H), 2.61 (s, 3H), 2.48 (s, 3H), 2.44 (s, 3H), 2.29-2.13 (m, 2H), 2.00-1.94 (m, 2H).

$^{19}$F NMR (376 MHz, CDCl$_3$): δ −184.16 (s, 1F).

LC-MS: [mobile phase: from 95% water (0.1% NH$_4$Ac) and 5% CH$_3$CN to 5% water (0.1% NH$_4$Ac) and 95% CH$_3$CN in 6.5 min], purity is >95%, Rt=4.053 min; MS Calcd.: 410, MS Found: 411 [M+H]$^+$.

Chiral condition: Supercritical Fluid Chromatography (SFC), 1E, CO$_2$/CH$_3$OH=70/30, CO$_2$ Flow Rate: 2.1 ml/min, 254 nm, T=41.8° C., Rt=6.12 min, 100% ee.

Example 42

(cis)-1-(6-(6-(3-Fluoro-1-(oxetan-3-yl)piperidin-4-yl)-5-methyl-1H-indazol-1-yl)-2-methylpyrimidin-4-yl)azetidin-3-ol (Enantiomer 1) (E42)

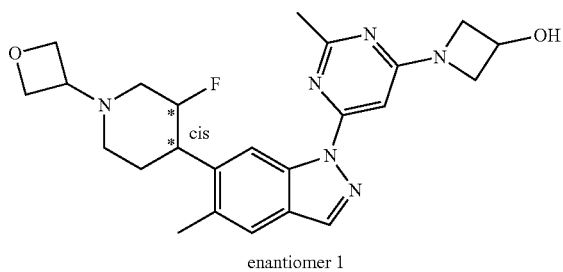 [SMILES: Cc1nc(N2CC(O)C2)cc(-n2ncc3cc(C)c(C4CCN(C5COC5)CC4F)cc32)n1]

enantiomer 1

To a solution of (cis)-1-(6-(6-(3-fluoropiperidin-4-yl)-5-methyl-1H-indazol-1-yl)-2-methyl pyrimidin-4-yl)azetidin-3-ol hydrochloride (enantiomer 1) (50 mg, 0.12 mmol) and oxetan-3-one (334 mg, 4.64 mmol) in methanol (2 mL) and 1,2-dichloroethane (8 mL) was added NaBH$_3$CN (72 mg, 1.1 mmol). Then the mixture was stirred at rt for 4 hrs. The reaction mixture was diluted with water (30 mL) and EtOAc (30 mL). The aqueous phase was extracted with EtOAc (30 mL×2). The combined organic layers were dried over Na$_2$SO$_4$, filtered, concentrated in vacuo and purified by C18 column eluting with CH$_3$CN/H$_2$O (from 5/95 to 95/5) to give the title compound (35 mg, yield 67%) as a white solid. E42 is a single unknown enantiomer.

$^1$H NMR (400 MHz, CDCl$_3$): δ 8.91 (s, 1H), 8.08 (s, 1H), 7.53 (s, 1H), 6.60 (s, 1H), 5.01-4.81 (m, 2H), 4.76-4.66 (m 4H), 4.46-4.39 (m, 2H), 4.05-3.98 (m, 2H), 3.70-3.63 (m, 1H), 3.30-3.24 (m, 1H), 3.16-3.09 (m, 1H), 2.90-2.84 (m, 1H), 2.66 (s, 3H), 2.48 (s, 3H), 2.37-2.32 (m, 1H), 2.17-1.87 (m, 4H).

$^{19}$F NMR (376 MHz, CDCl$_3$): δ183.98 (s, 1F).

LC-MS (mobile phase: from 95% water (0.02% NH$_4$OAc) and 5% CH$_3$CN to 5% water (0.02% NH$_4$OAc) and 95% CH$_3$CN in 6.0 min, purity is >95%, Rt=3.871 min; MS Calcd.: 452; MS Found: 453 [M+H]$^+$.

Chiral HPLC (Chiral condition: Chiralpak IE—5 μm 4.6*250 mm, Hex/IPA/DEA=60/40/0.2, Flow Rate: 1.0 ml/min, 254 nm, T=30° C.), Rt=10.527 min, 100% ee.

Example 43

(cis)-1-(6-(6-(3-Fluoro-1-(oxetan-3-yl)piperidin-4-yl)-5-methyl-1H-indazol-1-yl)-2-methylpyrimidin-4-yl)azetidin-3-ol (Enantiomer 2) (E43)

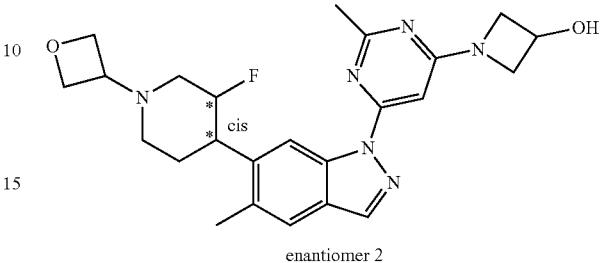

enantiomer 2

To a solution of (cis)-1-(6-(6-(3-fluoropiperidin-4-yl)-5-methyl-1H-indazol-1-yl)-2-methyl pyrimidin-4-yl)azetidin-3-ol hydrochloride (enantiomer 2) (66 mg, 0.15 mmol) and oxetan-3-one (440 mg, 6.11 mmol) in methanol (4 mL) and 1,2-dichloroethane (16 mL) was added NaBH$_3$CN (96 mg, 1.5 mmol). Then the mixture was stirred at rt for 3 hrs. The reaction mixture was diluted with water (30 mL) and EtOAc (30 mL). The organic layer was collected and the aqueous phase was extracted with EtOAc (30 mL×2). The combined organic layers were dried over Na$_2$SO$_4$, filtered, concentrated in vacuo and purified by C18 column eluting with CH$_3$CN/H$_2$O (from 5/95 to 100/0) to give the title compound (55 mg, yield 80%) as a white solid. E43 is a single unknown enantiomer.

$^1$H NMR (400 MHz, CDCl$_3$): δ 8.91 (s, 1H), 8.08 (s, 1H), 7.53 (s, 1H), 6.60 (s, 1H), 5.01-4.81 (m, 2H), 4.76-4.67 (m 4H), 4.46-4.40 (m, 2H), 4.04-3.99 (m, 2H), 3.70-3.63 (m, 1H), 3.31-3.24 (m, 1H), 3.16-3.08 (m, 1H), 2.90-2.83 (m, 1H), 2.66 (s, 3H), 2.48 (s, 3H), 2.43-2.38 (m, 1H), 2.15-2.07 (m, 1H), 2.07-1.88 (m, 3H).

$^{19}$F NMR (376 MHz, CDCl$_3$): δ 183.98 (s, 1F).

LC-MS (mobile phase: from 70% water (0.02% NH$_4$OAc) and 30% CH$_3$CN to 30% water (0.02% NH$_4$OAc) and 70% CH$_3$CN in 6.0 min, purity is >95%, Rt=3.425 min; MS Calcd.: 452; MS Found: 453 [M+H]$^+$.

Chiral HPLC (Chiral condition: Chiralpak IE-5 um 4.6*250 mm, Hex/IPA/DEA=60/40/0.2, Flow Rate: 1.0 ml/min, 254 nm, T=30° C.), Rt=9.043 min, 100% ee.

Example 44

(cis)-(1s,3s)-3-(6-(6-(3-Fluoro-1-(oxetan-3-yl)piperidin-4-yl)-5-methyl-1H-indazol-1-yl)-2-methylpyrimidin-4-yl)cyclobutanol (Enantiomer 1) (E44)

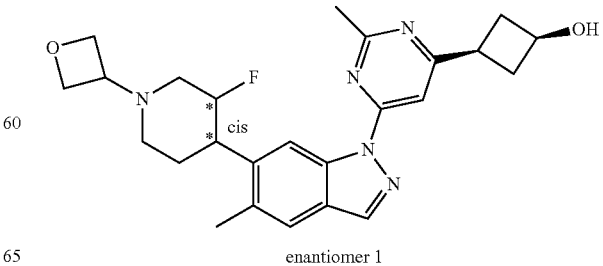

enantiomer 1

To a solution of (cis)-(1s,3s)-3-(6-(6-(3-fluoropiperidin-4-yl)-5-methyl-1H-indazol-1-yl)-2-methylpyrimidin-4-yl)cyclobutanol hydrochloride (enantiomer 1) (35 mg, 0.081 mmol) in methanol (0.5 mL) was added 1,2-dichloro-ethane (2.5 mL) and oxetan-3-one (0.2 mL). The mixture was stirred at rt for 30 min. To the reaction mixture was added NaBH₃CN (25 mg, 0.40 mmol) and stirred at rt for 2 hrs. To the reaction mixture was added a solution of sat. Na₂CO₃ solution (10 mL). The mixture was stirred at rt for 10 min. The mixture was extracted with DCM (10 mL×3). The combined organic layers were washed with brine (10 mL), dried over Na₂SO₄ and concentrated. The residue was purified by prep-TLC (DCM:CH₃OH=15:1) to give the title compound (3.6 mg, yield 10%) as a white solid. E44 is a single unknown enantiomer.

¹H NMR (400 MHz, CDCl₃): 8.90 (s, 1H), 8.12 (s, 1H), 7.64 (s, 1H), 7.56 (s, 1H), 5.02-4.83 (m, 1H), 4.76-4.64 (m, 4H), 4.38-4.29 (m, 1H), 3.71-3.55 (m, 2H), 3.32-3.22 (m, 2H), 3.18-3.09 (m, 1H), 2.90-2.81 (m, 6H), 2.49 (s, 3H), 2.28-2.21 (m, 2H), 2.15-1.89 (m, 4H).

¹⁹F NMR (376 MHz, CDCl₃): δ −184.01 (s, 1F).

LC-MS [mobile phase: from 95% water (0.02% NH₄OAc) and 5% CH₃CN to 5% water (0.02% NH₄OAc) and 95% CH₃CN in 6.5 min], purity is >95%, Rt=4.026 min; MS Calcd.: 451, MS Found: 452 [M+H]⁺.

Chiral condition: Chiralpak IF 5 um 4.6*250 mm, Hex/EtOH=90/10, Flow Rate: 1 ml/min, 230 nm, T=30° C., Rt=34.514 min, 100% ee.

Example 45

(cis)-(1s,3s)-3-(6-(6-(3-Fluoro-1-(oxetan-3-yl)piperidin-4-yl)-5-methyl-1H-indazol-1-yl)-2-methylpyrimidin-4-yl)cyclobutanol (Enantiomer 2) (E45)

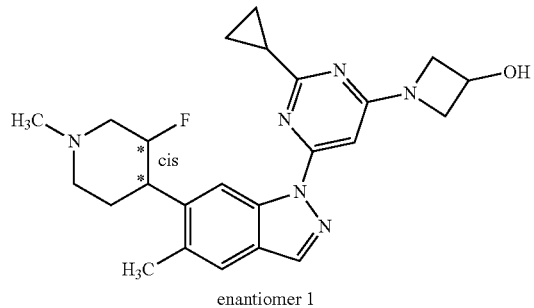

enantiomer 2

To a solution of (cis)-(1s,3s)-3-(6-(6-(3-fluoropiperidin-4-yl)-5-methyl-1H-indazol-1-yl)-2-methylpyrimidin-4-yl)cyclobutanol hydrochloride (enantiomer 2) (35 mg, 0.81 mmol) in methanol (0.5 mL) was added 1,2-dichloro-ethane (2.5 mL) and oxetan-3-one (0.2 mL). The mixture was stirred at rt for 30 min. To the reaction mixture was added NaBH₃CN (25 mg, 0.40 mmol) and stirred at rt for 2 hrs. To the reaction mixture was added a solution of sat. Na₂CO₃ solution (10 mL). The mixture was stirred at rt for 10 min. The mixture was extracted with DCM (10 mL×3). The combined organic layers were washed with brine (10 mL), dried over Na₂SO₄ and concentrated. The residue was purified by prep-TLC (DCM: CH₃OH=15:1) to give the title compound (12 mg, yield 33%) as a white solid. E45 is a single unknown enantiomer.

¹H NMR (400 MHz, CDCl₃): 8.91 (s, 1H), 8.12 (s, 1H), 7.64 (s, 1H), 7.56 (s, 1H), 5.03-4.84 (m, 1H), 4.78-4.67 (m, 4H), 4.39-4.30 (m, 1H), 3.73-3.62 (m, 2H), 3.33-3.22 (m, 2H), 3.17-3.09 (m, 1H), 2.90-2.82 (m, 6H), 2.49 (s, 3H), 2.28-2.20 (m, 2H), 2.15-1.88 (m, 4H).

¹⁹F NMR (376 MHz, CDCl₃): δ −184.00 (s, 1F).

LC-MS [mobile phase: from 95% water (0.02% NH₄OAc) and 5% CH₃CN to 5% water (0.02% NH₄OAc) and 95% CH₃CN in 6.5 min], purity is >95%, Rt=4.020 min; MS Calcd.: 451, MS Found: 452 [M+H]⁺.

Chiral condition: Chiralpak IF 5 μm 4.6*250 mm, Hex/EtOH=90/10, Flow Rate: 1 ml/min, 230 nm, T=30° C., Rt=31.842 min, 100% ee.

Example 46

(cis)-1-(2-Cyclopropyl-6-(6-(3-fluoro-1-methylpiperidin-4-yl)-5-methyl-1H-indazol-1-yl)pyrimidin-4-yl)azetidin-3-ol (Enantiomer 1) (E46)

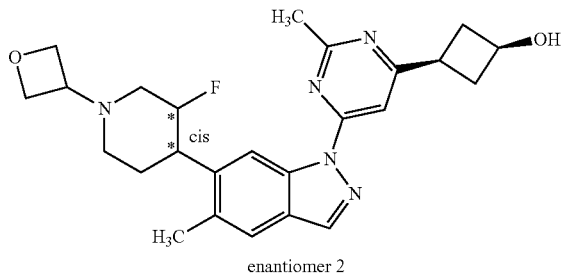 [SMILES: Cc1nc(-n2ncc3cc(C)c(C4CCN(C5COC5)CC4F)cc32)cc([C@H]2C[C@@H](O)C2)n1]

enantiomer 1

The mixture of (cis)-tert-butyl 4-(1-(2-cyclopropyl-6-(3-((tetrahydro-2H-pyran-2-yl)oxy) azetidin-1-yl)pyrimidin-4-yl)-5-methyl-1H-indazol-6-yl)-3-fluoropiperidine-1-carboxylate (enantiomer 1) (120 mg, 0.198 mmol) in HCl/MeOH (4 M, 15 mL) was stirred at rt for 2 hours. The reaction mixture was concentrated.

LCMS: (mobile phase: 5-95% acetonitrile in 3 min), Rt=1.78 min; MS Calcd: 422; MS Found: 423 [M+1]⁺.

The residue was dissolved in methanol (10 mL). Then formaldehyde (37%, 2 mL) and CH₃COOH (cat.) was added. The mixture was stirred at rt for 1 h. Then NaBH₃CN (37 mg, 0.59 mmol) was added at rt. Then the mixture was stirred at 35° C. overnight. The reaction mixture was added saturated aqueous NaHCO₃ (15 mL). After stirring for 20 min the aqueous layer was extracted with DCM (15 mL×2). The combined organic layers were dried over Na₂SO₄ and concentrated. The crude was purified by prep-TLC (DCM:MeOH=10:1) to give a crude. The crude was further purified by prep-HPLC to give the title compound (10.7 mg, yield 12%) as a white solid. E46 is a single unknown enantiomer.

¹H NMR (400 MHz, CDCl₃): δ 8.83 (s, 1H), 8.06 (s, 1H), 7.52 (s, 1H), 6.55 (s, 1H), 5.02-4.77 (m, 2H), 4.41-4.36 (m, 2H), 4.00-3.95 (m, 2H), 3.39-3.32 (m, 1H), 3.12-3.01 (m, 1H), 2.94-2.89 (m, 1H), 2.47 (s, 3H), 2.42 (s, 3H), 2.23-2.07 (m, 3H), 1.98-1.84 (m, 2H), 1.25-1.22 (m, 2H), 1.08-1.05 (m, 2H). ¹⁹F NMR (376 MHz, CDCl₃): δ −184.22 (s, 1F).

LC-MS: [mobile phase: from 80% water (0.02% NH₄OAc) and 20% CH₃CN to 5% water (0.02% NH₄OAc) and 95% CH₃CN in 6.5 min], purity is >95%, Rt=4.168 min; MS Calcd.: 436, MS Found: 437 [M+H]⁺.

Chiral HPLC: [Chiral condition: Chiralpak ID-3 3 um 4.6*150 mm, Phase: HEX:IPA:DEA=90:10:0.2, Flow Rate: 1 ml/min, 230 nm, T=30° C., Rt=3.992 min, 100% ee.

Example 47

(cis)-1-(2-Cyclopropyl-6-(6-(3-fluoro-1-methylpiperidin-4-yl)-5-methyl-1H-indazol-1-yl)pyrimidin-4-yl)azetidin-3-ol (Enantiomer 2) (E47)

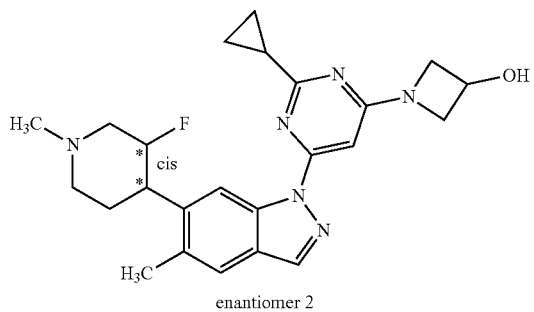 [SMILES: Cc1cc2cnn(-c3cc(N4CC(O)C4)nc(C4CC4)n3)c2cc1C1CCN(C)CC1F]

enantiomer 2

The mixture of (cis)-tert-butyl 4-(1-(2-cyclopropyl-6-(3-((tetrahydro-2H-pyran-2-yl)oxy) azetidin-1-yl)pyrimidin-4-yl)-5-methyl-1H-indazol-6-yl)-3-fluoropiperidine-1-carboxylate (enantiomer 2) (110 mg, 0.180 mmol) in HCl/MeOH (4 M, 15 mL) was stirred at rt for 2 hours. The reaction mixture was concentrated. LCMS: (mobile phase: 5-95% CH$_3$CN in 3 min), Rt=1.32 min; MS Calcd: 422; MS Found: 423 [M+1]$^+$. The residue was diluted with methanol (10 mL). Then, formaldehyde (37%, 2 mL) and CH$_3$COOH (cat.) were added and stirred for 1 h. Then NaBH$_3$CN (34 mg, 0.54 mmol) was added at rt. Then the mixture was stirred at 35° C. overnight. The reaction mixture was added to saturated aqueous NaHCO$_3$ (15 mL). After stirring for 20 min the aqueous layer was extracted with DCM (15 mL×2). The combined organic layers were dried over Na$_2$SO$_4$ and concentrated. The crude was purified by prep-TLC (DCM:MeOH=10:1) to give a light yellow solid. The solid was further purified by prep-HPLC to give the title compound (10.7 mg, yield 13%) as a white solid. E47 is a single unknown enantiomer.

$^1$H NMR (400 MHz, CDCl$_3$): δ 8.83 (s, 1H), 8.06 (s, 1H), 7.52 (s, 1H), 6.56 (s, 1H), 5.02-4.79 (m, 2H), 4.43-4.36 (m, 2H), 4.02-3.95 (m, 2H), 3.37-3.34 (m, 1H), 3.10-3.02 (m, 1H), 2.95-2.93 (m, 1H), 2.47 (s, 3H), 2.42 (s, 3H), 2.27-2.08 (m, 4H), 1.94-1.87 (m, 2H), 1.28-1.25 (m, 2H), 1.08-1.05 (m, 2H). $^{19}$F NMR (376 MHz, CDCl$_3$): δ −184.23 (s, 1F).

LC-MS [mobile phase: from 70% water (0.02% NH$_4$OAc) and 30% CH$_3$CN to 5% water (0.02% NH$_4$OAc) and 95% CH$_3$CN in 6.5 min], purity is >95%, Rt=3.804 min; MS Calcd.: 436, MS Found: 437 [M+H]$^+$.

Chiral HPLC [Chiral condition: Chiralpak ID-3 3 μm 4.6*150 mm, Phase: HEX:IPA:DEA=90:10:0.2, Flow Rate: 1 ml/min, 230 nm, T=30° C., Rt=4.881 min, 100% ee.

Example 48

(cis)-1-(2-(Difluoromethoxy)-6-(6-(3-fluoro-1-methylpiperidin-4-yl)-5-methyl-1H-indazol-1-yl)pyrimidin-4-yl)azetidin-3-ol (Enantiomer 2) (E48)

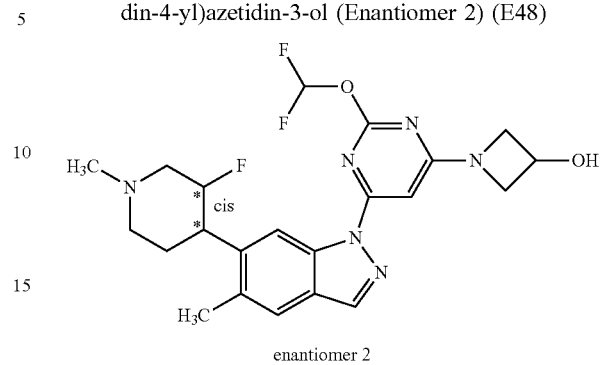

enantiomer 2

A mixture of solution of 1-(2-(difluoromethoxy)-6-iodopyrimidin-4-yl)azetidin-3-ol (50 mg, 0.14 mmol), (cis)-6-(3-fluoro-1-methylpiperidin-4-yl)-5-methyl-1H-indazole (enantiomer 2) (36 mg, 0.14 mmol), N$^1$,N$^2$-dimethyl cyclohexane-1,2-diamine (21 mg, 0.14 mmol), CuI (27 mg, 0.14 mmol), K$_3$PO$_4$ (31 mg, 0.14 mmol) in toluene (5 mL) stirred at 115° C. under N$_2$ for 2 hrs. The reaction mixture was cooled to rt, diluted with EtOAc (20 mL) and washed with water (10 mL×2). The organic layer was dried over Na$_2$SO$_4$, filtered and concentrated. The residue was purified by prep-TLC to give the title compound (14 mg, yield 21%) as a white solid. E48 is a single unknown enantiomer.

$^1$H NMR (300 MHz, CDCl$_3$): δ 8.64 (s, 1H), 8.08 (s, 1H), 7.53 (s, 1H), 7.41 (t, J=72.6 Hz, 1H), 6.55 (s, 1H), 5.08-4.83 (m, 2H), 4.42 (t, J=8.7 Hz, 2H), 4.03 (dd, J=10.2, 3.9 Hz, 2H), 3.43-3.36 (m, 1H), 3.14-2.96 (m, 2H), 2.48 (s, 3H), 2.44 (s, 3H), 2.29-2.12 (m, 2H), 1.96-1.87 (m, 2H). $^{19}$F NMR (376 MHz, CDCl$_3$): δ −88.47 (dd, J=410.6, 174.1 Hz, 2F).

LC-MS (mobile phase: from 70% water (0.02% NH$_4$OAc) and 30% CH$_3$CN to 5% water (0.02% NH$_4$OAc) and 95% CH$_3$CN in 6.5 min), Rt=3.813 min; MS Calcd.: 462, MS Found: 463 [M+H]$^+$.

Chiral HPLC: (Chiralpak AD-3 3 μm 4.6×150 mm, Phase: Hex/EtOH=70/30, flow rate: 1 mL/min, temperature: 30° C., 230 nm), Rt=6.562 min, 100% ee.

Example 49

(cis)-1-(2-(Difluoromethoxy)-6-(6-(3-fluoro-1-methylpiperidin-4-yl)-5-methyl-1H-indazol-1-yl)pyrimidin-4-yl)azetidin-3-ol (Enantiomer 1) (E49)

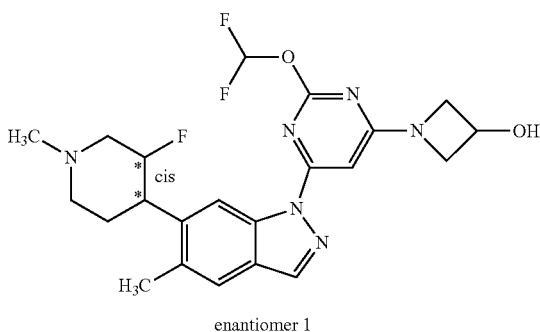 [SMILES: Cc1cc2cnn(-c3cc(N4CC(O)C4)nc(OC(F)F)n3)c2cc1C1CCN(C)CC1F]

enantiomer 1

A mixture of solution of 1-(2-(difluoromethoxy)-6-iodopyrimidin-4-yl)azetidin-3-ol (50 mg, 0.14 mmol), (cis)-6-(3-fluoro-1-methylpiperidin-4-yl)-5-methyl-1H-indazole (enantiomer 1) (36 mg, 0.14 mmol), N1,N2-dimethylcyclohexane-1,2-diamine (21 mg, 0.14 mmol), CuI (27 mg, 0.14 mmol), $K_3PO_4$ (31 mg, 0.14 mmol) in toluene (5 mL) was stirred at 115° C. under $N_2$ for 2 hrs. The reaction mixture was cooled to rt, diluted with EtOAc (20 mL) and washed with water (10 mL×2). The organic layer was dried over $Na_2SO_4$, filtered and concentrated. The residue was purified by prep-TLC to give the title compound (12 mg, yield 18%) as a white solid. E49 is a single unknown enantiomer.

$^1$H NMR (300 MHz, $CDCl_3$): δ 8.64 (s, 1H), 8.08 (s, 1H), 7.53 (s, 1H), 7.39 (t, J=72.9 Hz, 1H), 6.65 (s, 1H), 5.04-4.79 (m, 2H), 4.42 (t, J=8.4 Hz, 2H), 4.03 (dd, J=10.2, 3.9 Hz, 2H), 3.40-3.33 (m, 1H), 3.12-3.00 (m, 1H), 2.95-2.92 (m, 1H), 2.48 (s, 3H), 2.41 (s, 3H), 2.24-2.07 (m, 2H), 1.96-1.84 (m, 2H). $^{19}$F NMR (376 MHz, $CDCl_3$): δ −88.46 (dd, J=424.5, 175.6 Hz, 2F).

LC-MS (mobile phase: from 70% water (0.02% $NH_4OAc$) and 30% $CH_3CN$ to 5% water (0.02% $NH_4OAc$) and 95% $CH_3CN$ in 6.5 min), Rt=3.823 min; MS Calcd.: 462, MS Found: 463 $[M+H]^+$.

Chiral HPLC: (Chiralpak AD-3 3 μm 4.6×150 mm, Phase: Hex/EtOH=70/30, flow rate: 1 mL/min, temperature: 30° C., 230 nm), Rt=4.453 min, 97.7% ee.

Example 50

(cis)-2-((1-(6-(6-(3-Fluoro-1-methylpiperidin-4-yl)-5-methyl-1H-indazol-1-yl)-2-methoxypyrimidin-4-yl)azetidin-3-yl)oxy)ethanol (Enantiomer 1) (E50)

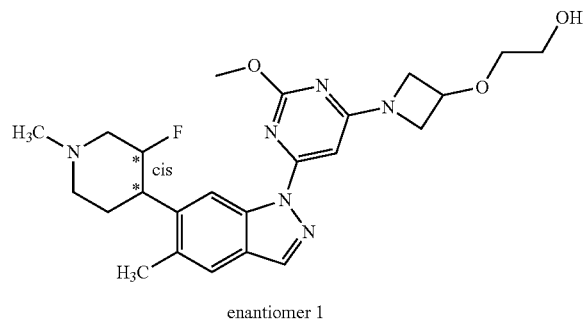 [SMILES: COc1nc(N2CC(OCCO)C2)cc(-n2ncc3cc(C)c(C4CCN(C)CC4F)cc32)n1]

enantiomer 1

To a solution of (cis)-2-((1-(6-(6-(3-fluoropiperidin-4-yl)-5-methyl-1H-indazol-1-yl)-2-methoxypyrimidin-4-yl)azetidin-3-yl)oxy)ethanol hydrochloride (enantiomer 1) (60 mg, 0.13 mmol) in methanol (5 mL) was added HCHO (35% in water, 0.5 mL) and stirred at rt for 10 min. To the reaction mixture was added $NaBH_3CN$ (31 mg, 0.50 mmol) and stirred at rt for 20 min. To the reaction mixture was added a solution of sat. $NaHCO_3$ solution (10 mL). The mixture was extracted with EtOAc (20 mL×3). The combined organic layers were washed with brine (20 mL), dried over $Na_2SO_4$ and concentrated. The residue was triturated with EtOAc (5 mL) to give the title compound (38 mg, yield 65%) as a white solid. E50 is a single unknown enantiomer.

$^1$H NMR (300 MHz, $CDCl_3$): 8.85 (s, 1H), 8.07 (s, 1H), 7.53 (s, 1H), 6.48 (s, 1H), 4.94-4.73 (m, 1H), 4.54-4.48 (m, 1H), 4.38-4.32 (m, 2H), 4.12 (s, 3H), 4.09-4.04 (m, 2H), 3.82-3.77 (m, 2H), 3.59-3.56 (m, 2H), 3.36-3.28 (m, 1H), 3.11-3.01 (m, 1H), 2.94-2.88 (m, 1H), 2.48 (s, 3H), 2.39 (s, 3H), 2.22-2.04 (m, 2H), 1.97-1.80 (m, 3H).

$^{19}$F NMR (376 MHz, $CDCl_3$): δ −184.26 (s, 1F).

LC-MS [mobile phase: from 95% water (0.02% $NH_4OAc$) and 5% $CH_3CN$ to 5% water (0.02% $NH_4OAc$) and 95% $CH_3CN$ in 6.5 min], purity is >95%, Rt=4.144 min; MS Calcd.: 470, MS Found: 471 $[M+H]^+$.

Chiral condition: Chiralpak IE 5 μm 4.6*250 mm, Hex/EtOH=40/50, Flow Rate: 1 ml/min, 230 nm, T=30° C., Rt=9.711 min, 98.3% ee.

Example 51

(cis)-2-((1-(6-(6-(3-Fluoro-1-methylpiperidin-4-yl)-5-methyl-1H-indazol-1-yl)-2-methoxypyrimidin-4-yl)azetidin-3-yl)oxy)ethanol (Enantiomer 2) (E51)

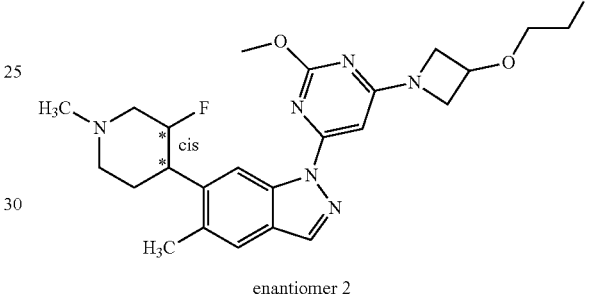

enantiomer 2

To a solution of (cis)-2-((1-(6-(6-(3-fluoropiperidin-4-yl)-5-methyl-1H-indazol-1-yl)-2-methoxypyrimidin-4-yl)azetidin-3-yl)oxy)ethanol hydrochloride (enantiomer 2) (60 mg, 0.13 mmol) in methanol (5 mL) was added HCHO (35% in water, 0.5 mL) and stirred at rt for 10 min. To the reaction mixture was added $NaBH_3CN$ (31 mg, 0.50 mmol) and stirred at rt for 1 h. A solution of sat. $NaHCO_3$ solution (10 mL) was added to the reaction mixture. The mixture was extracted with EtOAc (20 mL×3). The combined organic layers were washed with brine (20 mL), dried over $Na_2SO_4$ and concentrated. The residue was triturated with EtOAc (5 mL) to give the title compound (30 mg, yield 51%) as a white solid. E51 is a single unknown enantiomer.

$^1$H NMR (300 MHz, $CDCl_3$): 8.85 (s, 1H), 8.07 (s, 1H), 7.53 (s, 1H), 6.48 (s, 1H), 4.97-4.72 (m, 1H), 4.54-4.47 (m, 1H), 4.39-4.32 (m, 2H), 4.12 (s, 3H), 4.09-4.04 (m, 2H), 3.82-3.77 (m, 2H), 3.59-3.56 (m, 2H), 3.36-3.28 (m, 1H), 3.11-3.00 (m, 1H), 2.95-2.86 (m, 1H), 2.48 (s, 3H), 2.39 (s, 3H), 2.22-2.06 (m, 2H), 1.99-1.80 (m, 3H).

$^{19}$F NMR (376 MHz, $CDCl_3$): δ −184.25 (s, 1F).

LC-MS [mobile phase: from 95% water (0.02% $NH_4OAc$) and 5% $CH_3CN$ to 5% water (0.02% $NH_4OAc$) and 95% $CH_3CN$ in 6.5 min], purity is >95%, Rt=4.143 min; MS Calcd.: 470, MS Found: 471 $[M+H]^+$.

Chiral condition: Chiralpak IE 5 μm 4.6*250 mm, Hex/EtOH=40/60, Flow Rate: 1 ml/min, 230 nm, T=30° C., Rt=11.938 min, 99.7% ee.

Example 52

(cis)-(3S)-1-(6-(6-(3-Fluoro-1-methylpiperidin-4-yl)-5-methyl-1H-indazol-1-yl)-2-methoxypyrimidin-4-yl)pyrrolidin-3-ol (Diastereoisomer 1) (E52)

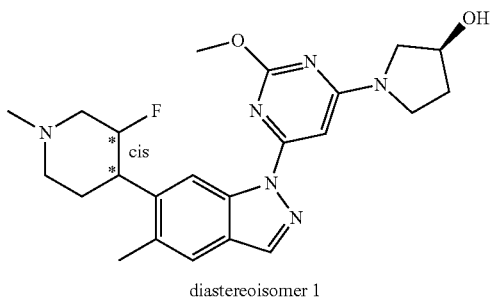 [SMILES: COc1nc(N2CC[C@H](O)C2)cc(-n2ncc3cc(C)c(C4CCN(C)CC4F)cc32)n1]

diastereoisomer 1

To a solution of (cis)-(3S)-1-(6-(6-(3-fluoropiperidin-4-yl)-5-methyl-1H-indazol-1-yl)-2-methoxypyrimidin-4-yl)pyrrolidin-3-ol hydrochloride (diastereoisomer 1) (140 mg crude, 0.24 mmol) in methanol (8 mL) was added CH$_2$O (37%, 2 mL) and NaBH$_3$CN (30 mg, 0.48 mmol) at rt. The resulting mixture was stirred for 1 h. The reaction mixture was partitioned between water (50 mL) and EtOAc (50 mL). The aqueous layer was extracted with EtOAc (50 mL). The combined organic layers were washed with brine, dried over MgSO$_4$ and concentrated. The crude was purified by prep. TLC (DCM:MeOH=10:1) to give the title compound (32.8 mg, yield 31% for 3 steps) as a white solid. E52 is a single unknown diastereoisomer.

$^1$H NMR (400 MHz, CD$_3$OD): δ 8.79 (s, 1H), 8.14 (s, 1H), 7.59 (s, 1H), 6.62 (s, 1H), 4.93-4.73 (m, 1H), 4.52 (br s, 1H), 4.09 (s, 3H), 3.80-3.457 (m, 4H), 3.41-3.32 (m, 2H), 3.21-3.10 (m, 1H), 2.98-2.95 (m, 1H), 2.47 (s, 3H), 2.44 (s, 3H), 2.31-2.21 (m, 2H), 2.18-2.93 (m, 3H), 1.88-1.77 (m, 1H). $^{19}$F NMR (376 MHz, CD$_3$OD): δ −185.71 (s, 1F).

LC-MS [mobile phase: from 95% water (0.02% NH$_4$OAc) and 5% CH$_3$CN to 5% water (0.02% NH$_4$OAc) and 95% CH$_3$CN in 6.5 min], purity >95%, Rt=4.211 min; MS Calcd.: 440, MS Found: 441 [M+H]$^+$.

Chiral HPLC [Chiral condition: Chiralpak IE 5 μm 4.6*250 mm, Phase: Hex/EtOH=40/60, flow rate: 1.0 mL/min, 230 nm, T=30° C.], Rt=7.436 min, 100% de.

Example 53

(cis)-(3S)-1-(6-(6-(3-Fluoro-1-methylpiperidin-4-yl)-5-methyl-1H-indazol-1-yl)-2-methoxypyrimidin-4-yl)pyrrolidin-3-ol (Diastereoisomer 2) (E53)

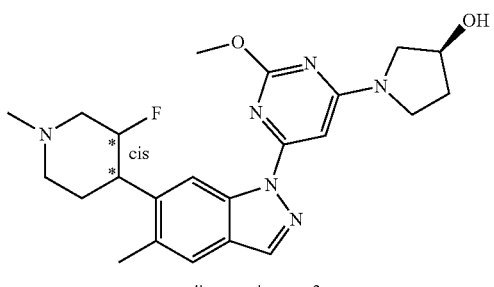

diastereoisomer 2

To a solution of (cis)-(3S)-1-(6-(6-(3-Fluoropiperidin-4-yl)-5-methyl-1H-indazol-1-yl)-2-methoxypyrimidin-4-yl)pyrrolidin-3-ol hydrochloride (diastereoisomer 2) (140 mg crude, 0.24 mmol) in methanol (8 mL) was added CH$_2$O (37%, 2 mL) and NaBH$_3$CN (30 mg, 0.48 mmol) at rt. The resulting mixture was stirred at rt for 1 h. The reaction mixture was partitioned between water (50 mL) and EtOAc (50 mL). The aqueous layer was extracted with EtOAc (50 mL). The combined organic layers were washed with brine, dried over MgSO$_4$ and concentrated. The crude was purified by prep. TLC (DCM/MeOH=10/1) to give the title compound (44.5 mg, yield 42% for 3 steps) as a white solid. E53 is a single unknown diastereoisomer.

$^1$H NMR (400 MHz, CD$_3$OD): δ 8.78 (s, 1H), 8.14 (s, 1H), 7.58 (s, 1H), 6.62 (s, 1H), 4.92-4.73 (m, 1H), 4.52 (br s, 1H), 4.09 (s, 3H), 3.78-3.48 (m, 4H), 3.41-3.33 (m, 2H), 3.20-3.11 (m, 1H), 3.00-2.96 (m, 1H), 2.46 (s, 3H), 2.45 (s, 3H), 2.33-2.18 (m, 2H), 2.18-1.93 (m, 3H), 1.88-1.78 (m, 1H). $^{19}$F NMR (376 MHz, CD$_3$OD): δ −185.73 (s, 1F).

LC-MS [mobile phase: from 95% water (0.02% NH$_4$OAc) and 5% CH$_3$CN to 5% water (0.02% NH$_4$OAc) and 95% CH$_3$CN in 6.5 min], purity 96.74% (214 nm), Rt=4.214 min; MS Calcd.: 440, MS Found: 441 [M+H]$^+$.

Chiral HPLC [Chiral condition: Chiralpak IE 5 μm 4.6*250 mm, Phase: Hex/EtOH=40/60, flow rate: 1.0 mL/min, 230 nm, T=30° C.], Rt=10.803 min, 100% de.

Example 54

(cis)-(3R)-1-(6-(6-(3-Fluoro-1-methylpiperidin-4-yl)-5-methyl-1H-indazol-1-yl)-2-methoxypyrimidin-4-yl)pyrrolidin-3-ol (Diastereoisomer 1) (E54)

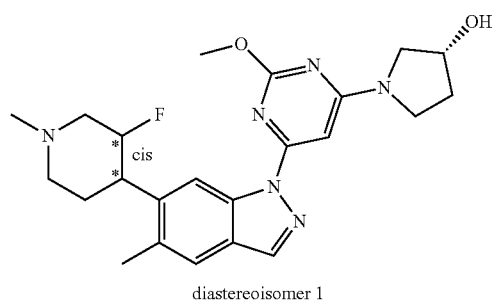 [SMILES: COc1nc(N2CC[C@@H](O)C2)cc(-n2ncc3cc(C)c(C4CCN(C)CC4F)cc32)n1]

diastereoisomer 1

To a solution of (cis)-(3R)-1-(6-(6-(3-fluoropiperidin-4-yl)-5-methyl-1H-indazol-1-yl)-2-methoxypyrimidin-4-yl)pyrrolidin-3-ol hydrochloride (diastereoisomer 1) (200 mg crude, 0.24 mmol) in methanol (8 mL) was added CH$_2$O (37%, 2 mL) and NaBH$_3$CN (30 mg, 0.48 mmol) at rt. The resulting mixture was stirred for 1.5 hrs. The reaction mixture was poured into water (100 mL) and extracted with EtOAc (40 mL×3). The combined organic layers were washed with brine, dried over MgSO$_4$ and concentrated. The crude was purified by prep. TLC (DCM/MeOH=10/1) to give the title compound (24.4 mg, yield 23% for 3 steps) as a white solid. E54 is a single unknown diastereoisomer.

$^1$H NMR (400 MHz, CDCl$_3$): δ 8.87 (s, 1H), 8.08 (s, 1H), 7.54 (s, 1H), 6.62 (s, 1H), 5.01-4.78 (m, 1H), 4.67 (s, 1H), 4.13 (s, 3H), 3.96-3.49 (m, 4H), 3.40-3.31 (m, 1H), 3.13-3.02 (m, 1H), 3.02-2.90 (m, 1H), 2.48 (s, 3H), 2.43 (s, 3H), 2.29-2.05 (m, 4H), 2.02-1.86 (m, 2H), 1.74-1.68 (m, 1H). $^{19}$F NMR (376 MHz, CDCl$_3$): δ −184.32 (s, 1F).

LC-MS [mobile phase: from 95% water (0.02% NH₄Ac) and 5% CH₃CN to 5% water (0.02% NH₄Ac) and 95% CH₃CN in 6.5 min], purity 98.88% (214 nm), Rt: 4.216 min; MS Calcd.: 440, MS Found: 441 [M+H]⁺.

Chiral HPLC [Chiral condition: Chiralpak IE 5 µm 4.6*250 mm, Phase: Hex/EtOH=40/60, flow rate: 1.0 mL/min, 230 nm, T=30° C.], Rt=7.588 min, 100% de.

Example 55

(cis)-(3R)-1-(6-(6-(3-Fluoro-1-methylpiperidin-4-yl)-5-methyl-1H-indazol-1-yl)-2-methoxypyrimidin-4-yl)pyrrolidin-3-ol (Diastereoisomer 2) (E55)

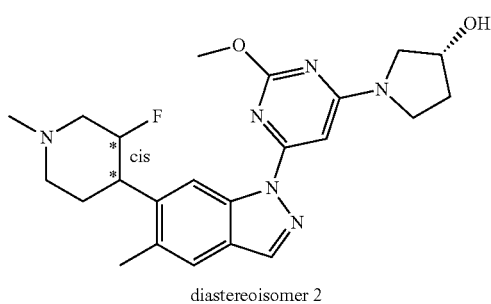 [SMILES: COc1nc(N2CC[C@@H](O)C2)cc(-n2ncc3cc(C)c(C4CCN(C)CC4F)cc32)n1]

diastereoisomer 2

To a solution of (cis)-(3R)-1-(6-(6-(3-fluoropiperidin-4-yl)-5-methyl-1H-indazol-1-yl)-2-methoxypyrimidin-4-yl)pyrrolidin-3-ol hydrochloride (diastereoisomer 2) (180 mg crude, 0.240 mmol) in methanol (8 mL) was added CH₂O (37%, 2 mL) and NaBH₃CN (30 mg, 0.48 mmol) at rt. The resulting mixture was stirred for 1.5 hrs. The reaction mixture was poured into water (100 mL) and extracted with EtOAc (40 mL×3). The combined organic layers were washed with brine, dried over MgSO₄ and concentrated. The crude was purified by prep. TLC (DCM/MeOH=10/1) to give the title compound (27.5 mg, yield 26% for 3 steps) as a white solid. E55 is a single unknown diastereoisomer.

¹H NMR (400 MHz, CDCl₃): δ 8.87 (s, 1H), 8.08 (s, 1H), 7.54 (s, 1H), 6.62 (s, 1H), 4.97-4.76 (m, 1H), 4.64 (s, 1H), 4.13 (s, 3H), 3.93-3.52 (m, 4H), 3.36-3.30 (m, 1H), 3.11-3.02 (m, 1H), 2.94-2.88 (m, 1H), 2.48 (s, 3H), 2.40 (s, 3H), 2.23-2.05 (m, 4H), 1.99-1.83 (m, 2H), 1.66-1.60 (m, 1H). ¹⁹F NMR (376 MHz, CDCl₃): δ −184.24 (s, 1F).

LC-MS [mobile phase: from 95% water (0.02% NH₄Ac) and 5% CH₃CN to 5% water (0.02% NH₄Ac) and 95% CH₃CN in 6.5 min], purity 97.29% (214 nm), Rt: 4.247 min; MS Calcd.: 440, MS Found: 441 [M+11]⁺.

Chiral HPLC [Chiral condition: Chiralpak IE 5 µm 4.6*250 mm, Phase: Hex/EtOH=40/60, flow rate: 1.0 mL/min, 230 nm, T=30° C.], Rt=8.508 min, 100% de.

Example 56

(cis)-6-(6-(3-Fluoro-1-methylpiperidin-4-yl)-5-methyl-1H-indazol-1-yl)-2-methoxy-N-methylpyrimidine-4-carboxamide (Enantiomer 2) (E56)

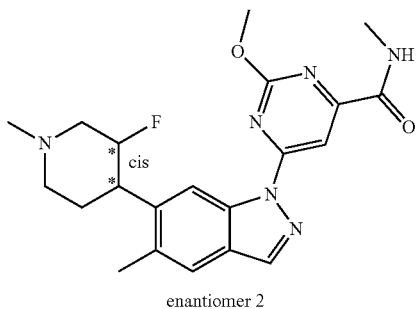 [SMILES: CNC(=O)c1cc(-n2ncc3cc(C)c(C4CCN(C)CC4F)cc32)nc(OC)n1]

enantiomer 2

(cis)-Methyl-6-(6-(3-fluoro-1-methylpiperidin-4-yl)-5-methyl-1H-indazol-1-yl)-2-methoxy pyrimidine-4-carboxylate (enantiomer 2) (40 mg, 0.097 mmol) was dissolved in methylamine alcohol solution (27%, 5 mL) and stirred at rt for 2 h. The reaction mixture was concentrated and the crude was triturated with Et₂O and filtered to give the title compound (29.4 mg, yield 74%) as a white solid. E56 is a single unknown enantiomer.

¹H NMR (400 MHz, CDCl₃): δ 8.82 (s, 1H), 8.41 (s, 1H), 8.18 (s, 1H), 7.92-7.84 (m, 1H), 7.58 (s, 1H), 4.97-4.79 (m, 1H), 4.22 (s, 3H), 3.38-3.33 (m, 1H), 3.14-3.07 (m, 1H), 3.05 (d, J=5.2 Hz, 3H), 2.95-2.92 (m, 1H), 2.50 (s, 3H), 2.42 (s, 3H), 2.25-2.10 (m, 2H), 1.99-1.91 (s, 2H). ¹⁹F NMR (376 MHz, CDCl₃): δ −184.28 (s, 1F).

LC-MS [mobile phase: from 95% water (0.02% NH₄OAc) and 5% CH₃CN to 5% water (0.02% NH₄OAc) and 95% CH₃CN in 6.5 min], purity is >95% (214 nm), Rt=4.373 min; MS Calcd.: 412, MS Found: 413 [M+H]⁺.

Chiral HPLC [Chiral condition: Chiralpak IB 5 µm 4.6*250 mm, Phase: Hex/EtOH/DEA=50/50/0.2, flow rate: 1.0 mL/min, 230 nm, T=30° C.], Rt=6.880 min, 100% ee.

Example 57

(cis)-6-(6-(3-Fluoro-1-methylpiperidin-4-yl)-5-methyl-1H-indazol-1-yl)-2-methoxy-N-methylpyrimidine-4-carboxamide (Enantiomer 1) (E57)

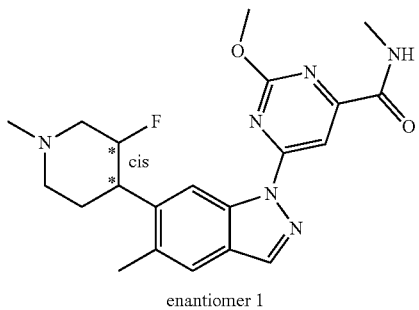 [SMILES: CNC(=O)c1cc(-n2ncc3cc(C)c(C4CCN(C)CC4F)cc32)nc(OC)n1]

enantiomer 1

(cis)-Methyl-6-(6-(3-fluoro-1-methylpiperidin-4-yl)-5-methyl-1H-indazol-1-yl)-2-methoxy pyrimidine-4-carboxylate (enantiomer 1) (40 mg, 0.097 mmol) was dissolved in methylamine alcohol solution (27%, 5 mL) and stirred at rt for 2 hrs. The reaction mixture was concentrated and the crude was triturated with Et$_2$O and filtered to give the title compound (35.7 mg, yield 89%) as a white solid. E57 is a single unknown enantiomer.

$^1$H NMR (400 MHz, CDCl$_3$): δ 8.82 (s, 1H), 8.41 (s, 1H), 8.18 (s, 1H), 7.92-7.84 (m, 1H), 7.58 (s, 1H), 4.97-4.79 (m, 1H), 4.22 (s, 3H), 3.38-3.33 (m, 1H), 3.14-3.07 (m, 1H), 3.05 (d, J 4.8 Hz, 3H), 2.95-2.92 (m, 1H), 2.50 (s, 3H), 2.42 (s, 3H), 2.25-2.10 (m, 2H), 1.99-1.87 (s, 2H). $^{19}$F NMR (376 MHz, CDCl$_3$): δ −184.29 (s, 1F).

LC-MS [mobile phase: from 95% water (0.02% NH$_4$OAc) and 5% CH$_3$CN to 5% water (0.02% NH$_4$OAc) and 95% CH$_3$CN in 6.5 min], purity is >95% (214 nm), Rt=4.385 min; MS Calcd.: 412, MS Found: 413 [M+H]$^+$.

Chiral HPLC [Chiral condition: Chiralpak IB 5 μm 4.6*250 mm, Phase: Hex/EtOH/DEA=50/50/0.2, flow rate: 1.0 mL/min, 230 nm, T=30° C.], Rt=5.423 min, 100% ee.

Example 58

(cis)-N-(6-(6-(3-Fluoro-1-methylpiperidin-4-yl)-5-methyl-1H-indazol-1-yl)-2-methoxypyrimidin-4-yl)acetamide (Enantiomer 2) (E58)

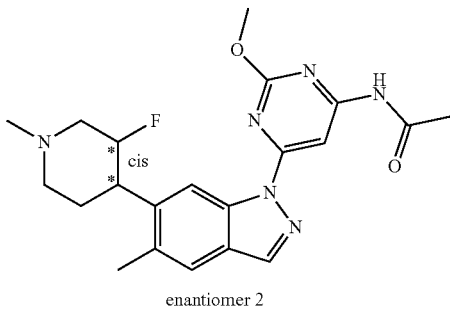 [SMILES: COc1nc(NC(C)=O)cc(-n2ncc3cc(C)c(C4CCN(C)CC4F)cc32)n1]

enantiomer 2

The mixture of (cis)-6-(6-(3-fluoro-1-methylpiperidin-4-yl)-5-methyl-1H-indazol-1-yl)-2-methoxy pyrimidin-4-amine (enantiomer 2) (80 mg, 0.216 mmol) and DMAP (cat.) in Ac$_2$O (10 mL) was heated to 110° C. for 1 h. The mixture was concentrated and the residue was dissolved in DCM (5 mL). The solution was washed with H$_2$O (10 mL). The aqueous layer was extracted with DCM/MeOH (DCM/MeOH=10/1, 5 mL×4). The combined organic solutions were concentrated to give brown oil. The oil was purified by prep-HPLC to give the title compound (37.5 mg, yield 42%) as a white solid. E58 is a single unknown enantiomer.

$^1$H NMR (400 MHz, CDCl$_3$): δ 8.80 (s, 2H), 8.37 (s, 1H), 8.13 (s, 1H), 7.91 (s, 1H), 7.55 (s, 1H), 4.99-4.75 (m, 1H), 4.14 (s, 3H), 3.37-3.29 (m, 1H), 3.11-3.02 (m, 1H), 2.96-2.89 (m, 2H), 2.49 (s, 3H), 2.41 (s, 3H), 2.25 (s, 3H), 2.22-2.10 (m, 2H), 1.96-1.82 (m, 2H).

$^{19}$F NMR (376 MHz, CDCl$_3$): δ −184.24 (s, 1F).

LC-MS [mobile phase: from 95% water (0.02% NH$_4$OAc) and 5% CH$_3$CN to 5% water (0.02% NH$_4$OAc) and 95% CH$_3$CN in 6.5 min], purity is >95%, Rt=3.211 min; MS Calcd.: 412, MS Found: 413 [M+H]$^+$.

Chiral condition: Chiralpak AD-3 3 μm 4.6*150 mm, HEX/EtOH/DEA=70/30/0.2, Flow Rate: 1.0 ml/min, 230 nm, T=30° C., Rt=5.360 min, 88.3% ee.

Example 59

(cis)-N-(6-(6-(3-Fluoro-1-methylpiperidin-4-yl)-5-methyl-1H-indazol-1-yl)-2-methoxypyrimidin-4-yl)acetamide (Enantiomer 1) (E59)

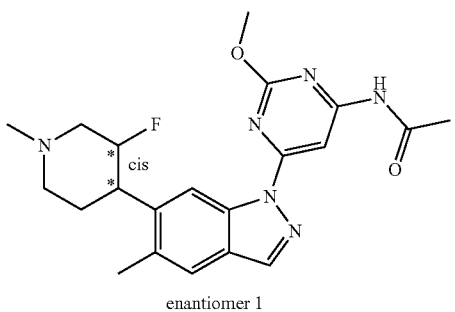 [SMILES: COc1nc(NC(C)=O)cc(-n2ncc3cc(C)c(C4CCN(C)CC4F)cc32)n1]

enantiomer 1

The mixture of (cis)-6-(6-(3-fluoro-1-methylpiperidin-4-yl)-5-methyl-1H-indazol-1-yl)-2-methoxy pyrimidin-4-amine (enantiomer 1) (37 mg, 0.10 mmol) and DMAP (cat.) in Ac$_2$O (6 mL) was heated to 110° C. for 1 h. The mixture was concentrated and dissolved in DCM (5 mL). The solution was washed with H$_2$O (10 mL). The aqueous layer was extracted with DCM/MeOH (DCM/MeOH=10/1, 5 mL×4). The combined organic solutions were concentrated to give brown oil. The oil was purified by prep-HPLC to give the title compound (11.1 mg, yield 27%) as a white solid. E59 is a single unknown enantiomer.

$^1$H NMR (400 MHz, CDCl$_3$): δ 8.80 (s, 1H), 8.37 (s, 1H), 8.13 (s, 1H), 7.85 (s, 1H), 7.56 (s, 1H), 4.95-4.75 (m, 1H), 4.13 (s, 3H), 3.36-3.30 (m, 1H), 3.12-3.02 (m, 1H), 2.93-2.87 (m, 1H), 2.49 (s, 3H), 2.41 (s, 3H), 2.25 (s, 3H), 2.19-2.06 (m, 2H), 1.99-1.82 (m, 2H).

$^{19}$F NMR (376 MHz, CDCl$_3$): δ −184.25 (s, 1F).

LC-MS [mobile phase: from 70% water (0.02% NH$_4$OAc) and 30% CH$_3$CN to 5% water (0.02% NH$_4$OAc) and 95% CH$_3$CN in 6.5 min], purity >95%, Rt=3.573 min; MS Calcd.: 412, MS Found: 413 [M+H]$^+$.

Chiral condition: Chiralpak AD-3 3 μm 4.6*150 mm, Hex/EtOH/DEA=70/30/0.2, Flow Rate: 1.0 ml/min, 230 nm, T=30° C., Rt=4.130 min, 81.9% ee.

Example 60

(cis)-4-(6-(6-(3-Fluoro-1-methylpiperidin-4-yl)-5-methyl-1H-indazol-1-yl)-2-methoxypyrimidin-4-yl)thiomorpholine 1,1-dioxide (Enantiomer 1) (E60)

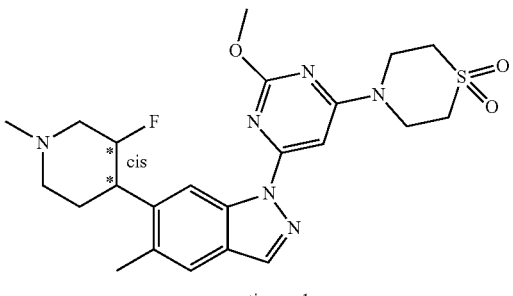

enantiomer 1

A solution of (cis)-4-(6-(6-(3-fluoropiperidin-4-yl)-5-methyl-1H-indazol-1-yl)-2-methoxypyrimidin-4-yl)thiomorpholine 1,1-dioxide hydrochloride (enantiomer 1) (37 mg of crude, 0.066 mmol) and formaldehyde solution (14%, 1 mL) in methanol (2 mL) was stirred at rt for 30 min. Then NaBH$_3$CN (21 mg, 0.33 mmol) was added. The resulting mixture was stirred at rt overnight. The mixture was poured into sat. Na$_2$CO$_3$ (5 mL) and stirred for 10 min. Then the mixture was extracted with dichloromethane (10 mL×2). The combined organic layers were washed with brine (10 mL), dried over Na$_2$SO$_4$ and concentrated. The residue was purified by prep. TLC (DCM:MeOH=10:1) to give the title compound (15.5 mg, yield 48%) as white solid. E60 is a single unknown enantiomer.

$^1$H NMR (300 MHz, CDCl$_3$): δ 8.83 (s, 1H), 8.09 (s, 1H), 7.55 (s, 1H), 6.96 (s, 1H), 4.97-4.74 (m, 1H), 4.29-4.22 (m, 4H), 4.15 (s, 3H), 3.36-3.30 (m, 1H), 3.11-3.01 (m, 5H), 2.96-2.86 (m, 1H), 2.49 (s, 3H), 2.43 (s, 3H), 2.31-2.13 (m, 2H), 2.01-1.85 (m, 2H). $^{19}$F NMR (376 MHz, DMSO-d$_6$): δ −182.36 (s, 1F).

LC-MS [mobile phase: from 70% water (0.02% NH$_4$OAc) and 30% CH$_3$CN to 5% water (0.02% NH$_4$OAc) and 95% CH$_3$CN in 6.5 min], purity is >95%, Rt=3.462 min; MS Calcd.: 488, MS Found: 489 [M+H]$^+$.

Chiral HPLC: Chiralpak IB 5 μm 4.6*250 mm, Phase: HEX:EtOH:DEA=70:30:0.2, Flow Rate: 1 ml/min, 254 nm, T=30° C., Rt=16.979 min, 100% ee.

Example 61

(cis)-4-(6-(6-(3-Fluoro-1-methylpiperidin-4-yl)-5-methyl-1H-indazol-1-yl)-2-methoxypyrimidin-4-yl)thiomorpholine 1,1-dioxide (Enantiomer 2) (E61)

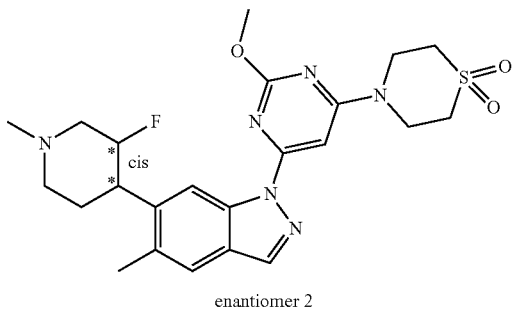 [SMILES: COc1nc(N2CCS(=O)(=O)CC2)cc(-n2ncc3cc(C)c(C4CCN(C)CC4F)cc32)n1]

enantiomer 2

A solution of (cis)-4-(6-(6-(3-fluoropiperidin-4-yl)-5-methyl-1H-indazol-1-yl)-2-methoxypyrimidin-4-yl)thiomorpholine 1,1-dioxide hydrochloride (enantiomer 2) (45 mg of crude, 0.088 mmol) and formaldehyde solution (14%, 1 mL) in methanol (3 mL) was stirred at rt for 30 min. Then NaBH$_3$CN (28 mg, 0.44 mmol) was added. The resulting mixture was stirred at rt overnight. The mixture was poured into sat. Na$_2$CO$_3$ (10 mL) and stirred for 10 min. Then the mixture was extracted with dichloromethane (10 mL×2). The combined organic layers were washed with brine (10 mL), dried over Na$_2$SO$_4$ and concentrated. The residue purified by prep. TLC (DCM:MeOH=10:1) to give the title compound (24.7 mg, yield 58%) as white solid. E61 is a single unknown enantiomer.

$^1$H NMR (300 MHz, CDCl$_3$): δ 8.83 (s, 1H), 8.09 (s, 1H), 7.56 (s, 1H), 6.96 (s, 1H), 5.02-4.77 (m, 1H), 4.34-4.27 (m, 4H), 4.16 (s, 3H), 3.50-3.36 (m, 1H), 3.26-3.11 (m, 5H), 3.05-2.86 (m, 1H), 2.49-2.33 (m, 6H), 2.31-2.10 (m, 2H), 2.01-1.85 (m, 2H). $^{19}$F NMR (376 MHz, CDCl$_3$): δ −184.30 (s, 1F).

LC-MS [mobile phase: from 70% water (0.02% NH$_4$OAc) and 30% CH$_3$CN to 5% water (0.02% NH$_4$OAc) and 95% CH$_3$CN in 6.5 min], purity is >95%, Rt=3.710 min; MS Calcd.: 488, MS Found: 489 [M+H]$^+$.

Chiral HPLC: Chiralpak IB 5 μm 4.6*250 mm, Phase: HEX:EtOH:DEA=70:30:0.2, Flow Rate: 1 ml/min, 254 nm, T=30° C., Rt=19.420 min, 100% ee.

Example 62

(cis)-4-(6-(6-(3-Fluoropiperidin-4-yl)-5-methyl-1H-indazol-1-yl)-2-methoxypyrimidin-4-yl)morpholine hydrochloride (Enantiomer 2) (E62)

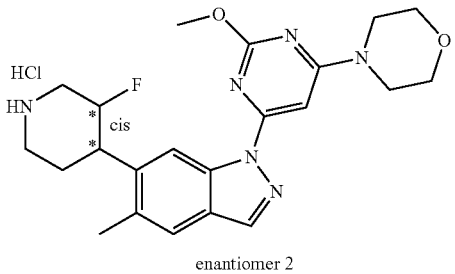

enantiomer 2

A mixture of (cis)-tert-butyl 3-fluoro-4-(1-(2-methoxy-6-morpholinopyrimidin-4-yl)-5-methyl-1H-indazol-6-yl)piperidine-1-carboxylate (enantiomer 2) (35 mg, 0.067 mmol) in HCl/dioxane (2.5 M, 10 mL) was stirred at rt for 1 h. The reaction mixture was concentrated. The residue was triturated with EtOAc (5 mL) to give the title compound (12 mg, yield 39%) as a white solid. E62 is a single unknown enantiomer.

$^1$H NMR (300 MHz, DMSO-d$_6$): δ 9.69 (s, 2H), 8.68 (s, 1H), 8.36 (s, 1H), 7.68 (s, 1H), 6.85 (s, 1H), 5.20-4.96 (m, 1H), 4.01 (s, 3H), 3.66-3.51 (m, 10H), 3.34-3.30 (m, 1H), 3.21-3.04 (m, 2H), 2.44 (s, 3H), 2.09-2.01 (m, 1H), 1.96-1.87 (m, 1H).

$^{19}$F NMR (376 MHz, DMSO-d$_6$): δ −185.58 (s, 1F).

LC-MS [mobile phase: from 80% water (0.02% NH$_4$OAc) and 20% CH$_3$CN to 5% water (0.02% NH$_4$OAc) and 95% CH$_3$CN in 6.5 min], purity >95%, Rt=4.154 min; MS Calcd.: 426, MS Found: 427 [M+H]$^+$.

Chiral condition: Chiralpak IF 5 μm 4.6*250 mm, CH$_3$OH/EtOH/DEA=50/50/0.2, Flow Rate: 1.0 ml/min, 230 nm, T=30° C. Rt=9.310 min, 100% ee.

Example 63

(cis)-4-(6-(6-(3-Fluoropiperidin-4-yl)-5-methyl-1H-indazol-1-yl)-2-methoxypyrimidin-4-yl)morpholine hydrochloride (Enantiomer 1) (E63)

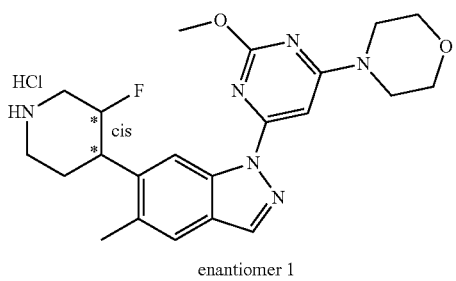 [SMILES: Cl ; COc1nc(N2CCOCC2)cc(-n2ncc3cc(C)c(C4CCNCC4F)cc32)n1]

enantiomer 1

A mixture of (cis)-tert-butyl 3-fluoro-4-(1-(2-methoxy-6-morpholinopyrimidin-4-yl)-5-methyl-1H-indazol-6-yl)piperidine-1-carboxylate (enantiomer 1) (35 mg, 0.067 mmol) in HCl/dioxane (2.5 M, 10 mL) was stirred at rt for 1 h. The reaction mixture was concentrated. The residue was triturated with EtOAc (5 mL) to give the title compound (12 mg, yield 39%) as a white solid. E63 is a single unknown enantiomer.

$^1$H NMR (300 MHz, DMSO-$d_6$): δ 9.57 (br s, 2H), 8.68 (s, 1H), 8.36 (s, 1H), 7.69 (s, 1H), 6.86 (s, 1H), 5.17-4.94 (m, 1H), 4.01 (s, 3H), 3.66-3.51 (m, 10H), 3.36-3.30 (m, 1H), 3.22-3.06 (m, 2H), 2.44 (s, 3H), 2.11-2.02 (m, 1H), 1.93-1.85 (m, 1H).

$^{19}$F NMR (376 MHz, CDCl$_3$): δ −185.58 (s, 1F).

LC-MS [mobile phase: from 80% water (0.02% NH$_4$OAc) and 20% CH$_3$CN to 5% water (0.02% NH$_4$OAc) and 95% CH$_3$CN in 6.5 min], purity >95%, Rt=4.141 min; MS Calcd.: 426, MS Found: 427 [M+H]$^+$.

Chiral condition: Chiralpak IF 5 μm 4.6*250 mm, CH$_3$OH/EtOH/DEA=50/50/0.2, Flow Rate: 1.0 ml/min, 230 nm, T=30° C. Rt=8.228 min, 100% ee.

Example 64

(cis)-4-(6-(6-(3-Fluoropiperidin-4-yl)-5-methyl-1H-indazol-1-yl)-2-methylpyrimidin-4-yl)morpholine hydrochloride (Enantiomer 1) (E64)

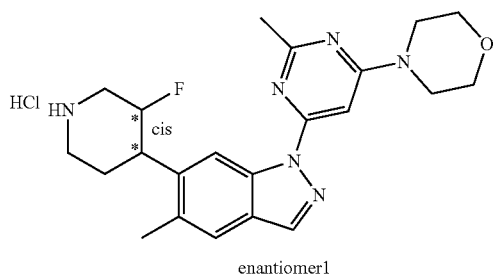 [SMILES: Cl ; Cc1nc(N2CCOCC2)cc(-n2ncc3cc(C)c(C4CCNCC4F)cc32)n1]

enantiomer1

The mixture of (cis)-tert-butyl 3-fluoro-4-(5-methyl-1-(2-methyl-6-morpholino pyrimidin-4-yl)-1H-indazol-6-yl)piperidine-1-carboxylate (enantiomer 1) (60 mg, mixture with 60% of de-Boc compound) in HCl/methanol (4 mol/L, 4 mL) was stirred at rt for 1 h. The reaction mixture was concentrated to give the title compound (38.4 mg, yield 68%) as a light yellow solid. 1H NMR (400 MHz, DMSO-$d_6$): δ 10.13 (br s, 1H), 9.63 (br s, 1H), 8.84 (s, 1H), 8.38 (s, 1H), 7.69 (s, 1H), 7.01 (s, 1H), 5.31-5.12 (m, 1H), 3.69-3.67 (m, 9H), 3.58-3.49 (m, 1H), 3.39-3.37 (m, 1H), 3.31-3.08 (m, 2H), 2.64 (s, 3H), 2.46 (s, 3H), 2.10-2.02 (m, 2H). $^{19}$F NMR (376 MHz, DMSO-$d_6$): δ −185.55 (s, 1F). E64 is a single unknown enantiomer.

LC-MS [mobile phase: from 95% water (0.1% TFA) and 5% CH$_3$CN to 5% water (0.1% TFA) and 95% CH$_3$CN in 6.5 min], purity is >95%, Rt=3.142 min; MS Calcd.: 410, MS Found: 411 [M+H]$^+$.

Chiral HPLC [Chiral condition: Chiralpak IE 5 μm 4.6*250 mm, Phase: HEX: IPA=50/50, Flow Rate: 1 ml/min, 230 nm, T=30° C., Rt=8.342 min, 100% ee.

Example 65

(cis)-4-(6-(6-(3-Fluoropiperidin-4-yl)-5-methyl-1H-indazol-1-yl)-2-methylpyrimidin-4-yl)morpholine hydrochloride (Enantiomer 2) (E65)

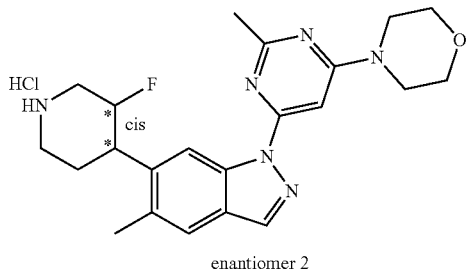 [SMILES: Cl ; Cc1nc(N2CCOCC2)cc(-n2ncc3cc(C)c(C4CCNCC4F)cc32)n1]

enantiomer 2

The mixture of (cis)-tert-butyl 3-fluoro-4-(5-methyl-1-(2-methyl-6-morpholinopyrimidin-4-yl)-1H-indazol-6-yl) piperidine-1-carboxylate (enantiomer 2) (60 mg, mixture with 60% of de-Boc compound) in HCl/methanol (4 mol/L, 4 mL) was stirred at rt for 1 h. The reaction mixture was concentrated to give the title compound (48.5 mg, yield 87%) as a light yellow solid. E65 is a single unknown enantiomer.

$^1$H NMR (400 MHz, DMSO-$d_6$): δ 10.13 (br s, 1H), 9.63 (br s, 1H), 8.84 (s, 1H), 8.38 (s, 1H), 7.69 (s, 1H), 7.01 (s, 1H), 5.33-5.12 (m, 1H), 3.69-3.67 (m, 9H), 3.57-3.51 (m, 1H), 3.38-3.33 (m, 1H), 3.22-3.06 (m, 2H), 2.63 (s, 3H), 2.46 (s, 3H), 2.10-2.02 (m, 2H). $^{19}$F NMR (376 MHz, DMSO-$d_6$): δ −185.54 (s, 1F).

LC-MS [mobile phase: from 95% water (0.02% NH$_4$Ac) and 5% CH$_3$CN to 5% water (0.02% NH$_4$Ac) and 95% CH$_3$CN in 6.5 min], purity is >95%, Rt=3.960 min; MS Calcd.: 410, MS Found: 411 [M+H]$^+$.

Chiral HPLC [Chiral condition: Chiralpak IE 5 um 4.6*250 mm, Phase: HEX: IPA=50/50, Flow Rate: 1 ml/min, 230 nm, T=30° C., Rt=6.798 min, 100% ee.

Example 66

1-(6-(6-(3,3-Difluoropiperidin-4-yl)-5-methyl-1H-indazol-1-yl)-2-methoxypyrimidin-4-yl)azetidine-3-carbonitrile (Enantiomer 1) (E66)

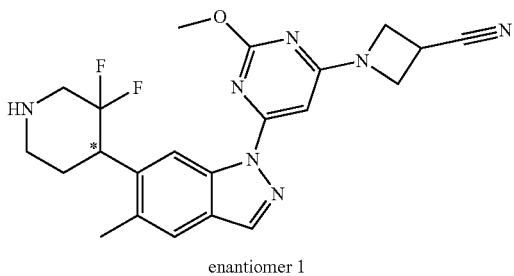 [SMILES: COc1nc(N2CC(C#N)C2)cc(-n2ncc3cc(C)c(C4CCNCC4(F)F)cc32)n1]

enantiomer 1

To a solution of tert-butyl 4-(1-(6-(3-cyanoazetidin-1-yl)-2-methoxypyrimidin-4-yl)-5-methyl-1H-indazol-6-yl)-3,3-difluoropiperidine-1-carboxylate (enantiomer 1) (65 mg, 0.12 mmol) in DCM (5 mL) was added TFA (1 mL) dropwise at 0° C. The resulting mixture was stirred at rt for 1 h. The mixture was concentrated under reduced pressure at rt. The residue was dissolved in EtOAc (25 mL), basified with aqueous $Cs_2CO_3$ (2 M) to pH=12. The organic layer was washed with brine (10 mL), dried over $Na_2SO_4$ and concentrated. The residue was washed with 1 mL of $Et_2O$ to give the title compound (36 mg, yield 68%) as a white solid. E66 is a single unknown enantiomer.

$^1$H NMR (400 MHz, $CDCl_3$): δ 8.98 (s, 1H), 8.10 (s, 1H), 7.56 (s, 1H), 6.51 (s, 1H), 4.49-4.44 (m, 2H), 4.41-4.37 (m, 2H), 4.15 (m, 3H), 3.68-3.60 (m, 1H), 3.57-3.47 (m, 1H), 3.37-3.31 (m, 1H), 3.27-3.23 (m, 1H), 3.04-2.93 (m, 1H), 2.81 (t, J=13.2 Hz, 2H), 2.49 (s, 3H), 2.14-2.10 (m, 1H), 1.98-1.95 (m, 1H). $^{19}$F NMR (376 MHz, $CDCl_3$): δ −105.64 (d, J=241.39 Hz, 1F), −117.23 (d, J=241.77 Hz, 1F).

LC-MS [mobile phase: from 70% water (0.02% $NH_4OAc$) and 30% $CH_3CN$ to 5% water (0.02% $NH_4OAc$) and 95% $CH_3CN$ in 6.5 min], purity >95%, Rt=3.318 min; MS Calcd.: 439, MS Found: 440 [M+H]$^+$.

Chiral HPLC: [Chiral condition: Chiralpak IB 5 μm 4.6*250 mm, Phase: MeOH/EtOH/DEA=50/50/0.2, flow rate: 1.0 mL/min, 230 nm, T=30° C.], Rt=6.612 min, 100% ee.

Example 67

1-(6-(6-(3,3-Difluoropiperidin-4-yl)-5-methyl-1H-indazol-1-yl)-2-methoxypyrimidin-4-yl)azetidine-3-carbonitrile (Enantiomer 2) (E67)

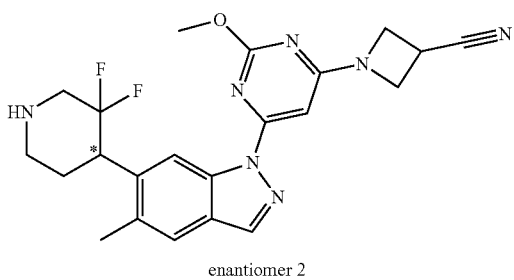 [SMILES: COc1nc(N2CC(C#N)C2)cc(-n2ncc3cc(C)c(C4CCNCC4(F)F)cc32)n1]

enantiomer 2

To a solution of tert-butyl 4-(1-(6-(3-cyanoazetidin-1-yl)-2-methoxypyrimidin-4-yl)-5-methyl-1H-indazol-6-yl)-3,3-difluoropiperidine-1-carboxylate (enantiomer 2) (80 mg, 0.15 mmol) in DCM (2 mL) was added TFA (0.5 mL), and the mixture was stirred at rt for 1 h. The mixture was concentrated under reduced pressure. The residue was dissolved in EtOAc (40 mL), and basified with $Cs_2CO_3$ (2 M) to pH=12. The organic layers was separated and washed with brine (10 mL), dried over $Na_2SO_4$, filtered, and concentrated to give the title compound (42 mg, yield 64%) as a white solid. E67 is a single unknown enantiomer.

$^1$H NMR (300 MHz, $CDCl_3$): δ 8.97 (s, 1H), 8.10 (s, 1H), 7.56 (s, 1H), 6.51 (s, 1H), 4.50-4.35 (m, 4H), 4.15 (s, 3H), 3.70-3.45 (m, 2H), 3.38-3.21 (m, 2H), 2.98 (dd, J=30.6, 13.2 Hz, 1H), 2.86-2.76 (m, 1H), 2.49 (s, 3H), 2.20-2.10 (m, 1H), 2.00-1.92 (m, 1H). $^{19}$F NMR (376 MHz, $CDCl_3$): δ −105.66 (d, J=243.27 Hz, 1F), −117.28 (d, J=241.02 Hz, 1F).

LC-MS [mobile phase: from 70% water (0.02% $NH_4OAc$) and 30% $CH_3CN$ to 5% water (0.02% $NH_4OAc$) and 95% $CH_3CN$ in 6.5 min], purity >95%, Rt=3.282 min; MS Calcd.: 439, MS Found: 440 [M+H]$^+$.

Chiral HPLC: [Chiral condition: Chiralpak IB 5 μm 4.6*250 mm, Phase: MeOH/EtOH/DEA=50/50/0.2, flow rate: 1.0 mL/min, 230 nm, T=30° C.], Rt=8.160 min, 100% ee.

Example 68

(cis)-1-(6-(5-fluoro-6-(3-fluoro-1-methylpiperidin-4-yl)-1H-indazol-1-yl)-2-methoxypyrimidin-4-yl)azetidin-3-ol (Enantiomer 1) (E68)

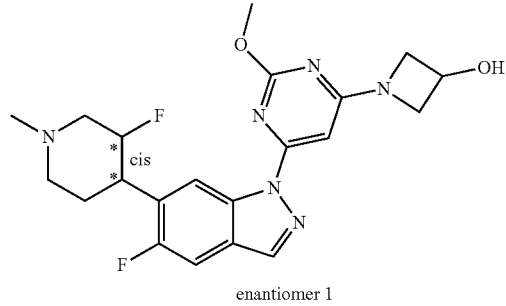 [SMILES: COc1nc(N2CC(O)C2)cc(-n2ncc3cc(F)c(C4CCN(C)CC4F)cc32)n1]

enantiomer 1

To a suspension of (cis)-5-fluoro-6-(3-fluoro-1-methylpiperidin-4-yl)-1-(2-methoxy-6-(3-((tetrahydro-2H-pyran-2-yl)oxy)azetidin-1-yl)pyrimidin-4-yl)-1H-indazole (enantiomer 1) (50 mg, 0.097 mmol) in methanol (5 mL) was added TsOH (85 mg, 0.49 mmol). The mixture was heated to 65° C. and stirred at 65° C. for 30 min. The reaction mixture was poured into $Na_2CO_3$ (sat., 20 mL) and extracted with EtOAc (20 mL×3). The combined organic layers were washed with brine, dried over $MgSO_4$ and concentrated to give the title compound (38.2 mg, yield 66%) as a white solid. E68 is a single unknown enantiomer.

$^1$H NMR (400 MHz, $CDCl_3$): δ 8.89 (d, J=6.4 Hz, 1H), 8.11 (s, 1H), 7.37 (d, J=10.0 Hz, 1H), 6.47 (s, 1H), 4.98-4.80 (m, 2H), 4.41 (t, J=8.0 Hz, 2H), 4.09 (s, 3H), 4.01 (dd, J=9.6, 4.0 Hz, 2H), 3.33-3.29 (m, 1H), 3.17-3.09 (m, 1H), 2.91-2.88 (m, 1H), 2.52 (br s, 1H), 2.39 (s, 3H), 2.21-2.07 (m, 2H), 2.04-1.94 (m, 1H), 1.91-1.85 (m, 1H). $^{19}$F NMR (376 MHz, $CDCl_3$): δ −124.00 (s, 1F), −184.18 (s, 1F).

LC-MS [mobile phase: from 95% water (0.02% $NH_4OAc$) and 5% $CH_3CN$ to 5% water (0.02% $NH_4OAc$)

and 95% CH$_3$CN in 6.5 min], purity is >95%, Rt=3.940 min; MS Calcd.: 430, MS Found: 431 [M+H]$^+$.

Chiral HPLC [Chiral condition: Chiralpak IA 5 μm 4.6*250 mm, Phase: MeOH/EtOH/DEA=50/50/0.2, flow rate: 1.0 mL/min, 230 nm, T=30° C.], Rt=6.852 min, 96.7% ee.

Example 69

(cis)-1-(6-(5-Fluoro-6-(3-fluoro-1-methylpiperidin-4-yl)-1H-indazol-1-yl)-2-methoxypyrimidin-4-yl)azetidin-3-ol (Enantiomer 2) (E69)

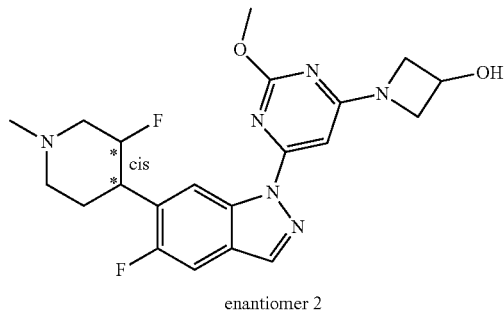 [SMILES: COc1nc(N2CC(O)C2)cc(-n2ncc3cc(F)c(C4CCN(C)CC4F)cc32)n1]

enantiomer 2

To a suspension of (cis)-5-fluoro-6-(3-fluoro-1-methylpiperidin-4-yl)-1-(2-methoxy-6-(3-((tetrahydro-2H-pyran-2-yl)oxy)azetidin-1-yl)pyrimidin-4-yl)-1H-indazole (enantiomer 2) (40 mg, 0.078 mmol) in methanol (4 mL) was added TsOH (67 mg, 0.39 mmol). The mixture was heated to 65° C. and stirred at 65° C. for 30 min. The reaction mixture was poured into Na$_2$CO$_3$ (sat., 20 mL) and extracted with EtOAc (20 mL×3). The combined organic layers were washed with brine, dried over MgSO$_4$ and concentrated to give the title compound (22.5 mg, yield 67%) as a white solid. E69 is a single unknown enantiomer.

$^1$H NMR (400 MHz, CDCl$_3$): δ 8.88 (d, J=6.4 Hz, 1 Hz), 8.11 (s, 1H), 7.36 (d, J=9.6 Hz, 1H), 6.47 (s, 1H), 4.98-4.79 (m, 2H), 4.41 (t, J=8.0 Hz, 2H), 4.09 (s, 3H), 4.01 (dd, J=9.2, 4.0 Hz, 2H), 3.33-3.29 (m, 1H), 3.17-3.09 (m, 1H), 2.90-2.87 (m, 1H), 2.46 (br s, 1H), 2.38 (s, 3H), 2.21-2.08 (m, 2H), 2.03-1.98 (m, 1H), 1.93-1.83 (m, 1H). $^{19}$F NMR (376 MHz, CDCl$_3$): δ −123.99 (s, 1F), −184.19 (s, 1F).

LC-MS [mobile phase: from 95% water (0.02% NH$_4$OAc) and 5% CH$_3$CN to 5% water (0.02% NH$_4$OAc) and 95% CH$_3$CN in 6.5 min], purity is >95%, Rt=3.989 min; MS Calcd.: 430, MS Found: 431 [M+H]$^+$.

Chiral HPLC [Chiral condition: Chiralpak IA 5 μm 4.6*250 mm, Phase: MeOH/EtOH/DEA=50/50/0.2, flow rate: 1.0 mL/min, 230 nm, T=30° C.], Rt=5.011 min, 100% ee.

Example 70

(cis)-1-(6-(5-Fluoro-6-(3-fluoro-1-methylpiperidin-4-yl)-1H-indazol-1-yl)-2-methylpyrimidin-4-yl)azetidin-3-ol (Enantiomer 1) (E70)

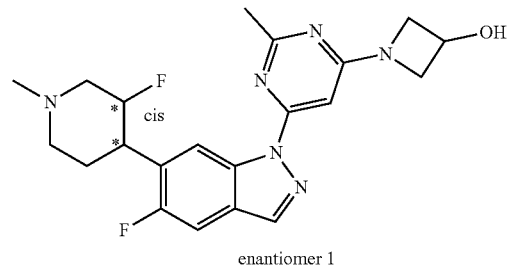 [SMILES: Cc1nc(N2CC(O)C2)cc(-n2ncc3cc(F)c(C4CCN(C)CC4F)cc32)n1]

enantiomer 1

To a suspension of (cis)-5-fluoro-6-(3-fluoro-1-methylpiperidin-4-yl)-1-(2-methyl-6-(3-((tetrahydro-2H-pyran-2-yl)oxy)azetidin-1-yl)pyrimidin-4-yl)-1H-indazole (enantiomer 1) (70 mg, 0.14 mmol) in methanol (10 mL) was added TsOH.H$_2$O (8 mg, 0.04 mmol). The resulting solution was stirred at rt overnight. The reaction mixture was poured into Na$_2$CO$_3$ (sat., 50 mL) and extracted with EtOAc (20 mL×3). The combined organic layers were washed with brine, dried over MgSO$_4$ and concentrated to give the title compound (38.2 mg, yield 66%) as a white solid. E70 is a single unknown enantiomer.

$^1$H NMR (300 MHz, CDCl$_3$): δ 8.94 (d, J=6.3 Hz, 1H), 8.11 (s, 1H), 7.36 (d, J=9.6 Hz, 1H), 6.60 (s, 1H), 5.10-4.80 (m, 2H), 4.44-4.39 (m, 2H), 4.03-3.99 (m, 2H), 3.41-3.31 (m, 1H), 3.22-3.09 (m, 1H), 2.99-2.89 (m, 1H), 2.61 (s, 3H), 2.43 (s, 3H), 2.28-2.11 (m, 2H), 2.06-1.97 (m, 2H). $^{19}$F NMR (376 MHz, CDCl$_3$): δ −124.21 (s, 1F), −184.16 (s, 1F).

LC-MS [mobile phase: from 95% water (0.1% TFA) and 5% CH$_3$CN to 5% water (0.1% TFA) and 95% CH$_3$CN in 6.5 min], purity 95.38% (214 nm), Rt=2.786 min; MS Calcd.: 414, MS Found: 415 [M+H]$^+$.

Chiral HPLC: [Chiral condition: Chiralpak IA 5 μm 4.6*250 mm, Phase: Hex/EtOH/DEA=60/40/0.2, flow rate: 1.0 mL/min, 230 nm, T=30° C.], Rt=6.693 min, 100% ee.

Example 71

(cis)-1-(6-(5-Fluoro-6-(3-fluoro-1-methylpiperidin-4-yl)-1H-indazol-1-yl)-2-methylpyrimidin-4-yl)azetidin-3-ol (Enantiomer 2) (E71)

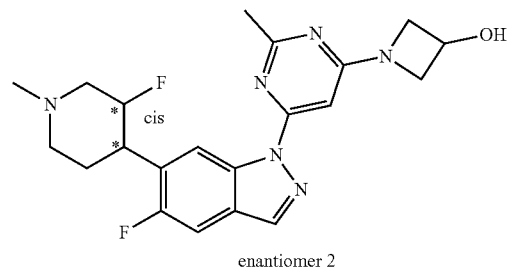 [SMILES: Cc1nc(N2CC(O)C2)cc(-n2ncc3cc(F)c(C4CCN(C)CC4F)cc32)n1]

enantiomer 2

To a suspension of (cis)-5-fluoro-6-(3-fluoro-1-methylpiperidin-4-yl)-1-(2-methyl-6-(3-((tetrahydro-2H-pyran-2-yl)

oxy)azetidin-1-yl)pyrimidin-4-yl)-1H-indazole (enantiomer 2) (68 mg, 0.14 mmol) in methanol (10 mL) was added TsOH.H$_2$O (8 mg, 0.04 mmol). The resulting solution was stirred overnight at rt. The reaction mixture was poured into Na$_2$CO$_3$ (sat., 50 mL) and extracted with EtOAc (20 mL×3). The combined organic layers were washed with brine, dried over MgSO$_4$ and concentrated to give the title compound (38.2 mg, yield 66%) as a white solid. E71 is a single unknown enantiomer.

$^1$H NMR (300 MHz, CDCl$_3$): δ 8.95 (d, J=6.3 Hz, 1H), 8.11 (s, 1H), 7.36 (d, J=9.6 Hz, 1H), 6.59 (s, 1H), 5.08-4.80 (m, 2H), 4.44-4.39 (m, 2H), 4.03-3.99 (m, 2H), 3.41-3.31 (m, 1H), 3.22-3.09 (m, 1H), 2.99-2.89 (m, 1H), 2.61 (s, 3H), 2.43 (s, 3H), 2.28-2.11 (m, 2H), 2.06-1.97 (m, 2H). $^{19}$F NMR (376 MHz, CDCl$_3$): δ −124.21 (s, 1F), −184.16 (s, 1F).

LC-MS [mobile phase: from 95% water (0.1% TFA) and 5% CH$_3$CN to 5% water (0.1% TFA) and 95% CH$_3$CN in 6.5 min], purity >95%, Rt=2.786 min, MS Calcd.: 414, MS Found: 415 [M+H]$^+$.

Chiral HPLC [Chiral condition: Chiralpak IA 5 μm 4.6*250 mm, Phase: Hex/EtOH/DEA=60/40/0.2, flow rate: 1.0 mL/min, 230 nm, T=30° C.], Rt=6.693 min, 100% ee.

Example 72 and 73

(cis)-1-(6-(6-(3-Fluoro-1-methylpiperidin-4-yl)-1H-indazol-1-yl)-2-methoxypyrimidin-4-yl)azetidin-3-ol (Enantiomer 1) (E72) and (cis)-1-(6-(6-(3-Fluoro-1-methylpiperidin-4-yl)-1H-indazol-1-yl)-2-methoxypyrimidin-4-yl)azetidin-3-ol (Enantiomer 2) (E73)

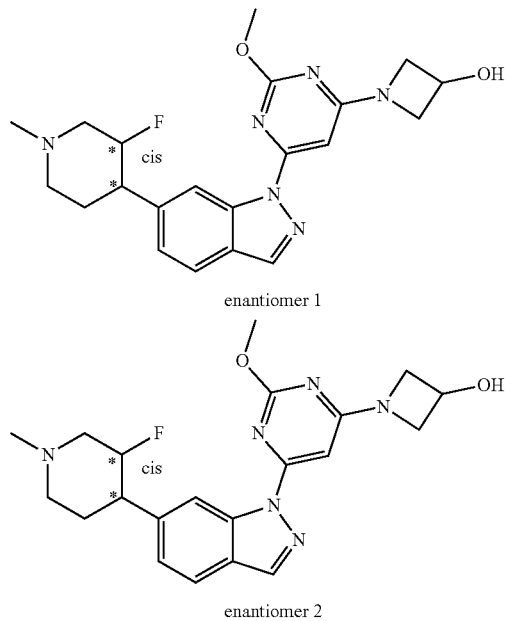

(cis)-1-(6-(6-(3-Fluoro-1-methylpiperidin-4-yl)-1H-indazol-1-yl)-2-methoxypyrimidin-4-yl)azetidin-3-ol (210 mg, 0.509 mmol) was separated by Chiral HPLC with the method (Chiralpak IC 5 μm 20*250 mm, Phase: Hex/EtOH=70/30, flow rate: 18 mL/min, 205 nm, T=30° C.) to give the title compounds (cis)-1-(6-(6-(3-Fluoro-1-methylpiperidin-4-yl)-1H-indazol-1-yl)-2-methoxypyrimidin-4-yl)azetidin-3-ol (enantiomer 1) (E72) (44.8 mg, yield 21%) and crude (cis)-1-(6-(6-(3-Fluoro-1-methylpiperidin-4-yl)-1H-indazol-1-yl)-2-methoxypyrimidin-4-yl)azetidin-3-ol (enantiomer 2) (E73) (80 mg, 75% purity) both as white solid. Crude E73 was further purified by prep. TLC (DCM/MeOH=15/1) to give the desire E73 (49.9 mg, yield 24%) as a white solid. E72 is a single unknown enantiomer. E73 is a single unknown enantiomer.

E72: $^1$H NMR (400 MHz, CDCl$_3$): δ 8.81 (s, 1H), 8.14 (s, 1H), 7.70 (d, J=6.3 Hz, 1H), 7.22 (d, J=7.2 Hz, 1H), 6.48 (s, 1H), 4.86-4.68 (m, 2H), 4.43-4.39 (m, 2H), 4.10 (s, 3H), 4.01 (dd, J=7.2, 4.0 Hz, 2H), 3.32-3.28 (m, 1H), 2.92-2.78 (m, 2H), 2.40 (s, 3H), 2.19-1.91 (m, 4H).

$^{19}$F NMR (376 MHz, CDCl$_3$): δ −183.28 (s, 1F).

LC-MS [mobile phase: from 95% water (0.1% TFA) and 5% CH$_3$CN to 5% water (0.1% TFA) and 95% CH$_3$CN in 6.5 min], purity >95%, Rt=2.871 min; MS Calcd.: 412, MS Found: 413 [M+H]$^+$.

Chiral HPLC [Chiral condition: Chiralpak IC 5 um 4.6*250 mm, Phase: Hex/EtOH=70/30, flow rate: 1.0 mL/min, 230 nm, T=30° C.], Rt=12.017 min, 100% ee.

E73: $^1$H NMR (400 MHz, CDCl$_3$): δ 8.81 (s, 1H), 8.14 (s, 1H), 7.70 (d, J=6.3 Hz, 1H), 7.22 (d, J=6.3 Hz, 1H), 6.48 (s, 1H), 4.93-4.72 (m, 2H), 4.43-4.39 (m, 2H), 4.10 (s, 3H), 4.01 (dd, J=7.5, 4.0 Hz, 2H), 3.38-3.31 (m, 1H), 2.98-2.79 (m, 2H), 2.43 (s, 3H), 2.25-2.00 (m, 4H).

$^{19}$F NMR (376 MHz, CDCl$_3$): δ −183.42 (s, 1F).

LC-MS [mobile phase: from 95% water (0.02% NH$_4$OAc) and 5% CH$_3$CN to 5% water (0.02% NH$_4$OAc) and 95% CH$_3$CN in 6.5 min], purity >95%, Rt=3.887 min; MS Calcd.: 412, MS Found: 413 [M+H]$^+$.

Chiral HPLC [Chiral condition: Chiralpak IC 5 μm 4.6*250 mm, Phase: Hex/EtOH=70/30, flow rate: 1.0 mL/min, 230 nm, T=30° C.], Rt=13.746 min, 100% ee.

Example 74

(cis)-1-(6-(6-(4-Fluoro-1-methylpyrrolidin-3-yl)-5-methyl-1H-indazol-1-yl)-2-methoxypyrimidin-4-yl) azetidin-3-ol (Enantiomer 2) (E74)

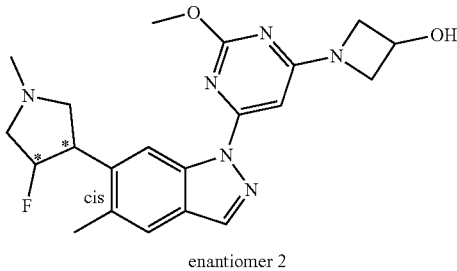 [SMILES: COc1nc(N2CC(O)C2)cc(-n2ncc3cc(C)c(C4CN(C)CC4F)cc32)n1]

To a suspension of (cis)-6-(4-fluoro-1-methylpyrrolidin-3-yl)-1-(2-methoxy-6-(3-((tetrahydro-2H-pyran-2-yl)oxy) azetidin-1-yl)pyrimidin-4-yl)-5-methyl-1H-indazole (enantiomer 2) (23 mg, 0.046 mmol) in methanol (1 mL) was added TsOH (cat). The resulting solution was stirred at 30° C. for 2 hrs. The reaction mixture was cooled and partitioned between Na$_2$CO$_3$ (10%, 20 mL) and EtOAc (20 mL). The aqueous was extracted with EtOAc (20 mL×2) and the combined organic layers were washed with brine, dried over Na$_2$SO$_4$ and concentrated to give the title compound (7.1 mg, yield 37%) as a white solid. E74 is a single unknown enantiomer.

$^1$H NMR (400 MHz, CDCl$_3$): δ 8.77 (s, 1H), 8.09 (s, 1H), 7.54 (s, 1H), 6.49 (s, 1H), 5.22-5.07 (m, 1H), 4.84 (brs, 1H), 4.42 (t, J=8.4 Hz, 2H), 4.13 (s, 3H), 4.04-4.00 (m, 2H), 3.97-3.85 (m, 1H), 3.34-3.30 (m, 1H), 3.11-3.02 (m, 1H), 2.91-2.79 (m, 1H), 2.64-2.60 (m, 1H), 2.51 (s, 3H), 2.42 (s, 3H), 2.24 (brs, 1H). $^{19}$F NMR (376 MHz, CDCl$_3$): δ −163.70 (s, 1F).

LC-MS [mobile phase: from 95% water (0.02% NH$_4$OAc) and 5% CH$_3$CN to 5% water (0.02% NH$_4$OAc) and 95% CH$_3$CN in 6.5 min], purity is >95%, Rt=4.051 min; MS Calcd.: 412, MS Found: 413 [M+H]$^+$.

Chiral HPLC: Chiralpak IA 5 um 4.6*250 mm, Phase: HEX: EtOH=60/40, Flow Rate: 1 ml/min, 230 nm, T=30° C., Rt=9.261 min, 95.4% ee.

Example 75

(cis)-1-(6-(6-(4-Fluoro-1-methylpyrrolidin-3-yl)-5-methyl-1H-indazol-1-yl)-2-methoxypyrimidin-4-yl)azetidin-3-ol (Enantiomer 1) (E75)

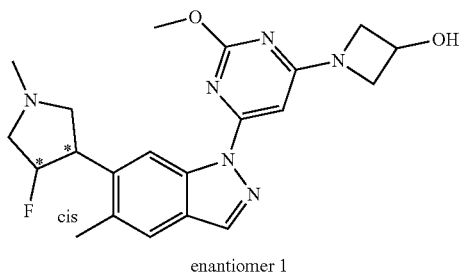 [SMILES: COc1nc(N2CC(O)C2)cc(-n2ncc3cc(C)c(C4CN(C)CC4F)cc32)n1]

enantiomer 1

To a suspension of 6-(4-fluoro-1-methylpyrrolidin-3-yl)-1-(2-methoxy-6-(3-((tetrahydro-2H-pyran-2-yl)oxy)azetidin-1-yl)pyrimidin-4-yl)-5-methyl-1H-indazole (enantiomer 1) (83 mg, 0.17 mmol) in methanol (5 mL) was added TsOH (cat.). The resulting solution was stirred at 30° C. for 3 hrs. The reaction mixture was cooled and partitioned between Na$_2$CO$_3$ (10%, 40 mL) and EtOAc (40 mL). The aqueous was extracted with EtOAc (30 mL×2). The combined organic layers were washed with brine, dried over Na$_2$SO$_4$ and concentrated to give the title compound (34.1 mg, yield 49%) as white solid. E75 is a single unknown enantiomer.

$^1$H NMR (400 MHz, CDCl$_3$): δ 8.77 (s, 1H), 8.09 (s, 1H), 7.54 (s, 1H), 6.49 (s, 1H), 5.22-5.07 (m, 1H), 4.84 (br s, 1H), 4.42-4.40 (m, 2H), 4.13 (s, 3H), 4.03-4.00 (m, 2H), 3.98-3.85 (m, 1H), 3.34-3.28 (m, 1H), 3.11-3.02 (m, 1H), 2.91-2.79 (m, 1H), 2.63-2.60 (m, 1H), 2.51 (s, 3H), 2.42 (s, 3H), 2.26 (brs, 1H). $^{19}$F NMR (376 MHz, CDCl$_3$): δ −163.70 (s, 1F).

LC-MS [mobile phase: from 95% water (0.02% NH$_4$OAc) and 5% CH$_3$CN to 5% water (0.02% NH$_4$OAc) and 95% CH$_3$CN in 6.5 min], purity is >95%, Rt=4.048 min; MS Calcd.: 412, MS Found: 413 [M+H]$^+$.

Chiral HPLC: Chiralpak IA 5 μm 4.6*250 mm, Phase: HEX: EtOH=60/40, Flow Rate: 1 ml/min, 230 nm, T=30° C., Rt=5.811 min, 97.7% ee.

Example 76

(cis)-4-(4-(6-(3-Fluoro-1-(2-methoxyethyl)piperidin-4-yl)-1H-pyrazolo[3,4-d]pyrimidin-1-yl)pyridin-2-yl)morpholine (Enantiomer 2) (E76)

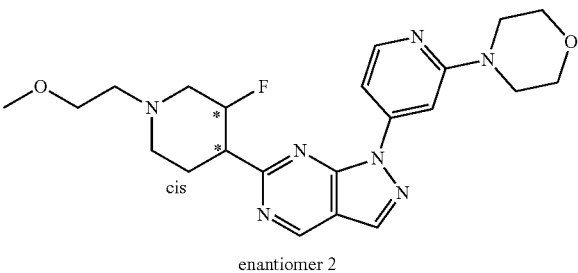 [SMILES: COCCN1CCC(c2ncc3cnn(-c4ccnc(N5CCOCC5)c4)c3n2)C(F)C1]

enantiomer 2

A suspension of (cis)-6-(3-fluoro-1-(2-methoxyethyl)piperidin-4-yl)-1H-pyrazolo[3,4-c]pyrimidine (enantiomer 2) (30 mg, 0.11 mmol), 4-(4-Iodo-2-pyridyl)morpholine (62 mg, 0.21 mmol), methyl[2-(methylamino)cyclohexyl]amine (30 mg, 0.21 mmol), CuI (61 mg, 0.32 mmol) and K$_3$PO$_4$ (68 mg, 0.32 mmol) in dry toluene (6 mL) was refluxed under N$_2$ atmosphere overnight. The mixture was cooled to room temperature, concentrated in vacuo. The residue was dissolved into MeOH (2 mL), filtered, and purified by prep. HPLC to give the title compound (15.4 mg, yield 33%) as a green solid. E76 is a single unknown enantiomer.

$^1$H NMR (300 MHz, CD$_3$OD): δ 9.30 (s, 1H), 8.47 (s, 1H), 8.24 (d, J=5.7 Hz, 1H), 7.94 (d, J=0.9 Hz, 1H), 7.83 (dd, J=5.7, 0.9 Hz, 1H), 5.41-5.15 (m, 1H), 3.86-3.83 (m, 4H), 3.60-3.56 (m, 6H), 3.44-3.35 (m, 4H), 3.27-3.18 (m, 1H), 3.07-3.00 (m, 1H), 2.74-2.70 (m, 2H), 2.40-2.25 (m, 2H), 2.19-2.06 (m, 1H), 2.06-1.92 (m, 1H).

LC-MS (mobile phase: from 95% water (0.02% NH$_4$OAc) and 5% CH$_3$CN to 5% water (0.02% NH$_4$OAc) and 95% CH$_3$CN in 6.5 min, purity is >98%, Rt=3.994 min; MS Calcd.: 441; MS Found: 442 [M+H]$^+$.

Chiral HPLC (Chiral condition: Chiralpak IF—5 μm 4.6*250 mm, Hex/EtOH=60/40, Flow Rate: 1.0 ml/min, 230 nm, T=ambient), Rt=20.178 min, 100% ee.

Example 77

(cis)-4-(4-(6-(3-Fluoro-1-(2-methoxyethyl)piperidin-4-yl)-1H-pyrazolo[3,4-d]pyrimidin-1-yl)pyridin-2-yl)morpholine (Enantiomer 1) (E77)

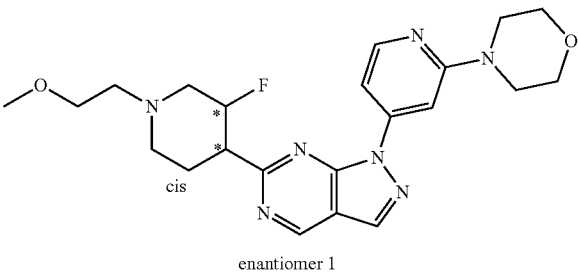 [SMILES: COCCN1CCC(c2ncc3cnn(-c4ccnc(N5CCOCC5)c4)c3n2)C(F)C1]

enantiomer 1

A suspension of (cis)-6-(3-fluoro-1-(2-methoxyethyl)piperidin-4-yl)-1H-pyrazolo[3,4-d]pyrimidine (enantiomer 1)

(30 mg, 0.11 mmol), 4-(4-iodopyridin-2-yl)morpholine (37 mg, 0.13 mmol), methyl[2-(methylamino)cyclohexyl]amine (15 mg, 0.11 mmol), CuI (21 mg, 0.11 mmol) and $K_3PO_4$ (46 mg, 0.22 mmol) in dry toluene (6 mL) was heated to 115° C. under $N_2$ atmosphere overnight. The mixture was cooled to room temperature, concentrated in vacuo. The residue was dissolved into MeOH (2 mL), filtered, and purified by prep. HPLC to give the crude product. The crude product was further purified by C18 column eluting with $CH_3CN/H_2O$ (from 0/100 to 100/0) to give the title compound (3.1 mg, yield 6.6%) as a white solid. E77 is a single unknown enantiomer.

$^1$H NMR (300 MHz, $CD_3OD$): δ 9.32 (s, 1H), 8.49 (s, 1H), 8.26 (d, J=6.0 Hz, 1H), 7.95 (s, 1H), 7.85 (dd, J=5.7, 1.2 Hz, 1H), 5.42-5.16 (m, 1H), 3.87-3.83 (m, 4H), 3.61-3.57 (m, 6H), 3.43-3.37 (m, 5H), 3.06-2.99 (m, 1H), 2.74-2.71 (m, 2H), 2.33-2.28 (m, 2H), 2.16-2.06 (m, 1H), 2.05-1.91 (m, 1H).

LC-MS (mobile phase: from 95% water (0.02% $NH_4OAc$) and 5% $CH_3CN$ to 5% water (0.02% $NH_4OAc$) and 95% $CH_3CN$ in 6.0 min, purity is >95%, Rt=3.995 min; MS Calcd.: 441; MS Found: 442, $[M+H]^+$.

Chiral HPLC (Chiral condition: Chiralpak IF—5 μm 4.6*250 mm, Hex/EtOH=60/40, Flow Rate: 1.0 ml/min, 230 nm, T=ambient), Rt=14.429 min, 100% ee.

Example 78

4-(6-(5-Methyl-6-(1-(oxetan-3-yl)piperidin-4-yl)-1H-indazol-1-yl)pyrimidin-4-yl)morpholine (E78)

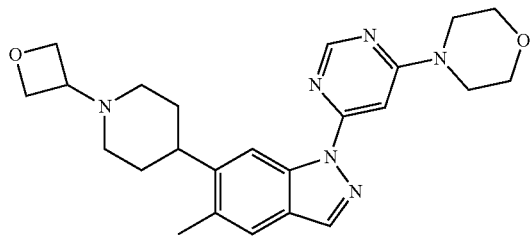 [SMILES: Cc1cc2cnn(-c3cc(N4CCOCC4)ncn3)c2cc1C1CCN(C2COC2)CC1]

A suspension of 5-methyl-6-(1-(oxetan-3-yl)piperidin-4-yl)-1H-indazole (100 mg, 0.37 mmol), 4-(6-chloro-pyrimidin-4-yl)-morpholine (110 mg, 0.55 mmol) and $Cs_2CO_3$ (240 mg, 0.74 mmol) in DMF (5 mL) was heated to 100° C. and stirred overnight. The reaction mixture was cooled to rt and then poured into water (40 mL) and extracted with EtOAc (20 mL×3). The combined organic layers were washed with brine, and dried over $Na_2SO_4$ and concentrated. The crude was purified by prep-TLC (PE:EtOAC=1:20) to give the title compound (13.1 mg, yield 8%) as a white solid.

$^1$H NMR (300 MHz, $CDCl_3$): δ 8.84 (s, 1H), 8.62 (s, 1H), 8.06 (s, 1H), 7.50 (s, 1H), 7.12 (s, 1H), 4.72-4.70 (m, 4H), 3.82 (brs, 4H), 3.72 (brs, 4H), 3.57-3.54 (m, 1H), 2.98-2.96 (m, 2H), 2.87-2.82 (m, 1H), 2.46 (s, 3H), 2.00-1.98 (m, 4H), 1.96-1.88 (m, 2H).

LC-MS (mobile phase: from 95% water (0.02% $NH_4OAc$) and 5% $CH_3CN$ to 5% water (0.02% $NH_4OAc$) and 95% $CH_3CN$ in 6 min, purity>95%, Rt=4.41 min; MS Calcd.: 434, MS Found: 435 $[M+H]^+$.

Example 79

1-(2-Methoxy-6-(5-methyl-6-(1-(oxetan-3-yl)piperidin-4-yl)-1H-indazol-1-yl)pyrimidin-4-yl)azetidin-3-ol (E79)

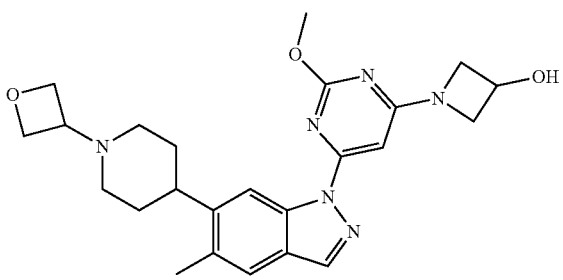 [SMILES: COc1nc(N2CC(O)C2)cc(-n2ncc3cc(C)c(C4CCN(C5COC5)CC4)cc32)n1]

To a mixture of 1-(2-methoxy-6-(3-((tetrahydro-2H-pyran-2-yl)oxy)azetidin-1-yl)pyrimidin-4-yl)-5-methyl-6-(1-(oxetan-3-yl)piperidin-4-yl)-1H-indazole (70 mg, 0.13 mmol) in methanol (5 mL) was added TsOH (22 mg, 0.13 mmol). The resulting solution was stirred at rt overnight. The mixture was poured into sat. $Na_2CO_3$ solution (20 mL). The reaction mixture was extracted with $CH_2Cl_2$ (3×20 mL). The combined organic layers were washed with brine (2×20 mL), dried over $Na_2SO_4$ and concentrated. The residue was triturated with EtOAc (5 mL) to give the title compound (35 mg, yield 60%) as white solid.

$^1$H NMR (300 MHz, $CDCl_3$): δ 8.75 (s, 1H), 8.06 (s, 1H), 7.49 (s, 1H), 6.45 (s, 1H), 4.87-4.80 (m, 1H), 4.70-4.67 (m, 4H), 4.43-4.38 (m, 2H), 4.13 (s, 3H), 4.02-3.98 (m, 2H), 3.59-3.50 (m, 1H), 2.94-2.75 (m, 4H), 2.44 (s, 3H), 2.05-1.83 (m, 6H).

LC-MS [mobile phase: from 95% water (0.02% $NH_4OAc$) and 5% $CH_3CN$ to 5% water (0.02% $NH_4OAc$) and 95% $CH_3CN$ in 6.5 min], purity >95%, Rt=4.019 min; MS Calcd.: 450; MS Found: 451 $[M+H]^+$.

Example 80

1-(2-Methoxy-6-(5-methyl-6-(1-(oxetan-3-yl)piperidin-4-yl)-1H-indazol-1-yl)pyrimidin-4-yl)-3-methyl-azetidin-3-ol (E80)

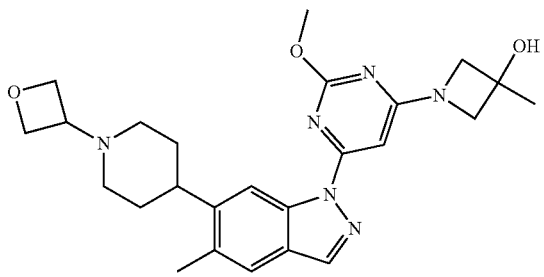 [SMILES: COc1nc(N2CC(C)(O)C2)cc(-n2ncc3cc(C)c(C4CCN(C5COC5)CC4)cc32)n1]

A suspension of 5-methyl-6-(1-(oxetan-3-yl)piperidin-4-yl)-1H-indazole (50 mg, 0.18 mmol), 1-(6-Iodo-2-methoxy-pyrimidin-4-yl)-3-methylazetidin-3-ol (70 mg, 0.22 mmol), $K_3PO_4$ (76 mg, 0.36 mmol), CuI (34 mg, 0.18 mmol) and N,N'-dimethyl-cyclohexane-1,2-diamine (51 mg, 0.34 mmol) in toluene (10 mL) was stirred at 110° C. for 3 hrs. The reaction mixture was concentrated and the residue was partitioned with EtOAc (30 mL) and NH₃.H₂O (30%, 20 mL). The organic layer was separated, dried over Na₂SO₄, filtered and concentrated. The residue was purified by prep-TLC (CH₂Cl₂: methanol=15:1) to afford crude as colorless oil. The crude was further purified by prep. chiral HPLC with the method (Chiralpak IB; Phase: Hex:EtOH=80:20; F: 15 mL/min; W: 254 nm) to give the title compound (17 mg, yield 20%) as a white solid.

¹H NMR (300 MHz, CDCl₃): δ 8.76 (s, 1H), 8.06 (s, 1H), 7.50 (s, 1H), 6.48 (s, 1H), 4.68 (d, J=6.6 Hz, 4H), 4.15-4.05 (m, 7H), 3.59-3.50 (m, 1H), 2.94-2.77 (m, 3H), 2.45 (s, 3H), 2.25-2.13 (m, 1H), 2.09-1.78 (m, 7H), 1.74-1.61 (m, 2H).

LC-MS [mobile phase: from 90% water (0.02% NH₄OAc) and 10% CH₃CN to 5% water (0.02% NH₄OAc) and 95% CH₃CN in 6.5 min], purity >95%, Rt=4.232 min; MS Calcd.: 464, MS Found: 465 [M+H]⁺.

Example 81

3-Methyl-1-(2-methyl-6-(5-methyl-6-(1-(oxetan-3-yl)piperidin-4-yl)-1H-indazol-1-yl)pyrimidin-4-yl) azetidin-3-ol (E81)

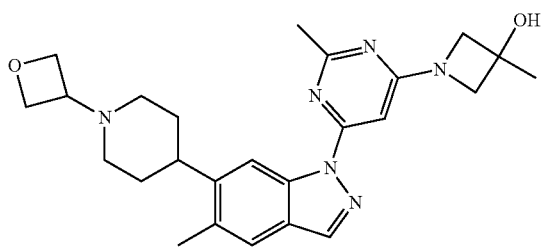 [SMILES: Cc1nc(N2CC(C)(O)C2)cc(-n2ncc3cc(C)c(C4CCN(C5COC5)CC4)cc32)n1]

To a suspension of 5-methyl-6-(1-(oxetan-3-yl)piperidin-4-yl)-1H-indazole (50 mg, 0.18 mmol), 1 1-(6-iodo-2-methylpyrimidin-4-yl)-3-methylazetidin-3-ol (61 mg, 0.20 mmol), CuI (34 mg, 0.18 mmol) and K₃PO₄ (76 mg, 0.36 mmol) in dry toluene (2 mL) was added N,N'-dimethylcyclohexane-1,2-diamine (51 mg, 0.36 mmol). The resulting mixture was degassed with N₂ and stirred at 110° C. for 2 hrs. The reaction mixture was cooled and then partitioned between dilute ammonia (30 mL) and EtOAc (30 mL). The organic layer was washed with brine, dried over MgSO₄ and concentrated. The crude was purified by prep. TLC (DCM: MeOH=10:1) to give the title compound (19 mg, yield 23%) as a white solid.

¹H NMR (300 MHz, CDCl₃): δ 8.81 (s, 1H), 8.06 (s, 1H), 7.49 (s, 1H), 6.60 (s, 1H), 4.73-4.71 (m, 4H), 4.11-4.04 (m, 4H), 3.63-3.51 (m, 1H), 3.02-2.93 (m, 2H), 2.89-2.78 (m, 1H), 2.66 (s, 3H), 2.45 (s, 3H), 2.15-1.94 (m, 7H), 1.63 (s, 3H).

LC-MS [mobile phase: from 90% water (0.02% NH₄OAc) and 10% CH₃CN to 5% water (0.02% NH₄OAc) and 95% CH₃CN in 6.5 min], purity >95%, Rt=4.060 min; MS Calcd.: 448, MS Found: 449 [M+H]⁺.

Example 82

1-(2-Methoxy-6-(5-methyl-6-(1-(methylsulfonyl) piperidin-4-yl)-1H-indazol-1-yl)pyrimidin-4-yl)azetidin-3-ol (E82)

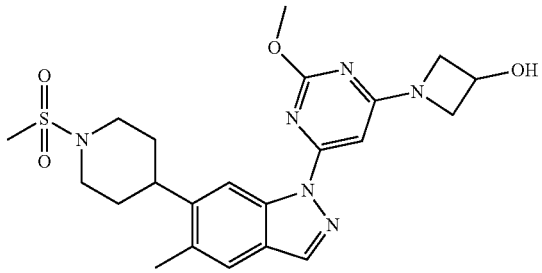 [SMILES: COc1nc(N2CC(O)C2)cc(-n2ncc3cc(C)c(C4CCN(S(C)(=O)=O)CC4)cc32)n1]

To a mixture of 1-(2-methoxy-6-(3-((tetrahydro-2H-pyran-2-yl)oxy)azetidin-1-yl)pyrimidin-4-yl)-5-methyl-6-(1-(methylsulfonyl)piperidin-4-yl)-1H-indazole (70 mg, 0.13 mmol) in methanol (5 mL) was added TsOH (5 mg, 0.03 mmol). The resulting solution was stirred at rt overnight. The mixture was filtered. The solid was collected to give the title compound (30 mg, yield 50%) as white solid.

¹H NMR (300 MHz, DMSO-d₆): δ 8.64 (s, 1H), 8.31 (s, 1H), 7.63 (s, 1H), 6.40 (s, 1H), 5.81 (br s, 1H), 4.60 (br s, 1H), 4.30-4.24 (m, 2H), 3.98 (s, 3H), 3.82-3.77 (m, 2H), 3.72-3.68 (m, 2H), 3.00-2.86 (m, 6H), 2.42 (s, 3H), 1.95-1.89 (m, 2H), 1.69-1.57 (m, 2H).

LC-MS [mobile phase: from 95% water (0.02% NH₄OAc) and 5% CH₃CN to 5% water (0.02% NH₄OAc) and 95% CH₃CN in 6.5 min], purity >95%, Rt=3.995 min; MS Calcd.: 472, MS Found: 473 [M+H]⁺.

Example 83

1-(4-(1-(6-(3-Hydroxyazetidin-1-yl)-2-methoxypyrimidin-4-yl)-5-methyl-1H-indazol-6-yl)piperidin-1-yl)ethanone (E83)

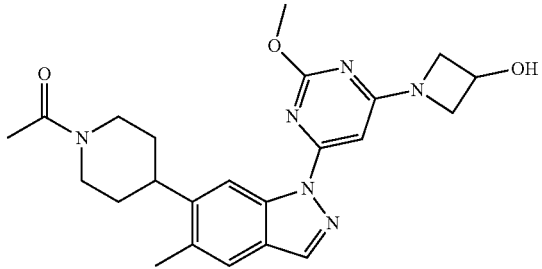 [SMILES: COc1nc(N2CC(O)C2)cc(-n2ncc3cc(C)c(C4CCN(C(C)=O)CC4)cc32)n1]

To a solution of 1-(4-(5-methyl-1H-indazol-6-yl)piperidin-1-yl)ethanone (51 mg, 0.20 mmol) in toluene (10 mL) was added 1-(6-iodo-2-methoxypyrimidin-4-yl)azetidin-3-ol (92 mg, 0.30 mmol), K₃PO₄ (127 mg, 0.600 mmol), CuI (114 mg, 0.600 mmol) and N,N'-dimethyl-cyclohexane-1,2-diamine (85 mg, 0.60 mmol). The reaction mixture was refluxed for 4 hrs. The reaction mixture was cooled to room temperature and poured into sat. NH₃.H₂O (10 mL). The desired compound was extracted with EtOAc (3×10 mL). The combined organic layers were washed with brine (20 mL), dried over Na$_2$SO$_4$ and concentrated. The residue was purified by prep. HPLC to give the title compound (15 mg, yield 17%) as white solid.

$^1$H NMR (300 MHz, CD$_3$OD): δ 8.66 (s, 1H), 8.12 (s, 1H), 7.57 (s, 1H), 6.44 (s, 1H), 4.72-4.68 (m, 2H), 4.35-4.30 (m, 2H), 4.10-4.05 (m, 4H), 3.91-3.88 (m, 2H), 3.39-3.35 (m, 1H), 3.26-3.16 (m, 1H), 2.82-2.73 (m, 1H), 2.49 (s, 3H), 2.15 (s, 3H), 2.00-1.90 (m, 2H), 1.72-1.60 (m, 2H).

LC-MS [mobile phase: from 95% water (0.02% NH$_4$OAc) and 5% CH$_3$CN to 5% water (0.02% NH$_4$OAc) and 95% CH$_3$CN in 6.5 min], purity >95%, Rt=3.799 min; MS Calcd.: 436; MS Found: 437 [M+H]$^+$.

Example 84

4-(6-(6-(1-Methylpiperidin-4-yl)-1H-indazol-1-yl)pyrimidin-4-yl)morpholine

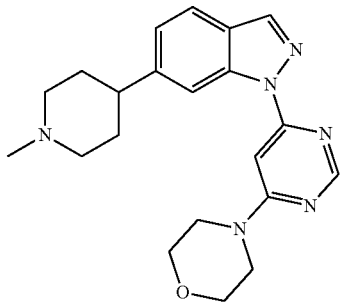 [SMILES: CN1CCC(c2ccc3cnn(-c4cc(N5CCOCC5)ncn4)c3c2)CC1]

A mixture of 4-(6-(6-(piperidin-4-yl)-1H-indazol-1-yl)pyrimidin-4-yl)morpholine (88.0 mg, 0.241 mmol), formaldehyde solution (390 mg, 5.20 mmol) and Pd—C (25.7 mg, 0.0240 mmol) in methanol (40 mL) was stirred at rt overnight under hydrogen. Then the reaction mixture was filtered and concentrated. Purification via Mass-Directed Autopreparation afforded the title product.

LC-MS (ESI) [mobile phase: from 95% water (0.05% TFA) and 5% CH$_3$CN to 5% water (0.1% TFA) and 95% CH$_3$CN in 5.0 min]: m/z 379 [M+H]$^+$; Rt=2.18 min.

$^1$H NMR (400 MHz, CD$_3$OD): 8.82 (s, 1H), 8.54 (s, 1H), 8.29 (s, 1H), 7.83 (d, J=8.0 Hz 1H), 7.29 (d, J=8.0 Hz, 1H), 7.28 (s, 1H), 3.82~3.67 (m, 11H), 3.27~3.13 (m, 2H), 2.97 (s, 3H), 2.28~2.24 (m, 2H), 2.11~2.08 (m, 2H).

Example 85

4-(6-(5-Methyl-6-(1,2,3,6-tetrahydropyridin-4-yl)-1H-indazol-1-yl)pyrimidin-4-yl)morpholine

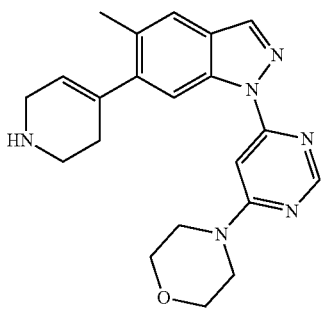 [SMILES: Cc1cc2cnn(-c3cc(N4CCOCC4)ncn3)c2cc1C1=CCNCC1]

A mixture of benzyl 4-(5-methyl-1-(6-morpholinopyrimidin-4-yl)-1H-indazol-6-yl)-5,6-dihydropyridine-1(2H)-carboxylate (1.8 g, 3.53 mmol) and Pd—C (0.375 g, 0.353 mmol) in THF (40 mL) and methanol (40.0 mL) was stirred at 60° C. under hydrogen (50 ps) overnight. The reaction mixture was filtered and concentrated. Purification via Mass-Directed autopreparation only afforded the title product.

LC-MS (ESI) [mobile phase: from 95% water (0.05% TFA) and 5% CH$_3$CN to 5% water (0.1% TFA) and 95% CH$_3$CN in 5.0 min]: m/z 377 [M+H]$^+$; Rt=2.49 min.

$^1$H NMR (400 MHz, CD$_3$OD): 8.64 (s, 1H), 8.49 (s, 1H), 8.25 (s, 1H), 7.69 (s, 1H), 7.26 (s, 1H), 5.79 (m, 1H), 3.91-3.53 (m, 12H), 2.18 (m, 2H), 3.34 (s, 3H).

Example 86

4-(6-(5-Methyl-6-(1-methyl-1,2,3,6-tetrahydropyridin-4-yl)-1H-indazol-1-yl)pyrimidin-4-yl)morpholine (E86)

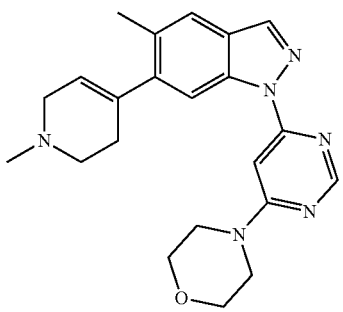 [SMILES: Cc1cc2cnn(-c3cc(N4CCOCC4)ncn3)c2cc1C1=CCN(C)CC1]

A mixture of 4-(6-(5-methyl-6-(1,2,3,6-tetrahydropyridin-4-yl)-1H-indazol-1-yl)pyrimidin-4-yl)morpholine (387 mg, 1.028 mmol), Pd—C (109 mg, 0.103 mmol) and HCHO (772 mg, 10.28 mmol) in THF (20 mL) and methanol (20.00 mL) was stirred at 60° C. under hydrogen (50 ps) overnight. Then the reaction mixture was filtered and concentrated. Direct purification via MDAP afforded the title product as a white solid.

$^1$H NMR (400 MHz, CD$_3$OD) d: 8.40 (s, 1H), 8.56 (s, 1H), 8.51 (s, 1H), 8.20 (s, 1H), 7.61 (s, 1H), 7.22 (s, 1H), 5.67 (s, 1H), 3.81, 3.73 (m, 8H), 2.23 (m, 2H), 2.80 (m, 2H), 2.53-2.40 (m, 8H)

LC-MS (ESI) [mobile phase: from 95% water (0.05% TFA) and 5% CH$_3$CN to 5% water (0.1% TFA) and 95% CH$_3$CN in 5.0 min]: m/z 391 [M+H]$^+$; Rt 2.49 min.

Example 87

4-(1-(6-(3-Hydroxyazetidin-1-yl)-2-methoxypyrimidin-4-yl)-5-methyl-1H-indazol-6-yl)-1-methylpiperidin-2-one (Enantiomer 2) (E87)

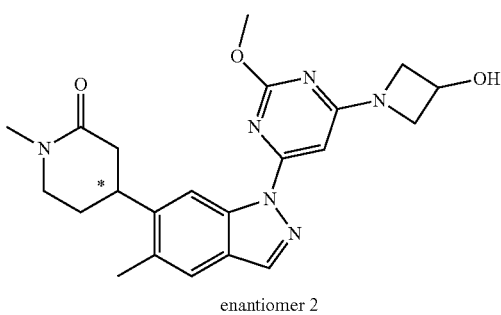 [SMILES: COc1nc(N2CC(O)C2)cc(-n2ncc3cc(C)c(C4CCN(C)C(=O)C4)cc32)n1]

enantiomer 2

To a mixture of 4-(1-(2-methoxy-6-(3-((tetrahydro-2H-pyran-2-yl)oxy)azetidin-1-yl) pyrimidin-4-yl)-5-methyl-1H-indazol-6-yl)-1-methylpiperidin-2-one (enantiomer 2) (50 mg, 0.099 mmol) in methanol (5 mL) was added TsOH (50 mg, 0.29 mmol). The resulting solution was stirred at rt for 2 hrs. The mixture was poured into sat. Na$_2$CO$_3$ solution (15 mL). The mixture was filtered. The solid was collected and dried to give the title compound (30 mg, yield 72%) as white solid. E87 is a single unknown enantiomer.

$^1$H NMR (300 MHz, CDCl$_3$): δ 8.70 (s, 1H), 8.07 (s, 1H), 7.53 (s, 1H), 6.47 (s, 1H), 4.87-4.79 (m, 1H), 4.44-4.38 (m, 2H), 4.09 (s, 3H), 4.03-3.98 (m, 2H), 3.52-3.33 (m, 3H), 3.02 (s, 3H), 2.81-2.73 (m, 1H), 2.56-2.53 (m, 1H), 2.52-2.46 (m, 4H), 2.19-2.04 (m, 2H).

LC-MS [mobile phase: from 95% water (0.02% NH$_4$OAc) and 5% CH$_3$CN to 5% water (0.02% NH$_4$OAc) and 95% CH$_3$CN in 6.5 min], purity >95%, Rt=3.661 min; MS Calcd.: 422, MS Found: 423 [M+H]$^+$.

Chiral HPLC: Chiralpak IA 5 μm 4.6×150 mm, Phase: Hex:EtOH=30:70, flowrate: 1 mL/min, temperature: 30° C., 230 nm, Rt=6.378 min, 100% ee.

Example 88

4-(1-(6-(3-Hydroxyazetidin-1-yl)-2-methoxypyrimidin-4-yl)-5-methyl-1H-indazol-6-yl)-1-methylpiperidin-2-one (Enantiomer 1) (E88)

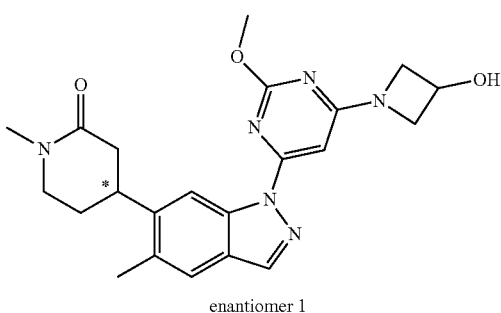 [SMILES: COc1nc(N2CC(O)C2)cc(-n2ncc3cc(C)c(C4CCN(C)C(=O)C4)cc32)n1]

enantiomer 1

To a mixture of 4-(1-(2-methoxy-6-(3-((tetrahydro-2H-pyran-2-yl)oxy)azetidin-1-yl) pyrimidin-4-yl)-5-methyl-1H-indazol-6-yl)-1-methylpiperidin-2-one (enantiomer 1) (52 mg, 0.10 mmol) in methanol (5 mL) was added TsOH (50 mg, 0.29 mmol). The resulting solution was stirred at rt for 2 hrs. The mixture was poured into sat. Na$_2$CO$_3$ solution (20 mL). The mixture was filtered. The solid was collected. The solid was washed with water (20 mL) and dried to give the title compound (23 mg, yield 53%) as white solid. E88 is a single unknown enantiomer.

$^1$H NMR (300 MHz, CDCl$_3$): δ 8.72 (s, 1H), 8.09 (s, 1H), 7.54 (s, 1H), 6.48 (s, 1H), 4.87-4.79 (m, 1H), 4.45-4.39 (m, 2H), 4.11 (s, 3H), 4.05-4.00 (m, 2H), 3.53-3.32 (m, 3H), 3.04 (s, 3H), 2.82-2.76 (m, 1H), 2.50-2.39 (m, 4H), 2.23-2.04 (m, 2H).

LC-MS: [mobile phase: from 95% water (0.02% NH$_4$OAc) and 5% CH$_3$CN to 5% water (0.02% NH$_4$OAc) and 95% CH$_3$CN in 6.5 min], purity >95%, Rt=3.678 min; MS Calcd.: 422, MS Found: 423 [M+H]$^+$.

Chiral HPLC: Chiralpak IA 5 μm 4.6×250 mm, Phase: Hex:EtOH=30:70, flowrate: 1 mL/min, temperature: 30° C., 230 nm, 100% ee.

Example 89

1-(2-Methyl-6-(5-methyl-6-(tetrahydro-2H-pyran-4-yl)-1H-indazol-1-yl)pyrimidin-4-yl)azetidin-3-ol (E89)

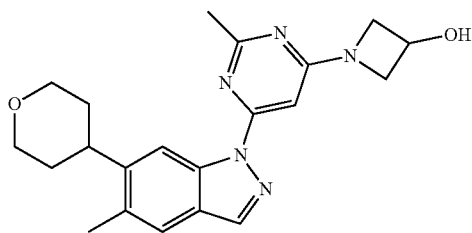 [SMILES: Cc1nc(N2CC(O)C2)cc(-n2ncc3cc(C)c(C4CCOCC4)cc32)n1]

To a round bottom bottle were added tripotassium phosphate (182 mg, 0.859 mmol), 5-methyl-6-(tetrahydro-2H-pyran-4-yl)-1H-indazole (78 mg, 0.361 mmol), copper(I) iodide (26.2 mg, 0.137 mmol), and a stir bar. The reaction vessel was fitted with a rubber septum, evacuated and back-filled with argon, and this order was repeated an additional time. 1-(6-iodo-2-methylpyrimidin-4-yl)azetidin-3-ol (100 mg, 0.344 mmol), N1,N2-dimethylcyclohexane-1,2-diamine (78 mg, 0.550 mmol) and toluene (5 mL) were then added successively under a stream of argon. The mixture was stirred at 120° C. for 16 hours. After filtration, the filtrate was concentrated and purified by MDAP to give 1-(2-methyl-6-(5-methyl-6-(tetrahydro-2H-pyran-4-yl)-1H-indazol-1-yl)pyrimidin-4-yl)azetidin-3-ol (4 mg, 10.54 μmol, 3.07% yield).

MS: 380.2 [M+H]$^+$.

1H NMR (400 MHz, DMSO-d$_6$) δ ppm 8.75 (1H, s) 8.31 (1H, s) 7.63 (1H, s) 6.55 (1H, s) 5.82 (1H, d) 4.63 (1H, m) 4.30 (2H, t) 4.01 (2H, d) 3.82 (2H, dd) 3.54 (2H, t) 3.11 (1H, t) 2.52 (3H, m) 2.45 (3H, s) 1.71 (4H, m).

Example 90

5-Methyl-1-(2-methyl-6-(4-(oxetan-3-yl)piperazin-1-yl)pyrimidin-4-yl)-6-(tetrahydro-2H-pyran-4-yl)-1H-indazole

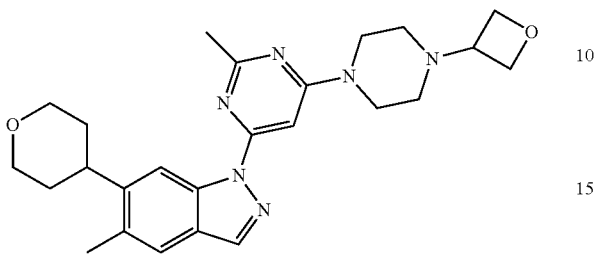

A solution of 5-methyl-1-(2-methyl-6-(piperazin-1-yl)pyrimidin-4-yl)-6-(tetrahydro-2H-pyran-4-yl)-1H-indazole (71 mg, 0.181 mmol), oxetan-3-one (130 mg, 1.809 mmol) and DMF (2 mL) was stirred for 30 min, before sodium triacetoxyborohydride (115 mg, 0.543 mmol) was added and the resulting solution was stirred at rt for 16 h. After filtration, the filtrate was concentrated and purified by MDAP to give 5-methyl-1-(2-methyl-6-(4-(oxetan-3-yl)piperazin-1-yl)pyrimidin-4-yl)-6-(tetrahydro-2H-pyran-4-yl)-1H-indazole (5 mg, 0.011 mmol, 6.16% yield).

MS: 449.1 [M+H]$^+$.

1H NMR (400 MHz, DMSO-d$_6$) δ ppm 8.74 (1H, s) 8.32 (1H, s) 7.63 (1H, s) 6.99 (1H, s) 4.53 (4H, m) 4.01 (2H, d) 3.70 (4H, br. s.) 3.49 (3H, m) 3.11 (1H, t) 2.54 (3H, s) 2.45 (3H, s) 2.35 (4H, d) 1.71 (4H, m).

Example 91

1-(2-Methoxy-6-(piperazin-1-yl)pyrimidin-4-yl)-5-methyl-6-(tetrahydrofuran-3-yl)-1H-indazole hydrochloride (Enantiomer 1) (E91)

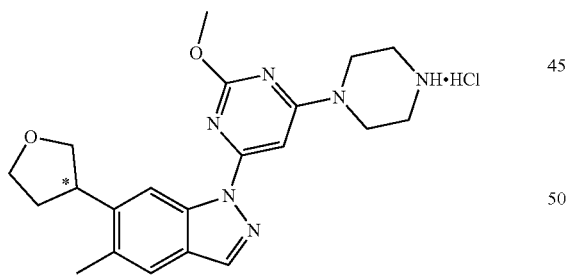

A mixture of tert-butyl 4-(2-methoxy-6-(5-methyl-6-(tetrahydrofuran-3-yl)-1H-indazol-1-yl)pyrimidin-4-yl) piperazine-1-carboxylate (enantiomer 1) (80 mg, 0.162 mmol) in HCl/CH$_3$OH (5M, 10 mL) was stirred at rt for 1 h. The mixture was concentrated to give the title compound (42 mg, yield 66%) as a white solid. E91 is a single unknown enantiomer.

$^1$H NMR (300 MHz, DMSO-d$_6$): δ 9.41 (s, 2H), 8.71 (s, 1H), 8.33 (s, 1H), 7.63 (s, 1H), 6.92 (s, 1H), 4.00-3.66 (m, 12H), 3.15 (br s, 4H), 2.48-2.34 (m, 4H), 1.89-1.79 (m, 1H).

LCMS: [mobile phase: 10-95% CH$_3$CN in water (0.1% TFA) in 6 min], purity >95%, Rt=3.250 min; MS Calcd: 394, MS Found: 395 (M+1)$^+$.

Chiral HPLC: (Chiralpak AD-3 3 μm 4.6×150 mm, Phase: Hex/EtOH=70/30, flow rate: 1 mL/min, temperature: 30° C.), Rt=13.570 min, 100% ee.

Example 92

1-(2-Methoxy-6-(piperazin-1-yl)pyrimidin-4-yl)-5-methyl-6-(tetrahydrofuran-3-yl)-1H-indazole hydrochloride (Enantiomer 2) (E92)

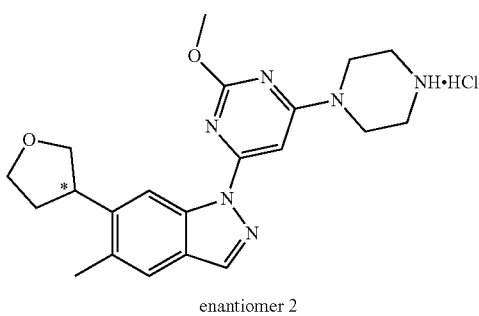

enantiomer 2

A mixture of tert-butyl 4-(2-methoxy-6-(5-methyl-6-(tetrahydrofuran-3-yl)-1H-indazol-1-yl)pyrimidin-4-yl)piperazine-1-carboxylate (enantiomer 2) (80 mg, 0.162 mmol) in HCl/CH$_3$OH (5M, 10 mL) was stirred at rt for 1 h. The mixture was concentrated to give the title compound (42 mg, yield 66%) as a white solid. E92 is a single unknown enantiomer.

$^1$H NMR (300 MHz, DMSO-d$_6$): δ 9.41 (s, 2H), 8.71 (s, 1H), 8.33 (s, 1H), 7.63 (s, 1H), 6.92 (s, 1H), 4.06-4.00 (m, 4H), 3.91-3.66 (m, 8H), 3.15 (br s, 4H), 2.48-2.34 (m, 4H), 1.89-1.78 (m, 1H).

LCMS: [mobile phase: 10-95% CH$_3$CN (0.1% TFA) in 6 min], purity >95%, Rt=3.255 min; MS Calcd: 394, MS Found: 395 (M+1)$^+$.

Chiral HPLC: (Chiralpak AD-3 3 μm 4.6×150 mm, Phase: Hex/EtOH=70/30, flow rate: 1 mL/min, temperature: 30° C.), Rt=17.043 min, 95.7% ee.

Example 93

3-(1-(2-Methoxy-6-morpholinopyrimidin-4-yl)-1H-indazol-6-yl)-4-methylmorpholine (Enantiomer 2) (E93)

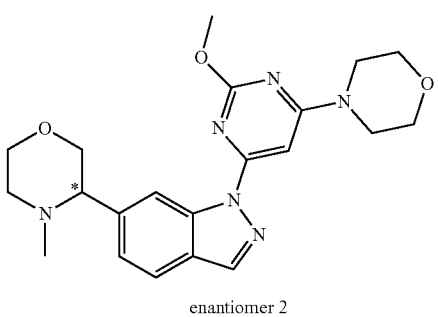 [SMILES: COc1nc(N2CCOCC2)cc(-n2ncc3ccc(C4COCCN4C)cc32)n1]

enantiomer 2

A suspension of 3-(1H-indazol-6-yl)-4-methylmorpholine (110 mg, 0.507 mmol) (enantiomer 2), 4-iodo-2-methoxy-6-(piperidin-1-yl)pyrimidine (324 mg, 1.01 mmol), methyl

[2-(methylamino)cyclohexyl]amine (216 mg, 1.52 mmol), CuI (290 mg, 1.52 mmol) and K₃PO₄ (322 mg, 1.52 mmol) in dry toluene (16 mL) was refluxed under N₂ atmosphere overnight. The mixture was cooled to room temperature and filtered. The filtrate was diluted with EtOAc (50 mL), and washed with water (100 mL×3). The organic layer was dried over Na₂SO₄, filtered and concentrated in vacuo to give the crude product. The crude product was further purified by prep. HPLC to give the title compound (105 mg, yield 50.5%) as a white solid. The white solid was further purified by Chiral HPLC with the method (Chiral condition: Chiralpak IC-5 um 20 mm*250 mm, Hex/IPA=60/40, Flow Rate: 14 ml/min, 205 nm, T=ambient) to give the title compound (52.0 mg, yield 25%) as a white solid. E93 is a single unknown enantiomer.

¹H NMR (300 MHz, CDCl₃): δ 8.86 (s, 1H), 8.15 (s, 1H), 7.70 (d, J=8.4 Hz, 1H), 7.34 (d, J=8.1 Hz, 1H), 6.85 (s, 1H), 4.12 (s, 3H), 3.97-3.93 (m, 1H), 3.81-3.71 (m, 10H), 3.50-3.43 (m, 1H), 3.29-3.24 (m, 1H), 2.87 (d, J=11.7 Hz, 1H), 2.53-2.43 (m, 1H), 2.11 (s, 3H).

LC-MS (mobile phase: from 95% water (0.02% NH₄Ac) and 5% CH₃CN to 5% water (0.02% NH₄Ac) and 95% CH₃CN in 6.0 min, purity is >95%, Rt=4.461 min; MS Calcd.: 410; MS Found: 411 [M+H]⁺.

Chiral HPLC (Chiral condition: Chiralpak IC-5 um 4.6*250 mm, Hex/IPA=60/40, Flow Rate: 1.0 ml/min, 230 nm, T=ambient), Rt=11.266 min, 100% ee.

Example 94

3-(1-(2-Methoxy-6-morpholinopyrimidin-4-yl)-1H-indazol-6-yl)-4-methylmorpholine (Enantiomer 1) (E94)

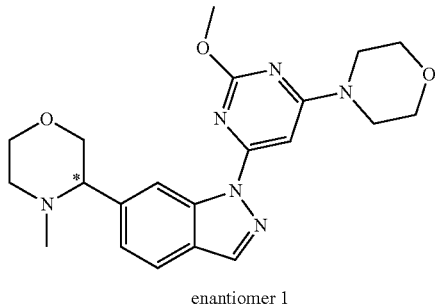 [SMILES: COc1nc(N2CCOCC2)cc(-n2ncc3ccc(C4COCCN4C)cc32)n1]

enantiomer 1

A suspension of 3-(1H-indazol-6-yl)-4-methylmorpholine (enantiomer 1) (95 mg, 0.44 mmol), 4-iodo-2-methoxy-6-(piperidin-1-yl)pyrimidine (280 mg, 0.876 mmol), N1,N2-dimethylcyclohexane-1,2-diamine (186 mg, 1.31 mmol), CuI (251 mg, 1.31 mmol) and K₃PO₄ (278 mg, 1.31 mmol) in dry toluene (16 mL) was refluxed under N₂ atmosphere overnight. The mixture was cooled to room temperature and filtered. The filtrate was diluted with EtOAc (50 mL) and washed with water (100 mL×3). The organic layer was dried over Na₂SO₄, filtered and concentrated in vacuo to give the crude product. The crude product was further purified by prep. HPLC to give the title compound (101 mg, yield 56%) as a white solid. E94 is a single unknown enantiomer.

¹H NMR (300 MHz, CDCl₃): δ 8.86 (s, 1H), 8.15 (s, 1H), 7.70 (d, J=8.1 Hz, 1H), 7.34 (d, J=7.8 Hz, 1H), 6.85 (s, 1H), 4.12 (s, 3H), 3.96-3.93 (m, 1H), 3.82-3.71 (m, 10H), 3.50-3.43 (m, 1H), 3.29-3.25 (m, 1H), 2.87 (d, J=12.3 Hz, 1H), 2.53-2.43 (m, 1H), 2.11 (s, 3H).

LC-MS (mobile phase: from 70% water (0.02% NH₄Ac) and 30% CH₃CN to 10% water (0.02% NH₄Ac) and 90% CH₃CN in 6.0 min, purity is >95%, Rt=3.647 min; MS Calcd.: 410; MS Found: 411 [M+H]⁺.

Chiral HPLC (Chiral condition: Chiralpak IC—5 μm 4.6*250 mm, Hex/IPA=60/40, Flow Rate: 1.0 ml/min, 230 nm, T=ambient), Rt=15.445 min, 99.2% ee.

Example 95

4-(6-(6-Isopropoxy-5-methyl-1H-indazol-1-yl)pyrimidin-4-yl)morpholine (E95)

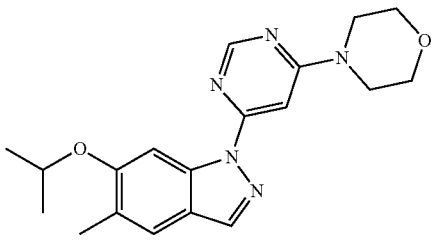 [SMILES: Cc1cc2cnn(-c3cc(N4CCOCC4)ncn3)c2cc1OC(C)C]

Step 1:

1-(6-isopropoxy-5-methyl-1H-indazol-1-yl)ethanone (140 mg, 0.6 mmol) was dissolved in MeOH (10 mL). HCl (12N, 1 mL) was added and the mixture was stirred at 40° C. for 1 hr. The solvent was then removed and the residue was re-dissolved in EtOAc (20 mL). Water (10 mL) was added and the pH value of the aqueous layer was adjusted to 8 using 1N NaOH. The organic layer was separated, dried over anhydrous Na₂SO₄ and concentrated. The crude product was purified by normal phase chromatography (PE:EtOAc=100:0 to 50:50) to afford 6-isopropoxy-5-methyl-1H-indazole (120 mg, 104% yield) as a white solid. LCMS: (mobile phase: 5-95% Acetonitrile), Rt=3.09 min in 5 min; MS Calcd: 190; MS Found: 191 [M+1]⁺.

Step 2:

To a solution of 6-isopropoxy-5-methyl-1H-indazole (60 mg, 0.31 mmol) was added 4-(6-chloropyrimidin-4-yl)morpholine (94 mg, 0.47 mmol) and Cs₂CO₃ (205 mg, 0.63 mmol). The mixture was stirred at 120° C. for 1 hr under microwave irradiation. The crude product was purified by reverse phase column (MDAP) to afford 4-(6-(6-isopropoxy-5-methyl-1H-indazol-1-yl)pyrimidin-4-yl)morpholine (12 mg, 10.8% yield) as a white solid.

LCMS: (mobile phase: 5-95% Acetonitrile), Rt=4.26 min in 5 min; MS Calcd: 353; MS Found: 354 [M+1]⁺.

¹H NMR (400M, CD₃OD): 8.53 (s, 1H), 8.29 (s, 1H), 8.09 (s, 1H), 7.51 (s, 1H), 7.19 (s, 1H), 4.77 (dt, J=12.1, 6.1 Hz, 1H), 3.81 (t, J=4.8 Hz, 4H), 3.68-3.74 (m, 4H), 2.28 (s, 3H), 1.44 (d, J=6.2 Hz, 6H).

Example 96

4-(6-(6-Isopropoxy-5-methyl-1H-indazol-1-yl)-2-methoxypyrimidin-4-yl)morpholine (E96)

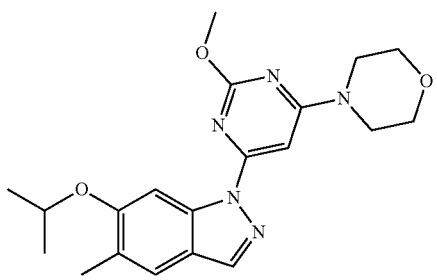 [SMILES: COc1nc(N2CCOCC2)cc(-n2ncc3cc(C)c(OC(C)C)cc32)n1]

To a solution of 6-isopropoxy-5-methyl-1H-indazole (60 mg, 0.31 mmol) was added 4-(6-chloro-2-methoxypyrimidin-4-yl)morpholine (108 mg, 0.47 mmol) and Cs$_2$CO$_3$ (205 mg, 0.63 mmol). The mixture was stirred at 120° C. for 1 hr under microwave irradiation. The crude product was purified by reverse phase column (MDAP) to afford 4-(6-(6-isopropoxy-5-methyl-1H-indazol-1-yl)-2-methoxypyrimidin-4-yl)morpholine (8 mg, 6.6% yield) as a white solid.

LCMS: (mobile phase: 5-95% Acetonitrile), Rt=4.45 min in 5 min; MS Calcd: 383; MS Found: 384 [M+1]$^+$.

$^1$H NMR (400M, CDCl$_3$): 8.33 (br. s., 1H), 8.01 (br. s., 1H), 7.45 (br. s., 1H), 6.87 (br. s., 1H), 4.70 (br. s., 1H), 4.11 (br. s., 3H), 3.80 (br. s., 4H), 3.73 (br. s., 4H), 2.31 (br. s., 3H), 1.44 (d, J=4.4 Hz, 6H).

Example 97

4-(6-(5-Methyl-6-((1-methylpiperidin-4-yl)oxy)-1H-indazol-1-yl)pyrimidin-4-yl)morpholine (E97)

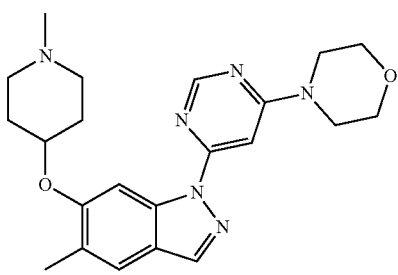 [SMILES: Cc1cc2cnn(-c3cc(N4CCOCC4)ncn3)c2cc1OC1CCN(C)CC1]

Step 1:

1-(5-methyl-6-((1-methylpiperidin-4-yl)oxy)-1H-indazol-1-yl)ethanone (90 mg, 368 µmol) was dissolved in MeOH (5 mL). HCl (12N, 0.5 mL) was added and the mixture was stirred at 40° C. for 1 hr. The solvent was then removed and the residue 5-methyl-6-((1-methylpiperidin-4-yl)oxy)-1H-indazole was used in next step without further purification.

LCMS: (mobile phase: 5-95% acetonitrile), Rt=1.89 min in 5 min; MS Calcd: 245; MS Found: 246 (M+1)+.

Step 2:

To a solution of 5-methyl-6-((1-methylpiperidin-4-yl)oxy)-1H-indazole (obtained in last step) were added 4-(6-chloropyrimidin-4-yl)morpholine (73 mg, 0.36 mmol) and Cs$_2$CO$_3$ (239 mg, 0.73 mmol). The mixture was stirred at 120° C. for 1 hr under microwave irradiation. The crude product was purified by reverse phase column (MDAP) to afford 4-(6-(5-methyl-6-((1-methylpiperidin-4-yl)oxy)-1H-indazol-1-yl)pyrimidin-4-I)morpholine (6.8 mg, 5.3% yield) as a white solid.

LCMS: (mobile phase: 5-95% acetonitrile), Rt=2.65 min in 5 min; MS Calcd: 408; MS Found: 409 [M+1]$^+$.

$^1$H NMR (400M, CD$_3$OD): 8.53 (br. s., 1H), 8.32-8.44 (m, 1H), 8.15 (br. s., 1H), 7.61 (br. s., 1H), 7.23 (br. s., 1H), 5.00 (br. s., 1H), 3.66-3.92 (m, 10H), 3.50 (d, J=10.8 Hz, 2H), 2.98 (br. s., 3H), 1.88-2.65 (m, 7H)

Example 98

4-(2-Methoxy-6-(5-methyl-6-((1-methylpiperidin-4-yl)oxy)-1H-indazol-1-yl)pyrimidin-4-yl)morpholine (E98)

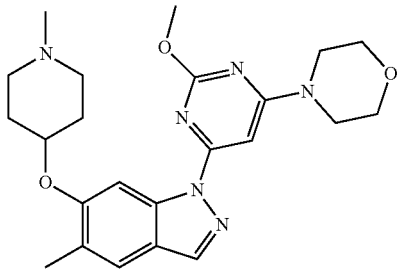 [SMILES: COc1nc(N2CCOCC2)cc(-n2ncc3cc(C)c(OC4CCN(C)CC4)cc32)n1]

Step 1:

1-(5-methyl-6-((1-methylpiperidin-4-yl)oxy)-1H-indazol-1-yl)ethanone (90 mg, 368 µmol) was dissolved in MeOH (5 mL). HCl (12N, 0.5 mL) was added and the mixture was stirred at 40° C. for 1 hr. The solvent was then removed and the residue 5-methyl-6-((1-methylpiperidin-4-yl)oxy)-1H-indazole was used in next step without further purification. LCMS: (mobile phase: 5-95% CH$_3$CN), Rt=1.89 min in 5 min; MS Calcd: 245; MS Found: 246 [M+1]$^+$.

Step 2:

To a solution of 5-methyl-6-((1-methylpiperidin-4-yl)oxy)-1H-indazole (obtained in step 1) was added 4-(6-chloro-2-methoxypyrimidin-4-yl)morpholine (84 mg, 0.36 mmol) and Cs$_2$CO$_3$ (239 mg, 0.73 mmol). The mixture was stirred at 120° C. for 1 hr under microwave irradiation. The product was purified by reverse phase column to afford a crude product. The crude product (40 mg, 0.09 mmol) was separated by chiral prep-HPLC with DEA to afford the target. The target was purified by C18 to remove DEA to give the title compound (2 mg, yield 5%) as a white solid.

$^1$H NMR (300 MHz, CD$_3$OD+CDCl$_3$): δ 8.30 (s, 1H), 8.06 (s, 1H), 7.52 (s, 1H), 6.88 (s, 1H), 4.70-4.65 (m, 1H), 4.09 (s, 3H), 3.82-3.80 (m, 4H), 3.73-3.70 (m, 4H), 2.84 (br s, 2H), 2.63 (br s, 2H), 2.46 (s, 3H), 2.33 (s, 3H), 2.15-2.01 (m, 4H);

LC-MS (mobile phase: from 90% water (0.02% NH$_4$OAc) and 10% CH$_3$CN to 5% water (0.02% NH$_4$OAc) and 95% CH$_3$CN in 6 min, purity is 93.78%, Rt=4.253 min; MS Calcd.: 438, MS Found: 439 [M+H]$^+$.

Example 99

(R)-4-(2-Methoxy-6-(5-methyl-6-((1-methylpiperidin-3-yl)oxy)-1H-indazol-1-yl)pyrimidin-4-yl)morpholine (E99)

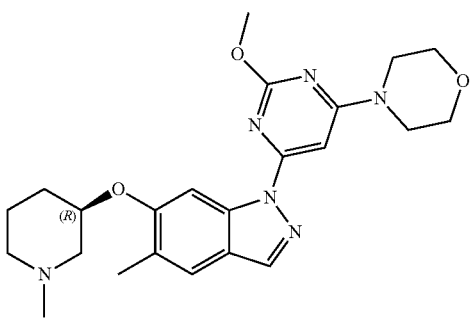

To a mixture of (R)-5-methyl-6-((1-methylpiperidin-3-yl)oxy)-1H-indazole (75 mg, 0.31 mmol) and Cs$_2$CO$_3$ (298 mg, 0.918 mmol) in DMF (3 mL) was added 4-(6-chloro-2-methoxypyrimidin-4-yl)morpholine (105 mg, 0.459 mmol). The mixture was heated to 110° C. and stirred overnight. After cooled to rt the mixture was partitioned with H$_2$O (10 mL) and EtOAc (15 mL). The organic layer was washed with water (10 mL) and brine (10 mL), dried over Na$_2$SO$_4$ and concentrated under vacuum. The residue was purified by prep. HPLC to give E99 (33 mg, yield 25%) as slight yellow solid.

$^1$H NMR (400 MHz, CDCl$_3$): δ 8.38 (s, 1H), 8.00 (s, 1H), 7.44 (s, 1H), 6.85 (s, 1H), 4.53-4.47 (m, 1H), 4.10 (s, 3H), 3.80-3.77 (m, 4H), 3.72-3.70 (m, 4H), 3.13-3.10 (m, 1H), 2.73-2.69 (m, 1H), 2.31 (s, 3H), 2.29 (s, 3H), 2.23-2.15 (m, 2H), 2.09-2.04 (m, 1H), 1.87-1.81 (m, 1H), 1.65-1.56 (m, 1H), 1.51-1.42 (m, 1H).

LC-MS: [mobile phase: from 80% water (0.02% NH$_4$OAc) and 20% CH$_3$CN to 5% water (0.02% NH$_4$OAc) and 95% CH$_3$CN in 6.5 min], purity >95%, Rt=4.091 min, MS Calcd.: 438, MS Found: 439 [M+H]$^+$.

Chiral condition: Chiralpak ID 5 μm 4.6*250 mm, Hex: EtOH=70:30, Flow Rate: 1.0 ml/min, 230 nm, T=30° C. Rt=7.566 min, 96.9% ee.

Example 100

(S)-4-(2-Methoxy-6-(5-methyl-6-((1-methylpiperidin-3-yl)oxy)-1H-indazol-1-yl)pyrimidin-4-yl)morpholine (E100)

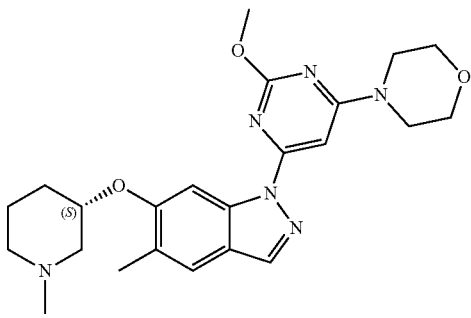

To a mixture of (S)-5-methyl-6-((1-methylpiperidin-3-yl)oxy)-1H-indazole (95 mg, 0.39 mmol) and Cs$_2$CO$_3$ (314 mg, 0.968 mmol) in DMF (3 mL) was added 4-(6-chloro-2-methoxypyrimidin-4-yl)morpholine (133 mg, 0.582 mmol). The mixture was heated to 110° C. and stirred overnight. After cooled to rt the mixture was partitioned with H$_2$O (10 mL) and EtOAc (15 mL). The organic layer was washed with water (10 mL) and brine (10 mL), dried over Na$_2$SO$_4$ and concentrated under vacuum. The residue was purified by prep. HPLC to give E100 (15 mg, yield 9%) as white solid.

$^1$H NMR (400 MHz, CDCl$_3$): δ 8.38 (s, 1H), 8.00 (s, 1H), 7.44 (s, 1H), 6.85 (s, 1H), 4.53-4.48 (m, 1H), 4.10 (s, 3H), 3.80-3.77 (m, 4H), 3.72-3.70 (m, 4H), 3.15-3.09 (m, 1H), 2.76-2.66 (m, 1H), 2.32 (s, 3H), 2.29 (s, 3H), 2.23-2.17 (m, 2H), 2.11-2.02 (m, 1H), 1.89-1.81 (m, 1H), 1.60-1.41 (m, 2H).

LC-MS: [mobile phase: from 80% water (0.02% NH$_4$OAc) and 20% CH$_3$CN to 5% water (0.02% NH$_4$OAc) and 95% CH$_3$CN in 6.5 min], purity >95%, Rt=4.092 min, MS Calcd.: 438, MS Found: 439 [M+H]$^+$.

Chiral condition: Chiralpak ID 5 μm 4.6*250 mm, Hex: EtOH=70:30, Flow Rate: 1.0 ml/min, 230 nm, T=30° C. Rt=9.138 min, 97.7% ee.

Example 101

(S)-4-(2-Methoxy-6-(5-methyl-6-((1-methylpyrrolidin-3-yl)oxy)-1H-indazol-1-yl)pyrimidin-4-yl)morpholine (E101)

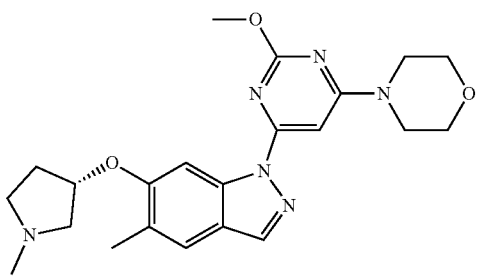

To a mixture of (S)-5-methyl-6-((1-methylpyrrolidin-3-yl)oxy)-1H-indazole (230 mg, 1.00 mmol) and Cs$_2$CO$_3$ (652 mg, 2.00 mmol) in DMF (10 mL) was added 4-(6-chloro-2-methoxypyrimidin-4-yl)morpholine (253 mg, 1.10 mmol). The mixture was heated to 100° C. and stirred overnight. The mixture was diluted with H$_2$O (30 mL) and extracted with EtOAc (3×15 mL). The combined organic layers were washed with brine, dried over Na$_2$SO$_4$ and concentrated under vacuum. The residue was purified by prep. TLC (DCM:MeOH=20:1) and further purified by prep. HPLC to give E101 (30 mg, yield 14%) as yellow solid.

E101: $^1$H NMR (300 MHz, CDCl$_3$): δ 8.20 (s, 1H), 8.00 (s, 1H), 7.44 (s, 1H), 6.85 (s, 1H), 5.00-4.96 (m, 1H), 4.08 (s, 3H), 3.80-3.71 (m, 8H), 3.03-2.98 (m, 1H), 2.85-2.75 (m, 2H), 2.61-2.53 (m, 1H), 2.42-2.35 (m, 4H), 2.30 (s, 3H), 2.16-2.05 (m, 1H).

LC-MS: [mobile phase: from 90% water (0.1% TFA) and 10% CH$_3$CN to 5% water (0.1% TFA) and 95% CH$_3$CN in 6.5 min], purity >95%, Rt=3.226 min MS Calcd.: 424, MS Found: 425 [M+H]$^+$.

Chiral condition: Chiralpak IA 5 um 4.6*250 mm, Hex:EtOH:DEA=70:30:0.2, Flow Rate: 1.0 ml/min, 230 nm, T=30° C. Rt=7.026 min, 100% ee.

Example 102

(R)-4-(2-Methoxy-6-(5-methyl-6-((1-methylpyrrolidin-3-yl)oxy)-1H-indazol-1-yl)pyrimidin-4-yl)morpholine (E102)

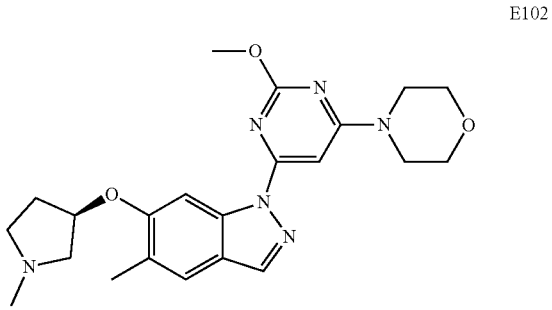 [SMILES: COc1nc(N2CCOCC2)cc(-n2ncc3cc(C)c(O[C@@H]4CCN(C)C4)cc32)n1]

E102

To a mixture of (R)-5-methyl-6-((1-methylpyrrolidin-3-yl)oxy)-1H-indazole (70 mg, 0.31 mmol) and $Cs_2CO_3$ (202 mg, 0.622 mmol) in DMF (3 mL) was added 4-(6-chloro-2-methoxypyrimidin-4-yl)morpholine (142 mg, 0.618 mmol). The mixture was heated to 100° C. and stirred for 6 hrs. After cooled to rt the mixture was diluted with $H_2O$ (20 mL) and extracted with EtOAc (3×15 mL). The combined organic layers were washed with brine, dried over $Na_2SO_4$ and concentrated under vacuum. The residue was purified by prep. TLC (DCM:MeOH=20:1) and further purified by prep. HPLC to give E102 (12 mg, yield 9%) as yellow solid.

E102: $^1$H NMR (300 MHz, $CDCl_3$): δ 8.20 (s, 1H), 7.99 (s, 1H), 7.44 (s, 1H), 6.85 (s, 1H), 4.99-4.95 (m, 1H), 4.08 (s, 3H), 3.79-3.71 (m, 8H), 3.03-2.98 (m, 1H), 2.85-2.75 (m, 2H), 2.60-2.53 (m, 1H), 2.42 (s, 3H), 2.39-2.35 (m, 1H), 2.30 (s, 3H), 2.15-2.07 (m, 1H).

LC-MS: [mobile phase: from 90% water (0.02% $NH_4OAc$) and 10% $CH_3CN$ to 5% water (0.02% $NH_4OAc$) and 95% $CH_3CN$ in 6.5 min], purity >95%, Rt=4.026 min MS Calcd.: 424, MS Found: 425 $[M+H]^+$.

Chiral condition: Chiralpak IA 5 μm 4.6*250 mm, Hex:EtOH:DEA=70:30:0.2, Flow Rate: 1.0 ml/min, 230 nm, T=30° C. Rt=8.303 min, 100% ee.

Example 103

(R)-1-(2-Methoxy-6-(piperazin-1-yl)pyrimidin-4-yl)-5-methyl-6-((tetrahydrofuran-3-yl)oxy)-1H-indazole hydrochloride (E103)

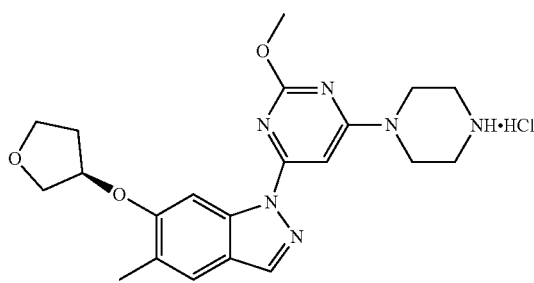

A mixture of (R)-tert-butyl 4-(2-methoxy-6-(5-methyl-6-((tetrahydrofuran-3-yl)oxy)-1H-indazol-1-yl)pyrimidin-4-yl)piperazine-1-carboxylate (210 mg, 0.410 mmol) in HCl/1,4-dioxane (6 M, 20 mL) was stirred at room temperature overnight. The reaction mixture was concentrated, and the residue was washed with 10 mL of EtOAc to get the title compound (160 mg, yield 95%) as a white solid. 50 mg of the crude product was further purified by prep-HPLC [Sunfire, C18, 5 μm, 19*150 mm, 20-65% B; A: $H_2O$ (0.1% HCl), B: $CH_3CN$; UV: 214 nm; flow rate: 20 mL/min] to get the title compound (10 mg, yield 20%) as a white solid.

$^1$H NMR (300 MHz, $CD_3OD$): δ 8.26 (s, 1H), 8.11 (s, 1H), 7.55 (s, 1H), 7.03 (s, 1H), 5.16-5.15 (m, 1H), 4.08 (s, 3H), 4.05-3.92 (m, 8H), 3.36-3.31 (m, 4H), 2.34-2.23 (m, 5H).

LC-MS: [mobile phase: from 95% water (0.02% $NH_4OAc$) and 5% $CH_3CN$ to 5% water (0.02% $NH_4OAc$) and 95% $CH_3CN$ in 6.5 min], purity is >95%, Rt=3.798 min, MS Calcd.: 410, MS Found: 411 $[M+H]^+$.

Example 104

(S)-1-(2-Methoxy-6-(piperazin-1-yl)pyrimidin-4-yl)-5-methyl-6-((tetrahydrofuran-3-yl)oxy)-1H-indazole hydrochloride (E104)

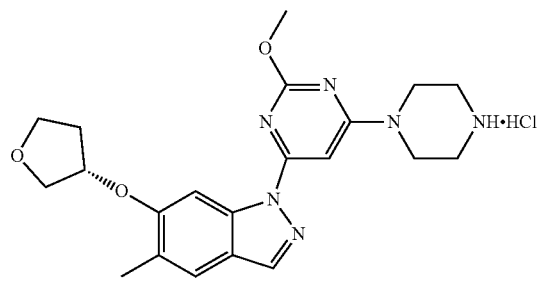

A mixture of (S)-tert-butyl 4-(2-methoxy-6-(5-methyl-6-((tetrahydrofuran-3-yl)oxy)-1H-indazol-1-yl)pyrimidin-4-yl)piperazine-1-carboxylate (40 mg, 0.08 mmol) in HCl/1,4-dioxane (6 M, 20 mL) was stirred at rt for 3 hrs. The reaction mixture was concentrated under reduced pressure, and the residue was purified by prep-HPLC [Sunfire, C18, 5 μm, 19*150 mm, 20-65% B; A: $H_2O$ (0.1% HCl), B: $CH_3CN$; UV: 214 nm; flow rate: 20 mL/min] to get the title compound (19 mg, yield 54%) as a white solid.

$^1$H NMR (300 MHz, $CD_3OD$): δ 8.24 (s, 1H), 8.11 (s, 1H), 7.54 (s, 1H), 7.02 (s, 1H), 5.18-5.12 (m, 1H), 4.08-3.92 (m, 11H), 3.36-3.32 (m, 4H), 2.35-2.21 (m, 5H).

LC-MS: [mobile phase: from 95% water (0.02% $NH_4OAc$) and 5% $CH_3CN$ to 5% water (0.02% $NH_4OAc$) and 95% $CH_3CN$ in 6.5 min], Rt=3.807 min, MS Calcd.: 410, MS Found: 411 $[M+H]^+$.

Example 105

(R)-1-(2-Methoxy-6-(4-methylpiperazin-1-yl)pyrimidin-4-yl)-5-methyl-6-((tetrahydrofuran-3-yl)oxy)-1H-indazole (E105)

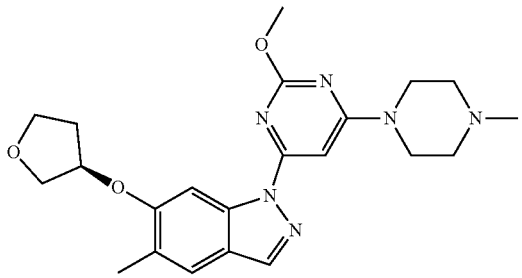 [SMILES: COc1nc(N2CCN(C)CC2)cc(-n2ncc3cc(C)c(O[C@@H]4CCOC4)cc32)n1]

To a mixture of (R)-1-(2-methoxy-6-(piperazin-1-yl)pyrimidin-4-yl)-5-methyl-6-((tetrahydrofuran-3-yl)oxy)-1H-indazole hydrochloride (66 mg, 0.15 mmol) and formaldehyde (37%, 2 mL) in methanol (10 mL) was added and NaBH$_3$CN (18 mg, 0.29 mmol). The mixture was stirred at rt for 1 h. The reaction mixture was diluted with water (30 mL), and extracted with EtOAc (20 mL×3). The combined organic layers were dried over MgSO$_4$, filtered and concentrated. The residue was purified by prep-HPLC to afford the product (63 mg, yield 92%) as a white solid.

$^1$H NMR (300 MHz, CDCl$_3$): δ 8.25 (s, 1H), 8.00 (s, 1H), 7.45 (s, 1H), 6.86 (s, 1H), 5.10-5.05 (m, 1H), 4.08-3.92 (m, 7H), 3.77 (br s, 4H), 2.53-2.51 (m, 4H), 2.36 (s, 3H), 2.30-2.22 (m, 5H).

LC-MS: [mobile phase: from 90% water (0.02% NH$_4$OAc) and 10% CH$_3$CN to 5% water (0.02% NH$_4$OAc) and 95% CH$_3$CN in 6.5 min], purity is >95%, Rt=4.760 min, MS Calcd.: 424, MS Found: 425 [M]$^+$.

Chiral-HPLC (Chiralpak IF 5 μm 4.6×250 mm, Phase: MeOH/EtOH=50/50, flowrate: 1 mL/min, temperature: 30° C.), Rt=14.544 min, 98.4% ee.

Example 106

(S)-1-(2-Methoxy-6-(4-methylpiperazin-1-yl)pyrimidin-4-yl)-5-methyl-6-((tetrahydrofuran-3-yl)oxy)-1H-indazole (E106)

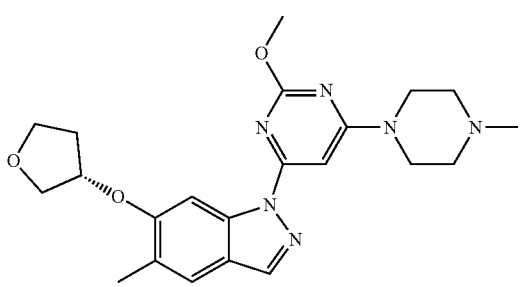 [SMILES: COc1nc(N2CCN(C)CC2)cc(-n2ncc3cc(C)c(O[C@H]4CCOC4)cc32)n1]

To a solution of (S)-1-(2-methoxy-6-(piperazin-1-yl)pyrimidin-4-yl)-5-methyl-6-((tetrahydrofuran-3-yl)oxy)-1H-indazole hydrochloride (55 mg, 0.13 mmol) and formaldehyde (37%, 2 mL) in methanol (10 mL) was added and NaBH$_3$CN (17 mg, 0.26 mmol). The mixture was stirred at rt for 1 h. The reaction mixture was diluted with water (30 mL), and extracted with EtOAc (20 mL×3). The combined organic layers were dried over MgSO$_4$, filtered and concentrated. The residue was purified by prep-HPLC to afford the product (30 mg, yield 52%) as a white solid.

$^1$H NMR (300 MHz, CDCl$_3$): δ 8.25 (s, 1H), 8.00 (s, 1H), 7.45 (s, 1H), 6.86 (s, 1H), 5.10-5.08 (m, 1H), 4.09-3.93 (m, 7H), 3.78 (br s, 4H), 2.53 (br s, 4H), 2.37 (s, 3H), 2.33-2.23 (m, 5H).

LC-MS: [mobile phase: from 60% water (0.02% NH$_4$OAc) and 40% CH$_3$CN to 5% water (0.02% NH$_4$OAc) and 95% CH$_3$CN in 6.5 min], Rt=3.245 min, MS Calcd.: 424, MS Found: 425 [M]$^+$.

Chiral-HPLC (Chiralpak IF 5 μm 4.6×250 mm, Phase: MeOH/EtOH=50/50, flowrate: 1 mL/min, temperature: 30° C.), Rt=16.145 min, 99.5% ee.

Example 107

(R)-1-(2-methoxy-6-(4-(oxetan-3-yl)piperazin-1-yl)pyrimidin-4-yl)-5-methyl-6-((tetrahydrofuran-3-yl)oxy)-1H-indazole (E107)

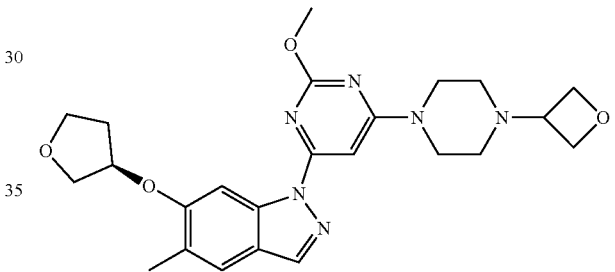

To a solution of (R)-1-(2-methoxy-6-(piperazin-1-yl)pyrimidin-4-yl)-5-methyl-6-((tetrahydrofuran-3-yl)oxy)-1H-indazole hydrochloride (44 mg, 0.11 mmol) and oxetan-3-one (38 mg, 0.54 mmol) in 1,2-dichloroethane (6 mL) and methanol (1 mL) was added NaBH$_3$CN (20 mg, 0.32 mmol). The mixture was stirred at rt for 1 h. The reaction mixture was diluted with water (40 mL) and extracted with DCM (10 mL×3). The combined organic layers were dried over MgSO$_4$, filtered and concentrated. The residue was dissolved in 2 mL of DCM and 2 mL of DMF, and then removed DCM under reduced pressure. The mixture was filtered, and the solid was washed with 10 mL of MeOH to afford the product (39 mg, yield 78%) as a white solid.

$^1$H NMR (400 MHz, CDCl$_3$): δ 8.23 (s, 1H), 8.01 (s, 1H), 7.45 (s, 1H), 6.86 (s, 1H), 5.06 (br s, 1H), 4.71-4.68 (m, 4H), 4.07-3.93 (m, 7H), 3.80 (brs, 4H), 3.58-3.53 (m, 1H), 2.44 (br s, 4H), 2.29-2.22 (m, 5H).

LCMS: [mobile phase: from 60% water (0.02% NH$_4$OAc) and 40% CH$_3$CN to 5% water (0.02% NH$_4$OAc) and 95% CH$_3$CN in 6.5 min], purity >95%, Rt=3.130 min, MS Calcd.: 466, MS Found: 467 [M]$^+$.

Chiral-HPLC (Chiralpak IA 5 μm 4.6×250 mm, Phase: MeOH/EtOH=50/50, flowrate: 1 mL/min, wave: 230 nm, temperature: 30° C.), Rt=13.295 min, 100% ee.

Example 108

(S)-1-(2-Methoxy-6-(4-(oxetan-3-yl)piperazin-1-yl)pyrimidin-4-yl)-5-methyl-6-((tetrahydrofuran-3-yl)oxy)-1H-indazole (E108)

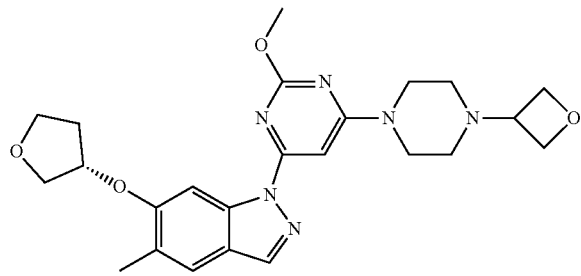 [SMILES: COc1nc(N2CCN(C3COC3)CC2)cc(-n2ncc3cc(C)c(O[C@H]4CCOC4)cc32)n1]

To a solution of (S)-1-(2-methoxy-6-(piperazin-1-yl)pyrimidin-4-yl)-5-methyl-6-((tetrahydrofuran-3-yl)oxy)-1H-indazole hydrochloride (55 mg, 0.13 mmol) and oxetan-3-one (44 mg, 0.61 mmol) in 1,2-dichloro-ethane (6 mL) and methanol (1 mL) was added NaBH$_3$CN (22 mg, 0.36 mmol). The mixture was stirred at rt for 1 h. The reaction mixture was diluted with water (20 mL), and extracted with DCM (10 mL×3). The combined organic layers were dried over MgSO$_4$, filtered and concentrated. The residue was purified by prep-HPLC to afford the product (36 mg, yield 63%) as a white solid.

$^1$H NMR (400 MHz, CDCl$_3$): δ 8.21 (s, 1H), 7.99 (s, 1H), 7.44 (s, 1H), 6.84 (s, 1H), 5.04 (br s, 1H), 4.72-4.70 (m, 4H), 4.06-3.95 (m, 7H), 3.81 (br s, 4H), 3.60 (br s, 1H), 2.48 (br s, 4H), 2.28-2.21 (m, 5H).

LC-MS: [mobile phase: from 60% water (0.02% NH$_4$OAc) and 40% CH$_3$CN to 5% water (0.02% NH$_4$OAc) and 95% CH$_3$CN in 6.5 min], Rt=3.151 min, MS Calcd.: 466, MS Found: 467 [M]$^+$.

Chiral-HPLC (Chiralpak IA 5 µm 4.6×250 mm, Phase: MeOH/EtOH=50/50, flowrate: 1 mL/min, temperature: 30° C.), Rt=14.649 min, 100% ee.

Example 109

4-(2-Methoxy-6-(5-methyl-6-((1-methylazetidin-3-yl)oxy)-1H-indazol-1-yl)pyrimidin-4-yl)morpholine (E109)

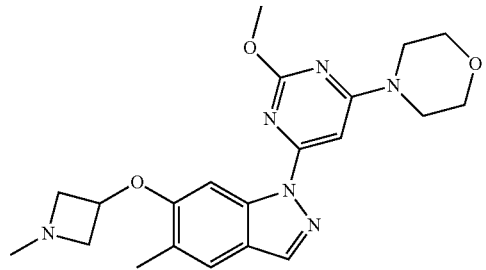 [SMILES: COc1nc(N2CCOCC2)cc(-n2ncc3cc(C)c(OC4CN(C)C4)cc32)n1]

To a mixture of 5-methyl-6-((1-methylazetidin-3-yl)oxy)-1H-indazole (270 mg, 1.24 mmol) and Cs$_2$CO$_3$ (808 mg, 2.48 mmol) in DMF (10 mL) was added 4-(6-chloro-2-methoxypyrimidin-4-yl)morpholine (343 mg, 1.49 mmol). The mixture was heated to 100° C. and stirred for 4 hrs. The mixture was diluted with H$_2$O (20 mL) and extracted with EtOAc (3×15 mL). The combined organic layers were washed with brine, dried over Na$_2$SO$_4$ and concentrated in vacuum. The residue was purified by prep. TLC (DCM:MeOH=20:1) and further purified by prep. HPLC to give the desired product (20.7 mg, yield 4%) as a yellow solid.

$^1$H NMR (300 MHz, CDCl$_3$): δ 8.05 (s, 1H), 8.00 (s, 1H), 7.46 (s, 1H), 6.83 (s, 1H), 4.97-4.94 (m, 1H), 4.11-4.03 (m, 5H), 3.81-3.78 (m, 4H), 3.73-3.71 (m, 4H), 3.34-3.28 (m, 2H), 2.52 (s, 3H), 2.33 (s, 3H).

LC-MS: [mobile phase: from 60% water (0.02% NH$_4$OAc) and 40% CH$_3$CN to 30% water (0.02% NH$_4$OAc) and 70% CH$_3$CN in 6.5 min], purity=91.7%, Rt=2.330 min MS Calcd.: 410, MS Found: 411 [M+H]$^+$.

Example 110

6-Isopropoxy-5-methyl-1-(2-(4-methyl piperazin-1-yl)pyridin-4-yl)-1H-pyrazolo[3,4-b]pyridine (E110)

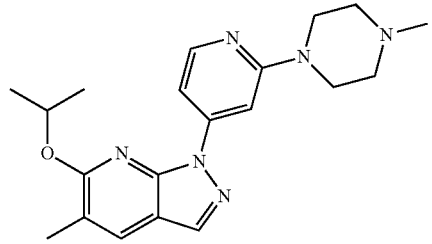 [SMILES: Cc1cc2cnn(-c3ccnc(N4CCN(C)CC4)c3)c2nc1OC(C)C]

To a solution of 6-isopropoxy-5-methyl-2H-pyrazolo[3,4-b]pyridine (40 mg, 0.21 mmol) in toluene (5 mL) was added 1-(4-Iodo-pyridin-2-yl)-4-methyl-piperazine (127 mg, 0.420 mmol), CuI (40 mg, 0.21 mmol), N,N'-dimethylcyclohexane-1,2-diamine (30 mg, 0.21 mmol) and K$_3$PO$_4$ (89 mg, 0.42 mmol). The reaction mixture was heated to 120° C. and stirred for 2 hrs. The mixture was cooled to rt and diluted with H$_2$O (10 mL) and EtOAc (10 mL). The aqueous layer was extracted with EtOAc (10 mL×3). The combined organic layers were dried over Na$_2$SO$_4$ and purified by prep. TLC (Eluent: EtOAc) to give the crude product. The crude was further purified by prep-HPLC to give the title compound (8.1 mg, yield: 11%) as a yellow solid. $^1$H NMR (300 MHz, CDCl$_3$): δ 8.25 (d, J=5.4 Hz, 1H), 7.97 (s, 1H), 7.89 (s, 1H), 7.73-7.71 (m, 2H), 5.49-5.44 (m, 1H), 3.69-3.66 (m, 4H), 2.58-2.55 (m, 4H), 2.37 (s, 3H), 2.26 (s, 3H), 1.46 (d, J=6.3 Hz, 6H). LC-MS (mobile phase: from 60% water (0.02% NH$_4$Ac) and 40% CH$_3$CN to 95% CH$_3$CN and 5% water (0.02% NH$_4$Ac) in 6 min, purity is >95%, Rt=3.742 min; MS Calcd.: 366, MS Found: 367 [M+H]$^+$.

Example 111

6-Isopropoxy-1-(2-(4-methylpiperazin-1-yl)pyridin-4-yl)-1H-pyrazolo[3,4-d]pyrimidine (E111)

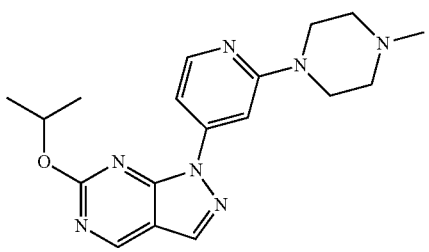 [SMILES: CC(C)Oc1ncc2cnn(-c3ccnc(N4CCN(C)CC4)c3)c2n1]

To a solution of 6-isopropoxy-1H-pyrazolo[3,4-d]pyrimidine (90 mg, 0.51 mmol) in toluene (10 mL) was added 1-(4-iodopyridin-2-yl)-4-methylpiperazine (307 mg, 1.05 mmol), $K_3PO_4 \cdot 3H_2O$ (214 mg, 1.05 mmol), CuI (96 mg, 0.51 mmol) and N,N'-dimethyl-cyclohexane-1,2-diamine (72 mg, 0.51 mmol) at $N_2$ atmosphere. The reaction mixture was refluxed overnight. The reaction mixture was cooled to room temperature and poured into $NH_3 \cdot H_2O$ (20 mL). EtOAc (2×20 mL) was added to extract the desired. The combined organic layers were washed with water (10 mL) and brine (10 mL), dried over $Na_2SO_4$ and concentrated. The residue was purified by prep. HPLC to give the crude product. The crude product was triturated with hexane (20 mL) to give the title compound (13 mg, 7%) as a white solid.

$^1$H NMR (400 MHz, $CDCl_3$): δ 8.99 (s, 1H), 8.28 (d, J=5.6 Hz, 1H), 8.16 (s, 1H), 7.71 (s, 1H), 7.66 (d, J=5.6 Hz, 1H), 5.43-5.37 (m, 1H), 3.68-3.65 (m, 4H), 2.57-2.54 (m, 4H), 2.36 (s, 3H), 1.49 (d, J=6.0 Hz, 6H). LC-MS (mobile phase: from 95% water (0.1% TFA) and 5% $CH_3CN$ to 5% water (0.1% TFA) and 95% $CH_3CN$ in 6.5 min, purity is >95%, Rt=2.791 min; MS Calcd.: 353, MS Found: 354 [M+H]$^+$.

Example 112

4-(6-(5-Methyl-6-(piperazin-1-yl)-1H-indazol-1-yl)pyrimidin-4-yl)morpholine (E112)

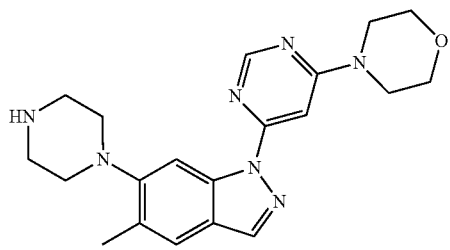 [SMILES: Cc1cc2cnn(-c3cc(N4CCOCC4)ncn3)c2cc1N1CCNCC1]

Tert-butyl 4-(5-methyl-1-(6-morpholinopyrimidin-4-yl)-1H-indazol-6-yl)piperazine-1-carboxylate (210 mg, 0.438 mmol) was dissolved in DCM (20 mL). TFA (2 mL) was added and the resulting solution was stirred at RT for 2 hrs. The solvent was then removed and the residue was used in next step without further purification.

LCMS: (mobile phase: 5-95% Acetonitrile), Rt=2.342 min in 5 min; MS Calcd: 379; MS Found: 380 [M+1]$^+$.

Purification was later performed for some portion of the residue (crude product) and it was described below:

The residue was further dissolved in MeOH (10 mL) and three drops of TFA. Then, the solution was added to Rxn CX 6 cc column (PoraPak™). Then the column was eluted with MeOH (20 mL). After that the column was eluted with MeOH with 5% ammonia (30 mL). After removing the solvent, the residue was dried in vacuo to give the solid. The FNMR showed there was TFA residue. The solid was dissolved in DCM (20 mL) and then the solution was washed with aqueous $NaHCO_3$ solution (1N) and water. The organic phase was dried over anhydrous sodium sulphate. After filtration and concentration, the residue was dissolved in MeOH and then MeOH was removed by rotary evaporator. Repeated this process three times. Then the residue was dissolved in ACN/water and dried in lyophilizer to give 4-(6-(5-methyl-6-(piperazin-1-yl)-1H-indazol-1-yl)pyrimidin-4-yl)morpholine (21.3 mg, 0.056 mmol).

LCMS: (mobile phase: 5-95% Acetonitrile), Rt=2.35 min in 5 min; MS Calcd: 379; MS Found: 380 [M+1]$^+$.

$^1$H NMR (METHANOL-$d_4$): δ 8.51 (s, 1H), 8.45 (s, 1H), 8.11 (s, 1H), 7.57 (s, 1H), 7.19 (s, 1H), 3.80-3.78 (m, 4H), 3.72-3.68 (m, 4H), 3.07-3.03 (m, 4H), 3.06-3.00 (m, 4H), 2.42 (s, 3H).

Example 113

4-(6-(5-Methyl-6-(4-methylpiperazin-1-yl)-1H-indazol-1-yl)pyrimidin-4-yl)morpholine (E113)

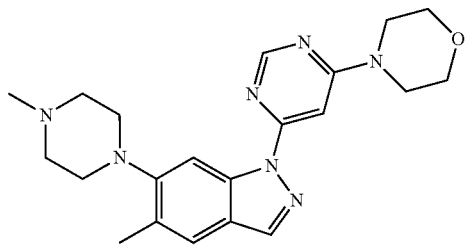 [SMILES: Cc1cc2cnn(-c3cc(N4CCOCC4)ncn3)c2cc1N1CCN(C)CC1]

The 4-(6-(5-methyl-6-(piperazin-1-yl)-1H-indazol-1-yl)pyrimidin-4-yl)morpholine was dissolved in DMF (5.00 mL). Formaldehyde (26.3 mg, 0.876 mmol), acetic acid (26.3 mg, 0.438 mmol) and $NaBH(OAc)_3$ (93 mg, 0.438 mmol) were added and the resulting solution was stirred at rt for 2 hrs. Water (20 mL) and EtOAc (30 mL) were added to the reaction mixture. The layers were separated and the aqueous layer was extracted by EtOAc (30 mL). The combined organic layers was washed with saturated aqueous NaCl (50 mL×2), dried over anhydrous $Na_2SO_4$ and then concentrated under the reduced pressure. The residue was then suspended in $Et_2O$ (5 mL) and then filtered and the solid was collected, and dried to afford 4-(6-(5-methyl-6-(4-methylpiperazin-1-yl)-1H-indazol-1-yl)pyrimidin-4-yl)morpholine (74 mg, 0.188 mmol, 42.9% yield) as a white solid.

LCMS: (mobile phase: 5-95% Acetonitrile), Rt=2.45 min in 5 min; MS Calcd: 393; MS Found: 394 [M+1]$^+$.

$^1$H NMR (DMSO-$d_6$): δ 8.59 (s, 1H), 8.41 (s, 1H), 8.30 (s, 1H), 7.63 (s, 1H), 7.15 (s, 1H), 3.68 (d, J=11.0 Hz, 8H), 2.88-3.04 (m, 4H), 2.53-2.50 (m, 4H), 2.36 (s, 3H), 2.27 (s, 3H)

Example 114

4-(6-(5-Methyl-6-(4-(oxetan-3-yl)piperazin-1-yl)-1H-indazol-1-yl)pyrimidin-4-yl)morpholine (E114)

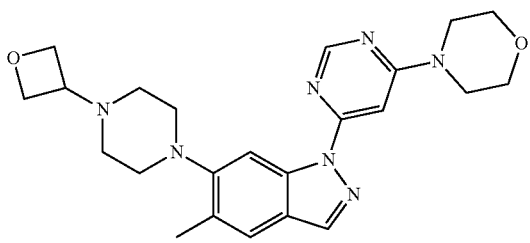 [SMILES: Cc1cc2cnn(-c3cc(N4CCOCC4)ncn3)c2cc1N1CCN(C2COC2)CC1]

The 4-(6-(5-methyl-6-(piperazin-1-yl)-1H-indazol-1-yl)pyrimidin-4-yl)morpholine (obtained in above step) was dissolved in DMF (5.00 mL). Cyclobutanone (61.4 mg, 0.876 mmol), acetic acid (26.3 mg, 0.438 mmol) and NaBH(OAc)$_3$ (93 mg, 0.438 mmol) were added and the resulting solution was stirred at rt overnight. Water (20 mL) and EtOAc (30 mL) were added to the reaction mixture. The layers were separated and the aqueous layer was extracted by EtOAc (30 mL). The combined organic layers was washed with saturated aqueous NaCl (50 mL×2), dried over anhydrous Na$_2$SO$_4$ and then concentrated under the reduced pressure. The residue was then suspended in Et$_2$O (5 mL) and then filtered, the solid was collected, and dried to afford 4-(6-(5-methyl-6-(4-(oxetan-3-yl)piperazin-1-yl)-1H-indazol-1-yl)pyrimidin-4-yl) morpholine (9 mg, 0.021 mmol, 4.72% yield) as a white solid.

LCMS: (mobile phase: 5-95% CH$_3$CN), Rt=2.44 min in 5 min; MS Calcd: 435; MS Found: 436 [M+1]$^+$.

$^1$H NMR (DMSO-d$_6$): δ 8.60 (s, 1H), 8.44 (s, 1H), 8.31 (s, 1H), 7.64 (s, 1H), 7.16 (s, 1H), 4.45-4.65 (m, 4H), 3.62-3.77 (m, 8H), 3.52 (br. s., 1H), 2.98 (br. s., 4H), 2.44-2.53 (br, s, 4H), 2.36 (s, 3H).

Example 115

4-(2-Methoxy-6-(5-methyl-6-(4-methylpiperazin-1-yl)-1H-indazol-1-yl)pyrimidin-4-yl)morpholine (E115)

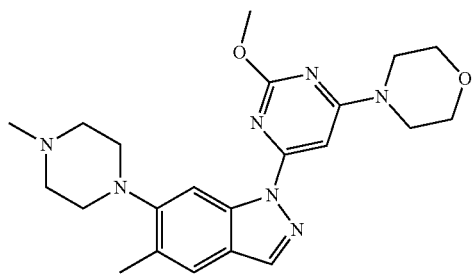 [SMILES: COc1nc(N2CCOCC2)cc(-n2ncc3cc(C)c(N4CCN(C)CC4)cc32)n1]

To a solution of 5-methyl-6-(4-methylpiperazin-1-yl)-1H-indazole (60 mg, 0.31 mmol) were added 4-(6-chloro-2-methoxypyrimidin-4-yl)morpholine (94 mg, 0.47 mmol) and Cs$_2$CO$_3$ (205 mg, 0.63 mmol). The mixture was stirred at 120° C. for 1 hr under microwave irradiation. The crude product was purified by reverse phase column (MDAP) to afford E115 as a white solid. The mixture was separated by chiral prep-HPLC with the method: chiralpal IB 5 um 4.6*250 mm, phase: Hex:EtOH=70:30, F: 1.0 mL/min, W: 230 nm, T=30° C. to obtain Peak 1 and Peak 2. The two compounds were further purified by C18 column eluting with CH$_3$CN/H$_2$O (from 05/95 to 100/0) to give E115 (8.6 mg, yield 17%, Rt=6.827 min, 100% ee) as a white solid as a white solid.

E115: $^1$H NMR (400 MHz, CD$_3$OD): δ 8.51 (s, 1H), 8.12 (s, 1H), 7.60 (s, 1H), 6.91 (s, 1H), 4.11 (s, 3H), 3.82-3.79 (m, 4H), 3.72-3.69 (m, 4H), 3.08 (s, 4H), 2.72 (br s, 4H), 2.43 (s, 3H), 2.41 (s, 3H); LC-MS (mobile phase: from 95% water (0.1% TFA) and 5% CH$_3$CN to 5% water (0.1% TFA) and 95% CH$_3$CN in 6 min, purity is >95%, Rt=3.396 min; MS Calcd.: 423, MS Found: 424 [M+H]$^+$.

Example 116

4-(2-Ethyl-6-(5-methyl-6-(4-methylpiperazin-1-yl)-1H-indazol-1-yl)pyrimidin-4-yl)morpholine (E116)

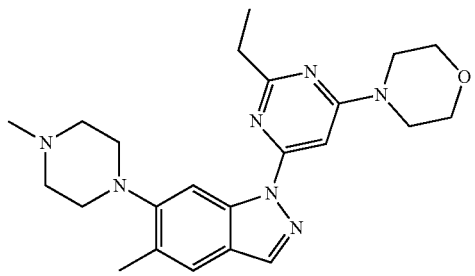 [SMILES: CCc1nc(N2CCOCC2)cc(-n2ncc3cc(C)c(N4CCN(C)CC4)cc32)n1]

To a solution of 4-(6-(6-bromo-5-methyl-1H-indazol-1-yl)-2-ethylpyrimidin-4-yl)morpholine (260 mg, 0.646 mmol) in toluene (20 mL) was added Pd$_2$(dba)$_3$ (59.2 mg, 0.065 mmol), BINAP (80 mg, 0.129 mmol), 1-methylpiperazine (129 mg, 1.293 mmol) and Cs$_2$CO$_3$ (421 mg, 1.293 mmol). The resulting mixture was stirred at 120° C. overnight under nitrogen atmosphere.

The reaction mixture was cooled to room temperature, ethyl acetate (50 mL) and water (50 mL) were added and the layers were separated. The aqueous layer was extracted by EtOAc (30 mL). The combined organic layers was washed with saturated aqueous NaCl (50 mL×2 times), dried over anhydrous Na$_2$SO$_4$ and then concentrated under the reduced pressure. The residue was purified by reverse phase chromatography (Biotage, Isolera One, 50 g column, water:acetonitrile=95:5→30:70) to afford 4-(2-ethyl-6-(5-methyl-6-(4-methylpiperazin-1-yl)-1H-indazol-1-yl)pyrimidin-4-yl)morpholine (60 mg, 0.128 mmol, 19.82% yield) as a pale yellow solid.

LCMS: (mobile phase: 5-95% CH$_3$CN), Rt=2.54 min in 5 min; MS Calcd: 421; MS Found: 422 (M+1)$^+$.

$^1$H NMR (DMSO-d$_6$): δ 8.52 (s, 1H), 8.27 (s, 1H), 7.62 (s, 1H), 6.98 (s, 1H), 3.57-3.78 (m, 8H), 3.35 (br. s., 4H), 3.02 (br. s., 3H), 2.62-2.88 (m, 5H), 2.31-2.44 (m, 4H), 1.39 (t, J=7.5 Hz, 3H).

Example 117

4-(1-(2-Methoxy-6-(piperazin-1-yl)pyrimidin-4-yl)-5-methyl-1H-indazol-6-yl)morpholine (E117)

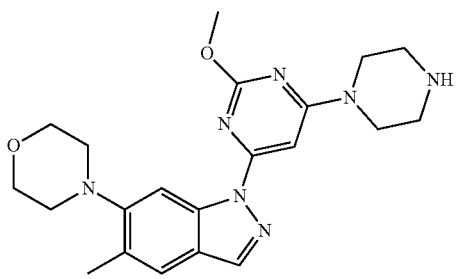 [SMILES: COc1nc(N2CCNCC2)cc(-n2ncc3cc(C)c(N4CCOCC4)cc32)n1]

Step 1:

To a solution of tert-butyl 4-(6-(6-bromo-5-methyl-1H-indazol-1-yl)-2-methoxypyrimidin-4-yl)piperazine-1-carboxylate (52 mg, 0.103 mmol) in toluene (5 mL) was added Pd$_2$(dba)$_3$ (18.92 mg, 0.021 mmol), xantphos (23.91 mg, 0.041 mmol), morpholine (0.045 mL, 0.516 mmol) and Cs$_2$CO$_3$ (67.3 mg, 0.207 mmol). The mixture was stirred at 120° C. under nitrogen atmosphere for 3 hrs. The mixture was cooled to room temperature. EtOAc (100 mL) and water (50 mL) were added. The layers were separated and the aqueous layer was extracted with EtOAc (30 mL). The combined layers were washed with saturated aqueous sodium chloride, dried over anhydrous Na$_2$SO$_4$ and then concentrated under the reduced pressure. The residue was then purified by normal phase chromatography (ISCO, 40 g column, PE:EtOAc=100:0 to 40:60) to afford tert-butyl 4-(2-methoxy-6-(5-methyl-6-morpholino-1H-indazol-1-yl)pyrimidin-4-yl)piperazine-1-carboxylate as a pale yellow solid. LCMS: (mobile phase: 5-95% CH$_3$CN), Rt=4.35 min in 5 min; MS Calcd: 509; MS Found: 510 [M+1]+.

Step 2:

The intermediate (obtained in step 1) was dissolved in DCM (5.00 mL), TFA (0.5 mL) was added and the solution was stirred at rt for 1 hr. The solvent was removed and the residue was redissolved in EtOAc (20 mL), water (10 mL) was added and the pH of the aqueous layer was adjusted to 8 using saturated aqueous NaHCO$_3$. The organic layer was separated, dried over anhydrous Na$_2$SO$_4$ and then concentrated to afford 4-(1-(2-methoxy-6-(piperazin-1-yl)pyrimidin-4-yl)-5-methyl-1H-indazol-6-yl)morpholine (5 mg, 0.012 mmol, 11.82% yield) as a white solid.

LCMS: (mobile phase: 5-95% CH$_3$CN), Rt=2.8 min in 5 min; MS Calcd: 409; MS Found: 410 [M+1]+.

$^1$H NMR (DMSO-d$_6$): δ 8.42 (s, 1H), 8.29 (s, 1H), 7.64 (s, 1H), 6.82 (s, 1H), 4.01 (s, 3H), 3.79 (br. s., 4H), 3.59 (br. s., 4H), 2.94 (br. s., 4H), 2.78 (br. s., 4H), 2.39 (s, 3H).

Example 118

4-(5-Methyl-1-(6-(4-methylpiperazin-1-yl)pyrimidin-4-yl)-1H-indazol-6-yl)morpholine (E118)

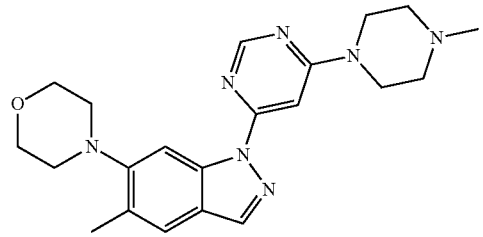 [SMILES: Cc1cc2cnn(-c3cc(N4CCN(C)CC4)ncn3)c2cc1N1CCOCC1]

Step 1:

tert-Butyl-4-(6-(5-methyl-6-morpholino-1H-indazol-1-yl)pyrimidin-4-yl)piperazine-1-carboxylate (100 mg, 0.209 mmol) was dissolved in DCM (10 mL), TFA (1 mL) was added and the resulting solution was stirred at RT for 2 hrs. The solvent was removed and the residue was used in next step without further purification.

LCMS: (mobile phase: 5-95% CH$_3$CN), Rt=2.66 min in 5 min; MS Calcd: 379; MS Found: 380 [M+1]+.

Step 2

The intermediate (obtained in step 1) was dissolved in DMF (6.00 mL). Formaldehyde (0.078 mL, 1.043 mmol), AcOH (0.020 mL, 0.349 mmol) and NaBH(OAc)$_3$ (133 mg, 0.626 mmol) were added and the solution was stirred at RT for 2 hrs. H$_2$O (30 mL) and EtOAc (50 mL) were added to the reaction mixture and pH value of the aqueous layer was adjusted to about 8 using saturated aqueous NaHCO$_3$. The layers were separated and the aqueous layer was extracted with EtOAc (20 mL). The organic layers were combined, washed with saturated aqueous NaCl (50 mL×2 times), dried over anhydrous Na$_2$SO$_4$ and then concentrated under the reduced pressure. The residue was then suspended in Et$_2$O (5 mL) and then filtered. The solid was collected, and dried to afford 4-(5-methyl-1-(6-(4-methylpiperazin-1-yl)pyrimidin-4-yl)-1H-indazol-6-yl)morpholine (35.9 mg, 0.091 mmol, 43.8% yield) as a white solid.

LCMS: (mobile phase: 5-95% CH$_3$CN), Rt=2.60 min in 5 min; MS Calcd: 393; MS Found: 394 [M+1]+.

$^1$H NMR (DMSO-d$_6$) δ: 8.57 (s, 1H), 8.41 (s, 1H), 8.30 (s, 1H), 7.65 (s, 1H), 7.15 (s, 1H), 3.75-3.83 (m, 4H), 3.68 (br. s., 4H), 2.87-3.03 (m, 4H), 2.36-2.44 (m, 7H), 2.23 (s, 3H).

Example 119

4-(5-Methyl-1-(6-(4-(oxetan-3-yl)piperazin-1-yl)pyrimidin-4-yl)-1H-indazol-6-yl)morpholine (E119)

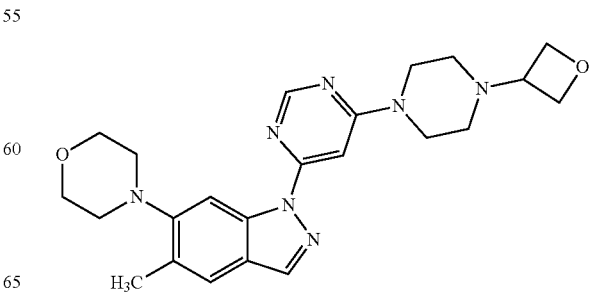

Step 1:

tert-Butyl-4-(6-(5-methyl-6-morpholino-1H-indazol-1-yl)pyrimidin-4-yl)piperazine-1-carboxylate (100 mg, 0.209 mmol) was dissolved in DCM (10 mL), TFA (1 mL) was added and the resulting solution was stirred at RT for 2 hrs. The solvent was removed and the residue was used in next step without further purification.

LCMS: (mobile phase: 5-95% CH$_3$CN), Rt=2.66 min in 5 min; MS Calcd: 379; MS Found: 380 [M+1]$^+$.

Step 2

The intermediate (obtained in step 1) was dissolved in DMF (6.00 mL). Oxetan-3-one (75 mg, 1.043 mmol), AcOH (0.020 mL, 0.349 mmol), NaBH(OAc)$_3$ (133 mg, 0.626 mmol) were added and the solution was stirred at RT overnight. H$_2$O (30 mL) and EtOAc (50 mL) were added to the reaction mixture and pH value of the aqueous layer was adjusted to 8 using saturated aqueous NaHCO$_3$. The layers were separated and the aqueous layer was extracted with EtOAc (20 mL). The organic layers were combined, washed with saturated aqueous NaCl (50 mL×2), dried over anhydrous Na$_2$SO$_4$ and then concentrated under the reduced pressure. The residue was then suspended in Et$_2$O (5 mL) and then filtered. The solid was collected, dried to afford 4-(5-methyl-1-(6-(4-(oxetan-3-yl)piperazin-1-yl)pyrimidin-4-yl)-1H-indazol-6-yl) morpholine (51 mg, 0.117 mmol, 56.2% yield) as a white solid.

LCMS: (mobile phase: 5-95% CH$_3$CN), Rt=2.60 min in 5 min; MS Calcd: 435; MS Found: 436 [M+1]$^+$.

$^1$H NMR (DMSO-d$_6$) δ: 8.58 (s, 1H), 8.41 (s, 1H), 8.31 (s, 1H), 7.65 (s, 1H), 7.16 (s, 1H), 4.54-4.61 (m, 2H), 4.45-4.52 (m, 2H), 3.76-3.83 (m, 4H), 3.71 (br. s., 4H), 3.43-3.50 (m, 1H), 2.95 (d, J=4.2 Hz, 4H), 2.34-2.44 (m, 7H).

Example 120

4-(2-Methoxy-6-(6-(piperazin-1-yl)-1H-indazol-1-yl)pyrimidin-4-yl)morpholine hydrochloride (E120)

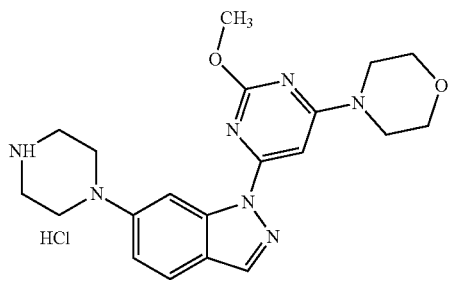 [SMILES: COc1nc(N2CCOCC2)cc(-n2ncc3ccc(N4CCNCC4)cc32)n1 ; Cl]

To a solution of tert-butyl 4-(1-(2-methoxy-6-morpholinopyrimidin-4-yl)-1H-indazol-6-yl)piperazine-1-carboxylate (60 mg, 0.12 mmol) was added HCl/MeOH (5 M, 5 mL) in MeOH (5 mL). The solution was stirred at room temperature for 1 h. The solution was directly concentrated in vacuum to give the desired product (46 mg, yield 90%) as a yellow solid.

$^1$H NMR (300 MHz, DMSO-d$_6$): δ 9.37 (br s, 2H), 8.30-8.26 (m, 2H), 7.73 (d, J=9.0 Hz, 1H), 7.17 (d, J=8.1, 1H), 6.86 (s, 1H), 3.99 (s, 3H), 3.70-3.63 (m, 8H), 3.50-3.48 (m, 4H), 3.30-3.24 (m, 4H).

LC-MS: [mobile phase: from 95% water (0.02% NH$_4$AC) and 5% CH$_3$CN to 5% water (0.02% NH$_4$AC) and 95% CH$_3$CN in 6.5 min], purity >95%, Rt=3.618 min MS Calcd.: 395, MS Found: 396 [M+H]$^+$.

Example 121

1-(1-(2-Methoxy-6-(4-methylpiperazin-1-yl)pyrimidin-4-yl)-5-methyl-1H-indazol-6-yl)piperidin-4-ol (E121)

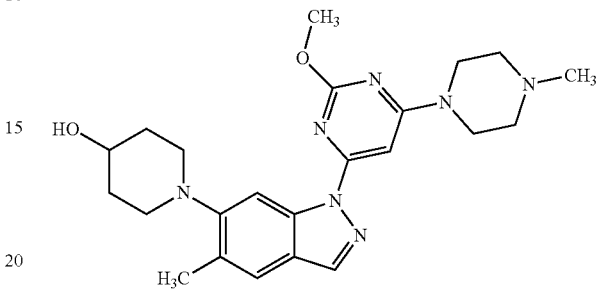

To a solution of 6-bromo-1-(2-methoxy-6-(4-methylpiperazin-1-yl)pyrimidin-4-yl)-5-methyl-1H-indazole (50 mg, 0.120 mmol) in THF (20 mL) was added Pd(OAc)$_2$ (5.38 mg, 0.024 mmol), 2'-(dicyclohexylphosphino)-N,N-dimethyl-[1,1'-biphenyl]-2-amine (18.86 mg, 0.048 mmol), piperidin-4-ol (36.4 mg, 0.359 mmol) and sodium 2-methylpropan-2-olate (23.03 mg, 0.240 mmol). The mixture was stirred at 70° C. under nitrogen atmosphere for 3 hrs. Water (20 mL) and EtOAc (70 mL) were added to the mixture. The layers were separated and the aqueous layer was extracted by EtOAc (30 mL). The combined organic layers was washed with saturated aqueous NaCl (50 mL×2), dried over anhydrous Na$_2$SO$_4$ and then concentrated under the reduced pressure. The residue was purified by reverse phase chromatography to afford 1-(1-(2-methoxy-6-(4-methylpiperazin-1-yl)pyrimidin-4-yl)-5-methyl-1H-indazol-6-yl)piperidin-4-ol, Trifluoroacetic acid salt (9.8 mg, 0.018 mmol, 14.83% yield) as a white solid.

LCMS: (mobile phase: 5-95% acetonitrile), Rt=2.29 min in 5 min; MS Calcd: 437; MS Found: 438.3 [M+1]$^+$.

$^1$H NMR (DMSO-d$_6$): δ 9.76 (br. s., 1H), 8.40 (s, 1H), 8.30 (s, 1H), 7.63 (s, 1H), 6.99 (s, 1H), 4.59 (d, J=11.7 Hz, 2H), 4.03 (s, 3H), 3.53-3.74 (m, 3H), 3.27 (t, J=13.0 Hz, 2H), 3.02-3.18 (m, 4H), 2.85 (br. s., 3H), 2.71 (t, J=10.9 Hz, 2H), 2.36 (s, 3H), 1.89 (br. s., 2H), 1.55-1.68 (m, 2H).

Example 122

(cis)-(1S,3S)-3-(6-(6-(3-Fluoro-1-methylpiperidin-4-yl)-5-methyl-1H-indazol-1-yl)-2-methoxypyrimidin-4-yl)cyclobutanol hydrochloride (Enantiomer 1) (E122)

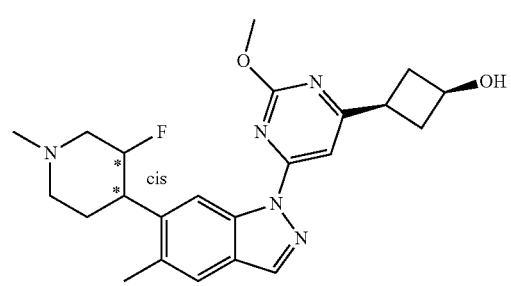 [SMILES: COc1nc(-n2ncc3cc(C)c(C4CCN(C)CC4F)cc32)cc([C@H]2C[C@@H](O)C2)n1]

To a solution of (cis)-(1S,3S)-3-(6-(6-(3-fluoropiperidin-4-yl)-5-methyl-1H-indazol-1-yl)-2-methoxypyrimidin-4-yl)cyclobutanol hydrochloride (enantiomer 1) (35 mg, 0.078 mmol) in methanol (5 mL) was added HCHO (35% in water, 0.5 mL). The mixture was stirred at rt for 10 min. To the reaction mixture was added NaBH₃CN (35 mg, 0.55 mmol) and stirred at rt for 1 h. To the reaction mixture was added sat. NaHCO₃ solution (10 mL). After stirred for 10 min the mixture was extracted with EtOAc (10 mL×3). The combined organic layers were washed with brine (10 mL), dried over Na₂SO₄ and concentrated. The residue was purified by prep-TLC (DCM: CH₃OH=15:1) to give the title compound (11 mg, yield 33%) as white solid.

E122 $^1$H NMR (300 MHz, CDCl₃): 8.84 (s, 1H), 8.11 (s, 1H), 7.55 (s, 1H), 7.46 (s, 1H), 4.99-4.75 (m, 1H), 4.36-4.27 (m, 1H), 4.19 (s, 3H), 3.37-3.31 (m, 1H), 3.19-3.04 (m, 2H), 2.95-2.91 (m, 1H), 2.85-2.74 (m, 2H), 2.49 (s, 3H), 2.41 (s, 3H), 2.34-2.08 (m, 4H), 1.95-1.82 (m, 2H).

$^{19}$F NMR (376 MHz, CDCl₃): δ −184.31 (s, 1F).

LC-MS [mobile phase: from 95% water (0.02% NH₄OAc) and 5% CH₃CN to 5% water (0.02% NH₄OAc) and 95% CH₃CN in 6.5 min], purity >95%, Rt=4.335 min; MS Calcd.: 425, MS Found: 426 [M+H]⁺.

Chiral condition: Chiralpak IA 5 um 4.6*250 mm, Hex/EtOH=70/30, Flow Rate: 1 ml/min, 230 nm, T=30° C., Rt=5.427 min, 100% ee.

Example 123

(cis)-(1S,3S)-3-(6-(6-(3-Fluoro-1-methylpiperidin-4-yl)-5-methyl-1H-indazol-1-yl)-2-methoxypyrimidin-4-yl)cyclobutanol hydrochloride (Enantiomer 2) (E123)

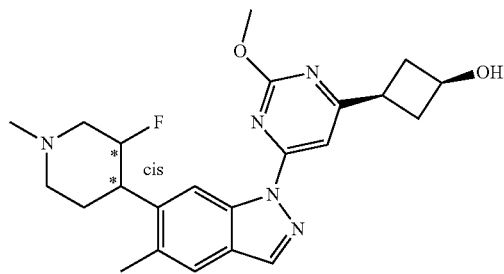 [SMILES: COc1nc(-n2ncc3cc(C)c(C4CCN(C)CC4F)cc32)cc([C@H]2C[C@@H](O)C2)n1]

To a solution of (cis)-(1S,3S)-3-(6-(6-(3-fluoropiperidin-4-yl)-5-methyl-1H-indazol-1-yl)-2-methoxypyrimidin-4-yl)cyclobutanol hydrochloride (enantiomer 2, 62 mg, 0.14 mmol) in methanol (10 mL) was added HCHO (35% in water, 0.5 mL). The mixture was stirred at rt for 10 min. To the reaction mixture was added NaBH₃CN (63 mg, 1.0 mmol) and stirred at rt for 1 h. To the reaction mixture was added sat. NaHCO₃ solution (20 mL). After stirred for 10 min the mixture was extracted with EtOAc (20 mL×2). The combined organic layers were washed with brine (20 mL), dried over Na₂SO₄ and concentrated. The residue was purified by prep-TLC (DCM: CH₃OH=15:1) to give the title compound (23 mg, yield 39%) as white solid.

E123 $^1$H NMR (400 MHz, CDCl₃): 8.84 (s, 1H), 8.12 (s, 1H), 7.56 (s, 1H), 7.46 (s, 1H), 4.97-4.79 (m, 1H), 4.35-4.28 (m, 1H), 4.19 (s, 3H), 3.37-3.31 (m, 1H), 3.18-3.05 (m, 2H), 2.95-2.91 (m, 1H), 2.84-2.77 (m, 3H), 2.49 (s, 3H), 2.41 (s, 3H), 2.33-2.08 (m, 4H), 1.97-1.85 (m, 2H).

$^{19}$F NMR (376 MHz, CDCl₃): δ −184.28 (s, 1F).

LC-MS [mobile phase: from 95% water (0.02% NH₄OAc) and 5% CH₃CN to 5% water (0.02% NH₄OAc) and 95% CH₃CN in 6.5 min], purity >95%, Rt=4.347 min; MS Calcd.: 425, MS Found: 426 [M+H]⁺.

Chiral condition: Chiralpak IA 5 um 4.6*250 mm, Hex/EtOH=70/30, Flow Rate: 1 ml/min, 230 nm, T=30° C., Rt=6.699 min, 100% ee.

Example 124

(cis)-(1R,3R)-3-(6-(6-(3-fluoro-1-methylpiperidin-4-yl)-5-methyl-1H-indazol-1-yl)-2-methoxypyrimidin-4-yl)cyclobutanol (Enantiomer 1, E124)

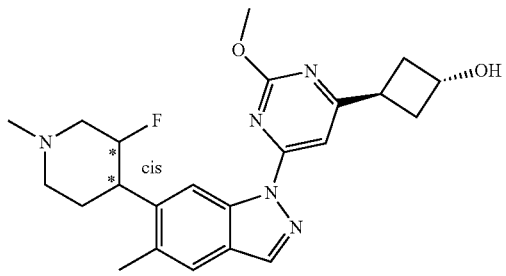 [SMILES: COc1nc(-n2ncc3cc(C)c(C4CCN(C)CC4F)cc32)cc([C@H]2C[C@H](O)C2)n1]

To a solution of (cis)-(1R,3R)-3-(6-(6-(3-fluoropiperidin-4-yl)-5-methyl-1H-indazol-1-yl)-2-methoxypyrimidin-4-yl)cyclobutanol hydrochloride (54 mg, 0.12 mmol) in methanol (5 mL) was added HCHO (35% in water, 0.5 mL). After stirred at rt for 10 min NaBH₃CN (50 mg, 0.79 mmol) was added. The resulting mixture was stirred at rt for 30 min. To the reaction mixture was added sat. NaHCO₃ solution (10 mL). The mixture was extracted with EtOAc (20 mL×2). The combined organic layers were washed with brine (20 mL), dried over Na₂SO₄ and concentrated. The residue was purified by prep-TLC (DCM: CH₃OH=15:1) to give the title compound (15 mg, yield 29%) as white solid.

E124 $^1$H NMR (400 MHz, CDCl₃): 8.85 (s, 1H), 8.11 (s, 1H), 7.56 (s, 1H), 7.46 (s, 1H), 4.96-4.74 (m, 2H), 4.18 (s, 3H), 3.63-3.56 (m, 1H), 3.37-3.32 (m, 1H), 3.12-3.03 (m, 1H), 2.95-2.90 (m, 1H), 2.75-2.68 (m, 2H), 2.49 (s, 3H), 2.44-2.37 (m, 5H), 2.23-2.09 (m, 2H), 1.97-1.83 (m, 3H).

$^{19}$F NMR (376 MHz, CDCl₃): δ −184.26 (s, 1F).

LC-MS [mobile phase: from 95% water (0.02% NH₄OAc) and 5% CH₃CN to 5% water (0.02% NH₄OAc) and 95% CH₃CN in 6.5 min], purity >95%, Rt=4.331 min; MS Calcd.: 425, MS Found: 426 [M+H]⁺.

Chiral condition: Chiralpak IA 5 um 4.6*250 mm, Hex/EtOH=70/30, Flow Rate: 1 ml/min, 230 nm, T=30° C., Rt=5.090 min, 99.5% ee.

Example 125

(cis)-(1R,3R)-3-(6-(6-(3-fluoro-1-methylpiperidin-4-yl)-5-methyl-1H-indazol-1-yl)-2-methoxypyrimidin-4-yl)cyclobutanol (Enantiomer 2, E125)

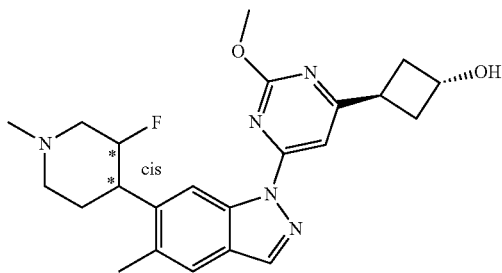 [SMILES: COc1nc(-n2ncc3cc(C)c(C4CCN(C)CC4F)cc32)cc([C@H]2C[C@H](O)C2)n1]

To a solution of (cis)-(1R,3R)-3-(6-(6-(3-fluoropiperidin-4-yl)-5-methyl-1H-indazol-1-yl)-2-methoxypyrimidin-4-yl)cyclobutanol hydrochloride (54 mg, 0.12 mmol) in methanol (5 mL) was added HCHO (35% in water, 0.5 mL). After stirred at rt for 10 min, NaBH$_3$CN (50 mg, 0.79 mmol) was added. The resulting mixture was stirred at rt for 30 min. To the reaction mixture was added sat. NaHCO$_3$ solution (10 mL). EtOAc (20 mL×2) was added to extract the desired compound. The combined organic layers were washed with brine (20 mL), dried over Na$_2$SO$_4$ and concentrated. The residue was purified by prep-TLC (DCM:CH$_3$OH=15:1) to give the title compound (22 mg, yield 43%) as white solid.

E125 $^1$H NMR (400 MHz, CDCl$_3$): 8.85 (s, 1H), 8.11 (s, 1H), 7.56 (s, 1H), 7.46 (s, 1H), 4.96-4.73 (m, 2H), 4.18 (s, 3H), 3.63-3.56 (m, 1H), 3.37-3.31 (m, 1H), 3.12-3.04 (m, 1H), 2.95-2.89 (m, 1H), 2.74-2.68 (m, 2H), 2.49 (s, 3H), 2.44-2.37 (m, 5H), 2.24-2.09 (m, 2H), 1.96-1.82 (m, 3H).

$^{19}$F NMR (376 MHz, CDCl$_3$): δ −184.26 (s, 1F).

LC-MS [mobile phase: from 95% water (0.02% NH$_4$OAc) and 5% CH$_3$CN to 5% water (0.02% NH$_4$OAc) and 95% CH$_3$CN in 6.5 min], purity >95%, Rt=4.338 min; MS Calcd.: 425, MS Found: 426 [M+H]$^+$.

Chiral condition: Chiralpak IA 5 um 4.6*250 mm, Hex/EtOH=70/30, Flow Rate: 1 ml/min, 230 nm, T=30° C., Rt=6.419 min, 96.5% ee.

Example 126

(R)-1-(6-(6-((cis)-3-fluoro-1-methylpiperidin-4-yl)-5-methyl-1H-indazol-1-yl)-2-methylpyrimidin-4-yl)pyrrolidin-3-ol (Diastereoisomer 1, E126)

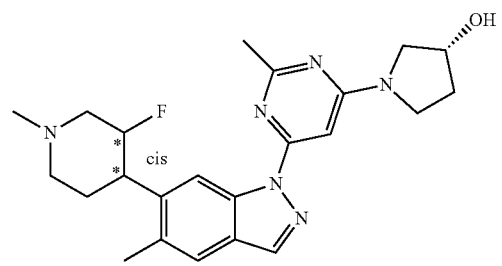 [SMILES: Cc1nc(N2CC[C@@H](O)C2)cc(-n2ncc3cc(C)c(C4CCN(C)CC4F)cc32)n1]

To a solution of (R)-1-(6-(6-((cis)-3-fluoropiperidin-4-yl)-5-methyl-1H-indazol-1-yl)-2-methylpyrimidin-4-yl)pyrrolidin-3-ol (diastereoisomer 1, 110 mg, 0.268 mmol, crude) in methanol (10 mL) was added 37% HCHO aqueous (1 mL) and stirred at room temperature for 30 min. Then, NaBH$_3$CN (60 mg, 0.13 mmol) was added and stirred at room temperature for 1 hr. The reaction mixture was poured into sat. NaHCO$_3$ solution (30 mL), and extracted with EtOAc (30 mL×3). The combined organic layers were washed with brine (30 mL), dried over anhydrous Na$_2$SO$_4$, filtered, and concentrated to dryness. The residue was purified by Prep-HPLC (method: Sepax C18-H 21.2*100 mm 5 um, phase: H$_2$O (0.1% TFA):ACN=90:10 to 10:90, 15 mL/min, 254/214 nm) to give the title product (R)-1-(6-(6-((cis)-3-fluoro-1-methyl piperidin-4-yl)-5-methyl-1H-indazol-1-yl)-2-methylpyrimidin-4-yl)pyrrolidin-3-ol (diastereoisomer 1) (40 mg, yield 35.2%) as a white solid.

E126 $^1$H NMR (400 MHz, CDCl$_3$): δ 8.90 (s, 1H), 8.06 (s, 1H), 7.52 (s, 1H), 6.71 (s, 1H), 4.97-4.84 (m, 1H), 4.63 (s, 1H), 3.70 (s, 4H), 3.37-3.34 (m, 1H), 3.09-2.93 (m, 2H), 2.62 (s, 3H), 2.48 (d, J=22.4, 6H), 2.24-2.09 (m, 4H), 1.94 (s, 2H), 1.71 (s, 1H).

$^{19}$F NMR (400 MHz, CDCl$_3$): δ −184.08 (s, 1F).

LC-MS [mobile phase: from 90% water (0.1% FA) and 10% CH$_3$CN (0.1% FA) to 5% water (0.1% FA) and 95% CH$_3$CN (0.1% FA) in 10 min], purity: 97.9%; Rt=4.86 min; MS Calcd: 424, MS Found: 425 [M+H]$^+$.

Chiral condition: Chiralpak AD-H 5 um 4.6*250 mm, Hexane/IPA=85/15, Flow Rate: 1 mL/min, 214 nm, T=30° C., Rt=7.64 min, 99% ee.

Example 127

(R)-1-(6-(6-((cis)-3-fluoro-1-methylpiperidin-4-yl)-5-methyl-1H-indazol-1-yl)-2-methylpyrimidin-4-yl)pyrrolidin-3-ol (Diastereoisomer 2, E127)

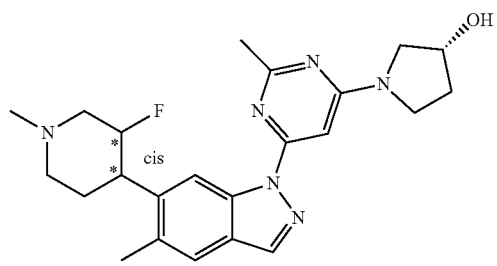 [SMILES: Cc1nc(N2CC[C@@H](O)C2)cc(-n2ncc3cc(C)c(C4CCN(C)CC4F)cc32)n1]

To a solution of (R)-1-(6-(6-((cis)-3-fluoropiperidin-4-yl)-5-methyl-1H-indazol-1-yl)-2-methylpyrimidin-4-yl)pyrrolidin-3-ol (diastereoisomer 2, 110 mg, 0.268 mmol, crude) in methanol (15 mL) was added 37% HCHO aqueous (1 mL) and stirred at room temperature for 30 min. Then, NaBH$_3$CN (60 mg, 0.13 mmol) was added and stirred at room temperature for 2 hr. The reaction mixture was poured into sat. NaHCO$_3$ solution (30 mL), and extracted with DCM (30 mL×3). The combined organic layers were washed with brine (30 mL), dried over anhydrous Na$_2$SO$_4$, filtered, and concentrated to dryness. The residue was purified by Prep-HPLC (method: Sepax C18-H 21.2*100 mm 5 um, phase: H$_2$O (0.1% TFA):ACN=90:10 to 10:90, 15 mL/min, 254/214 nm) to give the title product (R)-1-(6-(6-((cis)-3-fluoro-1-methyl piperidin-4-yl)-5-methyl-1H-indazol-1-yl)-2-methylpyrimidin-4-yl)pyrrolidin-3-ol (diastereoisomer 2) (40 mg, yield 38.2%) as a white solid.

E127 $^1$H NMR (400 MHz, CDCl$_3$): δ 8.90 (s, 1H), 8.06 (s, 1H), 7.52 (s, 1H), 6.71 (s, 1H), 4.97-4.84 (m, 1H), 4.63

(s, 1H), 3.70 (s, 4H), 3.37-3.34 (m, 1H), 3.09-2.93 (m, 2H), 2.62 (s, 3H), 2.48 (d, J=22.4, 6H), 2.24-2.09 (m, 4H), 1.94 (s, 2H), 1.71 (s, 1H).

$^{19}$F NMR (400 MHz, CDCl$_3$): δ −184.08 (s, 1F).

Example 128

(S)-1-(6-(6-((cis)-3-fluoro-1-methylpiperidin-4-yl)-5-methyl-1H-indazol-1-yl)-2-methylpyrimidin-4-yl)pyrrolidin-3-ol (Diastereoisomer 1, E128)

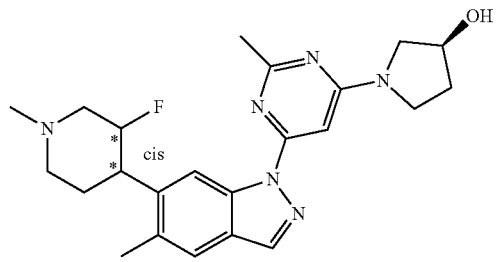 [SMILES: Cc1nc(N2CC[C@H](O)C2)cc(-n2ncc3cc(C)c(C4CCN(C)CC4F)cc32)n1]

To a solution of (S)-1-(6-(6-((cis)-3-fluoropiperidin-4-yl)-5-methyl-1H-indazol-1-yl)-2-methylpyrimidin-4-yl)pyrrolidin-3-ol (diastereoisomer 1) (50 mg, 0.122 mmol, crude) in methanol (10 mL) was added 37% HCHO aqueous (1 mL) and stirred at room temperature for 30 min. Then, NaBH$_3$CN (16 mg, 0.244 mmol) was added and stirred at room temperature for 1 hr. The reaction mixture was poured into sat. NaHCO$_3$ solution (30 mL), and extracted with EtOAc (30 mL×3). The combined organic layers were washed with brine (30 mL), dried over anhydrous Na$_2$SO$_4$, filtered, and concentrated to dryness. The residue was purified by Prep-HPLC (method: Sepax C18-H 21.2*100 mm 5 um, phase: H$_2$O (0.1% TFA):ACN=90:10 to 10:90, 15 mL/min, 254/214 nm) to give the title product (S)-1-(6-(6-((cis)-3-fluoro-1-methylpiperidin-4-yl)-5-methyl-1H-indazol-1-yl)-2-methylpyrimidin-4-yl)pyrrolidin-3-ol (diastereoisomer 1) (32 mg, yield=61.9%) as a white solid.

E128 $^1$H NMR (400 MHz, CDCl$_3$): δ 8.90 (s, 1H), 8.06 (s, 1H), 7.52 (s, 1H), 6.71 (s, 1H), 5.00-4.82 (m, 1H), 4.62 (s, 1H), 3.69 (s, 4H), 3.37-3.34 (m, 1H), 3.09-2.93 (m, 2H), 2.62 (s, 3H), 2.47 (s, 3H), 2.42 (s, 3H), 2.24-2.09 (m, 4H), 1.93 (s, 2H), 1.79 (s, 1H).

$^{19}$F NMR (376 MHz, CDCl$_3$): δ −184.07 (s, 1F).

LC-MS [mobile phase: from 90% water (0.1% FA) and 10% CH$_3$CN (0.1% FA) to 5% water (0.1% FA) and 95% CH$_3$CN (0.1% FA) in 10 min], purity: 98.9%; Rt=4.87 min; MS Calcd: 424, MS Found: 425[M+H]$^+$.

Chiral condition: Chiralpak AD-H 5 um 4.6*250 mm, Hexane/IPA=85/15, Flow Rate: 1 mL/min, 214 nm, T=30° C., Rt=10.73 min, 99% ee.

Example 129

(S)-1-(6-(6-((cis)-3-fluoro-1-methylpiperidin-4-yl)-5-methyl-1H-indazol-1-yl)-2-methylpyrimidin-4-yl)pyrrolidin-3-ol (Diastereoisomer 2, E129)

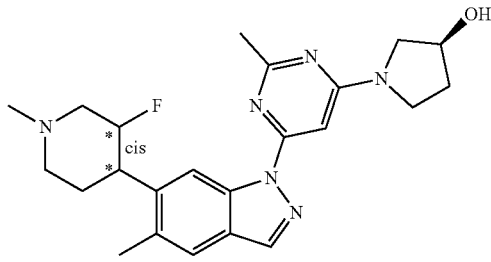 [SMILES: Cc1nc(N2CC[C@H](O)C2)cc(-n2ncc3cc(C)c(C4CCN(C)CC4F)cc32)n1]

To a solution of (S)-1-(6-(6-((cis)-3-fluoropiperidin-4-yl)-5-methyl-1H-indazol-1-yl)-2-methylpyrimidin-4-yl)pyrrolidin-3-ol (diastereoisomer 2) (90 mg, 0.219 mmol, crude) in methanol (10 mL) was added 37% HCHO aqueous (1 mL) and stirred at room temperature for 30 min. Then, NaBH$_3$CN (28 mg, 0.438 mmol) was added and stirred at room temperature for 2 hr. The reaction mixture was poured into sat. NaHCO$_3$ solution (50 mL), extracted with EtOAc (30 mL×3). The combined organic layers were washed with brine (30 mL), dried over anhydrous Na$_2$SO$_4$, filtered, and concentrated to dryness. The residue was purified by Prep-HPLC (method: Sepax C18-H 21.2*100 mm 5 um, phase: H$_2$O (0.1% TFA):ACN=90:10 to 10:90, 15 mL/min, 254/214 nm) to give the title product (S)-1-(6-(6-((cis)-3-fluoro-1-methylpiperidin-4-yl)-5-methyl-1H-indazol-1-yl)-2-methylpyrimidin-4-yl)pyrrolidin-3-ol (diastereoisomer 2) (43 mg, yield 46.3%) as a light yellow solid.

E129 $^1$H NMR (400 MHz, CDCl$_3$): δ 8.90 (s, 1H), 8.06 (s, 1H), 7.52 (s, 1H), 6.71 (s, 1H), 5.00-4.82 (m, 1H), 4.63 (s, 1H), 3.70 (s, 4H), 3.37-3.33 (m, 1H), 3.11-2.93 (m, 2H), 2.62 (s, 3H), 2.47 (s, 3H), 2.42 (s, 3H), 2.24-2.12 (m, 4H), 1.94 (s, 2H), 1.71 (s, 1H).

$^{19}$F NMR (376 MHz, CDCl$_3$): δ −184.08 (s, 1F).

LC-MS [mobile phase: from 90% water (0.1% FA) and 10% CH$_3$CN (0.1% FA) to 5% water (0.1% FA) and 95% CH$_3$CN (0.1% FA) in 10 min], purity: 96.7%; Rt=4.92 min; MS Calcd: 424, MS Found: 425[M+H]$^+$.

Chiral condition: Chiralpak AD-H 5 um 4.6*250 mm, Hexane/IPA=85/15, Flow Rate: 1 mL/min, 214 nm, T=30° C., Rt=12.99 min, 99% ee.

Example 130

1-(6-(6-((cis)-3-Fluoro-1-methylpiperidin-4-yl)-5-methyl-1H-indazol-1-yl)-2-methylpyrimidin-4-yl)pyrrolidine-3,4-diol (Diastereoisomer 1, E130)

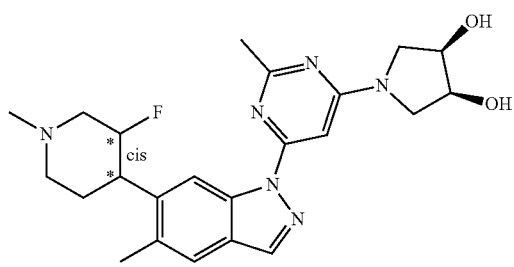 [SMILES: Cc1nc(N2C[C@@H](O)[C@@H](O)C2)cc(-n2ncc3cc(C)c(C4CCN(C)CC4F)cc32)n1]

To a solution of 1-(6-(6-((cis)-3-fluoropiperidin-4-yl)-5-methyl-1H-indazol-1-yl)-2-methyl pyrimidin-4-yl)pyrrolidine-3,4-diol (diastereoisomer 1) (42 mg, 0.098 mmol, crude) in methanol (10 mL) was added 37% HCHO aqueous (1 mL) and stirred at room temperature for 30 min. Then, NaBH$_3$CN (12 mg, 0.196 mmol) was added and stirred at room temperature for 1 hr. The reaction mixture was poured into sat. NaHCO$_3$ solution (20 mL), extracted with EtOAc (30 mL×3). The combined organic layers were washed with brine (30 mL), dried over anhydrous Na$_2$SO$_4$, filtered, and concentrated to dryness. The residue was purified by Prep-HPLC (method: Sepax C18-H 21.2*100 mm 5 um, phase: H$_2$O (0.1% TFA):ACN=90:10 to 10:90, 15 mL/min, 254/214 nm) to give the title product 1-(6-(6-((cis)-3-fluoro-1-(diastereoisomer 1) (9 mg, yield 20.9%) as a white solid.

E130 $^1$H NMR (400 MHz, CDCl$_3$): δ 8.89 (s, 1H), 8.06 (s, 1H), 7.52 (s, 1H), 6.69 (s, 1H), 4.97-4.84 (m, 1H), 4.42 (s, 2H), 3.84 (s, 2H), 3.61 (s, 2H), 3.36 (s, 1H), 3.11-2.93 (m, 2H), 2.61 (s, 3H), 2.48 (s, 3H), 2.42 (s, 3H), 2.21-2.12 (m, 2H), 1.94 (s, 2H).

$^{19}$F NMR (376 MHz, CDCl$_3$): δ −184.09 (s, 1F).

LC-MS [mobile phase: from 90% water (0.1% FA) and 10% CH$_3$CN (0.1% FA) to 5% water (0.1% FA) and 95% CH$_3$CN (0.1% FA) in 10 min], purity: 97.9%; Rt=4.77 min; MS Calcd: 440.5, MS Found: 441.8[M+H]$^+$.

Chiral condition: Chiralpak AD-H 5 um 4.6*250 mm, Hexane:EtOH=75/25, Flow Rate: 1 mL/min, 214 nm, T=30° C., Rt=5.12 min, 99% ee.

Example 131

1-(6-(6-((cis)-3-Fluoro-1-methylpiperidin-4-yl)-5-methyl-1H-indazol-1-yl)-2-methylpyrimidin-4-yl)pyrrolidine-3,4-diol (Diastereoisomer 2, E131)

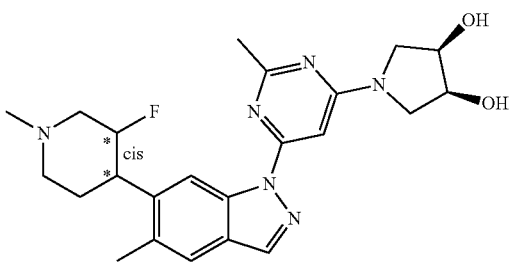 [SMILES: Cc1nc(N2C[C@@H](O)[C@@H](O)C2)cc(-n2ncc3cc(C)c(C4CCN(C)CC4F)cc32)n1]

To a solution of 1-(6-(6-((cis)-3-fluoropiperidin-4-yl)-5-methyl-1H-indazol-1-yl)-2-methyl pyrimidin-4-yl)pyrrolidine-3,4-diol (diastereoisomer 2) (120 mg, 0.28 mmol, crude) in methanol (10 mL) was added 37% HCHO aqueous (1 mL) and stirred at room temperature for 30 min. Then, NaBH$_3$CN (35 mg, 0.56 mmol) was added and stirred at room temperature for 1 hr. The reaction mixture was poured into sat. NaHCO$_3$ solution (50 mL), and extracted with EtOAc (30 mL×3). The combined organic layers were washed with brine (30 mL), dried over anhydrous Na$_2$SO$_4$, filtered, and concentrated to dryness. The residue was purified by Prep-HPLC (method: Waters XBridge 30*150 mm 5 um, phase: H$_2$O (0.1% TFA):ACN=90: 10 to 10:90, 20 mL/min, 254/214 nm) to give the title product 1-(6-(6-((cis)-3-fluoro-1-methylpiperidin-4-yl)-5-methyl-1H-indazol-1-yl)-2-methylpyrimidin-4-yl)pyrrolidine-3,4-diol (diastereoisomer 2) (38 mg, yield 30.8%) as a white solid.

E131 $^1$H NMR (400 MHz, CDCl$_3$): δ 8.89 (s, 1H), 8.06 (s, 1H), 7.52 (s, 1H), 6.69 (s, 1H), 4.98-4.84 (m, 1H), 4.42 (s, 2H), 3.82 (s, 2H), 3.60 (s, 2H), 3.37 (s, 1H), 3.09-2.94 (m, 2H), 2.61 (s, 3H), 2.48 (s, 3H), 2.42 (s, 3H), 2.23-2.10 (m, 2H), 1.94 (s, 2H).

$^{19}$F NMR (376 MHz, CDCl$_3$): δ −184.09 (s, 1F).

LC-MS [mobile phase: from 90% water (0.1% FA) and 10% CH$_3$CN (0.1% FA) to 5% water (0.1% FA) and 95% CH$_3$CN (0.1% FA) in 10 min], purity: 98.8%; Rt=4.72 min; MS Calcd: 440.5, MS Found: 441.7[M+H]$^+$.

Chiral condition: Chiralpak AD-H 5 um 4.6*250 mm, Hexane:EtOH=75/25, Flow Rate: 1 mL/min, 214 nm, T=30° C., Rt=6.32 min, 99% ee.

Example 132

(cis)-2-((1-(6-(6-(3-Fluoro-1-methylpiperidin-4-yl)-5-methyl-1H-indazol-1-yl)-2-methylpyrimidin-4-yl)azetidin-3-yl)oxy)ethanol (Enantiomer 1, D132)

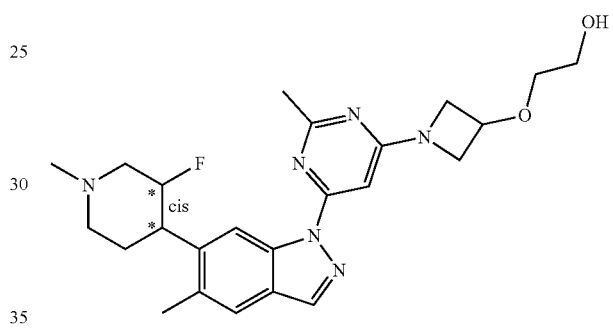

To a solution of (cis)-2-((1-(6-(6-(3-fluoropiperidin-4-yl)-5-methyl-1H-indazol-1-yl)-2-methylpyrimidin-4-yl)azetidin-3-yl)oxy)ethanol hydrochloride (enantiomer 1, 85 mg, 0.18 mmol) in methanol (5 mL) was added HCHO (14%, 1 mL) and stirred for 30 min. NaBH$_3$CN (23 mg, 0.36 mmol) was added slowly and the mixture was stirred for 2 hrs. To the mixture was added sat. NaHCO$_3$ (20 mL). The mixture was extracted with EtOAc (20 mL×3). The combined organic layers were washed with brine (20 mL), dried over Na$_2$SO$_4$ and concentrated. The residue was purified by prep. TLC (CH$_2$Cl$_2$:CH$_3$OH=10:1) to give the crude product (55 mg). The crude was then purified by prep. HPLC (condition: from 80% water (0.1% NH$_4$HCO$_3$) and 20% CH$_3$CN to 20% water (0.1% NH$_4$HCO$_3$) and 80% CH$_3$CN in 12 min) to give the title compound (41 mg, yield 50%) as white solid.

E132 $^1$H NMR (400 MHz, CDCl$_3$): 8.89 (s, 1H), 8.06 (s, 1H), 7.52 (s, 1H), 6.60 (s, 1H), 4.97-4.84 (m, 1H), 4.53-4.50 (m, 1H), 4.36-4.32 (m, 2H), 4.07-4.04 (m, 2H), 3.80-3.78 (m, 2H), 3.59-3.57 (m, 2H), 3.37-3.35 (m, 1H), 3.09-3.05 (m, 1H), 2.96-2.93 (m, 1H), 2.62 (s, 3H), 2.47 (s, 3H), 2.42 (s, 3H), 2.23-2.11 (m, 2H), 1.95-1.91 (m, 2H).

$^{19}$F NMR (376 MHz, CDCl$_3$): δ −184.13 (s, 1F).

LC-MS: [mobile phase: from 95% water (0.1% TFA) and 5% CH$_3$CN to 5% water (0.1% TFA) and 95% CH$_3$CN in 6.5 min], purity is >95%, Rt=3.897 min; MS Calcd.: 454, MS Found: 455 [M+H]$^+$.

Chiral condition: AD-H, Hex/IPA/DEA=70/30/0.2, Flow Rate: 1.0, 230 nm, T=30° C., Rt=5.688 min, 100% ee.

Example 133

(cis)-2-((1-(6-(6-(3-Fluoro-1-methylpiperidin-4-yl)-5-methyl-1H-indazol-1-yl)-2-methylpyrimidin-4-yl)azetidin-3-yl)oxy)ethanol (Enantiomer 2, E133)

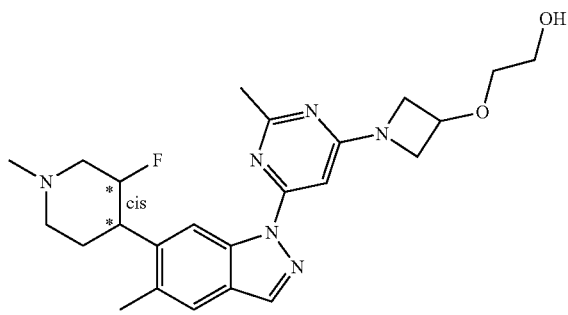 [SMILES: Cc1nc(N2CC(OCCO)C2)cc(-n2ncc3cc(C)c(C4CCN(C)CC4F)cc32)n1]

To a solution of (cis)-2-((1-(6-(6-(3-fluoropiperidin-4-yl)-5-methyl-1H-indazol-1-yl)-2-methylpyrimidin-4-yl)azetidin-3-yl)oxy)ethanol hydrochloride (enantiomer 2, 75 mg, 0.16 mmol) in methanol (5 mL) was added HCHO (14%, 1 mL) and stirred for 30 min. NaBH$_3$CN (20 mg, 0.32 mmol) was added slowly and the mixture was stirred for 2 hrs. To the mixture was added sat. NaHCO$_3$ (20 mL). The mixture was extracted with EtOAc (20 mL×3). The combined organic layers were washed with brine (20 mL), dried over Na$_2$SO$_4$ and concentrated. The residue was purified by prep. TLC (CH$_2$Cl$_2$:CH$_3$OH=10:1) to give the crude product (55 mg). The crude was then purified by prep. HPLC (condition: from 80% water (0.1% NH$_4$HCO$_3$) and 20% CH$_3$CN to 20% water (0.1% NH$_4$HCO$_3$) and 80% CH$_3$CN in 12 min) to give the title compound (47 mg, yield 65%) as white solid.

E133 $^1$H NMR (400 MHz, CDCl$_3$): 8.89 (s, 1H), 8.06 (s, 1H), 7.52 (s, 1H), 6.60 (s, 1H), 4.97-4.85 (m, 1H), 4.52-4.49 (m, 1H), 4.36-4.32 (m, 2H), 4.07-4.04 (m, 2H), 3.80-3.78 (m, 2H), 3.59-3.56 (m, 2H), 3.37-3.34 (m, 1H), 3.09-3.05 (m, 1H), 2.95-2.93 (m, 1H), 2.62 (s, 3H), 2.48 (s, 3H), 2.42 (s, 3H), 2.23-2.12 (m, 2H), 1.95-1.94 (m, 2H).

$^{19}$F NMR (376 MHz, CDCl$_3$): δ −184.12 (s, 1F).

LC-MS: [mobile phase: from 95% water (0.02% NH$_4$HCO$_3$) and 5% CH$_3$CN to 5% water (0.02% NH$_4$HCO$_3$) and 95% CH$_3$CN in 6.5 min], purity is >95%, Rt=3.898 min; MS Calcd.: 454, MS Found: 455 [M+H]$^+$.

Chiral condition: AD H, Hex/IPA/DEA=70/30/0.2, Flow Rate: 1.0, 230 nm, T=30° C., Rt=7.222 min, 100% ee.

Example 134

((R)-4-(6-(6-((cis)-3-fluoro-1-methylpiperidin-4-yl)-5-methyl-1H-indazol-1-yl)-2-methylpyrimidin-4-yl)morpholin-2-yl)methanol (Diastereoisomer 1, E134)

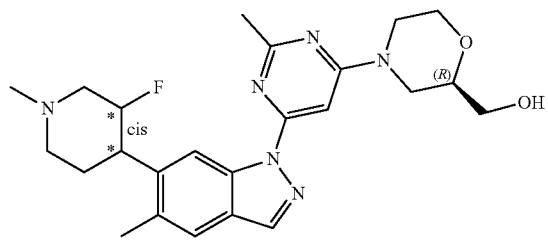

To a solution of ((R)-4-(6-(6-((cis)-3-fluoropiperidin-4-yl)-5-methyl-1H-indazol-1-yl)-2-methyl pyrimidin-4-yl)morpholin-2-yl)methanol (diastereoisomer 1, 100 mg, 0.23 mmol) in MeOH (15 mL) was added aq. HCHO (37%, 1.5 mL). The resulting mixture was a stirred at room temperature for 30 min. NaBH$_3$CN (28 mg, 0.46 mmol) was added and the reaction was stirred at room temperature for 30 min. Sat. NaHCO$_3$ (10 mL) was added and the resulting mixture was extracted with EtOAc (3×20 mL). The combined extracts were washed with water (30 mL), dried over anhydrous Na$_2$SO$_4$ and concentrated under reduced pressure The residue was purified by pre-HPLC (Waters 2767/Qda, Waters XBridge 30*150 mm 5 um, Phase: MeCN/H$_2$O (0.1% TFA): 10%~95%, Flow rate: 20 mL/min, 214 nm/254 nm) to give product (49 mg, yield 47.6%) as a white sold.

E134 $^1$H NMR (400 MHz, CDCl$_3$): δ 8.88 (s, 1H), 8.07 (s, 1H), 7.53 (s, 1H), 6.95 (s, 1H), 5.00~4.83 (m, 1H), 4.30 (t, J=12.0 Hz, 2H), 4.08 (dd, J=11.6, 2.4 Hz, 1H), 3.80~3.67 (m, 4H), 3.38~3.33 (m, 1H), 3.15~3.03 (m, 2H), 2.98~2.92 (m, 2H), 2.62 (s, 3H), 2.48 (s, 3H), 2.42 (s, 3H), 2.24~2.04 (m, 3H), 1.95~1.90 (m, 2H).

$^{19}$F NMR (376 MHz, CDCl$_3$): −184.12 (s, 1F).

LC-MS (mobile phase: from 90% water (0.1% FA) and 10% CH$_3$CN (0.1% FA) to 5% water (0.1% FA) and 95% CH$_3$CN (0.1% FA) in 10 min, purity 99.2%, Rt=5.30 min; MS Calcd.: 454.5, MS Found: 455.7 (M+H)$^+$.

Chiral purity: Rt=6.549 min; ee %=99.82%.

Chiral method: Chiralpak AD-H 5 um 4.6*250 mm, Phase: Hex:EtOH=70/30, F: 1.0 mL/min, W: 214 nm, T: 30° C.

Example 135

((R)-4-(6-(6-((cis)-3-fluoro-1-methylpiperidin-4-yl)-5-methyl-1H-indazol-1-yl)-2-methylpyrimidin-4-yl)morpholin-2-yl)methanol (Diastereoisomer 2, E135)

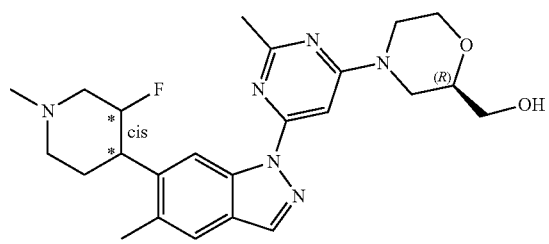

To a solution of ((R)-4-(6-(6-((cis)-3-fluoropiperidin-4-yl)-5-methyl-1H-indazol-1-yl)-2-methyl pyrimidin-4-yl)morpholin-2-yl)methanol (diastereoisomer 2, 100 mg, 0.23 mmol) in MeOH (15 mL) was added aq. HCHO (37%, 1.5 mL). The resulting mixture was a stirred at room temperature for 30 min. NaBH$_3$CN (29 mg, 0.45 mmol) was added and the reaction was stirred at room temperature for 30 min. Sat. NaHCO$_3$ (20 mL) was added and the resulting mixture was extracted with EtOAc (3×20 mL). The combined extracts were washed with brine (2×15 mL), dried over anhydrous Na$_2$SO$_4$ and concentrated under reduced pressure The residue was purified by pre-HPLC (Waters 2767/Qda, Waters XBridge 30*150 mm 5 um, Phase: MeCN/H2O (0.1% TFA): 10%~95%, Flow rate: 20 mL/min, 214 nm/254 nm) to give product (49 mg, yield 47.6%) as a white sold.

E135 $^1$H NMR (400 MHz, CDCl$_3$): δ 8.88 (s, 1H), 8.07 (s, 1H), 7.53 (s, 1H), 6.95 (s, 1H), 5.00~4.81 (m, 1H), 4.30

(t, J=12.0 Hz, 2H), 4.08 (dd, J=11.6, 2.4 Hz, 1H), 3.80~3.65 (m, 4H), 3.38~3.35 (m, 1H), 3.14~3.03 (m, 2H), 2.98~2.91 (m, 2H), 2.62 (s, 3H), 2.48 (s, 3H), 2.43 (s, 3H), 2.24~2.04 (m, 3H), 1.95~1.90 (m, 2H).

$^{19}$F NMR (376 MHz, CDCl$_3$): −184.13 (s, 1F).

LC-MS (mobile phase: from 90% water (0.1% FA) and 10% CH$_3$CN (0.1% FA) to 5% water (0.1% FA) and 95% CH$_3$CN (0.1% FA) in 10 min, purity 99.2%, Rt=4.17 min; MS Calcd.: 454.5, MS Found: 455.6 (M+H)$^+$.

Chiral purity: Rt=5.569 min; ee %=99.35%.

Chiral method: Chiralpak AD-H 5 um 4.6*250 mm, Phase: Hex:EtOH=70/30, F: 1.0 mL/min, W: 214 nm, T: 30° C.

Example 136

((S)-4-(6-(6-((cis)-3-fluoro-1-methylpiperidin-4-yl)-5-methyl-1H-indazol-1-yl)-2-methylpyrimidin-4-yl)morpholin-2-yl)methanol (Diastereoisomer 1, E136)

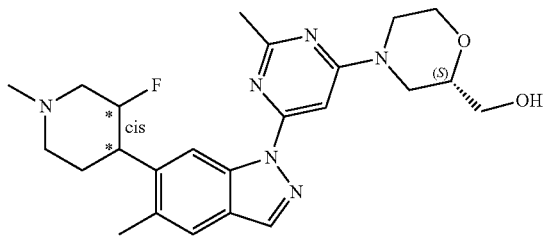

To a solution of ((S)-4-(6-(6-((cis)-3-fluoropiperidin-4-yl)-5-methyl-1H-indazol-1-yl)-2-methyl pyrimidin-4-yl)morpholin-2-yl)methanol (diastereoisomer 1, 130 mg, 0.303 mmol) in MeOH (15 mL) was added aq. HCHO (37%, 1.5 mL). The resulting mixture was a stirred at room temperature for 30 min. NaBH$_3$CN (38 mg, 0.60 mmol) was added and the reaction was stirred at room temperature for 30 min. Sat. NaHCO$_3$ (20 mL) was added and the resulting mixture was extracted with EtOAc (3×20 mL). The combined extracts were washed with brine (2×20 mL), dried over anhydrous Na$_2$SO$_4$ and concentrated under reduced pressure The residue was purified by pre-HPLC (Waters 2767, Sepax C18-H 21.2*100 mm 5 um, Phase: MeCN/H2O (0.1% TFA): 10%~95%, Flow rate: 15 mL/min, 214 nm/254 nm) to give product (58 mg, yield 43.2%) as a white sold.

E136 $^1$H NMR (400 MHz, CDCl$_3$): δ 8.88 (s, 1H), 8.07 (s, 1H), 7.53 (s, 1H), 6.95 (s, 1H), 5.00~4.81 (m, 1H), 4.30 (t, J=12.0 Hz, 2H), 4.08 (dd, J=11.6, 2.4 Hz, 1H), 3.80~3.67 (m, 4H), 3.38~3.35 (m, 1H), 3.14~3.03 (m, 2H), 2.98~2.92 (m, 2H), 2.62 (s, 3H), 2.48 (s, 3H), 2.42 (s, 3H), 2.24~2.06 (m, 3H), 1.95~1.91 (m, 2H).

$^{19}$F NMR (376 MHz, CDCl$_3$): −184.12 (s, 1F).

LC-MS (mobile phase: from 90% water (0.1% FA) and 10% CH$_3$CN (0.1% FA) to 5% water (0.1% FA) and 95% CH$_3$CN (0.1% FA) in 10 min, purity 99.2%, Rt=5.38 min; MS Calcd.: 454.5, MS Found: 455.7 (M+H)$^+$.

Chiral purity: Rt=6.875 min; ee %=99.97%.

Chiral method: Chiralpak AD-H 5 um 4.6*250 mm, Phase: Hex:EtOH=70/30, F: 1.0 mL/min, W: 214 nm, T: 30° C.

Example 137

((S)-4-(6-(6-((cis)-3-fluoro-1-methylpiperidin-4-yl)-5-methyl-1H-indazol-1-yl)-2-methylpyrimidin-4-yl)morpholin-2-yl)methanol (Diastereoisomer 2, D137)

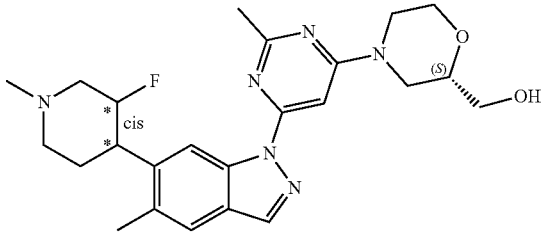

To a solution of ((S)-4-(6-(6-((cis)-3-fluoropiperidin-4-yl)-5-methyl-1H-indazol-1-yl)-2-methyl pyrimidin-4-yl)morpholin-2-yl)methanol (diastereoisomer 2, 115 mg, 0.26 mmol) in MeOH (15 mL) was added aq. HCHO (37%, 1.5 mL). The resulting mixture was stirred at room temperature for 30 min. NaBH$_3$CN (33 mg, 0.52 mmol) was added and the reaction was stirred at room temperature for 30 min. Sat. NaHCO$_3$ (10 mL) was added and the resulting mixture was extracted with EtOAc (3×20 mL). The combined extracts were washed with brine (2×30 mL), dried over anhydrous Na$_2$SO$_4$ and concentrated under reduced pressure The residue was purified by pre-HPLC (Waters 2767/Qda, Waters XBridge 30*150 mm 5 um, Phase: MeCN/H2O (0.1% TFA): 10%~95%, Flow rate: 20 mL/min, 214 nm/254 nm) to give product (36 mg, yield 30.3%) as a white sold.

E137 $^1$H NMR (400 MHz, CDCl$_3$): δ 8.88 (s, 1H), 8.07 (s, 1H), 7.53 (s, 1H), 6.95 (s, 1H), 5.00~4.82 (m, 1H), 4.30 (t, J=12.0 Hz, 2H), 4.08 (dd, J=11.6, 2.4 Hz, 1H), 3.80~3.67 (m, 4H), 3.37~3.33 (m, 1H), 3.15~3.03 (m, 2H), 2.98~2.92 (m, 2H), 2.62 (s, 3H), 2.48 (s, 3H), 2.42 (s, 3H), 2.24~2.04 (m, 3H), 1.95~1.90 (m, 2H).

$^{19}$F NMR (376 MHz, CDCl$_3$): −184.12 (s, 1F).

LC-MS (mobile phase: from 90% water (0.1% FA) and 10% CH$_3$CN (0.1% FA) to 5% water (0.1% FA) and 95% CH$_3$CN (0.1% FA) in 10 min, purity 99.2%, Rt=4.15 min; MS Calcd.: 454.5, MS Found: 455.6 (M+H)$^+$.

Chiral purity: Rt=7.953 min; ee %=99.94%.

Chiral method: Chiralpak AD-H 5 um 4.6*250 mm, Phase: Hex:EtOH=70/30, F: 1.0 mL/min, W: 214 nm, T: 30° C.

Example 138

((R)-4-(6-(6-((cis)-3-fluoro-1-methylpiperidin-4-yl)-5-methyl-1H-indazol-1-yl)-2-methoxypyrimidin-4-yl)morpholin-2-yl)methanol (Diastereoisomer 1, D138)

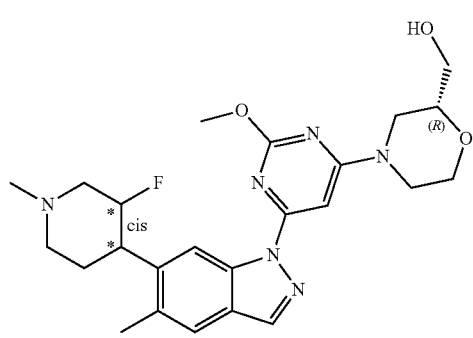

CH$_2$O (0.2 mL, 2.5 mmol) was added to the solution of ((R)-4-(6-(6-((cis)-3-fluoropiperidin-4-yl)-5-methyl-1H-indazol-1-yl)-2-methoxypyrimidin-4-yl)morpholin-2-yl)methanol (diastereoisomer 1, 135 mg, 0.30 mmol) in MeOH (10 mL) at RT and the resulting solution was stirred at room temperature overnight. NaBH$_3$CN (63 mg, 1.0 mmol) was added and the reaction was stirred at room temperature for 10 min. The reaction quenched with sat. NaHCO$_3$ (20 mL) and the mixture was extracted with EtOAc (3×20 mL). The obtained organic solution was dried over anhydrous Na$_2$SO$_4$ and concentrated under reduced pressure. The residue was purified by prep-HPLC to give pure solution. The solution was concentrated to remove acetonitrile and the obtained aq. solution was adjusted to pH-9 with the addition of K$_2$CO$_3$. The formed solid was filtered and the obtained solid was dried to give the desired product (95 mg, 67% yield) as a white solid.

D138 $^1$H NMR (400 MHz, CDCl$_3$): δ 8.84 (s, 1H), 8.08 (s, 1H), 7.54 (s, 1H), 6.84 (s, 1H), 4.95~4.76 (m, 1H), 4.32~4.24 (m, 2H), 4.12 (s, 3H), 4.08~4.03 (m, 1H), 3.80~3.65 (m, 2H), 3.35~3.30 (m, 1H), 3.18~2.89 (m, 4H), 2.48 (s, 3H), 2.40 (s, 3H), 2.22~1.79 (m, 5H).

$^{19}$F NMR (400 MHz, CDCl$_3$): δ -184.2 (s, 1F).

LC-MS (mobile phase: from 80% water (0.1% FA) and 20% CH$_3$CN (0.1% FA) to 5% water (0.1% FA) and 95% CH$_3$CN (0.1% FA) in 10 min, purity 98.7%, Rt=4.42 min; MS Calcd.: 470.2, MS Found: 471.7 (M+H)$^+$.

Chiral purity: Rt=7.645 min; ee %=99.7%.

Chiral method: Chiralpak AD-H 5 um 4.6*250 mm, Phase: Hex:EtOH=75/25, F: 1.0 mL/min, W: 214 nm, T: 30° C.

Example 139

((R)-4-(6-(6-((cis)-3-fluoro-1-methylpiperidin-4-yl)-5-methyl-1H-indazol-1-yl)-2-methoxypyrimidin-4-yl)morpholin-2-yl)methanol (Diastereoisomer 2, D139)

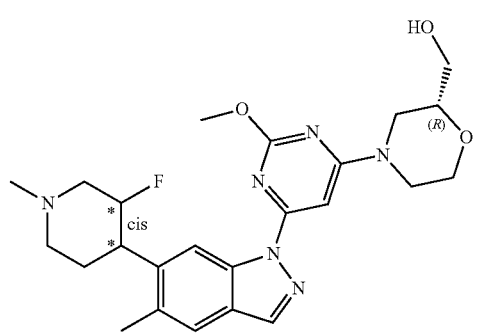

CH$_2$O (0.2 mL, 2.5 mmol) was added to the solution of ((R)-4-(6-(6-((cis)-3-fluoropiperidin-4-yl)-5-methyl-1H-indazol-1-yl)-2-methoxypyrimidin-4-yl)morpholin-2-yl)methanol (diastereoisomer 2, 140 mg, 0.30 mmol) in MeOH (10 mL) at RT and the resulting solution was stirred at room temperature overnight. NaBH$_3$CN (63 mg, 1.0 mmol) was added and the reaction was stirred at room temperature for 10 min. The reaction quenched with sat. NaHCO$_3$ (20 mL) and the mixture was extracted with EtOAc (3×20 mL). The obtained organic solution was dried over anhydrous Na$_2$SO$_4$ and concentrated under reduced pressure. The residue was purified by prep-HPLC to give pure solution. The solution was concentrated to remove acetonitrile and the obtained aq. solution was adjusted to pH-9 with the addition of K$_2$CO$_3$. The formed solid was filtered and the obtained solid was dried to give the desired product (73 mg, 50% yield) as a white solid.

D139 $^1$H NMR (400 MHz, CDCl$_3$): δ 8.84 (s, 1H), 8.08 (s, 1H), 7.54 (s, 1H), 6.84 (s, 1H), 4.95~4.76 (m, 1H), 4.32~4.24 (m, 2H), 4.12 (s, 3H), 4.08~4.03 (m, 1H), 3.80~3.65 (m, 2H), 3.35~3.30 (m, 1H), 3.18~2.89 (m, 4H), 2.48 (s, 3H), 2.40 (s, 3H), 2.22~1.79 (m, 5H).

$^{19}$F NMR (400 MHz, CDCl$_3$): δ -184.2 (s, 1F).

LC-MS (mobile phase: from 80% water (0.1% FA) and 20% CH$_3$CN (0.1% FA) to 5% water (0.1% FA) and 95% CH$_3$CN (0.1% FA) in 10 min, purity 95.8%, Rt=4.44 min; MS Calcd.: 470.2, MS Found: 471.7 (M+H)$^+$.

Chiral purity: Rt=11.123 min; ee %=98.9%.

Chiral method: Chiralpak AD-H 5 um 4.6*250 mm, Phase: Hex:EtOH=75/25, F: 1.0 mL/min, W: 214 nm, T: 30° C.

Example 140

((S)-4-(6-(6-(((cis)-3-fluoro-1-methylpiperidin-4-yl)-5-methyl-1H-indazol-1-yl)-2-methoxypyrimidin-4-yl)morpholin-2-yl)methanol (Diastereoisomer 1, D140)

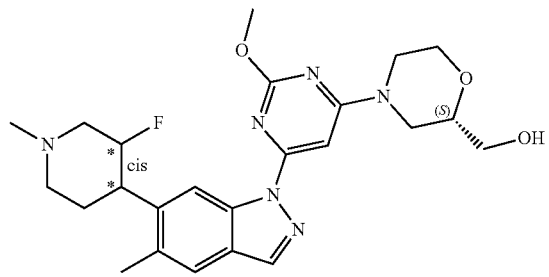

CH$_2$O (1.0 mL) was added to the solution of ((S)-4-(6-(6-((cis)-3-fluoropiperidin-4-yl)-5-methyl-1H-indazol-1-yl)-2-methoxypyrimidin-4-yl)morpholin-2-yl)methanol (diastereoisomer 1, 80 mg, 0.175 mmol) in MeOH (8 mL) at RT and the resulting solution was stirred at room temperature overnight. NaBH$_3$CN (30 mg, 0.35 mmol) was added and the reaction was stirred at room temperature for 2 hours. The reaction quenched with sat. NaHCO$_3$ (100 mL) and the mixture was extracted with EtOAc (2×70 mL). The obtained organic solution was dried over anhydrous Na$_2$SO$_4$ and concentrated under reduced pressure. The residue was purified by prep-HPLC to give solution. The solution was concentrated to remove acetonitrile and the obtained aq. solution was adjusted to pH=9-10 with the addition of Na$_2$CO$_3$. The formed solid was filtered and the obtained solid was dried to give the desired product (40 mg, 48% yield) as a white solid.

D140 $^1$H NMR (400 MHz, CDCl$_3$): δ 8.84 (s, 1H), 8.08 (s, 1H), 7.54 (s, 1H), 6.84 (s, 1H), 4.95~4.76 (m, 1H), 4.32~4.24 (m, 2H), 4.12 (s, 3H), 4.08~4.03 (m, 1H), 3.80~3.65 (m, 2H), 3.35~3.30 (m, 1H), 3.18~2.89 (m, 4H), 2.48 (s, 3H), 239 (s, 3H), 2.22~1.80 (m, 5H).

$^{19}$F NMR (400 MHz, CDCl$_3$): δ −184.242 (s, 1F).

LC-MS (mobile phase: from 80% water (0.1% FA) and 20% CH$_3$CN (0.1% FA) to 5% water (0.1% FA) and 95% CH$_3$CN (0.1% FA) in 10 min, purity 97%, Rt=4.46 min; MS Calcd.: 470.2, MS Found: 471.7 (M+H)$^+$.

Chiral purity: Rt=6.960 min; ee %=99.23%.

Chiral method: Chiralpak AD-H 5 um 4.6*250 mm, Phase: Hex:EtOH=75/35, F: 1.0 mL/min, W: 214 nm, T: 30° C.

Example 141

((S)-4-(6-(6-(((cis)-3-fluoro-1-methylpiperidin-4-yl)-5-methyl-1H-indazol-1-yl)-2-methoxypyrimidin-4-yl)morpholin-2-yl)methanol (Diastereoisomer 2, D141)

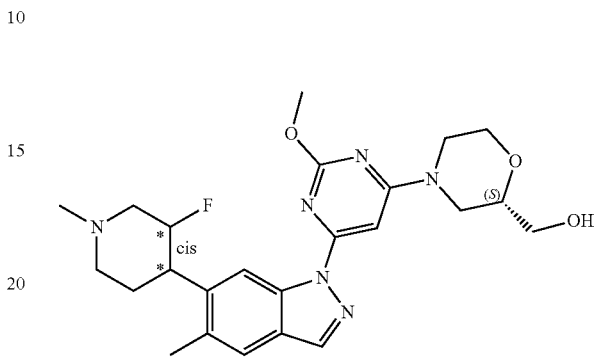

CH$_2$O (1.0 mL) was added to the solution of ((S)-4-(6-(6-(3-fluoropiperidin-4-yl)-5-methyl-1H-indazol-1-yl)-2-methoxypyrimidin-4-yl)morpholin-2-yl)methanol (diastereoisomer 2, 130 mg, 0.285 mmol) in MeOH (10 mL) at RT and the resulting solution was stirred at room temperature overnight. NaBH$_3$CN (36 mg, 0.57 mmol) was added and the reaction was stirred at room temperature for 2 hours. The reaction quenched with sat. NaHCO$_3$ (100 mL) and the mixture was extracted with EtOAc (2×80 mL). The obtained organic solution was dried over anhydrous Na$_2$SO$_4$ and concentrated under reduced pressure. The residue was purified by prep-HPLC to give pure solution. The solution was concentrated to remove acetonitrile and the obtained aq. solution was adjusted to pH=9-10 with the addition of Na$_2$CO$_3$. The formed solid was filtered and the obtained solid was dried to give the desired product (95 mg, 71% yield) as a white solid.

D141 $^1$H NMR (400 MHz, CDCl$_3$): δ 8.84 (s, 1H), 8.08 (s, 1H), 7.54 (s, 1H), 6.84 (s, 1H), 4.95~4.76 (m, 1H), 4.32~4.24 (m, 2H), 4.12 (s, 3H), 4.08~4.03 (m, 1H), 3.80~3.65 (m, 2H), 3.35~3.30 (m, 1H), 3.18~2.89 (m, 4H), 2.48 (s, 3H), 239 (s, 3H), 2.22~1.80 (m, 5H).

$^{19}$F NMR (400 MHz, CDCl$_3$): δ −184.246 (s, 1F).

LC-MS (mobile phase: from 80% water (0.1% FA) and 20% CH$_3$CN (0.1% FA) to 5% water (0.1% FA) and 95% CH$_3$CN (0.1% FA) in 10 min, purity 96.8%, Rt=4.42 min; MS Calcd.: 470.2, MS Found: 471.7 (M+H)$^+$.

Chiral purity: Rt=9.335 min; ee %=99.6%.

Chiral method: Chiralpak AD-H 5 um 4.6*250 mm, Phase: Hex:EtOH=75/35, F: 1.0 mL/min, W: 214 nm, T: 30° C.

Example 142

(cis)-1-(6-(6-(3-Fluoropiperidin-4-yl)-5-methyl-1H-indazol-1-yl)-2-methylpyrimidin-4-yl)azetidin-3-ol hydrochloride (Enantiomer 1, E142)

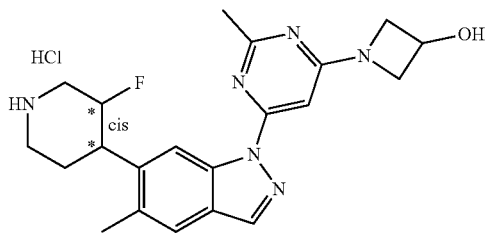 [SMILES: Cc1nc(N2CC(O)C2)cc(-n2ncc3cc(C)c(C4CCNCC4F)cc32)n1 ; Cl]

To a solution of (cis)-tert-butyl 3-fluoro-4-(5-methyl-1-(2-methyl-6-(3-((tetrahydro-2H-pyran-2-yl)oxy)azetidin-1-yl)pyrimidin-4-yl)-1H-indazol-6-yl)piperidine-1-carboxylate (enantiomer 1) (25 mg, 0.043 mmol) in methanol (2 mL) was added HCl/methanol (8 mol/L, 2 mL) at rt. The resulting mixture was stirred for 2 hrs. The reaction mixture was concentrated to give the title compound (18 mg, yield 97%) as a yellow solid.

E142 $^1$H NMR (400 MHz, CD$_3$OD): δ 8.75 (s, 1H), 8.36 (s, 1H), 7.70 (s, 1H), 6.87 (s, 1H), 5.33-5.20 (m, 1H), 4.92-4.85 (m, 2H), 4.66-4.62 (m, 2H), 4.22-4.20 (m, 2H), 3.84-3.82 (m, 1H), 3.63-3.54 (m, 2H), 3.29-3.25 (m, 1H), 2.86 (s, 3H), 2.53 (s, 3H), 2.30-2.17 (m, 2H).

$^{19}$F NMR (376 MHz, CD$_3$OD): δ −188.03 (s, 1F).

LCMS [mobile phase: from 95% water (0.1% TFA) and 5% CH$_3$CN to 5% water (0.1% TFA) and 95% CH$_3$CN in 6.5 min], purity >95%, Rt=2.883 min; MS Calcd: 396; MS Found: 397[M+H]$^+$.

Example 143

(cis)-1-(6-(6-(3-Fluoropiperidin-4-yl)-5-methyl-1H-indazol-1-yl)-2-methylpyrimidin-4-yl)azetidin-3-ol hydrochloride (Enantiomer 2, E143)

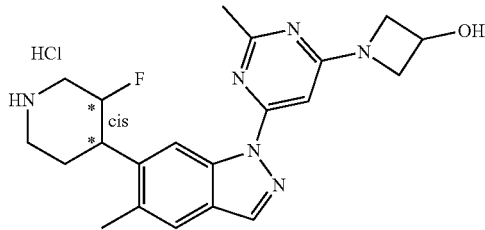 [SMILES: Cc1nc(N2CC(O)C2)cc(-n2ncc3cc(C)c(C4CCNCC4F)cc32)n1 ; Cl]

To a solution of (cis)-tert-butyl 3-fluoro-4-(5-methyl-1-(2-methyl-6-(3-((tetrahydro-2H-pyran-2-yl) oxy)azetidin-1-yl)pyrimidin-4-yl)-1H-indazol-6-yl)piperidine-1-carboxylate (enantiomer 2) (25 mg, 0.04 mmol) in methanol (2 mL) was added HCl/methanol (8 mol/L, 2 mL) at rt. The resulting mixture was stirred for 2 hrs. The reaction mixture was concentrated to give the title compound (15 mg, yield >100%) as a yellow solid.

E143 $^1$H NMR (400 MHz, CD$_3$OD): δ 8.76 (s, 1H), 8.36 (s, 1H), 7.70 (s, 1H), 6.86 (s, 1H), 5.33-5.22 (m, 1H), 4.94-4.91 (m, 2H), 4.66-4.62 (m, 2H), 4.21-4.18 (m, 2H), 3.84-3.81 (m, 1H), 3.63-3.53 (m, 2H), 3.31-3.27 (m, 1H), 2.87 (s, 3H), 2.53 (s, 3H), 2.30-2.20 (m, 2H).

$^{19}$F NMR (376 MHz, CD$_3$OD): δ −188.07 (s, 1F).

LC-MS [mobile phase: from 95% water (0.1% TFA) and 5% CH$_3$CN to 5% water (0.1% TFA) and 95% CH$_3$CN in 6.5 min], purity >95%, Rt=2.876 min; MS Calcd.: 396, MS Found: 397 [M+H]$^+$.

Example 144

1-(6-(Azetidin-1-yl)-2-methylpyrimidin-4-yl)-6-((cis)-3-fluoropiperidin-4-yl)-5-methyl-1H-indazole (Enantiomer 1, E144)

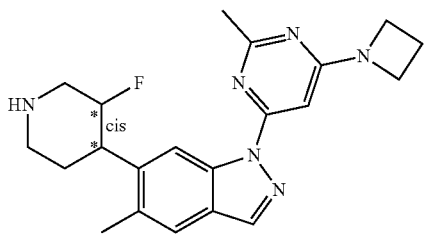 [SMILES: Cc1nc(N2CCC2)cc(-n2ncc3cc(C)c(C4CCNCC4F)cc32)n1]

To a solution of 4-(1-(6-(azetidin-1-yl)-2-methylpyrimidin-4-yl)-5-methyl-1H-indazol-6-yl)-3-fluoropiperidine-1-carboxylate (enantiomer 1, 60 mg, 0.12 mmol), in DCM (3 mL) was added TFA (0.5 mL) at 0° C. The reaction was warmed to room temperature and stirred at room temperature for 3 h. The solvent and TFA was removed under vacuum and 0.5 mL NH$_3$.H$_2$O was added. White solid was participated from the solution and collected via filtration. The solid was washed with H$_2$O and Et$_2$O to give product (22.2 mg, yield 68%) as a white solid.

E144 $^1$H NMR (400 MHz, DMSO-d$_6$): δ 8.78 (s, 1H), 8.25 (s, 1H), 7.57 (s, 1H), 6.45 (s, 1H), 4.72-4.53 (m, 1H), 4.04-4.00 (t, J=7.6 Hz, 4H), 3.16-3.06 (m, 1H), 2.89-2.86 (d, J=12.0 Hz, 1H), 2.59-2.53 (m, 2H), 2.45 (s, 3H), 2.36 (s, 3H), 2.33-2.27 (m, 2H), 1.80-1.77 (d, J=12 Hz, 1H), 1.55-1.47 (m, 1H).

$^{19}$F NMR (400 MHz, DMSO): δ −180.3 (s, 1F).

LC-MS (mobile phase: from 90% water (0.1% FA) and 10% CH$_3$CN (0.1% FA) to 5% water (0.1% FA) and 95% CH$_3$CN (0.1% FA) in 10 min, purity 99%, Rt=5.09 min; MS Calcd.: 380.21, MS Found: 381.2 (M+H)$^+$.

Chiral purity: Rt=6.01 min; ee %=99.4%.

Example 145

1-(6-(Azetidin-1-yl)-2-methylpyrimidin-4-yl)-6-((cis)-3-fluoropiperidin-4-yl)-5-methyl-1H-indazole (Enantiomer 2, E145)

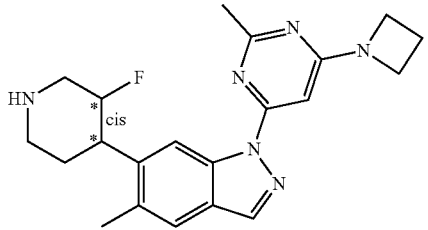 [SMILES: Cc1nc(N2CCC2)cc(-n2ncc3cc(C)c(C4CCNCC4F)cc32)n1]

To a solution of 4-(1-(6-(azetidin-1-yl)-2-methylpyrimidin-4-yl)-5-methyl-1H-indazol-6-yl)-3-fluoropiperidine-1-carboxylate (enantiomer 2, 38 mg, 0.08 mmol), in DCM (3 mL) was added TFA (0.5 mL) at 0° C. The reaction was warmed to room temperature and stirred at room temperature for 3 h. The solvent and TFA was removed under vacuum and 0.5 mL NH$_3$.H$_2$O was added. White solid was participated from the solution and collected via filtration. The solid was washed with H$_2$O and Et$_2$O to give product (21 mg, yield 69.8%) as a white solid.

E145 $^1$H NMR (400 MHz, DMSO) δ 8.85 (s, 1H), 8.32 (s, 1H), 7.64 (s, 1H), 6.53 (d, J=14.4 Hz, 1H), 4.69 (m, 1H), 4.09 (t, J=7.4 Hz, 4H), 3.16 (dd, J=18.1, 8.8 Hz, 1H), 2.94 (d, J=11.8 Hz, 1H), 2.69-2.55 (m, 2H), 2.52 (s, 3H), 2.43 (s, 3H), 2.41-2.27 (m, 2H), 1.85 (d, J=12.8 Hz, 1H), 1.57 (dd, J=21.9, 11.9 Hz, 1H).

$^{19}$F NMR (400 MHz, DMSO): δ −180.2 (s, 1F).

LC-MS (mobile phase: from 90% water (0.1% FA) and 10% CH$_3$CN (0.1% FA) to 90% water (0.1% FA) and 10% CH$_3$CN (0.1% FA) in 10 min, purity 100%, Rt=5.06 min; MS Calcd.: 380.21, MS Found: 381.3 (M+H)$^+$.

Chiral purity: Rt=12.93 min; ee %=99.4%.

Example 146

(cis)-1-(6-(6-(1-Ethyl-3-fluoropiperidin-4-yl)-5-methyl-1H-indazol-1-yl)-2-methylpyrimidin-4-yl)azetidin-3-ol (Enantiomer 1, E146)

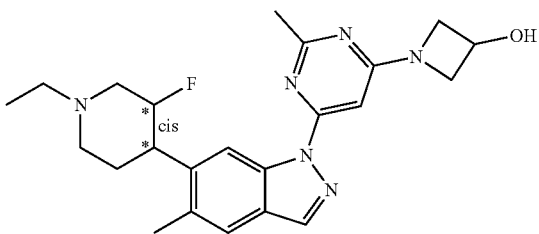 [SMILES: CCN1CCC(c2cc3c(cnn3-c3cc(N4CC(O)C4)nc(C)n3)cc2C)C(F)C1]

To a solution of (cis)-1-(6-(6-(3-fluoropiperidin-4-yl)-5-methyl-1H-indazol-1-yl)-2-methylpyrimidin-4-yl)azetidin-3-ol hydrochloride (enantiomer 1, 147 mg, 0.340 mmol) in methanol (4 mL) was added CH$_2$O (37%, 1 mL) and NaBH$_3$CN (108 mg, 1.71 mmol) at rt. The resulting mixture was stirred for 2 hrs. The reaction mixture was poured into sat. NaHCO$_3$ (20 mL) and stirred for 20 min. The mixture was extracted with EtOAc (20 mL×3). The combined organic layers were washed with brine (20 mL), dried over Na$_2$SO$_4$ and concentrated. The crude was purified by prep. TLC (DCM/MeOH=10/1) to give the title compound (27 mg, yield 19%) as a white solid.

E146 $^1$H NMR (400 MHz, CDCl$_3$): δ 8.91 (s, 1H), 8.06 (s, 1H), 7.52 (s, 1H), 6.58 (s, 1H), 5.04-4.79 (m, 2H), 4.43-4.37 (m, 2H), 4.03-3.98 (m, 2H), 3.50-3.42 (m, 1H), 3.17-2.97 (m, 3H), 2.66-2.56 (m, 5H), 2.48 (s, 3H), 2.26-2.10 (m, 2H), 2.00-1.89 (m, 2H), 1.18 (t, J=7.2 Hz, 3H). $^{19}$F NMR (376 MHz, CDCl$_3$): δ −183.72 (s, 1F).

LC-MS [mobile phase: from 90% water (0.1% TFA) and 10% CH$_3$CN to 5% water (0.1% TFA) and 95% CH$_3$CN in 6.5 min], purity>95%, Rt=2.737 min; MS Calcd.: 424, MS Found: 425 [M+H]$^+$.

Example 147

(cis)-1-(6-(6-(1-Ethyl-3-fluoropiperidin-4-yl)-5-methyl-1H-indazol-1-yl)-2-methylpyrimidin-4-yl)azetidin-3-ol (Enantiomer 2, E147)

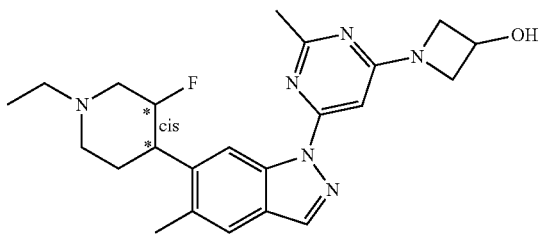 [SMILES: CCN1CCC(c2cc3c(cnn3-c3cc(N4CC(O)C4)nc(C)n3)cc2C)C(F)C1]

To a solution of (cis)-1-(6-(6-(3-fluoropiperidin-4-yl)-5-methyl-1H-indazol-1-yl)-2-methylpyrimidin-4-yl)azetidin-3-ol hydrochloride (enantiomer 2, 147 mg, 0.340 mmol) in methanol (4 mL) was added CH$_2$O (37%, 1 mL) and NaBH$_3$CN (108 mg, 1.71 mmol) at rt. The resulting mixture was stirred for 2 hrs. The reaction mixture was poured into sat. NaHCO$_3$ (20 mL) and stirred for 20 min. The mixture was extracted with EtOAc (20 mL×3). The combined organic layers were washed with brine (20 mL), dried over Na$_2$SO$_4$ and concentrated. The crude was purified by prep. TLC (DCM/MeOH=10/1) to give the title compound (28 mg, yield 19%) as a white solid.

E147 $^1$H NMR (400 MHz, CDCl$_3$): δ 8.91 (s, 1H), 8.06 (s, 1H), 7.52 (s, 1H), 6.58 (s, 1H), 5.02-4.79 (m, 2H), 4.43-4.37 (m, 2H), 4.03-3.98 (m, 2H), 3.50-3.42 (m, 1H), 3.16-3.00 (m, 3H), 2.66-2.56 (m, 5H), 2.48 (s, 3H), 2.23-2.10 (m, 2H), 2.00-1.89 (m, 2H), 1.17 (t, J=7.2 Hz, 3H). $^{19}$F NMR (376 MHz, CDCl$_3$): δ −183.69 (s, 1F).

LC-MS [mobile phase: from 95% water (0.02% NH$_4$OAc) and 5% CH$_3$CN to 5% water (0.02% NH$_4$OAc) and 95% CH$_3$CN in 6.5 min], purity>95%, Rt=4.282 min; MS Calcd.: 424, MS Found: 425 [M+H]$^+$.

Example 148

(cis)-1-(6-(6-(3-Fluoro-1-isopropylpiperidin-4-yl)-5-methyl-1H-indazol-1-yl)-2-methylpyrimidin-4-yl)azetidin-3-ol (Enantiomer 1, E148)

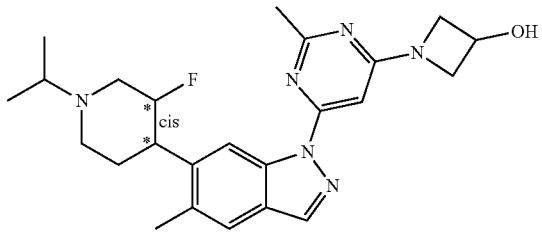 [SMILES: Cc1nc(N2CC(O)C2)cc(-n2ncc3cc(C)c(C4CCN(C(C)C)CC4F)cc32)n1]

To a solution of (cis)-1-(6-(6-(3-fluoropiperidin-4-yl)-5-methyl-1H-indazol-1-yl)-2-methylpyrimidin-4-yl)azetidin-3-ol hydrochloride (enantiomer 1, 108 mg, 0.250 mmol) in CH$_3$CN (1 mL) and DMF (0.2 mL) was added 2-iodopropane (148 mg, 0.900 mmol) and K$_2$CO$_3$ (160 mg, 1.20 mmol). The mixture was stirred at 80° C. overnight. The mixture was partitioned with H$_2$O (20 mL) and DCM (20 mL×2). The combined organic layers were washed by brine (50 mL), dried over Na$_2$SO$_4$ and concentrated. The mixture was purified by prep-TLC (DCM:CH$_3$OH=12:1) to give the crude compound. The crude compound was triturated with DMF (2 mL) to give the title compound (18 mg, yield 14%).

E148 $^1$H NMR (400 MHz, CDCl$_3$): δ 8.91 (s, 1H), 8.06 (s, 1H), 7.52 (s, 1H), 6.59 (s, 1H), 4.96-4.82 (m, 2H), 4.42-4.39 (m, 2H), 4.02-3.99 (m, 2H), 3.40-3.34 (m, 1H), 3.11-3.04 (m, 1H), 2.95-2.88 (m, 2H), 2.62 (s, 4H), 2.49 (s, 3H), 2.40-2.31 (m, 2H), 1.98-1.84 (m, 2H), 1.13-1.11 (m, 6H). $^{19}$F NMR (376 MHz, CDCl$_3$): δ −182.85 (s, 1F).

LC-MS [mobile phase: from 95% water (0.1% TFA) and 20% CH$_3$CN to 20% water (0.1% TFA) and 95% CH$_3$CN in 6.5 min], purity is 98.38%, Rt=2.348 min; MS Calcd.: 438, MS Found: 439 [M+H]$^+$.

Chiral condition: Chiralpak AD-H 5 um 4.6*250 mm, Hex/EtOH=70/30, Flow Rate: 1.0 ml/min, 230 nm, T=30° C. Rt=4.617 min, 100% ee.

Example 149

(cis)-1-(6-(6-(3-Fluoro-1-isopropylpiperidin-4-yl)-5-methyl-1H-indazol-1-yl)-2-methylpyrimidin-4-yl) azetidin-3-ol (Enantiomer 2, E149)

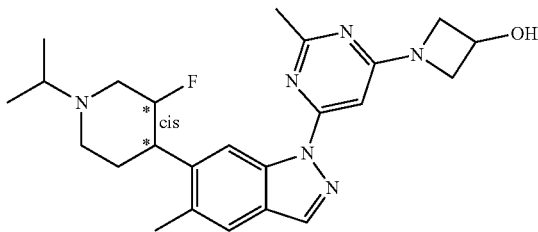

To a solution of (cis)-1-(6-(6-(3-fluoropiperidin-4-yl)-5-methyl-1H-indazol-1-yl)-2-methylpyrimidin-4-yl)azetidin-3-ol hydrochloride (enantiomer 2, 108 mg, 0.250 mmol) in CH$_3$CN (1 mL) and DMF (0.2 mL) was added 2-iodopropane (128 mg, 0.75 mmol) and K$_2$CO$_3$ (138 mg, 1.00 mmol). The mixture was stirred at 80° C. overnight. The mixture was washed with Na$_2$CO$_3$ (10 mL) and extracted by DCM (20 mL×2). The combined organic layers were washed with brine, dried over Na$_2$SO$_4$ and concentrated. The mixture was purified by prep-TLC (DCM:CH$_3$OH=12:1) to give the crude compound. The crude compound was triturated with Hex/EtOAc (4/1, 5 mL) to give the title compound (25 mg, yield 23%) as white solid.

E149 $^1$H NMR (400 MHz, CDCl$_3$): δ 8.91 (s, 1H), 8.06 (s, 1H), 7.52 (s, 1H), 6.59 (s, 1H), 4.97-4.79 (m, 2H), 4.42-4.38 (m, 2H), 4.02-3.99 (m, 2H), 3.39-3.35 (m, 1H), 3.12-3.03 (m, 1H), 2.95-2.86 (m, 2H), 2.62 (s, 4H), 2.48 (s, 3H), 2.40-2.31 (m, 2H), 1.98-1.80 (m, 2H), 1.14-1.11 (m, 6H). $^{19}$F NMR (376 MHz, CDCl$_3$): δ −182.83 (s, 1F).

LC-MS [mobile phase: from 95% water (0.1% TFA) and 10% CH$_3$CN to 10% water (0.1% TFA) and 95% CH$_3$CN in 6.5 min], purity is 97.56%, Rt=2.831 min; MS Calcd.: 438, MS Found: 439 [M+H]$^+$.

Chiral condition: Chiralpak AD-H 5 um 4.6*250 mm, Hex/EtOH=70/30, Flow Rate: 1.0 ml/min, 230 nm, T=30° C. Rt=6.510 min, 99.5% ee.

Example 150

(cis)-(1R,3R)-3-(6-(6-(3-fluoro-1-(oxetan-3-yl)piperidin-4-yl)-5-methyl-1H-indazol-1-yl)-2-methylpyrimidin-4-yl)cyclobutanol (Enantiomer 1, E150)

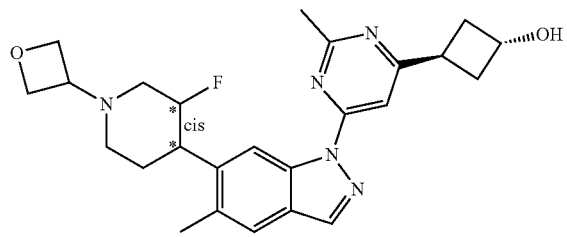 [SMILES: Cc1nc(-n2ncc3cc(C)c(C4CCN(C5COC5)CC4F)cc32)cc([C@H]2C[C@H](O)C2)n1]

To a solution of (cis)-(1R,3R)-3-(6-(6-(3-fluoropiperidin-4-yl)-5-methyl-1H-indazol-1-yl)-2-methylpyrimidin-4-yl)cyclobutanol hydrochloride (enantiomer 1, 21 mg, 0.05 mmol) in methanol (0.3 mL) was added 1,2-dichloro-ethane (2 mL) and oxetan-3-one (0.13 mL). After stirred at rt for 30 min the reaction mixture was added NaBH$_3$CN (20 mg, 0.30 mmol). The resulting mixture was stirred at rt for 2 hrs. To the reaction mixture was added a solution of sat. Na$_2$CO$_3$ solution (10 mL). The mixture was stirred at rt for 10 min and DCM (20 mL×3) was added to extract the desired compound. The combined organic layers were washed with brine (30 mL), dried over Na$_2$SO$_4$ and concentrated. The mixture was purified by prep-TLC (DCM: CH$_3$OH=15:1) to give the title compound (12 mg, yield 54%) as white solid.

E150 $^1$H NMR (400 MHz, CDCl$_3$): δ 8.91 (s, 1H), 8.12 (s, 1H), 7.66 (s, 1H), 7.56 (s, 1H), 5.01-4.84 (m, 1H), 4.76-4.67 (m, 5H), 3.71-3.63 (m, 2H), 3.31-3.26 (m, 1H), 3.18-3.09 (m, 1H), 2.89-2.81 (m, 4H), 2.73-2.68 (m, 2H), 2.49-2.42 (m, 5H), 2.17-1.85 (m, 5H).

$^{19}$F NMR (376 MHz, CDCl$_3$): δ −184.00 (s, 1F).

LC-MS [mobile phase: from 95% water (0.02% NH$_4$OAc) and 5% CH$_3$CN to 5% water (0.02% NH$_4$OAc) and 95% CH$_3$CN in 6.5 min], purity is >95%, Rt=3.992 min; MS Calcd.: 451, MS Found: 452 [M+H]$^+$.

Chiral condition: Chiralpak IF 5 um 4.6*250 mm, Hex/EtOH=80/20, Flow Rate: 1 ml/min, 230 nm, T=30° C., Rt=13.538 min, 99.3% ee.

Example 151

(cis)-(1R,3R)-3-(6-(6-(3-fluoro-1-(oxetan-3-yl)piperidin-4-yl)-5-methyl-1H-indazol-1-yl)-2-methylpyrimidin-4-yl)cyclobutanol (Enantiomer 2, E151)

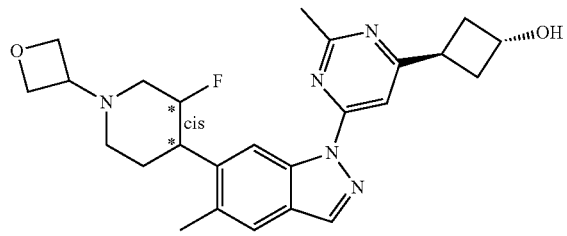 [SMILES: Cc1nc(-n2ncc3cc(C)c(C4CCN(C5COC5)CC4F)cc32)cc([C@H]2C[C@H](O)C2)n1]

To a solution of (cis)-(1R,3R)-3-(6-(6-(3-fluoropiperidin-4-yl)-5-methyl-1H-indazol-1-yl)-2-methylpyrimidin-4-yl) cyclobutanol hydrochloride (enantiomer 2, 32 mg, 0.07 mmol) in methanol (0.3 mL) was added 1,2-dichloro-ethane (2 mL) and oxetan-3-one (0.2 mL). The mixture was stirred at rt for 30 min. To the reaction mixture was added NaBH₃CN (30 mg, 0.48 mmol) and stirred at rt for 2 hrs. Then the reaction mixture was added a solution of sat. Na₂CO₃ solution (10 mL) and stirred at rt for 10 min. The mixture was extracted with DCM (20 mL×3). The combined organic layers were washed with brine (30 mL), dried over Na₂SO₄ and concentrated. The mixture was purified by prep-TLC (DCM: CH₃OH=15:1) to give the title compound (18 mg, yield 57%) as white solid.

E151 ¹H NMR (400 MHz, CDCl₃): δ 8.91 (s, 1H), 8.12 (s, 1H), 7.66 (s, 1H), 7.56 (s, 1H), 4.98-4.86 (m, 1H), 4.72-4.69 (m, 5H), 3.69-3.66 (m, 2H), 3.30-3.28 (m, 1H), 3.14-3.12 (m, 1H), 2.89-2.83 (m, 4H), 2.71-2.70 (m, 2H), 2.49-2.44 (m, 5H), 2.16-1.90 (m, 5H).

¹⁹F NMR (376 MHz, CDCl₃): δ −184.00 (s, 1F).

LC-MS [mobile phase: from 95% water (0.02% NH₄OAc) and 5% CH₃CN to 5% water (0.02% NH₄OAc) and 95% CH₃CN in 6.5 min], purity is 99.21%, Rt=3.990 min; MS Calcd.: 451, MS Found: 452 [M+H]⁺.

Chiral condition: Chiralpak IF 5um 4.6*250 mm, Hex/EtOH=80/20, Flow Rate: 1 ml/min, 230 nm, T=30° C., Rt=13.427 min, 100% ee.

Example 152

4-(6-(6-(3-Fluoro-1-(oxetan-3-yl)piperidin-4-yl)-5-methyl-1H-indazol-1-yl)-2-methoxypyrimidin-4-yl)morpholine (Enantiomer 1, E152)

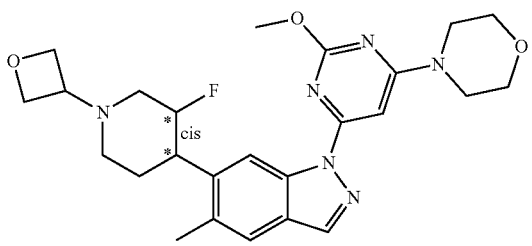 [SMILES: COc1nc(N2CCOCC2)cc(-n2ncc3cc(C)c(C4CCN(C5COC5)CC4F)cc32)n1]

To a solution of 4-(6-(6-(3-fluoropiperidin-4-yl)-5-methyl-1H-indazol-1-yl)-2-methoxypyrimidin-4-yl)morpholine (enantiomer 1, 88 mg, 0.21 mmol) in CH₂Cl₂ (5 mL) was added oxetan-3-one (45 mg, 0.62 mmol) and HAc (27 mg, 0.62 mmol). The resulting mixture was stirred at room temperature for 3 h. NaBH₃CN (39 mg, 0.62 mmol) was added and the reaction was stirred at room temperature for 2 h. The reaction was quenched was sat. NaHCO₃. CH₂Cl₂ (15 mL) was added and the resulting suspension was washed with brine (20 mL). The organic layer was collected and dried over anhydrous Na₂SO₄ and concentrated under reduced pressure. The residue was purified by pre-HPLC (Gilson GX-281, Sepax C18-H 21.2*100 mm 5 um, Phase: MeCN/H2O (0.1% TFA): 10%~95%, Flow rate: 15 mL/min, 214 nm/254 nm) to give product (50 mg, yield 50.2%), TFA salt, as a white sold.

E152 ¹H NMR (400 MHz, CDCl₃): δ 8.83 (s, 1H), 8.09 (s, 1H), 7.58 (s, 1H), 6.84 (s, 1H), 5.25~5.07 (m, 1H), 5.01~4.97 (m, 2H), 4.85~4.81 (m, 2H), 4.27~4.19 (m, 1H), 4.09 (s, 3H), 3.81~3.72 (m, 9H), 3.53 (d, J=10.8 Hz, 1H), 3.36~3.27 (m, 1H), 2.77~2.67 (m, 2H), 2.49 (s, 3H), 2.25~2.20 (m, 2H).

¹⁹F NMR (376 MHz, CDCl₃): δ−75.7 (s, 3F), −184.3 (s, 1F).

LC-MS (mobile phase: from 90% water (0.1% FA) and 10% CH₃CN (0.1% FA) to 5% water (0.1% FA) and 95% CH₃CN (0.1% FA) in 10 min, purity 96.2%, Rt=7.76 min; MS Calcd.: 482.2, MS Found: 483.7 (M+H)⁺.

Chiral purity: Rt=12.60 min; ee %=99.9%.

Chiral method: Chiralpak AD-H 5 um 4.6*250 mm, Phase: Hex:EtOH=70/30, F: 1.0 mL/min, W: 214 nm, T: 30° C.

Example 153

4-(6-(6-(3-Fluoro-1-(oxetan-3-yl)piperidin-4-yl)-5-methyl-1H-indazol-1-yl)-2-methoxypyrimidin-4-yl)morpholine (Enantiomer 2, E153)

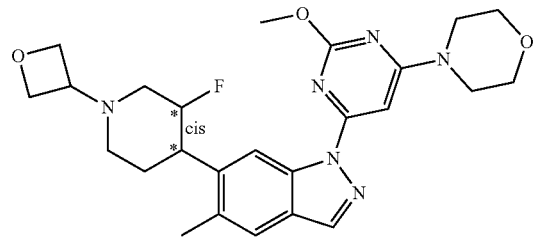 [SMILES: COc1nc(N2CCOCC2)cc(-n2ncc3cc(C)c(C4CCN(C5COC5)CC4F)cc32)n1]

To a solution of 4-(6-(6-(3-fluoropiperidin-4-yl)-5-methyl-1H-indazol-1-yl)-2-methoxypyrimidin-4-yl)morpholine (enantiomer 2, 78 mg, 0.18 mmol) in CH₂Cl₂ (5 mL) was added oxetan-3-one (40 mg, 0.55 mmol) and HAc (24 mg, 0.55 mmol). The resulting mixture was stirred at room temperature for 3 h. NaBH₃CN (34 mg, 0.55 mmol) was added and the reaction was stirred at room temperature for 2 h. The reaction was quenched was sat. NaHCO₃. CH₂Cl₂ (15 mL) was added and the resulting suspension was washed with brine (20 mL). The organic layer was collected and dried over anhydrous Na₂SO₄ and concentrated under reduced pressure. The residue was purified by pre-HPLC (Waters 2767/Qda, Waters XBridge 30*150 mm 5 um, Phase: MeCN/H₂O (0.1% TFA): 10%~95%, Flow rate: 20 mL/min, 214 nm/254 nm) to give product (47 mg, yield 53.0%), TFA salt, as a pale yellow sold.

E153 ¹H NMR (400 MHz, CDCl₃): δ 8.81 (s, 1H), 8.10 (s, 1H), 7.58 (s, 1H), 6.84 (s, 1H), 5.28~5.10 (m, 1H), 5.04~5.00 (m, 2H), 4.87~4.82 (m, 2H), 4.33~4.27 (m, 1H), 4.09 (s, 3H), 3.86~3.73 (m, 9H), 3.60 (d, J=10.4 Hz, 1H), 3.39~3.29 (m, 1H), 2.85~2.74 (m, 2H), 2.49 (s, 3H), 2.29~2.25 (m, 2H).

¹⁹F NMR (376 MHz, CDCl₃): δ−75.7 (s, 3F), −184.5 (s, 1F).

LC-MS (mobile phase: from 90% water (0.1% FA) and 10% CH₃CN (0.1% FA) to 5% water (0.1% FA) and 95% CH₃CN (0.1% FA) in 10 min, purity 96.2%, Rt=7.76 min; MS Calcd.: 482.2, MS Found: 483.7 (M+H)⁺.

Chiral purity: Rt=19.29 min; ee %=99.7%.

Chiral method: Chiralpak AD-H 5 um 4.6*250 mm, Phase: Hex:EtOH=70/30, F: 1.0 mL/min, W: 214 nm, T: 30° C.

Example 154

6-((cis)-3-Fluoro-1-(oxetan-3-yl)piperidin-4-yl)-1-(2-methoxy-6-(4-methylpiperazin-1-yl)pyrimidin-4-yl)-5-methyl-1H-indazole (Enantiomer 1, E154)

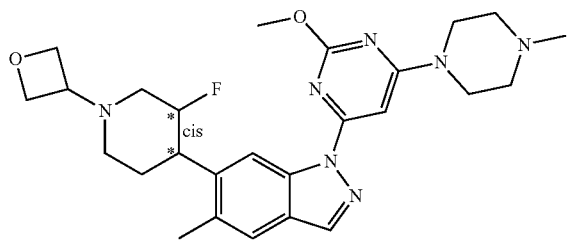 [SMILES: COc1nc(N2CCN(C)CC2)cc(-n2ncc3cc(C)c(C4CCN(C5COC5)CC4F)cc32)n1]

To a solution of 6-((cis)-3-fluoropiperidin-4-yl)-1-(2-methoxy-6-(4-methylpiperazin-1-yl) pyrimidin-4-yl)-5-methyl-1H-indazole TFA salt (enantiomer 1, 220 mg, 0.33 mmol) in DCM (5 mL) was added oxetan-3-one (72 mg, 1.0 mmol) and MeOH (1.0 mL). The resulting solution was stirred at room temperature for 2 h. NaBH$_3$CN (63 mg, 1.0 mmol) was added and the reaction was stirred at room temperature for 10 min. The reaction solution was concentrated and the residue was diluted with EtOAc (20 mL). The obtained solution was washed with brine (20 mL). The organic layer was collected and dried over anhydrous Na$_2$SO$_4$ and concentrated under reduced pressure. The residue was purified by silica column chromatography (MeOH:EtOAc=0:100~10:100, 5 g of silica gel) to give the desired product (80 mg, 49% yield) as a white solid.

D154 $^1$H NMR (400 MHz, CDCl$_3$): δ 8.88 (s, 1H), 8.07 (s, 1H), 7.54 (s, 1H), 6.85 (s, 1H), 4.93~4.79 (m, 1H), 4.73~4.63 (m, 4H), 4.13 (s, 3H), 3.77 (br, 4H), 3.68~3.64 (m, 1H), 3.25~3.21 (m, 1H), 3.13~3.10 (m, 1H), 2.84~2.81 (m, 1H), 2.51 (t, J=4.8 Hz, 4H), 2.48 (s, 3H), 2.35 (s, 3H), 2.12~1.88 (m, 4H).

19F NMR (400 MHz, CDCl$_3$): δ −184.0 (s, 1F).

LC-MS (mobile phase: from 90% water (0.1% FA) and 10% CH$_3$CN (0.1% FA) to 5% water (0.1% FA) and 95% CH$_3$CN (0.1% FA) in 10 min, purity 97.9%, Rt=5.07 min; MS Calcd.: 495.3, MS Found: 496.8 (M+H)$^+$.

Chiral purity: Rt=10.89 min; ee %=99.6%.

Chiral method: Chiralpak AD-H 5 um 4.6*250 mm, Phase: Hex:EtOH=70/30, F: 1.0 mL/min, W: 214 nm, T: 30° C.

Example 155

6-((cis)-3-Fluoro-1-(oxetan-3-yl)piperidin-4-yl)-1-(2-methoxy-6-(4-methylpiperazin-1-yl)pyrimidin-4-yl)-5-methyl-1H-indazole (Enantiomer 2, E155)

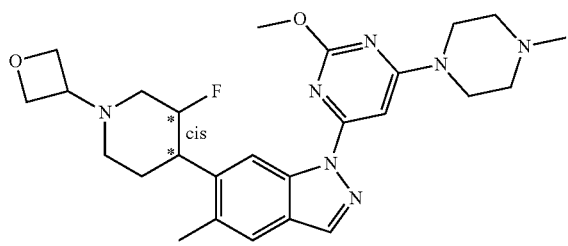 [SMILES: COc1nc(N2CCN(C)CC2)cc(-n2ncc3cc(C)c(C4CCN(C5COC5)CC4F)cc32)n1]

To a solution of 6-((cis)-3-fluoropiperidin-4-yl)-1-(2-methoxy-6-(4-methylpiperazin-1-yl)pyrimidin-4-yl)-5-methyl-1H-indazole (enantiomer 2, 280 mg, 0.58 mmol) in DCM (15 mL) was added oxetan-3-one (300 mg, 6.0 mmol). The resulting solution was stirred at room temperature overnight. NaBH$_3$CN (300 mg, 7.0 mmol) was added and the reaction was stirred at room temperature overnight till the material was consumed. The reaction solution was diluted with sat. NaHCO$_3$ (80 mL). The solution was extracted by DCM (2×100 mL). The combined organic layers were washed with brine (2×100 mL) and dried over Na$_2$SO$_4$ and concentrated. The residue was purified by silica column chromatography (MeOH:EtOAc=0:100~10:100, 4 g of silica gel) to give the desired product (50 mg, 22.5% yield) as a white solid.

E155 $^1$H NMR (400 MHz, CDCl$_3$): δ 8.87 (s, 1H), 8.08 (s, 1H), 7.54 (s, 1H), 6.86 (s, 1H), 4.93~4.79 (m, 1H), 4.73~4.63 (m, 4H), 4.14 (s, 3H), 3.77 (br, 4H), 3.68~3.64 (m, 1H), 3.25~3.21 (m, 1H), 3.13~3.10 (m, 1H), 2.84~2.81 (m, 1H), 2.57 (t, J=4.8 Hz, 4H), 2.47 (s, 3H), 2.40 (s, 3H), 2.12~1.88 (m, 4H).

$^{19}$F NMR (400 MHz, CDCl$_3$): δ −183.982 (s, 1F).

LC-MS (mobile phase: from 90% water (0.1% FA) and 10% CH$_3$CN (0.1% FA) to 5% water (0.1% FA) and 95% CH$_3$CN (0.1% FA) in 10 min, purity 97%, Rt=5.11 min; MS Calcd.: 495.3, MS Found: 496.8 (M+H)$^+$.

Chiral purity: Rt=10.89 min; ee %=99.53%.

Chiral method: Chiralpak AD-H 5 um 4.6*250 mm, Phase: Hex:EtOH=70/30, F: 1.0 mL/min, W: 214 nm, T: 30° C.

Example 156

(R)-4-(6-(6-((cis)-3-fluoro-1-(oxetan-3-yl)piperidin-4-yl)-5-methyl-1H-indazol-1-yl)-2-methoxypyrimidin-4-yl)-2-methylmorpholine (Diastereoisomer 1, E156)

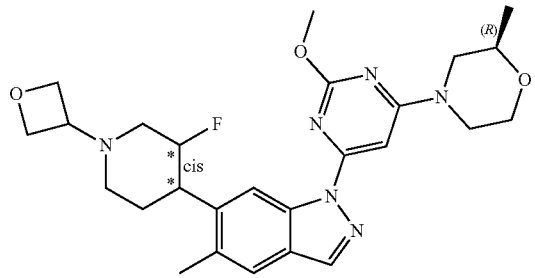

To a solution of (R)-4-(6-iodo-2-methoxypyrimidin-4-yl)-2-methylmorpholine (139 mg, 0.42 mmol) in toluene (10 mL) was added 6-((cis)-3-fluoro-1-(oxetan-3-yl)piperidin-4-yl)-5-methyl-1H-indazole (enantiomer 1) (100 mg, 0.35 mmol), K$_3$PO$_4$ (149 mg, 0.70 mmol), CuI (67 mg, 0.35 mmol) and N$^1$,N$^2$-dimethylethane-1,2-diamine (62 mg, 0.70 mmol). The mixture was stirred at 90° C. for 2 hrs under N$_2$. The reaction mixture was poured into water (100 mL), extracted with EtOAc (50 mL×3). The combined organic layers were washed with brine (50 mL), dried over anhydrous Na$_2$SO$_4$ and concentrated to dryness. The residue was purified by silica gel chromatography eluted with (EtOAc: petroleum ether=1:5~1:0) to give the product (R)-4-(6-(6-((cis)-3-fluoro-1-(oxetan-3-yl)piperidin-4-yl)-5-methyl-1H- indazol-1-yl)-2-methoxypyrimidin-4-yl)-2-methylmorpholine (diastereoisomer 1) (40 mg, 23.0% yield) as a white solid.

E156 $^1$H NMR (400 MHz, CDCl$_3$): δ 8.87 (s, 1H), 8.08 (s, 1H), 7.54 (s, 1H), 6.83 (s, 1H), 4.93~4.79 (m, 1H), 4.72~4.63 (m, 4H), 4.32~4.21 (m, 2H), 4.14 (s, 3H), 4.00 (d, J=9.6 Hz, 1H), 3.70~3.64 (m, 3H), 3.25~3.08 (m, 3H), 2.85~2.72 (m, 2H), 2.48 (s, 3H), 2.14~1.85 (m, 4H), 1.27 (d, J=6.0 Hz, 3H).

$^{19}$F NMR (376 MHz, CDCl$_3$): δ −183.97 (s, 1F).

LC-MS [mobile phase: from 90% water (0.1% FA) and 10% CH$_3$CN (0.1% FA) to 5% water (0.1% FA) and 95% CH$_3$CN (0.1% FA) in 10 min], purity: 98.9%; Rt=4.51 min; MS Calcd: 496, MS Found: 497[M+H]$^+$.

Chiral condition: Chiralpak AD-H 5 um 4.6*250 mm, Hexane:IPA (0.2% DEA)=65/35, Flow Rate: 1.0 mL/min, 214 nm, T=25° C., Rt=10.67 min, 99% ee.

Example 157

(R)-4-(6-(6-((cis)-3-fluoro-1-(oxetan-3-yl)piperidin-4-yl)-5-methyl-1H-indazol-1-yl)-2-methoxypyrimidin-4-yl)-2-methylmorpholine (Diastereoisomer 2, E157)

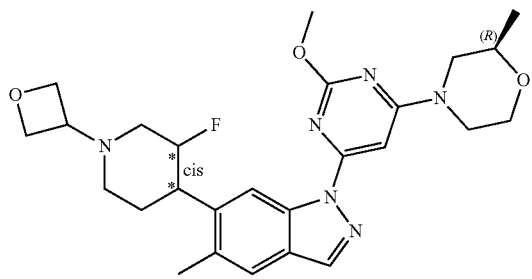

To a solution of (R)-4-(6-iodo-2-methoxypyrimidin-4-yl)-2-methylmorpholine (111 mg, 0.33 mmol) in toluene (10 mL) was added 6-((cis)-3-fluoro-1-(oxetan-3-yl)piperidin-4-yl)-5-methyl-1H-indazole (enantiomer 2) (80 mg, 0.28 mmol), K$_3$PO$_4$ (119 mg, 0.56 mmol), CuI (54 mg, 0.28 mmol) and N1,N2-dimethylethane-1,2-diamine (50 mg, 0.56 mmol). The mixture was stirred at 90° C. for 2 hrs under N$_2$. The reaction mixture was poured into water (100 mL), extracted with EtOAc (50 mL×3). The combined organic layers were washed with brine (50 mL), dried over anhydrous Na$_2$SO$_4$ and concentrated to dryness. The residue was purified by silica gel chromatography eluted with (EtOAc:petroleum ether=1:5~1:0) to give the product (R)-4-(6-(6-((cis)-3-fluoro-1-(oxetan-3-yl)piperidin-4-yl)-5-methyl-1H-indazol-1-yl)-2-methoxypyrimidin-4-yl)-2-methylmorpholine (diastereoisomer 2) (30 mg, 21.6% yield) as a white solid.

E157 $^1$H NMR (400 MHz, CDCl$_3$): δ 8.87 (s, 1H), 8.08 (s, 1H), 7.54 (s, 1H), 6.83 (s, 1H), 4.93~4.79 (m, 1H), 4.72~4.63 (m, 4H), 4.32~4.21 (m, 2H), 4.14 (s, 3H), 4.00 (d, J=9.6 Hz, 1H), 3.70~3.64 (m, 3H), 3.25~3.08 (m, 3H), 2.85~2.72 (m, 2H), 2.48 (s, 3H), 2.14~1.85 (m, 4H), 1.27 (d, J=6.0 Hz, 3H).

$^{19}$F NMR (376 MHz, CDCl$_3$): δ −183.97 (s, 1F).

LC-MS [mobile phase: from 90% water (0.1% FA) and 10% CH$_3$CN (0.1% FA) to 5% water (0.1% FA) and 95% CH$_3$CN (0.1% FA) in 10 min], purity: 98.9%; Rt=3.75 min; MS Calcd: 496, MS Found: 497[M+H]$^+$.

Chiral condition: Chiralpak AD-H 5 um 4.6*250 mm, Hexane:IPA (0.2% DEA)=65/35, Flow Rate: 1.0 mL/min, 214 nm, T=25° C., Rt=14.740 min, 99% ee.

Example 158

(S)-4-(6-(6-((cis)-3-Fluoro-1-(oxetan-3-yl)piperidin-4-yl)-5-methyl-1H-indazol-1-yl)-2-methoxypyrimidin-4-yl)-2-methylmorpholine (Diastereoisomer 1, E158)

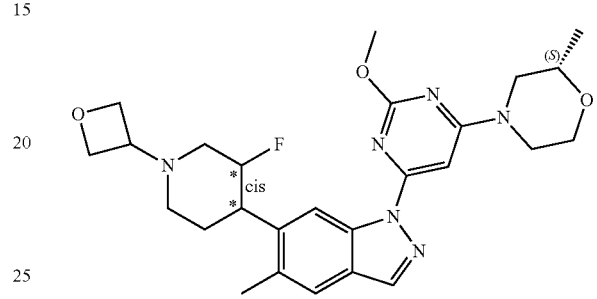

To a solution of (S)-4-(6-(6-((cis)-3-fluoropiperidin-4-yl)-5-methyl-1H-indazol-1-yl)-2-methoxypyrimidin-4-yl)-2-methylmorpholine (diastereoisomer 1) (140 mg, 0.32 mmol, crude) and oxetan-3-one (46 mg, 0.64 mmol) in DCE (10 mL) was added AcOH (19 mg, 0.32 mmol) and NaBH$_3$CN (40 mg, 0.64 mmol), the reaction was stirred at room temperature for overnight. The reaction mixture was poured into sat. NaHCO$_3$ solution (100 mL), and extracted with DCM (30 mL×3). The combined organic layers were washed with brine (30 mL), dried over anhydrous Na$_2$SO$_4$, filtered, concentrated to dryness. The residue was purified by Prep-HPLC (method: Sepax C18-H 21.2*100 mm 5 um, phase: H$_2$O (0.1% TFA):ACN=90:10 to 10:90, 15 mL/min, 254/214 nm) to give the title product (S)-4-(6-(6-((cis)-3-fluoro-1-(oxetan-3-yl)piperidin-4-yl)-5-methyl-1H-indazol-1-yl)-2-methoxypyrimidin-4-yl)-2-methylmorpholine (Single unknown isomer 1) (22 mg, yield=13.8%) as a white solid.

E158 $^1$H NMR (400 MHz, CDCl$_3$): δ 8.87 (s, 1H), 8.08 (s, 1H), 7.54 (s, 1H), 6.83 (s, 1H), 4.93~4.79 (m, 1H), 4.72~4.63 (m, 4H), 4.32~4.21 (m, 2H), 4.14 (s, 3H), 4.00 (d, J=9.6 Hz, 1H), 3.70~3.64 (m, 3H), 3.25~3.08 (m, 3H), 2.85~2.72 (m, 2H), 2.48 (s, 3H), 2.14~1.85 (m, 4H), 1.26 (d, J=6.0 Hz, 3H).

$^{19}$F NMR (376 MHz, CDCl$_3$): δ −183.97 (s, 1F).

LC-MS [mobile phase: from 90% water (0.1% FA) and 10% CH$_3$CN (0.1% FA) to 5% water (0.1% FA) and 95% CH$_3$CN (0.1% FA) in 10 min], purity: 98.9%; Rt=5.34 min; MS Calcd: 496, MS Found: 497[M+H]$^+$.

Chiral condition: Chiralpak AD-H 5 um 4.6*250 mm, Hexane:IPA (0.2% DEA)=65/35, Flow Rate: 1.0 mL/min, 214 nm, T=25° C., Rt=14.74 min 99% ee.

Example 159

(S)-4-(6-(6-((cis)-3-Fluoro-1-(oxetan-3-yl)piperidin-4-yl)-5-methyl-1H-indazol-1-yl)-2-methoxypyrimidin-4-yl)-2-methylmorpholine (Diastereoisomer 2, E159)

Example 160

(2S,6R)-4-(6-(6-(3-fluoro-1-(oxetan-3-yl)piperidin-4-yl)-5-methyl-1H-indazol-1-yl)-2-methoxypyrimidin-4-yl)-2,6-dimethylmorpholine (Diastereoisomer 1, E160)

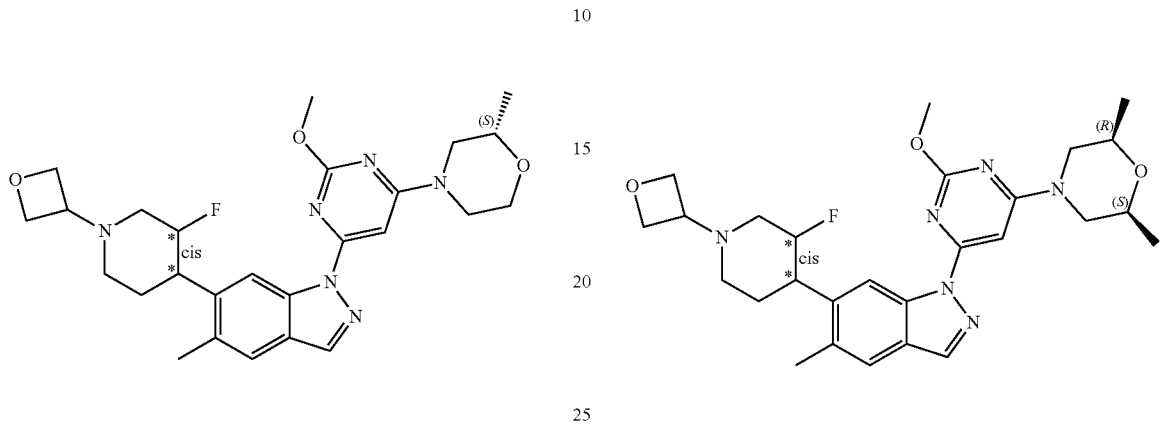

To a solution of (S)-4-(6-(6-((cis)-3-fluoropiperidin-4-yl)-5-methyl-1H-indazol-1-yl)-2-methoxypyrimidin-4-yl)-2-methylmorpholine (diastereoisomer 2) (95 mg, 0.22 mmol, crude) and oxetan-3-one (32 mg, 0.44 mmol) in DCE (10 mL) was added AcOH (13 mg, 0.22 mmol) and NaBH$_3$CN (28 mg, 0.44 mmol), the reaction was stirred at room temperature for overnight. LCMS showed the reaction was completed. The reaction mixture was poured into sat. NaHCO$_3$ solution (100 mL), extracted with DCM (30 mL×3). The combined organic layers were washed with brine (30 mL), dried over anhydrous Na$_2$SO$_4$, filtered, concentrated to dryness. The residue was purified by Prep-HPLC (method: Sepax C18-H 21.2*100 mm 5 um, phase: H$_2$O (0.1% TFA):ACN=90:10 to 10:90, 15 mL/min, 254/214 nm) to give the title product (S)-4-(6-(6-((cis)-3-fluoro-1-(oxetan-3-yl)piperidin-4-yl)-5-methyl-1H-indazol-1-yl)-2-methoxypyrimidin-4-yl)-2-methylmorpholine (diastereoisomer 2) (16 mg, yield=14.6%) as a white solid.

E159 $^1$H NMR (400 MHz, CDCl$_3$): δ 8.87 (s, 1H), 8.08 (s, 1H), 7.54 (s, 1H), 6.83 (s, 1H), 4.93~4.79 (m, 1H), 4.72~4.63 (m, 4H), 4.32~4.21 (m, 2H), 4.14 (s, 3H), 4.00 (d, J=9.6 Hz, 1H), 3.70~3.64 (m, 3H), 3.25~3.08 (m, 3H), 2.85~2.72 (m, 2H), 2.48 (s, 3H), 2.14~1.85 (m, 4H), 1.27 (d, J=6.0 Hz, 3H).

$^{19}$F NMR (376 MHz, CDCl$_3$): δ −183.98 (s, 1F).

LC-MS [mobile phase: from 90% water (0.1% FA) and 10% CH$_3$CN (0.1% FA) to 5% water (0.1% FA) and 95% CH$_3$CN (0.1% FA) in 10 min], purity: 98.9%; Rt=5.37 min; MS Calcd: 496, MS Found: 497[M+H]$^+$.

Chiral condition: Chiralpak AD-H 5 um 4.6*250 mm, Hexane: IPA (0.2% DEA)=65/35, Flow Rate: 1.0 mL/min, 214 nm, T=25° C., Rt=16.60 min, 99% ee.

The mixture of 6-(3-fluoro-1-(oxetan-3-yl)piperidin-4-yl)-5-methyl-1H-indazole (enantiomer 1, 70 mg, 0.24 mmol), (2S,6R)-4-(6-iodo-2-methoxypyrimidin-4-yl)-2,6-dimethylmorpholine (100 mg, 0.28 mmol), CuI (95 mg, 0.5 mmol) and K$_3$PO$_4$ (106 mg, 0.5 mmol) in toluene (10 mL) was degassed and protected with N$_2$ before N,N-dimethyl-1,2-ethanediamine (44 mg, 0.5 mmol) was added. Then, the reaction mixture was stirred at 90° C. for 2 hours. The reaction mixture was diluted with EtOAc (20 mL) and washed with brine (2×20 mL). The organic solution was dried over anhydrous Na$_2$SO$_4$ and concentrated. The residue was purified by prep-HPLC (method: Waters 2767/Qda; Waters XBridge 30*150 mm 5 um; 20 ml/min; 214 nm/254 nm; phase: H$_2$O (0.1% NH$_3$.H$_2$O)/ACN) to give the desired product as a white solid. (90 mg, 73% yield)

E160 $^1$H NMR (400 MHz, CDCl$_3$): δ 8.88 (s, 1H), 8.09 (s, 1H), 7.54 (s, 1H), 6.83 (s, 1H), 4.93~4.79 (m, 1H), 4.72~4.62 (m, 4H), 4.33~4.26 (br, 2H), 4.15 (s, 3H), 3.68~3.63 (m, 3H), 3.25~3.10 (m, 2H), 2.83 (d, J=10.4 Hz, 1H), 2.67 (t, J=12.0 Hz, 2H), 2.14~1.85 (m, 4H), 1.27 (d, J=6.0 Hz, 6H).

$^{19}$F NMR (400 MHz, CDCl$_3$): δ −184.0 (s, 1F).

LC-MS (mobile phase: from 60% water (0.1% FA) and 40% CH$_3$CN (0.1% FA) to 5% water (0.1% FA) and 95% CH$_3$CN (0.1% FA) in 10 min, purity 97.4%, Rt=6.52 min; MS Calcd.: 510.3, MS Found: 511.8 (M+H)$^+$.

Chiral purity: Rt=10.825 min; ee %=99.6%.

Chiral method: Chiralpak AD-H 5 um 4.6*250 mm, Phase: Hexane: Isopropanol (0.2% diethylamine)=65/35, F: 1.0 mL/min, W: 214 nm, T: 25° C.

Example 161

(2S,6R)-4-(6-(6-(3-fluoro-1-(oxetan-3-yl)piperidin-4-yl)-5-methyl-1H-indazol-1-yl)-2-methoxypyrimidin-4-yl)-2,6-dimethylmorpholine (Diastereoisomer 2, E161)

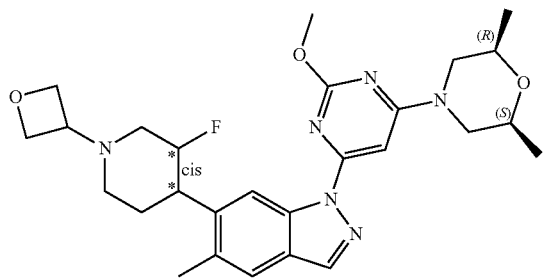

The mixture of 6-(3-fluoro-1-(oxetan-3-yl)piperidin-4-yl)-5-methyl-1H-indazole (enantiomer 2, 70 mg, 0.24 mmol), (2S,6R)-4-(6-iodo-2-methoxypyrimidin-4-yl)-2,6-dimethylmorpholine (100 mg, 0.28 mmol), CuI (95 mg, 0.5 mmol) and $K_3PO_4$ (106 mg, 0.5 mmol) in toluene (10 mL) was degassed and protected with $N_2$ before N,N-dimethyl-1,2-ethanediamine (44 mg, 0.5 mmol) was added. Then, the reaction mixture was stirred at 100° C. for 1 hour. The reaction mixture was diluted with EtOAc (20 mL) and washed with brine (2×20 mL). The organic solution was dried over anhydrous $Na_2SO_4$ and concentrated. The residue was purified by prep-HPLC (method: Waters 2767; Sepax Amethyst 21.2*100 mm 5 um; 15 ml/min; 214 nm/254 nm; phase: $H_2O$ (0.1% TFA)/ACN) to give the desired product as a white solid.

(70 mg, 57% yield)

E161 $^1$H NMR (400 MHz, $CDCl_3$): δ 8.88 (s, 1H), 8.09 (s, 1H), 7.54 (s, 1H), 6.83 (s, 1H), 4.93~4.79 (m, 1H), 4.72~4.62 (m, 4H), 4.33~4.26 (br, 2H), 4.15 (s, 3H), 3.68~3.63 (m, 3H), 3.25~3.10 (m, 2H), 2.83 (d, J=10.4 Hz, 1H), 2.67 (t, J=12.0 Hz, 2H), 2.14~1.85 (m, 4H), 1.27 (d, J=6.0 Hz, 6H).

$^{19}$F NMR (400 MHz, $CDCl_3$): δ −184.0 (s, 1F).

LC-MS (mobile phase: from 50% water (0.1% FA) and 50% $CH_3CN$ (0.1% FA) to 5% water (0.1% FA) and 95% $CH_3CN$ (0.1% FA) in 10 min, purity 96.8%, Rt=4.83 min; MS Calcd.: 510.3, MS Found: 511.7 (M+H)$^+$.

Chiral purity: Rt=14.684 min; ee %=99.6%.

Chiral method: Chiralpak AD-H 5 um 4.6*250 mm, Phase: Hexane: Isopropanol (0.2% diethylamine)=65/35, F: 1.0 mL/min, W: 214 nm, T: 25° C.

Example 162

(2S,6S)-4-(6-(6-(3-Fluoro-1-(oxetan-3-yl)piperidin-4-yl)-5-methyl-1H-indazol-1-yl)-2-methoxypyrimidin-4-yl)-2,6-dimethylmorpholine (Diastereoisomer 1, E162)

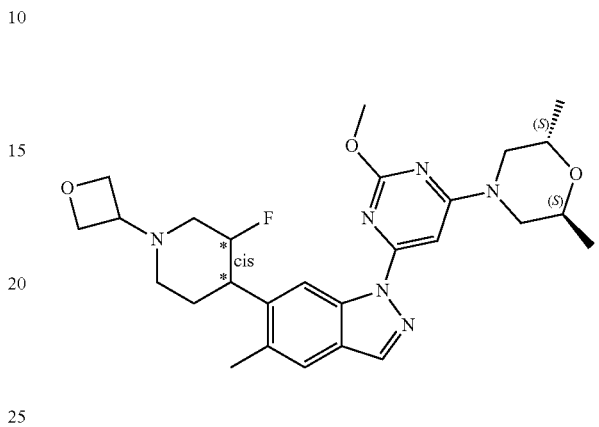

The mixture of 6-(3-fluoro-1-(oxetan-3-yl)piperidin-4-yl)-5-methyl-1H-indazole (enantiomer 1, 80 mg, 0.27 mmol), (2S,6S)-4-(6-iodo-2-methoxypyrimidin-4-yl)-2,6-dimethylmorpholine (106 mg, 0.304 mmol), CuI (105 mg, 0.55 mmol) and $K_3PO_4$ (117 mg, 0.55 mmol) in toluene (15 mL) was degassed and protected with $N_2$ before N,N-dimethyl-1,2-ethanediamine (50 mg, 0.5 mmol) was added. Then, the reaction mixture was stirred at 90° C. for 2 hours. The reaction mixture was diluted with EtOAc (120 mL) and washed with brine (2×100 mL). The organic solution was dried over anhydrous $Na_2SO_4$ and concentrated. The residue was purified by prep-HPLC (method: Waters 2767/Qda; Waters XBridge 30*150 mm 5 um; 20 ml/min; 214 nm/254 nm; phase: $H_2O$ (0.1% $NH_3.H_2O$)/ACN) to give the desired product as a white solid. (86 mg, 71% yield)

E162 $^1$H NMR (400 MHz, $CDCl_3$): δ 8.88 (s, 1H), 8.09 (s, 1H), 7.54 (s, 1H), 6.83 (s, 1H), 4.93~4.79 (m, 1H), 4.72~4.62 (m, 4H), 4.33~4.26 (br, 2H), 4.15 (s, 3H), 3.68~3.63 (m, 3H), 3.25~3.10 (m, 2H), 2.83 (d, J=10.4 Hz, 1H), 2.67 (t, J=12.0 Hz, 2H), 2.14~1.85 (m, 4H), 1.27 (d, J=6.0 Hz, 6H).

$^{19}$F NMR (400 MHz, $CDCl_3$): δ −184.0 (s, 1F).

LC-MS (mobile phase: from 50% water (0.1% FA) and 50% $CH_3CN$ (0.1% FA) to 5% water (0.1% FA) and 95% $CH_3CN$ (0.1% FA) in 10 min, purity 96.8%, Rt=4.83 min; MS Calcd.: 510.3, MS Found: 511.8 (M+H)$^+$.

Chiral purity: Rt=11.791 min; ee %=99.7%.

Chiral method: Chiralpak AD-H 5 um 4.6*250 mm, Phase: Hexane: Isopropanol (0.2% diethylamine)=65/35, F: 1.0 mL/min, W: 214 nm, T: 25° C.

Example 163

(2S,6S)-4-(6-(6-(3-Fluoro-1-(oxetan-3-yl)piperidin-4-yl)-5-methyl-1H-indazol-1-yl)-2-methoxypyrimidin-4-yl)-2,6-dimethylmorpholine (Enantiomer 2, E163)

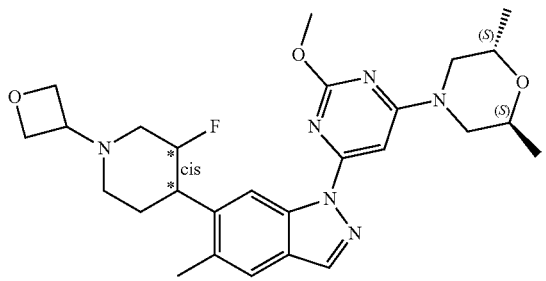

The mixture of 6-(3-fluoro-1-(oxetan-3-yl)piperidin-4-yl)-5-methyl-1H-indazole (diastereoisomer 2, 80 mg, 0.27 mmol), (2S,6S)-4-(6-iodo-2-methoxypyrimidin-4-yl)-2,6-dimethylmorpholine (106 mg, 0.304 mmol), CuI (105 mg, 0.55 mmol) and $K_3PO_4$ (117 mg, 0.55 mmol) in toluene (15 mL) was degassed and protected with $N_2$ before N,N-dimethyl-1,2-ethanediamine (50 mg, 0.5 mmol) was added. Then, the reaction mixture was stirred at 90° C. for 2 hours. The reaction mixture was diluted with EtOAc (120 mL) and washed with brine (2×100 mL). The organic solution was dried over anhydrous $Na_2SO_4$ and concentrated. The residue was purified by prep-HPLC (method: Waters 2767/Qda; Waters XBridge 30*150 mm 5 um; 20 ml/min; 214 nm/254 nm; phase: $H_2O$ (0.1% $NH_3.H_2O$)/ACN) to give the desired product as a white solid. (84 mg, 69% yield).

E163 $^1$H NMR (400 MHz, $CDCl_3$): δ 8.88 (s, 1H), 8.09 (s, 1H), 7.54 (s, 1H), 6.83 (s, 1H), 4.93~4.79 (m, 1H), 4.72~4.62 (m, 4H), 4.33~4.26 (br, 2H), 4.15 (s, 3H), 3.68~3.63 (m, 3H), 3.25~3.10 (m, 2H), 2.83 (d, J=10.4 Hz, 1H), 2.67 (t, J=12.0 Hz, 2H), 2.14~1.85 (m, 4H), 1.27 (d, J=6.0 Hz, 6H).

$^{19}$F NMR (400 MHz, $CDCl_3$): δ −184.0 (s, 1F).

LC-MS (mobile phase: from 50% water (0.1% FA) and 50% $CH_3CN$ (0.1% FA) to 5% water (0.1% FA) and 95% $CH_3CN$ (0.1% FA) in 10 min, purity 96.8%, Rt=4.21 min; MS Calcd.: 510.3, MS Found: 511.8 (M+H)$^+$.

Chiral purity: Rt=16.608 min; ee %=99.5%.

Chiral method: Chiralpak AD-H 5 um 4.6*250 mm, Phase: Hexane: Isopropanol (0.2% diethylamine)=65/35, F: 1.0 mL/min, W: 214 nm, T: 25° C.

Example 164

(R)-4-(6-(6-(3-fluoro-1-(oxetan-3-yl)piperidin-4-yl)-5-methyl-1H-indazol-1-yl)-2-methoxypyrimidin-4-yl)-3-methylmorpholine (Diastereoisomer 1, E164)

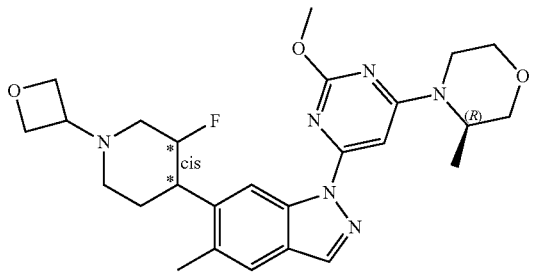

The mixture of 6-(3-fluoro-1-(oxetan-3-yl)piperidin-4-yl)-5-methyl-1H-indazole (enantiomer 1, 80 mg, 0.27 mmol), (R)-4-(6-iodo-2-methoxypyrimidin-4-yl)-3-methyl morpholine (102 mg, 0.30 mmol), CuI (103 mg, 0.54 mmol) and $K_3PO_4$ (115 mg, 0.54 mmol) in toluene (18 mL) was degassed and protected with $N_2$ before N,N-dimethyl-1,2-ethanediamine (48 mg, 0.54 mmol) was added. Then, the reaction mixture was stirred at 90° C. for 2 hours. The reaction mixture was diluted with EtOAc (2×100 mL) and washed with brine (150 mL). The organic solution was dried over anhydrous $Na_2SO_4$ and concentrated. The residue was purified by chromatography (EtOAc/PE=1/2~2/1) to give the desired product as a white solid. (80 mg, 58% yield)

E164 $^1$H NMR (400 MHz, $CDCl_3$): δ 8.88 (s, 1H), 8.07 (s, 1H), 7.54 (s, 1H), 6.81 (s, 1H), 4.92~4.79 (m, 1H), 4.72~4.63 (m, 4H), 4.48 (br, 1H), 4.14 (s, 3H), 4.14~3.99 (m, 2H), 3.81~3.58 (m, 4H), 3.34~3.08 (m, 3H), 2.81 (m, 1H), 2.48 (s, 3H), 2.11~1.85 (m, 4H), 1.35 (d, J=6.8 Hz, 3H).

$^{19}$F NMR (400 MHz, $CDCl_3$): δ −184.0 (s, 1F).

LC-MS (mobile phase: from 60% water (0.1% FA) and 40% $CH_3CN$ (0.1% FA) to 5% water (0.1% FA) and 95% $CH_3CN$ (0.1% FA) in 10 min, purity 99.4%, Rt=5.29 min; MS Calcd.: 496.3, MS Found: 497.8 (M+H)$^+$.

Chiral purity: Rt=7.637 min; ee %=99.7%.

Chiral method: Chiralpak AD-H 5 um 4.6*250 mm, Phase: Hexane: Isopropanol (0.2% diethylamine)=65/35, F: 1.0 mL/min, W: 214 nm, T: 25° C.

Example 165

(R)-4-(6-(6-(3-fluoro-1-(oxetan-3-yl)piperidin-4-yl)-5-methyl-1H-indazol-1-yl)-2-methoxypyrimidin-4-yl)-3-methylmorpholine (Diastereoisomer 2, E165)

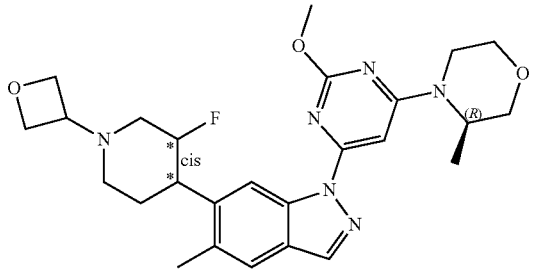

The mixture of 6-(3-fluoro-1-(oxetan-3-yl)piperidin-4-yl)-5-methyl-1H-indazole (enantiomer 2, 70 mg, 0.24 mmol), (R)-4-(6-iodo-2-methoxypyrimidin-4-yl)-3-methyl morpholine (100 mg, 0.30 mmol), CuI (95 mg, 0.5 mmol) and K$_3$PO$_4$ (106 mg, 0.5 mmol) in toluene (10 mL) was degassed and protected with N$_2$ before N,N-dimethyl-1,2-ethanediamine (44 mg, 0.5 mmol) was added. Then, the reaction mixture was stirred at 90° C. for 2 hours. The reaction mixture was diluted with EtOAc (50 mL) and washed with brine (50 mL). The organic solution was dried over anhydrous Na$_2$SO$_4$ and concentrated. The residue was purified by chromatography (EtOAc/PE=1/2~2/1) to give the desired product as a white solid. (65 mg, 55% yield).

E165 $^1$H NMR (400 MHz, CDCl$_3$): δ 8.88 (s, 1H), 8.07 (s, 1H), 7.54 (s, 1H), 6.81 (s, 1H), 4.92~4.79 (m, 1H), 4.72~4.63 (m, 4H), 4.48 (br, 1H), 4.14 (s, 3H), 4.14~3.99 (m, 2H), 3.81~3.58 (m, 4H), 3.34~3.08 (m, 3H), 2.81 (m, 1H), 2.48 (s, 3H), 2.11~1.85 (m, 4H), 1.35 (d, J=6.8 Hz, 3H).

$^{19}$F NMR (400 MHz, CDCl$_3$): δ -184.0 (s, 1F).

LC-MS (mobile phase: from 60% water (0.1% FA) and 40% CH$_3$CN (0.1% FA) to 5% water (0.1% FA) and 95% CH$_3$CN (0.1% FA) in 10 min, purity 98.0%, Rt=5.46 min; MS Calcd.: 496.3, MS Found: 497.9 (M+H)$^+$.

Chiral purity: Rt=11.471 min; ee %=98.8%.

Chiral method: Chiralpak AD-H 5 um 4.6*250 mm, Phase: Hexane: Isopropanol (0.2% diethylamine)=65/35, F: 1.0 mL/min, W: 214 nm, T: 25° C.

Example 166

(S)-4-(6-(6-(3-fluoro-1-(oxetan-3-yl)piperidin-4-yl)-5-methyl-1H-indazol-1-yl)-2-methoxypyrimidin-4-yl)-3-methylmorpholine (Diastereoisomer 1, E166)

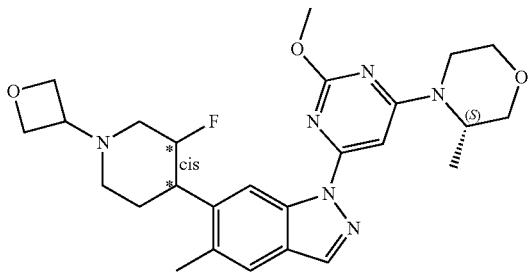

The mixture of 6-(3-fluoro-1-(oxetan-3-yl)piperidin-4-yl)-5-methyl-1H-indazole (enantiomer 1, 80 mg, 0.27 mmol), (S)-4-(6-iodo-2-methoxypyrimidin-4-yl)-3-methyl morpholine (102 mg, 0.30 mmol), CuI (103 mg, 0.54 mmol) and K$_3$PO$_4$ (115 mg, 0.54 mmol) in toluene (18 mL) was degassed and protected with N$_2$ before N,N-dimethyl-1,2-ethanediamine (48 mg, 0.54 mmol) was added. Then, the reaction mixture was stirred at 90° C. for 2 hours. The reaction mixture was diluted with EtOAc (2×100 mL) and washed with brine (150 mL). The organic solution was dried over anhydrous Na$_2$SO$_4$ and concentrated. The residue was purified by chromatography (EtOAc/PE=1/2~2/1) to give the desired product as a white solid. (75 mg, 55% yield).

E166 $^1$H NMR (400 MHz, CDCl$_3$): δ 8.88 (s, 1H), 8.07 (s, 1H), 7.54 (s, 1H), 6.81 (s, 1H), 4.92~4.79 (m, 1H), 4.72~4.63 (m, 4H), 4.48 (br, 1H), 4.14 (s, 3H), 4.14~3.99 (m, 2H), 3.81~3.58 (m, 4H), 3.34~3.08 (m, 3H), 2.81 (m, 1H), 2.48 (s, 3H), 2.11~1.85 (m, 4H), 1.35 (d, J=6.8 Hz, 3H).

$^{19}$F NMR (400 MHz, CDCl$_3$): δ -184.0 (s, 1F).

LC-MS (mobile phase: from 60% water (0.1% FA) and 40% CH$_3$CN (0.1% FA) to 5% water (0.1% FA) and 95% CH$_3$CN (0.1% FA) in 10 min, purity 99.2%, Rt=5.19 min; MS Calcd.: 496.3, MS Found: 497.8 (M+H)$^+$.

Chiral purity: Rt=7.349 min; ee %=99.8%.

Chiral method: Chiralpak AD-H 5 um 4.6*250 mm, Phase: Hexane: Isopropanol (0.2% diethylamine)=65/35, F: 1.0 mL/min, W: 214 nm, T: 25° C.

Example 167

(S)-4-(6-(6-(3-fluoro-1-(oxetan-3-yl)piperidin-4-yl)-5-methyl-1H-indazol-1-yl)-2-methoxypyrimidin-4-yl)-3-methylmorpholine (Diastereoisomer 2, E167)

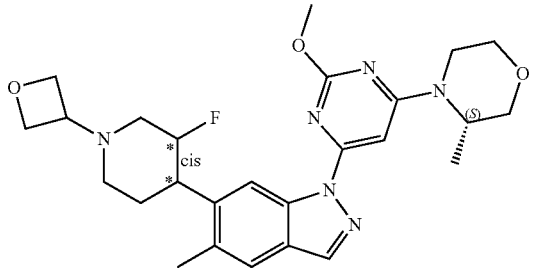

The mixture of 6-(3-fluoro-1-(oxetan-3-yl)piperidin-4-yl)-5-methyl-1H-indazole (enantiomer 2, 70 mg, 0.24 mmol), (S)-4-(6-iodo-2-methoxypyrimidin-4-yl)-3-methyl morpholine (100 mg, 0.30 mmol), CuI (95 mg, 0.5 mmol) and K$_3$PO$_4$ (106 mg, 0.5 mmol) in toluene (10 mL) was degassed and protected with N$_2$ before N,N-dimethyl-1,2-ethanediamine (44 mg, 0.5 mmol) was added. Then, the reaction mixture was stirred at 90° C. for 2 hours. The reaction mixture was diluted with EtOAc (50 mL) and washed with brine (50 mL). The organic solution was dried over anhydrous Na$_2$SO$_4$ and concentrated. The residue was purified by chromatography (EtOAc/PE=1/2~2/1) to give the desired product as a white solid. (60 mg, 50% yield).

E167 $^1$H NMR (400 MHz, CDCl$_3$): δ 8.88 (s, 1H), 8.07 (s, 1H), 7.54 (s, 1H), 6.81 (s, 1H), 4.92~4.79 (m, 1H), 4.72~4.63 (m, 4H), 4.48 (br, 1H), 4.14 (s, 3H), 4.14~3.99 (m, 2H), 3.81~3.58 (m, 4H), 3.34~3.08 (m, 3H), 2.81 (m, 1H), 2.48 (s, 3H), 2.11~1.85 (m, 4H), 1.35 (d, J=6.8 Hz, 3H).

$^{19}$F NMR (400 MHz, CDCl$_3$): δ -184.0 (s, 1F).

LC-MS (mobile phase: from 60% water (0.1% FA) and 40% CH$_3$CN (0.1% FA) to 5% water (0.1% FA) and 95% CH$_3$CN (0.1% FA) in 10 min, purity 98.5%, Rt=5.30 min; MS Calcd.: 496.3, MS Found: 497.9 (M+H)$^+$.

Chiral purity: Rt=10.125 min; ee %=99.1%.

Chiral method: Chiralpak AD-H 5 um 4.6*250 mm, Phase: Hexane: Isopropanol (0.2% diethylamine)=65/35, F: 1.0 mL/min, W: 214 nm, T: 25° C.

Example 168

6-(6-(6-(3-Fluoro-1-(oxetan-3-yl)piperidin-4-yl)-5-methyl-1H-indazol-1-yl)-2-methoxypyrimidin-4-yl)-2-oxa-6-azaspiro[3.4]octane (Enantiomer 1, E168)

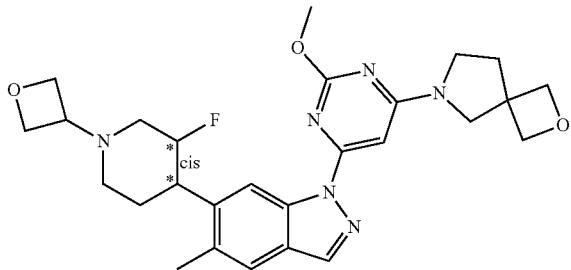 [SMILES: COc1nc(N2CCC3(COC3)C2)cc(-n2ncc3cc(C)c(C4CCN(C5COC5)CC4F)cc32)n1]

The mixture of 6-(3-fluoro-1-(oxetan-3-yl)piperidin-4-yl)-5-methyl-1H-indazole (enantiomer 1, 90 mg, 0.311 mmol), (R)-4-(6-iodo-2-methoxypyrimidin-4-yl)-3-methyl morpholine (118 mg, 0.342 mmol), CuI (118 mg, 0.622 mmol) and K$_3$PO$_4$ (132 mg, 0.622 mmol) in toluene (20 mL) was degassed and protected with N$_2$ before N,N-dimethyl-1,2-ethanediamine (55 mg, 0.622 mmol) was added. Then, the reaction mixture was stirred at 90° C. for 2 hours. The reaction mixture was diluted with EtOAc (2×100 mL) and washed with brine (150 mL). The organic solution was dried over anhydrous Na$_2$SO$_4$ and concentrated. The crude product was purified by chromatography (EtOAc/MeOH=10/1) to give the desired product as a white solid (110 mg, 69% yield). then further purified by Pre-HPLC (Waters 2767/Qda; Waters XBridge 30*150 mm 5 um; 20 ml/min; 214 nm/254 nm; Phase: ACN/H$_2$O (0.1% TFA)) to give the target product (72 mg) as a white solid.

E168 $^1$H NMR (400 MHz, CDCl$_3$): δ 8.89 (s, 1H), 8.08 (s, 1H), 7.54 (s, 1H), 6.61 (s, 1H), 4.95~4.81 (m, 1H), 4.80~4.62 (m, 8H), 4.15 (s, 3H), 3.88~3.62 (m, 5H), 3.24~3.11 (m, 2H), 2.84~2.81 (m, 1H), 2.48 (s, 3H), 2.34 (br, 2H), 2.11~1.87 (m, 4H).

$^{19}$F NMR (400 MHz, CDCl$_3$): δ −184.0 (s, 1F).

LC-MS (mobile phase: from 70% water (0.1% FA) and 30% CH$_3$CN (0.1% FA) to 5% water (0.1% FA) and 95% CH$_3$CN (0.1% FA) in 10 min, purity 99.7%, Rt=5.61 min; MS Calcd.: 508.3, MS Found: 509.7 (11/1+H)$^+$.

Chiral purity: Rt=28.440 min; ee %=99.9%.

Chiral method: Chiralpak AD-H 5 um 4.6*250 mm, Phase: Hexane: Isopropanol (0.2% diethylamine)=45/55, F: 0.6 mL/min, W: 214 nm, T: 25° C.

Example 169

6-(6-(6-(3-Fluoro-1-(oxetan-3-yl)piperidin-4-yl)-5-methyl-1H-indazol-1-yl)-2-methoxypyrimidin-4-yl)-2-oxa-6-azaspiro[3.4]octane (Enantiomer 2, E169)

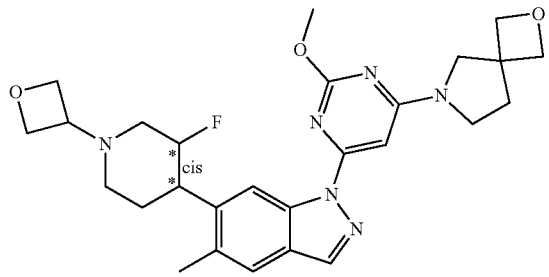 [SMILES: COc1nc(N2CCC3(COC3)C2)cc(-n2ncc3cc(C)c(C4CCN(C5COC5)CC4F)cc32)n1]

The mixture of 6-(3-fluoro-1-(oxetan-3-yl)piperidin-4-yl)-5-methyl-1H-indazole (enantiomer 2, 75 mg, 0.26 mmol), (S)-4-(6-iodo-2-methoxypyrimidin-4-yl)-3-methyl morpholine (107 mg, 0.31 mmol), CuI (100 mg, 0.52 mmol) and K$_3$PO$_4$ (110 mg, 0.52 mmol) in toluene (20 mL) was degassed and protected with N$_2$ before N,N-dimethyl-1,2-ethanediamine (46 mg, 0.52 mmol) was added. Then the reaction mixture was stirred at 90° C. for 2 hours. The reaction mixture was diluted with EtOAc (2×100 mL) and washed with brine (150 mL). The organic solution was dried over anhydrous Na$_2$SO$_4$ and concentrated. The residue was purified by chromatography (EtOAc/MeOH=10/1) to give the desired product (80 mg, 60% yield). then further purified by Pre-HPLC (Waters 2767/Qda; Waters XBridge 30*150 mm 5 um; 20 ml/min; 214 nm/254 nm; Phase: ACN/H$_2$O (0.1% TFA)) to give the target product (29 mg) as a white solid.

E169 $^1$H NMR (400 MHz, CDCl$_3$): δ 8.89 (s, 1H), 8.08 (s, 1H), 7.54 (s, 1H), 6.61 (s, 1H), 4.95~4.81 (m, 1H), 4.80~4.62 (m, 8H), 4.15 (s, 3H), 3.88~3.62 (m, 5H), 3.24~3.11 (m, 2H), 2.84~2.81 (m, 1H), 2.48 (s, 3H), 2.34 (br, 2H), 2.11~1.87 (m, 4H).

$^{19}$F NMR (400 MHz, CDCl$_3$): δ −184.0 (s, 1F).

LC-MS (mobile phase: from 60% water (0.1% FA) and 40% CH$_3$CN (0.1% FA) to 5% water (0.1% FA) and 95% CH$_3$CN (0.1% FA) in 10 min, purity 98.8%, Rt=3.45 min; MS Calcd.: 508.3, MS Found: 509.7 (M+H)$^+$.

Chiral purity: Rt=39.822 min; ee %=99.5%.

Chiral method: Chiralpak AD-H 5 um 4.6*250 mm, Phase: Hexane: Isopropanol (0.2% diethylamine)=45/55, F: 0.6 mL/min, W: 214 nm, T: 25° C.

Example 170

((R)-4-(6-(6-(3-fluoro-1-(oxetan-3-yl)piperidin-4-yl)-5-methyl-1H-indazol-1-yl)-2-methoxypyrimidin-4-yl)morpholin-2-yl)methanol (Diastereoisomer 1, E170)

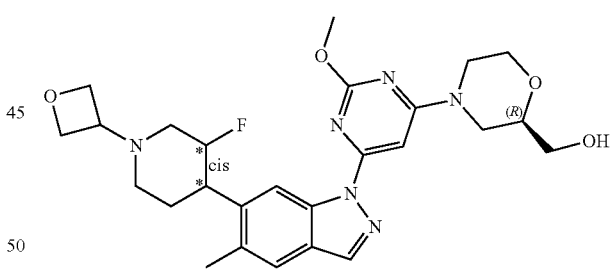

The mixture of 6-(3-fluoro-1-(oxetan-3-yl)piperidin-4-yl)-5-methyl-1H-indazole (enantiomer 1, 80 mg, 0.27 mmol), (R)-(4-(6-iodo-2-methoxy pyrimidin-4-yl)morpholin-2-yl)methanol (126 mg, 0.36 mmol), CuI (105 mg, 0.54 mmol) and K$_3$PO$_4$ (117 mg, 0.54 mmol) in toluene (15 mL) was degassed and protected with N$_2$ before N,N-dimethyl-1,2-ethanediamine (50 mg, 0.54 mmol) was added. Then, the reaction mixture was stirred at 90° C. for 2 hours. The reaction mixture was diluted with EtOAc (2×100 mL) and washed with brine (150 mL). The organic solution was dried over anhydrous Na$_2$SO$_4$ and concentrated. The residue was purified by Pre-HPLC to give the desired product as a white solid. (42 mg, 71% yield).

The crude product was purified by Pre-HPLC (Waters 2767/Qda; Sepax Amethyst 21.2*100 mm 5 um; 15 ml/min;

214 nm/254 nm; Phase: ACN/H₂O (0.1% TFA)) to give the desired product as a white solid. (42 mg, 71% yield)

E170 ¹H NMR (400 MHz, CDCl₃): δ 8.87 (s, 1H), 8.08 (s, 1H), 7.54 (s, 1H), 6.86 (s, 1H), 4.95~4.80 (m, 1H), 4.80~4.60 (m, 4H), 4.31~4.25 (br, 2H), 4.15 (s, 3H), 4.08~4.05 (m, 1H), 3.78~3.74 (m, 2H), 3.71~3.66 (m, 3H), 3.23~3.12 (m, 3H), 2.96~2.94 (m, 1H), 2.84~2.82 (m, 1H), 2.48 (s, 3H), 2.13~1.83 (m, 5H).

¹⁹F NMR (400 MHz, CDCl₃): δ −184.0 (s, 1F).

LC-MS (mobile phase: from 70% water (0.1% FA) and 30% CH₃CN (0.1% FA) to 5% water (0.1% FA) and 95% CH₃CN (0.1% FA) in 10 min, purity 97.6%, Rt=4.47 min; MS Calcd.: 512, MS Found: 513.9 (M+H)⁺.

Chiral purity: Rt=9.12 min; ee %=99.8%.

Chiral method: Chiralpak AD-H 5 um 4.6*250 mm, Phase: Hexane: Isopropanol (0.2% diethylamine)=65/35, F: 1.0 mL/min, W: 214 nm, T: 25° C.

Example 171

((R)-4-(6-(6-(3-fluoro-1-(oxetan-3-yl)piperidin-4-yl)-5-methyl-1H-indazol-1-yl)-2-methoxypyrimidin-4-yl)morpholin-2-yl)methanol (Diastereoisomer 2, E171)

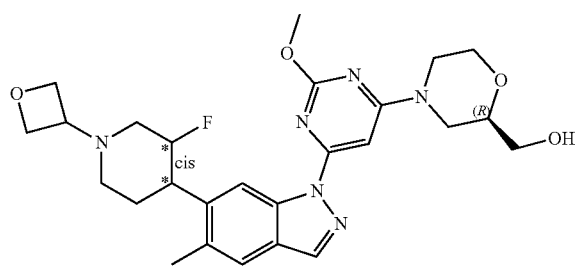

The mixture of 6-(3-fluoro-1-(oxetan-3-yl)piperidin-4-yl)-5-methyl-1H-indazole (enantiomer 2; 80 mg, 0.27 mmol), (R)-(4-(6-iodo-2-methoxy pyrimidin-4-yl)morpholin-2-yl)methanol (150 mg, 0.45 mmol), CuI (105 mg, 0.54 mmol) and K₃PO₄ (117 mg, 0.54 mmol) in toluene (15 mL) was degassed and protected with N₂ before N,N-dimethyl-1,2-ethanediamine (50 mg, 0.54 mmol) was added. Then, the reaction mixture was stirred at 90° C. for 2 hours. The reaction mixture was diluted with EtOAc (2×100 mL) and washed with brine (150 mL). The organic solution was dried over anhydrous Na₂SO₄ and concentrated. The residue was purified by Pre-HPLC (Waters 2767/Qda; Sepax Amethyst 21.2*100 mm 5 um; 15 ml/min; 214 nm/254 nm; Phase: ACN/H₂O (0.1% TFA)) to give the desired product as a white solid. (55 mg, 71% yield)

E171 ¹H NMR (400 MHz, CDCl₃): δ 8.87 (s, 1H), 8.08 (s, 1H), 7.54 (s, 1H), 6.86 (s, 1H), 4.95~4.80 (m, 1H), 4.80~4.60 (m, 4H), 4.31~4.25 (br, 2H), 4.15 (s, 3H), 4.08~4.05 (m, 1H), 3.78~3.74 (m, 2H), 3.71~3.66 (m, 3H), 3.23~3.12 (m, 3H), 2.96~2.94 (m, 1H), 2.84~2.82 (m, 1H), 2.48 (s, 3H), 2.13~1.83 (m, 5H).

¹⁹F NMR (400 MHz, CDCl₃): δ −184.0 (s, 1F).

LC-MS (mobile phase: from 70% water (0.1% FA) and 30% CH₃CN (0.1% FA) to 5% water (0.1% FA) and 95% CH₃CN (0.1% FA) in 10 min, purity 95%, Rt=4.62 min; MS Calcd.: 512, MS Found: 513.9 (M+H)⁺.

Chiral purity: Rt=12.15 min; ee %=99.5%.

Chiral method: Chiralpak AD-H 5 um 4.6*250 mm, Phase: Hexane: Isopropanol (0.2% diethylamine)=65/35, F: 1.0 mL/min, W: 214 nm, T: 25° C.

Example 172

((S)-4-(6-(6-(3-fluoro-1-(oxetan-3-yl)piperidin-4-yl)-5-methyl-1H-indazol-1-yl)-2-methoxypyrimidin-4-yl)morpholin-2-yl)methanol (Diastereoisomer 1, E172)

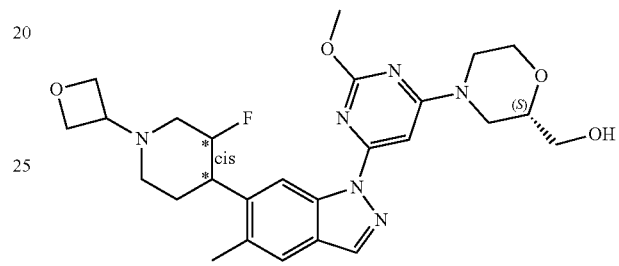

The mixture of 6-(3-fluoro-1-(oxetan-3-yl)piperidin-4-yl)-5-methyl-1H-indazole (enantiomer 1, 80 mg, 0.27 mmol), (S)-(4-(6-iodo-2-methoxy pyrimidin-4-yl)morpholin-2-yl)methanol (150 mg, 0.45 mmol), CuI (105 mg, 0.54 mmol) and K₃PO₄ (117 mg, 0.54 mmol) in toluene (15 mL) was degassed and protected with N₂ before N,N-dimethyl-1,2-ethanediamine (50 mg, 0.54 mmol) was added. Then, the reaction mixture was stirred at 90° C. for 2 hours. The reaction mixture was diluted with EtOAc (2×100 mL) and washed with brine (150 mL). The organic solution was dried over anhydrous Na₂SO₄ and concentrated. The residue was purified by Pre-HPLC (Waters 2767/Qda; Waters XBridge 30*150 mm 5 um; 20 ml/min; 214 nm/254 nm; Phase: ACN/H₂O (0.1% TEA)) to give the desired product as a white solid. (57 mg, 75% yield).

E172 ¹H NMR (400 MHz, CDCl₃): δ 8.87 (s, 1H), 8.08 (s, 1H), 7.54 (s, 1H), 6.86 (s, 1H), 4.95~4.80 (m, 1H), 4.80~4.60 (m, 4H), 4.31~4.25 (br, 2H), 4.15 (s, 3H), 4.08~4.05 (m, 1H), 3.78~3.74 (m, 2H), 3.71~3.66 (m, 3H), 3.23~3.12 (m, 3H), 2.96~2.94 (m, 1H), 2.84~2.82 (m, 1H), 2.48 (s, 3H), 2.13~1.83 (m, 5H).

¹⁹F NMR (400 MHz, CDCl₃): δ −184.0 (s, 1F).

LC-MS (mobile phase: from 70% water (0.1% FA) and 30% CH₃CN (0.1% FA) to 5% water (0.1% FA) and 95% CH₃CN (0.1% FA) in 10 min, purity 95%, Rt=4.52 min; MS Calcd.: 512, MS Found: 513.9 (M+H)⁺.

Chiral purity: Rt=10.09 min; ee %=99.8%.

Chiral method: Chiralpak AD-H 5 um 4.6*250 mm, Phase: Hexane: Isopropanol (0.2% diethylamine)=65/35, F: 1.0 mL/min, W: 214 nm, T: 25° C.

Example 173

((S)-4-(6-(6-(3-fluoro-1-(oxetan-3-yl)piperidin-4-yl)-5-methyl-1H-indazol-1-yl)-2-methoxypyrimidin-4-yl)morpholin-2-yl)methanol (Diastereoisomer 2, E173)

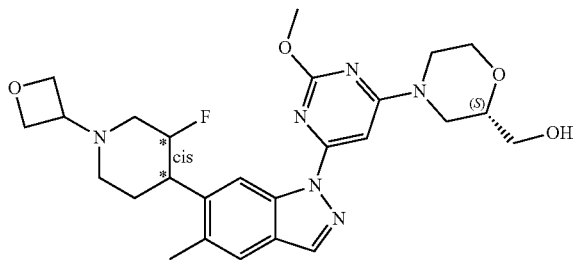

The mixture of 6-(3-fluoro-1-(oxetan-3-yl)piperidin-4-yl)-5-methyl-1H-indazole (enantiomer 2; 50 mg, 0.17 mmol), (S)-(4-(6-iodo-2-methoxy pyrimidin-4-yl)morpholin-2-yl)methanol (120 mg, 0.34 mmol), CuI (66 mg, 0.35 mmol) and $K_3PO_4$ (73 mg, 0.35 mmol) in toluene (15 mL) was degassed and protected with $N_2$ before N,N-dimethyl-1,2-ethanediamine (31 mg, 0.35 mmol) was added. Then, the reaction mixture was stirred at 90° C. for 2 hours. The reaction mixture was diluted with EtOAc (2×100 mL) and washed with brine (150 mL). The organic solution was dried over anhydrous $Na_2SO_4$ and concentrated.

The residue was purified by Pre-HPLC (Waters 2767/Qda; Waters XBridge 30*150 mm 5 um; 20 ml/min; 214 nm/254 nm; Phase: ACN/$H_2O$ (0.1% TFA)) to give the desired product as a white solid. (26 mg, 50% yield).

E173 $^1$H NMR (400 MHz, $CDCl_3$): δ 8.87 (s, 1H), 8.08 (s, 1H), 7.54 (s, 1H), 6.86 (s, 1H), 4.95~4.80 (m, 1H), 4.80~4.60 (m, 4H), 4.31~4.25 (br, 2H), 4.15 (s, 3H), 4.08~4.05 (m, 1H), 3.78~3.74 (m, 2H), 3.71~3.66 (m, 3H), 3.23~3.12 (m, 3H), 2.96~2.94 (m, 1H), 2.84~2.82 (m, 1H), 2.48 (s, 3H), 2.13~1.83 (m, 5H).

$^{19}$F NMR (400 MHz, $CDCl_3$): δ −184.0 (s, 1F).

LC-MS (mobile phase: from 70% water (0.1% FA) and 30% $CH_3CN$ (0.1% FA) to 5% water (0.1% FA) and 95% $CH_3CN$ (0.1% FA) in 10 min, purity 95%, Rt=4.48 min; MS Calcd.: 512, MS Found: 513.9 $(M+H)^+$.

Chiral purity: Rt=12.80 min; ee %=99.3%.

Chiral method: Chiralpak AD-H 5 um 4.6*250 mm, Phase: Hexane: Isopropanol (0.2% diethylamine)=65/35, F: 1.0 mL/min, W: 214 nm, T: 25° C.

Example 174

((R)-4-(6-(6-(3-fluoro-1-(oxetan-3-yl)piperidin-4-yl)-5-methyl-1H-indazol-1-yl)-2-methylpyrimidin-4-yl)morpholin-2-yl)methanol (Diastereoisomer 1, E174)

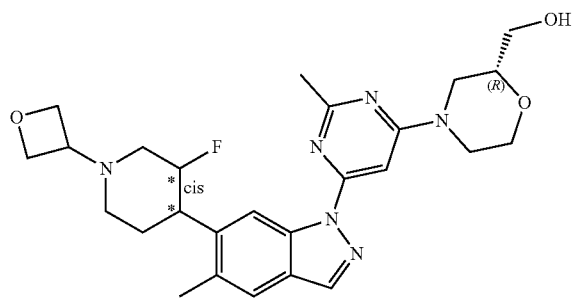

To a suspension of 6-(3-fluoro-1-(oxetan-3-yl)piperidin-4-yl)-5-methyl-1H-indazole (enantiomer 1, 80 mg, 0.28 mmol), (R)-(4-(6-iodo-2-methylpyrimidin-4-yl)morpholin-2-yl)methanol (111 mg, 0.33 mmol), CuI (54 mg, 0.28 mmol) and $K_3PO_4$ (119 mg, 0.56 mmol) in dry toluene (10 mL) was added N,N-dimethyl-1,2-ethanediamine (50 mg, 0.56 mmol). The mixture was stirred at 90° C. for 2 hrs under $N_2$. The reaction mixture was poured into water (100 mL), extracted with EtOAc (50 mL×3). The combined organic layers were washed with brine (50 mL), dried over anhydrous $Na_2SO_4$ and concentrated to dryness. The residue was purified by silica gel chromatography eluted with (EtOAc:petroleum ether=1:5~1:0) to give the desired product ((R)-4-(6-(6-(3-fluoro-1-(oxetan-3-yl)piperidin-4-yl)-5-methyl-1H-indazol-1-yl)-2-methylpyrimidin-4-yl)morpholin-2-yl)methanol (diastereoisomer 1) (50 mg, 36.5% yield) as a white solid.

E174 $^1$H NMR (400 MHz, $CDCl_3$): δ 8.90 (s, 1H), 8.07 (s, 1H), 7.53 (s, 1H), 6.97 (s, 1H), 4.97~4.82 (m, 1H), 4.75~4.67 (m, 4H), 4.31 (t, J=11.2 Hz, 2H), 4.09 (d, J=9.2, 2.0 Hz, 1H), 3.81~3.60 (m, 5H), 3.30~3.23 (m, 1H), 3.16~3.06 (m, 2H), 2.98~2.85 (m, 2H), 2.66 (s, 3H), 2.48 (s, 3H), 2.15~2.19 (m, 5H).

$^{19}$F NMR (376 MHz, $CDCl_3$): δ −183.96 (s, 1F).

LC-MS (mobile phase: from 90% water (0.1% FA) and 10% $CH_3CN$ (0.1% FA) to 5% water (0.1% FA) and 95% $CH_3CN$ (0.1% FA) in 10 min, purity 98.6%, Rt=5.62 min; MS Calcd.: 496.6, MS Found: 497.8 $(M+H)^+$.

Chiral purity: Rt=6.170 min; ee %=99.7%.

Chiral method: Chiralpak AD-H 5 um 4.6*250 mm, Phase: Hexane: Isopropanol (0.2% diethylamine)=65/35, F: 1.0 mL/min, W: 214 nm, T: 25° C.

Example 175

((R)-4-(6-(6-(3-fluoro-1-(oxetan-3-yl)piperidin-4-yl)-5-methyl-1H-indazol-1-yl)-2-methylpyrimidin-4-yl)morpholin-2-yl)methanol (Diastereoisomer 2, E175)

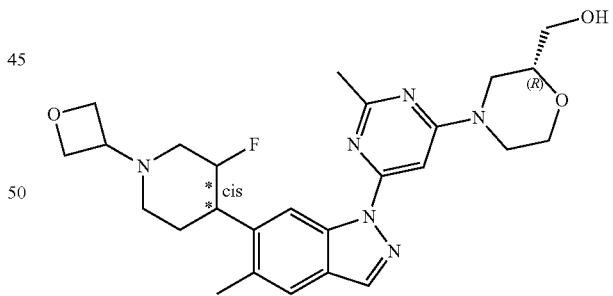

To a suspension of 6-(3-fluoro-1-(oxetan-3-yl)piperidin-4-yl)-5-methyl-1H-indazole (enantiomer 2, 80 mg, 0.28 mmol), (R)-(4-(6-iodo-2-methylpyrimidin-4-yl)morpholin-2-yl)methanol (111 mg, 0.33 mmol), CuI (54 mg, 0.28 mmol) and $K_3PO_4$ (119 mg, 0.56 mmol) in dry toluene (10 mL) was added N,N-dimethyl-1,2-ethanediamine (50 mg, 0.56 mmol). The mixture was stirred at 90° C. for 2 hrs under $N_2$. The reaction mixture was poured into water (100 mL), extracted with EtOAc (50 mL×3). The combined organic layers were washed with brine (50 mL), dried over anhydrous $Na_2SO_4$ and concentrated to dryness. The crude product was purified by silica gel chromatography eluted with (EtOAc:petroleum ether=1:5~1:0) to give the desired product ((R)-4-(6-(6-(3-fluoro-1-(oxetan-3-yl)piperidin-4-yl)-5-methyl-1H-indazol-1-yl)-2-methylpyrimidin-4-yl)morpholin-2-yl)methanol (diastereoisomer 2) (65 mg, 47.3% yield) as a white solid.

E175 $^1$H NMR (400 MHz, CDCl$_3$): δ 8.90 (s, 1H), 8.07 (s, 1H), 7.53 (s, 1H), 6.97 (s, 1H), 4.97~4.82 (m, 1H), 4.75~4.67 (m, 4H), 4.31 (t, J=11.2 Hz, 2H), 4.09 (d, J=9.2, 2.0 Hz, 1H), 3.81~3.60 (m, 5H), 3.30~3.23 (m, 1H), 3.16~3.06 (m, 2H), 2.98~2.85 (m, 2H), 2.66 (s, 3H), 2.48 (s, 3H), 2.15~2.19 (m, 5H).

$^{19}$F NMR (376 MHz, CDCl$_3$): δ −183.96 (s, 1F).

LC-MS (mobile phase: from 90% water (0.1% FA) and 10% CH$_3$CN (0.1% FA) to 5% water (0.1% FA) and 95% CH$_3$CN (0.1% FA) in 10 min, purity 98.6%, Rt=5.47 min; MS Calcd.: 496.6, MS Found: 497.8 (M+H)$^+$.

Chiral purity: Rt=7.247 min; ee %=99.3%.

Chiral method: Chiralpak AD-H 5 um 4.6*250 mm, Phase: Hexane: Isopropanol (0.2% diethylamine)=65/35, F: 1.0 mL/min, W: 214 nm, T: 25° C.

Example 176

((S)-4-(6-(6-(3-fluoro-1-(oxetan-3-yl)piperidin-4-yl)-5-methyl-1H-indazol-1-yl)-2-methylpyrimidin-4-yl)morpholin-2-yl)methanol (Diastereoisomer 1, E176)

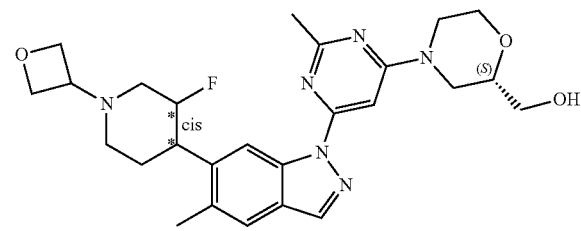

To a suspension of 6-((3S,4R)-3-fluoro-1-(oxetan-3-yl)piperidin-4-yl)-5-methyl-1H-indazole (enantiomer 1, 70 mg, 0.24 mmol), (S)-(4-(6-iodo-2-methylpyrimidin-4-yl)morpholin-2-yl)methanol (97 mg, 0.29 mmol), CuI (46 mg, 0.24 mmol) and K$_3$PO$_4$ (108 mg, 0.51 mmol) in dry toluene (5 mL) was added N,N-dimethyl-1,2-ethanediamine (43 mg, 0.48 mmol). The suspension was degassed with N$_2$ and stirred at 90° C. for 2 hr. EtOAc (50 mL) was added and the resulting mixture was washed with brine (2×40 mL), dried over anhydrous Na$_2$SO$_4$ and concentrated under reduced pressure. The residue was purified by pre-HPLC (Waters 2767/Qda, Waters XBridge 30*150 mm 5 urn, Phase: MeCN/H$_2$O (0.1%0NH$_3$): 10%~95%, Flow rate: 20 mL/min, 214 nm/254 nm) to give product (74 mg, yield 61.6%) as a white solid.

E176 $^1$H NMR (400 MHz, CDCl$_3$): δ 8.90 (s, 1H), 8.07 (s, 1H), 7.54 (s, 1H), 6.97 (s, 1H), 5.00~4.82 (m, 1H), 4.75~4.67 (m, 4H), 4.31 (t, J=11.2 Hz, 2H), 4.09 (dd, J=11.2, 2.0 Hz, 1H), 3.81~3.60 (m, 5H), 3.30~3.23 (m, 1H), 3.16~3.06 (m, 2H), 2.99 (dd, J=13.2, 10.8 Hz, 1H), 2.88 (d, J=10.4 Hz, 1H), 2.66 (s, 3H), 2.48 (s, 3H), 2.15-2.19 (m, 5H).

$^{19}$F NMR (376 MHz, CDCl$_3$): δ −183.96 (s, 1F).

LC-MS (mobile phase: from 90% water (0.1% FA) and 10% CH$_3$CN (0.1% FA) to 5% water (0.1% FA) and 95% CH$_3$CN (0.1% FA) in 10 min, purity 98.6%, Rt=5.56 min; MS Calcd.: 496.6, MS Found: 497.8 (M+H)$^+$.

Chiral purity: Rt=8.071 min; ee %=99.7%.

Chiral method: Chiralpak AD-H 5 um 4.6*250 mm, Phase: Hexane: Isopropanol (0.2% diethylamine)=65/35, F: 1.0 mL/min, W: 214 nm, T: 25° C.

Example 177

((S)-4-(6-(6-((3-fluoro-1-(oxetan-3-yl)piperidin-4-yl)-5-methyl-1H-indazol-1-yl)-2-methylpyrimidin-4-yl)morpholin-2-yl)methanol (Diastereoisomer 2, E177)

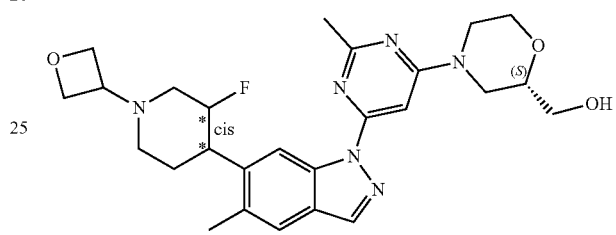

To a suspension of 6-((cis)-3-fluoro-1-(oxetan-3-yl)piperidin-4-yl)-5-methyl-1H-indazole (enantiomer 2, 70 mg, 0.24 mmol), (S)-(4-(6-iodo-2-methylpyrimidin-4-yl)morpholin-2-yl)methanol (97 mg, 0.29 mmol), CuI (46 mg, 0.24 mmol) and K$_3$PO$_4$ (108 mg, 0.51 mmol) in dry toluene (5 mL) was added N,N-dimethyl-1,2-ethanediamine (43 mg, 0.48 mmol). The suspension was degassed with N$_2$ and stirred at 90° C. for 2 h. EtOAc (50 mL) was added and the resulting mixture was washed with brine (2×50 mL), dried over anhydrous Na$_2$SO$_4$ and concentrated under reduced pressure. The residue was purified by pre-HPLC (Waters 2767/Qda, Waters XBridge 30*150 mm 5 urn, Phase: MeCN/H$_2$O (0.1% NH$_3$): 10%~95%, Flow rate: 20 mL/min, 214 nm/254 nm) to give product (80 mg, yield 66.6%) as a white solid.

E177 $^1$H NMR (400 MHz, CDCl$_3$): δ 8.90 (s, 1H), 8.07 (s, 1H), 7.54 (s, 1H), 6.97 (s, 1H), 5.00~4.82 (m, 1H), 4.73~4.66 (m, 4H), 4.31 (t, J=12.0 Hz, 2H), 4.09 (dd, J=12.0, 2.0 Hz, 1H), 3.81~3.63 (m, 5H), 3.30~3.25 (m, 1H), 3.16~3.09 (m, 2H), 2.99 (dd, J=12.8, 10.0 Hz, 1H), 2.88 (d, J=10.4 Hz, 1H), 2.66 (s, 3H), 2.48 (s, 3H), 2.15~2.18 (m, 5H).

$^{19}$F NMR (376 MHz, CDCl$_3$): δ −183.96 (s, 1F).

LC-MS (mobile phase: from 90% water (0.1% FA) and 10% CH$_3$CN (0.1% FA) to 5% water (0.1% FA) and 95% CH$_3$CN (0.1% FA) in 10 min, purity 98.6%, Rt=5.57 min; MS Calcd.: 496.6, MS Found: 497.8 (M+H)$^+$.

Chiral purity: Rt=8.963 min; ee %=99.3%.

Chiral method: Chiralpak AD-H 5 um 4.6*250 mm, Phase: Hexane: Isopropanol (0.2% diethylamine)=65/35, F: 1.0 mL/min, W: 214 nm, T: 25° C.

Example 178

1-(6-(6-((cis)-3-Fluoro-1-(oxetan-3-yl)piperidin-4-yl)-5-methyl-1H-indazol-1-yl)-2-methylpyrimidin-4-yl)-3-methylazetidin-3-ol (Enantiomer 1, E178)

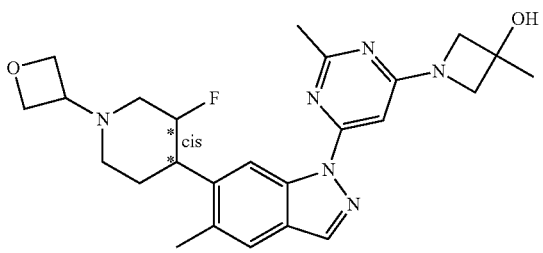 [SMILES: Cc1nc(N2CC(C)(O)C2)cc(-n2ncc3cc(C)c(C4CCN(C5COC5)CC4F)cc32)n1]

$N^1,N^2$-dimethylethane-1,2-diamine (31 mg, 0.35 mmol) was added to a solution of 1-(6-iodo-2-methoxypyrimidin-4-yl)-3-methylazetidin-3-ol (53 mg, 0.17 mmol), 6-((cis)-3-fluoro-1-(oxetan-3-yl)piperidin-4-yl)-5-methyl-1H-indazole (enantiomer 1, 50 mg, 0.17 mmol), CuI (32 mg, 0.17 mmol) and $K_3PO_4$ (74 mg, 0.35 mmol) in toluene (5 mL) under Ar. The reaction was stirred at 100° C. for 3h. The mixture was filtered, concentrated and purified by column (DCM:MeOH=50:1) to give product as a white solid (20 mg, yield 27.3%).

E178 $^1$H NMR (400 MHz, DMSO-$d_6$): δ 8.83 (s, 1H), 8.34 (s, 1H), 7.66 (s, 1H), 6.57 (s, 1H), 5.74 (s, 1H), 4.88-4.75 (md, J=48.0 Hz, 1H), 4.59-4.50 (m, 4H), 3.99-3.96 (d, J=8.8 Hz, 2H), 3.92-3.90 (d, J=8.4 Hz, 2H), 3.61-3.60 (m, 1H), 3.26-3.25 (m, 1H), 3.14-3.12 (m, 1H), 2.82-2.79 (m, 1H), 2.53 (s, 3H), 2.43 (s, 3H), 2.09-1.91 (m, 3H), 1.71-1.62 (q, 1H), 1.45 (s, 3H).

LC-MS (mobile phase: from 80% water (0.1% FA) and 20% $CH_3CN$ (0.1% FA), Rt=4.49 min; MS Calcd.: 466.6; MS Found: 467.6[M+H]$^+$.

Example 179

1-(6-(6-((cis)-3-Fluoro-1-(oxetan-3-yl)piperidin-4-yl)-5-methyl-1H-indazol-1-yl)-2-methylpyrimidin-4-yl)-3-methylazetidin-3-ol (Diastereoisomer 2, E179)

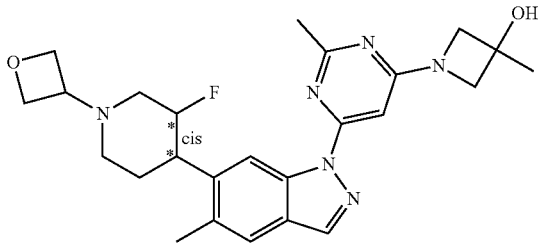 [SMILES: Cc1nc(N2CC(C)(O)C2)cc(-n2ncc3cc(C)c(C4CCN(C5COC5)CC4F)cc32)n1]

$N^1,N^2$-dimethylethane-1,2-diamine (31 mg, 0.35 mmol) was added to a solution of 1-(6-iodo-2-methoxypyrimidin-4-yl)-3-methylazetidin-3-ol (53 mg, 0.17 mmol), 6-((cis)-3-fluoro-1-(oxetan-3-yl)piperidin-4-yl)-5-methyl-1H-indazole (enantiomer 2, 50 mg, 0.17 mmol), CuI (32 mg, 0.17 mmol) and $K_3PO_4$ (74 mg, 0.35 mmol) in toluene (5 mL) under Ar. The reaction was stirred at 100° C. for 3h. The mixture was filtered and concentrated. Purified by column (DCM:MeOH=50:1) to give product as a white solid (30 mg, yield 37.2%).

E179 $^1$H NMR (400 MHz, DMSO-$d_6$): δ 8.83 (s, 1H), 8.34 (s, 1H), 7.66 (s, 1H), 6.57 (s, 1H), 5.74 (s, 1H), 4.88-4.75 (md, J=48 Hz, 1H), 4.59-4.50 (m, 4H), 3.99-3.97 (d, J=8.4 Hz, 2H), 3.92-3.90 (d, J=8.4 Hz, 2H), 3.61-3.60 (m, 1H), 3.27-3.26 (m, 1H), 3.14-3.12 (m, 1H), 2.82-2.79 (m, 1H), 2.53 (s, 3H), 2.43 (s, 3H), 2.09-1.92 (m, 3H), 1.71-1.62 (q, 1H), 1.45 (s, 3H).

LC-MS (mobile phase: from 80% water (0.1% FA) and 20% $CH_3CN$ (0.1% FA), Rt=4.91 min; MS Calcd.: 466.6; MS Found: 467.5[M+H]$^+$.

Example 180

1-(6-(6-((cis)-3-Fluoro-1-(oxetan-3-yl)piperidin-4-yl)-5-methyl-1H-indazol-1-yl)-2-methoxypyrimidin-4-yl)-3-methylazetidin-3-ol (Enantiomer 1, E180)

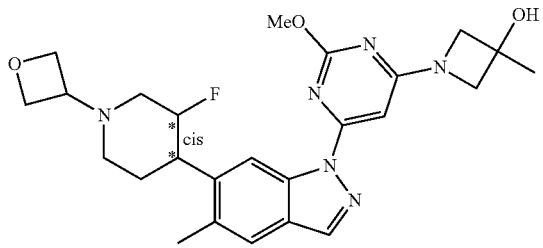 [SMILES: COc1nc(N2CC(C)(O)C2)cc(-n2ncc3cc(C)c(C4CCN(C5COC5)CC4F)cc32)n1]

$N^1,N^2$-dimethylethane-1,2-diamine (18 mg, 0.2 mmol) was added to a solution of 1-(6-iodo-2-methoxypyrimidin-4-yl)-3-methylazetidin-3-ol (33 mg, 0.1 mmol), 6-((cis)-3-fluoro-1-(oxetan-3-yl)piperidin-4-yl)-5-methyl-1H-indazole (enantiomer 1, 30 mg, 0.1 mmol), CuI (19 mg, 0.1 mmol) and $K_3PO_4$ (44 mg, 0.2 mmol) in toluene (2 mL) under Ar. The reaction was stirred at 100° C. for 3 h. The mixture was filtered, concentrated and then purified by column (DCM:MeOH=50:1) to give product as a white solid (21 mg, yield 42%).

E180 $^1$H NMR (400 MHz, $CDCl_3$): δ 8.83 (s, 1H), 8.40 (s, 1H), 7.72 (s, 1H), 6.49 (s, 1H), 5.82 (s, 1H), 4.76, 4.77, 4.88, 4.89 (dd, $J_1$=4 Hz, $J_2$=3.6 Hz, 1H), 4.52~4.65 (m, 4H), 4.96~4.06 (m, 6H), 3.63, 3.65, 3.66 (t, J=6 Hz, 1H), 3.16~3.28 (m, 2H), 2.84, 3.16 (d, J=9.6 Hz, 1H), 2.48 (s, 3H), 1.96~2.14 (m, 3H), 1.68, 1.71 (d, J=7.2 Hz, 1H), 1.50 (s, 3H).

LC-MS (mobile phase: from 80% water (0.1% FA) and 20% $CH_3CN$ (0.1% FA), Rt=4.25 min; MS Calcd.: 482.2; MS Found: 483.3 [M+H]$^+$.

Example 181

1-(6-(6-((cis)-3-Fluoro-1-(oxetan-3-yl)piperidin-4-yl)-5-methyl-1H-indazol-1-yl)-2-methoxypyrimidin-4-yl)-3-methylazetidin-3-ol (Diastereoisomer 2, E181)

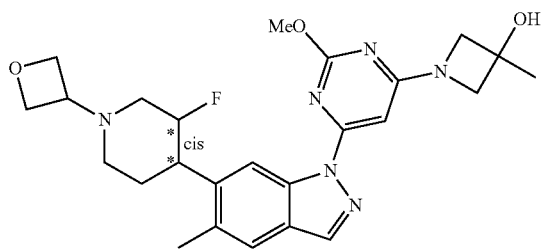 [SMILES: COc1nc(N2CC(C)(O)C2)cc(-n2ncc3cc(C)c(C4CCN(C5COC5)CC4F)cc32)n1]

N1,N2-dimethylethane-1,2-diamine (31 mg, 0.35 mmol) was added to a solution of 1-(6-iodo-2-methoxypyrimidin-4-yl)-3-methylazetidin-3-ol (53 mg, 0.17 mmol), 6-((cis)-3-fluoro-1-(oxetan-3-yl)piperidin-4-yl)-5-methyl-1H-indazole (enantiomer 2, 50 mg, 0.17 mmol), CuI (32 mg, 0.17 mmol) and $K_3PO_4$ (74 mg, 0.35 mmol) in toluene (5 mL) under Ar. The reaction was stirred at 100° C. for 3h. The mixture was filtered and concentrated. Purified by column (DCM: MeOH=50:1) to give product as a white solid (21 mg, yield 42%).

E181 $^1$H NMR (400 MHz, CDCl$_3$): δ 8.83 (s, 1H), 8.40 (s, 1H), 7.72 (s, 1H), 6.49 (s, 1H), 5.82 (s, 1H), 4.76, 4.77, 4.88, 4.89 (dd, J$_1$=4 Hz, J$_2$=3.6 Hz, 1H), 4.52~4.65 (m, 4H), 4.96~4.06 (m, 6H), 3.63, 3.65, 3.66 (t, J=6 Hz, 1H), 3.16~3.28 (m, 2H), 2.84, 3.16 (d, J=9.6 Hz, 1H), 2.48 (s, 3H), 1.96~2.14 (m, 3H), 1.68, 1.71 (d, J=7.2 Hz, 1H), 1.50 (s, 3H).

LC-MS (mobile phase: from 80% water (0.1% FA) and 20% CH$_3$CN (0.1% FA), Rt=5.93 min; MS Calcd.: 482.2; MS Found: 483.5 [M+H]$^+$.

Example 182

(R)-(4-(2-Methyl-6-(5-methyl-6-(1-(oxetan-3-yl)piperidin-4-yl)-1H-indazol-1-yl)pyrimidin-4-yl)morpholin-2-yl)methanol (E182)

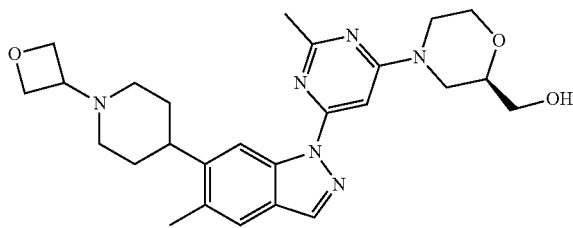 [SMILES: Cc1nc(N2CCO[C@@H](CO)C2)cc(-n2ncc3cc(C)c(C4CCN(C5COC5)CC4)cc32)n1]

To a solution of (R)-(4-(2-methyl-6-(5-methyl-6-(piperidin-4-yl)-1H-indazol-1-yl)pyrimidin-4-yl)morpholin-2-yl)methanol hydrochloride (119 mg crude, 0.194 mmol) in methanol (1 mL) was added 1,2-dichloro-ethane (15 mL) and oxetan-3-one (0.5 mL) at rt. After stirred for 30 min NaBH$_3$CN (82 mg, 1.30 mmol) was added and the resulting mixture stirred at rt for 2 hrs. To the mixture was added sat. Na$_2$CO$_3$ (20 mL) and stirred for 10 min. The mixture was extracted with DCM (50 mL×3) and the combined organic layers were washed with brine, dried over Na$_2$SO$_4$ and concentrated. The residue was purified by prep-TLC (CH$_2$Cl$_2$: CH$_3$OH=15:1) to give the title compound (39 mg, yield 31%) as white solid.

E182 $^1$H NMR (300 MHz, CDCl$_3$): δ 8.80 (s, 1H), 8.05 (s, 1H), 7.50 (s, 1H), 6.95 (s, 1H), 4.73-4.71 (m, 4H), 4.33-4.27 (m, 2H), 4.10-4.04 (m, 1H), 3.78-3.60 (m, 4H), 3.60-3.55 (m, 1H), 3.17-3.07 (m, 1H), 3.00-2.94 (m, 3H), 2.87-2.81 (m, 1H), 2.65 (s, 3H), 2.45 (s, 3H), 2.05-1.91 (m, 7H).

LC-MS (XB-C18, ¢4.6*50 mm*5 um; mobile phase: from 95% water (0.02% NH$_4$OAc) and 5% CH$_3$CN to 5% water (0.02% NH$_4$OAc) and 95% CH$_3$CN in 6.5 min), purity is >95%, Rt=4.057 min; MS Calcd: 478; MS Found: 479 (M+H)$^+$.

Chiral condition: Chiralpak AS-H 5 um 4.6*250 mm; Phase: Hex:EtOH=80:20:0.2; F: 1 mL/min, W: 230 nm; T: 30° C.; Rt=7.732 min, 100% ee.

Example 183

(S)-(4-(2-Methyl-6-(5-methyl-6-(1-(oxetan-3-yl)piperidin-4-yl)-1H-indazol-1-yl)pyrimidin-4-yl)morpholin-2-yl)methanol (E183)

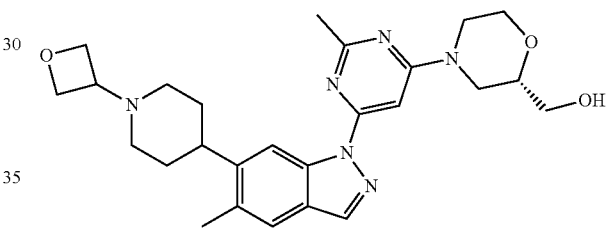

To a solution of tert-butyl 4-(5-methyl-1-(2-methyl-6-((2S)-2-(((tetrahydro-2H-pyran-2-yl)oxy)methyl)morpholino)pyrimidin-4-yl)-1H-indazol-6-yl)piperidine-1-carboxylate (118 mg, 0.194 mmol) in dioxane (4 mL) was added HCl/dioxane (4 M, 4 mL). The reaction mixture was stirred at rt for 1 h. The reaction mixture was concentrated. The crude was dissolved in CH$_3$OH (0.2 mL) and then oxetan-3-one (1 mL) and 1,2-dichloroethane (3 mL) was added. After stirred at rt for 30 min NaBH$_3$CN (90 mg, 1.4 mmol) was added to the mixture. The resulting mixture stirred at rt for 2 hrs. The mixture was washed with Na$_2$CO$_3$ (20 mL) and extracted with DCM (50 mL×3). The combined organic layers were washed with brine, dried over Na$_2$SO$_4$ and concentrated. The crude was purified by prep-HPLC to give the title compound (21.4 mg, yield 22%) as white solid.

E183 $^1$H NMR (300 MHz, CDCl$_3$): δ 8.80 (s, 1H), 8.05 (s, 1H), 7.50 (s, 1H), 6.95 (s, 1H), 4.72-4.70 (m, 4H), 4.33-4.29 (m, 2H), 4.08-4.04 (m, 1H), 3.80-3.65 (m, 4H), 3.58-3.54 (m, 1H), 3.16-3.08 (m, 1H), 2.98-2.91 (m, 3H), 2.86-2.81 (m, 1H), 2.65 (s, 3H), 2.45 (s, 3H), 2.07-1.93 (m, 7H).

LC-MS (XB-C18, ¢4.6*50 mm*5 um; mobile phase: from 95% water (0.02% NH$_4$OAc) and 5% CH$_3$CN to 5% water (0.02% NH$_4$OAc) and 95% CH$_3$CN in 6.5 min), purity is >95%, Rt=4.056 min; MS Calcd: 478; MS Found: 479 (M+H)$^+$.

Chiral condition: Chiralpak AS-H 5 um 4.6*250 mm; Phase: Hex:EtOH=80:20; F: 1 mL/min, W: 230 nm; T: 30° C.; Rt=8.662 min, 100% ee.

Example 184

1-(2-Methyl-6-(5-methyl-6-(1-(oxetan-3-yl)piperidin-4-yl)-1H-indazol-1-yl)pyrimidin-4-yl)azetidin-3-ol (E184)

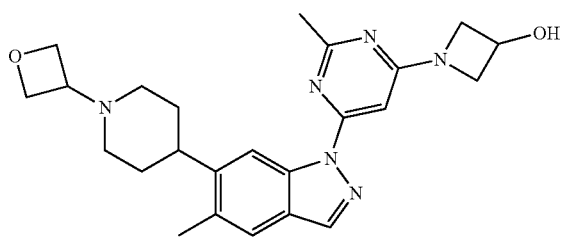 [SMILES: Cc1nc(N2CC(O)C2)cc(-n2ncc3cc(C)c(C4CCN(C5COC5)CC4)cc32)n1]

To a solution of 5-methyl-1-(2-methyl-6-(3-((tetrahydro-2H-pyran-2-yl)oxy)azetidin-1-yl)pyrimidin-4-yl)-6-(1-(oxetan-3-yl)piperidin-4-yl)-1H-indazole (100 mg, 0.193 mmol) in methanol (5 mL) was added TsOH (17 mg, 0.097 mmol) at room temperature. Then, the mixture was stirred at room temperature for 16 hrs. The reaction mixture was cooled to 0° C. Sat. $Na_2CO_3$ aqueous (16 mL) was added to the mixture. The mixture was extracted with EtOAc (50 mL×3). The combined organic layers were dried over $Na_2SO_4$, filtered and concentrated in vacuo. The residue was purified by column on C18 using $CH_3CN/H_2O$ (10%-60%) to give the desired product (39 mg, yield 47%) as a white solid.

E184 $^1$H NMR (300 MHz, DMSO-$d_6$): δ 8.72 (s, 1H), 8.27 (s, 1H), 7.59 (s, 1H), 6.52 (s, 1H), 5.77 (d, J=6.6 Hz, 1H), 4.63-4.45 (m, 5H), 4.27 (t, J=8.4 Hz, 2H), 3.82-3.77 (m, 2H), 3.48-3.39 (m, 1H), 2.87-2.76 (m, 3H), 2.50 (s, 3H), 2.40 (s, 3H), 1.94 (t, J=10.2 Hz, 2H), 1.83-1.79 (m, 2H), 1.73-1.60 (m, 2H).

LC-MS [mobile phase: from 95% water (0.02% $NH_4OAc$) and 5% $CH_3CN$ to 5% water (0.02% $NH_4OAc$) and 95% $CH_3CN$ in 6.5 min], purity is >95%, Rt=3.918 min; MS Calcd.: 434; MS Found: 435 $[M+H]^+$.

Example 185

1-(2-Methyl-6-(5-methyl-6-(piperidin-4-yl)-1H-indazol-1-yl)pyrimidin-4-yl)azetidin-3-ol hydrochloride (E185)

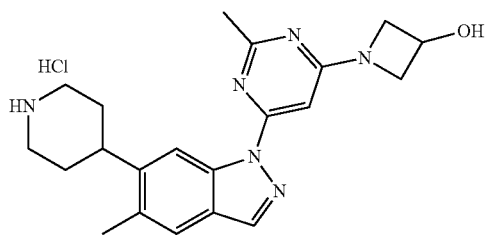 [SMILES: Cc1nc(N2CC(O)C2)cc(-n2ncc3cc(C)c(C4CCNCC4)cc32)n1 ; Cl]

To a solution of tert-butyl 4-(5-methyl-1-(2-methyl-6-(3-((tetrahydro-2H-pyran-2-yl)oxy)azetidin-1-yl)pyrimidin-4-yl)-1H-indazol-6-yl)piperidine-1-carboxylate (68 mg, 0.12 mmol) in dioxane (7 mL) was added HCl/dioxane (4 M, 1 mL) at 0° C. The resulting mixture was warmed to room temperature and stirred overnight. Then, the mixture was concentrated. EtOAc (5 mL) was added and then stirring was continued at room temperature for 30 min. The mixture was filtered and the solid was collected to give the title compound (46 mg, yield 92%) as a pink solid.

E185 $^1$H NMR (300 MHz, DMSO-$d_6$): δ 9.64 (br s, 1H), 9.24 (br s, 1H), 8.64 (s, 1H), 8.44 (s, 1H), 7.66 (s, 1H), 6.63 (s, 1H), 4.65 (s, 1H), 4.49-4.46 (m, 2H), 4.05-3.95 (m, 2H), 3.39-3.37 (m, 2H), 3.24-3.06 (m, 3H), 2.74 (s, 3H), 2.45 (s, 3H), 2.13-2.05 (m, 2H), 1.98-1.88 (m, 2H).

LC-MS [mobile phase: from 95% water (0.02% $NH_4OAc$) and 5% $CH_3CN$ to 5% water (0.02% $NH_4OAc$) and 95% $CH_3CN$ in 6.5 min], purity is >95%, Rt=3.001 min; MS Calcd.: 378, MS Found: 379 $[M+H]^+$.

Example 186

1-(2-Methyl-6-(5-methyl-6-(1-methylpiperidin-4-yl)-1H-indazol-1-yl)pyrimidin-4-yl)azetidin-3-ol (E186)

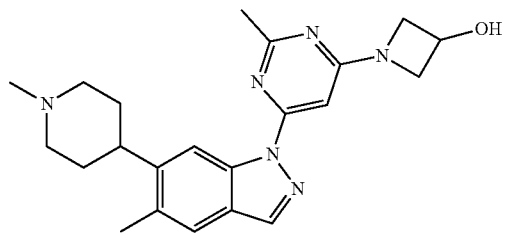 [SMILES: Cc1nc(N2CC(O)C2)cc(-n2ncc3cc(C)c(C4CCN(C)CC4)cc32)n1]

To a mixture of 1-(2-methyl-6-(5-methyl-6-(piperidin-4-yl)-1H-indazol-1-yl)pyrimidin-4-yl)azetidin-3-ol hydrochloride (90 mg, 0.24 mmol) and HCHO (37%, 0.5 mL) in methanol (10 mL) was added $NaBH(OAc)_3$ (151 mg, 0.714 mmol). Then, the mixture was stirred at room temperature for 16 hrs under $N_2$. The mixture was concentrated in vacuo. The residue was purified by column on C18 using $CH_3CN/H_2O$ (30%-60%) to give the desired product (25.7 mg, yield 28%) as a white solid.

E186 $^1$H NMR (300 Hz, $CD_3OD$): δ 8.78 (s, 1H), 8.11 (s, 1H), 7.54 (s, 1H), 6.58 (s, 1H), 4.77-4.65 (m, 1H), 4.42-4.29 (m, 2H), 4.01-3.84 (m, 2H), 3.16-2.99 (m, 2H), 2.94-2.83 (m, 1H), 2.57 (s, 3H), 2.44 (s, 3H), 2.35 (s, 3H), 2.29-2.14 (m, 2H), 1.99-1.81 (m, 4H).

LC-MS (XB-C18, ¢4.6*50 mm*5 um; mobile phase: from 95% water (0.1% TFA) and 5% $CH_3CN$ to 5% water (0.1% TFA) and 95% $CH_3CN$ in 6.5 min, purity is >95%, Rt=2.898 min; MS Calcd.: 392, MS Found: 393 $(M+H)^+$.

Example 187

(S)-(4-(2-Methyl-6-(5-methyl-6-(piperidin-4-yl)-1H-indazol-1-yl)pyrimidin-4-yl)morpholin-2-yl)methanol (E187)

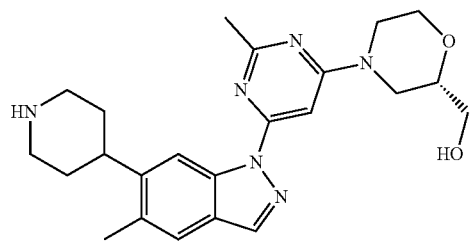 [SMILES: Cc1nc(N2CCO[C@H](CO)C2)cc(-n2ncc3cc(C)c(C4CCNCC4)cc32)n1]

A solution of (S)-tert-butyl 4-(1-(6-(2-(hydroxymethyl)morpholino)-2-methylpyrimidin-4-yl)-5-methyl-1H-indazol-6-yl)piperidine-1-carboxylate (50 mg, 0.096 mmol) in MeOH (5 mL) was added conc. HCl (2 mL) dropwise at rt. The reaction mixture was stirred at rt for 3 hrs. The reaction mixture was poured into Na₂CO₃ (sat., 50 mL) and extracted with EtOAc (40 mL×2). The combined organic layers were washed with brine, dried over MgSO₄ and concentrated. The compound was lyophilized to give the title compound (25 mg, yield 63%) as white solid.

E187 ¹H NMR (CDCl₃, 300 MHz): δ 8.78 (s, 1H), 8.06 (s, 1H), 7.50 (s, 1H), 6.95 (s, 1H), 4.34-4.27 (m, 2H), 4.09-4.04 (s, 1H), 3.82-3.63 (m, 4H), 3.31-3.26 (m, 2H), 3.16-3.07 (m, 1H), 3.01-2.80 (m, 4H), 2.64 (s, 3H), 2.47 (s, 3H), 1.95-1.80 (m, 4H).

LC-MS [mobile phase: from 95% water (0.02% NH₄Ac) and 5% CH₃CN to 5% water (0.02% NH₄Ac) and 95% CH₃CN in 6.5 min], purity is >95%, Rt=3.078 min; MS Calcd.: 422, MS Found: 423 [M+H]⁺.

Example 188

(R)-(4-(2-Methyl-6-(5-methyl-6-(piperidin-4-yl)-1H-indazol-1-yl)pyrimidin-4-yl)morpholin-2-yl)methanol (E188)

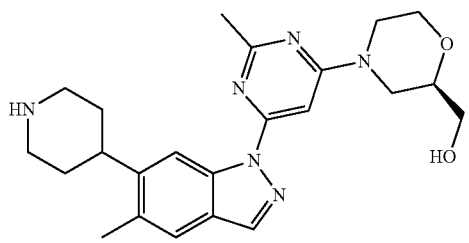 [SMILES: Cc1nc(N2CCO[C@@H](CO)C2)cc(-n2ncc3cc(C)c(C4CCNCC4)cc32)n1]

A solution of tert-butyl 4-(5-methyl-1-(2-methyl-6-((2R)-2-(((tetrahydro-2H-pyran-2-yl)oxy)methyl)morpholino)pyrimidin-4-yl)-1H-indazol-6-yl)piperidine-1-carboxylate (52 mg, 0.086 mmol) in MeOH (5 mL) was added conc. HCl (1 mL) dropwise at rt. The reaction mixture was stirred at rt for 3 hrs. The reaction mixture was poured into Na₂CO₃ (sat., 50 mL) and extracted with EtOAc (40 mL×2). The combined organic layers were washed with brine, dried over MgSO₄ and concentrated. The compound was lyophilized to give the title compound (23 mg, yield 64%) as white solid.

E188 ¹H NMR (CDCl₃, 300 MHz): δ 8.78 (s, 1H), 8.06 (s, 1H), 7.50 (s, 1H), 6.95 (s, 1H), 4.34-4.26 (m, 2H), 4.09-4.03 (s, 1H), 3.81-3.64 (m, 4H), 3.32-3.28 (m, 2H), 3.16-3.07 (m, 1H), 3.02-2.81 (m, 4H), 2.64 (s, 3H), 2.47 (s, 3H), 1.94-1.84 (m, 4H).

LC-MS [mobile phase: from 95% water (0.02% NH₄Ac) and 5% CH₃CN to 5% water (0.02% NH₄Ac) and 95% CH₃CN in 6.5 min], purity is >95%, Rt=3.081 min; MS Calcd.: 422, MS Found: 423 [M+H]⁺.

Example 189

(R)-(4-(2-Methoxy-6-(5-methyl-6-(1-(oxetan-3-yl)piperidin-4-yl)-1H-indazol-1-yl)pyrimidin-4-yl)morpholin-2-yl)methanol (E189)

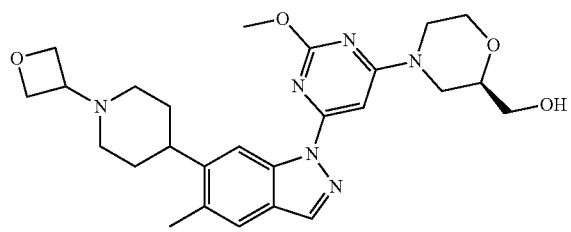 [SMILES: COc1nc(N2CCO[C@@H](CO)C2)cc(-n2ncc3cc(C)c(C4CCN(C5COC5)CC4)cc32)n1]

To a solution of (R)-(4-(2-methoxy-6-(5-methyl-6-(piperidin-4-yl)-1H-indazol-1-yl)pyrimidin-4-yl)morpholin-2-yl)methanol hydrochloride (42 mg, 0.09 mmol) in methanol (0.5 mL) and 1,2-dichloroethane (8 mL) was added oxetan-3-one (0.2 mL) at rt and stirred for 30 min. Then, NaBH₃CN (28 mg, 0.44 mmol) was added and the resulting mixture was stirred at rt for 2 hrs. To the mixture was added sat. NaHCO₃ (15 mL) and stirred for 10 min. DCM (20 mL×3) was added to extract the desired compound. The combined organic layers were washed with brine, dried over Na₂SO₄ and concentrated. The residue was purified by prep-TLC (CH₂Cl₂:CH₃OH=40:1) to give the title compound (10.4 mg, yield 24%) as a white solid.

E189 ¹H NMR (300 MHz, CDCl₃): δ 8.76 (s, 1H), 8.06 (s, 1H), 7.51 (s, 1H), 6.84 (s, 1H), 4.70-4.68 (m, 4H), 4.32-4.22 (m, 2H), 4.15 (s, 3H), 4.08-4.04 (m, 1H), 3.79-3.73 (m, 1H), 3.70-3.66 (m, 3H), 3.60-3.53 (m, 1H), 3.19-3.09 (m, 1H), 3.01-2.82 (m, 4H), 2.45 (s, 3H), 2.07-1.83 (s, 7H).

LC-MS (XB-C18, ¢4.6*50 mm*5 um; mobile phase: from 95% water (0.02% NH₄OAc) and 5% CH₃CN to 5% water (0.02% NH₄OAc) and 95% CH₃CN in 6.5 min), purity is >95%, Rt=3.631 min; MS Calcd: 494; MS Found: 495 (M+H)⁺.

Chiral condition: Chiralpak ID 5 um 4.6*250 mm, Hex:EtOH:DEA=50:50:0.2, Flow Rate:
1.0 mL/min, 230 nm, T=30° C. Rt=13.077 min, 99.05% ee.

Example 190

(S)-(4-(2-Methoxy-6-(5-methyl-6-(1-(oxetan-3-yl)piperidin-4-yl)-1H-indazol-1-yl)pyrimidin-4-yl)morpholin-2-yl)methanol (E190)

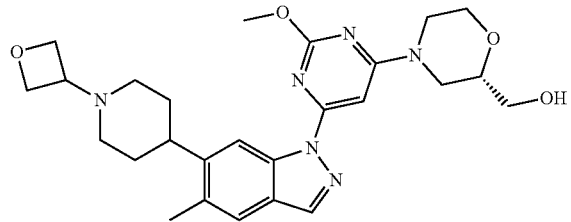 [SMILES: COc1nc(N2CCO[C@H](CO)C2)cc(-n2ncc3cc(C)c(C4CCN(C5COC5)CC4)cc32)n1]

To a solution of (S)-(4-(2-methoxy-6-(5-methyl-6-(piperidin-4-yl)-1H-indazol-1-yl)pyrimidin-4-yl)morpholin-2- yl)methanol hydrochloride (40 mg, 0.08 mmol) in methanol (0.5 mL) and 1,2-dichloroethane (8 mL) was added oxetan-3-one (0.2 mL) at rt and stirred for 30 min. Then, NaBH₃CN (27 mg, 0.42 mmol) was added and the resulting mixture was stirred at rt. for 2 hrs. To the mixture was added sat. NaHCO₃ (15 mL) and stirred for 10 min. DCM (20 mL×3) was added to extract the desired compound. The combined organic layers were washed with brine, dried over Na₂SO₄ and concentrated. The residue was purified by prep-TLC (CH₂Cl₂:CH₃OH=40:1) to give the title compound (25.3 mg, yield 61%) as white solid.

E190 ¹H NMR (300 MHz, CDCl₃): δ 8.76 (s, 1H), 8.06 (s, 1H), 7.51 (s, 1H), 6.85 (s, 1H), 4.70-4.68 (m, 4H), 4.32-4.23 (m, 2H), 4.15 (s, 3H), 4.09-4.03 (m, 1H), 3.79-3.74 (m, 1H), 3.71-3.66 (m, 3H), 3.58-3.54 (m, 1H), 3.18-3.10 (m, 1H), 3.01-2.81 (m, 4H), 2.45 (s, 3H), 2.06-1.85 (s, 7H).

LC-MS (XB-C18, ∅4.6*50 mm*5 um; mobile phase: from 95% water (0.02% NH₄OAc) and 5% CH₃CN to 5% water (0.02% NH₄OAc) and 95% CH₃CN in 6.5 min), purity is >95%, Rt=3.619 min; MS Calcd: 494; MS Found: 495 (M+H)⁺.

Chiral condition: Chiralpak ID 5 um 4.6*250 mm, Hex: EtOH:DEA=50:50:0.2, Flow Rate: 1.0 mL/min, 230 nm, T=30° C. Rt=11.534 min, 100% ee.

Example 191

(R)-(4-(2-Methoxy-6-(5-methyl-6-(piperidin-4-yl)-1H-indazol-1-yl)pyrimidin-4-yl)morpholin-2-yl)methanol (E191)

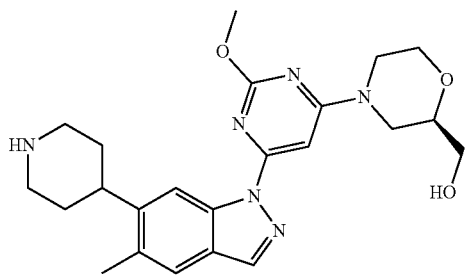 [SMILES: COc1nc(N2CCO[C@@H](CO)C2)cc(-n2ncc3cc(C)c(C4CCNCC4)cc32)n1]

A mixture of (R)-tert-butyl 4-(1-(6-(2-(hydroxymethyl)morpholino)-2-methoxypyrimidin-4-yl)-5-methyl-1H-indazol-6-yl)piperidine-1-carboxylate (40 mg, 0.074 mmol) in HCl/CH₃OH (2 M, 10 mL) was stirred at rt for 2 hrs. The mixture was partitioned with Na₂CO₃ (sat., 20 mL) and EtOAc (50 mL). The organic solution was concentrated and purified by prep-TLC (DCM:CH₃OH=10:1) to give the title compound (12.6 mg, yield 41%) as a white solid.

E191 ¹H NMR (300 MHz, CD₃OD): δ 8.72 (s, 1H), 8.17 (s, 1H), 7.63 (s, 1H), 6.93 (s, 1H), 4.40-4.24 (m, 2H), 4.07-4.00 (m, 4H), 3.70-3.52 (m, 7H), 3.26-3.07 (m, 3H), 2.94-2.85 (m, 1H), 2.51 (s, 3H), 2.17-1.98 (m, 4H).

LC-MS (mobile phase: from 95% water (0.1% TFA) and 5% CH₃CN to 5% water (0.1% TFA) and 95% CH₃CN in 6.5 min), purity is >95%, Rt=3.073 min; MS Calcd.: 438, MS Found: 439 [M+H]⁺.

Chiral condition: Chiralpak IC 5 um 4.6*250 mm, Phase: Hex:EtOH:DEA=50:50:0.2, Flow Rate: 1 mL/min, 230 nm, T=30° C. Rt=14.945 min, 100% ee.

Example 192

(S)-(4-(2-Methoxy-6-(5-methyl-6-(piperidin-4-yl)-1H-indazol-1-yl)pyrimidin-4-yl)morpholin-2-yl)methanol (E192)

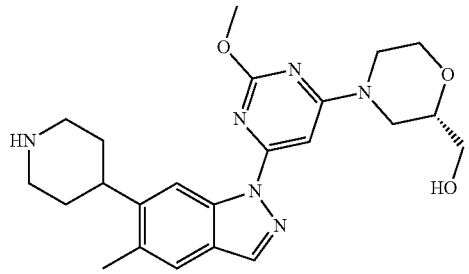 [SMILES: COc1nc(N2CCO[C@H](CO)C2)cc(-n2ncc3cc(C)c(C4CCNCC4)cc32)n1]

A mixture of (S)-tert-butyl 4-(1-(6-(2-(hydroxymethyl)morpholino)-2-methoxypyrimidin-4-yl)-5-methyl-1H-indazol-6-yl)piperidine-1-carboxylate (60 mg, 0.11 mmol) in HCl/CH₃OH (2 M, 10 mL) was stirred at rt for 2 hrs. The mixture was partitioned with Na₂CO₃ (sat., 20 mL) and EtOAc (50 mL). The organic solution was concentrated and purified by prep-TLC (DCM:CH₃OH=10:1) to give the title compound (15.5 mg, yield 32%) as a white solid.

E192 ¹H NMR (300 MHz, CD₃OD): δ 8.71 (s, 1H), 8.16 (s, 1H), 7.62 (s, 1H), 6.91 (s, 1H), 4.38-4.23 (m, 2H), 4.07-4.01 (m, 4H), 3.70-3.54 (m, 7H), 3.25-3.06 (m, 3H), 2.93-2.84 (m, 1H), 2.51 (s, 3H), 2.16-1.93 (m, 4H).

LC-MS (mobile phase: from 95% water (0.1% TFA) and 5% CH₃CN to 5% water (0.1% TFA) and 95% CH₃CN in 6.5 min), purity is >95%, Rt=3.074 min; MS Calcd.: 438, MS Found: 439 [M+H]⁺.

Chiral condition: Chiralpak IC 5 um 4.6*250 mm, Phase: Hex:EtOH:DEA=50:50:0.2, Flow Rate: 1 mL/min, 230 nm, T=30° C. Rt=18.530 min, 100% ee.

Example 193

4-(2-Methyl-6-(5-methyl-6-(1-(oxetan-3-yl)piperidin-4-yl)-1H-indazol-1-yl)pyrimidin-4-yl)morpholine (E193)

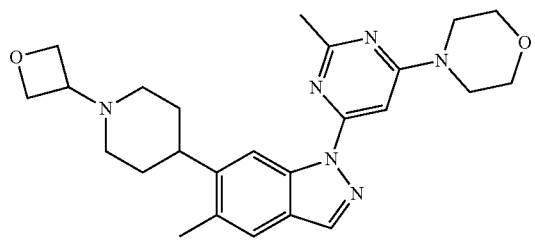 [SMILES: Cc1nc(N2CCOCC2)cc(-n2ncc3cc(C)c(C4CCN(C5COC5)CC4)cc32)n1]

To a solution of 4-(2-methyl-6-(5-methyl-6-(piperidin-4-yl)-1H-indazol-1-yl)pyrimidin-4-yl)morpholine hydrochloride (91 mg, 0.21 mmol) in methanol (0.5 mL) was added 1,2-dichloroethane (8 mL) and oxetan-3-one (0.5 mL) at rt and the mixture was stirred for 30 min. Then, NaBH₃CN (68 mg, 1.1 mmol) was added and the resulting mixture was stirred at rt overnight. To the mixture was added sat. NaHCO₃ (20 mL) and stirred for 10 min. DCM (20 mL×3) was added to extract the desired compound. The combined organic layers were washed with brine, dried over Na₂SO₄ and concentrated. The residue was purified by prep-TLC (PE:EA=1:1) to give the title compound (33.1 mg, yield 35%) as a white solid.

E193 ¹H NMR (400 MHz, CDCl₃): δ 8.82 (s, 1H), 8.05 (s, 1H), 7.50 (s, 1H), 6.95 (s, 1H), 4.73-4.71 (m, 4H), 3.82-3.80 (m, 4H), 3.73-3.70 (m, 4H), 3.58-3.55 (m, 1H), 2.99-2.96 (m, 2H), 2.88-2.80 (m, 1H), 2.65 (s, 3H), 2.45 (s, 3H), 2.07-1.94 (m, 6H).

LC-MS (XB-C18, ¢4.6*50 mm*5 um; mobile phase: from 95% water (0.02% NH₄OAc) and 5% CH₃CN to 5% water (0.02% NH₄OAc) and 95% CH₃CN in 6.5 min), purity is >95%, Rt=4.297 min; MS Calcd: 448; MS Found: 449 (M+H)⁺.

Example 194

4-(2-Methoxy-6-(5-methyl-6-(1-(oxetan-3-yl)piperidin-4-yl)-1H-indazol-1-yl)pyrimidin-4-yl)morpholine (E194)

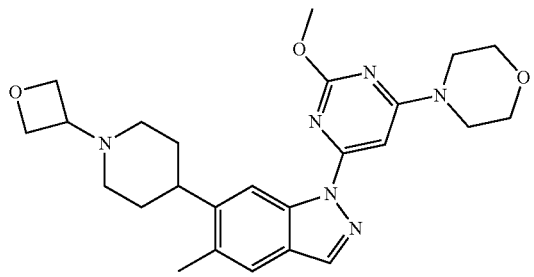 [SMILES: COc1nc(N2CCOCC2)cc(-n2ncc3cc(C)c(C4CCN(C5COC5)CC4)cc32)n1]

To a solution of 4-(2-methoxy-6-(5-methyl-6-(piperidin-4-yl)-1H-indazol-1-yl)pyrimidin-4-yl)morpholine hydrochloride (52 mg, 0.11 mmol) in methanol (0.5 mL) was added 1,2-dichloroethane (8 mL) and oxetan-3-one (0.5 mL) at rt and the mixture was stirred for 30 min. Then, NaBH₃CN (35 mg, 0.55 mmol) was added and the resulting mixture was stirred at rt overnight. To the mixture was added sat. NaHCO₃ (20 mL) and stirred for 10 min. DCM (20 mL×3) was added to extract the desired compound. The combined organic layers were washed with brine, dried over Na₂SO₄ and concentrated. The residue was purified by prep-TLC (CH₂Cl₂:EtOAc=1:1) to give the title compound (25.5 mg, yield 50%) as white solid.

E194 ¹H NMR (400 MHz, CDCl₃): δ 8.77 (s, 1H), 8.06 (s, 1H), 7.51 (s, 1H), 6.84 (s, 1H), 4.70-4.69 (m, 4H), 4.15 (s, 3H), 3.81-3.79 (m, 4H), 3.73-3.71 (m, 4H), 3.57-3.54 (m, 1H), 2.95-2.92 (m, 2H), 2.87-2.82 (m, 1H), 2.46 (s, 3H), 2.05-1.86 (m, 6H).

LC-MS (XB-C18, ¢4.6*50 mm*5 um; mobile phase: from 95% water (0.02% NH₄OAc) and 5% CH₃CN to 5% water (0.02% NH₄OAc) and 95% CH₃CN in 6.5 min), purity is >95%, Rt=4.287 min; MS Calcd: 464; MS Found: 465 (M+H)⁺.

Example 195

(R)-4-(2-Methoxy-6-(5-methyl-6-(1-(oxetan-3-yl)piperidin-4-yl)-1H-indazol-1-yl)pyrimidin-4-yl)-2-methylmorpholine (E195)

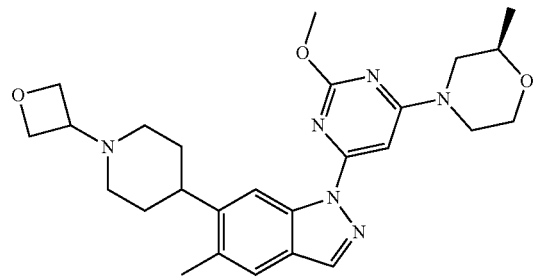 [SMILES: COc1nc(N2CCO[C@H](C)C2)cc(-n2ncc3cc(C)c(C4CCN(C5COC5)CC4)cc32)n1]

To a solution of (R)-4-(2-methoxy-6-(5-methyl-6-(piperidin-4-yl)-1H-indazol-1-yl)pyrimidin-4-yl)-2-methylmorpholine hydrochloride (100 mg of crude, 0.096 mmol) in ClCH₂CH₂Cl (4 mL) and MeOH (0.5 mL) was added oxetan-3-one (0.5 mL). The resulting mixture was stirred at rt for 30 min. Then, NaBH₃CN (18 mg, 0.23 mmol) was added and the resulting mixture was stirred overnight. The resulting mixture was poured into sat. Na₂CO₃ (60 mL) and extracted with EtOAc (60 mL). The organic solution was washed with brine, dried over Na₂SO₄ and then concentrated. The crude was purified by prep-TLC (DCM:MeOH=15:1) to give the title compound (32 mg, yield 70%) as white solid.

E195 ¹H NMR (300 MHz, CDCl₃): δ 8.77 (s, 1H), 8.07 (s, 1H), 7.51 (s, 1H), 6.83 (s, 1H), 4.70-4.68 (m, 4H), 4.40-4.20 (m, 2H), 4.15 (s, 3H), 4.05-3.96 (m, 1H), 3.73-3.51 (m, 1H), 3.18-3.04 (m, 1H), 2.98-2.70 (m, 4H), 2.46 (s, 3H), 2.10-1.82 (m, 6H), 1.26 (d, J=6.3 Hz, 3H).

LC-MS [mobile phase: from 70% water (0.02% NH₄OAc) and 30% CH₃CN to 5% water (0.02% NH₄OAc) and 95% CH₃CN in 6.5 min], purity is >95%, Rt=3.793 min; MS Calcd.: 478, MS Found: 479 [M+H]⁺.

Example 196

(S)-4-(2-Methoxy-6-(5-methyl-6-(1-(oxetan-3-yl)piperidin-4-yl)-1H-indazol-1-yl)pyrimidin-4-yl)-2-methylmorpholine (E196)

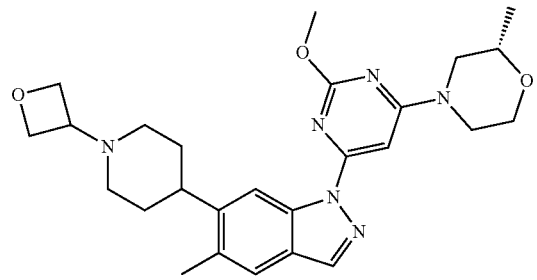 [SMILES: COc1nc(N2CCO[C@@H](C)C2)cc(-n2ncc3cc(C)c(C4CCN(C5COC5)CC4)cc32)n1]

To a solution of (S)-4-(2-methoxy-6-(5-methyl-6-(piperidin-4-yl)-1H-indazol-1-yl)pyrimidin-4-yl)-2-methylmorpholine hydrochloride (60 mg, 0.096 mmol) in ClCH₂CH₂Cl (4 mL) and MeOH (0.5 mL) was added oxetan-3-one (0.5 mL). The resulting mixture was stirred at rt for 30 min. Then, NaBH₃CN (18 mg, 0.23 mmol) was added and the resulting mixture was stirred overnight. The resulting mixture was poured into sat. Na₂CO₃ (60 mL) and extracted with EtOAc (60 mL). The organic solution was washed with brine, dried over Na₂SO₄ and then concentrated. The crude was purified by prep-TLC (DCM:MeOH=15:1) to give the title compound (23 mg, yield 50%) as white solid.

E196 $^1$H NMR (300 MHz, CDCl₃): δ 8.77 (s, 1H), 8.07 (s, 1H), 7.51 (s, 1H), 6.83 (s, 1H), 4.70-4.68 (m, 4H), 4.47-4.19 (m, 2H), 4.15 (s, 3H), 4.04-3.96 (m, 1H), 3.73-3.48 (m, 3H), 3.17-2.69 (m, 5H), 2.46 (s, 3H), 2.08-1.80 (m, 6H), 1.26 (d, J=6.0 Hz, 3H).

LC-MS [mobile phase: from 70% water (0.02% NH₄OAc) and 30% CH₃CN to 5% water (0.02% NH₄OAc) and 95% CH₃CN in 6.5 min], purity is >95%, Rt=3.798 min; MS Calcd.: 478, MS Found: 479 [M+H]⁺.

Example 197

(R)-2-Methyl-4-(2-methyl-6-(5-methyl-6-(1-(oxetan-3-yl)piperidin-4-yl)-1H-indazol-1-yl)pyrimidin-4-yl)morpholine (E197)

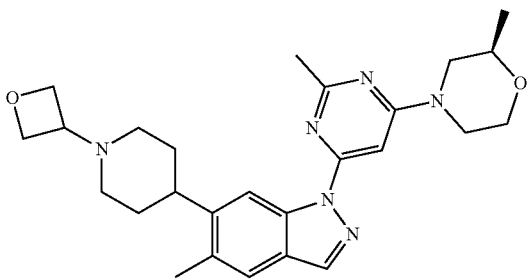 [SMILES: Cc1nc(N2CCO[C@H](C)C2)cc(-n2ncc3cc(C)c(C4CCN(C5COC5)CC4)cc32)n1]

To a solution of (R)-2-methyl-4-(2-methyl-6-(5-methyl-6-(piperidin-4-yl)-1H-indazol-1-yl)pyrimidin-4-yl)morpholine hydrochloride (140 mg, 0.198 mmol) in ClCH₂CH₂Cl (5 mL) and MeOH (0.6 mL) was added oxetan-3-one (0.5 mL). The resulting mixture was stirred at rt for 30 min. Then, NaBH₃CN (38 mg, 0.59 mmol) was added and the resulting mixture was stirred overnight. The resulting mixture was poured into sat. Na₂CO₃ (60 mL) and extracted with EtOAc (60 mL). The organic solution was washed with brine, dried over Na₂SO₄ and then concentrated. The crude was purified by prep-TLC (EtOAc) to give the title compound (43 mg, yield 47%) as white solid.

E197 $^1$H NMR (300 MHz, CDCl₃): δ 8.82 (s, 1H), 8.07 (s, 1H), 7.51 (s, 1H), 6.94 (s, 1H), 4.73-4.71 (m, 4H), 4.37-4.24 (m, 2H), 4.06-3.97 (m, 1H), 3.73-3.52 (m, 3H), 3.13-2.69 (m, 5H), 2.65 (s, 3H), 2.46 (s, 3H), 2.08-1.90 (m, 6H), 1.28 (d, J=6.0 Hz, 3H).

LC-MS [mobile phase: from 80% water (0.02% NH₄OAc) and 20% CH₃CN to 5% water (0.02% NH₄OAc) and 95% CH₃CN in 6.5 min], purity is >95%, Rt=4.195 min; MS Calcd.: 462, MS Found: 463 [M+H]⁺.

Chiral condition: Chiralpak IE 5 um 4.6*250 mm, Phase: Hex:EtOH=70:30, Flow Rate: 1 ml/min, 230 nm, T=30° C. Rt=12.265 min, 99.1% ee.

Example 198

(S)-2-Methyl-4-(2-methyl-6-(5-methyl-6-(1-(oxetan-3-yl)piperidin-4-yl)-1H-indazol-1-yl)pyrimidin-4-yl)morpholine (E198)

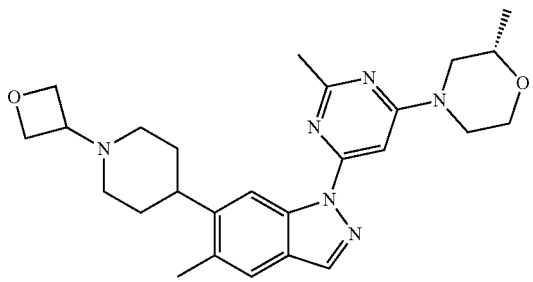 [SMILES: Cc1nc(N2CCO[C@@H](C)C2)cc(-n2ncc3cc(C)c(C4CCN(C5COC5)CC4)cc32)n1]

To a solution of (S)-2-methyl-4-(2-methyl-6-(5-methyl-6-(piperidin-4-yl)-1H-indazol-1-yl)pyrimidin-4-yl)morpholine hydrochloride (120 mg of crude, 0.154 mmol) in ClCH₂CH₂Cl (5 mL) and MeOH (0.6 mL) was added oxetan-3-one (0.5 mL). The resulting mixture was stirred at rt for 30 min. Then. NaBH₃CN (29 mg, 0.46 mmol) was added and the resulting mixture was stirred overnight. The resulting mixture was poured into sat. Na₂CO₃ (60 mL) and extracted with EtOAc (60 mL). The organic solution was washed with brine, dried over Na₂SO₄ and then concentrated. The crude was purified by prep-TLC (EtOAc) to give the title compound (51 mg, yield 72%) as white solid.

E198 $^1$H NMR (300 MHz, CDCl₃): δ 8.82 (s, 1H), 8.06 (s, 1H), 7.50 (s, 1H), 6.93 (s, 1H), 4.73-4.71 (m, 4H), 4.36-4.24 (m, 2H), 4.06-3.96 (m, 1H), 3.74-3.51 (m, 3H), 3.13-2.68 (m, 5H), 2.65 (s, 3H), 2.45 (s, 3H), 2.10-1.90 (m, 6H), 1.28 (d, J=6.3 Hz, 3H).

LC-MS [mobile phase: from 80% water (0.02% NH₄OAc) and 20% CH₃CN to 5% water (0.02% NH₄OAc) and 95% CH₃CN in 6.5 min], purity is >95%, Rt=4.194 min; MS Calcd.: 462, MS Found: 463 [M+H]⁺.

Chiral condition: Chiralpak IE 5 um 4.6*250 mm, Phase: Hex:EtOH=70:30, Flow Rate: 1 mL/min, 230 nm, T=30° C. Rt=11.245 min, 99.3% ee.

Example 199

4-(2-Ethyl-6-(5-methyl-6-(1-(oxetan-3-yl)piperidin-4-yl)-1H-indazol-1-yl)pyrimidin-4-yl)morpholine (E199)

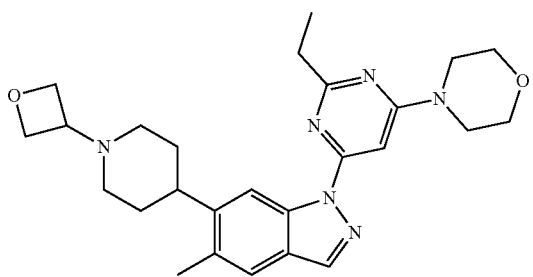 [SMILES: CCc1nc(N2CCOCC2)cc(-n2ncc3cc(C)c(C4CCN(C5COC5)CC4)cc32)n1]

To a solution of 4-(2-ethyl-6-(5-methyl-6-(piperidin-4-yl)-1H-indazol-1-yl)pyrimidin-4-yl)morpholine hydrochloride (30 mg, 0.05 mmol) in CH₃OH (0.5 mL) was added ClCH₂CH₂Cl (8 mL) and oxetan-3-one (0.5 mL). The resulting mixture was stirred at rt for 30 min. Then NaBH₃CN (17 mg, 0.27 mmol) was added and the mixture was stirred at rt overnight. To the reaction mixture was added sat. Na₂CO₃ (15 mL) and extracted with DCM (20 mL×3). The organic layers were washed with brine, dried over Na₂SO₄ and concentrated. The residue was purified by prep-TLC (DCM: EtOAc=4:1) to give the title compound (14.2 mg, yield 58%) as a white solid.

E199 $^1$H NMR (300 MHz, CDCl₃): δ 8.86 (s, 1H), 8.06 (s, 1H), 7.51 (s, 1H), 6.96 (s, 1H), 4.73-4.71 (m, 4H), 3.83-3.79 (m, 4H), 3.76-3.69 (m, 4H), 3.61-3.56 (m, 1H), 3.00-2.82 (m, 5H), 2.46 (s, 3H), 2.07-1.90 (m, 6H), 1.47 (t, J=7.2 Hz, 3H).

LC-MS (mobile phase: from 70% water (0.02% NH₄OAc) and 30% CH₃CN to 5% water (0.02% NH₄OAc) and 95% CH₃CN in 6.5 min), Rt=3.847 min, purity is 97.30%; MS Calcd.: 462, MS Found: 463 [M+H]⁺.

Example 200

(S)-(4-(2-Ethyl-6-(5-methyl-6-(1-(oxetan-3-yl)piperidin-4-yl)-1H-indazol-1-yl)pyrimidin-4-yl)morpholin-2-yl)methanol (E200)

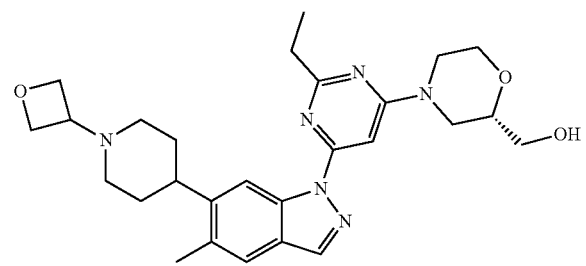 [SMILES: CCc1nc(N2CCO[C@H](CO)C2)cc(-n2ncc3cc(C)c(C4CCN(C5COC5)CC4)cc32)n1]

To a solution of (S)-(4-(2-ethyl-6-(5-methyl-6-(piperidin-4-yl)-1H-indazol-1-yl)pyrimidin-4-yl)morpholin-2-yl) methanol hydrochloride (40 mg, 0.085 mmol) in ClCH₂CH₂Cl (5 mL) and CH₃OH (0.3 mL) was added oxetan-3-one (0.5 mL). The resulting mixture was stirred at rt for 30 min. NaBH₃CN (22 mg, 0.34 mmol) was added and the mixture was stirred at rt overnight. The mixture was poured into water (10 mL) and extracted with EtOAc (50 mL). The organic layer was purified by prep-TLC (DCM: MeOH=13:1) to give the title compound (16.6 mg, yield 40%) as a white solid.

E200 $^1$H NMR (300 MHz, CDCl₃): δ 8.85 (s, 1H), 8.06 (s, 1H), 7.50 (s, 1H), 6.97 (s, 1H), 4.72-4.70 (m, 4H), 4.34-4.30 (m, 2H), 4.09-4.05 (m, 1H), 3.81-3.70 (m, 4H), 3.59-3.55 (m, 1H), 3.16-3.07 (m, 1H), 2.99-2.82 (m, 6H), 2.45 (s, 3H), 2.07-1.93 (m, 7H), 1.49-1.45 (m, 3H).

LC-MS (mobile phase: from 95% water (0.02% NH₄OAc) and 5% CH₃CN to 5% water (0.02% NH₄OAc) and 95% CH₃CN in 6.5 min), Rt=3.976 min, purity is >95%, MS Calcd.: 492, MS Found: 493 [M+H]⁺.

Chiral condition: Chiralpak IC 5 um 4.6*250 mm, Hex: IPA=55:45, Flow Rate: 1 mL/min, 230 nm, T=30° C. Rt=19.492 min, 100% ee.

Example 201

(R)-(4-(2-Ethyl-6-(5-methyl-6-(1-(oxetan-3-yl)piperidin-4-yl)-1H-indazol-1-yl)pyrimidin-4-yl)morpholin-2-yl)methanol (E201)

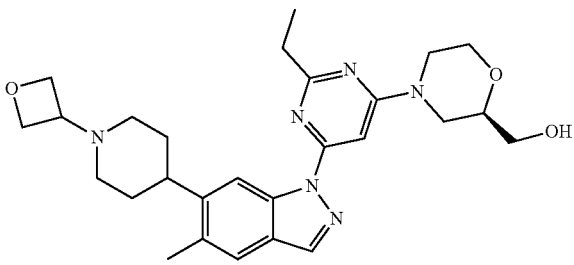 [SMILES: CCc1nc(N2CCO[C@@H](CO)C2)cc(-n2ncc3cc(C)c(C4CCN(C5COC5)CC4)cc32)n1]

To a solution of (R)-(4-(2-ethyl-6-(5-methyl-6-(piperidin-4-yl)-1H-indazol-1-yl)pyrimidin-4-yl)morpholin-2-yl) methanol hydrochloride (20 mg, 0.04 mmol) in ClCH₂CH₂Cl (6 mL) and CH₃OH (0.5 mL) was added oxetan-3-one (0.5 mL). The resulting mixture was stirred at r.t for 30 min. Then, NaBH₃CN (11 mg, 0.17 mmol) was added and the mixture was stirred at r.t overnight. To the reaction mixture was added sat. Na₂CO₃ (20 mL) and extracted with DCM (20 mL×3). The combined organic layers were washed with brine, dried over Na₂SO₄ and concentrated. The residue was purified by prep-TLC (DCM: MeOH=15:1) to give the title compound (9.6 mg, yield 65%) as a white solid.

E201 $^1$H NMR (300 MHz, CDCl₃): δ 8.85 (s, 1H), 8.06 (s, 1H), 7.51 (s, 1H), 6.97 (s, 1H), 4.72-4.70 (m, 4H), 4.35-4.30 (m, 2H), 4.10-4.05 (m, 1H), 3.81-3.67 (m, 4H), 3.61-3.54 (m, 1H), 3.16-3.07 (m, 1H), 2.99-2.82 (m, 6H), 2.46 (s, 3H), 2.08-1.93 (m, 7H), 1.47 (t, J=7.5 Hz, 3H).

LC-MS (mobile phase: from 95% water (0.02% NH₄OAc) and 5% CH₃CN to 5% water (0.02% NH₄OAc) and 95% CH₃CN in 6.5 min), Rt=3.971 min, purity is >95%; MS Calcd.: 492, MS Found: 493 [M+H]⁺.

Chiral condition: Chiralpak IC 5 um 4.6*250 mm, Hex: IPA=55:45, Flow Rate: 1 mL/min, 230 nm, T=30° C. Rt=16.800 min, 100% ee.

Example 202

(R)-2-methyl-4-(2-methyl-6-(5-methyl-6-(piperidin-4-yl)-1H-indazol-1-yl)pyrimidin-4-yl)morpholine (HCl Salt) (E202)

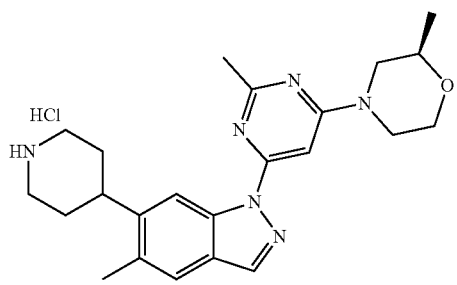 [SMILES: Cc1nc(N2CCO[C@H](C)C2)cc(-n2ncc3cc(C)c(C4CCNCC4)cc32)n1 ; Cl]

To a solution of (R)-tert-butyl 4-(5-methyl-1-(2-methyl-6-(2-methylmorpholino)pyrimidin-4-yl)-1H-indazol-6-yl)

piperidine-1-carboxylate (96 mg, 0.19 mmol) in dioxane (6 mL) was added HCl/dioxane (5 M, 6 mL) at rt. The resulting mixture was stirred at rt for 2 hrs. The resulting mixture was concentrated to give the title compound (38.6 mg, yield 46%) as a yellow solid.

E202 $^1$H NMR (300 MHz, CD$_3$OD): δ 8.50 (s, 1H), 8.34 (s, 1H), 7.72 (s, 1H), 7.35 (s, 1H), 4.39-4.24 (m, 2H), 4.12-4.07 (m, 1H), 3.80-3.72 (m, 2H), 3.60-3.56 (m, 2H), 3.43-3.35 (m, 2H), 3.27-3.22 (m, 2H), 3.09-3.01 (m, 1H), 2.84 (s, 3H), 2.54 (s, 3H), 2.22-2.10 (m, 4H), 1.29 (d, J=6.0 Hz, 3H).

LC-MS: mobile phase: from 95% water (0.1% TFA) and 5% CH$_3$CN to 5% water (0.1% TFA) and 95% CH$_3$CN in 6.5 min), Rt=3.340 min, purity is >95%; MS Calcd.: 406, MS Found: 407 [M+H]$^+$.

Example 203

(S)-2-Methyl-4-(2-methyl-6-(5-methyl-6-(piperidin-4-yl)-1H-indazol-1-yl)pyrimidin-4-yl)morpholine (HCl Salt) (E203)

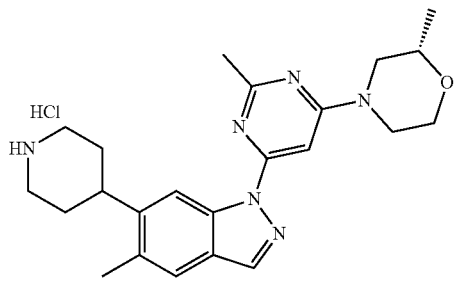 [SMILES: Cc1nc(N2CCO[C@@H](C)C2)cc(-n2ncc3cc(C)c(C4CCNCC4)cc32)n1 ; Cl]

To a solution of (S)-tert-butyl 4-(5-methyl-1-(2-methyl-6-(2-methylmorpholino)pyrimidin-4-yl)-1H-indazol-6-yl)piperidine-1-carboxylate (73 mg, 0.14 mmol) in dioxane (6 mL) was added HCl/dioxane (5 M, 6 mL) at rt. The resulting mixture was stirred at rt for 2 hrs. The resulting mixture was concentrated to give the title compound (14.6 mg, yield 23%) as a yellow solid.

E203 $^1$H NMR (300 MHz, CD$_3$OD): δ 8.51 (s, 1H), 8.38 (s, 1H), 7.72 (s, 1H), 7.35 (s, 1H), 4.39-4.24 (m, 2H), 4.12-4.06 (m, 1H), 3.78-3.71 (m, 2H), 3.60-3.56 (m, 2H), 3.43-3.34 (m, 2H), 3.27-3.21 (m, 2H), 3.07-2.99 (m, 1H), 2.83 (s, 3H), 2.54 (s, 3H), 2.17-2.10 (m, 4H), 1.29 (d, J=6.0 Hz, 3H).

LC-MS: mobile phase: from 95% water (0.1% TFA) and 5% CH$_3$CN to 5% water (0.1% TFA) and 95% CH$_3$CN in 6.5 min), Rt=3.341 min, purity is >95%; MS Calcd.: 406, MS Found: 407 [M+H]$^+$.

Example 204

4-(2-Methyl-6-(5-methyl-6-(piperidin-4-yl)-1H-indazol-1-yl)pyrimidin-4-yl)morpholine (HCl Salt) (E204)

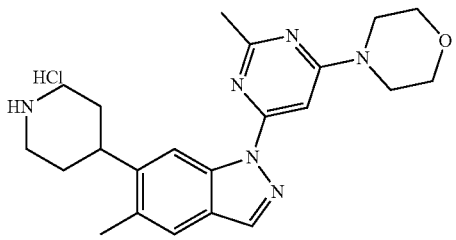 [SMILES: Cc1nc(N2CCOCC2)cc(-n2ncc3cc(C)c(C4CCNCC4)cc32)n1 ; Cl]

A mixture of tert-butyl 4-(5-methyl-1-(2-methyl-6-morpholinopyrimidin-4-yl)-1H-indazol-6-yl)piperidine-1-carboxylate (80 mg, 0.16 mmol) in HCl/dioxane (5 M, 10 mL) was stirred at rt overnight. The mixture was concentrated to give the title compound (68 mg, yield 97%) as a white solid.

E204 $^1$H NMR (300 MHz, CD$_3$OD): δ 8.45 (s, 1H), 8.39 (s, 1H), 7.72 (s, 1H), 7.32 (s, 1H), 3.89 (s, 8H), 3.60-3.56 (m, 2H), 3.40-3.21 (m, 3H), 2.84 (s, 3H), 2.54 (s, 3H), 2.21-2.06 (m, 4H).

LC-MS (mobile phase: from 95% water (0.1% TFA) and 5% CH$_3$CN to 5% water (0.1% TFA) and 95% CH$_3$CN in 6.5 min), Rt=3.140 min, purity is >95%; MS Calcd.: 392; MS Found: 393 [M+H]$^+$.

Example 205

4-(2-Methoxy-6-(5-methyl-6-(piperidin-4-yl)-1H-indazol-1-yl)pyrimidin-4-yl)morpholine (HCl Salt) (E205)

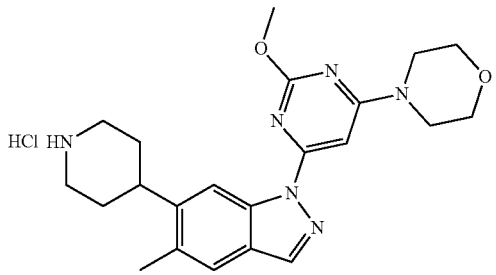 [SMILES: Cl ; COc1nc(N2CCOCC2)cc(-n2ncc3cc(C)c(C4CCNCC4)cc32)n1]

A mixture of tert-butyl 4-(1-(2-methoxy-6-morpholinopyrimidin-4-yl)-5-methyl-1H-indazol-6-yl)piperidine-1-carboxylate (80 mg, 0.14 mmol) in HCl/dioxane (5 M, 10 mL) was stirred at rt overnight. The mixture was concentrated to give the title compound (58 mg, yield 94%) as a white solid.

E205 $^1$H NMR (300 MHz, CD$_3$OD): δ 8.49 (s, 1H), 8.29 (s, 1H), 7.68 (s, 1H), 7.01 (s, 1H), 4.24 (s, 3H), 3.82-3.80 (m, 8H), 3.60-3.55 (m, 2H), 3.33-3.21 (m, 3H), 2.53 (s, 3H), 2.15-2.03 (m, 4H).

LC-MS (mobile phase: from 95% water (0.1% TFA) and 5% CH$_3$CN to 5% water (0.1% TFA) and 95% CH$_3$CN in 6.5 min), Rt=3.413 min, purity is >95%; MS Calcd.: 408, MS Found: 409 [M+H]$^+$.

Example 206

(R)-4-(2-Methoxy-6-(5-methyl-6-(piperidin-4-yl)-1H-indazol-1-yl)pyrimidin-4-yl)-2-methylmorpholine (TFA Salt) (E205)

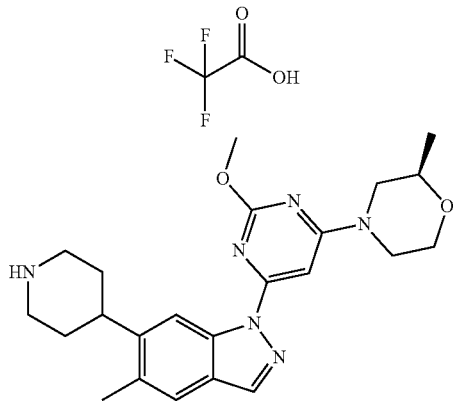

To the solution of (R)-tert-butyl 4-(1-(2-methoxy-6-(2-methylmorpholino)pyrimidin-4-yl)-5-methyl-1H-indazol-6-yl)piperidine-1-carboxylate (80 mg, 0.15 mmol) in CH$_2$Cl$_2$ (2 mL) was added TFA (0.5 mL) at rt. The resulting mixture was stirred at 30° C. for 2 hrs. The resulting mixture was concentrated to give the title compound (95 mg, yield 100%) as a yellow solid.

E206 $^1$H NMR (400 MHz, DMSO-d$_6$): δ 8.70 (br s, 1H), 8.63 (s, 1H), 8.48 (br s, 1H), 8.36 (s, 1H), 7.68 (s, 1H), 6.89 (s, 1H), 4.34-4.19 (m, 2H), 4.01 (s, 3H), 3.96-3.90 (m, 1H), 3.61-3.39 (m, 4H), 3.24-2.94 (m, 4H), 2.76-2.64 (m, 1H), 2.46 (s, 3H), 2.04-1.94 (m, 2H), 1.90-1.75 (m, 2H), 1.18 (d, J=6.0 Hz, 3H). $^{19}$F NMR (376 MHz, DMSO-d$_6$): δ −74.52 (s, 3F).

LC-MS [mobile phase: from 95% water (0.1% TFA) and 5% CH$_3$CN to 5% water (0.1% TFA) and 95% CH$_3$CN in 6.5 min], Rt=3.595 min, purity is >95%; MS Calcd.: 422, MS Found: 423 [M+H]$^+$.

Example 207

(S)-4-(2-Methoxy-6-(5-methyl-6-(piperidin-4-yl)-1H-indazol-1-yl)pyrimidin-4-yl)-2-methylmorpholine 2,2,2-trifluoroacetate (E207)

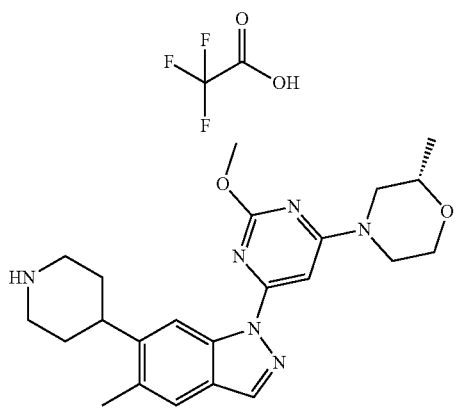

To the solution of (S)-tert-butyl 4-(1-(2-methoxy-6-(2-methylmorpholino)pyrimidin-4-yl)-5-methyl-1H-indazol-6-yl)piperidine-1-carboxylate (100 mg, 0.192 mmol) in CH$_2$Cl$_2$ (2 mL) was added TFA (0.5 mL) at rt. The resulting mixture was heated to 30° C. and stirred for 2 hrs. The resulting mixture was concentrated to give the title compound (106 mg, yield 100%) as a yellow solid.

E207 $^1$H NMR (300 MHz, CDCl$_3$): δ 8.68 (br s, 1H), 8.63 (s, 1H), 8.45 (br s, 1H), 8.36 (s, 1H), 7.68 (s, 1H), 6.89 (s, 1H), 4.34-4.18 (m, 2H), 4.01 (s, 3H), 3.97-3.87 (m, 1H), 3.60-3.38 (m, 4H), 3.25-2.95 (m, 4H), 2.76-2.63 (m, 1H), 2.46 (s, 3H), 2.04-1.93 (m, 2H), 1.88-1.74 (m, 2H), 1.18 (d, J=6.4 Hz, 3H). $^{19}$F NMR (376 MHz, DMSO-d$_6$): δ −74.45 (s, 3F).

LC-MS [mobile phase: from 95% water (0.1% TFA) and 5% CH$_3$CN to 5% water (0.1% TFA) and 95% CH$_3$CN in 6.5 min], Rt=3.596 min, purity is >95%; MS Calcd.: 422, MS Found: 423 [M+H]$^+$.

Example 208

(S)-(4-(6-(5-Chloro-6-(1-(oxetan-3-yl)piperidin-4-yl)-1H-indazol-1-yl)-2-methylpyrimidin-4-yl)morpholin-2-yl)methanol (E208)

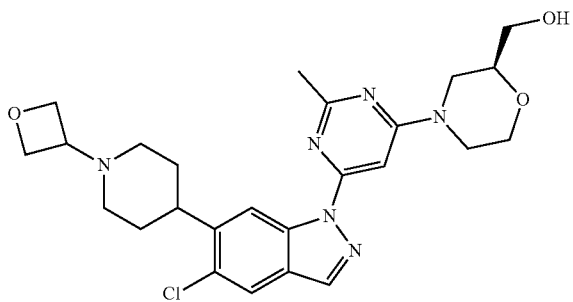 [SMILES: Cc1nc(N2CCO[C@H](CO)C2)cc(-n2ncc3cc(Cl)c(C4CCN(C5COC5)CC4)cc32)n1]

To a suspension of 5-chloro-6-(1-(oxetan-3-yl)piperidin-4-yl)-1H-indazole (50 mg, 0.17 mmol), (S)-(4-(6-iodo-2-methylpyrimidin-4-yl)morpholin-2-yl)methanol (57 mg, 0.17 mmol), CuI (32 mg, 0.17 mmol) and K$_3$PO$_4$ (72 mg, 0.34 mmol) in toluene (3 mL) was added N,N'-dimethylcyclohexane-1,2-diamine (48 mg, 0.34 mmol) at rt. The resulting mixture was stirred at 110° C. under N$_2$ atmosphere for 3 hrs. Then, the reaction mixture was cooled and partitioned between NH$_4$Cl (sat., 30 mL) and EtOAc (30 mL). The organic layer was washed with brine, dried over Na$_2$SO$_4$ and concentrated. The crude was purified by prep-TLC (EtOAc:MeOH=25:1) to give the title compound (42 mg, yield 49%) as a white solid.

E208 $^1$H NMR (300 MHz, CDCl$_3$): δ 8.92 (s, 1H), 8.08 (s, 1H), 7.75 (s, 1H), 6.96 (s, 1H), 4.73-4.70 (m, 4H), 4.34-4.27 (m, 2H), 4.10-4.05 (m, 1H), 3.84-3.65 (m, 4H), 3.61-3.51 (m, 1H), 3.18-3.07 (m, 2H), 3.02-2.91 (m, 3H), 2.65 (s, 3H), 2.13-2.00 (m, 5H), 1.96-1.82 (m, 2H).

LC-MS [mobile phase: from 95% water (0.02% NH$_4$OAc) and 5% CH$_3$CN to 5% water (0.02% NH$_4$OAc) and 95% CH$_3$CN in 6.5 min], purity is >95%, Rt=3.967 min; MS Calcd.: 498, MS Found: 499 [M+H]$^+$.

Chiral HPLC [Chiralpak OD-H 5 um 4.6*250 mm, Phase: Hex/EtOH=70/30, flow rate: 1 mL/min, 230 nm, T=30° C.], Rt=7.740 min, 100% ee.

Example 209

(R)-(4-(6-(5-Chloro-6-(1-(oxetan-3-yl)piperidin-4-yl)-1H-indazol-1-yl)-2-methylpyrimidin-4-yl)morpholin-2-yl)methanol (E209)

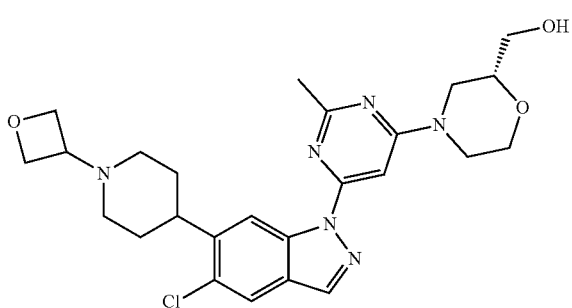

To a suspension of 5-chloro-6-(1-(oxetan-3-yl)piperidin-4-yl)-1H-indazole (50 mg, 0.17 mmol), (R)-(4-(6-iodo-2-methylpyrimidin-4-yl)morpholin-2-yl)methanol (57 mg, 0.17 mmol), CuI (32 mg, 0.17 mmol) and $K_3PO_4$ (72 mg, 0.34 mmol) in toluene (3 mL) was added N,N'-dimethylcyclohexane-1,2-diamine (48 mg, 0.34 mmol) at rt. The resulting mixture was stirred at 110° C. under $N_2$ atmosphere for 3 hrs. Then, the reaction mixture was cooled and partitioned between $NH_4Cl$ (sat., 30 mL) and EtOAc (30 mL). The organic layer was washed with brine, dried over $Na_2SO_4$ and concentrated. The crude was purified by prep-TLC (EtOAc:MeOH=25:1) to give the title compound (28 mg, yield 33%) as a white solid.

E209 $^1$H NMR (300 MHz, $CDCl_3$): δ 8.92 (s, 1H), 8.08 (s, 1H), 7.75 (s, 1H), 6.96 (s, 1H), 4.73-4.70 (m, 4H), 4.35-4.27 (m, 2H), 4.11-4.06 (m, 1H), 3.82-3.65 (m, 4H), 3.61-3.52 (m, 1H), 3.18-3.08 (m, 2H), 3.00-2.92 (m, 3H), 2.65 (s, 3H), 2.12-2.00 (m, 5H), 1.96-1.81 (m, 2H).

LC-MS [mobile phase: from 95% water (0.02% $NH_4OAc$) and 5% $CH_3CN$ to 5% water (0.02% $NH_4OAc$) and 95% $CH_3CN$ in 6.5 min], purity is >95%, Rt=3.970 min; MS Calcd.: 498, MS Found: 499 [M+H]$^+$.

Chiral HPLC [Chiralpak OD-H 5 um 4.6*250 mm, Phase: Hex/EtOH=70/30, flow rate: 1 mL/min, 230 nm, T=30° C.], Rt=8.621 min, 99.24% ee.

Example 210

1-(6-(5-Chloro-6-(1-(oxetan-3-yl)piperidin-4-yl)-1H-indazol-1-yl)-2-methylpyrimidin-4-yl)azetidin-3-ol (E210)

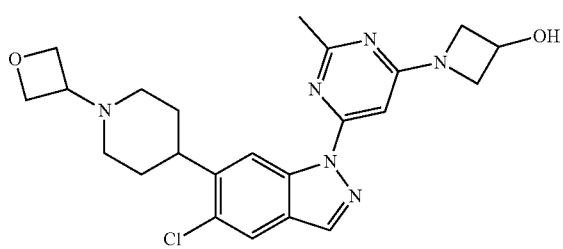 [SMILES: Cc1nc(N2CC(O)C2)cc(-n2ncc3cc(Cl)c(C4CCN(C5COC5)CC4)cc32)n1]

To a suspension of 5-chloro-1-(2-methyl-6-(3-((tetrahydro-2H-pyran-2-yl)oxy)azetidin-1-yl)pyrimidin-4-yl)-6-(1-(oxetan-3-yl)piperidin-4-yl)-1H-indazole (34 mg, 0.063 mmol) in MeOH (5 mL) was added TsOH (16 mg, 0.095 mmol) at rt. The resulting solution was stirred for 3 hrs. The reaction mixture was poured into sat. $Na_2CO_3$ (50 mL) and extracted with EtOAc (100 mL×2). The organic layers were washed with brine, dried over $Na_2SO_4$ and concentrated to give the title compound (26 mg, yield 90%) as a white solid.

E210 $^1$H NMR (400 MHz, $CDCl_3$): δ 8.94 (s, 1H), 8.09 (s, 1H), 7.75 (s, 1H), 6.61 (s, 1H), 4.90-4.82 (m, 1H), 4.73-4.71 (m, 4H), 4.46-4.40 (m, 2H), 4.06-4.00 (m, 2H), 3.63-3.52 (m, 1H), 3.19-3.09 (m, 1H), 3.02-2.93 (m, 2H), 2.65 (s, 3H), 2.12-2.01 (m, 5H), 1.97-1.83 (m, 2H).

LC-MS [mobile phase: from 95% water (0.02% $NH_4OAc$) and 5% $CH_3CN$ to 5% water (0.02% $NH_4OAc$) and 95% $CH_3CN$ in 6.5 min], purity is >95%, Rt=3.785 min; MS Calcd.: 454, MS Found: 455[M+H]$^+$.

Example 211

(S)-(4-(6-(5-Chloro-6-(piperidin-4-yl)-1H-indazol-1-yl)-2-methylpyrimidin-4-yl)morpholin-2-yl)methanol (E211)

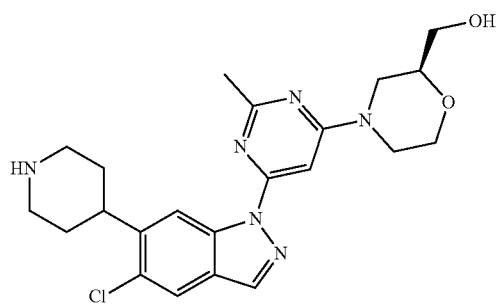 [SMILES: Cc1nc(N2CCO[C@H](CO)C2)cc(-n2ncc3cc(Cl)c(C4CCNCC4)cc32)n1]

To a solution of (S)-tert-butyl 4-(5-chloro-1-(6-(2-(hydroxymethyl)morpholino)-2-methylpyrimidin-4-yl)-1H-indazol-6-yl)piperidine-1-carboxylate (80 mg, 0.15 mmol) in MeOH (3 mL) was added conc. HCl (1 mL) at rt and the mixture was stirred for 7 hrs. Then, $Na_2CO_3$ (sat, 20 mL) was added and the mixture was stirred for 15 min. The aqueous was extracted with EtOAc (20 mL×3). The combined organic layers were washed with brine, dried over $MgSO_4$ and concentrated to give the title compound (23 mg, yield 35%) as a white solid.

E211 $^1$H NMR (300 MHz, $CDCl_3$): δ 8.92 (s, 1H), 8.07 (s, 1H), 7.74 (s, 1H), 6.95 (s, 1H), 4.36-4.24 (m, 2H), 4.10-4.03 (m, 1H), 3.82-3.63 (m, 4H), 3.30-3.20 (m, 3H), 3.16-3.06 (m, 1H), 2.99-2.80 (m, 3H), 2.62 (s, 3H), 2.04-1.97 (m, 2H), 1.74-1.63 (m, 2H).

LC-MS [mobile phase: from 95% water (0.02% $NH_4OAc$) and 5% $CH_3CN$ to 5% water (0.02% $NH_4OAc$) and 95% $CH_3CN$ in 6.5 min], Rt: 3.178 min, purity is >95%; MS Calcd.: 442, MS Found: 443 [M+H]$^+$.

Chiral HPLC [Chiralpak OD-H 5 um 4.6*250 mm, Phase: Hex/EtOH/DEA=70/30/0.2, flow rate: 1 mL/min, 230 nm, T=30° C.], Rt=6.433 min, 100% ee.

Example 212

(R)-(4-(6-(5-Chloro-6-(piperidin-4-yl)-1H-indazol-1-yl)-2-methylpyrimidin-4-yl)morpholin-2-yl)methanol (E212)

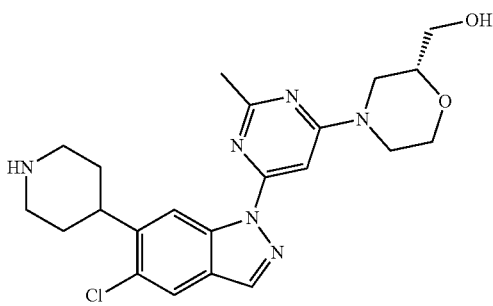 [SMILES: Cc1nc(N2CCO[C@@H](CO)C2)cc(-n2ncc3cc(Cl)c(C4CCNCC4)cc32)n1]

To a solution of (R)-tert-butyl 4-(5-chloro-1-(6-(2-(hydroxymethyl)morpholino)-2-methylpyrimidin-4-yl)-1H-indazol-6-yl)piperidine-1-carboxylate (74 mg, 0.14 mmol) in MeOH (3 mL) was added conc. HCl (1 mL) at rt and stirred for 7 hrs. Then, Na$_2$CO$_3$ (sat, 20 mL) was added and the mixture was stirred for 15 min. The aqueous was extracted with EtOAc (20 mL×3). And the combined organic layers were washed with brine, dried over MgSO$_4$ and concentrated to give the title compound (18 mg, yield 30%) as a white solid.

E212 $^1$H NMR (400 MHz, CDCl$_3$): δ 8.90 (s, 1H), 8.08 (s, 1H), 7.74 (s, 1H), 6.95 (s, 1H), 4.37-4.24 (m, 2H), 4.11-4.03 (m, 1H), 3.82-3.63 (m, 4H), 3.30-3.20 (m, 3H), 3.17-3.07 (m, 1H), 3.00-2.81 (m, 3H), 2.63 (s, 3H), 2.04-2.00 (m, 2H), 1.73-1.64 (m, 2H).

LC-MS [mobile phase: from 95% water (0.02% NH$_4$OAc) and 5% CH$_3$CN to 5% water (0.02% NH$_4$OAc) and 95% CH$_3$CN in 6.5 min], Rt: 3.179 min, purity is >95%; MS Calcd.: 442, MS Found: 443 [M+H]$^+$.

Chiral HPLC [Chiralpak OD-H 5 um 4.6*250 mm, Phase: Hex/EtOH/DEA=70/30/0.2, flow rate: 1 mL/min, 230 nm, T=30° C.], Rt=7.028 min, 100% ee.

Example 213

1-(6-(5-Chloro-6-(piperidin-4-yl)-1H-indazol-1-yl)-2-methylpyrimidin-4-yl)azetidin-3-ol (E213)

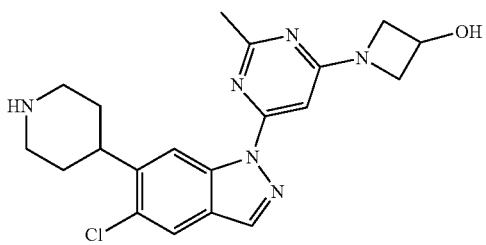 [SMILES: Cc1nc(N2CC(O)C2)cc(-n2ncc3cc(Cl)c(C4CCNCC4)cc32)n1]

To a solution of tert-butyl 4-(5-chloro-1-(2-methyl-6-(3-((tetrahydro-2H-pyran-2-yl)oxy)azetidin-1-yl)pyrimidin-4-yl)-1H-indazol-6-yl)piperidine-1-carboxylate (70 mg, 0.14 mmol) in DCM (5 mL) was added TFA (1 mL) at rt and stirred overnight. The reaction mixture was concentrated and the residue was dissolved in DCM (20 mL). Then, Na$_2$CO$_3$ (sat, 10 mL) was added to the solution and stirred for 20 min. The organic layer was separated and the aqueous was extracted with DCM/MeOH=10/1 (20 mL×2). The combined organic layers were dried over MgSO$_4$ and concentrated. The crude was triturated with PE/EtOAc (5 mL, 1/1) and filtered to give the title compound (15 mg, yield 27%) as a white solid.

E213 $^1$H NMR (400 MHz, DMSO-d$_6$): δ 8.87 (s, 1H), 8.38 (s, 1H), 7.98 (s, 1H), 6.55 (s, 1H), 4.65-4.59 (m, 1H), 4.32-4.28 (m, 2H), 3.84-3.80 (m, 2H), 3.16-3.06 (m, 3H), 2.75-2.62 (m, 2H), 2.51 (s, 3H), 1.86-1.83 (m, 2H), 1.60-1.51 (m, 2H).

LC-MS [mobile phase: from 95% water (0.02% NH$_4$OAc) and 5% CH$_3$CN to 5% water (0.02% NH$_4$OAc) and 95% CH$_3$CN in 6.5 min], Rt=3.142 min, purity 94.25% (254 nm); MS Calcd.: 398, MS Found: 399 [M+H]$^+$.

Example 214

(S)-1-(2-Methyl-6-(5-methyl-6-(1-(oxetan-3-yl)piperidin-4-yl)-1H-indazol-1-yl)pyrimidin-4-yl)pyrrolidin-3-ol (D214)

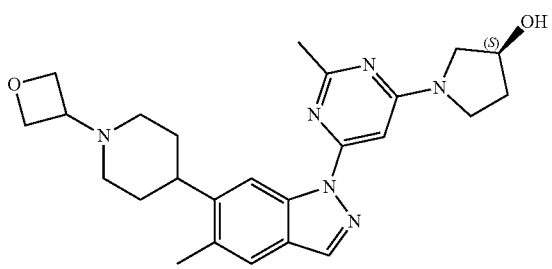

To a solution of 5-methyl-6-(1-(oxetan-3-yl)piperidin-4-yl)-1H-indazole (100 mg, 0.37 mmol) and (S)-1-(6-iodo-2-methylpyrimidin-4-yl)pyrrolidin-3-ol (113 mg, 0.37 mmol), K$_3$PO$_4$ (157 mg, 0.74 mmol), CuI (70 mg, 0.37 mmol) in toluene (2 ml) was added N1,N2-dimethylethane-1,2-diamine (65 mg, 0.74 mmol) under Ar. Then, the reaction was stirred at 100° C. for 3 hours. Then it was filtered and washed with DCM. The filtrate was concentrated and purified by column (PE:EtOAc=1:1-EtOAc-DCM:MeOH=30:1) to get a yellow solid. The residue was washed with ether and concentrated, dried to give the title compound as a white solid (59 mg, yield: 35.7%).

D214 $^1$H NMR (400 MHz, DMSO-d$_6$): δ 8.75 (s, 1H), 8.29 (s, 1H), 7.61 (s, 1H), 6.65 (s, 1H), 5.07-5.00 (d, J=27.2 Hz, 1H), 4.56-4.50 (m, 4H), 4.45-4.38 (m, 1H), 3.55-3.46 (m, 4H), 2.89-2.81 (m, 3H), 2.53 (s, 3H), 2.41 (s, 3H), 1.96 (s, 4H), 1.85-1.82 (d, J=11.6 Hz, 2H), 1.74-1.65 (m, 2H).

LC-MS [mobile phase: from 90% water (0.1% FA) and 10% CH$_3$CN (0.1% FA) to 5% water (0.1% FA) and 95% CH$_3$CN (0.1% FA) in 10 min], purity: 96.3%; Rt=4.85 min; MS Calcd: 448, MS Found: 449 [M+H]$^+$.

Example 215

(R)-1-(2-methyl-6-(5-methyl-6-(1-(oxetan-3-yl)piperidin-4-yl)-1H-indazol-1-yl)pyrimidin-4-yl)pyrrolidin-3-ol (D215)

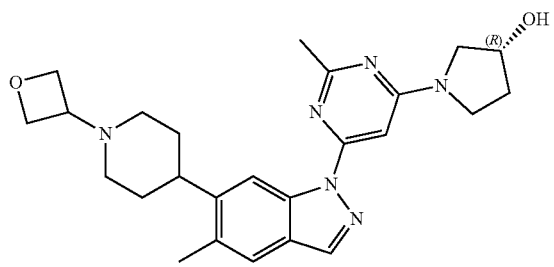

To a solution of 5-methyl-6-(1-(oxetan-3-yl)piperidin-4-yl)-1H-indazole (200 mg, 0.74 mmol) and (R)-1-(6-iodo-2-methylpyrimidin-4-yl)pyrrolidin-3-ol (338 mg, 1.11 mmol), $K_3PO_4$ (314 mg, 1.48 mmol), CuI (140 mg, 0.74 mmol) in toluene (2 ml) was added N1,N2-dimethylethane-1,2-diamine (130 mg, 1.48 mmol) under Ar. Then the reaction was stirred at 100° C. for 3 hours. Then it was filtered and washed with DCM. The filtrate was concentrated and purified by column (PE:EtOAc=1:1-EtOAc-DCM:MeOH=30:1-25:1) to get a yellow solid. (56 mg, yield: 17%).

E215 $^1$H NMR (400 MHz, DMSO-$d_6$): δ 8.76 (s, 1H), 8.30 (s, 1H), 7.61 (s, 1H), 6.66 (s, 1H), 5.09-5.02 (d, J=28 Hz, 1H), 4.58-4.55 (t, J=6.4 Hz, 2H), 4.51-4.48 (t, J=6.0 Hz, 2H), 4.44-4.38 (d, J=24 Hz, 1H), 3.63-3.38 (m, 4H), 2.89-2.79 (m, 2H), 2.54 (s, 3H), 2.42 (m, 3H), 2.05-1.93 (m, 4H), 1.85-1.82 (d, J=11.6 Hz, 2H), 1.74-1.65 (q, J=11.2 Hz, 2H).

LC-MS [mobile phase: from 90% water (0.1% FA) and 10% $CH_3CN$ (0.1% FA) to 5% water (0.1% FA) and 95% $CH_3CN$ (0.1% FA) in 10 min], purity: 96.3%; Rt=4.85 min; MS Calcd: 448, MS Found: 449 [M+H]$^+$.

Example 216 and 217

(trans)-4-Gluoro-1-(2-methyl-6-(5-methyl-6-(1-(oxetan-3-yl)piperidin-4-yl)-1H-indazol-1-yl)pyrimidin-4-yl)pyrrolidin-3-ol (Enantiomer 1, E216) and (trans)-4-Fluoro-1-(2-methyl-6-(5-methyl-6-(1-(oxetan-3-yl)piperidin-4-yl)-1H-indazol-1-yl)pyrimidin-4-yl)pyrrolidin-3-ol (Enantiomer 2, E217)

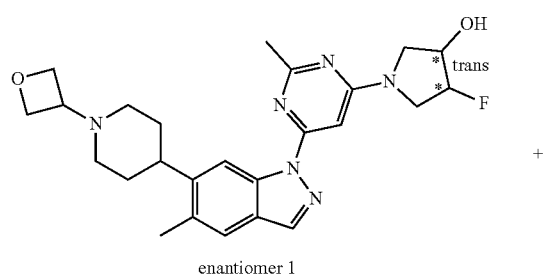

enantiomer 1

+

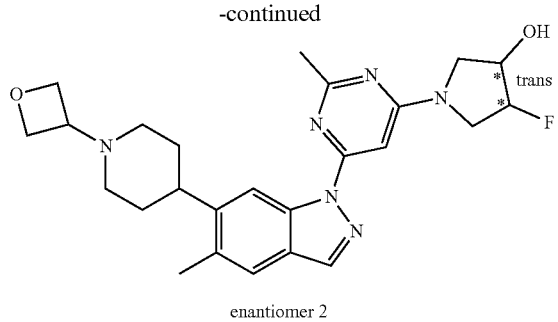

enantiomer 2

The racemate (trans)-4-fluoro-1-(2-methyl-6-(5-methyl-6-(1-(oxetan-3-yl)piperidin-4-yl)-1H-indazol-1-yl)pyrimidin-4-yl)pyrrolidin-3-ol (80 mg, 0.12 mmol) was separated by Chiral-HPLC (Chiralpak IC 5 μm 4.6×150 mm, Phase: HEP:ETOH (0.1% DEA)=60:40, flowrate: 0.5 mL/min, temperature: 25° C.) to give (trans)-4-fluoro-1-(2-methyl-6-(5-methyl-6-(1-(oxetan-3-yl)piperidin-4-yl)-1H-indazol-1-yl)pyrimidin-4-yl)pyrrolidin-3-ol (enantiomer 1) (Rt: 2.597 min, 30 mg, yield 37%) as a white solid and (trans)-4-fluoro-1-(2-methyl-6-(5-methyl-6-(1-(oxetan-3-yl)piperidin-4-yl)-1H-indazol-1-yl)pyrimidin-4-yl)pyrrolidin-3-ol (enantiomer 2) (30 mg, yield 37%) as a white solid.

E216 $^1$H NMR (400 MHz, CDCl$_3$) δ 8.84 (s, 1H), 8.05 (s, 1H), 7.50 (s, 1H), 6.70 (s, 1H), 5.02-5.15 (d, J=10.8 Hz, 1H), 4.72 (d, J=6.4 Hz, 4H), 4.56 (s, 1H), 3.93 (s, 1H), 3.78-3.84 (m, 4H), 3.55-3.58 (m, 1H); 2.96-2.99 (m, 2H); 2.83-2.86 (m, 1H), 2.62 (s, 3H); 2.45 (m, 3H); 1.94-2.03 (m, 7H).

E217 $^1$H NMR (400 MHz, CDCl$_3$) δ 8.83 (s, 1H), 8.05 (s, 1H), 7.50 (s, 1H), 6.70 (s, 1H), 5.02-5.15 (m, 1H), 4.73 (d, J=6.0 Hz, 4H), 4.56 (s, 1H), 3.78-3.94 (m, 4H), 3.59 (s, 1H); 2.99-3.01 (m, 2H), 2.85 (s, 1H), 2.63 (s, 3H); 2.45 (s, 3H); 2.17 (s, 1H), 1.95-2.06 (m, 7H).

Example 218 and 219

(trans)-4-Fluoro-1-(2-methoxy-6-(5-methyl-6-(1-(oxetan-3-yl)piperidin-4-yl)-1H-indazol-1-yl)pyrimidin-4-yl)pyrrolidin-3-ol (Enantiomer 1, E218) and (trans)-4-Fluoro-1-(2-methoxy-6-(5-methyl-6-(1-(oxetan-3-yl)piperidin-4-yl)-1H-indazol-1-yl)pyrimidin-4-yl)pyrrolidin-3-ol (Enantiomer 2, E219)

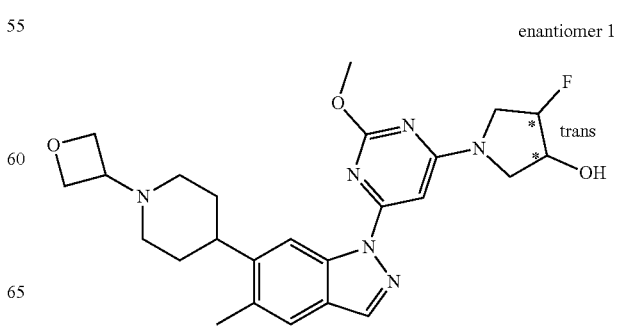

enantiomer 1

-continued enantiomer 2

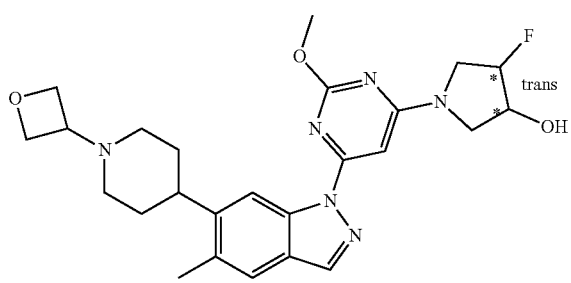

The racemate (trans)-4-fluoro-1-(2-methoxy-6-(5-methyl-6-(1-(oxetan-3-yl)piperidin-4-yl)-1H-indazol-1-yl)pyrimidin-4-yl)pyrrolidin-3-ol (210 mg, 0.43 mmol) was separated by Chiral-HPLC (Chiralpak IC 5 μm 4.6×150 mm, Phase: HEP:ETOH (0.1% DEA)=60:40, flowrate: 0.5 mL/min, temperature: 25° C.) to give (trans)-4-fluoro-1-(2-methoxy-6-(5-methyl-6-(1-(oxetan-3-yl)piperidin-4-yl)-1H-indazol-1-yl)pyrimidin-4-yl)pyrrolidin-3-ol (enantiomer 1, E218) (100 mg, yield 47%) as a white solid and (trans)-4-fluoro-1-(2-methoxy-6-(5-methyl-6-(1-(oxetan-3-yl)piperidin-4-yl)-1H-indazol-1-yl)pyrimidin-4-yl)pyrrolidin-3-ol (enantiomer 2, E219) (Rt: 6.795 min, 95 mg, yield 45%) as a white solid.

E218 $^1$H NMR (400 MHz, CDCl$_3$) δ 8.77 (s, 1H), 8.06 (s, 1H), 7.51 (s, 1H), 6.63 (s, 1H), 5.04 (d, J=50.4 Hz, 1H), 4.69 (d, J=6.4 Hz, 4H); 4.65 (d, J=6.4 Hz, 4H), 4.57-4.58 (m, 1H), 4.15 (s, 3H), 3.83-3.95 (m, 3H), 3.52-3.56 (m, 1H); 2.92-2.95 (m, 3H); 2.45 (s, 3H); 1.91-3.02 (m, 7H).

E219 $^1$H NMR (400 MHz, CDCl$_3$) δ 8.77 (s, 1H), 8.07 (s, 1H), 7.51 (s, 1H), 6.64 (s, 1H), 5.03-5.16 (d, J=50.4 Hz, 1H), 4.69 (d, J=6.4 Hz, 1H); 4.58 (s, 1H), 4.16 (s, 3H), 3.84-3.87 (m, 4H), 3.54-3.57 (m, 1H); 2.94 (m, 2H); 2.92 (m, 1H), 2.46 (s, 3H); 1.86-2.04 (m, 7H).

Example 220

N-Methyl-1-(2-methyl-6-(5-methyl-6-(1-(oxetan-3-yl)piperidin-4-yl)-1H-indazol-1-yl)pyrimidin-4-yl)azetidine-3-carboxamide (E220)

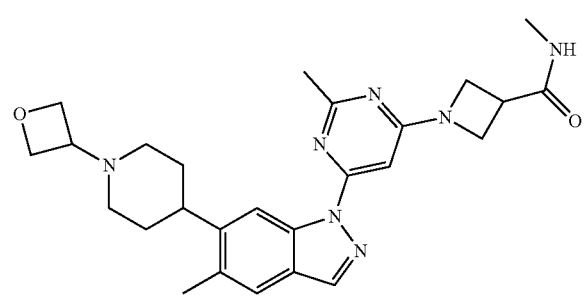 [SMILES: CNC(=O)C1CN(c2cc(-n3ncc4cc(C)c(C5CCN(C6COC6)CC5)cc43)nc(C)n2)C1]

Methylamine (2 mL) was added to a solution of 1-(2-methyl-6-(5-methyl-6-(1-(oxetan-3-yl)piperidin-4-yl)-1H-indazol-1-yl)pyrimidin-4-yl)azetidine-3-carboxylate (30 mg, 0.06 mmol) in MeOH (3 mL). The mixture was stirred at 60° C. for 4h. The reaction was concentrated and purified by column (DCM/MeOH=50/1) to give product as a white solid (5.1 mg, 6.5%).

E220 $^1$H NMR (400 MHz, CDCl$_3$): δ 8.75 (s, 1H), 8.31 (s, 1H), 8.04, 8.05 (d, J$_1$=4.4 Hz, 1H), 7.63 (s, 1H), 6.56 (s, 1H), 4.50~4.59 (m, 4H). 4.06~4.23 (m, 4H), 3.45~3.54 (m, 4H), 2.80~2.90 (m, 3H), 2.67 (s, 3H), 2.54 (s, 3H), 2.43 (s, 3H), 2.38 (m, 1H), 1.68~1.99 (m, 6H).

LC-MS (mobile phase: from 90% water (0.1% FA) and 10% CH$_3$CN (0.1% FA), Rt=1.29 min; MS Calcd.: 475.3; MS Found: 476.3 [M+H]$^+$.

Example 221 and 222

1-(6-(6-(3-Fluoro-1-methylpiperidin-3-yl)-5-methyl-1H-indazol-1-yl)-2-methoxypyrimidin-4-yl)azetidin-3-ol (Enantiomer 1, E221) and 1-(6-(6-(3-fluoro-1-methyl piperidin-3-yl)-5-methyl-1H-indazol-1-yl)-2-methoxypyrimidin-4-yl)azetidin-3-ol (Enantiomer 2, E222)

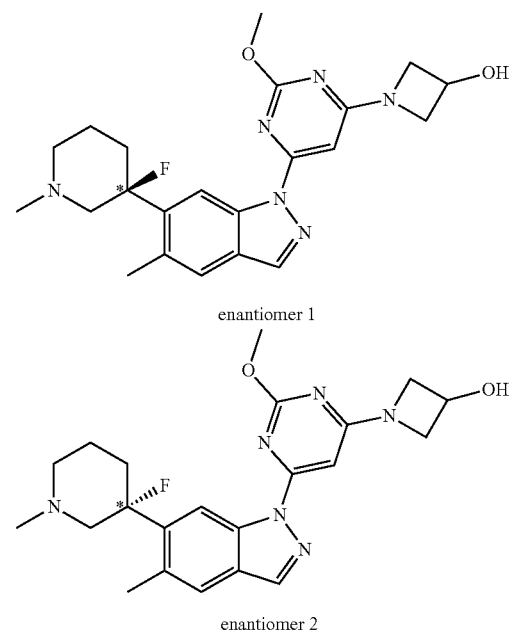

To a solution of 6-(3-fluoro-1-methylpiperidin-3-yl)-1-(2-methoxy-6-(3-((tetrahydro-2H-pyran-2-yl) oxy)azetidin-1-yl)pyrimidin-4-yl)-5-methyl-1H-indazole (180 mg, 0.35 mmol) in CH$_2$Cl$_2$ (3.0 mL) was added TFA (0.5 mL). The reaction was stirred at room temperature for 2.0 h. Solvent and most of TFA was removed in vacuum and the residue was diluted with CH$_2$Cl$_2$ (10 mL). The resulting solution was washed with sat. NaHCO$_3$ (2 mL) and brine (5 mL), dried over anhydrous Na$_2$SO$_4$ and concentrated under reduced pressure. The residue was purified by silica column chromatography (MeOH/DCM=1/20) to give an off-white solid (135 mg, 70% yield). The solid was washed with EtOAc/hexane=1/2 (2×5 mL) to give pure product as an off-white solid (91 mg). The solid was chiral separated by Daicel to give two solids: E221 (enantiomer 1) (37 mg, 39% yield)

$^1$H NMR (400 MHz, CDCl$_3$): δ 8.96 (s, 1H), 8.09 (s, 1H), 7.54 (s, 1H), 6.49 (s, 1H), 4.85~4.82 (m, 1H), 4.45~4.40 (m, 2H), 4.11 (s, 3H), 4.04~4.00 (m, 2H), 3.29 (m, 1H), 3.01~2.99 (m, 1H), 2.66 (d, J=4.4 Hz, 3H), 2.50 (m, 1H), 2.38 (s, 3H), 2.32~2.26 (m, 2H), 2.16~2.05 (m, 4H), 1.77~1.61 (m, 1H).

$^{19}$F NMR (400 MHz, CDCl$_3$): δ −75.59 (s, CF$_3$COOH), −153.69 (m, 1F).

LC-MS (mobile phase: from 90% water (0.1% FA) and 10% CH$_3$CN (0.1% FA) to 5% water (0.1% FA) and 95% CH$_3$CN (0.1% FA) in 10 min, purity 96.4%, Rt=5.27 min; MS Calcd.: 426.2, MS Found: 427.6 (M+H)$^+$.

Chiral purity: Rt=3.009 min; ee %=98.6%.

Chiral method: Chiralpak IA, 0.46 cm I.D.×15 cm L, Phase: MeOH: DEA=100/0.1, F: 1.0 mL/min, W: 254 nm, T: 25° C.

E222 (enantiomer 2): (41 mg, 43% yield)

$^1$H NMR (400 MHz, CDCl$_3$): δ 8.96 (s, 1H), 8.09 (s, 1H), 7.54 (s, 1H), 6.49 (s, 1H), 4.85~4.82 (m, 1H), 4.45~4.40 (m, 2H), 4.11 (s, 3H), 4.04~4.00 (m, 2H), 3.29 (m, 1H), 3.01~2.99 (m, 1H), 2.66 (d, J=4.4 Hz, 3H), 2.50 (m, 1H), 2.38 (s, 3H), 2.32~2.26 (m, 2H), 2.16~2.05 (m, 4H), 1.77~1.61 (m, 1H).

$^{19}$F NMR (400 MHz, CDCl$_3$): δ −75.59 (s, CF$_3$COOH), −153.69 (m, 1F).

LC-MS (mobile phase: from 80% water (0.1% FA) and 20% CH$_3$CN (0.1% FA) to 5% water (0.1% FA) and 95% CH$_3$CN (0.1% FA) in 10 min, purity 95.0%, Rt=5.28 min; MS Calcd.: 426.2, MS Found: 427.6 (M+H)$^+$.

Chiral purity: Rt=3.490 min; ee %=97.1%.

Chiral method: Chiralpak IA, 0.46 cm I.D.×15 cm L, Phase: MeOH: DEA=100/0.1, F: 1.0 mL/min, W: 254 nm, T: 25° C.

Example 223

(trans)-1-Methyl-4-(5-methyl-1-(2-methyl-6-morpholinopyrimidin-4-yl)-1H-indazol-6-yl)piperidin-3-ol (Enantiomer 1, E223)

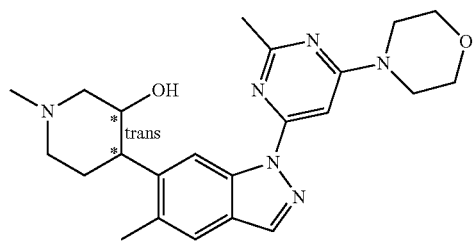 [SMILES: Cc1nc(N2CCOCC2)cc(-n2ncc3cc(C)c(C4CCN(C)CC4O)cc32)n1]

To a solution of (trans)-4-(5-methyl-1-(2-methyl-6-morpholinopyrimidin-4-yl)-1H-indazol-6-yl)piperidin-3-ol hydrochloride (enantiomer 1, 70 mg crude, 0.12 mmol) in methanol (5 mL) was added HCHO aqueous (37%, 1.2 mL). After the mixture was stirred at rt for 30 min NaBH$_3$CN (15 mg, 0.24 mmol) was added. The mixture was stirred at rt for 14 hrs. The mixture was concentrated and the residue was partitioned with CH$_2$Cl$_2$ (20 mL) and water (10 mL). The organic phase was separated and the aqueous phase was extracted with CH$_2$Cl$_2$ (20 mL×2). The combined organic phase was dried over Na$_2$SO$_4$ and concentrated. The crude was purified by prep-TLC (CH$_2$Cl$_2$:methanol=10:1) to give the title compound (28 mg, yield 54%) as white solid.

E223 $^1$H NMR (300 MHz, CDCl$_3$): δ 8.82 (s, 1H), 8.02 (s, 1H), 7.53 (s, 1H), 6.91 (s, 1H), 4.25-4.17 (m, 1H), 3.81-3.78 (m, 4H), 3.70-3.67 (m, 4H), 3.29-3.24 (m, 1H), 2.98-2.95 (m, 1H), 2.87-2.82 (m, 1H), 2.60 (s, 3H), 2.49 (s, 3H), 2.41 (s, 3H), 2.19-2.01 (m, 3H), 1.88-1.86 (m, 2H).

LC-MS (XB-C18, ¢4.6*50 mm*5 um; mobile phase: from 95% water (0.1% TFA) and 5% CH$_3$CN to 5% water (0.1% TFA) and 95% CH$_3$CN in 6.5 min, Rt=2.817 min; MS Calcd.: 422; MS Found: 423 (M+H)$^+$.

Chiral condition: Chiral pak OD-H 5 um 4.6*250 nm, Hex:EtOH:DEA=80:20:0.2; Flow: 1.0 ml/min; 230 nm, T=30° C. Rt=5.472 min, 99.3% ee.

Example 224

(trans)-1-Methyl-4-(5-methyl-1-(2-methyl-6-morpholinopyrimidin-4-yl)-1H-indazol-6-yl)piperidin-3-ol (Enantiomer 2, E224)

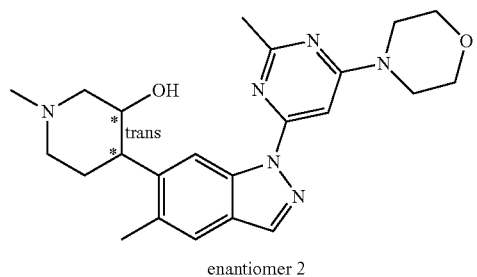 [SMILES: Cc1nc(N2CCOCC2)cc(-n2ncc3cc(C)c(C4CCN(C)CC4O)cc32)n1]

enantiomer 2

To a solution of (trans)-4-(5-methyl-1-(2-methyl-6-morpholinopyrimidin-4-yl)-1H-indazol-6-yl)piperidin-3-ol hydrochloride (enantiomer 2, 75 mg crude, 0.12 mmol) in methanol (5 mL) was added HCHO aqueous (37%, 1.2 mL). After the mixture was stirred at rt for 30 min NaBH$_3$CN (15 mg, 0.24 mmol) was added. The mixture was stirred at rt for 14 hrs. The mixture was concentrated and the residue was partitioned with CH$_2$Cl$_2$ (20 mL) and water (10 mL). The organic phase was separated and the aqueous phase was extracted with CH$_2$Cl$_2$ (20 mL×2). The combined organic phase was dried over Na$_2$SO$_4$ and concentrated. The crude was purified by prep-TLC (CH$_2$Cl$_2$:methanol=10:1) to give the title compound (30 mg, yield 57%) as white solid.

E224 $^1$H NMR (300 MHz, CDCl$_3$): δ 8.82 (s, 1H), 8.02 (s, 1H), 7.52 (s, 1H), 6.92 (s, 1H), 4.26-4.17 (m, 1H), 3.81-3.78 (m, 4H), 3.70-3.67 (m, 4H), 3.30-3.25 (m, 1H), 2.99-2.96 (m, 1H), 2.88-2.82 (m, 1H), 2.60 (s, 3H), 2.49 (s, 3H), 2.42 (s, 3H), 2.14-2.00 (m, 3H), 1.89-1.87 (m, 2H).

LC-MS (XB-C18, ¢4.6*50 mm*5 um; mobile phase: from 95% water (0.1% TFA) and 5% CH$_3$CN to 5% water (0.1% TFA) and 95% CH$_3$CN in 6.5 min, Rt=2.814 min; MS Calcd.: 422; MS Found: 423 (M+H)$^+$.

Chiral condition: Chiral pak OD-H 5 um 4.6*250 nm, Hex:EtOH:DEA=80:20:0.2; Flow: 1.0 ml/min; 230 nm, T=30° C. Rt=6.777 min, 99.5% ee.

Example 225

(trans)-4-(1-(2-Methoxy-6-morpholinopyrimidin-4-yl)-5-methyl-1H-indazol-6-yl)-1-methylpiperidin-3-ol (Enantiomer 1, E225)

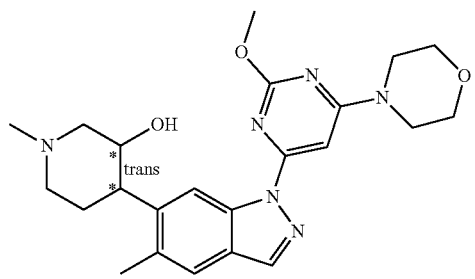 [SMILES: COc1nc(N2CCOCC2)cc(-n2ncc3cc(C)c(C4CCN(C)CC4O)cc32)n1]

To a solution of (trans)-4-(1-(2-methoxy-6-morpholinopyrimidin-4-yl)-5-methyl-1H-indazol-6-yl)piperidin-3-ol hydrochloride (enantiomer 1, 43 mg, 0.09 mmol) in methanol (4 mL) was added HCHO aqueous (37%, 1.2 mL). After the mixture was stirred at rt for 30 min NaBH$_3$CN (20 mg, 0.32 mmol) was added. The mixture was stirred at rt for 2 hrs. The mixture was poured into water (10 mL) and extracted with ethyl acetate (10 mL×2). The combined organic phase was washed with brine, dried over Na$_2$SO$_4$ and concentrated. The crude was purified by prep-TLC (CH$_2$Cl$_2$:methanol=9:1) to give the title compound (21 mg, yield 51%) as white solid.

E225 $^1$H NMR (300 MHz, CDCl$_3$): δ 8.79 (s, 1H), 8.01 (s, 1H), 7.53 (s, 1H), 6.79 (s, 1H), 4.20-4.09 (m, 4H), 3.78-3.69 (m, 8H), 3.26-3.22 (m, 1H), 2.97-2.82 (m, 2H), 2.49 (s, 3H), 2.40 (s, 3H), 2.16-2.05 (m, 2H), 1.89-1.85 (m, 2H).

LC-MS (XB-C18, ¢4.6*50 mm*5 um; mobile phase: from 95% water (0.1% TFA) and 5% CH$_3$CN to 5% water (0.1% TFA) and 95% CH$_3$CN in 6.5 min, Rt=3.122 min; MS Calcd.: 438; MS Found: 439 (M+H)$^+$.

Chiral condition: Chiral pak IA 5 um 4.6*250 mm, Hex:EtOH:DEA=50:50:0.2; Flow: 1.0 ml/min; 230 nm, T=30° C. Rt=7.547 min, 99.3% ee.

Example 226

(trans)-1-Methyl-4-(5-methyl-1-(2-methyl-6-morpholinopyrimidin-4-yl)-1H-indazol-6-yl)piperidin-3-ol (Enantiomer 2, E226)

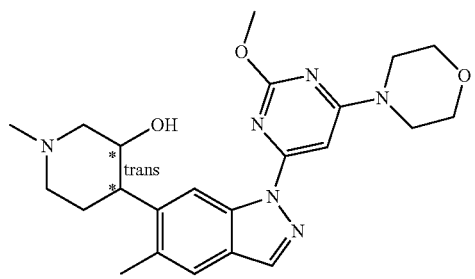 [SMILES: COc1nc(N2CCOCC2)cc(-n2ncc3cc(C)c(C4CCN(C)CC4O)cc32)n1]

To a solution of (trans)-4-(1-(2-methoxy-6-morpholinopyrimidin-4-yl)-5-methyl-1H-indazol-6-yl)piperidin-3-ol hydrochloride (enantiomer 2, 62 mg, 0.14 mmol) in methanol (4 mL) was added HCHO aqueous (37%, 1.2 mL). After the mixture was stirred at rt for 30 min NaBH$_3$CN (20 mg, 0.32 mmol) was added. The mixture was stirred at rt for 2 hrs. The mixture was poured into water (10 mL) and extracted with ethyl acetate (10 mL×2). The combined organic phase was washed with brine, dried over Na$_2$SO$_4$ and concentrated. The crude was purified by prep-TLC (CH$_2$Cl$_2$:methanol=9:1) to give the title compound (33 mg, yield 55%) as white solid.

E226 $^1$H NMR (300 MHz, CDCl$_3$): δ 8.79 (s, 1H), 8.02 (s, 1H), 7.53 (s, 1H), 6.80 (s, 1H), 4.21-4.09 (m, 4H), 3.80-3.77 (m, 4H), 3.71-3.68 (m, 4H), 3.27-3.21 (m, 1H), 2.97-2.81 (m, 2H), 2.48 (s, 3H), 2.40 (s, 3H), 2.16-2.04 (m, 3H), 1.90-1.80 (m, 2H).

LC-MS (XB-C18, ¢4.6*50 mm*5 um; mobile phase: from 95% water (0.1% TFA) and 5% CH$_3$CN to 5% water (0.1% TFA) and 95% CH$_3$CN in 6.5 min, Rt=3.122 min; MS Calcd.: 438; MS Found: 439 (M+H)$^+$.

Chiral condition: Chiral pak IA 5 um 4.6*250 mm, Hex:EtOH:DEA=50:50:0.2; Flow: 1.0 ml/min; 230 nm, T=30° C. Rt=8.986 min, 95.1% ee.

Example 227

1-(2-Methyl-6-(5-methyl-6-(4-methylmorpholin-2-yl)-1H-indazol-1-yl)pyrimidin-4-yl)azetidin-3-ol (Enantiomer 1, E227)

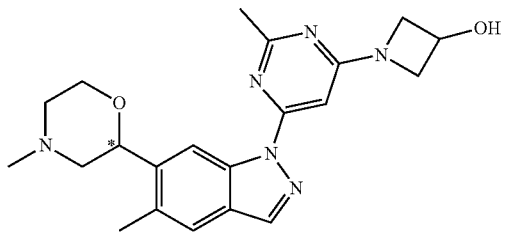 [SMILES: Cc1nc(N2CC(O)C2)cc(-n2ncc3cc(C)c(C4CN(C)CCO4)cc32)n1]

A mixture of 1-(2-methyl-6-(5-methyl-6-(morpholin-2-yl)-1H-indazol-1-yl)pyrimidin-4-yl)azetidin-3-ol hydrochloride (enantiomer 1, 58 mg, 0.12 mmol), formaldehyde solution (37%, 1 mL) and sodium cyanoborohydride (16 mg, 0.25 mmol) in methanol (4 mL) was stirred at room temperature overnight. The reaction mixture was poured into water (50 mL) and extracted with EtOAc (30 mL×2). The combined organic layers were washed with brine (50 mL), dried over Na$_2$SO$_4$ and concentrated to give a white solid. The solid was purified by prep-HPLC (ACN/H$_2$O, 10-95%) to give the title compound (25 mg, yield 51%) as white solid.

E227 $^1$H NMR (300 MHz, CDCl$_3$+1 drop of CD$_3$OD): δ 8.88 (s, 1H), 8.05 (s, 1H), 7.48 (s, 1H), 6.52 (s, 1H), 5.10-5.07 (m, 1H), 4.70-4.67 (m, 1H), 4.35-4.30 (m, 2H), 4.18-4.09 (m, 2H), 3.94-3.91 (m, 2H), 3.26-3.12 (m, 2H), 2.77-2.46 (m, 11H).

LC-MS (XB-C18, ¢4.6*50 mm*5 um; mobile phase: from 90% water (0.02% NH$_4$OAc) and 10% CH$_3$CN to 5% water (0.02% NH$_4$OAc) and 95% CH$_3$CN in 6.5 min, Rt=3.618 min; MS Calcd.: 394; MS Found: 395 (M+H)$^+$.

Chiral condition: Chiralpak IA 5 um 4.6*250 mm, Hex:IPA:DEA=60:40:0.2, Flow: 1.0 ml/min, 230 nm, T=30° C. Rt=4.320 min, 93.3% ee.

Example 228

1-(2-Methyl-6-(5-methyl-6-(4-methylmorpholin-2-yl)-1H-indazol-1-yl)pyrimidin-4-yl)azetidin-3-ol (Enantiomer 2, E228)

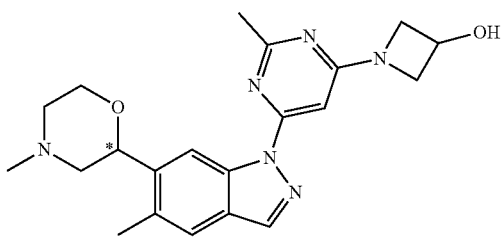 [SMILES: Cc1nc(N2CC(O)C2)cc(-n2ncc3cc(C)c(C4CN(C)CCO4)cc32)n1]

A mixture of 1-(2-methyl-6-(5-methyl-6-(morpholin-2-yl)-1H-indazol-1-yl)pyrimidin-4-yl)azetidin-3-ol hydrochloride (enantiomer 2, 110 mg, 0.222 mmol), formaldehyde solution (37%, 1 mL) and sodium cyanoborohydride (28 mg, 0.44 mmol) in methanol (4 mL) was stirred at room temperature for 18 hours. The reaction was poured into water (50 mL) and extracted with EtOAc (50 mL×2). The combined organic layers were washed with brine (50 mL), dried over $Na_2SO_4$ and concentrated. The residue was purified by prep-HPLC (ACN/$H_2O$, 10-95%) to give the title compound (34 mg, yield 39%) as white solid.

E228 $^1$H NMR (300 MHz, $CDCl_3$): δ 8.99 (s, 1H), 8.07 (s, 1H), 7.48 (s, 1H), 6.57 (s, 1H), 4.83-4.79 (m, 2H), 4.42-4.36 (m, 2H), 4.13-4.08 (m, 1H), 4.00-3.87 (m, 3H), 2.99-2.96 (m, 1H), 2.82-2.78 (m, 1H), 2.62 (s, 3H), 2.48 (s, 3H), 2.37 (s, 3H), 2.36-2.18 (m, 2H).

LC-MS (XB-C18, ¢4.6*50 mm*5 um; mobile phase: from 95% water (0.02% $NH_4OAc$) and 5% $CH_3CN$ to 95% water (0.02% $NH_4OAc$) and 5% $CH_3CN$ in 6.5 min), Rt=3.606 min; MS Calcd.: 394; MS Found: 395 (M+H)$^+$.

Chiral condition: Chiral pak IA 5 um 4.6*250 nm, Hex:IPA:DEA=60:40:0.2, Flow: 1.0 ml/min, 230 nm, T=30° C. Rt=7.182 min, 99.3% ee.

Example 229

1-(2-Methoxy-6-(5-methyl-6-(4-methyl morpholin-2-yl)-1H-indazol-1-yl)pyrimidin-4-yl)azetidin-3-ol (Enantiomer 1, E229)

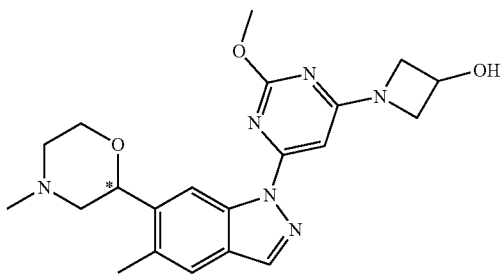 [SMILES: COc1nc(N2CC(O)C2)cc(-n2ncc3cc(C)c(C4CN(C)CCO4)cc32)n1]

A mixture of 1-(2-methoxy-6-(5-methyl-6-(morpholin-2-yl)-1H-indazol-1-yl)pyrimidin-4-yl)azetidin-3-ol hydrochloride (enantiomer 1, 109 mg, 0.262 mmol), formaldehyde solution (37%, 1 mL) and sodium cyanoborohydride (33 mg, 0.53 mmol) in methanol (4 mL) was stirred at room temperature for 18 hrs. The reaction mixture was poured into water (50 mL) and extracted with EtOAc (30 mL×2). The combined organic layers were washed with brine (50 mL), dried and concentrated. The residue was purified by prep-HPLC (ACN/$H_2O$, 10-95%) to give the title compound (33 mg, yield 31%) pale yellow solid.

E229 $^1$H NMR (400 MHz, $CDCl_3$): δ 9.05 (s, 1H), 8.08 (s, 1H), 7.49 (s, 1H), 6.45 (s, 1H), 4.86-4.80 (m, 2H), 4.42-4.38 (m, 2H), 4.16 (s, 3H), 4.06-3.90 (m, 4H), 2.99-2.96 (m, 1H), 2.81-2.78 (m, 1H), 2.47 (s, 3H), 2.33 (s, 3H), 2.20-2.03 (m, 2H).

LC-MS (XB-C18, ¢4.6*50 mm*5 um; mobile phase: from 95% water (0.02% $NH_4OAc$) and 5% $CH_3CN$ to 95% water (0.02% $NH_4OAc$) and 5% $CH_3CN$ in 6.5 min, Rt=3.704 min; MS Calcd.: 410; MS Found: 411 (M+H)$^+$.

Chiral condition: Chiral pak IA 5 um 4.6*250 nm, Hex:IPA:DEA=60:40:0.2; Flow: 1.0 ml/min; 230 nm, T=30° C. Rt=4.720 min, 93.7% ee.

Example 230

1-(2-Methoxy-6-(5-methyl-6-(4-methylmorpholin-2-yl)-1H-indazol-1-yl)pyrimidin-4-yl)azetidin-3-ol (Enantiomer 2, E230)

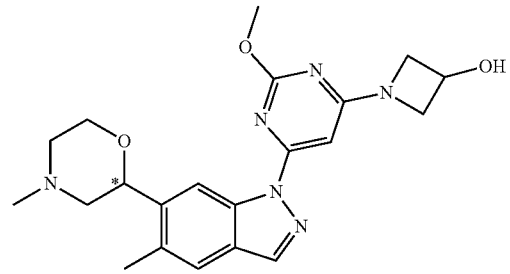 [SMILES: COc1nc(N2CC(O)C2)cc(-n2ncc3cc(C)c(C4CN(C)CCO4)cc32)n1]

A mixture of 1-(2-methoxy-6-(5-methyl-6-(morpholin-2-yl)-1H-indazol-1-yl)pyrimidin-4-yl)azetidin-3-ol hydrochloride (enantiomer 2, 150 mg crude, 0.262 mmol), formaldehyde solution (37%, 1 mL) and sodium cyanoborohydride (33 mg, 0.52 mmol) in methanol (4 mL) was stirred at room temperature for 18 hrs. The reaction mixture was poured into water (50 mL) and extracted with EtOAc (30 mL×2). The combined organic layers were washed with brine (50 mL), dried and concentrated. The residue was purified by prep-HPLC (ACN/$H_2O$, 10-95%) to give the title compound (56 mg, yield 52%) as pale yellow solid.

E230 $^1$H NMR (400 MHz, $CDCl_3$): δ 9.05 (s, 1H), 8.07 (s, 1H), 7.49 (s, 1H), 6.45 (s, 1H), 4.86-4.80 (m, 2H), 4.42-4.38 (m, 2H), 4.16 (s, 3H), 4.06-3.87 (m, 4H), 2.98-2.96 (m, 1H), 2.81-2.78 (m, 1H), 2.47 (s, 3H), 2.33 (s, 3H), 2.23-2.16 (m, 1H), 2.08-2.02 (m, 1H).

LC-MS (XB-C18, ¢4.6*50 mm*5 um; mobile phase: from 95% water (0.02% $NH_4OAc$) and 5% $CH_3CN$ to 95% water (0.02% $NH_4OAc$) and 5% $CH_3CN$ in 6.5 min, Rt=3.695 min; MS Calcd.: 410; MS Found: 411 (M+H)$^+$.

Chiral condition: Chiral pak IA 5 um 4.6'250 nm, Hex:IPA:DEA=60:40:0.2; Flow: 1.0 ml/min; 230 nm, T=30° C. Rt=6.565 min, 99.2% ee.

Example 231

1-(6-Methoxy-4-(5-methyl-6-(1-(oxetan-3-yl)piperidin-4-yl)-1H-pyrazolo[3,4-b]pyridin-1-yl)pyridin-2-yl)azetidin-3-ol (E231)

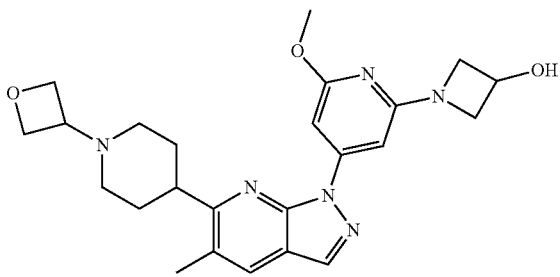 [SMILES: COc1cc(-n2ncc3cc(C)c(C4CCN(C5COC5)CC4)nc32)cc(N2CC(O)C2)n1]

To a solution of 1-(2-(3-(benzyloxy)azetidin-1-yl)-6-methoxypyridin-4-yl)-5-methyl-6-(1-(oxetan-3-yl)piperidin-4-yl)-1H-pyrazolo[3,4-b]pyridine (50 mg, 0.093 mmol) in EtOAc (50 mL) was added $CH_3OH$ (10 mL) and Pd/C (10%, 100 mg). The mixture was stirred at rt under a $H_2$ balloon for 2 days. The mixture was filtered and the filtrate was concentrated. The residue was purified by prep-TLC (DCM: $CH_3OH$=15:1) to give the title compound (9 mg, yield 22%) as white solid.

E231 $^1H$ NMR (300 MHz, $CDCl_3$): δ 8.04 (s, 1H), 7.80 (s, 1H), 7.59 (d, J=1.2 Hz, 1H), 7.15 (d, J=1.5 Hz, 1H), 4.86-4.80 (m, 1H), 4.75 (t, J=6.6 Hz, 2H), 4.63 (t, J=6.0 Hz, 2H), 4.43-4.38 (m, 2H), 4.03 (dd, J=9.0, 4.5 Hz, 2H), 3.95 (s, 3H), 3.53-3.45 (m, 1H), 3.10-3.00 (m, 2H), 2.93-2.90 (m, 2H), 2.47 (s, 3H), 2.31-2.18 (m, 2H), 2.03-1.95 (m, 2H), 1.89-1.84 (m, 2H).

LC-MS [mobile phase: from 95% water (0.02% $NH_4OAc$) and 5% $CH_3CN$ to 5% water (0.02% $NH_4OAc$) and 95% $CH_3CN$ in 6.5 min], purity >95%, Rt=3.396 min; MS Calcd.: 450, MS Found: 451 $[M+H]^+$.

Example 232

1-(6-(6-(3,3-Difluoro-1-(oxetan-3-yl)piperidin-4-yl)-5-methyl-1H-indazol-1-yl)-2-methylpyrimidin-4-yl)azetidin-3-ol (Enantiomer 1, E232)

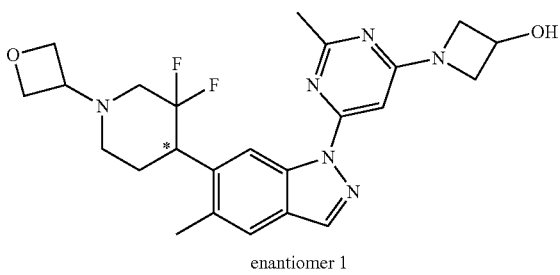 [SMILES: Cc1nc(N2CC(O)C2)cc(-n2ncc3cc(C)c(C4CCN(C5COC5)CC4(F)F)cc32)n1]

enantiomer 1

To a solution of 6-(3,3-difluoro-1-(oxetan-3-yl)piperidin-4-yl)-5-methyl-1-(2-methyl-6-(3-((tetrahydro-2H-pyran-2-yl)oxy)azetidin-1-yl)pyrimidin-4-yl)-1H-indazole (isomer 1, 68 mg, 0.12 mmol) in $CH_3OH$ (5 mL) was added TsOH (63 mg, 0.37 mmol). The mixture was stirred at rt overnight. To the mixture was added sat. $K_2CO_3$ (10 mL) and extracted with DCM (15 mL×3). The combined organic layers were washed with brine, dried over $Na_2SO_4$ and concentrated. The residue was purified by prep-HPLC (from 95% water (0.1% $NH_4HCO_3$) and 5% $CH_3CN$ to 50% water (0.1% $NH_4HCO_3$) and 50% $CH_3CN$ in 20 min, Flow rate: 20 mL/min) to give the title compound (29 mg, yield 50%) as white solid.

E232 $^1H$ NMR (400 MHz, $CDCl_3$): δ 9.01 (s, 1H), 8.08 (s, 1H), 7.54 (s, 1H), 6.62 (s, 1H), 4.84-4.79 (m, 1H), 4.77-4.71 (m, 4H), 4.42-4.38 (m, 2H), 4.01-3.98 (m, 2H), 3.76-3.73 (m, 1H), 3.43-3.32 (dd, J=27.2, 12.8 Hz, 1H), 3.15-3.13 (m, 1H), 3.05-3.02 (m, 1H), 2.64 (s, 3H), 2.47 (s, 3H), 2.44-2.30 (m, 3H), 2.20 (t, J=12.0 Hz, 1H), 2.00-1.96 (m, 1H). $^{19}F$ NMR (376 MHz, $CDCl_3$): δ −102.42 (d, J=241.8 Hz, 1F), −112.23 (d, J=241.8 Hz, 1F).

LC-MS (XB-C18, ¢4.6*50 mm*5 um; mobile phase: from 95% water (0.02% $NH_4OAc$) and 5% $CH_3CN$ to 5% water (0.02% $NH_4OAc$) and 95% $CH_3CN$ in 6.5 min, purity is >95%, Rt=3.874 min; MS Calcd: 470, MS Found: 471 $(M+H)^+$.

Chiral condition: Chiralpak ID 5 um 4.6*250 mm; Phase: Hex:IPA=40:60; F: 1 mL/min, W: 230 nm; T: 30° C.; Rt=6.274 min, 100% ee.

Example 233

1-(6-(6-(3,3-Difluoro-1-(oxetan-3-yl)piperidin-4-yl)-5-methyl-1H-indazol-1-yl)-2-methylpyrimidin-4-yl)azetidin-3-ol (Enantiomer 2, E233)

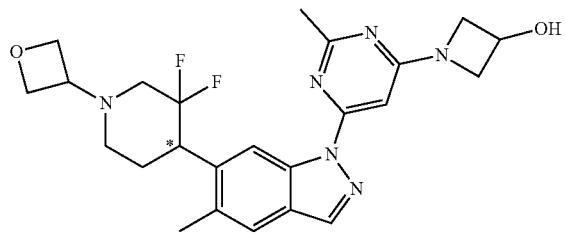 [SMILES: Cc1nc(N2CC(O)C2)cc(-n2ncc3cc(C)c(C4CCN(C5COC5)CC4(F)F)cc32)n1]

To a solution of 6-(3,3-difluoro-1-(oxetan-3-yl)piperidin-4-yl)-5-methyl-1-(2-methyl-6-(3-((tetrahydro-2H-pyran-2-yl)oxy)azetidin-1-yl)pyrimidin-4-yl)-1H-indazole (isomer 2, 93 mg, 0.16 mmol) in $CH_3OH$ (5 mL) was added TsOH (85 mg, 0.49 mmol). The mixture was stirred at rt overnight. To the mixture was added sat. $K_2CO_3$ (10 mL) and extracted with DCM (15 mL×3). The combined organic layers were washed with brine, dried over $NaSO_4$ and concentrated. The residue was purified by prep-HPLC (from 95% water (0.1% $NH_4HCO_3$) and 5% $CH_3CN$ to 50% water (0.1% $NH_4HCO_3$) and 50% $CH_3CN$ in 20 min, Flow rate: 20 mL/min) to give the title compound (32 mg, yield 37%) as white solid.

E233 $^1H$ NMR (400 MHz, $CDCl_3$): δ 9.01 (s, 1H), 8.08 (s, 1H), 7.54 (s, 1H), 6.62 (s, 1H), 4.85-4.80 (m, 1H), 4.77-4.71 (m, 4H), 4.44-4.39 (m, 2H), 4.02-3.98 (m, 2H), 3.78-3.73 (m, 1H), 3.43-3.32 (dd, J=27.2, 12.8 Hz, 1H), 3.18-3.12 (m, 1H), 3.05-3.02 (m, 1H), 2.64 (s, 3H), 2.47 (s, 3H), 2.42-2.31 (m, 3H), 2.20 (t, J=12.0 Hz, 1H), 1.99-1.95 (m, 1H). $^{19}F$ NMR (376 MHz, $CDCl_3$): δ −102.42 (d, J=242.5 Hz, 1F), −112.24 (d, J=244.0 Hz, 1F).

LC-MS (XB-C18, ¢4.6*50 mm*5 um; mobile phase: from 95% water (0.02% $NH_4OAc$) and 5% $CH_3CN$ to 5% water (0.02% $NH_4OAc$) and 95% $CH_3CN$ in 6.5 min, purity is >95%, Rt=3.877 min; MS Calcd: 470, MS Found: 471 $(M+H)^+$.

Chiral condition: Chiralpak ID 5 um 4.6*250 mm; Phase: Hex:IPA=40:60; F: 1 mL/min, W: 230 nm; T: 30° C.; Rt=11.719 min, 99.09% ee.

Example 234

2-(4-(2-Methyl-6-(5-methyl-6-(tetrahydro-2H-pyran-4-yl)-1H-indazol-1-yl)pyrimidin-4-yl)piperazin-1-yl)ethanol (E234)

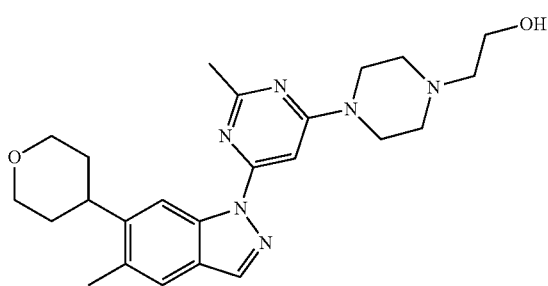 [SMILES: Cc1nc(N2CCN(CCO)CC2)cc(-n2ncc3cc(C)c(C4CCOCC4)cc32)n1]

To a mixture of 5-methyl-6-(tetrahydro-2H-pyran-4-yl)-1H-indazole (60 mg, 0.28 mmol), 2-(4-(6-iodo-2-methylpyrimidin-4-yl)piperazin-1-yl)ethanol (116 mg, 0.333 mmol), CuI (53 mg, 0.28 mmol) and K₃PO₄ (177 mg, 0.834 mmol) in toluene (5 mL) was added N,N'-dimethyl-cyclohexane-1,2-diamine (40 mg, 0.28 mmol) under N₂ atmosphere. The resulting mixture was stirred in reflux for 5 hrs. After cooled the mixture was partitioned with ethyl acetate (20 mL) and water (20 mL). Then ammonia hydrate (30%, 3 mL) was added and the mixture was stirred for 10 min. The organic layer was separated and washed with water (10 mL) and brine (10 mL), dried over Na₂SO₄ and concentrated. The residue was purified by prep-HPLC (HCl) to give the title compound (45 mg) as HCl salt. The salt was dissolved in sat. K₂CO₃ solution (5 mL) and extracted with ethyl acetate (5 mL×2). The combined organic layers were washed with water (5 mL), dried over Na₂SO₄ and concentrated to give the title compound (34 mg, yield 28%) as white solid.

E234 $^1$H NMR (300 MHz, CDCl₃): δ 8.81 (s, 1H), 8.05 (s, 1H), 7.50 (s, 1H), 6.95 (s, 1H), 4.18-4.13 (m, 2H), 3.77-3.74 (m, 4H), 3.69-3.58 (m, 4H), 3.13-3.05 (m, 1H), 2.62-2.56 (m, 9H), 2.47 (s, 3H), 2.04-1.89 (m, 3H), 1.84-1.79 (m, 2H).

LC-MS (mobile phase: from 95% water (0.1% TFA) and 30% CH₃CN to 5% water (0.1% TFA) and 95% CH₃CN in 6.5 min), purity >95%, Rt=3.490 min; MS Calcd.: 436, MS Found: 437 [M+H]⁺.

Example 235

(3S,4S)-1-(2-Methyl-6-(5-methyl-6-(tetrahydro-2H-pyran-4-yl)-1H-indazol-1-yl)pyrimidin-4-yl)pyrrolidine-3,4-diol (E235)

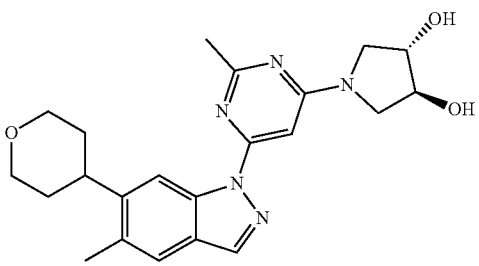 [SMILES: Cc1nc(N2C[C@H](O)[C@@H](O)C2)cc(-n2ncc3cc(C)c(C4CCOCC4)cc32)n1]

A mixture of 5-methyl-6-(tetrahydro-2H-pyran-4-yl)-1H-indazole (60 mg, 0.28 mmol), (3S,4S)-1-(6-iodo-2-methylpyrimidin-4-yl)pyrrolidine-3,4-diol (89 mg, 0.28 mmol), N,N'-dimethyl-cyclohexane-1,2-diamine (79 mg, 0.56 mmol), CuI (106 mg, 0.566 mmol) and K₃PO₄ (118 mg, 0.566 mmol) in toluene (5 mL) was stirred at 115° C. for 3 hrs under N₂. The mixture was cooled to room temperature and filtered. The filtrate was concentrated in vacuo. The residue was purified by column on C18 using CH₃CN/H₂O (30%-60%) to give the desired product (20 mg, yield 30%) as yellow solid.

E235 $^1$H NMR (300 Hz, CD₃OD): δ 8.61 (s, 1H), 8.35 (s, 1H), 7.67 (s, 1H), 7.13 (s, 1H), 4.35 (d, J=3.0 Hz, 2H), 4.14-4.11 (m, 2H), 3.98-3.95 (m, 2H), 3.76-3.64 (m, 4H), 3.33-3.29 (m, 1H), 2.82 (s, 3H), 2.52 (s, 3H), 1.91-1.82 (m, 4H).

LC-MS (XB-C18, ¢4.6*50 mm*5 um; mobile phase: from 95% water (0.1% TFA) and 5% CH₃CN to 5% water (0.1% TFA) and 95% CH₃CN in 6.5 min, purity is >95%, Rt=3.353 min; MS Calcd.: 409, MS Found: 410 (M+H)⁺.

Example 236

1-(2-Methoxy-6-(4-(oxetan-3-yl)piperazin-1-yl)pyrimidin-4-yl)-5-methyl-6-(tetrahydro-2H-pyran-4-yl)-1H-indazole (E236)

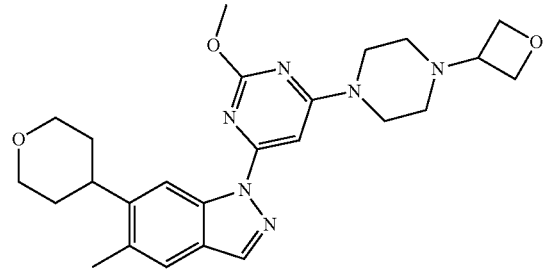 [SMILES: COc1nc(N2CCN(C3COC3)CC2)cc(-n2ncc3cc(C)c(C4CCOCC4)cc32)n1]

To a solution of 1-(2-methoxy-6-(piperazin-1-yl)pyrimidin-4-yl)-5-methyl-6-(tetrahydro-2H-pyran-4-yl)-1H-indazole hydrochloride (50 mg, 0.11 mmol) in ClCH₂CH₂Cl (4 mL) and MeOH (0.5 mL) was added oxetan-3-one (0.5 mL). The resulting mixture was stirred at rt for 30 min. Then, NaBH₃CN (35 mg, 0.56 mmol) was added and the mixture was stirred at rt for 3 hrs. The resulting mixture was poured into sat. Na₂CO₃ (30 mL) and extracted with EtOAc (20 mL×2). The combined organic solutions were washed with brine, dried over Na₂SO₄ and then concentrated. The crude was purified by prep-TLC (CH₂Cl₂:MeOH=20:1) and further purified by prep-HPLC (from 65% water (0.1% NH₄HCO₃) and 35% CH₃CN to 20% water (0.1% NH₄HCO₃) and 80% CH₃CN in 12 min, flow rate: 15 mL/min) to give the title compound (18 mg, yield 35%) as white solid.

E236 ¹H NMR (300 MHz, CDCl₃): δ 8.76 (s, 1H), 8.07 (s, 1H), 7.52 (s, 1H), 6.86 (s, 1H), 4.71-4.64 (m, 4H), 4.15-4.10 (m, 5H), 3.86-3.71 (m, 4H), 3.64-3.57 (m, 2H), 3.55-3.49 (m, 1H), 3.15-3.06 (m, 1H), 2.48 (s, 3H), 2.42-2.40 (m, 4H), 1.95-1.79 (m, 4H).

LC-MS [mobile phase: from 95% water (0.1% TFA) and 5% CH₃CN to 5% water (0.1% TFA) and 95% CH₃CN in 6.5 min], purity is >95%, Rt=3.580 min; MS Calcd.: 464, MS Found: 465 [M+H]⁺.

Example 237

2-((1-(2-Methoxy-6-(5-methyl-6-(tetrahydro-2H-pyran-4-yl)-1H-indazol-1-yl)pyrimidin-4-yl)azetidin-3-yl)oxy)ethanol (E237)

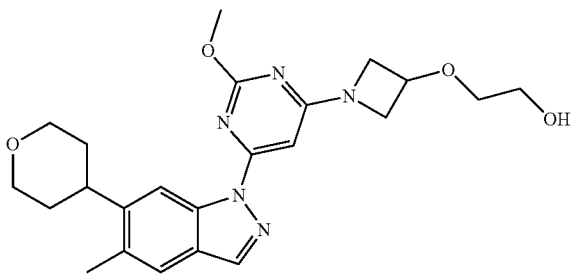 [SMILES: COc1nc(N2CC(OCCO)C2)cc(-n2ncc3cc(C)c(C4CCOCC4)cc32)n1]

To a solution of 5-methyl-6-(tetrahydro-2H-pyran-4-yl)-1H-indazole (50 mg, 0.23 mmol), 4-iodo-2-methoxy-6-(3-(2-((tetrahydro-2H-pyran-2-yl)oxy)ethoxy)azetidin-1-yl)pyrimidine (100 mg, 0.23 mmol), CuI (44 mg, 0.23 mmol) and K₃PO₄ (98 mg, 0.46 mmol) in dry toluene (2 mL) was added N,N'-dimethyl-cyclohexane-1,2-diamine (65 mg, 0.46 mmol) at rt. The resulting mixture was stirred at 110° C. for 3 hrs. TLC showed the reaction was completed. The resulting mixture was poured into diluted ammonia (10%, 50 mL) and extracted with EtOAc (40 mL). The organic solution was washed with brine, dried over Na₂SO₄ and concentrated. The crude was purified by prep-HPLC (from 50% water (0.1% TFA) and 50% CH₃CN to 15% water (0.1% TFA) and 85% CH₃CN in 12 min, flow rate: 15 mL/min). The fractions were concentrated and the product was dissolved in CH₂Cl₂ (20 mL). The organic solution was washed with sat. Cs₂CO₃ (5 mL×2), dried over Na₂SO₄ and concentrated to give the title compound (15 mg, yield 15%) as white solid.

E237 ¹H NMR (300 MHz, CDCl₃): δ 8.76 (s, 1H), 8.07 (s, 1H), 7.52 (s, 1H), 6.49 (s, 1H), 4.55-4.46 (m, 1H), 4.38-4.32 (m, 2H), 4.15-4.04 (m, 7H), 3.83-3.74 (m, 2H), 3.66-3.53 (m, 4H), 3.16-3.03 (m, 1H), 2.48 (s, 3H), 1.98-1.59 (m, 5H).

LC-MS [mobile phase: from 95% water (0.02% NH₄OAc) and 5% CH₃CN to 5% water (0.02% NH₄OAc) and 95% CH₃CN in 6.5 min], purity is >95%, Rt=3.930 min; MS Calcd.: 438, MS Found: 439 [M+H]⁺.

Example 238

(S)-(4-(2-Methyl-6-(5-methyl-6-(tetrahydro-2H-pyran-4-yl)-1H-indazol-1-yl)pyrimidin-4-yl)morpholin-2-yl)methanol (E238)

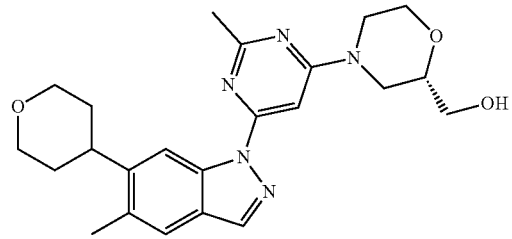 [SMILES: Cc1nc(N2CCO[C@H](CO)C2)cc(-n2ncc3cc(C)c(C4CCOCC4)cc32)n1]

To a solution of (2S)-4-(2-methyl-6-(5-methyl-6-(tetrahydro-2H-pyran-4-yl)-1H-indazol-1-yl)pyrimidin-4-yl)-2-(((tetrahydro-2H-pyran-2-yl)oxy)methyl)morpholine (180 mg, 0.355 mmol) in MeOH (15 mL) was added TsOH (31 mg, 0.18 mmol). The resulting mixture was stirred at rt overnight. The mixture was concentrated and the crude was dissolved in DCM (20 mL). The organic solution was washed with sat. Na₂CO₃ (20 mL) and water (20 mL), dried over Na₂SO₄ and concentrated to give the desired product (78 mg, yield 51%) as white solid.

E238 ¹H NMR (300 MHz, CDCl₃): δ 8.81 (s, 1H), 8.06 (s, 1H), 7.51 (s, 1H), 6.96 (s, 1H), 4.37-4.02 (m, 5H), 3.86-3.56 (m, 6H), 3.17-3.02 (m, 2H), 3.01-2.89 (m, 1H), 2.63 (s, 3H), 2.47 (s, 3H), 2.06-1.88 (m, 2H), 1.87-1.75 (m, 2H).

LC-MS (mobile phase: from 70% water (0.02% NH₄OAc) and 30% CH₃CN to 30% water (0.02% NH₄OAc) and 70% CH₃CN in 6.5 min), purity >95%, Rt=4.352 min; MS Calcd.: 423, MS Found: 424 [M+1]⁺.

Chiral condition: Chiralpak IA 5 um 4.6*250 nm, Hex: EtOH=60:40, Flow: 1.0 ml/min, 230 nm, T=30° C. Rt=6.190 min, 100% ee.

Example 239

(R)-(4-(2-Methyl-6-(5-methyl-6-(tetrahydro-2H-pyran-4-yl)-1H-indazol-1-yl)pyrimidin-4-yl)morpholin-2-yl)methanol (E239)

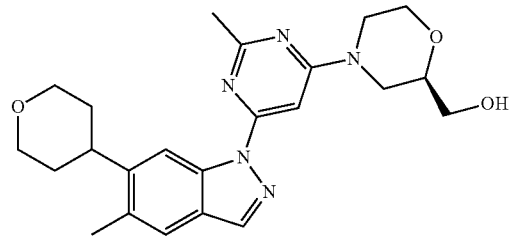 [SMILES: Cc1nc(N2CCO[C@@H](CO)C2)cc(-n2ncc3cc(C)c(C4CCOCC4)cc32)n1]

To a solution of (2R)-4-(2-methyl-6-(5-methyl-6-(tetrahydro-2H-pyran-4-yl)-1H-indazol-1-yl)pyrimidin-4-yl)-2-(((tetrahydro-2H-pyran-2-yl)oxy)methyl)morpholine (165 mg, 0.325 mmol) in MeOH (15 mL) was added TsOH (28 mg, 0.17 mmol). The resulting mixture was stirred at rt overnight. The mixture was concentrated and the crude was dissolved in DCM (20 mL). The organic solution was washed with sat. Na₂CO₃ (20 mL) and water (20 mL), dried over Na₂SO₄ and concentrated to give the desired product (83 mg, yield 59%) as white solid.

E239 $^1$H NMR (300 MHz, CDCl₃): δ 8.82 (s, 1H), 8.06 (s, 1H), 7.51 (s, 1H), 6.96 (s, 1H), 4.36-4.02 (m, 5H), 3.83-3.57 (m, 6H), 3.19-3.04 (m, 2H), 3.00-2.89 (m, 1H), 2.63 (s, 3H), 2.47 (s, 3H), 2.05-1.88 (m, 3H), 1.87-1.76 (m, 2H).

LC-MS (mobile phase: from 70% water (0.02% NH₄OAc) and 30% CH₃CN to 30% water (0.02% NH₄OAc) and 70% CH₃CN in 6.5 min, purity >95%, Rt=4.346 min; MS Calcd.: 423, MS Found: 424 [M+1]⁺.

Chiral condition: Chiralpak IA 5 um 4.6*250 nm, Hex: EtOH=60:40, Flow: 1.0 mL/min, 230 nm, T=30° C. Rt=7.856 min, 100% ee.

Example 240

((2R)-4-(2-Methyl-6-(5-methyl-6-(tetrahydro-2H-pyran-3-yl)-1H-indazol-1-yl)pyrimidin-4-yl)morpholin-2-yl)methanol (Diastereoisomer 1, E240)

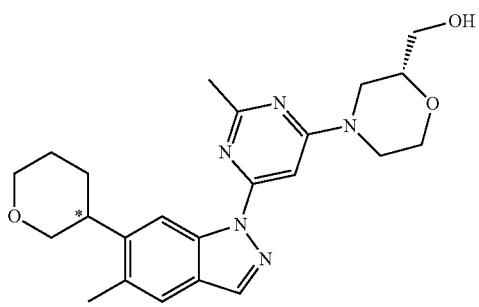 [SMILES: Cc1nc(N2CCO[C@@H](CO)C2)cc(-n2ncc3cc(C)c(C4CCCOC4)cc32)n1]

A mixture of 5-methyl-6-(tetrahydro-2H-pyran-3-yl)-1H-indazole (enantiomer 1, 22 mg, 0.10 Mmol), (2R)-4-(6-iodo-2-methylpyrimidin-4-yl)-2-(((tetrahydro-2H-pyran-2-yl)oxy)methyl)morpholine (50 mg, 0.12 mmol), CuI (15 mg. 0.08 mmol), N,N'-dimethyl-cyclohexane-1,2-diamine (23 mg, 0.16 mmol) and potassium phosphate (34 mg, 0.16 mmol) in toluene (2 mL) was degassed with nitrogen and stirred at 110° C. for 4 hrs. After cooled to room temperature the reaction mixture was poured into diluted ammonia solution (10%, 30 mL) and extracted with ethyl acetate (30 mL×2). The combined organic layers were washed with brine (50 mL), dried and concentrated. The residue was purified by prep-TLC (petroleum ether:EtOAc=4:1) to give THP-protected product as yellow gel. The gel was dissolved in HCl/dioxane (4 M, 2 mL) and stirred at room temperature for 1 h. The reaction mixture was directly concentrated and the crude was triturated in EtOAc (5 mL) to give the title compound (15 mg, yield 35%) as yellow solid.

E240 $^1$H NMR (300 MHz, CD₃OD): δ 8.55 (s, 1H), 8.28 (s, 1H), 7.64 (s, 1H), 7.16 (s, 1H), 4.41-4.28 (m, 2H), 4.11-3.96 (m, 3H), 3.75-3.53 (m, 6H), 3.25-3.09 (m, 3H), 2.69 (s, 3H), 2.49 (s, 3H), 2.11-2.08 (m, 1H), 1.90-1.81 (m, 3H).

LC-MS (XB-C18, ¢4.6*50 mm*5 um; mobile phase: from 95% water (0.1% TFA) and 5% CH₃CN to 5% water (0.1% TFA) and 95% CH₃CN in 6.5 min), purity >95%, Rt=4.115 min; MS Calcd.: 423; MS Found: 424 (M+H)⁺.

Chiral condition: Chiral pak IA 5 um 4.6*250 mm, Hex:EtOH=70:30, Flow: 1.0 ml/min, 230 nm, T=30° C. Rt=7.621 min, 99.13% ee.

Example 241

((2R)-4-(2-Methyl-6-(5-methyl-6-(tetrahydro-2H-pyran-3-yl)-1H-indazol-1-yl)pyrimidin-4-yl)morpholin-2-yl)methanol (Enantiomer 2, E241)

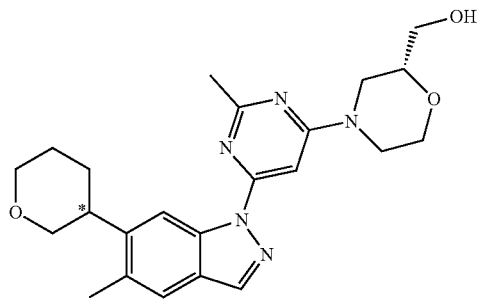 [SMILES: Cc1nc(N2CCO[C@@H](CO)C2)cc(-n2ncc3cc(C)c(C4CCCOC4)cc32)n1]

A mixture of 5-methyl-6-(tetrahydro-2H-pyran-3-yl)-1H-indazole (enantiomer 2, 40 mg, 0.19 mmol) (enantiomer 2), (2R)-4-(6-iodo-2-methylpyrimidin-4-yl)-2-(((tetrahydro-2H-pyran-2-yl)oxy)methyl)morpholine (93 mg, 0.22 mmol), CuI (28 mg. 0.15 mmol), N,N'-dimethyl-cyclohexane-1,2-diamine (42 mg, 0.30 mmol) and potassium phosphate (63 mg, 0.30 mmol) in toluene (2 mL) was degassed with nitrogen and then stirred at 110° C. for 4 hrs. After cooled to room temperature the reaction mixture was poured into diluted ammonia solution (10%, 30 mL) and extracted with ethyl acetate (30 mL×2). The combined organic layers were washed with brine (50 mL), dried and concentrated. The residue was purified by prep-TLC (petroleum ether: EtOAc=4:1) to give THP-protected product as yellow solid. The solid was dissolved in HCl/dioxane (4 M, 2 mL) and stirred at room temperature for 1 h. The reaction was directly concentrated and the crude was triturated in EtOAc (5 mL) to give the title compound (12 mg, yield 15%) as pale yellow solid.

E241 $^1$H NMR (300 MHz, CD₃OD): δ 8.50 (s, 1H), 8.33 (s, 1H), 7.68 (s, 1H), 7.23 (s, 1H), 4.42-4.32 (m, 2H), 4.14-4.08 (m, 1H), 4.00-3.96 (m, 2H), 3.78-3.56 (m, 6H), 3.40-3.36 (m, 1H), 3.25-3.17 (m, 2H), 2.74 (s, 3H), 2.50 (s, 3H), 2.13-2.08 (m, 1H), 1.91-1.77 (m, 3H).

LC-MS (XB-C18, ¢4.6*50 mm*5 um; mobile phase: from 95% water (0.1% TFA) and 5% CH₃CN to 5% water (0.1% TFA) and 95% CH₃CN in 6.5 min), purity >95%, Rt=4.119 min; MS Calcd.: 423; MS Found: 424 (M+H)⁺.

Chiral condition: Chiral pak IA 5 um 4.6*250 mm, Hex:EtOH=70:30, Flow: 1.0 ml/min, 230 nm, T=30° C. Rt=6.797 min, 97.51% ee.

Example 242

((2S)-4-(2-Methyl-6-(5-methyl-6-(tetrahydro-2H-pyran-3-yl)-1H-indazol-1-yl)pyrimidin-4-yl)morpholin-2-yl)methanol (Enantiomer 1, E242)

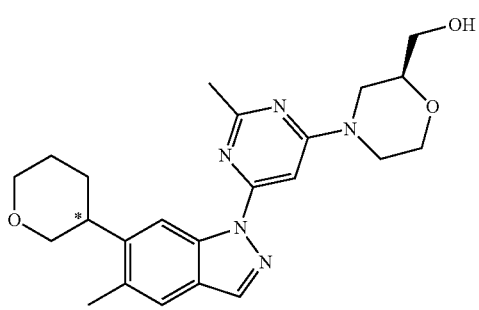 [SMILES: Cc1nc(N2CCO[C@H](CO)C2)cc(-n2ncc3cc(C)c(C4CCCOC4)cc32)n1]

A mixture of 5-methyl-6-(tetrahydro-2H-pyran-3-yl)-1H-indazole (22 mg, 0.10 mmol) (enantiomer 1), (2S)-4-(6-iodo-2-methylpyrimidin-4-yl)-2-(((tetrahydro-2H-pyran-2-yl)oxy)methyl)morpholine (40 mg, 0.12 mmol), CuI (15 mg. 0.08 mmol), N,N'-dimethyl-cyclohexane-1,2-diamine (23 mg, 0.16 mmol) and potassium phosphate (34 mg, 0.16 mmol) in toluene (2 mL) was degassed with nitrogen and then stirred at 110° C. for 3 hrs. After cooled to room temperature the reaction mixture was poured into diluted ammonia solution (10%, 30 mL) and extracted with ethyl acetate (30 mL×2). The combined organic layers were washed with brine (50 mL), dried and concentrated. The residue was purified by prep-TLC (petroleum ether:EtOAc=3:1) to give the title compound (10 mg, yield 24%) as pale yellow solid.

E242 $^1$H NMR (300 MHz, CD$_3$OD): δ 8.77 (s, 1H), 8.11 (s, 1H), 7.56 (s, 1H), 7.00 (s, 1H), 4.42-4.24 (m, 2H), 4.04-3.97 (m, 3H), 3.69-3.44 (m, 6H), 3.24-3.01 (m, 2H), 2.87-2.79 (m, 1H), 2.57 (s, 3H), 2.47 (s, 3H), 2.18-2.00 (m, 1H), 1.92-1.80 (m, 3H).

LC-MS (XB-C18, ¢4.6*50 mm*5 um; mobile phase: from 80% water (0.02% NH$_4$OAc) and 20% CH$_3$CN to 5% water (0.02% NH$_4$OAc) and 95% CH$_3$CN in 6.5 min), purity is >95%, Rt=4.110 min; MS Calcd.: 423; MS Found: 424 (M+H)$^+$.

Chiral condition: Chiral pak IA 5 um 4.6*250 mm, Hex:EtOH=80:20, Flow: 1.0 ml/min, 230 nm, T=30° C. Rt=8.950 min, 99.15% ee.

Example 243

((2S)-4-(2-Methyl-6-(5-methyl-6-(tetrahydro-2H-pyran-3-yl)-1H-indazol-1-yl)pyrimidin-4-yl)morpholin-2-yl)methanol (Diastereoisomer 2, E243)

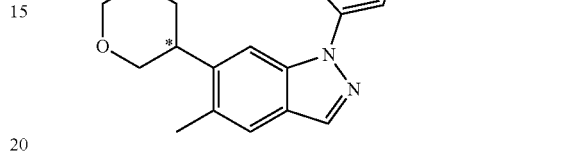

A mixture of 5-methyl-6-(tetrahydro-2H-pyran-3-yl)-1H-indazole (22 mg, 0.10 mmol) (enantiomer 2), (S)-(4-(6-iodo-2-methylpyrimidin-4-yl)morpholin-2-yl)methanol (40 mg, 0.12 mmol), CuI (15 mg. 0.08 mmol), N,N'-dimethyl-cyclohexane-1,2-diamine (23 mg, 0.16 mmol) and potassium phosphate (34 mg, 0.16 mmol) in toluene (2 mL) was degassed with nitrogen and then stirred at 110° C. for 3 hrs. After cooled to room temperature, the reaction mixture was poured into diluted ammonia solution (10%, 30 mL) and extracted with ethyl acetate (30 mL×2). The combined organic layers were washed with brine (50 mL), dried and concentrated. The residue was purified by prep-TLC (petroleum ether:EtOAc=2:1) to give the title compound (9 mg, yield 21%) as pale yellow solid.

E243 $^1$H NMR (300 MHz, CD$_3$OD): δ 8.77 (s, 1H), 8.12 (s, 1H), 7.57 (s, 1H), 7.01 (s, 1H), 4.42-4.25 (m, 2H), 4.05-3.97 (m, 3H), 3.70-3.44 (m, 6H), 3.21-3.07 (m, 2H), 2.88-2.79 ((m, 1H), 2.57 (s, 3H), 2.48 (s, 3H), 2.11-2.00 (m, 2H), 1.92-1.80 (m, 2H).

LC-MS (XB-C18, ¢4.6*50 mm*5 um; mobile phase: from 70% water (0.1% TFA) and 30% CH$_3$CN to 5% water (0.1% TFA) and 95% CH$_3$CN in 6.5 min), purity is >95%, Rt=3.320 min; MS Calcd.: 423; MS Found: 424 (M+H)$^+$.

Chiral condition: Chiral pak IA 5 um 4.6*250 mm, Hex:EtOH=80:20, Flow: 1.0 ml/min, 230 nm, T=30° C. Rt=8.308 min, 99.01% ee.

Example 244

((2R)-4-(2-Methyl-6-(5-methyl-6-(tetrahydro-2H-pyran-2-yl)-1H-indazol-1-yl)pyrimidin-4-yl)morpholin-2-yl)methanol (Diastereoisomer 1, E244)

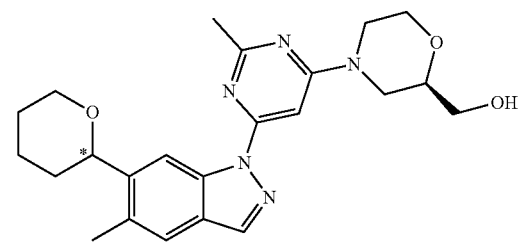 [SMILES: Cc1nc(N2CCO[C@@H](CO)C2)cc(-n2ncc3cc(C)c(C4CCCCO4)cc32)n1]

To a solution of 5-methyl-6-(tetrahydro-pyran-2-yl)-1H-indazole (61 mg, 0.28 mmol) (enantiomer 1) and (R)-(4-(6-iodo-2-methylpyrimidin-4-yl)morpholin-2-yl)methanol (104 mg, 0.311 mmol) in toluene (10 mL) was added N1,N2-dimethylcyclohexane-1,2-diamine (80 mg, 0.56 mmol), CuI (54 mg, 0.28 mmol) and $K_3PO_4$ (120 mg, 0.564 mmol). The mixture was stirred at 110° C. under nitrogen for 3 hrs. The reaction mixture was cooled to rt and filtered. The filtrate was concentrated under vacuum. The residue was purified by pre-TLC (PE:EtOAc=1:1, twice) and re-crystallized from ethanol (8 mL) to give the title compound (45 mg, yield 37%) as a white solid.

E244 $^1$H NMR (300 MHz, $CDCl_3$): δ 9.00 (s, 1H), 8.08 (s, 1H), 7.50 (s, 1H), 6.96 (s, 1H), 4.60 (d, J=9.9 Hz, 1H), 4.35-4.20 (m, 3H), 4.11-4.06 (m, 1H), 3.82-3.68 (m, 5H), 3.18-3.08 (m, 1H), 3.00-2.93 (m, 1H), 2.65 (s, 3H), 2.49 (s, 3H), 2.07-1.88 (m, 3H), 1.83-1.60 (m, 4H).

LC-MS [mobile phase: from 70% water (0.02% $NH_4OAc$) and 30% $CH_3CN$ to 5% water (0.02% $NH_4OAc$) and 95% $CH_3CN$ in 6.5 min], purity is >95%, Rt=3.876 min; MS Calcd.: 423, MS Found: 424 $[M+H]^+$.

Chiral HPLC [Chiralpak IC, Phase: $CO_2$/MeOH=60/40, MeOH (0.2 DEA), flow rate ($CO_2$: 1.799 mL/min; MeOH (0.2 DEA): 1.2 mL/min), T=40.1° C.], Rt=5.12 min, 100% ee.

Example 245

((2R)-4-(2-Methyl-6-(5-methyl-6-(tetrahydro-2H-pyran-2-yl)-1H-indazol-1-yl)pyrimidin-4-yl)morpholin-2-yl)methanol (Diastereoisomer 2, E245)

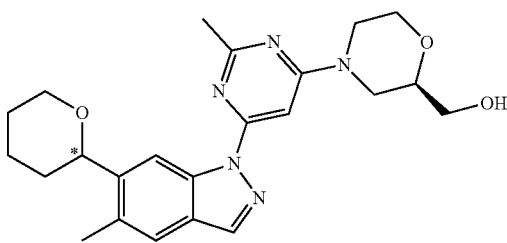 [SMILES: Cc1nc(N2CCO[C@@H](CO)C2)cc(-n2ncc3cc(C)c(C4CCCCO4)cc32)n1]

To a solution of 5-methyl-6-(tetrahydro-pyran-2-yl)-1H-indazole (64 mg, 0.30 mmol) (enantiomer 2) and (R)-(4-(6-iodo-2-methylpyrimidin-4-yl)morpholin-2-yl)methanol (109 mg, 0.326 mmol) in toluene (10 mL) was added N1,N2-dimethylcyclohexane-1,2-diamine (84 mg, 0.592 mmol), CuI (56 mg, 0.296 mmol) and $K_3PO_4$ (126 mg, 0.592 mmol). The mixture was stirred at 110° C. under nitrogen for 16 hrs. The reaction mixture was cooled to rt and filtered. The filtrate was concentrated under vacuum. The residue was purified by pre-TLC (PE:EtOAc=1:1, 4 times) and re-crystallized from ethanol to give the title compound (49 mg, yield 39%) as a white solid.

E245 $^1$H NMR (300 MHz, $CDCl_3$): δ 8.98 (s, 1H), 8.06 (s, 1H), 7.48 (s, 1H), 6.95 (s, 1H), 4.59 (d, J=8.7 Hz, 1H), 4.33-4.26 (m, 2H), 4.20 (d, J=11.7 Hz, 1H), 4.09-4.05 (m, 1H), 3.81-3.67 (m, 5H), 3.16-3.07 (m, 1H), 2.98-2.91 (m, 1H), 2.63 (s, 3H), 2.47 (s, 3H), 2.05-1.76 (m, 4H), 1.72-1.61 (m, 3H).

LC-MS [mobile phase: from 70% water (0.02% $NH_4OAc$) and 30% $CH_3CN$ to 5% water (0.02% $NH_4OAc$) and 95% $CH_3CN$ in 6.5 min], purity is >95%, Rt=3.836 min; MS Calcd.: 423, MS Found: 424 $[M+H]^+$.

Chiral HPLC [Chiralpak IC, Phase: $CO_2$/MeOH=60/40, MeOH (0.2 DEA), flow rate ($CO_2$: 1.799 mL/min; MeOH (0.2 DEA): 1.2 mL/min), T=39.9° C.], Rt=6.28 min, 99.53% ee.

Example 246

1-(6-(6-(3-Fluorotetrahydro-2H-pyran-4-yl)-5-methyl-1H-indazol-1-yl)-2-methylpyrimidin-4-yl)azetidin-3-ol (Enantiomer 1, E246)

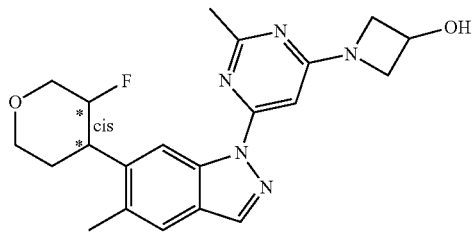 [SMILES: Cc1nc(N2CC(O)C2)cc(-n2ncc3cc(C)c(C4CCOCC4F)cc32)n1]

To a suspension of 6-(3-fluorotetrahydro-2H-pyran-4-yl)-5-methyl-1-(2-methyl-6-(3-((tetrahydro-2H-pyran-2-yl)oxy)azetidin-1-yl)pyrimidin-4-yl)-1H-indazole (isomer 1, 60 mg, 0.12 mmol) in MeOH (6 mL) was added TsOH (31 mg, 0.18 mmol) at rt and stirred for 3 hrs. $Na_2CO_3$ (sat. 50 mL) was added and the mixture was stirred for 15 min. The aqueous layer was extracted with EtOAc (30 mL×2) and the combined organic layers were washed with brine, dried over $Na_2SO_4$ and concentrated to give the title compound (20 mg, yield 41%) as a white solid.

E246 $^1$H NMR (300 MHz, $CDCl_3$): δ 8.94 (s, 1H), 8.08 (s, 1H), 7.54 (s, 1H), 6.60 (s, 1H), 5.12-4.79 (m, 2H), 4.45-4.39 (m, 2H), 4.23-4.12 (m, 1H), 4.11-3.97 (m, 3H), 3.69-3.36 (m, 3H), 2.62 (s, 3H), 2.51 (s, 3H), 2.34-2.20 (m, 2H), 2.07-1.97 (m, 1H). $^{19}$F NMR (376 MHz, $CDCl_3$): δ −174.96 (s, 1H).

LC-MS [mobile phase: from 95% water (0.02% $NH_4OAc$) and 5% $CH_3CN$ to 5% water (0.02% $NH_4OAc$) and 95% $CH_3CN$ in 6.5 min], purity is >95%, Rt=3.850 min; MS Calcd.: 397, MS Found: 398 $[M+H]^+$.

Chiral HPLC [Chiralpak IC 5 um 4.6*250 mm, Phase: Hex/EtOH=70/30, flow rate: 1 mL/min, 230 nm, T=30° C.], Rt=8.224 min, 100% ee.

Example 247

1-(6-(6-(3-Fluorotetrahydro-2H-pyran-4-yl)-5-methyl-1H-indazol-1-yl)-2-methylpyrimidin-4-yl)azetidin-3-ol (Enantiomer 2, E247)

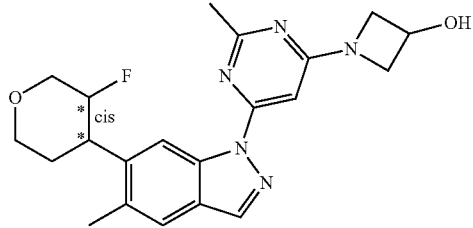 [SMILES: Cc1nc(N2CC(O)C2)cc(-n2ncc3cc(C)c(C4CCOCC4F)cc32)n1]

To a suspension of 6-(3-fluorotetrahydro-2H-pyran-4-yl)-5-methyl-1-(2-methyl-6-(3-((tetrahydro-2H-pyran-2-yl)

oxy)azetidin-1-yl)pyrimidin-4-yl)-1H-indazole (isomer 2, 100 mg, 0.208 mmol) in MeOH (8 mL) was added TsOH (54 mg, 0.31 mmol) at rt and stirred for 3 hrs. Na$_2$CO$_3$ (sat., 50 mL) was added and the mixture was stirred for 15 min. The aqueous layer was extracted with EtOAc (30 mL×2) and the combined organic layers were washed with brine, dried over Na$_2$SO$_4$ and concentrated to give the title compound (46 mg, yield 56%) as a white solid.

E247 $^1$H NMR (300 MHz, CDCl$_3$): δ 8.94 (s, 1H), 8.08 (s, 1H), 7.54 (s, 1H), 6.60 (s, 1H), 5.12-4.78 (m, 2H), 4.44-4.39 (m, 2H), 4.24-4.13 (m, 1H), 4.10-3.97 (m, 3H), 3.69-3.37 (m, 3H), 2.62 (s, 3H), 2.51 (s, 3H), 2.35-2.19 (m, 2H), 2.11-1.96 (m, 1H). $^{19}$F NMR (376 MHz, CDCl$_3$): δ −174.97 (s, 1H).

LC-MS [mobile phase: from 95% water (0.02% NH$_4$Ac) and 5% CH$_3$CN to 5% water (0.02% NH$_4$Ac) and 95% CH$_3$CN in 6.5 min], purity is >95%, Rt=3.846 min; MS Calcd.: 397, MS Found: 398 [M+H]$^+$.

Chiral HPLC [Chiralpak IC 5 um 4.6*250 mm, Phase: Hex/EtOH=70/30, flow rate: 1 mL/min, 230 nm, T=30° C.], Rt=7.305 min, 100% ee.

Example 248

((2S)-4-(6-(6-(3-Fluorotetrahydro-2H-pyran-4-yl)-5-methyl-1H-indazol-1-yl)-2-methylpyrimidin-4-yl)morpholin-2-yl)methanol (Diastereoisomer 1, E248)

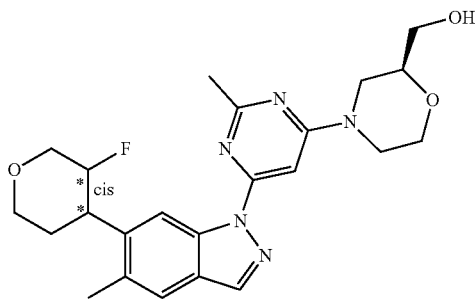 [SMILES: Cc1nc(N2CCO[C@H](CO)C2)cc(-n2ncc3cc(C)c(C4CCOCC4F)cc32)n1]

To a suspension of 6-(3-fluorotetrahydro-2H-pyran-4-yl)-5-methyl-1H-indazole (enantiomer 1) (60 mg, 0.26 mmol), (S)-(4-(6-iodo-2-methylpyrimidin-4-yl)morpholin-2-yl)methanol (87 mg, 0.26 mmol), CuI (50 mg, 0.26 mmol) and K$_3$PO$_4$ (110 mg, 0.52 mmol) in toluene (3 mL) was added N,N'-dimethyl-cyclohexane-1,2-diamine (74 mg, 0.52 mmol) at rt. The resulting mixture was stirred at 110° C. under N$_2$ atmosphere for 3 hrs. Then the reaction mixture was cooled and partitioned between diluted ammonia (10%, 30 mL) and EtOAc (30 mL). The organic layer was washed with brine, dried over Na$_2$SO$_4$ and concentrated. The crude was purified by prep-HPLC [Preparative HPLC was performed under conditions: Column: XBridge C18 5 μm 19*150 mm; Mobile phase: A acetonitrile; B water (0.1% NH$_4$HCO$_3$); Method: 40% to 60% A; Flow rate: 15 mL/min] and then lyophilized to give the title compound (35 mg, yield 30%) as a white solid.

E248 $^1$H NMR (400 MHz, CDCl$_3$): δ 8.93 (s, 1H), 8.08 (s, 1H), 7.55 (s, 1H), 6.96 (s, 1H), 5.09-4.90 (m, 1H), 4.35-4.26 (m, 2H), 4.23-4.15 (m, 1H), 4.09-4.02 (m, 2H), 3.83-3.63 (m, 5H), 3.54 (t, J=10.8 Hz, 1H), 3.46-3.38 (m, 1H), 3.15-3.08 (m, 1H), 2.98-2.92 (m, 1H), 2.62 (s, 3H), 2.51 (s, 3H), 2.34-2.24 (m, 1H), 2.10-1.96 (m, 2H). $^{19}$F NMR (376 MHz, CDCl$_3$): δ −174.97 (s, 1H).

LC-MS [mobile phase: from 95% water (0.02% NH$_4$Ac) and 5% CH$_3$CN to 5% water (0.02% NH$_4$Ac) and 95% CH$_3$CN in 6.5 min], purity is >95%, Rt=4.066 min; MS Calcd.: 441, MS Found: 442 [M+H]$^+$.

Chiral HPLC [Chiralpak IB 5 um 4.6*250 mm, Phase: Hex/EtOH=70/30, flow rate: 1 mL/min, 230 nm, T=30° C.], Rt=5.628 min, 98.70% ee.

Example 249

((2S)-4-(6-(6-(3-Fluorotetrahydro-2H-pyran-4-yl)-5-methyl-1H-indazol-1-yl)-2-methylpyrimidin-4-yl)morpholin-2-yl)methanol (Diastereoisomer 2, E249)

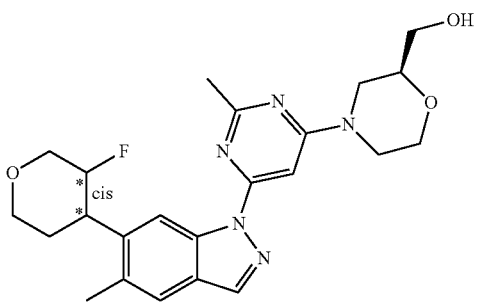 [SMILES: Cc1nc(N2CCO[C@H](CO)C2)cc(-n2ncc3cc(C)c(C4CCOCC4F)cc32)n1]

To a suspension of 6-(3-fluorotetrahydro-2H-pyran-4-yl)-5-methyl-1H-indazole (enantiomer 2) (50 mg, 0.21 mmol), (S)-(4-(6-iodo-2-methylpyrimidin-4-yl)morpholin-2-yl)methanol (70 mg, 0.21 mmol), CuI (40 mg, 0.21 mmol) and K$_3$PO$_4$ (89 mg, 0.42 mmol) in toluene (3 mL) was added N,N'-dimethyl-cyclohexane-1,2-diamine (60 mg, 0.42 mmol) at rt. The resulting mixture was stirred at 110° C. under N$_2$ atmosphere for 3 hrs. Then, the reaction mixture was cooled and partitioned between diluted ammonia (10%, 30 mL) and EtOAc (30 mL). The organic layer was washed with brine, dried over Na$_2$SO$_4$ and concentrated. The crude was purified by prep-TLC (PE:EtOAc=1:1) and then further purified by prep-HPLC [Preparative HPLC was performed at conditions: Column: XBridge C18 5 μm 19*150 mm; Mobile phase: A acetonitrile; B water (0.1% NH$_4$HCO$_3$); Method: 25-80% A; Flow rate: 15 mL/min] and lyophilized to give the title compound (27 mg, yield 29%) as white solid.

E249 $^1$H NMR (400 MHz, CDCl$_3$): δ 8.93 (s, 1H), 8.08 (s, 1H), 7.55 (s, 1H), 6.96 (s, 1H), 5.08-4.90 (m, 1H), 4.34-4.27 (m, 2H), 4.22-4.15 (m, 1H), 4.09-4.02 (m, 2H), 3.83-3.62 (m, 5H), 3.54 (t, J=10.8 Hz, 1H), 3.46-3.38 (m, 1H), 3.15-3.08 (m, 1H), 2.98-2.92 (m, 1H), 2.62 (s, 3H), 2.51 (s, 3H), 2.33-2.24 (m, 1H), 2.11-1.96 (m, 2H). $^{19}$F NMR (376 MHz, CDCl$_3$): δ −174.97 (s, 1H).

LC-MS [mobile phase: from 95% water (0.02% NH$_4$OAc) and 5% CH$_3$CN to 5% water (0.02% NH$_4$OAc) and 95% CH$_3$CN in 6.5 min], purity is >95%, Rt=4.068 min; MS Calcd.: 441, MS Found: 442 [M+H]$^+$.

Chiral HPLC [Chiralpak IB 5 um 4.6*250 mm, Phase: Hex/EtOH=70/30, flow rate: 1 mL/min, 230 nm, T=30° C.], Rt=6.660 min, 100% ee.

Example 250

((2R)-4-(6-(6-(3-Fluorotetrahydro-2H-pyran-4-yl)-5-methyl-1H-indazol-1-yl)-2-methylpyrimidin-4-yl)morpholin-2-yl)methanol (Diastereoisomer 1, E250)

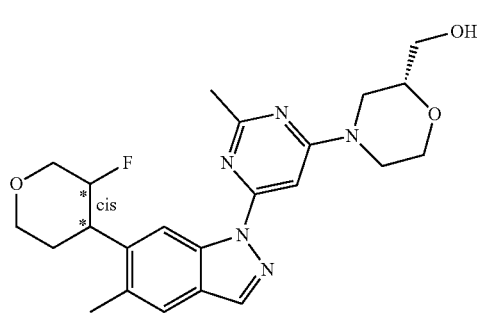 [SMILES: Cc1nc(N2CCO[C@@H](CO)C2)cc(-n2ncc3cc(C)c(C4CCOCC4F)cc32)n1]

To a suspension of 6-(3-fluorotetrahydro-2H-pyran-4-yl)-5-methyl-1H-indazole (60 mg, 0.26 mmol) (enantiomer 1) with 18% of 6-(4-fluorotetrahydro-2H-pyran-4-yl)-5-methyl-1H-indazole), (R)-(4-(6-iodo-2-methylpyrimidin-4-yl)morpholin-2-yl)methanol (87 mg, 0.26 mmol), CuI (50 mg, 0.26 mmol) and $K_3PO_4$ (110 mg, 0.520 mmol) in toluene (3 mL) was added N,N'-dimethyl-cyclohexane-1,2-diamine (74 mg, 0.52 mmol) at rt. The resulting mixture was stirred at 110° C. under $N_2$ atmosphere for 3 hrs. Then the reaction mixture was cooled and partitioned between diluted ammonia (10%, 30 mL) and EtOAc (30 mL). The organic layer was washed with brine, dried over $Na_2SO_4$ and concentrated. The crude was purified by prep-HPLC [Preparative HPLC was performed at conditions: Column: XBridge C18 5 μm 19*150 mm; Mobile phase: A acetonitrile; B water (0.1% $NH_4HCO_3$); Method: 35-75% A; Flow rate: 15 mL/min] and lyophilized to give the title compound the title compound (30 mg, yield 26%) as a white solid.

E250: $^1$H NMR (400 MHz, $CDCl_3$): δ 8.93 (s, 1H), 8.08 (s, 1H), 7.55 (s, 1H), 6.96 (s, 1H), 5.08-4.90 (m, 1H), 4.33-4.26 (m, 2H), 4.21-4.16 (m, 1H), 4.10-4.02 (m, 2H), 3.82-3.63 (m, 5H), 3.54 (t, J=11.2 Hz, 1H), 3.46-3.38 (m, 1H), 3.15-3.08 (m, 1H), 2.98-2.92 (m, 1H), 2.62 (s, 3H), 2.51 (s, 3H), 2.32-2.24 (m, 1H), 2.09-1.96 (m, 2H). $^{19}$H NMR (376 MHz, $CDCl_3$): δ −174.97 (s, 1F).

LC-MS [mobile phase: from 95% water (0.02% $NH_4OAc$) and 5% $CH_3CN$ to 5% water (0.02% $NH_4OAc$) and 95% $CH_3CN$ in 6.5 min], purity is >95%, Rt=4.068 min; MS Calcd.: 441, MS Found: 442 $[M+H]^+$.

Chiral HPLC [Chiralpak IB 5 um 4.6*250 mm, Phase: Hex/EtOH=70/30, flow rate: 1 mL/min, 230 nm, T=30° C.], Rt=5.767 min, 97.28% ee.

Example 251

((2R)-4-(6-(6-(3-Fluorotetrahydro-2H-pyran-4-yl)-5-methyl-1H-indazol-1-yl)-2-methylpyrimidin-4-yl)morpholin-2-yl)methanol (Diastereoisomer 2, E251)

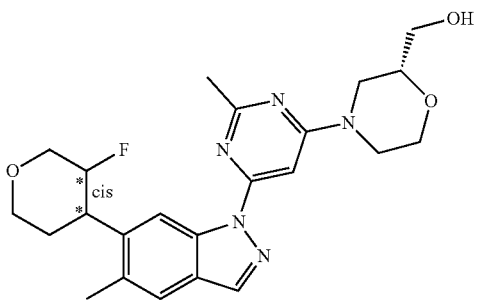 [SMILES: Cc1nc(N2CCO[C@@H](CO)C2)cc(-n2ncc3cc(C)c(C4CCOCC4F)cc32)n1]

To a suspension of 6-(3-fluorotetrahydro-2H-pyran-4-yl)-5-methyl-1H-indazole (50 mg, 0.21 mmol) (enantiomer 2), (R)-(4-(6-iodo-2-methylpyrimidin-4-yl)morpholin-2-yl)methanol (70 mg, 0.21 mmol), CuI (40 mg, 0.21 mmol) and $K_3PO_4$ (89 mg, 0.42 mmol) in toluene (3 mL) was added N,N'-dimethyl-cyclohexane-1,2-diamine (60 mg, 0.42 mmol) at rt. The resulting mixture was stirred at 110° C. under $N_2$ atmosphere for 3 hrs. Then the reaction mixture was cooled and partitioned between diluted ammonia (10%, 30 mL) and EtOAc (30 mL). The organic layer was washed with brine, dried over $Na_2SO_4$ and concentrated. The crude was purified by prep-HPLC (Preparative HPLC was performed at conditions: Column: XBridge C18 5 μm 19*150 mm; Mobile phase: A acetonitrile; B water (0.1% $NH_4HCO_3$); Method: 40-70% A; Flow rate: 15 mL/min) and lyophilized to give the title compound (24 mg, yield 26%) as a white solid.

E251 $^1$H NMR (400 MHz, $CDCl_3$): δ 8.93 (s, 1H), 8.08 (s, 1H), 7.55 (s, 1H), 6.96 (s, 1H), 5.08-4.90 (m, 1H), 4.32-4.27 (m, 2H), 4.21-4.17 (m, 1H), 4.09-4.02 (m, 2H), 3.81-3.63 (m, 5H), 3.54 (t, J=10.8 Hz, 1H), 3.46-3.38 (m, 1H), 3.15-3.08 (m, 1H), 2.98-2.92 (m, 1H), 2.62 (s, 3H), 2.51 (s, 3H), 2.33-2.24 (m, 1H), 2.11-1.96 (m, 2H). $^{19}$H NMR (376 MHz, $CDCl_3$): δ −174.97 (s, 1F).

LC-MS [mobile phase: from 95% water (0.02% $NH_4OAc$) and 5% $CH_3CN$ to 5% water (0.02% $NH_4OAc$) and 95% $CH_3CN$ in 6.5 min], purity is >95%, Rt=4.066 min; MS Calcd.: 441, MS Found: 442 $[M+H]^+$.

Chiral HPLC [Chiralpak IB 5 um 4.6*250 mm, Phase: Hex/EtOH=70/30, flow rate: 1 mL/min, 230 nm, T=30° C.], Rt=6.662 min, 100% ee.

Example 252

1-(6-(6-Isopropoxy-5-methyl-1H-indazol-1-yl)-2-methylpyrimidin-4-yl)azetidin-3-ol (HCl salt) (E252)

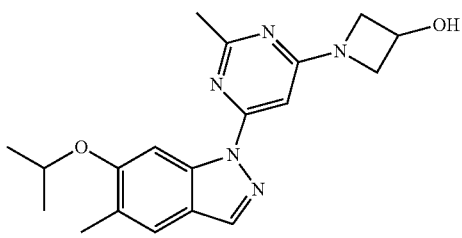 [SMILES: Cc1nc(N2CC(O)C2)cc(-n2ncc3cc(C)c(OC(C)C)cc32)n1]

Step 1:

To a 50 mL round bottle charged with the 6-isopropoxy-5-methyl-1H-indazole (141 mg, 0.74 mmol) were added copper(I) iodide (141 mg, 0.740 mmol), 4-iodo-2-methyl-6-(3-((tetrahydro-2H-pyran-2-yl)oxy)azetidin-1-yl) pyrimidine (278 mg, 0.740 mmol), potassium phosphate (157 mg, 0.740 mmol) and Toluene (6 mL). Subsequently, N1,N2-dimethylcyclohexane-1,2-diamine (0.117 mL, 0.740 mmol) were added under the nitrogen atmosphere. The mixture was then stirred at 120° C. for 2 hrs under nitrogen atmosphere. The mixture was cooled to room temperature, EtOAc (40 mL) and water (20 mL) were added and the layers were separated. The aqueous layer was extracted by EtOAc (40 mL). The combined organic layers was washed with saturated aqueous NaCl (30 mL), dried over anhydrous $Na_2SO_4$. Then the mixture was evaporated in vacuo and purified by normal phase column chromatography (EA/PE: 0% to 60%) to afford 6-isopropoxy-5-methyl-1-(2-methyl-6-(3-((tetrahydro-2H-pyran-2-yl)oxy)azetidin-1-yl)pyrimidin-4-yl)-1H-indazole (50 mg, 0.114 mmol, 15.44% yield)

LC-MS (mobile phase: from 95% water (0.1% TFA) and 5% $CH_3CN$ (0.1% TFA) to 5% water (0.1% TFA) and 95% $CH_3CN$ (0.1% TFA) in 5 min, Rt=3.832 min; MS Calcd.: 438.2 MS Found: 438.1 $(M+H)^+$.

Step 2:

To a 25 mL round bottle charged with 6-isopropoxy-5-methyl-1-(2-methyl-6-(3-((tetrahydro-2H-pyran-2-yl)oxy)azetidin-1-yl)pyrimidin-4-yl)-1H-indazole (50 mg, 0.114 mmol) were added Ethanol (2 mL) and concentrated hydrochloric acid(conc.) (1 ml, 32.9 mmol). The mixture was stirred for 30 mins at room temperature. The mixture changed turbid. Then the mixture was filtered and furnished 1-(6-(6-isopropoxy-5-methyl-1H-indazol-1-yl)-2-methylpyrimidin-4-yl)azetidin-3-ol, hydrochloride (29 mg, 0.071 mmol, 61.8% yield) as white powder.

E252 LC-MS (mobile phase: from 95% water (0.1% TFA) and 5% $CH_3CN$ (0.1% TFA) to 5% water (0.1% TFA) and 95% $CH_3CN$ (0.1% TFA) in 5 min, Rt=3.051 min; MS Calcd.: 354.1 MS Found: 354.0 $(M+H)^+$.

$^1$H NMR (400 MHz, $CD_3OD$) ppm 1.46 (d, J=5.99 Hz, 6H) 2.28 (s, 3H) 2.73 (s, 3H) 4.19 (d, J=7.58 Hz, 2H) 4.54-4.66 (m, 2H) 4.70-4.79 (m, 1H) 4.83 (br. s., 1H) 6.88 (s, 1H) 7.56 (s, 1H) 8.24 (br. s., 2H).

Example 253

1-(6-(6-Isopropoxy-5-methyl-1H-indazol-1-yl)-2-methoxypyrimidin-4-yl)azetidin-3-ol (TFA Salt) (E253)

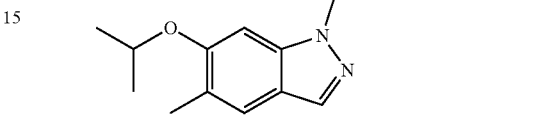

To a 25 mL round bottle charged with 6-isopropoxy-1-(2-methoxy-6-(3-((tetrahydro-2H-pyran-2-yl)oxy)azetidin-1-yl)pyrimidin-4-yl)-5-methyl-1H-indazole (59 mg, 0.130 mmol) were added ethanol (2 mL) and concentrated hydrochloric acid(conc.) (1 ml, 32.9 mmol). The mixture was stirred for 30 mins at room temperature. Then, the mixture was concentrated in vacuo and the residue was purified by reverse phase chromatography (KP-C18-HS column, ACN:H2O (0.5% TFA)=5:95→95:5) to afford the desired product 1-(6-(6-isopropoxy-5-methyl-1H-indazol-1-yl)-2-methoxypyrimidin-4-yl)azetidin-3-ol, trifluoroacetic acid salt (13 mg, 0.026 mmol, 19.64% yield) as white powder.

E253 LC-MS (mobile phase: from 95% water (0.1% TFA) and 5% $CH_3CN$ (0.1% TFA) to 5% water (0.1% TFA) and 95% $CH_3CN$ (0.1% TFA) in 5 min, Rt=3.552 min; MS Calcd.: 370.2 MS Found: 370.1 $(M+H)^+$.

$^1$H NMR (400 MHz, DMSO-$d_6$) ppm 1.37 (d, J=5.99 Hz, 6H) 2.22 (s, 3H) 3.71-3.86 (m, 2H) 3.99 (s, 3H) 4.28 (br.s., 2H) 4.55-4.73 (m, 2H) 5.74-5.90 (m, 1H) 6.42 (s, 1H) 7.59 (s, 1H) 8.24 (s, 1H) 8.28 (s, 1H)

Example 254

1-(6-(5-Chloro-6-isopropoxy-1H-indazol-1-yl)-2-methylpyrimidin-4-yl)azetidin-3-ol (E254)

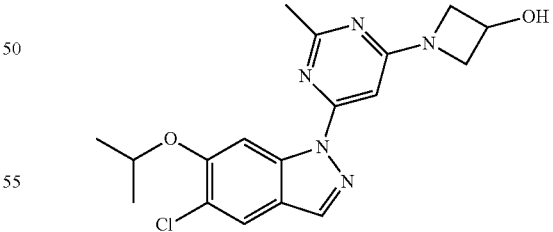

To a solution of 5-chloro-6-isopropoxy-1-(2-methyl-6-(3-((tetrahydro-2H-pyran-2-yl)oxy)azetidin-1-yl)pyrimidin-4-yl)-1H-indazole (32 mg, 0.07 mmol) in DCM (5 mL) was added TFA (0.5 mL) drop-wise at 0° C. The reaction was warmed to room temperature and stirred at room temperature for 4 hours. Solvent and most of TFA was removed in vacuum and the residue was diluted with $CH_2Cl_2$ (20 mL). The resulting solution was washed with sat. $Na_2CO_3$ (5 mL) and brine (5 mL), dried over anhydrous $Na_2SO_4$ and concentrated under reduced pressure The solvent was removed under vacuum and the residue was purified by silica gel chromatography (eluted with DCM/MeOH=30:1) to give product to give product (22 mg, yield 84%) as a white solid.

E254 $^1$H NMR (400 MHz, DMSO) δ 8.57 (s, 1H), 8.30 (s, 1H), 7.96 (s, 1H), 6.54 (s, 1H), 5.82 (d, J=6.4 Hz, 1H), 4.74 (dt, J=12.1, 6.1 Hz, 1H), 4.63 (d, J=6.2 Hz, 1H), 4.55-4.12 (m, 2H), 3.82 (dd, J=9.1, 4.1 Hz, 2H), 1.43 (d, J=6.0 Hz, 6H).

LC-MS (mobile phase: from 90% water (0.1% FA) and 10% CH$_3$CN (0.1% FA) to 5% water (0.1% FA) and 95% CH$_3$CN (0.1% FA) in 10 min, purity 99.24%, Rt=5.91 min; MS Calcd.: 373.1, MS Found: 374.5 (M+H)$^+$.

Example 255

1-(1-(6-(3-Hydroxyazetidin-1-yl)-2-methylpyrimidin-4-yl)-5-methyl-1H-indazol-6-yl)piperidin-4-ol (E255)

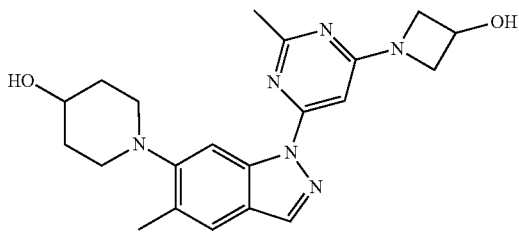 [SMILES: Cc1nc(N2CC(O)C2)cc(-n2ncc3cc(C)c(N4CCC(O)CC4)cc32)n1]

Step 1:

To a solution of 6-bromo-5-methyl-1-(2-methyl-6-(3-((tetrahydro-2H-pyran-2-yl)oxy)azetidin-1-yl) pyrimidin-4-yl)-1H-indazole (100 mg, 0.218 mmol) in THF (10 mL) was added piperidin-4-ol (66.2 mg, 0.655 mmol), diacetoxypalladium (9.80 mg, 0.044 mmol), dicyclohexyl (2',6'-diisopropoxy-[1,1'-biphenyl]-2-yl)phosphine (RuPhos) (40.7 mg, 0.087 mmol) and sodium 2-methylpropan-2-olate (0.218 mL, 0.436 mmol). The mixture was stirred at 70° C. under nitrogen atmosphere for 3 hrs. The reaction mixture was cooled down to room temperature and then water (20 mL) and EtOAc (70 mL) were added to the mixture. The layers were separated and the aqueous layer was extracted by EtOAc (30 mL). The combined organic layers were washed with brine (50 mL×2 times), dried over anhydrous Na$_2$SO$_4$ and then concentrated under the reduced pressure. The residue was purified by reverse phase chromatography (KP-C18-HS 50 g column, ACN:H$_2$O=5:95→95:5) to afford the desired product 1-(5-methyl-1-(2-methyl-6-(3-((tetrahydro-2H-pyran-2-yl)oxy)azetidin-1-yl)pyrimidin-4-yl)-1H-indazol-6-yl)piperidin-4-ol (25 mg, 0.052 mmol, 23.94% yield) as a colorless gel.

LC-MS (mobile phase: from 95% water (0.1% TFA) and 5% CH$_3$CN (0.1% TFA) to 5% water (0.1% TFA) and 95% CH$_3$CN (0.1% TFA) in 5 min, Rt=2.946 min; MS Calcd.: 479.2. MS Found: 479.0 (M+H)$^+$.

Step 2:

To a 50 mL round bottle charged with 1-(5-methyl-1-(2-methyl-6-(3-((tetrahydro-2H-pyran-2-yl)oxy) azetidin-1-yl)pyrimidin-4-yl)-1H-indazol-6-yl)piperidin-4-ol (25 mg, 0.052 mmol) were added ethanol (2 mL) and concentrated hydrochloric acid(conc.) (0.5 ml, 16.46 mmol). The mixture was stirred for 1 hr at room temperature. Then the mixture was evaporated in vacuo and purified by reverse phase column chromatography (ACN/water: 0% to 95%) to provide 1-(1-(6-(3-hydroxy-azetidin-1-yl)-2-methylpyrimidin-4-yl)-5-methyl-1H-indazol-6-yl)piperidin-4-ol (12 mg, 0.027 mmol, 52.4% yield).

E255 LC-MS (mobile phase: from 95% water (0.1% TFA) and 5% CH$_3$CN (0.1% TFA) to 5% water (0.1% TFA) and 95% CH$_3$CN (0.1% TFA) in 5 min, Rt=2.232 min; MS Calcd.: 395.2 MS Found: 395.0 (M+H)$^+$.

$^1$H NMR (400 MHz, DMSO-d$_6$) ppm 1.55 (q, J=9.33 Hz, 2H) 1.84 (d, J=10.27 Hz, 2H) 2.28 (s, 3H) 2.42 (br. s., 3H) 2.67 (t, J=10.03 Hz, 2H) 3.07 (d, J=11.98 Hz, 2H) 3.62 (br. s., 1H) 3.74 (dd, J=9.05, 4.16 Hz, 2H) 4.22 (t, J=7.89 Hz, 2H) 4.55 (d, J=5.50 Hz, 1H) 4.66 (d, J=3.30 Hz, 1H) 5.74 (d, J=6.36 Hz, 1H) 6.46 (s, 1H) 7.52 (s, 1H) 8.17 (s, 1H) 8.40 (s, 1H).

Example 256

(R)-1-(1-(6-(3-hydroxyazetidin-1-yl)-2-methylpyrimidin-4-yl)-5-methyl-1H-indazol-6-yl)pyrrolidin-3-ol (HCl Salt) (E256)

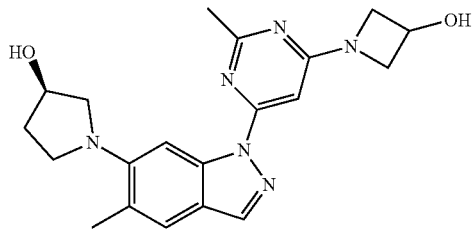 [SMILES: Cc1nc(N2CC(O)C2)cc(-n2ncc3cc(C)c(N4CC[C@@H](O)C4)cc32)n1]

To a 25 mL round bottle charged with (3R)-1-(5-methyl-1-(2-methyl-6-(3-((tetrahydro-2H-pyran-2-yl)oxy)azetidin-1-yl)pyrimidin-4-yl)-1H-indazol-6-yl)pyrrolidin-3-ol (20 mg, 0.043 mmol) were added ethanol (2 mL) and concentrated hydrochloric acid (conc.) (1.000 ml, 32.9 mmol). The mixture was stirred for 30 mins at room temperature. The mixture changed turbid. Then the mixture was filtered and furnished (R)-1-(1-(6-(3-hydroxyazetidin-1-yl)-2-methylpyrimidin-4-yl)-5-methyl-1H-indazol-6-yl)pyrrolidin-3-ol, Hydrochloride (16 mg, 0.036 mmol, 85% yield) as yellow powder.

E256 LC-MS (mobile phase: from 95% water (0.1% TFA) and 5% CH$_3$CN (0.1% TFA) to 5% water (0.1% TFA) and 95% CH$_3$CN (0.1% TFA) in 5 min, Rt=2.065 min; MS Calcd.: 381.2 MS Found: 381.0 (M+H)$^+$.

$^1$H NMR (400 MHz, Methanol-d$_4$) ppm 2.29 (br. s., 1H) 2.37 (br. s., 1H) 2.64 (s, 3H) 2.77 (s, 3H) 3.68 (br. s., 1H) 3.81 (d, J=7.21 Hz, 1H) 3.94-4.13 (m, 2H) 4.21 (d, J=9.54 Hz, 2H) 4.54-4.69 (m, 2H) 4.72-4.86 (m, 2H) 6.93 (s, 1H) 7.79 (br. s., 1H) 8.41 (s, 1H) 8.87-9.26 (m, 1H).

Example 257

(S)-1-(1-(6-(3-hydroxyazetidin-1-yl)-2-methylpyrimidin-4-yl)-5-methyl-1H-indazol-6-yl)pyrrolidin-3-ol (HCl Salt) (E257)

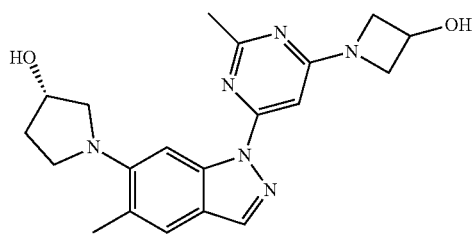 [SMILES: Cc1nc(N2CC(O)C2)cc(-n2ncc3cc(C)c(N4CC[C@H](O)C4)cc32)n1]

To a 25 mL round bottle charged with (3S)-1-(5-methyl-1-(2-methyl-6-(3-((tetrahydro-2H-pyran-2-yl)oxy)azetidin-1-yl)pyrimidin-4-yl)-1H-indazol-6-yl)pyrrolidin-3-ol (124 mg, 0.267 mmol) were added ethanol (5 mL) and concentrated hydrochloric acid(conc.) (1.000 ml, 32.9 mmol). The mixture was stirred for 30 mins at room temperature. The mixture changed turbid. Then, the mixture was filtered and furnished (S)-1-(1-(6-(3-hydroxyazetidin-1-yl)-2-methylpyrimidin-4-yl)-5-methyl-1H-indazol-6-yl)pyrrolidin-3-ol, hydrochloride (54 mg, 0.117 mmol, 43.7% yield) as yellow powder.

E257 LC-MS (mobile phase: from 95% water (0.1% TFA) and 5% $CH_3CN$ (0.1% TFA) to 5% water (0.1% TFA) and 95% $CH_3CN$ (0.1% TFA) in 5 min, Rt=2.024 min; MS Calcd.: 381.2 MS Found: 381.0 $(M+H)^+$.

$^1H$ NMR (400 MHz, DMSO-$d_6$) ppm 1.94 (br. s., 1H) 2.11 (br. s., 1H) 2.45 (br. s., 3H) 2.66 (s, 3H) 3.19 (br. s., 1H) 3.41 (br. s., 1H) 3.48-3.60 (m, 1H) 3.71 (br. s., 1H) 4.05 (br. s., 2H) 4.36-4.55 (m, 3H) 4.65 (br. s., 1H) 6.65 (s, 1H) 7.58 (br. s., 1H) 8.15-8.51 (m, 2H).

Example 258

1-(5-Chloro-1-(6-(3-hydroxyazetidin-1-yl)-2-methylpyrimidin-4-yl)-1H-indazol-6-yl)piperidin-4-ol (E258)

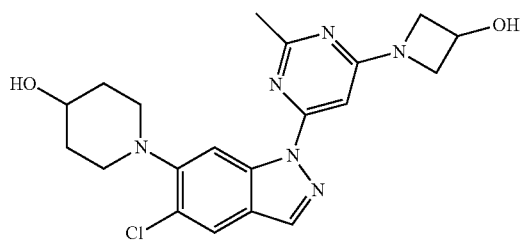 [SMILES: Cc1nc(N2CC(O)C2)cc(-n2ncc3cc(Cl)c(N4CCC(O)CC4)cc32)n1]

To a solution of 1-(5-chloro-1-(6-(3-hydroxyazetidin-1-yl)-2-methylpyrimidin-4-yl)-1H-indazol-6-yl)piperidin-4-one (95 mg, 0.23 mmol) in MeOH (10 mL) was added $NaBH_4$ (17.4 mg, 0.46 mmol) under 0° C. The mixture was stirred overnight at room temperature. The solvent was evaporated and water (20 mL) was added. The mixture was extracted with EtOAc (50 mL×3). The combined organic layer was dried over $Na_2SO_4$, concentrated and purified with prep-HPLC. The eluent was freeze-dried overnight to get the final compound 1-(5-chloro-1-(6-(3-hydroxyazetidin-1-yl)-2-methylpyrimidin-4-yl)-1H-indazol-6-yl)piperidin-4-ol in TFA form as a white solid (50 mg, yield 52%).

E258 $^1H$ NMR (400 MHz, DMSO-d6): δ 8.57 (s, 1H), 8.32 (s, 1H), 7.94 (s, 1H), 6.57 (s, 1H), 4.63 (s, 1H), 4.34-4.30 (t, 2H), 3.85-3.83 (t, 2H), 3.70 (s, 1H), 3.30-3.28 (t, 2H), 2.86-2.81 (t, 2H), 2.40 (s, 3H), 1.92-1.90 (s, 2H), 1.66-1.61 (t, 2H).

$^{19}F$ NMR (400 MHz, DMSO-d6): 74.74 (s).

LC-MS (mobile phase: from 70% water (0.1% TFA) and 30% $CH_3CN$ (0.1% TFA) to 30% water (0.1% TFA) and 70% $CH_3CN$ (0.1% TFA) in 10 min, purity 99.2%, Rt=4.72 min. MS Calcd.: 414.8, MS Found: 415.6 $(M+H)^+$.

Example 259

5-Methyl-1-(2-methyl-6-(1-(oxetan-3-yl)piperidin-4-yl)pyrimidin-4-yl)-6-(tetrahydro-2H-pyran-4-yl)-1H-indazole (E259)

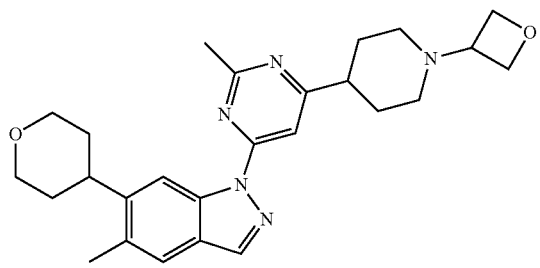 [SMILES: Cc1nc(C2CCN(C3COC3)CC2)cc(-n2ncc3cc(C)c(C4CCOCC4)cc32)n1]

To a solution of 6-(3,6-dihydro-2H-pyran-4-yl)-5-methyl-1-(2-methyl-6-(1-(oxetan-3-yl)-1,2,3,6-tetrahydropyridin-4-yl)pyrimidin-4-yl)-1H-indazole (42 mg, 0.095 mmol) in methanol (20 mL) was added palladium (25.2 mg, 0.024 mmol) on carbon (10% w/w) and the mixture was stirred at rt under hydrogen atmosphere overnight. The mixture was filtered and the filtrate was concentrated. The residue was directly purified by reverse phase chromatography (ACN:$H_2O$=5:95→95:5) to afford 5-methyl-1-(2-methyl-6-(1-(oxetan-3-yl)piperidin-4-yl)pyrimidin-4-yl)-6-(tetrahydro-2H-pyran-4-yl)-1H-indazole, Trifluoroacetic acid salt (4.8 mg, 7.69 μmol, 8.12% yield).

E259 LCMS: (mobile phase: 5-95% acetonitrile), Rt=2.835 min in 5 min; MS Calcd: 447. MS Found: 448.3 $(M+1)^+$.

$^1H$ NMR (DMSO-$d_6$) δ: 8.73 (s, 1H), 8.44 (s, 1H), 7.69 (s, 2H), 4.72-4.85 (m, 4H), 4.44 (br. s., 1H), 4.02 (d, J=10.5 Hz, 2H), 3.49-3.60 (m, 4H), 3.05-3.20 (m, 2H), 2.98 (br. s., 2H), 2.70-2.79 (m, 3H), 2.48 (s, 3H), 2.14-2.25 (m, 2H), 1.95-2.13 (m, 2H), 1.66-1.88 (m, 4H).

Example 260 and 261

1-(2-Methoxy-6-(5-methyl-6-(1-(oxetan-3-yl)piperidin-4-yl)-1H-indazol-1-yl)pyrimidin-4-yl)-3-methylpyrrolidin-3-ol (Enantiomer 1, E260; Enantiomer 2, E261)

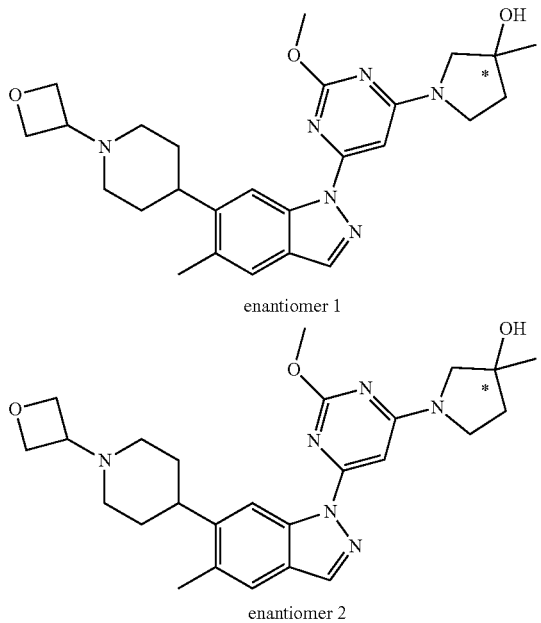

enantiomer 1 enantiomer 2

The racemate 1-(2-methoxy-6-(5-methyl-6-(1-(oxetan-3-yl)piperidin-4-yl)-1H-indazol-1-yl)pyrimidin-4-yl)-3-methylpyrrolidin-3-ol (56 mg, 0.12 mmol) was separated by Chiral-HPLC (Chiralpak IC 5 μm 4.6×150 mm, Phase: HEP:ETOH (0.1% DEA)=60:40, flowrate: 0.5 mL/min, temperature: 25° C.) to give single unknown isomer 1 (Rt: 3.062 min, 23.4 mg, yield 41.7%) as a white solid and single unknown isomer 2 (Rt: 4.071 min, 23.6 mg, yield 42.1%) as a white solid.

E260 (enantiomer 1) $^1$H NMR (400 MHz, CDCl$_3$) δ 8.77 (s, 1H), 8.05 (s, 1H), 7.49 (s, 1H), 6.59 (s, 1H), 4.69 (d, J=6.4 Hz, 4H), 4.14 (s, 3H), 3.50-3.76 (m, 5H), 2.92-2.95 (m, 3H); 2.44 (s, 3H); 1.86-2.05 (m, 8H), 1.51 (s, 3H).

LC-MS [mobile phase: from 80% water (0.1% FA) and 20% CH$_3$CN (0.1% FA) to 80% water (0.1% FA) and 20% CH$_3$CN (0.1% FA) in 1 min, from 80% water (0.1% FA) and 20% CH$_3$CN (0.1% FA) 5% water (0.1% FA) and 95% CH$_3$CN (0.1% FA) in 9 min]. MS Calcd: 478, MS Found: 479.3[M+H]$^+$, Rt=4.832 min Chiral condition: Chiralpak AD-H 0.46 cm I.D.×15 cm L, HEP:ETOH (0.1% DEA)=60:40 (V/V), Flow Rate: 0.5 mL/min, 254 nm, T=25° C., Rt=3.058 min, 100% ee.

E261 (enantiomer 2) $^1$H NMR (400 MHz, CDCl$_3$) δ 8.77 (s, 1H), 8.05 (s, 1H), 7.49 (s, 1H), 6.58 (s, 1H), 4.69 (d, J=6.0 Hz, 4H), 4.14 (s, 3H), 3.49-3.73 (m, 5H), 2.92-2.95 (m, 3H); 2.45 (s, 3H); 1.86-2.05 (m, 8H), 1.50 (s, 3H).

LC-MS [mobile phase: from 90% water (0.1% FA) and 10% CH$_3$CN (0.1% FA) to 90% water (0.1% FA) and 10% CH$_3$CN (0.1% FA) in 1 min, from 90% water (0.1% FA) and 10% CH$_3$CN (0.1% FA) to 5% water (0.1% FA) and 95% CH$_3$CN (0.1% FA) in 9 min]. MS Calcd: 478, MS Found: 479.3[M+H]$^+$, Rt=5.816 min Chiral condition: Chiralpak AD-H 0.46 cm I.D.×15 cm L, HEP:ETOH (0.1% DEA)=60:40 (V/V), Flow Rate: 0.5 mL/min, 254 nm, T=25° C., Rt=4.001 min, 100% ee.

Example 262, 263, 264 and 265

1-(4-(2-Methoxy-6-(5-methyl-6-(1-(oxetan-3-yl)piperidin-4-yl)-1H-indazol-1-yl)pyrimidin-4-yl)morpholin-2-yl)ethanol (Diastereoisomer 1, E262; Diastereoisomer 2, E263; Diastereoisomer 3, E264 and Diastereoisomer 4, E265)

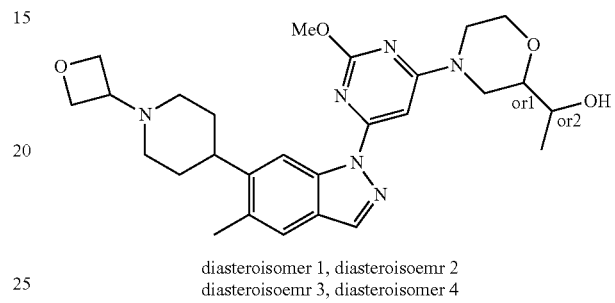

diasteroisomer 1, diasteroisoemr 2
diasteroisoemr 3, diastereoisomer 4

1-(4-(2-methoxy-6-(5-methyl-6-(1-(oxetan-3-yl)piperidin-4-yl)-1H-indazol-1-yl)pyrimidin-4-yl)morpholin-2-yl)ethanol (150 mg, 0.30 mmol, 98% purity by LCMS) was separated by chiral prep. HPLC with the method (Column: AD-H, Column size: 0.46 cm I.D.×15 cm L, Injection: 2 ul, Mobile phase: Hep:EtOH (0.05% DEA)=60:40, Flow rate: 0.5 mL, Wave length: UV 205 nm, T=25° C., Sample solution: X mg/ml in ETOH) to give diastereoisomer 1 as a white solid (12.28 mg, yield 6.6%), diastereoisomer 2 as a white solid (12.88 mg, yield 3.6%), diastereoisomer 3 as a white solid (24.81 g, yield 16.6%), diastereoisomer 4 as a white solid (24.23 mg, yield 16.6%).

E262 LC-MS (mobile phase: from 80% water (0.1% FA) and 20% CH$_3$CN (0.1% FA), Rt=4.849 min; MS Calcd.: 508.6; MS Found: 509.8 [M+H]$^+$.

$^1$H NMR (400 MHz, CDCl$_3$): δ 8.75 (s, 1H), 8.06 (s, 1H), 7.51 (s, 1H), 6.85 (s, 1H), 4.70-4.68 (d, J=6.4 Hz, 4H), 4.36-4.26 (m, 2H), 4.14 (s, 3H), 4.05-4.02 (d, J=10.8 Hz, 1H), 3.96-3.93 (m, 1H), 3.71-3.66 (t, J=10.8 Hz, 1H), 3.57-3.53 (m, 1H), 3.46-3.43 (d, J=10.0 Hz, 1H), 3.16-3.10 (m, 1H), 3.07-3.01 (t, J=12.0 Hz, 1H), 2.94-2.92 (d, J=10.4 Hz, 2H), 2.86-2.82 (m, 1H), 2.45 (s, 3H), 2.11 (s, 1H), 2.04-1.99 (t, J=10.4 Hz, 1H), 1.91-1.86 (m, 4H), 1.30-1.28 (d, J=6.4 Hz, 3H).

E263 LC-MS (mobile phase: from 80% water (0.1% FA) and 20% CH$_3$CN (0.1% FA), Rt=4.883 min; MS Calcd.: 508.6; MS Found: 509.8 [M+H]$^+$.

$^1$H NMR (400 MHz, CDCl$_3$): δ 8.75 (s, 1H), 8.06 (s, 1H), 7.51 (s, 1H), 6.85 (s, 1H), 4.70-4.68 (d, J=6.4 Hz, 4H), 4.36-4.26 (m, 2H), 4.14 (s, 3H), 4.05-4.02 (d, J=11.2 Hz, 1H), 3.96-3.93 (m, 1H), 3.71-3.66 (t, J=10.8 Hz, 1H), 3.58-3.53 (m, 1H), 3.45-3.43 (d, J=9.2 Hz, 1H), 3.16-3.10 (t, J=11.6 Hz, 1H), 3.07-3.01 (t, J=12.0 Hz, 1H), 2.94-2.92 (d, J=10.0 Hz, 2H), 2.86-2.81 (m, 1H), 2.45 (s, 3H), 2.11 (s, 1H), 2.04-1.99 (t, J=10.4 Hz, 1H), 1.91-1.86 (m, 4H), 1.30-1.28 (d, J=6.4 Hz, 3H).

E264 LC-MS (mobile phase: from 80% water (0.1% FA) and 20% CH$_3$CN (0.1% FA), Rt=4.682 min; MS Calcd.: 508.6; MS Found: 509.8 [M+H]$^+$.

¹H NMR (400 MHz, CDCl₃): δ 8.76 (s, 1H), 8.06 (s, 1H), 7.51 (s, 1H), 6.84 (s, 1H), 4.69-4.68 (d, J=6.0 Hz, 4H), 4.31-4.23 (m, 2H), 4.15 (s, 3H), 4.09-4.06 (d, J=10.4 Hz, 1H), 3.79-3.76 (m, 1H), 3.70-3.65 (t, J=11.2 Hz, 1H), 3.56-3.53 (m, 1H), 3.35-3.31 (m, 1H), 3.15-3.09 (1, J=11.6 Hz, 1H), 2.94-2.81 (m, 4H), 2.45 (s, 4H), 2.04-1.86 (m, 6H), 129-1.28 (d, J=6.4 Hz, 3H).

E265 LC-MS (mobile phase: from 80% water (0.1% FA) and 20% CH₃CN (0.1% FA), Rt=5.217 min; MS Calcd.: 508.6; MS Found: 509.8 [M+H]⁺.

¹H NMR (400 MHz, CDCl₃): δ 8.76 (s, 1H), 8.06 (s, 1H), 7.51 (s, 1H), 6.84 (s, 1H), 4.70-4.68 (d, J=6.4 Hz, 4H), 4.33-4.22 (m, 2H), 4.15 (s, 3H), 4.09-4.06 (d, J=11.2 Hz, 1H), 3.78-3.77 (m, 1H), 3.71-3.65 (t, J=11.6 Hz, 1H), 3.57-3.53 (m, 1H), 3.35-3.31 (m, 1H), 3.15-3.09 (t, J=11.6 Hz, 1H), 2.94-2.81 (m, 4H), 2.45 (s, 4H), 2.04-1.83 (m, 6H), 1.29-1.28 (d, J=6.0 Hz, 3H).

Example 266, 267, 268 and 269

1-(4-(2-Methyl-6-(5-methyl-6-(1-(oxetan-3-yl)piperidin-4-yl)-1H-indazol-1-yl)pyrimidin-4-yl)morpholin-2-yl)ethanol (Diastereoisomer 1, E266; Diastereoisomer 2, E267; Diastereoisomer 3, E268; Diastereoisomer 4, E269)

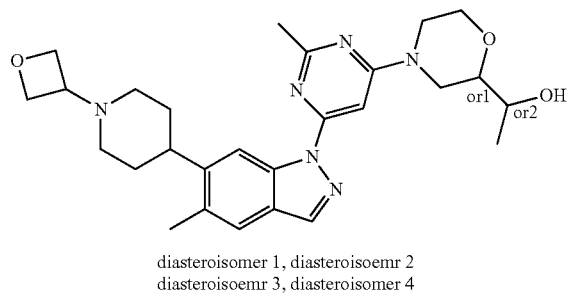 [SMILES: Cc1nc(N2CCOC(C(C)O)C2)cc(-n2ncc3cc(C)c(C4CCN(C5COC5)CC4)cc32)n1]

diasteroisomer 1, diasteroisoemr 2
diasteroisoemr 3, diasteroisomer 4

1-(4-(2-methyl-6-(5-methyl-6-(1-(oxetan-3-yl)piperidin-4-yl)-1H-indazol-1-yl)pyrimidin-4-yl)morpholin-2-yl)ethanol (122 mg, 0.25 mmol, 100% purity by LCMS) was separated by chiral prep. HPLC with the method (Column: AD-H, Column size: 0.46 cm I.D.×15 cm L, Injection: 2 ul, Mobile phase: Hep:EtOH (0.05% DEA)=60:40, Flow rate: 0.5 mL, Wave length: UV 205 nm, T=25° C., Sample solution: X mg/ml in ETOH) to give diasteroisomer 1 as a white solid (24.21 mg, yield 25%), diasteroisomer 2 as a white solid (24.48 mg, yield 25%), diasteroisomer 3 as a white solid (24.85 mg, yield 25%), diasteroisomer 4 as a white solid (25.56 mg, yield 25%).

E266 LC-MS (mobile phase: from 80% water (0.1% FA) and 20% CH₃CN (0.1% FA), Rt=6.019 min; MS Calcd.: 492.6; MS Found: 493.8 [M+H]⁺.

¹H NMR (400 MHz, CDCl₃): δ 8.80 (s, 1H), 8.06 (s, 1H), 7.50 (s, 1H), 6.96 (s, 1H), 4.72 (s, 4H), 4.36-4.27 (m, 2H), 4.05-4.02 (d, J=11.2 Hz, 1H), 3.94 (m, 1H), 3.72-3.67 (t, J=10.4 Hz, 1H), 3.61 (s, 1H), 3.46-3.42 (m, 1H), 3.16-2.83 (m, 5H), 2.66 (s, 3H), 2.45 (s, 3H), 2.09-1.97 (m, 7H), 1.31-1.29 (d, J=6.0 Hz, 3H).

E267 LC-MS (mobile phase: from 80% water (0.1% FA) and 20% CH₃CN (0.1% FA), Rt=6.052 min; MS Calcd.: 492.6; MS Found: 493.8 [M+H]⁺.

¹H NMR (400 MHz, CDCl3): δ 8.79 (s, 1H), 8.06 (s, 1H), 7.50 (s, 1H), 6.96 (s, 1H), 4.73-4.72 (d, J=5.6 Hz, 4H), 4.36-4.33 (d, J=13.6 Hz, 1H), 4.30-4.27 (d, J=12.8 Hz, 1H), 4.05-4.02 (d, J=11.6 Hz, 1H), 3.96-3.94 (m, 1H), 3.73-3.67 (m, 1H), 3.59 (s, 1H), 3.46-3.44 (m, 1H), 3.15-2.97 (m, 4H), 2.85 (s, 1H), 2.65 (s, 3H), 2.45 (s, 3H), 2.08-1.96 (m, 7H), 1.31-1.29 (d, J=6.0 Hz, 3H).

E268 LC-MS (mobile phase: from 80% water (0.1% FA) and 20% CH₃CN (0.1% FA), Rt=6.019 min; MS Calcd.: 492.6; MS Found: 493.7 [M+H]⁺.

¹H NMR (400 MHz, CDCl₃): δ 8.82 (s, 1H), 8.06 (s, 1H), 7.50 (s, 1H), 6.95 (s, 1H), 4.73 (s, 4H), 4.37-4.34 (d, J=11.6 Hz, 1H), 4.28-4.25 (d, J=12.8 Hz, 1H), 4.10-4.07 (d, J=11.6 Hz, 1H), 3.82-3.77 (m, 1H), 3.71-3.66 (t, J=11.6 Hz, 1H), 3.62-3.57 (m, 1H), 3.36-3.34 (m, 1H), 3.11-2.97 (m, 3H), 2.90-2.84 (t, J=11.2 Hz, 2H), 2.66 (s, 3H), 2.50 (s, 1H), 2.45 (s, 3H), 2.07-1.91 (m, 6H), 1.30-1.29 (d, J=6.0 Hz, 3H).

E269 LC-MS (mobile phase: from 80% water (0.1% FA) and 20% CH₃CN (0.1% FA), Rt=5.952 min; MS Calcd.: 492.6; MS Found: 493.8 [M+H]⁺.

¹H NMR (400 MHz, CDCl₃): δ 8.81 (s, 1H), 8.06 (s, 1H), 7.50 (s, 1H), 6.95 (s, 1H), 4.72-4.71 (d, J=6.4 Hz, 4H), 4.37-4.34 (d, J=12.4 Hz, 1H), 4.28-4.25 (d, J=12.4 Hz, 1H), 4.10-4.07 (d, J=11.6 Hz, 1H), 3.80-3.76 (m, 1H), 3.71-3.66 (t, J=11.6 Hz, 1H), 3.57-3.56 (m, 1H), 3.36-3.33 (m, 1H), 3.11-3.06 (m, 1H), 2.99-2.97 (d, J=7.2 Hz, 2H), 2.90-2.82 (m, 2H), 2.65 (s, 3H), 2.45 (s, 1H), 2.45 (s, 3H), 2.03-1.94 (m, 7H), 1.30-1.29 (d, J=6.0 Hz, 3H).

Example 270

((2S)-4-(2-Methyl-6-(5-methyl-6-(tetrahydro-2H-pyran-2-yl)-1H-indazol-1-yl)pyrimidin-4-yl)morpholin-2-yl)methanol (Diastereoisomer 1, E270)

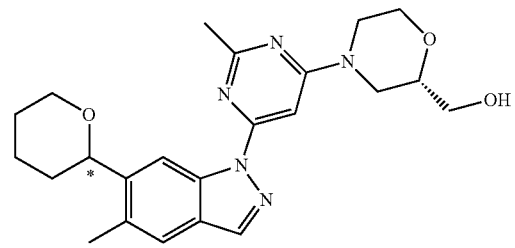 [SMILES: Cc1nc(N2CCO[C@H](CO)C2)cc(-n2ncc3cc(C)c(C4CCCCO4)cc32)n1]

To a solution of 5-methyl-6-(tetrahydro-pyran-2-yl)-1H-indazole (enantiomer 1, 66 mg, 0.30 mmol) and (S)-(4-(6-iodo-2-methylpyrimidin-4-yl)morpholin-2-yl)methanol (102 mg, 0.30 mmol) in toluene (10 mL) was added N1,N2-dimethylcyclohexane-1,2-diamine (85 mg, 0.60 mmol), CuI (57 mg, 0.30 mmol) and K₃PO₄ (127 mg, 0.60 mmol). The mixture was stirred at 110° C. under nitrogen for 3 hrs. The reaction mixture was cooled to rt and filtered. The filtrate was concentrated. The residue was purified by pre-TLC (PE:EtOAc=1:1, twice) and column C18 (5-70% ACN in water) to give the title compound (33 mg, yield 39%) as a brown solid.

E270 ¹H NMR (300 MHz, CDCl₃): δ 8.98 (s, 1H), 8.06 (s, 1H), 7.48 (s, 1H), 6.95 (s, 1H), 4.58 (d, J=11.7 Hz, 1H), 4.29 (t, J=12.3 Hz, 2H), 4.20 (d, J=12.0 Hz, 1H), 4.07 (d, J=13.2 Hz, 1H), 3.80-3.67 (m, 5H), 3.11 (t, J=12.3 Hz, 1H), 2.95 (t, J=12.6 Hz, 1H), 2.63 (s, 3H), 2.47 (s, 3H), 2.04-1.84 (m, 4H), 1.82-1.57 (m, 4H).

LC-MS [mobile phase: from 70% water (0.02% NH₄OAc) and 30% CH₃CN to 5% water (0.02% NH₄OAc)

and 95% CH$_3$CN in 6.5 min], purity is >95%, Rt=3.804 min; MS Calcd.: 423, MS Found: 424 [M+H]$^+$.

Chiral HPLC [Chiralpak IC, Phase: CO$_2$/MeOH=60/40, MeOH (0.2DEA), flow rate (CO$_2$: 1.799 mL/min; MeOH (0.2DEA): 1.2 mL/min, T=38.6° C.], Rt=5.35 min, 100% ee.

Example 271

((2S)-4-(2-Methyl-6-(5-methyl-6-(tetrahydro-2H-pyran-2-yl)-1H-indazol-1-yl)pyrimidin-4-yl)morpholin-2-yl)methanol (Diastereoisomer 2, E271)

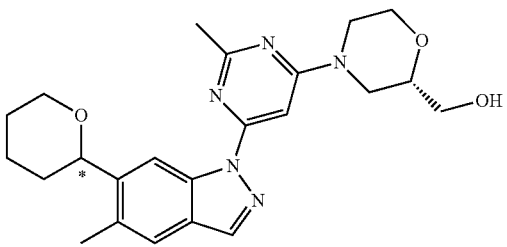 [SMILES: Cc1nc(N2CCO[C@H](CO)C2)cc(-n2ncc3cc(C)c(C4CCCCO4)cc32)n1]

To a solution of 5-methyl-6-(tetrahydro-pyran-2-yl)-1H-indazole (diastereoisomer 2, 66 mg, 0.30 mmol) and (S)-(4-(6-iodo-2-methylpyrimidin-4-yl)morpholin-2-yl)methanol (100 mg, 0.33 mmol) in toluene (10 mL) was added N1,N2-dimethylcyclohexane-1,2-diamine (85 mg, 0.60 mmol), CuI (57 mg, 0.30 mmol) and K$_3$PO$_4$ (127 mg, 0.60 mmol). The mixture was stirred at 110° C. under nitrogen for 3 hrs. The reaction mixture was cooled to rt and filtered. The filtrate was concentrated under vacuum. The residue was purified by pre-TLC (PE:EtOAc=1:1, 4 times) and re-crystallized from ethanol to give the title compound (24 mg, yield 19%) as a white solid.

E271 $^1$H NMR (300 MHz, CDCl$_3$): δ 8.98 (s, 1H), 8.06 (s, 1H), 7.48 (s, 1H), 6.94 (s, 1H), 4.58 (d, J=11.7 Hz, 1H), 4.29-4.17 (m, 3H), 4.05 (d, J=12.3 Hz, 1H), 3.75-3.69 (m, 5H), 3.14-3.06 (m, 1H), 2.93 (t, J=12.3 Hz, 1H), 2.63 (s, 3H), 2.47 (s, 3H), 2.06-1.76 (m, 4H), 1.74-1.64 (m, 3H).

LC-MS [mobile phase: from 70% water (0.02% NH$_4$OAc) and 30% CH$_3$CN to 5% water (0.02% NH$_4$OAc) and 95% CH$_3$CN in 6.5 min], purity is >95%, Rt=3.838 min; MS Calcd.: 423, MS Found: 424 [M+H]$^+$.

Chiral HPLC [Chiralpak IC, Phase: CO$_2$/MeOH=60/40, MeOH (0.2DEA), flow rate (CO$_2$: 1.799 mL/min; MeOH (0.2DEA): 1.2 mL/min, T=39.2° C.], Rt=7.08 min, 99.35% ee.

Example 272

1-(2-Methyl-6-(5-methyl-6-(tetrahydro-2H-pyran-3-yl)-1H-indazol-1-yl)pyrimidin-4-yl)azetidin-3-ol (Enantiomer 1, E272)

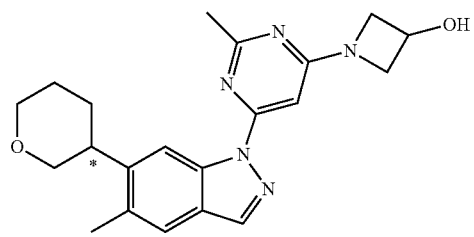 [SMILES: Cc1nc(N2CC(O)C2)cc(-n2ncc3cc(C)c(C4CCCOC4)cc32)n1]

A mixture of 5-methyl-6-(tetrahydro-2H-pyran-3-yl)-1H-indazole (enantiomer 1, 22 mg, 0.10 mmol), 4-iodo-2-methyl-6-(3-((tetrahydro-2H-pyran-2-yl)oxy)azetidin-1-yl)pyrimidine (45 mg, 0.12 mmol), CuI (15 mg. 0.08 mmol), N,N'-dimethyl-cyclohexane-1,2-diamine (23 mg, 0.16 mmol) and potassium phosphate (34 mg, 0.16 mmol) in toluene (2 mL) was degassed with nitrogen and then stirred at 110° C. for 2 hrs. After cooled to rt the reaction mixture was poured into diluted ammonia solution (10%, 50 mL) and EtOAc (50 mL). The organic layer was separated and the aqueous layer was extracted with ethyl acetate (50 mL). The combined organic layers were washed with brine (50 mL), dried and concentrated. The residue was purified by prep-TLC (petroleum ether:EtOAc=4:1) to give pale yellow solid. The solid was dissolved in HCl/dioxane (4 M, 2 mL) and stirred at room temperature for 2 hrs. The reaction mixture was directly concentrated under reduced pressure to give the title compound (12 mg, yield 32%) as white solid.

E272 $^1$H NMR (300 MHz, CD$_3$OD): δ 8.68 (s, 1H), 8.31 (s, 1H), 7.64 (s, 1H), 6.87 (s, 1H), 4.94-4.85 (m, 1H), 4.65-4.60 (m, 2H), 4.21-4.17 (m, 2H), 4.02-3.95 (m, 2H), 3.65-3.48 (m, 2H), 3.24-3.21 (m, 1H), 2.76 (s, 3H), 2.49 (s, 3H), 2.11-2.08 (m, 1H), 1.88-1.79 (m, 3H).

LC-MS (XB-C18, ¢4.6*50 mm*5 um; mobile phase: from 95% water (0.02% NH$_4$OAc) and 5% CH$_3$CN to 5% water (0.02% NH$_4$OAc) and 95% CH$_3$CN in 6.5 min), purity >95%, Rt=4.163 min; MS Calcd.: 379; MS Found: 380 (M+H)$^+$.

Chiral condition: Chiral pak IA 5 um 4.6*250 mm, Hex:EtOH=70:30, Flow: 1.0 ml/min, 230 nm, T=30° C. Rt=5.792 min, 100% ee.

Example 273

1-(2-Methyl-6-(5-methyl-6-(tetrahydro-2H-pyran-3-yl)-1H-indazol-1-yl)pyrimidin-4-yl)azetidin-3-ol (Enantiomer 2, E273)

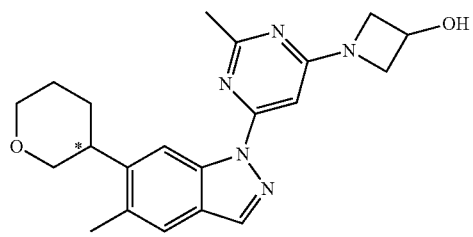 [SMILES: Cc1nc(N2CC(O)C2)cc(-n2ncc3cc(C)c(C4CCCOC4)cc32)n1]

A mixture of 5-methyl-6-(tetrahydro-2H-pyran-3-yl)-1H-indazole (enantiomer 2, 22 mg, 0.10 mmol), 4-iodo-2-methyl-6-(3-((tetrahydro-2H-pyran-2-yl)oxy)azetidin-1-yl)pyrimidine (45 mg, 0.12 mmol), CuI (15 mg. 0.08 mmol), N,N'-dimethyl-cyclohexane-1,2-diamine (23 mg, 0.16 mmol) and potassium phosphate (34 mg, 0.16 mmol) in toluene (2 mL) was degassed with nitrogen and then stirred at 110° C. for 3 hrs. After cooled to rt the reaction mixture was poured into diluted ammonia solution (10%, 30 mL) and EtOAc (30 mL). The organic layer was separated and the aqueous layer was extracted with ethyl acetate (30 mL). The combined organic layers were washed with brine (50 mL), dried and concentrated. The residue was purified by prep-TLC (petroleum ether:EtOAc=4:1) to give THP-protected product as yellow gel. The gel was dissolved in HCl/dioxane (4 M, 2 mL) and stirred at room temperature for 2 hrs. The reaction mixture was directly concentrated and the crude was triturated in EtOAc (10 mL) to give the title compound (11 mg, yield 29%) as white solid.

E273 $^1$H NMR (300 MHz, CD$_3$OD): δ 8.68 (s, 1H), 8.31 (s, 1H), 7.64 (s, 1H), 6.86 (s, 1H), 4.93-4.91 (m, 1H), 4.65-4.58 (m, 2H), 4.20-4.16 (m, 2H), 4.04-3.96 (m, 2H), 3.22-3.19 (m, 1H), 2.76 (s, 3H), 2.49 (s, 3H), 2.08-1.78 (m, 4H).

LC-MS (XB-C18, ⌀4.6*50 mm*5 um; mobile phase: from 95% water (0.02% NH$_4$OAc) and 5% CH$_3$CN to 5% water (0.02% NH$_4$OAc) and 95% CH$_3$CN in 6.5 min), purity >95%, Rt=4.164 min; MS Calcd.: 379; MS Found: 380 (M+H)$^+$.

Chiral condition: Chiral pak IA 5 um 4.6*250 mm, Hex:EtOH=70:30, Flow: 1.0 ml/min, 230 nm, T=30° C. Rt=7.300 min, 98.28% ee.

F. Biological Data

As stated above, the compounds of the present invention are LRRK2 kinase inhibitors, and are useful in the treatment of diseases mediated by LRRK2. The biological activities of the compounds of the present invention can be determined using any suitable assay for determining the activity of a candidate compound as a LRRK2 kinase inhibitor, as well as tissue and in vivo models.

1) Truncated G2019 Human LRRK2 (1326-2527) Inhibition Mass Spectrometry Assay

Production of 6his-Tev-LRRK2 (1326-2527)

A LRRK2 cDNA encoding residues 1326-2527 was received from Dundee University (described in M. Jaleel et al., 2007, Biochem J, 405: 407-417). This gene fragment was subcloned into pFB-HTb (Invitrogen) using BamHI and NotI restriction sites. The LRRK2 plasmid was recombined into the baculovirus genome according to the BAC-to-BAC protocol described by Invitrogen. Transfection into *Spodoptera frugiperda* (Sf9) insect cells was performed using Cellfectin (Invitrogen), according to the manufacturer's protocol to generate P1 and P2 baculovirus stocks.

Sf9 cells were grown in HyClone SFX (Thermo Scientific) growth media at 27° C., 80 rpm in shake flask until of a sufficient volume to inoculate a bioreactor. The cells were grown in a 20 litre working volume Wave bioreactor (GE Healthcare) at 27° C., 50% dissolved oxygen and an agitation rate 22 rocks per minute, 10 degree rock angle, 200 ml/min air with a cell concentration of approximately 6xe6 cells/ml. The cells were infected with P2 Baculovirus at a multiplicity of infection (MOI) of 3. The cultivation was continued for a 48 hour expression phase. The infected cells were removed from the growth media by centrifugation at 2500 g using a Sorvall RC 3C Plus centrifuge at 2500 g for 20 minutes. The cell pellet was immediately frozen and subsequently supplied for purification.

A 260 g pellet was allowed to thaw in a water bath at 27° C. with 800 ml lysis buffer/buffer A (50 mm Tris-HCl pH 8.5, 300 mM NaCl, 1 mm DTT, 10% glycerol, 1 ml/L Calbiochem complete protease inhibitor cocktail and benzonase (50 ul/800 ml)) before being dounce homogenised on ice using 20 strokes per 100 ml. The suspension was packed in ice and sonicated at 50% amplitude for 3 min 10 sec on/off using a ¾" probe. The suspension was then centrifuged at 100,000 g for 90 min, at 4° C.

The lysate (700 ml) was decanted from the insoluble pellet and contacted for 3h at 4° C. with 10 ml His bind Ni NTA resin by end over end mixing. The resin was recovered by centrifugation, 3000 g, 5 min at 4° C., and packed in an XK16 column. The column was then washed with 10 column volumes buffer A, 10 column volumes buffer B (buffer A+1M NaCl) and 10 column volumes buffer C (buffer A+20 mM imidazole). The column was then eluted with 15 column volumes buffer D (buffer A+300 mM imidazole) collecting 2 ml fractions. All washes and elution were conducted at 4 ml/min.

Fractions identified by SDS-PAGE as containing protein of interest were pooled and loaded directly onto a 320 ml SEC Superdex 200 pg column that was pre-equilibrated with buffer E (50 mM Tris-HCl pH 8.5, 300 mM NaCl, 10% glycerol, 1 mM DTT). The column was loaded and eluted with 1.2 column volumes buffer E at 2 ml/min collecting 2 ml fractions. Fractions identified by SDS-PAGE as containing protein of interest were tested for activity.

Production of LRRKtide for LRRK2 Inhibition Mass Spectrometry Assay

The 'LRRKtide' peptide (SEQ ID NO. 10) was synthesized as follows. The protected peptide was assembled on a solid-phase synthesiser using preloaded Wang resin and utilising standard Fmoc synthesis protocols. The crude peptide was obtained after cleavage from the resin with a mixture of trifluoroacetic acid (TFA), triisopropylsilane and water (95:2.5:2.5) for 3 hours at room temperature and was then purified using a C18 reverse-phase column utilising a 0.1% TFA-buffered water/acetonitrile gradient. The resulting fractions were analysed and fractions which were >95% pure by analytical HPLC and giving the correct molecular weight (mw) (by MALDiTOF mass spectroscopy) were pooled and freeze dried. The final material was analysed by HPLC and MALDiTOF mass spectroscopy.

Truncated G2019 Human LRRK2 (1326-2527) Inhibition Mass Spectrometry Assay

This assay for Leucine Rich Repeat Kinase 2 (LRRK2) inhibition is based on the direct measurement of the peptide 'LRRKtide' (LRRKtide: RLGRDKYKT*LRQIRQ and "*" refers to the site of phosphorylation) and phosphorylated 'LRRKtide' using a high throughput RapidFire mass spectrometry assay. Inhibitors are defined as compounds which reduce the conversion of LRRKtide to phospho-LRRKtide.

Assay Protocol

1. A 10 mM test compound was dissolved in 100% DMSO and serially diluted 1 in 4. 100 nL of this dilution series was then added to a 384 well, v bottom polypropylene plate, excluding columns 6 and 18. 100 nL of DMSO was added to columns 6 and 18 as controls wells. Assay dilution gave a top final assay concentration of test compound of 100 μM 2. 5 uL of 'enzyme solution' containing 120 nM of purified recombinant 6HIS-Tev-LRRK2 (1326-2527) in assay buffer (50 mM Hepes (pH 7.2), 10 mM MgCl2, 150 mM NaCl, 5% glycerol, 0.0025% triton X-100 and 1 mM DTT) was added to all wells except column 18 using a multidrop combi dispenser, giving a final assay concentration of 60 nM LRRK2 enzyme. 5 uL assay buffer only was added to column 18 using a multidrop combi dispenser as a 100% inhibition control, column 6 (enzyme plus DMSO) gave 0% inhibition. Test plates were then incubated for 30 minutes at room temperature.

3. 5 uL 'substate solution' containing 50 uM LRRKtide peptide substrate and 40 uM ATP was added to all wells of the plate using a multidrop combi dispenser giving a final assay concentration of 25 uM LRRKtide and 20 uM ATP. Test plates were then incubated for 1 hour at room temperature. (Incubation may vary depending on rate and linearity of reaction with different enzyme batches).

4. 50 ul of 1% formic acid in laboratory grade water was added to all wells to quench the reaction, and plates were centrifuged at 3000 rpm for 10 minutes. Test plates were then analysed on an Agilent RapidFire High Throughput solid phase extraction system coupled to AB Sciex API 4000 triple quadropole mass spectrometer with the following setting:

RapidFire settings:
  Sip Height=2 mm, Aspirate=500 ms, Load time=3000 ms, Elution time=3000 ms, Requilibration=500 ms,
  Flow rates: pump 1=1.5 mL/min, pump 2 1.25 mL/min pump 3=0.8 mL/min Mass Spectrometer Settings
  LRRKtide Detection settings: Q1 mass 644.8 Da, Q3 mass 638.8, declustering potential 76 volts, collision energy 37 volts, CXP 34 volts
  Phospho-LRRKtide Detection settings: Q1 mass 671.4 Da, Q3 mass 638.8, Declustering potential 76 volts, Collision energy 37 volts, CXP 34 volts.
  A C4 cartridge was used and running buffers were: A (aqueous) 0.1% formic acid in water B (organic) 0.1% formic acid, 80% acetonitrile, 20% water 5. Data was analysed using ActivityBase software (IDBS). A percent conversion from LRRKtide to Phospho-LRRKtide was calculated using the following formula:

$$\% \text{ conversion} = (\text{Phospho-LRRKtide product peak area}/(\text{Phospho-LRRKtide product peak area} + \text{LRRKtide substrate peak area})) \times 100$$

2) Full Length G2019 Human LRRK2 Inhibition Mass Spectrometry Assay

Insect Cell Cultures

Sf9 insect cells (Invitrogen Life Technologies, Carlsbad, Calif.) were maintained at 27° C. in SF 900 II SFM in 500-ml stationary flasks. The cells were maintained in exponential growth phase and subcultured twice per week. For larger volumes, cells were grown in 2-liter shaker flasks (Erlenmeyer, Corning) while being agitated with 120 rpm at 27° C. incubator shaker.

Human G2019 LRRK2 Plasmids Preparation

Primers Used for PCR Cloning:
  pHTBV-F: SEQ ID No: 1
  LRRK2 wt-F1: SEQ ID No: 2
  LRRK2 wt-R1: SEQ ID No: 3
  LRRK2 wt-F2: SEQ ID No: 4
  LRRK2 wt-R2: SEQ ID No: 5
  LRRK2 wt-F3: SEQ ID No: 6
  pHTBV-R: SEQ ID No: 7

The primers described above were used to amplify full length human LRRK2 (amino acids from 1-2527) with N terminal Flag tag from BioCat 116313 using high fidelity PCR polymerase KOD-Plus according to the manufacturer's instructions (KOD-211, TOYOBO). The PCR product was digested with BamHI and KpnI and ligated into BamHI and KpnI digested pHTBV1mcs3 (BioCat 127555). The sequence of the target fragment was confirmed by DNA sequencing. The construct BioCat141351 was generated by Novoprotein.

The G2019 full length Flag-LRRK2 coding sequence is SEQ ID No: 8.

The translated protein sequence for human G2019 full length LRRK2 flag tagged protein is SEQ ID No: 9.

Generation of the BacMam Virus

To generate the recombinant BacMam virus, SF9 cells were seeded in 6-well tissue culture dishes at $9 \times 10^5$ cells/well and allowed to attach for 20 min. Transfection procedure was followed using AESOP AP5911v2. Briefly, DH10Bac competent cells (10361-012, Invitrogen) were transformed by the genotypically normal human LRRK2 BacMam plasmid to generate the recombinant baculovirus DNA. The Sf9 insect cells were co-transfected with the mixture of recombinant baculovirus DNA and cellfectin (10362-100, Invitrogen). After 4 h of incubation at 27° C., the transfection media was replaced with Sf-900 III SFM medium containing 5% HI FBS (Ser. No. 10/100,147, Invitrogen). The cells were further incubated for 4 days. The infected cell culture medium containing the baculovirus (P0 virus stock) was collected and amplified by further infecting the Sf9 cells at multiplicity of infection (MOI) (pfu/cell) of 0.1.

Quantification of BacMam Viral Titre by BacPAKRapid Titer

The viral titre, measured as plaque forming unit (pfu)/ml was determined using BacPAK Papid Titer Kit (631406, Clontech) according to the manufacturer's protocol. The Sf9 cells seeded in 96-well plate with $3 \times 10^5$ cells per well were incubated with serial dilution of the viral stocks for 1 h at 27° C., 50 µl methyl cellulose overlay was added to each well followed by 43-47 h incubation. The cells were then fixed in 4% paraformaldehyde (PFA). After blocking the cells with diluted normal goat serum, Mouse anti-gp64 antibody was added to the cells. After 30 min incubation, the cells were washed with phosphate buffered saline containing 0.1% Triton-X100 (PBST) and incubated for another 30 min with goat anti-mouse antibody/HRP conjugate. This was followed by blue peroxidase substrate which detects the single infected cells and foci of infected cells by their dark blue color.

Protein Expression

Expression of Flag Tagged Full Length G2019 Human LRRK2

HEK293 6E cells (BioCat: 120363) were incubated in a 37° C. incubator with a humidified atmosphere of 5% $CO_2$ on an orbital shaker rotating at 110 rpm. On the day of transduction, the cell viability was higher than 98% and the cell density was in the range of $1 \times 10^6 \sim 1.5 \times 10^6$ cells/ml.

HEK293 6E cells were centrifuged at 1,000 rpm for 10 min, and then the cells were resuspended in fresh Freestyle 293 expression medium (Invitrogen: 12338) with 0.1% F-68 (Invitrogen: 24040-032) but without antibiotics (G418) at density of $1 \times 10^6$ cells/ml. BacMam virus with Flag-hu LRRK2 (genotypically normal) gene was centrifuged at 40,000 g for 2 hours, then resuspended in fresh Freestyle 293 expression medium. The resuspended virus was added into the cells in at MOI of 10. The cells were incubated in a 37° C. incubator with a humidified atmosphere of 5% $CO_2$ in air on an orbital shaker rotating at 110 rpm. Cultures were harvested at approximately 48 hours post-transduction by centrifugation at 4,000 rpm for 20 min and pellets were frozen for purification.

Protein Purification

Purification of Flag Tagged Full Length G2019 Human LRRK2

The cell pellet was resuspended in 20 mL lysis buffer (50 mM TrisHCl pH7.5 at 4° C., 500 mM NaCl, 0.5 mM EDTA, 0.1% TritonX-100, 10% glycerol, freshly add 2 mM DTT), with protease inhibitors (Roche: 04693132001) and benzonase (Merck Millipore: 70746-3CN) at recommended concentration suggested by suppliers. The suspended cells were lysed by sonication on ice for 30 min (2 secs on/4 sec off, 20% amplitude), and centrifuged at 10,000 rpm for 30 minutes at 4° C. The supernatant was incubated with 1 mL per litre of cell culture of anti-Flag magnetic beads (Sigma- Aldrich: M8823) at 4° C. for 3 hours, then the beads were washed by 5 mL per litre of cell culture binding buffer (50 mM Tris pH7.5@ 4 C, 500 mM NaCl, 0.5 mM EDTA, 0.1% TritonX-100, 10% glycerol, freshly add 2 mM DTT) for three times. The Flag tagged LRRK2 proteins were eluted by Elution buffer (50 mM Tris pH7.5@ 4C, 500 mM NaCl, 0.5 mM EDTA, 0.1% TritonX-100, 10% glycerol, freshly add 2 mM DTT, 250 ug/ml Flag peptide (Sigma-Aldrich: F3290)) at 4° C. for 2 hours. Flag peptide was removed by Zeba Spin Desalting Columns, 7K MWCO (Thermo-Fisher: 89893) and the buffer of eluted LRRK2 proteins was exchanged into Storage Buffer (50 mM Tris pH7.5@4C, 150 mM NaCl, 0.5 mM EDTA, 0.02% Triton X-100, 2 mM DTT and 50% Glycerol) using Amicon Ultra Centrifugal Filter Units (100 kD) (Merck: UFC910096). Fractions containing LRRK2 proteins were pooled, aliquoted and stored at −80° C. Protein concentration was determined by Bradford protein assay, and protein purity was analyzed by NuPAG Novex 4-12% Bis-Tris Protein Gels (Invitrogen: NP0322BOX).

Full Length G2019 Human LRRK2 Inhibition Mass Spectrometry Assay

This assay for Leucine Rich Repeat Kinase 2 (LRRK2) inhibition is based on the direct measurement of the peptide 'LRRKtide' (LRRKtide: RLGRDKYKT*LRQIRQ and "*" refers to the site of phosphorylation) and phosphorylated 'LRRKtide' using a high throughput RapidFire mass spectrometry assay. Inhibitors are defined as compounds which reduce the conversion of LRRKtide to phospho-LRRKtide.

Assay Protocol
1. A 10 mM test compound was dissolved in 100% DMSO and serially diluted 1 in 4. 100 nL of this dilution series was then added to a 384 well, v bottom polypropylene plate, excluding columns 6 and 18. 100 nL of DMSO was added to columns 6 and 18 as controls wells. Assay dilution gave a top final assay concentration of test compound of 100 μM
2. 50 ul of 1% formic acid in laboratory grade water was added to column 18 using a multidrop combi dispenser to act as a pre stopped assay control.
3. 5 uL of 'enzyme solution' containing 50 nM of purified recombinant Full length Flag-LRRK2 in assay buffer (50 mM Hepes (pH 7.2), 10 mM MgCl2, 150 mM NaCl, 5% glycerol, 0.0025% triton X-100 and 1 mM DTT) was added to all wells using a multidrop combi dispenser, giving a final assay concentration of 25 nM LRRK2 enzyme. This resulted in column 6 (enzyme plus DMSO) giving 0% inhibition and column 18 giving 100% inhibition (pre stopped control). Test plates were then incubated for 30 minutes at room temperature.
4. 5 uL 'substate solution' containing 50 uM LRRKtide peptide substrate and 4 mM ATP was added to all wells of the plate using a multidrop combi dispenser giving a final assay concentration of 25 uM LRRKtide and 2 mM ATP. Test plates were then incubated for 1 hour at room temperature. (Incubation may vary depending on rate and linearity of reaction with different enzyme batches).
5. 50 ul of 1% formic acid in laboratory grade water was added to all wells (minus column 18) to quench the reaction, and plates were centrifuged at 3000 rpm for 10 minutes. Test plates were then analysed on an Agilent RapidFire High Throughput solid phase extraction system coupled to AB Sciex API 4000 triple quadropole mass spectrometer with the following setting:

RapidFire Settings:
Sip Height=2 mm, Aspirate=500 ms, Load time=3000 ms, Elution time=3000 ms, Requilibration=500 ms,
Flow rates: pump 1=1.5 mL/min, pump 2 1.25 mL/min pump 3=0.8 mL/min Mass Spectrometer Settings
LRRKtide Detection settings: Q1 mass 644.8 Da, Q3 mass 638.8, declustering potential 76 volts, collision energy 37 volts, CXP 34 volts
Phospho-LRRKtide Detection settings: Q1 mass 671.4 Da, Q3 mass 638.8, Declustering potential 76 volts, Collision energy 37 volts, CXP 34 volts.
A C4 cartridge was used and running buffers were: A (aqueous) 0.1% formic acid in water B (organic) 0.1% formic acid, 80% acetonitrile, 20% water 6. Data was analysed using ActivityBase software (IDBS). A percent conversion from LRRKtide to Phospho-LRRKtide was calculated using the following formula:

% conversion=(Phospho-LRRKtide product peak area/(Phospho-LRRKtide product peak area+ LRRKtide substrate peak area))*100

3) Recombinant Cellular LRRK2 AlphaScreen Assay

To determine the activity of compounds against LRRK2 kinase activity in cells, the observed LRRK2 kinase-dependent modulation of LRRK2 Ser 935 phosphorylation (Dzamko et al., 2010, Biochem. J. 430: 405-413) was utilized to develop a quantitative 384 well plate-based immunoassay of LRRK2 Ser935 phosphorylation in the human neuroblastoma cell line SH-SY5Y, engineered to over-express recombinant full length LRRK2 protein.

A BacMam virus expressing full length recombinant LRRK2 was purchased from Invitrogen and amplified by inoculation of SF-9 cells at MOI 0.3 for 4-5 days in Sf-900 III SFM medium supplemented with 3% fetal bovine serum. Infected cell cultures were then centrifuged at 2000 g for 20 minutes, viral supernatant titer determined by anti-gp64 plaque assay and stored at 4° C.

Affinity-purified anti-phospho LRRK2 Ser935 sheep polyclonal antibody (Dzamko et al., 2010, Biochem. J. 430: 405-413) was biotinylated by standard methods (PerkinElmer). Anti-LRRK2 rabbit polyclonal antibody was purchased from Novus Biologicals. AlphaScreen Protein A IgG Kit (including acceptor and donor beads) was purchased from Perkin Elmer.

SH-SY5Y cells were grown in DMEM/F12 medium with 10% dialysed fetal bovine serum and harvested by treatment with 0.5% trypsin-EDTA for 5 minutes at 37° C. followed by centrifugation at 1000 rpm for 4 minutes. The cell pellet was resuspended in Opti-MEM reduced serum media (Invitrogen) at 200,000 cells/ml and mixed with the BacMam LRRK2 virus at M01=50. 50 μl cell solutions were then dispensed to each well of a 384-well plate and incubated at 37° C., 5% $CO_2$ for 24 hours.

Serial dilutions of test compounds were prepared in Opti-MEM reduced serum media (Invitrogen) and 5.6 ul transferred from compound plate to cell assay plate to achieve a top final assay concentration of 10 uM. DMSO was used in certain wells as controls. Cells were incubated at 37° C., 5% $CO_2$ for 60 minutes. The medium was then removed and cells lysed by addition of 20 ul cell lysis buffer (Cell Signaling Technology) and incubation at 4° C. for 20 minutes. 10 ul of antibody/acceptor bead mix [(1/1000 biotinylated-pS935 LRRK2 antibody, 1/1000 total-LRRK2 antibody, 1/100 Acceptor beads in AlphaScreen detection buffer (25 mM Hepes (pH 7.4), 0.5% Triton X-100, 1 mg/ml Dextran 500 and 0.1% BSA)] was then added to each well and plates incubated for 2 hours at ambient temperature in the dark. 10 μl of donor beads solution (1/33.3 donor beads in AlphaScreen detection buffer) was then added to each well. Following incubation for a further 2 hours at ambient temperature in the dark, plates were read on an EnVision™ plate reader at emission 520-620 nm with excitation 680 nm. Dose response curve data was based on sigmoidal dose-response model.

Pharmacological Data

Compounds of Examples E1-E273 were tested in the truncated G2019 human LRRK2 inhibition mass spectrometry assay, full length G2019 human LRRK2 Inhibition mass spectrometry assay and/or recombinant cellular LRRK2 alphaScreen assay. Compounds of E1-E273 were found to inhibit LRRK2 kinase activity in one or two assays described above.

The pIC50 value for each compound was either reported in at least one experiment or the average of multiple experiments. It is understood that the data described herein may have reasonable variations depending on the specific conditions and procedures used by the person conducting the experiments.

The compounds of Examples E1-E19, E21-E41, E48, E49, E56-E60, E62-E79, E81-E83, E85-E88, E91-E114, and E116-E121 were tested in the truncated G2019 human LRRK2 inhibition mass spectrometry assay, and exhibited a $pIC_{50} \geq 5.0$. The compounds of Examples E2-E4, E6, E14, E21-E24, E28-E30, E34-E36, E38, E39, E48, E56-E58, E62, E72, E73, E82, E92, E96, E104-E108, E110, E114, and E121 exhibited The compounds of Examples E42, E43, E45, E50-E55, E80, E122-E185, E187-E192, E195-E201, E205-E209, E211-E235, E237-E242, E244-E252, E254-E260, E264-E266 and E268-E273 were tested in the full length G2019 human LRRK2 Inhibition mass spectrometry assay and exhibited a $pIC_{50} \geq 5.0$. The compounds of Examples E50-E55, E80, E123-125, E136, E138-E140, E142, E146, E152-E156, E158, E160-E163, E166, E169-E171, E173, E180-E181, E211, E212, E237, E248, E252 and E265 exhibited Compounds of Examples E1-E273 were tested in the recombinant cellular LRRK2 alphaScreen assay. All tested compounds except Examples E7, E9, E11, E25, E74, E76, E77, E87, E221, E228, E229, E240, E245, E271 and E272 exhibited a $pIC_{50} \geq 5.0$. The compounds of Examples E4, E18, E22, E24, E29, E30, E34, E35, E38, E39, E40, E42, E44, E45, E46, E49-E55, E62-E64, E79, E80, E89, E122-E126, E128, E132, E134-E142, E146, E152-E177, E180-E183, E188-E192, E195-E196, E205, E207-E209, E211-E213, E219, E237, E246, E250, E258, E260-E266, and E268 exhibited $pIC_{50} \geq 7.0$.

For example, the pIC50 values of recombinant cellular LRRK2 alphaScreen assay and LRRK2 Inhibition Mass Spectrometry Assay for following examples are:

| Example No | Recombinant cellular LRRK2 alphaScreen assay (pIC50) | Truncated G2019 human LRRK2 inhibition mass spectrometry assay (pIC50) | Full length G2019 human LRRK2 Inhibition mass spectrometry assay (pIC50) |
|---|---|---|---|
| E4 | 7.6 | 8.1 | |
| E18 | 7.9 | 7.9 | |
| E22 | 7.9 | 8.1 | |
| E38 | 7.5 | 8 | |
| E39 | 8.3 | 8.0 | |
| E40 | 7.3 | 7.9 | |
| E41 | 6.9 | 7.9 | |
| E62 | 7.3 | 8.1 | |
| E66 | 6.9 | 7.5 | |
| E79 | 8.0 | 7.9 | |
| E117 | 6.2 | 7.6 | |
| E170 | 8.3 | | 8.1 |
| E183 | 7.2 | | 7.9 |
| E188 | 7.1 | | 7.6 |
| E205 | 7.3 | | 7.7 |
| E208 | 7.4 | | 7.7 |
| E230 | 6.2 | | 6.6 |
| E239 | 6.8 | | 7.9 |

```
Sequence listing

SEQ ID NO: 1 Primers used for PCR cloning of Human G2019 LRRK2 plasmids preparation: pHTBV-F
5'-GATCTCGACGGGCGCGGATCCACCATGGATTACAAGGATGACGACGAT-3'

SEQ ID NO: 2 Primers used for PCR cloning of Human G2019 LRRK2 plasmids preparation: LRRK2
wt-F1
5'-CATGGATTACAAGGATGACGACGATAAGATGGCTAGTGGCAGCTGTCAG-3'

SEQ ID NO: 3 Primers used for PCR cloning of Human G2019 LRRK2 plasmids preparation: LRRK2
wt-R1
5'-GTTCACGAGATCCACTATTCAGTAAGAGTTCCACCAATTTGGGACTG-3'

SEQ ID NO: 4 Primers used for PCR cloning of Human G2019 LRRK2 plasmids preparation: LRRK2
wt-F2
5'-GAATAGTGGATCTCGTGAACAAG-3'

SEQ ID NO: 5 Primers used for PCR cloning of Human G2019 LRRK2 plasmids preparation: LRRK2
wt-R2
5'-GTCAGACAAACTGCTTGGAACCAGC-3'

SEQ ID NO: 6 Primers used for PCR cloning of Human G2019 LRRK2 plasmids preparation: LRRK2
wt-F3
5'-CTGGTTCCAAGCAGTTTGTCTGACCACAGGCCTGTGATAG-3'

SEQ ID NO: 7 Primers used for PCR cloning of Human G2019 LRRK2 plasmids preparation: pHTBV-R
5'-GTTCTAGCCAAGCTTGGTACCCTATTACTCAACAGATGTTCGTCTC-3'
```

SEQ ID NO: 8 G2019 full length Flag-LRRK2 coding sequence
atggattacaaggatgacgacgataagATGGCTAGTGGCAGCTGTCAGGGGTGCGAAGAGGACGAGGAAAC
TCTGAAGAAGTTGATAGTCAGGCTGAACAATGTCCAGGAAGGAAAACAGATAGAAACGCTGGTC
CAAATCCTGGAGGATCTGCTGGTGTTCACGTACTCCGAGCACGCCTCCAAGTTATTTCAAGGCAA
AAATATCCATGTGCCTCTGTTGATCGTCTTGGACTCCTATATGAGAGTCGCGAGTGTGCAGCAGG
TGGGTTGGTCACTTCTGTGCAAATTAATAGAAGTCTGTCCAGGTACAATGCAAAGCTTAATGGGA
CCCCAGGATGTTGGAAATGATTGGGAAGTCCTTGGTGTTCACCAATTGATTCTTAAAATGCTAAC
AGTTCATAATGCCAGTGTAAACTTGTCAGTGATTGGACTGAAGACCTTAGATCTCCTCCTAACTTC
AGGTAAAATCACCTTGCTGATACTGGATGAAGAAAGTGATATTTTCATGTTAATTTTTGATGCCAT
GCACTCATTTCCAGCCAATGATGAAGTCCAGAAACTTGGATGCAAAGCTTTACATGTGCTGTTTG
AGAGAGTCTCAGAGGAGCAACTGACTGAATTTGTTGAGAACAAAGATTATATGATATTGTTAAGT
GCGTTAACAAATTTTAAAGATGAAGAGGAAATTGTGCTTCATGTGCTGCATTGTTTACATTCCCTA
GCGATTCCTTGCAATAATGTGGAAGTCCTCATGAGTGGCAATGTCAGGTGTTATAATATTGTGGT
GGAAGCTATGAAAGCATTCCCTATGAGTGAAAGAATTCAAGAAGTGAGTTGCTGTTTGCTCCATA
GGCTTACATTAGGTAATTTTTTCAATATCCTGGTATTAAACGAAGTCCATGAGTTTGTGGTGAAAG
CTGTGCAGCAGTACCCAGAGAATGCAGCATTGCAGATCTCAGCGCTCAGCTGTTTGGCCCTCCT
CACTGAGACTATTTTCTTAAATCAAGATTTAGAGGAAAAGAATGAGAATCAAGAGAATGATGATGA
GGGGGAAGAAGATAAATTGTTTTGGCTGGAAGCCTGTTACAAAGCATTAACGTGGCATAGAAAGA
ACAAGCACGTGCAGGAGGCCGCATGCTGGGCACTAAATAATCTCCTTATGTACCAAAACAGTTTA
CATGAAGAAGATTGGAGATGAAGATGGCCATTTCCCAGCTCATAGGGAAGTGATGCTCTCCATGC
TGATGCATTCTTCATCAAAGGAAGTTTTCCAGGCATCTGCGAATGCATTGTCAACTCTCTTAGAAC
AAAATGTTAATTTCAGAAAAATACTGTTATCAAAAGGAATACACCTGAATGTTTGGAGTTAATGCA
GAAGCATATACATTCTCCTGAAGTGGCTGAAAGTGGCTGTAAAATGCTAAATCATCTTTTTGAAGG
AAGCAACACTTCCCTGGATATAATGGCAGCAGTGGTCCCCAAAATACTAACAGTTATGAAACGTC
ATGAGACATCATTACCAGTGCAGCTGGAGGCGCTTCGAGCTATTTTACATTTTATAGTGCCTGGC
ATGCCAGAAGAATCCAGGGAGGATACAGAATTTCATCATAAGCTAAATATGGTTAAAAAACAGTG
TTTCAAGAATGATATTCACAAACTGGTCCTAGCAGCTTTGAACAGGTTCATTGGAAATCCTGGGAT
TCAGAAATGTGGATTAAAAGTAATTTCTTCTATTGTACATTTTCCTGATGCATTAGAGATGTTATCC
CTGGAAGGTGCTATGGATTCAGTGCTTCACACACTGCAGATGTATCCAGATGACCAAGAAATTCA
GTGTCTGGGTTTAAGTCTTATAGGATACTTGATTACAAAGAAGAATGTGTTCATAGGAACTGGACA
TCTGCTGGCAAAAATTCTGGTTTCCAGCTTATACCGATTTAAGGATGTTGCTGAAATACAGACTAA
AGGATTTCAGACAATCTTAGCAATCCTCAAATTGTCAGCATCTTTTTCTAAGCTGCTGGTGATCA
TTCATTTGACTTAGTAATATTCCATCAAATGTCTTCCAATATCATGGAACAAAAGGATCAACAGTTT
CTAAACCTCTGTTGCAAGTGTTTTGCAAAAGTAGCTATGGATGATTACTTAAAAAATGTGATGCTA
GAGAGAGCGTGTGATCAGAATAACAGCATCATGGTTGAATGCTTGCTTCTATTGGGAGCAGATG
CCAATCAAGCAAAGGAGGGATCTTCTTTAATTTGTCAGGTATGTGAGAAAGAGAGCAGTCCCAAA
TTGGTGGAACTCTTACTGAATAGTGGATCTCGTGAACAAGATGTACGAAAAGCGTTGACGATAAG
CATTGGGAAAGGTGACAGCCAGATCATCAGCTTGCTCTTAAGGAGGCTGGCCCTGGATGTGGCC
AACAATAGCATTTGCCTTGGAGGATTTTGTATAGGAAAAGTTGAACCTTCTTGGCTTGGTCCTTTA
TTTCCAGATAAGACTTCTAATTTAAGGAAACAAACAAATATAGCATCTACACTAGCAAGAATGGTG
ATCAGATATCAGATGAAAAGTGCTGTGGAAGAAGGAACAGCCTCAGGCAGCGATGGAAATTTTC
TGAAGATGTGCTGTCTAAATTTGATGAATGGACCTTTATTCCTGACTCTTCTATGGACAGTGTGTT
TGCTCAAAGTGATGACCTGGATAGTGAAGGAAGTGAAGGCTCATTTCTTGTGAAAAAGAAATCTA
ATTCAATTAGTGTAGGAGAATTTTACCGAGATGCCGTATTACAGCGTTGCTCACCAAATTTGCAAA
GACATTCCAATTCCTTGGGGCCCATTTTTGATCATGAAGATTTACTGAAGCGAAAAAGAAAAATAT
TATCTTCAGATGATTCACTCAGGTCATCAAAACTTCAATCCCATATGAGGCATTCAGACAGCATTT
CTTCTCTGGCTTCTGAGAGAGAATATATTACATCACTAGACCTTTCAGCAAATGAACTAAGAGATA
TTGATGCCCTAAGCCAGAAATGCTGTATAAGTGTTCATTTGGAGCATCTTGAAAAGCTGGAGCTT
CACCAGAATGCACTCACGAGCTTTCCACAACAGCTATGTGAAACTCTGAAGAGTTTGACACATTT
GGACTTGCACAGTAATAAATTTACATCATTTCCTTCTTATTGTTGAAAATGAGTTGTATTGCTAAT
CTTGATGTCTCTCGAAATGACATTGGACCCTCAGTGGTTTTAGATCCTACAGTGAAATGCCAACT
CTGAAACAGTTTAACCTGTCATATAACCAGCTGTCTTTTGTACCTGAGAACCTCACTGATGTGGTA
GAGAAACTGGAGCAGCTCATTTTAGAAGGAAATAAAATATCAGGGATATGCTCCCCCTTGAGACT
GAAGGAACTGAAGATTTTAAACCTTAGTAAGAACCACATTTCATCCCTATCAGAGAACTTTCTTGA
GGCTTGTCCTAAAGTGGAGAGTTTCAGTGCCAGAATGAATTTTCTTGCTGCTATGCCTTTCTTGC
CTCCTTCTATGCAACATCCTAAAATTATCTCAGAACAAATTTTCCTGTATTCCAGAAGCAATTTTAAA
TCTTCCACACTTGCGGTCTTTAGATATGAGCAGCAATGATATTCAGTACCTACCAGGTCCCGCAC
ACTGGAAATCTTTGAACTTAAGGGAACTCTTATTTAGCCATAATCAGATCAGCATCTTGGACTTGA
GTGAAAAAGCATATTTATGGTCTAGAGTAGAGAAACTGCATCTTTCTCACAATAAACTGAAAGAGA
TTCCTCCTGAGATTGGCTGTCTTGAAAATCTGACATCTCTGGATGTCAGTTACAACTTGGAACTAA
GATCCTTTCCCAATGAAATGGGGAAATTAAGCAAAATATGGGATCTTCCTTTGGATGAACTGCAT
CTTAACTTTGATTTTAAACATATAGGATGTAAAGCCAAAGACATCATAAGGTTTCTTCAACAGCGA
TTAAAAAAGGCTGTGCCTTATAACCGAATGAAACTTATGATTGTGGGAAATACTGGGAGTGGTAA
AACCACCTTATTGCAGCAATTAATGAAAACCAAGAAATCAGATCTTGGAATGCAAAGTGCCACAG
TTGGCATAGATGTGAAAGACTGGCCTATCCAAATAAGAGACAAAAGAAAGAGATCTCGTCCTA
AATGTGTGGGATTTTGCAGGTCGTGAGGAATTCTATAGTACTCATCCCCATTTTATGACGCAGCG
AGCATTGTACCTTGCTGTCTATGACCTCAGCAAGGGACAGGCTGAAGTTGATGCCATGAAGCCTT
GGCTCTTCAATATAAAGGCTCGCGCTTCTTCTTCCCCTGTGATTCTCGTTGGCACACATTTGGAT
GTTTCTGATGAGAAGCAACGCAAAGCCTGCATGAGTAAAATCACCAAGGAACTCCTGAATAAGCG
AGGGTTCCCTGCCATACGAGATTACCACTTTGTGAATGCCACCGAGGAATCTGATGCTTTGGAA
AACTTCGGAAAACCATCATAAACGAGAGCCTTAATTTCAAGATCCGAGATCAGCTTGTTGTTGGA
CAGCTGATTCCAGACTGCTATGTAGAACTTGAAAAAATCATTTTATCGGAGCGTAAAAATGTGCCA
ATTGAATTTCCCGTAATTGACCGGAAACGATTATTACAACTAGTGAGAGAAAATCAGCTGCAGTTA
GATGAAAATGAGCTTCCTCACGCAGTTCACTTTCTAAATGAATCAGGAGTCCTTCTTCATTTTCAA
GACCCAGCACTGCAGTTAAGTGACTTGTACTTTGTGGAACCCAAGTGGCTTTGTAAAATCATGGC
ACAGATTTTGACAGTGAAAGTGGAAGGTTGTCCAAAACACCCTAAGGGAATTATTTCGCGTAGAG

| Sequence listing |
|---|
| ATGTGGAAAAATTTCTTTCAAAGAAAAGGAAATTTCCAAAGAACTACATGTCACAGTATTTTAAGC
TCCTAGAAAAATTCCAGATTGCTTTGCCAATAGGAGAAGAATATTTGCTGGTTCCAAGCAGTTTGT
CTGACCACAGGCCTGTGATAGAGCTTCCCCATTGTGAGAACTCTGAAATTATCATCCGACTATAT
GAAATGCCTTATTTTCCAATGGGATTTTGGTCAAGATTAATCAATCGATTACTTGAGATTTCACCTT
ACATGCTTTCAGGGAGAGAACGAGCACTTCGCCCAAACAGAATGTATTGGCGACAAGCATTTA
CTTAAATTGGTCTCCTGAAGCTTATTGTCTGGTAGGATCTGAAGTCTTAGACAATCATCCAGAGA
GTTTCTTAAAAATTACAGTTCCTTCTTGTAGAAAAGGCTGTATTCTTTTTGGGCCAAGTTGTGGACC
ACATTGATTCTCTCATGGAAGAATGGTTTCCTGGGTTGCTGGAGATTGATATTTGTGGTGAAGGA
GAAACTCTGTTGAAGAATGGGCATTATATAGTTTTAATGATGGTGAAGAACATCAAAAAATCTTA
CTTGATGACTTGATGAAAAGCAGAGGAAGGAGATCTCTTAGTAAATCCAGATCAACCAAGGCT
CACCATTCCAATATCTCAGATTGCCCCTGACTTGATTTTGGCTGACCTGCCTAGAAATATTATGTT
GAATAATGATGAGTTGGAATTTGAACAAGCTCCAGAGTTTCTCCTAGGTGATGGCAGTTTTGGAT
CAGTTTACCGAGCAGCCTATGAAGGAGAAGAAGTGGCTGTGAAGATTTTTAATAAACATACATCA
CTCAGGCTGTTAAGACAAGAGCTTGTGGTGCTTTGCCACCTCCACCACCCCAGTTTGATATCTTT
GCTGGCAGCTGGGATTCGTCCCCGGATGTTGGTGATGGAGTTAGCCTCCAAGGGTTCCTTGGAT
CGCCTGCTTCAGCAGGACAAAGCCAGCCTCACTAGAACCCTACAGCACAGGATTGCACTCCACG
TAGCTGATGGTTTGAGATACCTCCACTCAGCCATGATTATATACCGAGACCTGAAACCCCACAAT
GTGCTGCTTTTCACACTGTATCCCAATGCTGCCATCATTGCAAAGATTGCTGACTACGGCATTGC
TCAGTACTGCTGTAGAATGGGGATAAAAACATCAGAGGGCACACCAGGGTTTCGTGCACCTGAA
GTTGCCAGAGGAAATGTCATTTATAACCAACAGGCTGATGTTTATTCATTTGGTTTACTACTCTAT
GACATTTTGACAACTGGAGGTAGAATAGTAGAGGGTTTGAAGTTTCCAAATGAGTTTGATGAATTA
GAAATACAAGGAAAATTACCTGATCCAGTTAAAGAATATGGTTGTGCCCCATGGCCTATGGTTGA
GAAATTAATTAAACAGTGTTTGAAAGAAAATCCTCAAGAAAGGCCTACTTCTGCCCAGGTCTTTGA
CATTTTGAATTCAGCTGAATTAGTCTGTCTGACGAGACGCATTTTAATTACCTAAAAACGTAATTGTT
GAATGCATGGTTGCTACACATCACAACAGCAGGAATGCAAGCATTTGGCTGGGCTGTGGGCACA
CCGACAGAGGACAGCTCTCATTTCTTGACTTAAATACTGAAGGATACACTTCTGAGGAAGTTGCT
GATAGTAGAATATTGTGCTTAGCCTTGGTGCATCTTCCTGTTGAAAAGGAAAGCTGGATTGTGTC
TGGGACACAGTCTGGTACTCTCCTGGTCATCAATACCGAAGATGGGAAAAAGGACATACCCTA
GAAAAGATGACTGATTCTGTCACTTGTTTGTATTGCAATTCCTTTTCCAAGCAAAGCAAACAAAAA
AATTTTCTTTTGGTTGGAACCGCTGATGGCAAGTTAGCAATTTTTGAAGATAAGACTGTTAAGCTT
AAAGGAGCTGCTCCTTTGAAGATACTAAATATAGGAAATGTCAGTACTCCATTGATGTGTTTGAGT
GAATCCACAAATTCAACGGAAAGAAATGTAATGTGGGGAGGATGTGGCACAAAGATTTTCTCCTT
TTCTAATGATTTCACCATTCAGAAACTCATTGAGACAAGAACAAGCCAACTGTTTTCTTATGCAGC
TTTCAGTGATTCCAACATCATAACAGTGGTGGTAGACACTGCTCTCTATATTGCTAAGCAAAATAG
CCCTGTTGTGGAAGTGTGGGATAAGAAAACTGAAAAACTCTGTGGACTAATAGACTGCGTGCACT
TTTTAAGGGAGGTAATGGTAAAAGAAAACAAGGAATCAAAACACAAAATGTCTTATTCTGGGAGA
GTGAAAACCCTCTGCCTTCAGAAGAACACTGCTCTTTGGATAGGAACTGGAGGAGGCCATATTTT
ACTCCTGGATCTTTCAACTCGTCGACTTATACGTGTAATTTACAACTTTTGTAATTCGGTCAGAGT
CATGATGACAGCACAGCTAGGAAGCCTTAAAAATGTCATGCTGGTATTGGGCTACAACCGGAAAA
ATACTGAAGGTACACAAAAGCAGAAAGAGATACAATCTTGCTTGACCGTTTGGGACATCAATCTT
CCACATGAAGTGCAAAATTTAGAAAAACACATTGAAGTGAGAAAAGAATTAGCTGAAAAAATGAG
ACGAACATCTGTTGAGTAA |

SEQ ID NO: 9 Translated protein sequence for human G2019 full length LRRK2 flag tagged protein
MDYKDDDDKMASGSCQGCEEDEETLKKLIVRLNNVQEGKQIETLVQILEDLLVFTYSEHASKLFQGKN
IHVPLLIVLDSYMRVASVQQVGWSLLCKLIEVCPGTMQSLMGPQDVGNDWEVLGVHQLILKMLTVHN
ASVNLSVIGLKTLDLLLTSGKITLLILDEESDIFMLIFDAMHSFPANDEVQKLGCKALHVLFERVSEEQLT
EFVENKDYMILLSALTNFKDEEEIVLHVLHCLHSLAIPCNNVEVLMSGNVRCYNIVVEAMKAFPMSERI
QEVSCCLLHRLTLGNFFNILVLNEVHEFVVKAVQQYPENAALQISALSCLALLTETIFLNQDLEEKNEN
QENDDEGEEDKLFWLEACYKALTWHRKNKHVQEEAACWALNNLLMYQNSLHEKIGDEDGHFPAHRE
VMLSMLMHSSSKEVFQASANALSTLLEQNVNFRKILLSKGIHLNVLELMQKIHSPEVAESGCKMLNH
LFEGSNTSLDIMAAVVPKILTVMKRHETSLPVQLEALRAILHFIVPGMPEESREDTEFHHKLNMVKKQC
FKNDIHKLVLAALNRFIGNPGIQKCGLKVISSSIVHFPDALEMLSLEGAMDSVLHTLQMYPDDQEIQCLG
LSLIGYLITKKNVFIGTGHLLAKILVSSLYRFKDVAEIQTKGFQTILAILKLSASFSKLLVHHSFDLVIFHQM
SSNIMEQKDQQFLNLCCKCFAKVAMDDYLKNVMLERACDQNNSIMVECLLLLGADANQAKEGSSLIC
QVCEKESSPKLVELLLNSGSREQDVRKALTISIGKGDSQIISLLLRRLALDVANNSICLGGFCIGKVEPS
WLGPLFPDKTSNLRKQTNIASTLARMVIRYQMKSAVEEGTASGSDGNFSEDVLSKFDEWTFIPDSSM
DSVFAQSDDLDSEGSEGSFLVKKKSNSISVGEFYRDAVLQRCSPNLQRHSNSLGPIFDHEDLLKRKR
KILSSDDSLRSSKLQSHMRHSDSISSLASEREYITSDLLSANELRDIDALSQKCCISVHLEHLEKLELHQ
NALTSFPQQLCETLKSLTHLDLHSNKFTSFPSYLLKMSCIANLDVSRNDIGPSVVLDPTVKCPTLKQFN
LSYNQLSFVPENLTDVVEKLEQLILEGNKISGICSPLRLKELKILNLSKNHISSLSENFLEACPKVESFSA
RMNFLAAMPFLPPSMTILKLSQNKFSCIPEAILNLPHLRSLDMSSNDIQYLPGPAHWKSLNLRELLFSH
NQISILDLSEKAYLWSRVEKLHLSHNKLKEIPPEIGCLENLTSLDVSYNLELRSFPNEMGKLSKIWDLPL
DELHLNFDFKHIGCKAKDIIRFLQQRLKKAVPYNRMKLMIVGNTGSGKTTLLQQLMKTKKSDLGMQSA
TVGIDVKDWPIQIRDKRKRDLVLNVWDFAGREEFYSTHPHFMTQRALYLAVYDLSKGQAEVDAMKP
WLFNIKARASSSPVILVGTHLDVSDEKQRKACMSKITKELLNKRGFPAIRDYHFVNATEESDALAKLRK
TIINESLNFKIRDQLVVGQLIPDCYVELEKIILSERKNVPIEFPVIDRKRLLQLVRENQLQLDENELPHAVH
FLNESGVLLHFQDPALQLSDLYFVEPKWLCKIMAQILTVKVEGCPKHPKGIISRRDVEKFLSKKRKFPK
NYMSQYFKLLEKFQIALPIGEEYLLVPSSLSDHRPVIELPHCENSEIIIRLYEMPYFPMGFWSRLINRLLE
ISPYMLSGRERALRPNRMYWRQGIYLNWSPEAYCLVGSEVLDNHPESFLKITVPSCRKGCILLGQVV
DHIDSLMEEWFPGLLEIDICGEGETLLKKWALYSFNDGEEHQKILLDDLMKKAEEGDLLVNPDQPRLTI
PISQIAPDLILADLPRNIMLNNDELEFEQAPEFLLGDGSFGSVYRAAYEGEEVAVKIFNKHTSLRLLRQE
LVVULCHLHHPSLISLLAAGIRPRMLVMELASKGSLDRLLQQDKASLTRTLQHRIALHVADGLRYLHSAM
IIYRDLKPHNVLLFTLYPNAAIIAKIADYGIAQYCCRMGIKTSEGTPGFRAPEVARGNVIYNQQADVYSF
GLLLYDILTTGGRIVEGLKFPNEFDELEIQGKLPDPVKEYGCAPWPMVEKLIKQCLKENPQERPTSAQ
VFDILNSAELVCLTRRILLPKNVIVECMVATHHNSRNASIWLGCGHTDRGQLSFLDLNTEGYTSEEVAD
SRILCLALVHLPVEKESWIVSGTQSGTLLVINTEDGKKRHTLEKMTDSVTCLYCNSFSKQSKQKNFLLV GTADGKLAIFEDKTVKLKGAAPLKILNIGNVSTPLMCLSESTNSTERNVMWGGCGTKIFSFSNDFTIQK
LIETRTSQLFSYAAFSDSNIITVVVDTALYIAKQNSPVVEVWDKKTEKLCGLIDCVHFLREVMVKENKES
KHKMSYSGRVKTLCLQKNTALWIGTGGGHILLLDLSTRRLIRVIYNFCNSVRVMMTAQLGSLKNVMLV
LGYNRKNTEGTQKQKEIQSCLTVWDINLPHEVQNLEKHIEVRKELAEKMRRTSVE SEQ ID NO: 10: 'LRRKtide' peptide
H-RLGRDKYKTLRQIRQ-OH

What is claimed is:

1. A compound of Formula (I) or a salt thereof

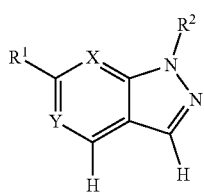

Formula (I)

Wherein

X is selected from CH or N;

Y is selected from CH, N or $CR_3$, wherein $R_3$ is selected from the group consisting of halo, $C_{1-3}$ alkyl, CN, and $C_{1-3}$ haloalkyl;

$R^1$ is selected from the group consisting of 5 or 6 membered heterocyclyl optionally substituted with one two or three substituents independently selected from the group consisting of $C_{1-3}$ alkyl optionally further substituted with one $C_{1-3}$ alkoxyl, $C_{1-3}$ alkoxyl, halo, hydroxyl,

—$SO_2CH_3$,

—$COCH_3$, oxo group, and oxetanyl,

—O-4 to 6 membered heterocyclyl optionally substituted with one or two substituents of $C_{1-3}$ alkyl, which may be the same or different, and $C_{1-6}$ alkoxyl; and $R^2$ is

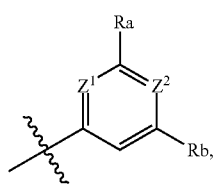

wherein $Z^1$ and $Z^2$ are independently N or $CR_7$, and wherein $R_7$ is H or $C_{1-3}$alkoxyl, but $Z^1$ and $Z^2$ cannot both be $CR_7$, $R_a$ is selected from the group consisting of

H,

CN, $C_{1-3}$ alkyl, $C_{1-3}$ alkoxyl,

—O—$C_{1-3}$haloalkyl, and $C_{3-6}$cycloalkyl; and $R_b$ is selected from the group consisting of 2-oxa-6-azaspiro[3.4]octanyl, $C_{3-6}$cycloalkyl, optionally substituted with one hydroxyl,

—$CONHCH_3$,

—$NHCOCH_3$, 4 to 6 membered heterocyclyl optionally substituted with one or two substituents independently selected from the group consisting of hydroxyl,

CN,

—$CONHCH_3$, oxetanyl, $C_{1-3}$alkyl, optionally substituted with one hydroxyl, and $C_{1-3}$ alkoxyl, optionally substituted with one hydroxyl.

2. A compound according to claim 1 has the structure of Formula (I) or a pharmaceutically acceptable salt thereof.

3. The compound or a pharmaceutically acceptable salt thereof according to claim 1, wherein X is CH.

4. The compound or a pharmaceutically acceptable salt thereof according to claim 1, wherein Y is $CR_3$ and $R_3$ is F or methyl.

5. The compound or a pharmaceutically acceptable salt thereof according to claim 1, wherein $R^1$ is 5 or 6 membered heterocyclyl optionally substituted with one, two or three substituents independently selected from the group consisting of halo, hydroxyl, $SO_2CH_3$, $COCH_3$, oxetanyl, oxo group and $C_{1-3}$ alkyl optionally further substituted with one $C_{1-3}$ alkoxyl and wherein the 5 or 6 membered heterocyclyl is saturated or contains one double bond and contains one or two heteroatom ring members selected from nitrogen or oxygen.

6. The compound or a pharmaceutically acceptable salt thereof according to claim 1, wherein $R^1$ is 6 membered heterocyclyl optionally substituted with one or two substituents independently selected from the group consisting of halo, oxetanyl and $C_{1-3}$ alkyl, and wherein the heterocyclyl is saturated and contains one or two heteroatom ring members selected from nitrogen or oxygen.

7. The compound or a pharmaceutically acceptable salt thereof according to claim 1, wherein $R^2$ is

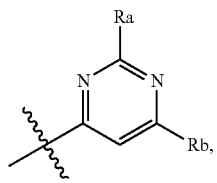

wherein $R_a$ is selected from the group consisting of

H,

CN, $C_{1-3}$ alkyl, $C_{1-3}$ alkoxyl, and $C_{3-6}$cycloalkyl; and $R_b$ is selected from the group consisting of 2-oxa-6-azaspiro[3.4]octanyl, $C_{3-6}$cycloalkyl, optionally substituted with one hydroxyl,

—CONHCH$_3$,

—NHCOCH$_3$, and 4 to 6 membered heterocyclyl optionally substituted with one or two substituents independently selected from the group consisting of hydroxyl,

CN,

—CONHCH$_3$, $C_{1-3}$ alkyl, optionally substituted with one hydroxyl, and $C_{1-3}$ alkoxyl, optionally substituted with one hydroxyl.

8. The compound or a pharmaceutically acceptable salt thereof according to claim 1, wherein R$^2$ is

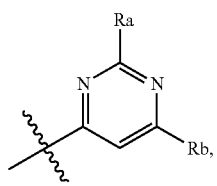

wherein $R_a$ is $C_{1-3}$ alkyl or $C_{1-3}$ alkoxyl, and $R_b$ is 4 to 6 membered heterocyclyl optionally substituted with one substituent selected from the group consisting of hydroxyl, $C_{1-3}$alkyl optionally substituted with one hydroxyl, and $C_{1-3}$ alkoxyl optionally substituted with one hydroxyl, and the 4 to 6 membered heterocyclyl is selected from the group consisting of morpholinyl, azetinidyl, piperazinyl, and oxetanyl.

9. The compound according to claim 1 or a pharmaceutically acceptable salt thereof has a structure of Formula (B)

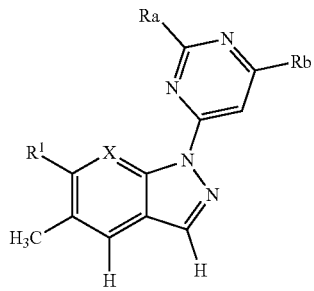

Formula (B)

wherein,

R$^1$ is piperidinyl substituted with one or two substituents independently selected from the group consisting of halo, $C_{1-3}$ alkyl and oxetanyl;

$R_a$ is $C_{1-3}$ alkyl or $C_{1-3}$ alkoxyl; and $R_b$ is 4 to 6 membered heterocyclyl substituted with one substituent selected from the group consisting of hydroxyl, $C_{1-3}$ alkyl optionally substituted with one hydroxyl, and $C_{1-3}$ alkoxyl optionally substituted with one hydroxyl, and the 4 to 6 membered heterocyclyl is selected from the group consisting of morpholinyl, azetinidyl, piperazinyl, and oxetanyl.

10. The compound or a pharmaceutically acceptable salt thereof according to claim 9, which is

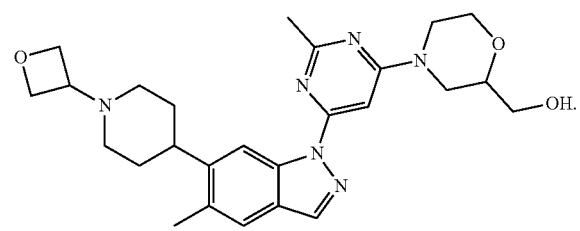 [SMILES: Cc1nc(N2CCOC(CO)C2)cc(-n2ncc3cc(C)c(C4CCN(C5COC5)CC4)cc32)n1]

11. The compound or a pharmaceutically acceptable salt thereof according to claim 9, which is

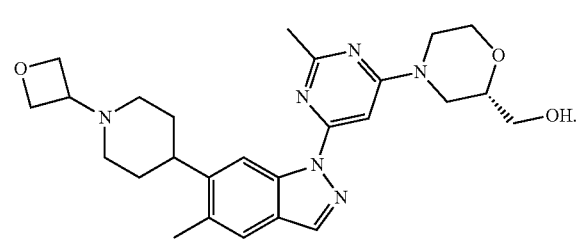

12. The compound or a pharmaceutically acceptable salt thereof according to claim 9, which is

13. The compound or a pharmaceutically acceptable salt thereof according to claim 9, which is

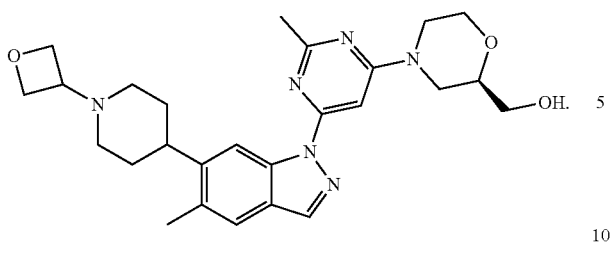

14. The compound or a pharmaceutically acceptable salt thereof according to claim 9, which is

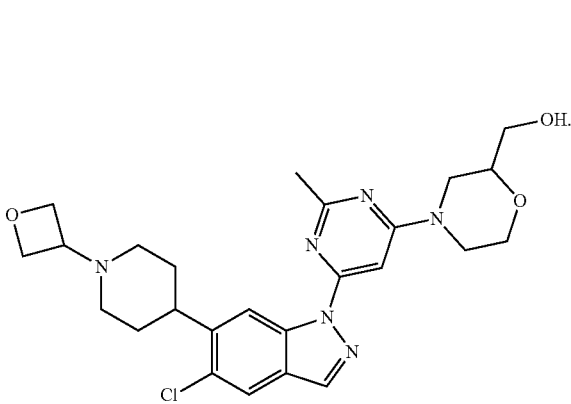

15. The compound or a pharmaceutically acceptable salt thereof according to claim 9, which is

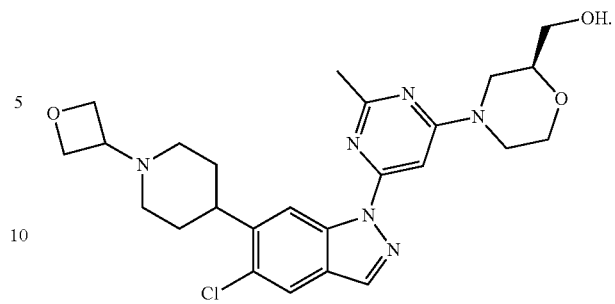

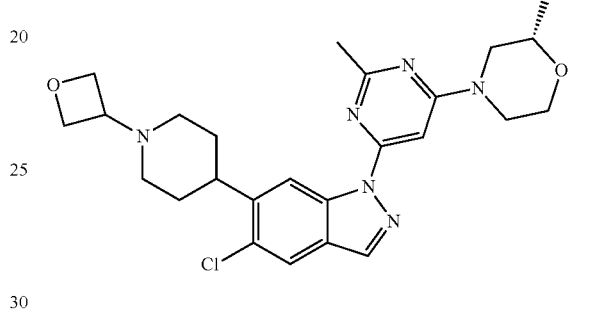

16. A pharmaceutical composition comprising the compound of Formula (I) or a pharmaceutically acceptable salt thereof according to claim 1 and a pharmaceutically acceptable excipient.

17. A method of treatment of Parkinson's disease which comprises administering to a subject in need thereof a therapeutically effective amount of a compound or a pharmaceutically acceptable salt thereof according to claim 1.

18. The method of claim 17, wherein the subject is a human.

* * * * *